(12) United States Patent
Wang et al.

(10) Patent No.: US 11,021,444 B2
(45) Date of Patent: Jun. 1, 2021

(54) ANTIVIRAL COMPOUNDS

(71) Applicant: Janssen BioPharma, Inc., South San Francisco, CA (US)

(72) Inventors: Guangyi Wang, Carlsbad, CA (US); Leonid Beigelman, San Mateo, CA (US); Anh Truong, Burlingame, CA (US); Carmela Napolitano, Verona (IT); Daniele Andreotti, Verona (IT); Haiying He, Shanghai (CN); Karin Ann Stein, Moutain View, CA (US)

(73) Assignee: Janssen BioPharma, Inc., South San Francisco, CA (US)

( * ) Notice: Subject to any disclaimer, the term of this patent is extended or adjusted under 35 U.S.C. 154(b) by 0 days.

(21) Appl. No.: 16/165,865

(22) Filed: Oct. 19, 2018

(65) Prior Publication Data

US 2019/0263754 A1 Aug. 29, 2019

Related U.S. Application Data

(63) Continuation of application No. 15/678,901, filed on Aug. 16, 2017, now abandoned, which is a
(Continued)

(51) Int. Cl.

| | | |
|---|---|---|
| *C07D 213/40* | (2006.01) |
| *A61K 45/06* | (2006.01) |
| *A61K 31/4355* | (2006.01) |
| *A61K 31/505* | (2006.01) |
| *A61K 31/427* | (2006.01) |
| *A61K 31/4196* | (2006.01) |
| *A61K 31/422* | (2006.01) |
| *A61K 31/4365* | (2006.01) |
| *A61K 31/4439* | (2006.01) |
| *A61K 31/4178* | (2006.01) |
| *A61K 31/4418* | (2006.01) |
| *A61K 31/4436* | (2006.01) |
| *C07D 491/052* | (2006.01) |
| *C07D 207/273* | (2006.01) |
| *C07D 417/12* | (2006.01) |
| *C07D 405/12* | (2006.01) |
| *C07D 401/06* | (2006.01) |
| *C07D 413/06* | (2006.01) |
| *C07D 413/12* | (2006.01) |
| *C07D 417/06* | (2006.01) |
| *C07D 409/14* | (2006.01) |
| *C07D 233/64* | (2006.01) |
| *C07D 491/048* | (2006.01) |
| *C07D 401/12* | (2006.01) |
| *C07D 213/65* | (2006.01) |
| *C07D 471/04* | (2006.01) |

(Continued)

(52) U.S. Cl.
CPC ........ *C07D 213/40* (2013.01); *A61K 31/4178* (2013.01); *A61K 31/4196* (2013.01); *A61K 31/422* (2013.01); *A61K 31/427* (2013.01); *A61K 31/437* (2013.01); *A61K 31/4355* (2013.01); *A61K 31/4365* (2013.01); *A61K 31/444* (2013.01); *A61K 31/4418* (2013.01); *A61K 31/4436* (2013.01); *A61K 31/4439* (2013.01); *A61K 31/4709* (2013.01); *A61K 31/505* (2013.01); *A61K 45/06* (2013.01); *C07D 207/273* (2013.01); *C07D 213/65* (2013.01); *C07D 233/64* (2013.01); *C07D 239/34* (2013.01); *C07D 401/04* (2013.01); *C07D 401/06* (2013.01); *C07D 401/12* (2013.01); *C07D 405/12* (2013.01); *C07D 409/04* (2013.01); *C07D 409/14* (2013.01); *C07D 413/04* (2013.01); *C07D 413/06* (2013.01); *C07D 413/12* (2013.01); *C07D 417/04* (2013.01); *C07D 417/06* (2013.01); *C07D 417/12* (2013.01); *C07D 471/04* (2013.01); *C07D 491/048* (2013.01); *C07D 491/052* (2013.01); *C07D 495/14* (2013.01); *A61K 2300/00* (2013.01); *C12N 2760/18511* (2013.01)

(58) Field of Classification Search
None
See application file for complete search history.

(56) References Cited

U.S. PATENT DOCUMENTS

| | | |
|---|---|---|
| 2,516,098 A | 7/1950 | Bambas |
| 4,876,346 A | 10/1989 | Musser et al. |

(Continued)

FOREIGN PATENT DOCUMENTS

| | | |
|---|---|---|
| CN | 1261276 A | 7/2000 |
| CN | 1869008 A | 11/2006 |

(Continued)

OTHER PUBLICATIONS

Chemical Abstract Registry No. 1290350-29-6, indexed in the Registry File on STN CAS Online May 5, 2011.*
(Continued)

*Primary Examiner* — Po-Chih Chen
(74) *Attorney, Agent, or Firm* — Morrison & Foerster LLP

(57) ABSTRACT

Disclosed herein are new antiviral compounds, together with pharmaceutical compositions that include one or more antiviral compounds, and methods of synthesizing the same. Also disclosed herein are methods of ameliorating and/or treating a paramyxovirus viral infection with one or more small molecule compounds. Examples of paramyxovirus infection include an infection caused by human respiratory syncytial virus (RSV).

25 Claims, 9 Drawing Sheets

Specification includes a Sequence Listing.

Related U.S. Application Data continuation of application No. 14/462,937, filed on Aug. 19, 2014, now abandoned.

(60) Provisional application No. 61/945,048, filed on Feb. 26, 2014, provisional application No. 61/868,519, filed on Aug. 21, 2013.

(51) Int. Cl.
| | | |
|---|---|---|
| *C07D 239/34* | (2006.01) |
| *C07D 417/04* | (2006.01) |
| *C07D 413/04* | (2006.01) |
| *C07D 401/04* | (2006.01) |
| *C07D 495/14* | (2006.01) |
| *C07D 409/04* | (2006.01) |
| *A61K 31/437* | (2006.01) |
| *A61K 31/444* | (2006.01) |
| *A61K 31/4709* | (2006.01) |

(56) References Cited

U.S. PATENT DOCUMENTS

| | | | |
|---|---|---|---|
| 5,618,938 | A | 4/1997 | Emonds-Alt |
| 6,623,741 | B1 | 9/2003 | Antczak et al. |
| 9,724,351 | B2 | 8/2017 | Wang et al. |
| 10,358,453 | B2 | 7/2019 | Wang |
| 2004/0127574 | A1 | 7/2004 | Kori et al. |
| 2007/0037752 | A1 | 2/2007 | Ansorge et al. |
| 2009/0238772 | A1 | 9/2009 | Vaishnaw et al. |
| 2012/0128669 | A1 | 5/2012 | Depla et al. |
| 2012/0225867 | A1 | 9/2012 | Wohlfahrt et al. |
| 2013/0090328 | A1 | 4/2013 | Liang et al. |
| 2013/0164280 | A1 | 6/2013 | Boojamra et al. |
| 2013/0210839 | A1 | 8/2013 | Masui et al. |
| 2013/0273037 | A1 | 10/2013 | Siegel et al. |
| 2014/0072554 | A1 | 3/2014 | Babaoglu et al. |
| 2015/0065504 | A1 | 3/2015 | Wang et al. |
| 2016/0244460 | A1 | 8/2016 | Wang et al. |
| 2017/0283429 | A1 | 10/2017 | Wang et al. |
| 2018/0065932 | A1 | 3/2018 | Wang et al. |

FOREIGN PATENT DOCUMENTS

| | | |
|---|---|---|
| EA | 201590197 A1 | 7/2015 |
| JP | S60-500669 A | 5/1984 |
| JP | 2002-293764 A | 10/2002 |
| JP | 2002-539115 A | 11/2002 |
| JP | 2007-501788 A | 2/2007 |
| JP | 2007-501803 A | 2/2007 |
| JP | 2008-521787 A | 6/2008 |
| JP | 2009-539791 A | 11/2009 |
| JP | 2013-517278 A | 5/2013 |
| WO | WO-1984/02907 A1 | 8/1984 |
| WO | WO-1998/048799 A1 | 11/1998 |
| WO | WO-1999/61437 A1 | 12/1999 |
| WO | WO-1999/066925 A1 | 12/1999 |
| WO | WO-2000/053583 A1 | 9/2000 |
| WO | WO-2002/034745 A1 | 5/2002 |
| WO | WO-2003/024955 A2 | 3/2003 |
| WO | WO-2003/029245 A1 | 4/2003 |
| WO | WO-2003/045381 A1 | 6/2003 |
| WO | WO-2004/039366 A1 | 5/2004 |
| WO | WO-2005/014540 A1 | 2/2005 |
| WO | WO-2005/016876 A2 | 2/2005 |
| WO | WO-2005/016876 A3 | 2/2005 |
| WO | WO-2005/035514 A2 | 4/2005 |
| WO | WO-2005/042530 A1 | 5/2005 |
| WO | WO-2005/058869 A1 | 6/2005 |
| WO | WO-2005/094514 A2 | 10/2005 |
| WO | WO-2006/056815 A1 | 6/2006 |
| WO | WO-2006/136561 A1 | 12/2006 |
| WO | WO-2007/141009 A1 | 12/2007 |
| WO | WO-2008/098239 A2 | 8/2008 |
| WO | WO-2008/150486 A2 | 12/2008 |
| WO | WO-2009/005638 A2 | 1/2009 |
| WO | WO-2009/016460 A2 | 2/2009 |
| WO | WO-2009/045503 A1 | 4/2009 |
| WO | WO-2009/055077 A1 | 4/2009 |
| WO | WO-2009/087379 A2 | 7/2009 |
| WO | WO-2009/154780 A1 | 12/2009 |
| WO | WO-2010/103306 A1 | 9/2010 |
| WO | WO-2010/132992 A1 | 11/2010 |
| WO | WO-2010/150281 A2 | 12/2010 |
| WO | WO-2011/005842 A1 | 1/2011 |
| WO | WO-2011/088181 A1 | 7/2011 |
| WO | WO-2011/097607 A1 | 8/2011 |
| WO | WO-2012/020786 A1 | 2/2012 |
| WO | WO-2012/057247 A1 | 5/2012 |
| WO | WO-2012/068622 A1 | 5/2012 |
| WO | WO-2012/080446 A1 | 6/2012 |
| WO | WO-2012/080447 A1 | 6/2012 |
| WO | WO-2012/080449 A1 | 6/2012 |
| WO | WO-2012/080450 A1 | 6/2012 |
| WO | WO-2012/080451 A1 | 6/2012 |
| WO | WO-2013/007663 A1 | 1/2013 |
| WO | WO-2013/010380 A1 | 1/2013 |
| WO | WO-2013/055645 A1 | 4/2013 |
| WO | WO-2013/059119 A1 | 4/2013 |
| WO | WO-2013/064518 A1 | 5/2013 |
| WO | WO-2013/186332 A1 | 12/2013 |
| WO | WO-2013/186333 A1 | 12/2013 |
| WO | WO-2013/186334 A1 | 12/2013 |
| WO | WO-2013/186335 A1 | 12/2013 |
| WO | WO-2014/009302 A1 | 1/2014 |
| WO | WO-2014/031784 A1 | 2/2014 |
| WO | WO-2015/026792 A1 | 2/2015 |

OTHER PUBLICATIONS

Chinese Office Action dated May 7, 2019 for Chinese Application 201480055176.5, filed Aug. 19, 2014.
Ukraine Office Action dated Apr. 18, 2019 for UA Application No. a201601391 filed Aug. 19, 2014.
Eurasian Office Action dated Aug. 26, 2019, for Eurasian Application No. 201690224/28, filed Aug. 19, 2014, 4 pages.
European Office Action dated Nov. 21, 2019 for European Application No. 14837913.4, filed Mar. 10, 2016, 6 pages.
Israeli Notice of Allowance dated Nov. 6, 2019, for IL Application No. 244163, filed Aug. 19, 2014, 75 pages.
Mexican Office Action dated Dec. 13, 2019 for Mexican Application No. MX/a/2016/002199, filed Aug. 19, 2014, 8 pages.
Philippines Substantive Examination Report dated Aug. 7, 2019, for PH Application No. 1/2016/500332, filed Feb. 18, 2016, 4 pages.
Al-Afaleq et al., "L-Amino Acid Esters Studies: Part II: Synthesis of N-(Dimethoxy/3,5 Diacetoxybenzoyl)-L-Amino Acid Hydrazides and their Reactions with Aldehydes and Ketones" *Syn. Comm: An International Journal for Rapid Communication of Synthetic Organic Chemistry* (1999) 29(8):1317-1331.
Barbayianni et al., "Enzymatic Removal of Carboxyl Protecting Groups. 2. Cleavage of the Benzyl and Mthyl Moieties" *J. Org. Chem.* (2005) 70(22):8730-8733.
Bhattacharjee et al., "Discovery of non-oxime reactivators using an in silica pharmacophore model of oxime reactivators of OP-inhibited acetylcholinesterase" *Eur. J. Med. Chem.* (2012) 49:229-238.
CAS Registry No. 1276363-72-4, Entered Apr. 7, 2011.
CAS Registry No. 1235682-49-1, Entered Aug. 10, 2010.
CAS Registry No. 817189-89-2, Entered Jan. 20, 2005.
CAS Registry No. 817189-87-0, Entered Jan. 20, 2005.
CAS Registry No. 476430-91-8, Entered Dec. 17, 2002.
CAS Registry No. 476430-75-8, Entered Dec. 17, 2002.
CAS Registry No. 391891-52-4, Entered Feb. 13, 2002.
CAS Registry No. 391891-51-3, Entered Feb. 13, 2002.
CAS Registry No. 374606-62-9, Entered Dec. 10, 2001.
CAS Registry No. 373613-54-8, Entered Dec. 5, 2001.
CAS Registry No. 373373-41-2, Entered Dec. 4, 2001.
CAS Registry No. 349568-79-2, Entered Jul. 31, 2001.
CAS Registry No. 339005-10-6, Entered May 30, 2001.
CAS Registry No. 328126-15-4, Entered Mar. 20, 2001.

(56) References Cited

OTHER PUBLICATIONS

CAS Reg No. 1025828-66-3, Entry Date of Jun. 5, 2008, Retrieved Oct. 21, 2013.
CAS Reg No. 1235686-10-8, Entry Date of Aug. 10, 2010, Retrieved Oct. 21, 2013.
CAS Reg No. 1294568-99-2, Entry Date of May 15, 2011, Retrieved Oct. 21, 2013.
CAS Reg No. 1299457-43-4, Entry Date of May 24, 2011, Retrieved Oct. 21, 2013.
CAS Reg No. 1321772-62-6, Entry Date of Aug. 23, 2011, Retrieved Oct. 21, 2013.
CAS Reg No. 1321793-72-9, Entry Date of Aug. 23, 2011, Retrieved Oct. 21, 2013.
CAS Reg No. 1371789-14-8, Entry Date of May 1, 2012, Retrieved Oct. 21, 2013.
CAS Reg No. 1386825-26-8, Entry Date of Aug. 6, 2012, Retrieved Oct. 21, 2013.
CAS Reg No. 327988-51-2, Entry Date of Mar. 19, 2001, Retrieved Oct. 21, 2013.
CAS Reg No. 382157-09-7, Entry Date of Jan. 11, 2002, Retrieved Oct. 21, 2013.
CAS Reg No. 383168-68-1, Entry Date of Jan. 15, 2002, Retrieved Oct. 21, 2013.
CAS Reg No. 847596-86-5, Entry Date of Mar. 30, 2005, Retrieved Oct. 21, 2013.
CAS Reg. No. 1379766-28-5, entered Sep. 26, 2012.
CAS Reg. No. 1379766-66-1, entered Sep. 26, 2012.
CAS Reg. No. 1379768-94-1, entered Sep. 26, 2012.
CAS Reg. No. 1379773-83-7, entered Sep. 26, 2012.
CAS Reg. No. 1379776-61-0, entered Sep. 26, 2012.
CAS Reg. No. 1379776-73-4, entered Sep. 26, 2012.
CAS Reg. No. 1379779-69-7, entered Sep. 26, 2012.
CAS Reg. No. 1379780-05-8, entered Sep. 26, 2012.
CAS Reg. No. 1379780-19-4, entered Sep. 26, 2012.
CAS Reg. No. 1379791-03-3, entered Sep. 26, 2012.
CAS Reg. No. 1379791-59-9, entered Sep. 26, 2012.
CAS Reg. No. 1390085-61-6, entered Sep. 26, 2012.
CAS Reg. No. 1390085-85-4, entered Sep. 26, 2012.
CAS Reg. No. 1390247-93-4, entered Sep. 26, 2012.
CAS Reg. No. 1390455-41-0, entered Sep. 26, 2012.
CAS Reg. No. 1396400-48-8, entered Sep. 26, 2012.
CAS Reg. No. 1396400-78-4, entered Sep. 26, 2012.
CAS Reg. No. 1396401-17-4, entered Sep. 26, 2012.
CAS Reg. No. 1396403-91-0, entered Sep. 26, 2012.
CAS Reg. No. 1396494-02-2, entered Sep. 26, 2012.
CAS Reg. No. 1396499-00-5, entered Sep. 26, 2012.
CAS Reg. No. 1436095-55-4, entered Sep. 26, 2012.
CAS Reg. No. 1396495-67-2, entered Sep. 26, 2012.
CAS Registry No. 1276808-00-4 (registered by FCH Group) entered STN Apr. 8, 2011 Chemical Abstract Registry No. 1276808-004, indexed in the Registry File on STN CAS Online Apr. 8, 2011.
Franck et al., "Investigations into the synthesis, radiofluorination and conjugation of a new [18F]fluorocyclobutyl prosthetic group and its in vitro stability using a tyrosine model system" *Bioorganic & Medicinal Chemistry*, (2013) 21 (3):643-652.
Granzhan et al., "Combining Metallasupramolecular Chemistry with Dynamic Covalent Chemistry: Synthesis of Large Molecular Cages" *Angew. Chem. Int'l Ed.* (2010) 49(32): 5515-5518, and Supporting Information S1-S29.
Greene, et al., Protective Groups in Organic Synthesis, 3. Ed., John Wiley & Sons, (1999) Cover & Contents pages.
Hay et al., "4-Pyridylanilinothiazoles That Selectively Target von Hippel-Lindau Deficient Renal Cell Carcinoma Cells by Inducing Autophagic Cell Death" *J. Med. Chem.* (2010) 53(2):787-797.
Henichart, J. et al., "Synthesis of 6-phenyl and 6-styrylthiazolo[3,2-b] [1,2,4]triazoles" *J. Het. Chem.* (1986), 23(5):1531-1533.
Hotard, A.L., "A stabilized respiratory syncytial virus reverse genetics system amendable to recombination-mediated mutagenesis" *Virology* (2012) 434(1):129-136.

"IUPAC-IUB Commission on Biochemical Nomenclature Abbreviated Nomenclature of Synthetic Polypeptides (Polymerized Amino Acids)* Revised Recommendations (1971 )" Biochemistry. (1972) 11 (5) :942-944.
Jang et al., "Regioselective cross-coupling reactions and nucleophilic aromatic substitutions on a 5,7-dichloropyrido[4,3-d]pyrimidine scaffold" *Tet. Lett.* (2006) 47(50):8917-8920.
Kametani et al., "Syntheses of Imidazoquinoline Derivatives. II. Synthesis of 9, 10 Dimethoxy-3-veratryl-5,6-dihydrobenzoglyoxacoline" *Yakugaku Zasshi* (1950) 70:263-265.
Kuzuhara, H. et al. (1963). "Studies on the D-xylose Series. Part I. Synthesis of 3-Acetamido-3,5-Dideoxy-D-Xylofuranose and its Derivatives," *Agricultural and Biological Chemistry* 27(10):689-694.
McOmie, J. F. W., Protective Groups in Organic Chemistry, Plenum Press, 1973. Cover & Contents pages only.
Mello et al., "Reversing the Discovery Paradigm: A New Approach to the Combinatorial Discovery of Fluorescent Chemosensory" *J. Am. Chem. Soc.* (2005) 127(29):10124-10125.
Mina, J.G. et al. (2011). "Exploring Leishmania Major Inositol Phosphorylceramide Synthase (LmjIPCS): Insights into the Ceramide Binding Domain," *Organic & Biomolecular Chemistry* 9(6):1823-1830.
Pascal, R., et al., „Synthesis of the Novel Amino Acid 4-Amno-3-(aminomethyl)benzoicAcid (AmAbz) and Its Protected Devivatives as Building Sleeks for Psedopeptide Synthesis *Eur. J. Org. Chem.* (2000) 2000(22):3755-3761.
Perni, R. T., et al., "Inhibitors of hepatitis C virus NS3-4A protease 2. Warhead SAR and optimization" Bioorg. & Med. Chem. Letters (2004) 14:1441-1446.
Podlech et al., "99, Azetitin-3-ones from (S)-a-amino Acids and Their Reactions with Nucleophiles: Preparation of Some Azetidine-Containing Amino-Alcohol and Amino-Acid Derivatives" *Helv. Chimica Acta* (1995) 78(5):1238-1246.
Rydzewski, R.M., Real World Drug Discovery, A Chemist's Guide to Biotech and Pharmaceutical Research (Elsevier, 2008):42-43
Rydzewski, Real World Drug Discovery 2008, 42-43.
Rye et al., "Asymmetric synthesis and anti-protozoa! Activity of the 8,4'-oxyneolignans virolin and analogues" *Eur. J. Med. Chem.* (2013) 60:240-248.
Shao et al., "Synthesis and evaluation of tacrine-E2020 hybrids as acetylcholinesterase inhibitors for the treatment of Alzheimer's disease" *Bio. Med. Chem. Lett.* (2004) 14:4639-4642.
Sidwell et al., "Use of Disposable Mircro Tissue Culture Plates for Antiviral and Interferon Induction Studies" *Appl. Microbial.* (1971) 22(5):797-801.
USPTO. (Feb. 9, 2011). "Supplementary Examination Guidelines for Determining Compliance With 35 U.S.C. 112 and for Treatment of Related Issues in Patent Applications," *Federal Register* 76(27):7162-7175, located at <https://www.gpo.gov/fdsys/pkg/FR-2011-02-09/pdf/2011-2841.pdf>, last visited on Dec. 18, 2018.
Vorozhtsov, N.I. et al. (2005) Synthesis and some reactions of 1-"-cyanoalkyl(aralkyl)-2-pyrazolines. Chem Heterocycl Compd, 41(10):1307-1313.
Wuitschik et al., "Oxetanes in Drug Discovery: Structural and Synthetic Insights" *J. Med. Chem.* (2010) 53(8):3327-3246 and Supporting Information pp. 1-26.
Xu et al., "Asymmetric Synthesis of Chiral 1,3-Diaminopropanols: Bisoxazolidine-Catalyzed C-C Bond Formation with a-Keto Amides" *Angew. Chem. Int. Ed.* (2011) 50(51):12249-12252 and Supporting Information pp. 1-79.
Zornik et al., "Designing Structural Motifs for Clickamers: Exploiting the 1,2,3-Triazole Moiety to Generate Conformationally Restricted Molecular Architectures" *Chem. Eur. J.* (2011) 17(5):1473-1484 and Supporting Information pp. S1-S120.
Australian Office Action dated Feb. 2, 2018 for Australian Application 2014308991, filed Aug. 19, 2014.
Australian Office Action dated Feb. 4, 2019 for Australian Application 2014308991, filed Aug. 19, 2014.
Australian Office Action dated Jan. 29, 2019 for Australian Application 2014308991, filed Aug. 19, 2014.
Chinese Office Action dated Aug. 2, 2018 for Chinese Application 201480055176.5, filed Aug. 19, 2014.

(56) References Cited

OTHER PUBLICATIONS

Chinese Office Action dated Mar. 22, 2017 in Chinese Application No. 201480055176.5, filed on Aug. 19, 2014. (Eng. Translation only).
Chinese Office Action dated Nov. 3, 2017 for Chinese Application 201480055176.5, filed Aug. 19, 2014.
Chinese Search Report dated Mar. 8, 2017 in Chinese Application No. 201480055176.5, filed on Aug. 19, 2014. (Eng. Translation only).
Colombian Office Action dated Apr. 12, 2016 for Colombian Patent Application No. 16068.345, filed Aug. 19, 2014.
Eurasian Office Action dated Dec. 10, 2018 for Eurasian Application No. 201690224/28, filed Aug. 19, 2016.
Eurasian Office Action dated Nov. 29, 2016 for Eurasian Application No. 201690224/28, filed Aug. 19, 2016.
European Extended Search Report dated Mar. 13, 2017 for European Application No. 14837913, filed Mar. 10, 2016.
European Office Action dated Jan. 15, 2019 for European Application No. 14837913.4, filed Mar. 10, 2016.
European Office Action dated Mar. 14, 2018 for European Application No. 14837913.4, filed Mar. 10, 2016.
Georgian Documentary Conclusion dated May 22, 2017 for Georgian Patent Application No. 14095/01, filed Aug. 19, 2014.
Georgian Notice of Allowance dated Sep. 25, 2017, for Georgia Application No. 14095/01, filed Aug. 19, 2014.
Georgian Notification—Demand dated Nov. 10, 2016 for Georgian Patent Application No. 14095/01, filed Aug. 19, 2014.
International Preliminary Report on Patentability dated Dec. 2, 2015 for PCT Application No. PCT/US2014/051642, filed Aug. 19, 2014.
International Search Report and Written Opinion dated Nov. 24, 2014 for PCT Application No. PCT/US2014/051642, filed Aug. 19, 2014.
Israeli Office Action dated Aug. 28, 2018 for IL Application No. 244163, filed Aug. 19, 2014.
Japanese Notice of Allowance dated Jan. 15, 2019 for Japanese Application No. 2016-536372, filed Aug. 19, 2014.
Japanese Office Action dated May 29, 2018 for Japanese Application No. 2016-536372, filed Aug. 19, 2014.
Mexican Office Action dated Apr. 12, 2019 for Mexican Application No. MX/a/2016/002199, filed Aug. 19, 2014.
New Zealand Examination Report—Postponed Acceptance Notice dated Oct. 18, 2017 for New Zealand Application No. 716822, filed Aug. 19, 2014.
New Zealand Examination Report dated Jun. 19, 2017 for New Zealand Application No. 716822.
New Zealand Examination Report dated Oct. 5, 2017 for New Zealand Application No. 716822, filed Aug. 19, 2014.
New Zealand Examination Report dated Sep. 5, 2017 for New Zealand Application No. 716822.
New Zealand First Examination Report dated Oct. 25, 2016 for NZ Application No. 716822, filed Aug. 19, 2016.
Singaporean Search Report dated Feb. 2, 2017 in Singapore Application No. 11201600977X, filed on Aug. 19, 2014.
Singaporean Written Opinion dated Feb. 2, 2017 in Singapore Application No. 11201600977X, filed on Aug. 19, 2014.
Singaporean Written Opinion dated Nov. 20, 2018 in Singapore Application No. 11201600977X, filed on Aug. 19, 2014.
Singaporean Written Opinion dated Nov. 28, 2017 for Singapore Application No. 11201600977X, filed Aug. 19, 2014.
Taiwanese Notice of Allowance dated Aug. 29, 2018 for Taiwanese Application No. 103128871, filed Aug. 21, 2014.
Taiwanese Office Action dated Apr. 20, 2018 for Taiwanese Application No. 103128871, filed Aug. 21, 2014.
Thai Office Action dated Dec. 2, 2016 in Thai Application No. 1601000934, filed on Aug. 19, 2014. (Eng. translation only).
U.S. Office Action dated Nov. 2, 2016 for U.S. Appl. No. 14/462,937, filed Aug. 19, 2014.
Uzbekistan Office Action dated Dec. 24, 2018 for UZ Application No. IAP20160095 filed on Aug. 19, 2014.
Written Opinion (Second) dated Jul. 24, 2015 for PCT Application No. PCT/US2014/051642, filed Aug. 19, 2014.
Written Opinion (Third) dated Oct. 9, 2015 for PCT Application No. PCT/US2014/051642, filed Aug. 19, 2014.
CAS Registry No. 1379769-64-8, Jun. 22, 2012, "Benzeneacetamide, 4-chloro-N-[(1R,2S,3R,5R)-2,3-dihydroxy-5-[6-(4-morpholinyl)-3-pyridinyl]cyclopentyl]," Source: Analyticon Discovery Gmbh, 1 page.
CAS Registry No. 1379791-60-2, (Jun. 22, 2012). "Benzeneacetamide, 4-chloro-N-[(1R,2S,3R,5R)-2,3-dihydroxy-5-[6-(4-morpholinyl)-3-pyridinyl]cyclopentyl]," Source: Analyticon Discovery Gmbh, 1 page.

\* cited by examiner

FIG. 1A

| Name or CAS No. | IUPAC Name | Structure |
|---|---|---|
| BMS-433771 | 1-cyclopropyl-3-[[1-(4-hydroxybutyl)benzimidazol-2-yl]methyl]imidazo[4,5-c]pyridin-2-one | 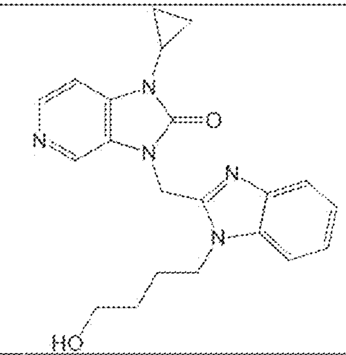 |
| VP-14637 (MDT-637) | 5,5'-bis[1-(((5-amino-1H-tetrazolyl)imino)methyl)]2,2',4''-methylidynetrisphenol | 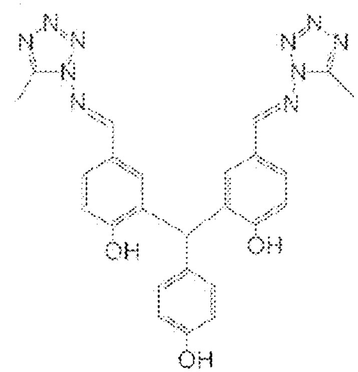 |
| JNJ-2408068 | 2-[[2-[[1-(2-aminoethyl)-4-piperidinyl]amino]-4-methyl-1H-benzimidazol-1-yl]-6-methyl-3-pyridinol | 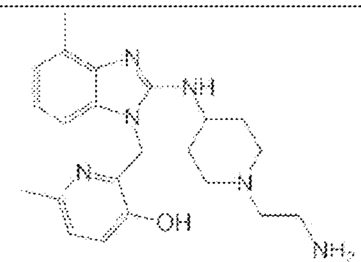 |

FIG. 1B

| Name or CAS No. | IUPAC Name | Structure |
|---|---|---|
| TMC-353121 | 2-[[6-[[[2-(3-Hydroxypropyl)-5-methylphenyl]amino]methyl]-2-[[3-(morpholin-4-yl)propyl]amino]benzimidazol-1-yl]methyl]-6-methylpyridin-3-ol | 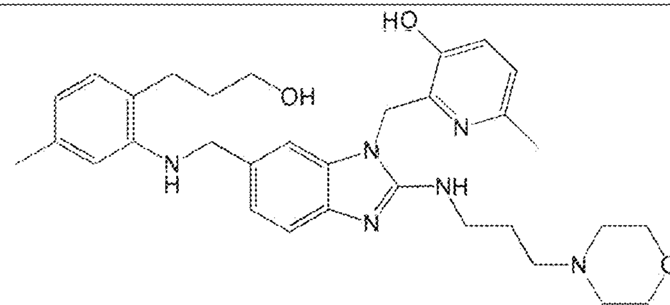 |
| P13 | N-(2-hydroxyethyl)-4-methoxy-N-methyl-3-(6-methyl-[1,2,4]triazolo[3,4-a]phthalazin-3-yl)benzenesulfonamide | 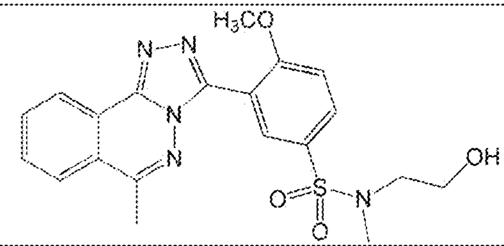 |
| C15 | 1,4-bis(3-methylpyridin-4-yl)-1,4-diazepane | 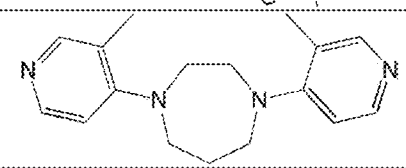 |

FIG. 1C

| Name or CAS No. | IUPAC Name | Structure |
|---|---|---|
| R170591 | 2-((2-((1-(2-aminoethyl)piperidin-4-yl)amino)-4-methyl-1H-benzo[d]imidazol-1-yl)methyl)-6-methylpyridin-3-ol | 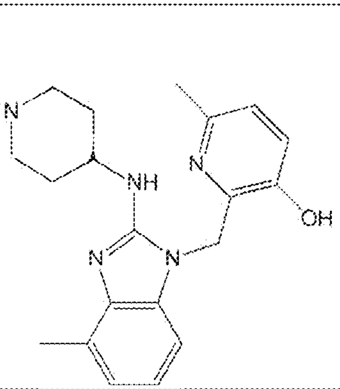 |
| BTA9981 | (R)-9b-(4-chlorophenyl)-1-(4-fluorobenzoyl)-2,3-dihydro-1H-imidazo[1',2':1,2]pyrrolo[3,4-c]pyridin-5(9bH)-one (BTA9981) | 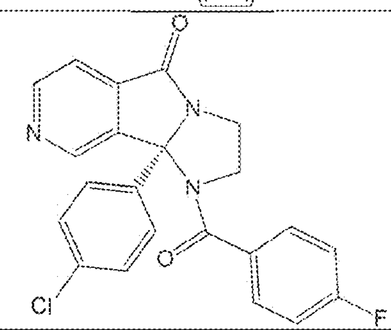 |
| RSV-604 | (S)-1-(2-fluorophenyl)-3-(2-oxo-5-phenyl-2,3-dihydro-1H-benzo[e][1,4]diazepin-3-yl)urea | 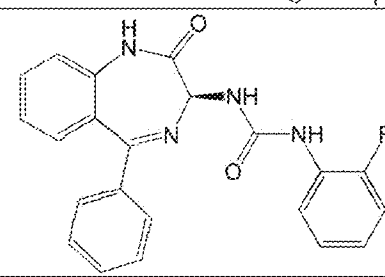 |

FIG. 1D

| Name or CAS No. | IUPAC Name | Structure |
|---|---|---|
| YM-53403 | 6-{4-[(biphenyl-2-ylcarbonyl) amino]benzoyl}-N-cyclopropyl-5,6-dihydro-4H-thieno[3,2-d][1]benzazepine-2-carboxamide | 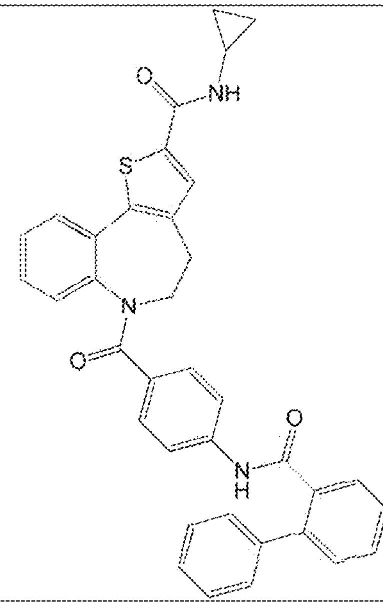 |

FIG. 1E

| Name or CAS No. | IUPAC Name | Structure |
|---|---|---|
| RFI-641 | 4,4''-bis-{4,6-bis-[3-(bis-carbamoylmethyl)-sulfamoyl)-phenylamino]-(1,3,5)triazin-2-ylamino}-biphenyl-2,2''-disulfonic-acid | 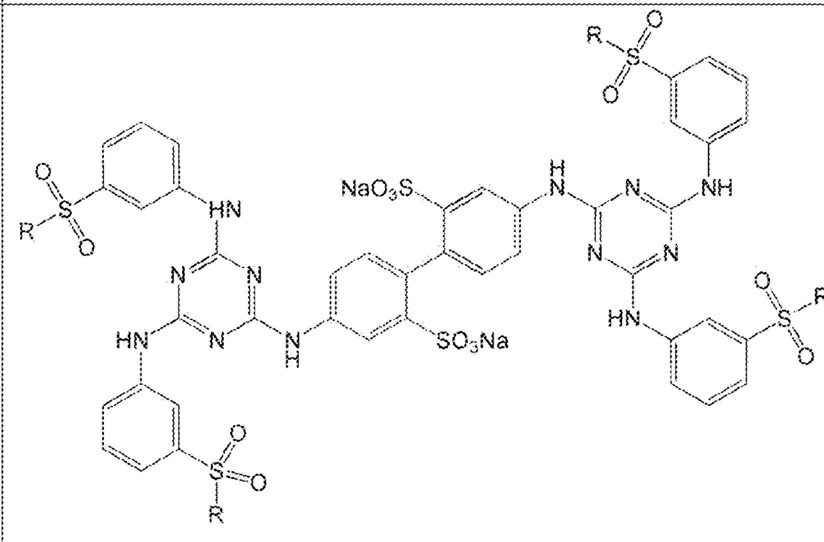 |
| EICAR | 5-ethynyl-1-beta-D-ribofuranosylimidazole-4-carboxamide | 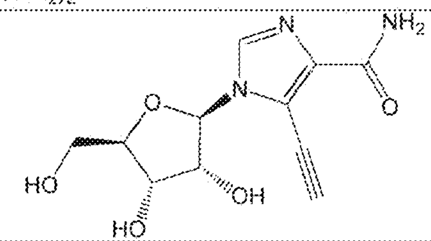 |
| leflunomide | 5-methyl-N-[4-(trifluoromethyl) phenyl]-isoxazole-4-carboxamide | |

FIG. 1F

| Name or CAS No. | IUPAC Name | Structure |
|---|---|---|
| JMN3-003 | N-(2-chloro-4-methylphenyl)-2-((1-(4-methoxyphenyl)-1H-benzo[d]imidazol-2-yl)thio)propanamide | 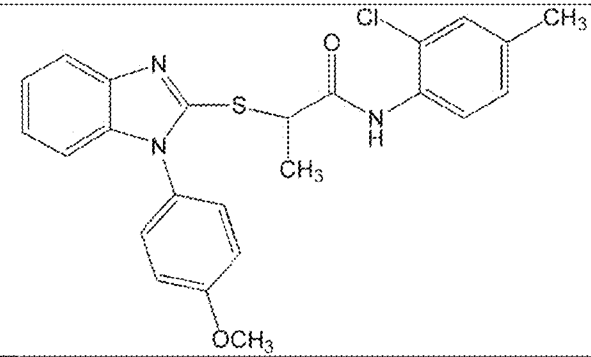 |
| MBX300 | [2,2-bis(docosyloxy-oxymethyl)propyl-5-acetaamido-3,5-dideoxy-4,7,8,9-tetra-O-(sodium-oxysulfonyl)-D-glycero-D-galacto-2-nonulopyranosid]onate | 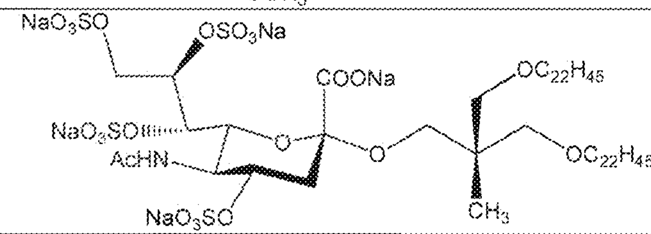 |
| GS-5806 | N-(2-((S)-2-(5-((S)-3-aminopyrrolidin-1-yl)-6-methylpyrazolo[1,5-a]pyrimidin-2-yl)piperidine-1-carbonyl)-4-chlorophenyl)methanesulfonamide | 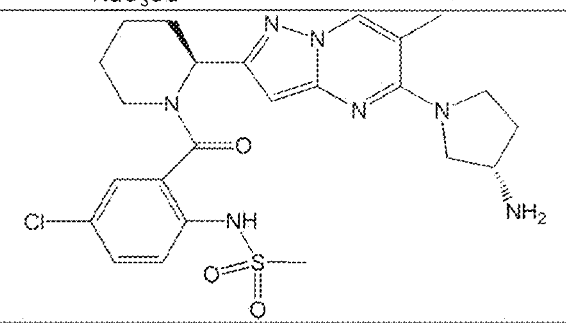 |

FIG. 1G

| Name or CAS No. | IUPAC Name | Structure |
|---|---|---|
| | N-cyclopropyl-5-(4-(2-(pyrrolidin-1-yl)benzamido)benzoyl)-5,6,7,10-tetrahydrobenzo[b]cyclopenta[d]azepine-9-carboxamide | |
| 851658-10-1 | 4-amino-8-(3-{[2-(3,4-dimethoxyphenyl)ethyl]amino}propyl)-6,6-dimethyl-2-(4-methyl-3-nitrophenyl)-1H-imidazo[4,5-h]-isoquinoline-7,9(6H,8H)-dione | 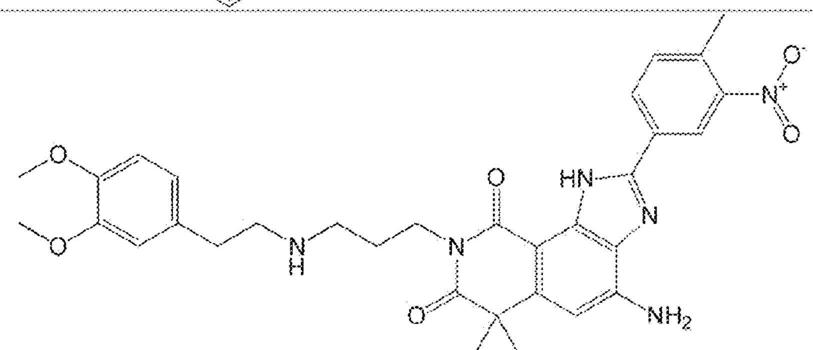 |

FIG. 1H

| Name or CAS No. | IUPAC Name | Structure |
|---|---|---|
| pyrazofurin | 4-hydroxy-3-beta-D-ribofuranosylpyrazole-5-carboxamide | 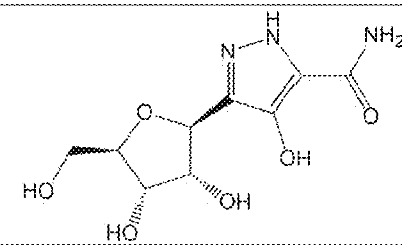 |
| Taribavirin (viramidine) | 1-((2R,3R,4S,5R)-3,4-dihydroxy-5-(hydroxymethyl)tetrahydrofuran-2-yl)-1H-1,2,4-triazoie-3-carboximidamide | 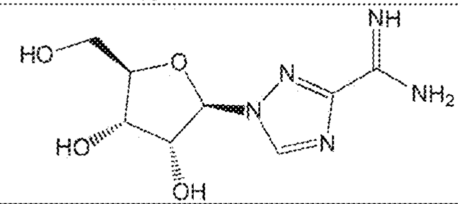 |
| ribavirin | 1-[(2R,3R,4S,5R)-3,4-dihydroxy-5-(hydroxymethyl)oxolan-2-yl]-1H-1,2,4-triazole-3-carboxamide | 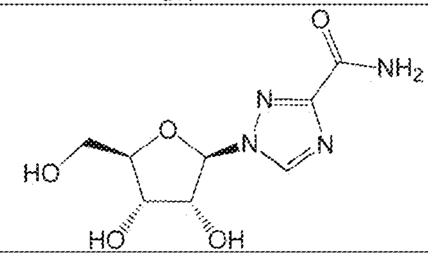 |
| LY253963 | 1,3,4-thiadiazol-2-ylcyanamide | 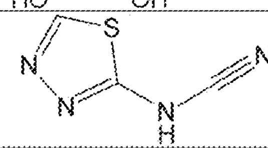 |
| VX-497 | tetrahydrofuran-3-yl 3-(3-(3-methoxy-4-(oxazol-5-yl)phenyl)ureido)benzylcarbamate | 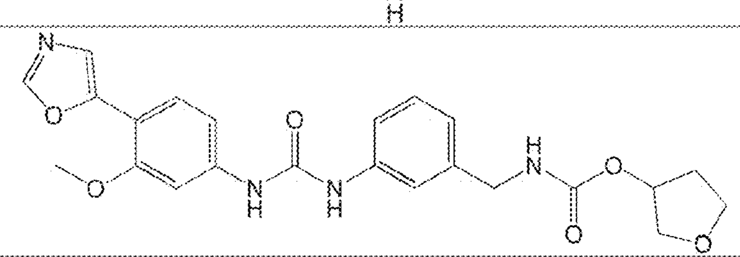 |

FIG. 11

| Name or CAS No. | IUPAC Name | Structure |
|---|---|---|
| Mycophenolic acid | (4E)-6-(4-Hydroxy-6-methoxy-7-methyl-3-oxo-1,3-dihydro-2-benzofuran-5-yl)-4-methylhex-4-enoic acid | 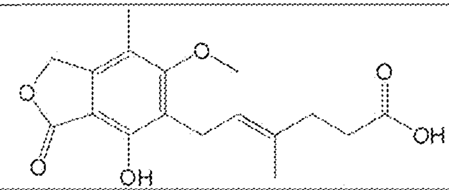 |
| Mycophenolate Mofetil | 2-morpholin-4-ylethyl (E)-6-(4-hydroxy-6-methoxy-7-methyl-3-oxo-1H-2-benzofuran-5-yl)-4-methylhex-4-enoate | 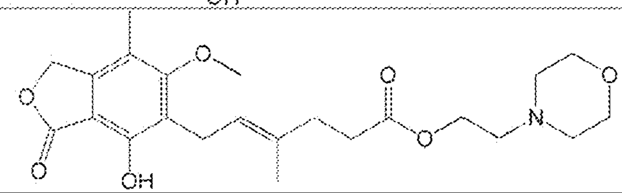 |

SEQUENCE LISTING

<160> NUMBER OF SEQ ID NOS: 4

<210> SEQ ID NO 1
<211> LENGTH: 28

```
<212> TYPE: PRT
<213> ORGANISM: Artificial Sequence
<220> FEATURE:
<223> OTHER INFORMATION: Core polypeptide

<400> SEQUENCE: 1

Asp Glu Phe Asp Ala Ser Ile Ser Gln Val Asn Glu Lys Ile Asn Gln
1               5                   10                  15

Ser Leu Ala Phe Ile Arg Lys Ser Asp Glu Leu Leu
            20                  25

<210> SEQ ID NO 2
<211> LENGTH: 35
<212> TYPE: PRT
<213> ORGANISM: Artificial Sequence
<220> FEATURE:
<223> OTHER INFORMATION: Core polypeptide

<400> SEQUENCE: 2

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 3
<211> LENGTH: 21
<212> TYPE: DNA
<213> ORGANISM: Artificial Sequence
<220> FEATURE:
<223> OTHER INFORMATION: Combined DNA/RNA Molecule: Synthetic
      oligonucleotide

<400> SEQUENCE: 3
ggcucuuagc aaagucaagt t                                            21

<210> SEQ ID NO 4
<211> LENGTH: 21
<212> TYPE: DNA
<213> ORGANISM: Artificial Sequence
<220> FEATURE:
<223> OTHER INFORMATION: Combined DNA/RNA Molecule: Synthetic
      oligonucleotide

<400> SEQUENCE: 4
cuugacuuug cuaagagcct t                                            21
```

ANTIVIRAL COMPOUNDS

CROSS REFERENCE TO RELATED APPLICATIONS

This application is a continuation application of U.S. patent application Ser. No. 15/678,901, filed Aug. 16, 2017, which is a continuation application of U.S. patent application Ser. No. 14/462,937, filed Aug. 19, 2014, which claims priority benefit of U.S. Provisional Application Nos. 61/945,048, filed Feb. 26, 2014, and 61/868,519, filed Aug. 21, 2013, the disclosures of each of which are hereby incorporated by reference in their entireties for all purposes.

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

REFERENCE TO SEQUENCE LISTING

The present application is being filed along with a Sequence Listing in electronic format. The Sequence Listing is provided as a file entitled 756982000902SEQLIST.TXT, created May 13, 2019, size: 2 KB. The information in the electronic format of the Sequence Listing is incorporated by reference in its entirety.

BACKGROUND

Field

The present application relates to the fields of chemistry, biochemistry and medicine. More particularly, disclosed herein are new antiviral compounds, together with pharmaceutical compositions, and methods of synthesizing the same. Also disclosed herein are methods of ameliorating and/or treating a paramyxovirus viral infection with one or more small molecule compounds.

Description

Respiratory viral infections, including upper and lower respiratory tract viral infections, are a leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs. Human respiratory syncytial virus (RSV) is a common cause of respiratory tract infections. Up to 60% of human infants are infected with RSV within their first year of life. Children and adults are also infected with RSV, where it is often manifesting as a lower respiratory tract infection with possible complications of bronchiolitis. RSV infections can be particularly severe in infants and elderly patients. RSV is a negative-sense, single-stranded RNA virus classified within the Paramyxoviridae family, which also includes viruses that cause Newcastle disease, parainfluenza, mumps, measles, and canine distemper.

SUMMARY

Some embodiments disclosed herein relate to a compound of Formula (I), or a pharmaceutically acceptable salt thereof. Some embodiments disclosed herein relate to a method of ameliorating and/or treating a paramyxovirus viral infection that can include administering to a subject suffering from the paramyxovirus viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a paramyxovirus viral infection. Still other embodiments described herein relate to compounds of Formula (I), or a pharmaceutically acceptable salt thereof, that can be used for ameliorating and/or treating a paramyxovirus viral infection. Yet still other embodiments disclosed herein relate to a method of ameliorating and/or treating a paramyxovirus viral infection that can include contacting a cell infected with the paramyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. Some embodiments disclosed herein relate to a method of inhibiting the replication of a paramyxovirus that can include contacting a cell infected with the paramyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. For example, the paramyxovirus viral infection can be caused by a henipavirus, a morbillivirus, a respirovirus, a rubulavirus, a pneumovirus (including a respiratory syncytial viral infection), a metapneumovirus, hendravirus, nipahvirus, measles, sendai virus, mumps, a human parainfluenza virus (HPIV-1, HPIV-2, HPIV-3 and HPIV-4) and/or a metapneumovirus.

Some embodiments disclosed herein relate to a method of ameliorating and/or treating a paramyxovirus viral infection that can include administering to a subject suffering from the viral infection an effective amount of a compound described herein or a pharmaceutically acceptable salt thereof (for example, one or more compounds of Formula (I), or a pharmaceutically acceptable salt thereof), or a pharmaceutical composition that includes one or more compounds described herein, in combination with one or more agents described herein. Some embodiments disclosed herein relate to a method of ameliorating and/or treating a paramyxovirus viral infection that can include contacting a cell infected with the paramyxovirus with an effective amount of a compound described herein or a pharmaceutically acceptable salt thereof (for example, one or more compounds of Formula (I), or a pharmaceutically acceptable salt thereof), or a pharmaceutical composition that includes one or more compounds described herein, in combination with one or more agents described herein.

BRIEF DESCRIPTION OF THE DRAWINGS

FIG. 1A, FIG. 1B, FIG. 1C, FIG. 1D, FIG. 1E, FIG. 1F, FIG. 1G, FIG. 1H, and FIG. 1I show examples of additional agents.

DETAILED DESCRIPTION

Paramyxoviridae family is a family of single stranded RNA viruses. Several genera of the paramyxoviridae family include henipavirus, morbillivirus, respirovirus, rubulavirus, pneumovirus and metapneumovirus. These viruses can be transmitted person to person via direct or close contact with contaminated respiratory droplets or fomites. Species of henipavirus include hendravirus and nipahvirus. A species of morbillivirus is measles. Species of respirovirus include sendai virus and human parainfluenza viruses 1 and 3; and species of rubulavirus include mumps virus and human parainfluenza viruses 2 and 4. A species of metapneumovirus is human metapneumovirus.

Human Respiratory Syncytial Virus (RSV), a species of pneumovirus, can cause respiratory infections, and can be associated with bronchiolitis and pneumonia. Symptoms of an RSV infection include coughing, sneezing, runny nose, fever, decrease in appetite, and wheezing. RSV is the most common cause of bronchiolitis and pneumonia in children under one year of age in the world, and can be the cause of tracheobronchitis in older children and adults. In the United States, between 75,000 and 125,000 infants are hospitalized each year with RSV. Among adults older than 65 years of age, an estimated 14,000 deaths and 177,000 hospitalizations have been attributed to RSV.

Treatment options for people infected with RSV are currently limited. Antibiotics, usually prescribed to treat bacterial infections, and over-the-counter medication are not effective in treating RSV. In severe cases, a nebulized bronchodilator, such as albuterol, may be prescribed to relieve some of the symptoms, such as wheezing. Respi-Gram® (RSV-IGIV, MedImmune, approved for high risk children younger than 24 months of age), Synagis® (palivizumab, MedImmune, approved for high risk children younger than 24 months of age), and Virzole® (ribavirin by aerosol, ICN pharmaceuticals) have been approved for treatment of RSV.

Symptoms of the measles include fever, cough, runny nose, red eyes and a generalized rash. Some individuals with measles can develop pneumonia, ear infections and bronchitis. Mumps leads to swelling of the salivary glands. Symptoms of mumps include fever, loss of appetite and fatigue. Individuals are often immunized against measles and mumps via a three-part MMR vaccine (measles, mumps, and rubella). Human parainfluenza virus includes four serotypes types, and can cause upper and lower respiratory tract infections. Human parainfluenza virus 1 (HPIV-1) can be associated with croup; human parainfluenza virus 3 (HPIV-3) can be associated with bronchiolitis and pneumonia. According to the Centers of Disease Control and Prevention (CDC), there are no vaccines against human parainfluenza virus.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, and $R^A$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

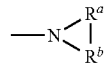

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, acylalkyl, hydroxy, alkoxy, alkoxyalkyl, aminoalkyl, amino acid, aryl, heteroaryl, heterocyclyl, aryl(alkyl), heteroaryl(alkyl), heterocyclyl(alkyl), hydroxyalkyl, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one, two, three or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl or heteroalicyclic groups may be unsubstituted or substituted. Examples of such "heterocyclyl" or "heteroalicyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "acylalkyl" refers to an acyl connected, as a substituent, via a lower alkylene group. Examples include aryl-C(=O)—$(CH_2)_n$— and heteroaryl-C(=O)—$(CH_2)_n$—, where n is an integer in the range of 1 to 6.

As used herein, "alkoxyalkyl" refers to an alkoxy group connected, as a substituent, via a lower alkylene group. Examples include $C_{1-4}$ alkyl-O—$(CH_2)_n$—, wherein n is an integer in the range of 1 to 6.

As used herein, "aminoalkyl" refers to an optionally substituted amino group connected, as a substituent, via a lower alkylene group. Examples include $H_2N(CH_2)_n$—, wherein n is an integer in the range of 1 to 6.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydropropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, chlorofluoroalkyl, chloro-difluoroalkyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, chloro-fluoroalkyl, chloro-difluoroalkoxy and 2-fluoroisobutoxy. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—$SO_2N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carbamyl" group refers to a "—OC(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "urea" group refers to "N(R)—C(=O)—$NR_AR_B$ group in which R can be hydrogen or an alkyl, and $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A urea may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, "-------" indicates a single or double bond, unless stated otherwise.

The term "interferon" is used herein as is commonly understood by one of ordinary skill in the art. Several types of interferons are known to those skilled in the art, such as Type 1 interferons, Type 2 interferons and Type 3 interferons. A non-limiting list of examples include: alpha-interferons, beta-interferons, delta-interferons, gamma interferons, lambda interferons, omega-interferons, tau-interferons, x-interferons, consensus interferons and asialo-interferons. Interferons can be pegylated. Examples of type 1 interferons include interferon alpha 1A, interferon alpha 1B, interferon alpha 2A, interferon alpha 2B, pegylated-interferon alpha 2a (PEGASYS, Roche), recombinant interferon alpha 2a (ROFERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical). Examples of type 2 interferons include interferon gamma 1, interferon gamma 2 and pegylated interferon gamma; and examples of type 3 interferons include interferon lambda 1, interferon lambda 2 and interferon lambda 3.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. As used herein, "amino acid" also includes amino acids wherein the main-chain carboxylic acid group has been converted to an ester group.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propyl silyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Formula (I)

Some embodiments disclosed herein relate to a compound of Formula (I), or a pharmaceutically acceptable salt thereof, having the structure:

A-L-Y (I)

wherein: L can be selected from:

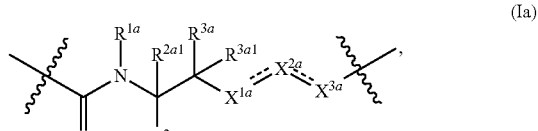

(Ia)

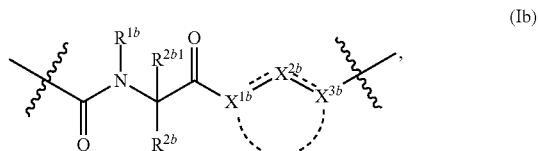

(Ib)

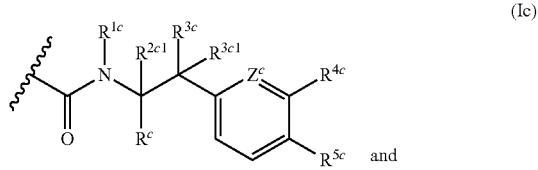

(Ic)

and

-continued

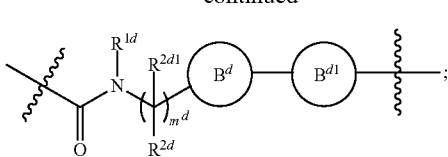
(Id)

A can be selected from an optionally substituted cycloalkyl, an optionally substituted cycloalkenyl, an optionally substituted aryl, an optionally substituted aryl($C_{1-2}$ alkyl), an optionally substituted heteroaryl and an optionally substituted heterocyclyl; Y can be selected from an optionally substituted cycloalkyl, an optionally substituted cycloalkenyl, an optionally substituted aryl, an optionally substituted heteroaryl and an optionally substituted heterocyclyl; $R^{1a}$, $R^{1b}$, $R^{1c}$ and $R^{1d}$ can be each independently hydrogen or an unsubstituted $C_{1-4}$ alkyl; $R^{2a}$, $R^{2a1}$, $R^{2b}$, $R^{2b1}$, $R^{2c}$, $R^{2c1}$, $R^{2d}$ and $R^{2d1}$ can be each independently selected from hydrogen, an optionally substituted $C_{1-4}$ alkyl, an optionally substituted aryl($C_{1-6}$ alkyl), an optionally substituted heterocyclyl($C_{1-6}$ alkyl), an alkoxyalkyl, an aminoalkyl, a hydroxyalkyl and hydroxy; or $R^{2a1}$ can be hydrogen, and $R^{1a}$ and $R^{2a}$ can be joined together with the atoms to which they are attached to form an optionally substituted 5 membered heterocyclyl or an optionally substituted 6 membered heterocyclyl, $R^{2b1}$ can be hydrogen, and $R^{1b}$ and $R^{2b}$ can be joined together with the atoms to which they are attached to form an optionally substituted 5 membered heterocyclyl or an optionally substituted 6 membered heterocyclyl; ------ between $X^{1a}$ and $X^{2a}$ represents a single or double bond between $X^{1a}$ and $X^{2a}$; ------ between $X^{2a}$ and $X^{3a}$ represents a single or double bond between $X^{2a}$ and $X^{3a}$; provided that ------ between $X^{1a}$ and $X^{2a}$ and ------ between $X^{2a}$ and $X^{3a}$ cannot be both double bonds and at least one of ------ is a double bond; when ------ between $X^{1a}$ and $X^{2a}$ represents a double bond and ------ between $X^{2a}$ and $X^{3a}$ is a single bond, then $X^{1a}$ can be N (nitrogen) or $CR^{4a1}$, $X^{2a}$ can be N (nitrogen) or $CR^{5a}$ and $X^{3a}$ can be $NR^{6a1}$, C(=O) or $CR^{6a2}R^{6a3}$; and when ------ between $X^{1a}$ and $X^{2a}$ represents a single bond and ------ between $X^{2a}$ and $X^{3a}$ is a double bond, then $X^{1a}$ can be $NR^{4a}$ or $CR^{4a2}R^{4a3}$, $X^{2a}$ can be N (nitrogen) or $CR^{5a}$ and $X^{3a}$ can be N (nitrogen) or $CR^{6a}$; or $X^{1a}$, $X^{2a}$ and $X^{3a}$ can be each independently C (carbon), N (nitrogen), O (oxygen) or C(=O), and form a ring or ring system selected from an optionally substituted aryl, an optionally substituted heteroaryl and an optionally substituted heterocyclyl by joining $X^{1a}$ and $X^{3a}$ together; with the proviso that the valencies of $X^{1a}$, $X^{2a}$ and $X^{3a}$ can be each independently satisfied with a substituent selected from hydrogen and an optionally substituted $C_{1-4}$ alkyl, and $X^{1a}$, $X^{2a}$ and $X^{3a}$ are uncharged; $R^{3a}$ and $R^{3a1}$ can be each independently selected from hydrogen, hydroxy, halogen, amino, an optionally substituted $C_{1-4}$ alkyl, an optionally substituted $C_{2-4}$ alkenyl, an optionally substituted $C_{2-4}$ alkynyl, an optionally substituted $C_{3-6}$ cycloalkyl, an optionally substituted $C_{1-4}$ alkoxy, —O-carboxy, an optionally substituted heteroaryl, an optionally substituted heterocyclyl, $CHF_2$, $CF_3$ and

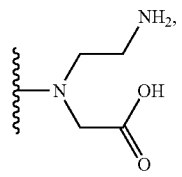 [SMILES: *N(CCN)CC(=O)O]

provided that $R^{3a}$ and $R^{3a1}$ cannot be both hydrogen; or $R^{3a}$ and $R^{3a1}$ can together form =N—$OR^a$; or $R^{3a}$ and $R^{3a1}$ can together with the atom to which they are attached can be joined to form an optionally substituted 3 membered ring, an optionally substituted 4 membered ring, an optionally substituted 5 membered ring or an optionally substituted 6 membered ring; $R^{4a}$, $R^{4a1}$, $R^{4a2}$ and $R^{4a3}$ can be each independently hydrogen or an unsubstituted $C_{1-4}$ alkyl; $R^{5a}$ and $R^{5a1}$ can be each independently be hydrogen or an unsubstituted $C_{1-4}$ alkyl; $R^{6a}$ and $R^{6a1}$ can be each independently hydrogen, an optionally substituted $C_{1-4}$ alkyl or an optionally substituted alkoxyalkyl; $R^{6a2}$ and $R^{6a3}$ can be each independently hydrogen or an unsubstituted $C_{1-4}$ alkyl; $X^{1b}$, $X^{2b}$ and $X^{3b}$ can be each independently C (carbon), N (nitrogen), O (oxygen) or C(=O), and form a bi-cyclic ring selected from an optionally substituted aryl, an optionally substituted heteroaryl and an optionally substituted heterocyclyl by joining $X^{1b}$ and $X^{3b}$ together; provided that at least one of $X^{1b}$, $X^{2b}$ and $X^{3b}$ comprises a nitrogen atom; with the proviso that the valencies of $X^{1b}$, $X^{2b}$ and $X^{3b}$ can be each independently satisfied with a substituent selected from hydrogen and an optionally substituted $C_{1-4}$ alkyl, and $X^{1b}$, $X^{2b}$ and $X^{3b}$ are uncharged; $R^{3c}$ and $R^{3c1}$ can be each independently selected from hydrogen, hydroxy, halogen, amino, an optionally substituted $C_{1-4}$ alkyl, an optionally substituted $C_{2-4}$ alkenyl, an optionally substituted $C_{2-4}$ alkynyl, an optionally substituted $C_{3-6}$ cycloalkyl, an optionally substituted $C_{1-4}$ alkoxy, —O-carboxy, an optionally substituted heteroaryl, an optionally substituted heterocyclyl, $CHF_2$, $CF_3$ and

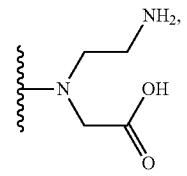 [SMILES: *N(CCN)CC(=O)O]

provided that $R^{3c}$ and $R^{3c1}$ cannot be both hydrogen; or $R^{3c}$ and $R^{3c1}$ can together form =N—$ORC$; or $R^{3c}$ and $R^{3c1}$ can together with the atom to which they are attached can be joined to form an optionally substituted 3 membered ring, an optionally substituted 4 membered ring, an optionally substituted 5 membered ring or an optionally substituted 6 membered ring; $R^a$ and $R^c$ can be each independently hydrogen or an unsubstituted $C_{1-4}$ alkyl; $R^{4c}$ and $R^{5c}$ can be taken together to form an unsubstituted aryl, an unsubstituted heteroaryl or an optionally substituted heterocyclyl; $Z^c$ can be N or CH; $m^d$ can be 0 or 1; and ring $B^d$ can be an optionally substituted $C_5$ cycloalkyl; ring $B^{d1}$ can be an optionally substituted pyridinyl; and provided that when L is Formula (IIc), then Y is absent.

Formula (Ia)

In some embodiments, L can be Formula (Ia):

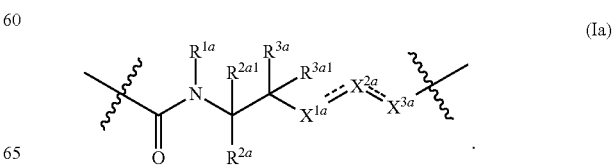
(Ia)

In some embodiments of Formula (Ia), $X^{1a}$ can be $CR^{4a1}$ or $CR^{4a2}R^{4a3}$, $X^{2a}$ can be N (nitrogen), and $X^{3a}$ can be $CR^{6a}$ or $CR^{6a2}R^{6a3}$. In some embodiments of Formula (Ia), ------- between $X^{1a}$ and $X^{2a}$ can be a single bond, ------- between $X^{2a}$ and $X^{3a}$ can be a double bond, $X^{1a}$ can be $CR^{4a2}R^{4a3}$, $X^{2a}$ can be N (nitrogen), and $X^{3b}$ can be $CR^{6a}$. In other embodiments of Formula (Ia), ------- between $X^{1a}$ and $X^{2a}$ can be a double bond, ------- between $X^{2a}$ and $X^{3a}$ can be a single bond, $X^{1a}$ can be $CR^{4a1}$, $X^{2b}$ can be N (nitrogen), and $X^{3b}$ can be $CR^{6a2}R^{6a3}$. In some embodiments, including those of this paragraph, $R^{5a}$ can be hydrogen. In some embodiments including those of this paragraph, $R^{5a1}$ can be hydrogen. In some embodiments, —$X^{1a}$------- $X^{2a}$------- $X^{3a}$— can be —$CH_2$—N=CH— or —CH=N—$CH_2$—. In other embodiments, —$X^{1a}$------- $X^{2a}$------- $X^{3a}$— can be —N=N—$CH_2$—, —N=CH—$CH_2$— or —N=CH—NH—. In still other embodiments, —$X^{1a}$------- $X^{2a}$------- $X^{3a}$— can be —$CH_2$—CH=N—, —NH—CH=NH— or —NH—N=CH—. In some embodiments, $X^{1a}$, $X^{2a}$ and $X^{3a}$ can be each independently C (carbon), N (nitrogen), O (oxygen) or C(=O), and form a ring or ring system selected from an optionally substituted aryl, an optionally substituted heteroaryl and an optionally substituted heterocyclyl by joining $X^{1a}$ and $X^{3a}$ together; with the proviso that the valencies of $X^{1a}$, $X^{2a}$ and $X^{3a}$ can be each independently satisfied with a substituent selected from hydrogen and an optionally substituted $C_{1-4}$ alkyl; and $X^{1a}$, $X^{2a}$ and $X^{3a}$ are uncharged.

Formula (Ia1)

In some embodiments, L of Formula (Ia) can be Formula (Ia1):

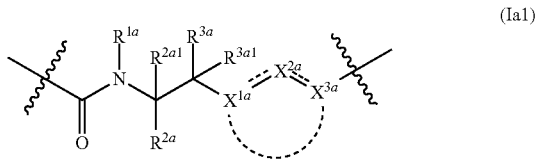

(Ia1)

wherein: $X^{1a}$, $X^{2a}$ and $X^{3a}$ can be each independently C (carbon), N (nitrogen), O (oxygen) or C(=O), and form a ring or ring system selected from an optionally substituted aryl, an optionally substituted heteroaryl and an optionally substituted heterocyclyl by joining $X^{1a}$ and $X^{3a}$ together; with the proviso that the valencies of $X^{1a}$, $X^{2a}$ and $X^{3a}$ can be each independently satisfied with a substituent selected from hydrogen and an optionally substituted $C_{1-4}$ alkyl; and $X^{1a}$, $X^{2a}$ and $X^{3a}$ are uncharged.

In some embodiments of Formula (Ia1), $X^{1a}$ can be C, $X^{2a}$ can be N and $X^{3a}$ can be C. In some embodiments of Formula (Ia1), ------- between $X^{1a}$ and $X^{2a}$ can be a single bond, ------- between $X^{2a}$ and $X^{3a}$ can be a double bond, $X^{1a}$ can be C, $X^{2a}$ can be N and $X^{3a}$ can be C. In other embodiments of Formula (Ia1), ------- between $X^{1a}$ and $X^{2a}$ can be a double bond, ------- between $X^{2a}$ and $X^{3a}$ can be a single bond, $X^{1a}$ can be C, $X^{2a}$ can be N and $X^{3a}$ can be C. In still other embodiments of Formula (Ia1), ------- between $X^{1a}$ and $X^{2a}$ can be a single bond, ------- between $X^{2a}$ and $X^{3a}$ can be a single bond, $X^{1a}$ can be C, $X^{2a}$ can be O and $X^{3a}$ can be C. In some embodiments, the valencies of $X^{1a}$, $X^{2a}$ and $X^{3a}$ can be each independently satisfied with hydrogen or an unsubstituted $C_{1-4}$ alkyl, such as $CH_3$.

In some embodiments, the ring or ring system of Formula (Ia1) can be an optionally substituted aryl. In other embodiments, the ring or ring system of Formula (Ia1) can be an optionally substituted mono-cyclic heteroaryl. In still other embodiments, the ring or ring system of Formula (Ia1) can be an optionally substituted bi-cyclic heteroaryl. In some embodiments, the ring or ring system of Formula (Ia1) can be an optionally substituted mono-cyclic heterocyclyl. In some embodiments, the ring or ring system of Formula (Ia1) can be an optionally substituted bi-cyclic heterocyclyl.

In some embodiments of Formula (Ia1),

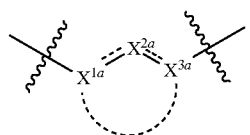

can be selected from an optionally substituted

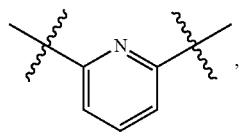 [SMILES: *c1cccc(*)n1]

an optionally substituted

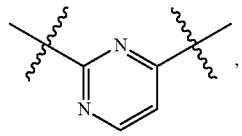 [SMILES: *c1ccnc(*)n1]

an optionally substituted

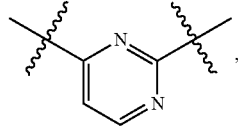 [SMILES: *c1ccnc(*)n1]

an optionally substituted

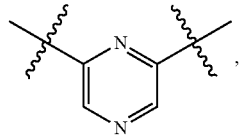 [SMILES: *c1cncc(*)n1]

an optionally substituted

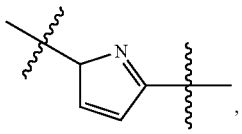 [SMILES: *C1=NC(*)C=C1]

an optionally substituted

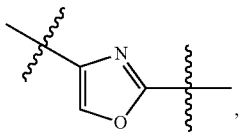 [SMILES: *c1coc(*)n1]

an optionally substituted

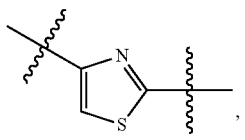 [SMILES: *c1csc(*)n1]

an optionally substituted

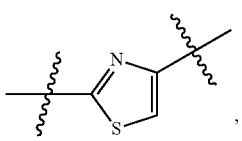 [SMILES: *c1csc(*)n1]

an optionally substituted an optionally substituted

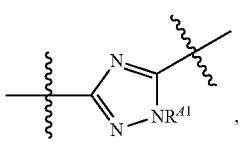

an optionally substituted

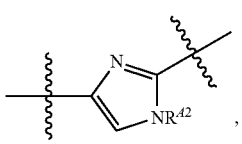

an optionally substituted

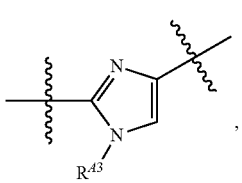

an optionally substituted

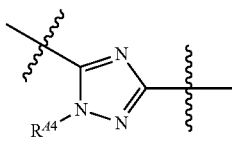

and an optionally substituted

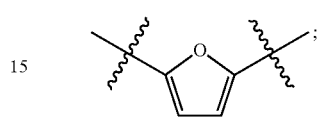

wherein $R^{41}$, $R^{42}$, $R^{43}$ and $R^{44}$ can be each independently hydrogen or an unsubstituted $C_{1-6}$ alkyl.

In some embodiments,

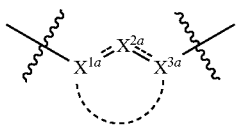

can be an optionally substituted

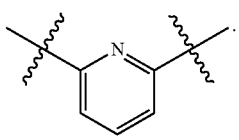

In some embodiments,

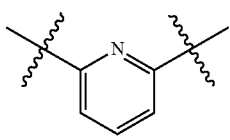 [SMILES: *c1cccc(*)n1]

can be substituted with one or more substituents selected from amino, mono-substituted amino, di-substituted amino, hydroxyalkyl, alkyl and alkoxy. In some embodiments,

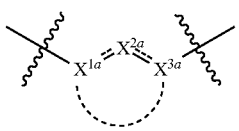

can be an unsubstituted

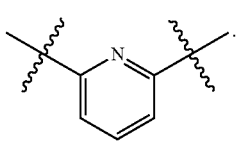 [SMILES: *c1cccc(*)n1]

In other embodiments,

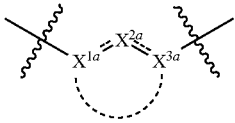

can be a substituted

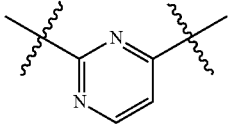 [SMILES: *c1ccnc(*)n1]

or a substituted

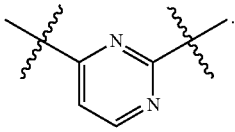

In some embodiments,

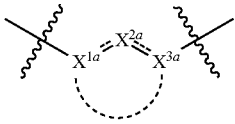

can be an optionally substituted

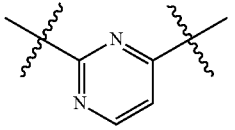 [SMILES: *c1ccnc(*)n1]

or an optionally substituted

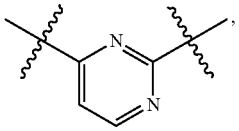 [SMILES: *c1ccnc(*)n1]

, $R^{3a}$ can be hydroxy and $R^{3a1}$ can be selected from amino, an unsubstituted $C_{1-4}$ alkyl, an unsubstituted $C_{2-4}$ alkenyl, an unsubstituted $C_{2-4}$ alkynyl, an unsubstituted $C_{3-6}$ cycloalkyl (for example, cyclopropyl), an unsubstituted $C_{1-4}$ alkoxy (such as $OCH_3$), hydroxy, halogen and an unsubstituted heteroaryl (for example, thiazole).

In some embodiments, when one of $R^{3a}$ and $R^{3a1}$ is H and the other of $R^{3a}$ and $R^{3a1}$ is OH, then

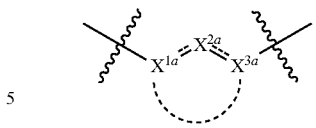

is not an unsubstituted

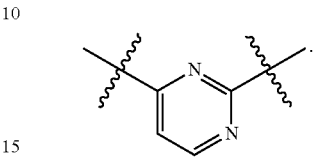

In other embodiments, when one of $R^{3a}$ and $R^{3a1}$ is H, then the other of $R^{3a}$ and $R^{3a1}$ is not OH. In some embodiments,

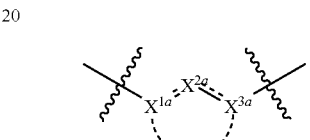

is not an optionally substituted pyrimidine. In some embodiments, a compound of Formula (I) cannot be

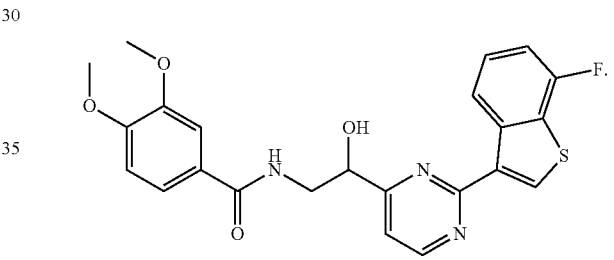

Formula (Ia2)

In some embodiments, L of Formula (Ia) can be Formula (Ia2):

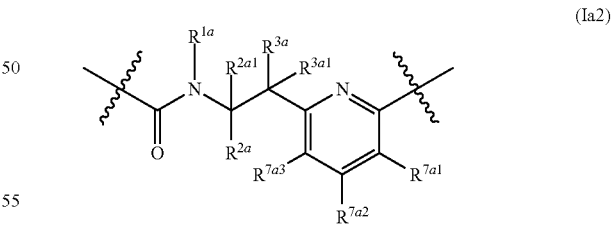

(Ia2)

wherein $R^{7a1}$, $R^{7a2}$ and $R^{7a3}$ can be each independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl, an optionally substituted O-amido and an optionally substituted C-carboxy. In some embodiments, $R^{7a1}$ can be an unsubstituted $C_{1-4}$ alkoxy, and $R^{7a2}$ and $R^{7a3}$ can be both hydrogen. In other embodiments, $R^{7a}$ can be a substituted $C_{1-4}$ alkoxy, and $R^{7a2}$ and $R^{7a3}$ can be both hydrogen. For example, $R^{7a1}$ can be a substituted $C_{1-4}$ alkoxy substituted with an amino, mono-substituted amino or a di-substituted amino. In some embodiments, $R^{7a1}$ can be hydrogen, $R^{7a2}$ can be an optionally substituted $C_{1-4}$ alkyl, and $R^{7a3}$ can be hydrogen. In other embodiments, $R^{7a1}$ can be hydrogen, $R^{7a2}$ can be a substituted $C_{3-6}$ cycloalkyl, and $R^{7a3}$ can be hydrogen. In still other embodiments, $R^{7a}$ can be hydrogen, $R^{7a2}$ can be a mono-substituted amino, and $R^{7a3}$ can be hydrogen. In yet still other embodiments, $R^{7a1}$ can be a mono-substituted amino or an optionally substituted O-amido (such as —C(=O)NH$_2$) and $R^{7a2}$ and $R^{7a3}$ can be both hydrogen. For example, the mono-substituted amino of $R^{7a1}$ or $R^{7a2}$ can be —N(C$_{1-4}$ alkyl), such as —NCH$_3$. In some embodiments, $R^{7a1}$ can be a substituted $C_{1-8}$ alkyl (such as an amino substituted $C_{1-8}$ alkyl) and $R^{7a2}$ and $R^{7a3}$ can be both hydrogen. In other embodiments, $R^{7a}$ and $R^{7a2}$ can be both hydrogen and $R^{7a3}$ can be halogen. In other embodiments, $R^{7a}$ and $R^{7a3}$ can be both hydrogen and $R^{7a2}$ can be an optionally substituted heterocyclyl, such as an optionally substituted mono-cyclic heterocyclyl. Examples of optionally substituted mono-cyclic heterocyclyl at $R^{7a2}$ include, but are not limited to, an optionally substituted azetidine, an optionally substituted pyrrolidine, an optionally substituted pyrrolidinone, an optionally substituted piperidine and an optionally substituted oxetane.

When $R^{7a1}$, $R^{7a2}$ and/or $R^{7a3}$ are substituted, possible substituent(s) includes those provided in the list of "substituted" along with urea, amidine and acetylurea. For example, the $C_{1-4}$ alkyl, $C_{3-6}$ cycloalkyl and mono-cyclic heterocyclyl of $R^{7a2}$ can be substituted with various substituent(s), such as, halo, hydroxy, $C_{1-4}$ alkoxy, an optionally substituted aryl(C$_{1-4}$ alkyl), an optionally substituted C-carboxy, amino, an optionally substituted mono-substituted amino, an optionally substituted di-substituted amino, an optionally substituted C-amido, an optionally substituted N-amido, an optionally substituted N-carbamyl, an optionally substituted N-sulfonamido, an optionally substituted urea, an optionally substituted amidine and an optionally substituted acetylurea (e.g., halogenated acetylurea). Non-limiting examples of substituted $C_{1-4}$ alkyls and substituted $C_{3-6}$ cycloalkyls of $R^{7a2}$ are as follows:

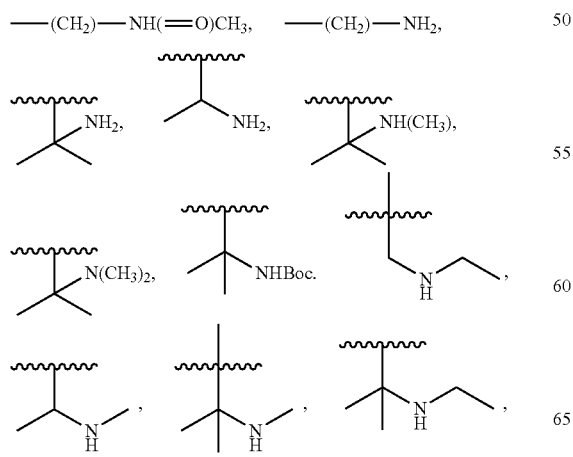

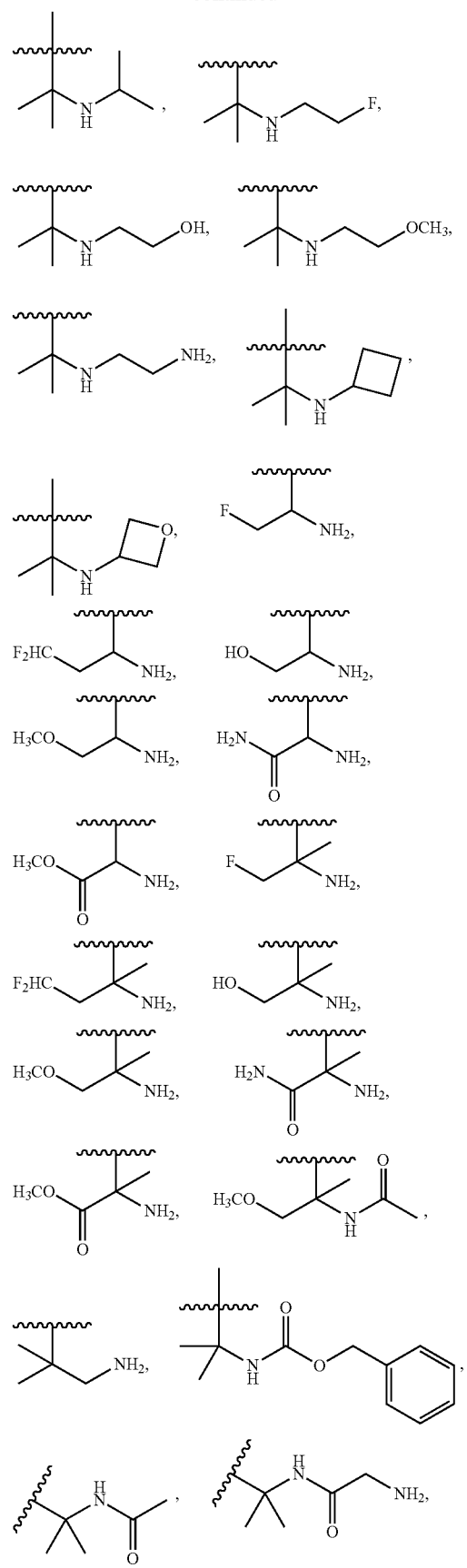

-continued

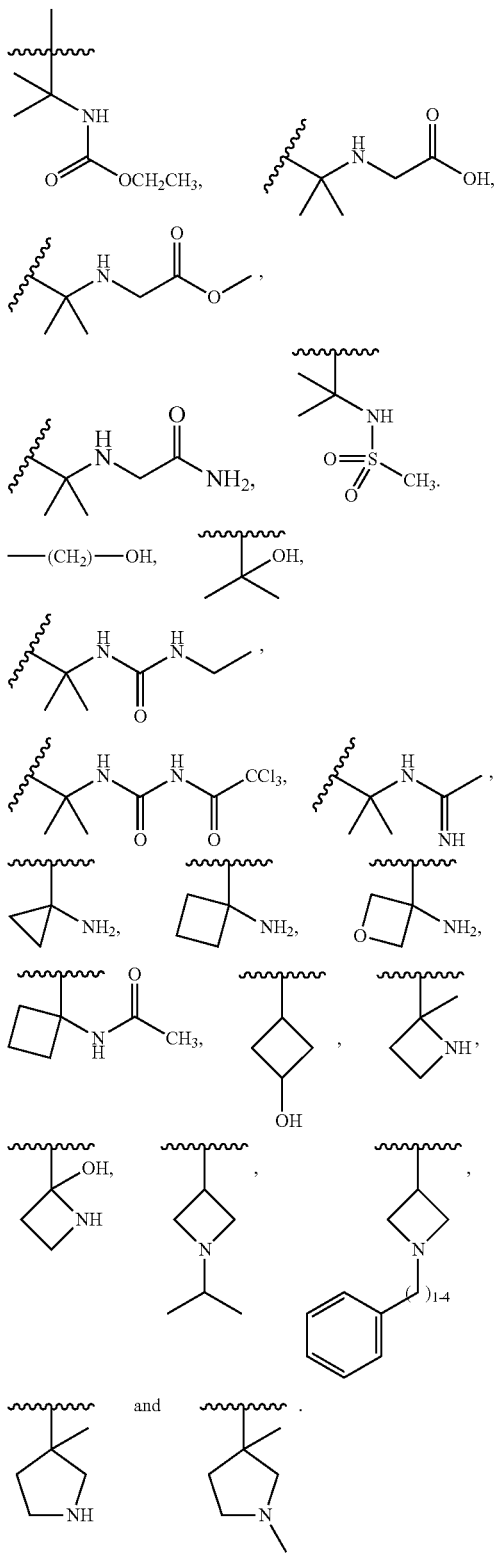

Formula (Ia3)

In some embodiments, L of Formula (Ia) can be Formula (Ia3):

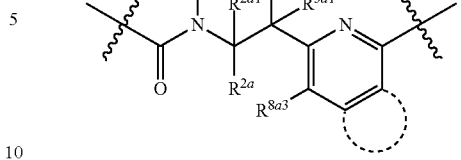

wherein: the dashed semi-circle along with the two carbon atoms to which it is connected can form an optionally substituted cycloalkyl an optionally substituted aryl, an optionally substituted heteroaryl or an optionally substituted heterocyclyl; and $R^{8a3}$ can be selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy.

In some embodiments of Formula (Ia3), the dashed semi-circle along with the two carbon atoms to which it is connected can form an optionally substituted 5-membered cycloalkyl. In other embodiments of Formula (Ia3), the dashed semi-circle along with the two carbon atoms to which it is connected can form an optionally substituted 6-membered cycloalkyl. In still other embodiments of Formula (Ia3), the dashed semi-circle along with the two carbon atoms to which it is connected can form an optionally substituted aryl (for example, phenyl). In some embodiments of Formula (Ia3), the dashed semi-circle along with the two carbon atoms to which it is connected can form an optionally substituted 5-membered heteroaryl. In other embodiments of Formula (Ia3), the dashed semi-circle along with the two carbon atoms to which it is connected can form an optionally substituted 6-membered heteroaryl. In still other embodiments of Formula (Ia3), the dashed semi-circle along with the two carbon atoms to which it is connected can form an optionally substituted 5-membered heterocyclyl. In yet still other embodiments of Formula (Ia3), the dashed semi-circle along with the two carbon atoms to which it is connected can form an optionally substituted 6-membered heterocyclyl.

In some embodiments, the bicyclic ring system can be selected from an optionally substituted

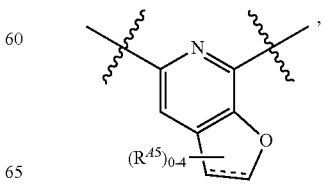

an optionally substituted

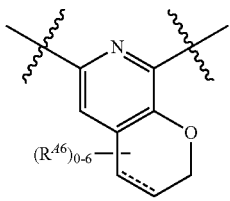

and an optionally substituted

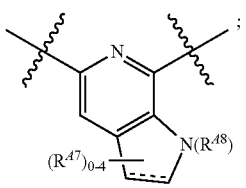;

wherein each ------ can be independently absent or a bond; each $R^{A5}$, each $R^{A6}$, each $R^{A7}$ can be halogen, an unsubstituted $C_{1-6}$ alkyl, hydroxy, amino, an optionally substituted mono-substituted amino, an optionally substituted di-substituted amino, —$(CH_2)_{1-4}$OH, —$(CH_2)_{1-4}$NH$_2$ or N-sulfinamido (for example, —NH—S(=O)$C_{1-4}$ alkyl), or two $R^{A5}$, two $R^{A6}$ or two $R^{A7}$ are taken together to form an optionally substituted 5-membered ring to an optionally substituted 6-membered ring (such as an optionally substituted cycloalkyl or an optionally substituted heterocyclyl); and $R^{A8}$ can be hydrogen or an unsubstituted $C_{1-6}$ alkyl. In some embodiments of this paragraph, ------ can be absent. In some embodiments of this paragraph, ------ can be a bond such that a double bond is present between the between carbons. In some embodiments, at least two $R^{A5}$ groups can be an unsubstituted $C_{1-6}$ alkyl (for example, $CH_3$). In some embodiments, at least two $R^{A6}$ groups can be an unsubstituted $C_{1-6}$ alkyl (for example, $CH_3$). Examples of these bi-cyclic groups include the following:

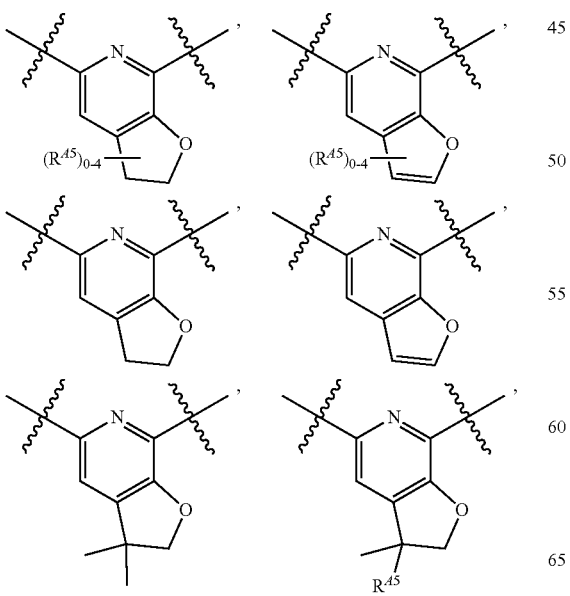

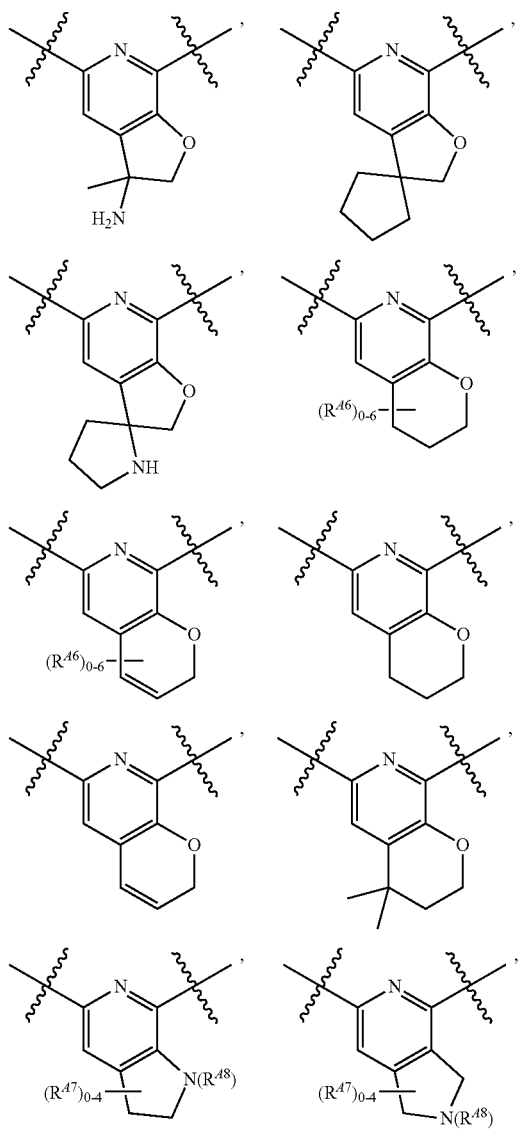

and

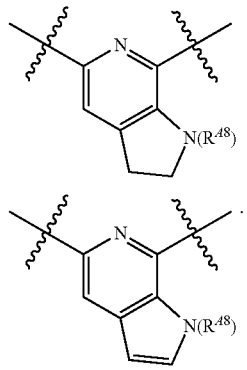.

In some embodiments of Formulae (Ia), (Ia1), (Ia2) and/or (Ia3), $R^{1a}$ can be hydrogen. In other embodiments of Formulae (Ia), (Ia1), (Ia2) and/or (Ia3), $R^{1a}$ can be an unsubstituted $C_{1-4}$ alkyl.

In some embodiments of Formulae (Ia), (Ia1), (Ia2) and/or (Ia3), both $R^{2a}$ and $R^{2a1}$ can be hydrogen. In other embodiments of Formulae (Ia), (Ia1), (Ia2) and/or (Ia3), $R^{2a}$ can be hydrogen and $R^{2a1}$ can be an unsubstituted $C_{1-4}$ alkyl. In still other embodiments of Formulae (Ia), (Ia1), (Ia2) and/or (Ia3), $R^{2a}$ can be hydrogen and $R^{2a1}$ can be a substituted $C_{1-4}$ alkyl. In yet still other embodiments of Formulae (Ia), (Ia1), (Ia2) and/or (Ia3), $R^{2a}$ can be hydrogen and $R^{2a1}$ can be an optionally substituted aryl($C_{1-6}$ alkyl) or an optionally substituted heterocyclyl($C_{1-6}$ alkyl). In some embodiments of Formulae (Ia), (Ia1), (Ia2) and/or (Ia3), $R^{2a}$ can be hydrogen and $R^{2a1}$ can be an alkoxyalkyl, an aminoalkyl or a hydroxyalkyl. In other embodiments of Formulae (Ia), (Ia1), (Ia2) and/or (Ia3), $R^{2a}$ can be hydrogen and $R^{2a1}$ can be hydroxy. In still other embodiments of Formulae (Ia), (Ia1), (Ia2) and/or (Ia3), $R^{2a1}$ can be hydrogen, and $R^{1a}$ and $R^{2a}$ can be joined together with the atoms to which they are attached to form an optionally substituted 5 membered heterocyclyl (for example, pyrrolidinyl) or an optionally substituted 6 membered heterocyclyl (for example, piperdinyl). In yet still other embodiments of Formulae (Ia), (Ia1), (Ia2) and/or (Ia3), $R^{2a}$ and $R^{2a1}$ both can be an optionally substituted $C_{1-4}$ alkyl.

In some embodiments of Formulae (Ia), (Ia1), (Ia2) and/or (Ia3), $R^{3a}$ can be hydrogen, and $R^{3a1}$ can be selected from amino, an unsubstituted $C_{1-4}$ alkyl, an unsubstituted $C_{2-4}$ alkenyl, an unsubstituted $C_{2-4}$ alkynyl, an unsubstituted $C_{3-6}$ cycloalkyl (for example, cyclopropyl), an unsubstituted $C_{1-4}$ alkoxy (such as $OCH_3$), an unsubstituted —O-carboxy (such as —OC(=O)$C_{1-4}$ alkyl), hydroxy, halogen, an unsubstituted heteroaryl (for example, thiazole) and an optionally substituted heterocyclyl (for example, azetidine). In some embodiments of Formulae (Ia), (Ia1), (Ia2) and/or (Ia3), $R^{3a}$ can be hydrogen, and $R^{3a1}$ can be hydroxy. In other embodiments or Formulae (Ia), (Ia1), (Ia2) and/or (Ia3), $R^{3a}$ and $R^{3a1}$ can be both halogen. In still other embodiments of Formulae (Ia), (Ia1), (Ia2) and/or (Ia3), $R^{3a}$ can be hydrogen, and $R^{3a1}$ can be unsubstituted $C_{1-4}$ alkyl. In yet still other embodiments of Formulae (Ia), (Ia1), (Ia2) and/or (Ia3), $R^{3a}$ can be hydroxy, and $R^{3a1}$ can be selected from amino, an unsubstituted $C_{1-4}$ alkyl, an unsubstituted $C_{2-4}$ alkenyl, an unsubstituted $C_{2-4}$ alkynyl, an unsubstituted $C_{3-6}$ cycloalkyl (for example, cyclopropyl), an unsubstituted $C_{1-4}$ alkoxy (such as $OCH_3$), hydroxy, halogen, an unsubstituted heteroaryl (for example, thiazole) and an optionally substituted heterocyclyl (for example, azetidine). In some embodiments of Formulae (Ia), (Ia1), (Ia2) and/or (Ia3), $R^{3a}$ can be hydroxy, and $R^{3a1}$ can be an unsubstituted $C_{1-4}$ alkyl. In other embodiments of Formulae (Ia), (Ia1), (Ia2) and/or (Ia3), $R^{3a}$ can be hydroxy, and $R^{3a1}$ can be an unsubstituted $C_{2-4}$ alkenyl (such as ethenyl or propenyl) or an unsubstituted $C_{2-4}$ alkynyl (such as ethynyl or propynyl). In still other embodiments of Formulae (Ia), (Ia1), (Ia2) and/or (Ia3), $R^{3a}$ can be hydroxy, and $R^{3a1}$ can be $CF_3$. In yet still other embodiments of Formulae (Ia), (Ia1), (Ia2) and/or (Ia3), $R^{3a}$ can be hydroxy, and $R^{3a1}$ can be $CHF_2$. In some embodiments of Formulae (Ia), (Ia1), (Ia2) and/or (Ia3), $R^{3a}$ can be halogen, and $R^{3a1}$ can be $CF_3$ or $CHF_2$. In other embodiments of Formulae (Ia), (Ia1), (Ia2) and/or (Ia3), $R^{3a}$ can be halogen, and $R^{3a1}$ can be $CHF_2$. In some embodiments of Formulae (Ia), (Ia1), (Ia2) and/or (Ia3), $R^{3a}$ can be hydroxy, and $R^{3a1}$ can be an unsubstituted $C_{3-6}$ cycloalkyl, for example, an unsubstituted cyclopropyl. In some embodiments of Formulae (Ia), (Ia1), (Ia2) and/or (Ia3), $R^{3a}$ can be halogen, and $R^{3a1}$ can be an unsubstituted $C_{3-6}$ cycloalkyl, for example, an unsubstituted cyclopropyl. In other embodiments of Formulae (Ia), (Ia1), (Ia2) and/or (Ia3), $R^{3a}$ can be an unsubstituted $C_{1-4}$ alkoxy (such as methoxy), and $R^{3a1}$ can be an unsubstituted $C_{1-4}$ alkyl (such as methyl). In still other embodiments of Formulae (Ia), (Ia1), (Ia2) and/or (Ia3), $R^{3a}$ and $R^{3a1}$ can be both an unsubstituted $C_{1-4}$ alkyl, for example, $R^{3a}$ and $R^{3a1}$ can be both methyl. In yet sill other embodiments of Formulae (Ia), (Ia1), (Ia2) and/or (Ia3), one of $R^{3a}$ and $R^{3a1}$ can be an optionally substituted mono-cyclic heteroaryl; and the other of $R^{3a}$ and $R^{3a1}$ can be hydroxy. In some embodiments of Formulae (Ia), (Ia1), (Ia2) and/or (Ia3), one of $R^{3a}$ and $R^{3a1}$ can be an unsubstituted $C_{1-4}$ alkyl (such as methyl); and the other of $R^{3a}$ and $R^{3a1}$ can be an unsubstituted —O-carboxy (such as —OC(=O) $C_{1-4}$ alkyl).

When one of $R^{3a}$ and $R^{3a1}$ is a substituted $C_{1-4}$ alkyl, the $C_{1-4}$ alkyl can be substituted with various substituents. For example, in some embodiments, one of $R^{3a}$ and $R^{3a1}$ is a substituted $C_{1-4}$ alkyl substituted with substituent selected from halogen, hydroxy, amino, mono-substituted amino (for example, —NH($C_{1-4}$ alkyl)), di-substituted amino, —N-amido, mono-cyclic heteroaryl and mono-cyclic heterocyclyl. In some embodiments, one of $R^{3a}$ and $R^{3a1}$ can be an optionally substituted mono-cyclic heteroaryl or an optionally substituted mono-cyclic heterocyclyl and the other of $R^{3a}$ and $R^{3a1}$ can be hydroxy. The mono-cyclic heteroaryl substituted on the $C_{1-4}$ alkyl of one of $R^{3a}$ and $R^{3a1}$ can be 5-membered or 6-membered heteroaryl. The mono-cyclic heterocyclyl substituted on the $C_{1-4}$ alkyl of one of $R^{3a}$ and $R^{3a1}$ can be 4-membered, 5-membered or 6-membered heterocyclyl. For example, one of $R^{3a}$ and $R^{3a1}$ can be a substituted $C_{1-4}$ alkyl substituted with substituent selected from an optionally substituted imidazole, an optionally substituted pyrazole, an optionally substituted pyrrolidine, an optionally substituted piperidine, an optionally substituted piperazine, an optionally substituted morpholine, an optionally substituted triazole, an optionally substituted piperazinone and an optionally substituted azetidine.

In some embodiments of Formulae (Ia), (Ia1), (Ia2) and/or (Ia3), $R^{3a}$ and $R^{3a1}$ can together form N=$OR^a$. In some embodiments of Formulae (Ia), (Ia1), (Ia2) and/or (Ia3), $R^{3a}$ and $R^{3a1}$ together form N=OH. In other embodiments of Formulae (Ia), (Ia1), (Ia2) and/or (Ia3), $R^{3a}$ and $R^{3a1}$ can together form N=$OCH_3$. In some embodiments of Formulae (Ia), (Ia1), (Ia2) and/or (Ia3), $R^{3a}$ and $R^{3a1}$ can join together with the atom to which they are attached to form an optionally substituted 3 to 6 membered ring. In some embodiments of Formulae (Ia), (Ia1), (Ia2) and/or (Ia3), the 3 to 6 membered ring can be a $C_{3-6}$ cycloalkyl. In other embodiments of Formulae (Ia), (Ia1), (Ia2) and/or (Ia3), the ring can be a 3 to 6 membered heterocyclyl, for example, an optionally substituted oxetane or an optionally substituted oxazolidinone. In some embodiments of Formulae (Ia), (Ia1), (Ia2) and/or (Ia3), the carbon to which $R^{3a}$ and $R^{3a1}$ are attached can be a chiral center. When the carbon to which $R^{3a}$ and $R^{3a1}$ are attached a chiral center, in some embodiments of Formulae (Ia), (Ia1), (Ia2) and/or (Ia3), the carbon can have a (R)-configuration. In other embodiments of Formulae (Ia), (Ia1), (Ia2) and/or (Ia3), the carbon to which $R^{3a}$ and $R^{3a1}$ are attached can have a (S)-configuration.

Formula (Ib)

In some embodiments, L of Formula (I) can be Formula (Ib):

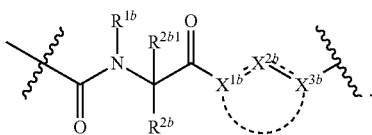

(Ib)

wherein the dotted curved line between $X^{1b}$ and $X^{3b}$ indicates a bi-cyclic ring selected from an optionally substituted bi-cyclic heteroaryl and an optionally substituted bi-cyclic heterocyclyl by joining $X^{1b}$ and $X^{3b}$ together, wherein ------- between $X^{1b}$ and $X^{2b}$ represents a single or double bond between $X^{1b}$ and $X^{2b}$, ------- between $X^{2b}$ and $X^{3b}$ represents a single or double bond between $X^{2b}$ and $X^{3b}$; wherein $X^{1b}$, $X^{2b}$ and $X^{3b}$ can be each independently C (carbon), N (nitrogen), O (oxygen) or C($=$O); and provided that at least one of $X^{1b}$, $X^{2b}$ and $X^{3b}$ comprises a nitrogen atom and both ------- cannot be double bonds; with the proviso that the valencies of $X^{1b}$, $X^{2b}$ and $X^{3b}$ can be each independently satisfied with a substituent selected from hydrogen and an optionally substituted $C_{1-4}$ alkyl; and $X^{1b}$, $X^{2b}$ and $X^{3b}$ are uncharged. In some embodiments, the valencies of $X^{1b}$, $X^{2b}$ and $X^{3b}$ can be each independently satisfied with a substituent selected from hydrogen and an unsubstituted $C_{1-4}$ alkyl. In some embodiments, the valencies of $X^{1b}$, $X^{2b}$ and $X^{3b}$ can be each independently satisfied with hydrogen or methyl.

In some embodiments of Formula (Ib), the bi-cyclic ring can be an optionally substituted 9-membered bi-cyclic heteroaryl. In other embodiments of Formula (Ib), the bi-cyclic ring can be an optionally substituted 9-membered bi-cyclic heterocyclyl. In still other embodiments of Formula (Ib), the bi-cyclic ring can be an optionally substituted 10-membered bi-cyclic heteroaryl. In yet still some embodiments of Formula (Ib), the bi-cyclic ring can be an optionally substituted 10-membered bi-cyclic heterocyclyl.

In some embodiments of Formula (Ib), $X^{1b}$ can be C, $X^{2b}$ can be N and $X^{3b}$ can be C. In other embodiments of Formula (Ib), $X^{1b}$ can be N, $X^{2b}$ can be N and $X^{3b}$ can be C. In still other embodiments of Formula (Ib), $X^{1b}$ can be N, $X^{2b}$ can be C($=$O) and $X^{3b}$ can be N. In yet still other embodiments of Formula (Ib), $X^{1b}$ can be C, $X^{2b}$ can be O and $X^{3b}$ can be C.

In some embodiments of Formula (Ib), when $X^{1b}$ can be C, $X^{2b}$ can be N and $X^{3b}$ can be C, the bi-cyclic ring can be an optionally substituted bi-cyclic heteroaryl ring. In other embodiments of Formula (Ib), when $X^{1b}$ can be C, $X^{2b}$ can be N and $X^{3b}$ can be C, the bi-cyclic ring can be an optionally substituted bi-cyclic heterocyclyl ring.

Formula (Ib1)

In some embodiments, L of Formula (Ib) can be Formula (Ib1):

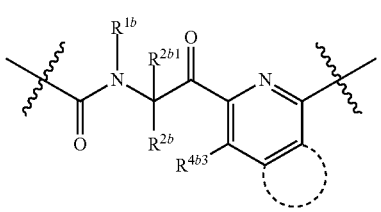

(Ib1)

wherein: the dashed semi-circle along with the two carbon atoms to which it is connected can form an optionally substituted cycloalkenyl, an optionally substituted aryl, an optionally substituted heteroaryl or an optionally substituted heterocyclyl; and $R^{4b3}$ can be selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy.

In some embodiments of Formula (Ib1), the dashed semi-circle along with the two carbon atoms to which it is connected can form an optionally substituted 5-membered cycloalkenyl. In other embodiments of Formula (Ib1), the dashed semi-circle along with the two carbon atoms to which it is connected can form an optionally substituted 6-membered cycloalkenyl. In still other embodiments of Formula (Ib1), the dashed semi-circle along with the two carbon atoms to which it is connected can form an optionally substituted aryl (for example, phenyl). In some embodiments of Formula (Ib1), the dashed semi-circle along with the two carbon atoms to which it is connected can form an optionally substituted 5-membered heteroaryl. In other embodiments of Formula (Ib1), the dashed semi-circle along with the two carbon atoms to which it is connected can form an optionally substituted 6-membered heteroaryl. In still other embodiments of Formula (Ib1), the dashed semi-circle along with the two carbon atoms to which it is connected can form an optionally substituted 5-membered heterocyclyl. In yet still other embodiments of Formula (Ib1), the dashed semi-circle along with the two carbon atoms to which it is connected can form an optionally substituted 6-membered heterocyclyl.

In some embodiments, the bi-cyclic ring system can be selected from an optionally substituted

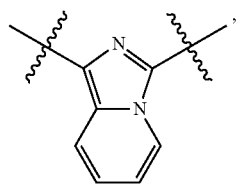 [SMILES: *c1nc(*)n2ccccc12]

an optionally substituted

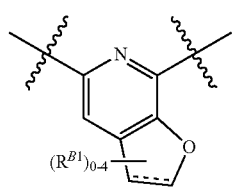

an optionally substituted an optionally substituted

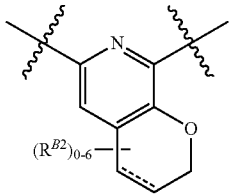

and an optionally substituted

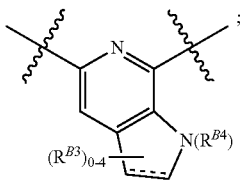

wherein each ----- can be independently absent or a bond; each $R^{B1}$, each $R^{B2}$ and each $R^{B3}$ can be an unsubstituted $C_{1-6}$ alkyl, halogen, hydroxy, amino, mono-substituted amino, di-substituted amino or —NH—S(=O)$C_{1-4}$ alkyl; and $R^{B4}$ can be hydrogen or an unsubstituted $C_{1-6}$ alkyl. In some embodiments of this paragraph, ------ can be absent. In some embodiments of this paragraph, ------ can be a bond such that a double bond is present between the between carbons. In some embodiments, at least two $R^{B2}$ groups can be an unsubstituted $C_{1-6}$ alkyl (for example, $CH_3$). In some embodiments, at least two $R_B3$ groups can be an unsubstituted $C_{1-6}$ alkyl (for example, $CH_3$). Examples of these bi-cyclic groups include the following:

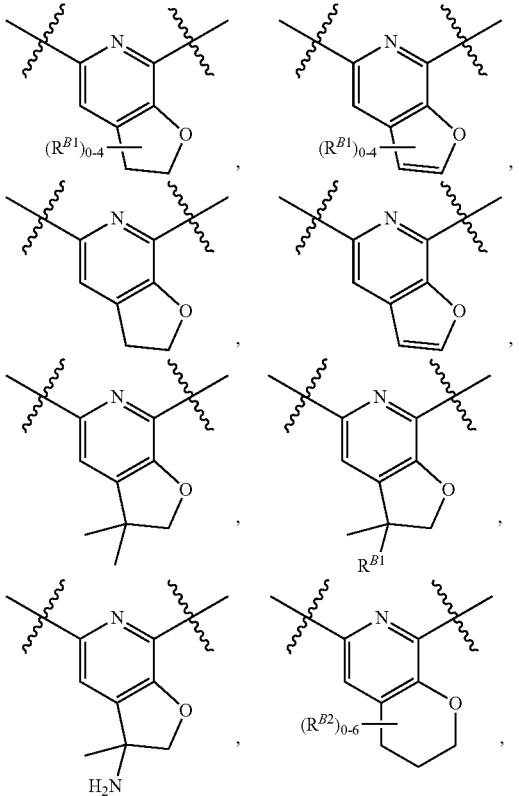

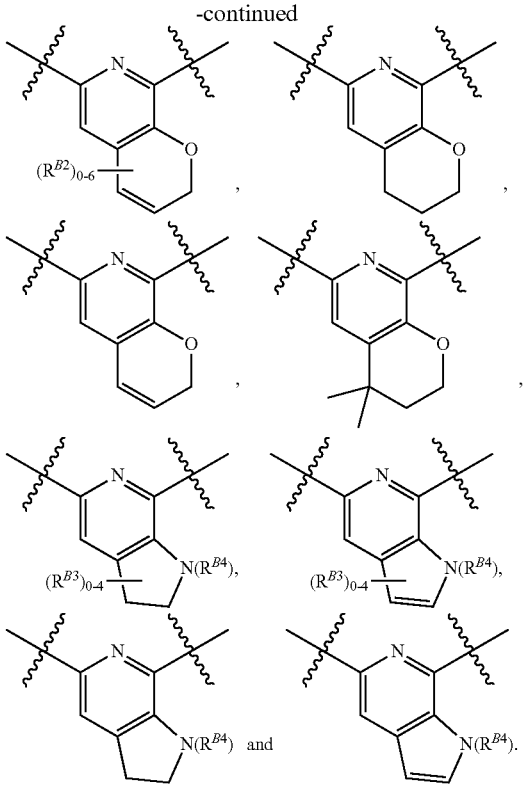

In some embodiments of Formulae (Ib) and (Ib1), $R^{1b}$ can be hydrogen.

In some embodiments of Formulae (Ib) and (Ib1), both $R^{2b}$ and $R^{2b1}$ can be hydrogen. In other embodiments of Formulae (Ib) and (Ib1), $R^{2b}$ can be hydrogen and $R^{2b1}$ can be an unsubstituted $C_{1-4}$ alkyl. In still other embodiments of Formulae (Ib) and (Ib1), $R^{2b}$ can be hydrogen and $R^{2b1}$ can be a substituted $C_{1-4}$ alkyl. In yet still other embodiments of Formulae (Ib) and (Ib1), $R^{2b}$ can be hydrogen and $R^{2b1}$ can be an optionally substituted aryl($C_{1-6}$ alkyl) or an optionally substituted heterocyclyl($C_{1-6}$ alkyl). In some embodiments of Formulae (Ib) and (Ib1), $R^{2b}$ can be hydrogen and $R^{2b1}$ can be an alkoxyalkyl, an aminoalkyl or a hydroxyalkyl. In other embodiments of Formulae (Ib) and (Ib1), $R^{2b}$ can be hydrogen and $R^{2b1}$ can be hydroxy. In still other embodiments of Formulae (Ib) and (Ib1), $R^{2b1}$ can be hydrogen, and $R^{1b}$ and $R^{2b}$ can be joined together with the atoms to which they are attached to form an optionally substituted 5 membered heterocyclyl or an optionally substituted 6 membered heterocyclyl.

Formula (Ic)

In some embodiments, L can be Formula (Ic):

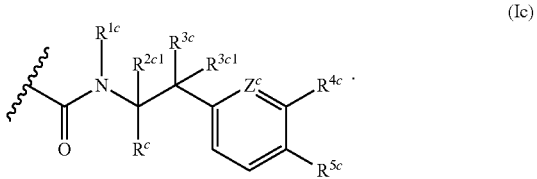

In some embodiments of Formula (Ic), $R^{1c}$ can be hydrogen. In other embodiments of Formula (Ic), $R^{1c}$ can be an unsubstituted $C_{1-4}$ alkyl.

In some embodiments of Formula (Ic), both $R^{2c}$ and $R^{2c1}$ can be hydrogen. In other embodiments of Formula (Ic), $R^{2c}$ can be hydrogen and $R^{2c1}$ can be an unsubstituted $C_{1-4}$ alkyl. In still other embodiments of Formula (Ic), $R^{2c}$ can be hydrogen and $R^{2c1}$ can be a substituted $C_{1-4}$ alkyl. In yet still other embodiments of Formula (Ic), $R^{2c}$ can be hydrogen and $R^{2c1}$ can be an optionally substituted aryl($C_{1-6}$ alkyl) or an optionally substituted heterocyclyl($C_{1-6}$ alkyl). In some embodiments of Formula (Ic), $R^{2c}$ can be hydrogen and $R^{2c1}$ can be an alkoxyalkyl, an aminoalkyl or a hydroxyalkyl. In other embodiments of Formula (Ic), $R^{2c}$ can be hydrogen and $R^{2c1}$ can be hydroxy. In still other embodiments of Formula (Ic), $R^{2c}$ and $R^{2c1}$ both can be an optionally substituted $C_{1-4}$ alkyl.

In some embodiments of Formula (Ic), $R^{3c}$ can be hydrogen, and $R^{3c1}$ can be selected from amino, an unsubstituted $C_{1-4}$ alkyl, an unsubstituted $C_{2-4}$ alkenyl, an unsubstituted $C_{2-4}$ alkynyl, an unsubstituted $C_{3-6}$ cycloalkyl (for example, cyclopropyl), an unsubstituted $C_{1-4}$ alkoxy (such as $OCH_3$), hydroxy, halogen and an unsubstituted heteroaryl (for example, thiazole). In some embodiments, $R^{3c}$ can be hydrogen, and $R^{3c1}$ can be hydroxy. In other embodiments, $R^{3c}$ and $R^{3c1}$ can be both halogen. In still other embodiments, $R^{3c}$ can be hydrogen, and $R^{3c1}$ can be unsubstituted $C_{1-4}$ alkyl. In yet still other embodiments of Formula (Ic), $R^{3c}$ can be hydroxy, and $R^{3c1}$ can be selected from amino, an unsubstituted $C_{1-4}$ alkyl, an unsubstituted $C_{2-4}$ alkenyl, an unsubstituted $C_{2-4}$ alkynyl, an unsubstituted $C_{3-6}$ cycloalkyl (for example, cyclopropyl), an unsubstituted $C_{1-4}$ alkoxy (such as $OCH_3$), hydroxy, halogen and an unsubstituted heteroaryl (for example, thiazole). In some embodiments of Formula (Ic), $R^{3c}$ can be hydroxy, and $R^{3c1}$ can be an unsubstituted $C_{1-4}$ alkyl. In some embodiments of Formula (Ic), $R^{3c}$ and $R^{3c1}$ can together form N=$OR^c$, for example, N=OH or N=$OCH_3$. In some embodiments of Formula (Ic), $R^{3c}$ and $R^{3c1}$ can join together with the atom to which they are attached to form an optionally substituted 3 to 6 membered ring. In some embodiments, the 3 to 6 membered ring can be a $C_{3-6}$ cycloalkyl. In other embodiments, the ring can be a 3 to 6 membered heterocyclyl, for example, an optionally substituted oxetane. In some embodiments, the carbon to which $R^{3c}$ and $R^{3c1}$ are attached can be a chiral center. When the carbon to which $R^{3c}$ and $R^{3c1}$ are attached a chiral center, in some embodiments, the carbon can have a (R)-configuration. In other embodiments, the carbon to which $R^{3c}$ and $R^{3c1}$ are attached can have a (S)-configuration.

In some embodiments of Formula (Ic), $Z^c$ can be N. In some embodiments of Formula (Ic), $Z^c$ can be CH.

In some embodiments of Formula (Ic), $R^{4c}$ and $R^{5c}$ can be taken together to form an unsubstituted aryl (for example, phenyl). In other embodiments of Formula (Ic), $R^{4c}$ and $R^{5c}$ can be taken together to form an unsubstituted heteroaryl, such as piperdinyl. In still other embodiments of Formula (Ic), $R^{4c}$ and $R^{5c}$ can be taken together to form an optionally substituted heterocyclyl. In some embodiments, the optionally substituted heterocyclyl can be an optionally substituted tricyclic heterocyclyl, such as an optionally substituted

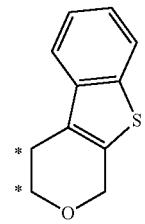

wherein * each indicate a point of attachment to the 6-membered ring.

Formula (Id)

In some embodiments, L can be Formula (Id):

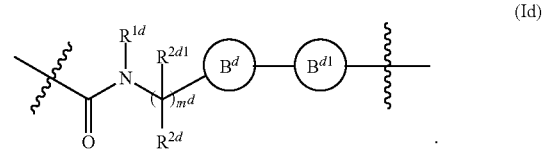

In some embodiments of Formula (Id), $R^{1d}$ can be hydrogen. In other embodiments of Formula (Id), $R^{1d}$ can be an unsubstituted $C_{1-4}$ alkyl.

In some embodiments of Formula (Id), both $R^{2d}$ and $R^{2d1}$ can be hydrogen. In other embodiments of Formula (Id), $R^{2d}$ can be hydrogen and $R^{2d1}$ can be an unsubstituted $C_{1-4}$ alkyl. In still other embodiments of Formula (Id), $R^{2d}$ can be hydrogen and $R^{2d1}$ can be a substituted $C_{1-4}$ alkyl. In yet still other embodiments of Formula (Id), $R^{2d}$ can be hydrogen and $R^{2d1}$ can be an optionally substituted aryl($C_{1-6}$ alkyl) or an optionally substituted heterocyclyl($C_{1-6}$ alkyl). In some embodiments of Formula (Id), $R^{2d}$ can be hydrogen and $R^{2d1}$ can be an alkoxyalkyl, an aminoalkyl or a hydroxyalkyl. In other embodiments of Formula (Id), $R^{2d}$ can be hydrogen and $R^{2d1}$ can be hydroxy. In still other embodiments of Formula (Id), $R^{2d}$ and $R^{2d1}$ both can be an optionally substituted $C_{1-4}$ alkyl.

In some embodiments of Formula (Id), $m^d$ can be 0. In other embodiments of Formula (Id), $m^d$ can be 1.

In some embodiments of Formula (Id), ring $B^d$ can be an optionally substituted $C_5$ cycloalkyl. In some embodiments, ring $B^d$ can be an optionally substituted

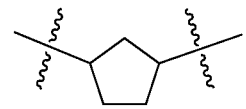

In some embodiments of Formula (Id), ring $B^{d1}$ can be an optionally substituted pyridinyl having the structure

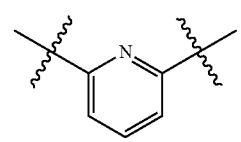

The $C_5$ cycloalkyl and/or pyridinyl ring can be unsubstituted or substituted with one or more substituents. Suitable substituents include, but are not limited to, amino, mono-substituted amino, di-substituted amino, hydroxyalkyl, alkyl and alkoxy.

In some embodiments, A can be substituted. In other embodiments, A can be unsubstituted. When A is substituted, possible substituent(s) includes those provided in the list of "substituted" along with those described herein.

In some embodiments, A can be an optionally substituted aryl. For example, A can be an optionally substituted phenyl. In some embodiments, A can be a para-substituted phenyl, a meta-substituted phenyl or an ortho-substituted phenyl. In some embodiments, A can be a di-substituted phenyl. For example, A can be a 3,4-substituted phenyl, such as

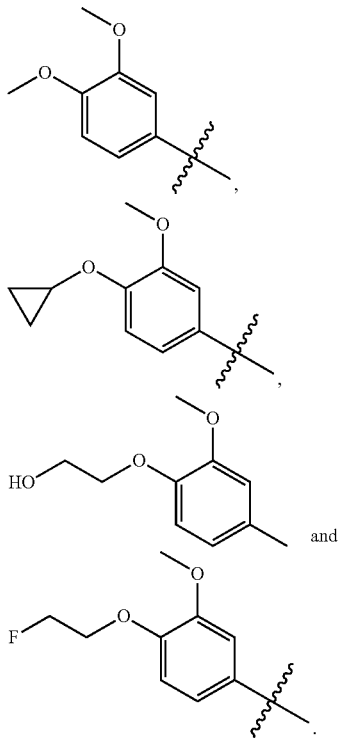

In some embodiments, A can be a substituted phenyl that is substituted with 3 more substituents. In other embodiments, A can be unsubstituted phenyl. In some embodiments, A can be an optionally substituted naphthyl.

In some embodiments and without limitation, A can be a phenyl substituted with one or more substituents selected from an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amino, —O-amido, sulfenyl, alkyoxyalkyl, an optionally substituted aryl (for example, an optionally substituted phenyl), an optionally substituted monocyclic heteroaryl, an optionally substituted monocyclic heterocyclyl, an optionally substituted aryl($C_{1-4}$ alkyl), an optionally substituted monocyclic heteroaryl($C_{1-4}$ alkyl), an optionally substituted monocyclic heterocyclyl($C_{1-4}$ alkyl), hydroxyalkyl and aminoalkyl. In some embodiments, the optionally substituted $C_{1-4}$ alkoxy can be further substituted, for example, further substituted with a substituent selected from $C_{1-4}$ alkyl, halo, hydroxy, C-carboxy, C-amido, amino, mono-alkyl amine, di-alkyl amine and an amino acid. In some embodiments, the optionally substituted haloalkoxy can be further substituted, for example, further substituted with an $C_{1-4}$ alkoxy. In some embodiments, the optionally substituted heteroaryl can be further substituted, for example, further substituted with an $C_{1-4}$ alkyl.

Examples of suitable substituents include, but are not limited to, methyl, ethyl, propyl (n-propyl and iso-propyl), butyl (n-butyl, iso-butyl and t-butyl), hydroxy, methoxy, ethoxy, propoxy (n-propoxy and iso-propoxy), butoxy (n-butoxy, iso-butoxy and t-butoxy), phenoxy, bromo, chloro, fluoro, trifluoromethyl, difluoromethoxy, trifluoromethoxy, cyano, N,N-di-methyl-amine, N,N-di-ethyl-amine, N-methyl-N-ethyl-amine, N-methyl-amino, N-ethyl-amino, amino, N-amido (for example, —NH—C(=O)$C_{1-4}$ alkyl), alkylthio (such as $CH_3CH_2S$—), N-sulfonamido (for example, —NH—S(O)$_2C_{1-4}$ alkyl), an optionally substituted phenyl, an optionally substituted imidazole, an optionally substituted morpholinyl, an optionally substituted pyrazole, an optionally substituted pyrrolidinyl, an optionally substituted pyridinyl, an optionally substituted piperidinyl, an optionally substituted piperidinone, an optionally substituted pyrrolidinone, an optionally substituted pyrimidine, an optionally substituted pyrazine, an optionally substituted 1,2,4-oxadiazole, —(CH$_2$)$_{1-4}$—OH, —(CH$_2$)$_{1-2}$—NH(CH$_3$), an optionally substituted —(CH$_2$)$_{1-2}$-imidazole, an optionally substituted —(CH$_2$)$_{1-2}$-pyrrolidinone, an optionally substituted —(CH$_2$)$_{1-2}$-imidazolidinone, —O(CH$_2$)$_2$—NH$_2$, —O(CH$_2$)$_2$—NH(CH$_3$), —O(CH$_2$)$_2$—N(CH$_3$)$_2$, —O—(CH$_2$)$_{2-4}$OH, —O(CH$_2$)$_2$OCH$_3$, an optionally substituted —O(CH$_2$)$_{0-2}$-cyclopentanone, an optionally substituted —O(CH$_2$)$_{0-2}$pyrrolidinone, an optionally substituted —O(CH$_2$)$_{0-2}$-morpholinyl, an optionally substituted —O(CH$_2$)$_{0-2}$-triazole, an optionally substituted —O(CH$_2$)$_{0-2}$-imidazole, an optionally substituted —O(CH$_2$)$_{0-2}$-pyrazole, an optionally substituted —O(CH$_2$)$_{0-2}$-tetrahydrofuran, an optionally substituted —O(CH$_2$)$_{0-2}$-pyrrolidinone, an optionally substituted —O(CH$_2$)$_{0-2}$-tetrazole, an optionally substituted —O(CH$_2$)$_{0-2}$-tetrazolone,

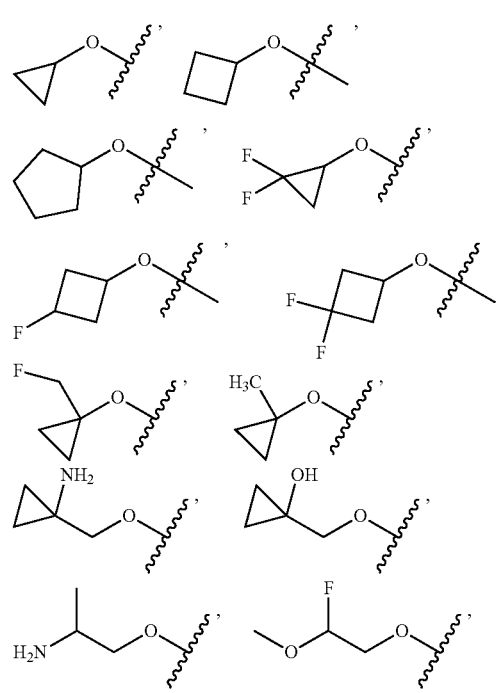

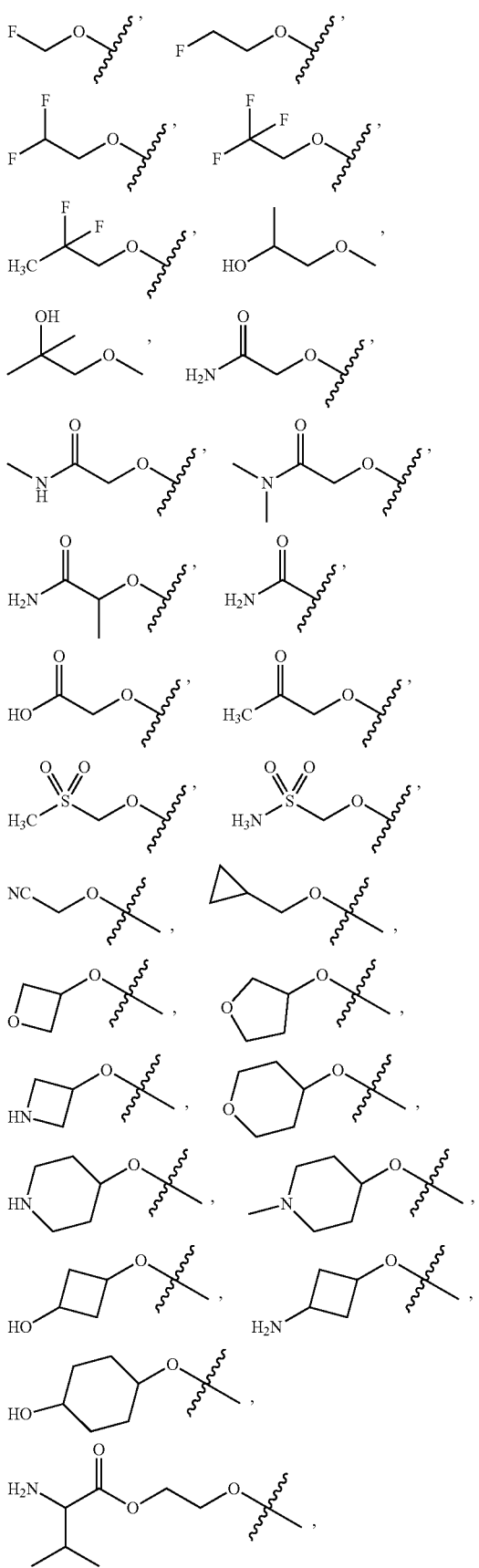

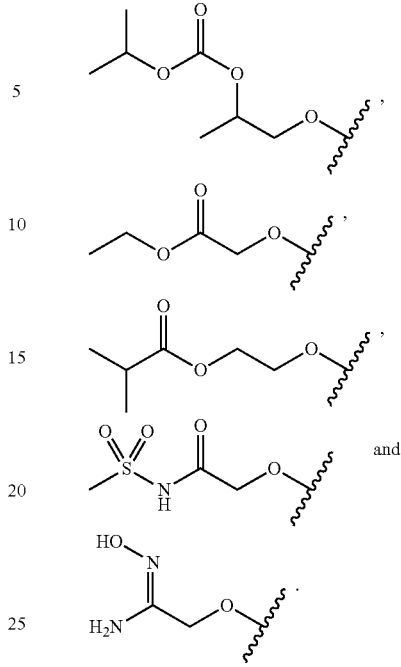

In some embodiments, A can be an optionally substituted cycloalkyl. Suitable examples of optionally substituted cycloalkyls include, but are not limited to, an optionally substituted cyclohexyl and an optionally substituted cycloheptyl. In other embodiments, A can be an optionally substituted cycloalkenyl, for example, an optionally substituted cyclohexenyl. In some embodiments, A can be an optionally substituted bi-cyclic cycloalkenyl, such as

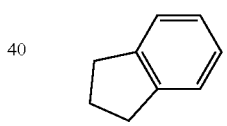

In some embodiments, A can be an optionally substituted aryl($C_{1-2}$ alkyl). In some embodiments, A can be an optionally substituted benzyl.

In some embodiments, A can be an optionally substituted mono-cyclic heteroaryl. In some embodiments, A can be an optionally substituted mono-cyclic 5-membered heteroaryl. In other embodiments, A can be an optionally substituted mono-cyclic 6-membered heteroaryl. In some embodiments, A can be an optionally substituted bi-cyclic heteroaryl.

In some embodiments, the optionally substituted heteroaryl can be selected from an optionally substituted imidazole, an optionally substituted thiazole, an optionally substituted furan, an optionally substituted thiophene, an optionally substituted pyrrole, an optionally substituted pyridine, an optionally substituted pyrimidine, an optionally substituted pyrazine, an optionally substituted quinoline, an optionally substituted imidazole, an optionally substituted oxazole, an optionally substituted isoxazole, an optionally substituted benzoimidazole, an optionally substituted benzoxazole, an optionally substituted benzothiazole and an optionally substituted imidazo[1,2-a]pyrimidine. In some embodiments, A can be an optionally substituted thiophene. In other embodiments, A can be an optionally substituted thiazole. In still other embodiments, A can be an optionally substituted pyridine. In yet still other embodiments, A can be an optionally substituted pyrimidine. In some embodiments, A can be an optionally substituted pyrazine. In other embodiments, A can be an optionally substituted imidazole. In still other embodiments, A can be an optionally substituted benzoimidazole, an optionally substituted benzooxazole or an optionally substituted benzothiazole.

In some embodiments, A can be an optionally substituted heterocyclyl, for example, an optionally substituted monocyclic heterocyclyl or an optionally substituted bi-cyclic heterocyclyl. In some embodiments, A can be an optionally substituted

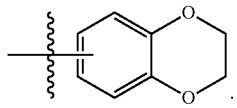

In other embodiments, A can be an optionally substituted

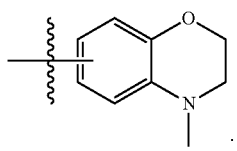

In still other embodiments, A can be an optionally substituted

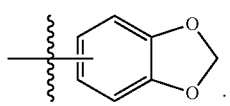

In yet still other embodiments, A can be an optionally substituted

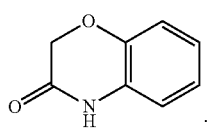

In some embodiments, A can be an optionally substituted

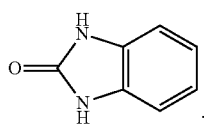

In other embodiments, A can be an optionally substituted

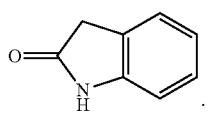

In still other embodiments, A can be an optionally substituted

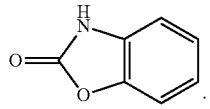

In yet still other embodiments, A can be an optionally substituted

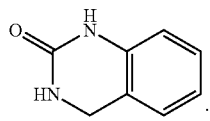 [SMILES: O=C1NCc2ccccc2N1]

In some embodiments, A can be an optionally substituted

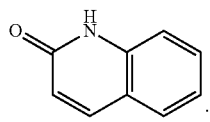 [SMILES: O=c1ccc2ccccc2[nH]1]

In some embodiments, A can be substituted with one or more $R^A$'s. In some embodiments, one $R^A$ can be present. In some embodiments, two $R^A$'s can be present. In some embodiments, three $R^A$'s can be present. In some embodiments, four or more $R^A$'s can be present. When two or more $R^A$'s are present, two or more $R^A$'s can be the same or two or more $R^A$'s can be different. In some embodiments, at least two $R^A$'s can be the same. In some embodiments, at least two $R^A$'s can be different. In some embodiments, all the $R^A$'s can be the same. In other embodiments, all the $R^A$'s can be different. In some embodiments, A can have one of the following structures:

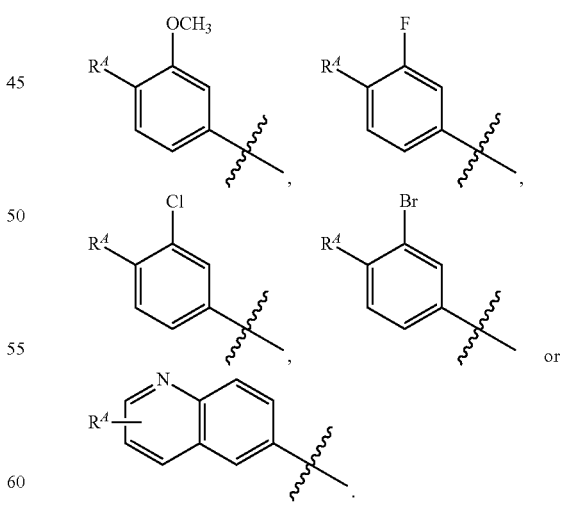

In some embodiments, $R^A$ can be each independently selected from an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amine, sulfenyl, alkyoxyalkyl, aryl, monocyclic heteroaryl, monocyclic heterocyclyl and aminoalkyl. In some embodiments, the optionally substituted $C_{1-4}$ alkoxy can be further substituted, for example, further substituted with a substituent selected from $C_{1-4}$ alkyl, halo, hydroxy, C-carboxy, C-amido, N-amido, amino, mono-alkyl amine, di-alkyl amine and an amino acid. In some embodiments, the optionally substituted haloalkoxy can be further substituted, for example, further substituted with an $C_{1-4}$ alkoxy. In some embodiments, the optionally substituted heteroaryl can be further substituted, for example, further substituted with an $C_{1-4}$ alkyl.

In some embodiments, each $R^A$ can be an alkyl, such as methyl, ethyl, propyl (n-propyl and iso-propyl) and/or butyl (n-butyl, iso-butyl and t-butyl).

In some embodiments, each $R^A$ can be an optionally substituted alkoxy, for example, methoxy, ethoxy, propoxy (n-propoxy and iso-propoxy), butoxy (n-butoxy, iso-butoxy and t-butoxy), phenoxy, —O(CH$_2$)$_2$—NH$_2$, —O(CH$_2$)$_2$—NH(CH$_3$), —O(CH$_2$)$_2$—N(CH$_3$)$_2$, —O—(CH$_2$)$_{2-4}$OH,

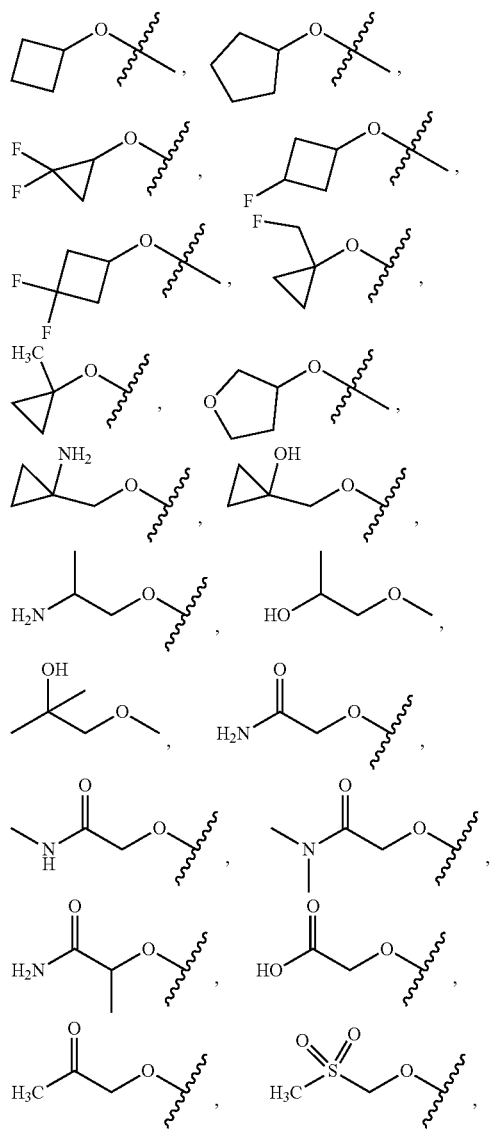

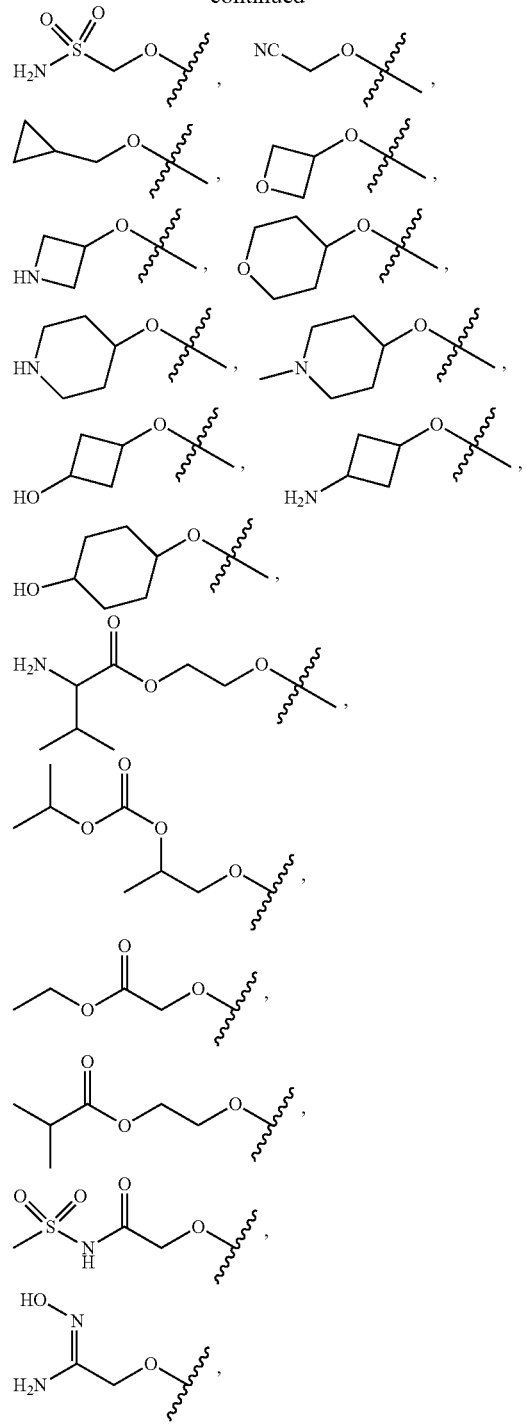

—O(CH$_2$)$_2$OCH$_3$, an optionally substituted —O(CH$_2$)$_{0-2}$-morpholinyl, an optionally substituted —O(CH$_2$)$_{0-2}$-triazole, an optionally substituted —O(CH$_2$)$_{0-2}$-imidazole, an optionally substituted —O(CH$_2$)$_{0-2}$-cyclopentanone, an optionally substituted —O(CH$_2$)$_{0-2}$pyrrolidinone, an optionally substituted —O(CH$_2$)$_{0-2}$-pyrazole, an optionally substituted —O(CH$_2$)$_{0-2}$-tetrahydrofuran, an optionally substituted —O(CH$_2$)$_{0-2}$-pyrrolidinone, an optionally substituted —O(CH$_2$)$_{0-2}$-tetrazole, an optionally substituted —O(CH$_2$)$_{0-2}$-tetrazolone and/or

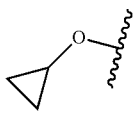

In some embodiments, $R^4$ can be substituted $C_{1-6}$ alkoxy substituted by one or more of the following: halo, hydroxy, $C_{1-4}$ alkyl, cyano, amino, mono-substituted amino, di-substituted amino, sulfonamidocarbonyl, hydroxamidine, C-amido, acyl, C-carboxy, O-carboxy, sulfonyl, S-sulfonamido, O-linked amino acid and carbonate ester.

In some embodiments, each $R^4$ can be haloalkyl, for example, trifluoromethyl.

In some embodiments, each $R^4$ can be an optionally substituted haloalkoxy, for example, difluoromethoxy, trifluoromethoxy,

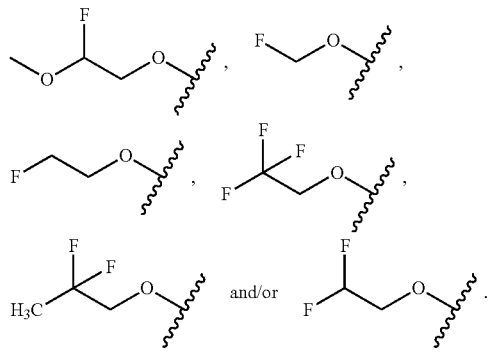

In some embodiments, each $R^4$ can be halogen, for example, chloro, bromo and/or fluoro.

In some embodiments, each $R^4$ can be amino, a mono-substituted amine or a di-substituted amine. For examples, $R^4$ can be N,N-di-methyl-amine, N,N-di-ethyl-amine, N-methyl-N-ethyl-amine, N-methyl-amino, N-ethyl-amino and/or amino.

In some embodiments, each $R^4$ can be hydroxy.

In some embodiments, each $R^4$ can be alkylthio, for example ethylthio.

In some embodiments, each $R^4$ can be aminoalkyl, such as —$(CH_2)_{1-2}$—$NH(CH_3)$.

In some embodiments, each $R^4$ can be alkoxyalkyl, for example, —$CH_2$—O—$CH_3$.

In some embodiments, each $R^4$ can be an optionally substituted aryl($C_{1-4}$ alkyl). In some embodiments, each $R^4$ can be an optionally substituted monocyclic heteroaryl($C_{1-4}$ alkyl). In some embodiments, each $R^4$ can be an optionally substituted monocyclic heterocyclyl($C_{1-4}$ alkyl). Non-limiting examples include an optionally substituted —$(CH_2)_{1-2}$-imidazole, an optionally substituted —$(CH_2)_{1-2}$-pyrrolidinone, an optionally substituted —$(CH_2)_{1-2}$-imidazolidinone.

In some embodiments, each $R^4$ can be hydroxyalkyl, for example, —$(CH_2)_{1-4}$—OH.

In some embodiments, each $R^4$ can be —O-amido, for example,

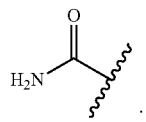

In some embodiments, each $R^4$ can be —N-amido, for example,

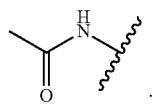

In some embodiments, each $R^4$ can be —N-sulfonamido, for example,

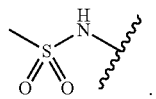

In some embodiments, each $R^4$ can be aminoalkyl, for example, —$CH_2$—$NH_2$ and/or —$CH_2$—$N(CH_3)H$.

In some embodiments, each $R^4$ can be an optionally substituted aryl, for example, an optionally substituted phenyl.

In some embodiments, each $R^4$ can be an optionally substituted mono-cyclic heteroaryl, such as an optionally substituted imidazole, an optionally substituted pyrazole, an optionally substituted pyridinyl, an optionally substituted pyrimidine, an optionally substituted pyrazine and/or an optionally substituted 1,2,4-oxadiazole.

In some embodiments, each $R^4$ can be an optionally substituted mono-cyclic heterocyclyl, for example, an optionally substituted pyrrolidinyl, an optionally substituted piperidinyl, an optionally substituted morpholinyl and/or an optionally substituted pyrrolidinone.

In some embodiments, Y can be an optionally substituted aryl. In some embodiments, Y can be a para-substituted phenyl, a meta-substituted phenyl or an ortho-substituted phenyl. In some embodiments, Y can be a mono-substituted phenyl, such as a mono-halo substituted phenyl. In some embodiments, Y can be a di-substituted phenyl, for example a di-halo substituted phenyl. For example, mono-halo substituted phenyls and di-halo substituted phenyls include, but are not limited to,

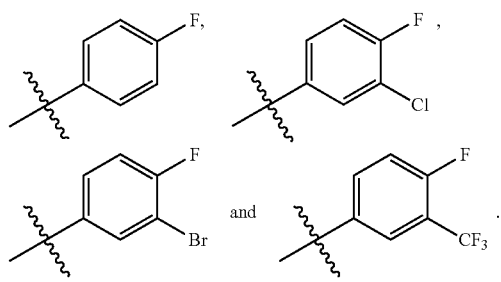

In some embodiments, Y can be di-substituted phenyl of the structure

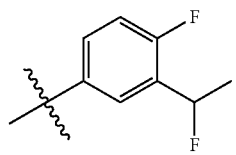

In some embodiments, Y can be a substituted phenyl that is substituted with 3 more substituents. In other embodiments, Y can be unsubstituted phenyl. In some embodiments, Y can be a substituted naphthyl. In other embodiments, Y can be an unsubstituted naphthyl.

In some embodiments, Y can be an optionally substituted cycloalkyl (e.g., an optionally substituted cyclohexyl and an optionally substituted cycloheptyl). In other embodiments, Y can be an optionally substituted cycloalkenyl, for example, an optionally substituted cyclohexenyl. In some embodiments, Y can be an optionally substituted bi-cyclic cycloalkenyl, such as

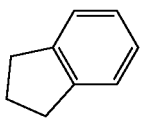

In some embodiments, Y can be an optionally substituted mono-cyclic heteroaryl. In some embodiments, Y can be selected from an optionally substituted imidazole, an optionally substituted furan, an optionally substituted thiophene, an optionally substituted pyrrole, an optionally substituted pyrimidine, an optionally substituted pyrazine, an optionally substituted pyridine, an optionally substituted pyrazole, an optionally substituted oxazole and an optionally substituted isoxazole. In some embodiments, Y can be a substituted mono-cyclic heteroaryl, including those described herein. In some embodiments, Y can be an unsubstituted mono-cyclic heteroaryl, including those described herein.

In some embodiments, Y can be an optionally substituted bi-cyclic heteroaryl. In some embodiments, Y can be selected from an optionally substituted benzothiophene, an optionally substituted benzofuran, an optionally substituted indole, an optionally substituted quinoline, an optionally substituted isoquinoline, an optionally substituted benzoxazole, an optionally substituted benzoisoxazole, an optionally substituted benzoisothiazole, an optionally substituted benzothiazole, an optionally substituted benzoimidazole, an optionally substituted benzotriazole, an optionally substituted 1H-indazole and an optionally substituted 2H-indazole. In some embodiments, Y can be selected from an optionally substituted

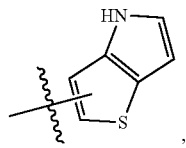

an optionally substituted

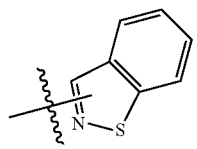

an optionally substituted

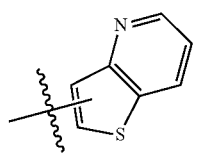

an optionally substituted

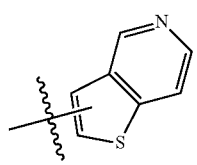

an optionally substituted

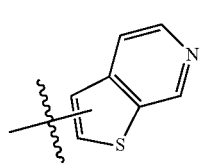

an optionally substituted

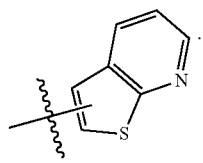

an optionally substituted

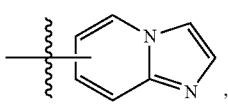

and an optionally substituted

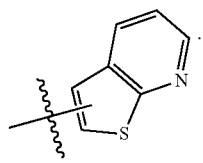

In some embodiments, Y can be a substituted bi-cyclic heteroaryl, including those described herein. In some embodiments, Y can be an unsubstituted bi-cyclic heteroaryl, including those described herein.

In some embodiments, Y can be an optionally substituted heterocyclyl. In some embodiments, Y can be an optionally substituted mono-cyclic heterocyclyl, such as an optionally substituted pyridinone. In other embodiment, Y can be an optionally substituted bi-cyclic heterocyclyl. For example, Y can be an optionally substituted

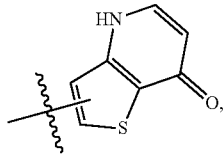

an optionally substituted

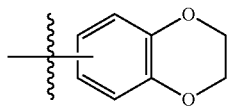

or an optionally substituted

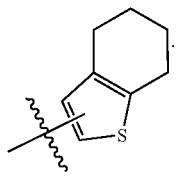

When Y is substituted, Y can be substituted with one or more $R^B$'s. In some embodiments, each $R^B$ can be independently selected from cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, alkoxyalkyl, $C_{1-4}$ haloalkyl, haloalkoxy, an unsubstituted acyl, an optionally substituted —C-carboxy, an optionally substituted —C-amido, sulfonyl, carbonyl, amino, mono-substituted amine, di-substituted amine and

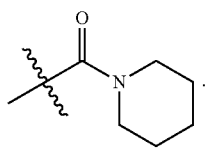 [SMILES: *C(=O)N1CCCCC1]

In some embodiments, when Y is an optionally substituted phenyl, the phenyl can be substituted 1, 2, 3 or more times with cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, $C_{1-4}$ haloalkyl (such as $CF_3$, $CHF_2$), haloalkoxy (such as $OCF_3$), an unsubstituted acyl, an optionally substituted —C-carboxy, an optionally substituted —C-amido, sulfonyl, amino, mono-$C_{1-4}$ alkyl amine, di-$C_{1-4}$ alkyl amine and/or

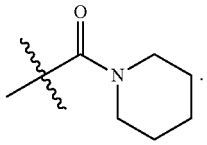 [SMILES: *C(=O)N1CCCCC1]

In other embodiments, when Y is an optionally substituted mono-cyclic heteroaryl, the mono-cyclic heteroaryl can be substituted 1, 2, 3 or more times with halo, an optionally substituted $C_{1-4}$ alkyl, an optionally substituted phenyl and/or an unsubstituted acyl. In still other embodiments, when Y is an optionally substituted bi-cyclic heteroaryl, the bi-cyclic heteroaryl can be substituted 1, 2, 3 or more times with halo, an optionally substituted $C_{1-4}$ alkyl, an optionally substituted phenyl, hydroxy, $C_{1-4}$ alkoxy, an unsubstituted acyl, carbonyl, cyano, amino, mono-$C_{1-4}$ alkyl amine and/or di-$C_{1-4}$ alkyl amine.

In some embodiments, Y can be an optionally substituted benzothiophene. In some embodiments, Y can be a substituted benzothiophene. In other embodiments, Y can be an unsubstituted benzothiophene. In some embodiments, the benzothiophene can be substituted with one or more of the following: halogen (such as fluoro, chloro and/or bromo), carbonyl, $C_{1-4}$ alkyl, hydroxy, $C_{1-4}$ alkoxy, $NH_2$ and/or mono-substituted amine. For example, the benzothiophene can be an optionally substituted

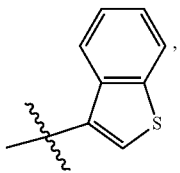 [SMILES: *c1csc2ccccc12]

such as an optionally substituted

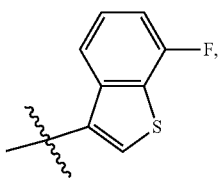 [SMILES: *c1csc2c(F)cccc12]

an optionally substituted

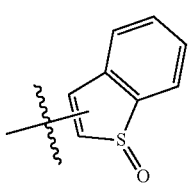

and an optionally substituted

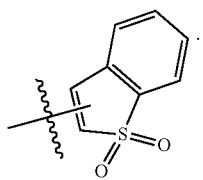

In some embodiments, Y can be an optionally substituted benzofuran.

In some embodiments, Y can be an optionally substituted indole. In some embodiments, Y can be a substituted indole. In some embodiments, the indole can be substituted 1, 2, 3 or more time with phenyl (substituted or unsubstituted), $C_{1-4}$ alkyl and/or halo. In other embodiments, Y can be an unsubstituted indole.

In some embodiments, Y can be substituted with one or more halogen. In some embodiments, Y can be substituted with one or more unsubstituted $C_{1-4}$ alkyl. In some embodiments, Y can be substituted with more or more hydroxy. In some embodiments, Y can be substituted with one or more optionally substituted phenyl. In some embodiments, Y can be substituted with one or more alkoxy. In some embodiments, Y can be substituted with one or more acyl. In some embodiments, Y can be substituted with one or more amino, mono-substituted amino, or di-substituted amino. In some embodiments, Y can be substituted with one or more haloalkyl. In some embodiments, Y can be substituted with one or more haloalkoxy. In some embodiments, Y can be substituted with one or more C-carboxy. In some embodiments, Y can be substituted with one or more C-amido. In some embodiments, Y can be substituted with one or more hydroxyalkyl.

In some embodiments, a compound of Formula (I) can be selected from the following compounds: 1, 13-1, 100, 101, 102, 103, 105, 106, 107, 108, 109, 110, 111, 112, 113, 114, 115, 116, 116a, 116b, 117, 117a, 117b, 118, 118a, 118b, 119, 120, 120a, 120b, 121, 122, 122a, 122b, 123, 124, 125, 126, 127, 128, 129, 131, 132, 133, 134, 138, 139, 142, 143, 144, 145, 146, 147, 148, 151, 152, 153, 154, 155, 158, 159, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 218, 219, 221, 223, 224, 225, 226, 227, 228, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 288, 289, 290, 291, 292, 293, 294, 295, 296, 297, 298, 299, 300, 301, 306, 307, 308, 309, 310, 312, 313, 314, 315, 316, 317, 318, 319, 320, 321, 322, 323, 324, 325, 326, 327, 328, 329, 330, 331, 332, 333, 334, 335, 336, 337, 338, 339, 340, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 475, 476, 477, 478, 479, 480, 481, 482, 483, 484, 485, 486, 487, 488, 489, 490, 491, 492, 493, 494, 495, 496, 497, 498a, 498b, 498c, 498d, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604a, 604b, 604c, 604d, 605a, 605b, 605c, 605d, 606, 607, 608, 609, 610, 611, 612, 613, 614, 615, 616, 617, 618, 619, 620, 621, 622, 623a, 623b, 624a, 624b, 625, 626, 627, 628, 629, 630, 631, 632, 633a, 633b, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 680, 681 and 682, or a pharmaceutically acceptable salt of the foregoing. In some embodiments, a compound of Formula (I) can be selected from: 149, 150, 156, 157, 160, 217, 220, 222, 229, 287, 302, 303, 304, 305, 311, 401, 473 and 474, or a pharmaceutically acceptable salt of the foregoing. In some embodiments, a compound of Formula (I) can be selected from: 130, 135, 140 and 141, or a pharmaceutically acceptable salt of the foregoing. In some embodiments, a compound of Formula (I) can be 104 or 161, or a pharmaceutically acceptable salt of the foregoing. In some embodiments, a compound of Formula (I) can be 136 or 137, or a pharmaceutically acceptable salt of the foregoing. In some embodiments, a compound of Formula (I), or a pharmaceutically acceptable salt thereof, cannot be a compound provided in PCT Publication WO 2014/031784, published Feb. 27, 2014.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments described herein relate to a method for ameliorating, treating and/or preventing a paramyxovirus viral infection, which can comprise administering an effective amount of one or more compounds described herein, or a pharmaceutical composition that includes one or more compounds described herein (e.g., a compound of Formula (I), or a pharmaceutically acceptable salt thereof).

Some embodiments described herein relate to a method for inhibiting viral replication of a paramyxovirus, which can comprise contacting a cell infected with the virus with an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof).

Some embodiments described herein relate to a method for contacting a cell infected with a paramyxovirus, which can comprise contacting a cell infected with the virus with an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof).

In some embodiments, the paramyxovirus infection is a human respiratory syncytial virus infection.

In some embodiments, an effective amount of one or more compounds of Formula (I), or a pharmaceutically acceptable salt thereof, one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a respiratory syncytial viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a respiratory syncytial viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a respiratory syncytial virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the RSV polymerase complex. In some embodiments, the RSV can be RSV A. In some embodiments, the RSV can be RSV B.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a hendraviral infection and/or nipahviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a hendraviral infection and/or nipahviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a hendravirus and/or nipahvirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the hendravirus polymerase complex and/or nipahvirus polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a measles. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a measles. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a measles virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the measles polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate mumps. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent mumps. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a mumps virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the mumps polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a sendai viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a sendai viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication a sendai virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the sendai virus polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a HPIV-1 infection and/or HPIV-3 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a HPIV-1 infection and/or HPIV-3 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a HPIV-1 and/or HPIV-3. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the HPIV-1 polymerase complex and/or HPIV-3 polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a HPIV-2 infection and/or HPIV-4 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a HPIV-2 infection and/or HPIV-4 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a HPIV-2 and/or HPIV-4. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the HPIV-2 polymerase complex and/or HPIV-4 polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a human metapneumoviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a human metapneumoviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a human metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the human metapneumovirus polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection caused by a virus selected from a henipavirus, a morbillivirus, a respirovirus, a rubulavirus, a pneumovirus, and a metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection caused by a virus selected from a henipavirus, a morbillivirus, a respirovirus, a rubulavirus, a pneumovirus, and a metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an infection caused by a virus selected from a henipavirus, a morbillivirus, a respirovirus, a rubulavirus, a pneumovirus, and a metapneumovirus (such as those described herein).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection caused by RSV infection, measles, mumps, parainfluenza infection, and/or metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection caused by RSV infection, measles, mumps, parainfluenza infection, and/or metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an infection caused by RSV infection, measles, mumps, parainfluenza infection, and/or metapneumovirus (such as those described herein).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate bronchiolitis and/or tracheobronchitis due to a RSV infection and/or human parainfluenza virus 3 (HPIV-3) infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate pneumonia due to a RSV infection and/or human parainfluenza virus 3 (HPIV-3) infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate croup due to a RSV infection and/or human parainfluenza virus 1 (HPIV-1) infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate due to fever, cough, runny nose, red eyes, a generalized rash, pneumonia, an ear infection and/or bronchitis due to measles. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate due to swelling of the salivary glands, fever, loss of appetite and/or fatigue due to mumps.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a human parainfluenza viral infection. In some embodiments, the human parainfluenza viral infection can be a human parainfluenza virus 1 (HPIV-1). In other embodiments, the human parainfluenza viral infection can be a human parainfluenza virus 2 (HPIV-2). In other embodiments, the human parainfluenza viral infection can be a human parainfluenza virus 3 (HPIV-3). In other embodiments, the human parainfluenza viral infection can be a human parainfluenza virus 4 (HPIV-4). In some embodiments, one or more compounds of Formula (I), or a pharmaceutically acceptable salt thereof, can be used to treat and/or ameliorate one or more subtypes of human parainfluenza virus. For example, one or more compounds of Formula (I), or a pharmaceutically acceptable salt thereof, can be used to treat HPIV-1 and/or HPIV-3.

The one or more compounds of Formula (I) or a pharmaceutically acceptable salt thereof, that can be used to treat, ameliorate and/or prevent a paramyxovirus viral infection can be a compound of Formula (I), or pharmaceutically acceptable salt thereof, provided in any of the embodiments described in the section under the "Compounds" heading above.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "prevent" and "preventing," mean lowering the efficiency of viral replication and/or inhibiting viral replication to a greater degree in a subject who receives the compound compared to a subject who does not receive the compound. Examples of forms of prevention include prophylactic administration to a subject who has been or may be exposed to an infectious agent, such as a paramyxovirus (e.g., RSV).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance, and may positively affect one or more symptoms or aspects of the disease while having effects on other aspects of the disease or on unrelated systems that may be considered undesireable.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, treat, alleviate or ameliorate one or more symptoms or conditions of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a viral infection, such as a paramyxovirus, are known to those skilled in the art. Example of suitable indicators include, but are not limited to, a reduction in viral load, a reduction in viral replication, a reduction in viral RNA, a reduction in time to seroconversion (virus undetectable in patient serum), a reduction of morbidity or mortality in clinical outcomes, and/or other indicator of disease response.

In some embodiments, an effective amount of a compound of Formula (I), or a pharmaceutically acceptable salt thereof, is an amount that is effective to reduce viral titers to essentially undetectable or very low levels, for example, to less than 1.7 $\log_{10}$ plaque forming units equivalents (PFUe)/mL, or less than 0.3 $\log_{10}$ plaque forming units equivalents (PFUe)/mL. In some embodiments, a compound of Formula (I), or a pharmaceutically acceptable salt thereof, can reduce the viral load compared to the viral load before administration of the combination (for example, 60 hours after receiving the initial dosage of the combination). In some embodiments, a compound of Formula (I), or a pharmaceutically acceptable salt thereof, described herein can reduce the viral load to lower than 1.7 $\log_{10}$ (PFUe)/mL, or lower than 0.3 $\log_{10}$ (PFUe)/mL. In some embodiments, a combination of compounds described herein can achieve a reduction in viral titer in the serum of the subject in the range of about 1.5-log to about a 2.5-log reduction, about a 3-log to about a 4-log reduction, or a greater than about 5-log reduction compared to the viral load before administration of the combination. For example, the viral load is measure before administration of the combination, and several hours after receiving the initial dosage of the combination (for example, 60 hours after receiving the initial dosage of the combination).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of a paramyxovirus relative to pre-treatment levels in a subject, as determined several hours after receiving the initial dosage of the combination (for example, 60 hours after receiving the initial dosage of the combination). In some embodiments, a compound of Formula (I), or a pharmaceutically acceptable salt thereof, described herein can result in a reduction of the replication of a paramyxovirus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of a paramyxovirus replication in the range of 1 to 1.5 log, 1.5 log to 2 log, 2 log to 2.5 log, 2.5 to 3 log, 3 log to 3.5 log or 3.5 to 4 log more reduction of a paramyxovirus replication compared to the reduction of a paramyxovirus reduction achieved by ribavirin (Virazole®), or may achieve the same reduction as that of ribavirin (Virazole®) therapy in a shorter period of time, for example, in one day, two days, three days, four days, or five days, as compared to the reduction achieved after 5 days of ribavirin (Virazole®) therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with RSV that is resistant to one or more different anti-RSV agents (for example, ribavirin). In some embodiments, development of resistant RSV strains is delayed when subjects are treated with a compound of Formula (I), or a pharmaceutically acceptable salt thereof, compared to the development of RSV strains resistant to other RSV drugs.

In some embodiments, a compound of Formula (I), or a pharmaceutically acceptable salt thereof, can decrease the percentage of subjects that experience complications from a RSV viral infection compared to the percentage of subjects that experience complication being treated with ribavirin. For example, the percentage of subjects being treated with a compound of Formula (I), or a pharmaceutically acceptable salt thereof, that experience complications can be 10%, 25%, 40%, 50%, 60%, 70%, 80% and 90% less compared to subjects being treated with ribavirin.

In some embodiments, a compound of Formula (I), or a pharmaceutically acceptable salt thereof, or a pharmaceutical composition that includes a compound described herein, can be used in combination with one or more additional agent(s). In some embodiments, a compound of Formula (I), or a pharmaceutically acceptable salt thereof, can be used in combination with one or more agents currently used in a conventional standard of care for treating RSV. For example, the additional agent can be ribavirin, palivizumab, and RSV-IGIV. For the treatment of RSV, additional anti-RSV agents include but are not limited to an anti-RSV antibody, a fusion protein inhibitor, an N-protein inhibitor, a RSV polymerase inhibitor, an IMPDH inhibitor, an interferon and an other compound that inhibits the RSV virus, or a pharmaceutically acceptable salt of any of the foregoing. A non-limiting list of examples of additional agents is provided herein.

| | |
|---|---|
| anti-RSV antibodies | RSV-IGIV (RespiGam ®) |
| | palivizumab (Synagis ®, a chimeric humanized IgG monoclonal antibody) |
| | motavizumab (MEDI-524, humanized monoclonal antibody) |
| fusion protein inhibitors | 1-cyclopropyl-3-[[1-(4-hydroxybutyl)benzimidazol-2-yl]methyl]imidazo[4,5-c]pyridin-2-one (BMS-433771) |
| | 4,4''-bis-{4,6-bis-[3-(bis-carbamoylmethyl-sulfamoyl)-phenylamino]-(1,3,5)triazin-2-ylamino}-biphenyl-2,2''-disulfonic-acid (RFI-641) |
| | 4,4'-Bis[4,6-di[3-aminophenyl-N,N-bis(2-carbamoylethyl)-sulfonilimino]-1,3,5-triazine-2-ylamino]-biphenyl-2,2'-disulfonic acid, disodium salt (CL387626) |
| | 2-[[2-[[1-(2-aminoethyl)-4-piperidinyl]amino]-4-methyl-1H-benzimidazol-1-yl]-6-methyl-3-pyridinol (JNJ-2408068) |
| | 2-[[6-[[[2-(3-Hydroxypropyl)-5-methylphenyl]amino]methyl]-2-[[3-(morpholin-4-yl)propyl]amino]benzimidazol-1-yl]methyl]-6-methylpyridin-3-ol (TMC-353121) |
| | 5,5'-bis[1-(((5-amino-1H-tetrazolyl)imino)methyl)]2,2',4''-methylidynetrisphenol (VP-14637, MDT-637) |
| | N-(2-hydroxyethyl)-4-methoxy-N-methyl-3-(6-methyl-[1,2,4]triazolo[3,4-a]phthalazin-3-yl)benzenesulfonamide (P13) |
| | 2-((2-((1-(2-aminoethyl)piperidin-4-yl)amino)-4-methyl-1H-benzo[d]imidazol-1-yl)methyl)-6-methylpyridin-3-ol (R170591) |
| | 1,4-bis(3-methylpyridin-4-yl)-1,4-diazepane (C15) |
| | (R)-9b-(4-chlorophenyl)-1-(4-fluorobenzoyl)-2,3-dihydro-1H-imidazo[1',2':1,2]pyrrolo[3,4-c]pyridin-5(9bH)-one (BTA9981) |
| | [2,2-bis(docosyloxy-oxymethyl)propyl-5-acetoamido-3,5-dideoxy-4,7,8,9-tetra-O-(sodium-oxysulfonyl)-D-glycero-D-galacto-2-nonulopyranosid]onate (MBX-300) |
| | BTA-C286 |
| | N-(2-((S)-2-(5-((S)-3-aminopyrrolidin-1-yl)-6-methylpyrazolo[1,5-a]pyrimidin-2-yl)piperidine-1-carbonyl)-4-chlorophenyl)methanesulfonamide (GS-5806) |
| | an anti-RSV nanobody (e.g., ALX-0171 (a trivalent nanobody, Ablynx) |
| | a peptide fusion inhibitor (such as a peptide having the sequence DEFDASISQVNEKINQSLAFIRKSDELL (T-67) |
| | a peptide having the sequence FDASISQVNEKINQSLAFIRKSDELLHNVNAGKST (T-118) |
| N-protein inhibitors | (S)-1-(2-fluorophenyl)-3-(2-oxo-5-phenyl-2,3-dihydro-1H-benzo[e][1,4]diazepin-3-yl)urea (RSV-604) |
| | STP-92 (siRNA delivered through nanoparticle based delivery systems, Sirnaomics) |
| | iKT-041 (Inhibikase) |
| RSV polymerase inhibitors | 6-{4-[(biphenyl-2-ylcarbonyl) amino]benzoyl}-N-cyclopropyl-5,6-dihydro-4H-thieno[3,2-d][1]benzazepine-2-carboxamide (YM-53403) |
| | N-cyclopropyl-5-(4-(2-(pyrrolidin-1-yl)benzamido)benzoyl)-5,6,7,10-tetrahydrobenzo[b]cyclopenta[d]azepine-9-carboxamide |
| | 6-(4-(2-(2-oxa-7-azaspiro[3.5]nonan-7-yl)nicotinamido)benzoyl)-N-cyclopropyl-5,6-dihydro-4H-benzo[b]thieno[2,3-d]azepine-2-carboxamide, 4-amino-8-(3-{[2-(3,4-dimethoxyphenyl)ethyl]amino}propyl)-6,6-dimethyl-2-(4-methyl-3-nitrophenyl)-1H-imidazo[4,5-h]-isoquinoline-7,9(6H,8H)-dione (CAS Reg. No. 851658-10-1) |
| | AZ27 |

| | |
|---|---|
| IMPDH inhibitors | ribavirin
5-ethynyl-1-beta-D-ribofuranosylimidazole-4-carboxamide (EICAR)
4-hydroxy-3-beta-D-ribofuranosylpyrazole-5-carboxamide (pyrazofurin)
1-((2R,3R,4S,5R)-3,4-dihydroxy-5-(hydroxymethyl)tetrahydrofuran-2-yl)-1H-1,2,4-triazole-3-carboximidamide (Taribavirin, viramidine)
1,3,4-thiadiazol-2-ylcyanamide (LY253963)
tetrahydrofuran-3-yl-3-(3-(3-methoxy-4-(oxazol-5-yl)phenyl)ureido)benzylcarbamate (VX-497)
(4E)-6-(4-Hydroxy-6-methoxy-7-methyl-3-oxo-1,3-dihydro-2-benzofuran-5-yl)-4-methylhex-4-enoic acid (Mycophenolic acid)
2-morpholin-4-ylethyl-(E)-6-(4-hydroxy-6-methoxy-7-methyl-3-oxo-1H-2-benzofuran-5-yl)-4-methylhex-4-enoate (Mycophenolate Mofetil) |
| Interferons | Type 1 interferon
Type 2 interferon
Type 3 interferon
an alpha-interferon (IFN-α)
Pegylated interferon-alpha-2a (PEGASYS ®)
Pegylated interferon-alpha-2b (PEG-INTRON ®)
interferon alfacon-1 (INFERGEN ®)
beta-interferon (IFN-β)
lambda-interferon (IFN-λ) |
| other compounds | a double stranded RNA oligonucleotide
5-methyl-N-[4-(trifluoromethyl) phenyl]-isoxazole-4-carboxamide (leflumomide), N-(2-chloro-4-methylphenyl)-2-((1-(4-methoxyphenyl)-1H-benzo[d]imidazol-2-yl)thio)propanamide (JMN3-003)
an intratracheal formulation of recombinant human CC10 (CG-100)
high titer, human immunoglobulin (RI-001, ADMA Biologics Inc.)
a non-neutralizing mAb against the G protein (mAb 131-2G)
ALN-RSV01 (an siRNA agent with the sense strand sequence (5' to 3') GGCUCUUAGCAAAGUCAAGdTdT (SEQ ID NO. 3) and the antisense strand sequence (5' to 3') CUUGACUUUGCUAAGAGCCdTdT (SEQ ID NO. 4)
ALN-RSV02
Medi-559
Medi-534
Medi-557 |

ALN-RSV01 and/or ALN-RSV02 can be found in U.S. Publication No. 2009/0238772, filed Dec. 15, 2008 (Alnylam Pharmaceuticals).
ALX-0171 described in U.S. Publication No. 2012/0128669, filed Jun. 7, 2010.
T-67, SEQ ID NO: 1, U.S. Pat. No. 6,623,741, filed Feb. 29, 2000.
T-118, SEQ ID NO: 2, U.S. Pat. No. 6,623,741, filed Feb. 29, 2000.

Other examples of compounds that can be used in combination with a compound of Formula (I), or a pharmaceutically acceptable salt, include those provided in WO 2013/186333, published Dec. 19, 2013; WO 2013/186332, published Dec. 19, 2013; WO 2013/186335, published Dec. 19, 2013; WO 2013/186334, published Dec. 19, 2013; WO 2012/080447, published Jun. 21, 2012; WO 2012/080449, published Jun. 21, 2012; WO 2012/080450, published Jun. 21, 2012; WO 2012/080451, published Jun. 21, 2012; WO 2012/080446, published Jun. 21, 2012; WO 2010/103306, published Sep. 16, 2010; WO 2012/068622, published May 31, 2012; WO 2005/042530, published May 12, 2005; WO 2006/136561, published Dec. 28, 2006; WO 2005/058869, published Jun. 30, 2005; U.S. 2013/0090328, published Apr. 11, 2013; WO 2014/009302, published Jan. 16, 2014; WO 2011/005842, published Jan. 13, 2011; U.S. 2013/0273037, published Oct. 17, 2013; U.S. 2013/0164280, published Jun. 27, 2013; U.S. 2014/0072554, published Mar. 13, 2014; WO 2014/031784, published Feb. 27, 2014 and WO 2014/031784, published Feb. 27, 2014, all of which are hereby incorporated by reference.

In combination therapy, the additional agents can be administered in amounts that have been shown to be effective for those additional agents. Such amounts are known in the art; alternatively, they can be derived from viral load or replication studies using the parameters for "effective amount" set forth above. Alternatively, the amount used can be less than the effective monotherapy amount for such additional agents. For example, the amount used could be between 90% and 5% of such amount, e.g., 90%, 80%, 70%, 60%, 50%, 40%, 30%, 20%, 10%, or 5%, or intermediate values between those points.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

A potential advantage of utilizing a compound of Formula (I), or a pharmaceutically acceptable salt thereof, in combination with one or more additional agent(s) described above (including the table), including pharmaceutically acceptable salts and prodrugs thereof, may be a reduction in the required amount(s) of one or more compounds of above (including the table) (including pharmaceutically acceptable salts and prodrugs thereof) that is effective in treating a disease condition disclosed herein (for example, RSV), as compared to the amount required to achieve same therapeutic result when one or more compounds described above (including the table), including pharmaceutically acceptable salts thereof, are administered without a compound of Formula (I), or a pharmaceutically acceptable salt thereof. For example, the amount of a compound described above (including the table), including a pharmaceutically acceptable salt and prodrug thereof, can be less compared to the amount of the compound described above (including the table), including a pharmaceutically acceptable salt and prodrug thereof, needed to achieve the same viral load reduction when administered as a monotherapy. Another potential advantage of utilizing a compound of Formula (I), or a pharmaceutically acceptable salt thereof, in combination with one or more additional agent(s) described above (including the table), including pharmaceutically acceptable salts and prodrugs thereof, is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) described above (including the table), including pharmaceutically acceptable salts and prodrugs thereof, may include little to no cross resistance between a compound of Formula (I), or a pharmaceutically acceptable salt thereof, and one or more additional agent(s) described above (including the table) (including pharmaceutically acceptable salts and prodrugs thereof); different routes for elimination of a compound of Formula (I), or a pharmaceutically acceptable salt thereof, and one or more additional agent(s) described above (including the table) (including pharmaceutically acceptable salts and prodrugs thereof); little to no overlapping toxicities between a compound of Formula (I), or a pharmaceutically acceptable salt thereof, and one or more additional agent(s) described above (including the table) (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) described above (including the table), including pharmaceutically acceptable salts and prodrugs thereof).

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Synthesis

Compounds of Formula (I), and those described herein may be prepared in various ways. Some compounds of Formula (I) can be obtained commercially and/or prepared utilizing known synthetic procedures. General synthetic routes to the compounds of Formula (I), and some examples of starting materials used to synthesize the compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

EXAMPLES

Additional embodiments are disclosed in further detail in the following examples, which are not in any way intended to limit the scope of the claims.

Example 1

Preparation of Compound 1

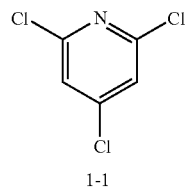

1-1

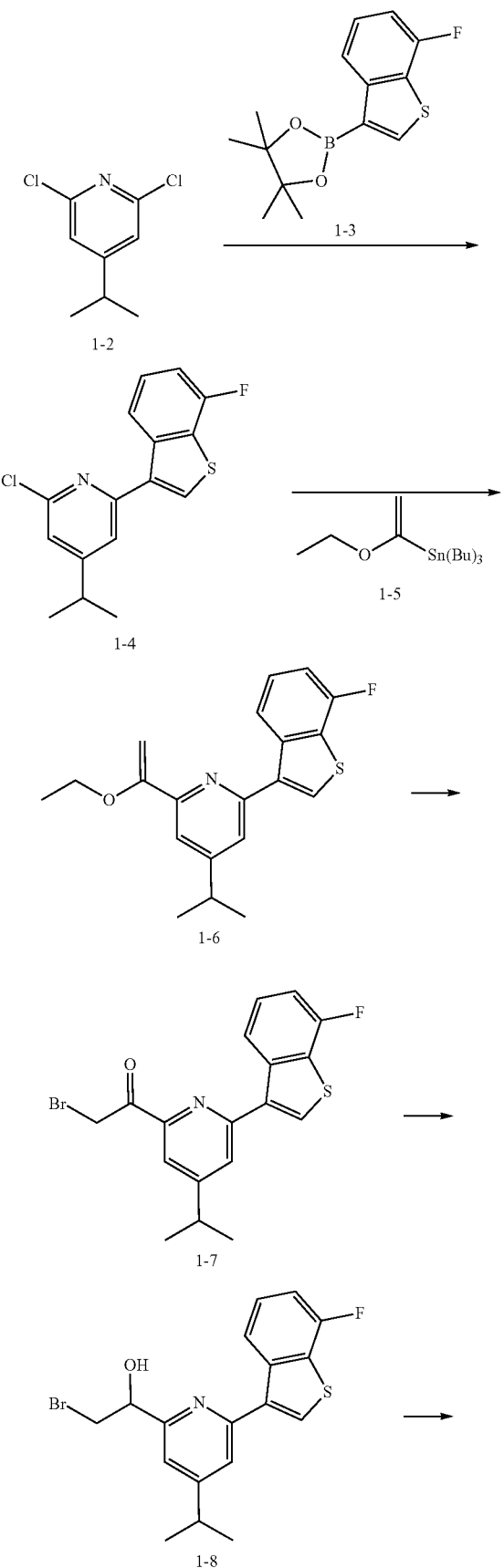

-continued

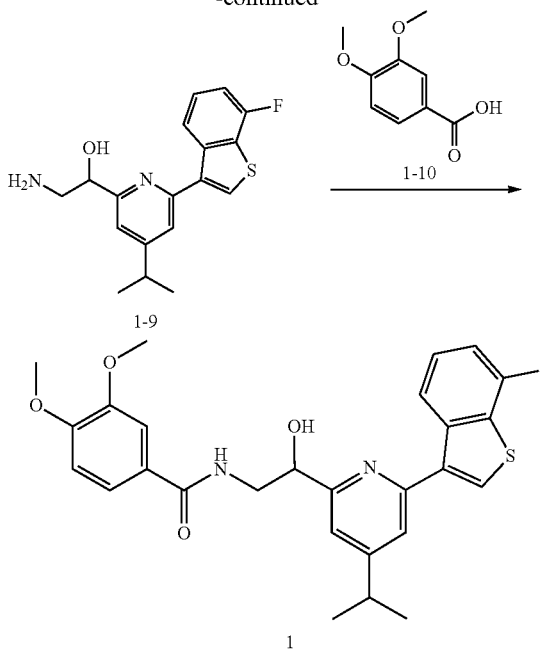

To a mixture of 1-1 (3.65 g, 20 mmol) in NMP:THF (2 mL/20 mL), Fe(acac)$_3$ (622 mg, 2 mmol) was added. The solution was cooled to 0° C. and i-PrMgCl (20 mL, 2N) was added slowly at 0° C. The solution was stirred for 2 h at 0° C. The solution was extracted with EA, and washed with brine. The organic phase was concentrated to give crude 1-2 as a colorless solid (2.4 g, 63.5%). +ESI-MS: m/z 190.1 [M+H]$^+$.

To a mixture of 1-2 (1 g, 5.29 mmol) and 1-3 (1.03 g, 5.29 mmol) in DMF (30 mL) were added Pd(dppf)Cl$_2$ (420 mg, 0.529 mmol) and a freshly prepared KF solution (2.57 g in 10 mL of water). The system was degassed and then charged with nitrogen 3 times. The mixture was stirred under nitrogen at 70° C. using an oil bath for 8 h. The reaction solution was cooled to r.t., diluted with EA and separated from the water layer. The EA solution was washed with brine, dried over Na$_2$SO$_4$ and concentrated. The residue was purified on a silica gel column to give 1-4 as a colorless solid (0.5 g, 31%). +ESI-MS: m/z 306.0 [M+H]$^+$.

To a mixture of 1-4 (900 mg, 2.95 mmol), 1-5 (1.07 g, 2.95 mmol) and KF (0.684 g, 11.8 mmol) in DMF (10 mL) was added Pd(dppf)Cl$_2$ (228 mg, 0.295 mmol). The system was degassed and then charged with nitrogen 3 times. The mixture was stirred under nitrogen at 70° C. using an oil bath for 8 h. The reaction solution was cooled to r.t., diluted with EA and H$_2$O. The organic phase was washed with brine, dried over Na$_2$SO$_4$ and concentrated to give crude 1-6 (1 g). +ESI-MS: m/z 342.1 [M+H]$^+$.

A mixture of 1-6 (1 g, 2.9 mmol) and NBS (516 mg, 2.9 mmol) in a mixture of THF (10 mL) and H$_2$O (1 mL) was stirred at r.t. for 30 mins. The solution was diluted with water and the aqueous layer was extracted with EtOAc. The combined organic layers were washed with a sat. Na$_2$S$_2$O$_3$ solution, followed by brine. The solution was dried over Na$_2$SO$_4$ and evaporated to give crude 1-7 (1 g). +ESI-MS: m/z 392.0 [M+H]$^+$.

To a solution of 1-7 (1 g, 2.55 mmol) in a mixture of THF (5 mL) and MeOH (0.5 mL) was added NaBH$_4$ (193 mg, 5.1 mmol) at 0° C. The mixture was stirred at 0° C. for 30 mins with TLC monitoring. The reaction was quenched by the addition of H$_2$O and extracted with EA. The combined organic layers were washed with brine, dried over Na$_2$SO$_4$ and concentrated. The residue was purified on a silica gel column to give 1-8 (200 mg, 20%). +ESI-MS: m/z 394.0 [M+H]$^+$.

A mixture of 1-8 (200 mg, 0.50 mmol) and sat. NH$_4$OH/EtOH (1 mL/5 mL) in a sealed tube was heated to 70° C. for 6 h. The solution was removed under reduced pressure to give crude 1-9 (160 mg, 90.0%), which was used for next step directly without purification. +ESI-MS: m/z 331.1 [M+H]$^+$.

To a solution of 1-9 (65 mg, 0.363 mmol), HATU (172 mg, 0.45 mmol) and DIPEA (117 mg, 0.909 mmol) in anhydrous DMF (1 mL) was added 1-10 (100 mg 0.303 mmol) at 25° C. The solution was stirred for 10 h at r.t. The solution was diluted with 1.0 N aqueous NaHCO$_3$ solution (2×40 mL) and extracted with EA (2×20 mL). The combined organic layers were washed with brine, dried over anhydrous Na$_2$SO$_4$, and concentrated under reduced pressure. The residue was purified on a silica gel column to give 1 (100 mg, 67.1%). +ESI-MS: m/z 495.1 [M+H]$^+$.

Example 2

Preparation of Compound 100

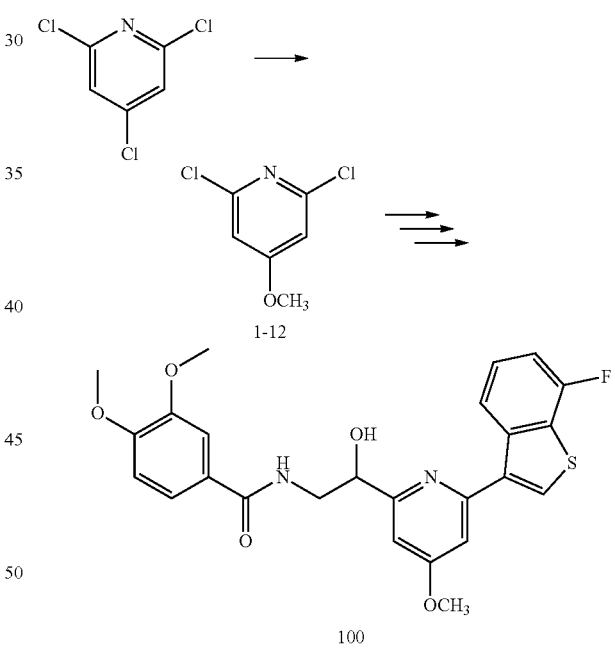

A solution of 2,4,6-trichloropyridine (6.5 g, 36 mmol) in anhydrous methanol (20 mL) was added MeONa (2.9 g, 54 mmol) at 0° C. The reaction mixture was stirred at r.t. for 12 h. The reaction was quenched with dry ice, and the mixture was filtered. The solution was concentrated under reduced pressure, and the residue was dissolved in EA. The mixture was washed with water, and the organic layers were dried over NaSO$_4$. The solvent was concentrated to give 1-12 (4.2 g, 67%).

Compound 100 was prepared using 1-12 and 4-(cyclopropylmethoxy)-3-methoxybenzoic acid, and by following a synthetic route, which closely follows that described for the preparation of 1. 100: +ESI-MS: m/z 483.1 [M+H]+.

Example 3

Preparation of Compound 101

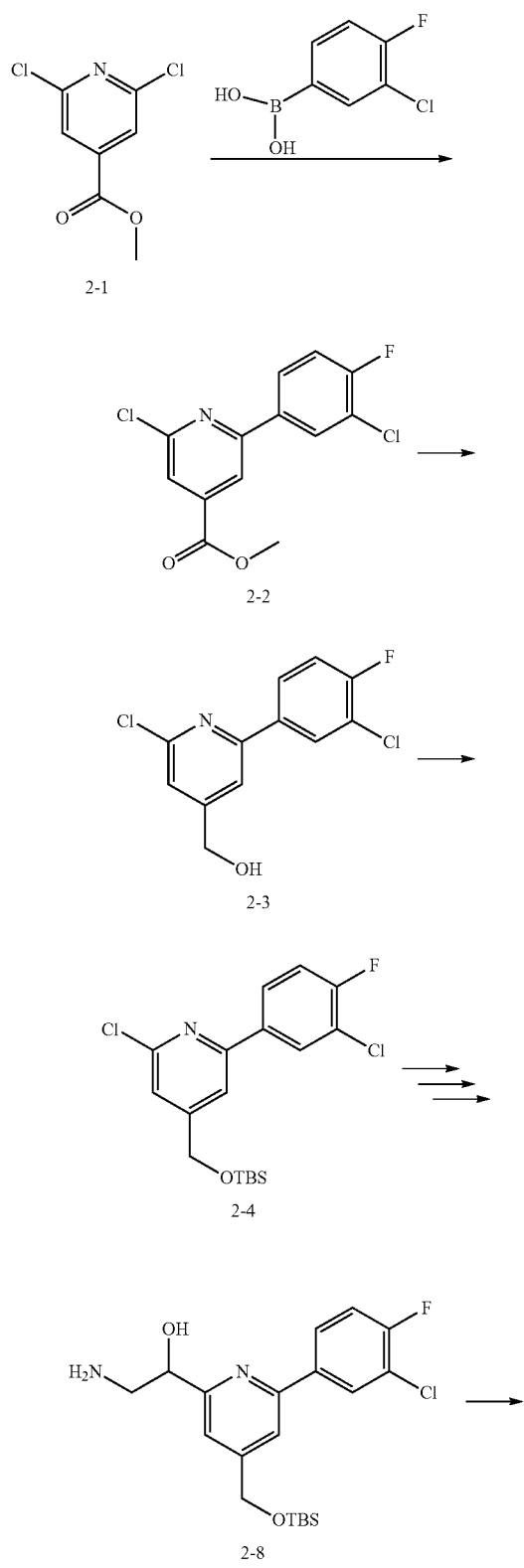

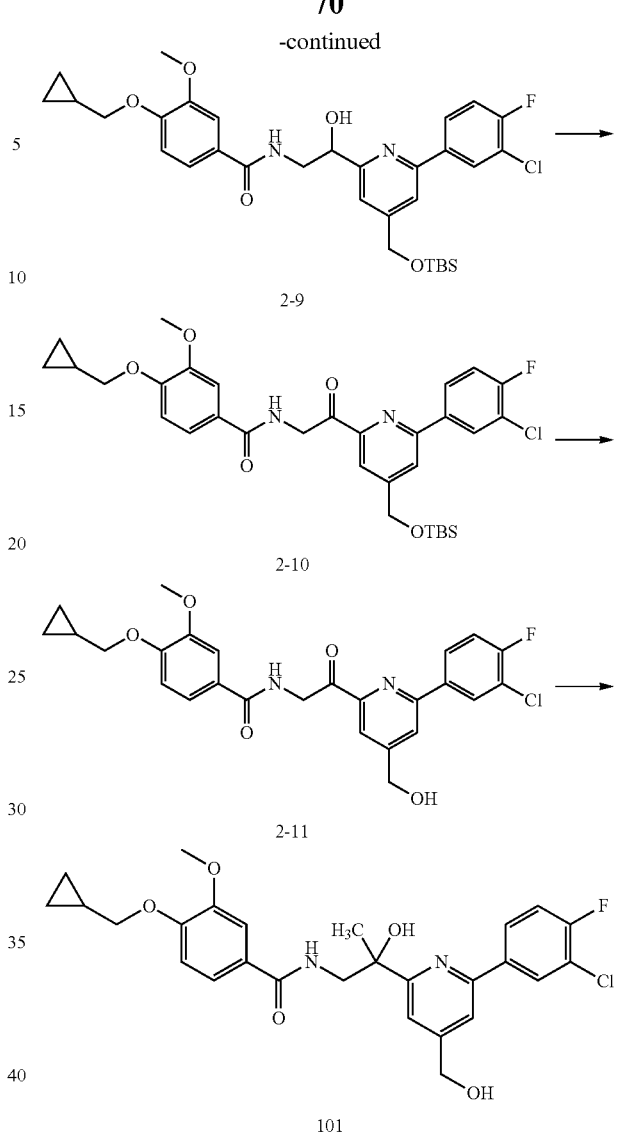

To a solution of 2-1 (3 g, 14 mmol) and the boronic acid (2.5 g, 14 mmol) in dioxane/H$_2$O (30 mL/5 mL) was added Pd(dppf)Cl$_2$ (1.02 g, 1.4 mmol) and Cs$_2$CO$_3$ (6.8 g, 21 mmol). The system was degassed and then charged with nitrogen for 3 times. The mixture was stirred under nitrogen at 80° C. in an oil bath for 2 h. The solution was cooled to r.t., diluted with EA and separated from the water layer. The EA solution was washed by brine, dried over Na$_2$SO$_4$ and concentrated. The residue was purified on a silica gel column to give 2-2 (2 g, 47.9%).

To a solution of 2-2 (2 g, 6.7 mmol) in MeOH/DCM (20 mL/20 mL) was added NaBH$_4$ (510 mg, 13.4 mmol) slowly at 0° C. The solution was stirred for 10 mins and heated to 50° C. and stirred for 2 h. The solution was quenched with H$_2$O and extracted with EA. The solution was concentrated to give crude 2-3 (1.81 g, 100%).

To a solution of 2-3 (1.81 g, 6.7 mmol) in DMF was added imidazole (1.36 g, 1.34 mmol) at r.t. TBSCl (201 mg, 1.34 mmol) was added. The solution was stirred for 18 h. The solution was washed with water and extracted with EA. The organic phase was concentrated to give 2-4 (1.8 g, 70.0%). ESI-LCMS: m/z 385.9 [M+H]$^+$.

Compound 2-10 was prepared using 2-4 and 4-(cyclopropylmethoxy)-3-methoxybenzoic acid, and by following a synthetic route, which closely follows that described for the preparation of 1. $^1$H-NMR (400 MHz, CDCl$_3$), δ=8.00 (d, J=5.51 Hz, 1H) 7.87 (br. s., 1H) 7.78 (s, 1H) 7.81 (s, 1H) 7.34 (s, 1H) 7.26 (d, J=8.38 Hz, 1H) 7.14 (t, J=8.71 Hz, 1H) 6.92 (br, 1H) 6.74 (d, J=8.38 Hz, 1H) 5.13 (d, J=4.41 Hz, 2H) 4.72 (s, 2H) 3.71-3.85 (m, 5H) 1.09 (br, 1H), 0.83 (s, 10H) 0.46-0.56 (m, 2H), 0.19-0.30 (m, 2H), 0.00 (s, 7H).

To a solution of 2-10 (100 mg, 0.163 mmol) in dioxane (2 mL) was added concentrated HCl (2 mL) at r.t. and the mixture was stirred for 30 mins. The solution was quenched by aqueous NaHCO$_3$ solution and extracted by EA. The combined organic layers were washed by brine, dried over Na$_2$SO$_4$ and concentrated. The residue was purified by prep-HPLC(FA) to give 2-11 (30 mg, 37.0%) as a white solid. +ESI-MS: m/z 498.9 [M+H]$^+$.

The solution of 2-11 (100 mg, 0.20 mmol) in THF (2 mL) was added MeMgBr (1 mL, 3 mmol) at r.t. and the mixture was stirred for 2 h. The solution was quenched with H$_2$O and extracted with EA. The combined organic layers were washed by brine, dried over Na$_2$SO$_4$ and concentrated. The residue was purified by prep-TLC (PE:EA=1:1) to give 101 (20 mg, 19.4%) as a white solid. +ESI-MS: m/z 514.9 [M+H]$^+$.

Example 4

Preparation of Compound 102

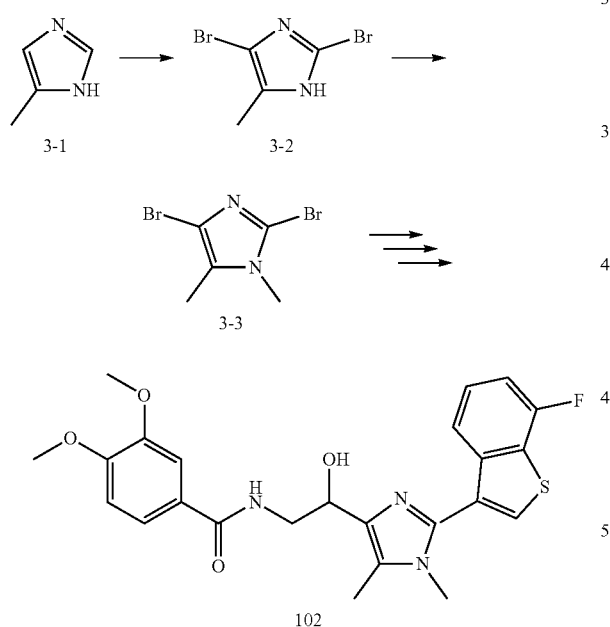

To a solution of 3-1 (3.4 g, 40 mmol) in THF (50 mL) at r.t. was added NBS (14 g, 80 mmol). The mixture was stirred for 1 h. The solvent were removed under reduced pressure. Purification by column chromatography on silica gel (PE: EA=2:1) provided 3-2 as white solid (9.6 g, 99%). +ESI-MS: m/z 239.0 [M+H]+

To a solution of 3-2 (9.6 g, 40 mmol) and K$_2$CO$_3$ (5.4 g, 40 mmol) in DMF (50 mL) at 40° C. was added CH$_3$I (6 g, 40 mmol). The mixture was stirred for 2 h at r.t. The solution was poured into water and extracted with EtOAc. The organic phase was dried over anhydrous Na$_2$SO$_4$ and concentrated under reduced pressure. The residue was purified by column chromatography on silica gel (PE:EA=20:1) to provide 3-3 (3 g, 30%). +ESI-MS: m/z 253.0 [M+H]+.

Compound 102 was obtained by closely following the procedure for obtaining 1 using 3-3 and 3,4-dimethoxybenzoic acid. Compound 102 was obtained as a white solid. +ESI-MS: m/z 470.1 [M+H]$^+$.

Example 5

Preparation of Compound 103

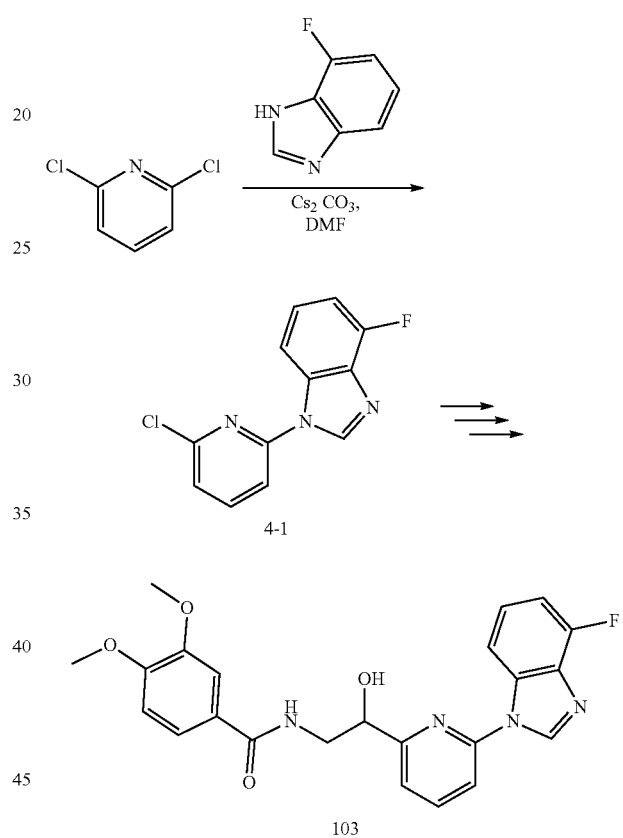

To a stirring mixture of 2,6-dichloropyridine (270 mg, 1.82 mmol) and 7-fluoro-1H-benzo[d]imidazole (248 mg, 1.82 mmol) in DMF (3 mL) was added Cs$_2$CO$_3$ (709 mg, 2.2 mmol). The mixture was reacted at 120° C. for 2 h and then cooled to r.t. The mixture was diluted with EtOAc and washed with a sat. NaCl solution. The layers were separated. The aqueous layer was extracted with EtOAc (2×25 mL). The combined organic layers were dried over MgSO$_4$, filtered, and concentrated under reduced pressure. Chromatography of the residue afforded 4-1 (300 mg) as a white solid. LCMS: m/z 248.1 [M+H]$^+$.

Compound 103 was obtained as a yellow oil (100 mg) by closely following the procedure for obtaining 1 using 4-1 and 3,4-dimethoxybenzoic acid. LCMS: m/z 437.25 [M+H]$^+$.

Example 6

Preparation of Compound 104

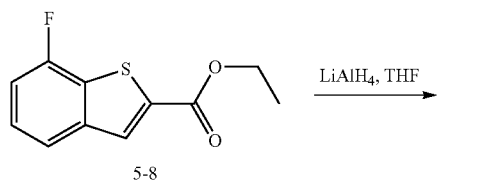
5-8

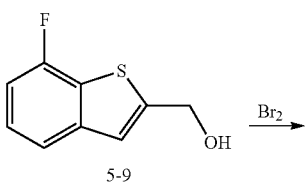
5-9

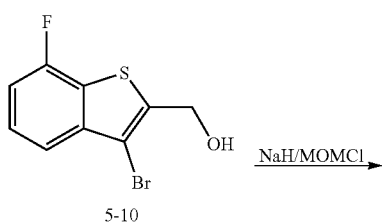
5-10

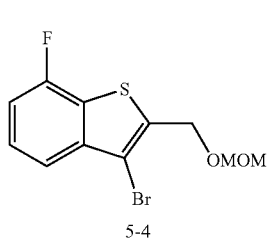
5-4

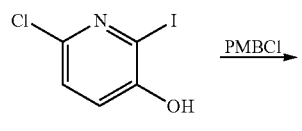
5-1

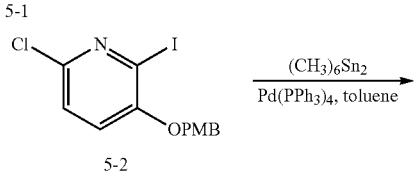
5-2

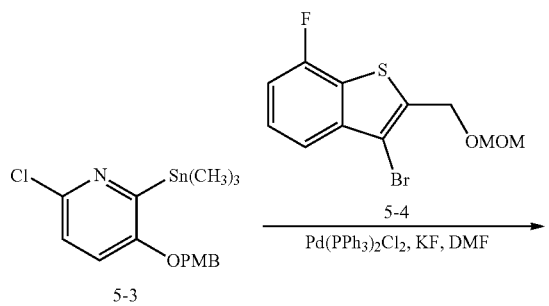
5-3

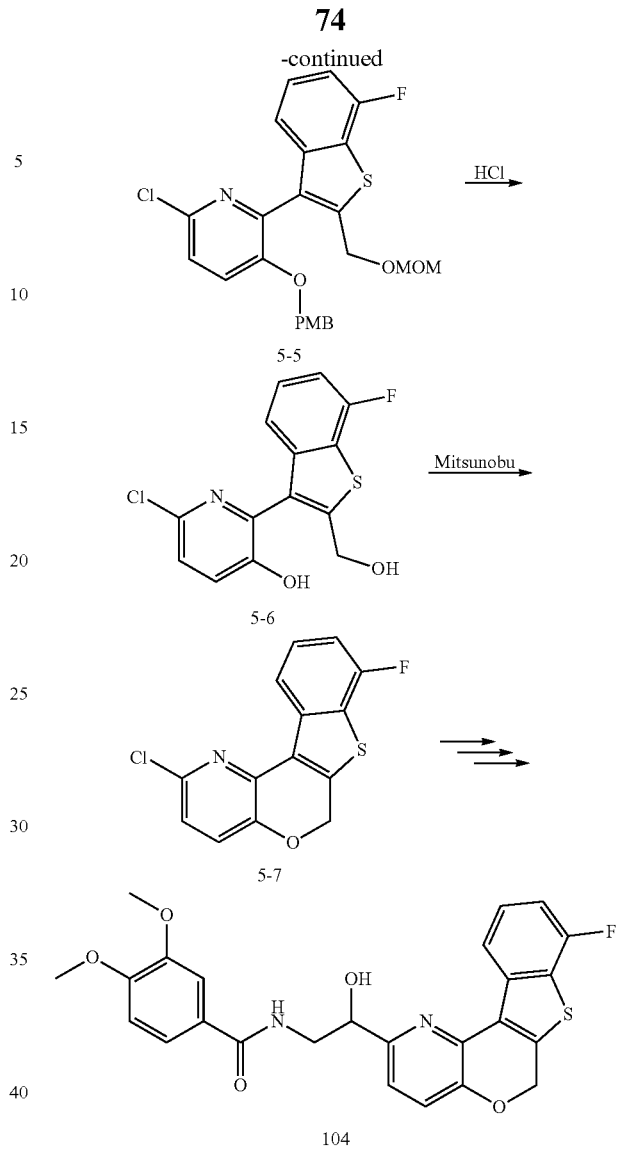

To a solution of 5-1 (10 g, 44.0 mmol) in DMF (150 mL) was added NaH (7.0 g, 0.177 mol), and the mixture was stirred at 0° C. for 30 mins. The solution was treated with PMBCl (11.67 g, 0.0748 mol), and stirred at r.t. overnight. After complete conversion, the reaction was quenched with MeOH and H$_2$O, and extracted with EA. The organic phase was concentrated to give 5-2 (11 g, 87.2%). +ESI-MS: m/z 375.9 [M+H]$^+$.

To a solution of 5-2 (36 g, 96 mmol) in toluene (400 mL) was added (CH$_3$)$_6$Sn$_2$ (47.0 g, 144.0 mmol). The mixture was bubbled with nitrogen gas and stirred at 100° C. for 3 h. The mixture was concentrated in vacuum to give the crude product, which was purified by column chromatography to give 5-3 (22 g). +ESI-MS: m/z 414.0 [M+H]$^+$.

To a solution of 5-8 (30 g, 134 mmol) in anhydrous THF (500 mL) was added LiAlH$_4$ (7.6 g, 200 mmol) in portions at 0° C., and the mixture was stirred at r.t. for 2 h (monitored by TLC). The reaction was quenched with a sat. NH$_4$Cl solution, and extracted with EA to give the crude product, which was purified by column chromatography to give 5-9 (22 g). +ESI-MS: m/z 183.0 [M+H]$^+$.

To a solution of 5-9 (22 g, 121 mmol) in THF (400 mL) was added NBS (25.7 g, 145 mmol), and the mixture was stirred at r.t. overnight (monitored by TLC). The reaction was quenched with a sat. Na₂S₂O₃ solution, and extracted with EA to give the crude product, which was purified by column chromatography to give 5-10 (23 g). +ESI-MS: m/z 460.9 [M+H]⁺.

To a solution of 5-10 (22 g, 84.6 mmol) in anhydrous THF (200 mL) was added NaH (8.12 g, 33.85 mmol) in portions at 0° C., and the mixture was stirred at 0° C. for 30 mins. MOMCl (27.08 g, 338.5 mmol) was added, and the mixture was stirred at r.t. for 4 h. The reaction was quenched with water and extracted with EA. The organic layer was dried over sodium sulfate, and concentrated in vacuum to give the crude product, which was purified by column chromatography to give 5-4 (21 g). +ESI-MS: m/z 304.9 [M+H]⁺.

To a solution of 5-3 (6.36 g, 15.4 mmol) in DMF (50 mL) were added 5-4 (4.7 g, 15.4 mmol), KF (3.7 g, 61.6 mmol) and Pd(PPh₃)₂Cl₂ (324 mg, 0.46 mmol). The mixture was bubbled with nitrogen gas and stirred at 100° C. overnight. The mixture was diluted with water and extracted with EA. The organic layer was dried over sodium sulfate, and concentrated in vacuum to give the crude product, which was purified by column chromatography to give 5-5 (3.8 g). +ESI-MS: m/z 474.1 [M+H]⁺.

To a solution of 5-5 (4.5 g, 9.51 mmol) in THF (30 mL) was added 10% HCl (30 mL), and stirred 110° C. overnight. The mixture was cooled to r.t., and the pH was adjusted to 7.0 by adding a sat. NaHCO₃ solution. The mixture was extracted with EA. The organic layer was dried over sodium sulfate, and concentrated in vacuum to give 5-6 (2.0 g), which was used in the next step without purification. +ESI-MS: m/z 310.0 [M+H]⁺.

To a solution of 5-6 (1.3 g, 4.2 mmol) in THF (100 mL) was added PPh₃ (1.32 g, 5.05 mmol), and the mixture was stirred at r.t. for 10 mins. DIAD (1.01 g, 5.05 mmol) was added in portions, and the mixture stirred at refluxed for 4 h. The mixture was concentrated in vacuum to give the crude product, which was purified by column chromatography to give 5-7 (0.7 g). +ESI-MS: m/z 292.0 [M+H]⁺.

Compound 104 was obtained as a white solid (50 mg) by closely following the procedure for obtaining 1 by using 5-7 and 3,4-dimethoxybenzoic acid. +ESI-MS: m/z 481.1 [M+H]⁺.

Example 7

Preparation of Compound 105

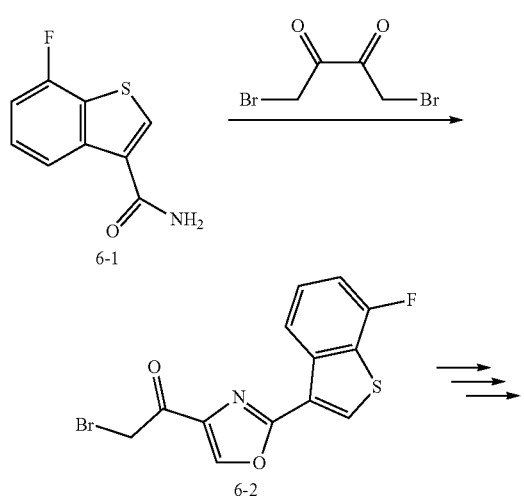

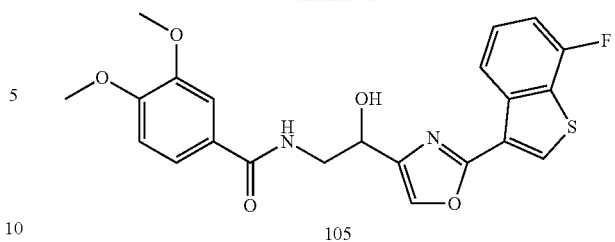

105

To a solution of 6-1 (196 mg, 1.0 mmol), 1,4-dibromobutane-2,3-dione (241 mg, 1.0 mmol) in DCM (3 mL) was added AgOTf (255 mg, 1.0 mmol). The reaction was carried out at 80° C. under microwave irradiation for 15 mins. The mixture was concentrated at low pressure. The residue was purified by silica gel column (PE/EA) to 6-2 (270 mg, 80%). +ESI-MS: m/z 339.9 [M+H]⁺.

Compound 105 was obtained (100 mg, 48%) by closely following the procedure for obtaining 1 using 6-2 and 3,4-dimethoxybenzoic acid. +ESI-MS: m/z 442.9 [M+H]⁺.

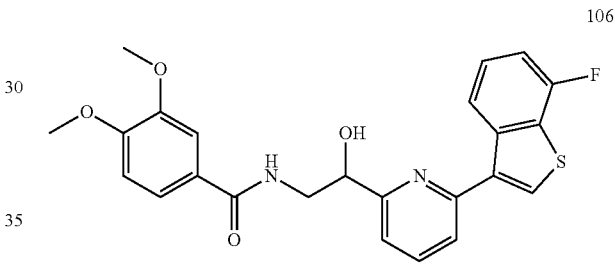

106

Compound 106 was prepared using 2,6-dibromopyridine, 2-(7-fluorobenzo[b]thiophen-3-yl)-4,4,5,5-tetramethyl-1,3, 2-dioxaborolane and 3,4-dimethoxybenzoic acid, and by closely following a synthetic route, which closely follows that described for the preparation of 1. +ESI-MS: m/z 452.9 [M+H]⁺.

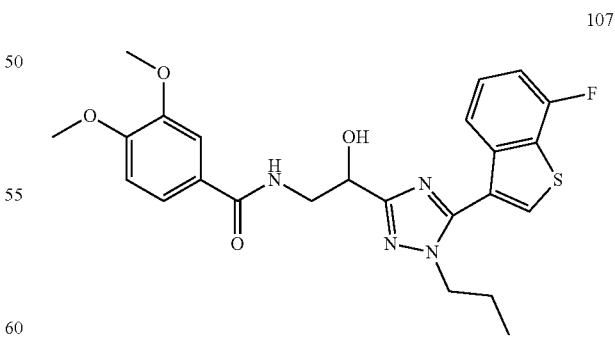

107

Compound 107 was prepared using 3,4-dimethoxybenzoic acid and 3-bromo-5-(7-fluorobenzo[b]thiophen-3-yl)-1-propyl-1H-1,2,4-triazole, and by closely following a synthetic route, which closely follows that described for the preparation of 1. +ESI-MS: m/z 485.0 [M+H]⁺.

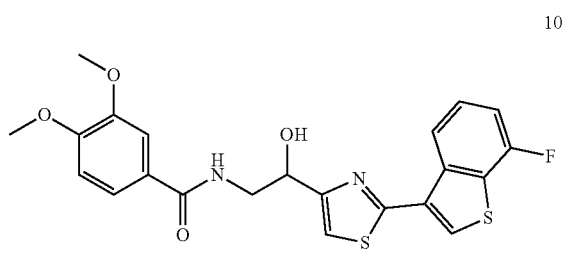

108

Compound 108 was prepared using 2,4-dibromothiazole, 2-(7-fluorobenzo[b]thiophen-3-yl)-4,4,5,5-tetramethyl-1,3,2-dioxaborolane and 3,4-dimethoxybenzoic acid, and by closely following a synthetic route, which closely follows that described for the preparation of 1. +ESI-LCMS: m/z 459.0 [M+H]+.

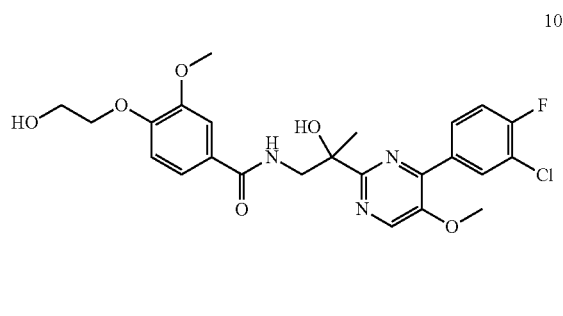

109

Compound 109 was prepared using 2,4-dichloro-5-methoxypyrimidine, (3-chloro-4-fluorophenyl) boronic acid and 4-(2-hydroxyethoxy)-3-methoxybenzoic acid, and by closely following a synthetic route, which closely follows that described for preparation of 1. +ESI-MS: m/z 506.1 [M+H]+.

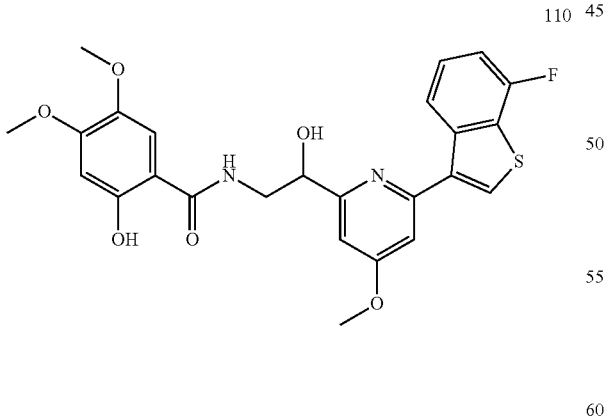

110

Compound 110 was prepared using 2-hydroxy-4,5-dimethoxybenzoic acid and 2-amino-1-(6-(7-fluorobenzo[b]thiophen-3-yl)-4-methoxypyridin-2-yl) ethanol, and by following a synthetic route, which closely follows that described for preparation of 1. Compound 110 was obtained as a white solid. +ESI-MS: m/z 498.9[M+H]+.

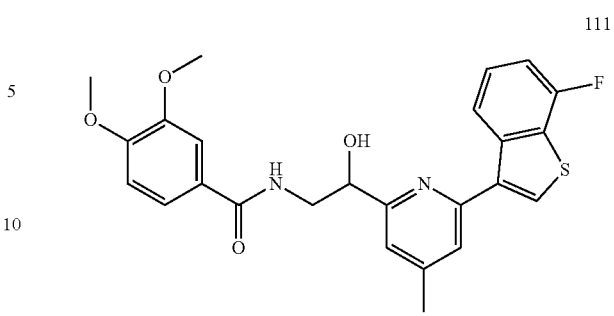

111

Compound 111 was obtained by closely following the procedure for obtaining 1 by using 2,4-dibromothiazole, 2-(7-fluorobenzo[b]thiophen-3-yl)-4,4,5,5-tetramethyl-1,3,2-dioxaborolane and 3,4-dimethoxybenzoic acid. Compound 111 was obtained as a white solid. +ESI-LCMS: m/z 466.9 [M+H]+.

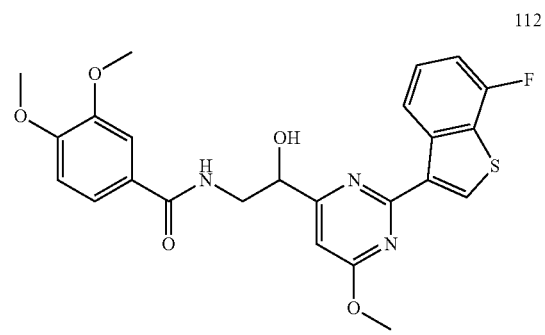 [SMILES: COc1cc(C(O)CNC(=O)c2ccc(OC)c(OC)c2)nc(-c2csc3c(F)cccc23)n1]

112

Compound 112 was prepared using 4-chloro-2-iodo-6-methoxypyrimidine, 2-(7-fluorobenzo[b]thiophen-3-yl)-4,4,5,5-tetramethyl-1,3,2-dioxaborolane and 3,4-dimethoxybenzoic acid, and by following a synthetic route, which closely follows that described for preparation of 1. +ESI-MS: m/z 484.1 [M+H]+.

Example 8

Preparation of Compound 113

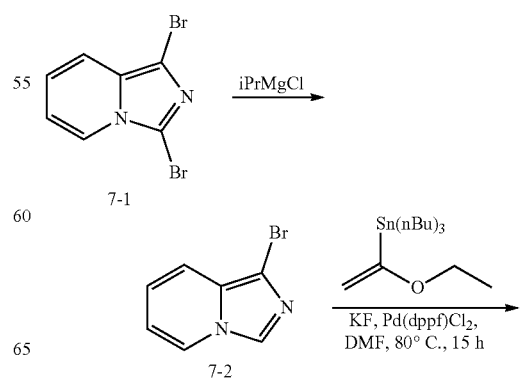

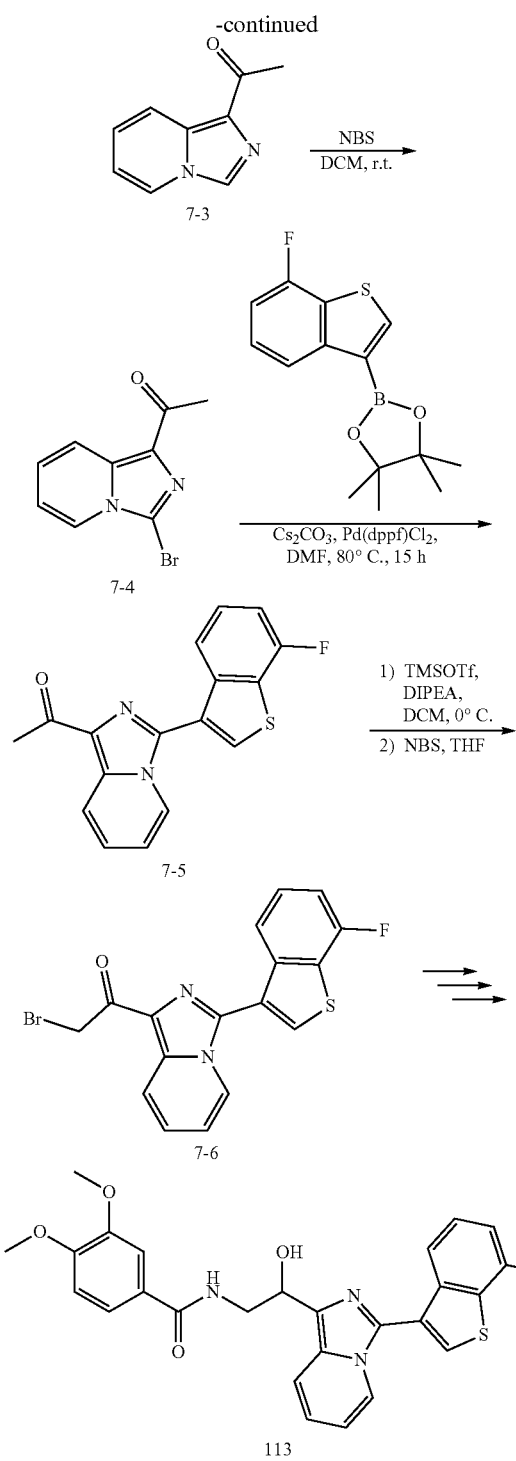

bath for 15 h. The solution was cooled to r.t. The mixture was diluted with EA. The EA solution was washed by brine, dried over $Na_2SO_4$ and concentrated to give crude 7-3 (360 mg, 44.2%)

To a solution of 7-3 (360 mg, 2.25 mmol) in DCM (5 mL) was added NBS (480 mg, 2.7 mmol). The mixture was stirred at r.t. for 30 mins with TLC monitoring. The solution was quenched by aqueous $Na_2S_2O_3$ solution and extracted by EA. The combined organic layers were dried over $Na_2SO_4$ and concentrated. The residue was purified by prep-HPLC(FA) to give 7-4 (250 mg, 46.2%)

To a solution of 7-4 (480 mg, 2 mmol) and the dioxaborolane reagent (558 mg, 2 mmol) in dioxane/$H_2O$ (10 mL/2 mL) were added Pd(dppf)$Cl_2$ (146 mg, 0.2 mmol) and $Cs_2CO_3$ (975 mg, 3 mmol). The system was degassed and then charged with nitrogen for 3 times. The mixture was stirred under nitrogen at 80° C. in an oil bath for 15 h. The solution was cooled to r.t., diluted with EA and separated from the water layer. The EA solution was washed by brine, dried over $Na_2SO_4$ and concentrated. The residue was purified on a silica gel column to give 7-5 (400 mg, 64.5%).

To a solution of 7-5 (550 mg, 1.77 mmol) in DCM (5 mL) was added DIPEA (685 mg, 5.31 mmol) and TMSOTf (589 mg, 2.65 mmol) at 0° C. The solution was stirred for 2 h at r.t. The solution was concentrated and the residue was dissolved in THF (10 mL) and $H_2O$ (1 mL). NBS (471 mg, 2.65 mmol) was added at r.t., and stirred for 1.5 h. The solution was evaporated at low pressure. The residue was purified by chromatography (PE:EA=3:1) to give 7-6 (600 mg, 86.9%).

Compound 113 was prepared from 7-6 and 3,4-dimethoxybenzoic acid by following a synthetic route, which closely follows that described for the preparation of 1. Compound 113 was obtained as white solids. +ESI-MS: m/z 492.0 $[M+H]^+$.

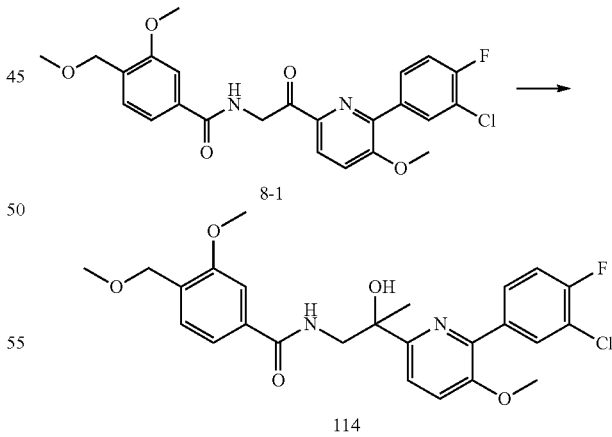

To a solution of 7-1 (7.5 g, 27.17 mmol) in THF (100 mL) was added slowly i-PrMgCl (25 mL, 2M in THF) at r.t., and the mixture stirred for 10 mins. The solution was quenched with MeOH and diluted with DCM (20 mL). The solution was washed by brine, dried over $Na_2SO_4$ and concentrated to give crude 7-2 (5 g, 94.3%).

To a solution of 7-2 (1 g, 5.1 mmol), the tin reagent (3.71 g, 10.2 mmol) and KF (1.18 g, 20.4 mmol) in DMF (10 mL) was added Pd(dppf)$Cl_2$ (372 mg, 0.51 mmol). The system was degassed and then charged with nitrogen for 3 times. The mixture was stirred under nitrogen at 80° C. in an oil To a solution of 8-1 (90 mg, 0.19 mmol) in THF (5 mL) was added $CH_3MgBr$ (3 M, 0.64 M) at 0° C., and stirred at r.t. overnight. The reaction was quenched with $NH_4Cl$ solution and extracted with EA. The organic layer was dried over sodium sulfate, then concentrated in vacuum to give the crude product, which was purified by prep-HPLC to give 114 (18 mg) as a white solid. +ESI-MS: m/z 498.1 $[M+H]^+$.

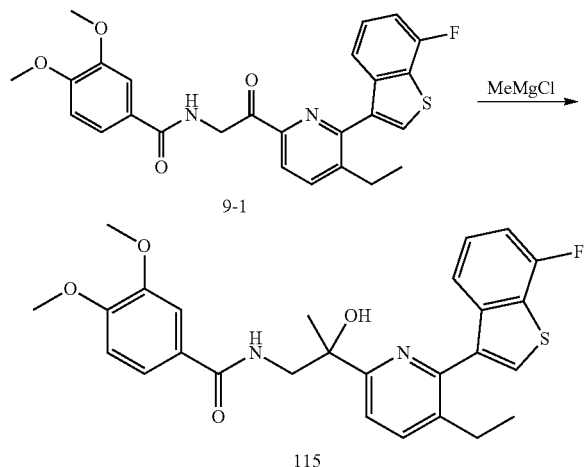

9-1

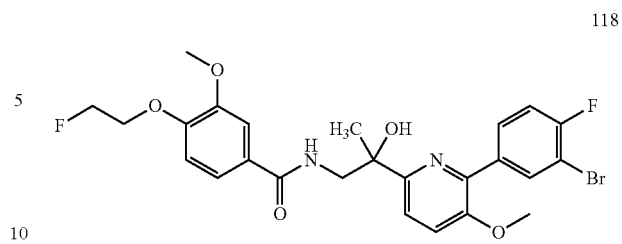

118

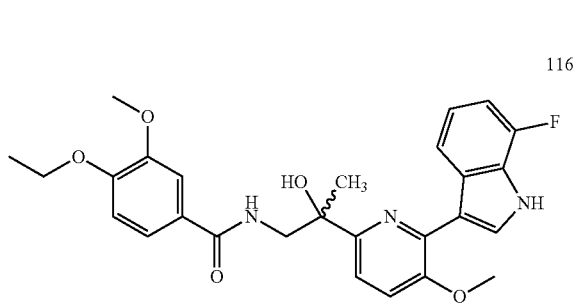 [SMILES: CCOc1ccc(C(=O)NCC(C)(O)c2ccc(OC)c(-c3c[nH]c4c(F)cccc34)n2)cc1OC]

115

Compound 115 (57 mg, 60%) was obtained by closely following the procedure for obtaining 114 by using 9-1 (120 mg, 0.2 mmol). Compound 115 was obtained as a white solid. +ESI-MS: m/z 494.9 [M+H]+.

Compound 118 was prepared using 1-amino-2-(6-(3-bromo-4-fluorophenyl)-5-methoxypyridin-2-yl)propan-2-ol and 4-(2-fluoroethoxy)-3-methoxybenzoic acid and 4-(2-fluoroethoxy)-3-methoxybenzoic acid, and by following a synthetic route, which closely follows that described for preparation of 100 and 114. +ESI-MS: m/z 551.9 [M+H]+.

Individual enantiomers of 118 (118a and 118b) were obtained by SFC separation of a racemic mixture of 118. +ESI-MS: m/z 551.9 [M+H]+.

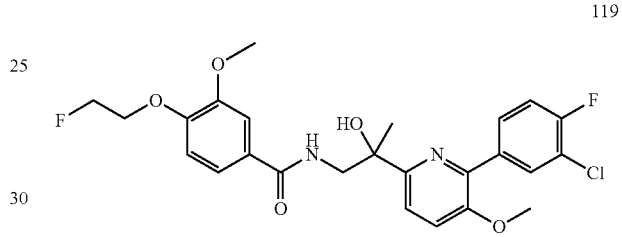

119

116

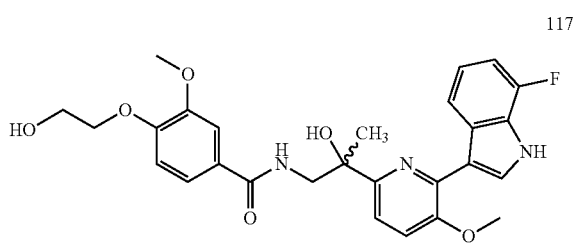 [SMILES: COc1cc(C(=O)NCC(C)(O)c2ccc(OC)c(-c3c[nH]c4c(F)cccc34)n2)ccc1OCCO]

Compound 116 was obtained by closely following the procedures for obtaining 100 and 114 using 7-fluoro-3-(4,4,5,5-tetramethyl-1,3,2-dioxaborolan-2-yl)-1-((2-(trimethylsilyl)ethoxy)methyl)-1H-indole and 4-ethoxy-3-methoxybenzoic acid. Compound 116 was obtained as a white solid. +ESI-MS: m/z 494.2 [M+H]+.

Individual enantiomers of 116 (116a and 116b) were obtained by SFC separation of a racemic mixture of 116. +ESI-MS: m/z 494.2 [M+H]+.

To a stirring mixture of N-(2-(6-(3-chloro-4-fluorophenyl)-5-methoxypyridin-2-yl)-2-oxoethyl)-4-(2-fluoroethoxy)-3-methoxybenzamide (50 mg, 0.1 mmol) in THF at r.t. under argon was added a solution of MeMgCl in THF (0.5 mL, 1.0 mmol). The mixture was reacted at r.t. for 2 h. The mixture was diluted with EtOAc and slowly quenched with a sat. NH4Cl solution. The mixture was stirred at r.t. for 10 mins and then the layers were separated. The aqueous layer was extracted with EtOAc. The organic layers were dried (Na2SO4), filtered and concentrated under reduced pressure. The crude mixture was purified via silica gel column and further purified via prep-HPLC to afford 119 as a white solid. LCMS: m/z 507.1 [M+H]+.

117

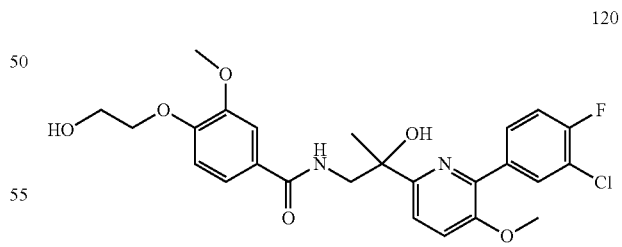

120

Compound 117 was obtained by closely following the procedures for obtaining 100 and 114 using 7-fluoro-3-(4,4,5,5-tetramethyl-1,3,2-dioxaborolan-2-yl)-1-((2-(trimethylsilyl)ethoxy)methyl)-1H-indole and 4-(2-hydroxyethoxy)-3-methoxybenzoic acid. Compound 117 was obtained as a white solid. +ESI-MS: m/z 510.2 [M+H]+.

Individual enantiomers of 117 (117a and 117b) were obtained by SFC separation of a racemic mixture of 117. +ESI-MS: m/z 510.1 [M+H]+.

Compound 120 was prepared using N-(2-(6-(3-chloro-4-fluorophenyl)-5-methoxypyridin-2-yl)-2-oxoethyl)-4-(2-hydroxyethoxy)-3-methoxybenzamide with MeMgBr in THF, and by closely following a synthetic route, which closely follows that described for preparation of 119. LCMS: m/z 505.15 [M+H]+.

Individual enantiomers of 120 (120a and 120b) were obtained by SFC separation of a racemic mixture of 120. +ESI-MS: m/z 505.1 [M+H]+.

121

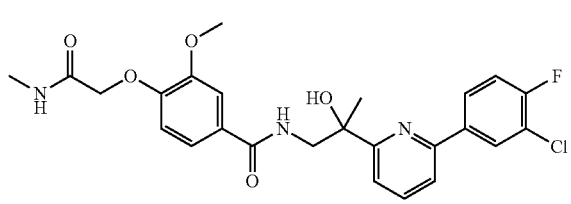

Compound 121 was prepared using N-(2-(6-(3-chloro-4-fluorophenyl)pyridin-2-yl)-2-oxoethyl)-3-methoxy-4-(2-(methylamino)-2-oxoethoxy)benzamide with MeMgBr in THF, and by following a synthetic route, which closely follows that described for preparation of 119. LCMS: m/z 502.05 [M+H]+.

122

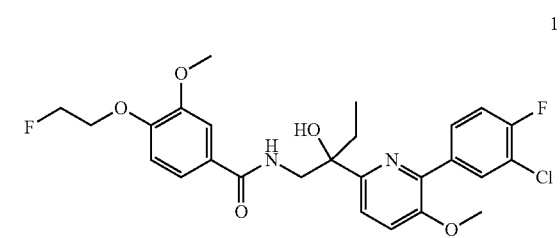

123

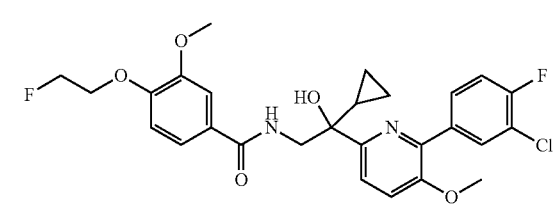

124

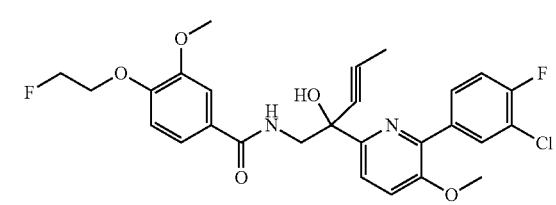

125

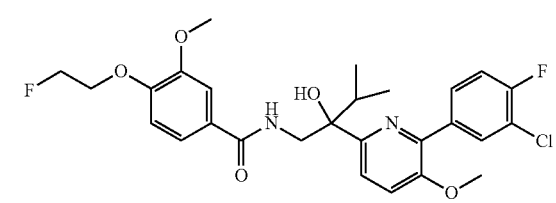

126

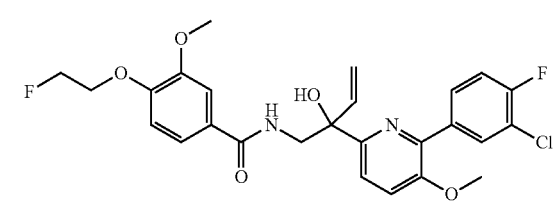

127

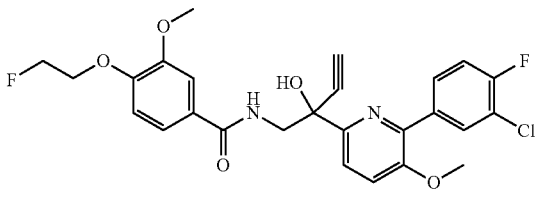

Compounds 122, 123, 124, 125, 126 and 127 were prepared using N-(2-(6-(3-chloro-4-fluorophenyl)-5-methoxypyridin-2-yl)-2-oxoethyl)-4-(2-fluoroethoxy)-3-methoxybenzamide with different Grignard reagents in THF, and by following a synthetic route, which closely follows that described for preparation of 119. 122: LCMS: m/z 521.15 [M+H]+. 123: LCMS: m/z 533.15 [M+H]+. 124: LCMS: m/z 531.10 [M+H]+. 125: LCMS: m/z 535.15 [M+H]+. 126: LCMS: m/z 519.15 [M+H]+. 127: LCMS: m/z 517.05 [M+H]+.

Individual enantiomers of 122 (122a and 122b) were obtained by SFC separation of a racemic mixture of 122.

128

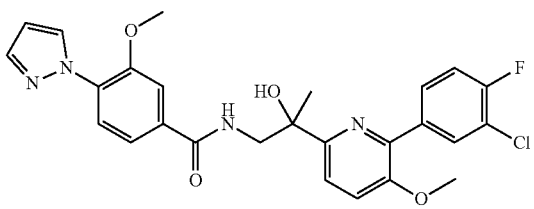

Compound 128 was prepared using N-(2-(6-(3-chloro-4-fluorophenyl)-5-methoxypyridin-2-yl)-2-oxoethyl)-3-methoxy-4-(1H-pyrazol-1-yl)benzamide with MeMgBr in THF, and by following a synthetic route, which closely follows that described for preparation of 119. LCMS: m/z 511.10 [M+H]+.

Example 9

Preparation of Compound 129

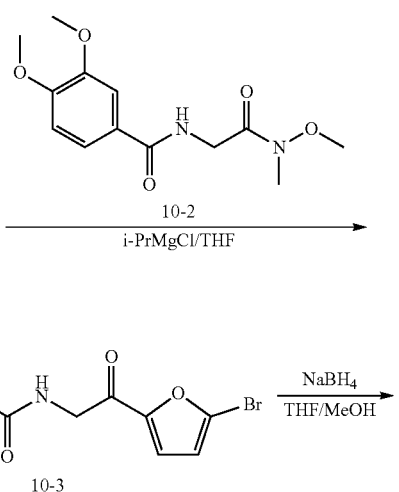

-continued

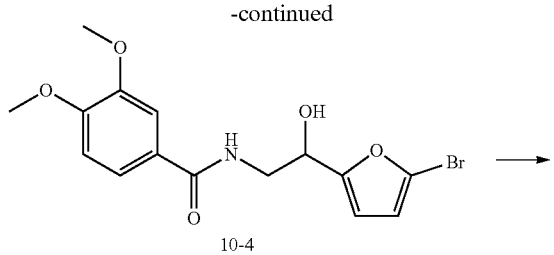

10-4

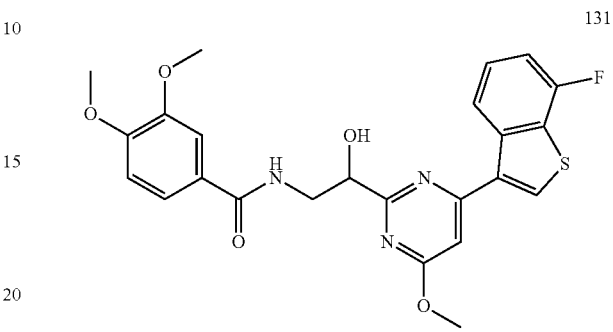

129

A 50 mL flask with a magnetic stirring bar was charged with 10-1 (223 mg, 1.0 mmol), Weinreb amide (10-2, 282 mg, 1.0 mmol), and THF (10 mL) under N₂ atmosphere. The solution was treated with i-PrMgCl (1.3 M, 2.0 eq.) dropwise at r.t. The mixture was stirred for 1 h at r.t. Water (50 mL) and EA (50 mL) were added. The organic layer was separated and the aqueous phase extracted with EA. The combined organic layers were dried with MgSO₄ and the volatiles were removed under reduced pressure. The residue was purified by column chromatography on silica gel (PE) to provide 10-3 as a solid (332 mg, 90%). +ESI-MS: m/z 367.0, 369.0 [M+H]⁺.

To a stirred solution of 10-3 (368 mg, 1.0 mmol) in MeOH/THF (5 mL/5 mL) was added NaBH₄ (380 mg, 10 mmol) in portions until the starting materials was consumed. The volatiles were removed under reduced pressure. The residue was purified by column chromatography on silica gel (PE:EtOAc=2:1) to give 10-4 as a colorless oil (370 mg, 100%). +ESI-MS: m/z 369.0, 371.0 [M+H]⁺.

A 50 mL flask with a magnetic stirring bar was charged with 10-4 (165 mg, 0.5 mmol), 2-(7-fluorobenzo[b]thiophen-3-yl)-dioxaborolane (278 mg, 1.0 mmol), Pd(dppf)Cl₂ (8 mg, 1 mol %), KF (180 mg, 3.0 mmol), and dioxane/H₂O (20 mL/5 mL) under N₂ atmosphere. The mixture was stirred for 10 h at 100° C. Water (50 mL) and EA (50 mL) were added. The organic layer was separated and the aqueous phase extracted with EA. The combined organic phases were dried with MgSO₄ and the volatiles were removed under reduced pressure. The residue was purified by column chromatography on silica gel to provide 129 as a white solid (176 mg, 80%). +ESI-MS: m/z 463.9 [M+Na]⁺.

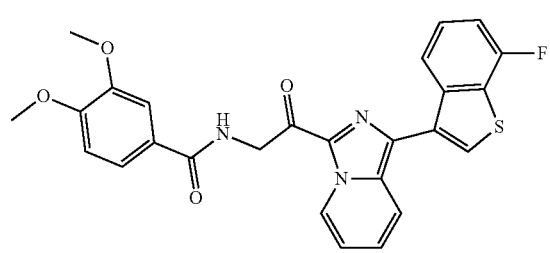

130

Compound 130 was obtained following the procedure for obtaining 129 by using 10-2,1,3-dibromoimidazo[1,5-a]pyridine and 2-(7-fluorobenzo[b]thiophen-3-yl)-4,4,5,5-tetramethyl-1,3,2-dioxaborolane as the starting materials, and then the oxidizing reagent DMP. Compound 130 was obtained as a white solid. +ESI-MS: m/z 489.8 [M+H]⁺.

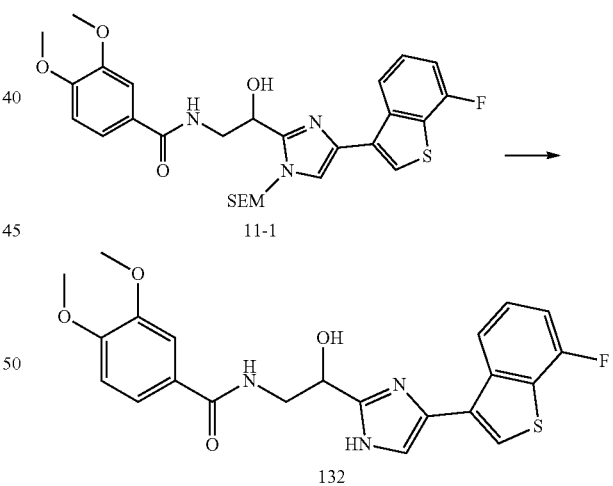

131

Compound 131 (176 mg, 80%) was obtained following the procedure for obtaining 129 by using 10-2,4-chloro-2-iodo-6-methoxypyrimidine and 2-(7-fluorobenzo[b]thiophen-3-yl)-4,4,5,5-tetramethyl-1,3,2-dioxaborolane. +ESI-MS: m/z 483.9 [M+H]⁺.

Example 10

Preparation of Compound 132

11-1

132

Compound 11-1 was prepared using 10-2,2,4,5-tribromo-1-((2-(trimethylsilyl)ethoxy)methyl)-1H-imidazole and 3,4-dimethoxy-N-(2-(methoxy(methyl)amino)-2-oxoethyl)benzamide, and by following a synthetic route, which closely follows that described for preparation of 129.

Compound 11-1 (402 mg, 0.62 mmol) was dissolved in TFA/DCM (1/1, 6 mL), and stirred at r.t. for 3 h. The solvent was removed and the residue was purified by column (DCM/MeOH=50:1 to 20:1) on silica gel to give 132 (149 mg, 72.4%). +ESI-MS: m/z 442.1 [M+H]⁺.

133

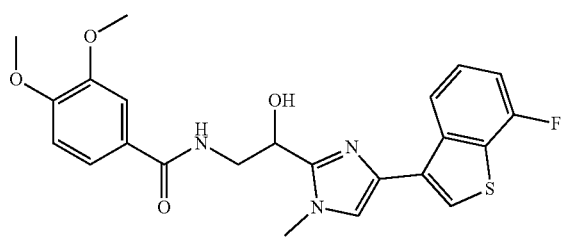

Compound 133 was prepared using 2,4,5-tribromo-1-methyl-1H-imidazole and 3,4-dimethoxy-N-(2-(methoxy(methyl)amino)-2-oxoethyl)benzamide, and by following a synthetic route, which closely follows that described for preparation of 129. +ESI-MS: m/z 455.9[M+H]⁺.

134

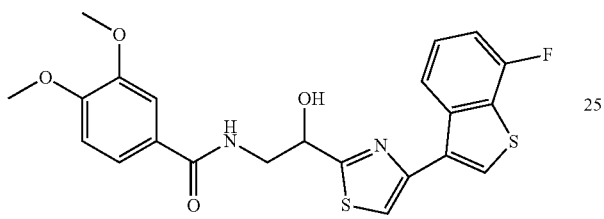

Compound 134 was prepared using 2,4-dibromothiazole and 3,4-dimethoxy-N-(2-(methoxy(methyl)amino)-2-oxoethyl)benzamide, and by following a synthetic route, which closely follows that described for preparation of 129. +ESI-MS: m/z 459.0 [M+H]⁺.

135

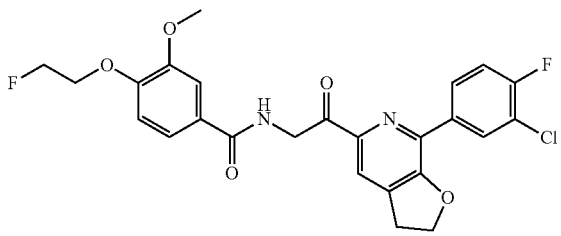

+ESI-MS: m/z 502.9 [M+]⁺.

Example 11

Preparation of Compounds 136 and 137

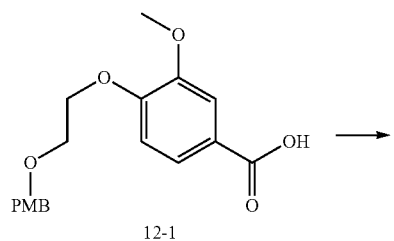

12-1

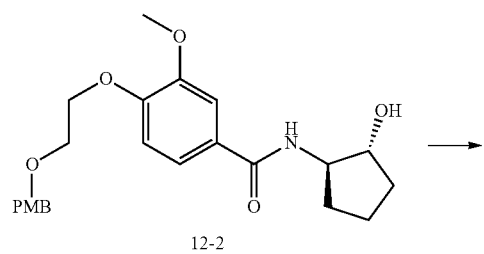

12-2

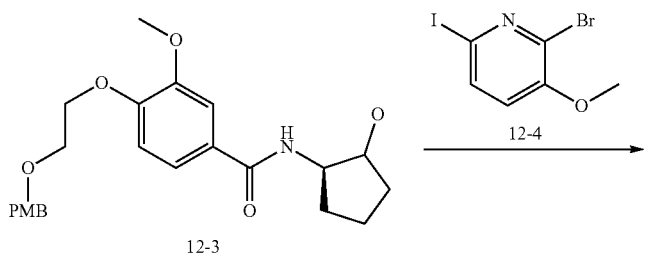

12-3

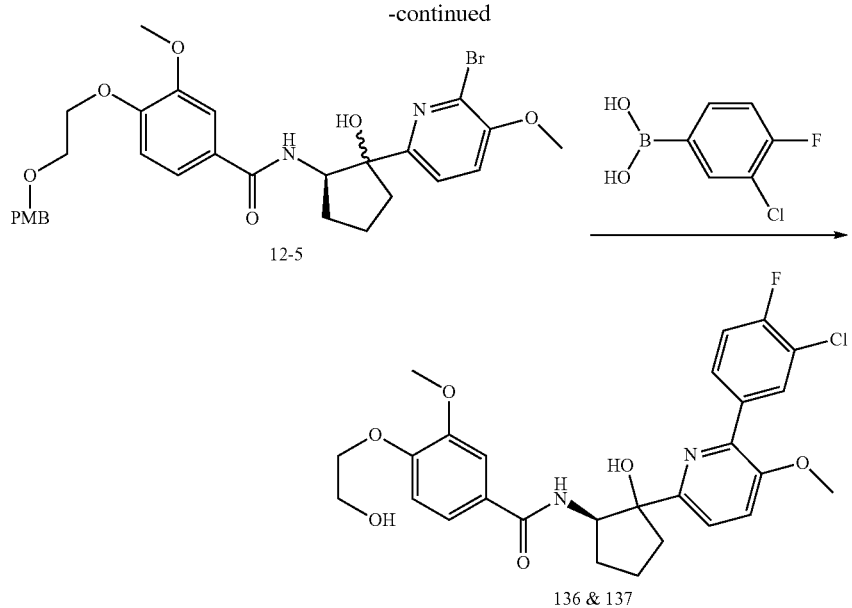

12-5

136 & 137

A mixture of 12-1 (3.26 g, 9.80 mmol), (1R,2R)-2-aminocyclopentan-1-ol hydrochloride (1.04 g, 7.55 mmol), EDC (2.17 g, 11.3 mmol), HOBT (1.53 g, 11.3 mmol) and TEA (2.60 mL, 18.9 mmol) in DCM (50 mL) was stirred at r.t. for 18 h. The mixture was washed twice with 1M aq. HCl solution, dried ($Na_2SO_4$), filtered and concentrated under reduced pressure. Chromatography of the residue (cyclohexane-EtOAc, 100:0 to 0:100) afforded 12-2 as a white solid (2.98 g, 95%). UPLC/MS (ES+): m/z 416.29 [M+H]+.

Dess-Martin periodinane (4.55 g, 10.7 mmol) was added to a solution of 12-2 (2.98 g, 7.16 mmol) in DCM (50 mL). The mixture was stirred at r.t. for 1.5 h. A 1:1 mixture of 10% aq. $Na_2S_2O_3$ solution and sat. aq. $NaHCO_3$ solution was added, and the mixture was stirred for 40 mins. The layers were separated and the organic portion was dried ($Na_2SO_4$), filtered and concentrated under reduced pressure. Chromatography of the residue (cyclohexane-EtOAc, 100:0 to 0:100) afforded 12-3 as a white solid (2.86 g, 96%). UPLC/MS (ES+): m/z 413.18 [M+H]+.

n-Butyllithium (1.6M solution in hexane, 1.50 mL, 2.42 mmol) was added dropwise to a stirred solution of 12-4 (760 mg, 2.42 mmol) in toluene (15 mL), which had been pre-cooled to −78° C. After 20 mins, a solution of 12-3 (500 mg, 1.21 mmol) in THF (10 mL) was added. The mixture was stirred at −78° C. for 30 mins. The mixture was allowed to warm to r.t. and then quenched with MeOH. The volatiles were removed under reduced pressure. The residue was partitioned between EtOAc and water. The layers were separated and the organic portion was dried with $Na_2SO_4$, filtered and concentrated under reduced pressure. The residue was purified by reverse phase chromathography (water: $CH_3CN$ 100:0 to 95:5) to afford 12-5 as a 2:1 diastereomeric mixture (470 mg, 65%). UPLC/MS (ES+): m/z 601.22 [M+H]+.

A mixture of (3-chloro-4-fluorophenyl)boronic acid (50.5 mg, 0.290 mmol), 12-5 (70 mg, 0.116 mmol), Pd(dppf)Cl$_2$ (4.3 mg, 0.006 mmol) and aq. Na$_2$CO3 (2M solution, 174 uL, 0.348 mmol) in DCE (2 mL) was degassed and heated to 85° C. After 1 h, water was added and the aqueous phase was extracted with DCM. The organic phase was dried with $Na_2SO_4$, filtered and concentrated under reduced pressure. The residue was dissolved in a 10:1 DCM-TFA solution (3 mL) and the mixture was stirred at r.t. for 30 mins. A 1M aq. NaOH solution was added and the mixture was stirred for further 30 mins. The phases were separated and the organic portion was dried with $Na_2SO_4$, filtered and concentrated under reduced pressure. Chromatography of the residue (DCM-MeOH, 98:2) afforded compounds 136 and 137. 136: UPLC/MS (ES+): m/z 531.26 [M+H]+. 137: UPLC/MS (ES+): m/z 531.26 [M+H]+.

Example 12

Preparation of Compound 138

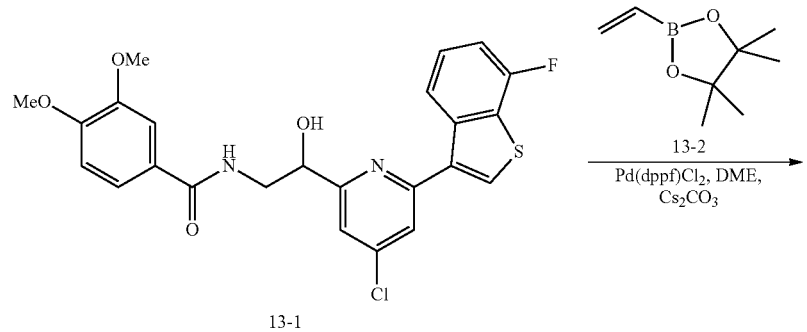

13-1

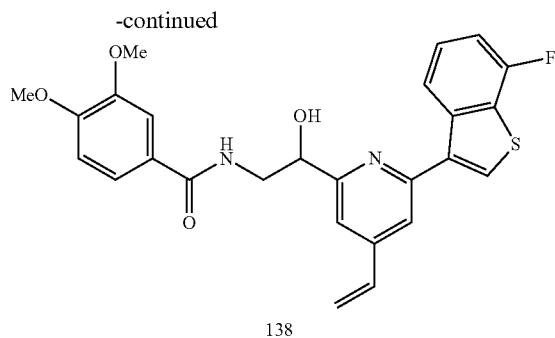

138

Compound 13-1 was obtained following the procedure for obtaining 1 by using 2,4,6-trichloropyridine, 2-(7-fluorobenzo[b]thiophen-3-yl)-4,4,5,5-tetramethyl-1,3,2-dioxaborolane and 3,4-dimethoxybenzoic acid.

To a solution of 13-1 (972 mg, 2 mmol) in DME (15 mL) was added 13-2 (616 mg, 4 mmol), Pd(dppf)Cl$_2$ (146 mg, 0.2 mmol) and Cs$_2$CO$_3$ (1.3 g, 4 mmol). The mixture was stirred for 16 h at 120° C. under N$_2$. The reaction solution was filtered and to give a clear solution. The solution was extracted with EtOAc (80 mL) and washed with brine (3×20 mL). Compound 138 was purification by silica column chromatography using EA:PE=1:1 as the elute (900 mg, 94%). ESI-MS: m/z 478.9 [M+H]$^+$.

Example 13

Preparation of Compound 139

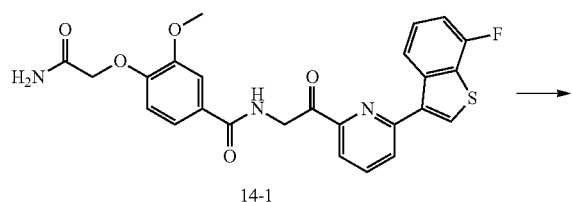

14-1

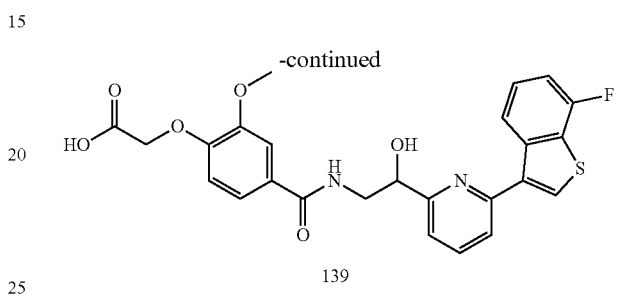

139

To a solution of 14-1 (495 mg, 1.0 mmol) in MeOH (10 mL) was added aqueous NaOH (10 mL, 1M). The mixture was stirred for 4 h at 60° C. The solution was cooled to r.t., acidified to pH=3 using 1N HCl solution and extracted with EtOAc. The organic phase was dried with anhydrous Na$_2$SO$_4$ and concentrated under reduced pressure to provide 139 (490 mg, 99%). +ESI-MS: m/z 497.1 [M+H]$^+$.

Example 14

Preparation of Compounds 140 and 141

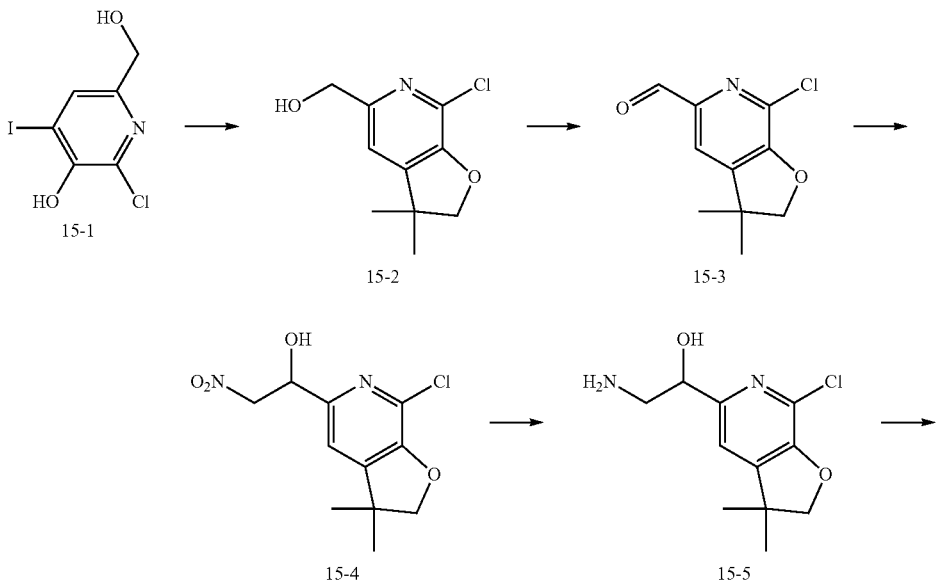

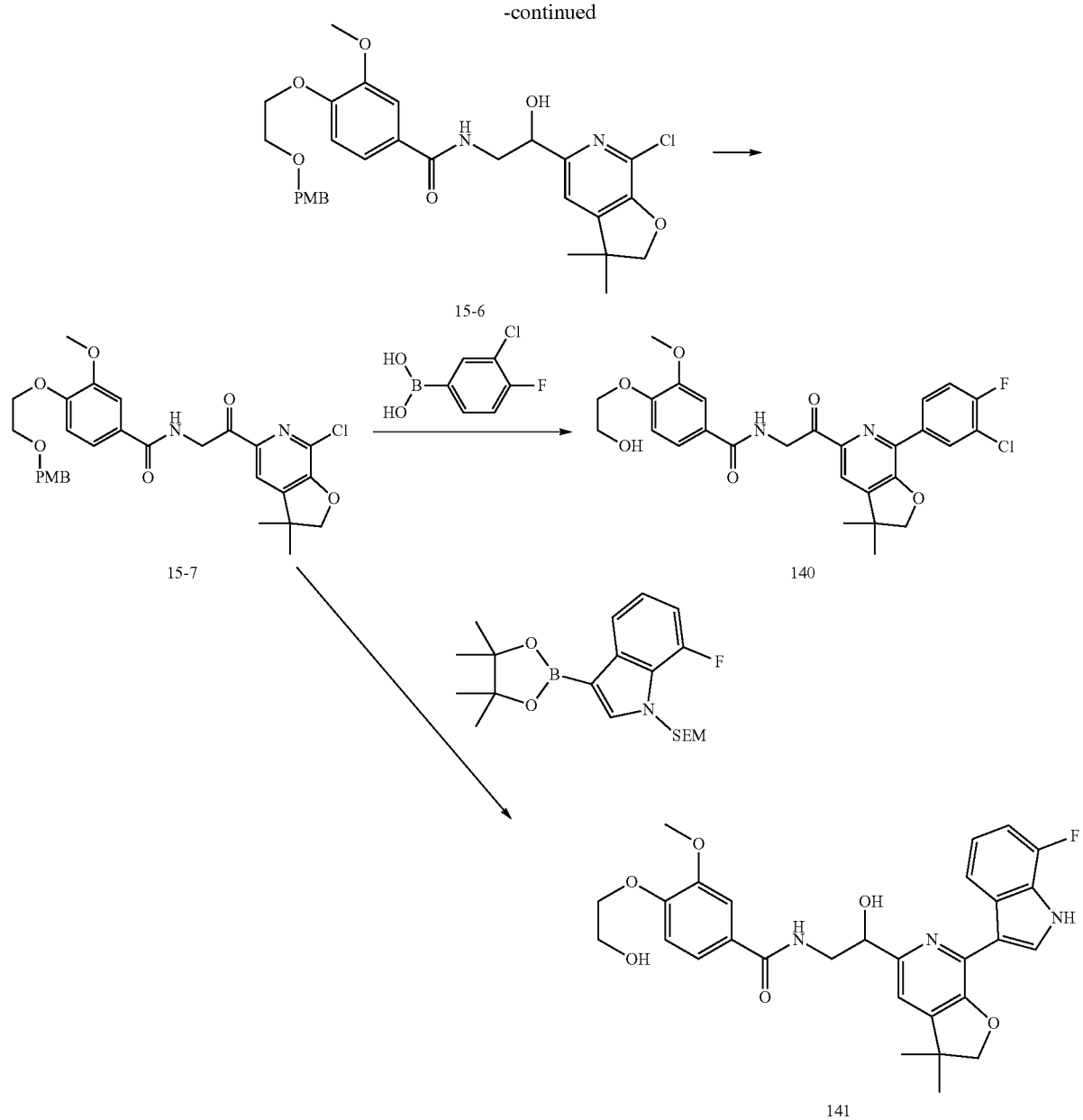

Compound 15-2 was prepared starting from 2-chloro-6-(hydroxymethyl)-4-iodopyridin-3-ol (15-1) according to procedures provided in PCT Publication No. WO 2004/039366, published May 13, 2004, which is hereby incorporated by reference for the limited purpose of its disclosure of the preparation of 15-2.

Dess-Martin periodinane (2.00 g, 4.21 mmol) was added to a stirred solution of 15-2 (835 mg) in dry DCM (5 mL). The mixture was stirred at r.t. for 40 mins. and quenched with a 1:1 mixture of 2M aq. $Na_2S_2O_3$ solution-sat. aq. $NaHCO_3$ sol (10 mL). After 30 mins., the layers were separated. The organic portion was washed with brine, dried ($Na_2SO_4$), filtered and concentrated under reduced pressure. Chromatography of the residue (cyclohexane-EtOAc, 100:0 to 60:40) afforded 15-3 as a white solid (250 mg). $^1$H NMR (400 MHz, $CDCl_3$) δ ppm 1.44 (s, 6H), 4.53 (s, 2H), 7.79 (s, 1H), 9.92 (s, 1H).

Nitromethane (191 uL, 3.54 mmol) and $K_2CO_3$ (32.5 mg, 0.236 mmol) were added to a solution of 15-3 (250 mg, 1.18 mmol) in dry THF (5 mL). The mixture was stirred at r.t. for 30 h and EtOAc was added. The organic portion was washed with water and brine, dried ($Na_2SO_4$), filtered and concentrated under reduced pressure to afford crude 15-4 (343 mg), which was used in the next step. $^1$H NMR (400 MHz, $CDCl_3$) δ ppm 1.36-1.49 (m, 6H), 4.45 (s, 2H), 4.68 (dd, J=13.6, 8.5 Hz, 1H), 4.85 (dd, J=13.4, 3.4 Hz, 1H), 5.43 (dd, J=8.5, 3.3 Hz, 1H), 7.26 (s, 1H).

$NaBH_4$ (21.0 mg, 0.550 mmol) was added to a solution of $NiCl_2$-$6H_2O$ (43.0 mg, 0.183 mmol) in MeOH (3 mL). After 30 mins, 15-4 (100 mg, 0.367 mmol) dissolved in MeOH (2 mL) was added, followed by additional solid $NaBH_4$ (28.0 mg, 0.730 mmol). The reaction was monitored by UPLC. When complete, the mixture was filtered through a pad of celite and the organic portion was concentrated under reduced pressure. The residue was eluted through a SCX-cartridge using MeOH and 2M NH₃-MeOH solution to afford 15-5. UPLC/MS (ES⁺): m/z 243.10 [M+H]⁺.

A mixture of 15-5, 3-methoxy-4-{2-[(4-methoxyphenyl) methoxy]ethoxy}benzoic acid (146 mg, 0.440 mmol), EDC (106 mg, 0.550 mmol), HOBT (74 mg, 0.550 mmol) and TEA (101 uL, 0.730 mmol) in DCM (4 mL) was stirred at r.t. for 18 h. The mixture was washed twice with 1M aq. HCl solution. The organic portion was dried with Na₂SO₄, filtered and concentrated under reduced pressure. Chromatography of the residue (cyclohexane:EtOAc, 80:20 to 0:100) afforded 15-6 as a pale yellow wax (90 mg, 44% over two steps). UPLC/MS (ES⁺): m/z 557.30 [M+H]⁺.

Dess-Martin periodinane (172 mg, 0.404 mmol) was added to a solution of 15-6 (90 mg, 0.162 mmol) in DCM (4 mL). The mixture was stirred at r.t. for 1 h. A 1:1 sat. aq. NaHCO₃ solution-sat. aq. Na₂S₂O₃ solution was added. The mixture was stirred at r.t. for 30 mins and the layers were separated. The organic portion was washed with water, dried (Na₂SO₄), filtered and concentrated under reduced pressure. Chromatography of the residue (cyclohexane-EtOAc, 50:50 to 10:90) afforded 15-7 as a pale yellow wax (70 mg, 78%). ¹H NMR (400 MHz, CDCl₃) δ ppm 1.45 (s, 6H), 3.83 (s, 3H), 3.86-3.92 (m, 2H), 3.96 (s, 3H), 4.27 (t, J=5.0 Hz, 2H), 4.52 (s, 2H), 4.60 (s, 2H), 5.11 (d, J=4.5 Hz, 2H), 6.91 (d, J=8.5 Hz, 2H), 6.95 (d, J=8.5 Hz, 1H), 7.02 (s, 1H), 7.32 (d, J=8.5 Hz, 2H), 7.41 (dd, J=8.3, 1.8 Hz, 1H), 7.51 (d, J=1.8 Hz, 1H), 7.90 (s, 1H).

A mixture of 15-7 (90.0 mg, 0.126 mmol), (3-chloro-4-fluorophenyl)boronic acid (55.0 mg, 0.316 mmol), Pd(dppf)Cl₂ (6.0 mg, 0.008 mmol) and aq. Na₂CO₃ (2M solution, 190 uL, 0.378 mmol) in DCE (3 mL) was degassed and heated to 85° C. After 20 h, the volatiles were removed under reduced pressure. Chromatography of the residue (cyclohexane-EtOAc, 80:20 to 0:100) afforded the PMB-ether (51 mg). The PMB-ether was dissolved in DCM (1.5 mL) and treated with TFA (200 uL). The mixture was stirred at r.t. for 30 mins and quenched with 2M aq. NaOH solution. The layers were separated and the aqueous portion was extracted with DCM. The combined organic portions were dried (Na₂SO₄), filtered and concentrated under reduced pressure. Chromatography of the residue (cyclohexane-EtOAc, 80:20 to 0:100) afforded 140 as a white solid (20 mg, 30% over two steps). ¹H NMR (400 MHz, CDCl₃) δ ppm UPLC/MS (ES⁺): m/z 529.15 [M+H]⁺.

Coupling of 15-7 with 7-fluoro-3-(tetramethyl-1,3,2-dioxaborolan-2-yl)-1-{[2-(trimethylsilyl)ethoxy]-methyl}-1H-indole followed removal of all protecting groups (TFA-DCM) afforded 141 as an off-white solid (9% over two steps). UPLC/MS (ES⁺): m/z 534.33 [M+H]⁺.

Example 15

Preparation of Compound 142

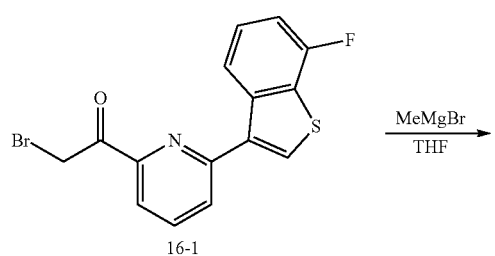

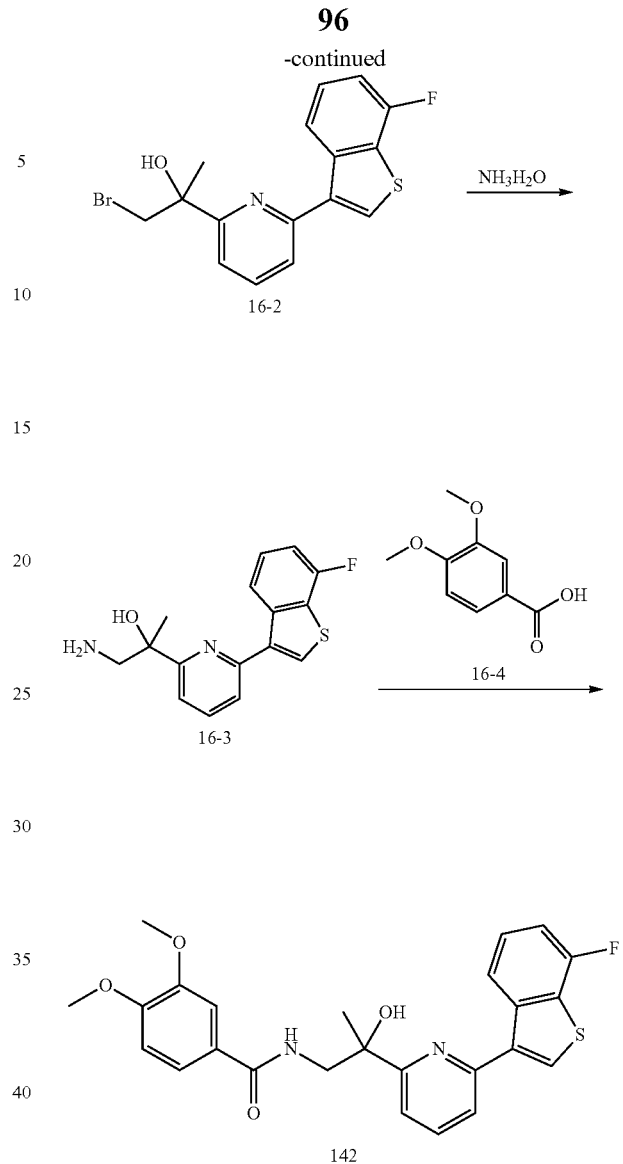

MeMgBr (0.7 mL, 2 mmol) was added dropwise to a stirred solution of 16-1 (700 mg, 0.3 mmol) in THF (5 mL) at −78° C. After 1 h, the mixture was allowed to warm to r.t. (approx. 2 h). The reaction was quenched with 1N HCl and extracted with EtOAc. The combined organic layers were washed with brine, dried over Na₂SO₄ and concentrated. The residue was purified by column on silica gel (PE:EA=10:1) to give 16-2 (350 mg, 41%).

A solution of 16-2 (350 mg, 0.96 mmol) in ammonia (6 mL) and EtOH (3 mL) was stirred at 90° C. for 10 h. The solvent was removed and the crude product was used in next step without purification.

To a solution of 16-4 (73 mg, 0.4 mmol) in DIPEA (0.2 mL) and DMF (1 mL) was added HATU (152 mg, 0.4 mmol), and stirred at 40° C. for 30 mins. Compound 16-3 (100 mg, 0.33 mmol) was added. The mixture was stirred at 40° C. for 10 h. The mixture was diluted with water and extracted with EtOAc. The organic layers was washed with brine, dried over Na₂SO₄, and concentrated. The crude product was purified by prep-HPLC to give 142 (60 mg, 39%). +ESI-MS: m/z 488.9 [M+Na]⁺.

Example 16

Preparation of Compound 143

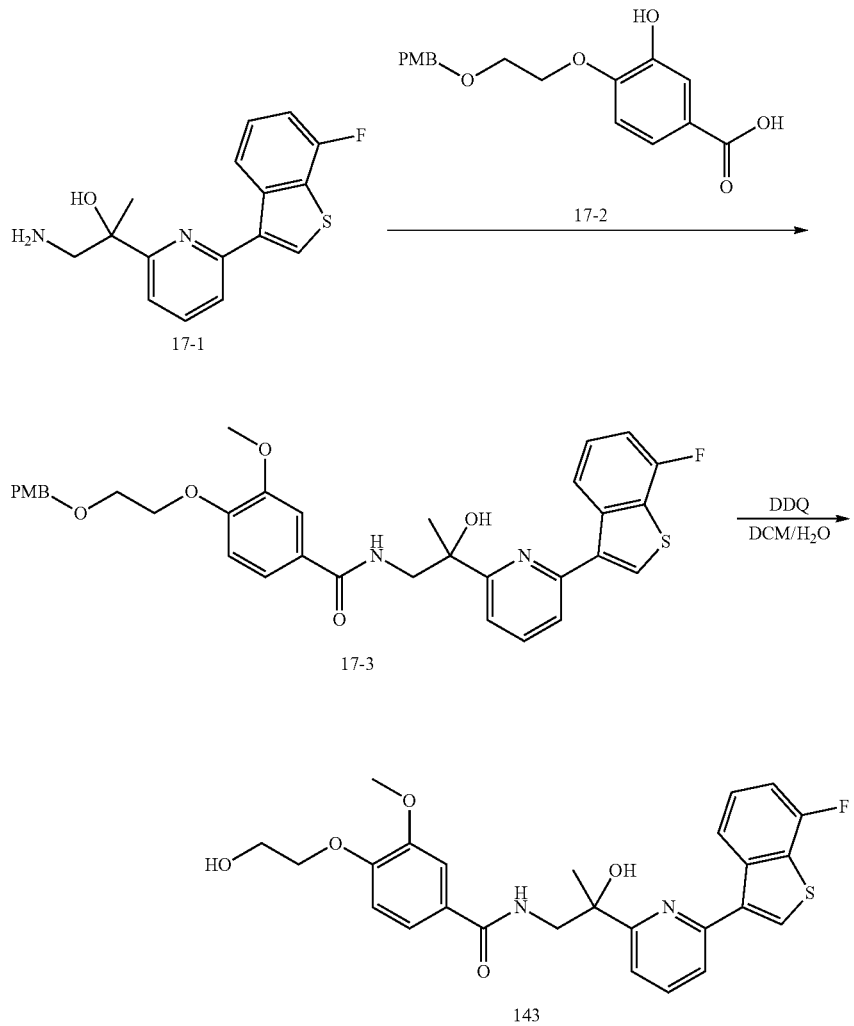

To a solution of 17-2 (132 mg, 0.4 mmol) in DIPEA (0.2 mL) and DMF (1 mL) was added HATU (152 mg, 0.4 mmol), and the mixture stirred at 40° C. for 30 mins. Compound 17-1 (100 mg, 0.33 mmol) was added. The mixture was stirred at 40° C. for 10 h. The mixture was diluted with water and extracted with EtOAc. The organic layers was washed with brine, dried over $Na_2SO_4$, and concentrated. The crude product was purified by column on silica gel (PE:EA=1:1) to give 17-3 (60 mg, 32%).

To a solution of 17-3 (60 mg, 0.1 mmol) in DCM (2 mL) and $H_2O$ (0.2 mL) was added DDQ (45 mg, 0.2 mmol). The mixture was stirred for 2 h. at r.t. The mixture was dissolved in DCM (30 mL). The solution was washed with sat. $NaHCO_3$, dried over Na2SO4, and concentrated. The residue was purified by prep-HPLC to give 143 (30 mg, 60%). +ESI-MS: m/z 496.9 $[M+H]^+$.

Example 17

Preparation of Compound 144

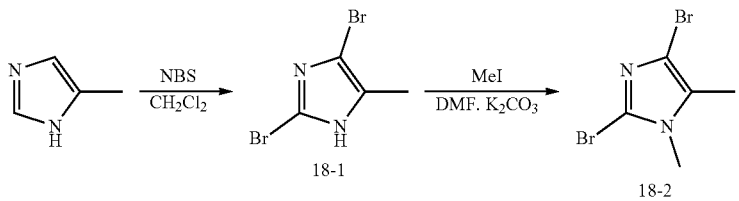

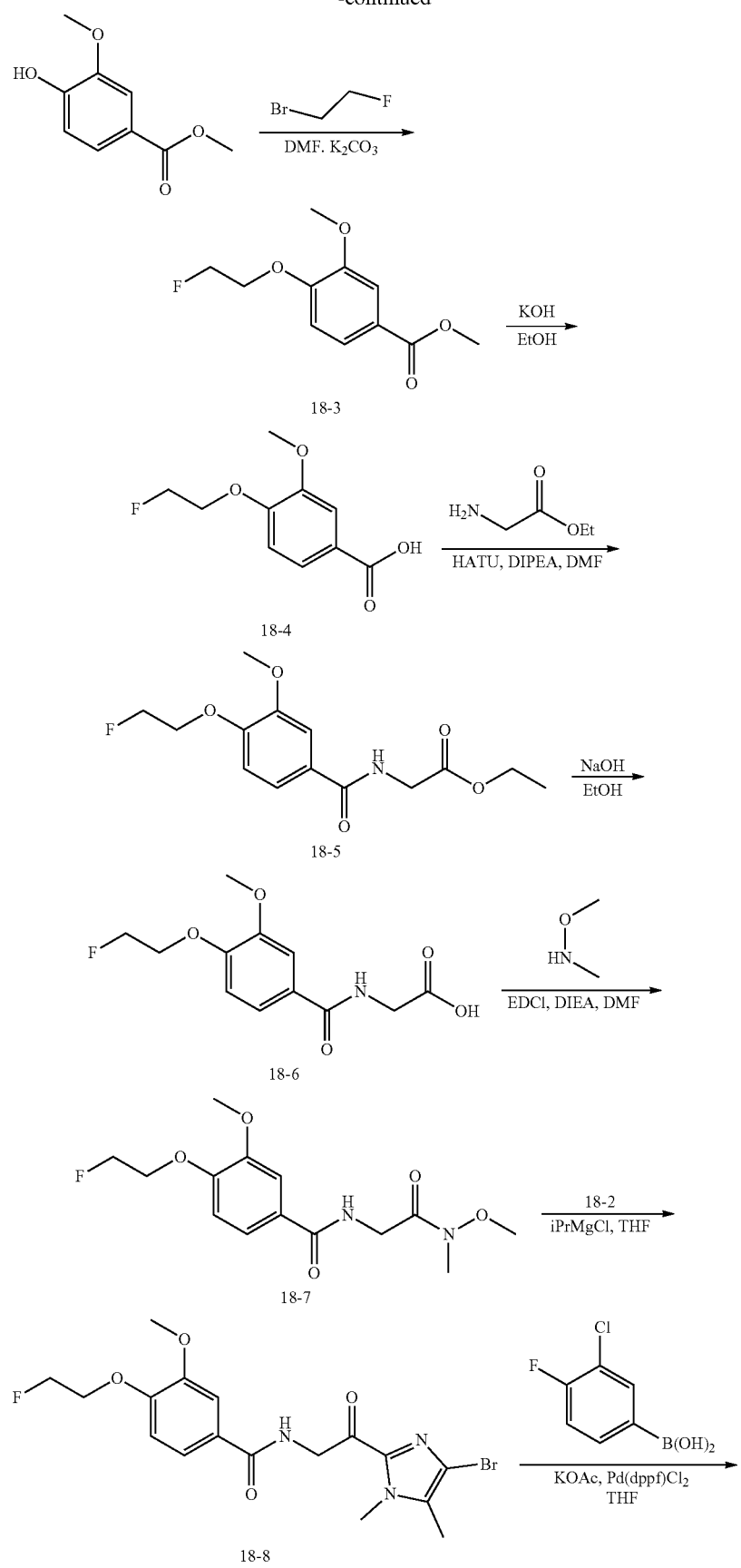

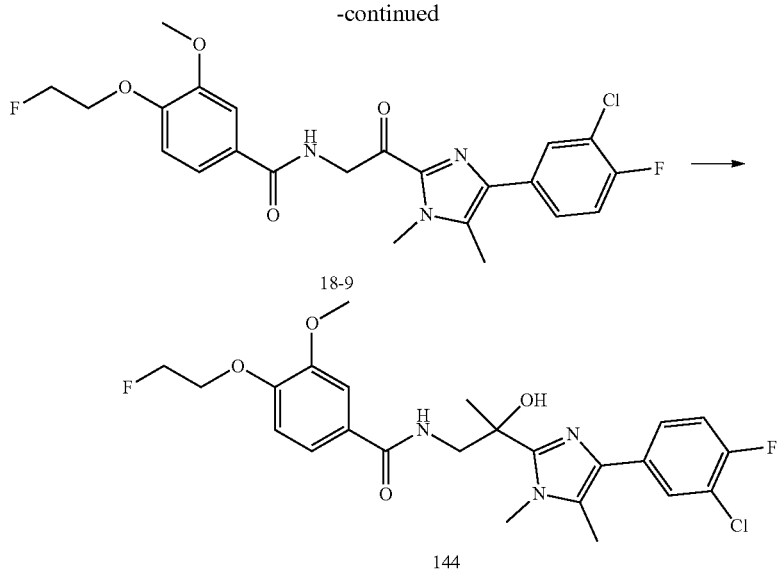

144

To a solution of 4(5)-methylimidazole (2 g, 24 mmol) in CH$_2$Cl$_2$ (150 mL) was added bromine (2.5 mL, 48 mmol) at 0° C. The solution was stirred for 1H at r.t. The product was filtered and partitioned between EA and sat. NaHCO$_3$. The product was precipitated from MeOH/CH$_2$Cl$_2$ to provide 18-1 (4.31 g, 75%). $^1$H NMR (400 MHz, DMSO-d$_6$): δ 2.06 (s, 3H).

To a solution of 18-1 (3.6 g, 15 mmol) and K$_2$CO$_3$ (4.1 g, 30 mmol) in DMF (18 mL) was added iodomethane (1.4 mL, 23 mmol) at 25° C. The solution was stirred for 15 h. The mixture was poured into water and extracted with EA The combined organic phase was dried over anhydrous Na$_2$SO$_4$, and the residue was purified by chromatography on silica gel (EA/hexane) to give 18-2 (1.6 g, 41%). $^1$H NMR (400 MHz, CDCl$_3$): δ 3.52 (s, 3H), 2.21 (s, 3H).

To a solution of methyl vanillate (7.06 g, 39 mmol) and K$_2$CO$_3$ (10.7 g, 78 mmol) in DMF (25 mL) was added 1-bromo-2-fluoroethane (4.3 mL, 58 mmol) at 25° C. The solution was stirred for 2 days. The mixture was poured into water and extracted with EA. The combined organic layers were dried over anhydrous Na$_2$SO$_4$, and concentrated. The residue was purified by chromatography on silica gel (EA/hexane) to give 18-3 (8.92 g, 103%).). $^1$H NMR (400 MHz, CDCl$_3$): δ 7.63 (dd, J=2.15, 8.41, 1H), 7.55 (d, J=8.41, 1H), 4.72-4.86 (m, 2H), 4.27-4.35 (m, 2H), 3.90 (s, 3H), 3.88 (s, 3H).

To a solution of 18-3 (8.92 g, 39 mmol) in MeOH (150 mL) was added 2 N NaOH (40 mL, 78 mmol). The solution was stirred for 2 h at 70° C. The mixture was concentrated, acidified with 2N HCl and extracted with EA to provide 18-4. (5.0 g, 30%). $^1$H NMR (400 MHz, DMSO-d$_6$): δ 7.47 (dd, J=1.96, 8.41, 1H), 7.38 (d, J=1.96, 1H), 6.99 (d, J=8.41, 1H), 4.61-4.76 (m, 2H), 4.17-4.27 (m, 2H).

To a solution of 18-4 (3.07 g, 14.3 mmol), glycine methyl ester HCl salt (3.6 g, 29 mmol), HATU (6.5 g, 17 mmol) in DMF (15 mL) was added DIEA (10 mL, 57 mmol). The solution was stirred for 18 h at r.t. The mixture was diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 18-5 (2.02 g, 51%). $^1$H NMR (400 MHz, CDCl$_3$): δ 7.43 (d, J=2.15, 1H), 7.30 (dd, J=2.15, 8.42), 6.90 (d, J-8.42, 1H), 6.57 (br. t, 1H), 4.72-4.85 (m, 2H), 4.22-4.35 (m, 2H), 4.25 (d, J=5.08, 2H) 3.85 (s, 3H), 3.79 (s, 3H).

To a solution of 18-5 (2.02 g, 7.1 mmol) in MeOH (50 mL) was added 2 N NaOH (10 mL, 20 mmol). The solution was stirred for 2 h at r.t. The mixture was concentrated, acidified with 2N HCl and extracted with EA to provide 18-6. (1.38 g, 72%). $^1$H NMR (400 MHz, CD$_3$OD): δ 7.49 (m, 2H), 7.04 (d, J=8.42, 1H), 4.62-4.85 (m, 2H), 4.25-4.34 (m, 2H), 4.08 (s, 2H), 3.90 (s, 3H).

To a solution of 18-6 (0.52 g, 1.9 mmol), N,O-dimethylhydroxylamine hydrochloride (0.23 g, 3.8 mmol), EDCI (0.38 g, 2.3 mmol) in DMF (3 mL) was DIEA (1.0 mL, 5.8 mmol). The solution was stirred for 2 h at r.t. The mixture was diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 18-7 (0.28 g, 47%). $^1$H NMR (400 MHz, CDCl$_3$): δ 7.43 (d, J=1.96, 1H), 7.33 (dd, J=1.96, 8.22, 1H), 6.90 (d, J=8.22, 1H), 4.71-4.84 (m, 2H), 4.26-4.36 (m, 4H), 3.91 (3, 3H), 3.76 (s, 3H), 3.25 (s, 3H).

Isopropylmagnesium chloride (2.0M, 0.48 mL, 0.95 mmol) was added dropwise to a solution of 18-7 (0.12 g, 0.38 mmol) and 18-2 (0.13 g, 0.50 mmol) in THF (1.0 mL). The solution was stirred for 2 h at r.t. The reaction was quenched with 1N HCl, diluted with EA and washed with brine. The organic solution was filtered to 18-8 (0.030 g, 20%). $^1$H NMR (400 MHz, CDCl$_3$): δ 7.49 (d, J=2.15, 1H), 7.38 (dd, J=2.15, 8.21, 1H), 7.03 (t, J=5.09, 1H), 4.93 (d, J=5.09, 2H), 4.74-4.96 (m, 2H), 4.28-4.37 (m, 2H), 3.96 (s, 3H), 3.93 (s, 3H), 2.22 (s, 3H).

A solution of 18-8 (30 mg, 0.070 mmol), 3-chloro-4-fluorophenylboronic acid (24 mg, 0.14 mmol), potassium acetate (21 mg, 0.21 mmol) and Pd(dppf)Cl$_2$ (10 mg, 0.014 mmol) was heated under microwave irradiation for 1 h at 110° C. The mixture was concentrated and purified by chromatography on silica gel (EA/hexane) to give 18-9 (24 mg, 72%). LCMS: m/z 478.10 [M+H]$^+$.

Methylmagnesium bromide (0.33 mL, 0.46 mmol) was added to a solution of 18-9 (22 mg, 0.046 mmol) in THF (1.0 mL). The mixture was stirred for 2 h at r.t., and then quenched with 1M HCl. The mixture was extracted with EA, washed with brine, dried and concentrated. The residue purified by reverse phase HPLC to give 144 (3.8 mg, 17%). LCMS: m/z 494.15 [M+H]⁺.

Example 18

Preparation of Compound 145

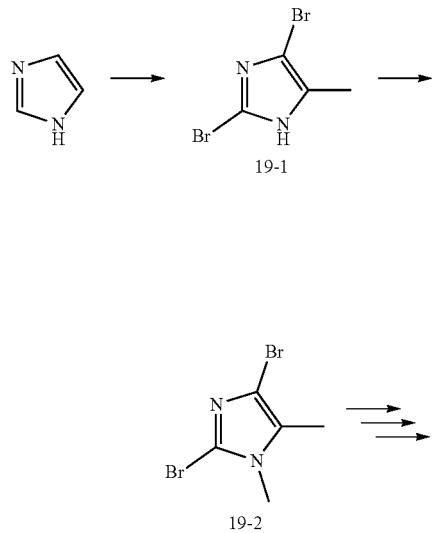

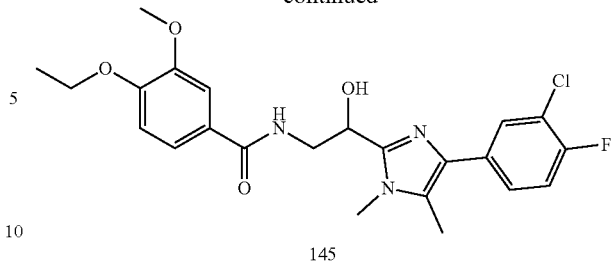

To a solution of 4(5)-methylimidazole (2 g, 24 mmol) in $CH_2Cl_2$ (150 mL) was added bromine (2.5 mL, 48 mmol) at 0° C. The solution was stirred for 1H at r.t. The product was filtered and partitioned between EA and sat. $NaHCO_3$. The product was precipitated from $MeOH/CH_2Cl_2$ to provide 19-1 (4.31 g, 75%). $^1$H NMR (400 MHz, DMSO-$d_6$): δ 2.06 (s, 3H).

To a solution of 19-1 (3.6 g, 15 mmol) and $K_2CO_3$ (4.1 g, 30 mmol) in DMF (18 mL) was added iodomethane (1.4 mL, 23 mmol) at 25° C. The solution was stirred for 15 h. The mixture was poured into water and extracted with EA The combined organic phase was dried over anhydrous $Na_2SO_4$, and the residue was purified by chromatography on silica gel (EA/hexane) to give 19-2 (1.6 g, 41%). $^1$H NMR (400 MHz, $CDCl_3$): δ 3.52 (s, 3H), 2.21 (s, 3H).

Compound 145 was prepared using iodoethane and closely following the procedure for preparing of 144. LCMS: m/z 476.10 [M+H]⁺.

Example 19

Preparation of Compound 146

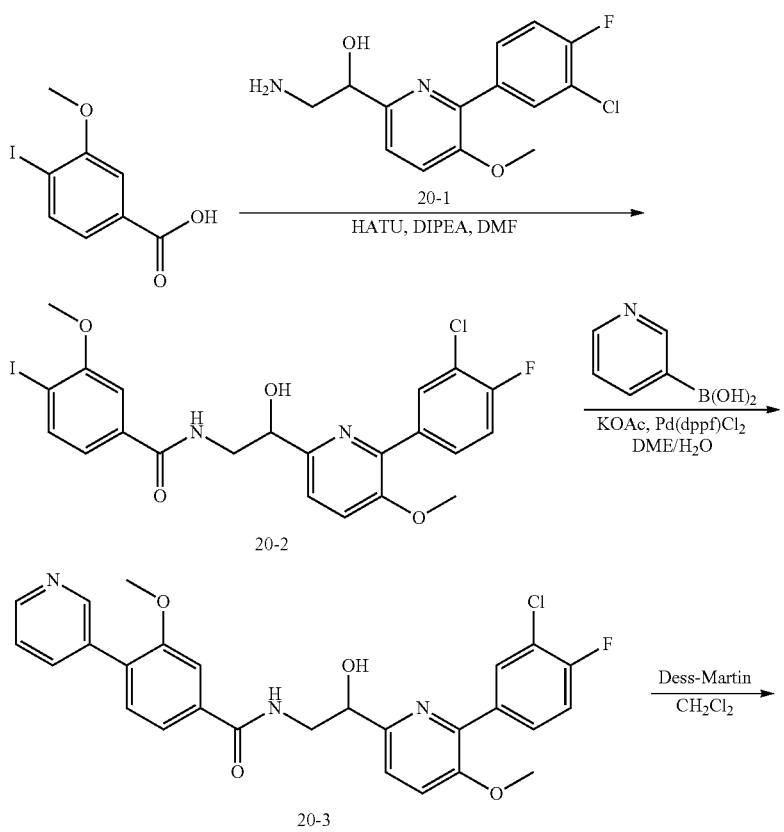

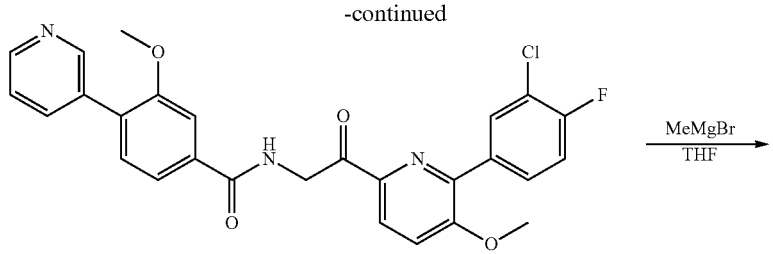

20-4

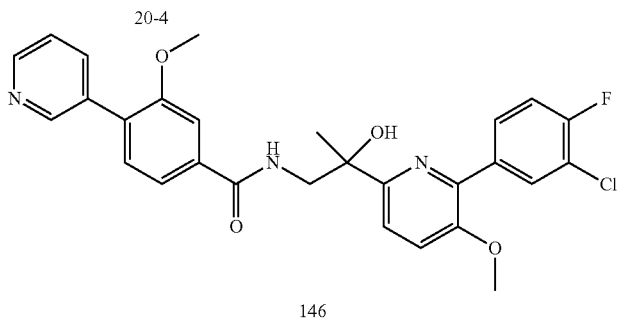

146

To a solution of 3-methoxy-4-iodobenzoic acid (0.45 g, 1.6 mmol), 20-1 (0.485 g, 1.6 mmol), HATU (0.75 g, 2.0 mmol) in DMF (3 mL) was added DIEA (0.71 mL, 4.1 mmol). The solution was stirred for 18 h at r.t. The mixture was diluted with EA. The organic phase was washed with water, 1N HCl, NaHCO$_3$ and brine, dried over anhydrous Na$_2$SO$_4$, and concentrated. The residue was purified by chromatography on silica gel (MeOH/CH$_2$Cl$_2$) to give 20-2 (0.176 g, 51%). $^1$H NMR (400 MHz, CDCl$_3$): δ 7.99 (dd, J=2.15, 7.24, 1H), 7.81-7.85 (m, 1H), 7.75 (d, J=8.02, 1H), 7.37-7.42 (m, 2H), 7.26-7.27 (m, 1H), 7.25 (t, J=8.71, 1H), 6.93 (dd, J=1.96, 8.02), 6.83-6.86 (m, 1H), 4.97-4.99 (m, 1H), 3.99-4.13 (m, 1H), 3.90 (s, 3H), 3.89 (s, 3H), 3.54-3.72 (m, 1H).

A solution of 20-2 (25 mg, 0.045 mmol), pyridine-3-boronic acid (11 mg, 0.09 mmol), potassium acetate (13 mg, 0.13 mmol) and Pd(dppf)Cl$_2$ (6 mg, 0.009 mmol) in DME (0.5 mL) and H$_2$O (0.05 mL) was heated under microwave irradiation for 1 h at 110° C. The mixture was concentrated and purified by chromatography on silica gel (MeOH/CH$_2$Cl$_2$) to give 20-3 (22 mg, 88%). $^1$H NMR (400 MHz, CDCl$_3$): δ 8.74-8.90 (br. s, 1H), 8.60-8.72 (br. s, 1H), 8.00, dd, J=2.15, 7.24), 7.85-7.88 (m, 2H), 7.34-7.45 (m, 5H), 7.17, (t, J=8.80, 1H), 6.94-6.97 (m, 1H), 4.98-5.01 (m, 1H), 4.00-4.09 (m, 1H), 3.88 (s, 3H), 3.82 (s, 3H0, 3.68-3.75 (m, 1H).

Dess-Martin periodinane (25 mg, 0.061 mmol) was added to a solution of 20-3 (22 mg, 0.043 mmol) in CH$_2$Cl$_2$, and stirred for 2 h. The mixture was diluted with CH$_2$Cl$_2$, washed with sat. Na$_2$CO$_3$, and brine, dried over MgSO$_4$, and concentrated under reduced pressure. The crude product was purified by chromatography on silica gel (EA/hexane) to give 20-4 (6.1 mg, 28%). LCMS: m/z 506.10 [M+H]$^+$.

Methylmagnesium bromide (1.4 M in THF, 0.39 mL, 0.39 mmol) was added to a solution of 20-4 (20 mg, 0.039 mmol) in THF (1.0 mL) and stirred for 2 h. The mixture was diluted with quenched with 1N HCl and extracted with EA. The organic extracts were washed with brine, dried over MgSO$_4$, and concentrated under reduced pressure. The crude product purified by reverse phase HPLC to provide 146 (0.9 mg, 4%). LCMS: m/z 522.15 [M+H]$^+$.

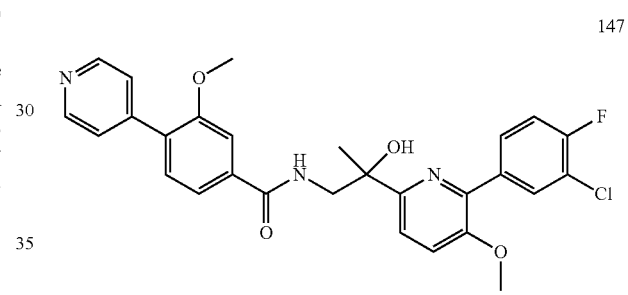

147

Compound 147 was prepared using pyridine-4-boronic acid pinacol ester in the Suzuki reaction and by following a synthetic route, which closely follows that described for preparation of 146. LCMS: m/z 522.15 [M+H]$^+$.

Example 20

Preparation of Compound 148

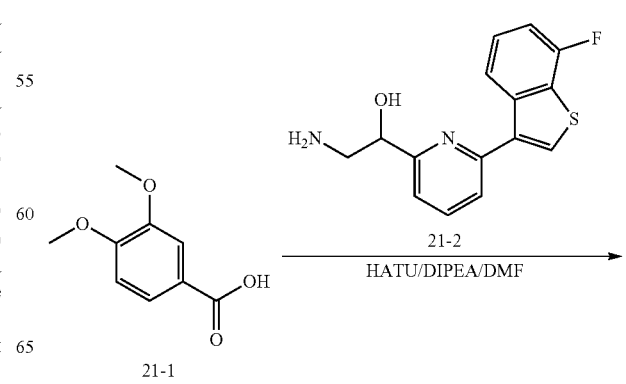

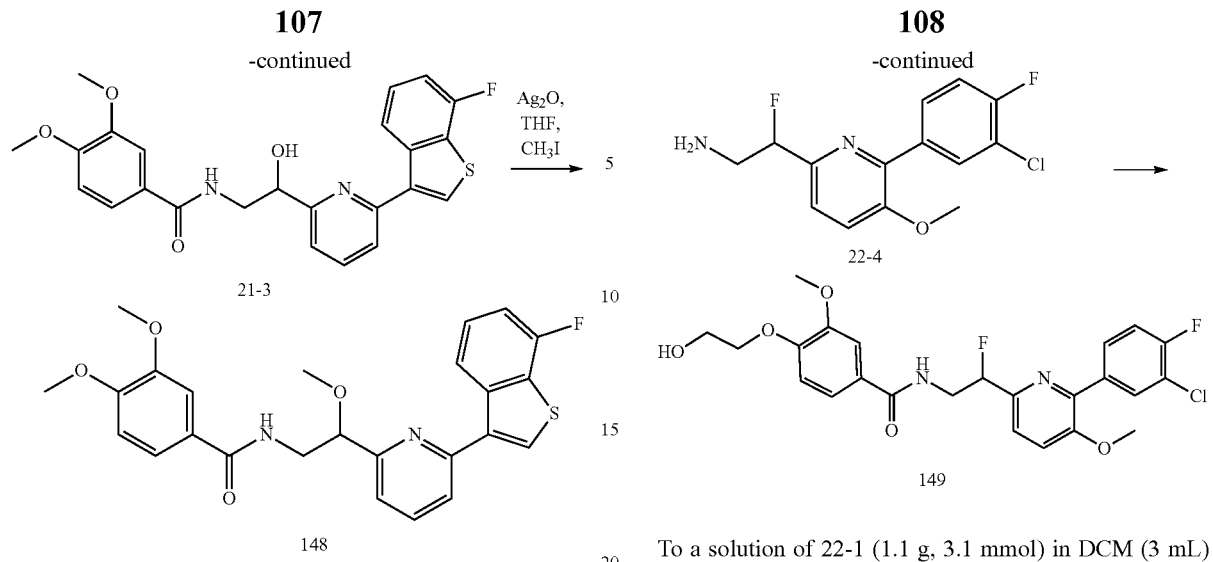

To a solution of 21-1 (100 mg, 0.549 mmol), HATU (208 mg, 0.549 mmol) and DIPEA (142 mg, 1.1 mmol) in anhydrous DMF (2 mL) was added 21-2 (100 mg 0.347 mmol) at 25° C. The solution was stirred for 10 h at this temperature and then diluted with 1.0 N aqueous NaHCO$_3$ solution (2×40 mL), extracted with EA (2×20 mL). The combined organic layers were washed with brine, dried over anhydrous Na$_2$SO$_4$, and concentrated under reduced pressure. The residue was purified on a silica gel column to give 21-3 (100 mg, 40.3%). +ESI-MS: m/z 433.1 [M+H]$^+$.

To a solution of 21-3 (100 mg, 0.22 mmol) in THF (2 mL) were added Ag$_2$O (20 mg) and CH$_3$I (100 mg, 0.72 mmol). The mixture was stirred for 15 h at 40° C. The solid was removed, and the filtrate was concentrated. The residue was purified by prep-HPLC (FA) to give 148 as a white solid (40 mg, 38.8%). +ESI-MS: m/z 466.9 [M+H]$^+$.

Example 21

Preparation of Compound 149

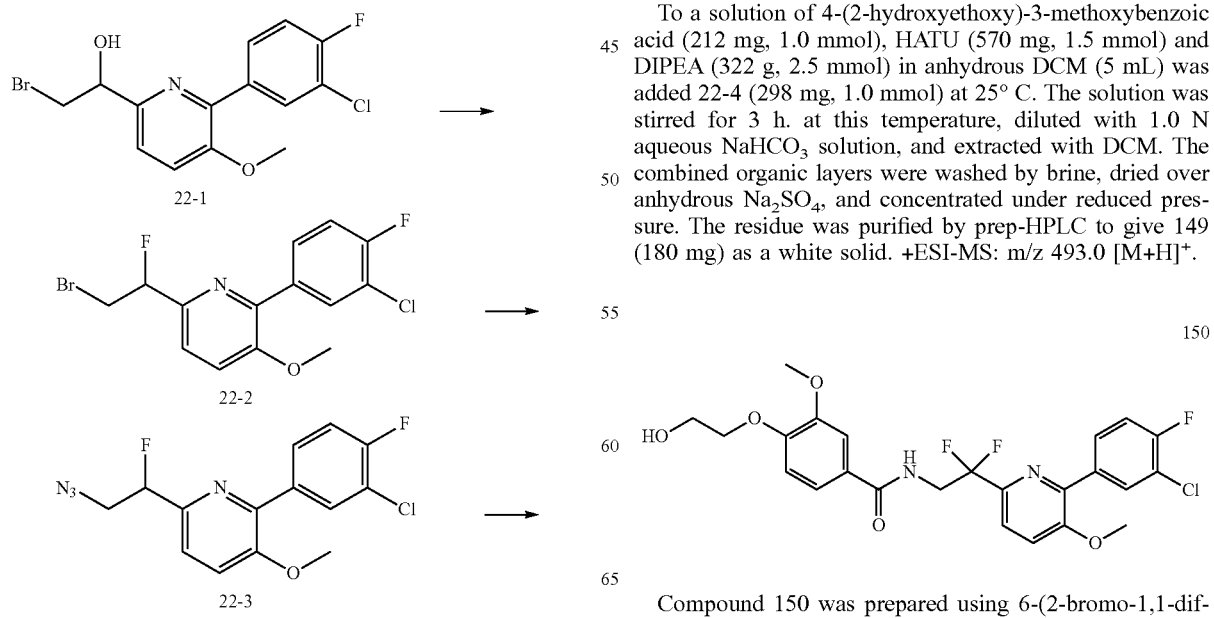

To a solution of 22-1 (1.1 g, 3.1 mmol) in DCM (3 mL) was added DAST (1.4 g; 8.7 mmol). The solution was stirred at r.t. for 1 h with TLC monitoring. The reaction was quenched with aq. NaHCO$_3$ at 0° C. and extracted with DCM. The combined organic solution was dried over anhydrous MgSO$_4$, and evaporated under reduced pressure. The residue was purified on a silica gel column (PE:EA=20:1 to 6:1) to give 22-2 (0.8 g).

To a solution of 22-2 (0.8 g, 2.2 mmol) in DMSO (5 mL) was added NaN$_3$ (300 mg 4.6 mmol). The solution was stirred at 60° C. for 3 h with LCMS monitoring. The reaction was quenched with aq. NaHCO$_3$ and extracted with EA. The combined organic solution was dried over anhydrous MgSO$_4$, and evaporated under reduced pressure to give crude 22-3 (0.7 g), which was used in next step directly without purification.

To a solution of 22-3 (0.7 g, 2.1 mmol) in EtOH (10 mL) and HCl (2 drops, 1.0 N) was added Pd/C (10%, 400 mg) under N$_2$. The suspension was degassed under vacuum and purged with H$_2$ 3 times. The mixture was stirred under H$_2$ (40 psi) at r.t. for 1 h. The suspension was filtered through a pad of Celite and the pad cake was washed with EtOH. The combined filtrates were concentrated to give crude 22-4 (0.4 g) used for next step directly without purification To a solution of 4-(2-hydroxyethoxy)-3-methoxybenzoic acid (212 mg, 1.0 mmol), HATU (570 mg, 1.5 mmol) and DIPEA (322 g, 2.5 mmol) in anhydrous DCM (5 mL) was added 22-4 (298 mg, 1.0 mmol) at 25° C. The solution was stirred for 3 h. at this temperature, diluted with 1.0 N aqueous NaHCO$_3$ solution, and extracted with DCM. The combined organic layers were washed by brine, dried over anhydrous Na$_2$SO$_4$, and concentrated under reduced pressure. The residue was purified by prep-HPLC to give 149 (180 mg) as a white solid. +ESI-MS: m/z 493.0 [M+H]$^+$.

Compound 150 was prepared using 6-(2-bromo-1,1-difluoroethyl)-2-(3-chloro-4-fluorophenyl)-3-methoxypyridine, and by following a synthetic route, which closely follows that described for preparation of 149. +ESI-MS: m/z 510.9 [M+H]+.

Example 22

Preparation of Compound 151

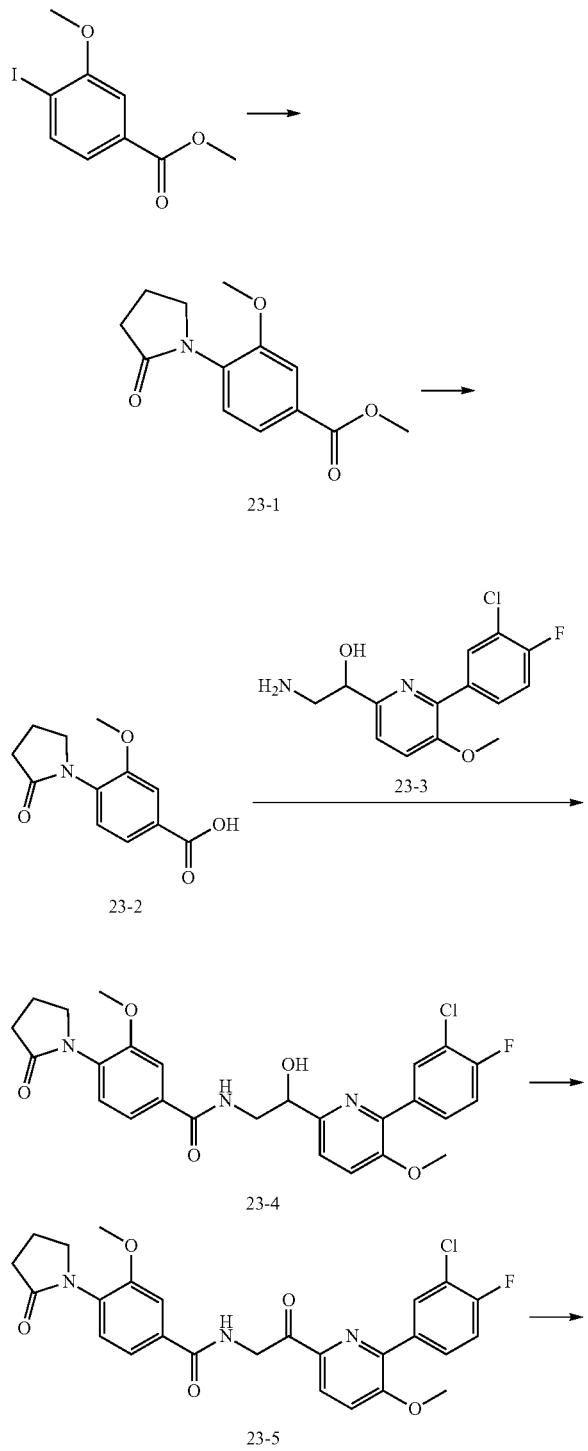

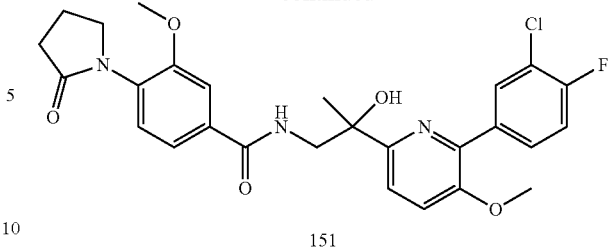

To a solution of methyl 3-methoxy-4-iodobenzoate (250 mg, 0.85 mmol) in toluene (2 mL) was added pyrrolidinone (150 mg, 1.7 mmol), potassium phosphate (0.55 g, 2.2 mmol), xantphos (25 mg, 0.43 mmol) and tris(dibenzylideneacetone)dipalladium(0) (40 mg, 0.43 mmol). The mixture was heated at 110° C. for 3 h. The mixture was then diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 23-1 (0.178 g, 83%). LCMS: m/z 478.10 [M+H]+.

To a solution of 23-1 (0.178 g, 0.72 mmol) in methanol (6 mL) was added NaOH (2.0 M, 2.0 mL) at 25° C. The solution was stirred for 15 h, acidified with 2N HCl and extracted with EA. The combined organic phase was dried over anhydrous Na$_2$SO$_4$ to give 23-2 (0.152 g, 90%). $^1$H NMR (400 MHz, CDCl$_3$): δ 7.52 (dd, J=1.77, 8.22 Hz, 1H), 7.51 (d, J=1.77 Hz, 1H), 7.30 (d, J=8.22 Hz, 1H), 3.82 (s, 3H), 3.75 (t, J=7.04 Hz, 2H), 2.55 (t, J=8.02 Hz, 2H), 2.0-2.3 (m, 2H).

To a solution of 23-2 (0.152 g, 0.65 mmol), 23-3 (0.19 g, 0.65 mmol), HATU (0.37 g, 0.97 mmol) in DMF (1 mL) was added DIEA (0.23 mL, 1.3 mmol). The solution was stirred for 2 h at r.t. The mixture was diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 23-4 (0.172 g, 51%). LCMS: m/z 478.10 [M+H]+.

Dess-Martin periodinane (220 mg, 0.50 mmol) was added to a solution of 23-4 (172 mg, 0.34 mmol) in CH$_2$Cl$_2$, and the mixture was stirred for 2 h. The mixture was diluted with CH$_2$Cl$_2$ and washed with sat. Na$_2$CO$_3$, and brine, dried over MgSO$_4$, and concentrated under reduced pressure. The crude product was purified by chromatography on silica gel (EA/hexane) to give 23-5 (77 mg, 45%) as white solid. LCMS: m/z 512.10 [M+H]+.

Methylmagnesium bromide (1.0 mL, 1.4 mmol) was added to a solution of 23-5 (72 mg, 0.14 mmol) in THF (1.0 mL). The mixture was stirred for 2 h at r.t., and then quenched with 1N HCl. The mixture was extracted with EA, washed with brine, dried and concentrated. The residue purified by reverse phase HPLC to give 151 (6.5 mg, 17%) as white solid. LCMS: m/z 528.15 [M+H]+.

Example 23

Preparation of Compound 152

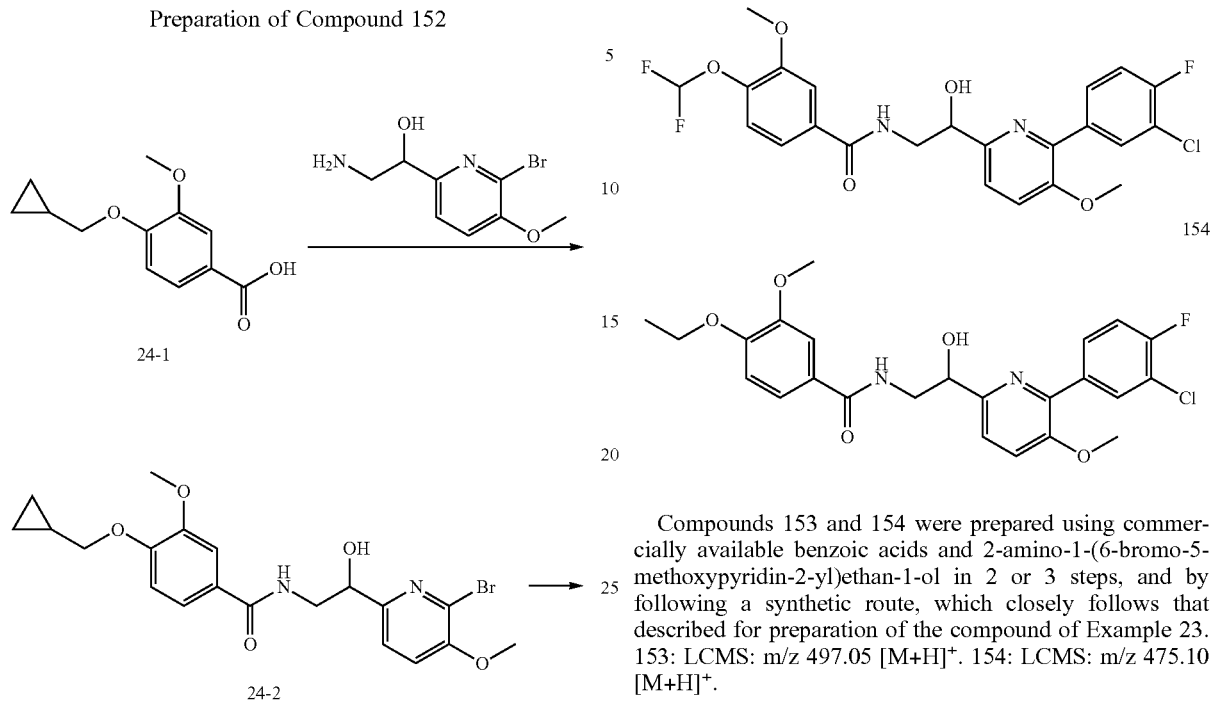

To a stirring mixture of 24-1 (44 mg, 0.197 mmol) in DMF were added HATU (83 mg, 0.218 mmol) and DIPEA (51 mg, 0.4 mmol). The mixture was stirred at r.t. for 10 mins and a solution of 2-amino-1-(6-bromo-5-methoxypyridin-2-yl)ethan-1-ol was added. The mixture was stirred at r.t. for 1 h, diluted with EtOAc and quenched with a sat. NaHCO$_3$ solution. The mixture was stirred at r.t. for 10 mins and the layers were separated. The aqueous layer was extracted with EtOAc. The organic layers were dried (Na$_2$SO$_4$), filtered and concentrated under reduced pressure. The crude product was purified via silica gel chromatography to afford 24-2. LCMS: m/z 451.05 [M+H]$^+$.

To a stirring mixture of 24-2 (28 mg, 0.062 mmol) in DME/water (10:1, 2.2 mL) were added Cs$_2$CO$_3$ (60 mg, 0.19 mmol), PdCl$_2$dppf (10 mg, 0.012 mmol), and (3-chloro-4-fluorophenyl)boronic acid (11 mg, 0.062 mmol). The mixture was stirred under microwave conditions at 110° C. for 1 h. The crude product mixture was cooled to r.t. and concentrated under reduced pressure. The crude mixture was purified via silica gel chromatography to afford 152. LCMS: m/z 501.15 [M+H]$^+$.

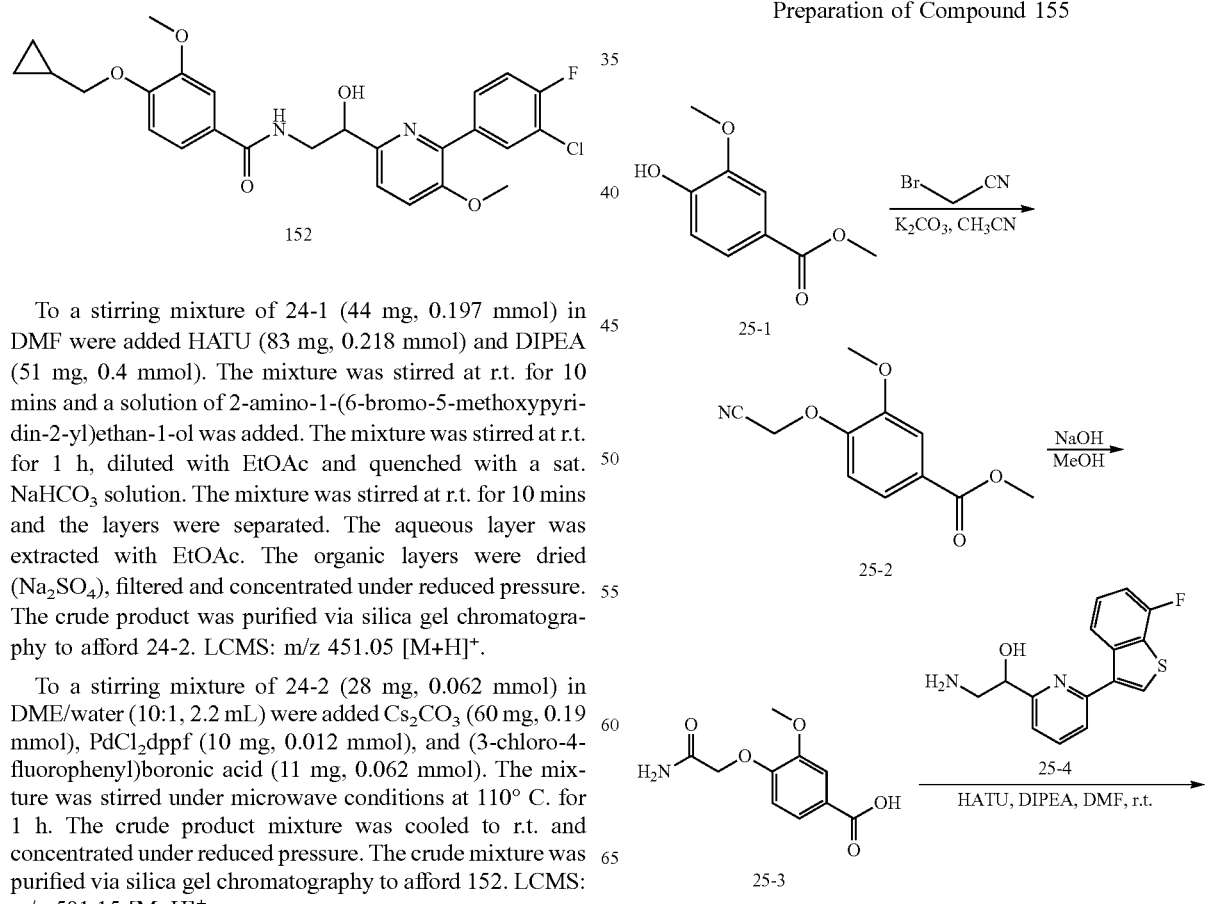

Compounds 153 and 154 were prepared using commercially available benzoic acids and 2-amino-1-(6-bromo-5-methoxypyridin-2-yl)ethan-1-ol in 2 or 3 steps, and by following a synthetic route, which closely follows that described for preparation of the compound of Example 23. 153: LCMS: m/z 497.05 [M+H]$^+$. 154: LCMS: m/z 475.10 [M+H]$^+$.

Example 24

Preparation of Compound 155

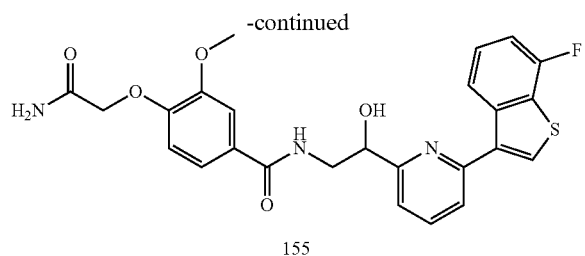

155

To a solution of 25-1 (1.82 g, 10 mmol) and K₂CO₃ (2.76 g, 20 mmol) in CH₃CN (20 mL) at r.t. was slowly added 2-bromoacetonitrile (2.4 g, 20 mmol). The mixture was heated to reflux and stirred for 15 h. The solvent were removed under reduced pressure. Purification by column chromatography on silica gel (PE:EA=3:1) provided 25-2 (2 g, 90%).

To a solution of 25-2 (2.21 g, 10 mmol) in methanol (10 mL) was added NaOH aqueous (10 mL, 1M). The mixture was stirred for 4 h at 60° C. The solution was cooled to r.t., acidified to pH=4 using 1N HCl solution and extracted with EtOAc. The organic phase was dried with anhydrous Na₂SO₄ and concentrated under reduced pressure to provide 25-3 (1.1 g, 50%).

To a solution of 25-3 (226 mg, 0.1 mmol) in DMF (3 mL) were added HATU (570 mg, 1.5 mmol) and DIPEA (387 mg, 3 mmol) at r.t. The solution was stirred for 10 mins at r.t. Compound 25-4 (287 mg, 1 mmol) was added and stirred for 1 h. The solution was extracted with EtOAc and washed with H₂O. The organic phase was concentrated and purified by prep-TLC to give 155 (200 mg, 40%). +ESI-MS: m/z 495.9 [M+H]⁺.

Example 25

Preparation of Compound 156

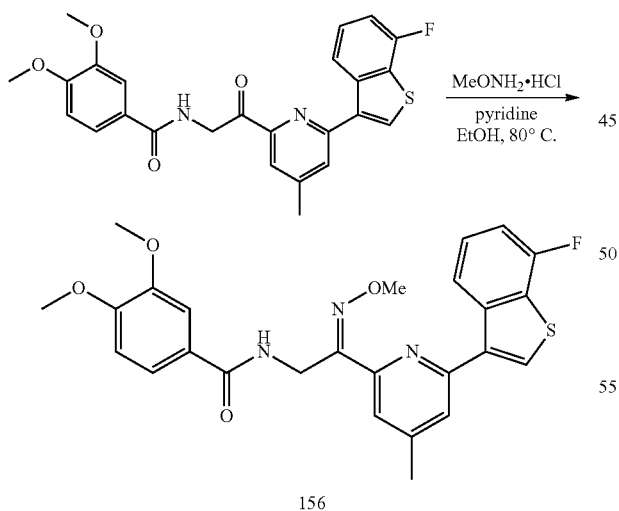

156

To a stirring mixture of N-(2-(6-(7-fluorobenzo[b]thiophen-3-yl)-4-methylpyridin-2-yl)-2-oxoethyl)-3,4-dimethoxybenzamide (20 mg, 0.043 mmol) in EtOH (0.25 mL) were added methoxy amine hydrochloride (4 mg, 0.048 mmol) followed by an addition of pyridine (34 mg, 0.43 mmol). The mixture was heated at 80° C. for 30 mins and then cooled to r.t. The mixture was concentrated under reduced pressure. The crude mixture was purified via prep-HPLC to afford 156. LCMS: m/z 494.10 [M+H]⁺.

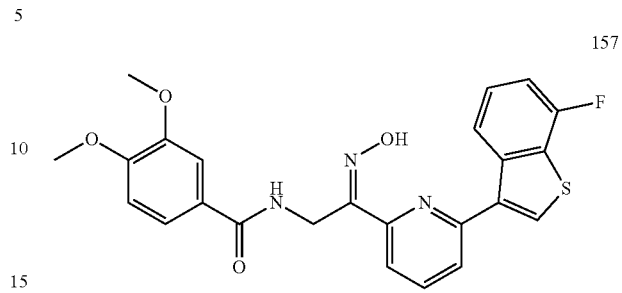

157

Compound 157 was prepared using N-(2-(6-(7-fluorobenzo[b]thiophen-3-yl)pyridin-2-yl)-2-oxoethyl)-3,4-dimethoxybenzamide and hydroxylamine hydrochloride, and by following a synthetic route, which closely follows that described for preparation of 156. LCMS: m/z 466.25 [M+H]⁺.

Example 26

Preparation of Compound 158

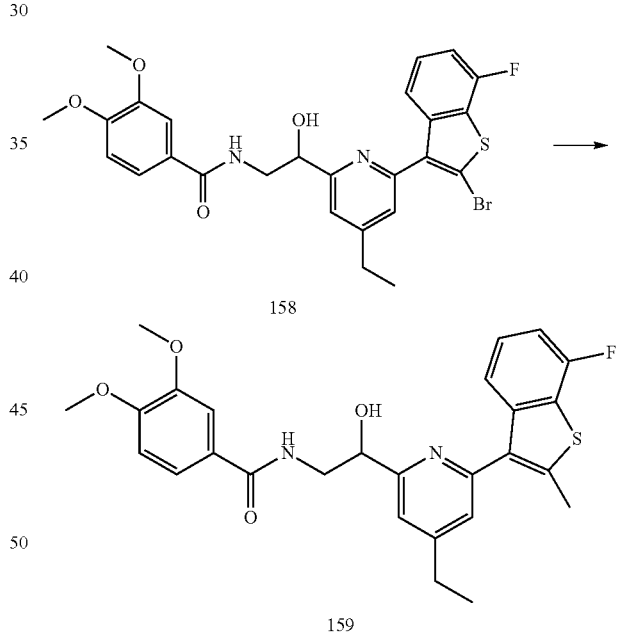

159

To a stirring mixture of 158 (20 mg, 0.036 mmol) in THF (1 mL) were added bis(tri-tert-butylphosphine)palladium(0) (3.6 mg, 0.008 mmol), and a solution of MeZnCl in THF (0.055 mL, 0.11 mmol). The mixture was stirred under microwave condition at 100° C. for 1 h. The mixture was cooled to r.t., diluted with EtOAc and slowly quenched with a sat. NH₄Cl solution. The mixture was stirred at r.t. for 20 mins and then the layers were separated. The aqueous layer was extracted with EtOAc. The organic layers were dried (Na₂SO₄), filtered and concentrated under reduced pressure. The crude product mixture was purified via silica gel column to afford 159 as a colorless oil. LCMS: m/z 495.1 [M+H]⁺.

Example 27

Preparation of Compound 160

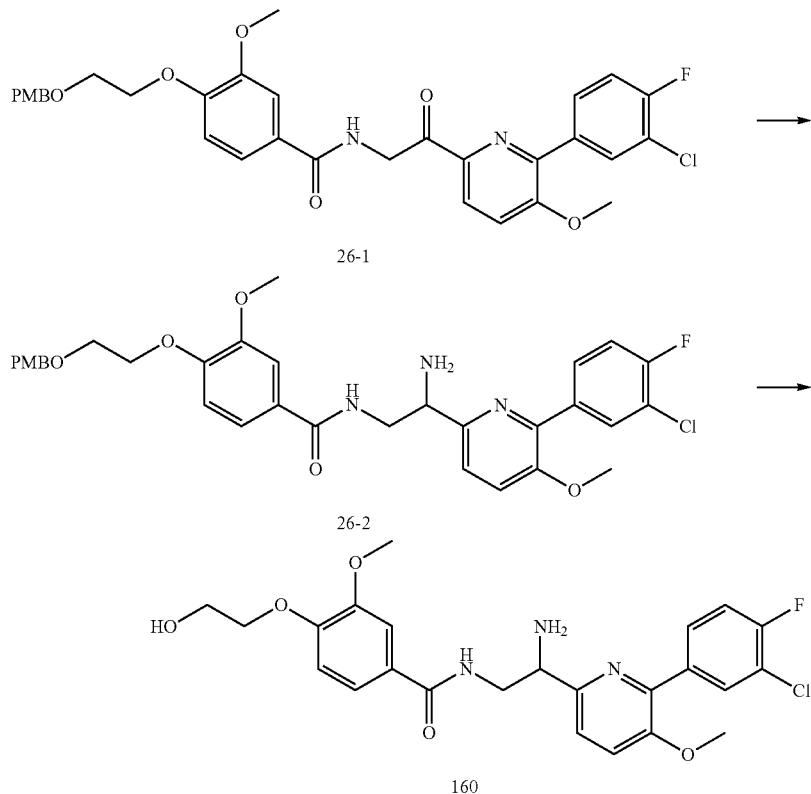

To a stirring mixture of 26-1 (50 mg, 0.082 mmol) in MeOH (1 mL) were added ammonium acetate (94 mg, 1.23 mmol), NaCNBH$_3$ (7.7 mg, 0.12 mmol). The mixture was heated at 70° C. for 1 h and then cooled to room temperature. The mixture was diluted with EtOAc and slowly quenched with a sat. NH$_4$Cl solution. The aqueous layer was extracted with EtOAc. The organic layers were dried (Na$_2$SO$_4$), filtered and concentrated under reduced pressure. The crude product mixture was purified via silica gel chromatography to afford 26-2. The PMB ether was removed using TFA in DCM at r.t. The crude product was concentrated under reduced pressure and purified via prep-HPLC to afford 160 (3.1 mg) as a white solid. LCMS: m/z 490.15 [M+H]$^+$.

Example 28

Preparation of Compound 161

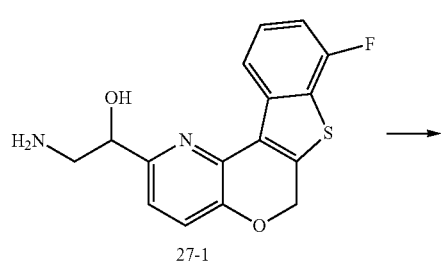

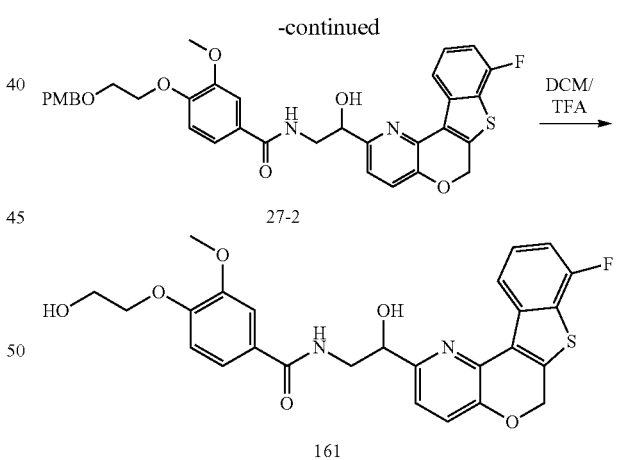

To a solution of 3-methoxy-4-(2-((4-methoxybenzyl)oxy)ethoxy)benzoic acid (205 mg, 0.62 mmol) in DMF (15 mL) were added DIPEA (320 mg, 2.48 mmol) and HATU (235.6 mg, 0.62 mmol). The mixture was stirred at r.t. for 30 mins, and 27-1 (195 mg, 0.62 mmol) was added. The mixture was stirred at r.t. overnight. The mixture was diluted with water and extracted with EA. The organic layer was dried over sodium sulfate, and concentrated in vacuum to give the crude product, which was purified by column chromatography to give 27-2 (180 mg). +ESI-MS: m/z 631.1 [M+H]$^+$.

Compound 27-2 (180 mg, 0.286 mmol) was dissolved in TFA/DCM (10 mL). The mixture was stirred at r.t. for 1 h (monitored by TLC). The mixture was extracted with EA, and washed with a sat. NaHCO₃ solution. The organic layer was dried over sodium sulfate, and concentrated in vacuum to give the crude product, which was purified by prep-HPLC to give 161 (50 mg) as a white solid. +ESI-MS: m/z 511.1 [M+H]⁺.

Example 29

Preparation of Compound 162

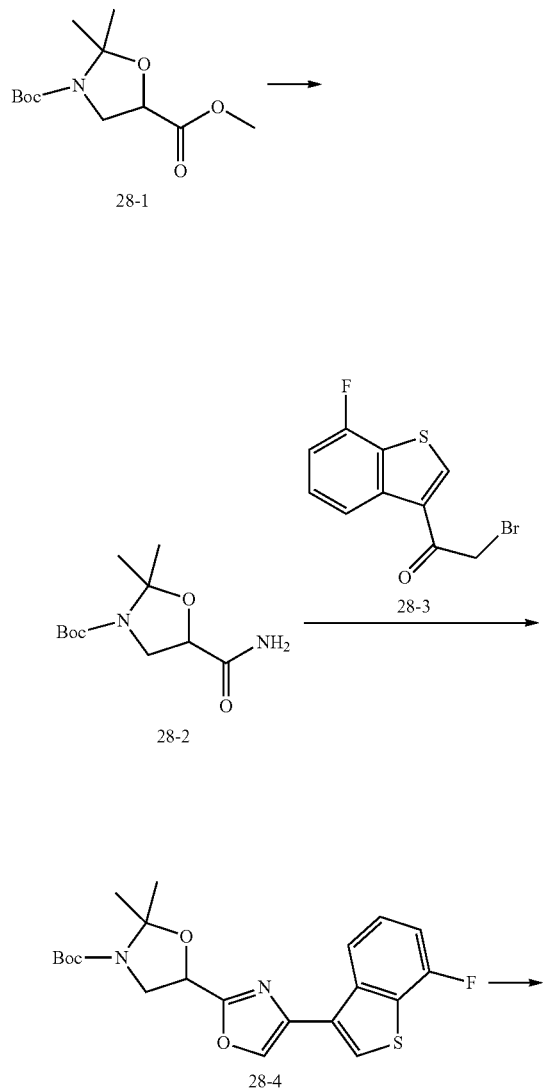

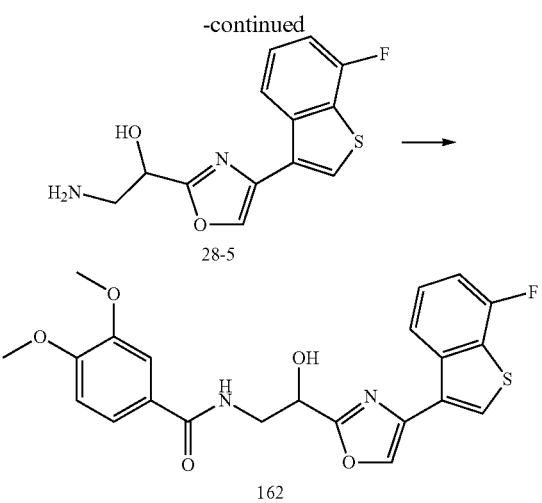

A solution of 28-1 (2.59 g, 0.01 mol) in NH₃/MeOH (20 mL) was stirred at r.t. for 30 mins. The solvent was removed by rotary evaporator. The residue, 28-2, was used in next step.

A mixture of 28-2 (2.44 g, 0.01 mol) 28-3 (2.73 g, 0.01 mol) and AgSbF₆ (5.14 g, 0.015 mol) in DME (20 mL) was stirred for 2 h at 120° C. under microwave irradiation. The mixture was filtered. The filtrate was concentrated by rotary evaporator to give crude 28-4 (5 g), which was used in next step without further purification.

To a solution of 28-4 (5 g) in EtOAc (10 mL) was added HCl-EtOAc (30 mL). The solution was stirred for 10 h. The solvent was concentrated by rotary evaporator. The product was purified by prep-HPLC to give 28-5 (250 mg). ESI-MS: m/z 278.8 [M+H]⁺.

To a solution of 28-5 (145 mg, 0.8 mmol) in DMF (10 mL) was added HATU (343 mg, 0.9 mmol), DIEA (155 mg, 1.2 mmol), and stirred for 5 mins. 3,4-dimethoxybenzoic acid (250 mg, 0.8 mmol) was added and the mixture was stirred for 5 h. Water (100 mL) was poured into the solution, and a solid precipitated. The solid was purified by silica column chromatography (PE:EA=1:1) to give 162 (158 mg, 45%). ESI-MS: m/z 442.9 [M+H]⁺.

Example 30

Preparation of Compound 163

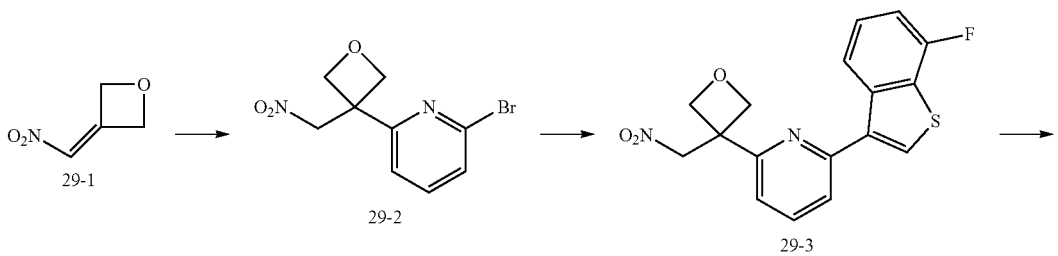

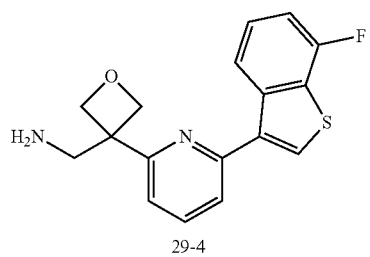

29-4

-continued

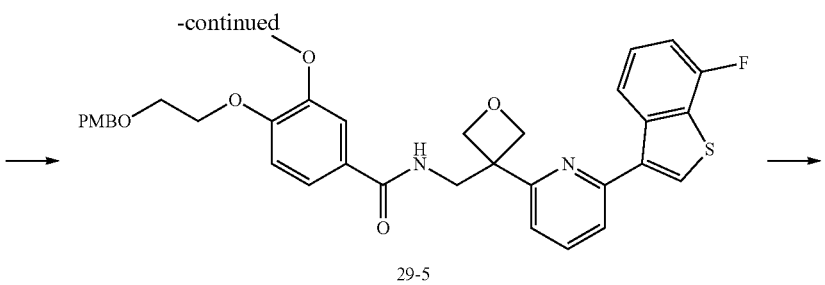

29-5

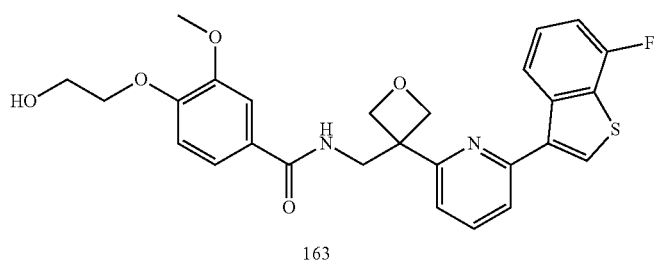

163

A 50 mL three-necked round bottle flask was charged with a solution of 2,6-dibromopyridine (1.15 g, 5 mmol, 5.0 eq.) in THF under nitrogen. The solution was cooled to −78° C., and n-BuLi (2 mL, 5 mmol, 5.0 eq.) was added dropwise. After addition, the mixture was stirred for 30 mins. A solution of 29-1 (115 mg, 1.0 mmol, 1.0 eq.) (prepared according to Wuitschik et al., *J. Med. Chem.* (2010) 53(8): 3327-3246, which hereby is incorporated by reference for the limited purpose of preparing 29-1) in THF (3~5 mL) was added dropwise. After addition, the mixture was stirred for 30 mins. The reaction was quenched with sat. NH$_4$Cl, and the mixture was extracted by EA (3×10 mL). The combined organic phase was concentrated to dryness, and the residue was purified by prep-TLC to give 29-2 as a yellow oil (80 mg). $^1$H-NMR (400 MHz, CDCl$_3$), δ=7.67-7.60 (m, 1H), 7.55 (d, J=7.5 Hz, 1H), 7.44 (d, J=8.0 Hz, 1H), 5.23 (s, 2H), 4.99 (d, J=7.0 Hz, 2H), 4.89 (d, J=7.0 Hz, 2H).

A 50 mL round bottom flask was charged with a mixture of 29-2 (0.4 g. 1.46 mmol), boric ester (0.6 g, 2.16 mmol, 1.5 eq.), Pd(dppf)Cl$_2$ (107 mg, 0.146 mmol, 0.1 eq.) and Na$_2$CO$_3$ (320 mg, 3.0 mmol, 3.0 eq.) in dioxane/H$_2$O (10 mL/2 mL). The mixture was degassed and refilled with nitrogen. The mixture was heated to reflux overnight. The mixture was cooled to r.t. and concentrated to dryness. The residue was purified by column on silica gel (5~10% EA in PE) to give 29-3 as a pink oil (0.44 g, 87% yield). $^1$H-NMR (400 MHz, CDCl$_3$), δ=8.02 (d, J=8.5 Hz, 1H), 7.92 (t, J=7.8 Hz, 1H), 7.81 (s, 1H), 7.67 (dd, J=7.8, 14.3 Hz, 2H), 7.42 (dt, J=5.5, 8.0 Hz, 1H), 7.16-7.07 (m, 1H), 5.33 (s, 2H), 5.10 (d, J=7.0 Hz, 2H), 5.00 (d, J=6.5 Hz, 2H).

A 250 mL round bottom flask was charged with a solution of 29-3 (0.4 g, 1.17 mmol) in EtOH (100 mL) and Pd/C (0.2 g). The mixture was stirred under hydrogen balloon overnight. The mixture was filtered, and concentrated to dryness. Crude 29-4 was used in the next step without further purification.

To a solution of 29-4 (270 mg, 0.86 mmol, 1.0 eq.), acid (313 mg, 0.942 mmol, 1.1 eq.) and DIEA (0.33 g, 3.0 eq.) in DMF (10 mL) was added HATU (360 mg, 0.942 mmol, 1.1 eq.), and the mixture was stirred at r.t. overnight. The mixture was diluted with EA and water. The organic phase was washed with brine, dried over anhydrous MgSO$_4$, and concentrated to dryness. The residue was purified by silica gel column (60% EA in PE) to give 29-5 as a pale yellow oil (0.4 g, 74%).

To a solution of 29-5 (0.35 g) in DCM (25 mL) was added TFA (5 mL), and the mixture was stirred at r.t. for 10 mins. The mixture was neutralized with sat. Na$_2$CO$_3$ solution. The organic phase was concentrated and purified by prep-TLC to give 163 as a white solid (70 mg). +ESI-MS: m/z 509.0 [M+H]$^+$.

Example 31

Preparation of Compound 164

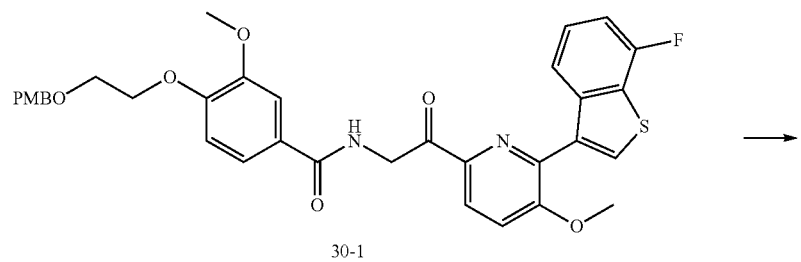

30-1

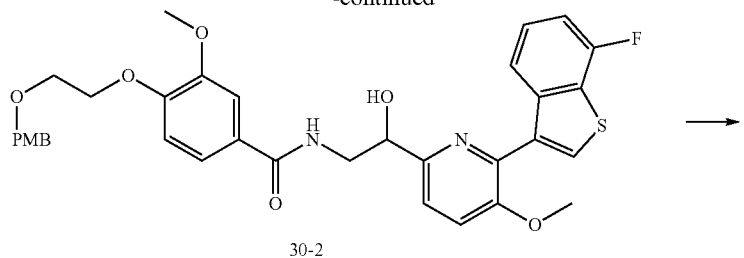

30-2

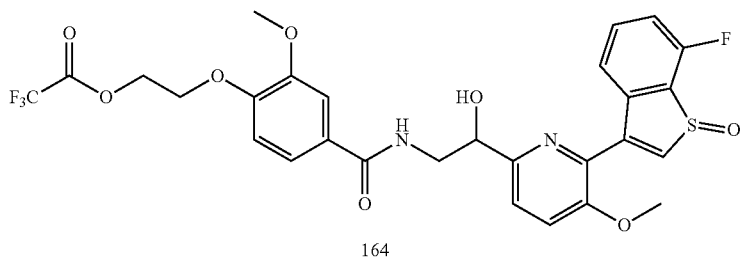

164

To a solution of 30-1 (190 mg, 0.30 mmol) in THF (5 mL) was added NaBH$_4$ (20 mg, 0.6 mmol) at r.t. MeOH (1 mL) was added, and the mixture was stirred at 20° C. for 1 h. The residue was purified by column chromatography on silica gel (PE) to provide 30-2 (190 mg, 99%).

To a solution of 30-2 (190 mg, 0.3 mmol) in DCM (3 mL) was added TFA (0.5 mL) and H$_2$O$_2$ (0.2 mL, 30%, 2 eq), and the mixture was stirred for 30 mins. The mixture was neutralized with a sat. NaHCO$_3$ solution, and extracted with DCM (3×10 mL). The solution was concentrated to give 164 in crude form (200 mg), +ESI-MS: m/z 625.0 [M+H]$^+$.

Example 32

Preparation of Compound 165

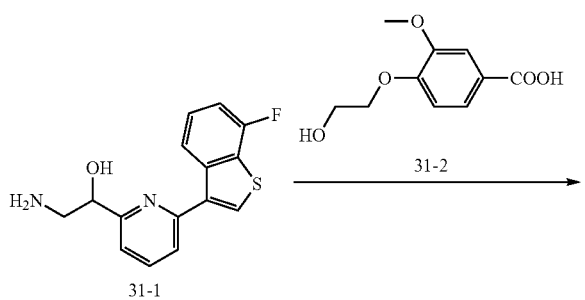

31-1

-continued

165

Compound 31-2 (106 mg, 0.5 mmol), 31-1 (140 mg, 0.5 mmol) and triethylamine (1 mmol) were dissolved in DMF (5 mL). HATU (380 mg, 1 mmol) was added to the solution. After 15-30 mins, the mixture was treated with sat. NaCl solution (100 mL), and extracted with EtOAc (3×10 mL). The combined organic phase was washed with 2N HCl solution and 5% NaHCO$_3$ solution. The organic layer were dried over anhydrous MgSO$_4$, and concentrated in vacuum to give the crude product. The crude product was purified by silica gel column chromatography eluting with EtOAc/PE (1/1) to give 165 as a white solid (24 mg, 10%). +ESI-MS: m/z 483.0 [M+H]$^+$.

Example 33

Preparation of Compound 166

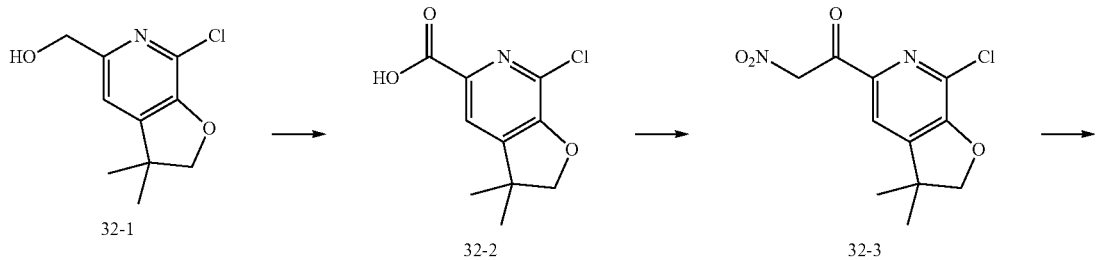

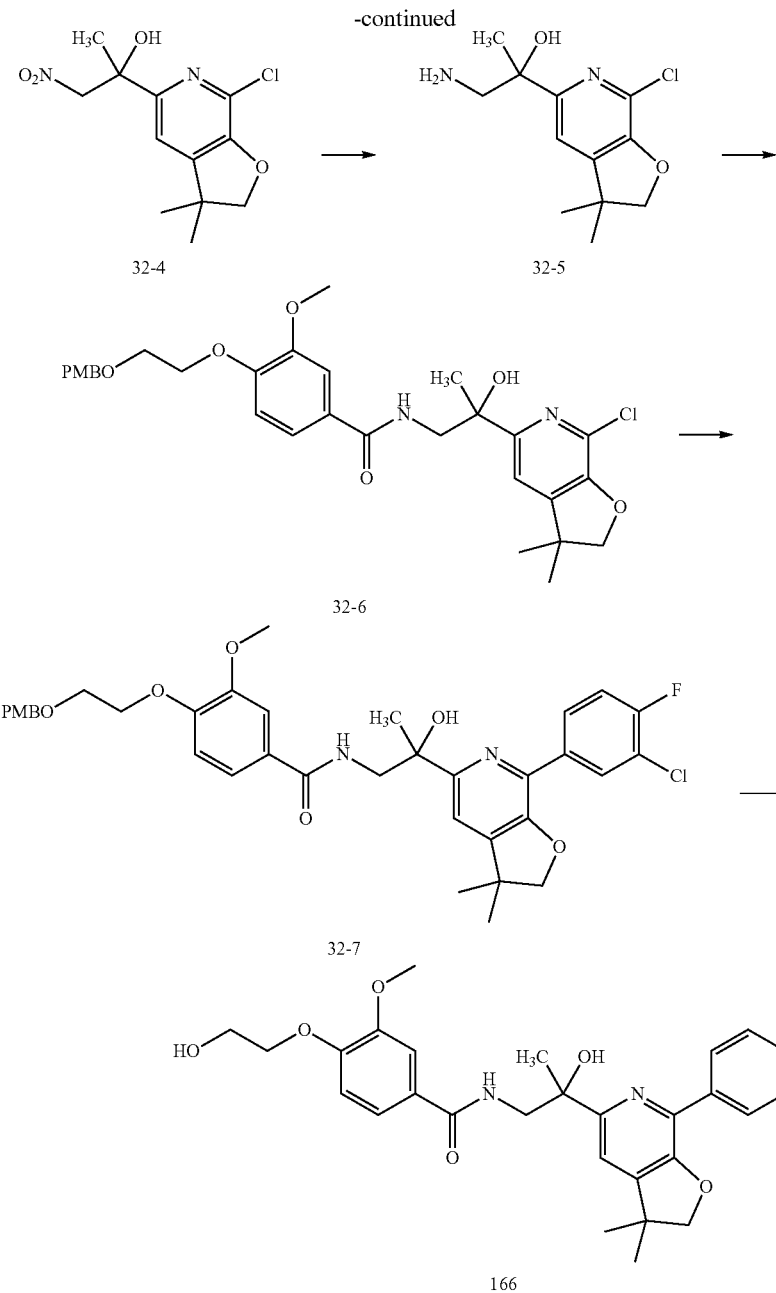

Dess-Martin periodinane (1.49 g, 3.52 mmol) was added to a stirred solution of 32-1 (300 mg, 1.40 mmol) in dry DCM (6.5 mL). The mixture was stirred at r.t. for 1 h and quenched with a 1:1 mixture of 2M aq. $Na_2S_2O_3$ solution and sat. aq. $NaHCO_3$ solution (10 mL). The mixture was stirred vigorously for 30 mins and the layers were separated. The organic portion was washed with brine, dried ($Na_2SO_4$), filtered and concentrated under reduced pressure. The crude aldehyde was progressed to the next step without further purification. The aldehyde was dissolved in tert-butanol (21 mL). To the solution, 2-methyl-2-butene (1.13 mL, 13.5 mmol) and a solution of sodium chlorite (244 mg, 2.70 mmol) and sodium phosphate monobasic dihydrate (1.36 g, 8.70 mmol) in water (21 mL) were added. The mixture was stirred at r.t. for 18 h. Brine was added and the mixture was extracted 3 times with EtOAc. The combined organic portions were dried ($Na_2SO_4$) and filtered. The volatiles were removed under reduced pressure. Acid 32-2 (310 mg) was progressed to the next step without further purification. UPLC/MS ($ES^+$): m/z 228.07 $[M+H]^+$.

1,1'-Carbonyldiimidazole (1.17 g, 7.21 mmol) was added to a solution of 32-2 (250 mg) in THF (9.6 mL). The mixture was stirred at r.t. for 30 mins and then nitromethane (671 mg, 11.0 mmol) and potassium carbonate (608 mg, 4.40 mmol) were added. After 3 h, the volatiles were removed under reduced pressure. The residue was taken up with EtOAc. The organic portion was washed with water, dried with $Na_2SO_4$, filtered and concentrated under reduced pressure. Crude 32-3 (300 mg) was progressed to the next step without further purification. UPLC/MS ($ES^+$): m/z 271.05 $[M+H]^+$.

Methylmagnesium bromide (3M solution in Et$_2$O, 204 uL, 0.612 mmol) was added to a solution of 32-3 (300 mg) in THF (8 mL), which had been pre-cooled to −40° C. The mixture was stirred at −40° C. for 1 h, allowed to reach r.t. and then quenched with 1M aq. HCl solution. The aqueous portion was extracted twice with EtOAc. The combined organic portions were dried with Na$_2$SO$_4$, filtered and concentrated under reduced pressure. Crude 32-4 was progressed to the next step without further purification. UPLC/MS (ES$^+$): m/z 287.10 [M+H]$^+$.

NaBH$_4$ (52.0 mg, 1.38 mmol) was added to a solution of NiCl$_2$-6H$_2$O (109 mg, 0.460 mmol) in MeOH (10 mL). After 30 mins, nitro-derivative 32-4 (250 mg) dissolved in MeOH (2 mL) was added, followed by additional solid NaBH$_4$ (70 mg). The reaction was monitored by UPLC. When complete, the mixture was filtered through a pad of celite and the organic portion was concentrated under reduced pressure. Crude 32-5 (235 mg) was progressed to the next step without further purification. UPLC/MS (ES$^+$): m/z 257.17 [M+H]$^+$.

A mixture of 32-5 (235 mg), 3-methoxy-4-{2-[(4-methoxyphenyl)methoxy]ethoxy}benzoic acid (365 mg, 1.10 mmol), EDC (263 mg, 1.38 mmol), HOBT (186 mg, 1.38 mmol) and TEA (255 uL, 1.84 mmol) in DCM (8 mL) was stirred at r.t. for 3 h. The mixture was washed twice with 1M aq. HCl solution. The organic portion was dried (Na$_2$SO$_4$), filtered and concentrated under reduced pressure. Chromatography of the residue (cyclohexane-EtOAc, 60:40 to 10:90) afforded 32-6 as an off-white solid (60 mg, 12% starting from 32-1). UPLC/MS (ES$^+$): m/z 571.20 [M+H]$^+$.

A mixture of 32-6 (60 mg, 0.100 mmol), (3-chloro-4-fluorophenyl)boronic acid (91.0 mg, 0.500 mmol), Pd(dppf)Cl$_2$ (3.6 mg, 0.005 mmol) and aq. Na$_2$CO$_3$ (2M solution, 0.500 mmol, 250 uL) in DCE (1 mL) was degassed and then stirred with heat to 85° C. for 4 h. Water and DCM were added, and the layers were separated. The organic phase was dried with Na$_2$SO$_4$, filtered and evaporated. Chromatography of residue (cyclohexane:EtOAc, 100:0 to 20:80) afforded 32-7 (46 mg, 69%). UPLC/MS (ES$^+$): m/z 665.47 [M+H]$^+$.

A solution of 32-7 (46.0 mg, 0.069 mmol) in 10:1 DCM-TFA (1.1 mL) was stirred at room temperature for 1 h. 1M aq. NaOH solution was added and the mixture was stirred for 15 mins. The layers were separated. The organic portion was dried (Na$_2$SO$_4$), filtered and concentrated under reduced pressure. The residue was purified by reverse phase chromatography (water:CH$_3$CN, 100:0 to 50:50) to afford 166 as a white solid (racemic mixture, 18 mg, 33%). UPLC/MS (ES$^+$): m/z 545.33 [M+H]$^+$.

Example 34

Preparation of Compound 167

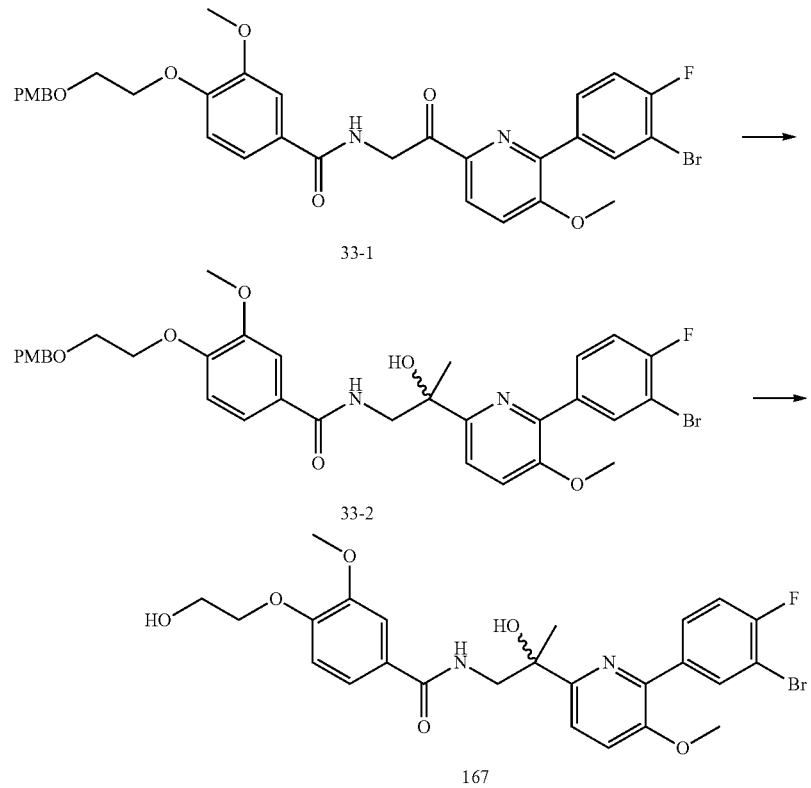

To a stirring mixture of 33-1 (40 mg, 0.061 mmol) in THF (1.0 mL) at r.t. under argon was added a solution of MeMgBr (1.4 M) in THF (0.5 mL) dropwise. The mixture was reacted at r.t. for 1 h. The mixture was diluted with EtOAc and quenched with a sat. NH$_4$Cl solution. The mixture was stirred at r.t. for 10 mins and the layers were separated. The aqueous layer was extracted with EtOAc. The organic layers were dried (Na$_2$SO$_4$), filtered and concentrated under reduced pressure. The crude mixture was purified via silica gel column to afford 33-2 as a white solid. LCMS: m/z 669.1 [M+H]$^+$.

To a stirring mixture of 33-2 (20 mg, 0.0299 mmol) in DCM (1.0 mL) at r.t. was added dropwise TFA (0.2 mL). The mixture was stirred at r.t. for 10 mins and then concentrated under reduced pressure. The crude product mixture was purified via prep-HPLC to afford 167. LCMS: m/z 549.05 [M+H]⁺.

Example 35

Preparation of Compound 168

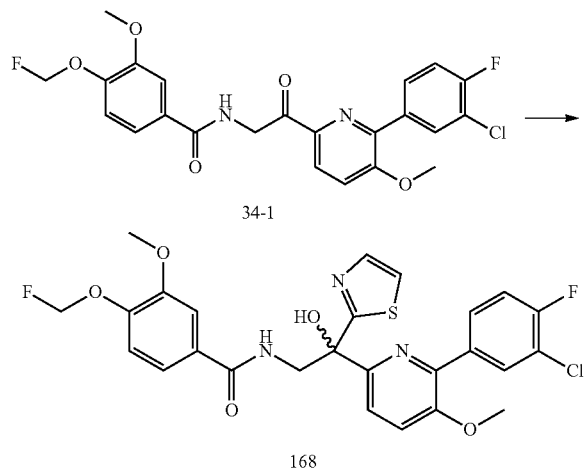

To a stirring mixture of 2-bromothiazole (0.2 g, 1.22 mmol) in THF under Ar at −78° C. was added dropwise a solution of n-BuLi (2.5 M) in hexane (0.49 mL, 1.22 mmol). The mixture was stirred at −78° C. for 15 mins and then a solution of 34-1 (40 mg, 0.081 mmol) in THF (0.5 mL) was added. The mixture was stirred at −78° C. for 1 h and then warmed to r.t. for 10 mins. The mixture was diluted with EtOAc and quenched with a sat. NH₄Cl solution. The mixture was stirred at r.t. for 10 mins and then the layers were separated. The aqueous layer was extracted with EtOAc (2×15 mL). The organic layers were dried (Na₂SO₄), filtered and concentrated under reduced pressure. The crude mixture was purified via silica gel chromatography and further purified via prep-HPLC to afford 168 as a tan solid. LCMS: m/z 576.1 [M+H]⁺.

Example 36

Preparation of Compound 169

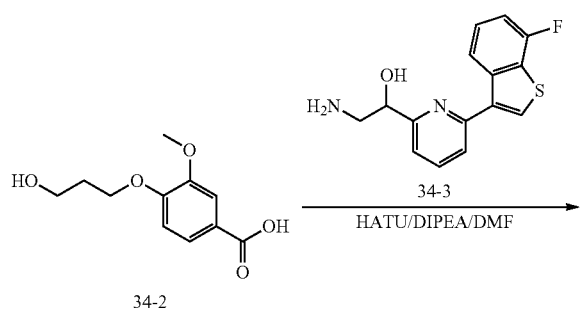

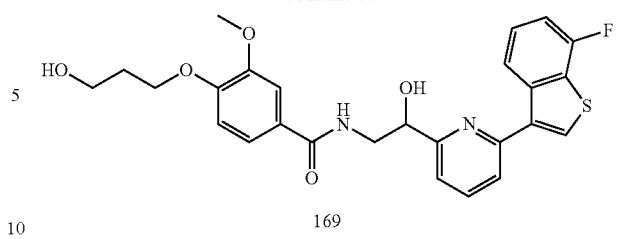

To a solution of 34-2 (100 mg, 0.442 mmol), HATU (251 mg, 0.66 mmol) and DIPEA (170 mg, 1.32 mmol) in anhydrous DMF (2 mL) was added 34-3 (127 mg 0.442 mmol) at 25° C. The solution was stirred for 10 h at r.t. and then diluted with 1.0 N aqueous NaHCO₃ solution (2×40 mL), extracted with EA (2×20 mL). The combined organic layers were washed with brine, dried over anhydrous Na₂SO₄, and concentrated under reduced pressure. The residue was purified on a silica gel column to give 169 (120 mg, 54.8%). +ESI-MS: m/z 497.1 [M+H]⁺.

Example 37

Preparation of Compound 170

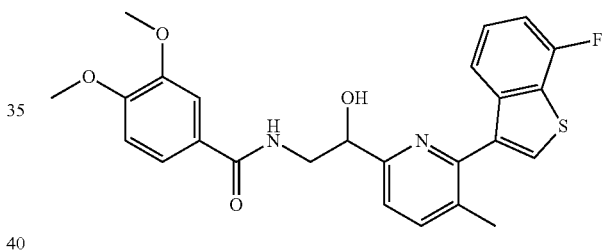

Compound 170 was prepared using 2,6-dichloro-3-methylpyridine, 2-(7-fluorobenzo[b]thiophen-3-yl)-4,4,5,5-tetramethyl-1,3,2-dioxaborolane and 3,4-dimethoxybenzoic acid, and by closely following a synthetic route, which closely follows that described for the preparation of 1. +ESI-MS: m/z 464.9 [M+H]⁺.

Example 38

Preparation of Compounds 171 and 172

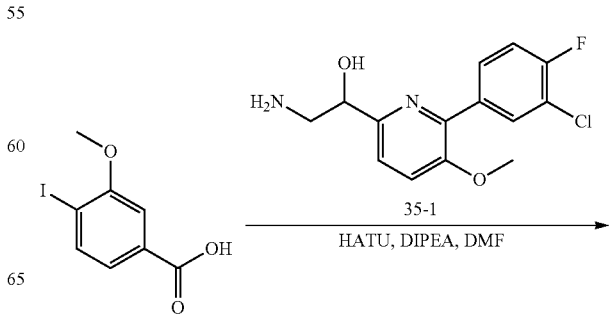

-continued

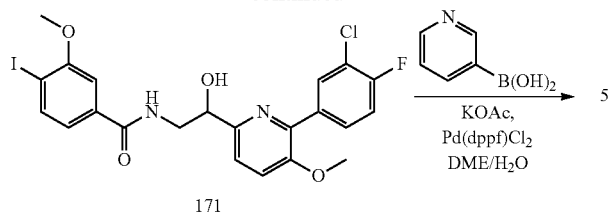

171

172

To a solution of 3-methoxy-4-iodobenzoic acid (0.45 g, 1.6 mmol), 35-1 (0.485 g, 1.6 mmol), HATU (0.75 g, 2.0 mmol) in DMF (3 mL) was added DIEA (0.71 mL, 4.1 mmol). The solution was stirred for 18 h at r.t. The mixture was diluted with EA. The organic phase was washed with water, 1N HCl, NaHCO$_3$ and brine, dried over anhydrous Na$_2$SO$_4$, and concentrated. The residue was purified by chromatography on silica gel (MeOH/CH$_2$Cl$_2$) to give 171 (0.176 g, 51%). $^1$H NMR (400 MHz, CDCl$_3$): δ 7.99 (dd, J=2.15, 7.24, 1H), 7.81-7.85 (m, 1H), 7.75 (d, J=8.02, 1H), 7.37-7.42 (m, 2H), 7.26-7.27 (m, 1H), 7.25 (t, J=8.71, 1H), 6.93 (dd, J=1.96, 8.02), 6.83-6.86 (m, 1H), 4.97-4.99 (m, 1H), 3.99-4.13 (m, 1H), 3.90 (s, 3H), 3.89 (s, 3H), 3.54-3.72 (m, 1H).

A solution of 171 (25 mg, 0.045 mmol), pyridine-3-boronic acid (11 mg, 0.09 mmol), potassium acetate (13 mg, 0.13 mmol) and Pd(dppf)Cl$_2$ (6 mg, 0.009 mmol) in DME (0.5 mL) and H$_2$O (0.05 mL) was heated under microwave irradiation for 1 h at 110° C. The mixture was concentrated and purified by chromatography on silica gel (MeOH/CH$_2$Cl$_2$) to give 172 (22 mg, 88%). $^1$H NMR (400 MHz, CDCl$_3$): δ 8.74-8.90 (br. s, 1H), 8.60-8.72 (br. s, 1H), 8.00, dd, J=2.15, 7.24), 7.85-7.88 (m, 2H), 7.34-7.45 (m, 5H), 7.17, (t, J=8.80, 1H), 6.94-6.97 (m, 1H), 4.98-5.01 (m, 1H), 4.00-4.09 (m, 1H), 3.88 (s, 3H), 3.82 (s, 3H0, 3.68-3.75 (m, 1H).

Example 39

Preparation of Compound 173

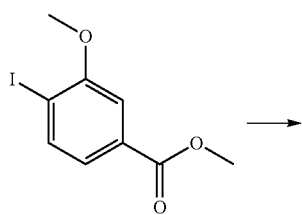

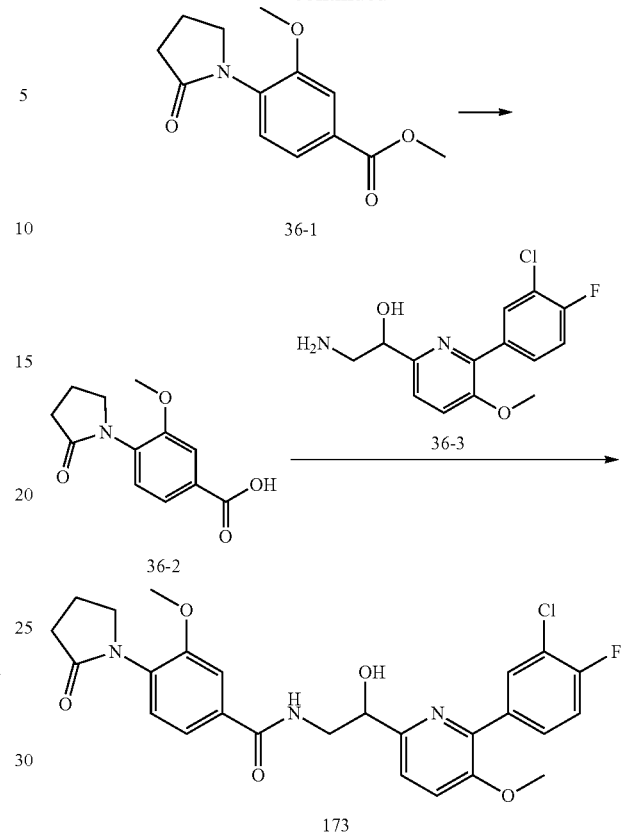

To a solution of methyl 3-methoxy-4-iodobenzoate (250 mg, 0.85 mmol) in toluene (2 mL) was added pyrrolidinone (150 mg, 1.7 mmol), potassium phosphate (0.55 g, 2.2 mmol), xantphos (25 mg, 0.43 mmol) and tris(dibenzylideneacetone)dipalladium(0) (40 mg, 0.43 mmol). The mixture was heated at 110° C. for 3 h. The mixture was then diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 36-1 (0.178 g, 83%). LCMS: m/z 478.10 [M+H]$^+$.

To a solution of 36-1 (0.178 g, 0.72 mmol) in methanol (6 mL) was added NaOH (2.0 M, 2.0 mL) at 25° C. The solution was stirred for 15 h, acidified with 2N HCl and extracted with EA. The combined organic phase was dried over anhydrous Na$_2$SO$_4$ to give 36-2 (0.152 g, 90%). $^1$H NMR (400 MHz, CDCl$_3$): δ 7.52 (dd, J=1.77, 8.22 Hz, 1H), 7.51 (d, J=1.77 Hz, 1H), 7.30 (d, J=8.22 Hz, 1H), 3.82 (s, 3H), 3.75 (t, J=7.04 Hz, 2H), 2.55 (t, J=8.02 Hz, 2H), 2.0-2.3 (m, 2H).

To a solution of 36-2 (0.152 g, 0.65 mmol), 36-3 (0.19 g, 0.65 mmol), HATU (0.37 g, 0.97 mmol) in DMF (1 mL) was added DIEA (0.23 mL, 1.3 mmol). The solution was stirred for 2 h at r.t. The mixture was diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 173 (0.172 g, 51%). LCMS: m/z 478.10 [M+H]$^+$.

Example 40
Preparation of Compound 174
Example 41
Preparation of Compound 175
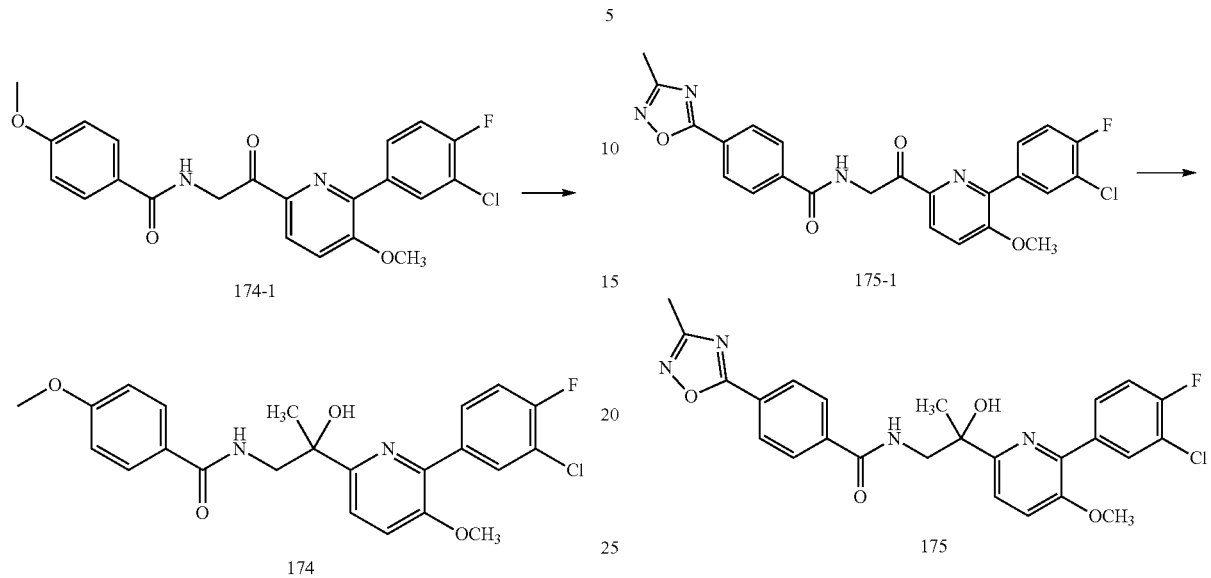
Addition of MeMgBr to 174-1 afforded 174 as a white solid (50%). UPLC/MS (ES+): m/z 445.27 [M+H]+.
Addition of MeMgBr to 175-1 afforded 175 as a white solid (10%). UPLC/MS (ES+): m/z 497.1 [M+H]+.
Example 42
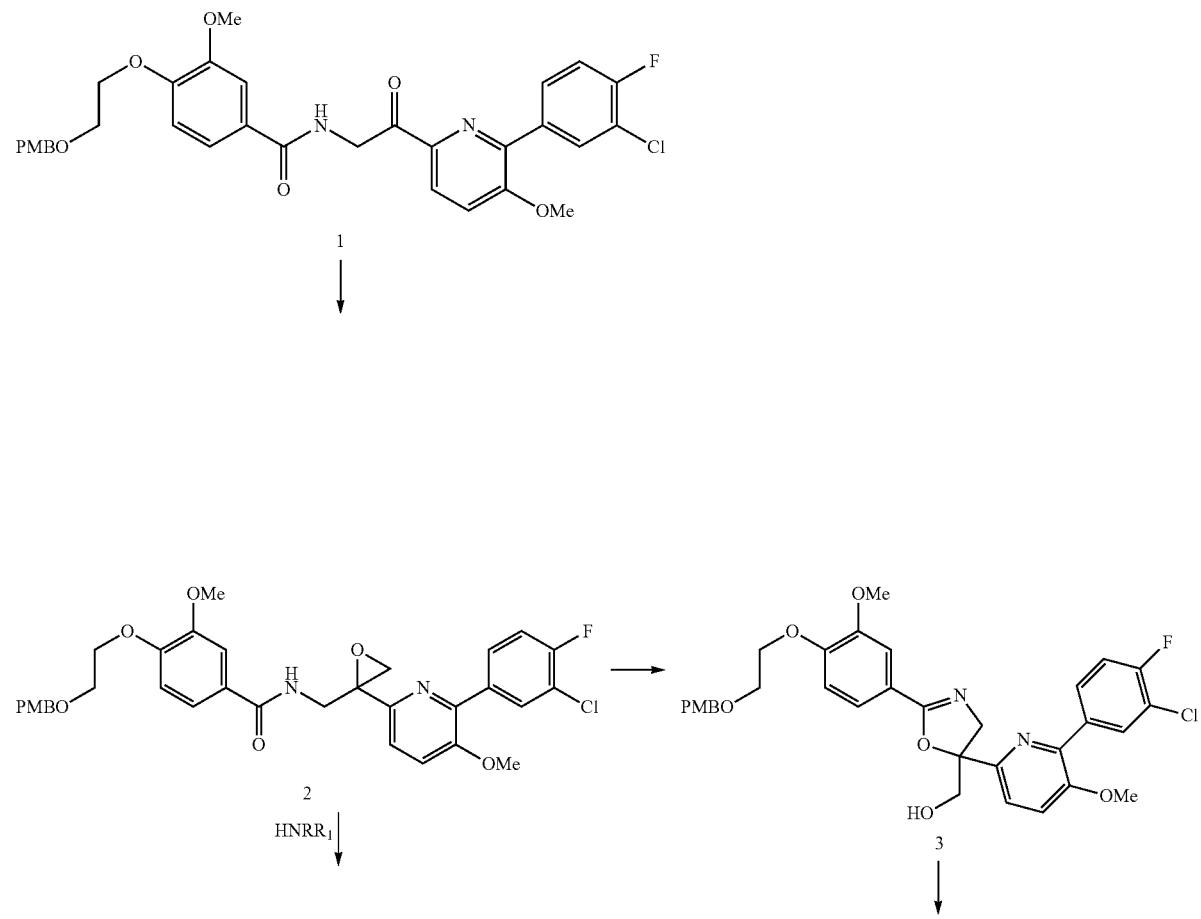

133

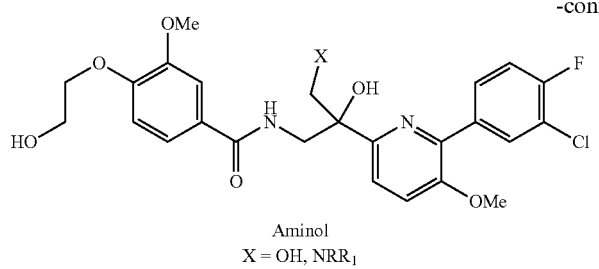

Aminol
X = OH, NRR₁

134

-continued

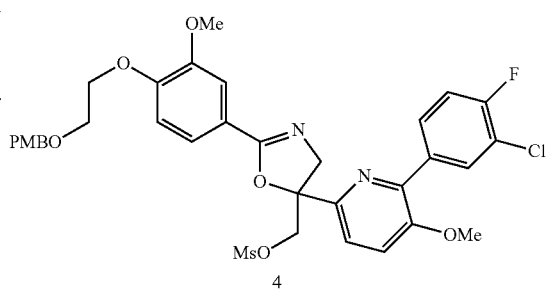

4

Trimethylsulfoxonium iodide (1.19 g, 5.41 mmol) was added to a solution of potassium tert-butoxide (551 mg, 4.92 mmol) in DMSO (10 mL). The mixture was stirred at r.t. for 30 mins. A solution of N-{2-[6-(3-chloro-4-fluorophenyl)-5-methoxypyridin-2-yl]-2-oxoethyl}-3-methoxy-4-{2-[(4-methoxyphenyl)methoxy]ethoxy}benzamide (1, 3.00 g, 4.92 mmol) in DMSO (20 mL) was added. The mixture was stirred at r.t. for 10 mins. The mixture was diluted with EtOAc and water. The layers were separated, and the aqueous portion was extracted with EtOAc. The combined organic extracts were washed with brine, dried with Na₂SO₄ and concentrated under reduced pressure to afford the crude epoxide 2 (3.34 g). Epoxide 2:UPLC/MS (ES⁺): m/z 623.40 [M+H+]. With chromatography (cyclohexane-EtOAc, 75:25 to 50:50), epoxide 2 quantitatively rearranged to oxazoline 3 (1.92 g recovered from 3 g of crude 2). Oxazoline 3: UPLC/MS (ES⁺): m/z 623.29 [M+H+].

Method A:

A mixture of epoxide 2 (100 mg, crude) and an amine (10 eq.) in MeOH (1 mL) was stirred at r.t. or heated to 100° C. When complete, the reaction was concentrated under reduced pressure. The residue was dissolved in a 10:1 DCM:TFA mixture (2.2 mL). After 30 mins of stirring at r.t., a 2M aq. NaOH solution was added. The mixture was stirred at r.t. for 10 mins. The layers were separated, and the aqueous portion extracted with DCM. The combined organic portions were dried with Na₂SO₄, filtered and concentrated under reduced pressure. Chromatography of the residue afforded the aminol.

Method B:

A mixture of epoxide 2 (150 mg, crude), an amine (2 eq.) and K₂CO₃ (66.0 mg, 2 eq.) in DMF (2 mL) was stirred at 50° C. When complete, the reaction was diluted with EtOAc. The organic portion was washed twice with water, dried with Na₂SO₄, filtered and concentrated under reduced pressure. The residue was dissolved in DCM (2 mL) and treated with TFA (300 uL). After 1 h, the reaction was quenched with 2M aq. NaOH solution. The layers were separated, and the organic portion was concentrated under reduced pressure. Chromatography of the residue afforded the aminol.

Method C:

TEA (270 uL, 1.93 mmol) and MsCl (150 uL, 1.93 mmol) were added to a solution of 3 (600 mg, 0.964 mmol) in DCM (4 mL). The mixture was stirred at r.t. for 2 h. The mixture was poured into 1M aq. HCl solution and extracted with DCM. The combined organic portions were dried with Na₂SO₄ and filtered. The volatiles were removed under reduced pressure to afford the crude mesylate 4, which was directly used in the next step. A mixture of 4 (80 mg) and an amine (50 uL) in MeOH (2 mL) was heated to 85° C. in a sealed vial. When complete, the reaction was concentrated under reduced pressure. The residue was dissolved in MeOH (1.5 mL) and treated with a 6M aq. HCl solution (1.5 mL). The mixture was heated to 65° C. for 2 h. After cooling to r.t., the mixture was purified by reverse phase chromatography to afford the aminol.

Method D:

A mixture of epoxide 2 (50 mg, crude) and an amine (10 eq.) was heated to 60° C. under microwave irradiation. When complete, the reaction was concentrated under reduced pressure. The residue was dissolved in DCM (2 mL) and treated with TFA (300 uL). After 1 h, the reaction was quenched with 2M aq. NaOH solution. The layers were separated, and the organic portion was concentrated under reduced pressure. Chromatography of the residue afforded the aminol.

Example 43

Preparation of Compound 176

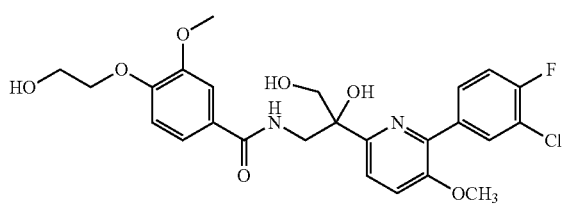

176

Epoxide 2 (200 mg, crude) was dissolved in a 1:1 MeOH: 6M aq. HCl solution (2 mL), and the mixture was stirred at 60° C. for 2 h. The mixture was basified with 6M aq. NaOH solution and purified by reverse phase chromatography (water:CH₃CN, 100:0 to 50:50) to afford 176 as an off-white solid (40.2 mg). UPLC/MS (ES⁺): m/z 521.10 [M+H]⁺.

Example 44

Preparation of Compound 177

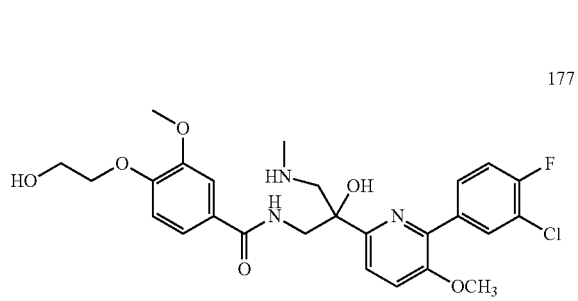 [SMILES: CNCC(O)(CNC(=O)c1ccc(OCCO)c(OC)c1)c1ccc(OC)c(-c2ccc(F)c(Cl)c2)n1]

177

Reaction of epoxide 2 with a 2M MeNH$_2$-MeOH solution followed by PMB-group removal according to Method A afforded 177 as a white solid (13% over 3 steps). UPLC/MS (ES$^+$): m/z 534.30 [M+H]$^+$.

Example 45

Preparation of Compound 178

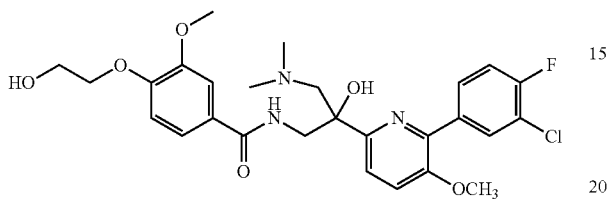

178

Reaction of epoxide 2 with a 2M Me$_2$NH-MeOH solution followed by PMB-group removal according to Method A afforded 178 as a white solid (37% over 3 steps). UPLC/MS (ES$^+$): m/z 548.30 [M+H]$^+$.

Example 46

Preparation of Compound 179

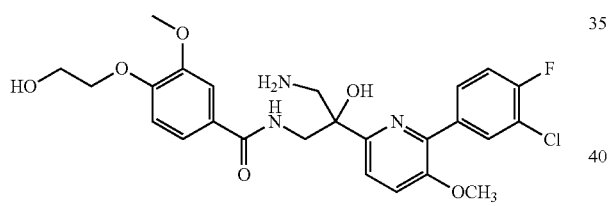

179

Reaction of epoxide 2 with a 7M NH$_3$-MeOH solution followed by PMB-group removal according to Method A afforded 179 as a white solid (24% over 3 steps). UPLC/MS (ES$^+$): m/z 520.40 [M+H]$^+$.

Example 47

Preparation of Compound 180

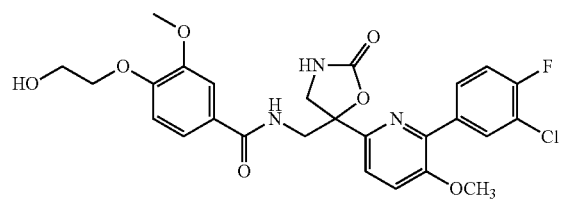

180

A solution of 179 (10.0 mg, 0.019 mmol) and triphosgene (5.0 mg, 0.019 mmol) in a 1:1 5% aq. NaHCO$_3$:MeOH mixture (1 mL) was stirred and heated at 40° C. for 3 h. The volatiles were removed under reduced pressure to afford a 30:70 mixture of 180 and the corresponding methyl carbamate. This mixture was dissolved in DMF (0.5 mL) and treated with NaH (60% oil dispersion, 1 mg). After 30 mins, the reaction was quenched with MeOH, and the volatiles were removed under reduced pressure. The residue was purified by reverse phase chromatography (0.1% HCOOH:water-0.1% HCOOH:CH$_3$CN, 100:0 to 30:70) to afford 180 as a white solid (4.0 mg, 39%). UPLC/MS (ES$^+$): m/z 546.30 [M+H]$^+$.

Example 48

Preparation of Compound 181

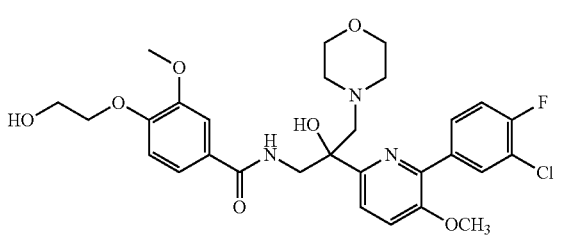

181

Reaction of epoxide 2 with morpholine followed by PMB-group removal according to Method B afforded 181 as a white solid (10% over 3 steps). UPLC/MS (ES$^+$): m/z 590.40 [M+H]$^+$.

Example 49

Preparation of Compound 182

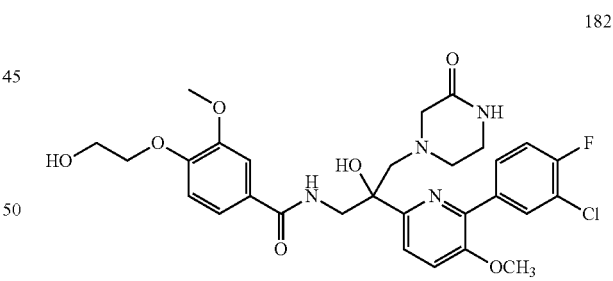

182

A mixture of epoxide 2 (100 mg, crude), ketopiperazine (80 mg, 0.80 mmol) and K$_2$CO$_3$ (155 mg, 1.13 mmol) in DMF (2 mL) was stirred at 60° C. for 18 h. The mixture was diluted with EtOAc, and the organic portion was washed with water (2×), dried with Na$_2$SO$_4$, filtered and concentrated under reduced pressure. The residue was dissolved in MeOH (2 mL) and treated with 3M aq. HCl solution (500 uL). The mixture was heated to 80° C. and stirred at 80° C. for 30 mins. The volatiles were removed under reduced pressure. The residue was purified by reverse phase chromatography (water-CH$_3$CN, 100:0 to 0:100) to afford 182 as a light yellow solid (14% over 3 steps). UPLC/MS (ES$^+$): m/z 603.30 [M+H]$^+$.

Example 50

Preparation of Compound 183

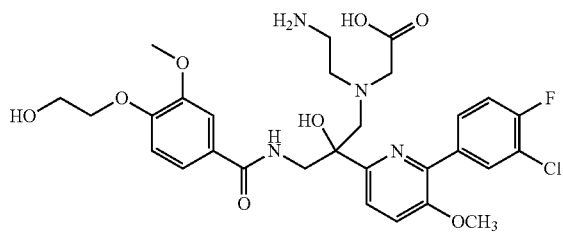
183

Reaction of epoxide 2 with ketopiperazine followed by PMB-group removal according to Method B afforded 183 as a light yellow solid (10% over 3 steps). UPLC/MS (ES+): m/z 621.40 [M+H]+.

Example 51

Preparation of Compounds 184, 185 and 186

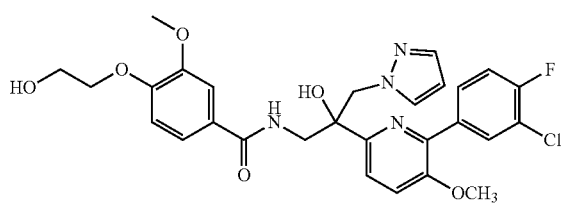
184, 185 and 186

Reaction of epoxide 2 with pyrazole followed by PMB-group removal according to Method B afforded 184 as a racemic mixture (32% over 3 steps). This mixture was resolved by using a prep-HPLC separation [Chiralpak AD-H (25×2.0 cm), 5 µM; mobile phase: Ethanol+0.1% isopropylamine 30%, flow rate: 46 mL/min, UV detection DAD 220 nm] to afford the two separated enantiomers 185 ($t_R$=11.0 min) and 186 ($t_R$=12.5 min). Analytical data for the single enantiomers: white solid. UPLC/MS (ES+): m/z 571.36

Example 52

Preparation of Compound 187

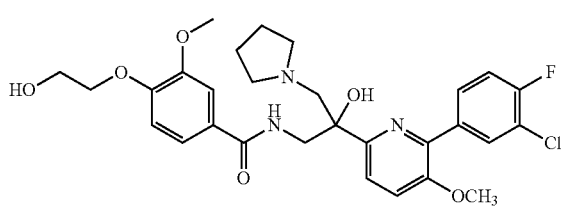
187

Reaction of mesylate 4 with pyrrolidine followed by PMB-group removal according to Method C afforded 187 as a white solid (55% over 3 steps). UPLC/MS (ES+): m/z 574.20 [M+H]+.

Example 53

Preparation of Compound 188

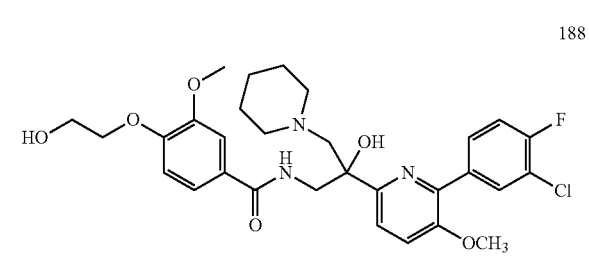 [SMILES: COc1cc(C(=O)NCC(O)(CN2CCCCC2)c2ccc(OC)c(-c3ccc(F)c(Cl)c3)n2)ccc1OCCO]
188

Reaction of mesylate 4 with piperidine followed by PMB-group removal according to Method C afforded 188 as a white solid (6% over 3 steps). UPLC/MS (ES+): m/z 588.20 [M+H]+.

Example 54

Preparation of Compound 189

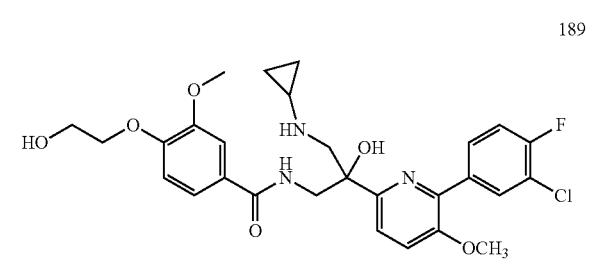 [SMILES: COc1cc(C(=O)NCC(O)(CNC2CC2)c2ccc(OC)c(-c3ccc(F)c(Cl)c3)n2)ccc1OCCO]
189

Reaction of epoxide 2 with cyclopropylamine followed by PMB-group removal according to Method D afforded 189 as a white solid (11% over 3 steps). UPLC/MS (ES+): m/z 560.10 [M+H]+.

Example 55

Preparation of Compound 190

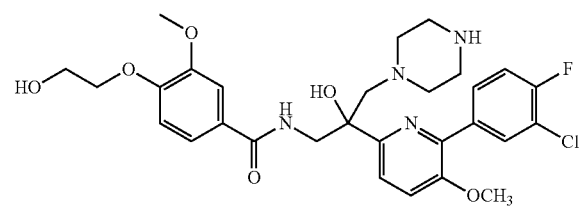
190

Reaction of epoxide 2 with 1-Boc-piperazine followed by PMB-group removal according to Method C afforded 190 (17% over 3 steps). UPLC/MS (ES⁺): m/z 589.30 [M+H]⁺.

Example 56

Preparation of Compound 191

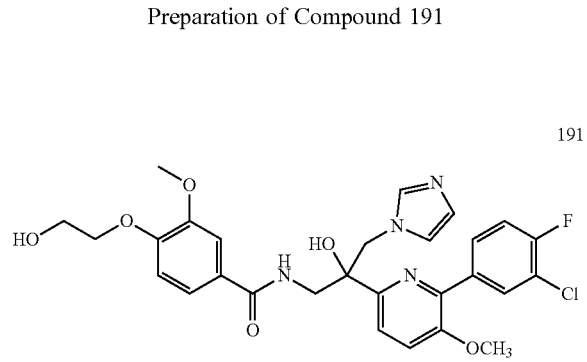

Reaction of epoxide 2 with imidazole followed by PMB-group removal according to Method B afforded 191 as a white solid (12% over 3 steps). UPLC/MS (ES⁺): m/z 571.30 [M+H]⁺.

Example 57

Preparation of Compounds 192 and 193

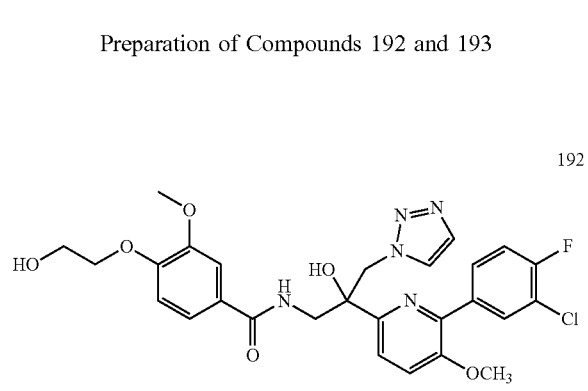

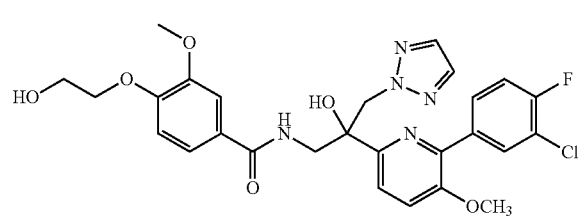

Reaction of epoxide 2 with 1H-1,2,3-triazole followed by PMB-group removal according to Method B afforded compounds 192 (10% over 3 steps) and 193 (18% over 3 steps). 192: UPLC/MS (ES⁺): m/z 572.30 [M+H]⁺. 193: UPLC/MS (ES⁺): m/z 572.30

Example 58

Preparation of Compound 194

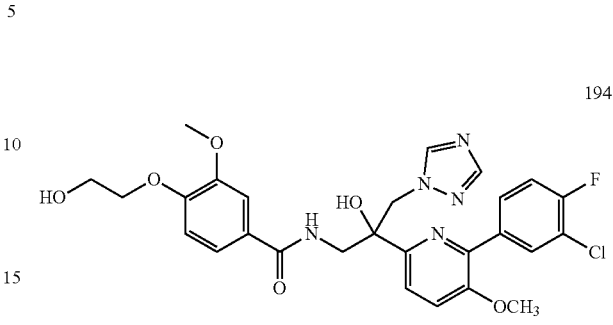

Reaction of epoxide 2 with 1H-1,2,4-triazole followed by PMB-group removal according to Method B afforded compound 194 (24% over 3 steps). UPLC/MS (ES⁺): m/z 572.30 [M+H]⁺.

Example 59

Preparation of Compound 195

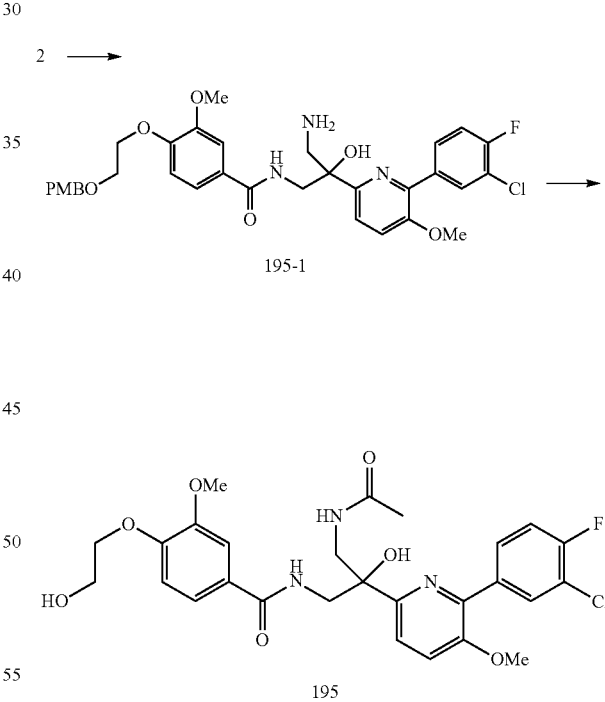

A mixture of epoxide 2 (80 mg, crude) and 7M NH₃-MeOH (1.5 mL) in MeOH (2 mL) was stirred at r.t. for 18 h. The volatiles were removed under reduced pressure. The resulting crude 195-1 was dissolved in DCM (1 mL) and treated with TEA (15 uL) and AcCl (11 uL). The mixture was stirred at r.t. for 1 h. The volatiles were removed under reduced pressure. Deprotection of the PMB-ether using TFA:DCM afforded 195 as a white solid (7% overall). UPLC/MS (ES⁺): m/z 562.30 [M+H]⁺.

Example 60

Preparation of Compound 196

2 ⟶

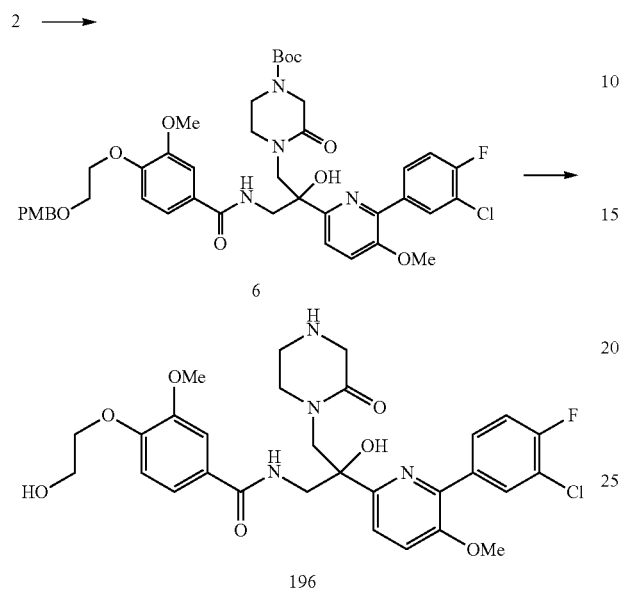

n-BuLi (1.6M solution in hexanes, 650 µL, 1.04 mmol) was added to a suspension of tert-butyl 3-oxopiperazine-1-carboxylate (160 mg, 0.800 mmol) in dry THF (2 mL), which had been pre-cooled to 0° C. The mixture was stirred for 5 mins at 0° C. and then warmed to r.t. After 5 mins, a solution of epoxide 2 (200 mg, crude) in THF (1 mL) was added. The mixture was heated to 50° C. and stirred at 50° C. for 12 h. Water and EtOAc were added. The layers were separated, and the aqueous portion was extracted with EtOA. The combined organic portions were dried with Na2SO4 and filtered. The volatiles were removed under reduced pressure. The crude 6 was dissolved in MeOH (5 mL) and treated with 6M aq. HCl solution (2 mL). The mixture was heated to 60° C. and stirred at 60° C. for 1.5 h. A majority of the volatiles were removed under reduced pressure. The residue was purified by reverse phase chromatography (water:CH$_3$CN 100:0 to 40:60) to afford 196 as a white solid (31 mg, 16% over 3 steps). UPLC/MS (ES$^+$): m/z 603.30 [M+H]$^+$.

Example 61

Preparation of Compound 197

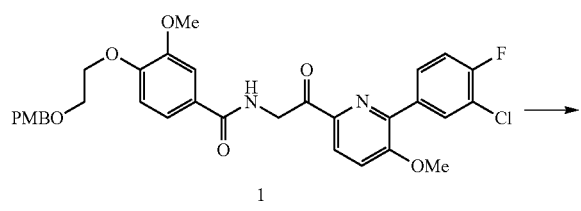

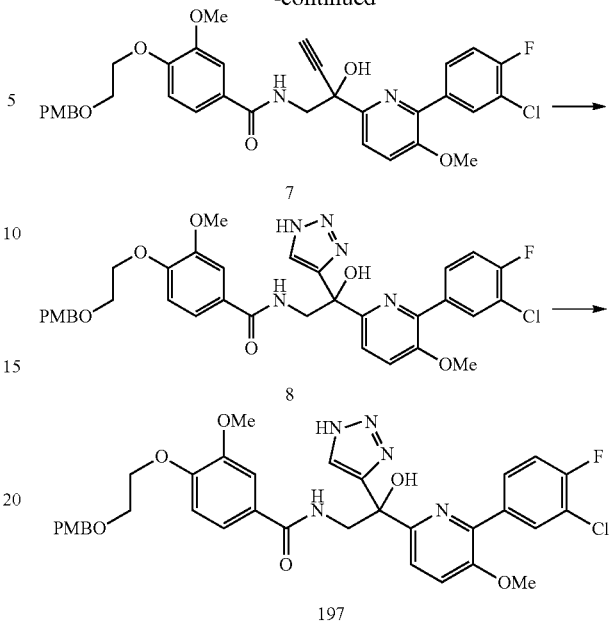

Bromo(ethynyl)magnesium (4.90 mL, 2.46 mmol) was added to a solution of 1 (300 mg, 0.493 mmol) in THF (15 mL), which had been warmed to 55° C. The mixture was stirred for 30 mins and quenched with sat. aq. NH4Cl solution. The aqueous portion was extracted with EtOAc (2×). The combined organic portions were dried with Na$_2$SO$_4$, filtered and concentrated under reduced pressure. Chromatography of the residue (DCM:EtOAc, 100:0 to 80:20) afforded 7 as a light yellow solid (130 mg, 41%). UPLC/MS (ES$^+$): m/z 635.20 [M+H]$^+$.

A mixture of aq formaldehyde (37% solution, 630 uL, 0.780 mmol) and glacial AcOH (7 uL, 0.117 mmol) in THF (500 uL) was stirred at r.t. for 15 mins. Sodium azide (7.6 mg, 0.117 mmol) and 7 (50.0 mg, 0.078 mmol) were sequentially added. After 10 mins, aq. sodium ascorbate (0.5 M solution, 32 uL, 0.016 mmol) and CuSO$_4$ (1.2 mg, 0.008 mmol) were added. The mixture was stirred at r.t. for 18 h. The volatiles were removed under reduced pressure. The residue was treated with a 3:1 MeOH:2N aq NaOH solution (4 mL), and the mixture was stirred at r.t. for 18 h. The volatiles were removed under reduced pressure, and the residue was partitioned between EtOAc and water. The layers were separated, and the organic portion was dried with Na$_2$SO$_4$, filtered and concentrated under reduced pressure to afford crude 8 (34 mg), which was used in next step without further purification. UPLC/MS (ES$^+$): m/z 678.25 [M+H]$^+$.

A solution of 8 (34 mg) in 10:1 DCM-TFA (5 mL) was stirred at r.t. for 20 mins. The reaction was quenched with 2M aq. NaOH solution. The layers were separated, and the organic portion was concentrated under reduced pressure. The residue was purified by reverse phase chromatography (water:CH$_3$CN, 95:5 to 0:100) to afford 197 as a white solid (5.5 mg, 13% over 2 steps). UPLC/MS (ES$^+$): m/z 558.11 [M+H]$^+$.

Example 62

Preparation of Compounds 198 and 199

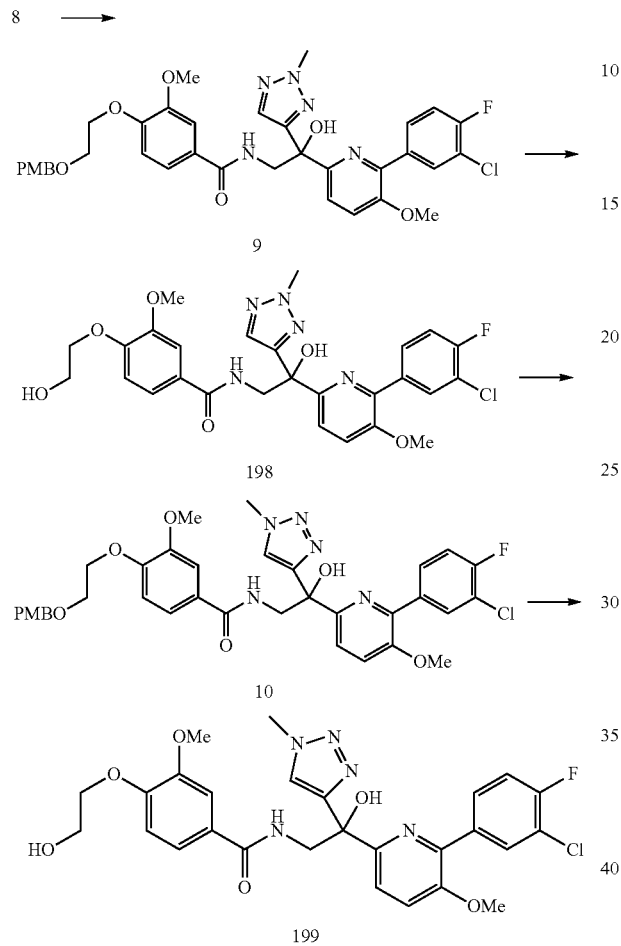

Potassium carbonate (40.0 mg, 0.295 mmol) and MeI (20.0 mg, 0.141 mmol) were added to a solution of 8 (80.0 mg, 0.118 mmol) in $CH_3CN$ (4 mL). The mixture was stirred at r.t. for 4 h, diluted with water and extracted with EtOAc (3×). The combined organic portions were dried with $Na_2SO_4$, filtered and concentrated under reduced pressure. Chromatography of the residue (DCM:EtOAc, 70:30 to 0:100) afforded the two separated regioisomers 9 (21 mg, 25%) and 10 (24 mg, 29%). 9: UPLC/MS (ES$^+$): m/z 692.29 [M+H]$^+$. 10: UPLC/MS (ES$^+$): m/z 692.28 [M+H]$^+$.

General Procedure for PMB-Removal:

A solution of PMB-ether (0.1 mmol) in 10:1 DCM:TFA (3 mL) was stirred at r.t. for 30 mins. The reaction was quenched with 2M aq. NaOH solution. The layers were separated, and the organic portion was concentrated under reduced pressure. Chromatography of the residue (EtOAc:MeOH, 100:0 to 90:10) afforded the product. 198. (derived from 9) UPLC/MS (ES$^+$): m/z 572.38 [M+H]$^+$. 199: (derived from 10) UPLC/MS (ES$^+$): m/z 572.43 [M+H]$^+$.

Example 63

Preparation of Compounds 200, 201, 202, 203 and 204

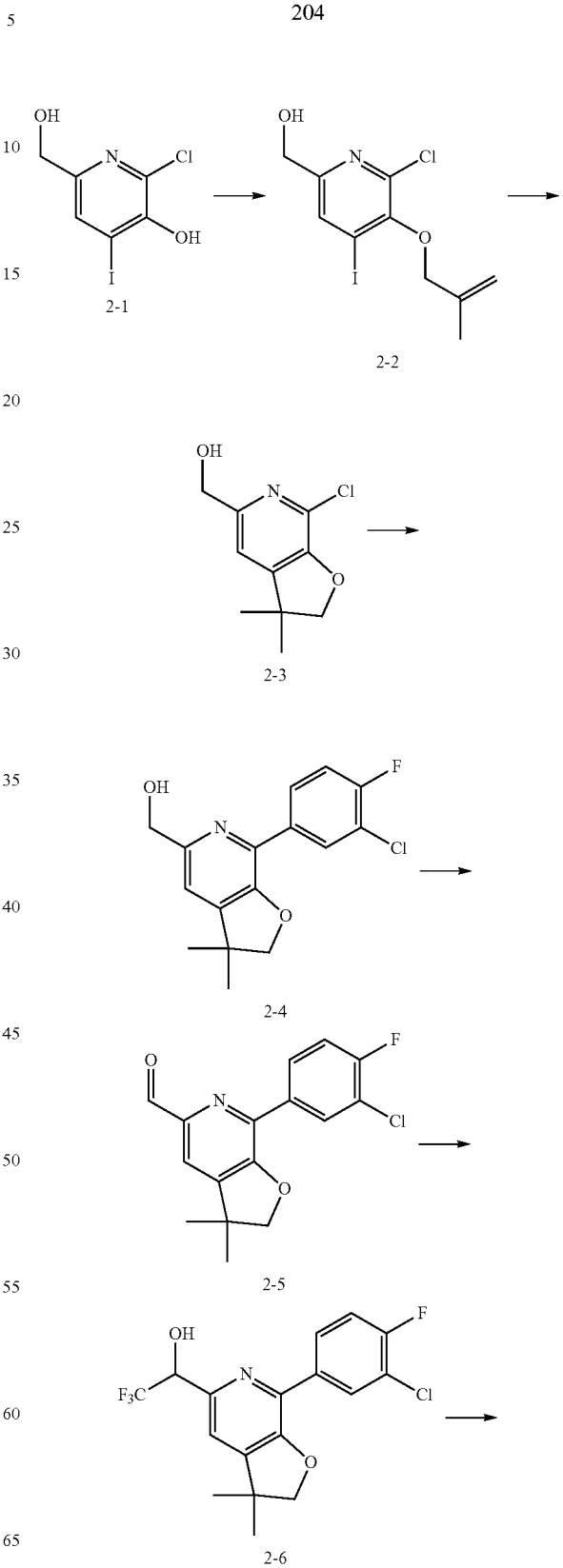

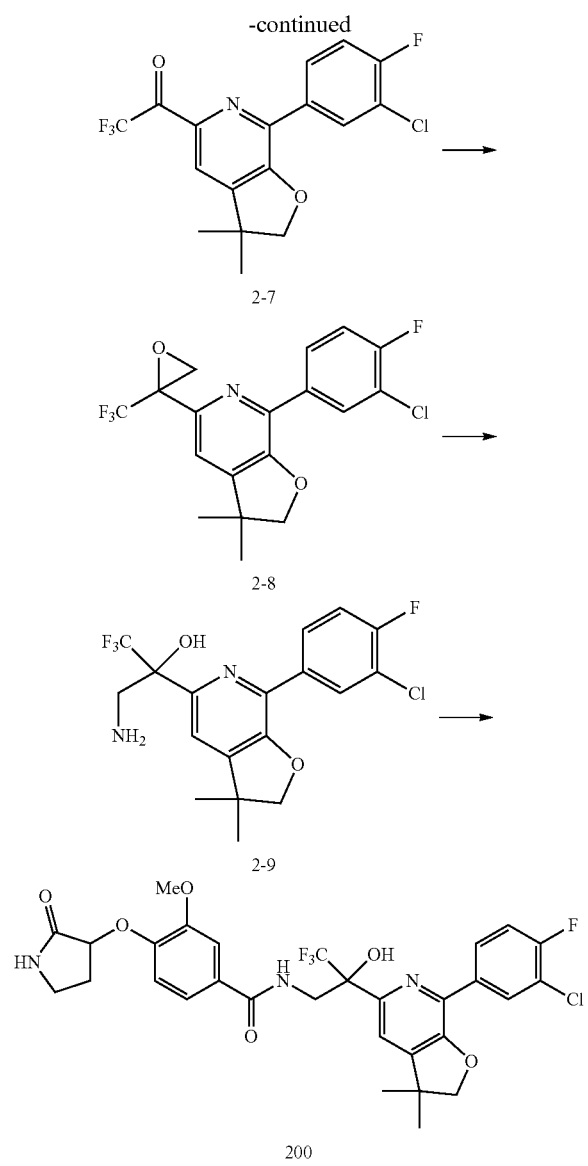

Sodium hydride (1.80 g, 44.7 mmol) was added to a stirred solution of 2-1 (11.6 g, 40.7 mmol) in dry DMF (75 mL), which had been pre-cooled to 0° C. The mixture was stirred at 0° C. for 10 mins, and then warmed to r.t. The mixture was then stirred for 30 mins. The reaction was cooled to 0° C. and 3-bromo-2-methylprop-1-ene (5.70 g, 42.7 mmol) was added dropwise. The mixture was allowed to gradually reach r.t., and stirring was continued for 20 h. EtOAc and sat. aq. NH₄Cl solution were added. The layers were separated, and the organic portion was washed with brine, dried with Na₂SO₄, filtered and concentrated under reduced pressure. Chromatography of the residue (cyclohexane:EtOAc, 100:0 to 50:50) afforded 2-2 (12.1 g, 87%). UPLC/MS (ES⁺): m/z 339.80 [M+H]⁺.

A mixture of 2-2 (12.0 g, 35.4 mmol), sodium formate (2.70 g, 40.7 mmol), tetrabutylammonium chloride (9.80 g, 35.4 mmol), Pd(OAc)₂ (396 mg, 1.7 mmol) and TEA (14.7 mL, 106 mmol) in dry DMF (300 mL) was degassed and heated to 100° C. for 3 h. EtOAc and sat. aq. NH₄Cl solution were added. The layers were separated, and the organic portion was washed with brine, dried with Na₂SO₄, filtered and concentrated under reduced pressure. Chromatography of the residue (cyclohexane:EtOAc, 100:0 to 50:50) afforded 2-3 as a pale yellow wax (6.15 g, 810). UPLC/MS (ES): m/z 213.91 [M+H]⁺.

A mixture of 2-3 (1.80 g, 8.45 mmol), (3-chloro-4-fluorophenyl)boronic acid (2.94 g, 16.9 mmol), [1,1'-bis(diphenylphosphino)ferrocene]dichloropalladium(II) (618 mg, 0.84 mmol) and aq. Na₂CO₃ (2M solution, 8.45 mL, 16.9 mmol) in DCE (80 mL) was degassed and heated to 100° C. under microwave irradiation. Water and DCM were added. The layers were separated, and the organic phase was dried with Na₂SO₄, filtered and concentrated under reduced pressure. Chromatography of the residue (cyclohexane:EtOAc, 100:0 to 50:50) afforded 2-4 as a white solid (1.97 g, 76%). UPLC/MS (ES⁺): m/z 307.18 [M+H]⁺.

Dess-Martin periodinane (6.8 g, 16.0 mmol) was added to a stirred solution of 2-4 (1.97 g, 6.40 mmol) in dry DCM (28 mL). The mixture was stirred at r.t. under N₂ atmosphere for 1 h. The reaction was quenched with a 1:1 2M aq. Na₂S₂O₃: sat. aq. NaHCO₃ solution (30 mL), the mixture was vigorously stirred for 30 mins. The layers were separated, and the organic portion was washed with brine, dried with Na₂SO₄, filtered and concentrated under reduced pressure. Chromatography of the residue (cyclohexane:EtOAc 100:0 to 70:30) afforded 2-5 as a white solid (1.40 g, 72%). UPLC/MS (ES⁺): m/z 306.15 [M+H]⁺.

TMSCF₃ (810 uL, 5.50 mmol) was added to a solution of 2-5 (1.40 g, 4.60 mmol) in dry DCM (25 mL). The mixture was cooled 0° C. and TBAF (1M sol in THF, 5.5 mL, 5.50 mmol) was added dropwise. The mixture was allowed to gradually reach r.t. and stirring was continued for 1 h. Water and DCM were added. The layers were separated, and the organic portion was dried with Na₂SO₄ and filtered. The volatiles were removed under reduced pressure. Chromatography of the residue (cyclohexane:EtOAc 100:0 to 80:20) afforded 2-6 (1.43 g, 82%). UPLC/MS (ES⁺): m/z 376.16 [M+H]⁺.

Dess-Martin periodinane (3.25 g, 7.68 mmol) was added to a stirred solution of 2-6 (1.43 g, 3.84 mmol) in dry DCM (17 mL). The mixture was stirred at r.t. for 1 h. A 1:1 2M aq. Na₂S₂O₃:sat. aq. NaHCO₃ solution was added. The mixture was stirred at r.t. for 30 mins. The layers were separated, and the aqueous portion was extracted with DCM (2×). The combined organic portions were dried with Na₂SO₄, filtered and concentrated under reduced pressure. Chromatography of the residue (cyclohexane:EtOAc 100:0 to 70:30) afforded 2-7 as a white solid (1.20 g, 84%). UPLC/MS (ES⁺): m/z 392.16 [M+H₃O]⁺

Trimethylsulfoxonium iodide (695 mg, 3.16 mmol) was added to a solution of potassium tert-butoxide (354 mg, 3.16 mmol) in DMSO (6 mL). The mixture was stirred at r.t. for 30 mins. A solution of 2-7 (1.18 g, 3.16 mmol) in DMSO (20 mL) was added, and the mixture was stirred at r.t. for 30 mins. EtOAc and water were added, and the layers were separated. The aqueous portion was extracted with EtOAc. The combined organic extracts were washed with brine, dried with Na₂SO₄ and filtered. The volatiles were removed under reduced pressure. Chromatography of the residue (cyclohexane:EtOAc 100:0 to 70:30) afforded 2-8 as a colourless wax (530 mg, 43%). UPLC/MS (ES⁺): m/z 388.18 [M+H]⁺.

A solution of 2-8 (530 mg, 1.37 mmol) in 7M NH₃-MeOH (50 mL) was stirred at 45° C. for 1 h. The volatiles were removed under reduced pressure. The crude was purified by reverse phase chromatography (water:CH₃CN 95:5 to 0:100) to afford 2-9 as a white solid (498 mg, 90%). UPLC/MS (ES⁺): m/z 405.21 [M+H]⁺.

Racemate 2-9 was resolved by using a prep-HPLC separation [Chiralpak AD-H (25×3 cm, 5 um), mobile phase: n-Hexane/(EtOH/MeOH+0.1% ipa) 96/4% v/v, flow rate: 32 mL/min, UV detection DAD 220 nm] to obtain the two separated enantiomers 2-9a ($t_R$=10.9 min) and 2-9b ($t_R$=140.5 min). UPLC and $^1$H NMR analyses for the two enantiomers were superimpossible.

General Amide Coupling Conditions—Method A:

A mixture of 2-9 (50.0 mg, 0.124 mmol), EDC (31.0 mg, 0.161 mmol), HOBT (22.0 mg, 0.161 mmol) and acid (0.124 mmol) in DCM:DMF (5:1, 6 mL) was stirred at 45° C. for 2 h. DCM was added. The organic portion was washed with sat. aq. NH$_4$Cl solution and brine, dried with Na$_2$SO$_4$, filtered and concentrated under reduced pressure. Chromatography of the residue afforded the product.

General Amide Coupling Conditions—Method B:

DIPEA (281 uL, 1.62 mmol) was added to a solution of acid (1.06 mmol) and HATU (461 mg, 1.21 mmol) in dry DMF (5 mL). After 20 mins, a solution of 2-9 (330 mg, 0.81 mmol) in DMF (5 mL) was added. The mixture was stirred at r.t. until complete. EtOAc and sat. aq. NH$_4$Cl solution were added. The layers were separated, and the aqueous portion was extracted with EtOAc. The combined organic portions were dried with Na$_2$SO$_4$ and filtered. The volatiles were removed under reduced pressure. Chromatography of the residue afforded the product.

Coupling of 2-9 with acid 2-10 according to Method A afforded 200 as a white solid (30%, mixture of 4 isomers). UPLC/MS (ES+): m/z 638.18 [M+H]$^+$. Racemate 200 was resolved by using a prep-HPLC separation [Chiralpak AD-H (25×2 cm, 5 um), mobile phase: Ethanol+0.1% isopropylamine 20% v/v, flow rate: 45 mL/min, UV detection DAD 220 nm] to obtain the four separated isomers 201 ($t_R$=12.9 min), 203 ($t_R$=14.8 min), 202 ($t_R$=16.6 min) and 204 ($t_R$=23.6 min).

Alternatively, 2-9a and 2-9b were separately coupled with 2-10 according to Method B. Each diastereomeric mixture was resolved by chiral HPLC. 2-9a provided a mixture of 204 ($t_R$=6.5 min) and 202 ($t_R$=14.1 min) [Whelk O1 (R,R) (25×2.0 cm), 5µ, mobile phase: n-Hexane/(Ethanol+0.1% isopropylamine) 30/70% v/v, flow rate: 17 mL/min, UV detection DAD 220 nm]. 2-9b provided a mixture of 201 and 203 ($t_R$ 6.4 min and 12.3 min) [Whelk O1 (R,R) (25×2.0 cm), 5µ, mobile phase: n-Hexane/(Ethanol+0.1% isopropylamine) 30/70% v/v, flow rate: 17 mL/min, UV detection DAD 220 nm].

Example 64

Preparation of 2-10

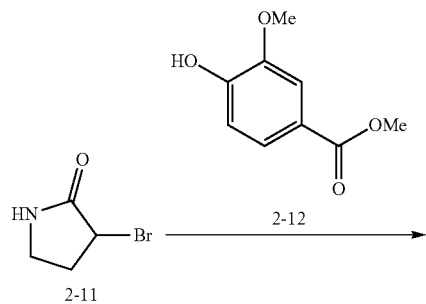

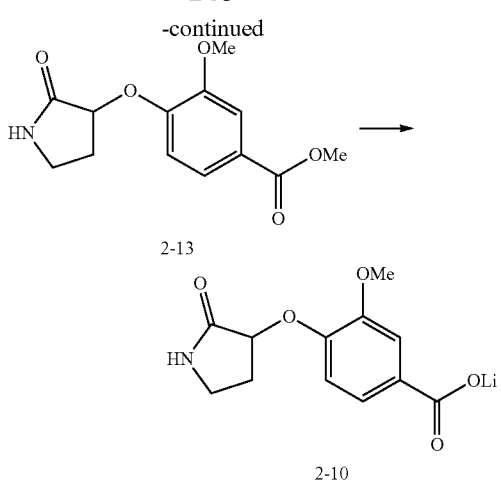

Compound 2-12 (4.86 g, 26.7 mmol) was added to a stirring suspension of cesium carbonate (15.4 g, 47.5 mmol) in DCM (120 mL). A solution of 2-11 (3.13 g, 19.0 mmol) in DCM (20 mL) was added. The mixture was stirred at r.t. for 5 h. The mixture was filtered through a pad of Celite, washed thoroughly with DCM and concentrated. The residue was dissolved in EtOAc. The organic portion was washed with water and brine, dried with Na$_2$SO$_4$, filtered and concentrated under reduced pressure. Chromatography of the residue (cyclohexane:EtOAc 100:0 to 0:100) afforded 2-13 as a white solid (4.50 g, 89%). UPLC/MS (ES$^+$): m/z 266.15 [M+H]$^+$.

Lithium hydroxide monohydrate (258 mg, 6.10 mmol) was added to a suspension of 2-13 (1.50 g, 5.60 mmol) in a 1:1:6 THF:MeOH:H$_2$O mixture (40 mL). The mixture was stirred at r.t. for 3 h, loaded on a reverse phase cartridge and eluted with water to afford 2-10 as a white solid (1.10 g, 78%). UPLC/MS (ES$^+$): m/z 252.13 [M+H]$^+$.

Example 65

Preparation of Compounds 205 and 206

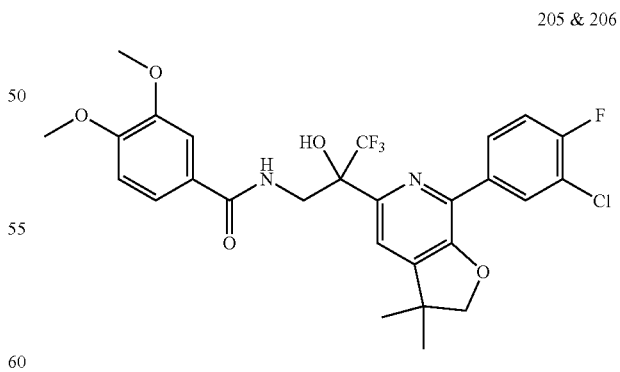

Coupling of 2-9a with 3,4-dimethoxybenzoic acid according to Method A afforded 205 as a white solid (51%). UPLC/MS (ES$^+$): m/z 569.40 [M+H]$^+$. Using 2-9b and 3,4-dimethoxybenzoic acid according to Method A afforded 206 as a white solid (50%). UPLC/MS (ES$^+$): m/z 569.40 [M+H]$^+$.

Example 66

Preparation of Compounds 207

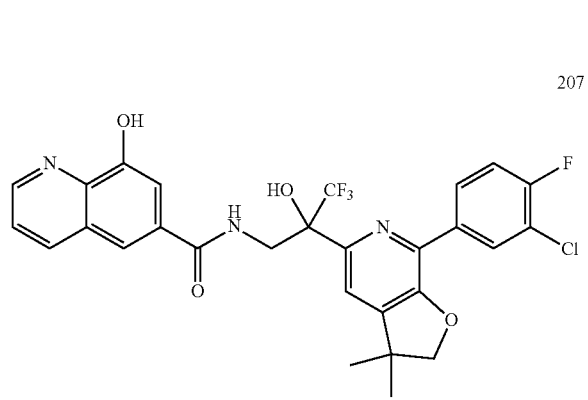 [SMILES: CC1(C)COc2c1cc(C(O)(CNC(=O)c1cc(O)c3ncccc3c1)C(F)(F)F)nc2-c1ccc(F)c(Cl)c1]

Coupling of 2-9 with 2-14 according to Method A afforded 207 as a white solid (43%). UPLC/MS (ES⁺): m/z 576.32 [M+H]⁺.

Example 67

Preparation of 2-14

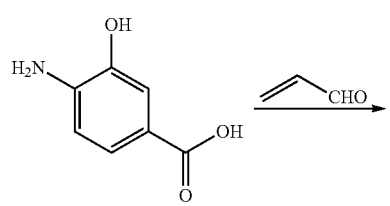

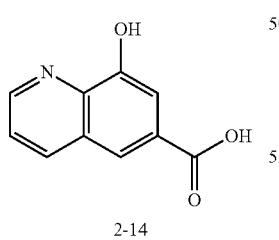

Acrolein (21.8 mL, 326 mmol) was added to a mixture of 4-amino-3-hydroxybenzoic acid (5.00 g, 33.0 mmol) in 12 N aq. HCl solution (50 mL). The mixture was refluxed for 1 h. After cooling to r.t., the mixture was concentrated under reduced pressure. The residue was purified by reverse phase chromatography (water:CH₃CN 100:0 to 50:50) to afford 2-14 (561 mg, 9%). UPLC/MS (ES⁺): m/z 190.04 [M+H]⁺.

Example 68

Preparation of Compound 208

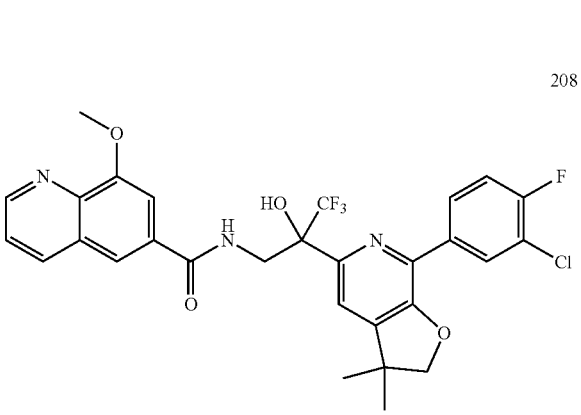 [SMILES: COc1cc(C(=O)NCC(O)(c2cc3c(c(-c4ccc(F)c(Cl)c4)n2)OCC3(C)C)C(F)(F)F)cc2cccnc12]

Coupling of 2-9 with 2-15 according to Method A afforded 208 as a white solid (67%). UPLC/MS (ES⁺): m/z 590.25 [M+H]⁺.

Example 69

Preparation of 2-15

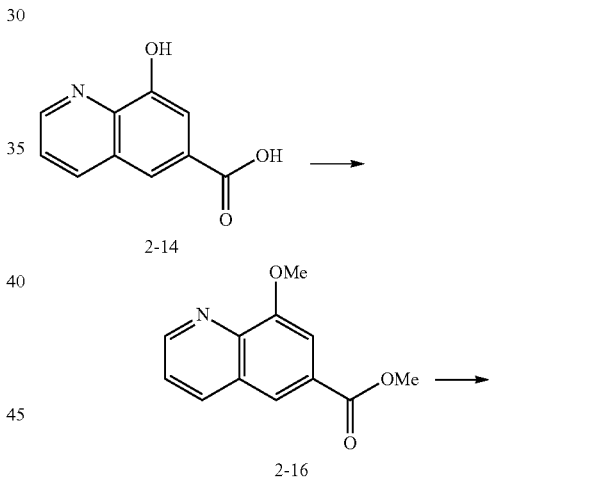

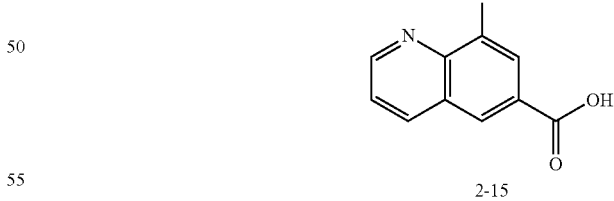

Cesium carbonate (2.58 g, 7.92 mmol) and MeI (822 uL, 13.2 mmol) were sequentially added to a solution of 2-14 (500 mg, 2.64 mmol) in DMF (30 mL). The mixture was stirred at r.t. for 18 h. EtOAc was added. The organic portion was washed with 2M aq. HCl solution and water, dried with Na₂SO₄, filtered and concentrated under reduced pressure. Crude 2-16 was dissolved in a 2:1:1 THF:MeOH:H₂O mixture (8 mL). Lithium hydroxide monohydrate (332 mg, 7.92 mmol) was added, and the mixture was stirred at r.t. for 1 h. The volatiles were removed under reduced pressure. The

Example 70

Preparation of Compound 209

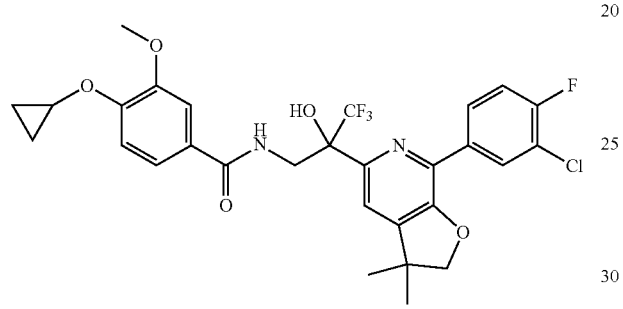

Coupling of 2-9 with 4-cyclopropoxy-3-methoxybenzoic acid according to Method A afforded 209 as a white solid (41%). UPLC/MS (ES+): m/z 595.30 [M+H]+.

Example 71

Preparation of Compound 210

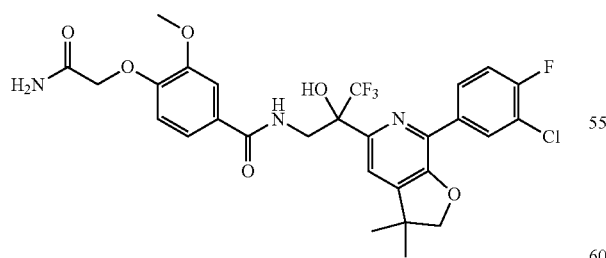

Coupling of 2-9 with 4-(carbamoylmethoxy)-3-methoxybenzoic acid according to Method B afforded 210 as a white solid (51%). UPLC/MS (ES+): m/z: 612.21 [M+H]+.

Example 72

Preparation of Compound 211

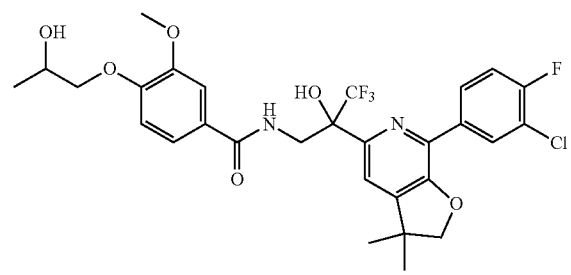

Coupling of 2-9 with 4-[(2R)-2-hydroxypropoxy]-3-methoxybenzoic acid according to Method B afforded 211 as a white solid (45%). UPLC/MS (ES+): m/z 613.27 [M+H]+.

Example 73

Preparation of Compound 212

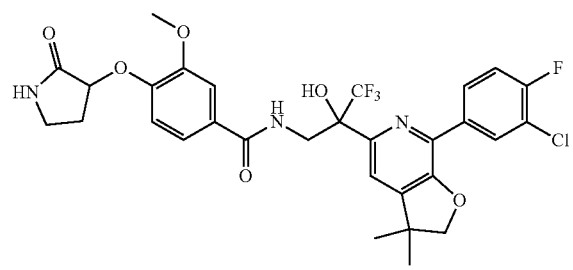

Coupling of 2-9 with 2-17 according to Method B afforded 212 as a white solid (33%). UPLC/MS (ES+): m/z 636.00 [M+H]+.

Example 74

Preparation of 2-17

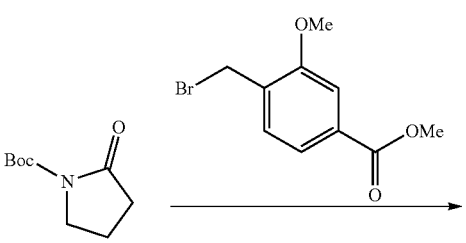

-continued

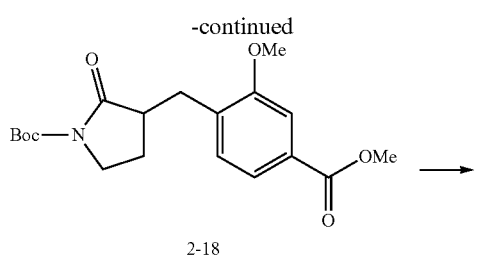

2-18

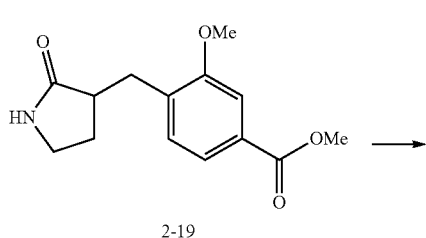

2-19

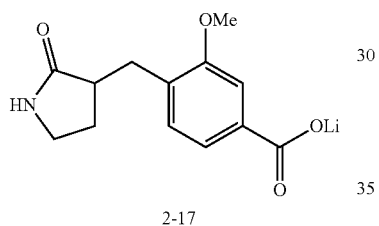

2-17

LDA (2M solution in THF, 1.05 mL, 2.10 mmol) was added to a stirred solution of 1-(tert-butoxycarbonyl)-2-pyrrolidinone (276 uL, 1.62 mmol) in THF (1 mL), which had been pre-cooled to −78° C. After 15 mins, a solution of methyl 4-(bromomethyl)-3-methoxybenzoate (460 mg, 1.78 mmol) in THF (1 mL) was added dropwise to the mixture and stirring at 78° C. was continued for 1 h. The reaction was quenched with water. The aqueous portion was extracted with EtOAc (2×). The combined organic portions were dried with $Na_2SO_4$, filtered and concentrated under reduced pressure. Chromatography of the residue (cyclohexane:EtOAc 70:30) afforded 2-18 (199 mg, 34%). UPLC/MS (ES$^+$): m/z 364.20 [M+H]$^+$.

A solution of 2-18 (199 mg, 0.547 mmol) in 5:1 DCM: TFA (3 mL) was stirred at r.t. for 5 mins. The mixture was diluted with DCM. The organic portion was washed with a sat. aq. $NaHCO_3$ solution, dried with $Na_2SO_4$, filtered and concentrated under reduced pressure. The residue was purified by reverse phase chromatography (0.1% HCOOH: water:0.1% HCOOH:$CH_3CN$ 100:0 to 0:100) to afford 2-19.

Compound 2-19 was dissolved in a 2:1:1 THF:MeOH: $H_2O$ mixture (10 mL). Lithium hydroxide monohydrate (45 mg, 1.10 mmol) was added. The mixture was stirred at r.t. for 2 h. The volatiles were removed under reduced pressure to afford crude 2-17, which was directly used in the next step without further purification. UPLC/MS (ES$^+$): m/z 250.20 [M+H]$^+$.

Example 75

Preparation of Compound 213

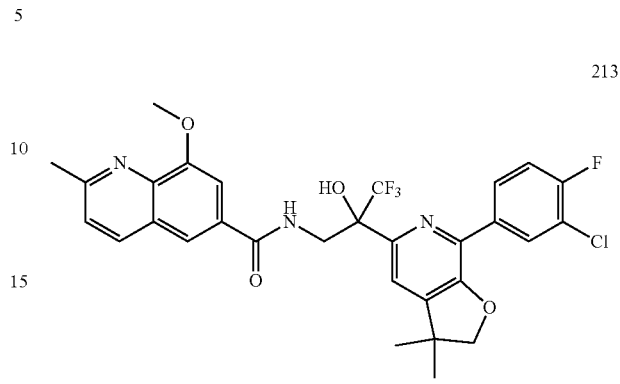

213

Coupling of 2-9 with 2-20 according to Method B afforded 213 as a white solid (73%). UPLC/MS (ES$^+$): m/z 604.00 [M+H]$^+$.

Example 76

Preparation of 2-20

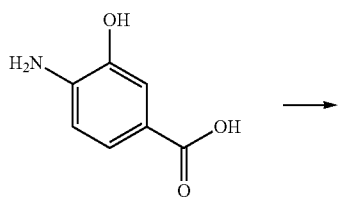

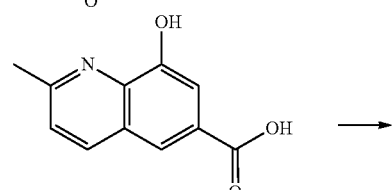

2-21

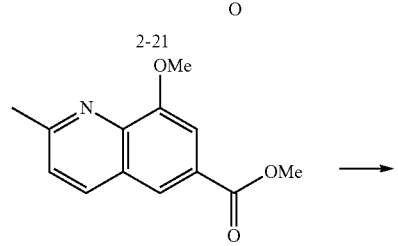

2-22

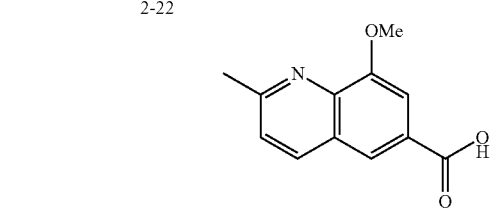

2-20

Crotonaldehyde (4.01 g, 48.9 mmol) was added dropwise to a mixture of 4-amino-3-hydroxybenzoic acid (5.00 g, 33.1 mmol) and 6M aq. HCl solution (60 mL, 360 mmol). The mixture was refluxed for 18 h. After cooling to r.t. a precipitate formed. The solid was filtered off, dried and collected. Acid 2-21 (3.44 g) was used in the next step without further purification. UPLC/MS (ES+): m/z 204.10 [M+H]+.

Cesium carbonate (15.8 g, 48.6 mmol) and MeI (5.88 mL, 94.5 mmol) were sequentially added to a solution of 2-21 (3.04 g) in DMF (80 mL). The mixture was stirred at r.t. for 12 h. DMF was removed under reduced pressure, and the residue was taken up with EtOAc. The organic portion was washed with water, dried with Na2SO4, filtered and concentrated under reduced pressure to afford crude 2-22 (2.76 g), which was used in the next step without further purification. UPLC/MS (ES+): m/z 232.10 [M+H]+.

Lithium hydroxide monohydrate (0.272 g, 6.49 mmol) was added to a stirred suspension of 2-22 (500 mg, 2.16 mmol) in a 2:1:2 THF:MeOH:H2O mixture. The mixture was stirred at r.t. for 3 h. The volatiles were removed under reduced pressure. The residue was purified by reverse phase chromatography (water:CH3CN 100:0 to 0:100) to afford 2-20 (291 mg). UPLC/MS (ES+): m/z 218.10 [M+H]+.

Example 77

Preparation of Compound 214

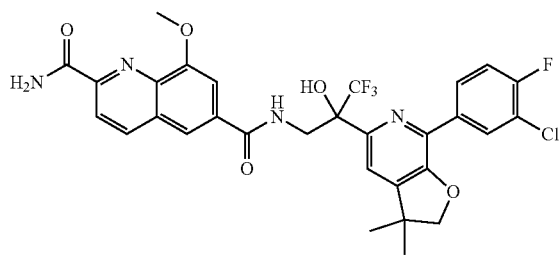

Coupling of 2-9 with 2-23 according to Method B afforded 214 as a white solid (49%). UPLC/MS (ES+): m/z 633.26 [M+H]+.

Example 78

Preparation of 2-23

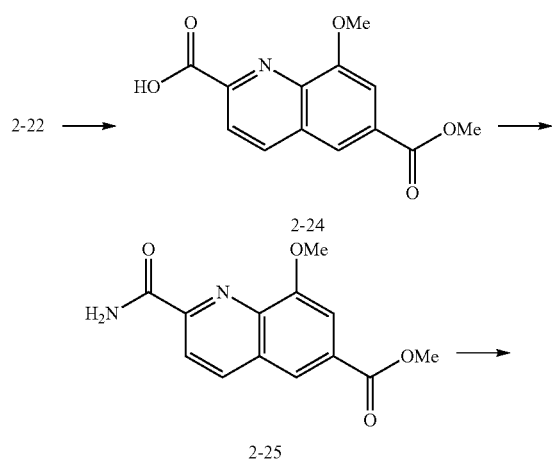

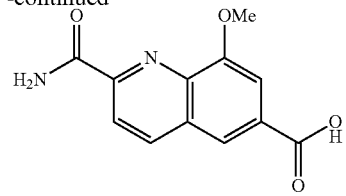

Ester 2-22 (1.50 g, 6.48 mmol) was added to a suspension of selenium dioxide (1.44 g, 13.0 mmol) in pyridine (24 mL). The mixture was refluxed for 3 h. The volatiles were removed under reduced pressure, and the residue was triturated with EtOAc. The solid was dried and collected to provide 2-24 (595 mg, 35%). UPLC/MS (ES+): m/z 262.10 [M+H]+.

Oxalyl chloride (100 uL, 1.14 mmol) and DMF (1 drop) were added to a solution of 2-24 (230 mg, 0.880 mmol) in DCM (7 mL). The mixture was stirred at r.t. for 30 mins. HMDS (400 uL, 1.89 mmol) and then MeOH were added. The mixture was concentrated under reduced pressure. Chromatography of the residue (EtOAc-DCM, 100:0 to 0:100) afforded 2-25. UPLC/MS (ES+): m/z 261.10 [M+H]+.

Lithium hydroxide monohydrate (44.0 mg, 1.05 mmol) was added to a stirred suspension of 2-25 (91.0 mg, 0.350 mmol) in a 2:1:2 THF:MeOH:H2O mixture. The mixture was stirred at r.t. for 2 h. The volatiles were removed under reduced pressure. The residue was purified by reverse phase chromatography (water:CH3CN 100:0 to 0:100) to afford 2-23 (76 mg, 89%). UPLC/MS (ES+): m/z 247.20 [M+H]+.

Example 79

Preparation of Compound 215

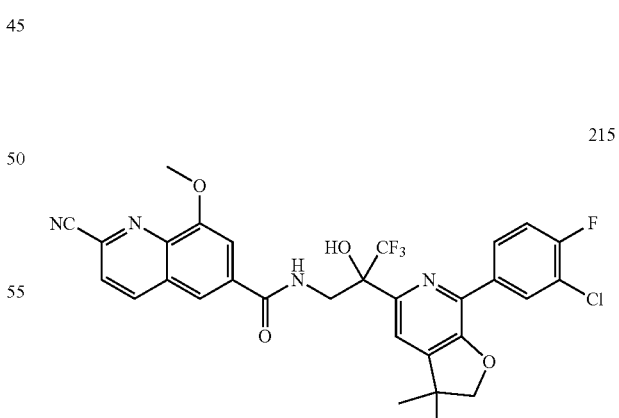

Coupling of 2-9 with 2-26 according to Method B afforded 215 as a white solid (41%). UPLC/MS (ES+): m/z 615.26 [M+H]+.

Example 80

Preparation of 2-26

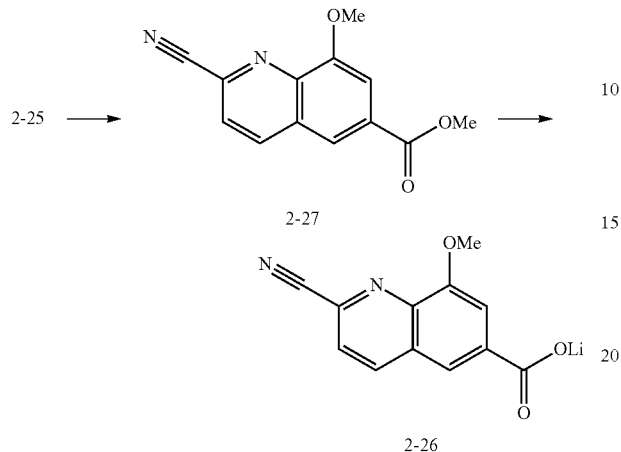

SOCl$_2$ (420 uL, 5.76 mmol) and TEA (800 uL, 5.76 mmol) were added to a solution of 2-25 (150 mg, 0.576 mmol) in DCE (10 mL), which had been pre-cooled to 0° C. The mixture was stirred at 0° C. for 3 h. The reaction was quenched with a sat. aq. NaHCO$_3$ solution. The layers were separated, and the aqueous portion was extracted with EtOAc. The combined organic portions were dried with Na$_2$SO$_4$, filtered and concentrated under reduced pressure. The residue was purified by reverse phase chromatography (water:CH$_3$CN 100:0 to 0:100) to afford 2-27 (100 mg, 71%). UPLC/MS (ES$^+$): m/z 243.18 [M+H]$^+$.

Lithium hydroxide monohydrate (21.0 mg, 0.49 mmol) was added to a stirred suspension of 2-27 (100 mg, 0.413 mmol) in a 2:2:1 THF:MeOH:H$_2$O mixture (10 mL). The mixture was stirred at r.t. for 2 h. The volatiles were removed under reduced pressure. Crude 2-26 was used in the next step without further purification. UPLC/MS (ES$^+$): m/z 229.14 [M+H]$^+$.

Example 81

Preparation of Compound 216

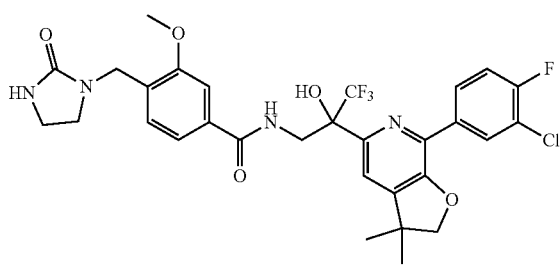

Coupling of 2-9 with 2-28 according to Method B afforded 216 as a white solid (46%). UPLC/MS (ES$^+$): m/z 637.30 [M+H]$^+$.

Example 82

Preparation of 2-28

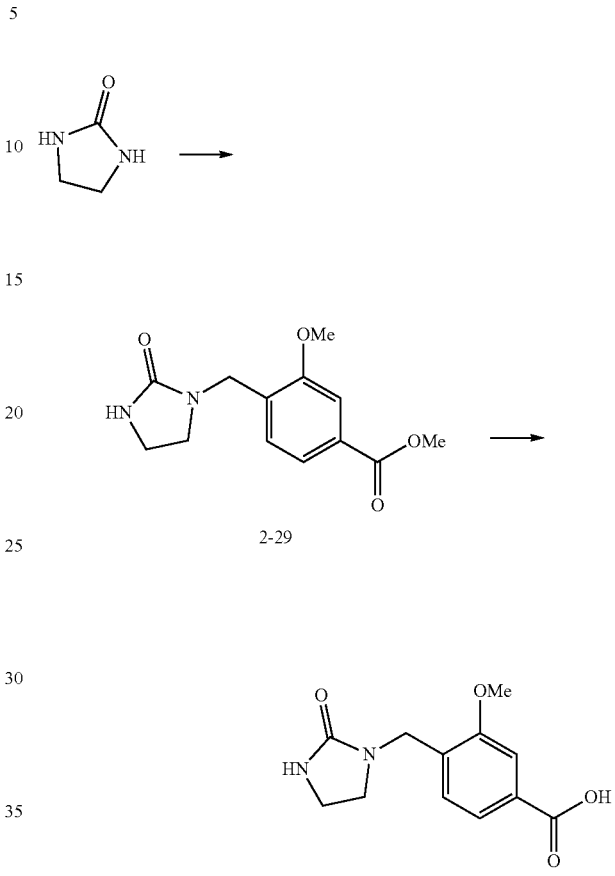

NaH (153 mg, 3.83 mmol) was added to a solution of imidazolidin-2-one (300 mg, 3.48 mmol) in THF (3 mL), which had been pre-cooled to 0° C. After 1 h, methyl 4-(bromomethyl)-3-methoxybenzoate (899 mg, 3.48 mmol) was added. The mixture was stirred at r.t. for 18 h, poured in to water and extracted with EtOAc (3×). The combined organic portions were dried with Na$_2$SO$_4$, filtered and concentrated under reduced pressure. Chromatography of the residue (EtOAc:MeOH 100:0 to 80:20) afforded 2-29 as a white solid (40 mg, 4%). UPLC/MS (ES$^+$): m/z 265.20 [M+H]$^+$.

Lithium hydroxide monohydrate (19.0 mg, 0.454 mmol) was added to a stirred suspension of 2-29 (40.0 mg, 0.151 mmol) in a 2:2:1 THF:MeOH:H$_2$O mixture (8 mL). The mixture was stirred at r.t. for 18 h. The volatiles were removed under reduced pressure. The residue was taken up with water, and the aqueous portion was extracted with EtOAc (2×). The combined organic portions were dried with Na$_2$SO$_4$, filtered and concentrated under reduced pressure. Chromatography of the residue (EtOAc:MeOH 100:0 to 80:20) afforded 2-28 as a white solid (32 mg, 84%). UPLC/MS (ES$^+$): m/z 251.20

Example 83

Preparation of Compound 217

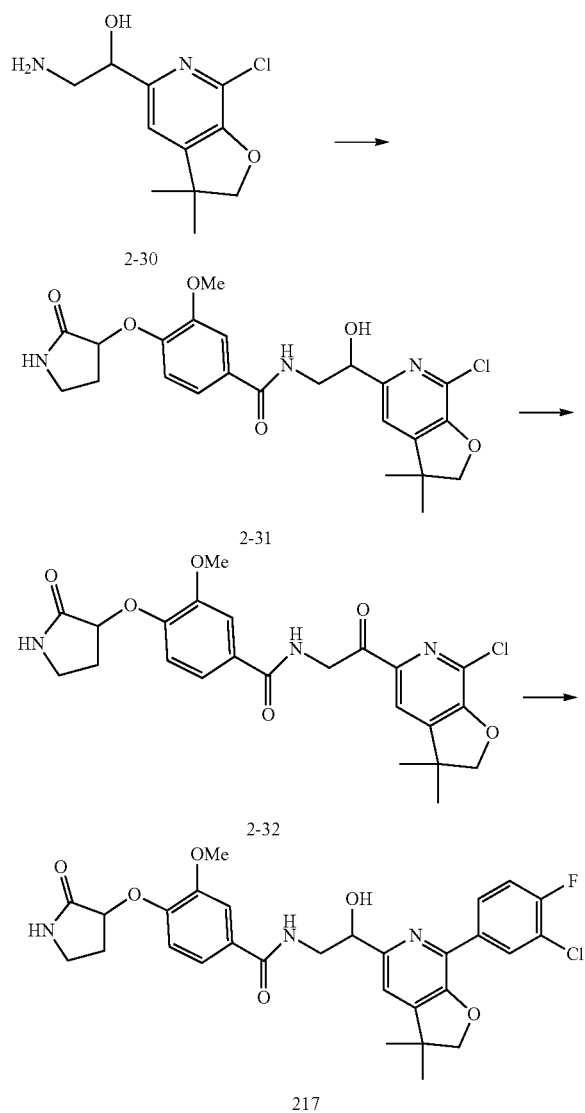

Triethylamine (0.240 mL, 1.72 mmol) was added to a mixture of 3-methoxy-4-[(2-oxopyrrolidin-3-yl)oxy]benzoic acid (130 mg, 0.517 mmol), HOBT (87.3 mg, 0.646 mmol), EDC (124 mg, 0.646 mmol) and 2-30 (104 mg, 0.431 mmol) in a 4:1 DCM:DMF (5 mL). The mixture was warmed to 45° C. and stirred at 45° C. for 18 h. A 1M aq. HCl solution was added, and the mixture was stirred at r.t. for 10 mins. The layers were separated. The organic portion was washed with 1M aq. HCl solution, dried with $Na_2SO_4$, filtered and concentrated under reduced pressure to afford crude 2-31 (203 mg), which was used in the next step without further purification. UPLC/MS (ES$^+$): m/z 476.30 [M+H]$^+$.

Dess-Martin periodinane (453 mg, 1.07 mmol) was added to a stirred solution of 2-31 (203 mg) in dry DCM (10 mL). The mixture was stirred at r.t. for 2 h, and the reaction was quenched with a 1:1 1M aq. $Na_2S_2O_3$:sat. aq. $NaHCO_3$ solution (3 mL). The mixture was stirred vigorously for 30 mins. The layers were separated, and the organic portion was washed with brine, dried with $Na_2SO_4$, filtered and concentrated under reduced pressure. Chromatography of the residue (EtOAc:MeOH, 100:0 to 75:25) afforded 2-32 (80 mg, 39% over two steps). UPLC/MS (ES$^+$): m/z 474.30 [M+H]$^+$.

A mixture of 2-32 (10.0 mg, 0.021 mmol), (3-chloro-4-fluorophenyl)boronic acid (18.4 mg, 0.105 mmol), Pd(dppf)Cl$_2$ (2.0 mg, 0.003 mmol) and aq. $Na_2CO_3$ (2M solution, 0.105 mmol, 0.05 mL) in DCE (0.3 mL) was degassed and stirred while heated to 85° C. under microwave irradiation (4 cycles for 10 mins each). After each run, a further aliquot of Pd(dppf)Cl$_2$ (2.0 mg, 0.003 mmol) was added. The reaction was diluted with water, and DCM were added. The layers were separated, and the organic portion was concentrated under reduced pressure. The residue was purified by reverse phase chromatography (water:CH$_3$CN 100:0 to 0:100) to afford 217. UPLC/MS (ES$^+$): m/z 568.30 [M+H]$^+$.

Example 84

Preparation of Compound 218

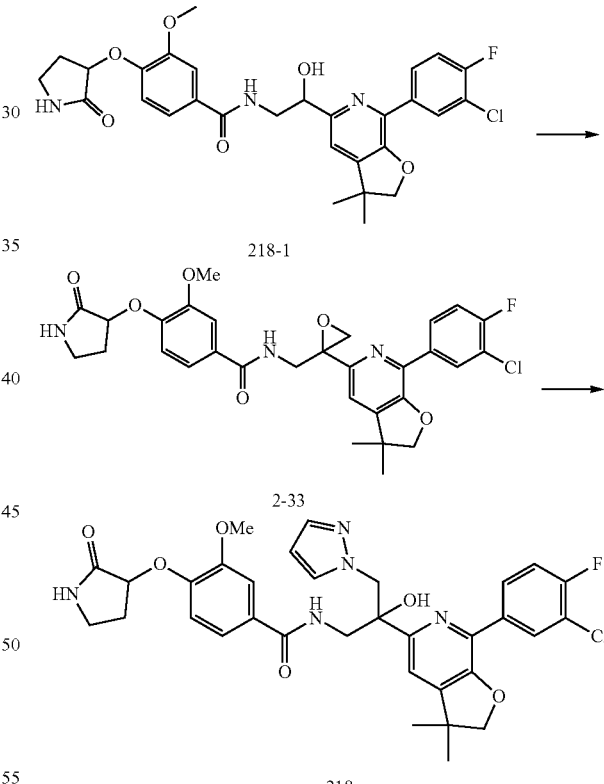

Trimethylsulfoxonium iodide (21.0 mg, 0.097 mmol) was added to a solution of potassium tert-butoxide (9.8 mg, 0.086 mmol) in DMSO (0.6 mL). The mixture was stirred at r.t. for 30 mins. A solution of 218-1 (50.0 mg, 0.088 mmol) in DMSO (0.6 mL) was added, and the mixture was stirred at r.t. for a further 30 mins. The mixture was diluted with EtOAc and water. The layers were separated, and the aqueous portion was extracted with EtOAc. The combined organic portions were washed with brine, dried with $Na_2SO_4$, filtered and concentrated under reduced pressure to afford crude 2-33 (50 mg), which was used next step without further purification. UPLC/MS (ES+): m/z 582.34 [M+H]+.

A mixture of 2-33 (50 mg), potassium carbonate (24.0 mg, 0.170 mmol) and pyrazole (24.0 mg, 0.350 mmol) in DMF (1 mL) was stirred at 40° C. for 18 h. The mixture was diluted with EtOAc and water. The layers were separated, and the aqueous portion was extracted with EtOAc. The combined organic portions were dried with Na₂SO₄, filtered and concentrated under reduced pressure. The residue was purified by reverse phase chromatography (water:CH₃CN 100:0 to 50:50) to afford 218 as a white solid (10 mg, 17% over two steps). UPLC/MS (ES+): m/z 650.40 [M+H]+.

Example 85

Preparation of Compound 219

2-33 ⟶

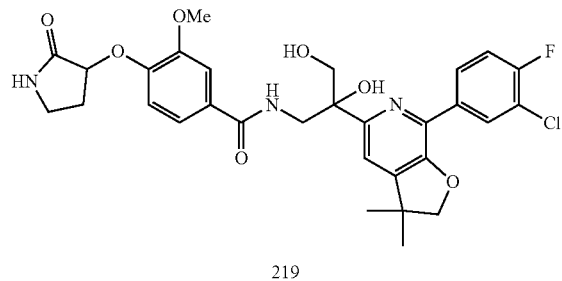

219

Epoxide 2-33 (60 mg, crude) was dissolved in a 1:1 3M aq. HCl sol:MeOH mixture (5 mL). The mixture was heated to 50° C. for 3 h. After cooling to r.t., the mixture was basified with 1M aq. NaOH solution and concentrated under reduced pressure. The residue was purified by reverse phase chromatography (water:CH₃CN 95:5 to 0:100) to afford 219 as a white solid (18 mg, 26% over two steps). UPLC/MS (ES+): m/z 600.36 [M+H]+.

Example 86

Preparation of Compound 220

2-30 ⟶

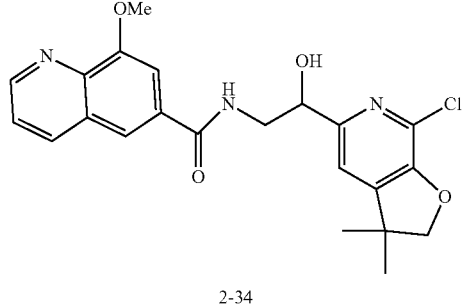

2-34

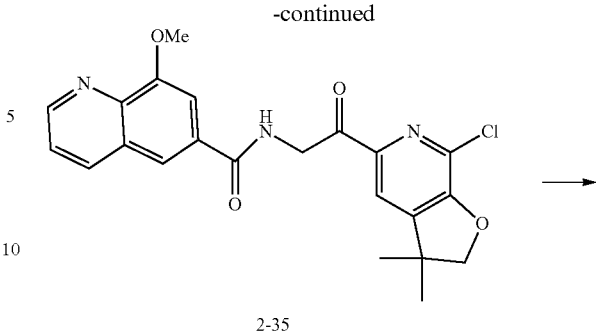

2-35

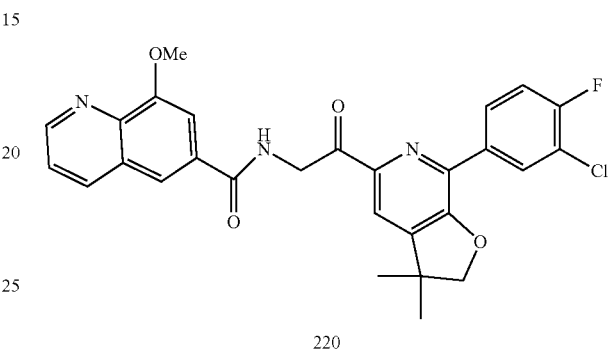

220

Triethylamine (0.35 mL, 2.51 mmol) was added to a mixture of 8-methoxyquinoline-6-carboxylic acid (286 mg, 1.18 mmol), HOBT (223 mg, 1.65 mmol), EDC (316 mg, 1.65 mmol) and 2-30 (239 mg, 1.18 mmol) in DCM (7 mL). The mixture was stirred at r.t. for 60 h. A 1M aq. HCl solution was added, and the mixture was stirred at r.t. for 10 mins. The layers were separated. The organic portion was washed with 1M aq. HCl solution, dried with Na₂SO₄, filtered and concentrated under reduced pressure to afford crude 2-34, which was used in the next step without further purification. UPLC/MS (ES+): m/z 428.30 [M+H]+.

Dess-Martin periodinane (1.20 g, 2.82 mmol) was added to a stirred solution of 2-34 in dry DCM (6 mL). The mixture was stirred at r.t. for 2 h, and the reaction quenched with a 1:1 1M aq. Na₂S₂O₃:sat. aq. NaHCO₃ solution. The mixture was stirred vigorously for 30 mins. The layers were separated, and the organic portion was washed with brine, dried with Na₂SO₄, filtered and concentrated under reduced pressure. The residue was purified by reverse phase chromatography (water:CH₃CN 80:20 to 0:100) to afford 2-35 (11.0 mg, 2% overall). UPLC/MS (ES+): m/z 426.20 [M+H]+.

A mixture of 2-35 (11.0 mg, 0.026 mmol), (3-chloro-4-fluorophenyl)boronic acid (11.2 mg, 0.065 mmol), Pd(dppf)Cl₂ (1.3 mg, 0.002 mmol) and aq. Na₂CO₃ (2M solution, 39 uL, 0.078 mmol) in DCE (1 mL) was degassed and heated to 85° C. for 24 h. The volatiles were removed under reduced pressure. The residue was purified by reverse phase chromatography (water:CH₃CN 100:0 to 30:70) to afford 220 as an off-white solid (2.3 mg, 17%). UPLC/MS (ES+): m/z 520.30 [M+H]+.

Example 87

Preparation of Compound 221

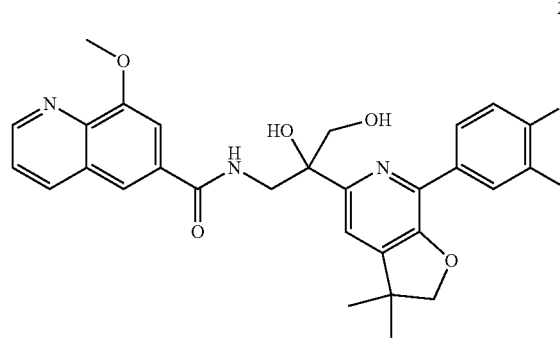

221

Trimethylsulfoxonium iodide (18.3 mg, 0.087 mmol) was added to a solution of potassium tert-butoxide (9.3 mg, 0.083 mmol) in DMSO (0.3 mL). The mixture was stirred at r.t. for 30 mins. A solution of 220 (43.0 mg, 0.083 mmol) in DMSO (0.7 mL) was added, and the mixture was stirred at r.t. for a further 30 mins. The mixture was partitioned between EtOAc and water. The layers were separated, and the aqueous portion was extracted with EtOAc. The combined organic portions were washed with brine, dried with $Na_2SO_4$, filtered and concentrated under reduced pressure. The residue was dissolved in a 1:1 3M aq. HCl sol:MeOH mixture (3 mL), and the mixture was heated to 50° C. for 3 h. The volatiles were removed under reduced pressure. The residue was purified by reverse phase chromatography (water:$CH_3CN$ 100:0 to 0:100) to afford 221 as an off-white solid. UPLC/MS ($ES^+$): m/z 552.38 $[M+H]^+$.

Example 88

Preparation of Compound 222

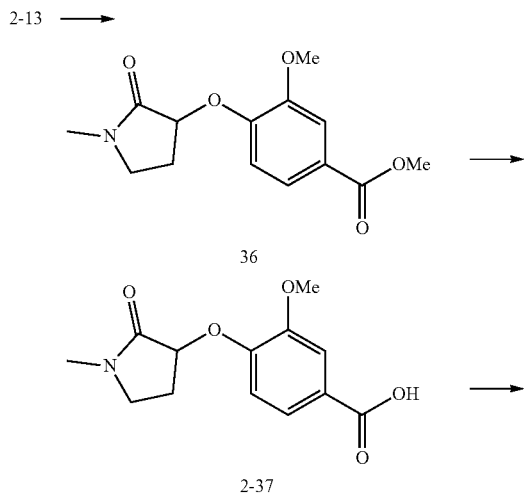

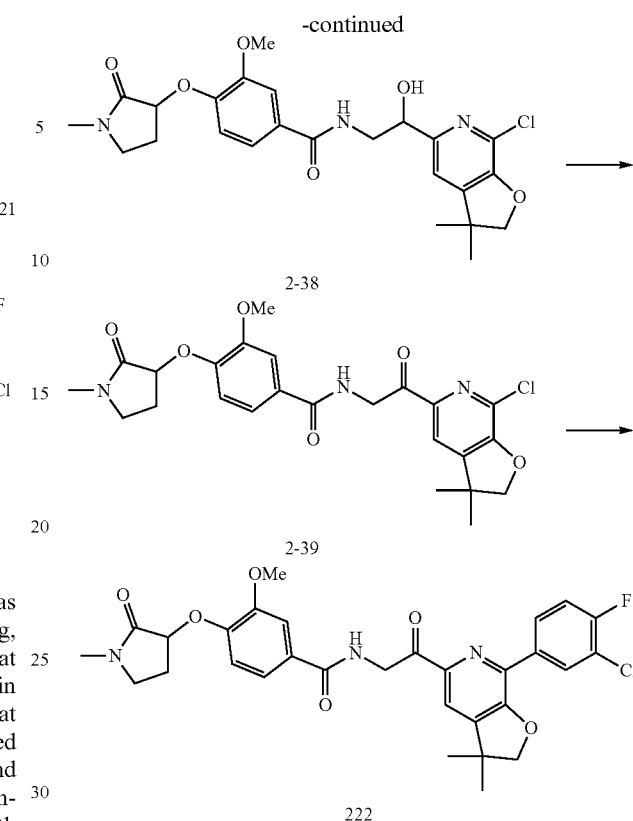

NaH (59.0 mg, 1.47 mmol) was added to a solution of 2-13 (300 mg, 1.13 mmol) in dry THF (4.5 mL). After 5 mins of stirring at r.t., MeI (192 mg, 1.35 mmol) was added. The reaction was stirred at r.t. for 3 h. EtOAc and 1M aq. HCl solution were added. The layers were separated, and the aqueous portion was extracted with EtOAc. The combined organic portions were dried with $Na_2SO_4$ and filtered. The volatiles were removed under reduced pressure to afford crude 2-36, which was in the next step without further purification. Lithium hydroxide monohydrate (95.0 mg, 2.26 mmol) was added to a stirred mixture of 2-36 in 2:1:1 THF:MeOH:$H_2O$ (8 mL). The reaction was stirred at r.t. for 3 h. Additional lithium hydroxide monohydrate (95 mg) was added and stirring was continued for 2 h. The mixture was poured in to 6M aq. HCl solution. The aqueous portion was saturated with NaCl and extracted with EtOAc and DCM. The combined organic portions were dried with $Na_2SO_4$, and filtered. The volatiles were removed under reduced pressure to afford crude 2-37, which was in the next step without further purification. UPLC/MS ($ES^+$): m/z 266.20 $[M+H]^+$.

A mixture of 2-37, 2-30 (273 mg, 1.13 mmol), EDC (282 mg, 1.47 mmol), HOBT (198 mg, 1.47 mmol) and TEA (267 uL, 1.92 mmol) in DMF (8 mL) was stirred at r.t. for 18 h. EtOAc and 2M aq. HCl solution were added. The layers were separated, and the organic portion was concentrated under reduced pressure. The residue was purified by reverse phase chromatography (water:$CH_3CN$ 100:0 to 0:100) to afford 2-38 as a colorless wax (90 mg, 16% over 3 steps). UPLC/MS ($ES^+$): m/z 490.30 $[M+H]^+$.

Dess-Martin periodinane (195 mg, 0.46 mmol) was added to a stirred solution of 2-38 (90.0 mg, 0.184 mmol) in dry DCM (2 mL). The mixture was stirred at r.t. for 2 h. The reaction was quenched with a 1:1 1M aq. $Na_2S_2O_3$:sat. aq.

NaHCO₃ solution. The mixture was stirred vigorously for 30 mins. The layers were separated, and the organic portion was washed with brine, dried with Na₂SO₄, filtered and concentrated under reduced pressure to afford crude 2-39 (92 mg), which was in the next step without further purification. UPLC/MS (ES⁺): m/z 488.30 [M+H]⁺.

A mixture of 2-39 (92 mg), (3-chloro-4-fluorophenyl) boronic acid (83.0 mg, 0.475 mmol), Pd(dppf)Cl₂ (27.6 mg, 0.038 mmol) and aq. Na₂CO₃ (2M solution, 285 uL, 0.570 mmol) in DCE (3 mL) was degassed and heated to 100° C. under microwave irradiation for 1.5 h. Water and DCM were added. The layers were separated, and the organic portion was dried with Na₂SO₄, filtered and concentrated under reduced pressure. The residue was purified by reverse phase chromatography (water:CH₃CN 100:0 to 0:100) to afford 222 as an off-white solid (27.0 mg, 25% over two steps). UPLC/MS (ES⁺): m/z 582.30 [M+H]⁺.

Example 89

Preparation of Compound 223

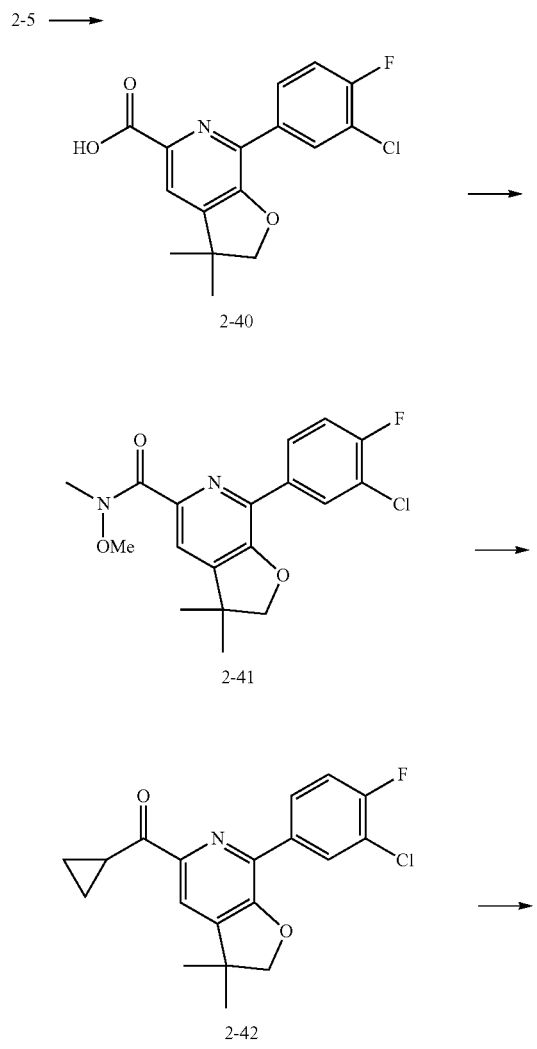

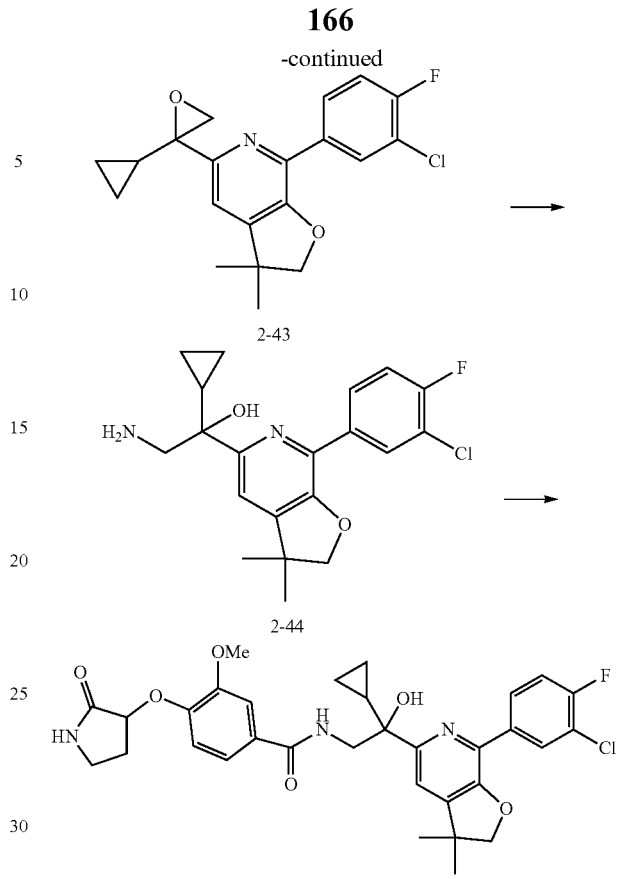

2-Methyl-2-butene (16.9 mL, 33.7 mmol, 2M solution in THF) was added to a solution of 2-5 (1.03 g, 3.37 mmol) in tert-butanol (60 mL). A solution of sodium chlorite (609 mg, 6.74 mmol) and sodium phosphate monobasic dihydrate (3.41 g, 21.9 mmol) in water (60 mL) was then added. The mixture was stirred at r.t. for 18 h. Brine was added, and the aqueous portion was extracted with EtOAc (3×). The combined organic portions were dried with Na₂SO₄, filtered and concentrated under reduced pressure. Chromatography of the residue (cyclohexane:EtOAc 100:0 to 0:100) afforded 2-40 as an off-white solid (688 mg, 63%). UPLC/MS (ES⁺): m/z 322.10 [M+H]⁺.

Triethylamine (0.160 mL, 1.12 mmol) was added to a mixture of 2-40 (200 mg, 0.622 mmol), HOBT (151 mg, 1.12 mmol), EDC (167 g, 0.870 mmol) and N,O-dimethylhydroxylamine hydrochloride (91.1 mg, 0.934 mmol) in DCM (15 mL). The mixture was stirred at r.t. for 18 h. A 1M aq. HCl solution was added, and the mixture was stirred at r.t. for 10 mins. The layers were separated. The organic portion was washed with 1M aq. HCl solution, dried with Na₂SO₄, filtered and concentrated under reduced pressure to afford crude 2-41 (255 mg) which was used in the next step without further purification. UPLC/MS (ES⁺): m/z found 365.20 [M+H]⁺.

Cyclopropylmagnesium bromide (1M solution in 2-methyl tetrahydrofuran, 1.96 mL, 1.96 mmol) was added to a solution of 2-41 (255 mg) in THF (10 mL). The mixture was stirred at r.t. for 1 h. The reaction was quenched with sat. aq. NH₄Cl solution and extracted with DCM (3×). The combined organic portions were dried with Na₂SO₄, filtered and concentrated under reduced pressure. Chromatography of the residue (cyclohexane-EtOAc, 100:0 to 50:50) afforded 2-42 (146 mg, 68% over 2 steps). UPLC/MS (ES⁺): m/z: 346.20 [M+H]⁺.

A mixture of trimethylsulfoxonium iodide (93.0 mg, 0.423 mmol) and NaH (16.9 mg, 0.423 mmol) in 1:1 DMSO:THF (1 mL) was stirred at r.t. for 1 h. A solution of 2-42 (146 mg, 0.423 mmol) in THF (1 mL) was added, and the mixture was stirred at r.t. for 18 h. The mixture was partitioned between EtOAc and water. The layers were separated, and the aqueous portion was extracted with EtOAc. The combined organic portions were dried with Na$_2$SO$_4$, filtered and concentrated under reduced pressure to afford crude 2-43 (180 mg), which was used in the next step without further purification.

A solution of 2-43 (180 mg) in 7M NH$_3$:MeOH (4 mL) was stirred at r.t. for 18 h and at 35° C. for an addition 24 h. The volatiles were removed under reduced pressure. The residue was purified by reverse phase chromatography (water:CH$_3$CN 100:0 to 0:100) to afford 2-44 (13 mg, 8% over 2 steps). UPLC/MS (ES$^+$): m/z 377.20 [M+H]$^+$.

A mixture of 2-10 (39.9 mg 0.159 mmol), HOBT (25.8 mg, 0.191 mmol), EDC (28.4 mg, 0.148 mmol), TEA (0.027 mL, 0.191 mmol) and 2-44 (40.0 mg, 0.106 mmol) in DMF (2 mL) was stirred at r.t. for 18 h. A 1M aq. HCl solution was added, and the mixture was stirred at r.t. for 10 mins. The layers were separated. The organic portion was washed with 1M aq. HCl solution, dried with Na$_2$SO$_4$, filtered and concentrated under reduced pressure. The residue was purified by reverse phase chromatography (water:CH$_3$CN 100:0 to 0:100) to afford 223 (8 mg, 12%). UPLC/MS (ES$^+$): m/z 610.50 [M+H]$^+$.

Example 90

Preparation of Compound 224

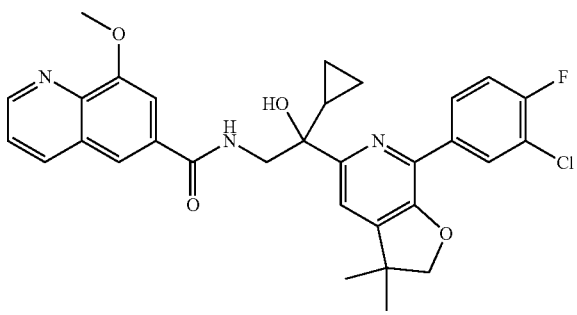

Coupling of 2-44 with 2-14 using conditions reported for the preparation of 223 (EDC, HOBT) afforded 224 as a white solid. UPLC/MS (ES$^+$): m/z 562.40 [M+H]$^+$.

Example 91

Preparation of Compound 225

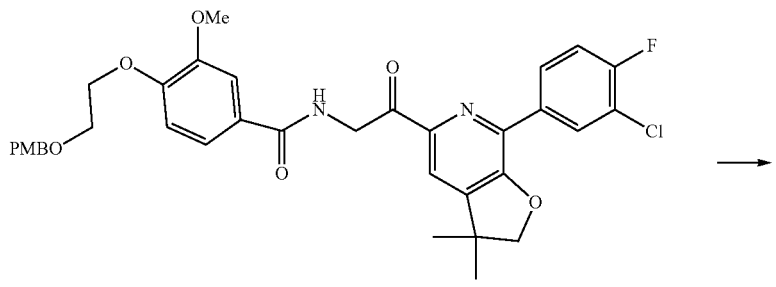

2-45

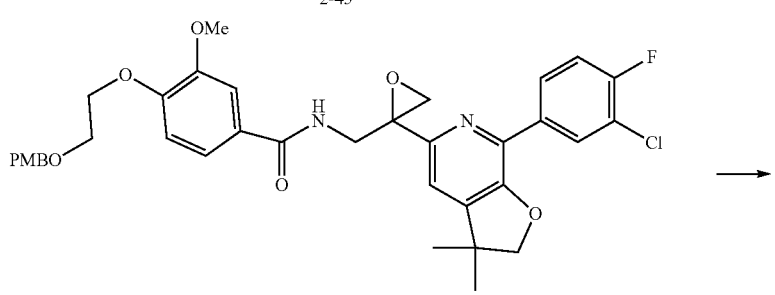

2-46

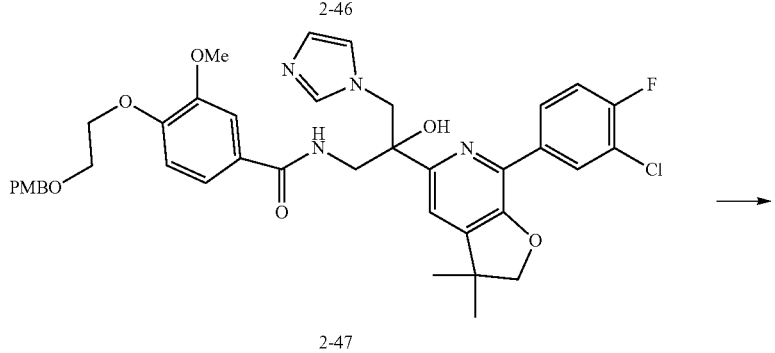

2-47

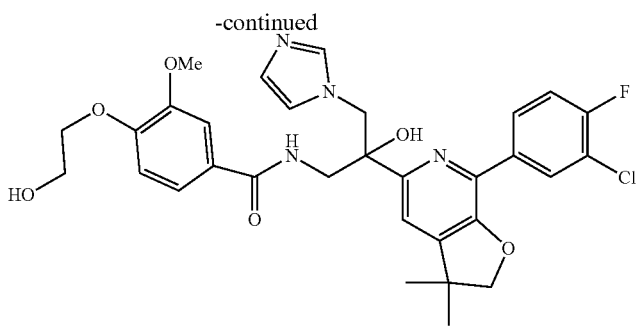

225

Trimethylsulfoxonium iodide (21.5 mg, 0.098 mmol) was added to a mixture of potassium tert-butoxide (9.98 mg, 0.089 mmol) in DMSO (2 mL). After 30 mins, 2-45 (57.8 mg, 0.089 mmol) was added, and the mixture was stirred at r.t. for 1.5 h. The mixture was partitioned between EtOAc and water. The layers were separated, and the aqueous portion was extracted with EtOAc. The combined organic portions were dried with $Na_2SO_4$, filtered and concentrated under reduced pressure to afford crude 2-46, which was used in the next step without purification. Crude 2-46 was dissolved in DMF (1 mL). $K_2CO_3$ (24.6 mg, 0.178 mmol) and imidazole (12.1 mg, 0,178 mmol) were then sequentially added. The mixture was heated to 80° C. and stirred at 80° C. for 48 h. The volatiles were removed under reduced pressure to afford crude 2-47, which was used in the next step without purification.

A solution of 2-47 in 1:1 TFA:DCM (0.9 mL) was stirred at r.t. for 1 h. The reaction was quenched with a 1M aq. NaOH solution. After 30 mins of stirring at r.t., the layers were separated. The organic portion was dried with $Na_2SO_4$, filtered and concentrated under reduced pressure. The residue was purified by reverse phase chromatography to afford 225 as a white solid (1 mg, 2% overall). UPLC/MS (ES$^+$): m/z 611.30 [M+H]$^+$.

Example 92

Preparation of Compound 226

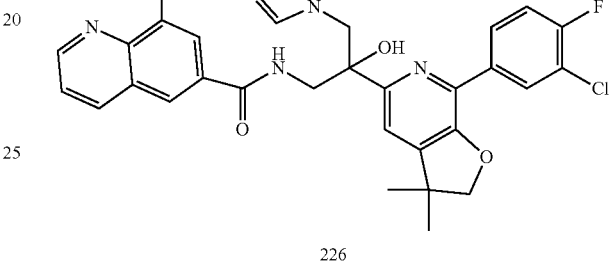

226

NaH (9.0 mg, 0.226 mmol) was added to a solution of trimethylsulfoxonium iodide (49.7 mg, 0.226 mmol) in DMSO (2 mL). After 40 mins a solution of 220 (117 mg, 0.226 mmol) in THF (2 mL) was added, and the mixture was stirred at r.t. for 6 h. The mixture was partitioned between water and EtOAc. The layers were separated, and the aqueous portion was extracted with EtOAc. The combined organic portions were dried with $Na_2SO_4$, filtered and concentrated under reduced pressure to afford crude 2-48, which was used in the next step without purification. UPLC/MS (ES$^+$): m/z 534.30 [M+H]$^+$.

Potassium carbonate (31.3 mg, 0.452 mmol) and imidazole (30.8 mg, 0.452 mmol) were sequentially added to a solution of 2-48 in DMF (2 mL). The mixture was heated to 120° C. for 18 h. The volatiles were removed under reduced pressure. The residue was purified by reverse phase chromatography (water:$CH_3CN$ 100:0 to 0:100) to afford 226 as a white solid (10 mg, 7% over 2 steps). UPLC/MS (ES$^+$): m/z 602.50 [M+H]$^+$.

Example 93

Preparation of Compound 227

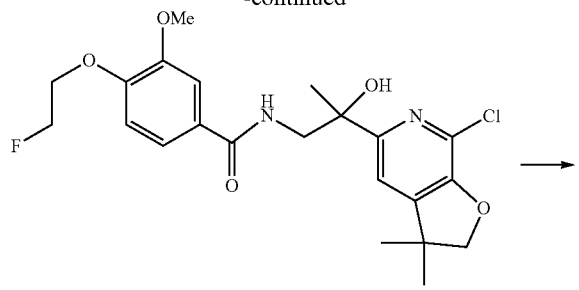

2-50

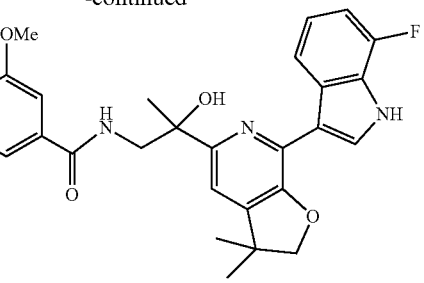

228

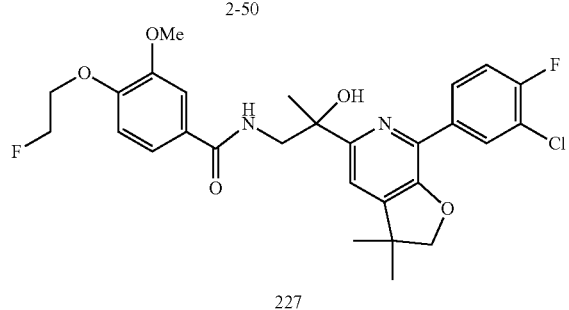

227

A mixture of 2-49 (110 mg, 0.0 mmol), HOBT (86.0 mg, 0.640 mmol), EDC (122 mg, 0.640 mmol), TEA (120 uL, 0.860 mmol) and 4-(2-fluoroethoxy)-3-methoxybenzoic acid (110 mg, 0.510 mmol) in DCM (4 mL) was stirred at r.t. for 3 h. The reaction was quenched with 1M aq. HCl solution, and the mixture was stirred at r.t. for 10 mins. The layers were separated, and the organic portion was washed with 1M aq. HCl solution, dried with $Na_2SO_4$, filtered and concentrated under reduced pressure. Chromatography of the residue (cyclohexane:EtOAc 60:40 to 10:90) afforded 2-50 as a white solid (95 mg, 48%). UPLC/MS (ES$^+$): m/z 453.09 [M+H]$^+$.

A mixture of 2-50 (45.0 mg, 0.100 mmol), (3-chloro-4-fluorophenyl)boronic acid (87.0 mg, 0.500 mmol), Pd(dppf)Cl$_2$ (3.6 mg, 0.005 mmol) and aq. $Na_2CO_3$ (2M solution, 250 uL, 0.500 mmol) in DCE (1 mL) was degassed and stirred with heating to 85° C. for 3 h. Water and DCM were added. The layers were separated, and the organic phase was dried with $Na_2SO_4$, filtered and concentrated under reduced pressure. The residue was purified by reverse phase chromatography (water:CH$_3$CN 100:0 to 50:50) to afford 227 (10.5 mg, 19%). UPLC/MS (ES$^+$): m/z 547.30 [M+H]$^+$.

Example 94

Preparation of Compound 228

2-50 ⟶

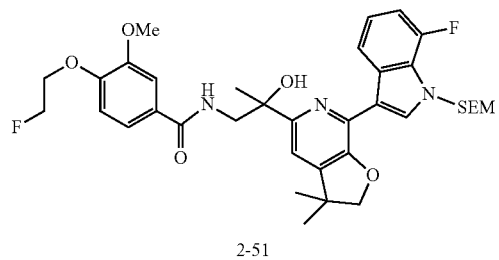

2-51

A mixture of 2-50 (50.0 mg, 0.110 mmol), 7-fluoro-3-(tetramethyl-1,3,2-dioxaborolan-2-yl)-1-{[2-(trimethylsilyl)ethoxy]methyl}-1H-indole (108 mg, 0.270 mmol), Pd(dppf)Cl$_2$ (4.0 mg, 0.005 mmol) and aq. $Na_2CO_3$ (2M solution, 135 uL, 0.270 mmol) in DCE (1 mL) was degassed and stirred with heating to 85° C. for 5 h. Water and DCM were added, and the layers were separated. The organic phase was dried with $Na_2SO_4$, filtered and concentrated under reduced pressure. The residue was purified by reverse phase chromatography (water:CH$_3$CN 100:0 to 0:100) to afford 2-51.

A solution of 2-51 in 10:1 DCM:TFA (1.1 mL) was stirred at r.t. for 3 h. A 1M aq. NaOH solution was added, and the mixture was stirred at r.t. for 18 h. The layers were separated, and the organic phase was dried with $Na_2SO_4$, filtered and concentrated under reduced pressure. The residue was purified by reverse phase chromatography (water:CH$_3$CN 100:0 to 50:50) to afford 228 (4.2 mg, 7% over 2 steps). UPLC/MS (ES$^+$): m/z 552.40 [M+H]$^+$.

Example 95

Preparation of Compound 229

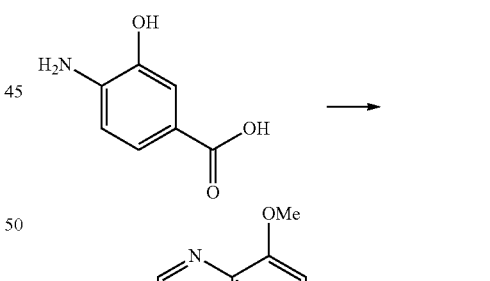

2-52

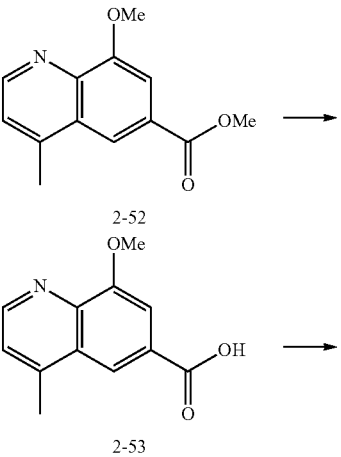

2-53

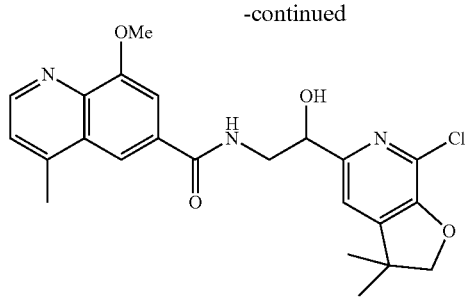

2-54

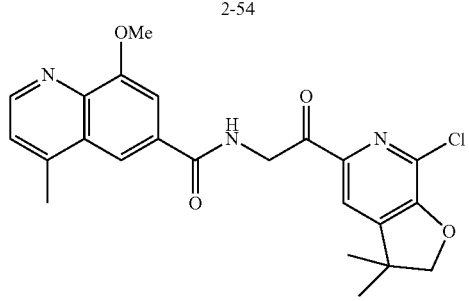

2-55

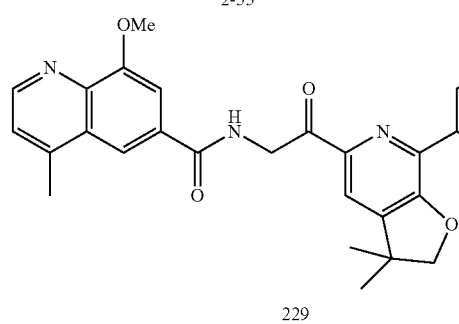

229

A mixture of 4-amino-3-hydroxybenzoic acid (2.01 g, 13.1 mmol), 12M aq. HCl solution (20 mL, 240 mmol) and 3-buten-2-one (1.59 mL, 19.6 mmol) was refluxed for 4 h. The volatiles were removed under reduced pressure, and the residue was purified by reverse phase chromatography (water:CH$_3$CN 100:0 to 0:100) to afford 8-hydroxy-4-methylquinoline-6-carboxylic acid (830 mg, 31%). This was dissolved in DMF (35 mL). Cesium carbonate (4.42 g, 13.6 mmol) and iodomethane (1.28 mL, 20.5 mmol) were sequentially added to the solution. The mixture was stirred at r.t. for 4 h. The volatiles were removed under reduced pressure, and the residue was taken up with EtOAc. The organic portion was washed with water, dried with Na$_2$SO$_4$, filtered and concentrated under reduced pressure to afford crude 2-52 (860 mg), which was used in the next step without further purification. UPLC/MS (ES$^+$): m/z 232.10 [M+H]$^+$.

Lithium hydroxide monohydrate (280 mg, 6.73 mmol) was added to a stirred suspension of 2-52 (220 mg) in a 2:1:1 THF:MeOH:H$_2$O mixture (4 mL). The mixture was stirred at r.t. for 1 h. The volatiles were removed under reduced pressure. The residue was dissolved in water, and the pH of the aqueous portion was adjusted to 6 with 1M aq. HCl solution. The mixture was purified by reverse phase chromatography (water:CH$_3$CN 100:0 to 0:100) to afford 2-53 (80 mg, 31%). UPLC/MS (ES$^+$): m/z 218.10 [M+H]$^+$.

Coupling of 2-53 with 2-30 according to Method A afforded 2-54, which was used in the next step without further purification.

Dess-Martin periodinane (127 mg, 0.299 mmol) was added to a stirred solution of 2-54 (66 mg) in dry DCM (32 mL). The mixture was stirred at r.t. for 1 h. The reaction was quenched with a 1:1 1M aq. Na$_2$S$_2$O$_3$:sat. aq. NaHCO$_3$ solution, and the mixture was stirred vigorously for 30 mins. The layers were separated, and the organic portion was washed with brine, dried with Na$_2$SO$_4$, filtered and concentrated under reduced pressure to afford crude 2-55, which was used in the next step without further purification.

A mixture of 2-55, (3-chloro-4-fluorophenyl)boronic acid (52.0 mg, 0.299 mmol), Pd(dppf)Cl$_2$ (16.0 mg, 0.022 mmol) and aq. Na$_2$CO$_3$ (2M solution, 222 uL, 0.447 mmol) in DCE (31 mL) was degassed and heated to 100° C. under microwave irradiation. After 2.5 h, the volatiles were removed under reduced pressure. The residue was purified by reverse phase chromatography (water:CH$_3$CN 100:0 to 50:50) to afford 229 (10.0 mg). UPLC/MS (ES$^+$): m/z 534.30 [M+H]$^+$.

Example 96

Preparation of Compounds 230 and 231

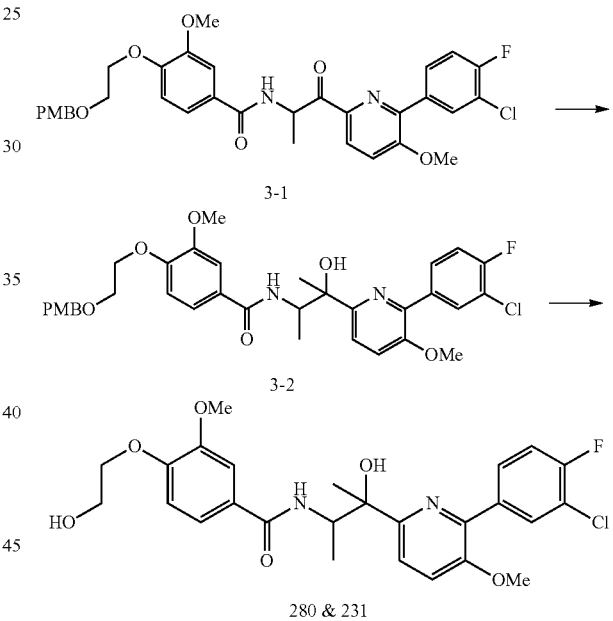

Methyl magnesiumbromide (3M solution in hexane, 300 uL, 0.892 mmol) was added to a solution of 3-1 (185 mg, 0.297 mmol) in dry THF (5 mL). The mixture was stirred at r.t. for 1 h. The reaction was quenched with 1M aq. HCl solution and EtOAc was added. The layers were separated, and the aqueous portion was extracted with EtOAc. The combined organic portions were dried with Na$_2$SO$_4$, filtered and concentrated under reduced pressure to afford crude 3-2 (201 mg), which was used in the next step without further purification.

A solution of 3-2 (201 mg) in a 10:1 DCM:TFA (3 mL) was stirred at r.t. for 40 mins. The reaction was quenched with 1M aq. NaOH solution, and the mixture was stirred at r.t. for 10 mins. The layers were separated, and the aqueous portion was extracted with DCM. The combined organic portions were dried with Na$_2$SO$_4$ and filtered. The volatiles were removed under reduced pressure. Chromatography of the residue (EtOAc:MeOH 100:0 to 80:20) afforded the two separated diastereomers (each as a racemic mixture, relative stereochemistry arbitrarily assigned). 230: white solid (10 mg, 7% overall) and UPLC/MS (ES+): m/z 519.30 [M+H]+. 231: white solid (37 mg, 24% overall) and UPLC/MS (ES+): m/z 519.30 [M+H]+.

Example 97

Preparation of Compound 232

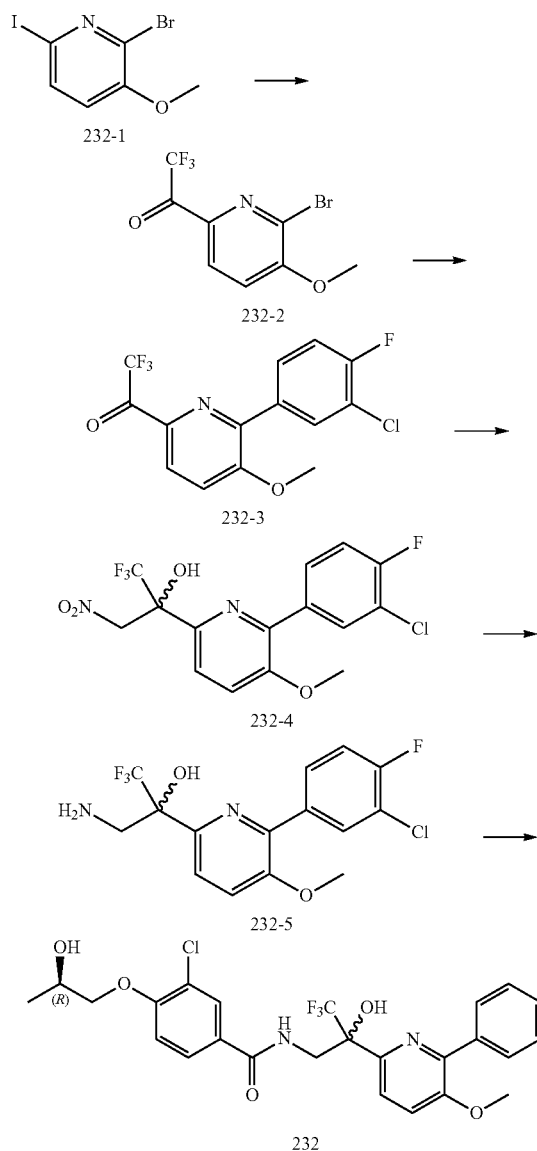

To a solution of 232-1 (21.8 g, 69.9 mmol) and ethyl 2,2,2-trifluoroacetate (12.9 g, 90.8 mmol) in THF (500 mL) was added isopropyl-magnesium chloride (46.0 mL, 2.3 N in THF) at 0° C. The mixture was stirred at 0° C. for 30 mins. The reaction was quenched with sat. NH$_4$Cl solution and extracted with EA. The combined organic phases were dried over anhydride MgSO$_4$ and evaporated under reduced pressure. The residue was purified by column chromatography on silica gel (PE:EA, 5:1) to give 232-2 as an oil (16.5 g, 83.8%).

To a solution of 232-2 (16.5 g, 58.5 mmol), (3-chloro-4-fluorophenyl)boronic acid (10.51 g, 58.6 mmol), KF (7.1 g, 117 mmol) in dioxane (300 mL) and H$_2$O (30 mL) was added Pd(dppf)Cl$_2$ (4.7 g, 5.8 mmol). The mixture was degassed and then charged with nitrogen (3×). The mixture was stirred at 70° C. in an oil bath for 6 h under N$_2$. The mixture was cooled to r.t., diluted with EA and separated from the water layer. The organic phase was washed with brine, dried over anhydrous Na$_2$SO$_4$ and concentrated at low pressure. The residue was purified by column chromatography on silica gel (PE:EA, 10:1) to give 232-3 as a white solid (17.0 g, 87.2%). ESI-MS: m/z 351.8 [M+H$_2$O]+.

A mixture of 232-3 (17.0 g, 51.1 mmol) and K$_2$CO$_3$ (13.8 g, 100 mmol) in nitro-methane (100 mL) was stirred at r.t. for 10 h. The solution was extracted with EA (3×200 mL). The combined organic phases were dried over anhydrous MgSO$_4$ and evaporated under reduced pressure. The residue was purified by column chromatography on silica gel using 15% EA in PE to give 232-4 as a white solid (16.0 g, 80.0%).

To a solution of 232-4 (16.0 g, 40.6 mmol) and NiCl$_2$.6H$_2$O (9.5 g, 40.4 mmol) in anhydrous MeOH (150 mL) and anhydrous THF (150 mL) was added NaBH$_4$ (15.2 g, 400.6 mmol) in portions at 0° C. After addition was complete, the solution was stirred at 0° C. for 1 h. The reaction was quenched with H$_2$O and then extracted with EA (3×200 mL). The combined organic layers were washed with brine, dried over anhydrous Na$_2$SO$_4$, and concentrated under reduced pressure. The residue was purified by column chromatography using EA to give 232-5 as an oil (11.0 g, 74.8%). ESI-MS: m/z 365 [M+H]+.

To a solution of (R)-3-chloro-4-(2-hydroxypropoxy)benzoic acid (115 mg, 0.5 mmol), HATU (260 mg, 0.7 mmol) and DIPEA (320 mg, 2.5 mmol) in anhydrous DCM (5 mL) was added 232-5 (180 mg, 0.5 mmol) at 25° C. The solution was stirred for 1 h at 25° C. The mixture was diluted with 1.0 N aqueous NaHCO$_3$ solution, and extracted with DCM (3×20 mL). The combined organic layers were washed with brine, dried over anhydrous Na$_2$SO$_4$, and concentrated under reduced pressure. The residue was purified by prep-HPLC to give 232 as a white solid (80 mg, 27.5%). ESI-MS: m/z 576.9 [M+H]+.

Example 98

Preparation of Compound 233

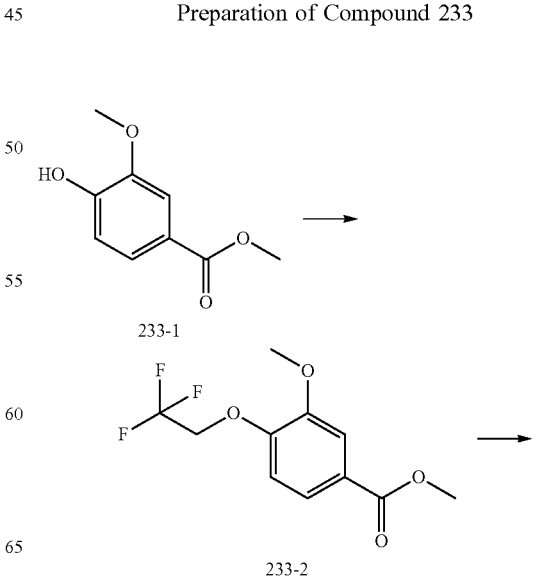

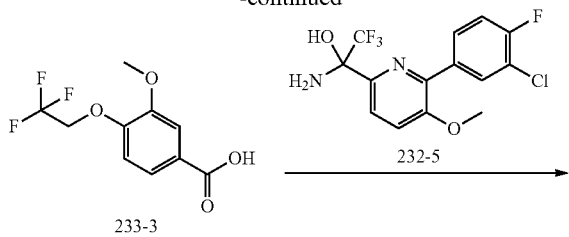

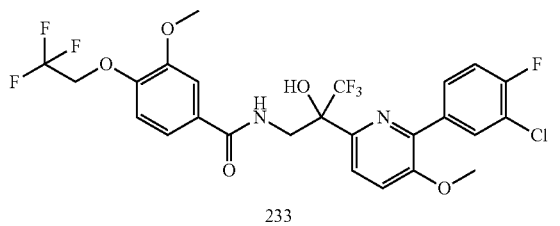

To a solution of 233-1 (1.8 g, 10.0 mmol) and F₃CCH₂I (2 g, 10.0 mmol) in DMF (100 mL) was added K₂CO₃ (2.6 g, 20.0 mmol). The mixture was stirred at 80° C. for 3 h. The mixture was concentrated at low pressure, and the residue was dissolved in EA (50 mL). The mixture was washed with brine, dried over anhydrous Na₂SO₄ and concentrated to dryness. The crude product was purified by column chromatography using 10% EA in PE to give 233-2 (1.6 g, 60%).

To a solution of 233-2 (1.5 g, 5.7 mmol) in CH₃OH and water (120 mL and 30 mL) was added LiOH (270 mg, 11.3 mmol). The mixture was stirred at 70° C. for 2 h, and then cooled to r.t. The mixture was extracted with EA, and the residue was neutralized using 2.0 N HCl solution. The mixture was extracted with EA (3×30 mL). The organic layer was washed with brine and dried over anhydrous Na₂SO₄. The solution was concentrated at low pressure to give 233-3 as a white solid (1.3 g, 85%).

Compound 233 was prepared essentially as described in the preparation of 232 by using 233-3 and 232-5. Compound 233 was obtained as a white solid. (100 mg, 67%) +ESI-MS: m/z 596.1 [M+H]⁺.

Example 99

Preparation of Compound 234

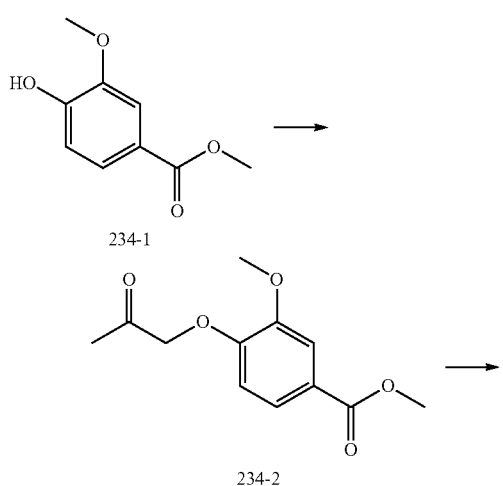

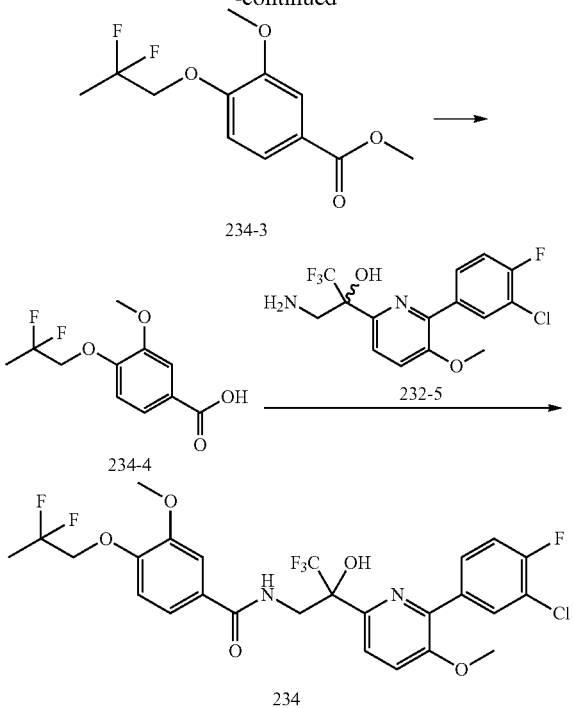

To a solution of 234-1 (1.0 g, 5.4 mmol) in MeCN (10 mL) were added 1-chloro-2-propanone (1.0 g, 10.0 mmol) and K₂CO₃ (3.5 g, 20.0 mmol). The mixture was stirred at 80° C. for 1 h. After filtration, the filtrate was concentrated at low pressure. The residue was purified by chromatography to give 234-2 (850 mg, 65.4%).

A mixture of 234-2 (500 mg, 2.1 mmol) and DAST (5 mL) was stirred at 50° C. for 12 h. The reaction was quenched with sat. NaHCO₃ solution, and extracted with EA (3×20 mL). The organic layer was washed with brine, dried over anhydrous Na₂SO₄, and concentrated to dryness. The residue was purified by column chromatography using 10% EA in PE to give 234-3 (310 mg, 56.8%).

Compound 234-4 was prepared essentially as described in the preparation of 233-3. Compound 234 was prepared essentially as described in the preparation of 232 by using 234-4 and 232-5. Compound 234 was obtained as white solid (58 mg, 24.1%). +ESI-MS: m/z 593.1 [M+H]⁺.

Example 100

Preparation of Compound 235

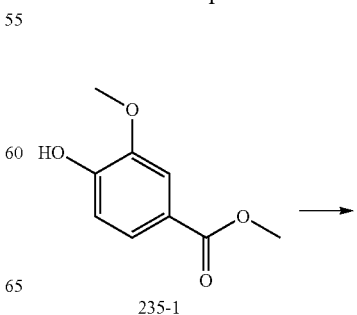

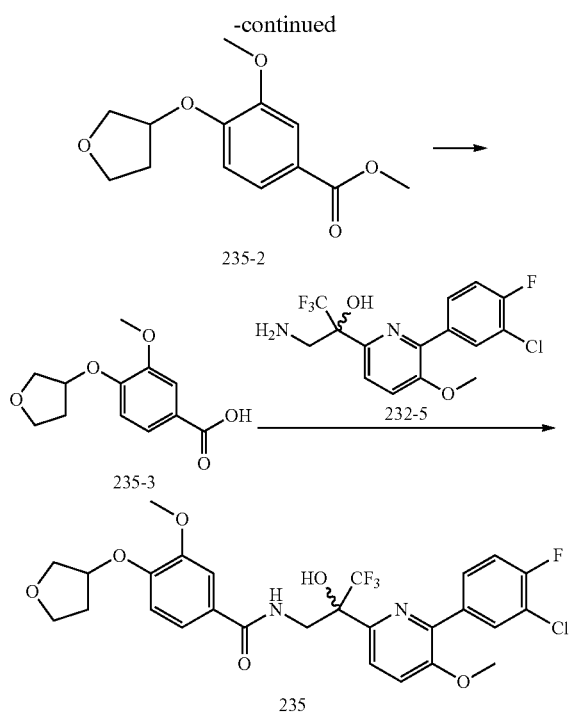

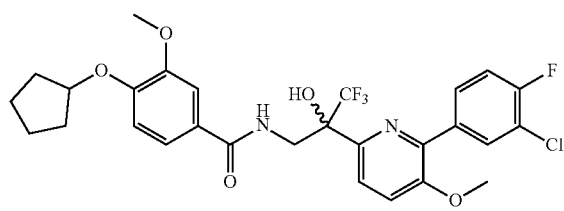

To a solution of 235-1 (1.82 g, 10.0 mmol), tetrahydrofuran-3-ol (880 mg, 10.0 mmol) and PPh₃ (2.62 g, 10.0 mmol) in THF (30 mL) at 0° C. was added DIAD (2.02 g, 10.0 mmol) dropwise. The mixture was stirred at 50° C. for 2 h, and the reaction was then quenched with sat. NaHCO₃ solution. The aqueous layer was extracted by DCM (3×). The combined organic layers were dried over MgSO₄, filtered and concentrated at low pressure. The residue was purified by flash column chromatography on silica gel to give 235-2 (2.4 g, 89.6%).

Compound 235-3 was prepared essentially as described in the preparation of 233-3. Compound 235 was prepared essentially as described in the preparation of compound 232 by using 235-3 and 232-5. Compound 235 was obtained as white solid (75 mg, 62.3%). +ESI-MS: m/z 585.2 [M+H]⁺.

Example 101

Preparation of Compound 236

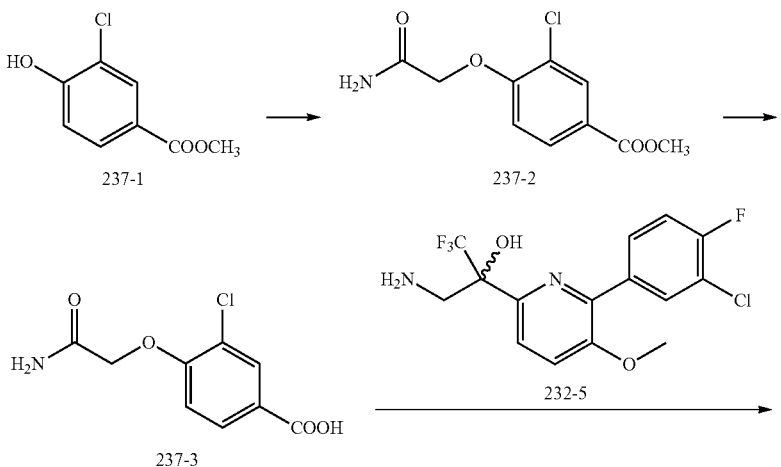

Compound 236 was prepared essentially as described in the preparation of compound 235 by using methyl 4-hydroxy-3-methoxybenzoate. Compound 236 was obtained as white solid (56 mg, 22.7%). +ESI-MS: m/z 583.1 [M+H]⁺.

Example 102

Preparation of Compound 237

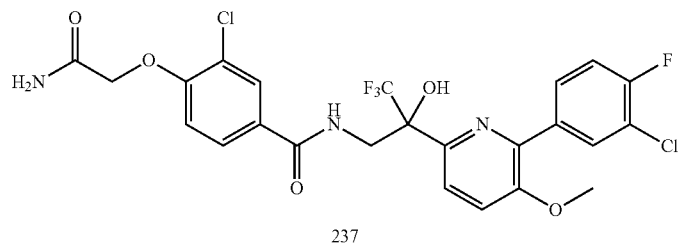

To a solution of 237-1 (0.93 g, 5 mmol) in acetone (30 mL) was added $K_2CO_3$ (2.08 g, 15 mmol) and 2-iodoacetamide (1.39 g, 7.5 mmol). The mixture was stirred at r.t. overnight. The mixture was diluted with water and extracted with EA (4×100 mL). The combined organic layers were dried over anhydrous $Na_2SO_4$ and concentrated in vacuum to give crude 237-2, which was further purified by column chromatography on silica gel (PE:EA=2:1) to 237-2 (1.01 g, 83.1%) as a white solid.

Compound 237-3 was prepared essentially as described in the preparation of 233. Compound 237 was prepared essentially as described in the preparation of 236 by using 237-3 and 232-5. Compound 237 was obtained as white solid (32 mg, 22.2%). +ESI-MS: m/z 576.1 [M+H]+.

Example 103

Preparation of Compounds 238, 239 and 240

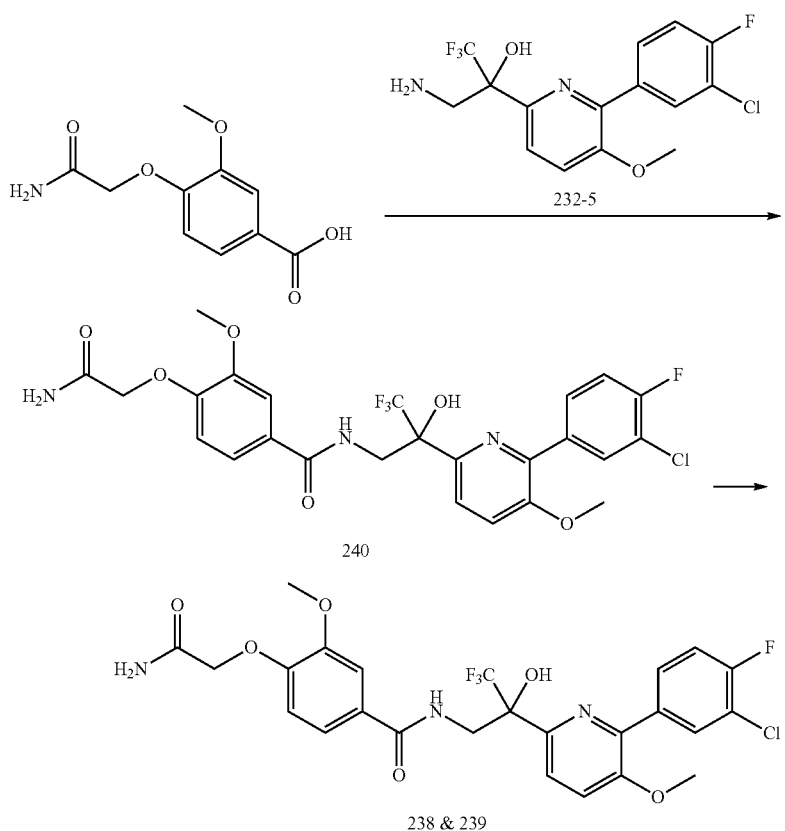

238 & 239

Compound 240 was prepared essentially as described in the preparation of 232 by using 4-(2-amino-2-oxoethoxy)-3-methoxybenzoic acid and 232-5. Compound 240 was obtained as a white solid (300 mg, 52.5%).

Compound 240 (300 mg, 0.53 mmol) was separated via SFC to give two enantiomers: 238 (140 mg, 93.3%) and 239 (100 mg, 66.7%). Compound 238: +ESI-MS: m/z 572.1 [M+H]+. Compound 239: +ESI-MS: m/z 572.0 [M+H]+.

Example 104

Preparation of Compounds 241, 242 and 243

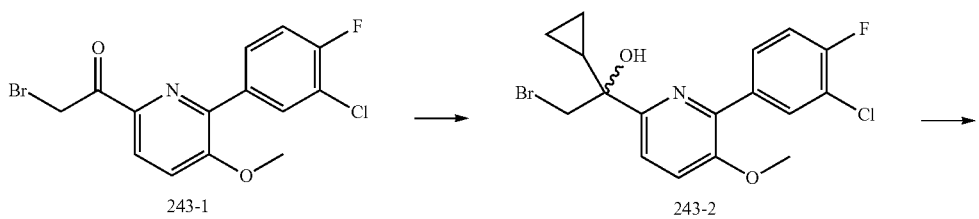

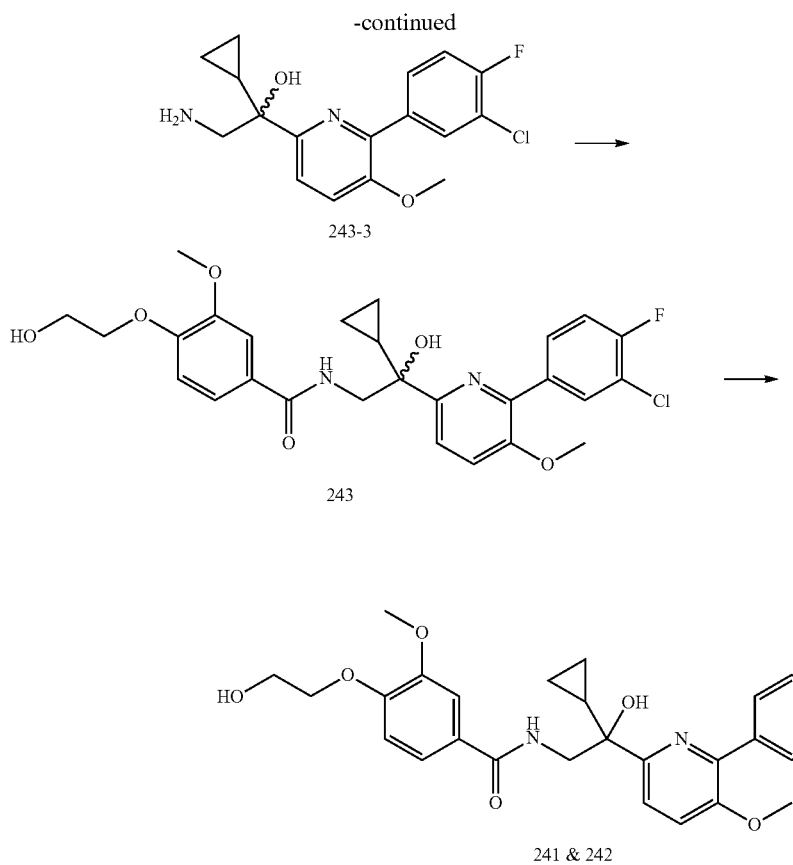

To a solution of 243-1 (714 mg, 2.0 mmol) in THF (4 mL) was added cyclopropylmagnesium bromide (4 mL, 0.5 M in THF). The mixture was stirred at 0° C. for 1 h. The reaction was quenched with water, and extracted with EA (3×20 mL). The combined organic layers was washed with brine, dried over anhydrous Na$_2$SO$_4$, and concentrated at low pressure. Crude 243-2 was directly used in the next step. +ESI-MS: m/z 399.0 [M+H]$^+$.

Compound 243-2 (600 mg), NH$_3$.H$_2$O (10 mL) and ethanol (10 mL) were put in an autoclave. After sealing, the reaction was stirred at r.t. for 10 h. The mixture was extracted by EA (3×10 mL), dried over anhydrous Na$_2$SO$_4$, and concentrated at low pressure to give 243-3, which was used without further purification. +ESI-MS: m/z 336.1 [M+H]$^+$.

Compound 243 was prepared essentially as described in the preparation of 232 by using 4-(2-hydroxyethoxy)-3-methoxybenzoic acid and 243-3. Compound 243 was obtained as a white solid (152 mg, 23%). +ESI-MS: m/z 531.2 [M+H]$^+$.

Compound 243 (152 mg, 0.28 mmol) was separated via SFC to give two isomers: 242 (40.0 mg, 26%) and 241 (43.0 mg, 26%). 241: +ESI-MS: m/z 531.1 [M+H]$^+$. 242: +ESI-MS: m/z 531.1 [M+H]$^+$.

Example 105

Preparation of Compound 244

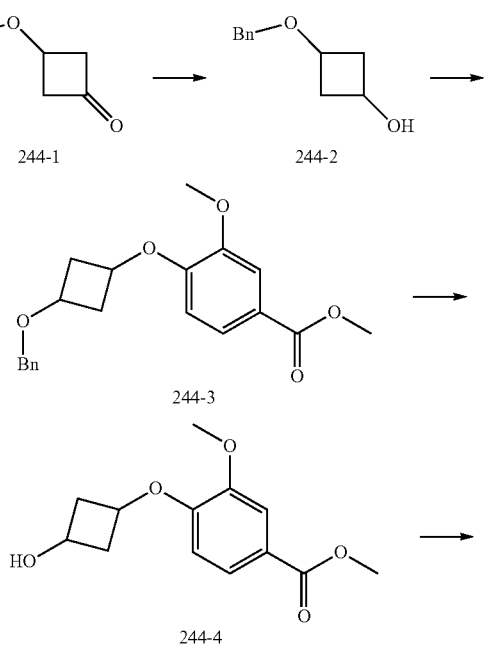

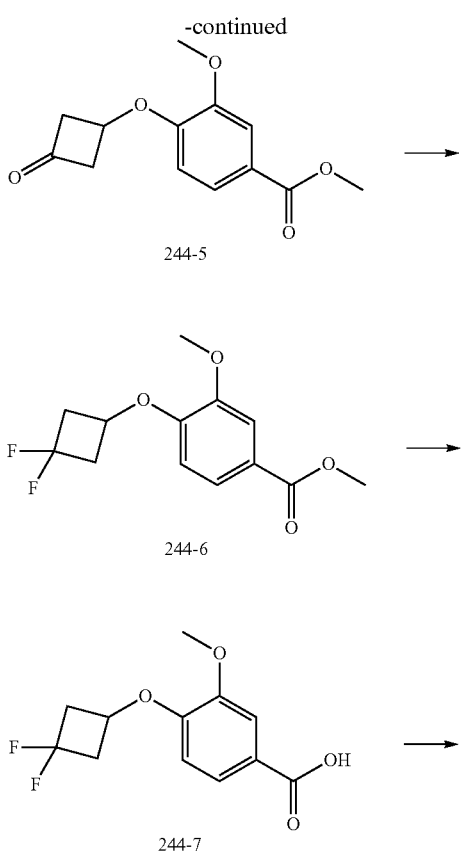

244-5

244-6

244-7

244

Compound 244-2 was prepared as described in Franck et al., *Bioorganic & Medicinal Chemistry*, (2013) 21(3):643-652. Compound 244-3 was prepared essentially as described in the preparation of 235 by using 244-4 and methyl 4-hydroxy-3-methoxybenzoate. Compound 244-3 was obtained as a white solid (2.8 g, 73.7%).

To a solution of 244-3 (2.8 g, 8.2 mmol) in methanol (15 mL) was added Pd(OH)$_2$ on charcoal (10%, 500 mg) under N$_2$. The suspension was degassed under vacuum and purged with H$_2$ (3×). The mixture was stirred under H$_2$ (40 psi) at r.t. for 3 h. The suspension was filtered through a pad of Celite, and the pad cake was washed with methanol. The combined filtrates were concentrated to give crude 244-4 (1.7 g, 84.5%), which was used in the next step without purification.

To a solution of 244-4 (1.3 g, 5.2 mmol) in DCM (10 mL) was added DMP (3.4 g, 8.0 mmol). The mixture was stirred at r.t. for 40 mins. The reaction was quenched by sat. Na$_2$S$_2$O$_3$ solution and extracted with EA. The combined organic layers were washed with sat. NaHCO$_3$ solution, brine and dried over anhydrous Na$_2$SO$_4$. The solution was concentrated to dryness, and the residue was purified by column chromatography on a silica gel column (PE:EA, 5:1) to give 244-5 as a white solid (0.8 g, 61.6%).

Compound 244-5 (500 mg, 2.0 mmol) was treated with DAST (5 mL), and stirred at 0° C. for 30 mins. The reaction was quenched by a sat. NaHCO$_3$ solution at 0° C., and then extracted with EA. The combined organic layers were washed with brine, dried over anhydrous Na$_2$SO$_4$ and concentrated to dryness. The residue was purified by column chromatography on silica gel (PE:EA, 10:1) to give 244-6 as a white solid (605 mg, 81.2%). +ESI-MS: m/z 273.1 [M+H]$^+$.

To a solution of 244-6 (300 mg, 1.1 mmol) in MeOH (35 mL) was added NaOH solution (2 N, 35 mL). The reaction was stirred under reflux for 1 h. The mixture was neutralized with 2.0 N HCl solution, and extracted with EA (3×20 mL). The combined organic layers were dried over anhydrous MgSO$_4$ and evaporated under reduced pressure to give 244-7 as a white solid (250 mg, 88.1%). +ESI-MS: m/z 259 [M+H]$^+$.

Compound 244 was prepared essentially as described in the preparation of compound 232 by using 244-7 and 232-5. Compound 244 was obtained as a white solid (60 mg, 25.5%). +ESI-MS: m/z 606.1 [M+H]$^+$.

Example 106

Preparation of Compound 245

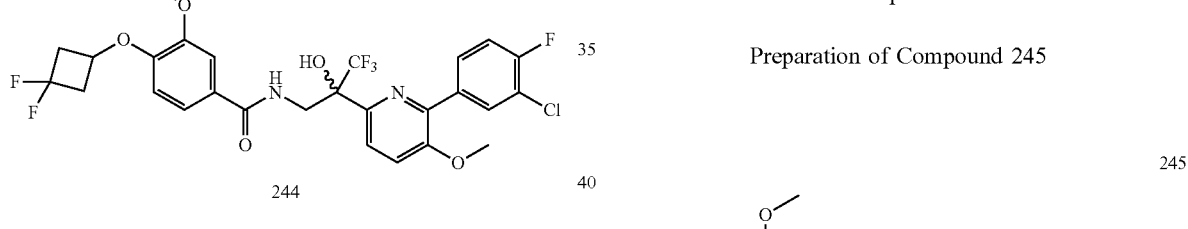

245

Compound 245 was prepared essentially as described in the preparation of 235. Compound 245 was obtained as a white solid (70 mg, 54.8%). +ESI-MS: m/z 569.1 [M+H]$^+$.

Example 107

Preparation of Compound 248

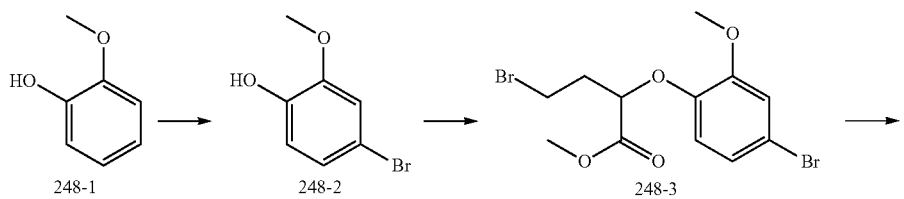

248-1  248-2  248-3

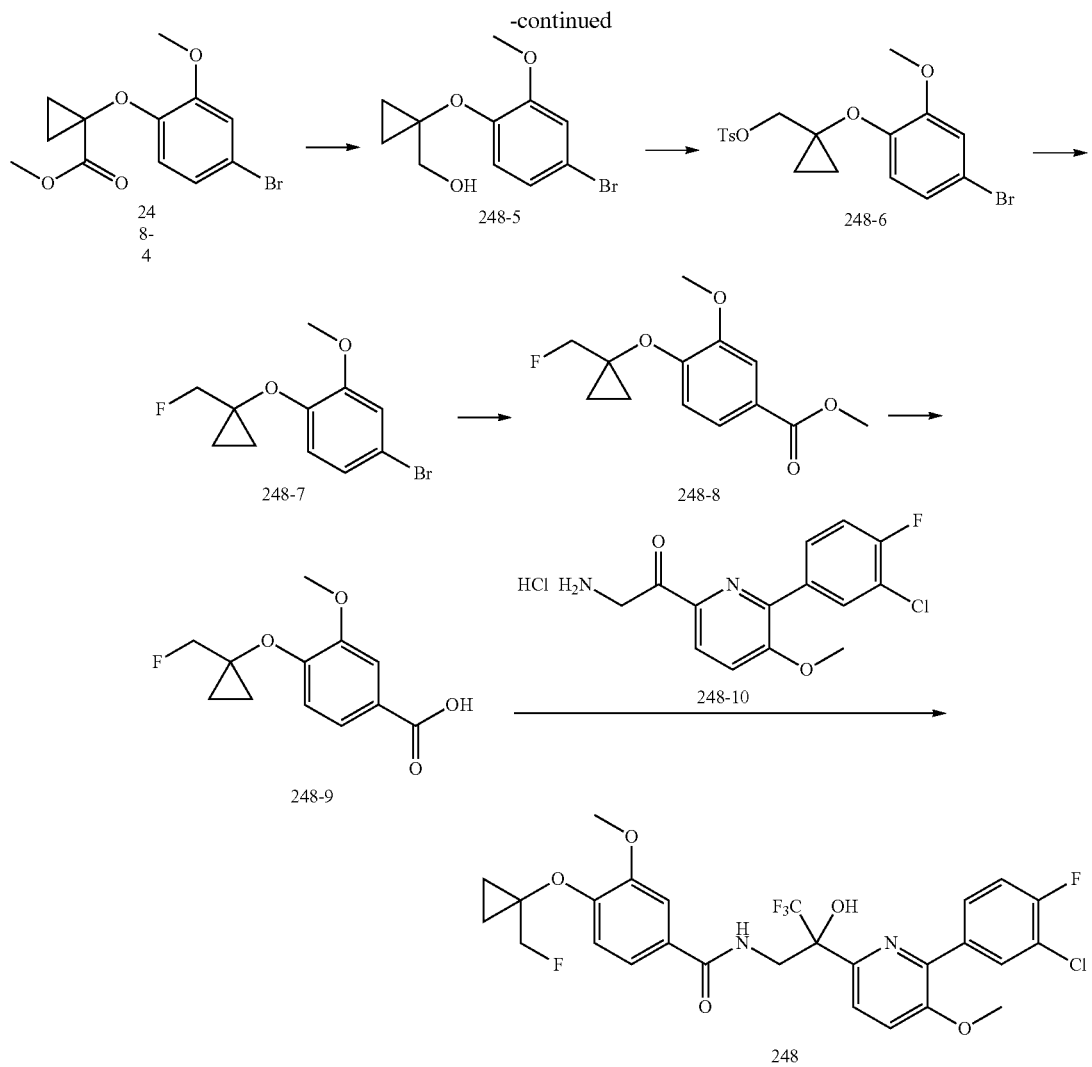

Compound 248-2 was prepared as described in Rye et al., *Eur. J Med. Chem.* (2013) 60:240-248. To a solution of 248-2 (6.0 g, 29.41 mmol) and $K_2CO_3$ (5.28 g, 38.23 mmol) in DMF (50 mL) was added methyl 2,4-dibromobutanoate (9.86 g, 38.23 mmol). The mixture was stirred at 80° C. for 12 h, and then diluted with water and extracted with EA (3×50 mL). The combined organic layers were dried over anhydrous $Na_2SO_4$ and concentrated in vacuum. The residue was purified by column chromatography on silica gel crude 248-3 (9.8 g).

To a solution of 248-3 (9.8 g, 25.8 mmol) in THF (100 mL) was added t-BuOK (28.37 mL, 28.37 mmol, 1 N in THF) at 0° C. The mixture was stirred at r.t. for 3 h. The mixture was diluted with water and extracted with EA (3×60 mL). The combined organic layer was dried over anhydrous $Na_2SO_4$ and concentrated at low pressure. The residue was purified by column chromatography to give 248-4 (6.0 g, 78.0%).

To a solution of 248-4 (6.0 g, 20.0 mmol) in EtOH (20 mL) was added $NaBH_4$ (2.10 g, 30.0 mmol) at r.t. The mixture was stirred at r.t. for 10 mins. The mixture was heated to reflux for 10 h and then cooled to r.t. The mixture was diluted with EA (60 mL) and washed with brine. The combined organic layer was dried over anhydrous $Na_2SO_4$ and concentrated at low pressure. The residue was purified by chromatography to give 248-5 (4.5 g) as a white solid.

To a solution of 248-5 (500 mg, 1.84 mmol) in DCM (10 mL) was added $Et_3N$ (370 mg, 3.68 mmol) and DMAP (10.0 mg, 0.082 mmol). TsCl (459 mg, 2.41 mmol) was added portionwise. The mixture was stirred at r.t. overnight. The reaction was quenched with water, and extracted with EA (3×30 mL). The combined organic layer were dried over anhydrous $Na_2SO_4$ and concentrated at low pressure. The residue was purified by column chromatography on silica gel to give 248-6 as a white solid (730 mg, 93.1%).

To a solution of 248-6 (730 mg, 1.80 mmol) in anhydrous THF (10 mL) was added TBAF (1M in THF) (5.0 mL, 5.0 mmol). The mixture was stirred at r.t. overnight. The mixture was diluted with EA (20 mL) and washed with brine. The combined organic layer was dried over anhydrous $Na_2SO_4$ and concentrated at low pressure. The residue was purified by column chromatography on silica gel to give 248-7 as a white solid (330 mg, 67.0%).

To a solution of 248-7 (330 mg, 1.2 mmol) in anhydrous THF (10 mL) was added n-BuLi (0.63 mL, 1.6 mmol) at −78° C. dropwise. The mixture was stirred at −78° C. for 0.5 h. $ClCOOCH_3$ (0.69 g, 7.2 mmol) was added in one portion and stirred at −78° C. for 1 h. The mixture was diluted with EA (20 mL) and washed with brine. The combined organic layer was dried over anhydrous Na₂SO₄ and concentrated at low pressure. The residue was purified by chromatography to give 248-8 as a white solid (203 mg, 66.0%).

Compound 248-9 was prepared essentially as described in the preparation of 233. Compound 248 was prepared essentially as described in the preparation of 232 by using 248-9 and 248-10. Compound 248 was obtained as a white solid (12 mg, 3.7%). +ESI-MS: m/z 587.1 [M+H]⁺.

Example 108

Preparation of Compound 249

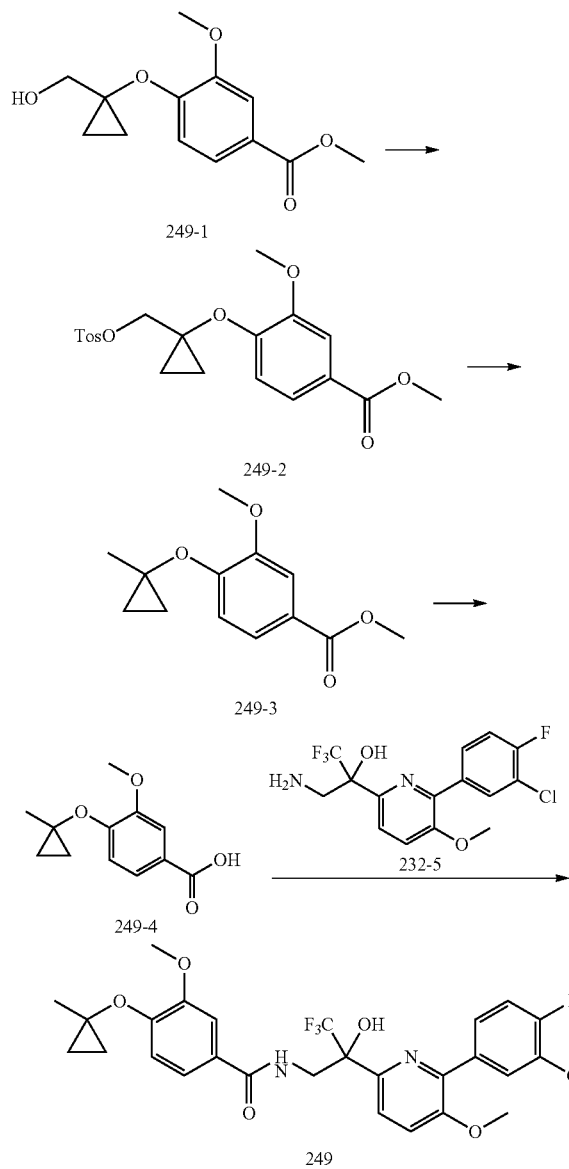

Compound 249-2 was prepared essentially as described in the preparation of 248. To a solution of 249-2 (1.02 mg, 2.5 mmol) in DMSO (10 mL) was added NaBH₄ (285 mg, 7.5 mmol) at r.t. under N₂ atmosphere. The solution was heated to 80° C. and stirred for 1 h. The solution was cooled to r.t. The reaction was quenched with water (20 mL) and extracted with EA (2×20 mL). The organic phase was concentrated at low pressure, and the residue was purified by column chromatography on silica gel (PE:EA=20:1) to give 249-3 as a colorless oil (280 mg, 47.4%)

Compound 249-4 was prepared essentially as described in the preparation of 233. Compound 249 was prepared essentially as described in the preparation of 232 by using 249-4 and 232-5. Compound 249 was obtained as a white solid (7 mg, 13.7%). +ESI-MS: m/z 569.0[M+H]⁺.

Example 109

Preparation of Compound 250

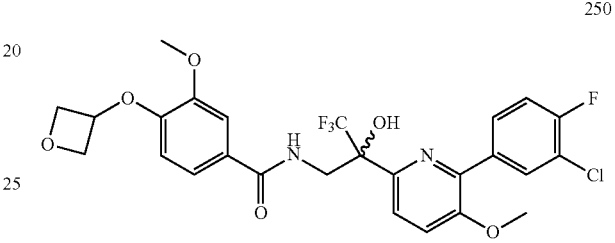

Compound 250 was prepared essentially as described in the preparation of 235 by using methyl 4-hydroxy-3-methoxybenzoate and 232-5. Compound 250 was obtained as white solid (19.8 mg, 8.7%). +ESI-MS: m/z 571.0[M+H]⁺.

Example 110

Preparation of Compound 251

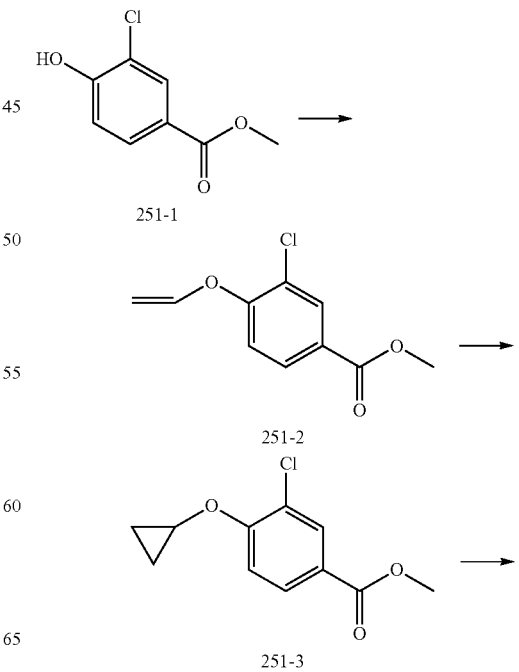

-continued

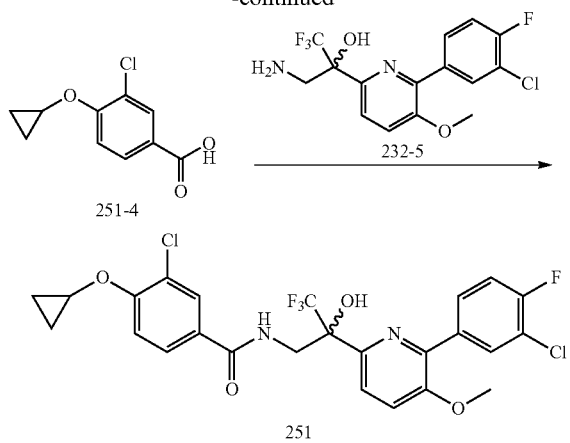

To a suspension of [IrCl(cod)]$_2$ (18 mg, 0.03 mmol) and sodium carbonate (171 mg, 1.6 mmol) in toluene (10 mL) was added 251-1 (500 mg, 2.68 mmol) and vinyl acetate (457 mg, 5.38 mmol) under Ar. The mixture was stirred at 100° C. for 2 h. The mixture was cooled to r.t., and treated with PE. The precipitate was removed by filtration, and the organic phase was concentrated at low pressure. The residue was purified by column chromatography on silica gel (PE: EA=30:1) to give 251-2 (410 mg, 72%).

TFA (468 mg, 4.1 mmol) was slowly added to anhydrous DCM (5 mL) and Et$_2$Zn (4.2 mL, 4.2 mmol) at 0° C. The mixture was stirred at 0° C. for 10 mins, followed by the addition of CH$_2$I$_2$ (1.9 g, 7.1 mL). The resulting solution was stirred at 0° C. for 10 mins, and then 251-2 (300 mg, 1.42 mmol) was added. The mixture was allowed to warm to r.t., and stirred at r.t. overnight. The reaction was quenched with sat. NH$_4$Cl solution and extracted with EA (3×20 mL). The organic layer was dried over anhydrous MgSO$_4$ and concentrated at low pressure. The residue was purified by column chromatography on silica gel (PE:EA=20:1) to give 251-3 (210 mg, 65.8%).

Compound 251-4 was prepared essentially as described in the preparation of 233. Compound 251 was prepared essentially as described in the preparation of 232 by using 251-4 and 232-5. Compound 251 was obtained as white solid (23 mg, 10.1%). +ESI-MS: m/z 559.0[M+H]$^+$.

Example 111

Preparation of Compound 252

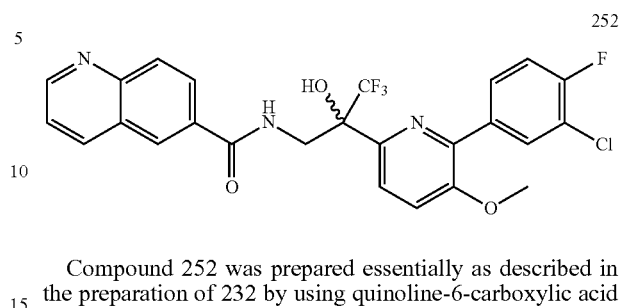

Compound 252 was prepared essentially as described in the preparation of 232 by using quinoline-6-carboxylic acid and 232-5. Compound 252 was obtained as a white solid (70 mg, 33%). +ESI-MS: m/z 520.1 [M+H]$^+$.

Example 112

Preparation of Compound 253

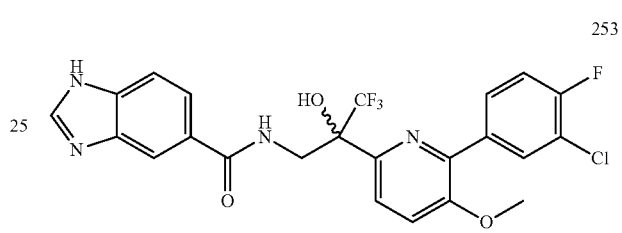

Compound 253 was prepared essentially as described in the preparation of 232 by using 1H-benzo[d]imidazole-5-carboxylic acid and 232-5. Compound 253 was obtained as a white solid (70 mg, 28%). +ESI-MS: m/z 509.1 [M+H]$^+$.

Example 113

Preparation of Compound 254

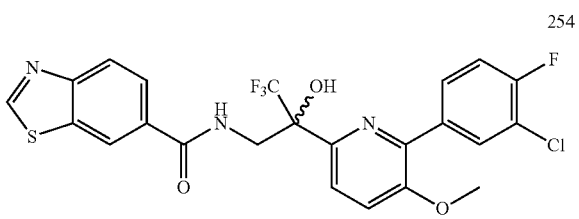 [SMILES: COc1ccc(C(O)(CNC(=O)c2ccc3ncsc3c2)C(F)(F)F)nc1-c1ccc(F)c(Cl)c1]

Compound 254 was prepared essentially as described in the preparation of 232 by using benzo[d]thiazole-6-carboxylic acid and 232-5. Compound 254 was obtained as a white solid (38 mg, 33%). +ESI-MS: m/z 525.9 [M+H]$^+$.

Example 114

Preparation of Compounds 255, 256 and 398

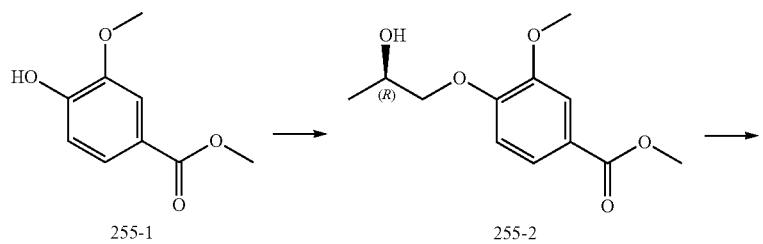

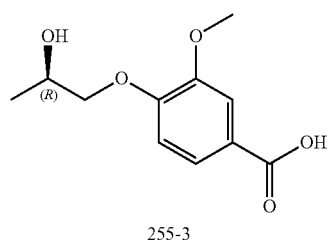
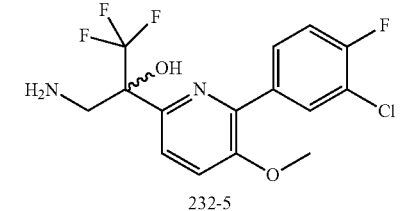
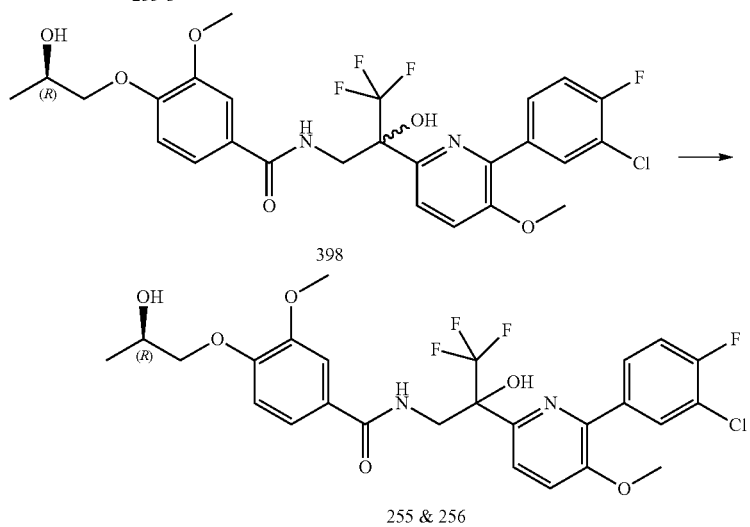

To a solution of 255-1 (5 g, 27 mmol) and (R)-2-methyloxirane (4.7 g, 82 mmol) in DMF (100 mL) was added K$_2$CO$_3$ (7.4 g, 54 mmol). The mixture was stirred at 80° C. for 3 h. The reaction was quenched with water and extracted by EA (3×50 mL). The organic layer was washed with brine, dried over anhydrous Na$_2$SO$_4$ and concentrated at low pressure. The residue was purified by column chromatography on silica gel to give 255-2 (6.5 g, 95%).

Compound 255-3 was prepared essentially as described in the preparation of 233. Compound 398 was prepared essentially as described in the preparation of 232 by using 255-3 and 232-5. Compound 398 was obtained as a white solid (687 mg, 68%).

Compound 398 (350 mg, 1.14 mmol) was separated via SFC to give two diastereomers: 255 (113 mg) and 256 (107 mg). 255: +ESI-MS: m/z 573.1 [M+H]$^+$. 256: +ESI-MS: m/z 573.1 [M+H]$^+$.

Example 115

Preparation of Compound 257

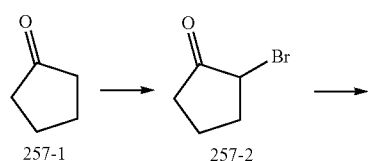
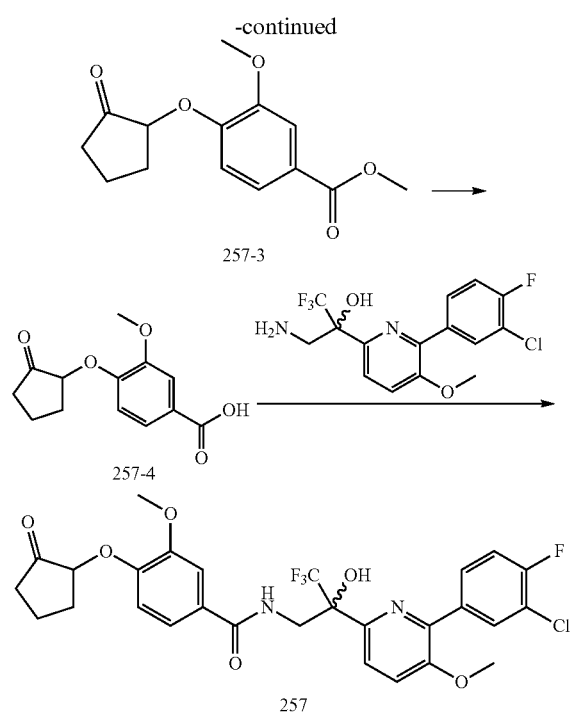

Compound 257-2 was prepared according to the procedure provided in Xu et al., *Angew. Chem. Int. Ed.* (2011) 50(51).12249-12252. Compound 257 was prepared essentially as described in the preparation of 234 by using 257-2 and 232-5. Compound 257 was obtained as a white solid (51 mg, 23.8%). +ESI-MS: m/z 597.1 [M+H]$^+$.

Example 116

Preparation of Compound 258

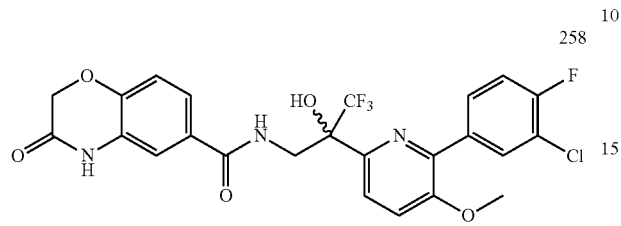

Compound 258 was prepared essentially as described in the preparation of 232 by using 3-oxo-3,4-dihydro-2H-benzo[b][1,4]oxazine-6-carboxylic acid and 232-5. Compound 258 was obtained as a white solid (80 mg, 41%). +ESI-MS: m/z 540.0 [M+H]$^+$.

Example 117

Preparation of Compounds 259, 260 and 261

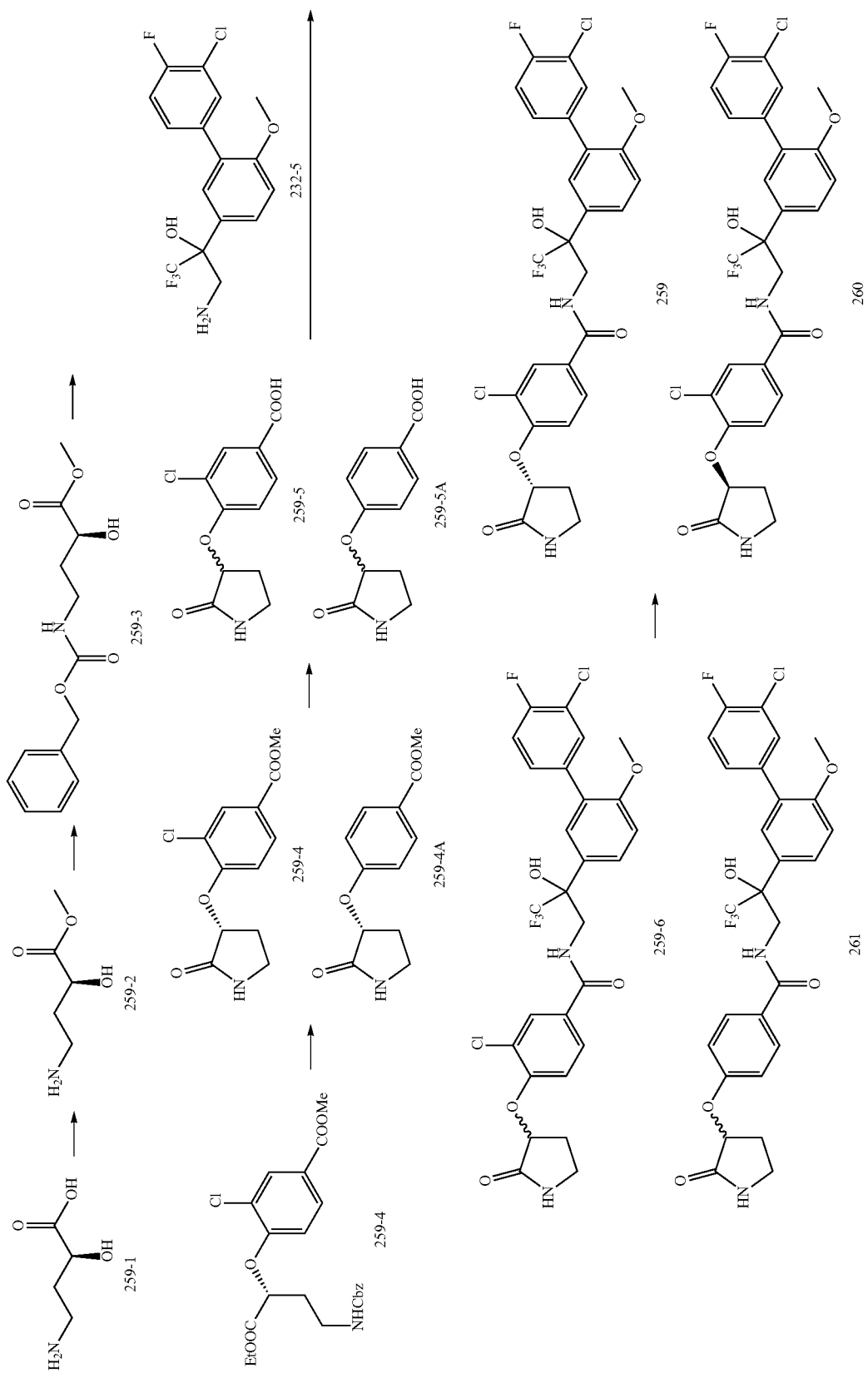

Compound 259-2 was prepared according to the procedure provided in Chinese Patent No. CN 1869008, published Nov. 29, 2006, which is hereby incorporated by reference for the limited purpose of its description of the preparation of 259-2. Compound 259-3 was prepared according to the procedure provided in Barbayianni et al., *J. Org. Chem.* (2005) 70(22):8730-8733, which is hereby incorporated by reference for the limited purpose of its description of the preparation of 259-3. Compound 259-4 was prepared essentially as described in the preparation of 235 by using 259-3 and methyl 3-chloro-4-hydroxybenzoate. Compound 259-4 was obtained as a white solid (4 g, 90%).

Under $H_2$ atmosphere, a mixture of 259-4 (4 g, 9 mmol) and Pd/C (200 mg) in MeOH (45 mL) was stirred at 30° C. for 10 h. Purification by column chromatography on silica gel provided 259-4 (2 g, 80%). +ESI-MS: m/z 269.8[M+H]$^+$.

To a solution of 259-4 and 259-4A (2 g, 7.4 mmol) in THF/$H_2O$ (10 mL/1 mL) was added NaOH (400 mg, 10 mmol) in portions until the starting material was consumed completely. The mixture was neutralized by addition of 2 N HCl solution. The mixture was extracted with EA (3×40 mL). The organic phase was washed with brine, dried over anhydrous $MgSO_4$ and concentrated at low pressure to give 259-5 and 259-5A.

Compound 259-6 and 261 were prepared essentially as described in the preparation of 232 by using 259-5 and 232-5. Compound 259-6 (100 mg) and 261 (30 mg) were each obtained as a white solid. 261: +ESI-MS: m/z 568.1 [M+H]$^+$.

Compound 259-6 (100 mg, 0.16 mmol) was separated by SFC to give 259 (80 mg, 80%) and 260 (20 mg, 20%). 259: +ESI-MS: m/z 602.1 [M+H]$^+$. 260: +ESI-MS: m/z 602.1 [M+H]$^+$.

Example 118

Preparation of Compound 262

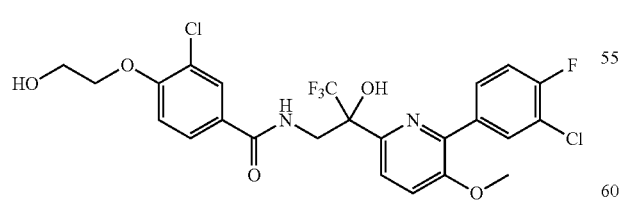

262

Compound 262 was prepared essentially as described in the preparation of 237 by using 2-oxo-2,3-dihydro-1H-benzo[d]imidazole-5-carboxylic acid and 232-5. Compound 262 was obtained as a white solid (58 mg, 24.5%). +ESI-MS: m/z 563.0 [M+H]$^+$.

Example 119

Preparation of Compounds 264 and 265

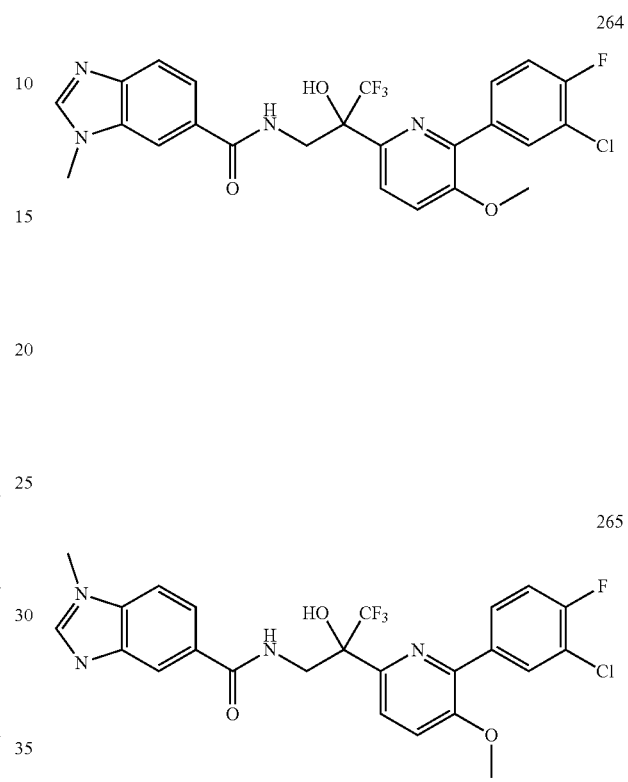

264

265

Compounds 264 and 265 were prepared essentially as described in the preparation of 232 by using 1-methyl-1H-benzo[d]imidazole-6-carboxylic acid or 1-methyl-1H-benzo[d]imidazole-5-carboxylic acid, and 232-5, respectively. Compounds 264 (47 mg, 26%) and 265 (51 mg, 28%) were each obtained as a white solid. 264: +ESI-MS: m/z 522.9 [M+H]$^+$. 265: +ESI-MS: m/z 523.0 [M+H]$^+$.

Example 120

Preparation of Compound 266

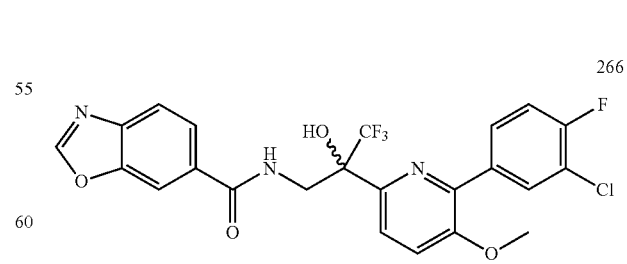

266

Compound 266 was prepared essentially as described in the preparation of 232 by using benzo[d]oxazole-6-carboxylic acid and 232-5. Compound 266 was obtained as a white solid (60 mg, 23%). +ESI-MS: m/z 509.9 [M+H]$^+$.

Example 121

Preparation of Compound 267

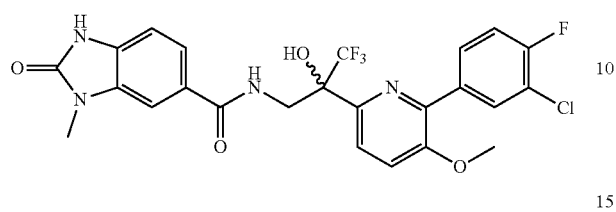

267

Compound 267 was prepared essentially as described in the preparation of 232 by using 3-methyl-2-oxo-2,3-dihydro-1H-benzo[d]imidazole-5-carboxylic acid and 232-5 as start material. Compound 267 was obtained as a white solid (10.7 mg, 7.6%). +ESI-MS: m/z 539.0 [M+H]$^+$.

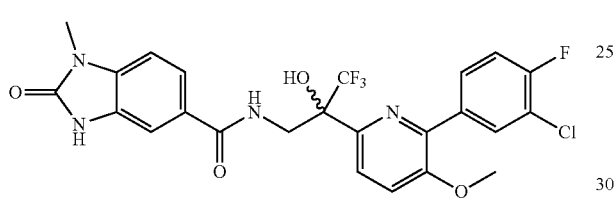

268

Compound 268 was prepared essentially as described in the preparation of 232 by using 1-methyl-2-oxo-2,3-dihydro-1H-benzo[d]imidazole-5-carboxylic acid and 232-5. Compound 268 was obtained as a white solid (14 mg, 8.4%). +ESI-MS: m/z 539.0 MS: m/z 539.0 [M+H]$^+$.

Example 123

Preparation of Compound 269

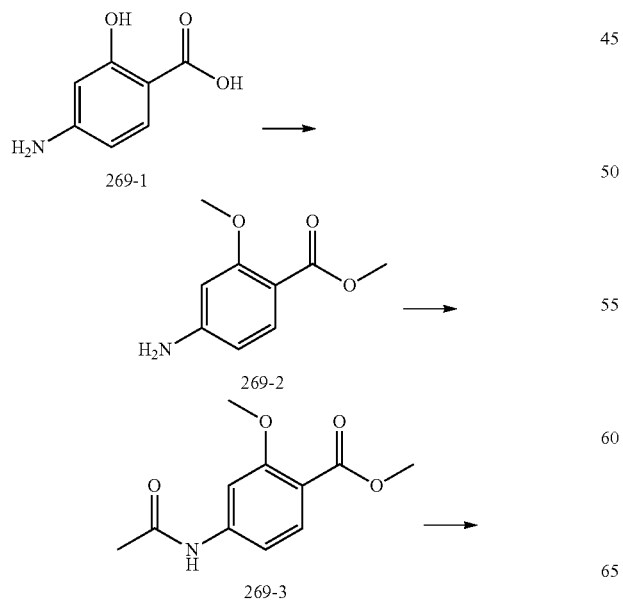

-continued

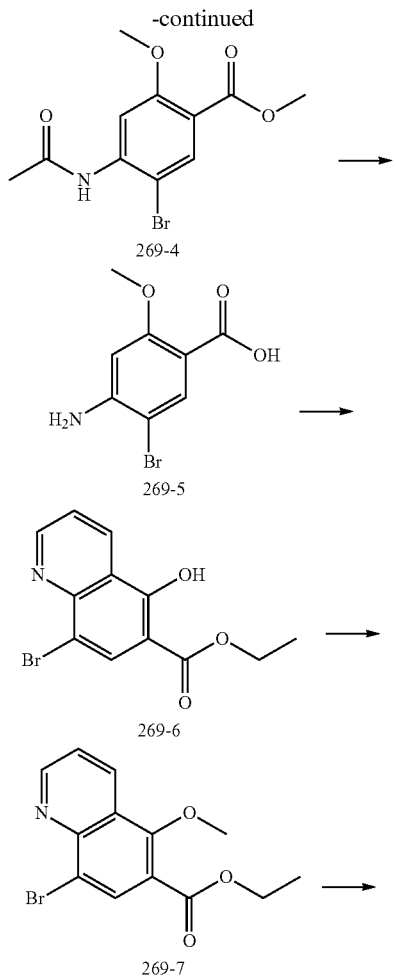

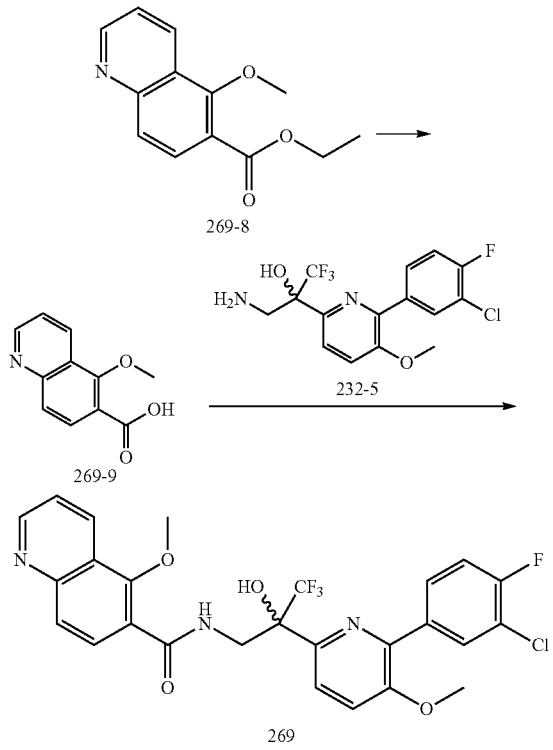

To a stirred solution of 269-1 (20.0 g, 130.68 mmol) in acetone (400 mL) was added KOH (18.4 g, 15 mmol) and (CH$_3$)$_2$SO$_4$ (29.4 mL, 318.9 mmol). The mixture was stirred at r.t. overnight. The solvent was evaporated at low pressure, and the residue was dissolved in hot water. The pH was adjusted to 9 with 1 N NaOH solution. After cooling to r.t., the precipitate was filtered off and thoroughly washed with cold EtOAc to give 269-2 as a light yellow powder (23.66 g, 63.4%). +ESI-MS: m/z 181.8 [M+H]$^+$.

To a solution of 269-2 (14.4 g, 8 mmol) in EtOH (120 mL) was added acetic anhydride (9.0 g, 88 mmol). The mixture was allowed to stir at 50° C. for 2 h. The mixture was cooled to r.t., and neutralized with aqueous NaHCO$_3$ solution. The mixture was extracted with EA (3×60 mL). The organic phase was dried over anhydrous sodium sulfate, and concentrated at low pressure. The residue was purified by flash column chromatography on silica gel (PE:EA 1:1) to give 269-3 (15.0 g, 84.1%). +ESI-MS: m/z 223.9 [M+H]$^+$.

To a solution of 269-3 (4.46 g, 20 mmol), PdOAc (0.45 g, 2 mmol) and Cu(OAc)$_2$ (7.26 g, 40 mmol) in 1,2-dichloroethane (150 mL) was added anhydrous CuBr$_2$ (8.93 g, 40 mmol) under N$_2$ atmosphere. The mixture was stirred at 90° C. for 72 h. After cooling to r.t., the reaction was quenched by water, and filtered through a celite pad. The solution was washed with brine, dried by anhydrous Na$_2$SO$_4$ and concentrated at low pressure. The residue was purified by flash column chromatography on silica gel (PE:EA 1:1) to give 269-4 (6.04 g, 51.3%). +ESI-MS: m/z 303.7 [M+H]$^+$.

To a solution of 269-4 (4.53 g, 15 mmol) in ethanol (60 mL) and water (60 mL) was added NaOH (6.0 g, 150 mmol), and the mixture was stirred at 70° C. overnight. After cooling to 0° C., the mixture was neutralized with 5% aqueous HCl. The precipitate was filtered and concentrated to give 269-5 as a light yellow powder (3.1 g, 82.0%), which was used without further purification. +ESI-MS: m/z 247.6 [M+H]$^+$.

A mixture of 269-5 (2.44 g, 10 mmol), glycerol (1.5 mL, 20 mmol), and 3-nitrobenzensulfonate (10 g, 45 mmol) were treated with conc. H$_2$SO$_4$ (25 mL) and H$_2$O (8.3 mL). The mixture was heated at 100° C. for 3 h., and then stirred at 140° C. for 1 h. The mixture was slowly cooled to 60° C. Ethanol (15 mL) was added, and the mixture was stirred overnight. The mixture was neutralized with ammonia water, and extracted with EA (3×50 mL). The solution was dried over anhydrous Na$_2$SO$_4$ and concentrated at low pressure. The residue was purified by flash column chromatography on silica gel (PE:EA 10:1) to give 269-6 (0.50 g, 16.9%). +ESI-MS: m/z 295.9 [M+H]$^+$.

To a stirred solution of 269-6 (0.295 g, 1 mmol) in DMF (3 mL) was added K$_2$CO$_3$ (145 mg, 1.05 mmol) and CH$_3$I (149 mg, 1.05 mmol). The mixture was stirred at r.t. overnight, and then concentrated at low pressure. The residue was dissolved in EA (20 mL). The solution was washed with brine, dried over Na$_2$SO$_4$ and concentrated in vacuum. The residue was purified by column chromatography on silica gel (PE:EA=5:1) to give 269-7 (216 mg, 70.0%) as a white solid. +ESI-MS: m/z 311.9 [M+H]$^+$.

To a stirred solution of 269-7 (240 g, 0.77 mmol) in methanol (30 mL) was added Pd/C (15 mg). The mixture was stirred at r.t. under H$_2$ (balloon) for 1 h. The mixture was filtered, and the filtrate was concentrated at low pressure. The residue was purified by column chromatography on silica gel (PE:EA=5:1) to give 269-8 (101 mg, 56.0%) as a white solid. +ESI-MS: m/z 231.9 [M+H]$^+$.

To a solution of 269-8 (0.1 g, 0.44 mmol) in CH$_3$OH (2 mL) and water (2 mL) was added NaOH (80 mg, 2 mmol), and the mixture was stirred at 50° C. for 0.5 h. The mixture was cooled to 0° C., and the pH was adjusted to 5 using 5% HCl solution. The mixture was extracted with EA (3×20 mL). The organic layer was dried over anhydrous sodium sulfate, and concentrated at low pressure to give crude 269-9 (66 mg, 75.8%) as a white solid, which was used without further purification.

To a solution of 269-9 (66 mg, 0.325 mmol) in DCM (5 mL) were added DMF (1 drop) and (COCl)$_2$ (0.23 mL, 1.3 mmol). The mixture was stirred at r.t. for 2 h, and then concentrated at low pressure. The residue was treated with a solution of 232-5 (117 mg, 0.325 mmol) and TEA (0.28 mL) in DCM (5 mL) at 50° C. The mixture was allowed to stir at r.t. overnight. The mixture was diluted with water, and extracted with EA (3×20 mL). The organic layer was dried over anhydrous sodium sulfate, and concentrated in vacuum. The residue was purified by HPLC to give 269 as a white solid (25 mg, 14.0%). +ESI-MS: m/z 550.0 [M+H]$^+$.

Example 124

Preparation of Compound 270

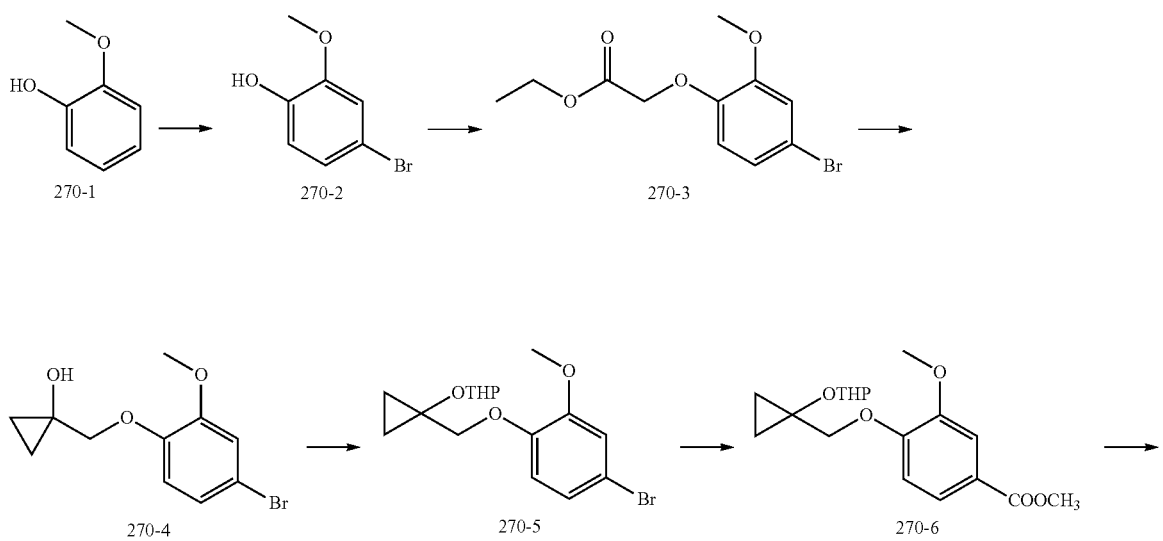

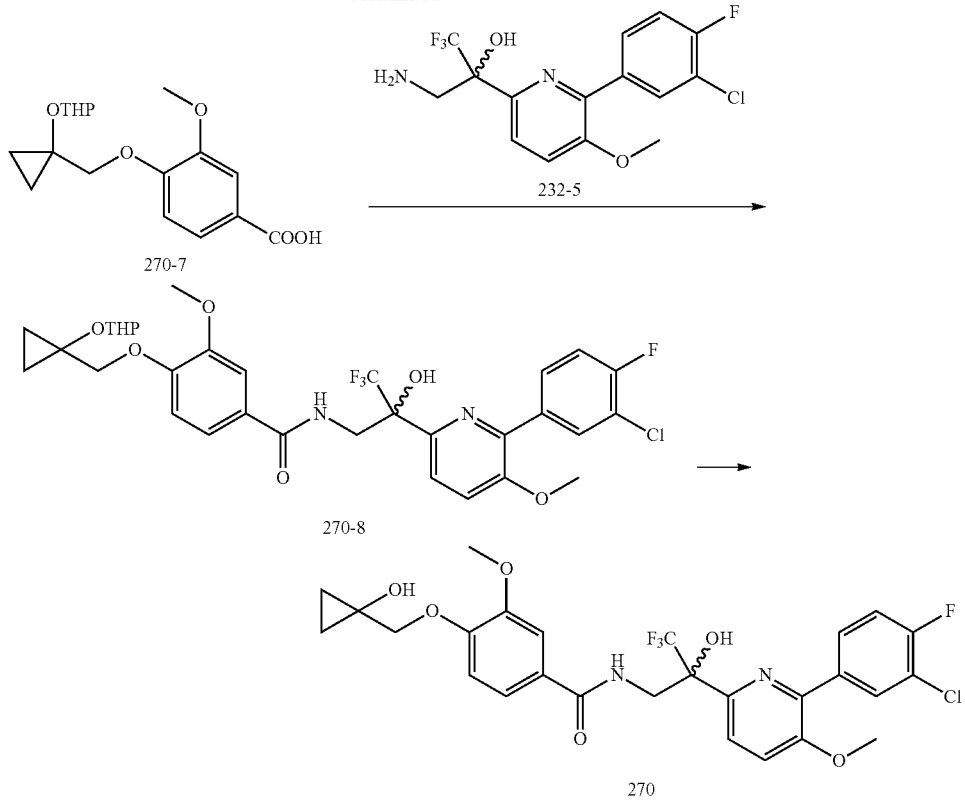

Compound 270-2 was prepared according to the procedure provided in Rye et al., *Eur. J. Med. Chem.* (2013) 60:240-248, which is hereby incorporated by reference for the limited purpose of its description of the preparation of 270-2. To a stirred solution of 270-2 (18.0 g, 89.1 mmol) in acetone (200 mL) were added ethyl 2-bromoacetate (29.6 g, 178.2 mmol) and $K_2CO_3$ (36.9 g, 270 mmol). The mixture was stirred at 80° C. for 12 h. The mixture was diluted with water and extracted with EA. The organic layers were dried over anhydrous sodium sulfate, and concentrated in vacuum. The residue was purified by column chromatography on silica gel to give crude 270-3 (25 g yield: 98%).

To a solution of 270-3 (11 g, 38.2 mmol) in anhydrous THF (100 mL) was added Ti(i-PrO)$_4$ (10.85 g, 38.2 mmol) under $N_2$ at 0° C., and then EtMgBr (34.4 mL, 103.14 mmol) was added dropwise. The mixture was stirred at r.t. overnight. The reaction was quenched with water, and extracted with EA (3×60 mL). The organic layer was dried over anhydrous sodium sulfate, and concentrated at low pressure. The residue was purified by column chromatography on silica gel to give 270-4 (4.2 g, 40.4%).

To a solution of 270-4 (2.5 g, 9.19 mmol) in DCM (20 mL) were added DHP (1.54 g, 18.38 mmol) and TsOH (158.2 mg, 0.92 mmol). The mixture was stirred at r.t. overnight. The reaction was quenched with water, and extracted with DCM. The organic layer was dried over anhydrous sodium sulfate and concentrated at low pressure. The residue was purified by column chromatography on silica gel to give 270-5 as a white solid (2.6 g, yield: 74.0%).

To a solution of 270-5 (1.5 g, 4.21 mmol) in anhydrous THF (15 mL) was added n-BuLi (2.0 mL, 5.0 mmol) at −78° C. dropwise. After the mixture was stirred at −78° C. for 0.5 h, ClCOOCH$_3$ (2.39 g, 25.28 mmol) was added in one portion. The mixture was stirred at −78° C. for 1 h, and then diluted with EA (50 mL) and washed with brine. The organic layer was dried over anhydrous sodium sulfate and concentrated at low pressure. The residue was purified by chromatography to generate 270-6 as a white solid (820 mg, yield: 58%).

To a stirred solution of 270-6 (410 mg, 1.22 mmol) in EtOH/H$_2$O (3:1, 10 mL) was added NaOH (195 mg, 4.88 mmol), and the mixture was stirred at 50° C. for 1 h. The mixture was diluted with water and extracted with EA. The pH of aqueous layers was adjusted to 4.0 by adding 5% HCl solution. The aqueous phase was extracted with EA. The organic layers were dried over anhydrous sodium sulfate and concentrated in vacuum to give crude 270-7 (198 mg).

To a solution of 270-7 (200 mg, 0.62 mmol) in DMF (15 mL) were added DIPEA (240 mg, 1.86 mmol) and HATU (236 mg, 0.62 mmol). The mixture was stirred at r.t. for 30 mins, and then 232-5 (226 mg, 0.62 mmol) was added. The mixture was stirred at r.t. for 2 h, and then diluted with water and extracted with EA (3×20 mL). The organic layer was dried over anhydrous sodium sulfate and concentrated at low pressure. The residue was purified by column chromatography on silica gel to give 270-8 (250 mg, 60.4%).

To a solution of 270-8 (250 mg, 0.37 mmol) in EtOH (10 mL) was added PPTS (19.4 mg, 0.075 mmol). The mixture was stirred at 70° C. for 2 h, and then diluted with EA (50 mL) and washed with brine. The organic layer was dried over anhydrous sodium sulfate and concentrated at low pressure. The residue was purified by prep-HPLC to give 270 as a white solid (80 mg, 37.0%). +ESI-MS: m/z 585.1 [M+H]$^+$.

Example 125
Preparation of Compounds 271, 272 and 314
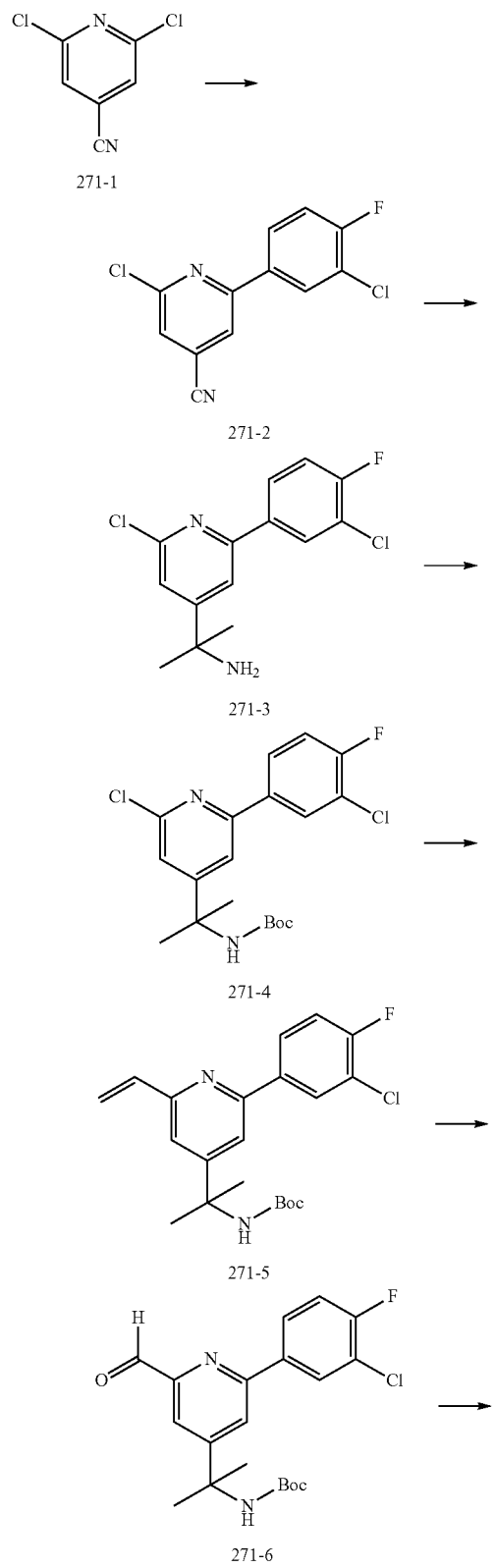 [SMILES: N#Cc1cc(Cl)nc(Cl)c1 ; N#Cc1cc(Cl)nc(-c2ccc(F)c(Cl)c2)c1 ; CC(C)(N)c1cc(Cl)nc(-c2ccc(F)c(Cl)c2)c1 ; CC(C)(C)OC(=O)NC(C)(C)c1cc(Cl)nc(-c2ccc(F)c(Cl)c2)c1 ; C=Cc1cc(C(C)(C)NC(=O)OC(C)(C)C)cc(-c2ccc(F)c(Cl)c2)n1 ; CC(C)(C)OC(=O)NC(C)(C)c1cc(C=O)nc(-c2ccc(F)c(Cl)c2)c1]
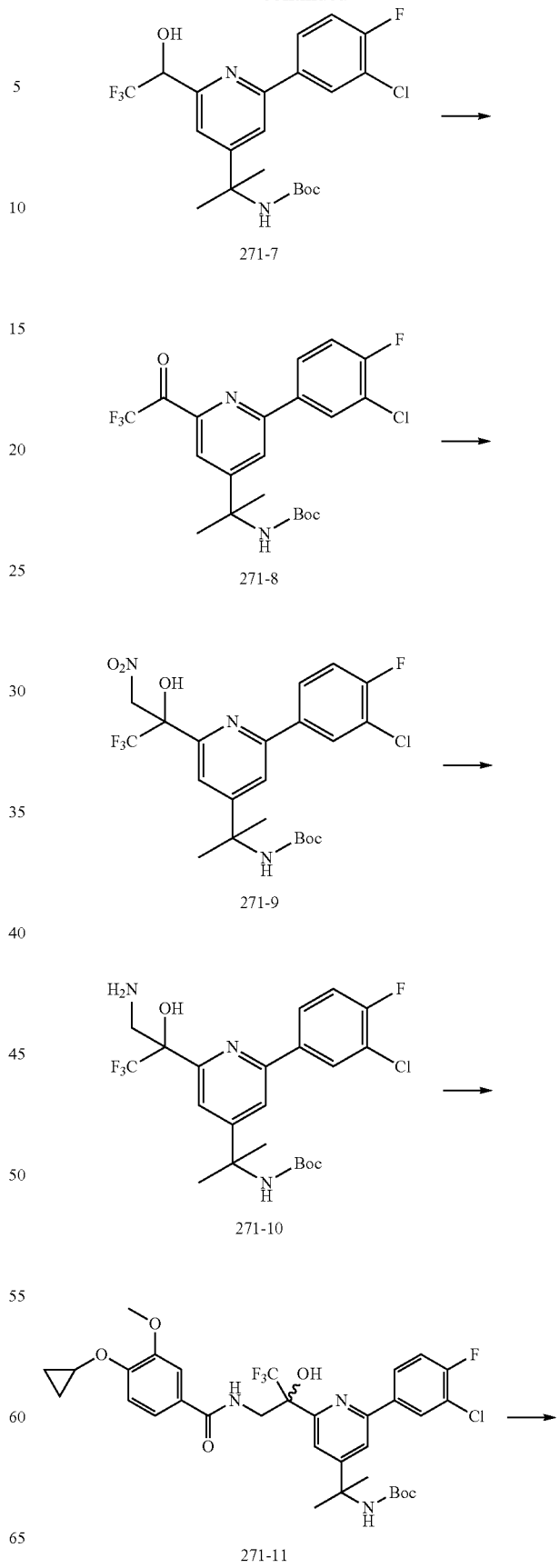

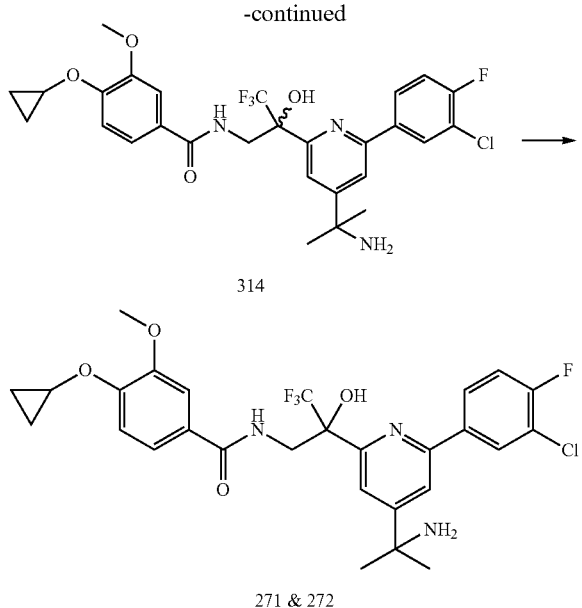

314

271 & 272

A 1 L round bottom flask was charged with a mixture of 271-1 (15 g, 86.71 mmol), (3-chloro-4-fluorophenyl)boronic acid (15 g, 86.03 mmol), [1,1'-bis(diphenylphosphino)ferrocene]dichloropalladium(II) (1.0 g, 1.37 mmol) and $K_2CO_3$ (23.7 g, 172 mmol) in dioxane/$H_2O$ (450 mL/50 mL) under $N_2$ atmosphere. The mixture was heated to 100° C. for 2 h. The mixture was cooled to r.t. and dioxane evaporated under reduced pressure. The residue was diluted with EA and water. The organic layer was dried over anhydrous $Na_2SO_4$ and concentrated under reduced pressure. Chromatography of the residue (PE:EtOAc 100:1 to 40:1) afforded 271-2 as a white solid (11 g, 47.8%).

To a solution of 271-2 (7.2 g, 26.9 mmol) in toluene (200 mL) was added MeMgBr (27 mL, 81 mmol) in 5 mins. The solution was stirred for 30 mins at r.t. Ti(OiPr)$_4$ (8 mL, 27.3 mmol) was added slowly at r.t. The solution was bathed in 100° C. oil and stirred for 20 mins. The mixture was cooled to r.t., and the reaction was quenched with a sat. aq. $Na_2CO_3$ solution. The mixture was separated by filtration, and the cake was washed with EA. The organic phase was concentrated to dryness, and crude 271-3 (7.0 g, brown oil) was used directly in the next step.

To a solution of 271-3 (7.0 g, 23.4 mmol) in toluene (100 mL), Et$_3$N (7.09 g, 70.2 mmol) and Boc$_2$O (5.6 g, 25.7 mmol) were added at r.t. The solution was bathed in 100° C. oil and stirred for 3 h. The solution was cooled to r.t., and separated between EA (300 mL) and water (200 mL). The organic phase was washed with brine and dried over $Na_2SO_4$. The organic phase was concentrated, and the residue was purified by chromatography on silica gel (PE:EA 20:1-10:1) to give 271-4 as a yellow solid (7.05 g, 75.5%). +ESI-MS: m/z 398.9 $[M+H]^+$.

To a solution of 271-4 (7.0 g, 17.5 mmol) in EtOH (70 mL) were added $K_2CO_3$ (3.62 g, 26.2 mmol) and potassium trifluoro(vinyl)borate (2.8 g, 21.0 mmol) at r.t. Pd(dppf)Cl$_2$ (256 g, 0.35 mmol) was added under $N_2$ atmosphere. The mixture was bathed in 100° C. oil and stirred for 3 h. The solution was concentrated at low pressure, and the residue was separated between EA (100 mL) and water (50 mL). The organic phase was washed with brine, dried over anhydrous $Na_2SO_4$ and concentrated at low pressure. The residue was purified by chromatography on silica gel (PE:EA 20:1-10:1) to give 271-5 as a yellow oil (6.1 g, 89.3%). +ESI-MS: m/z 391.0 $[M+H]^+$.

A solution of 271-5 (6.1 g, 15.6 mmol) in DCM (150 mL) was bubbled with $O_3$ at −78° C. until the solution turned blue. The solution was then bubbled with $N_2$ until the blue colour disappeared. PPh$_3$ (4.9 g, 18.72 mmol) was added at −78° C., and stirred for 2 h at −78° C. The mixture was concentrated at low pressure, and the residue was purified by chromatography on silica gel (PE:EA 10:1-5:1) to give 271-6 as a white solid (4.8 g, 78.4%).

To a solution of 271-6 (4.86 g, 12.38 mmol) in dry DMF (25 mL) was added TMSCF$_3$ (4.4 g, 31.0 mmol). The mixture was cooled down to −78° C., and TBAF (1M in THF, 7.3 mL, 7.3 mmol) was added dropwise. The mixture was allowed to gradually warm to r.t., and stirred for 0.5 h. The mixture was diluted with water and EtOAc. The organic layers was dried over anhydrous $Na_2SO_4$ and concentrated under reduced pressure. Chromatography of the residue (PE:EtOAc 100:0 to 80:20) afforded 271-7 (4.1 g, 72%).

To a stirred solution of 271-7 (4.1 g, 8.86 mmol) in dry DCM (45 mL) was added Dess-Martin periodinane (4.96 g, 17.7 mmol). The mixture was stirred at r.t. for 10 h. The mixture was concentrated under reduced pressure and chromatography of the residue (PE:EtOAc 100:0 to 70:30) afforded 271-8 (3.8 g, 93%).

To a solution of 271-8 (3.8 g, 8.25 mmol) in MeNO$_2$ (10 mL) was added Et$_3$N (2 mL, 14 mmol), and the mixture was stirred at r.t. for 30 mins. The mixture was concentrated under reduced pressure, and the residue was dissolved in co-solvent of EtOH:$H_2O$ (50 mL:5 mL). The mixture was treated with iron powder (1.85 g, 33 mmol) and NH$_4$Cl (1.8 g, 33 mmol), and then heated to 80° C. for 2 h. After filtration, the solution was concentrated under reduced pressure. The residue was purified by chromatography to give 271-10 (2.5 g, 61.7%). +ESI-MS: m/z 491.9 $[M+H]^+$.

A 100 mL round bottom flask was charged with a solution of 4-cyclopropoxy-3-methoxybenzoic acid (208 mg, 1.0 mmol), DIPEA (193 mg, 1.5 mmol) and HATU (380 mg, 1.0 mmol) in anhydrous DMF (10 mL). The mixture was stirred at r.t. for 30 mins. Compound 271-10 (490 mg, 1.0 mmol) was added in one portion, and the mixture was stirred at r.t. for 2-3 h. The mixture was diluted with EA and water, and the organic phase was washed with brine, dried over anhydrous sodium sulfate and concentrated at low pressure. The residue was purified by column chromatography on silica gel (PE:EA 1:1) to give 271-11 as a pale yellow oil (610 mg, 88%).

A 50 mL round bottom flask was charged with a solution of 271-11 (610 mg, 0.88 mmol) in EA (10 mL). The solution was treated with HCl in EA (10 mL, 4.0 M). The mixture was stirred at r.t. for 1-2 h. The mixture was concentrated at low pressure to give crude 314 (550 mg).

Compound 314 (550 mg) was separated via SFC separation to give two enantiomers. The two enantiomers were treated with 2 M HCl in EA and then concentrated to give 271 (120 mg) and 272 (124 mg). 271: +ESI-MS: m/z 582.1 $[M+H]^+$. 272: +ESI-MS: m/z 582.1 $[M+H]^+$.

Example 126

Preparation of Compound 273

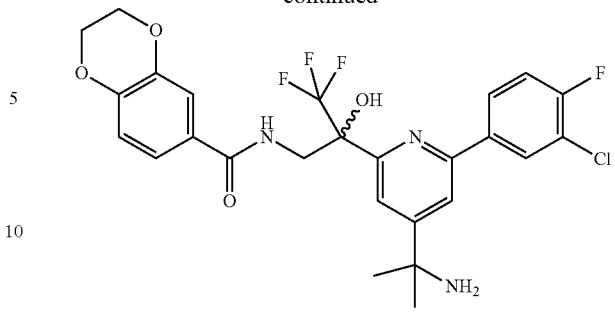

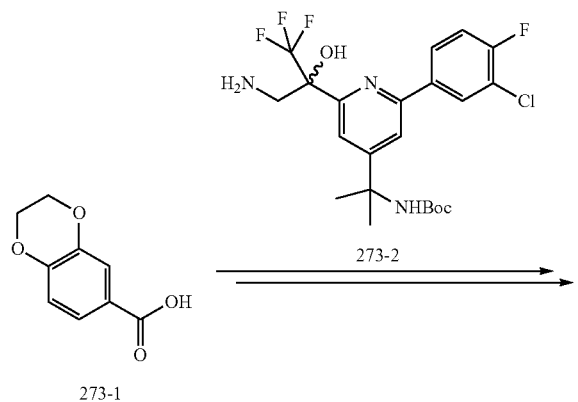

Compound 273 was prepared essentially as described in the preparation of compound 272 by 273-1 and 273-2. Compound 273 was obtained as a white solid (41 mg, 52.2%). +ESI-MS: m/z 554.0 [M+H]$^+$.

Example 127

Preparation of Compounds 274-285

The following compounds in Table 1 were prepared essentially as described in the preparation of 272 by using the listed acid and amine.

TABLE 1

| Compound | Acid | Amine | Yield and +ES-MS: m/z |
|---|---|---|---|
|  | benzo[d][1,3]dioxole-5-carboxylic acid | 273-2 | 32 mg, 58.8% 539.9 [M + H]$^+$ |
|  | 2,2-difluorobenzo[d][1,3]dioxole-5-carboxylic acid | 273-2 | 38 mg, 46.5% 576.0 [M + H]$^+$ |

TABLE 1-continued

| Compound | Acid | Amine | Yield and +ES-MS: m/z |
|---|---|---|---|
| 276 | 2-chlorothiazole-5-carboxylic acid | 273-2 | 30 mg, 54.5% 536.9 [M + H]+ |
| 277 | thiazole-4-carboxylic acid | 273-2 | 32 mg, 64.0% 502.9 [M + H]+ |
| 278 | thiazole-5-carboxylic acid | 273-2 | 18 mg, 36.0% 502.9 [M + H]+ |
| 279 | 2-methylthiazole-4-carboxylic acid | 273-2 | 23 mg, 45% 517.0 [M + H]+ |

TABLE 1-continued

| Compound | Acid | Amine | Yield and +ES-MS: m/z |
|---|---|---|---|
| 280 | 2-chlorothiazole-4-carboxylic acid | 273-2 | 24 mg, 45% 537.0 [M + H]+ |
| 281 | 3-chloro-4-((2-oxopyrrolidin-3-yl)oxy)benzoic acid | 273-2 | 28 mg, 45% 629.0 [M + H]+ |
| 282 | 3-chloro-4-cyclopropoxybenzoic acid | 273-2 | 20 mg, 34% 585.9 [M + H]+ |
| 283 | (S)-3-methoxy-4-((2-oxopyrrolidin-3-yl)oxy)benzoic acid | 273-2 | 28 mg, 45% 625.1 [M + H]+ |

TABLE 1-continued
| Compound | Acid | Amine | Yield and +ES-MS: m/z |
|---|---|---|---|
| 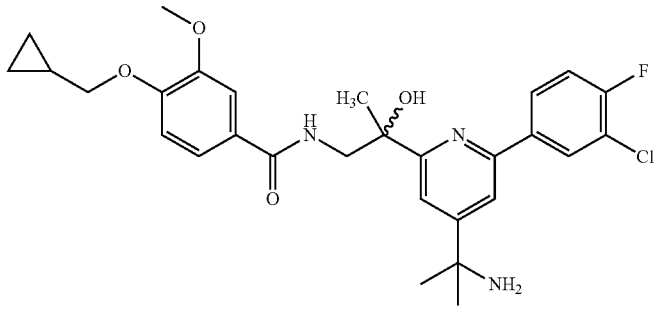 284 | 4-(cyclopropylmethoxy)-3-methoxybenzoic acid | 273-2 | 30 mg, 68.2% 596.1 [M + H]+ |
| 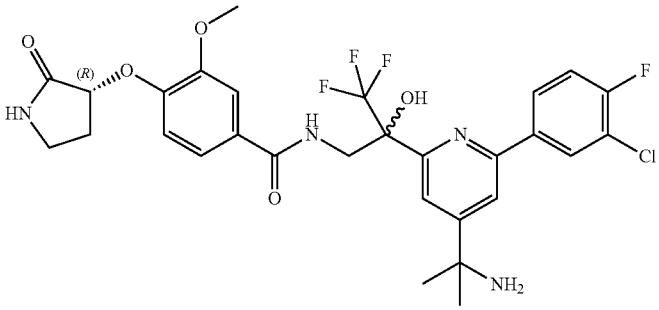 285 | (R)-3-methoxy-4-((2-oxopyrrolidin-3-yl)oxy)benzoic acid | 273-2 | 28 mg, 45% 625.0 [M + H]+ |
Example 128
Preparation of Compound 286
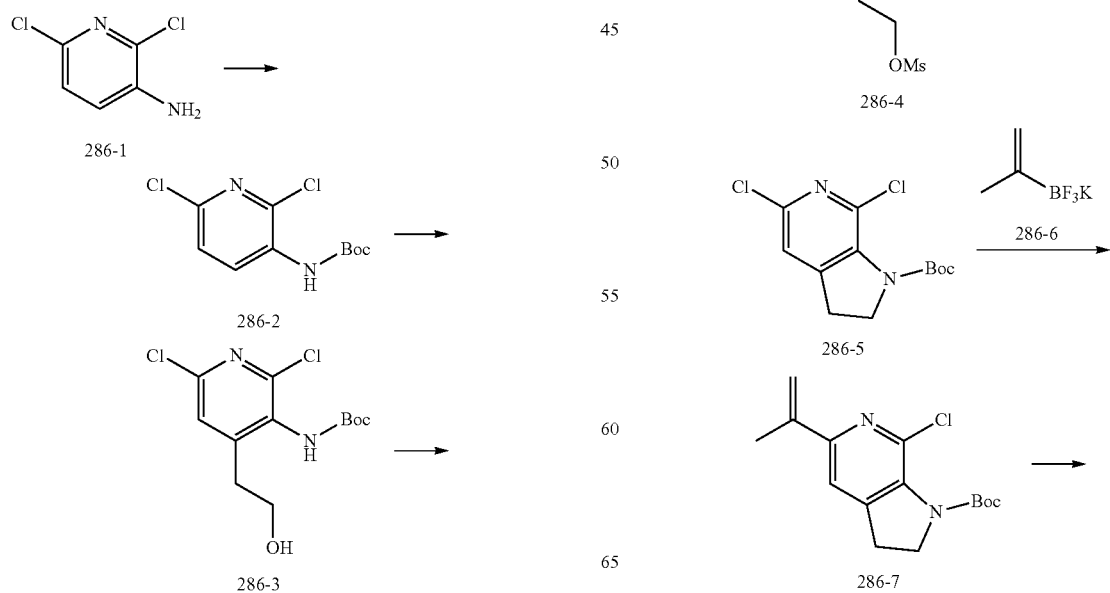

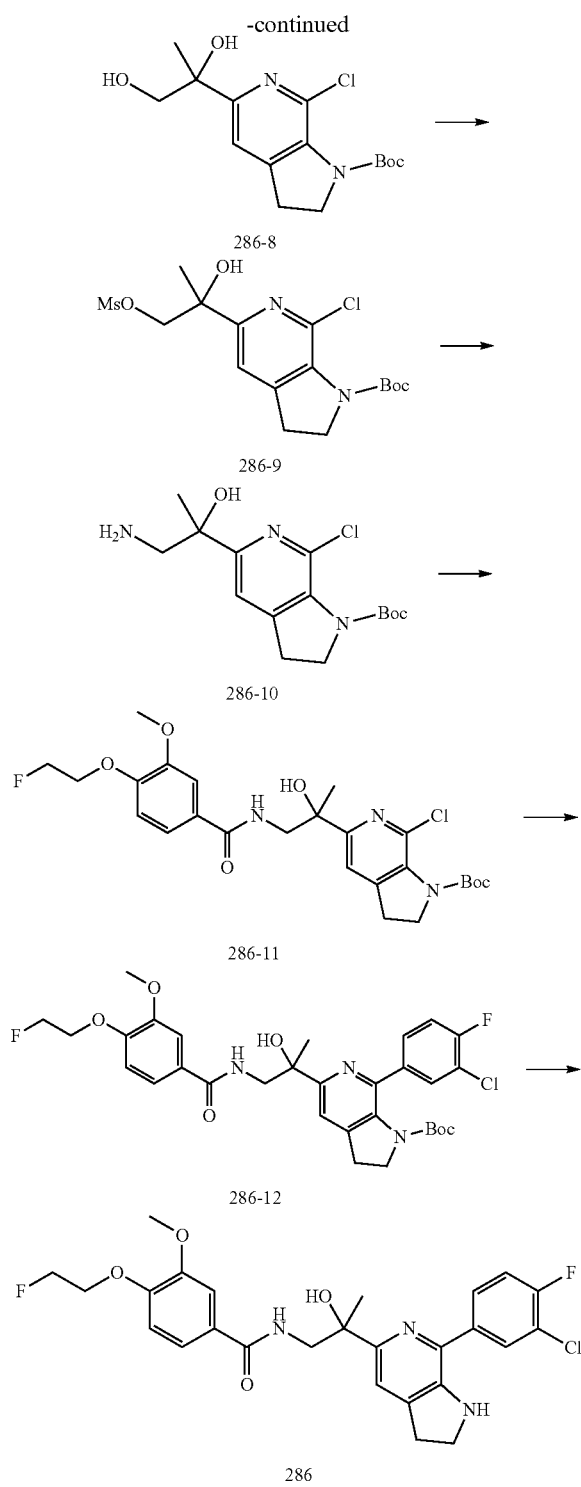

Compound 286-2 was prepared according to the procedure provided in PCT Publication No. WO 2009/005638, published Jan. 8, 2009, which is hereby incorporated by reference for the limited purpose of its description of the preparation of 286-2.

To a solution of 286-2 (1.83 g, 7 mmol) in THF (15 mL) was added n-BuLi (7 mL, 2.5 M in THF) at −78° C. After 5 mins, TMEDA (1.624 g, 14 mmol) was added at −78° C. The solution was warmed slowly to −30° C., and stirred for 30 mins at −30° C. The solution was cooled to −78° C. and oxirane (0.7 mL, 14 mmol) was added. The solution was stirred at −78° C. for 2 h., and stirred overnight at r.t. The reaction was quenched with $H_2O$ and extracted with EA (2×30 mL). The combined organic phase was washed with brine, dried over anhydrous $Na_2SO_4$ and concentrated at low pressure. The residue was purified by column chromatography (PE:EA 10:1) to give 286-3 (0.7 g, 32.7%).

To a solution of 286-3 (4.5 g, 14.7 mmol) in DCM (100 mL) was added TEA (4.45 g, 44.1 mmol). After cooled to 0° C., MsCl (3.36 g, 29.4 mmol) was added slowly. The solution was stirred for 30 mins. The reaction was quenched with $H_2O$, and extracted with DCM (3×100 mL). The organic phase was washed with brine, dried over anhydrate sodium sulfate and concentrated at low pressure to give crude 286-4 (5.6 g, 99.2%). +ESI-MS: m/z 384.8 $[M+H]^+$.

To a solution of 286-4 (5.6 g, 14.5 mmol) in DMF (50 mL) was added $K_2CO_3$ (4.02 g, 29.2 mmol). The mixture was heated up to 50-60° C., and stirred for 1 h. The solution was cooled to r.t., poured into cold water and extracted with EA (2×100 mL). The combined organic phase was washed with brine, dried over anhydrous $Na_2SO_4$ and concentrated at low pressure. The residue was purified by chromatography (PE:EA 10:1) to give 286-5 (3.1 g, 74.3%).

To a solution of 286-5 (1.68 g, 5.83 mmol), 286-6 (860 mg, 5.83 mmol) and $K_2CO_3$ (1.61 g, 11.66 mmol) in MeOH (50 mL) was added Pd(dppf)$Cl_2$ (426 mg, 0.583 mmol). The mixture was degassed and then refilled with $N_2$ (3 times). The mixture was stirred under nitrogen at 70° C. for 15 h, and then cooled to r.t., and extracted with EA (3×50 mL). The organic phase was washed by brine, dried over anhydrous $Na_2SO_4$ and concentrated at low pressure. The residue was purified by column chromatography (PE:EA 5:1) to give 286-7 as a white solid (1.2 g, 70%).

To a solution of 286-7 (2.94 g, 10 mmol) in DCM (50 mL) were added NMO (2.4 g, 20 mmol) and $OsO_4$ (500 mg, 0.2 mmol) at r.t. The mixture was stirred at r.t. for 1 h. The reaction was quenched with sat. aq. $Na_2SO_3$, and stirred for 2 h. The mixture was extracted with DCM (2×100 mL). The combined organic layers were washed with brine, dried over anhydrous $Na_2SO_4$ and concentrated at low pressure. The residue was purified by column chromatography (PE:EA 3:1) to give 286-8 (2.94 g, 89.6%). +ESI-MS: m/z 328.9 $[M+H]^+$.

To a solution of 286-8 (3.28 g, 10 mmol) and TEA (4.45 g, 44.1 mmol) in DCM (20 mL) was added MsCl (2.2 g, 20 mmol) slowly at 0° C. The solution was stirred for 30 mins, and then diluted with DCM (20 mL). The solution was washed with brine and dried over anhydrous sodium sulfate. The organic phase was concentrated at low pressure to give crude 286-9 (4.06 g, 100.0%).

A solution of 286-9 (4.0 g, 10 mmol) in ammonia water and ethanol (10 mL:10 mL) in a seal tube was stirred for 1 h at r.t. The solution was heated to 40° C. for 15 h. The mixture was concentrated to dryness under reduced pressure to give crude 286-10 (1.6 g, 50%), which was used without purification. +ESI-MS: m/z 327.9 $[M+H]^+$.

To a solution of 4-(2-fluoroethoxy)-3-methoxybenzoic acid (214 mg, 1 mmol), HATU (456 mg, 1.2 mmol) and DIPEA (258 mg, 2 mmol) in anhydrous DMF (5 mL) was added 286-10 (327 mg, 1 mmol) at 25° C. The solution was stirred for 2 h at 25° C. The reaction was quenched by a sat. aq. $NaHCO_3$ solution (40 mL), and then extracted with EA (2×20 mL). The combined organic layers were washed with brine, dried over anhydrous $Na_2SO_4$ and concentrated under reduced pressure. The residue was purified by column chromatography on silica gel (PE:EA 3:1) to give 286-11 (201 mg, 38.2%). +ESI-MS: m/z 524.0 $[M+H]^+$.

221

To a solution of 286-11 (150 mg, 0.3 mmol), (3-chloro-4-fluorophenyl)boronic acid (105 mg, 0.6 mmol) and $K_2CO_3$ (84 mg, 0.6 mmol) in dioxane (6 mL) was added $Pd(dppf)Cl_2$ (22 mg, 0.03 mmol). The mixture was degassed and then refilled with $N_2$ (3 times). The mixture was heated to 120° C. by microwave under $N_2$ for 2 h. The solution was cooled to r.t. and diluted with EA (20 mL). The solution was washed with brine, dried over anhydrous $Na_2SO_4$ and concentrated at low pressure. The residue was purified by column chromatography (PE:EA 1:1) to give 286-12 (123 mg, 65%).

To a solution of 286-12 (123 mg, 0.2 mmol) in DCM (2 mL) was added TFA (4 mL) at r.t. The mixture was stirred for 30 mins, concentrated to dryness and dissolved in EA (20 mL). The solution was washed with a sat. $NaHCO_3$ solution. The organic layer was washed with brine, dried over anhydrous $Na_2SO_4$ and concentrated at low pressure. The residue was purified by prep-HPLC to give 286 (80 mg, 77.6%) as a yellow solid. +ESI-MS: m/z 518.1 $[M+H]^+$.

Example 129

Preparation of Compound 287

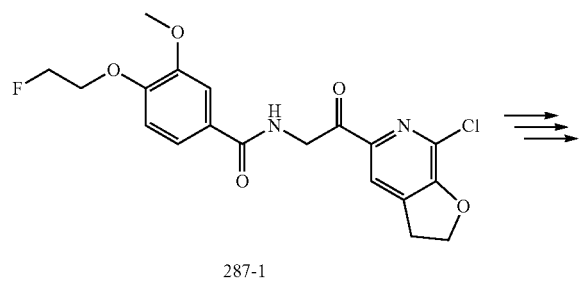

287-1

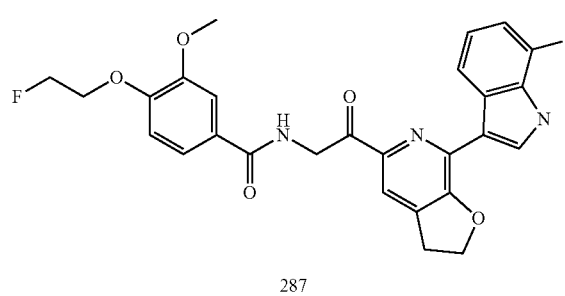

287

Compound 287 was prepared essentially as described in the preparation of 286 by using 7-fluoro-3-(4,4,5,5-tetramethyl-1,3,2-dioxaborolan-2-yl)-1-((2-(trimethylsilyl)ethoxy)methyl)-1H-indole and 287-1. Compound 287 was obtained as white solid. +ESI-MS: m/z 507.9 $[M+H]^+$.

Example 130

Preparation of Compounds 288 and 289

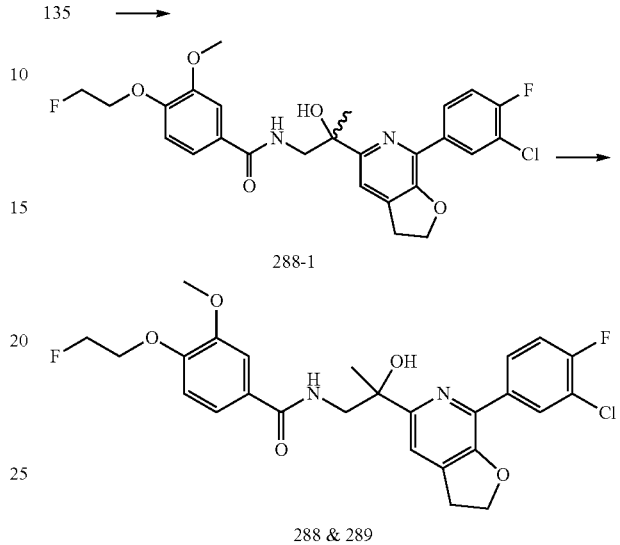

288-1

288 & 289

To a solution of 135 (400 mg, 0.80 mmol) in THF (10 mL) was added MeMgBr (3 mL, 1.3 N in THF) under $N_2$. The mixture was stirred at r.t. for 1 h under $N_2$. The reaction was quenched with sat. aq. $NH_4Cl$ and extracted with EA (3×20 mL). The combined organic layers were dried over anhydrous sodium sulfate and evaporated under reduced pressure. The residue was purified by prep-HPLC to give 288-1 (150 mg).

Compounds 288 (39 mg) and 289 (41 mg) were obtained by SFC separation of 288-1. 288: +ESI-MS: m/z 519.3 $[M+H]^+$. 289: +ESI-MS: m/z 519.3 $[M+H]^+$.

Example 131

Preparation of Compound 290

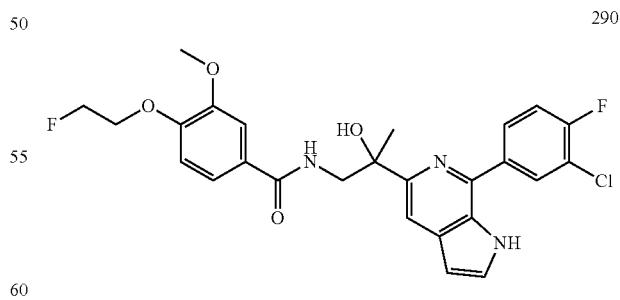

290

To a solution of 286 (400 mg, 0.77 mmol) in DCM (20 mL) was added $MnO_2$ (336 mg, 3.86 mmol) at r.t. The mixture was stirred for 2 h. The precipitate was removed by filtration, and the filtrate was concentrated at low pressure. The residue was purified by prep-HPLC to give 290 (150 mg, 37.5%) as a yellow solid. +ESI-MS: m/z 515.9 $[M+H]^+$.

Example 132

Preparation of Compounds 291 and 292

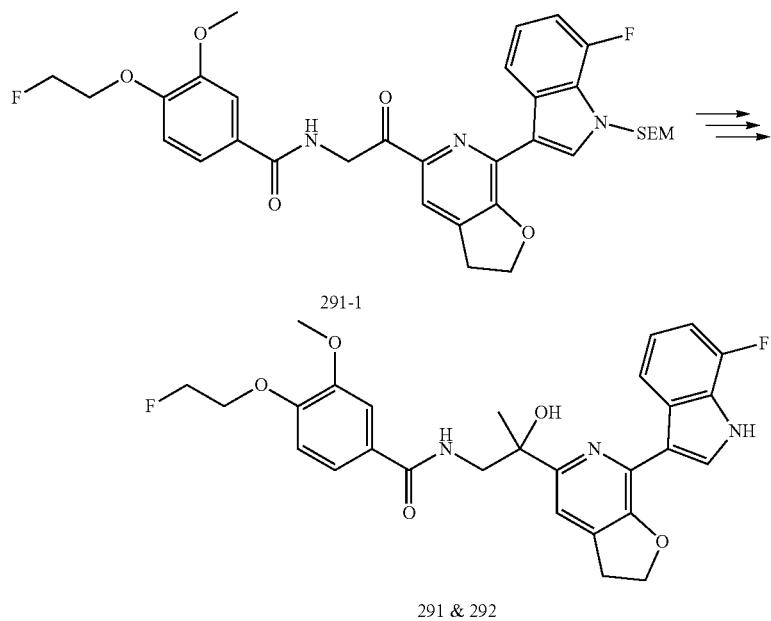

Compounds 291 and 292 were prepared essentially as described in the preparation of 288 and 289 by using 291-1. Compound 291 (31 mg) and 292 (30 mg) were obtained as white solids. 291: +ESI-MS: m/z 524.1 [M+H]$^+$. 292: +ESI-MS: m/z 524.1 [M+H]$^+$.

Example 133

Preparation of Compounds 293 and 294

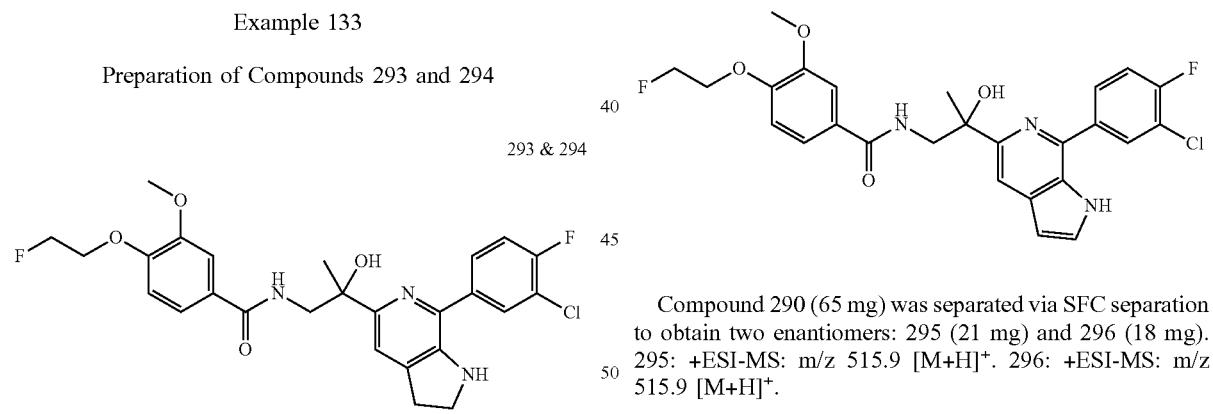

Compound 286 (60 mg) was separated via SFC separation to obtain two enantiomers: 293 (24 mg) and 294 (22 mg). 293: +ESI-MS: m/z 517.9 [M+H]$^+$. 294: +ESI-MS: m/z 517.9 [M+H]$^+$.

Example 134

Preparation of Compounds 295 and 296

Compound 290 (65 mg) was separated via SFC separation to obtain two enantiomers: 295 (21 mg) and 296 (18 mg). 295: +ESI-MS: m/z 515.9 [M+H]$^+$. 296: +ESI-MS: m/z 515.9 [M+H]$^+$.

Example 135

Preparation of Compound 297

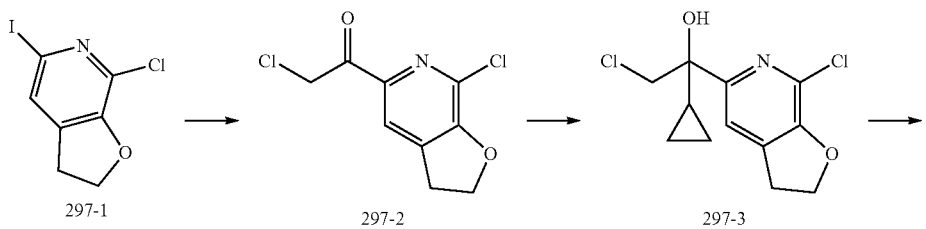

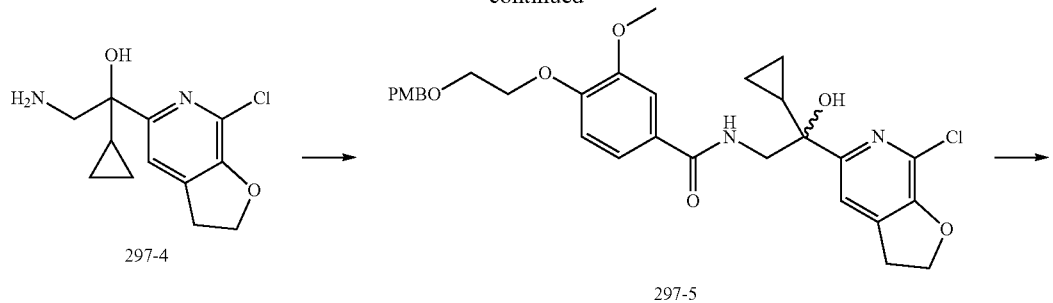

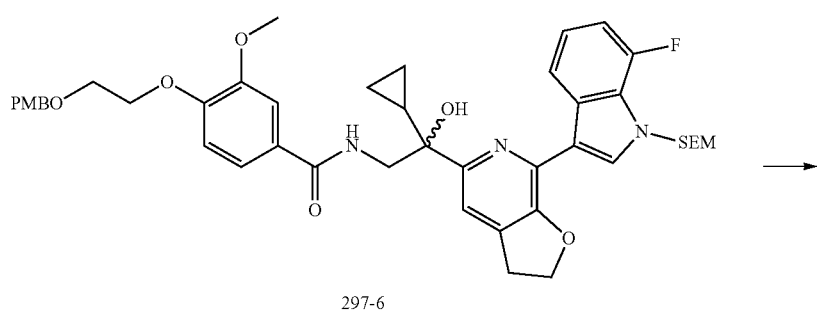

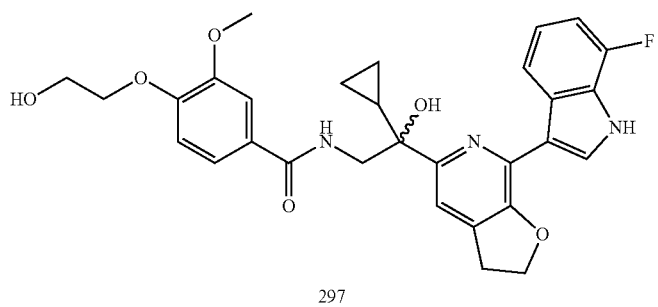

[0588] To a solution of 297-1 (1.4 g, 5.0 mmol) and 2-chloro-N-methoxy-N-methylacetamidein (700 mg, 5.0 mmol) in THF (20 mL) was added i-PrMgCl (3 mL, 2.0 M in THF) dropwise at 0° C. The mixture was stirred at 0° C. for 1 h. The reaction was quenched with water, and extracted with EA (3×20 mL). The combined organic layers were washed with brine, dried over anhydrous $Na_2SO_4$ and concentrated in vacuum. The residue was purified by column chromatography on silica gel to give 297-2 (1.0 g, 87%). +ESI-MS: m/z 232.0 $[M+H]^+$.

To a solution of 297-2 (460 mg, 2.0 mmol) in THF (4 mL) was added cyclopropylmagnesium bromide (4 mL, 0.5 M in THF) dropwise at 0° C. The mixture was stirred at 0° C. for 1 h. The reaction was quenched with water, and extracted with EA (3×20 mL). The combined organic layers were washed with brine, dried over anhydrous $Na_2SO_4$ and concentrated in vacuum. Compound 297-3 was used without further purification.

Compound 297 was prepared essentially as described in the preparation of 286 by using 297-3. Compound 297 was obtained as white solid (98 mg). +ESI-MS: m/z 548.3 $[M+H]^+$.

Example 136

Preparation of Compound 298

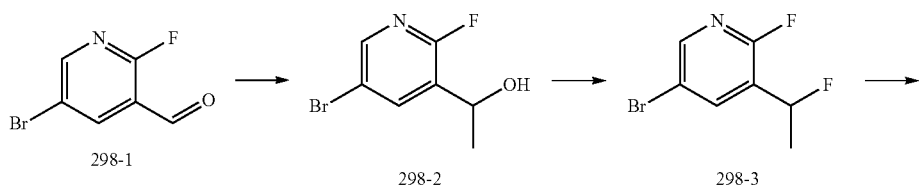

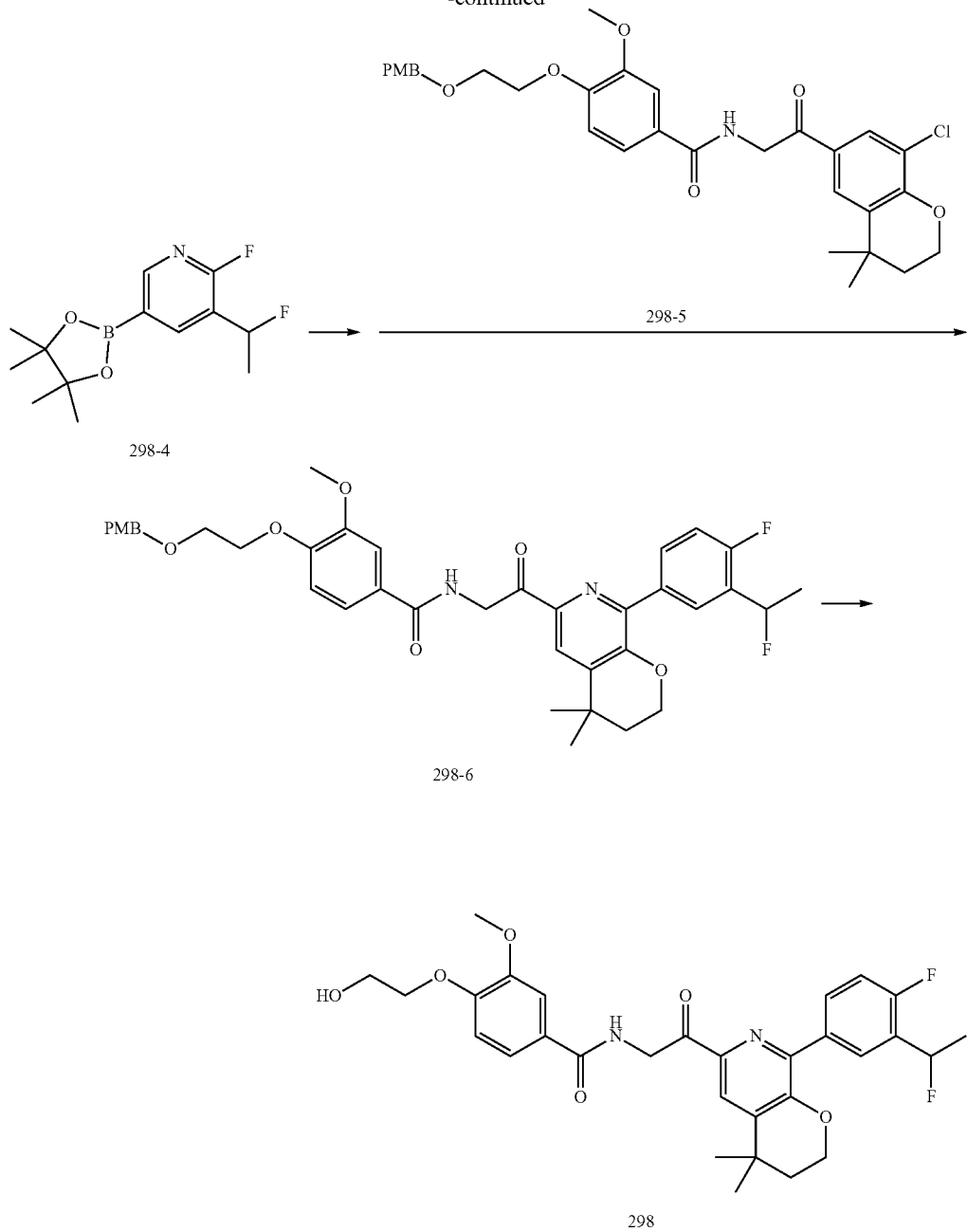

Compound 298-2 was prepared according to the procedure provided in PCT Publication No. WO 2009/016460, published Feb. 5, 2009, which is hereby incorporated by reference for the limited purpose of its description of the preparation of 298-2. To a solution of 298-2 (1.8 g, 8.3 mmol) in DCM (10 mL) was added DAST (2 mL) dropwise at 0° C. The mixture was stirred at r.t. for 30 mins. The reaction was quenched with sat. NaHCO$_3$ solution at 0° C. and extracted with EA (3×30 mL). The combined organic layers were washed by brine, dried over anhydrous Na$_2$SO$_4$ and concentrated in vacuum. The residue was purified by column chromatography on silica gel column (PE:EA 30:1) to give 298-3 as a white solid (1.4 g, 77.8%).

To a solution of 298-3 (1.4 g, 6.4 mmol) in THF (10 mL) was added n-BuLi (3.3 mL, 2.5 N in hexane) dropwise at −78° C. under N$_2$. The mixture was stirred at −78° C. for 30 mins. 2-isopropoxy-4,4,5,5-tetramethyl-1,3,2-dioxaborolane (1.6 g, 9.4 mmol) was added at −78° C., and the mixture was allowed to warm to r.t., and stirred 10 mins. The reaction was quenched with sat. NH$_4$Cl solution and extracted with EA. The combined organic solutions were washed with brine, dried over anhydrous sodium sulfate and concentrated under reduced pressure. The residue was purified by column chromatography on silica gel (PE:EA 50:1) to give 298-4 as an oil (1.0 g, 58.9%).

Compound 298 was prepared essentially as described in the preparation of 286 by using 298-4. Compound 298 was obtained as a white solid (70 mg). +ESI-MS: m/z 555.1 [M+H]$^+$.

Example 137

Preparation of Compound 299

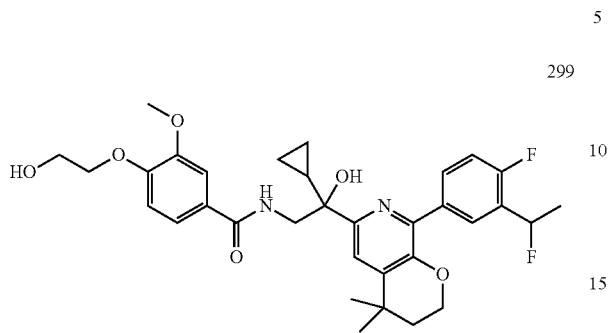

Compound 299 was prepared essentially as described in the preparation of 288 and 289 by using 298 and cyclopropylmagnesium bromide. Compound 299 (30 mg) was obtained as a white solid. +ESI-MS: m/z 597.2 [M+H]+.

Example 138

Preparation of Compounds 300 and 301

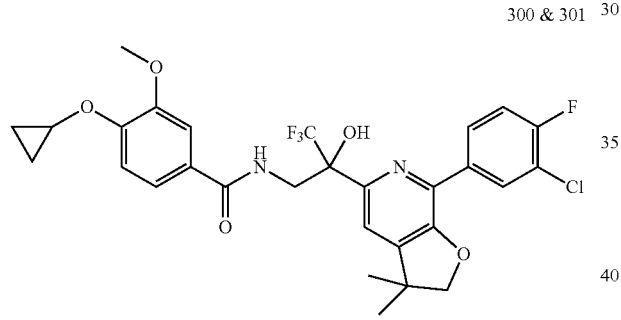

Compound 229 (28 mg, 0.047 mmol) was separated via SFC separation to give two enantiomers: 300 (3.8 mg) and 301 (4.5 mg) as white solids. 300: +ESI-MS: m/z 595.0 [M+H]+. 301: +ESI-MS: m/z 595.0 [M+H]+.

Example 139

Preparation of Compound 335

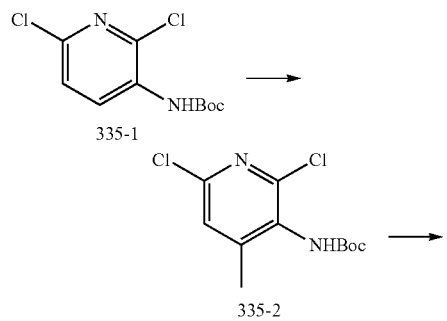

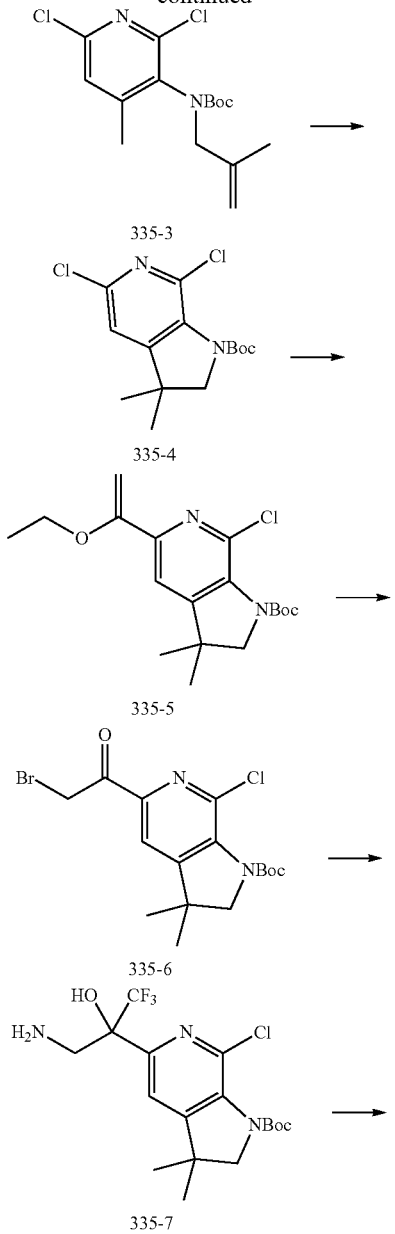

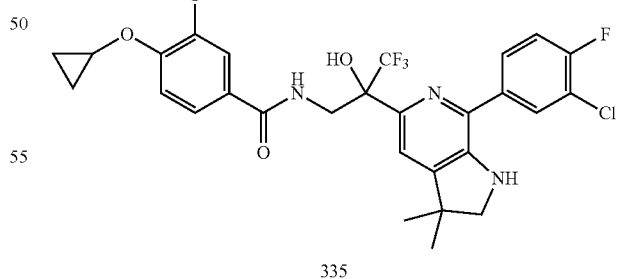

To a solution of 335-1 (5.2 g, 20 mmol) in THF (50 mL) was added n-BuLi (16 mL, 20 mmol, 2.5M) at −78° C. under N$_2$. After stirred at −78° C. for 0.5 h, a solution of I$_2$ (5.1 g 20 mmol) in THF (25 mL) was added slowly. The mixture was stirred at −78° C. for 1 h. The reaction was quenched with water and extracted with EA (3×50 mL). The combined organic phase was washed with brine, dried over anhydrous sodium sulfate and concentrated under reduced pressure. The residue was purified by column chromatography on silica gel (PE:EA 10:1) to give 335-2 (7.5 g, 95%). +ESI-MS: m/z 388.9 [M+H]$^+$.

To a solution of 335-2 (3.88 g, 10.0 mmol) in DMF (50 mL) was added sodium hydride (480 mg, 10 mmol, 60% in the mineral oil) at r.t. The mixture was stirred for 0.5 h and 3-chloro-2-methylprop-1-ene (1.0 g, 11 mmol) was added dropwise. The mixture was stirred for 2 h. The reaction was quenched with water and extracted with EA (2×30 mL). The combined organic phase was washed with brine, dried over anhydrous sodium sulfate and concentrated at low pressure to give crude 335-3 (4.4 g, 99%), which was used without further purification.

Under N$_2$ atmosphere, a mixture of 335-3 (4.4 g, 10 mmol), LiCl (420 mg, 10 mmol), sodium formate (1.36 g, 20 mmol) and Pd(OAc)$_2$ (111 mg, 0.1 mmol) in DMF (95 mL) was stirred at 100° C. for 2 h. After cooling to r.t, the mixture was diluted with EA (50 mL). The solution was washed with brine, dried over anhydrous sodium sulfate and concentrated at low pressure. The residue was purified by column chromatography on silica gel (PE:EA 10:1) to give 335-4 (1.5 g, 50%). +ESI-MS: m/z 316.9 [M+H]$^+$.

Under N$_2$ atmosphere, a mixture of 335-4 (1.5 g, 5 mmol), tributyl(1-ethoxyvinyl)stannane (3.6 g, 10 mmol) and Pd(dppf)Cl$_2$ (180 mg, 0.25 mmol) in toluene (15 mL) was stirred at 140° C. for 0.5 h. After cooling to r.t., the mixture was concentrated at low pressure. The residue was purified by column chromatography on silica gel (PE:EA 10:1) to give 335-5 (1.5 g, 88%). +ESI-MS: m/z 352.9 [M+H]$^+$.

To a solution of 335-5 (1.5 g, 1.35 mmol) in THF/H$_2$O (30 mL/1 mL) was added NBS (2.70 g, 15 mmol) in portions. The mixture was diluted with water and extracted with EA (3×30 mL). The combined organic phase was washed with brine, dried over anhydrous sodium sulfate and concentrated at low pressure. The residue was purified by column chromatography on silica gel (PE:EA 10:1) to give 335-6 (1.5 g, 75%).

To a solution of 335-6 (400 mg, 1.0 mmol) in DMF (5 mL) was added CF$_3$TMS (1 mL) and LiOAc (10 mg 0.02 eq.). After addition, the mixture was stirred at r.t. until 335-6 was consumed. The mixture was treated with ammonia water (5 mL), and then stirred at r.t. for 0.5 h. The mixture was diluted with EA (50 mL). The solution was washed with brine, dried over anhydrous sodium sulfate and concentrated at low pressure. The residue was purified by column chromatography on silica gel (PE:EA 1:1) to give 335-7 (205 mg, 50%). +ESI-MS: m/z 410.0 [M+H]$^+$.

Compound 335 was prepared essentially as described in the preparation of 286 by using 4-cyclopropoxy-3-methoxybenzoic acid and 335-7. Compound 335 was obtained as a white solid (25 mg). +ESI-MS: m/z 594.1 [M+H]$^+$.

Example 140

Preparation of Compound 302

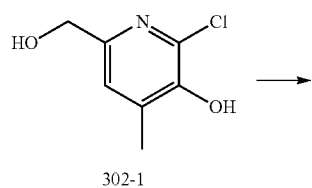

302-1

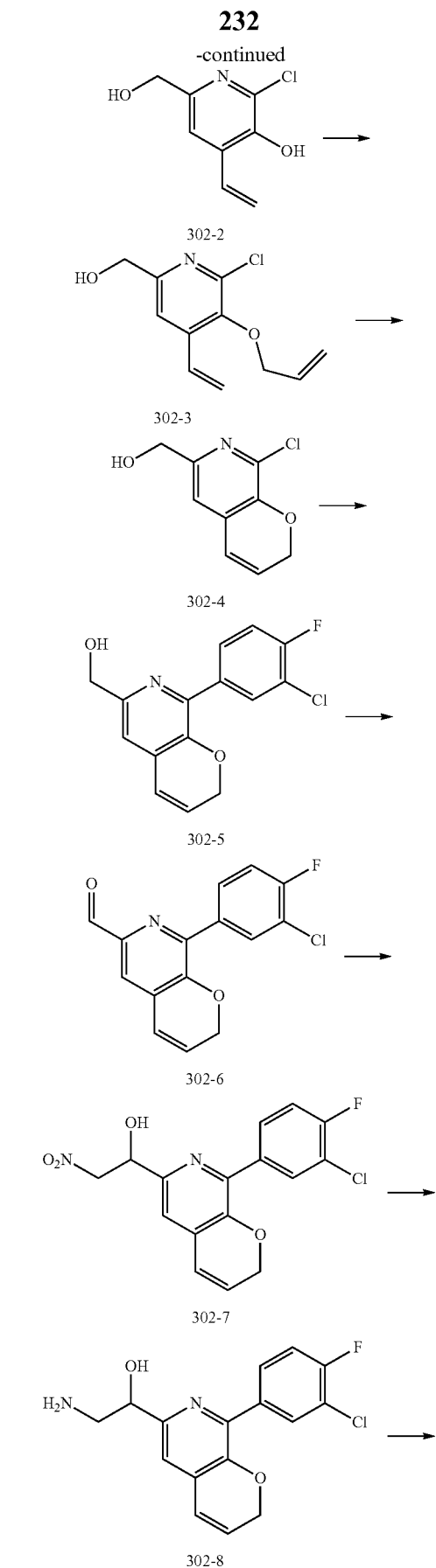

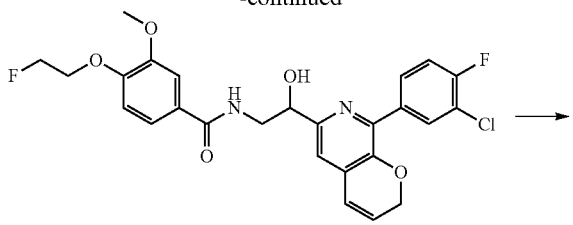

302-9

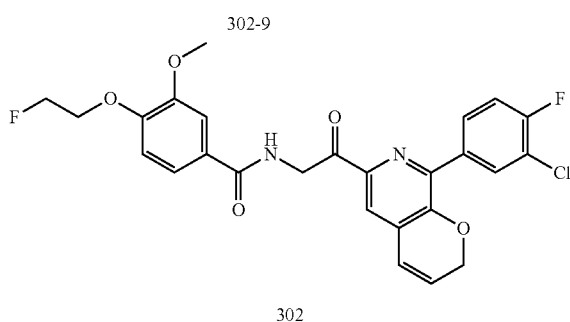

302

To a stirring mixture of 302-1 (460 mg, 1.6 mmol) in DMF (2 mL, deoxygenated prior to use) were added PdCl$_2$(PPh$_3$)$_2$ (114 mg, 0.16 mmol) and tributyl(vinyl)stannane (500 mg, 1.6 mmol). The reaction was carried out under microwave irradiation at 80° C. for 2 h. The mixture was cooled to r.t. and diluted with EtOAc. The mixture was washed with brine:water:NaHCO$_3$. The mixture was dried over MgSO$_4$, filtered and concentrated under reduced pressure. Crude 302-2 was purified via a silica gel column. LCMS: m/z 186.05 [M+H]$^+$.

To a stirring mixture of 302-2 (170 mg, 0.915 mmol) in DMF (3 mL) was added NaH (37 mg, 0.915 mmol). The mixture was stirred for 10 mins before allyl bromide (96 μL, 1.09 mmol) was added. The mixture was stirred for 1 h at r.t., and then diluted with EtOAc and a 10% NaHCO$_3$ aq. solution. The mixture was worked-up with EtOAc. The crude was purified via a silica gel column to afford 302-3 as a yellow oil. LCMS: m/z 226.05 [M+H]$^+$.

To a stirring mixture of 302-3 (100 mg, 0.44 mmol) in CH$_2$Cl$_2$ at r.t. (3.5 mL) was added benzylidene-bis(tricyclohexylphosphine) dichlororuthenium (12 mg, 0.014 mmol). The mixture was stirred for 3 h and then concentrated under reduced pressure. The crude was purified via a silica gel column to afford 302-4 as a tan solid. LCMS: m/z 198.0 [M+H]$^+$.

To a stirring mixture of 302-4 (70 mg, 0.35 mmol) in DME (2 mL, deoxygenated prior to use) were added (3-chloro-4-fluorophenyl)boronic acid (74 mg, 0.43 mmol), PdCl$_2$(PPh$_3$)$_2$, a solution of Cs$_2$CO$_3$ (0.4 mL, 2.65 M). The mixture was carried out under microwave irradition at 110° C. for 1 h and then diluted with EtOAc and water. A normal aqueous workup was followed. The crude was purified via a silica gel column to afford 302-5 as a white solid. LCMS: m/z 292.0 [M+H]$^+$.

To a stirring mixture of 302-5 (70 mg, 0.24 mmol) in CH$_2$Cl$_2$ (2 mL) at r.t. were added NaHCO$_3$ (114 mg, 1.7 mmol) and Dess-Martin periodinane (509 mg, 1.2 mmol). The mixture was stirred at r.t. until the alcohol was consumed. The reaction was quenched with 5% NaHSO$_3$ and sat. NaHCO$_3$ solution. The aqueous layer was extracted with EtOAc (2×25 mL). The organic layers were dried (Na$_2$SO$_4$), filtered and concentrated under reduced pressure. The crude was purified via a silica gel column to afford 302-6. LCMS: m/z 290.0 [M+H]$^+$.

To a stirring mixture of 302-6 (40 mg, 0.138 mmol) in THF (2 mL) were added K$_2$CO$_3$ and nitromethane (25 mg, 0.42 mmol). The mixture was stirred overnight at r.t. The reaction was diluted with EtOAc and quenched with water and brine. The aqueous layer was extracted with EtOAc (2×25 mL). The crude was purified via a silica gel chromatography to afford 302-7 as a white solid; LCMS: m/z 351.0 [M+H]$^+$.

To a stirring mixture of 302-7 (55 mg, 0.158 mmol) in EtOAc (0.5 mL) was added SnCl$_2$. 2H$_2$O (106 mg, 0.47 mmol). The mixture was heated at reflux for 1 h. The mixture was cooled and concentrated under reduced pressure. The crude was purified via a silica gel column to afford 302-8 as a colorless oil. LCMS: m/z 321.0 [M+H]$^+$.

To a stirring mixture of 4-(2-fluoroethoxy)-3-methoxybenzoic acid (33.8 mg, 0.156 mmol) in DMF (0.5 mL) were added HATU (59.3 mg, 0.156 mmol) and DIPEA (40 mg, 0.26 mmol). The mixture was stirred at r.t. for 10 mins. Compound 302-8 (50 mg, 0.156 mmol) in DMF (0.5 mL) was added, and then the mixture was stirred for 10 mins. The reaction was quenched with a 10% aq. solution of NaHCO$_3$ (10 mL). The mixture was diluted with DCM and a normal aqueous work up with DCM was followed. The crude was purified via prep-HPLC to afford 302-9 as a white solid. LCMS: m/z 517.10 [M+H].

To a stirring mixture of 302-9 (30 mg, 0.058 mmol) in DCM (1 mL) at r.t. was added Dess-Martin periodinane (172 mg, 0.41 mmol). The mixture was stirred at r.t. for 1 h and the reaction quenched with 5% NaHSO$_3$ and a sat. NaHCO$_3$ solution. The aqueous layer was extracted with EtOAc (2×25 mL). The organic layers were dried (Na$_2$SO$_4$), filtered and concentrated under reduced pressure. The crude product was purified via HPLC to afford 302 as a white solid. LCMS: m/z 515.05 [M+H].

Example 141

Preparation of Compound 303

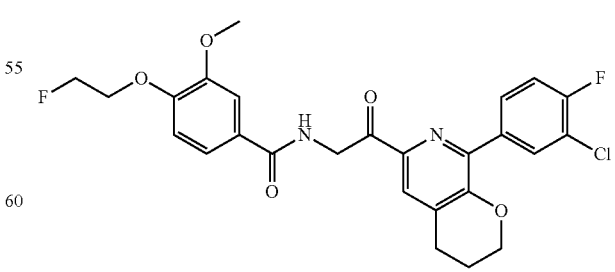

303

Compound 303 was synthesized by reacting 302 under hydrogenation reaction conditions using Pd/C in EtOAc/EtOH. LCMS: m/z 517.1 [M+H].

Example 142

Preparation of Compound 304

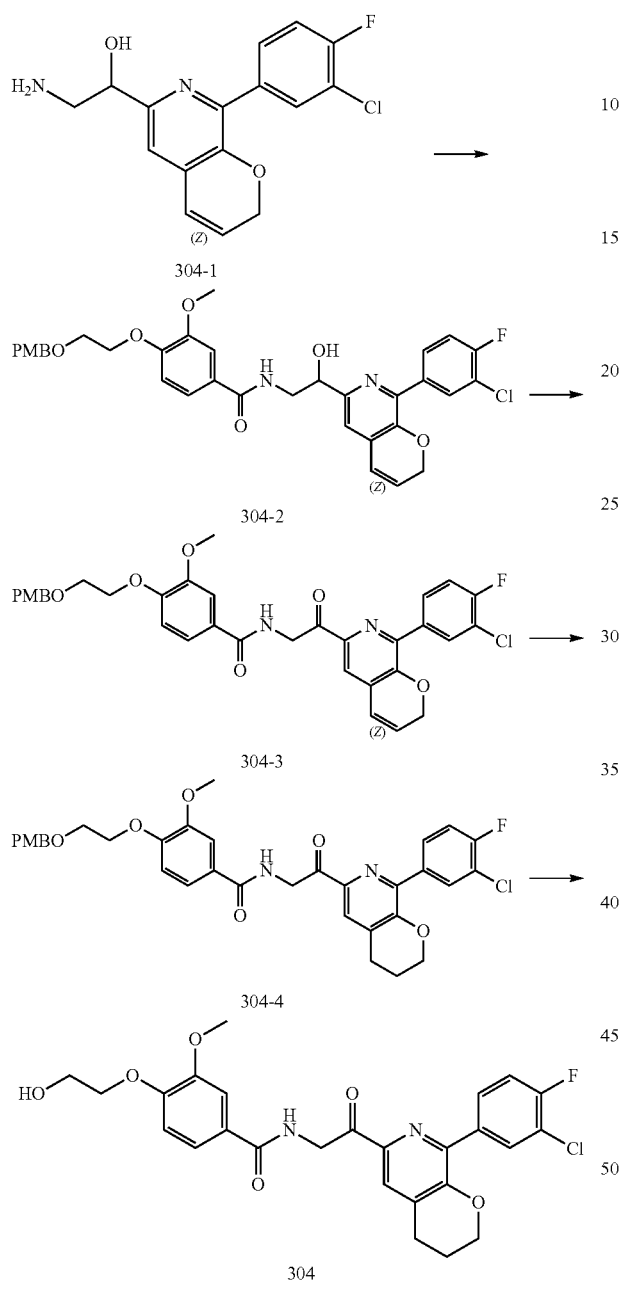

To a stirring mixture of 3-methoxy-4-(2-((4-methoxybenzyl)oxy)ethoxy)benzoic acid (40 mg, 0.12 mmol) in DMF (0.5 mL) were added HATU (36 mg, 0.096 mmol) and DIPEA (25 mg, 0.192 mmol). The mixture was stirred at r.t. for 10 mins. Compound 304-1 (31 mg, 0.096 mmol) in DMF (0.5 mL) was added, the mixture was stirred for 10 mins. The reaction was quenched with 10% NaHCO$_3$ (3 mL). The mixture was diluted with DCM and a normal aqueous workup with DCM was followed. The crude was purified via prep-HPLC to afford 304-2 as a white solid. LCMS: m/z 635.1 [M+H].

To a stirring mixture of 304-2 (30 mg, 0.047 mmol) in DCM (1 mL) at r.t. was added Dess-Martin periodinane (200 mg, 0.47 mmol). The mixture was stirred at r.t. for 1 h, and the reaction was quenched with 5% NaHSO$_3$ and a sat. NaHCO$_3$ solution. The aqueous layer was extracted with EtOAc (2×25 mL). The organic layers were dried (Na$_2$SO$_4$), filtered and concentrated under reduced pressure. The crude was purified via HPLC to afford 304-3 as a white solid; LCMS: m/z 633.15 [M+H]$^+$.

To a stirring mixture of 304-3 (20 mg, 0.031 mmol) in EtOH/EtOAc (1:1, 10 mL) was added Pd/C (10 mg). The mixture was reacted under H$_2$ balloon. The mixture was filtered through a plug of celite, and the filtrate was concentrated under reduced pressure. Crude 304-4 was used without further purification; LCMS: m/z 635.15 [M+H]$^+$.

To a stirring mixture of 304-4 in DCM (1 mL) at 0° C. was added TFA (0.3 mL) dropwise. The mixture was stirred at r.t. for 10 mins and then diluted with EtOAc. The reaction was quenched sat. NaHCO$_3$. The aqueous layer was extracted with EtOAc, dried over Na$_2$SO$_4$, filtered and concentrated under reduced pressure. The product was purified via prep-HPLC to afford 304 as a white solid. LCMS: m/z 515.10 [M+H]$^+$.

Example 143

Preparation of Compound 305

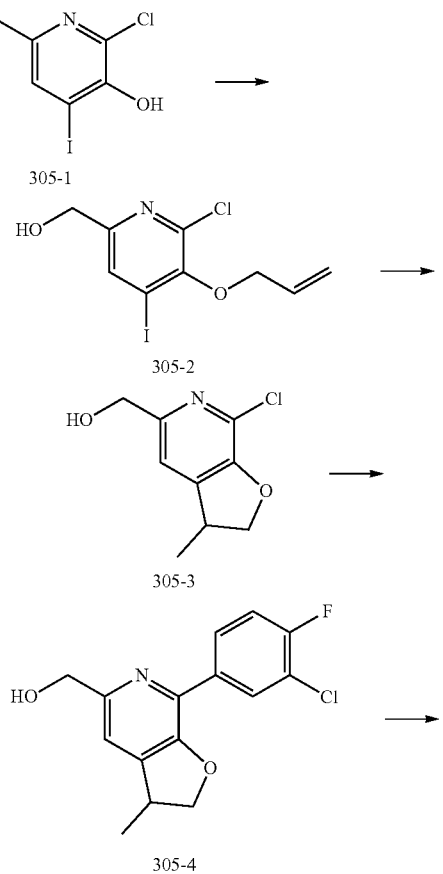

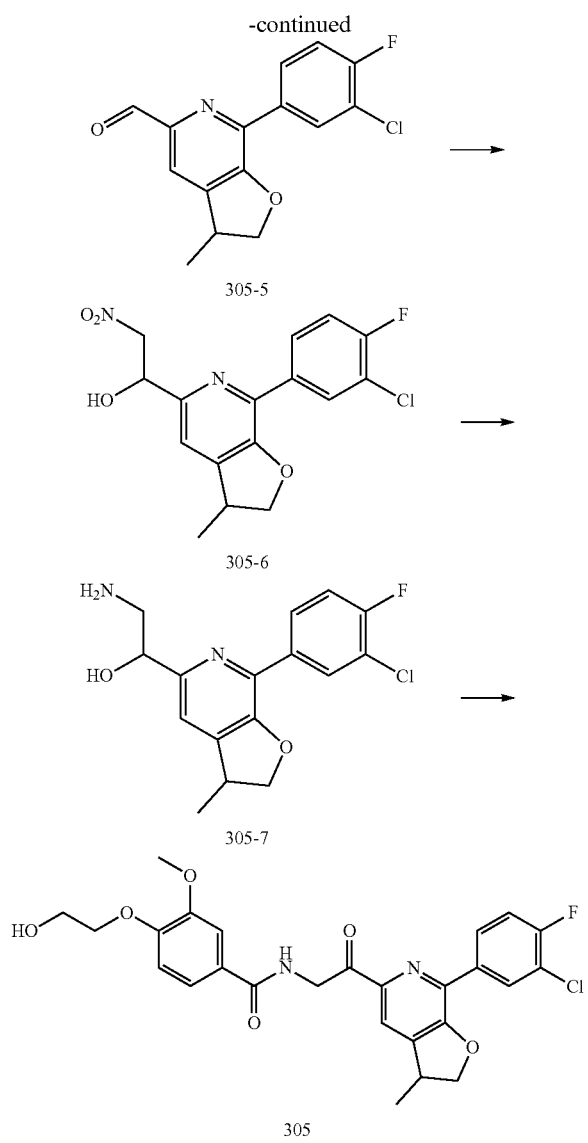

Cs₂CO₃ (0.6 mL, 4.25 M). The reaction was carried out under microwave irradition at 110° C. for 1 h. The mixture was diluted with EtOAc and water. The aqueous layer was extracted with EtOAc, dried over Na₂SO₄, filtered and concentrated under reduced pressure. The crude was purified via a silica gel column to afford 305-4 as a white solid. LCMS: m/z 294.0 [M+H].

Compound 305-7 was prepared in three steps similarly to the methods described for the synthesis of 302. Coupling of 305-7 with 3-methoxy-4-(2-((4-methoxybenzyl)oxy)ethoxy)benzoic acid followed by alcohol oxidation and deprotection afforded 305. LCMS: m/z 515.10 [M+H]⁺.

Example 144

Preparation of Compound 306

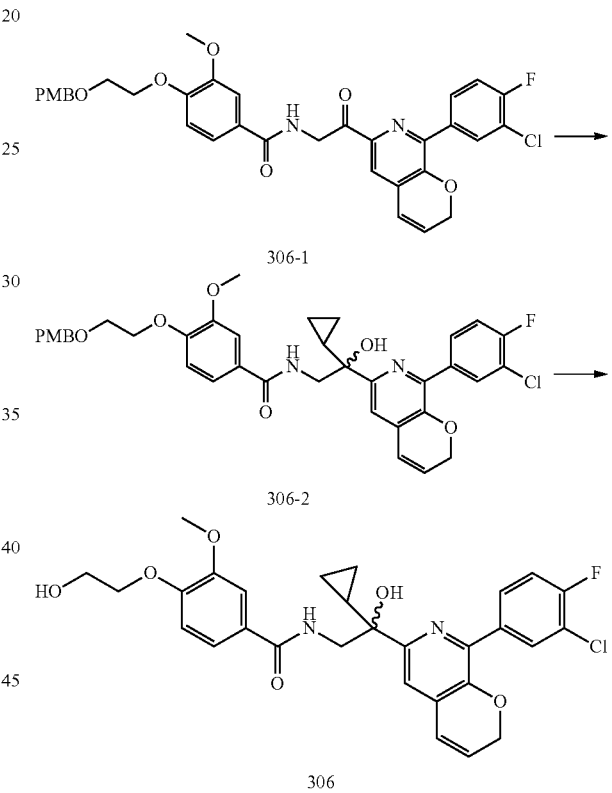

To a stirring mixture of 305-1 (500 mg, 1.75 mmol) in DMF (8.8 mL) at 0° C. was added NaH (144 mg, 3.6 mmol). The mixture was stirred at 0° C. for 5 mins. Allyl bromide (222 mg, 1.75 mmol) was added, and the mixture was stirred at 0° C. for 20 mins. The mixture was warmed to r.t. and stirred for 5 mins. The mixture was diluted with EtOAc and quenched with water. The aqueous layer was extracted with EtOAc, dried over Na₂SO₄, filtered and concentrated under reduced pressure. The crude was purified via a silica gel chromatography to afford 305-2. LCMS: m/z 325.9 [M+H]⁺.

To a stirring mixture of 305-2 (280 mg, 1.4 mmol) and AIBN (23 mg, 0.14 mmol) in toluene (3.5 mL) under Ar at reflux was added a solution of tributyltin hydride (407 mg, 1.4 mmol) in toluene (1 mL) dropwise over 5 mins. The mixture was stirred at reflux for 2 h. and then concentrated under reduced pressure. The crude was purified via a silica gel column to afford 305-3 as a colorless oil. LCMS: m/z 200.05 [M+H]⁺.

To a stirring mixture of 305-3 (170 mg, 0.85 mmol) in DME (2.4 mL, deoxygenated prior to use) were added (3-chloro-4-fluorophenyl)boronic acid (163 mg, 0.94 mmol), PdCl₂(PPh₃)₂ (93 mg, 0.13 mmol) and a solution of To a stirring mixture of 306-1 (30 mg, 0.047 mmol) in THF (0.45 mL) at r.t. under Ar was added cyclopropyl magnesium bromide (1.9 mL, 0.95 mmol). The mixture was stirred for 30 mins and then diluted with EtOAc. The reaction was quenched with a sat. NH₄Cl solution. A normal aqueous workup with EtOAc was followed. The crude was purified via a silica gel column to afford 306-2. LCMS: m/z 675.20 [M+H]⁺.

To a stirring mixture of 306-2 (30 mg, 0.052 mmol) in DCM (1 mL) was added TFA (0.2 mL) at r.t. The mixture was stirred for 10 mins, and then quenched with a cold sat. NaHCO₃ solution. The aqueous solution was extracted with DCM. The combined organic layers were washed with brine, dried over anhydrous Na₂SO₄, and concentrated under reduced pressure. The crude was purified via prep-HPLC to afford 306 as a white solid. LCMS: m/z 555.10 [M+H]⁺.

Example 145

Preparation of Compounds 307-312

TABLE 2

| Example Method | No. | Structure | LCMS: m/z |
|---|---|---|---|
| Compound 306 | 307 | | 529.10 [M + H]+ |
| Compound 306 | 308 | | 557.15 [M + H]+ |
| Compound 306 | 309 | | 557.15 [M + H]+ |
| Compound 306 | 310 | | 543.15 [M + H]+ |

TABLE 2-continued

| Example Method | No. | Structure | LCMS: m/z |
|---|---|---|---|
| Compound 298 | 311 | 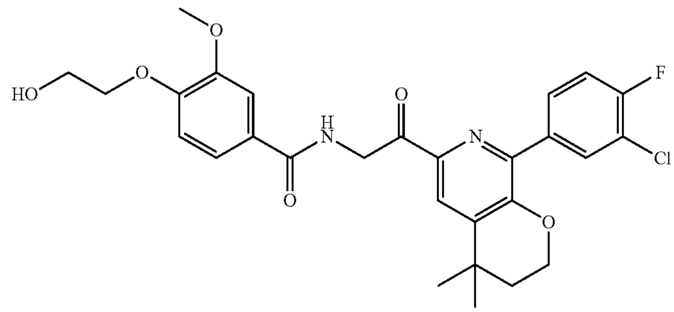 [SMILES: COc1cc(C(=O)NCC(=O)c2cc3c(c(-c4ccc(F)c(Cl)c4)n2)OCCC3(C)C)ccc1OCCO] | 543.15 [M + H]+ |
| Compound 306 | 312 | 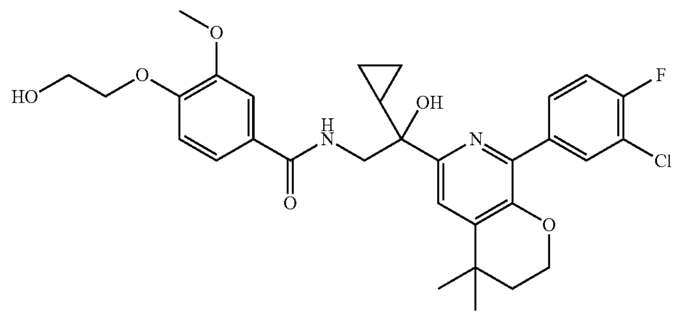 [SMILES: COc1cc(C(=O)NCC(O)(c2cc3c(c(-c4ccc(F)c(Cl)c4)n2)OCCC3(C)C)C2CC2)ccc1OCCO] | 585.15 [M + H]+ |

Example 146

Preparation of Compound 313

Example 147

Preparation of Compound 314

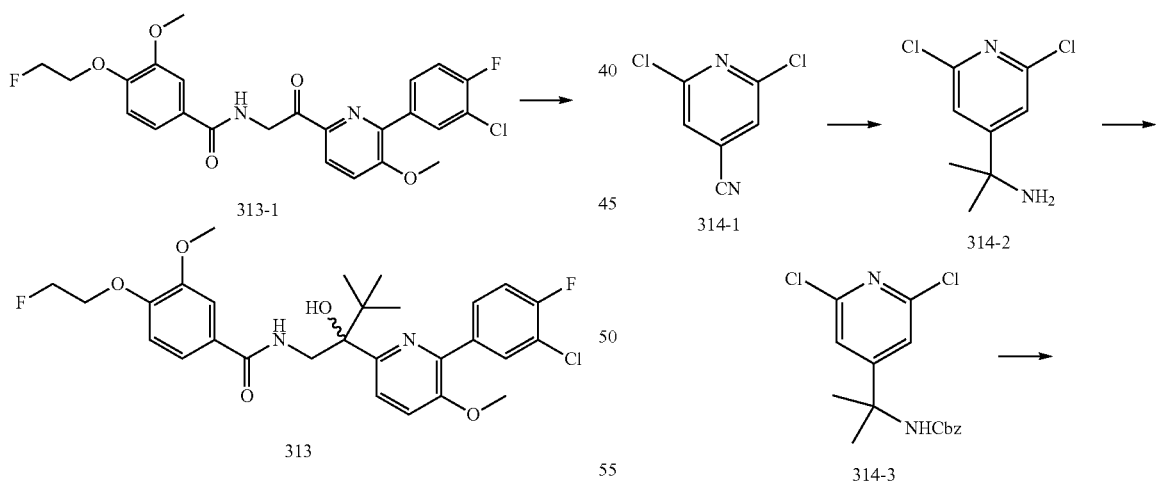

To a stirring mixture of 313-1 (45 mg, 0.092 mmol) in THF (1 mL) at r.t. under Ar was added a solution of t-BuMgCl in THF (0.91 mL, 0.91 mmol). The mixture was cooled to r.t., diluted with EtOAc and quenched with a sat. NH₄Cl solution. The mixture was stirred at r.t. for 20 mins and the layers were separated. The aqueous layer was extracted with EtOAc. The organic layers were dried (Na₂SO₄), filtered and concentrated under reduced pressure. The crude was purified via silica gel column and further purified via prep-HPLC to afford 313 as a white solid. LCMS: m/z 549.15 [M+H]+.

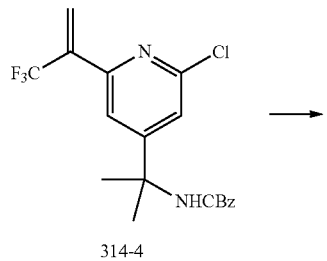

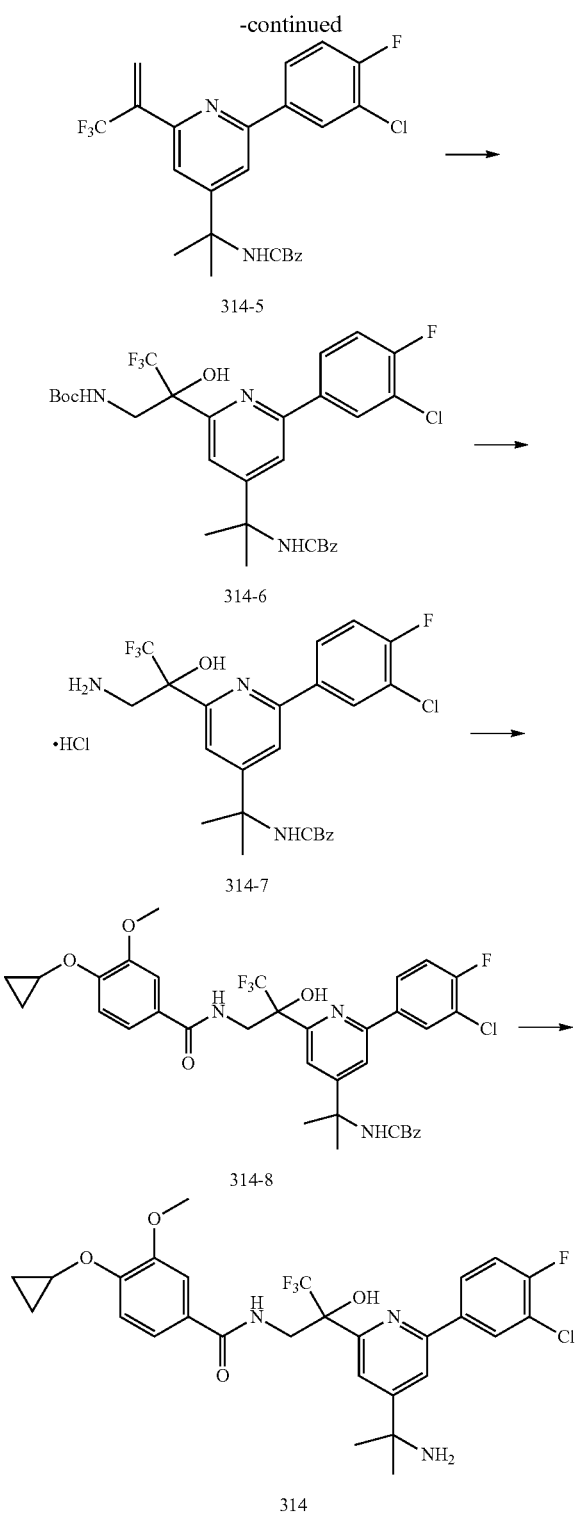

Methylmagnesium bromide (27 mL, 3.2 M in THF, 87 mmol) was added to a solution of 314-1 (5.0 g, 29 mmol) in Et₂O (80 mL) at 0° C. After 1 h of stirring, titanium isopropoxide (8.2 mL, 29 mmol) was added, and the reaction was heated at 50° C. for 2 h. Copious quantities of celite were added to the mixture which was cooled to r.t. The mixture was basified with 2N NaOH and filtered through celite and washing with CH₂Cl₂. The layers were separated, and the organic layer was concentrated. The mixture was re-dissolved in CH₂Cl₂ and extracted with 1N HCl (3×). The aqueous extracts were basified with solid K₂CO₃ and back-extracted with EA. The combined organic layers were washed with brine, dried and concentrated to provide crude 314-2 (3.25 g).

Crude 314-2 (3.28 g, 16 mmol) was dissolved in CH₂Cl₂. Benzyl chloroformate (2.3 mL, 16 mmol) and DIPEA (3.0 mL, 18 mmol) were added, and the reaction was stirred at r.t. for 3 h. The mixture was washed with 1N HCl, brine, dried (Na₂SO₄) and concentrated. The crude was purified via a silica gel chromatography to afford 314-3 as a white solid.

To a stirring mixture of 314-3 (2 g, 5.9 mmol) in DME (10 mL, deoxygenated prior to using) were added 4,4,6-trimethyl-2-(3,3,3-trifluoroprop-1-en-2-yl)-1,3,2-dioxaborinane (1.32 g, 5.9 mmol) and a solution of Cs₂CO₃ (6M, 3 mL), PdCl₂(dppf) (461 mg, 0.59 mmol). The mixture was stirred at 110° C. under microwave reaction conditions for 1 h. The mixture was diluted with EtOAc and water. A normal aqueous workup with EtOAc was followed. The crude was purified via a silica gel chromatography (EtOAc:hex 0-20%) to afford 314-4 (1.3 g), which was used without further purification.

To a stirring mixture of 314-4 (1.3 g, 3.2 mmol) in DME (5 mL, deoxygenated prior to using) were added 3-chloro-4-fluorophenylboronic acid (550 mg, 3.2 mmol), a solution of Cs₂CO₃ (6M, 1.5 mL), and PdCl₂(dppf) (230 mg, 0.32 mmol). The mixture was stirred at 110° C. under microwave reaction conditions for 1 h. The mixture was diluted with EtOAc and water. A normal aqueous workup with EtOAc was followed. The crude was purified via a silica gel chromatography (EtOAc:hex 0-20%) to afford 314-5. LCMS: m/z 493.05 [M+H]⁺.

To a stirring mixture of tert-butyl hydroxycarbamate (2 g, 15 mmol) in THF (10 mL) at 0° C. was added TsCl (2.8 g, 15 mmol) and TEA (2.2 mL, 15.8 mmol). The mixture was stirred at 0° C. for 20 mins, and then warmed to r.t. for 5 mins. The mixture was diluted with DCM and washed with water. A normal aqueous workup with DCM was followed. The crude was purified via a silica gel to afford tert-butyl tosyloxycarbamate as a white solid.

To a stirring mixture of 314-5 (950 mg, 1.9 mmol) in t-BuOH:water (3:1, 3 mL total volume) at r.t. were added potassium osmate dihydrate (105 mg, 0.3 mmol) and tert-butyl tosyloxycarbamate (1 g, 3.8 mmol). The mixture was stirred at r.t. overnight, and then diluted with water and DCM. A normal aqueous work up with DCM was followed. The crude was purified via a silica gel chromatography to afford 314-6 (1.3 g, 80% pure). LCMS: m/z 626.20 [M+H]⁺.

Compound 314-6 was dissolved in a solution of HCl (4N) in dioxane (10 mL) at r.t. The mixture was stirred at r.t. The mixture was concentrated under reduced pressure to afford crude 314-7, which was used without further purification. LCMS: m/z 526.05 [M+H]⁺.

To a stirring mixture of 4-cyclopropoxy-3-methoxybenzoic acid (350 mg, 1.69 mmol) in DMF (1.5 mL) were added HATU (642 mg, 1.69 mmol) and DIPEA (735 mL, 4.2 mmol). The mixture was stirred at r.t. for 10 mins. Compound 314-7 in DMF (2 mL) was added, and then stirred for 10 mins. The reaction was quenched with a 10% aqueous solution of NaHCO₃ (10 mL), and then diluted with DCM. A normal aqueous work up with DCM was followed. The crude was purified via prep-HPLC to afford 314-8 as a white solid. LCMS: m/z 716.2 [M+H]⁺.

To a stirring mixture of 314-8 (602 mg, 0.84 mmol) in AcCN (3 mL) at r.t. were added NaI (630 mg, 4.2 mmol) and TMSCl (453 mg, 4.2 mmol). The mixture was warmed to 60° C. until the starting material disappeared. The mixture was cooled to r.t. and purified by silica gel chromatography (EtOAc:hex 0-50% and then MeOH:DCM 0-20%). The product was further purified via prep-HPLC and then converted to the HCl salt to afford 314. LCMS: m/z 582.2 [M+H]⁺.

Example 148

Preparation of Compounds 315-317

TABLE 3

| Example Method | No. | Structure | LCMS: m/z |
|---|---|---|---|
| Compound 314 | 315 | | 570.10 [M + H]+ |
| Compound 314 | 316 | | 556.10 [M + H]+ |
| Compound 314 | 317 | | 600.15 [M + H]+ |

Example 149

Preparation of Compound 318

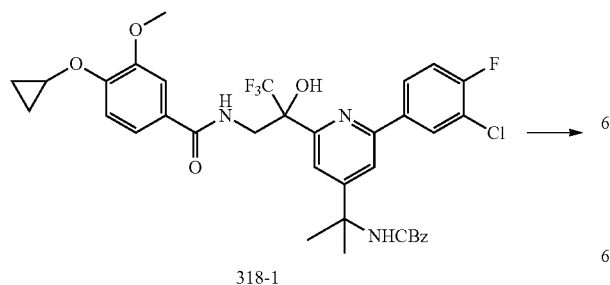

318-1

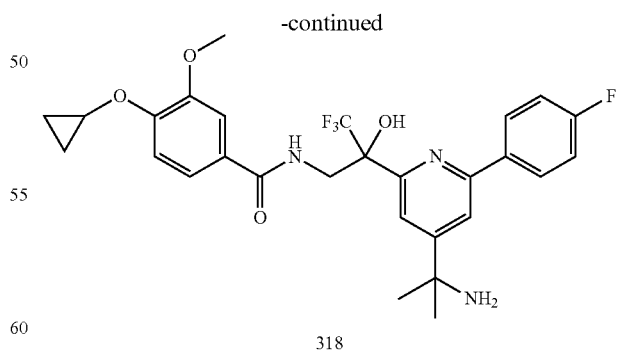

318

To a stirring solution of 318-1 (40 mg, 0.028 mmol) in EtOAc:EtOH:HOAc (5 mL:1.0 mL:0.1 mL) was added Pd/C (20 mg). The mixture was placed under a H₂ balloon. The mixture was stirred for several hours until the starting material was consumed. The mixture was filtered through a plug of celite, and the plug was washed with EtOAc (2×10 mL). The mixture was concentrated under reduced pressure and purified via prep-HPLC to afford 318 as a white solid. LCMS: m/z 548.15 [M+H]⁺.

Example 150

Preparation of Compounds 319-322

TABLE 4

| Example Method | No. | Structure | LCMS: m/z |
|---|---|---|---|
| Compound 319 | 318 | | 591.15 [M + H]⁺ |
| Compound 320 | 318 | | 522.15 [M + H]⁺ |
| Compound 321 | 318 | | 577.15 [M + H]⁺ |
| Compound 322 | 318 | | 599.10 [M + H]⁺ |

Example 151

Preparation of Compound 323

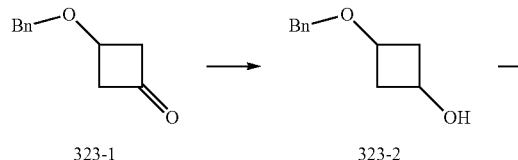

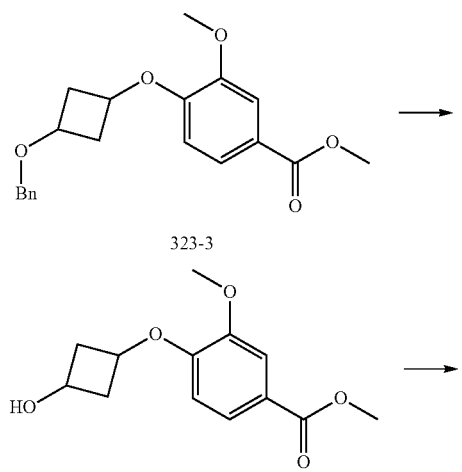

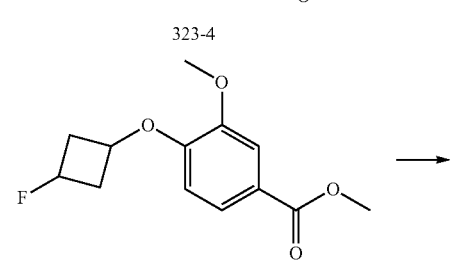

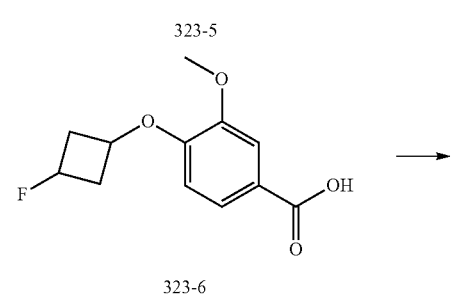

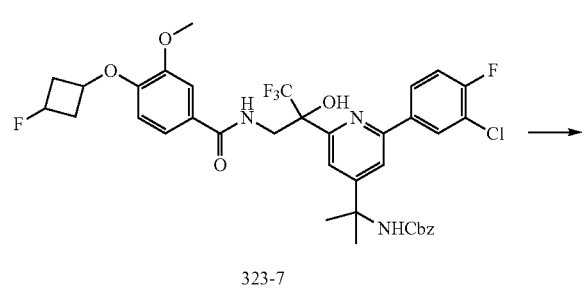

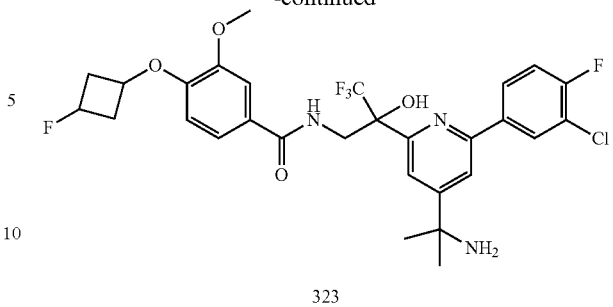

323

To a solution of 323-1 (2.5 g, 14.2 mmol) in THF (10 mL) and MeOH (10 mL) was added NaBH$_4$ (1.6 g, 42.1 mmol) at 0° C. The mixture was stirred at 0° C. for 30 mins. The reaction was quenched with 1.0 N HCl and extracted with EtOAc. The combined organic solutions were dried (MgSO$_4$) and evaporated under reduced pressure. The residue was purified on a silica gel column (PE:EA 5:1) to give 323-2 as a colorless oil (2.0 g, 79.1%).

A solution of 323-2 (2.0 g, 11.2 mmol), methyl 4-hydroxy-3-methoxybenzoate (2.1 g, 11.5 mmol) and PPh$_3$ (4.5 g, 17.3 mmol) was stirred in dry THF (40 mL) at 0° C. under a N$_2$ atmosphere. DIAD (3.5 g, 17.5 mmol) added dropwise over a period of 5 mins, and the solution was allowed to stir at 50° C. for 3 h. After disappearance of the starting material, the solvent was evaporated under reduced pressure. The residue was purified on by column chromatography on silica gel (PE:EA 10:1) to give 323-3 as a white solid (2.8 g, 73.7%); $^1$H-NMR (CDCl$_3$, 400 MHz), δ=7.62-7.60 (dd, J=1.6 Hz, J=10.0 Hz, 1H), 7.53 (s, 1H), 7.34-7.25 (m, 5H), 6.66 (d, J=8.4 Hz, 1H), 4.96-4.93 (m, 1H), 4.44 (s, 2H), 4.36-4.32 (m, 1H), 3.93 (s, 3H), 3.87 (s, 3H), 2.59-2.54 (m, 4H).

To a mixture of 323-3 (2.8 g, 8.2 mmol) in MeOH (15 mL) was added Pd(OH)$_2$ on carbon (10%, 500 mg) under N$_2$. The suspension was degassed under vacuum and purged with H$_2$ (3×). The mixture was stirred under H$_2$ (40 psi) at r.t. for 3 h. The suspension was filtered through a pad of Celite, and the cake was washed with MeOH. The combined filtrates were concentrated to give crude 323-4 (1.7 g, 84.5%) which was used without purification.

To a mixture of 323-4 (1.7 g, 6.7 mmol) in DCM (10 mL) was added DAST (3 mL) at 0° C. The mixture was stirred at 0° C. for 30 mins. The reaction was quenched by sat. aq. NaHCO$_3$ at 0° C. and then extracted with EtOAc. The combined organic layers were washed with brine, dried over Na$_2$SO$_4$ and concentrated to dryness. The residue was purified by column chromatography on silica gel (PE:EA 15:1) to give 323-5 as a white solid (800 mg, 47.1%).

A solution of 323-5 (254 mg, 1.0 mmol) and aq. lithium hydroxide (2 N, 1 mL) in THF (5 mL) was stirred at r.t. for 1 h. The mixture was neutralized by using 2N HCl and extracted with EtOAc. The combined organic solutions were dried (MgSO$_4$), and evaporated under reduced pressure to give 323-6 as a white solid (100 mg, 41.6%).

Compound 323 was prepared similarly to the preparation of 314. LCMS: m/z 614.15 [M+H]$^+$.

Example 152

Preparation of Compound 324

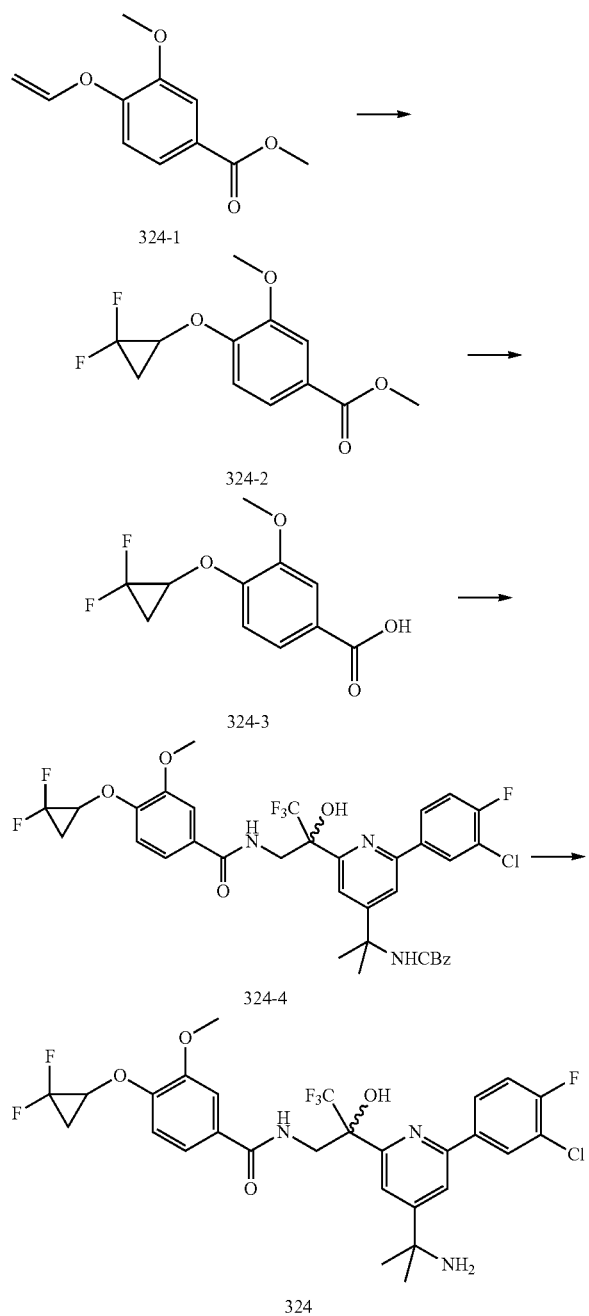

Example 153

Preparation of Compound 325

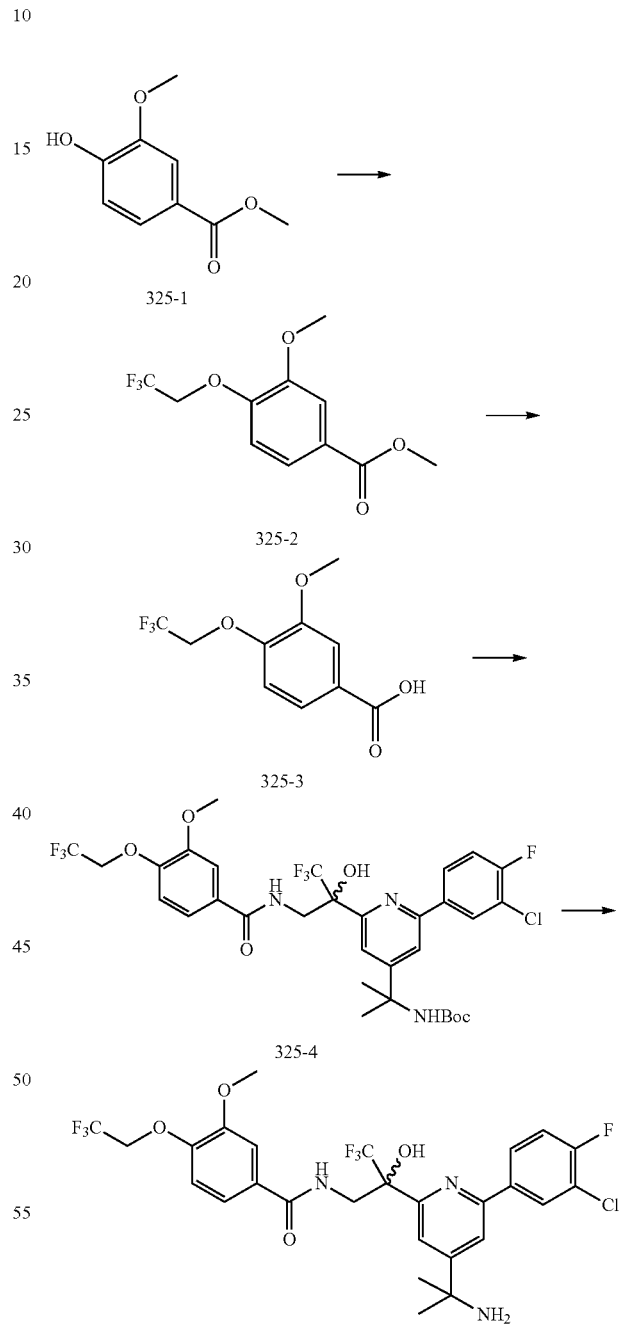

To a stirring mixture of 324-1 (360 mg, 1.73 mmol) and NaF (7.3 mg, 0.173 mmol) in toluene (2 mL) at reflux was added trimethylsilyl-2,2-difluoro-2-(fluorosulphonyl)acetate dropwise over 1 h. The mixture was heated at reflux for 1 h and then cooled to r.t. The mixture was concentrated under reduced pressure and loaded into a silica gel column to afford 324-2. LCMS: m/z 259.05 [M+H]$^+$.

To a stirring mixture of 324-2 (320 mg, 1.24 mmol) in THF:water (1.0 mL:0.2 mL) at r.t. was added aq. LiOH (155 mg, 3.7 mmol). The mixture was stirred for 2 d. The mixture was diluted with EtOAc and acidified with 10% aqueous HCl solution. A normal aqueous work up with EtOAc was followed. Crude 324-3 was used without further purification.

Compound 324 was prepared similarly to the preparation of 314. LCMS: m/z 618.15 [M+H]$^+$.

To a stirring mixture of 325-1 (0.5 g, 2.75 mmol) in DMF (7 mL) were added Cs$_2$CO$_3$ (1.35 g, 4.12 mmol), and 2,2,2-trifluoroethyl 1,1,2,2,3,3,4,4,4-nonafluorobutane-1-sulfonate (837 mg, 2.2 mmol). The mixture was heated at 55° C. overnight, and then diluted with EtOAc, and washed with water. The aqueous layer was extracted with EtOAc, dried over Na$_2$SO$_4$, filtered and concentrated under reduced pressure. The crude was purified via a silica gel column to afford 325-2 as a white solid; LCMS: m/z 265.05 [M+H]$^+$.

To a stirring mixture of 325-2 (300 mg, 1.13 mmol) in THF:water (1 mL:0.1 mL) was added aq. LiOH. The mixture was stirred at r.t. overnight. The mixture was diluted with EtOAc and acidified with a 1N HCl aqueous solution. The aqueous layer was extracted with EtOAc, dried over Na$_2$SO$_4$, filtered and concentrated under reduced pressure. Crude 325-3 was used without further purification.

Compound 325 was prepared similarly to the preparation of 314. LCMS: m/z 624.1 [M+H]$^+$.

Example 154

Preparation of Compound 326

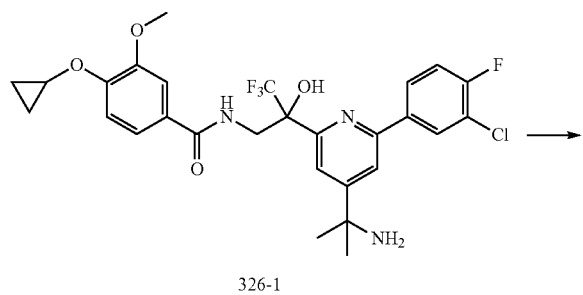

326-1

-continued

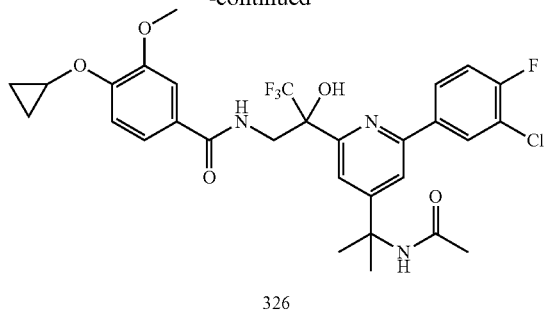

326

To a stirring mixture of acetic acid (5 mg, 0.083 mmol) in DMF (0.2 mL) were added HATU (3.1 mg, 0.083) and DIPEA (17 mg, 0.13 mmol). The mixture was stirred at r.t. for 5 mins. A solution of 326-1 in DMF (0.8 mL) was added, and the mixture was stirred for 10 mins. The reaction was quenched with a 10% aq. solution of NaHCO$_3$ (10 mL). The mixture was diluted with DCM, and a normal aqueous work up with DCM was followed. Crude product was purified via prep-HPLC to afford 326 as a white solid. LCMS: m/z 624.15 [M+H]$^+$.

Example 155

Preparation of Compounds 327-329

TABLE 5

| Example Method | Structure | LCMS: m/z |
|---|---|---|
| Compound 314 | ![structure 327] | 554.10 [M + H]$^+$ |
| Compound 326 | ![structure 328] | 596.1 [M + H]$^+$ |

TABLE 5-continued
| Example Method | Structure | LCMS: m/z |
|---|---|---|
| Compound 326 | 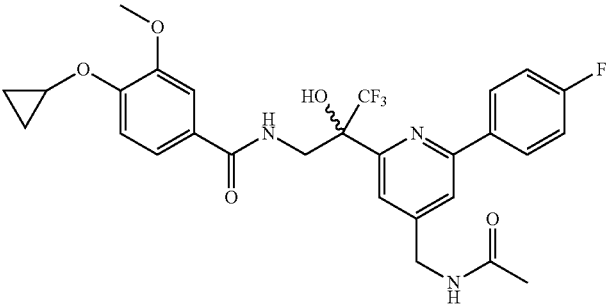<br>329 | 562.15 [M + H]+ |
| Compound 330 | 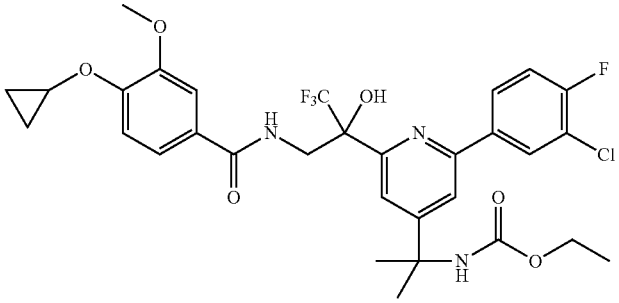<br>331 | 654.15 [M + H]+ |
| Compound 306 | 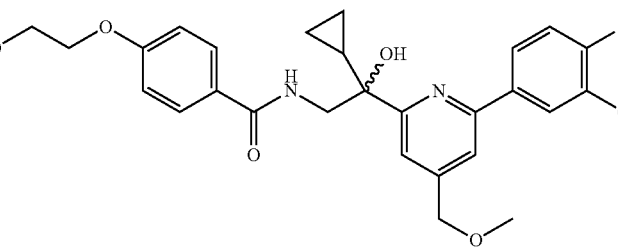<br>333 | 501.10 [M + H]+ |
| Compound 314 | 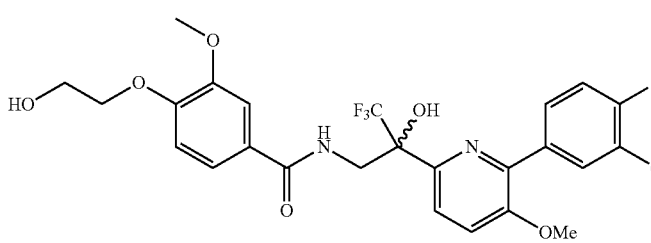<br>334 | 559.10 [M + H]+ |

TABLE 5-continued

| Example Method | Structure | LCMS: m/z |
|---|---|---|
| Compound 334 | 336 | 573.15 [M + H]+ |
| Compound 334 | 337 | 529.1 [M + H]+ |
| Compound 334 | 338 | 586.05 [M + H]+ |
| Compound 334 | 339 | 550.05 [M + H]+ |
| Compound 334 | 340 | 612.1 [M + H]+ |

TABLE 5-continued

| Example Method | Structure | LCMS: m/z |
|---|---|---|
| Compound 334 | 341 | 545.15 [M + H]⁺ |
| Compound 334 | 345 | 609.10 [M + H]⁺ |
| Compound 334 | 346 | 627.15 [M + H]⁺ |
| Compound 334 | 347 | 626.15 [M + H]⁺ |

TABLE 5-continued

| Example Method | Structure | LCMS: m/z |
|---|---|---|
| Compound 334 | 348 | 652.2 [M + H]+ |
| Compound 334 | 349 | 598.1 [M + H]+ |

Example 156

Preparation of Compound 330

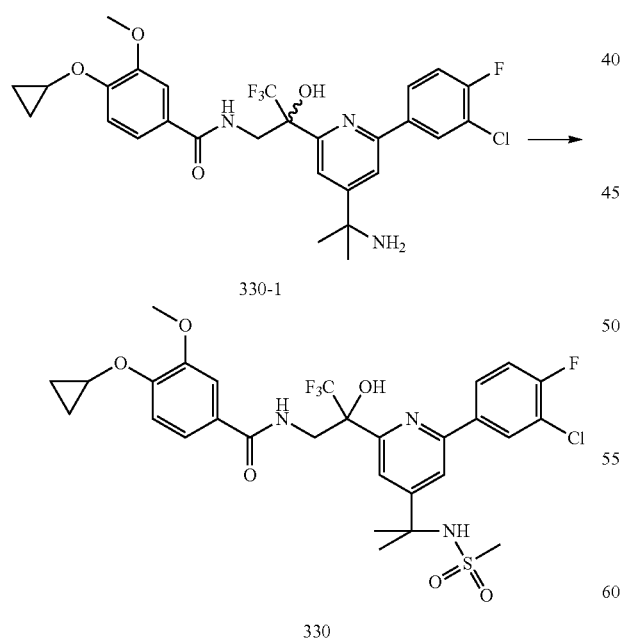

To a stirring mixture of 330-1 (20 mg, 0.034 mmol) in DCM (0.4 mL) were added TEA (7 mg, 0.069 mmol) and MsCl (1 drop). The mixture was stirred for 20 mins and slowly warmed to r.t. The mixture was diluted with DCM, and the reaction was quenched with a sat. NaHCO₃ solution. The aqueous layer was extracted with DCM. The organic layers were dried (Na₂SO₄), filtered and concentrated under reduced pressure. Crude product was purified via prep-HPLC to afford 330 as a white solid. LCMS: m/z 660.10 [M+H]⁺.

Example 157

Preparation of Compound 332

To a stirring mixture of 332-1 (8 mg, 0.014 mmol) in DMF (0.2 mL) was added DMF.DMA (0.2 mL). The mixture was stirred at 90° C. until the starting material was consumed. The crude mixture was concentrated under reduced pressure and used without further purification.

To a stirring mixture of crude product from the previous step in DCM (0.5 mL) at 0° C. were added hydrazine monohydrate (0.1 mL) and HOAc (0.05 mL). The mixture was warmed to r.t. and then reflux for 30 mins. The mixture was cooled to r.t., and the reaction was quenched with a sat. NaHCO₃ solution. The aqueous layer was extracted with DCM, dried over Na₂SO₄, filtered and concentrated under reduced product. Crude product was purified via prep-HPLC to afford 332 as a white solid. LCMS: m/z 595.1

Example 158

Preparation of Compound 342

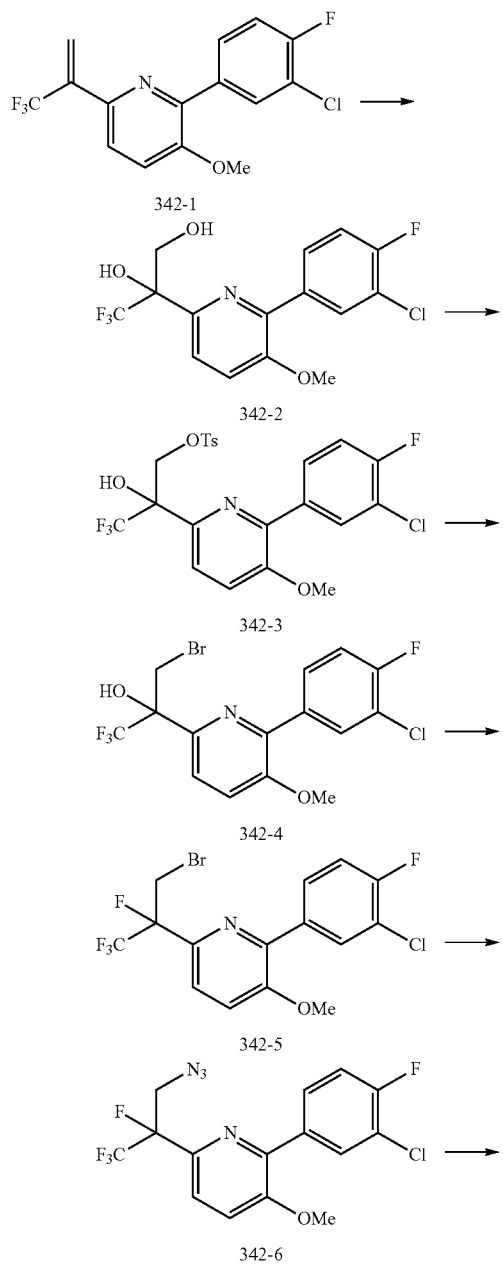

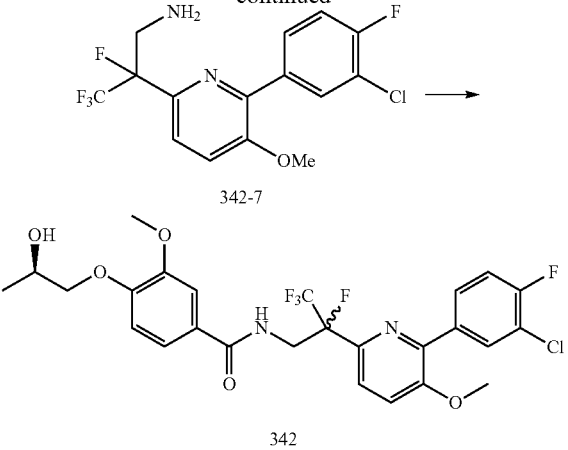

To a stirring mixture of 342-1 (50 mg, 0.15 mmol) in t-BuOH:water (3:1, 1.3 mL) at 0° C. were added NMO (26 mg, 0.23 mmol) and potassium osmate dehydrate (5.5 mg, 0.016 mmol). The mixture was warmed to r.t. overnight, and then diluted with DCM and water. The aqueous layer was extracted with DCM, dried over Na₂SO₄, filtered and concentrated under reduced pressure. The crude was purified on a silica gel column to afford 342-2 as a brownish oil (50 mg, 91% yield). LCMS: m/z 366.0 [M+H]⁺.

To a stirring mixture of 342-2 (50 mg, 0.136 mmol) in DCM (1 mL) at 0° C. were added TsCl (52 mg, 0.273 mmol), TEA (60 µL, 0.41 mmol) and DMAP (2 crystals). The mixture was warmed to r.t. for 1 h and then diluted with DCM. The reaction was quenched with sat. NaHCO₃ solution. The aqueous layer was extracted with DCM, dried over Na₂SO₄, filtered and concentrated under reduced pressure. The crude was purified via a silica gel column to afford 342-3 (65 mg, 92% yield). LCMS: m/z 520.0 [M+H]⁺.

To a stirring mixture of 342-3 (128 mg, 0.246 mmol) in acetone (1 mL) was added LiBr (64 mg, 0.74 mmol). The mixture was stirred at reflux for 2 h and loaded into a silica gel column to afford 342-4 as a colorless oil (75 mg, 71% yield). LCMS: m/z 427.95 [M+H]⁺.

To a stirring mixture of 342-4 in DCM (1 mL) at 0° C. was added DAST (58 mL, 0.44 mmol). The mixture was stirred at 0° C. for 30 mins and then warmed to r.t. for 5 mins. The reaction was quenched with a cold aq. NaHCO₃ solution. The aqueous layer was extracted with DCM, dried over Na₂SO₄, filtered and concentrated under reduced pressure. The crude was purified via a silica gel column to afford 342-5 (56 mg, 74% yield). LCMS: m/z 429.95 [M+H]⁺.

To a stirring mixture of 342-5 (50 mg, 0.116 mmol) in DMF (2 mL) were added tetrabutylammonium azide (330 mg, 1.2 mmol) and tetrabutylammonium iodide (5 mg). The mixture was stirred at 95° C. for 4 h. The mixture was loaded onto a silica gel column, eluting with hexane:EtOAc to afford 342-6 as a colorless oil. LCMS: m/z 393.0 [M+H]⁺.

To a stirring mixture of 342-6 (25 mg, 0.064 mmol) in THF:water (10:1, 1.1 mL) was added triphenylphosphine (polymer-bound, 167 mg, 0.64 mmol). The mixture was stirred at 70° C. for 30 mins, cooled to r.t. and filtered through a plug of celite. The plug was washed several times with EtOAc. The mixture was concentrated under reduced pressure and 342-7 used without further purification. LCMS: m/z 367.0 [M+H]⁺.

To a stirring mixture of (R)-4-(2-hydroxypropoxy)-3-methoxybenzoic acid (18 mg, 0.079 mmol) in DMF (0.5 mL) were added HATU (36 mg, 0.095 mmol) and DIPEA (35 μL, 0.191 mmol). The mixture was stirred at r.t. for 10 mins. A solution of 342-7 in DMF (0.5 mL) was added, and the mixture was stirred at for 10 mins. The reaction was quenched with a 10% aq. solution of NaHCO₃ (10 mL). The mixture was diluted with DCM and a normal aqueous work up with DCM was followed. The crude was purified via prep-HPLC to afford 342 as a white solid. LCMS: m/z 575.15 [M+H]⁺.

Example 159

Preparation of Compound 343

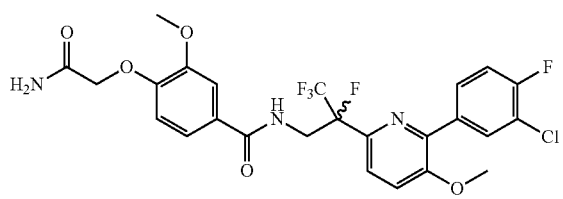

343

Compound 343 was prepared according to the method described for 342. LCMS: m/z 574.10 [M+H]⁺.

Example 160

Preparation of Compound 344

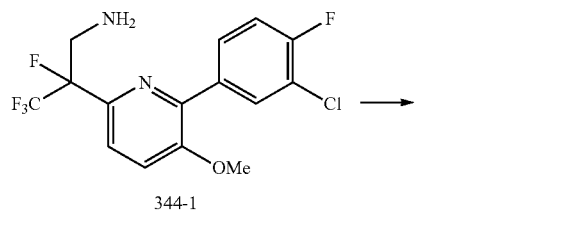

344-1

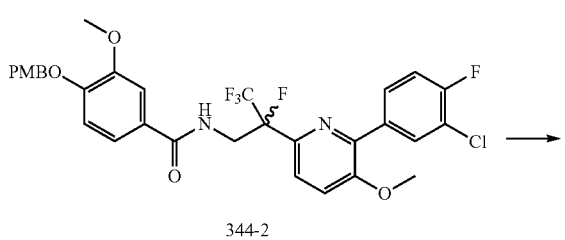

344-2

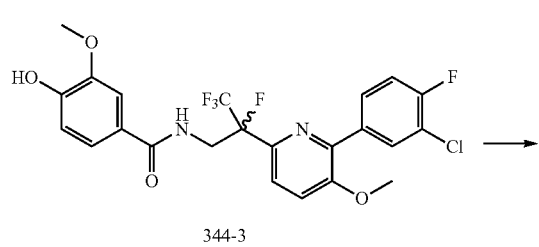

344-3

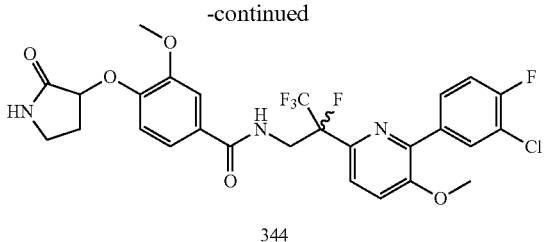

344

To a stirring mixture of 3-methoxy-4-((4-methoxybenzyl) oxy)benzoic acid (35 mg, 0.095 mmol) in DMF (0.5 mL) were added HATU (45 mg, 0.114 mmol) and DIPEA (35 μL, 0.19 mmol). The mixture was stirred at r.t. for 10 mins. A solution of 344-1 in DMF (0.5 mL) was added, and the mixture was stirred for 10 mins. The reaction was quenched with a 10% aq. solution of NaHCO₃ (5 mL). The mixture was diluted with DCM and a normal aqueous work up with DCM was followed. The crude was purified via a silica gel column to afford 344-2 as a colorless oil. LCMS: m/z 637.15 [M+H]⁺.

To a stirring mixture of 344-2 in DCM (1 mL) was added TFA (0.4 mL). The mixture was stirred at r.t. until 344-2 was consumed. The reaction was quenched with a cold sat. NaHCO₃ solution. The aqueous layer was extracted with DCM, dried over Na₂SO₄, filtered and concentrated under reduced pressure. The crude was purified via a silica gel column to give 344-3 as a colorless oil. LCMS: m/z 517.1 [M+H]⁺.

To a stirring mixture of 344-3 (30 mg, 0.058 mmol) in DCM was added Cs₂CO₃ (47 mg, 0.145 mmol) and 3-bromopyrrolidin-2-one (11.4 mg, 0.07 mmol). The mixture was heated under microwave irradiation at 70° C. for 1 h. The mixture was filtered through a plug of celite and washed several times with DCM. The mixture was concentrated under reduced pressure and further purified via HPLC to afford 344 as a white solid. LCMS: m/z 600.15 [M+H]⁺.

Example 161

Preparation of Compound 350

350-1

350-2

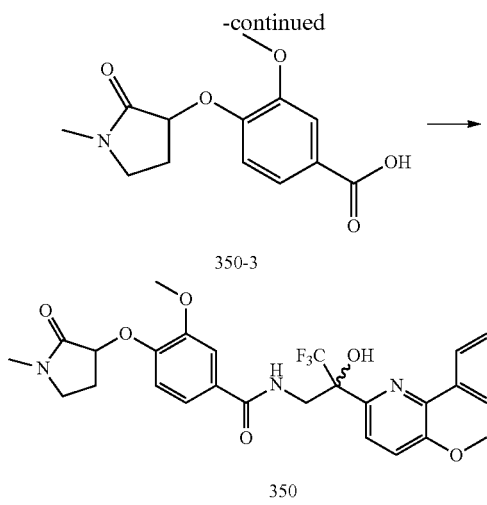

350-3

350

To a stirring mixture of 350-1 (57 mg, 0.21 mmol) in THF (1 mL) at 0° C. was added NaH (17 mg, 0.43 mmol). The mixture was stirred at 0° C. for 5 mins, and then methyl iodide (61 mg, 0.43 mmol) was added. The mixture was warmed to r.t. and then diluted with EtOAc. The reaction was quenched with a sat. NH$_4$Cl solution. The aqueous layer was extracted with EtOAc, dried over Na$_2$SO$_4$, filtered and concentrated under reduced pressure. The crude was purified via a silica gel column to give 350-2. LCMS: m/z 280.05 [M+H]$^+$.

To a stirring mixture of 350-2 (50 mg, 0.17 mmol) in THF:MeOH:water (1:0.4:0.1) at r.t. was added aq. LiOH (36 mg, 0.86 mmol). The mixture was stirred overnight at r.t. The mixture was diluted with EtOAc and acidified with a 1N HCl solution. The aqueous layer was extracted with EtOAc, dried over Na$_2$SO$_4$, filtered and concentrated under reduced pressure. Crude 350-3 was used without further purification. LCMS: m/z 266.05 [M+H]$^+$.

Compound 350 was prepared similarly according to the methods for 349. LCMS: m/z 612.1 [M+H]$^+$.

Example 162

Preparation of Compound 351

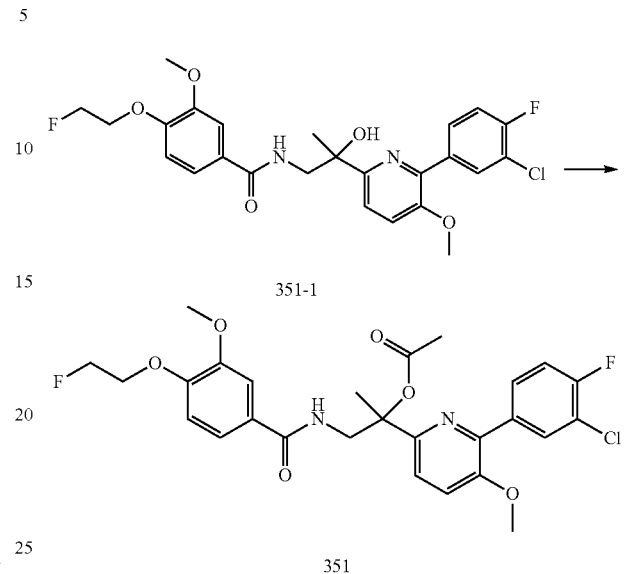

351-1

351

To a stirring mixture of 351-1 (15 mg, 0.0295 mmol) in DCM (1 mL) at 0° C. were added acetic anhydride (10 mg, 0.09 mmol), TEA (20 μl) and DMAP (1 crystal). The mixture was stirred at r.t. until the alcohol was consumed. The reaction was quenched with a sat. NaHCO$_3$ (5 mL). The aqueous layer was extracted with EtOAc, dried over Na$_2$SO$_4$, filtered and concentrated under reduced pressure. The crude was purified via HPLC to afford 352 as a white solid. LCMS: m/z 549.10 [M+H]$^+$.

Example 163

Preparation of Compound 352

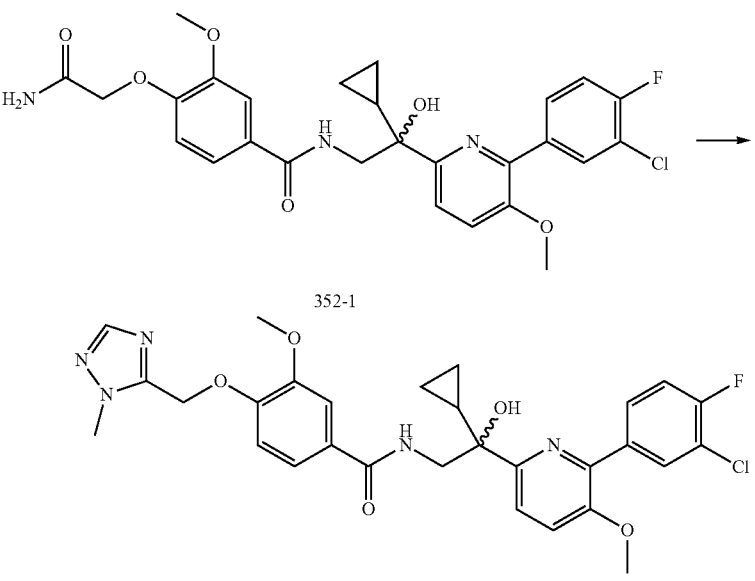

352-1

352

269

To a stirring mixture of 352-1 (25 mg, 0.047 mmol) in DMF (0.1 mL) was added DMF. DMA (0.1 mL). The mixture was stirred at 60° C. until the starting material was consumed. The mixture was cooled to r.t. and concentrated under reduced pressure. The crude used was without further purification. To the stirring crude in DCM at 0° C. were added HOAc (3 drops) and methyl hydrazine (3 drops). The mixture was warmed to r.t. for 20 mins and heated to reflux. The mixture was cooled to r.t., diluted with DCM and quenched with a cold sat. NaHCO₃ solution. The aqueous layer was extracted with DCM (3×10 mL), dried over Na₂SO₄, filtered and concentrated under reduced pressure. The crude was purified via prep-HPLC to afford 352 as a white solid. LCMS: m/z 582.15 [M+H]⁺.

Example 164

Preparation of Compound 353

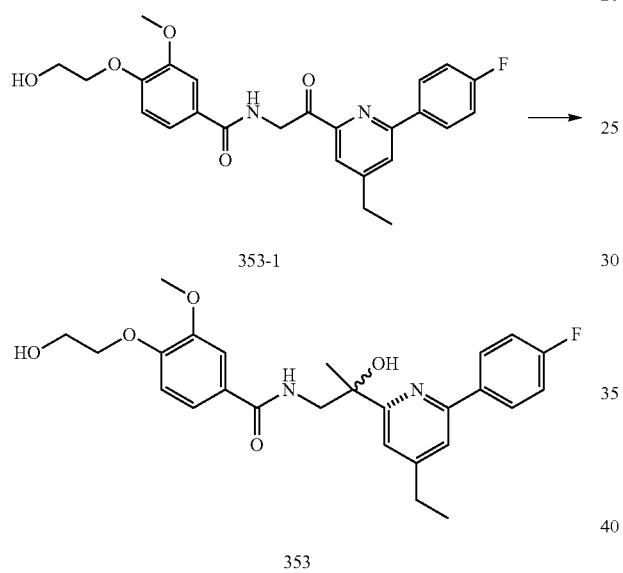

353-1

353

To a solution of 353-1 (53 mg, 0.11 mmol) in THF (4 mL) was added MeMgCl (1 mL). The mixture was stirred at 0° C. for 1 h. The reaction was quenched with a sat. NH₄Cl solution. The organic layers was washed with brine, dried over Na₂SO₄ and concentrated. The crude was purified by prep-HPLC to give 353 (20 mg, 40%) as a white solid. LCMS: m/z 469.3 [M+H]⁺.

Example 165

Preparation of Compound 354

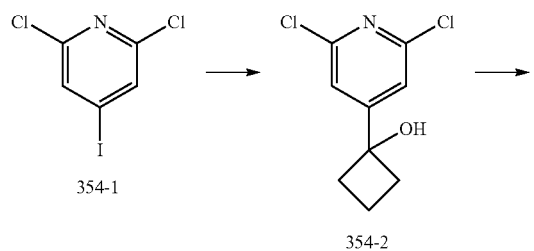

354-1

354-2

270

-continued

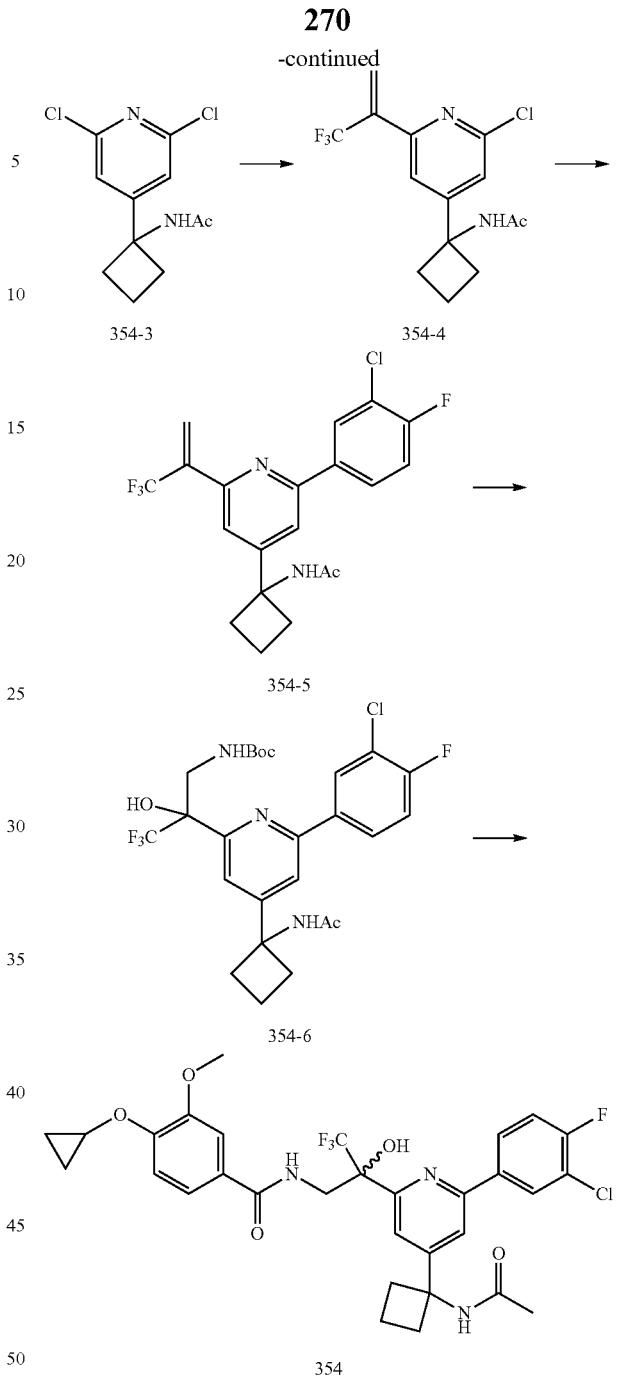

354-3

354-4

354-5

354-6

354

A solution of i-PrMgCl (2.75 mL, 3.84 mmol) in THF was added dropwise to a stirring mixture of 354-1 (1 g, 3.66 mmol) at −45° C. over 5 mins. The mixture was stirred for 1 h, and then cyclobutanone (256 mg, 3.66 mmol) in THF (1 mL) was added. The mixture was warmed to r.t. and stirred overnight. The mixture was diluted with EtOAc, and the reaction quenched with a sat. NH₄Cl solution. The aqueous layer was extracted with EtOAc, dried over Na₂SO₄, filtered and concentrated under reduced pressure. The crude was purified via a silica gel column to afford 354-2 as a colorless oil. LCMS: m/z 218 [M+H]⁺.

To a stirring mixture of 354-2 (0.4 g, 1.83) in CH₃CN (4 mL) at 0° C. was added dropwise H₂SO₄ (conc.) (490 µL, 9.2 mmol) over 5 mins. The mixture was warmed to r.t. for 1 h and then warmed to 80° C. for 30 mins. The mixture was cooled to r.t., and then diluted with EtOAc. The reaction was quenched with a sat. NaHCO₃ solution. The aqueous layer was extracted with EtOAc, dried over Na₂SO₄, filtered and concentrated under reduced pressure. The crude was purified via a silica gel column to afford 354-3 as a white solid. LCMS: m/z 258.95 [M+H]⁺.

Steps 3-6 were conducted in a similar manner as 314 to provide 354. LCMS: m/z 636.15 [M+H]⁺.

Example 166

Preparation of Compound 355

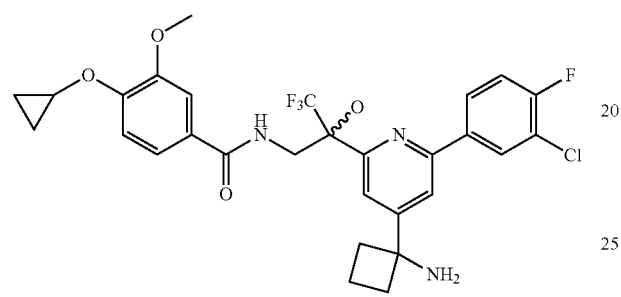

355

To a stirring mixture of 354 (16 mg, 0.025 mmol) in 4N HCl in dioxane (2 mL) was added a 6N HCl aqueous solution. The mixture was heated under microwave irradiation at 120° C. for 1 h. The mixture was cooled to r.t., diluted with DCM and neutralized with a cold sat. NaHCO₃ solution. The aqueous layer was extracted with DCM, dried over Na₂SO₄ and concentrated under reduced pressure. The crude was purified via prep-HPLC to afford 355 as a white solid. LCMS: m/z 594.10 [M+H]⁺.

Example 167

Preparation of Compound 356

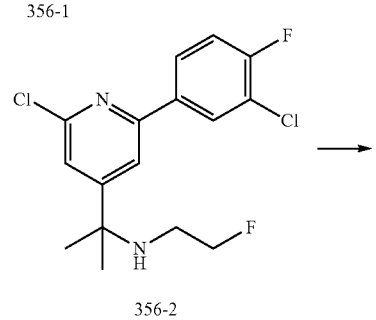

356-1

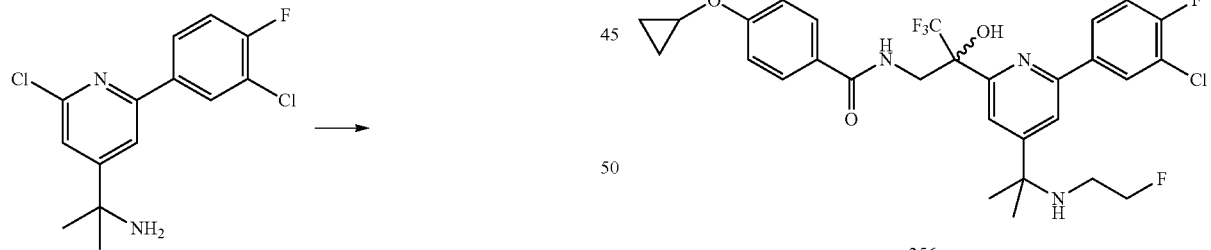

356-2

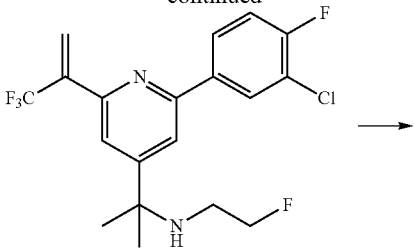

356-3

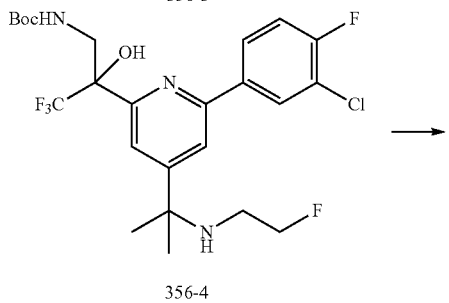

356-4

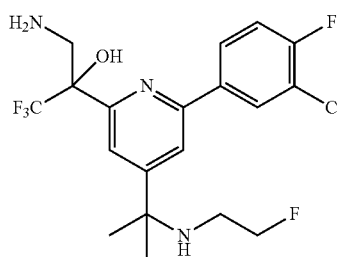

356-5

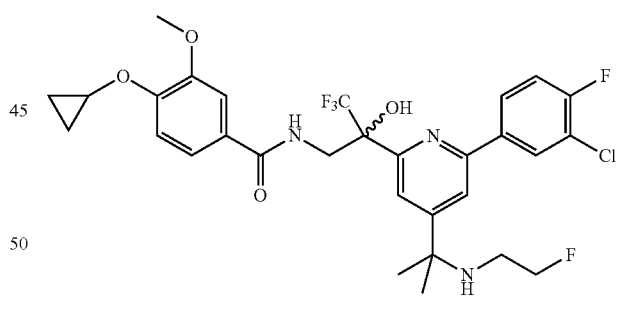

356

To a stirring mixture of 356-1 (0.3 g, 1 mmol) in DMF at r.t. were added Cs₂CO₃ (488 mg, 1.5 mmol), NaI (15 mg) and 1-bromo-2-fluoroethane (127 mg, 1 mmol). The mixture was heated to 45° C. overnight. The mixture was diluted with EtOAc and quenched with water. The aqueous layer was extracted with EtOAc, dried over Na₂SO₄ and concentrated under reduced pressure. The crude was purified via a silica gel column to afford 356-2. LCMS: m/z 345.1 [M+H]⁺.

Compound 356 was prepared in 4 steps using the similar methods as 314. LCMS: m/z 628.15 [M+H]⁺.

Example 168
Preparation of Compounds 357-361 and 363
TABLE 6
| Example Method | Structure | LCMS: m/z |
|---|---|---|
| Compound 327 | 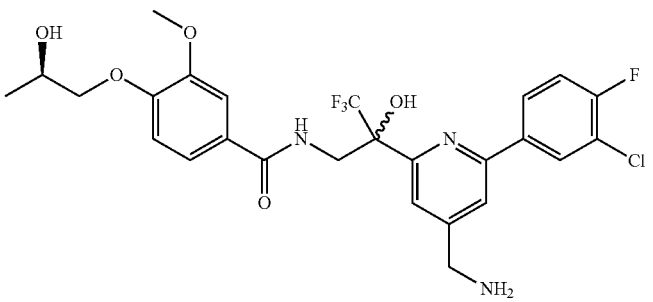 357 | 572.15 [M + H]+ |
| Compound 334 | 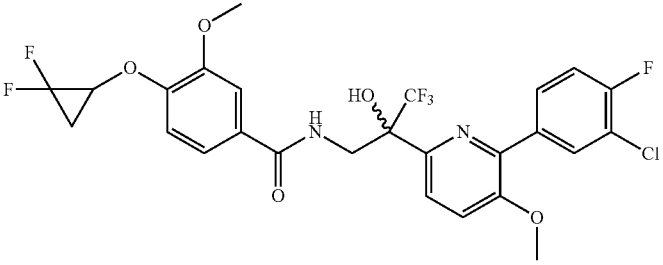 358 | 591.10 [M + H]+ |
| Compound 306 | 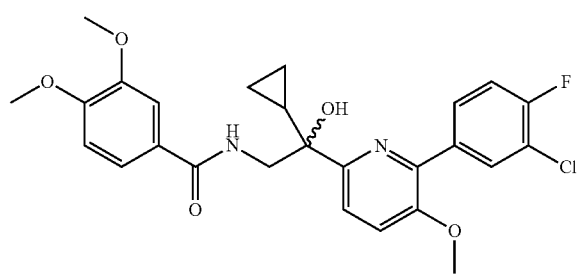 359 | 501.10 [M + H]+ |
| Compound 352 | 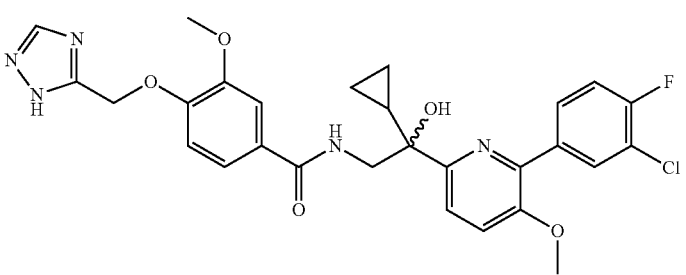 360 | 568.15 [M + H]+ |

TABLE 6-continued

| Example Method | Structure | LCMS: m/z |
|---|---|---|
| Compound 327 | 361 | 520.15 [M + H]⁺ |
| Compound 383 | 363 | 553.10 [M + H]⁺ |

Example 169

Preparation of Compound 362

362

To a stirring mixture of 336 (20 mg, 0.035 mmol) in DCM (1 mL) at r.t. was added Dess-Martin periodinane (150 mg, 0.175 mmol). The mixture was stirred at r.t. for 1 h and then quenched with 5% NaHSO₃ and a sat. NaHCO₃ solution. The aqueous layer was extracted with EtOAc (2×25 mL). The organic layers were dried (Na₂SO₄), filtered and concentrated under reduced pressure. The crude was purified via HPLC to afford 362 as a white solid. LCMS: m/z 571.1 [M+H]⁺.

Example 170

Preparation of Compound 364

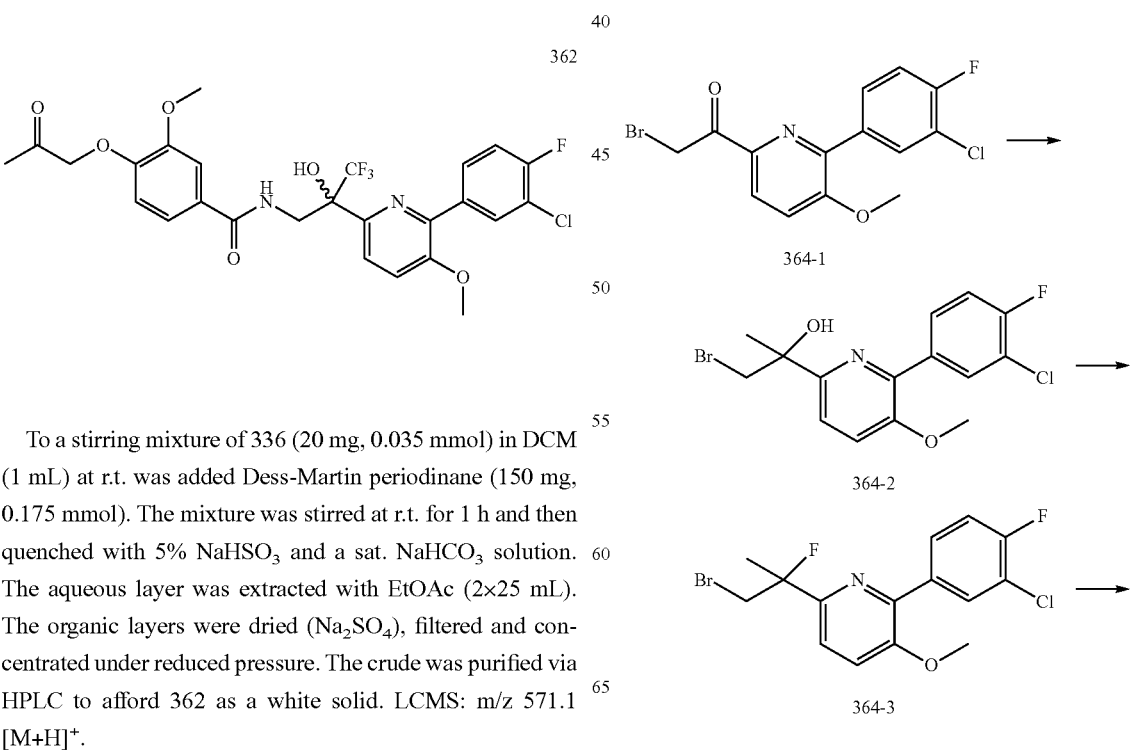

364-1

364-2

364-3

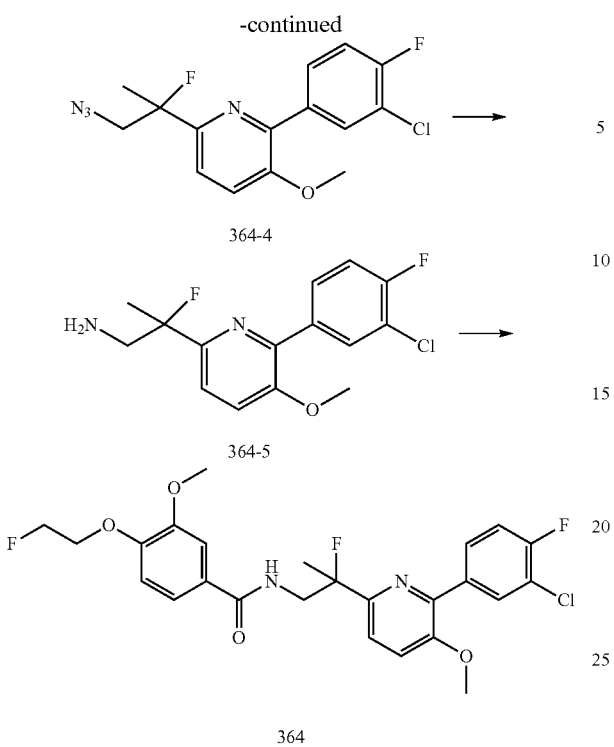

364-4

364-5

364

Methylmagnesium bromide (1.4 M in THF, 0.50 mL, 0.68 mmol) was added to a solution of bromoketone (0.163 g, 0.45 mmol) in THF (2 mL) at 0° C. After 30 mins, the reaction was quenched with NH$_4$Cl and extracted with EA, dried over anhydrous Na$_2$SO$_4$ and concentrated. The residue was purified by chromatography on silica gel (EA:hexane) to give 364-2 (0.115 g, 68%). LCMS: m/z 375.95 [M+H]$^+$.

To a solution of 364-2 (0.115 g, 0.31 mmol) in CH$_2$Cl$_2$ (3 mL) at 0° C. was added DAST (81 uL, 0.61 mmol). The solution was stirred for 1 h. The mixture was diluted with sat. NaHCO$_3$ and extracted with EA. The combined organic phase was dried over anhydrous Na$_2$SO$_4$ and concentrated. The residue was purified by chromatography on silica gel (EA:hexane) to give 364-3 (0.071 g, 61%). LCMS: m/z 377.95 [M+H]$^+$.

To a solution of 364-3 (0.071 g, 0.19 mmol) in DMF (1 mL) was added tetrabutylammonium azide (0.7 g, 0.94 mmol). The solution was stirred for 3 h at 90° C. and then diluted with EA. The organic phase was washed with water and brine, dried over anhydrous Na$_2$SO$_4$ and concentrated. The residue was purified by chromatography on silica gel (EA:hexane) to give 364-4 (0.054 g, 84%). LCMS: m/z 339.05 [M+H]$^+$.

To a solution of 364-4 (0.054 g, 0.16 mmol) in THF (1 mL) and water (1 drop) was added polymer supported triphenylphosphine (0.5 g, 1.5 mmol). The solution was stirred for 2 h at 60° C. The mixture was diluted with EA and filtered to remove resin. The organic phase was washed with brine, dried over anhydrous Na$_2$SO$_4$ and concentrated to provide crude 364-5 (0.032 g, 63%), which was used without further purification. LCMS: m/z 313.00 [M+H]$^+$.

Diisopropylethylamine (52 uL, 0.31 mmol) was added to a solution of 4-(2-fluoroethoxy)-3-methoxybenzoic acid (33 mg, 0.15 mmol), 364-5 (32 mg, 0.10 mmol) HBTU (62 mg, 0.16 mmol) in DMF (1 mL). The solution was stirred at r.t. for 3 h. The mixture was diluted with EtOAc, and washed with 1N HCl, sat. Na$_2$CO$_3$ and brine, dried over MgSO$_4$ and concentrated under reduced pressure. The crude was purified by reverse phase HPLC to give 364 (10.4 mg, 20%). LCMS: m/z 509.05 [M+H]$^+$.

Example 171

Preparation of Compound 365

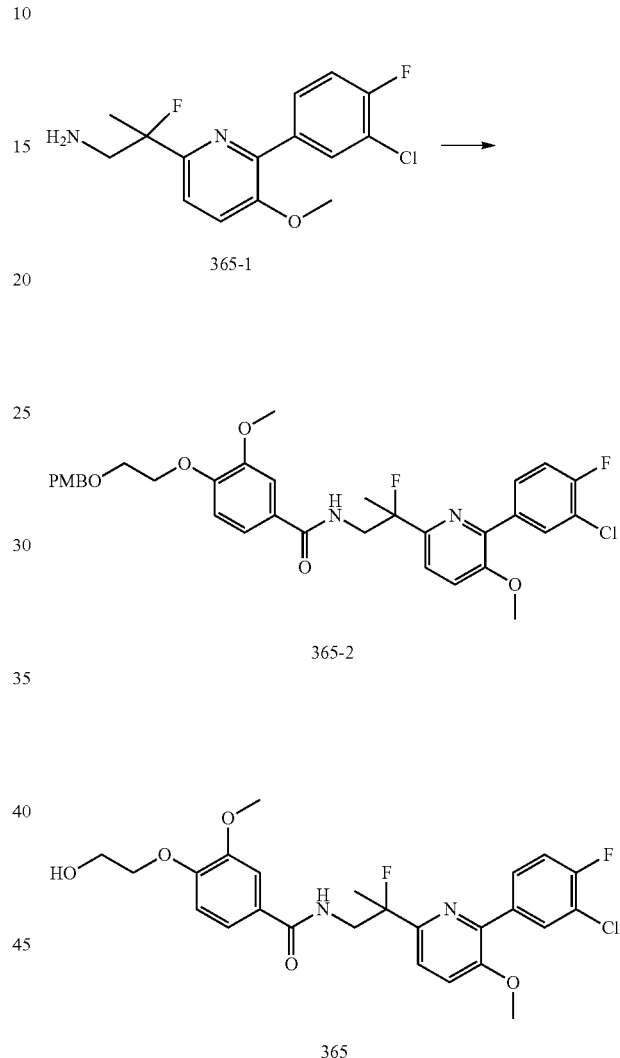

365-1

365-2

365

Diisopropylethylamine (0.13 mL, 0.75 mmol) was added to a solution of 3-methoxy-4-(2-((4-methoxybenzyl)oxy)ethoxy)benzoic acid (33 mg, 0.15 mmol), 365-1 (78 mg, 0.25 mmol) HATU (0.15 g, 0.40 mmol) in DMF (1 mL). The solution was stirred at r.t. for 3 h. The mixture was diluted with EtOAc, and washed with 1N HCl, sat. Na$_2$CO$_3$ and brine, dried over MgSO$_4$ and concentrated under reduced pressure. The crude was purified by chromatography on silica gel (EA:hexane) to give 365-2. LCMS: m/z 627.20 [M+H]$^+$.

Compound 365-2 was deprotected using TFA (0.25 mL) in CH$_2$Cl$_2$ (1.0 mL) at r.t. for 8 mins. The reaction was quenched with cold NaHCO$_3$ and extracted with CH$_2$Cl$_2$. The crude was purified by reverse phase HPLC to give 365 (10.4 mg, 8%). LCMS: m/z 507.01 [M+H]$^+$.

Example 172

Preparation of Compound 368

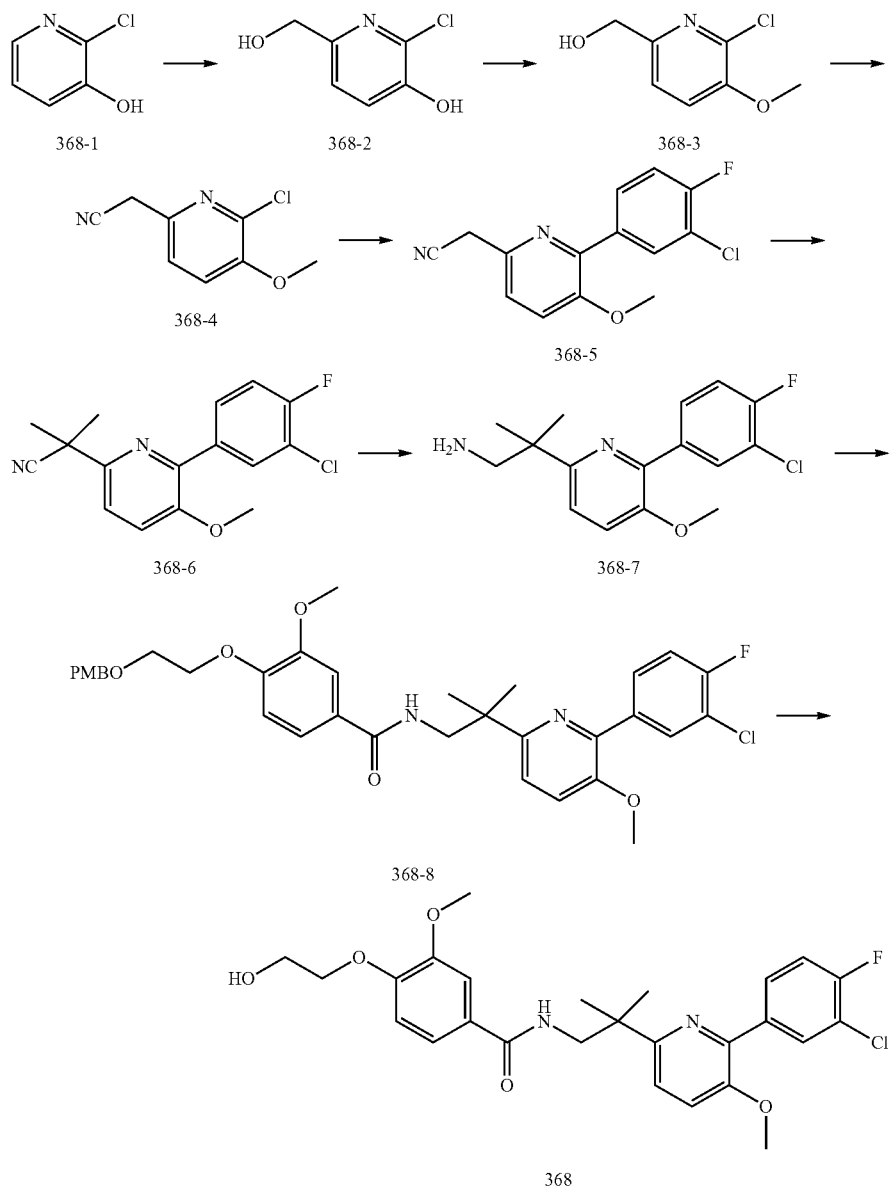

Compound 368-1 (5.0 g, 39 mmol) and solid NaHCO$_3$ (5.0 g, 60 mmol) were suspended in water (40 mL) and heated to 90° C. Formaldehyde (10 mL) was added portionwise over 8 h and the reaction was heated at 90° C. overnight. The mixture was cooled to 0° C. and acidified to pH 1 with 6N HCl. The solution was stirred at 0° C. for 1 h. The reaction was filtered, and the filtrate extracted with EA to provide 368-2 (4.9 g, 79%). $^1$H NMR (400 MHz, CDCl$_3$): δ 7.21 (d, J=4.6, 1H), 7.20 (d, J=4.6, 1H), 4.4 (s, 2H).

Iodomethane (4.5 mL, 72 mmol) was added to a solution of 368-2 (7.7 g, 48 mmol) and potassium carbonate (13 g, 144 mmol) in DMF (60 mL). The mixture was stirred at 50° C. for 1 h. The mixture was diluted with EA, washed with brine, dried over anhydrous Na$_2$SO$_4$ and concentrated. The residue was purified by chromatography on silica gel (EA: hexane) to give 368-3 (2.57 g, 31%). $^1$H NMR (400 MHz, CDCl$_3$): δ 7.20 (s, 2H), 4.6 (d, J=6.0, 2H).

Methanesulfonyl chloride (1.4 mL, 0.18 mmol) was added to a solution of 368-3 (2.57 g, 15 mmol) and diisopropylethyl amine (3.9 mL, 22 mmol) in CH$_2$Cl$_2$ (30 mL) at 0° C. After 30 mins, the mixture was diluted with CH$_2$Cl$_2$, washed with 1N HCl and brine, dried over anhydrous Na$_2$SO$_4$ and concentrated. The residue was dissolved in DMF (10 mL) and treated with sodium cyanide (2.2 g, 44 mmol) at 80° C. for 3 h. The mixture was diluted with EA, and the organic phase was washed with water and brine, dried over anhydrous Na$_2$SO$_4$ and concentrated. The residue was purified by chromatography on silica gel (EA:hexane) to give 368-4 (1.13 g, 41%). LCMS: m/z 183.03 [M+H]$^+$.

Pd(dppf)Cl$_2$ (0.45 g, 0.61 mmol) was added to a solution of 368-4 (0.56 g, 3.1 mmol), 3-chloro-4-fluorophenyl boronic acid (0.80 g, 4.6 mmol) in CH$_3$CN (10 mL) and 1M K$_2$CO$_3$ (5 mL). The reaction vessel was heated under micro wave irradiation for 3 h at 120° C. The mixture was diluted with EA. The organic phase was washed with water and brine, dried over anhydrous Na$_2$SO$_4$ and concentrated. The residue was purified by chromatography on silica gel (EA:hexane) to give 368-5 (0.70 g, 81%). LCMS: m/z 277.05 [M+H]$^+$.

Sodium hydride (76 mg, 1.9 mmol) was added to a solution of 368-5 (0.21 g, 0.76 mmol) in DMF (1 mL). After 5 mins, iodomethane (0.14 mL, 2.3 mmol) was added, and the mixture was stirred for 30 mins. The reaction was quenched with NH$_4$Cl, diluted with EA. The organic phase was washed with water and brine, dried over anhydrous Na$_2$SO$_4$ and concentrated. The residue was purified by chromatography on silica gel (EA:hexane) to give 368-6 (0.19 g, 81%). LCMS: m/z 305.00 [M+H]$^+$.

Lithium aluminum hydride (1.8 mL, 1M in THF, 1.8 mmol) was added to a solution of 368-6 (0.19 g, 0.61 mmol) in THF (5 mL), and the mixture was stirred at r.t. for 2 h. The reaction was quenched by the addition of solid sodium sulfate decahydrate and stirred for 10 mins. The solids were filtered, and the filtrate was concentrated to yield 368-7 (0.16 g, 85%). LCMS: m/z 309.05 [M+H]$^+$.

Compounds 368-8 and 368 were prepared in the same manner as 365. Compound 368-8: LCMS: m/z 624.3 [M+H]$^+$. Compound 368: LCMS: m/z 503.15

Example 173

Preparation of Compound 369

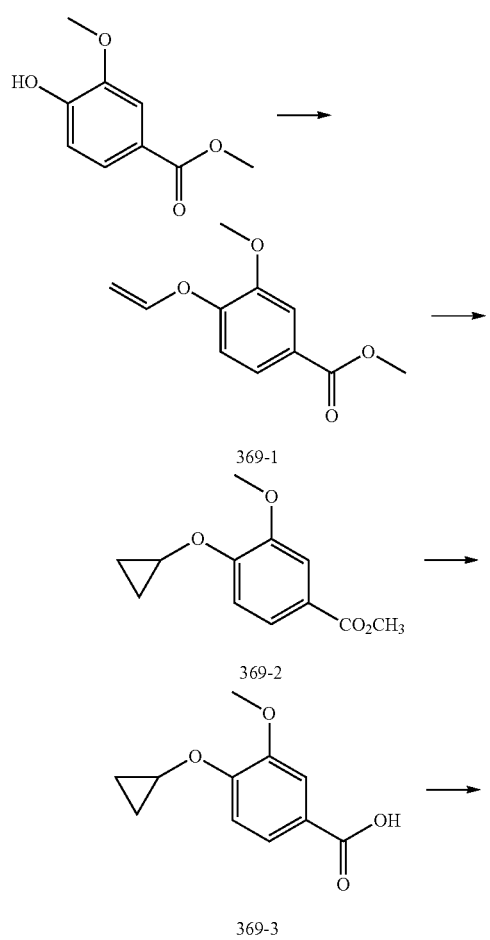

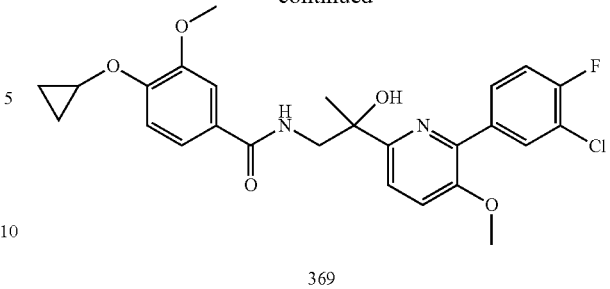

369

Methyl vanillate (0.25 g, 1.4 mmol) and vinyl acetate (0.25 mL, 2.7 mmol) were added to [IrCl(cod)]$_2$ (9 mg, 0.014) and sodium carbonate (52 mg, 0.49 mmol) in toluene (1 mL). The mixture was flushed with Ar and stirred at 110° C. for 1.5 h and then diluted with EA. The organic phase was washed with water and brine, dried over anhydrous Na$_2$SO$_4$ and concentrated. The residue was purified by chromatography on silica gel (EA:hexane) to give 369-1 (0.159 g, 55%). $^1$H NMR (400 MHz, CDCl$_3$): δ 7.61 (dd, J=1.6, 8.0, 1H), 7.0 (d, J=8.4, 1H), 6.63 (dd, J=6.0, 14, 1H), 4.87 (dd, J=2.4, 14, 1H), 4.55 (dd, J=2.0, 6.0, 1H), 2.92 (s, 2H), 3.91 (s, 3H).

Diethylzinc (9 mL, 9.0 mmol) was added dropwise to a solution of 369-1 (0.234 g, 1.1 mmol) and diiodoethane (0.72 mL, 9.0 mmol) in dichloroethane (3 mL) at 0° C. The mixture was stirred at r.t. overnight, and then diluted with EA. The organic phase was washed with water and brine, dried over anhydrous Na$_2$SO$_4$ and concentrated. The residue was purified by chromatography on silica gel (EA:hexane) to give 369-2 (0.121 g, 55%). $^1$H NMR (400 MHz, CDCl$_3$): δ 7.61 (dd, J=1.6, 8.0, 1H), 7.0 (d, J=8.4, 1H), 6.63 (dd, J=6.0, 14, 1H), 4.87 (dd, J=2.4, 14, 1H), 4.55 (dd, J=2.0, 6.0, 1H), 3.92 (s, 3H).

2N Sodium hydroxide (1 mL) was added to a solution of 369-2 (58 mg) in methanol (3 mL), and the mixture was stirred at r.t. overnight. The mixture was acidified with 1N HCl and extracted with EA to give 369-3 (50 mg, 86%). $^1$H NMR (400 MHz, CDCl$_3$): δ 7.78 (d, J=1.95, 1H), 7.58 (s, 1H), 7.30 (d, J=1.95, 1H), 3.91 (s, 3H), 3.80-3.83 (m, 1H), 0.85-0.89 (m, 4H).

Compound 369 was prepared in a similar manner as 364. LCMS: m/z 501.1 [M+H]$^+$.

Example 174

Preparation of Compound 371

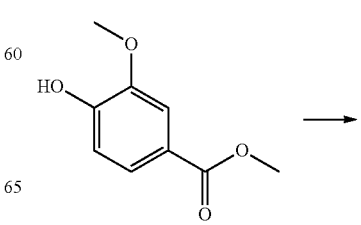

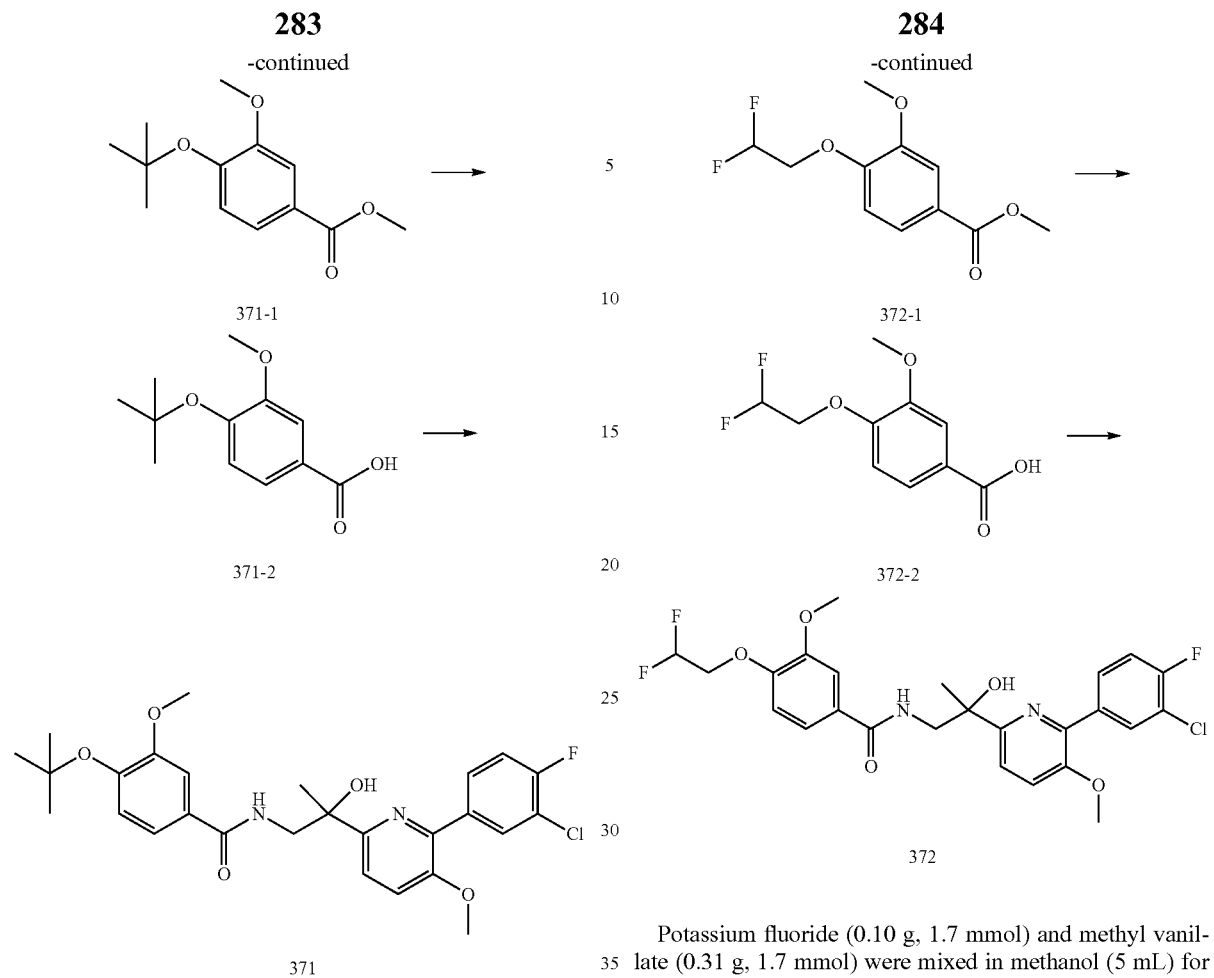

Isobutylene (10 mL, 105 mmol) was added to a solution of methyl vanillate (1 g, 5.5 mmol) and H₂SO₄ (3 drops) in CH₂Cl₂ (15 mL) in a sealed vessel at −40 OC. The mixture was warmed to r.t. and stirred over 2-3 d. The mixture was diluted with EA. The organic phase was washed with water and brine, dried over anhydrous Na₂SO₄ and concentrated. The residue was purified by chromatography on silica gel (EA:hexane) to give 371-2 (0.161 g, 12%). ¹H NMR (400 MHz, CDCl₃): δ 7.71 (d, J=6.26, 1H), 7.63 (d, J=1.96, 1H), 7.09 (d, J=8.26, 1H), 3.88 (s, 3H), 3.87 (s, 3H), 1.41 (s, 9H).

Compound 371 prepared in a similar manner as 364. LCMS: m/z 517.2 [M+H]⁺.

Example 175

Preparation of Compound 372

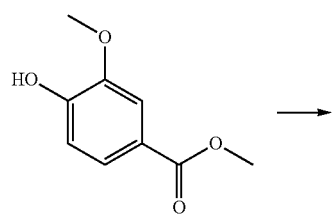

Potassium fluoride (0.10 g, 1.7 mmol) and methyl vanillate (0.31 g, 1.7 mmol) were mixed in methanol (5 mL) for 15 mins. The mixture was concentrated, co-evaporating with diethyl ether (2×). The residue was dissolved in DMSO (2.0 mL) and added to difluoroiodoethane (0.36 g, 1.9 mmol) in a vial. The vial was flushed with Ar, sealed, and heated at 120° C. overnight. The mixture was diluted with EA. The organic phase was washed with water and brine, dried over anhydrous Na₂SO₄ and concentrated. The residue was purified by chromatography on silica gel (EA:hexane) to give 372-1 (0.060 g, 14%). ¹H NMR (400 MHz, CDCl₃): δ 766 (dd, J=1.95, 8.41, 1H), 7.59 (d, J=1.95, 1H), 6.92 (d, J=8.41, 1H), 6.00-6.30 (m, 1H), 4.24-4.31 (m, 2H), 3.91 (s, 3H), 3.91 (s, 3H).

Compound 372 was prepared in a similar manner as 364. LCMS: m/z 525.10 [M+H]⁺.

Example 176

Preparation of Compound 374

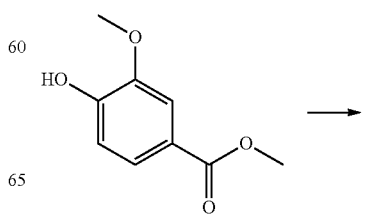

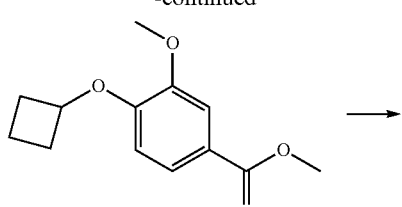

374-1

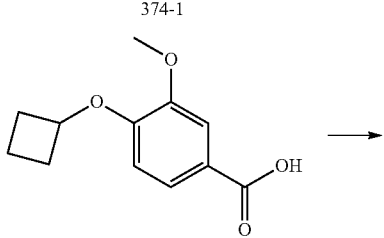

374-2

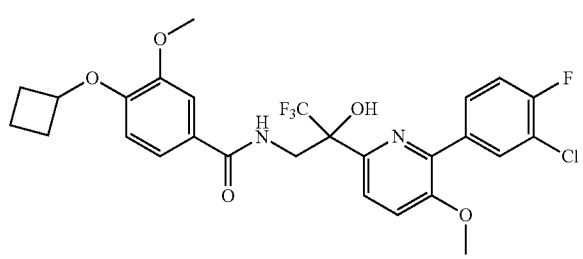

374

Sodium iodide (1 mg) was added to a solution of methyl vanillate (0.26 g, 1.4 mmol), bromocyclobutane (0.40 mL, 4.3 mmol), potassium carbonate (0.98 g, 4.3 mmol) in NMP (1.5 mL). The mixture was heated under microwave irradiation at 180° C. for 1.5 h and then diluted with EA. The organic phase was washed with water and brine, dried over anhydrous Na$_2$SO$_4$ and concentrated. The residue was purified by chromatography on silica gel (EA:hexane) to give 374-1 (0.18 g, 54%). $^1$H NMR (400 MHz, CDCl$_3$): δ 7.3 (d, J=8.41, 1H), 7.53 (s, 1H), 6.74 (d, J=8.41, 1H), 4.4-4.7 (m, 1H), 3.92 (s, 3H), 3.89 (s, 3H).

Compound 372-2 was hydrolyzed in a similar manner as 369, and 372 was prepared in a similar manner as 364. LCMS: m/z 568.9 [M+H]$^+$.

Example 177

Preparation of Compound 375

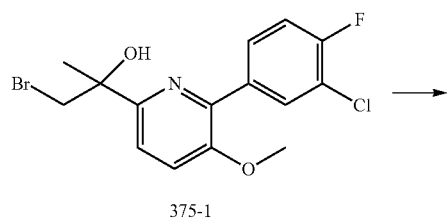

375-1

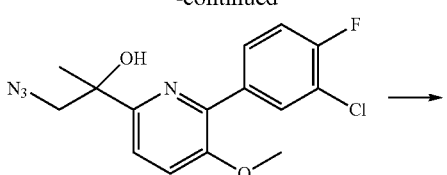

375-2

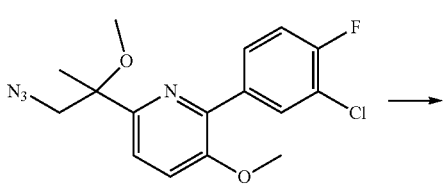

375-3

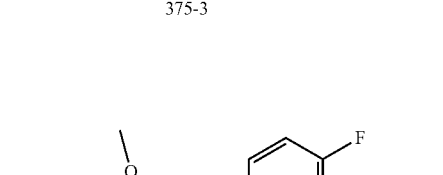

375-4

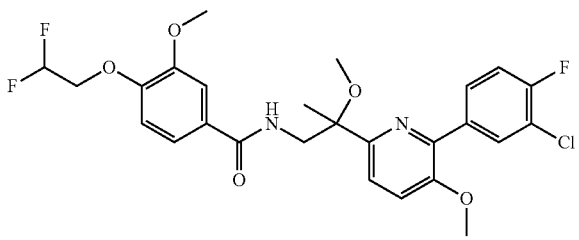

375

Tetrabutylammonium azide (0.33 g, 0.57 mmol) was added to 375-1 (60 mg, 0.16 mmol) in DMF (1 mL), and the mixture was heated at 80° C. for 5 h. The mixture was diluted with EA. The organic phase was washed with water and brine, dried over anhydrous Na$_2$SO$_4$ and concentrated. The residue was purified by chromatography on silica gel (EA:hexane) to give 375-2 (0.052 g, 96%). LCMS: m/z 337.05 [M+H]$^+$.

NaH (12 mg, 0.31 mmol) was added to 375-2 (52 mg, 0.15 mmol) in DMF (1 mL). The mixture was stirred at r.t. for 15 mins. Iodomethane (30 uL, 0.46 mmol) was added, and the mixture reaction was stirred for 2 h. The mixture was diluted with EA, and the organic phase was washed with water and brine, dried over anhydrous Na$_2$SO$_4$ and concentrated. The residue was purified by chromatography on silica gel (EA:hexane) to give 375-3 (0.052 g, 98%). LCMS: m/z 351.05 [M+H]$^+$.

Compound 375 was prepared in a similar manner as 364. LCMS: m/z 539.15 [M+H]$^+$.

Example 178

Preparation of Compound 377

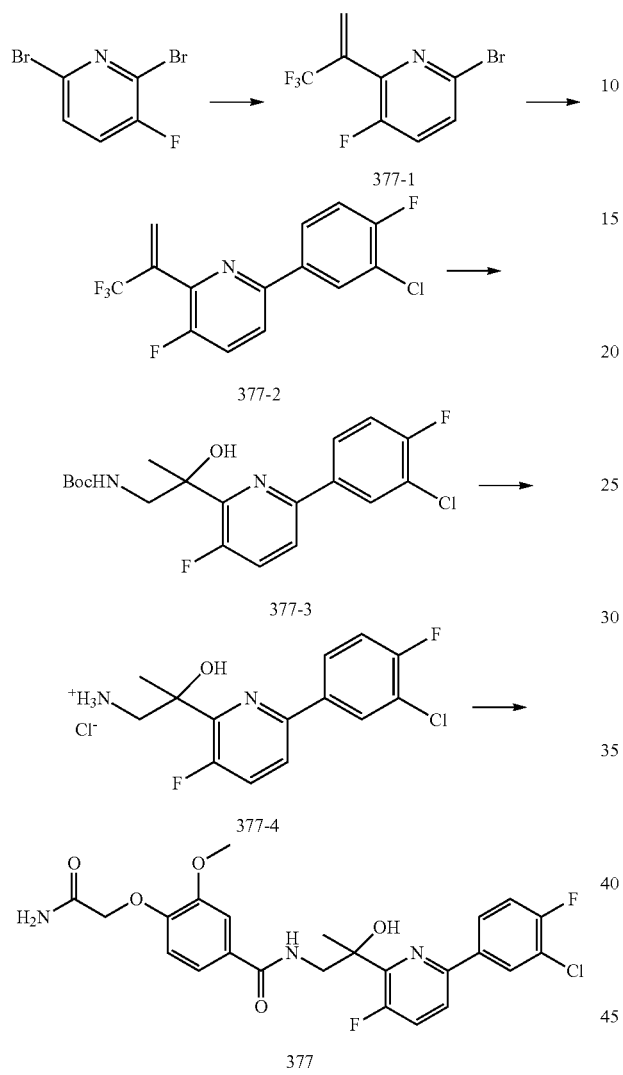

Pd(dppf)Cl$_2$ (20 mg, 0.02 mmol) was added to a solution of 2,6-dichloro-3-fluoropyridine (0.20 g, 0.78 mmol) and 1-(trifluoromethyl)vinylboronic acid hexylene glycol ester (0.18 g, 0.86 mmol) in CH$_3$CN (0.5 mL) and 1M K$_2$CO$_3$ (0.25 mL). The mixture was heated under microwave irradiation for 1 h at 110° C. The reaction was diluted with EA, and the organic phase was washed with water and brine, dried over anhydrous Na$_2$SO$_4$ and concentrated. The residue was purified by chromatography on silica gel (EA:hexane) to give 377-1 (0.10 g, 47%). LCMS: m/z 271.90 [M+H]$^+$.

Pd(dppf)Cl$_2$ (75 mg, 0.091 mmol) was added to 377-1 (0.493 g, 1.8 mmol) and 3-chloro-4-fluorophenyl boronic acid (0.38 g, 2.7 mmol) in CH$_3$CN (2 mL) and 1M K$_2$CO$_3$ (0.5 mL). The mixture was heated under microwave irradiation at 110° C. for 30 mins. The mixture was heated under microwave irradiation for 1 h at 110° C. The mixture was diluted with EA, and the organic phase was washed with water and brine, dried over anhydrous Na$_2$SO$_4$ and concentrated. The residue was purified by chromatography on silica gel (EA:hexane) to give 377-2 (0.286 g, 33%). LCMS: m/z 319.95 [M+H]$^+$.

Potassium osmate (50 mg, 0.13 mmol) was added to a suspension of 377-2 (0.286 g, 0.89 mmol) and tert-butyl (tosyloxy)carbamate (0.36 g, 1.3 mmol) in t-butanol (2 mL) and water (0.6 mL), and the mixture was stirred overnight at r.t. The crude was poured directly onto a silica gel column and chromatographed (EA:hexane) to give 377-3. (0.162 g, 40%). LCMS: m/z 398.83 [M+H]$^+$.

4N HCl in dioxane (2 mL) was added to 377-3 (0.16 g), and the mixture was stirred at r.t. for 1 h. The mixture was concentrated to give 377-4, which was used without further purification. Compound 377 was prepared in a similar manner as 364. LCMS: m/z 506.20 [M+H]$^+$.

Example 179

Preparation of Compound 378

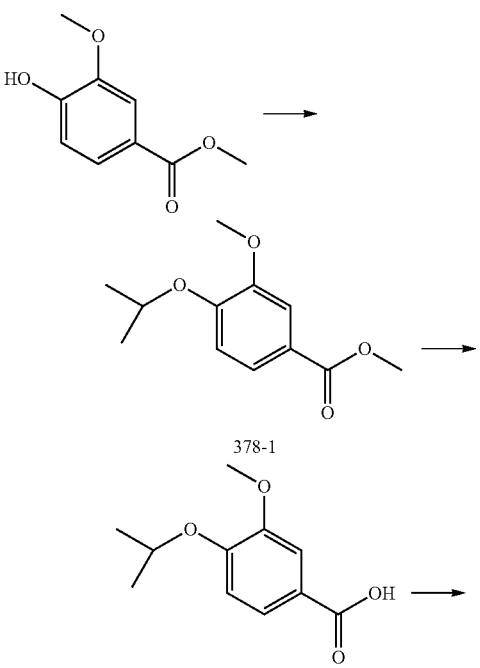

NaH (0.13 g, 3.1 mmol) was added to a solution of methyl vanillate (0.44 g, 2.4 mmol) and 2-iodopropane (1.2 mL, 12 mmol) in DMF (3.0 mL), and the mixture was heated at 65° C. for 1 h. The mixture was diluted with EA, and the organic phase was washed with water and brine, dried over anhydrous Na$_2$SO$_4$ and concentrated. The residue was purified by chromatography on silica gel (EA:hexane) to give 378-1 (0.50 g, 93%). $^1$H NMR (400 MHz, CDCl$_3$): δ 7.65 (dd, J=1.95, 8.6, 1H), 7.55 (d, J=1.96, 1H), 6.90 (d, J=8.6, 1H), 4.61-4.66 (m, 1H), 3.91 (s, 3H), 3.58 (s, 3H), 1.41 (s, 3H), 1.39 (s, 3H).

Compound 378-1 was hydrolyzed in a similar manner as 369 to give 378-2. $^1$H NMR (400 MHz, CDCl$_3$): δ 7.74 (dd, J=1.95, 8.6, 1H), 7.60 (d, J=1.96, 1H), 6.92 (d, J=8.6, 1H), 4.65-4.68 (m, 1H), 3.92 (s, 3H), 1.41 (s, 3H), 1.39 (s, 3H). Compound 378 was prepared in a similar manner as 364. LCMS: m/z 557.10 [M+H]$^+$.

Example 180

Preparation of Compound 379

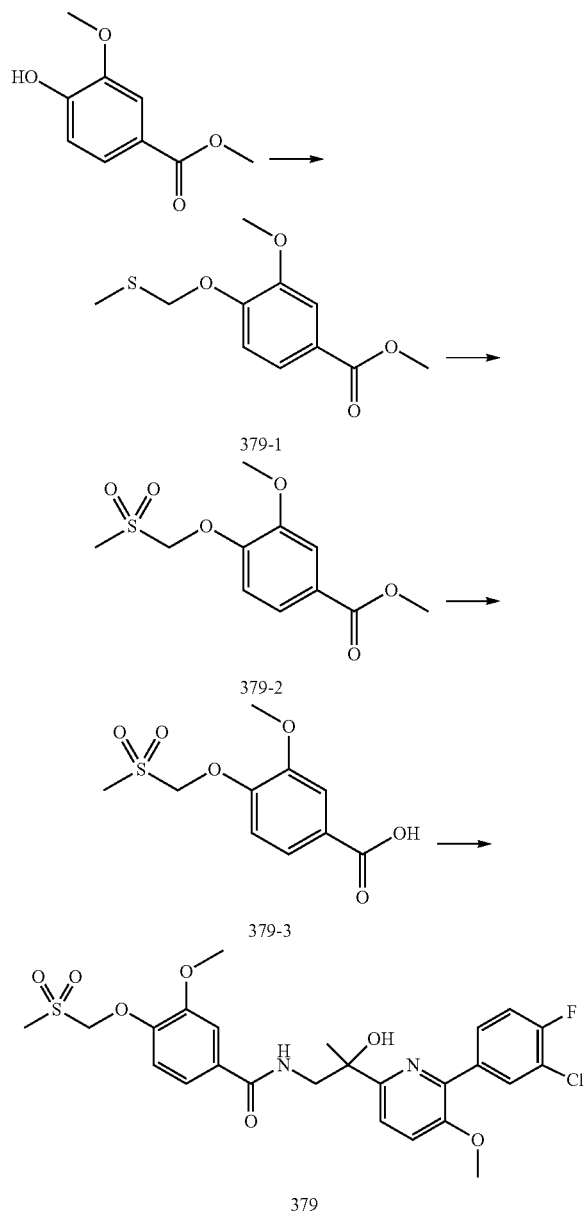

379

NaH (0.13 g, 3.1 mmol) was added to a solution of methyl vanillate (0.44 g, 2.4 mmol) and chloromethylmethyl sulfide (0.24 mL, 2.8 mmol) in DMF (3.0 mL), and the mixture was stirred for 1 h. The mixture was diluted with EA, and the organic phase was washed with water and brine, dried over anhydrous Na$_2$SO$_4$ and concentrated. The residue was purified by chromatography on silica gel (EA:hexane) to give 379-1 (0.57 g, 92%).

MCPBA (0.9 g, 5.2 mmol) was added to 379-1 (0.576 g, 2.4 mmol) in CH$_2$Cl$_2$ (3 mL), and the mixture was stirred at r.t. for 1 h. The mixture was washed with Na$_2$CO$_3$, dried over anhydrous Na$_2$SO$_4$ and concentrated. The residue was purified by chromatography on silica gel (EA:hexane) to give 379-2 (0.40 g, 70%).

Compound 379-2 was hydrolyzed in a similar manner as 369 to give 379-3. Compound 379 was prepared in a similar manner as 364. LCMS: m/z 553.10 [M+H]$^+$.

Example 181

Preparation of Compound 380 7

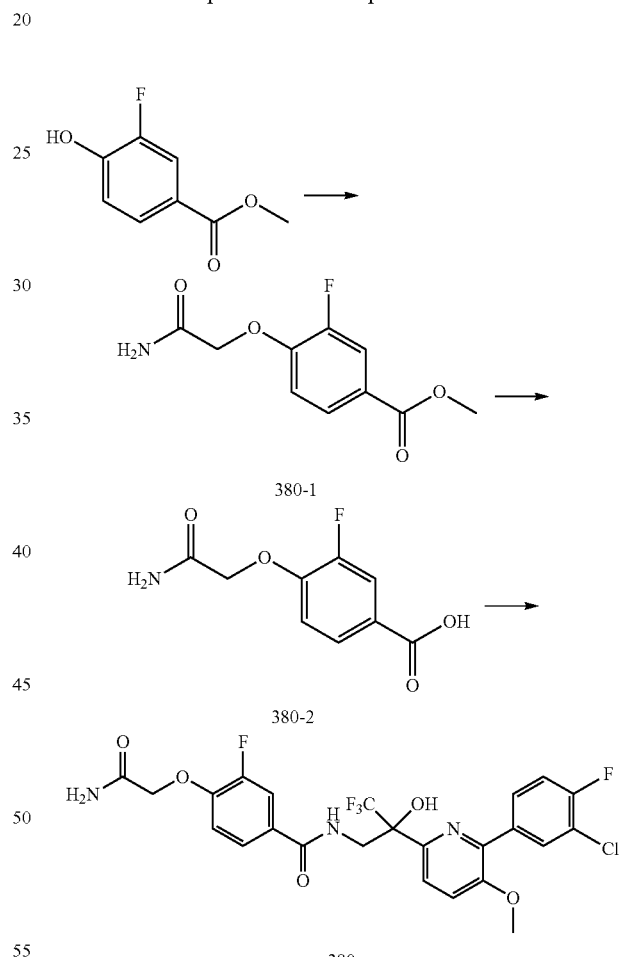

380

2-Bromoacetamide (0.46 g, 3.4 mmol) was added to methyl 3-fluoro-4-hydroxybenzoate (0.29 g, 1.7 mmol) and potassium carbonate (0.70 g, 5.0 mmol) in DMF (1 mL), and the mixture was heated to 65° C. for 1 h. The mixture was diluted with EA, and the organic phase was washed with water and brine, dried over anhydrous Na$_2$SO$_4$ and concentrated. Compound 380-1 was crystallized from EA and collected by filtration (0.27 g, 71%). $^1$H NMR (400 MHz, dmso-d$_6$): δ 7.67-7.42 (m, 2H), 7.50 (br. s, 1H), 7.38 (br. s, 1H), 7.11 (t, J=8.62, 1H), 4.62 (s, 2H), 3.79 (s, 3H).

Compound 380-1 was hydrolyzed in a similar manner as 369 to give 380-2. ¹H NMR (400 MHz, dmso-d₆): δ 7.63-7.69 (m, 2H), 7.49 (br. s, 1H), 7.38 (br. s, 1H), 7.08-7.11 (m, 1H), 4.61 (s, 2H). Compound 380 was prepared in a similar manner as 364. LCMS: m/z 560.05 [M+H]⁺.

Example 182

Preparation of Compound 381

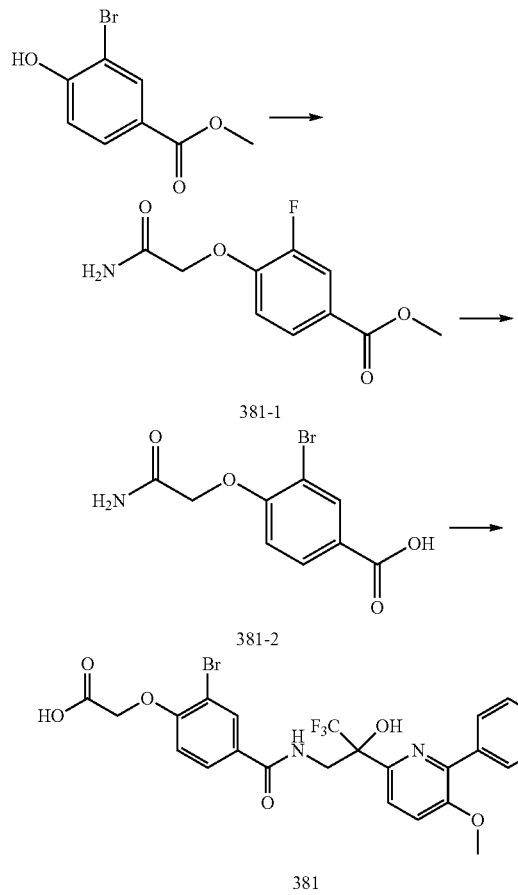

2-Bromoacetamide (0.46 g, 3.4 mmol) was added to methyl 3-bromo-4-hydroxybenzoate (0.46 g, 1.7 mmol) and potassium carbonate (0.70 g, 5.0 mmol) in DMF (1 mL), and the mixture was heated to 65° C. for 1 h. The mixture was diluted with EA, and the organic phase was washed with water and brine, dried over anhydrous Na₂SO₄ and concentrated. The residue was purified by chromatography on silica gel (EA:hexane) to give 381-1 (0.091 g, 24%). ¹H NMR (400 MHz, dmso-d₆): δ 7.95 (d, J=2.34, 1H), 7.90 (dd, J=2.34, 8.61, 1H), 7.45 (br. s, 1H), 7.34 (br. s, 1H), 7.06 (d, J=8.61, 1H), 4.65 (s, 2H), 3.78 (s, 3H).

381-1 was hydrolyzed in a similar manner as 369-2 to give 381-2. ¹H NMR (400 MHz, dmso-d₆): δ 8.12 (d, J=2.34, 1H), 7.87 (dd, J=2.35, 6.0, 1H), 7.15 (d, J=6.0, 1H), 4.87 (s, 2H).

Compound 381 was prepared in a similar manner as 364. LCMS: m/z 621.76 [M+H]⁺.

Example 183

Preparation of Compound 382

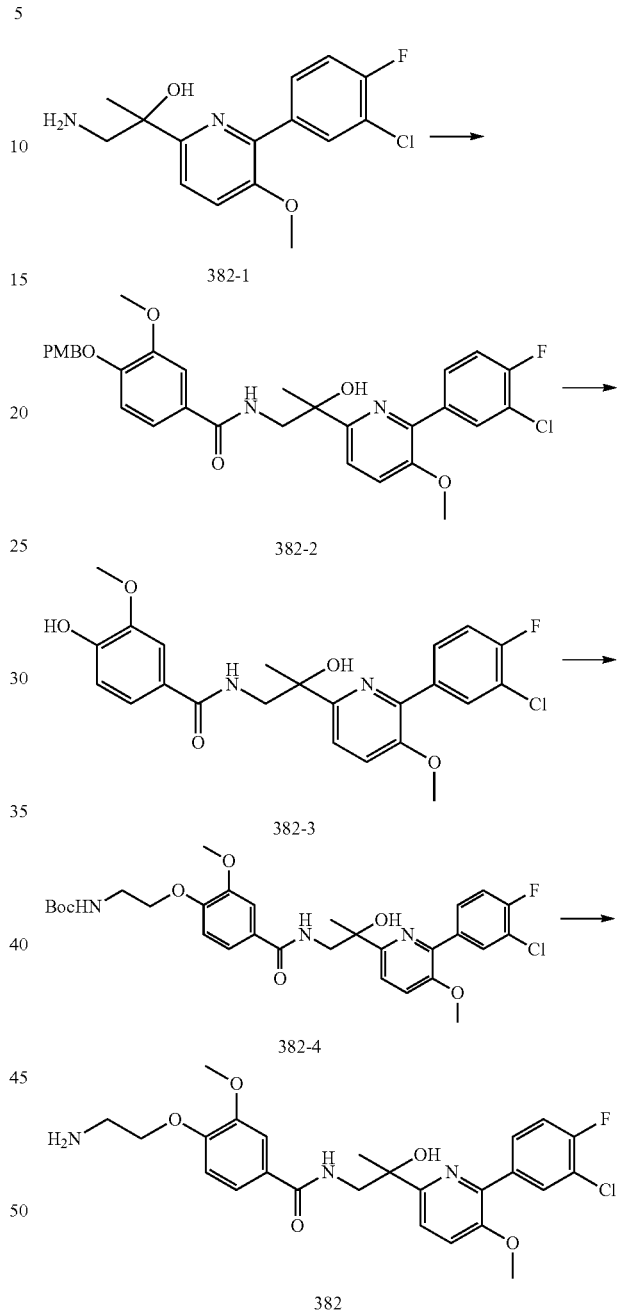

Diisopropylethylamine (0.15 mL, 0.84 mmol) was added to a solution of 382-1 (0.10 g, 0.34 mmol), 3-methoxy-4-(2-((methosybenzyl)oxy)ethoxy)benzoic acid (0.15 g, 0.51 mmol) and HATU (0.25 g, 0.67 mmol) in DMF (1 mL). The mixture was stirred at r.t. for 2 h. The mixture was diluted with EA, and the organic phase was washed with water and brine, dried over anhydrous Na₂SO₄ and concentrated. The residue was purified by chromatography on silica gel (EA: hexane) to give 382-2 (0.15 g, 76%). LCMS: m/z 581.15 [M+H]⁺.

Compound 382-2 was deprotected in a similar manner as 368 to give 382-3 LCMS: m/z 461.10 [M+H]⁺.

Cesium carbonate (0.11 g, 0.33 mmol) was added to a solution of 382-3 (0.050 g, 0.11 mmol) and 2-(Boc-amino)ethyl bromide (0.048 g, 0.22 mmol) in DMF (1 mL). The mixture was heated under microwave irradiation at 70° C. for 1 h. The mixture was diluted with EA, and the organic phase was washed with water and brine, dried over anhydrous Na$_2$SO$_4$ and concentrated. The residue was purified by chromatography on silica gel (EA:hexane) to give 382-4 (39 mg, 60%). LCMS: m/z 604.20 [M+H]$^+$.

Hydrochloric acid in dioxane (1.5 mL, 4N) was added to 382-4 (39 mg, 0.077 mmol). The mixture was stirred at r.t. for 1 h and then concentrated under reduced pressure. The crude was purified by reverse phase HPLC to give 382 (8 mg, 25%). LCMS: m/z 503.95 [M+H]$^+$.

Example 184

Preparation of Compound 383

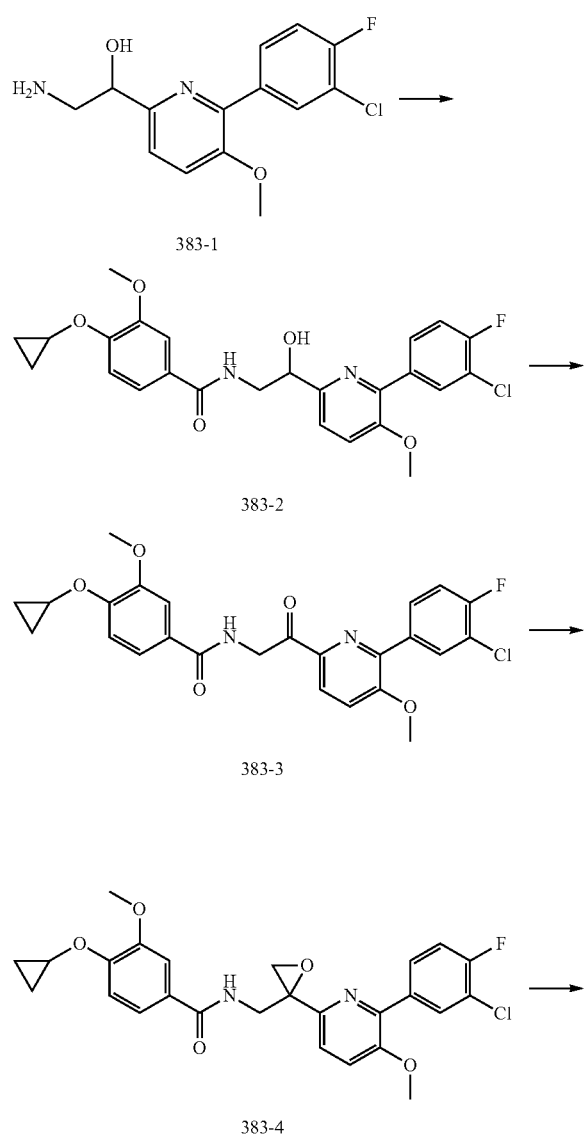

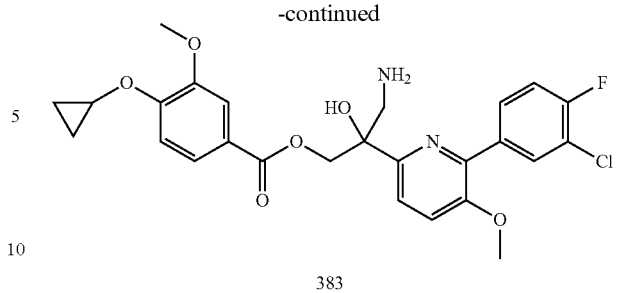

Compound 383-1 was prepared in a similar manner as 364 to give 383-2. LCMS: m/z 487.10 [M+H]$^+$.

Dess-Martin periodinane (0.58 g, 1.4 mmol) was added to 383-2 (0.337 g, 0.69 mmol) in CH$_2$Cl$_2$ (10 mL), and the mixture was stirred at r.t. for 1 h. The mixture was diluted with CH$_2$Cl$_2$, washed with Na$_2$CO$_3$ and brine, dried over anhydrous Na$_2$SO$_4$ and concentrated. The crude was purified by chromatography on silica gel (EA:hexane) to provide 383-3 (0.144 g, 43%). LCMS: m/z 485.10 [M+H]$^+$.

Potassium tert-butoxide (40 mg, 0.36 mmol) was added to trimethylsulfoxonium iodide (65 mg, 0.30 mmol) in DMSO (1 mL), and the mixture was stirred at r.t. for 30 mins. Compound 383-3 (0.144 g, 0.30 mmol) in DMSO (0.5 mL) was added, and the mixture was stirred for 1 h. The mixture was diluted with EA, and the organic phase was washed with water and brine, dried over anhydrous Na$_2$SO$_4$ and concentrated. The residue was purified by chromatography on silica gel (EA:hexane) to give 383-4 (0.050 g, 33%). LCMS: m/z 499.15 [M+H]$^+$.

Compound 383-4 (0.050 g, 0.10 mmol) was dissolved in 6N HCl (1 mL) and MeOH (1 mL) and heated at 60° C. for 2 h. The mixture was concentrated, and the crude was purified by reverse phase HPLC to give 383 (14 mg, 28%). LCMS: m/z 517.10 [M+H]$^+$.

Example 185

Preparation of Compound 384

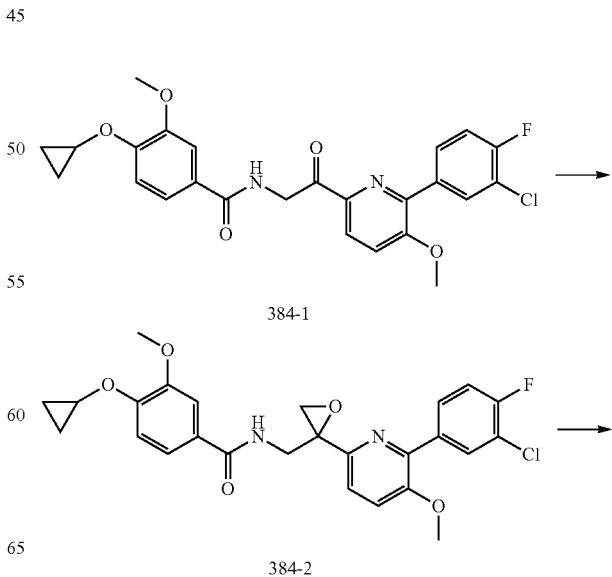

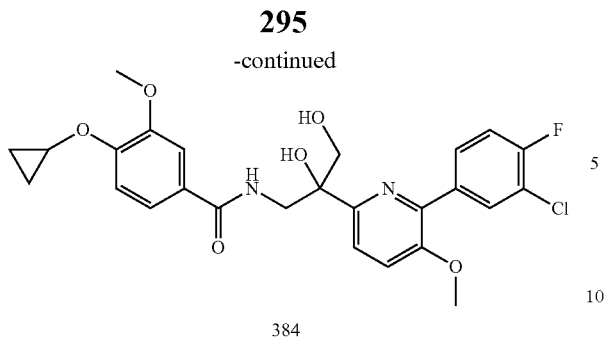

384

Potassium tert-butoxide (81 mg, 0.72 mmol) was added to trimethylsulfoxonium iodide (0.13 g, 0.60 mmol) in DMSO (1 mL), and the mixture was stirred at r.t. for 30 mins. Compound 384-1 (0.329 g, 0.60 mmol) in DMSO (0.5 mL) was added, and the mixture was stirred for 1 h. The mixture was diluted with EA, and the organic phase was washed with water and brine, dried over anhydrous $Na_2SO_4$ and concentrated. The residue was purified by chromatography on silica gel (EA:hexane) to give 384-2 (0.11 g, 37%). LCMS: m/z 499.15 $[M+H]^+$.

Compound 384-2 (0.11 g, 0.22 mmol) was dissolved in 6N HCl (1 mL) and MeOH (1 mL) and heated at 60° C. for 2 h. The mixture was concentrated and treated with 2N NaOH (2 mL) in MeOH (2 mL) for 2 h. The crude was purified by reverse phase HPLC to give 384 (17 mg, 5%). LCMS: m/z 517.10 $[M+H]^+$.

Example 186

Preparation of Compound 385

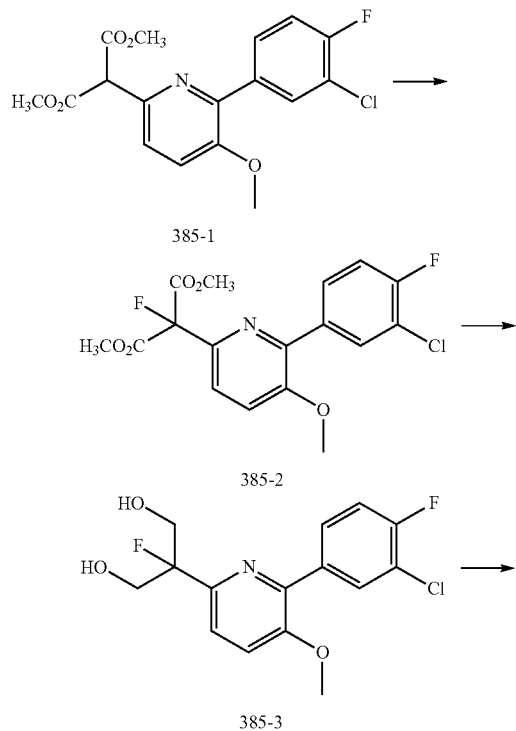

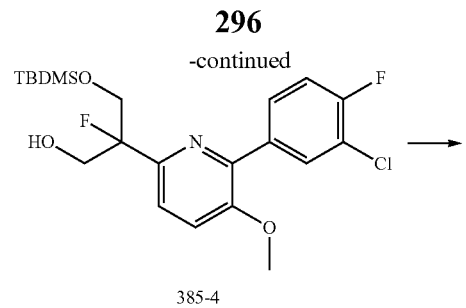

385-4

385-5

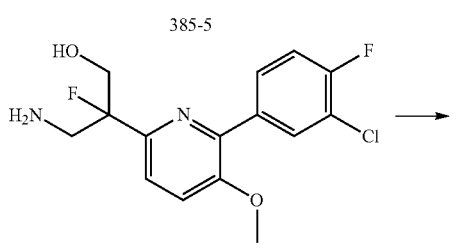

385-6

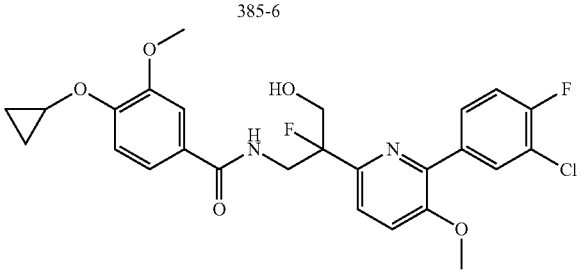

385

LDA (2 M in THF, 1.4 mL, 2.8 mmol) was added dropwise to a solution of 385-1 (0.93 g, 2.5 mmol) in THF (10 mL) at −78° C., and the mixture was stirred at −78° C. for 15 mins. N-fluorobenzenesulfonimide (1.2 g, 3.8 mmol) was added, and the mixture was stirred for 3 h. The mixture was warmed to r.t., and the reaction was quenched with 1N HCl. The mixture was extracted with EA, and the organic extracts were washed with brine, dried over sodium sulfate and concentrated. The residue was purified by chromatography on silica gel (EA:hexane) to give 385-2 (0.57 g, 59%). LCMS: m/z 386.10 $[M+H]^+$.

Sodium borohydride (0.12 g, 3.1 mmol) was added to a solution of 385-2 (0.14 g, 0.36 mmol) in EtOH. The mixture was stirred at r.t. for 2 h. The reaction was quenched with 1N HCl and extracted with EA. The organic extracts were washed with brine, dried over sodium sulfate and concentrated. The residue was purified by chromatography on silica gel (EA:hexane) to give 385-3 (0.040 g, 33%). LCMS: m/z 330.00 $[M+H]^+$.

Compound 385-3 (25 mg, 0.076 mmol) in THF (1 mL) was added to NaH (3.0 mg, 0.076 mmol) in THF (0.5 mL), and the mixture solution was stirred for 30 mins. TBDMSCl (11 mg, 0.076 mmol) was added, and the mixture was stirred at r.t. for 2 h. The reaction was quenched with 1N HCl and extracted with EA. The organic extracts were washed with brine, dried over sodium sulfate and concentrated. The residue was purified by chromatography on silica gel (EA:hexane) to give 385-4 (0.014 g, 41%). LCMS: m/z 444.10 [M+H]$^+$.

Triflic anhydride (45 uL, 0.27 mmol) was added to a solution of 385-4 (60 mg, 0.14 mmol) and 2,6-lutidine (47 uL, 0.40 mmol) in CH$_2$Cl$_2$ (1 mL) at −78° C. The mixture was warmed to r.t. The reaction was quenched with 1N HCl and extracted with EA. The organic extracts were washed with brine, dried over sodium sulfate and concentrated. The crude triflate was immediately dissolved in NMP (0.5 mL) and tetrabutylammonium azide (0.39 g, 1.4 mmol) was added, and the mixture was heated at 65° C. for 1 h. The mixture was diluted with EA, and organic extracts were washed with water and brine, dried over sodium sulfate and concentrated. The crude was purified by chromatography on silica gel (EA:hexane) to give 385-5 (0.057 g, 114%). LCMS: m/z 355.05 [M+H]$^+$.

Compound 385-5 was reduced in a similar manner as 364 to give 385-6. LC/MS: [M+H] 329.00. Diisopropylethylamine (62 uL, 0.36 mmol) was added to a solution of 385-6 (54 mg, 0.12 mmol), 4-cyclopropoxy-3-methoxybenzoic acid (37 mg, 0.18 mmol) and HBTU (81 mg, 0.21 mmol) in DMF (1 mL), and the mixture was stirred at r.t. for 1 h. The mixture was diluted with EA and washed with 1 N HCl, sodium bicarbonate, water and brine, dried over sodium sulfate and concentrated. The crude was purified by reverse phase HPLC to give 385 (14 mg, 22%). LCMS: m/z 520.15 [M+H]$^+$.

Example 187

Preparation of Compound 386

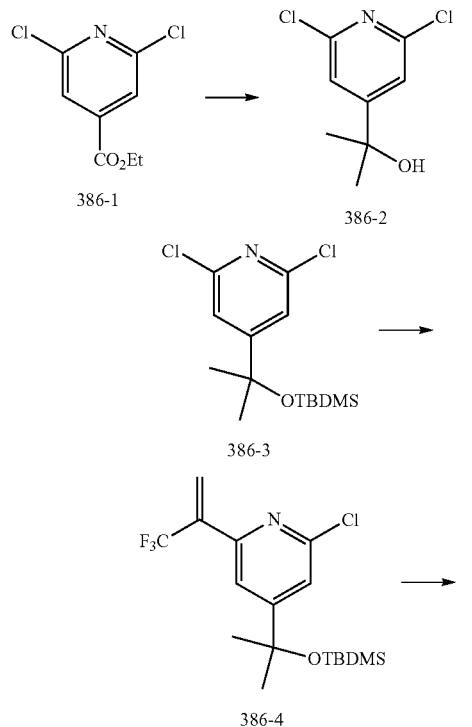

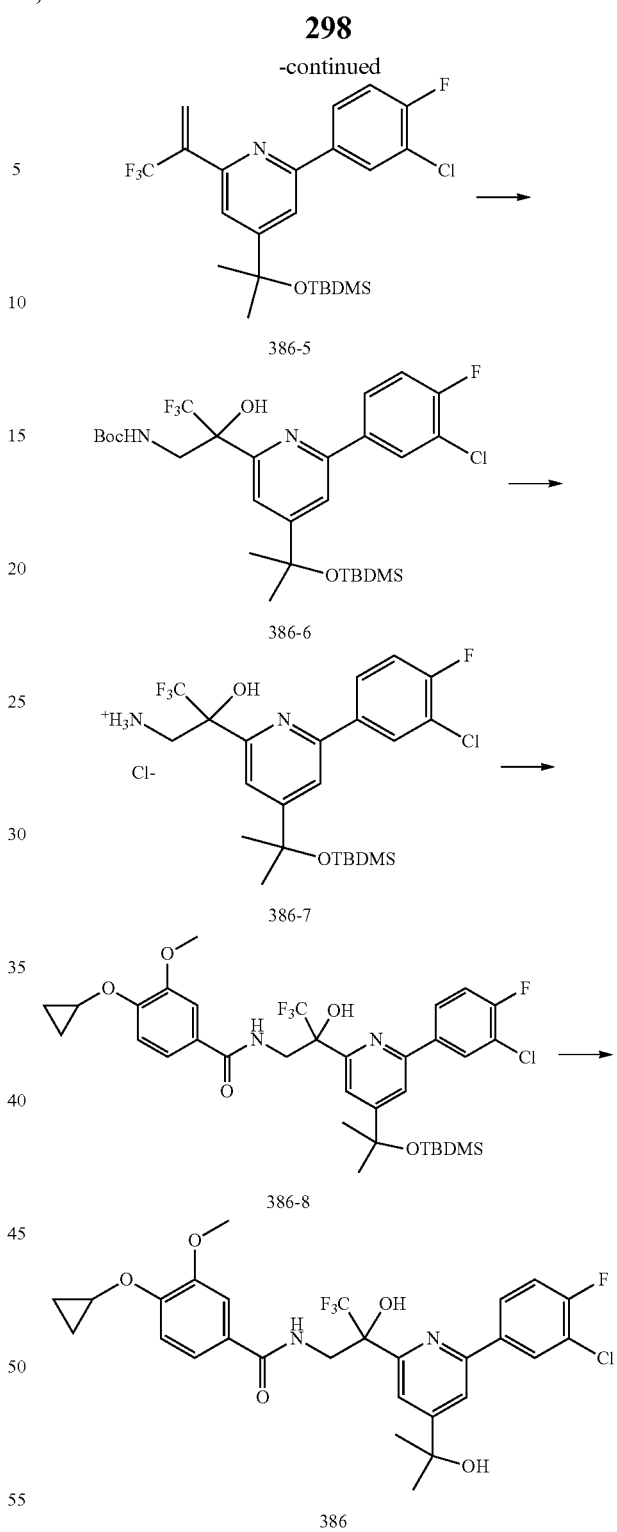

Methyl magnesium bromide (1.4 M in THF, 6.0 mL, 8.4 mmol) was added to a solution of ethyl 2,6-dichloroisonicotinate (0.74 g, 3.4 mmol) in THF (20 mL) at 0° C. The mixture was stirred at r.t. for 2 h. The reaction was quenched with 1N HCl and extracted with EA. The organic extracts were washed with brine, dried over sodium sulfate and concentrated. The crude was purified by chromatography on silica gel (EA:hexane) to give 386-2 (0.63 g, 88%). LCMS: m/z 206.00 [M+H]$^+$.

TBDMSOTf (2.6 mL, 12 mmol) was added dropwise to a solution of 386-2 (0.80 g, 3.9 mmol) and 2,6-lutidine (2.3 mL, 19 mmol) in CH$_2$Cl$_2$ (20 mL), and the mixture was stirred at r.t. for 3 h. The reaction was quenched with 1N HCl and extracted with EA. The organic extracts were washed with brine, dried over sodium sulfate and concentrated. The crude was purified by chromatography on silica gel (EA: hexane) to give 386-3 (1.2 g, 96%). LCMS: m/z 320.05 [M+H]$^+$.

Compounds 386-4, 386-5, 386-6, 386-7 and 386-8 were prepared in a similar manner as 377. 386-4: LCMS: m/z 350.10 [M+H]$^+$. 386-5: LCMS: m/z 474.15 [M+H]$^+$. 386-6: LCMS: m/z 607.20 [M+H]$^+$. 386-7: LCMS: m/z 507.15 [M+H]$^+$. 386-8: LCMS: m/z 697.25 [M+H]$^+$.

TBAF (1M in THF, 0.13 mL, 0.13 mmol) was added to a solution of 386-8 (25, mg, 0.043 mmol), and the mixture was stirred at r.t. for 1 h. The mixture was concentrated, and 386 was purified by reverse phase HPLC (5 mg, 20%). LCMS: m/z 583.20 [M+H]$^+$.

Example 188

Preparation of Compound 387

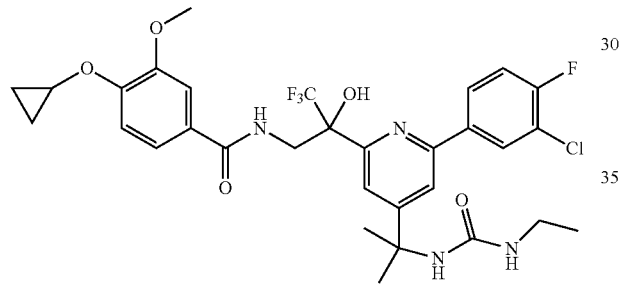

387

Compound 314 (10 mg, 0.021 mmol) was dissolved in CH$_2$Cl$_2$ (1 mL). Ethyl isocyanate (10 uL, 0.12 mmol) was added, and the mixture was stirred at r.t. for 5 h. The reaction was quenched with methanol (2 mL) and concentrated. Compound 314 was purified by HPLC (4.1 mg, 40%). LCMS: m/z 653.20 [M+H]$^+$.

Example 189

Preparation of Compound 388

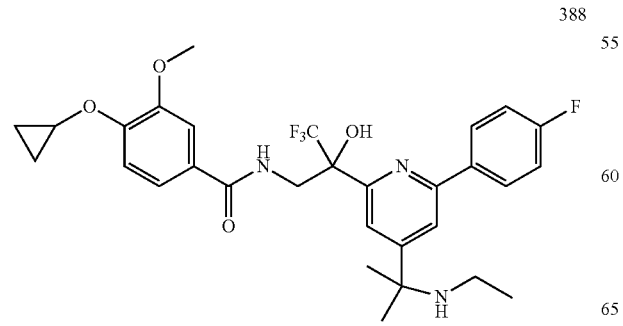

388

Sodium triacetoxyborohydride (48 mg, 0.23 mmol) was added to a solution of 318 (28 mg, 0.051 mmol) and acetaldehyde (9 uL, 0.16 mmol) in CH$_2$Cl$_2$ (1 mL). Additional acetaldehyde and reducing agent were added every 30 mins for 5 h. The reaction was quenched with ammonium chloride and extracted with CH$_2$Cl$_2$. Compound 388 was purified by reverse phase HPLC (14 mg, 50%) LCMS: m/z 576.20 [M+H]$^+$.

Example 190

Preparation of Compound 393

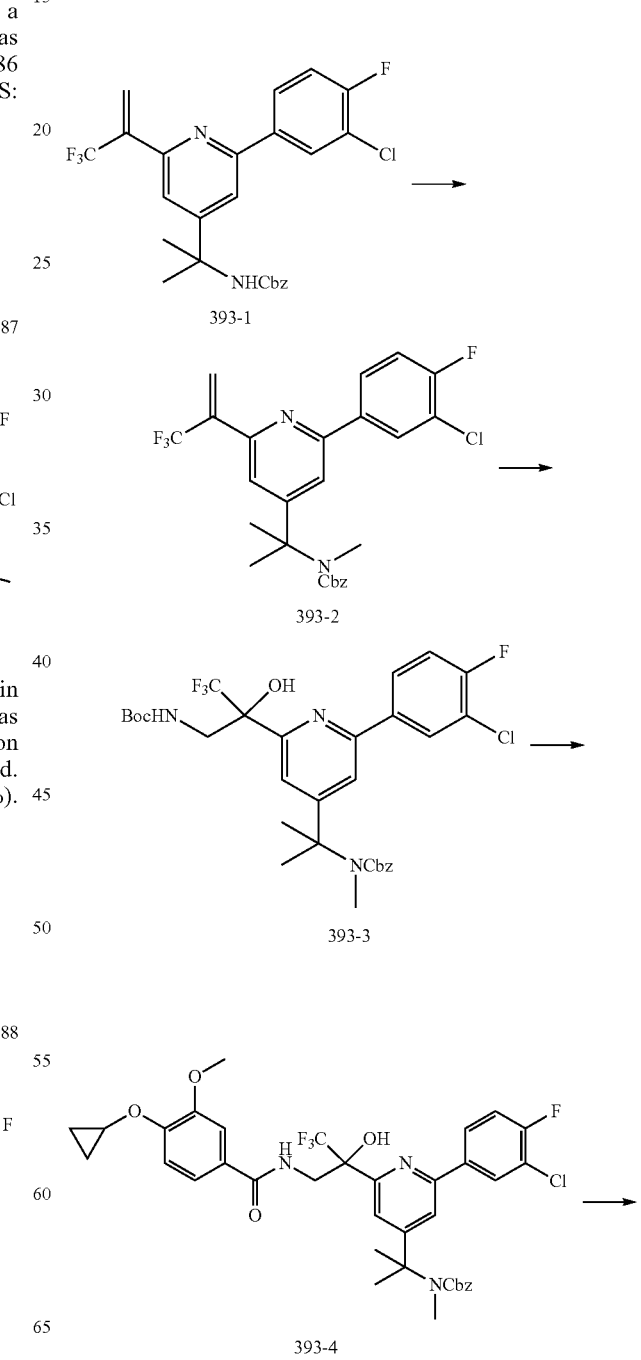

393-1

393-2

393-3

393-4

-continued

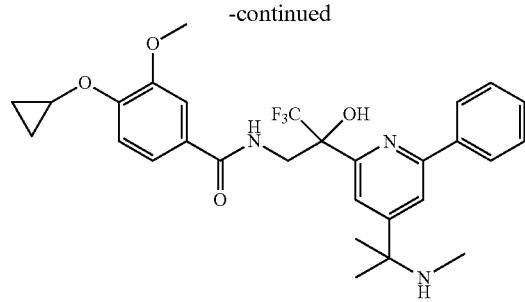

393

NaH (9 mg, 0.22 mmol) was added to a solution of 393-1 (72 mg, 0.15 mmol) in DMF (1 mL) and stirred for 15 mins. Iodomethane (18 uL, 0.29 mmol) was added, and the mixture was stirred at r.t. for 3 h. The reaction was quenched with sat. NH$_4$Cl and extracted with EA. The combined organic extracts were washed with water and brine, dried over sodium sulfate and concentrated. The crude was purified by chromatography on silica gel (EA:hexane) to give 393-2 (51 mg, 66%). LCMS: m/z 507.10 [M+H]$^+$.

Potassium osmate (6 mg, 0.015 mmol) was added to a solution of 393-2 (51 mg, 0.10 mmol) and tert-butyl (tosyloxy)carbamate (41 mg, 0.15 mmol) in t-butanol (1 mL) and water (0.33 mL), and the solution was stirred overnight at r.t. The crude was purified by chromatography on silica gel (EA:hexane) to give 393-3 (0.025 g, 50%). LCMS: m/z 640.20 [M+H]$^+$.

HCl (4N in dioxane, 1 mL) was added to 393-3 (0.025 g, 0.039 mmol), and the mixture was stirred for 1 h. The solvent was removed by evaporation and 4-cyclopropoxy-3-methoxybenzoic acid (24 mg, 0.12 mmol), HATU (60 mg, 0.16 mmol), and diisopropylethylamine (40 uL, 0.23 mmol) were added, and the mixture was stirred at r.t. for 1.5 h. The crude was diluted with EA and washed with 1N HCl, sodium bicarbonate and brine, dried over sodium sulfate and concentrated. The crude was purified by reverse phase HPLC to provide 393-4 (12 mg, 41%). LCMS: m/z 730.15 [M+H]$^+$.

Pd/C (10%, 3 mg) was added to a solution of 393-4 (12 mg, 0.025 mmol) in EtOH (3 mL), and the mixture was stirred under hydrogen atmosphere for 2 h. The catalyst was removed by filtration, and the crude was purified by reverse phase HPLC to provide 393 (2.5 mg, 28%) LCMS: m/z 563.20 [M+H]$^+$.

Example 191

Preparation of Compound 394

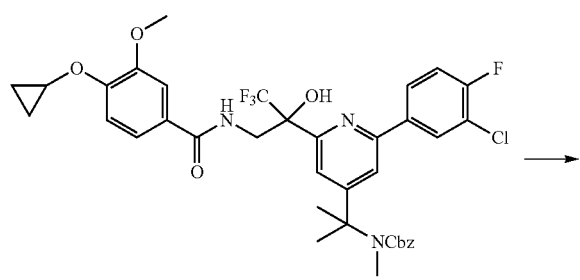

-continued

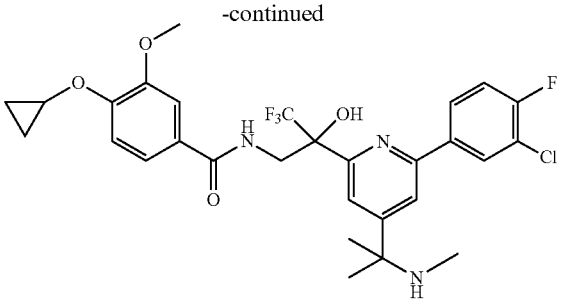

394

Sodium iodide (40 mg, 0.27 mmol) was added to a solution of 393-4 (40 mg, 0.55 mmol) and chlorotrimethylsilane (35 uL, 0.27 mmol) in acetonitrile (3 mL), and the mixture was stirred at r.t. for 2 h. The reaction mixture was diluted with EA and washed with sat. Na$_2$(SO$_2$)$_3$, and brine, dried over Na$_2$SO$_4$ and concentrated. The product was purified by reverse phase HPLC to provide 394. LCMS: m/z 597.15 [M+H]$^+$.

Example 192

Preparation of Compound 395

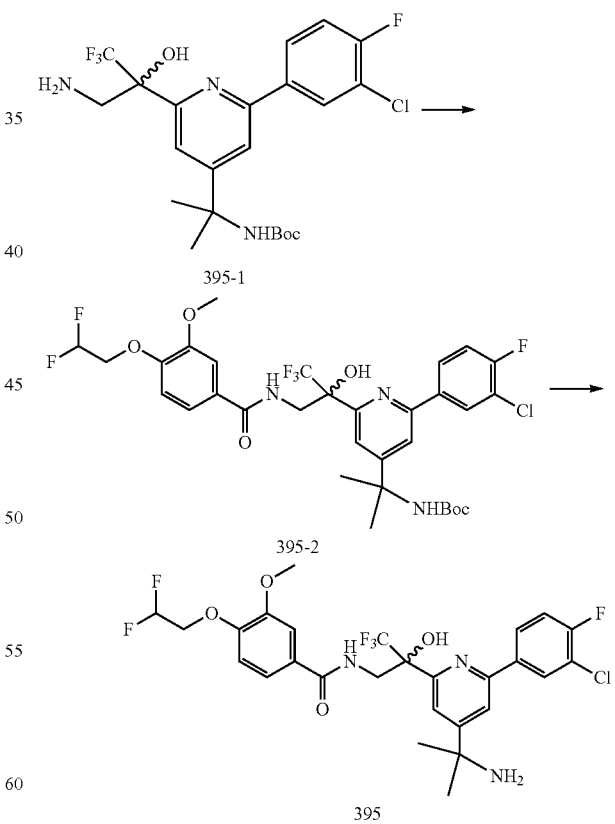

Compound 395-2 was prepared in a similar manner as 364. LCMS: m/z 706.20 [M+H]$^+$. Compound 395 was prepared in a similar manner as 396. LCMS: m/z 607.10 [M+H]$^+$.

Example 193
Preparation of Compound 396
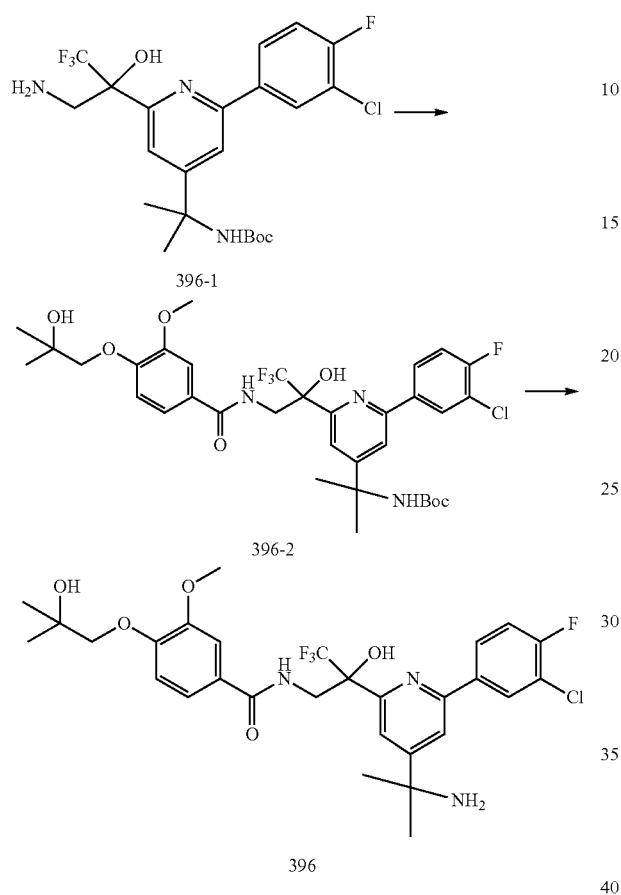
Compound 396-2 was prepared in a similar manner as 364. LC/MS: m/z 714.20 [M+H]. HCl (4N in dioxane, 2 mL) was added to 396-2 (80 mg, 0.11 mmol,) and the mixture was stirred for 2 h. The mixture was concentrated to remove volatile components, and 396 was purified by reverse phase HPLC (11 mg, 15%). LCMS: m/z 615.15 [M+H]$^+$.
Example 194
Preparation of Compound 397
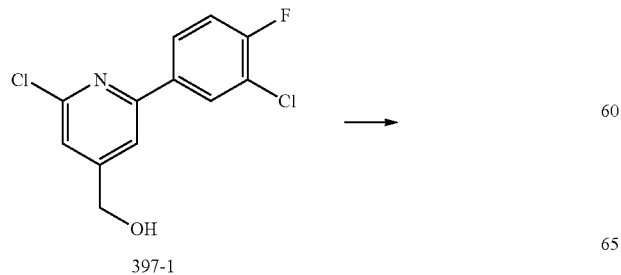
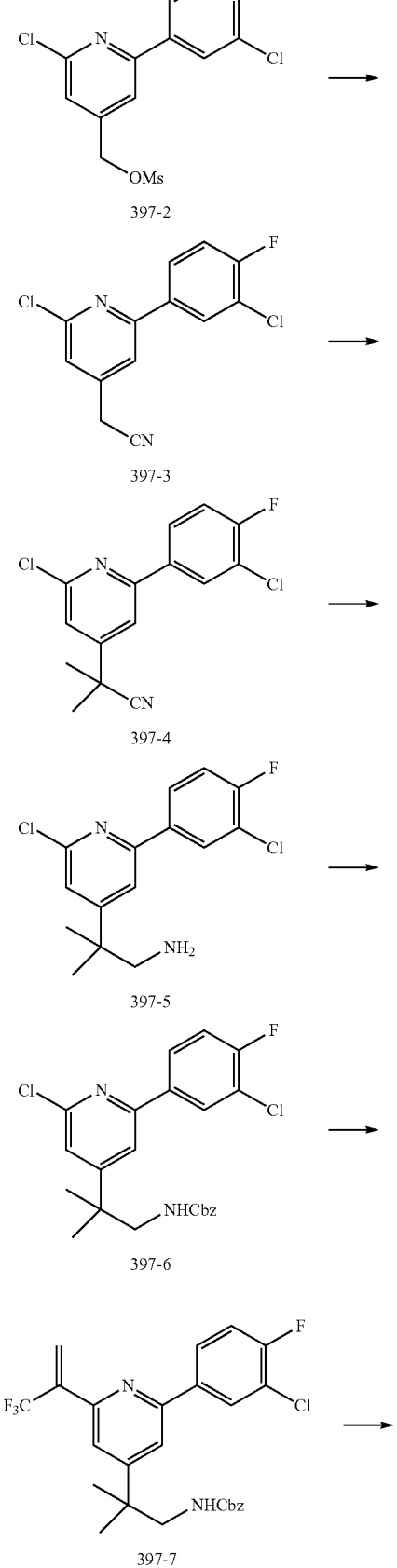

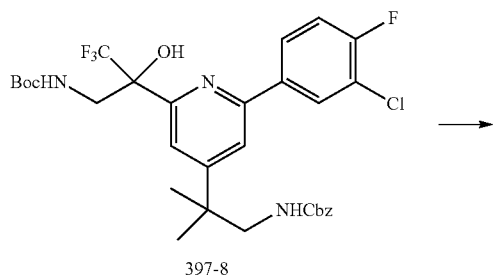

397-8

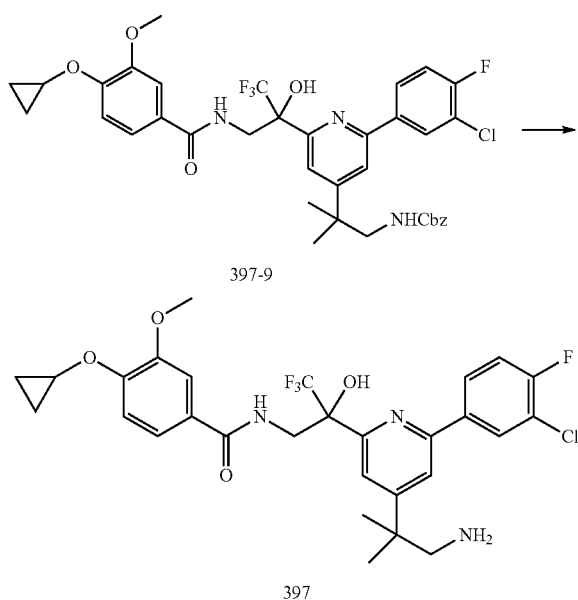

397-9

397

Methanesulfonyl chloride (0.30 mL, 4.0 mmol) was added dropwise to a solution of 397-1 (0.70 g, 2.7 mmol) and diisopropylethylamine (0.93 mL, 5.3 mmol) in $CH_2Cl_2$ (30 mL) at 0° C. for 30 mins. The mixture was washed with 1N HCl, and brine, dried over $Na_2SO_4$ and concentrated. The crude was purified by silica gel chromatography (EA: hexane) to provide 397-2 (0.59 g, 85%). LCMS: m/z 349.95 [M+H]$^+$.

Sodium cyanide (0.14 g, 2.8 mmol) was added to a solution of 397-2 (0.59 g, 2.3 mmol) in ethanol (10 mL) and water (2 mL). The mixture was heated at 50° C. for 30 mins. The mixture was diluted with EA and washed with water and brine, dried over $Na_2SO_4$ and concentrated. The crude was purified by silica gel chromatography (EA:hexane) to provide 397-3 (0.15 g, 23%). LCMS: m/z 280.95 [M+H]$^+$.

NaH (65 mg, 1.6 mmol) was added to a solution of 397-3 (0.15 g, 0.54 mmol) in DMF (1 mL) and stirred for 5 mins. Iodomethane (0.16 mL, 3.0 mmol) was added dropwise, and the mixture was stirred at r.t. for 1 h. The reaction was quenched with $NH_4Cl$ and extracted with EA. The organic extracts were washed with water and brine, dried over $Na_2SO_4$ and concentrated. The crude was purified by silica gel chromatography (eluent: EA:hexane) to provide 397-4 (0.123 g, 72%). LCMS: m/z 308.95 [M+H]$^+$.

Borane-dimethylsulfide (0.11 mL, 0.11 mmol) was added dropwise to a solution of 397-4 (0.123 g, 3.9 mmol) in THF (2 mL), and the mixture was heated at 55° C. for 1 h. The reaction was quenched with 6N HCl and heated at 55° C. for 15 mins. The volatile components were removed by evaporation, and 397-5 was used without further purification. LCMS: m/z 313.00 [M+H]$^+$.

Benzyl chloroformate (85 uL, 0.59 mmol) was added dropwise to a solution of 397-5 (3.9 mmol) and diisopropylethylamine (0.20 mL, 1.2 mmol) in $CH_2Cl_2$ (2 mL), and the mixture was stirred at r.t. for 1 h. The mixture was diluted with EA and washed with water and brine, dried over $Na_2SO_4$ and concentrated. The crude was purified by silica gel chromatography (EA:hexane) to provide 397-6 (0.15 g, 87%). LCMS: m/z 447.05 [M+H]$^+$.

Compound 397-7 was prepared in a similar manner as 364. LCMS: m/z 507.10 [M+H]$^+$. Compound 397-8 was prepared in a similar manner as 377. LCMS: m/z 640.15 [M+H]$^+$. Compound 397-9 was prepared in a similar manner as 377. LCMS: m/z 730.15 [M+H]$^+$. Compound 397 was prepared in a similar manner as 394. LCMS: m/z 597.20 [M+H]$^+$.

Example 195

Preparation of Compounds 366, 367, 370, 373, 376, 389, 390, 391 and 392

TABLE 7

| Example Method | Structure | LCMS: m/z |
|---|---|---|
| Compound 365 | ![structure 366] | 533.10 [M + H]$^+$ |

366

TABLE 7-continued

| Example Method | Structure | LCMS: m/z |
|---|---|---|
| Compound 424 | 367 | 500.1 [M + H]+ |
| Compound 369 | 370 | 555.10 [M + H]+ |
| Compound 364 | 373 | 579.05 [M + H]+ |
| Compound 364 | 376 | 515.05 [M + H]+ |

TABLE 7-continued

| Example Method | Structure | LCMS: m/z |
| --- | --- | --- |
| Compound 388 | 389 | 548.20 [M + H]+ |
| Compound 388 | 390 | 611.10 [M + H]+ |
| Compound 388 | 391 | 628.20 [M + H]+ |
| Compound 388 | 392 | 625.15 [M + H]+ |

Example 196

Preparation of Compounds 246 and 247

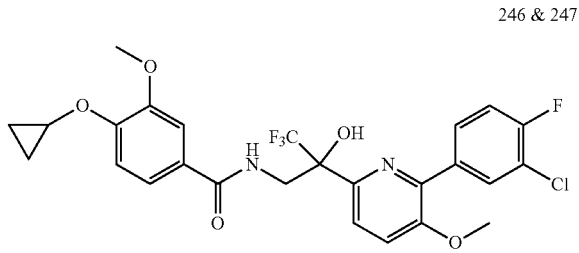 [SMILES: COc1cc(C(=O)NCC(O)(c2ccc(OC)c(-c3ccc(F)c(Cl)c3)n2)C(F)(F)F)ccc1OC1CC1]

246 & 247

Compound 370 (270 mg, 0.49 mmol) was separated via SFC to give two enantiomers: 246 (100 mg, 74.0%) and 247 (110 mg, 81.5%). 246: +ESI-MS: m/z 555.1 [M+H]$^+$. 247: +ESI-MS: m/z 555.1 [M+H]$^+$.

Example 197

Preparation of Compound 398

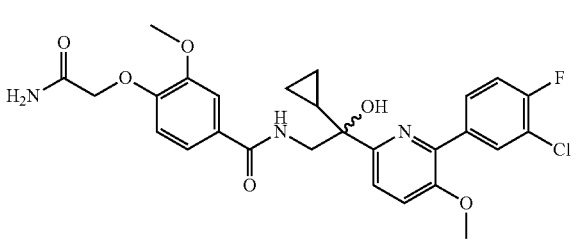

398

To a stirring mixture of 4-(2-amino-2-oxoethoxy)-3-methoxybenzoic acid (70 mg, 0.31 mmol) in DMF (1.5 mL) were added HATU (90 mg, 0.237 mmol) and DIPEA (84 μL, 0.474 mmol). The mixture was stirred at r.t. for 10 mins. 2-amino-1-(6-(3-chloro-4-fluorophenyl)-5-methoxypyridin-2-yl)-1-cyclopropylethan-1-ol in DMF (0.5 mL) as added. The mixture was stirred at for 10 mins, and then quenched with a 10% aq. solution of NaHCO$_3$ (10 mL). The mixture was diluted with DCM, and a normal aqueous work up with DCM was followed. The crude was purified via prep-HPLC to afford 398 as a white solid. LCMS: m/z 544.15 [M+H]$^+$.

Example 198

Preparation of Compound 399

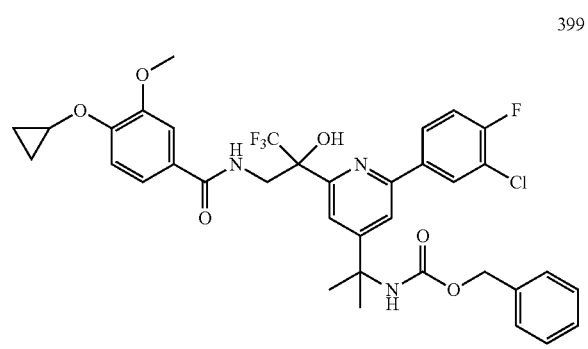 [SMILES: COc1cc(C(=O)NCC(O)(c2cc(C(C)(C)NC(=O)OCc3ccccc3)cc(-c3ccc(F)c(Cl)c3)n2)C(F)(F)F)ccc1OC1CC1]

399

Compound 399 was prepared in a manner similar to 398. LCMS: m/z 716.2 [M+H]$^+$.

Example 199

Preparation of Compound 400

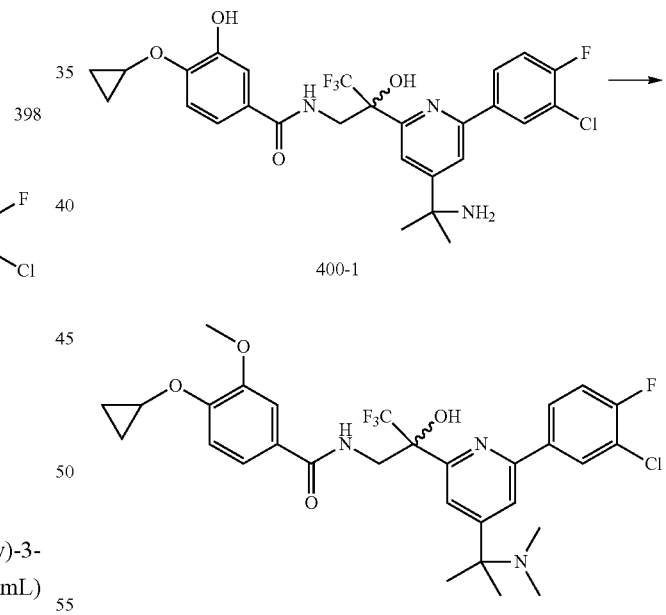

To a stirring mixture of 400-1 (50 mg, 0.088 mmol, obtained during the preparation of 314) in DMF (2.0 mL) were added Cs$_2$CO$_3$ (143 mg. 0.44 mmol) and MeI (38 mg. 0.264 mmol). The mixture was stirred at r.t. until the starting material was consumed. The crude was diluted EtOAc and water. The aqueous layer was extracted with EtOAc, dried over Na$_2$SO$_4$, filtered and concentrated under reduced pressure. Compound 400 was purified via HPLC to afford 400 as a white solid. LCMS: m/z 610.15 [M+H]$^+$.

Example 200
Preparation of Compound 401
To a stirring mixture of 401-1 (460 mg, 1.6 mmol) in DMF (2.5 mL, deoxygenated) were added PdCl$_2$(PPh$_3$)$_2$ (32 mg, 0.045 mmol), CuI (26 mg, 0.136 mmol), piperidine
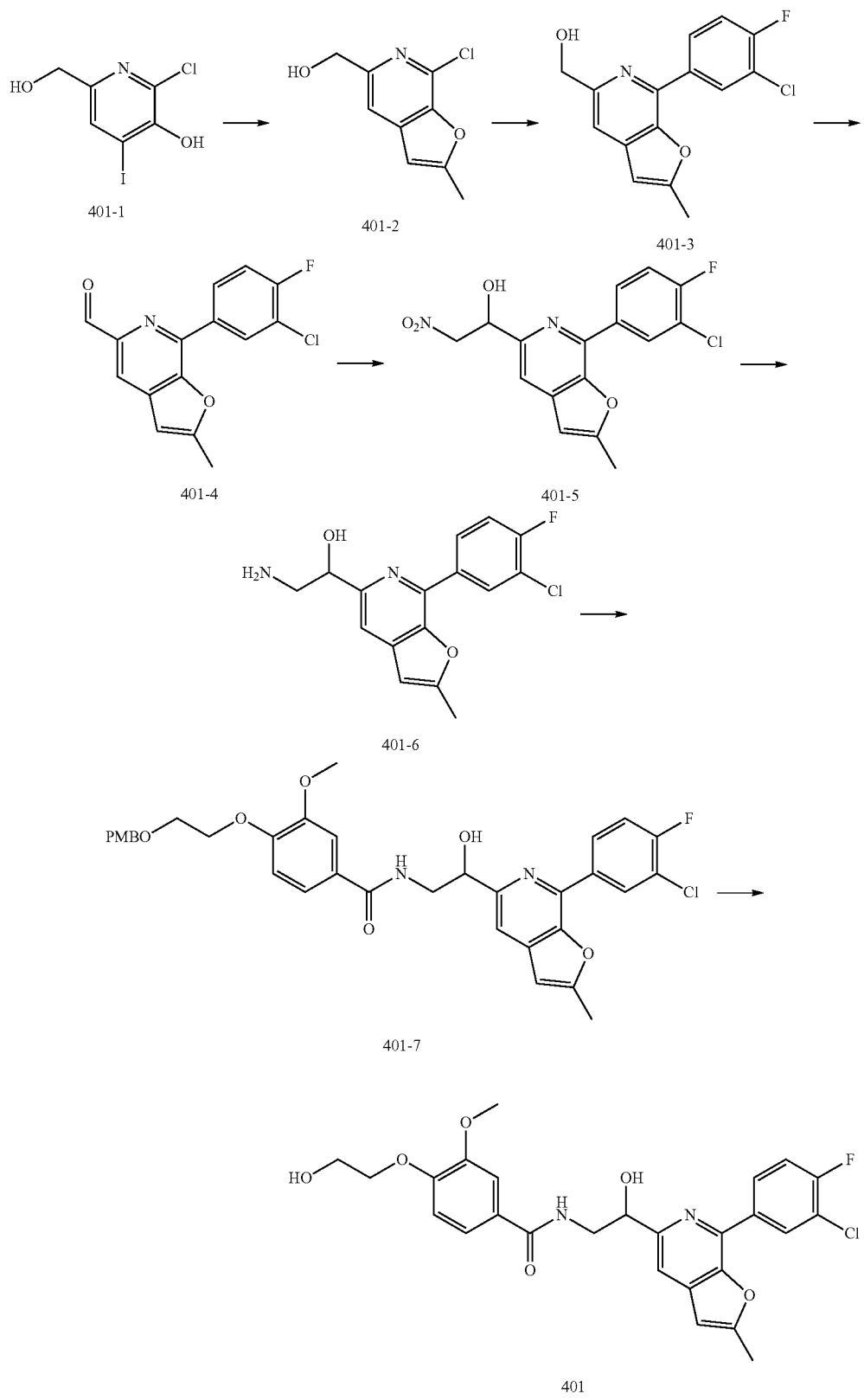

(0.35 mL) and trimethyl(prop-2-yn-1-yl)silane (180 mg, 1.6 mmol). The mixture subjected to microwave irradiation at 60° C. for 3 h. The mixture was cooled to r.t. and diluted with EtOAc. The mixture was washed with brine, water and NaHCO₃. The mixture was dried over MgSO₄, filtered and concentrated under reduced pressure. The crude was purified via a silica gel column to afford 401-2 as a yellow solid. LCMS: m/z 198.05 [M+H]⁺.

To a stirring mixture of 401-2 (110 mg, 0.56 mmol) in DME (3 mL, deoxygenated) were added (3-chloro-4-fluorophenyl)boronic acid (191 mg, 1.1 mmol), PdCl₂(dppf)₂ and a solution of Cs₂CO₃ (0.6 mL, 3.7 M). The mixture subjected to under microwave irradition at 110° C. for 4 h. The mixture was diluted with EtOAc and water. The aqueous layer was extracted with EtOAc, dried over MgSO₄, filtered and concentrated under reduced pressure. The crude was purified via a silica gel column to afford 401-3 as a white solid. LCMS: m/z 292.0 [M+H]⁺.

Compound 401-6 was prepared in 3 steps using methods similar to those for preparing 302. LCMS: m/z 321.0 [M+H]⁺. Compound 401-6 was coupled with 3-methoxy-4-(2-((4-methoxybenzyl)oxy)ethoxy)benzoic acid followed by alcohol oxidation and deprotection to afford 401. LCMS: m/z 513. 05 [M+H]⁺.

Example 201

Preparation of Compound 402

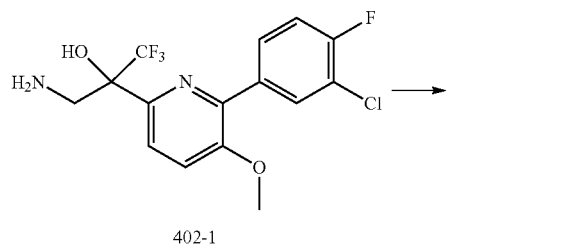

402-1

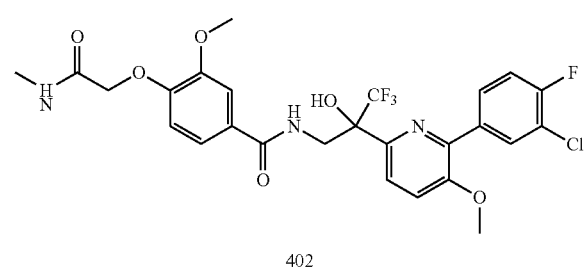

402

Diisopropylethylamine (24 uL, 0.14 mmol) was added to a solution of 402-1 (21 mg, 0.045 mmol), 3-methoxy-4-[(methylcarbamoyl)methoxy]benzoic acid (22 mg, 0.090 mmol) and HATU (38 mg, 0.099 mmol) in DMF (1 mL), and the mixture was stirred at r.t. for 2 h. The mixture was diluted with EA, washed with 1N HCl, water and brine, dried over Na₂SO₄ and concentrated. The crude was purified by reverse-phase HPLC to provide 402 (7.5 mg). LCMS: m/z 586.05 [M+H]⁺.

Example 202

Preparation of Compounds 403, 404 and 405

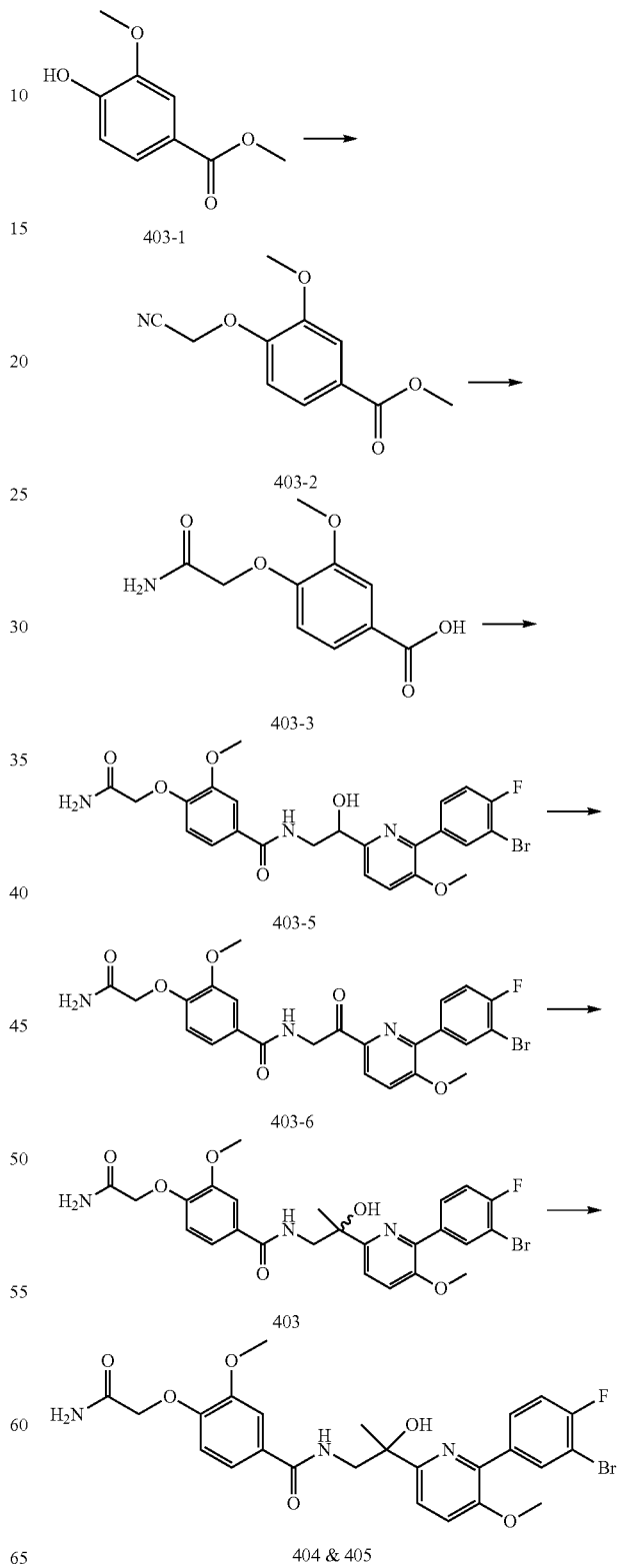

To a solution of 403-1 (6.0 g, 32.97 mmol) and K₂CO₃ (9.12 g, 66.1 mmol) in DMF (50 mL) was added 2-bromoacetonitrile (4.98 g, 39.52 mmol) dropwise. The mixture was stirred at 80° C. for 4 h. The mixture was diluted with water, and extracted with EA (3×100 mL). The combined organic layer was washed with brine, dried over anhydrous sodium sulfate and concentrated at low pressure. The residue was purified by column chromatography on silica gel (5~10% EA:PE) to give 402-2 as a colorless oil (5.1 g, 70%).

To a solution of 402-2 (8.0 g, 36.2 mmol) in MeOH:H₂O (2:1, 90 mL) was added NaOH (2.9 g, 72.4 mmol), and the mixture stirred at 50° C. for 1 h. The mixture was diluted with water and extracted with EA (2×50 mL). The aqueous layer was acidified to pH 4.0 using 2.0 M HCl solution. The aqueous phase was extracted with EA (2×150 mL). The combined organic layer was washed with brine, dried over sodium sulfate and concentrated at low pressure to give 403-3 (5.6 g, 70%).

To a solution of 403-3 (530 mg, 2.35 mmol) in DMF (15 mL) were added DIPEA (590 mg, 7.04 mmol) and HATU (885 mg, 2.35 mmol), and the mixture was stirred at r.t. for 30 mins. The mixture was treated with 2-amino-1-(6-(3-bromo-4-fluorophenyl)-5-methoxypyridin-2-yl)ethanol (403-4, 800 mg, 2.35 mmol), and the mixture was stirred at r.t. for 2 h. The mixture was diluted with water, and extracted with EA (3×20 mL). The combined organic layer was washed with brine, dried over anhydrous sodium sulfate and concentrated at low pressure. The residue was purified by column chromatography on silica gel (PE:EA 1:1) to give 403-5 (1.0 g, 77.5%). +ESI-MS: m/z 547.9 [M+H]⁺.

To a solution of 403-5 (600 mg, 1.10 mmol) in DCM (20 mL) was added DMP (948 mg, 2.2 mmol) in portions, and the mixture was stirred at r.t. for 1 h. The mixture was washed with sat. Na₂S₂O₃ solution and brine. The organic phase was dried over anhydrous sodium sulfate and concentrated at low pressure. The residue was purified by chromatography to give 403-6 as a white solid (400 mg, 66.7%). +ESI-MS: m/z 546.1 [M+H]⁺.

To a solution of 403-6 (400 mg, 0.73 mmol) in THF (20 mL) was added CH₃MgBr (2.4 mL, 7.3 mmol) dropwise, and the mixture was stirred at r.t. for 30 mins. The reaction was quenched with water, and extracted with EA (3×30 mL). The organic layer was washed with brine, dried over anhydrous sodium sulfate and concentrated at low pressure. The residue was purified by prep-HPLC to give 403 (60 mg) as a white solid. +ESI-MS: m/z 562.1 [M+H]⁺.

Compound 403 (~45 mg) was separated via SFC separation to give two isomers: 404 (10.0 mg) and 405 (12.5 mg). 404: +ESI-MS: m/z 562.1 [M+H]⁺. 405: +ESI-MS: m/z 562.0 [M+H]⁺.

Example 203

Preparation of Compounds 406 and 407

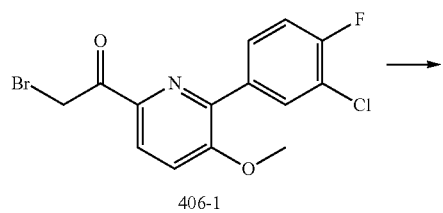

406-1

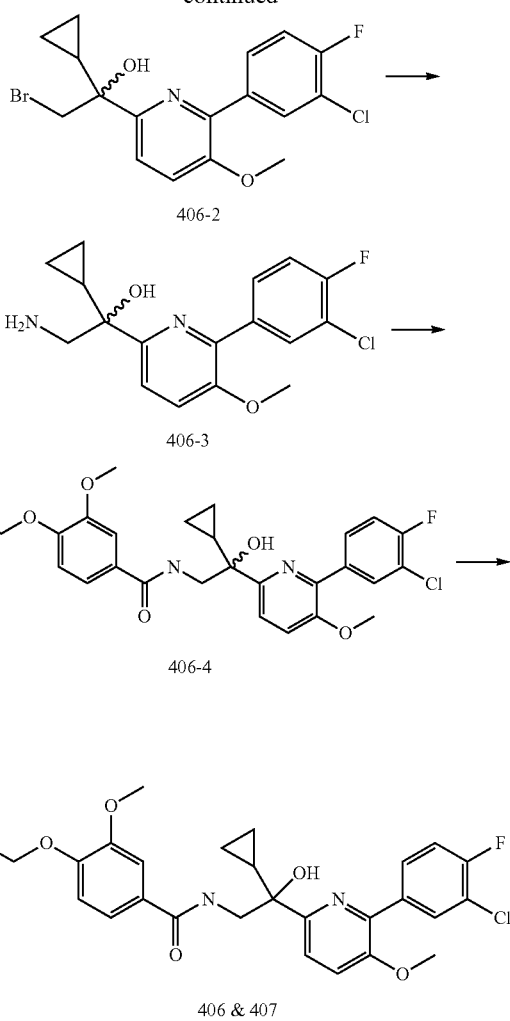

To a solution of 406-1 (540 mg, 1.53 mmol) in THF (4 mL) was added cyclopropylmagnesium bromide (4 mL, 0.5M in THF) dropwise at 0° C. The mixture was stirred at 0° C. for 1 h. The reaction was quenched with water, and extracted with EA (3×20 mL). The combined organic layer was washed with brine, dried over anhydrous Na₂SO₄ and concentrated at low pressure. The residue was purified by chromatography (PE:EA 10:1) to give 406-2 (400 mg, 70%).

Compound 406-2 (400 mg, 1.0 mmol) was treated with concentrated ammonia water (10 mL) and ethanol (10 mL) in an autoclave. After sealing, the mixture was heated to 80° C. for 10 h with stirring. The mixture was cooled to r.t., and diluted with EA (30 mL). The mixture was washed with brine, dried over anhydrous Na₂SO₄ and concentrated at low pressure to give 406-3, which was used without further purification. +ESI-MS: m/z 337.1 [M+H]⁺.

Compound 406-6 was prepared essentially as described in the preparation of 403 by using 4-(2-fluoroethoxy)-3-methoxybenzoic acid and 406-3. The crude was purified by column chromatography (EA:PE 1:1) to give 406-4 as a white solid (201 mg, 73%). +ESI-MS: m/z 533.1 [M+H]⁺.

Compound 406-4 was separated via SFC separation to give two isomers: 406 (60 mg) and 407 (65 mg). 406: +ESI-MS: m/z 533.1 [M+H]+. 407: +ESI-MS: m/z 533.1 [M+H]+.

Example 204
Preparation of Compounds 408 and 409
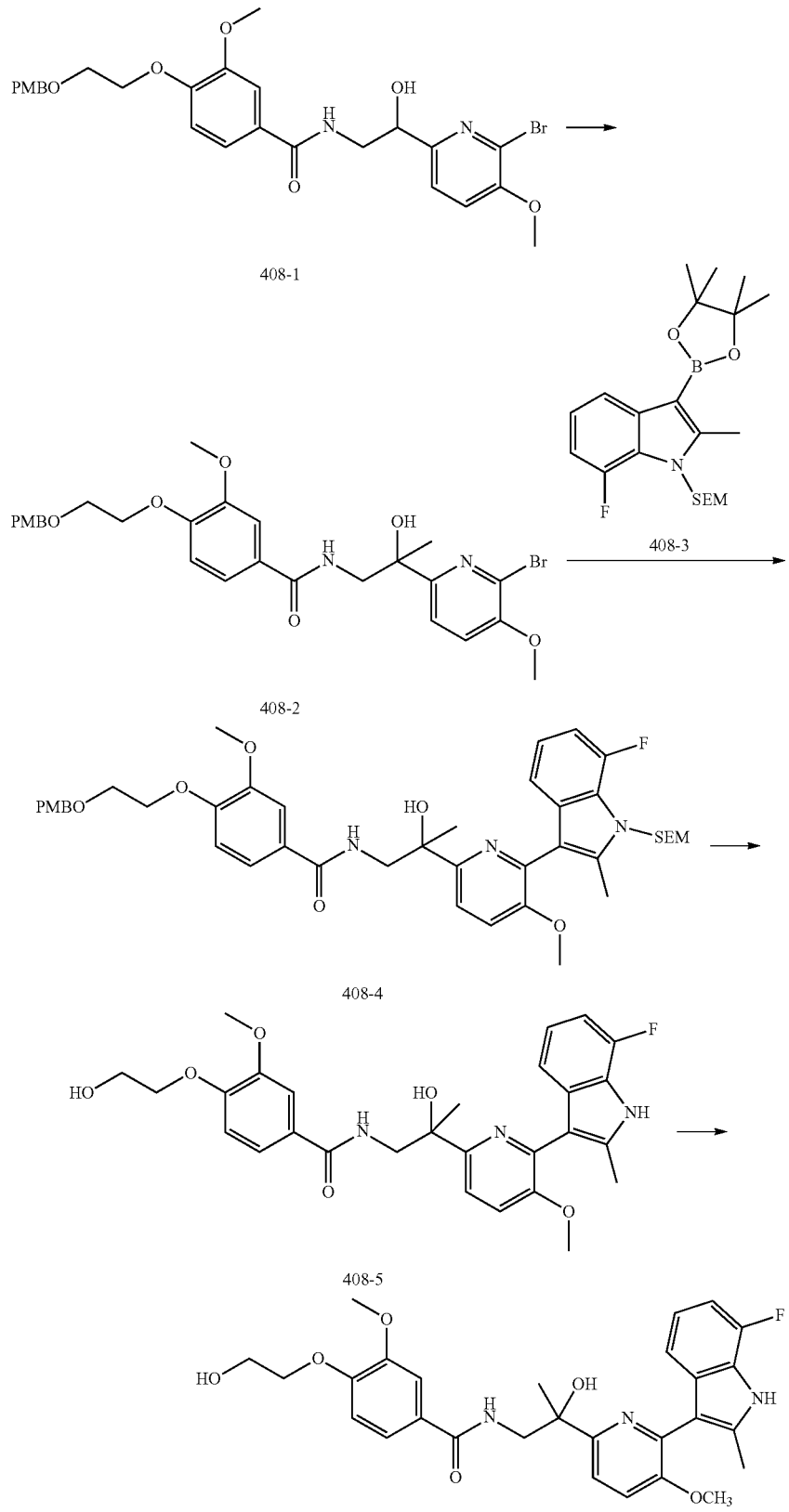

To a solution of 408-1 (560 mg, 0.2 mmol) in TH (4 mL) was added MeMgCl (1 mL, 3 M in Et$_2$O). The mixture was stirred at 0° C. for 1 h. The reaction was quenched with CBr$_4$ (5 g) in THF (10 mL). The mixture was diluted with EA (50 mL). The solution was washed with brine, dried over anhydrous Na$_2$SO$_4$ and concentrated at low pressure. The residue was purified by silica gel to give 408-2 (402 mg, 70%). +ESI-MS: m/z 577.1 [M+H]$^+$.

Under N$_2$ atmosphere, a 50 mL flask with a magnetic stirring bar was charged with 208-3 (300 mg, 0.75 mmol), 408-2 (290 mg, 0.5 mmol), Pd(dppf)Cl$_2$ (8 mg, 1 mmol %), KF (180 mg, 3.0 mmol), and dioxane:H$_2$O (20 mL:5 mL). The mixture was stirred for 10 h at 100° C. The mixture was cooled to r.t. and diluted with water (50 mL) and EA (50 mL). The organic layer was separated, and the aqueous phase was extracted with EA (2×20 mL). The combined organic phase was washed with brine, dried over anhydrous Na$_2$SO$_4$ and concentrated under reduced pressure. The residue was purified by column chromatography on silica gel (PE:EA 10:1) to give 408-3 as a solid (280 mg, 70%). +ESI-MS: m/z 774.5 [M+H]$^+$.

To a solution of 408-3 (280 mg, 0.36 mmol) in dioxane (8 mL) wad added conc. HCl (2 mL). The mixture was stirred at 80° C. for 1 h. The mixture was cooled to r.t. and diluted with water (15 mL) and EA (20 mL). The organic phase was washed with brine, dried over anhydrous Na$_2$SO$_4$ and concentrated at low pressure. The residue was purified by prep-HPLC to give 408-4 (189 mg).

Compound 408-4 (189 mg) was separated via SFC separation to give two enantiomers: 408 (60 mg) and 409 (65 mg). 408: +ESI-MS: m/z 524.1 [M+H]$^+$. 409: +ESI-MS: m/z 524.1 [M+H]$^+$.

Example 205

Preparation of Compounds 410 and 411

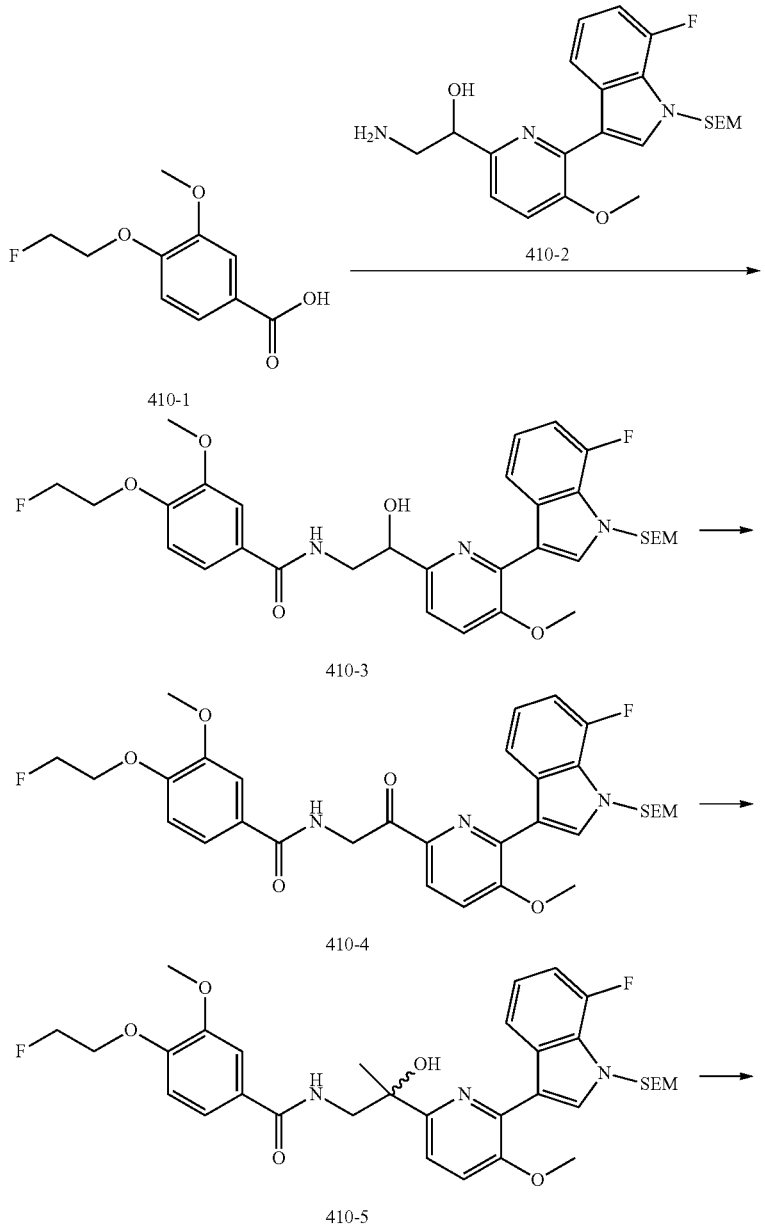

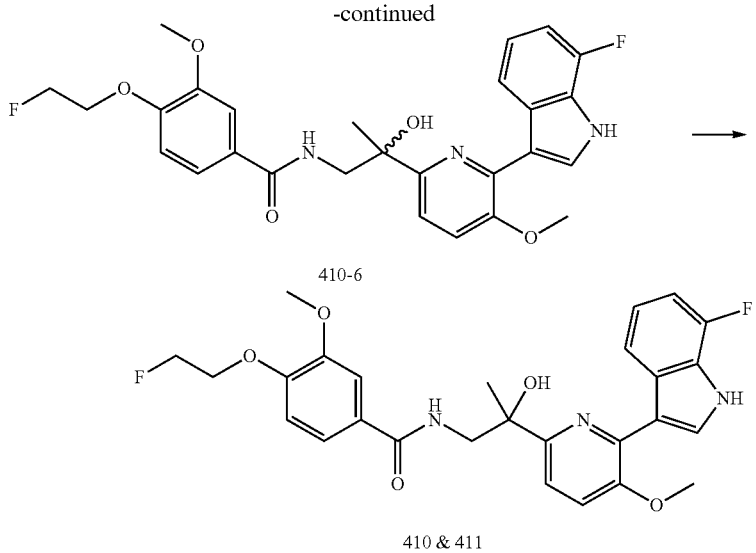

410-6

410 & 411

Compound 410-3 was prepared essentially as described in the preparation of 403 by using 410-1 and 410-2. The crude was purified by column chromatography on silica gel (PE: acetone 5:1) to give 410-3 (1.8 g, 89%). +ESI-MS: m/z 628.1 [M+H]$^+$.

Compound 410-4 was prepared essentially as described in the preparation of 403. Crude 410-4 was obtained (0.8 g, 52.3%). +ESI-MS: m/z 626.1 [M+H]$^+$. Compound 410-5 was prepared essentially as described in the preparation of 403. Crude 410-5 was purified by column chromatography on silica gel (PE:acetone 5:1) to give 410-5 (496 g, 51%). +ESI-MS: m/z 642.1 [M+H]$^+$. Compound 410-5 was prepared essentially as described in the preparation of 403. Crude 410-6 was purified by prep-HPLC to give 410-6 (302 mg, 70%). +ESI-MS: m/z 512.1 [M+H]$^+$. Compound 410-5 was separated via SFC separation to give 410 (30 mg) and 411 (28 mg). 410: +ESI-MS: m/z 512.1 [M+H]$^+$. 411: +ESI-MS: m/z 512.1 [M+H]$^+$.

Example 206

Preparation of Compounds 412 and 413

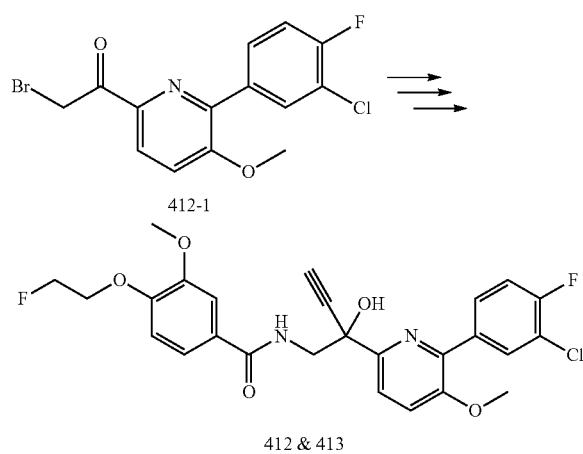

412-1

412 & 413

Compounds 412 and 413 were prepared essentially as described in the preparation of 403 by using 412-1 and ethynyl magnesium bromide. The product was purified by prep-HPLC and SFC separation. 412 (30 mg) and 413 (32 mg) were obtained as white solids. 412: +ESI-MS: m/z 516.9 [M+H]$^+$. 413: +ESI-MS: m/z 516.9 [M+H]$^+$.

Example 207

Preparation of Compounds 414,415 and 416

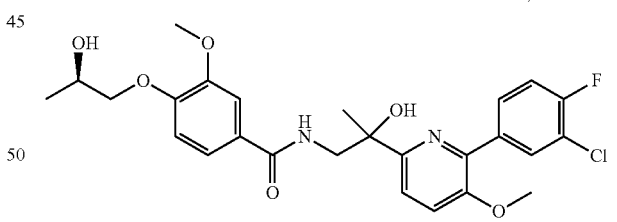

414, 415 & 416

Racemic 414 was prepared essentially as described in the preparation of 403 by using 412-1 and (R)-4-(2-hydroxypropoxy)-3-methoxybenzoic acid. Compound 414 was obtained as a white solid (150 mg). Compound 414 was separated via SFC separation to give two enantiomers: 415 (35 mg) and 416 (38 mg). 415: +ESI-MS: m/z 519.1 [M+H]$^+$. 416: +ESI-MS: m/z 519.0 [M+H]$^+$.

Example 208

Preparation of Compounds 417 and 418

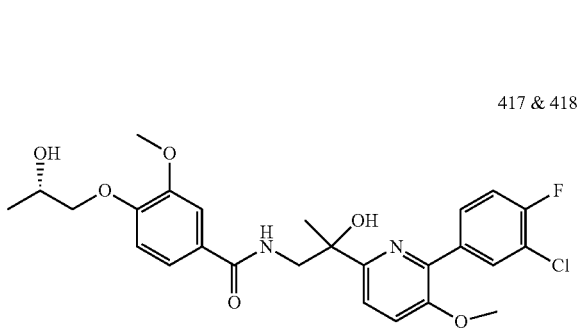 [SMILES: COc1cc(C(=O)NCC(C)(O)c2ccc(OC)c(-c3ccc(F)c(Cl)c3)n2)ccc1OC[C@H](C)O]

417 & 418

Compounds 417 and 418 were prepared essentially as described in the preparation of 403 by using 412-1 and (S)-4-(2-hydroxypropoxy)-3-methoxybenzoic acid. Compounds 417 (36 mg) and 418 (39 mg). 417: +ESI-MS: m/z 518.9 [M+H]$^+$. 418: +ESI-MS: m/z 518.9 [M+H]$^+$.

Example 209

Preparation of Compounds 419, 420 and 421

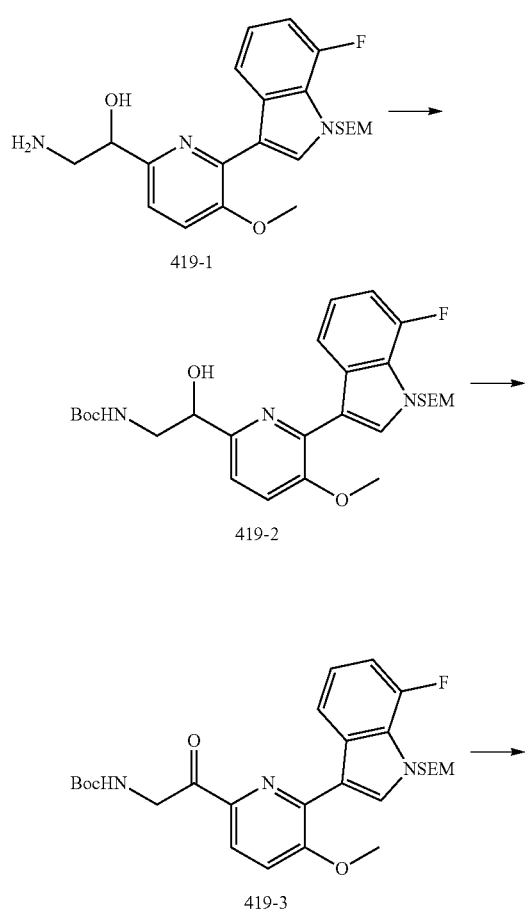

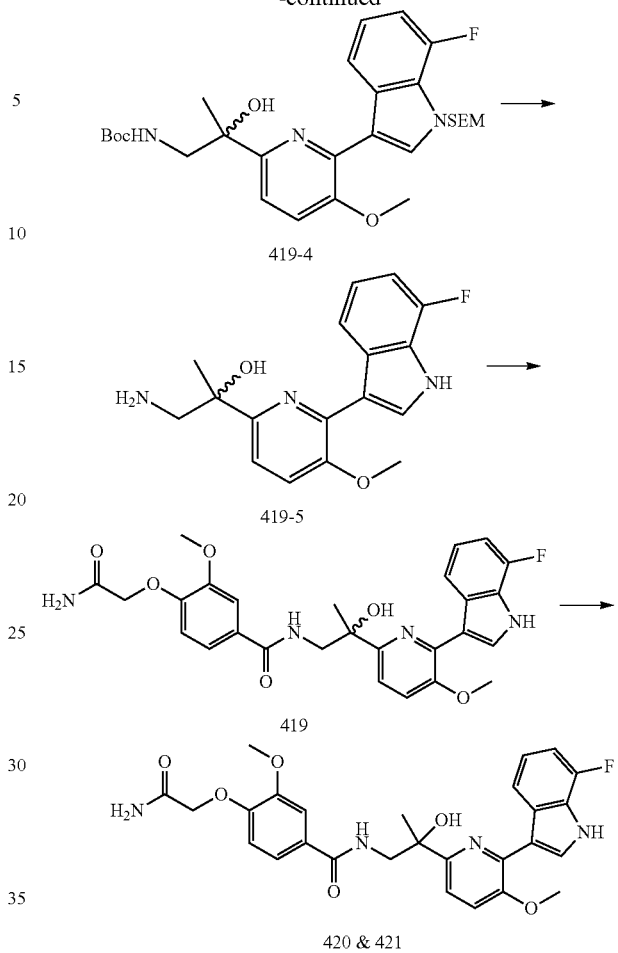

To a solution of 419-1 (1.0 g, 2.32 mmol) in dioxane:H$_2$O (4:1, 20 mL) was added NaHCO$_3$ (584.6 mg, 6.96 mmol) in one portion and Boc$_2$O (657.5 mg, 3.02 mmol) in portions. The mixture was stirred at r.t. for 2 h, and then diluted with water (50 mL) and EA (50 mL). The aqueous phase was extracted by EA (2×50 mL). The combined organic layers were washed with brine, dried over anhydrous sodium sulfate and concentrated in vacuum. The residue was purified by column chromatography on silica gel (PE:EA 4:1) to give 419-2 (1.2 g, 97%). +ESI-MS: m/z 532.3 [M+H]$^+$.

To a solution of 419-2 (1.2 g, 2.26 mmol) in DCM (20 mL) was added DMP (1.95 g, 4.52 mmol) in portions. The mixture was stirred at r.t. for 1 h. The reaction was quenched with sat. Na$_2$SO$_3$ solution (50 mL), and extracted with CH$_2$Cl$_2$ (3×50 mL). The combined organic phase was washed with brine, dried over anhydrous sodium sulfate and concentrated at low pressure. The residue was purified by chromatography to give 419-3 as a white solid (1.0 g, 83.3%). +ESI-MS: m/z 530.3 [M+H]$^+$.

To a solution of 419-3 (1.0 g, 1.89 mmol) in THF (15 mL) was added CH$_3$MgBr (6.30 mL, 18.90 mmol) dropwise at 0° C., and the mixture was stirred at r.t. for 30 mins. The reaction was quenched with water, and extracted with EA (3×30 mL). The combined organic phase was dried over anhydrous sodium sulfate and concentrated at low pressure. The crude was purified by column chromatography (PE:EA 3:1~2:1) to give 419-4 as a white solid (605 mg, 58.3%). +ESI-MS: m/z 546.2 [M+H]$^+$.

To a solution of 419-4 (600 mg, 1.1 mmol) in dioxane (16 mL) was added conc. HCl (8 mL). The mixture was stirred at 80° C. overnight. After cooled to r.t., the mixture was neutralized by sat. NaHCO$_3$ solution, and extracted with EA (3×50 mL). The combined organic phase was washed with brine, dried over anhydrous sodium sulfate and concentrated at low pressure to give 419-5 (301 mg, 87%).

Compound 419 was prepared essentially as described in the preparation of 403 by using 419-5 and 4-(2-amino-2-oxoethoxy)-3-methoxybenzoic acid. Compound 491 was obtained as a white solid (90 mg). +ESI-MS: m/z 523.1 [M+H]$^+$.

Compound 419 (90 mg, 0.172 mmol) was separated via SFC separation to give two enantiomers: 420 (15.0 mg) and 421 (22.0 mg). 420: +ESI-MS: m/z 523.1 [M+H]$^+$. 421: +ESI-MS: m/z 523.1 [M+H]$^+$.

Example 210

Preparation of Compounds 422 and 423

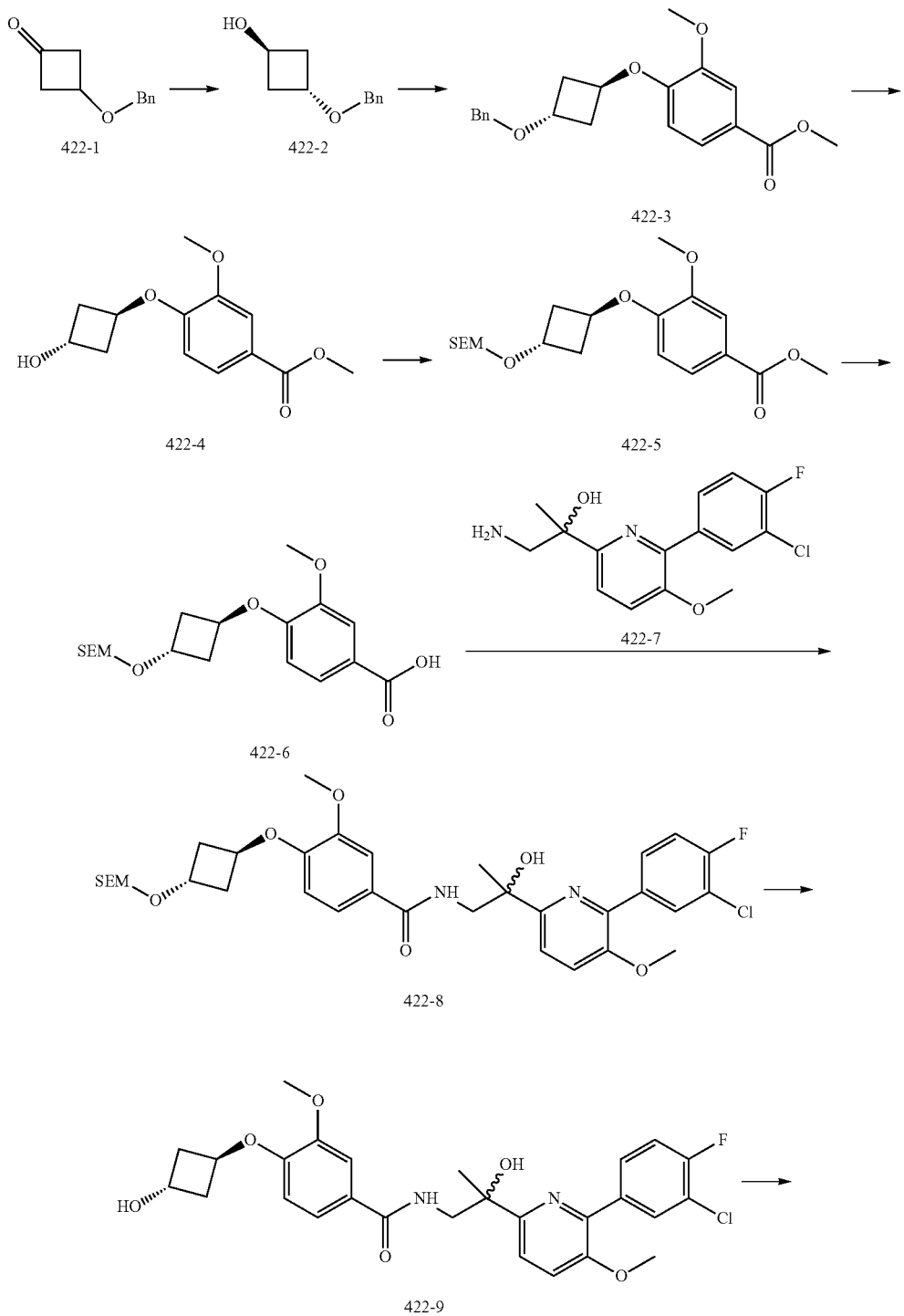

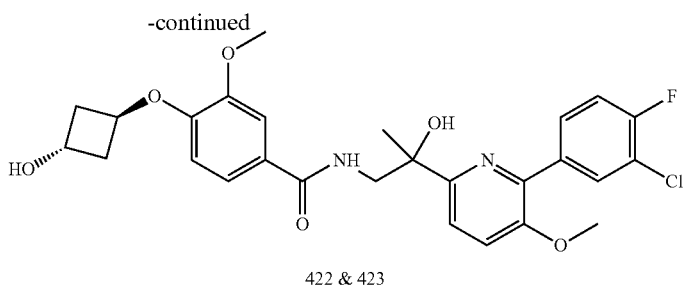

422 & 423

To a solution of 422-1 (100 mg, 0.575 mmol) in THF (10 mL) was NaBH₄ (44 mg, 1.1 mmol) was added, and the mixture was stirred at r.t. for 30 mins. The reaction was quenched by water, and extracted with EA (3×20 mL). The organic phase was washed with brine, dried over anhydrous Na₂SO₄ and concentrated at low pressure. The crude was purified by chromatography (PE:EA 20:1 to 5:1) to afford 422-2 (90 mg, 89.1%).

To a solution of 422-2 (534 mg, 3.0 mmol), methyl 4-hydroxy-3-methoxybenzoate (546 mg, 3.0 mmol) and PPh₃ (786 mg, 3.0 mmol) in THF (15 mL) at 0° C. was added DIAD (606 mg, 3.0 mmol) dropwise. The mixture was stirred at r.t. for 2 h. The reaction was quenched with sat. NaHCO₃ solution. The mixture was extracted with DCM (3×20 mL). The combined organic phase was washed with brine, dried over anhydrous sodium sulfate and concentrated at low pressure. The residue was purified by flash column chromatography on silica gel to give 422-3 (667 mg, 66%).

A solution of 422-3 (2.0 g, 5.85 mmol) and Pd(OH)₂ (0.2 g) in MeOH (20 mL) was stirred under H₂ atmosphere (50 psi) at r.t. overnight. The mixture was filtered, and the filtrate was evaporated to give crude 422-4 (1.5 g), which was used without further purification.

To a solution of 422-4 (150 mg, 0.597 mmol) in THF (10 mL) at 0° C. was added NaH (47.8 mg, 1.195 mmol), and the mixture was stirred at 0° C. for 0.5 h. The mixture was treated with SEMCl (149 mg, 0.896 mmol), and the mixture was allowed to warm to r.t. over 30 mins. The reaction was quenched with water, and extracted with EA (2×30 mL). The combined organic phase was washed with brine, dried over anhydrous Na₂SO₄ and concentrated under reduced pressure. The residue was purified by column chromatography on silica gel (PE:EA 20:1) to give 422-5 (110 mg, 48.2%).

To a solution of 422-5 (600 mg, 1.57 mmol) in co-solvent THF:H₂O (1:1, 10 mL) was added NaOH (126 mg, 3.14 mmol in 2 mL water). The mixture was stirred at r.t. for 1 h. The organic solvent was evaporated under reduced pressure, and the aqueous layer was acidified to pH 4~5 with 1M HCl solution. The mixture was extracted with EA (2×20 mL). The combined organic phase was dried over anhydrous sodium sulfate and concentrated at low pressure to give 422-6 (480 mg, 83.0%).

Compound 422-8 was prepared essentially as described in the preparation of 403 by using 422-6 and 422-7. Compound 422-8 was obtained as a white solid (180 mg, 66.9%). +ESI-MS: m/z 661.0 [M+H]⁺.

A suspension of 422-8 (180 mg, 0.273 mmol) in HCl: dioxane (4M, 15 mL) was stirred at r.t. for 30 mins. The mixture was concentrated under reduced pressure to give crude 422-9. The residue was diluted with sat. NaHCO₃ (10 mL), and extracted with EA (2×10 mL). The combined organic phase was washed with brine, dried over anhydrous sodium sulfate and concentrated at low pressure. The residue was purified by column chromatography on silica gel (PE: EA 5:1 to 1:1) to give 422-9 (90 mg, 62.3%).

Compound 422-9 (90 mg) was separated by SFC separation to give two enantiomers: 422 (25 mg) and 423 (27 mg). 422: +ESI-MS: m/z 531.0 [M+H]⁺. 423: +ESI-MS: m/z 531.0 [M+H]⁺.

Example 211

Preparation of Compound 424

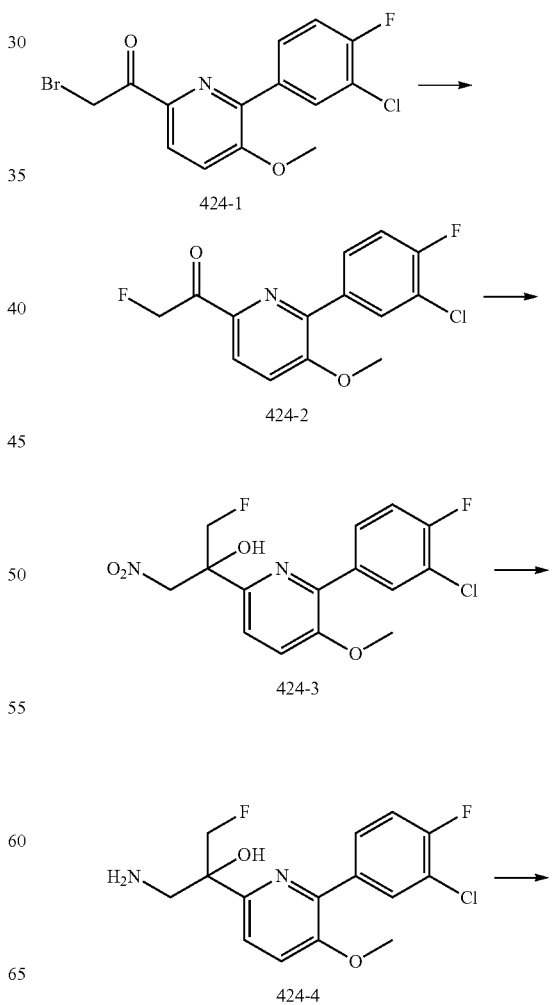

-continued

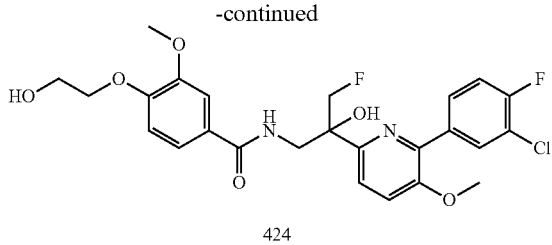

424

To a solution of 424-1 (1.05 g, 3.0 mmol) and 18-crowm-6 (800 mg, 3.1 mmol) in CH₃CN (50 mL) was added CsF (900 mg, 6.0 mmol). The mixture was heated to reflux for 1 h and the concentrated under reduced pressure. The residue was purified by column chromatography (PE: EA 10:1) to provide 424-2 as a white solid (360 mg, 40%).

A 50 mL round bottom flask with a magnetic stirring bar was charged with 424-2 (360 mg, 1.2 mmol), MeNO₂ (5 mL) and Et₃N (303 mg, 3.0 mmol). The mixture was stirred at r.t. for 10 h and then concentrated under reduced pressure. The residue was purified by column chromatography (PE: DCM 2:1) to give 424-3 (270 mg, 63%).

To a stirred mixture of 424-3 (271 mg, 0.75 mmol) and NiCl₂ (127 mg, 1 mmol) in MeOH (10 mL) was added NaBH₄ (380 mg, 1.0 mmol) in portions until the starting materials was consumed. The mixture was concentrated under reduced pressure, and the residue was purified by column chromatography (EA:EtOH 10:1) to give 424-4 as a colorless oil (130 mg, 50%). +ESI-MS: m/z 328.8 [M+H]⁺.

Compound 424 was prepared essentially as described in the preparation of 403 by using the 424-4 and 4-(2-hydroxy-ethoxy)-3-methoxybenzoic acid. The product was purified by prep-HPLC. Compound 424 was obtained as a white solid (180 mg, 66.9%). +ESI-MS: m/z 523.2 [M+H]⁺.

Example 212

Preparation of Compound 425

Compound 425-3 was prepared essentially as described in the preparation of 403 by using 425-1 and 425-2. The crude was purified by column chromatography (PE:EA 1:1) to give 425-3 (190 mg). +ESI-MS: m/z 654.9 [M+H]⁺.

To a solution of 425-3 (190 mg, 0.29 mmol) in dioxane (15 mL) was added conc. HCl (5.0 mL). The mixture was stirred at r.t. for 1 h, neutralized with sat. NaHCO₃ solution and extracted with EA (3×10 mL). The organic layer was dried over anhydrous sodium sulfate, and concentrated at low pressure. The residue was purified by prep-HPLC to give 425 (21 mg, 13.5%) as a white solid. +ESI-MS: m/z 534.9 [M+H]⁺.

Example 213

Preparation of Compound 426

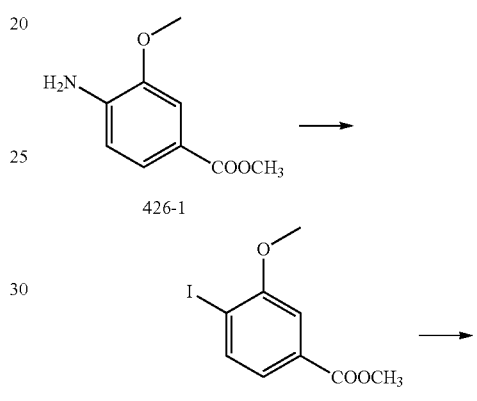

426-1

426-2

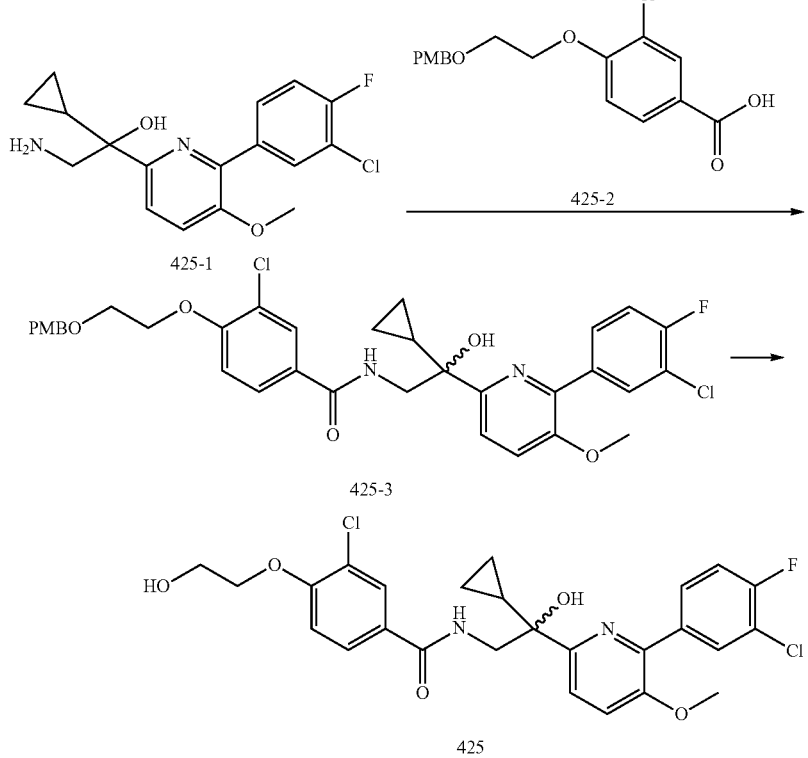

425-1

425-3

425

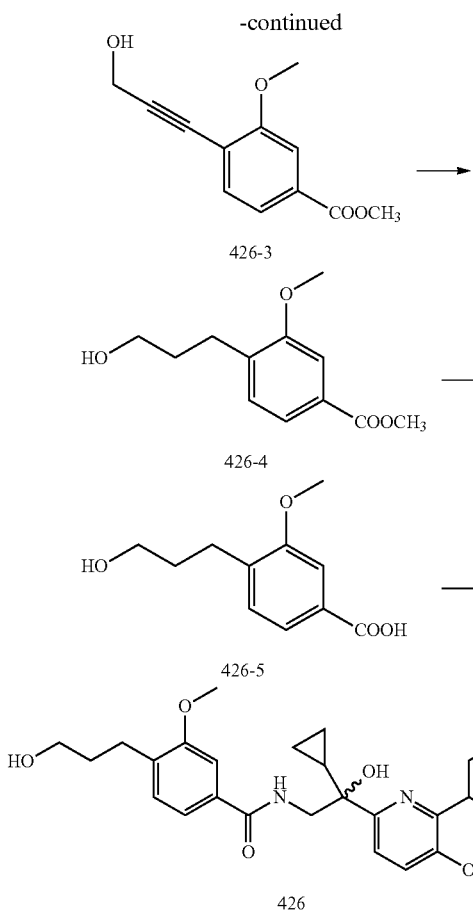

mixture was stirred at 50° C. for 1 h, cooled to 0° C., and acidified to pH 5 with HCl (2 M) solution. The mixture was extracted with EA (4×50 mL). The combined organic layer was dried over anhydrous sodium sulfate and concentrated in vacuum to give 426-5 (0.50 g, 80.0%) as a yellow solid, which was used without further purification.

Compound 426 was prepared essentially as described in the preparation of 403 by using 426-5 and 2-amino-1-(6-(3-chloro-4-fluorophenyl)-5-methoxypyridin-2-yl)-1-cyclopropylethanol. The crude was purified by prep-HPLC to give 426 (35 mg, 13.3%) as a white solid. +ESI-MS: m/z 529.0 [M+H]$^+$.

Example 214

Preparation of Compound 427

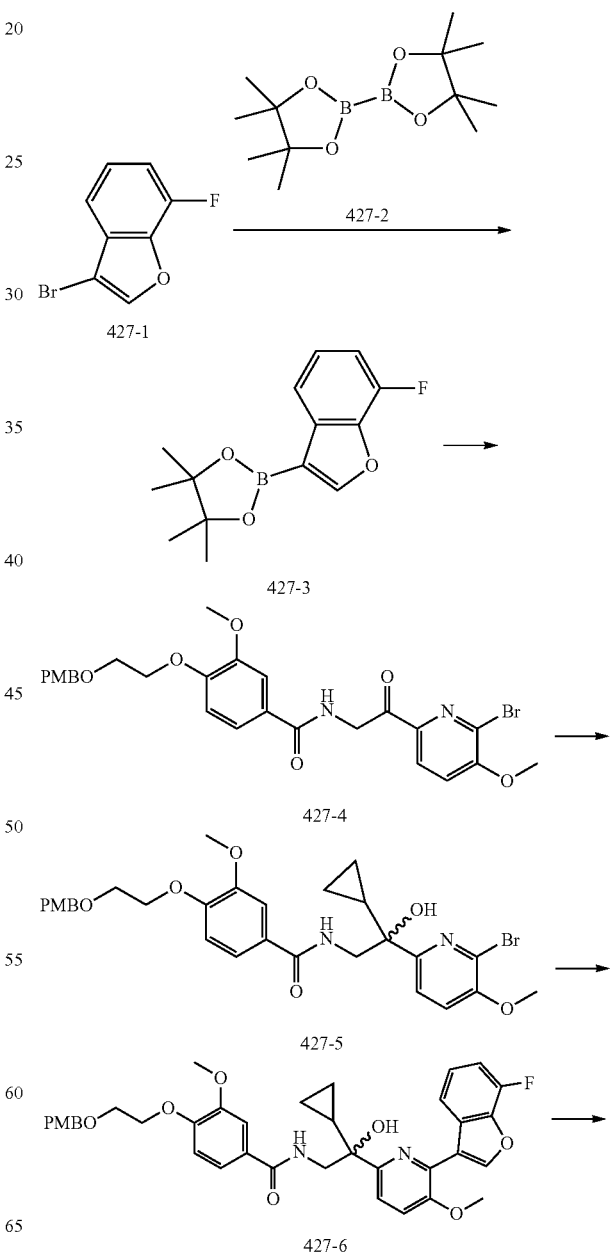

To a stirred solution of 426-1 (16.2 g, 90 mmol) in HCl (6 N, 300 mL) at 0° C. was added a solution of NaNO$_2$ (6.90 g, 99 mmol) in water (15 mL) dropwise. The mixture was stirred at 0° C. for 1 h and then treated with a solution of KI (75 g, 450 mmol) in water (150 mL). The mixture was stirred for 30 mins and then extracted with EA (4×100 mL). The combined organic layer was dried over anhydrous sodium sulfate and concentrated at low pressure. The residue was purified by column chromatography (PE:EA 10:1) to give 426-2 (21.2 g, 80.5%) as a light yellow solid.

To a suspension of 426-2 (8.77 g, 30 mmol), CuI (1.14 g, 6 mmol), PdCl$_2$(PPh$_3$)$_2$ (1.05 g, 1.5 mmol) and NEt$_3$ (21 mL, 150 mmol) in THF (150 mL) was added propiolic alcohol (3.36 g, 60 mmol) under N$_2$ atmosphere. The mixture was stirred at r.t. overnight and then filtered through a celite pad. The filtrate was concentrated to dryness and the residue was diluted with EA (200 mL). The solution was washed with brine, dried over anhydrous sodium sulfate and concentrated at low pressure. The residue was purified by column chromatography on silica gel (PE:EA 1:1) to give 426-3 (5.1 g, 77.3%) as a light yellow solid.

To a solution of 426-3 (2.2 g, 10 mmol) in MeOH (100 mL) was added Pd/C (0.5 g) under N$_2$. The mixture was degassed and refilled with hydrogen (3×). The mixture was stirred under H$_2$ atmosphere (40 psi) overnight. The mixture was filtered through a celite pad and the filtrate was concentrated in vacuum to give crude 426-4. The residue was purified by column chromatography on silica gel (PE:EA 1:1) to give 426-4 (1.62 g, 72.3%) as a light yellow oil.

To a solution of 426-4 (0.67 g, 3 mmol) in EtOH (7.5 mL) and water (2.5 mL) was added NaOH (0.48 g, 12 mmol). The

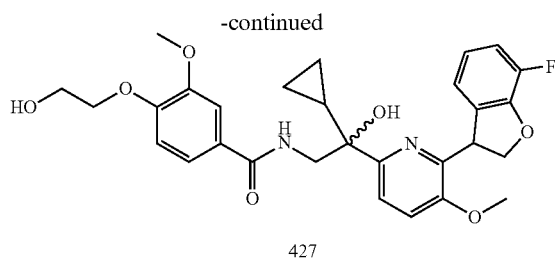

427

To a suspension of 427-1 (1.0 g, 4.67 mmol) in dioxane (30 mL) were added 427-2 (2.37 g, 9.346 mmol), AcOK (1.37 g, 14.0 mmol) and Pd(dppf)Cl$_2$ (0.346 g, 0.467 mmol). The mixture was stirred at 80° C. under N$_2$ atmosphere for 16 h. The mixture was cooled to r.t., poured into water (100 mL), and extracted with DCM (3×50 mL). The combined organic layer was washed with brine, dried over anhydrous sodium sulfate and concentrated at low pressure. The residue was purified by column chromatography (PE:EA 50:1) to give 427-3 (1.4 g, contain 0.3-0.4 g of 427-2).

To a solution of 427-4 (310 mg, 0.554 mmol) in THF (10 mL) at 0° C. was added cyclopropyl-magnesium bromide (11 mL, 0.5 M in THF) dropwise. The mixture was stirred for 1 h and then warmed to r.t. The reaction was quenched with sat. NH$_4$Cl (10 mL) solution, and extracted with EA (2×20 mL). The combined organic phase was washed with sat. NaHCO$_3$ solution, and brine. The organic layer was dried over anhydrous Na$_2$SO$_4$ and concentrated at low pressure. The residue was purified by column chromatography on silica gel (30% EA in PE) to give 427-5 (170 mg, 51.0%). +ESI-MS: m/z 601.1 [M+H]$^+$.

To a suspension of 427-5 (120 mg, 0.2 mmol) in a mixture of dioxane and H$_2$O (9:1, 10 mL) were added Cs$_2$CO$_3$ (195.6 mg, 0.6 mmol), 427-3 (108.6 mg, 0.3 mmol) and Pd(dppf)Cl$_2$ (16.3 mg, 0.02 mmol) under N$_2$ atmosphere. The mixture was stirred at 70° C. for 2 h. The mixture was cooled to r.t., poured into water (50 mL) and extracted with EA (2×50 mL). The combined organic phase was washed with brine, dried over anhydrous Na$_2$SO$_4$ and concentrated at low pressure. The residue was purified by column chromatography (10~30% EA in PE) to give 427-6 (121 mg, 92.2%). +ESI-MS: m/z 657.1 [M+H]$^+$.

A suspension of 427-6 (121 mg, 0.184 mmol) and Pd/C (20 mg) in MeOH (20 mL) was stirred under H$_2$ atmosphere (balloon) at r.t. overnight. The solution was filtered, and the filtrate was concentrated in vacuum. The residue was purified by prep-HPLC to give 427 (17 mg, 10.1%) as a white solid. +ESI-MS: m/z 539.1 [M+H]$^+$.

Example 215

Preparation of Compound 428

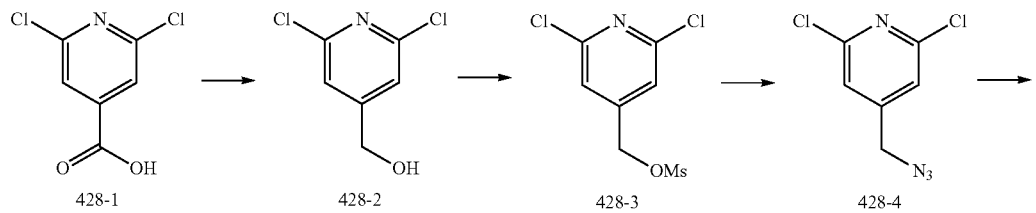

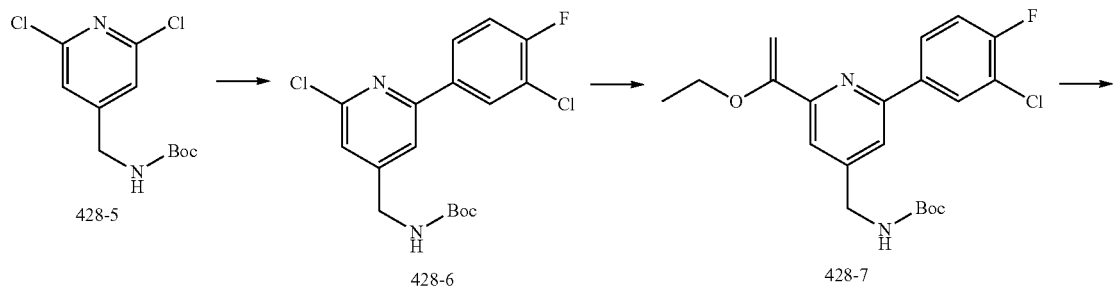

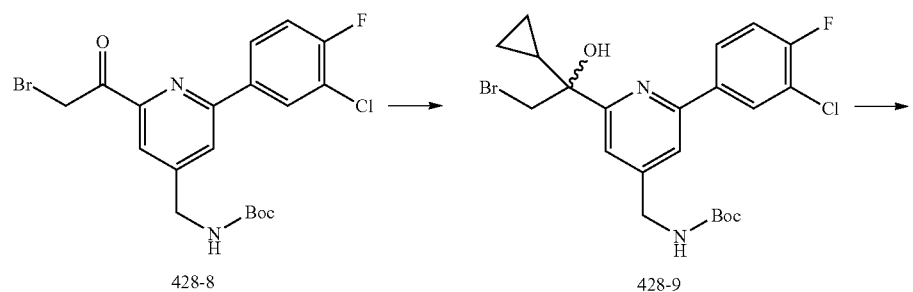

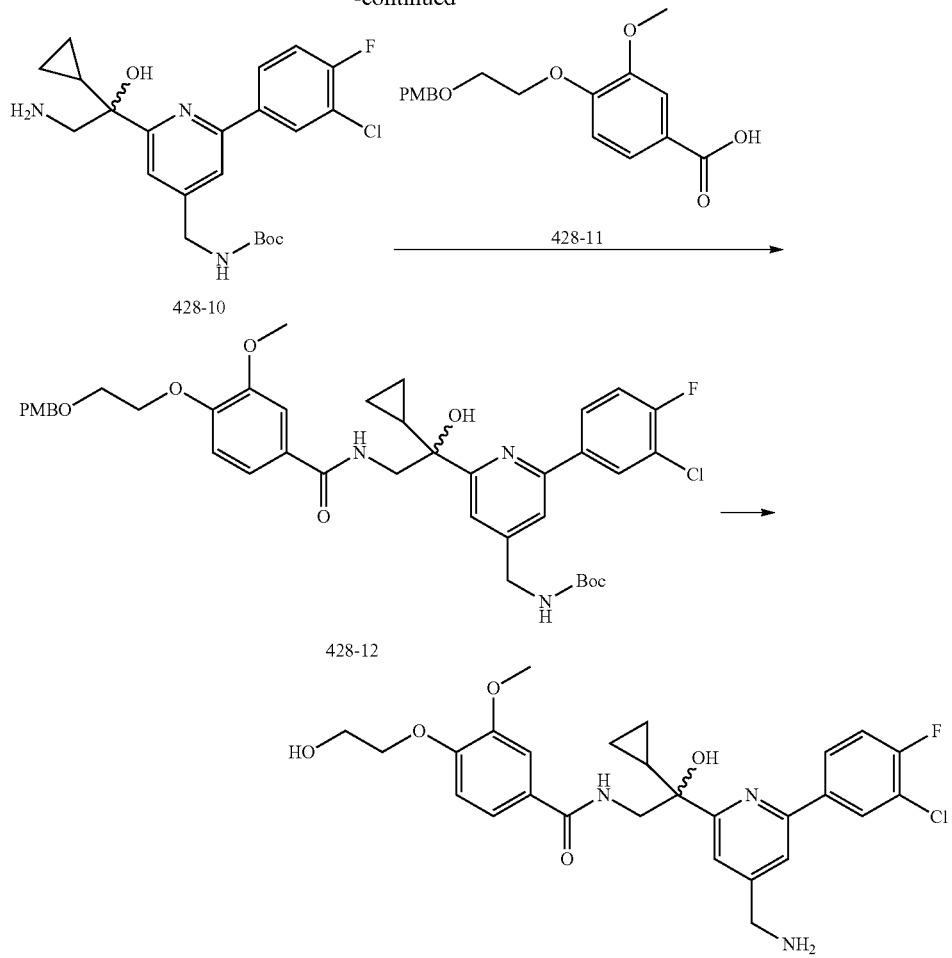

Compound 428-2 was prepared as provided in Mello et al., *J. Am. Chem. Soc.* (2005) 127(29):10124-10125, which is hereby incorporated by reference for the limited purpose of its description of the preparation of 428-2. Compound 428-3 was prepared as provided in PCT Publication No. WO 2002/034745, published May 2, 2002, which is hereby incorporated by reference for the limited purpose of its description of the preparation of 428-3.

To a solution of 428-3 (8 g, 38 mmol) in DMF (100 mL) were added $K_2CO_3$ (9.5 g, 69 mmol) and $NaN_3$ (3 g, 46 mmol) at r.t. The solution was stirred for 2 h, poured into $H_2O$ (100 mL) and extracted with EA (3×100 mL). The combined organic phase was washed with brine, dried over anhydrous sodium sulfate and concentrated at low pressure. The residue was purified by column chromatography (PE: EA 10:1) to give 428-4 (5.1 g, 66.1%).

To a solution of 428-4 (5 g, 23.4 mmol) in EtOH (50 mL) were added $Boc_2O$ (6.11 g, 28 mmol) and Pd/C (1 g) at r.t. under $N_2$. The solution was degassed and refilled with $H_2$ (3×). The mixture was stirred at r.t. under $H_2$ atmosphere (balloon) for 18 h. The solution was filtered, and the filtrate was concentrated to dryness. The residue was purified by chromatography on silica gel (PE:EA 10:1) to give 428-5 (2.2 g, 34.4%).

To a solution of 428-5 (2.2 g, 7.9 mmol) and (3-chloro-4-fluorophenyl)boronic acid (1.39 g, 7.9 mmol) in a mixture of dioxane and $H_2O$ (20 mL/5 mL) were added $Pd(dppf)Cl_2$ (289 g, 0.395 mmol) and $K_2CO_3$ (1.63 g, 11.85 mmol). The mixture was degassed and refilled with $N_2$ (3×). The mixture was stirred under $N_2$ at 40° C. for 3 h. The mixture was cooled to r.t., and diluted with EA (100 mL) and water (100 mL). The organic phase was washed with brine, dried over anhydrous sodium sulfate and concentrated at low pressure. The residue was purified by column chromatography on silica gel (PE:EA 10:1) to give 428-6 (2.923 g, 100%) as a white solid. +ESI-MS: m/z 370.8 $[M+H]^+$.

To a solution of 428-6 (1.2 g, 3.24 mmol), tributyl(1-ethoxyvinyl)stannane (2.34 g, 6.48 mmol) and KF (751 mg, 12.96 mmol) in DMF (15 mL) was added $Pd(dppf)Cl_2$ (237 mg, 0.324 mmol) under $N_2$. The mixture was stirred at 80° C. for 2 h. After cooling to r.t., the mixture was diluted with EA (100 mL) and water (50 mL). The organic phase was washed with brine, dried over anhydrous sodium sulfate and concentrated at low pressure to give crude 428-7 (1.35 g crude), which was used in the next step directly. +ESI-MS: m/z 407.1 $[M+H]^+$.

Compound 428-7 (1.315 g, 3.24 mmol) was dissolved in THF (20 mL) and $H_2O$ (2 mL). The solution was treated with NBS (1.13 g, 6.4 mmol) at r.t., and stirred for 20 mins. The mixture was concentrated at low pressure, and the residue was purified by column chromatography on silica gel (PE:EA 10:1) to give 428-8 (1.4 g, 94.5%). +ESI-MS: m/z 459.1 $[M+H]^+$.

Compound 428-9 was prepared essentially as described in the preparation of 406 by using 428-8. Crude 428-9 (410 mg, 63%) was used directly in the next step. Compound 428-10 was prepared essentially as described in the preparation of 406 by using crude 428-9. Crude 428-10 (205 mg, 57.6%) was used directly in the next step. +ESI-MS: m/z 436.3 [M+H]+. Compound 428-11 was prepared essentially as described in the preparation of 406 by using crude 428-10 and 3-methoxy-4-(2-((4-methoxybenzyl)oxy)ethoxy)benzoic acid. Crude 428-11 was purified by column chromatography on silica gel (50% EA in PE) to give purified 428-11 (106 mg, 30.1%).

To a solution of 428-11 (100 mg, 0.13 mmol) in dioxane (2 mL) was added conc. HCl (2 mL) at r.t., and the mixture was stirred for 30 mins. The mixture was neutralized using a sat. Na$_2$CO$_3$ solution, and extracted with EA (3×10 mL). The combined organic layer was washed with brine, dried over anhydrous Na$_2$SO$_4$ and concentrated at low pressure. The residue was purified by prep-HPLC to give 428 (15 mg, 21.2%) as a white solid. +ESI-MS: m/z 530.0 [M+H]+.

Example 216

Preparation of Compounds 429, 430 and 431

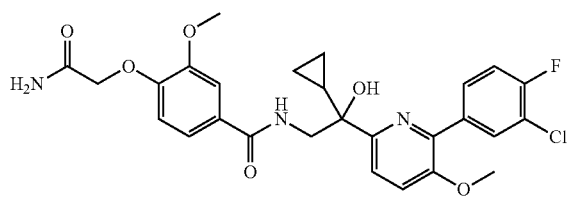

429, 430 & 431

Compound 429 was prepared essentially as described in the preparation of 403 by using 403-3 and 406-3. Compound 429 was obtained as a white solid (50 mg). +ESI-MS: m/z 544.1 [M+H]+.

Compound 429 was separated via SFC separation to give two enantiomers: 430 (3.22 mg, 12.9%) and 431 (3.45 mg, 13.8%). 430: +ESI-MS: m/z 544.1 [M+H]+. 431: +ESI-MS: m/z 544.1 [M+H]+.

Example 217

Preparation of Compound 432

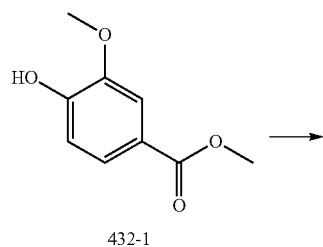

432-1

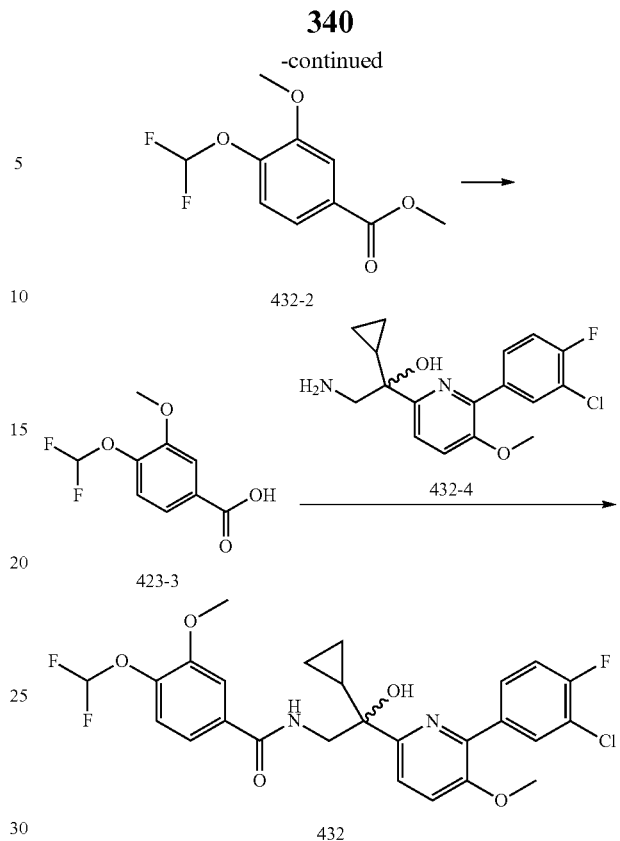

To a solution of 432-1 (2.0 g, 10.99 mmol) in DMF (20 mL) were added ClCF$_2$COONa (3.0 g, 19.74 mmol) and K$_2$CO$_3$ (4.4 g, 31.88 mmol). The mixture was stirred at 95° C. for 5 h. After cooling to r.t., the mixture was poured into water (100 mL) and extracted with EA (3×50 mL). The combined organic layers were washed with brine, dried over anhydrous sodium sulfate and concentrated at low pressure. The residue was purified by column chromatography on silica gel (5~20% EA in PE) to give 432-2 (1.3 g, 51.0%).

Compound 432-3 was prepared essentially as described in the preparation of 426 using 432-2. Compound 432-3 was obtained as a white solid (1.19 g, 97.5%). Compound 432 was prepared essentially as described in the preparation of 406 by using 432-3 and 432-4. Compound 432 was obtained after purification by prep-HPLC as a white solid (70 mg, 21.7%). +ESI-MS: m/z 537.1 [M+H]+.

Example 218

Preparation of Compound 433

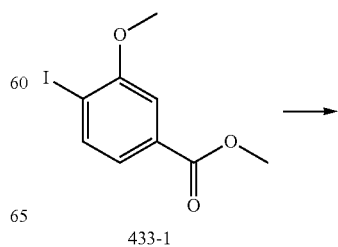

433-1 after purification by prep-HPLC as a white solid (32 mg, 8.2%). +ESI-MS: m/z 515.0 [M+H]+.

Example 219

Preparation of Compound 434

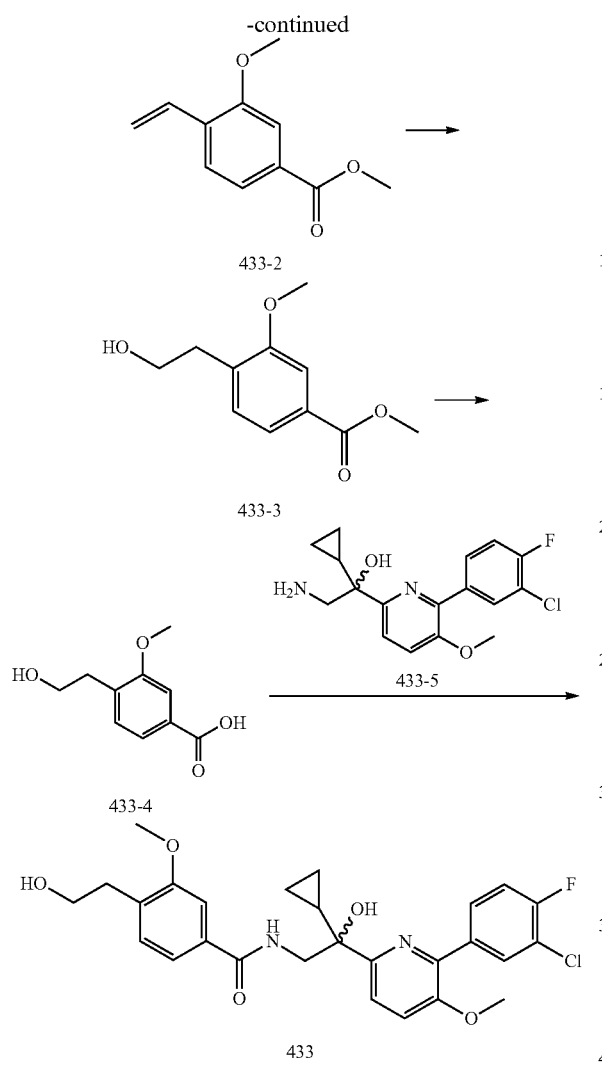
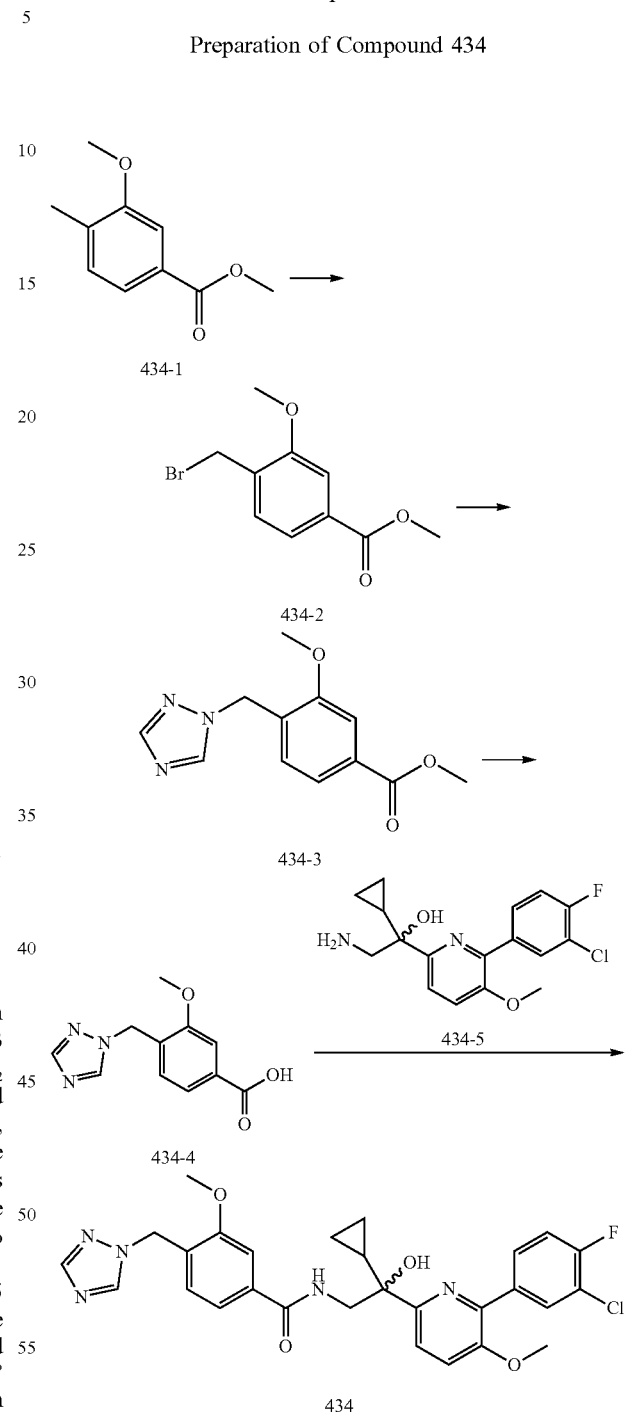

To a solution of 433-1 (2 g, 6.8 mmol), potassium trifluoro(vinyl)borate (0.917 mg, 6.8 mmol) and Et$_3$N (1.73 g, 17.12 mmol) in MeOH (30 mL) was added Pd(dppf)Cl$_2$ (497 mg, 0.68 mmol) under N$_2$. The mixture was stirred under N$_2$ at 70° C. for 15 h. The solution was cooled to r.t., and diluted with EA (100 mL) and water (50 mL). The organic phase was washed with brine, dried over anhydrous sodium sulfate and concentrated at low pressure. The residue was purified by column chromatography on silica gel (3% EA in PE) to give 433-2 as a colorless oil (1.1 g, 84.6%).

To a solution of 433-2 (730 mg, 3.84 mmol) in THF (15 mL) was added BH$_3$.THF (4 mL, 1 M) at 0° C., and the reaction was stirred at 0° C. for 1 h. The solution was treated with NaOH (10 mL, 1 M in water) and H$_2$O$_2$ (3 mL) at 0° C. The mixture was stirred at r.t. for 1 h, and extracted with EA (3×30 mL). The combined organic phase was washed with brine, dried over anhydrous sodium sulfate and concentrated at low pressure. The residue was purified by column chromatography (PE:EA 5:1) to give 433-3 (320 mg. 40.4%).

Compound 433-4 was prepared essentially as described in the preparation of 426 using 433-3. Compound 433-4 obtained as a white solid (210 mg, 70.7%). Compound 433 was prepared essentially as described in the preparation of 406 by using 433-4 and 433-5. Compound 433 was obtained Compound 434-2 was prepared as described in PCT Publication No. WO 2009/055077, published on Apr. 30, 2009, which is hereby incorporated by reference for the limited purpose of its description of the preparation of 434-2.

To a suspension of 1,2,4-triazole (0.52 g, 7.51 mmol), and K$_2$CO$_3$ (2.57 g, 20.49 mmol) in DMF (15 mL) was added 434-2 (1.77 g, 6.83 mmol) at 0° C., and stirred at r.t.

overnight. The mixture was poured into water (100 mL), and extracted by EA (4×100 mL). The combined organic layers were washed with brine, dried over anhydrous sodium sulfate and concentrated at low pressure. The residue was purified by column chromatography Compound 434-4 was prepared essentially as described in the preparation of 426 by using 434-3. Compound 434-4 was obtained as a white solid (0.4 g, 57.2%). Compound 434 was prepared essentially as described in the preparation of 406 by using 434-4 and 434-5. Compound 434 was obtained after purification by prep-HPLC as a white solid (135 mg, 27.2%). +ESI-MS: m/z 552.1 [M+H]⁺.

Example 220

Preparation of Compound 435

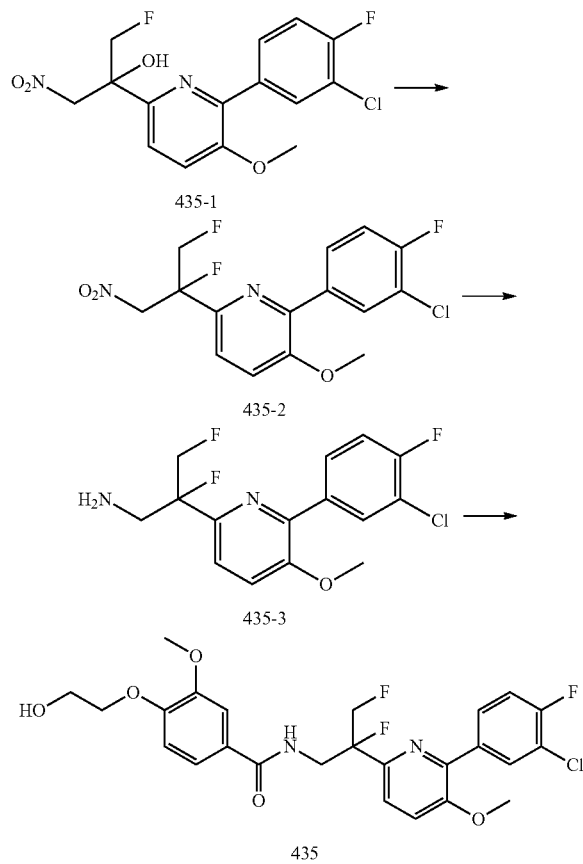

To a solution of 435-1 (270 mg, 0.75 mmol) in DCM (10 mL) was added BAST (220 mg, 1.0 mmol) at r.t. The mixture was stirred at r.t. for 1 h. The reaction was quenched with sat. NaHCO₃ solution (20 mL), extracted with EA (3×30 mL). The combined organic phase was washed with brine, dried over anhydrous sodium sulfate and concentrated under reduced pressure. Crude 435-2 (271 mg, 99%) was used without further purification.

To a solution of 435-2 (271 mg, 0.75 mmol) and NiCl₂ (127 mg, 1 mmol) in MeOH (10 mL) was added NaBH₄ (380 mg, 1.0 mmol) in portions until the starting materials was consumed. The reaction was quenched by water (10 mL), and extracted with EA (3×30 mL). The organic phase was washed with brine, dried over anhydrous Na₂SO₄, and concentrated under reduced pressure. The residue was purified by column chromatography on silica gel (10% EtOH in EA) to give 435-3 as a colorless oil (130 mg, 50%). +ESI-MS: m/z 331.1 [M+H]⁺.

Compound 435 was prepared essentially as described in the preparation of 406 by using 435-4 and 435-5. Compound 435 was obtained after purification by prep-HPLC as a white solid (85 mg, 47%). +ESI-MS: m/z 525.2 [M+H]⁺.

Example 221

Preparation of Compound 436

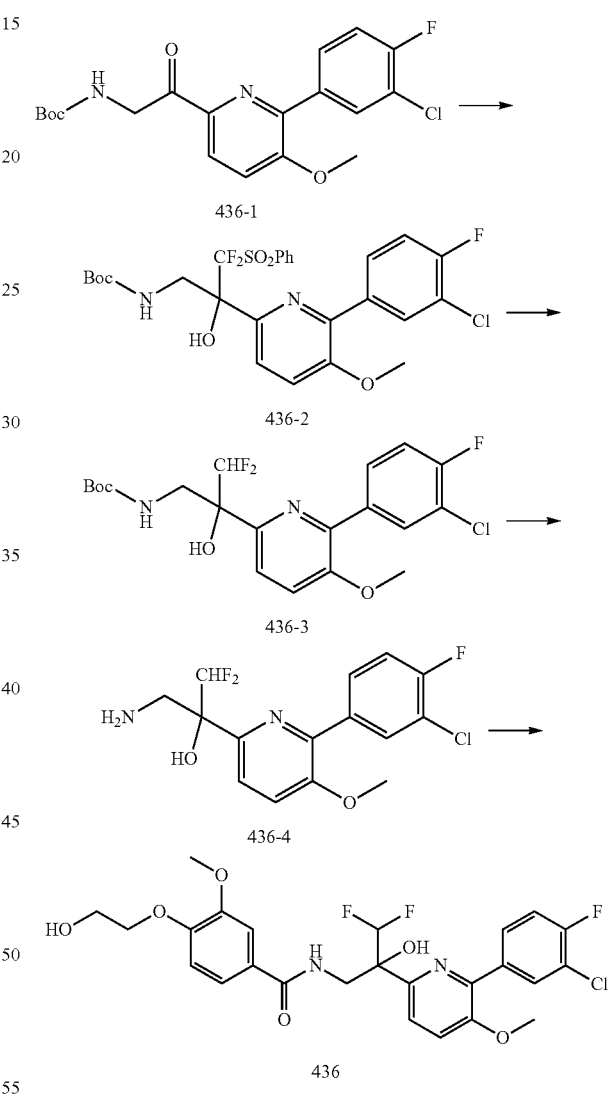

To a stirred solution of 436-1 (800 mg, 2.02 mmol) and PhSO₂CHF₂ (465 mg, 2.42 mmol) in THF (10 mL) was added LDA (2 mL, 4 mmol) dropwise at −78° C. under N₂ atmosphere. The mixture was stirred at −78° C. for 2 h, and warmed to 0° C. for 30 mins. The reaction was quenched with sat. NH₄Cl solution, and extracted with EA (3×30 mL). The combined organic phase was washed with brine, dried over anhydrous Na₂SO₄ and concentrated under reduced pressure. The residue was purified by column chromatography (PE:EA 3:1) to give 436-2 (610 mg, 51.6%). +ESI-MS: m/z 587.1 [M+H]⁺.

To a solution of 436-2 (610 mg, 1.04 mmol) in DMF (5 mL) were added HOAc (1 mL) and H₂O (1 mL) at r.t. The mixture was treated with magnesium (250 mg, 10.4 mmol) in portions. After stirring at r.t. for 6 h, the mixture was poured into ice-water (50 mL) and extracted with EA (3×30 mL). The combined organic phase was washed with brine, dried over anhydrous Na₂SO₄ and concentrated under reduced pressure to give 436-3 (320 mg, 68.9%). +ESI-MS: m/z 446.9 [M+H]⁺.

To a solution of 436-3 (320 mg, 0.72 mmol) in EA (3 mL) was added HCl/EA (3 mL, 4M). The solution was stirred at r.t. for 30 mins, and then concentrated to dryness. Crude 436-4 (220 mg, 90.9%) was used without purification.

Compound 436 was prepared essentially as described in the preparation of 406 by using 436-4 and 4-(2-hydroxy-ethoxy)-3-methoxybenzoic acid. Compound 436 was obtained after purification by prep-HPLC as white solid (40 mg, 11.7%). +ESI-MS: m/z 541.0 [M+H]⁺.

Example 222

Preparation of Compound 437

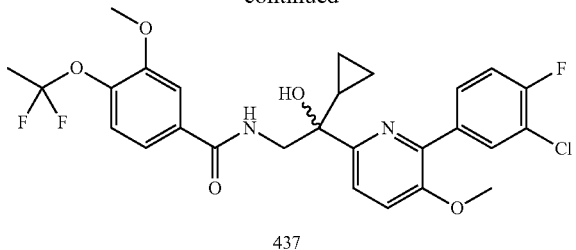

437

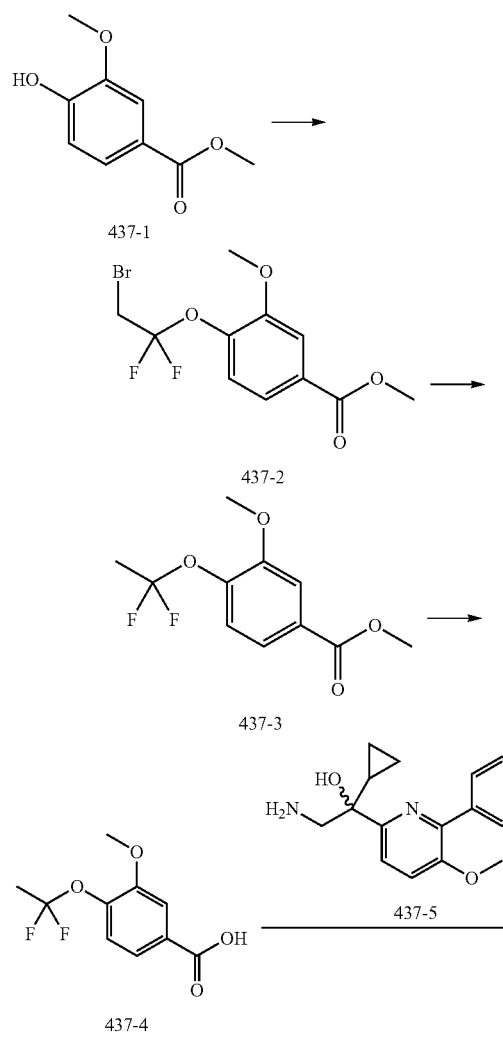

To a solution of 437-1 (1.0 g, 5.5 mmol) and K₂CO₃ (1.0 g, 7.3 mmol) in a mixture of CH₃CN (10 mL) and H₂O (2 mL) was added 2-bromo-1,1-difluoroethene (10.0 mL, ~2 M in acetonitrile) at 0° C. The mixture was stirred at 50° C. for 10 h. After cooling to r.t, the mixture was poured into water (50 mL) and extracted with EA (3×30 mL). The combined organic layers were washed with brine, dried over anhydrous Na₂SO₄ and concentrated under reduced pressure. The residue was purified by column chromatography (PE:EA 10:1) to give 437-2 as an oil (0.4 g crude).

To a solution of 437-2 (0.4 g, 1.2 mmol) in MeOH (20 mL) was added Pd/C (0.3 g) under N₂. The suspension was degassed and refilled with H₂ (3×). The mixture was stirred under H₂ (50 psi) at r.t. for 5 h. The suspension was filtered through a Celite pad, and the filtrate was concentrated to dryness. The residue was purified by column chromatography (PE:EA 9:1) to give 437-3 as a white solid (250 mg, 84.7%).

Compound 437-4 was prepared essentially as described in the preparation of 426 by using 437-3. Compound 437-4 was obtained as a white solid (201 mg, 85.1%). Compound 437 was prepared essentially as described in the preparation of 406 by using 437-4 and 437-5. Compound 437 was obtained after purification by prep-HPLC as white solid (50 mg, 36.4%). +ESI-MS: m/z 551.2 [M+H]⁺.

Example 223

Preparation of Compound 438

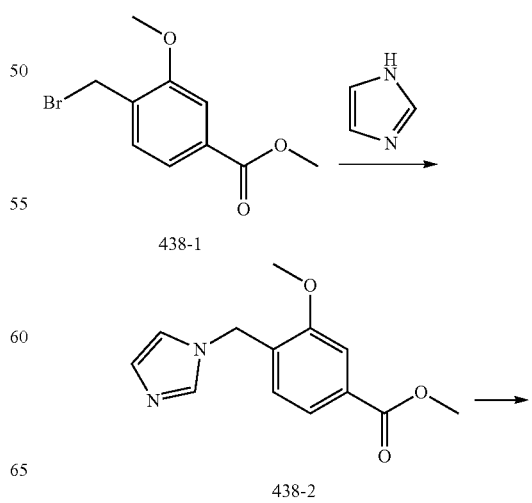

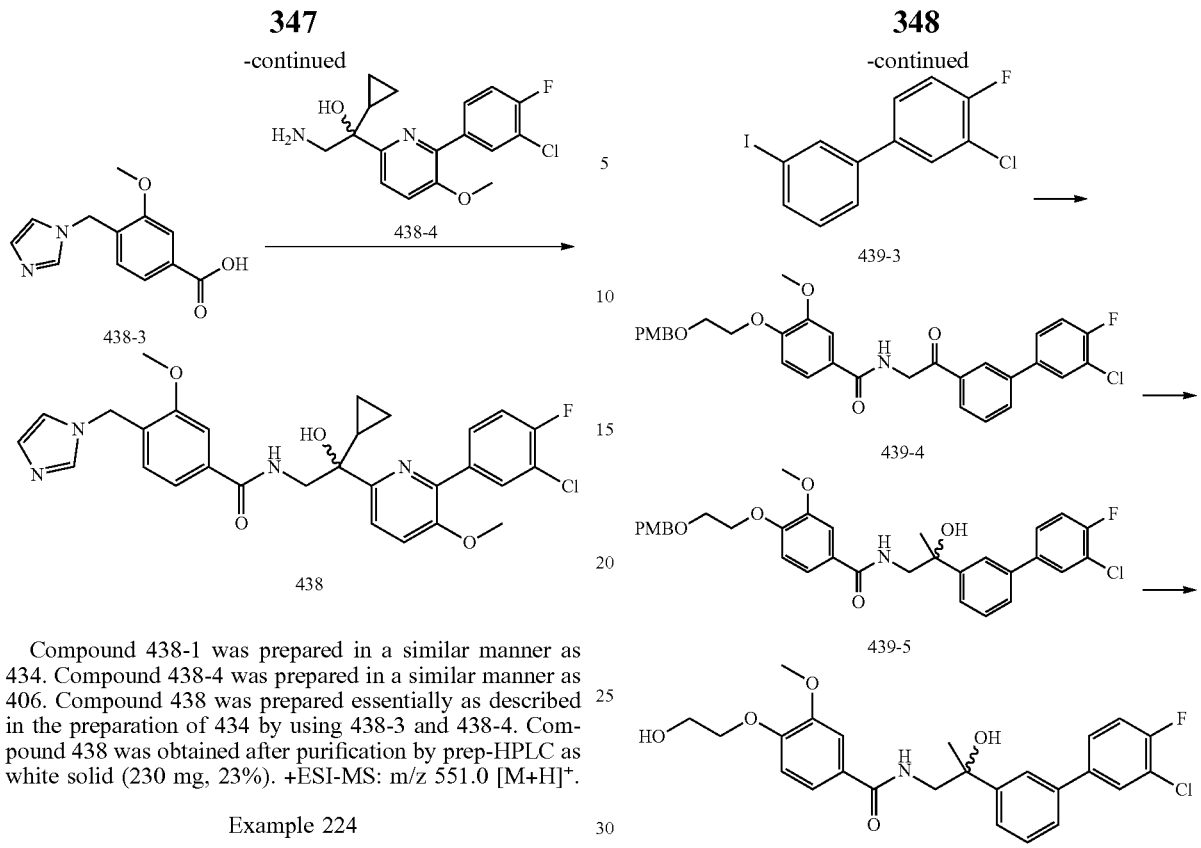

Compound 438-1 was prepared in a similar manner as 434. Compound 438-4 was prepared in a similar manner as 406. Compound 438 was prepared essentially as described in the preparation of 434 by using 438-3 and 438-4. Compound 438 was obtained after purification by prep-HPLC as white solid (230 mg, 23%). +ESI-MS: m/z 551.0 [M+H]+.

Example 224

Preparation of Compound 439

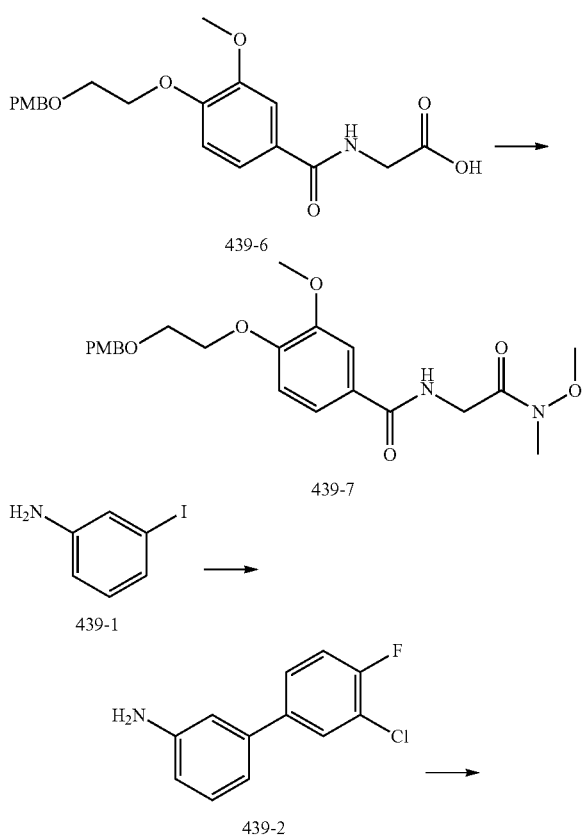

To a solution of 439-6 (2.334 g, 6 mmol) in DMF (20 mL) were added N,O-dimethyl-hydroxylamine hydrochloride (873 mg, 9 mmol), DIPEA (2.322 g, 18 mmol) and HATU (3.42 g, 9 mmol), and the mixture was stirred at r.t. for 1 h. The mixture was poured into water (50 mL), and extracted with EA (3×50 mL). The combined organic layer was washed with brine, dried over anhydrous Na$_2$SO$_4$ and concentrated under reduced pressure. The residue was purified by column chromatography (20-50% EA in PE) to give 439-7 (2.4 g, 92.7%). +ESI-MS: m/z 433.1 [M+H]+.

Compound 439-2 was prepared essentially as described in the preparation of 428 by using 439-1 and 3-chloro-4-fluorophenylboronic acid. Compound 439-2 was obtained as a white solid (0.61 g, 69.0%). Compound 439-3 was prepared essentially as described in the preparation of 426 by using 439-2. Compound 439-3 was obtained as a white solid (0.97 g, 58.8%).

To a solution of 439-3 (1.6 g, 4.8 mmol) and 439-7 (2.1 g, 4.8 mmol) in anhydrous THF (20 mL) was added isopropyl-magnesium chloride (18.5 mL, 24.1 mmol) dropwise at 0° C., and the mixture was stirred at r.t. for 1 h. The mixture was quenched with water, and extracted with EA (2×50 mL). The combined organic phase was washed with brine, dried over anhydrous Na$_2$SO$_4$ and concentrated under reduced pressure. The residue was purified by column chromatography (10~50% EA in PE) to give 439-4 (1.2 g, 64%). +ESI-MS: m/z 578.0 [M+H]+.

Compound 439-5 was prepared essentially as described in the preparation of 403 by using 439-4. Compound 439-5 was obtained as a white solid (160 mg, 27.0%). +ESI-MS: m/z 594.0 [M+H]+. Compound 439 was prepared essentially as described in the preparation of 425 by using 439-5. Compound 439 was obtained as a white solid (101 mg, 79.2%). +ESI-MS: m/z 473.8 [M+H]⁺.

Example 225

Preparation of Compound 440

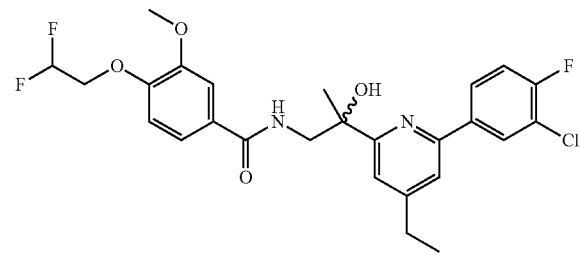

440

Compound 440 was prepared essentially as described in the preparation of 406 by using 2-bromo-1-(6-(3-chloro-4-fluorophenyl)-4-ethylpyridin-2-yl)ethanone. Compound 440 was obtained as a white solid (197 mg, 73%). +ESI-MS: m/z 523.1 [M+H]⁺.

Example 226

Preparation of Compound 441

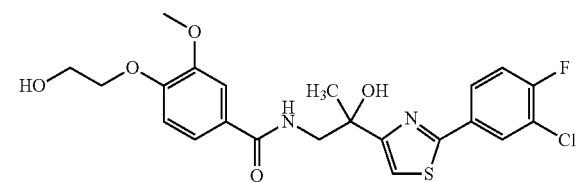

441

Compound 441 was prepared essentially as described in the preparation of 428 by using 2,4-dibromothiazole. Compound 441 was obtained as a white solid (60 mg, 35.7%). +ESI-MS: m/z 480.8 [M+H]⁺.

Example 227

Preparation of Compound 442

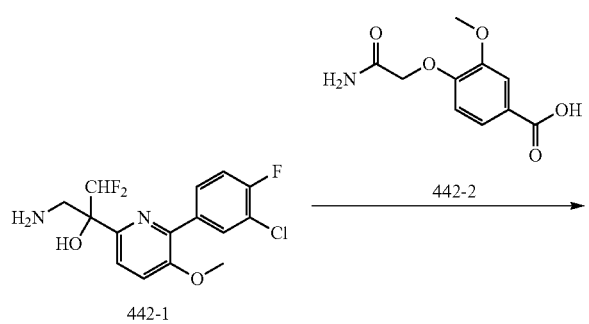

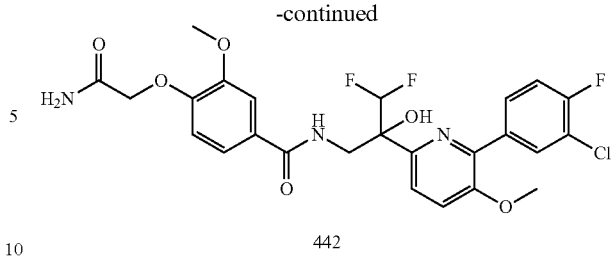

442

Compound 442-1 was prepared as essentially described in the preparation of 436. Compound 442-2 was prepared as essentially described in the preparation of 403. Compound 442 was prepared essentially as described in the preparation of 406 by using 442-1 and 442-2. Crude 442 was purified by prep-HPLC to give 442 as a white solid (65 mg, 13.3%). +ESI-MS: m/z 554.1 [M+H]⁺.

Example 228

Preparation of Compound 443

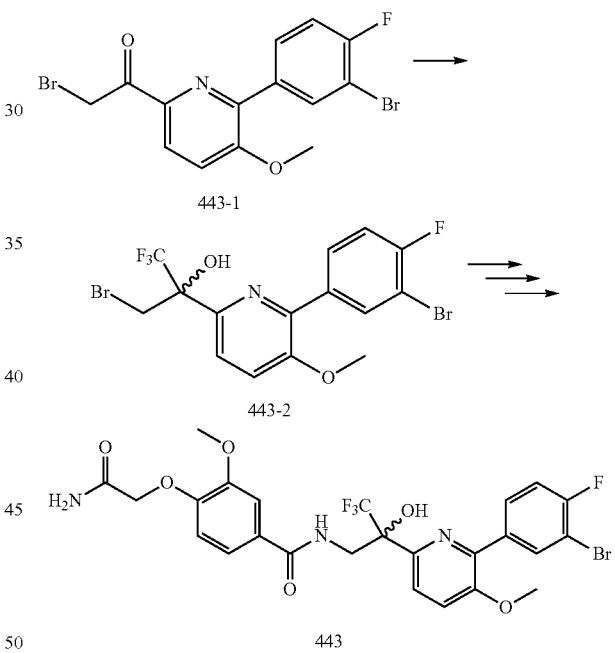

To a solution of 443-1 (511 mg, 1.27 mmol) in anhydrous DMF (5 mL) were added TMS-CF₃ (217 mg, 1.53 mmol) and LiOAc (8.4 mg, 0.127 mmol) at r.t., and the mixture was stirred for 24 h. The mixture was treated with HCl (1.5 mL, 1 M) solution, and stirred at r.t. for 1 h. The mixture was diluted with water (20 mL), and extracted with EA (2×40 mL). The combined organic layers were washed with brine, dried over anhydrous Na₂SO₄ and concentrated under reduced pressure. The residue was purified by flash column chromatography (PE:EA 5:1) to give 443-2 (131 mg, 21.8%).

Compound 443 was prepared essentially as described in the preparation of 428 by using 443-2 and 442-2. Compound 443 was obtained as a white solid (92 mg, 53.2%). +ESI-MS: m/z 616.0 [M+H]⁺.

Example 229

Preparation of Compound 444

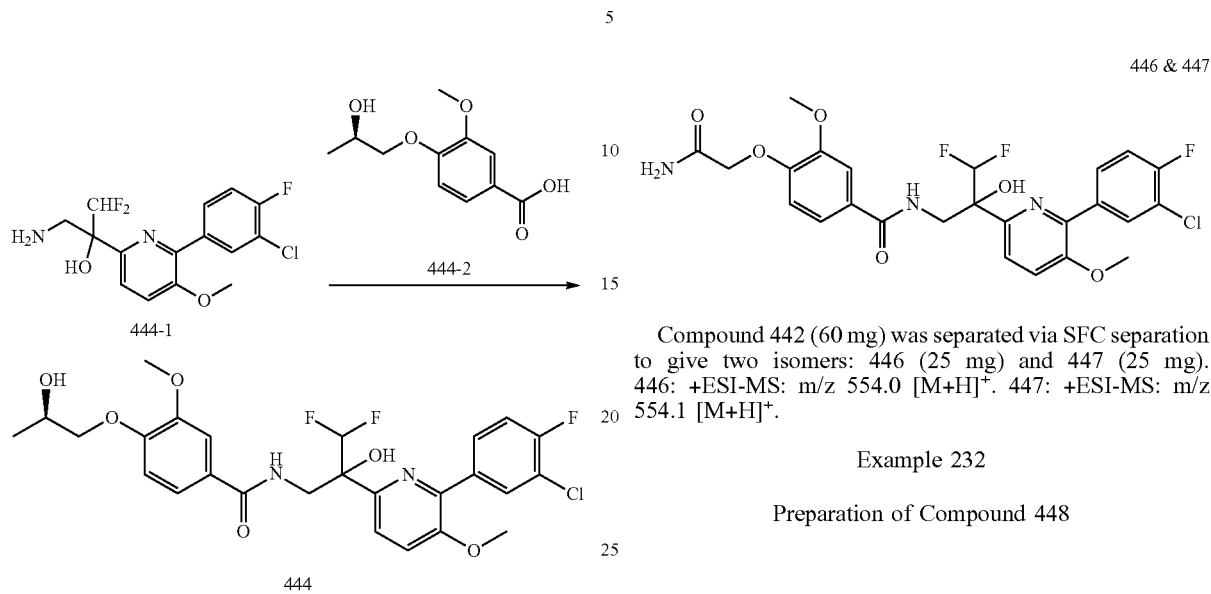

Compound 444 was prepared essentially as described in the preparation of 406 by using 444-1 and 444-2. Compound 444 was purified by prep-HPLC to give 444 as a white solid (55 mg, 25.4%). +ESI-MS: m/z 555.0 [M+H]$^+$.

Example 230

Preparation of Compound 445

Compound 445 was prepared essentially as described in the preparation of 406 by using 445-1 and 445-2. Compound 445 was purified by prep-HPLC to give 445 as a white solid (56 mg, 36.3%). +ESI-MS: m/z 537.0 [M+H]$^+$.

Example 231

Preparation of Compounds 446 and 447

Compound 442 (60 mg) was separated via SFC separation to give two isomers: 446 (25 mg) and 447 (25 mg). 446: +ESI-MS: m/z 554.0 [M+H]$^+$. 447: +ESI-MS: m/z 554.1 [M+H]$^+$.

Example 232

Preparation of Compound 448

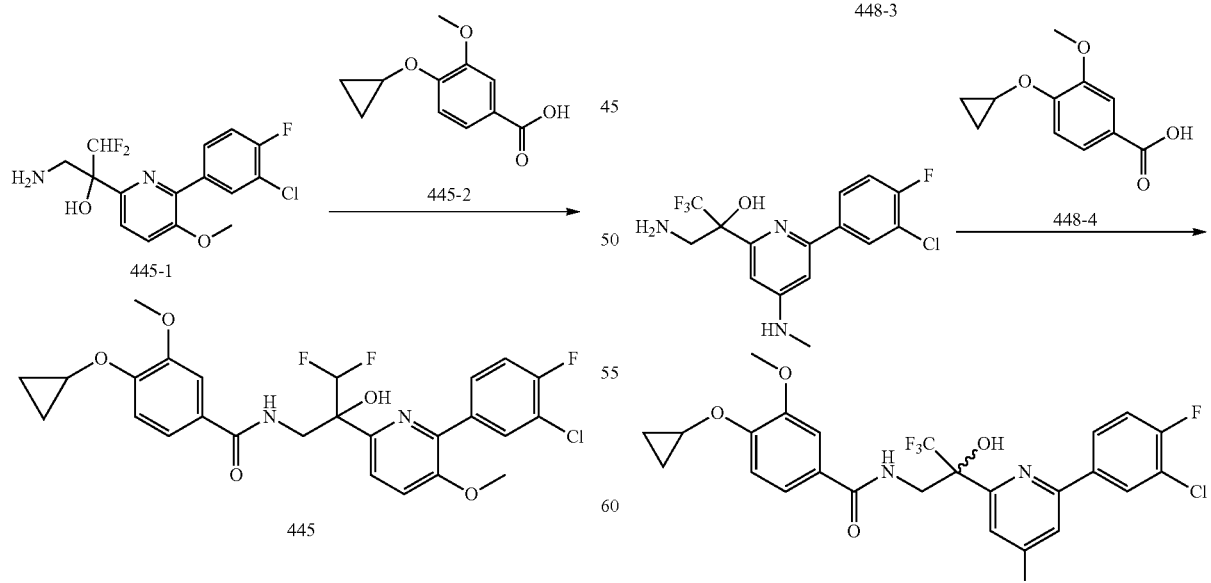

Compound 448-2 was prepared essentially as described in Jang et al., *Tet. Lett.* (2006) 47(50):8917-8920, which is hereby incorporated by reference for the limited purpose of its description of the preparation of 448-2. To a suspension of 448-2 (6.0 g, 22.9 mmol) and $K_2CO_3$ (6.3 g, 45.6 mmol) in $CH_3CN$ (40 mL) was added MeI (6.5 g, 45.6 mmol) at r.t. The solution was heated to 80° C. and stirred for 8 h. The precipitate was removed by filtration, and the organic layer was concentrated under reduced pressure. The residue was purified by column chromatography (PE:EA 20:1) to give 448-3 (5.5 g, 87.3%) as a white solid.

Compound 448 was prepared essentially as described in the preparation of 428 and 443 by using 448-3 and 448-4. Crude 448 was purified by prep-HPLC to give 448 as a white solid (40 mg, 51.9%). +ESI-MS: m/z 554.0 [M+H]$^+$.

Example 233

Preparation of Compounds 449 and 450

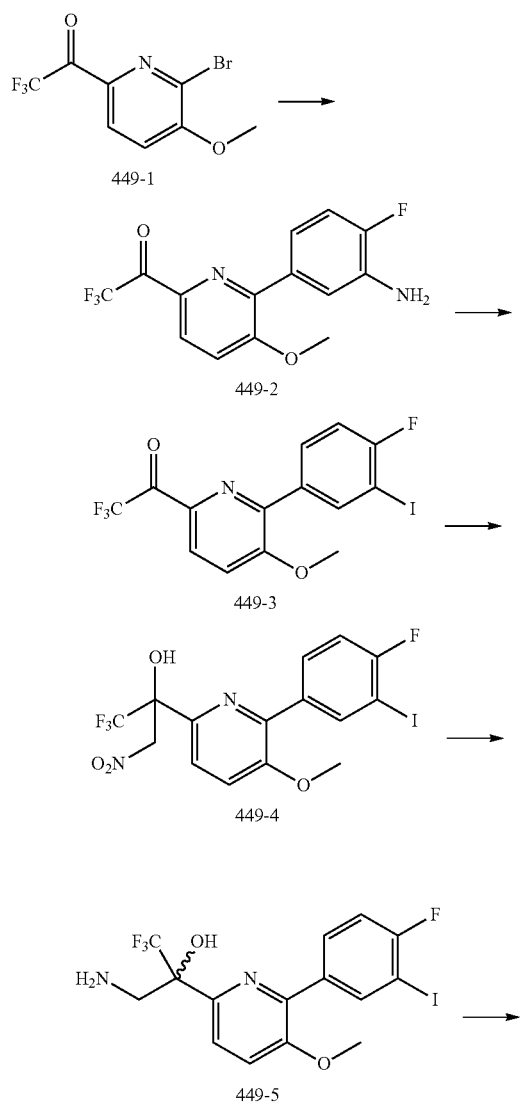

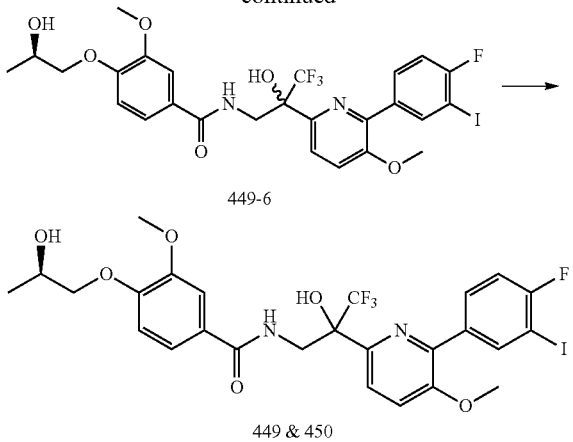

Step 1 and step 3 were conducted as essentially as described in the preparation of 232. Step 2 was conducted as essentially as described in the preparation of 426. To a solution of 449-4 (1.0 g, 2.06 mmol) in AcOH (10 mL) was added Fe (576 mg, 10.3 mmol) powder in portions. The mixture was stirred at 80° C. for 2 h. After cooling to r.t, the mixture was neutralized with sat. $Na_2CO_3$ solution, and extracted with EA (3×50 mL). The combined organic phase was washed with brine, dried over anhydrous $Na_2SO_4$ and concentrated under reduced pressure. The residue was purified by column (PE:EA 3:1) to give 449-5 (435 mg, 46.4%). +ESI-MS: m/z 457.0 [M+H]$^+$.

Compound 449-6 was prepared essentially as described in the preparation of 406 by using 449-5 and (R)-4-(2-hydroxypropoxy)-3-methoxybenzoic acid. Crude 449-6 was purified by prep-HPLC to give 449-6 (92 mg, 40.4%). +ESI-MS: m/z 665.0 [M+H]$^+$. Compound 449-6 (92 mg) was separated via SFC separation to give two isomers: 449 (32 mg) and 450 (33 mg). 449: +ESI-MS: m/z 665.0 [M+H]$^+$. 450: +ESI-MS: m/z 665.1 [M+H]$^+$.

Example 234

Preparation of Compound 451

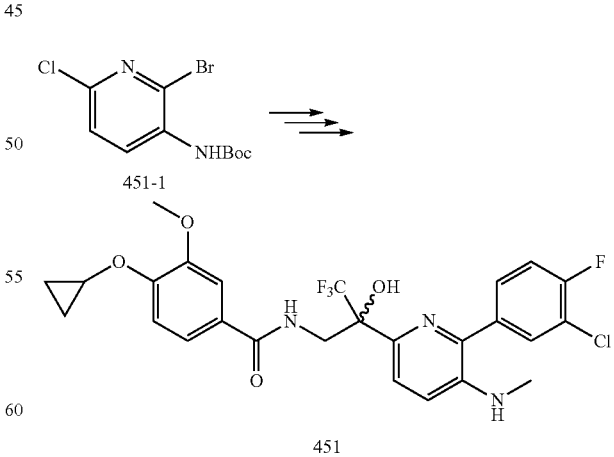

Compound 451 was prepared essentially as described in the preparation of 443 and 448 by using 451-1. Crude 451 was purified by prep-HPLC to give 451 as a white solid (42 mg, 16.0%). +ESI-MS: m/z 553.9 [M+H]$^+$.

Example 235

Preparation of Compound 452

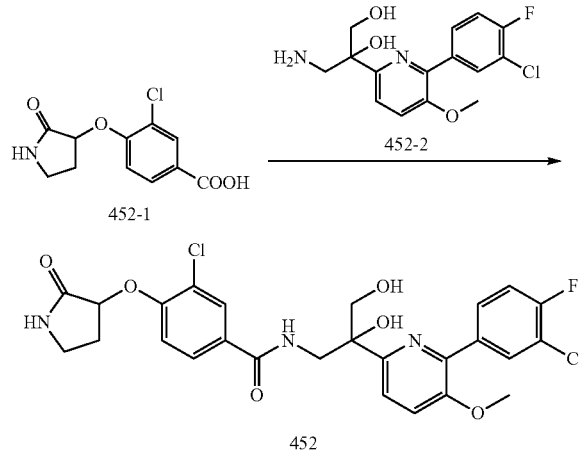 [SMILES: O=C(O)c1ccc(OC2CCNC2=O)c(Cl)c1 ; COc1ccc(C(O)(CN)CO)nc1-c1ccc(F)c(Cl)c1 ; COc1ccc(C(O)(CO)CNC(=O)c2ccc(OC3CCNC3=O)c(Cl)c2)nc1-c1ccc(F)c(Cl)c1]

Compound 452-1 was prepared essentially as described in the preparation of 259. Compound 452-2 was prepared essentially as described in the preparation of 471. Compound 452 was prepared essentially as described in the preparation of 406 by using 452-1 and 452-2. Crude 452 was purified by prep-HPLC to give 452 as a white solid (90 mg, 19%). +ESI-MS: m/z 564.0 [M+H]$^+$.

Example 236

Preparation of Compound 453

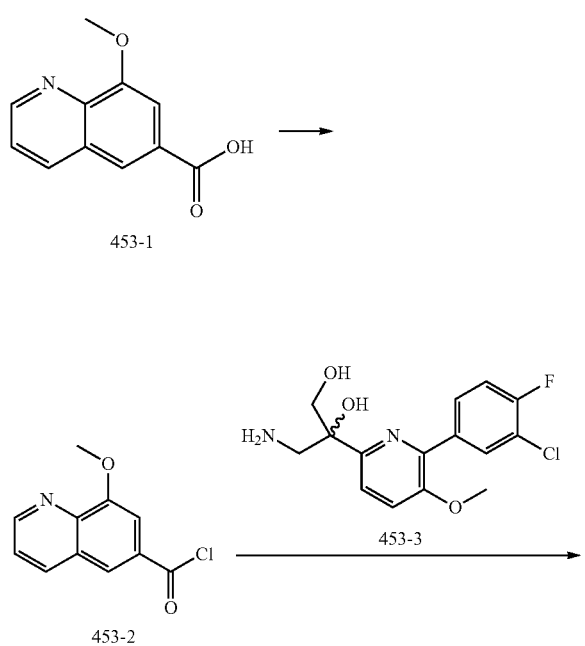

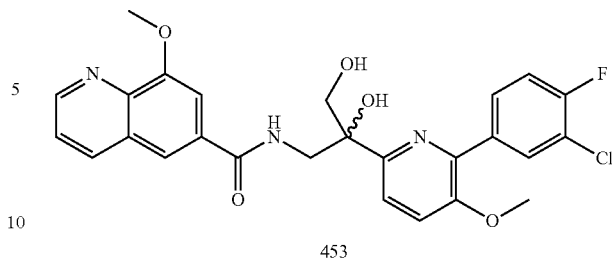

To a solution of 453-1 (100 mg, 0.493 mmol) in SOCl$_2$ (3 mL) was added DMF (one drop) at 0° C., and stirred at r.t. for 1 h. The mixture was co-evaporated with toluene (2×), and re-dissolved in anhydrous DCM (5 mL). The solution was treated with TEA (99.6 mg, 0.986 mol) and 453-3 (164.2 mg, 0.493 mol). The mixture was stirred at r.t. for 1 h. The mixture was diluted with DCM (20 mL) and washed with brine (20 mL). The organic phase was dried over anhydrous Na$_2$SO$_4$ and concentrated under reduced pressure. The residue was purified by prep-HPLC to give 453 (42 mg, yield: 16.7%). +ESI-MS: m/z 512.1 [M+H]$^+$.

Example 237

Preparation of Compound 454

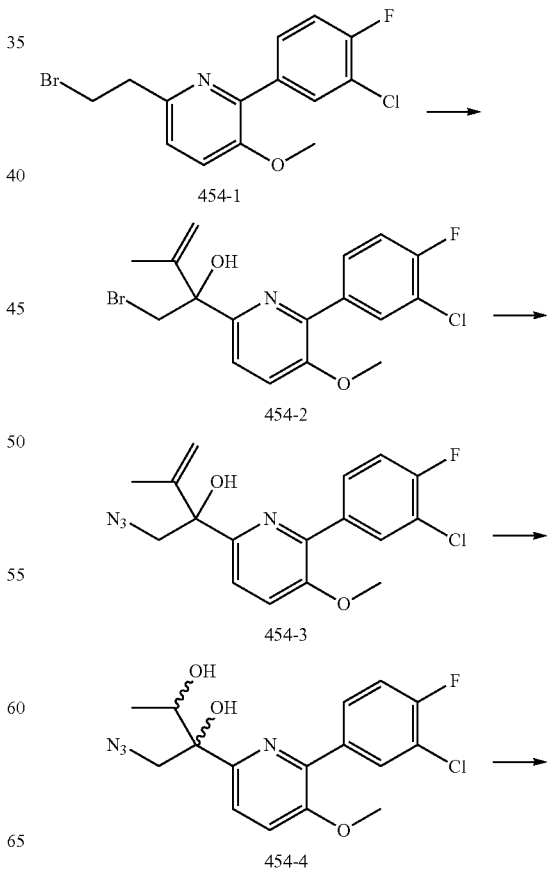

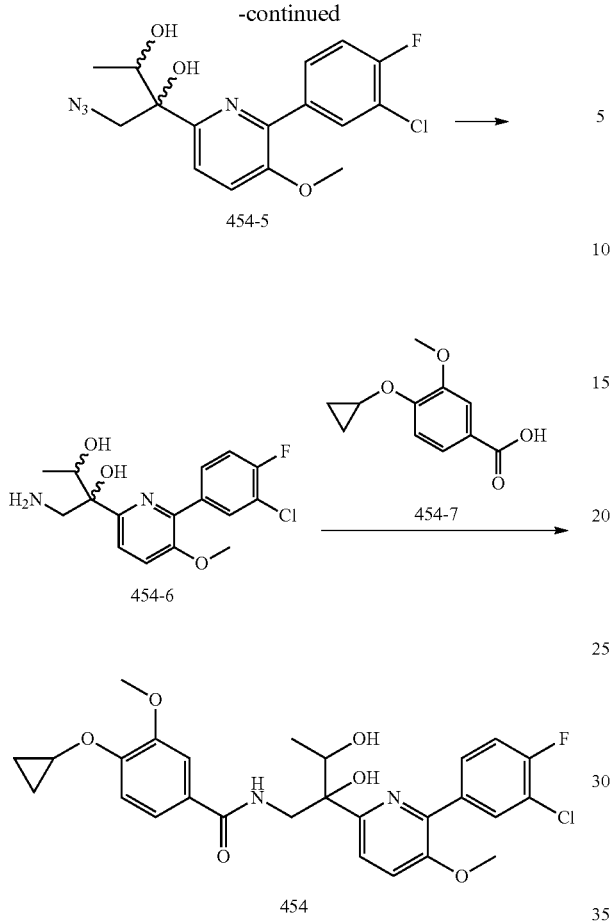

Example 238

Preparation of Compounds 455, 456, 457 and 458

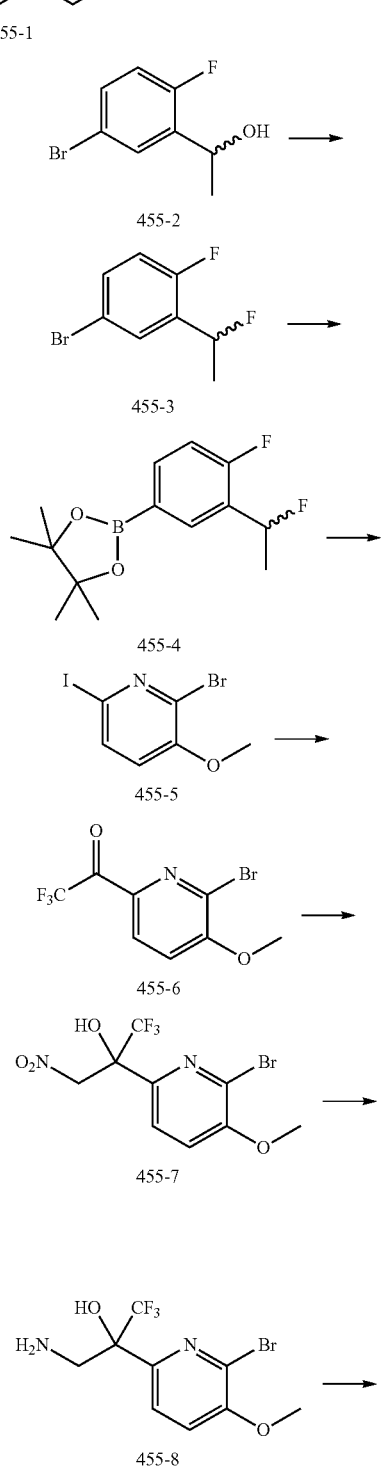

Compound 454-2 was prepared essentially as described in the preparation of 406 by using 454-1 and prop-1-en-2-ylmagnesium bromide. Crude 454-2 was purified by column chromatography (PE:EA 8:1) to give 454-2 as a solid (0.8 g). +ESI-MS: m/z 401.9 [M+H]$^+$.

To a solution of 454-2 (800 mg, 2.0 mmol) in DMSO (10 mL) was added NaN$_3$ (650 mg, 10.0 mmol) at r.t., and the mixture was stirred for 5 h. The reaction was quenched with water (30 mL), and extracted by EA (3×20 mL). The combined organic layers were washed with brine, dried over anhydrous Na$_2$SO$_4$ and concentrated under reduced pressure. The residue was purified by column chromatography (PE:EA 6:1) to give 454-3 (402 mg, 55.1%) as a white solid. +ESI-MS: m/z 362.9 [M+H]$^+$.

Ozone was bubbled into a solution of 454-3 (402 mg, 1.1 mmol) in anhydrous methanol (20 mL) at −78° C. for 10 mins. After excess ozone was purged by nitrogen, NaBH$_4$ (125 mg, 3.3 mmol) was added. The mixture was stirred at r.t. for 30 mins. The reaction was quenched with water and extracted with EA (3×30 mL). The combined organic phase was washed with brine, dried over anhydrous Na$_2$SO$_4$ and concentrated under reduced pressure. The residue was purified by column chromatography (PE:EA 5:1) to give 454-4 as an oil (303 mg, 74.6%).

Compound 454 was prepared essentially as described in the preparation of 428 from 454-4 and 454-7. Crude 454 was purified by prep-HPLC to give 454 as a white solid (40 mg, 31.4%). +ESI-MS: m/z 531.0 [M+H]$^+$.

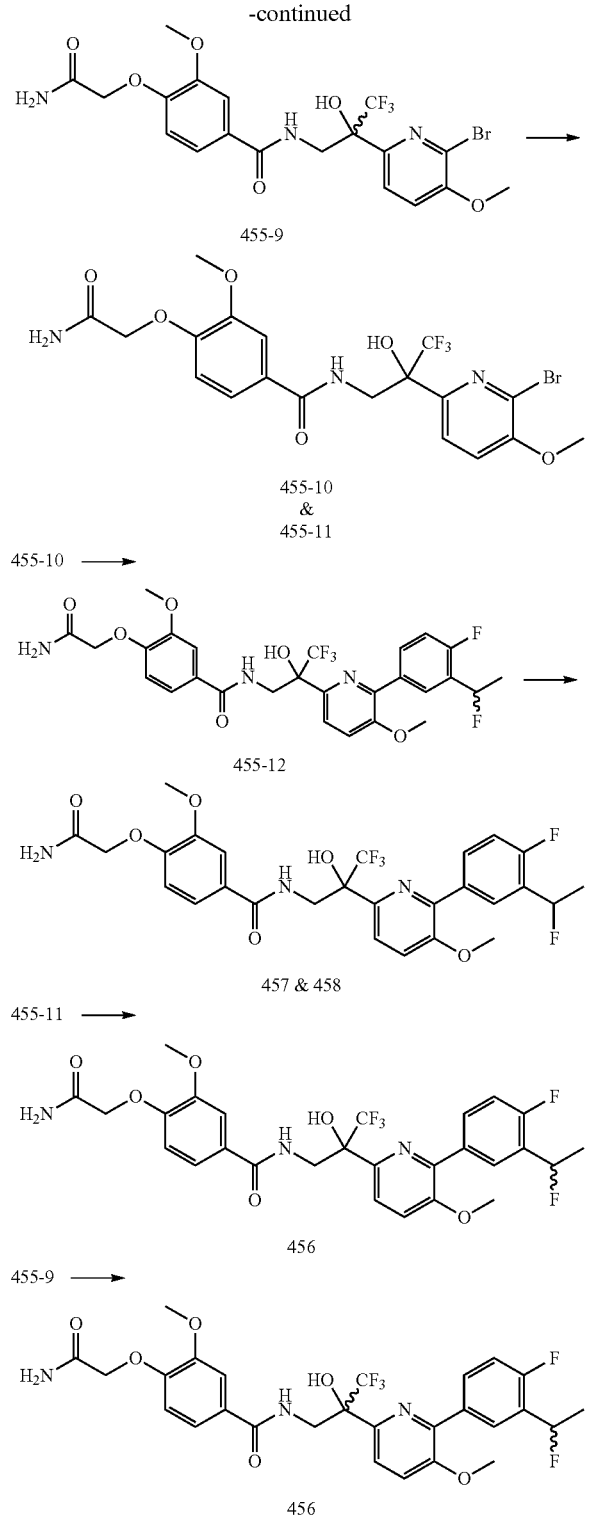

brine, dried over anhydrous Na₂SO₄ and concentrated under reduced pressure. The residue was purified by column chromatography (PE:EA 100:1) to give 455-3 (1.2 g, 60%).

To a solution of 455-3 (1.2 g, 5.4 mmol) in anhydrous THF (40 mL) was added n-BuLi (3 mL, 2.5M in hexane) dropwise at −78° C., and the solution was stirred for 1 h. 2-isopropoxy-4,4,5,5-tetramethyl-1,3,2-dioxaborolane (1.5 g, 8.1 mmol) was added dropwise, and the mixture was stirred at −78° C. for 1 h. The reaction was quenched with water (50 mL), and extracted with EA (2×50 mL). The combined organic phase was washed with brine, dried over anhydrous Na₂SO₄ and concentrated under reduced pressure. The residue was purified by column chromatography (PE:EA 100:1) to give 455-4 (0.4 g, 28%).

Compounds 455-5 to 455-7 was prepared essentially as described in the preparation of 449 by using 455-4. Crude 455-7 was purified by gel column to give 455-7 (0.9 g, 67%). A suspension of 455-7 (1.0 g, 2.9 mmol) and SnCl₂·2H₂O (2.6 g, 12 mmol) in EA (15 mL) was stirred at 70° C. overnight. After cooling to r.t., NH₃—H₂O (5 mL) was added, and the mixture was stirred for 30 mins. A white precipitate was formed and removed by filtration. The filtrate was washed with brine, dried over anhydrous Na₂SO₄ and concentrated under reduced pressure. Compound 455-8 (0.8 g) was used without further purification.

Compound 455-9 was prepared essentially as described in the preparation of 406 by using 455-8 and 4-(2-amino-2-oxoethoxy)-3-methoxybenzoic acid. Crude 455-9 was purified by prep-HPLC to give 455-9 as a white solid (570 mg, 41%). +ESI-MS: m/z 521.8 [M+H]⁺. Compound 455-9 (570 mg, 1.09 mmol) separated via SFC separation to give two enantiomers: 455-10 (230 mg) and 455-11 (220 mg, 42%).

To a solution of 455-10 (100 mg, 0.19 mmol) and 455-4 (150 mg, 0.56 mmol) in co-solvent dioxane (4 mL) and H₂O (0.5 mL) were added Pd(dppf)Cl₂ (10 mg, 0.012 mmol) and K₂CO₃ (55 mg, 0.4 mmol). The mixture was degassed and then refilled with N₂ (3×). The mixture was heated to 150° C. by microwave for 50 mins. The mixture was cooled to r.t., and diluted with EA (30 mL) and water (30 mL). The organic phase was washed with brine, dried over anhydrous Na₂SO₄ and concentrated under reduced pressure. The residue was purified by prep-HPLC to give 455-12 as a white solid (80 mg, 70%).

Compound 455-12 (80 mg, 0.15 mmol) was separated via SFC separation to give two isomers: 457 (30 mg) and 458 (29 mg). 457: +ESI-MS: m/z 584.1 [M+H]⁺. 458: +ESI-MS: m/z 584.1 [M+H]⁺.

Compound 456 was prepared by using 455-11 and 455-4. Crude 456 was purified by prep-HPLC to give 456 as a white solid (75 mg, 65%). +ESI-MS: m/z 584.1 [M+H]⁺. Compound 455 was prepared by using 455-9 and 455-4. Crude 455 was purified by prep-HPLC to give 455 as a white solid (40 mg, 23.3%). +ESI-MS: m/z 584.1 [M+H]⁺.

Example 239

Preparation of Compound 459

Compound 455-2 was prepared essentially as described in PCT Publication No. WO 2012/057247, published May 3, 2012, which is hereby incorporated by reference for the limited purpose of its description of the preparation of 455-2. To a solution of 455-2 (2.0 g, 9.17 mmol) in DCM (50 mL) was added DAST (6.0 g, 36 mmol) at 0° C., and the mixture was stirred at r.t. for 1 h. The reaction was quenched with water (50 mL). The organic layer was washed with

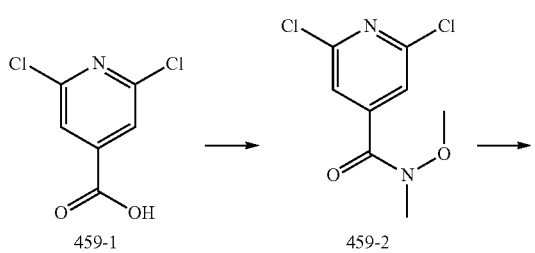

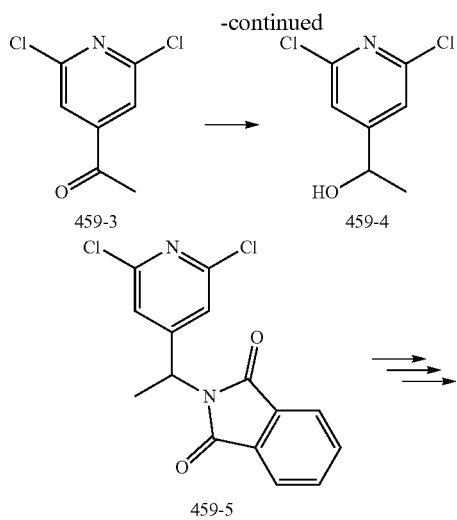

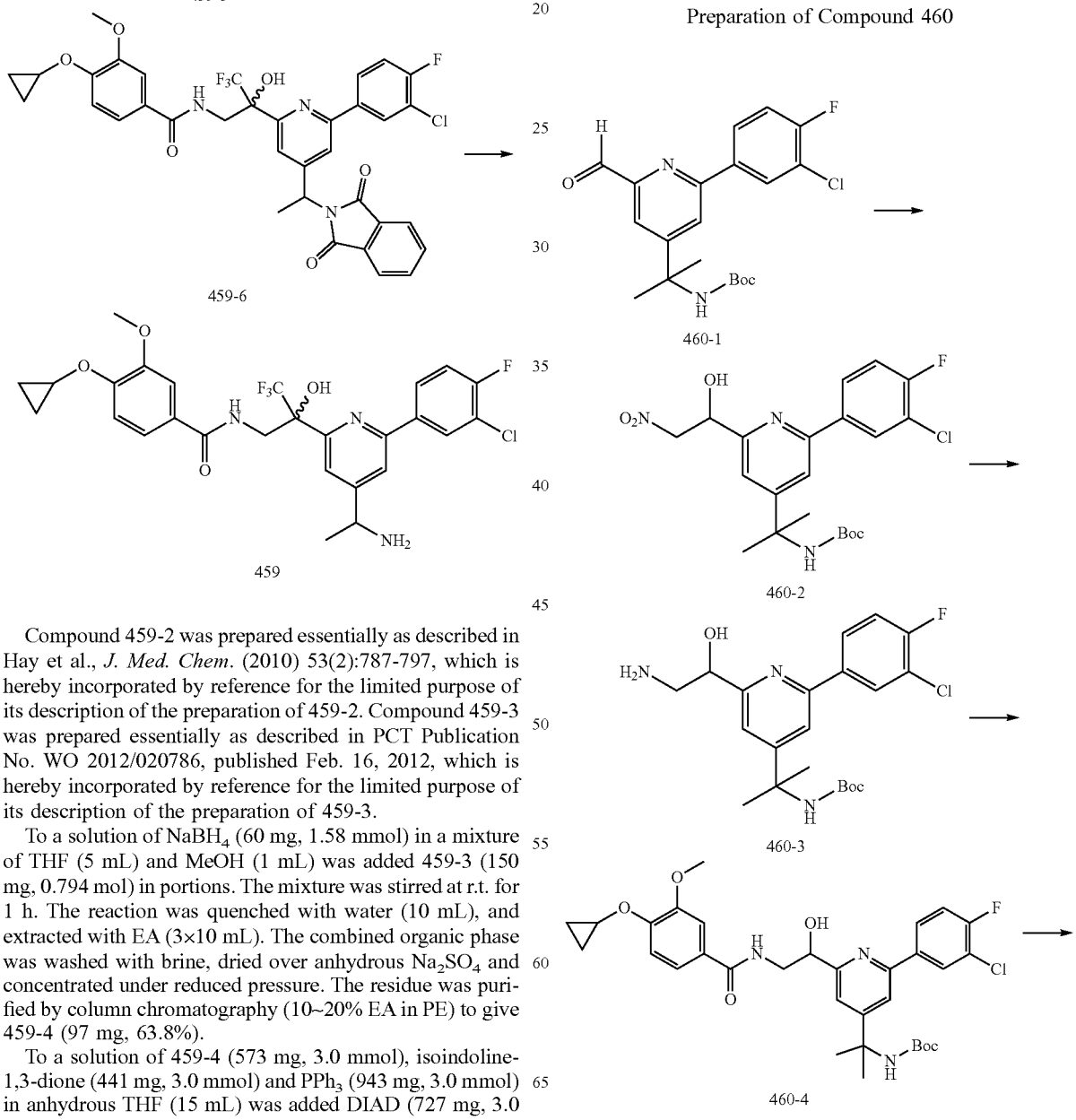

for 2 h at r.t. The reaction was quenched by sat. NaHCO₃ solution (30 mL). The mixture was extracted with DCM (3×20 mL). The combined organic layers were washed with brine, dried over anhydrous MgSO₄ and concentrated under reduced pressure. The residue was purified by column chromatography (PE:EA 10:1) to give 459-5 (604 mg, 62.9%).

Compounds 459-5 to 459-12 was prepared essentially as described in the preparation of 428. Crude 459-12 was purified by flash column chromatography (10~20% EA in PE) to give 459-12 (127 mg, 65.8%). A suspension of 459-12 (127 mg, 0.326 mmol) in N₂H₄.H₂O (10 mL) was stirred at r.t. for 2 h. The mixture was concentrated under reduced pressure. The residue was purified by prep-HPLC to give 459 (35 mg, 33.9%). +ESI-MS: m/z 568.0 [M+H]⁺.

Example 240

Preparation of Compound 460

Compound 459-2 was prepared essentially as described in Hay et al., *J. Med. Chem.* (2010) 53(2):787-797, which is hereby incorporated by reference for the limited purpose of its description of the preparation of 459-2. Compound 459-3 was prepared essentially as described in PCT Publication No. WO 2012/020786, published Feb. 16, 2012, which is hereby incorporated by reference for the limited purpose of its description of the preparation of 459-3.

To a solution of NaBH₄ (60 mg, 1.58 mmol) in a mixture of THF (5 mL) and MeOH (1 mL) was added 459-3 (150 mg, 0.794 mol) in portions. The mixture was stirred at r.t. for 1 h. The reaction was quenched with water (10 mL), and extracted with EA (3×10 mL). The combined organic phase was washed with brine, dried over anhydrous Na₂SO₄ and concentrated under reduced pressure. The residue was purified by column chromatography (10~20% EA in PE) to give 459-4 (97 mg, 63.8%).

To a solution of 459-4 (573 mg, 3.0 mmol), isoindoline-1,3-dione (441 mg, 3.0 mmol) and PPh₃ (943 mg, 3.0 mmol) in anhydrous THF (15 mL) was added DIAD (727 mg, 3.0 mmol) dropwise at 0° C. under N₂. The mixture was stirred

363

-continued

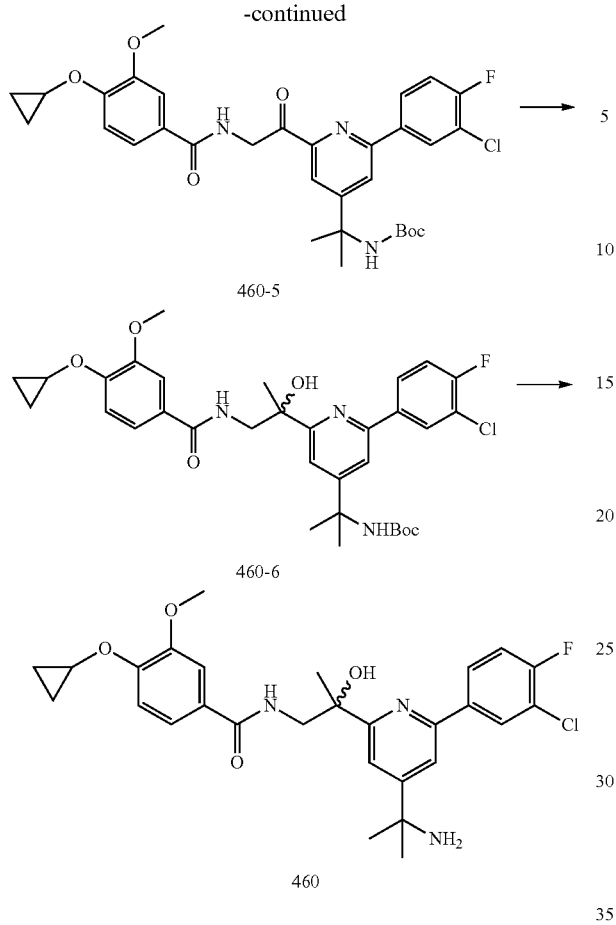

Compounds 460-1 to 460-6 were prepared essentially as described in the preparation of 272 and 403. Crude 460-6 was purified by prep-HPLC to give 460-6 as a white solid (67 mg, 50%). To a solution of 460-6 (100 mg, 0.16 mmol) in DCM (5 mL) was added TFA (1 mL). The mixture was stirred at r.t. for 1 h. and then concentrated under reduced pressure. The residue was purified by prep-HPLC to give 460 (30 mg, 60%). +ESI-MS: m/z 528.1 [M+H]$^+$.

Example 241

Preparation of Compound 461

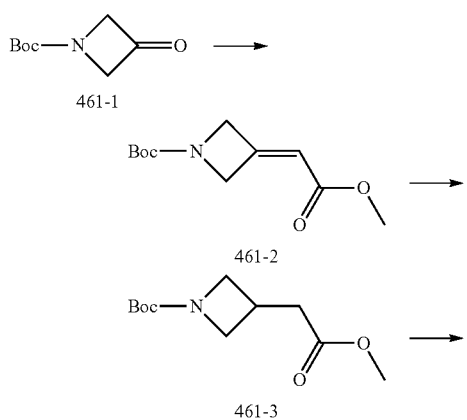

364

-continued

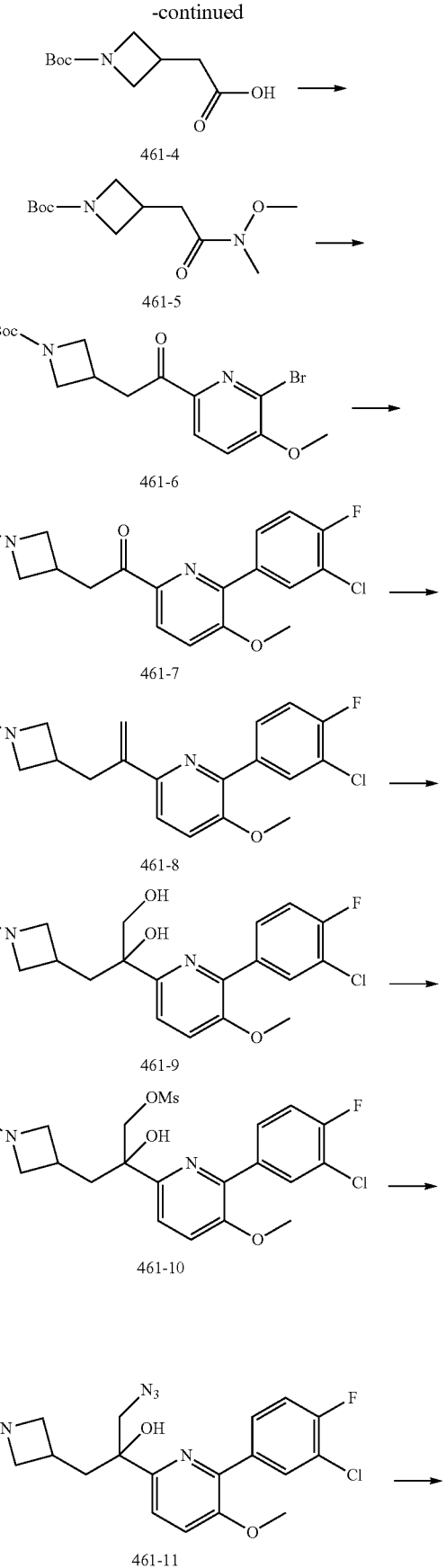

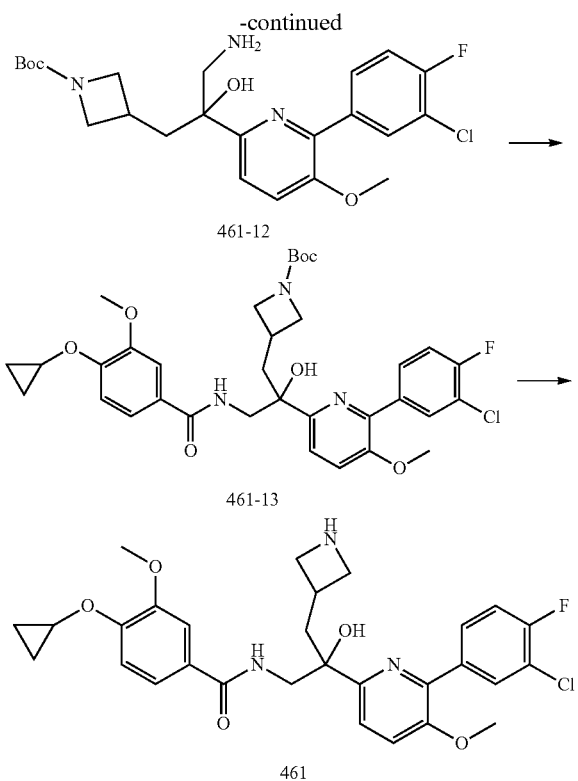

Compound 461-2 was prepared essentially as described in PCT Publication No. WO 2013/055645, published Apr. 18, 2013, which is hereby incorporated by reference for the limited purpose of its description of the preparation of 461-2. Compound 461-3 was prepared essentially as described in Podlech et al., *Helv. Chimica Acta* (1995) 78(5):1238-1246, which is hereby incorporated by reference for the limited purpose of its description of the preparation of 461-3. Compound 461-4 was prepared essentially as described in PCT Publication No. WO 2009/154780, published Dec. 23, 2009, which is hereby incorporated by reference for the limited purpose of its description of the preparation of 461-4.

To a solution of 461-4 (9.0 g, 39.3 mmol) in anhydrous DMF (50 mL) were added DIPEA (15.2 g, 117.9 mmol) and HATU (14.9 g, 39.3 mmol), and the mixture was stirred at r.t. for 30 mins. N,O-dimethylhydroxylamine (3.85 g, 39.3 mmol) was added, and the mixture was stirred at r.t. for 2 h. The mixture was diluted with water (100 mL), and extracted with EA (3×100 mL). The combined organic phase was washed brine, dried over anhydrous $Na_2SO_4$ and concentrated under reduced pressure. The residue was purified by column chromatography (PE:EA 10:1) to give 461-5 (8.5 g, 70.7%).

To a solution of 461-5 (8.0 g, 31.0 mmol) and 2-bromo-6-iodo-3-methoxypyridine (9.7 g, 31.0 mmol) in anhydrous THF (120 mL) was added i-PrMgCl (23.5 mL, 46.51 mmol) dropwise at 0° C., and the mixture was stirred at r.t. for 2 h. The reaction was quenched with water (50 mL) and extracted with EA (3×150 mL). The combined organic phase was washed with brine, dried over anhydrous $Na_2SO_4$ and concentrated under reduced pressure. The residue was purified by column chromatography (PE:EA 8:1) to give 461-6 (6.0 g, 49.6%). +ESI-MS: m/z 385.01 $[M+H]^+$.

Compound 461-7 was prepared as essentially as described in the preparation of 428 by using 461-6. Compound 461-7 (4.2 g) was obtained after purification by column chromatography.

To a suspension of $CH_3P^+Ph_3Br^-$ (2.46 g, 6.92 mmol) in toluene (20 mL) was added NaHMDS (6.92 mL, 1 M in THF) dropwise at 0° C. under $N_2$. The mixture was stirred for 30 mins. The mixture was cooled to −78° C. and 461-7 (2.0 g, 4.6 mmol) was added, and then stirred at −78° C. to reflux overnight. The reaction was quenched by water (30 mL) and extracted with EA (3×30 mL). The combined organic phase was washed with brine, dried over anhydrous $Na_2SO_4$ and concentrated under reduced pressure. The residue was purified by column chromatography (PE:EA 5:1) to give 461-8 (1.2 g, 61.0%).

To a solution of 461-8 (1.3 g, 3.0 mmol) in DCM (20 mL) were added NMO (1.05 g, 9.0 mmol) and $OsO_4$ (38.4 mg, 0.15 mmol), and the mixture was stirred at r.t. overnight. The reaction was quenched with sat. $Na_2SO_3$ solution (50 mL) and extracted with EA (3×50 mL). The combined organic phase was washed with brine, dried over anhydrous $Na_2SO_4$ and concentrated under reduced pressure. The residue was purified by column chromatography (PE:EA 3:1) to give 461-9 (0.85 g, 60.7%).

To an ice-cold solution of 461-9 (265 mg, 0.725 mmol) and TEA (220 mg, 2.2 mmol) in anhydrous DCM (20 mL) was added MsCl (1.0 g, 8.7 mmol) dropwise, and the mixture was stirred at r.t. for 1 h. The mixture was washed with brine (20 mL), dried over anhydrous $Na_2SO_4$ and concentrated under reduced pressure. The residue was purified by column chromatography (PE:EA 5:1) to give 461-10 (250 mg, 63.4%).

Compound 461 was prepared essentially as described in the preparation of 428 from 461-10. Crude 461 was purified by prep-HPLC to give 461 as a white solid (36 mg, 20.2%). +ESI-MS: m/z 556.1 $[M+H]^+$.

Example 242

Preparation of Compound 462

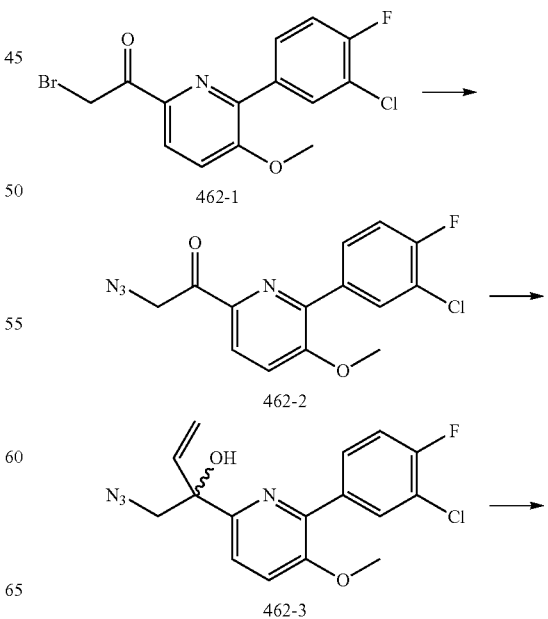

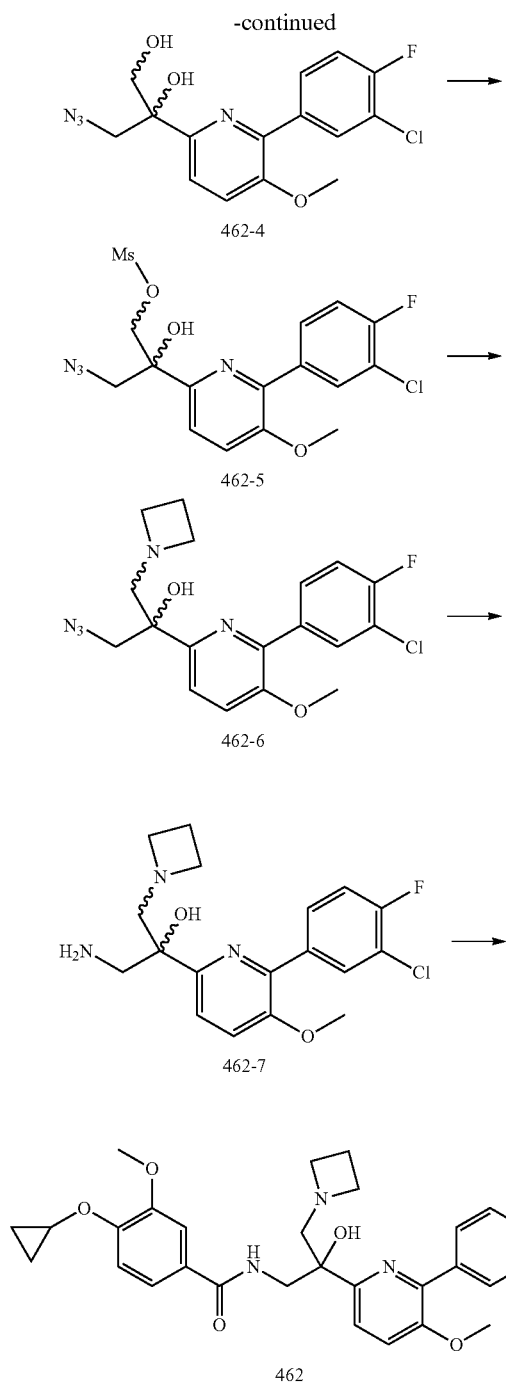

with sat. NH₄Cl solution (50 mL). The mixture was allowed to warm to r.t. and extracted with EA (3×50 mL). The combined organic layers were washed with brine, dried over anhydrous Na₂SO₄ and concentrated under reduced pressure. The residue was purified by column chromatography (PE:EA 5:1) to give 462-3 as a white solid (2.0 g, 76.9%). +ESI-MS: m/z 349.0 [M+H]⁺.

Ozone was bubbled into a solution of 462-3 (2.0 g, 5.7 mmol) in anhydrous MeOH (20 mL) at −78° C. for 10 mins. After excess Ozone was purged by N₂, NaBH₄ (800 mg, 21.1 mmol) was added at r.t. in portions. The mixture was stirred at r.t. for 30 mins. The reaction was quenched with water (30 mL) and extracted with EA (2×50 mL). The combined organic phase was washed with brine, dried over anhydrous Na₂SO₄ and concentrated under reduced pressure. The residue was purified by column chromatography (PE:EA 1:1) to give 462-4 as an oil (1.6 g, 80.1%). +ESI-MS: m/z 352.9 [M+H]⁺.

To a solution of 462-4 (1.6 g, 4.5 mmol) and TEA (900 mg, 8.9 mmol) in anhydrous DCM (20 mL) was added MsCl (500 mg, 4.4 mmol) dropwise at 0° C. The solution was stirred at r.t. for 30 mins. The reaction was quenched with H₂O (30 mL) and extracted with EA (3×30 mL). The combined organic phase was washed with brine, dried over anhydrous Na₂SO₄ and concentrated under reduced pressure. The residue was purified by column chromatography (PE:EA 4:1) to give 462-5 as a solid (1.6 g, 84.2%). +ESI-MS: m/z 431 [M+H]⁺.

To a solution of 462-5 (1.6 g, 3.7 mmol) in CH₃CN (20 mL) was added azetidine hydrochloride (1.6 g, 17.2 mmol) at r.t. The solution was heated to 70° C. and stirred for 8 h. After cooling to r.t., the reaction was quenched with H₂O (30 mL) and extracted with EA (3×30 mL). The combined organic phase was washed with brine, dried over anhydrous Na₂SO₄ and concentrated under reduced pressure. The residue was purified by column chromatography (PE:EA 1:1) to give 462-6 as an oil (500 mg, 35.7%). +ESI-MS: m/z 391.9 [M+H]⁺.

Compound 462 was prepared essentially as described in the preparation of 428 by using 462-6. Crude 462 was purified by prep-HPLC to give 462 as a white solid (10 mg, 6.5%). +ESI-MS: m/z 556.1 [M+H]⁺.

Example 243

Preparation of Compound 463

To a solution of 462-1 (3.56 g, 10.0 mmol) in DMSO (30 mL) was added NaN₃ (1.95 g, 30.0 mmol) at 25° C. in portions, and the mixture was stirred for 30 mins. The mixture was poured into water (50 mL), and extracted with EA (3×30 mL). The combined organic layers were washed with brine, dried over anhydrous Na₂SO₄ and concentrated under reduced pressure. The residue was purified by column chromatography (PE:EA 5:1) to give 462-2 (2.4 g, 75.1%) as a white solid. +ESI-MS: m/z 320.9 [M+H]⁺.

To a solution of 462-2 (2.4 g, 7.5 mmol) in anhydrous THF (30 mL) was added vinyl-magnesium bromide (7.5 mL, 1.0M in THF) dropwise at −30° C. under N₂, and the mixture was stirred for 30 mins. The reaction was quenched

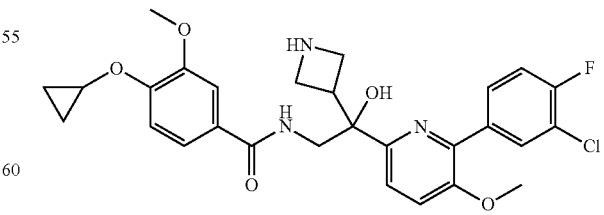

Compound 463 was prepared essentially as described in the preparation of 461 by using 1-(tert-butoxycarbonyl)azetidine-3-carboxylic acid. Compound 463 was obtained as white solid (40 mg, 40%). +ESI-MS: m/z 542.1 [M+H]⁺.

Example 244

Preparation of Compound 464

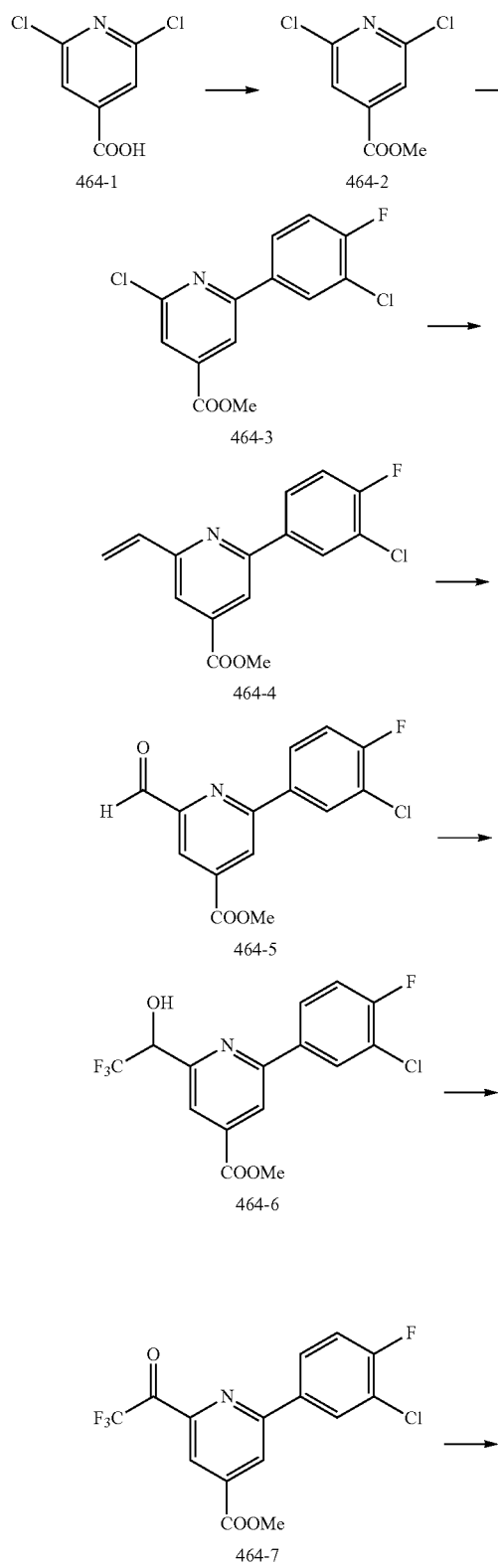

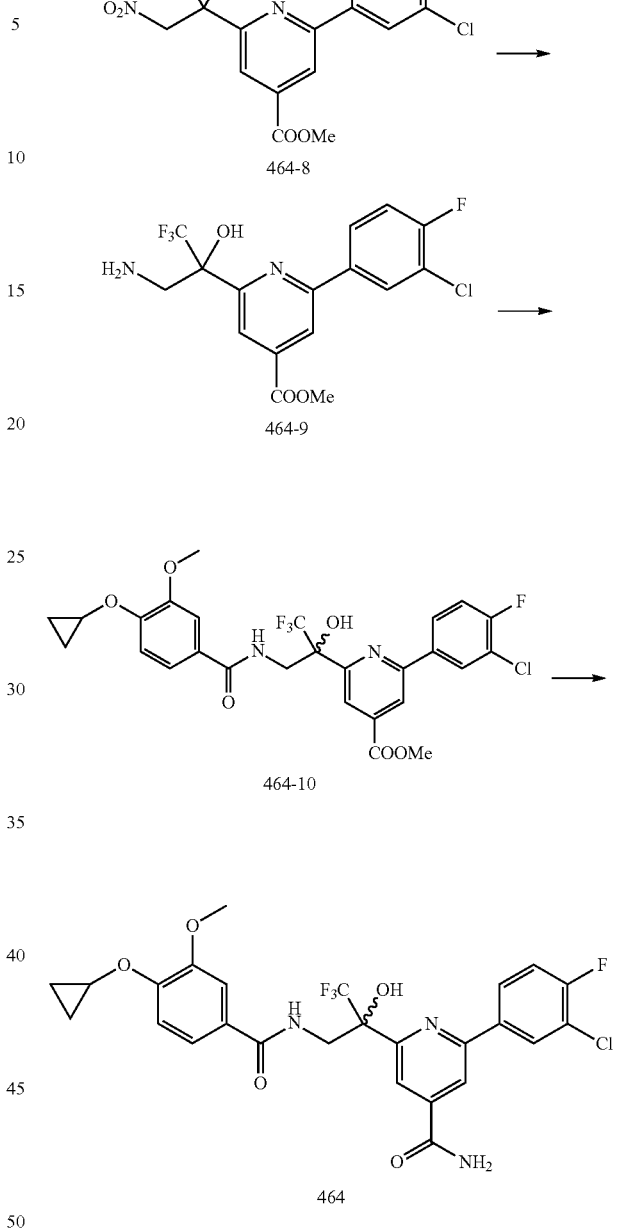

Compound 464-2 was prepared essentially as described in Zornik et al., *Chem. Eur. J.* (2011) 17(5):1473-1484 and S1473/1-S1473/121, which is hereby incorporated by reference for the limited purpose of its description of the preparation of 464-2. Compound 464-10 was prepared essentially as described in the preparation of 272 by using 464-2. Compound 464-10 was obtained as white solid (300 mg, 68.5%). +ESI-MS: m/z 582.9 [M+H]$^+$.

To a solution of 464-10 (50 mg, 0.086 mmol) in 1,4-dioxane (5 mL) was added ammonia water (2 mL) in a sealed tube. The mixture was then stirred at 100° C. overnight. After cooling to r.t., the mixture was concentrated to dryness, and the residue was purified by prep-HPLC to give 464 (15 mg, 30.8%) as a white solid. +ESI-MS: m/z 568.0 [M+H]$^+$.

Example 245

Preparation of Compound 465

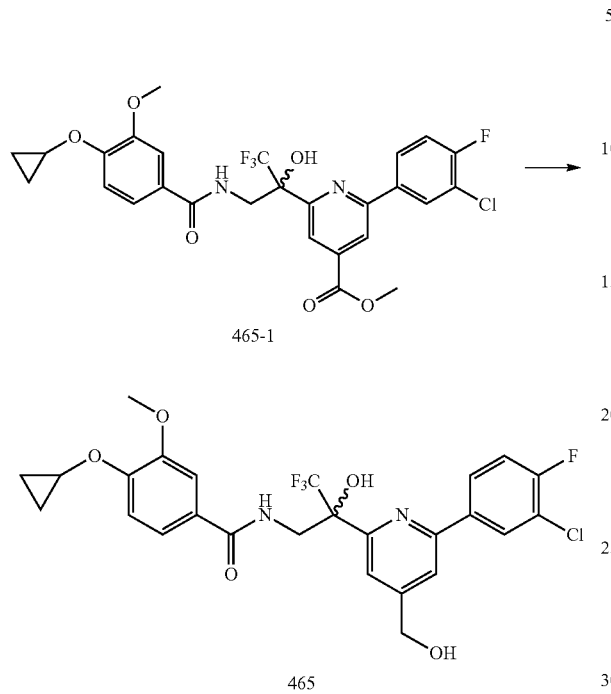

465-1

465

To a stirred solution of 465-1 (87.3 mg, 0.15 mmol) in THF (5 mL) at 0° C. was added LAH (5.7 mg, 0.15 mmol) under $N_2$. After stirring at 0° C. for 1 h, the reaction was quenched by water (10 mL), and extracted by EA (3×10 mL). The combined organic phase was washed with brine, dried over anhydrous $Na_2SO_4$ and concentrated to dryness. The residue was purified by prep-HPLC to give 465 (50 mg, 60.2%) as a white solid. +ESI-MS: m/z 555.0 $[M+H]^+$.

Example 246

Preparation of Compound 466

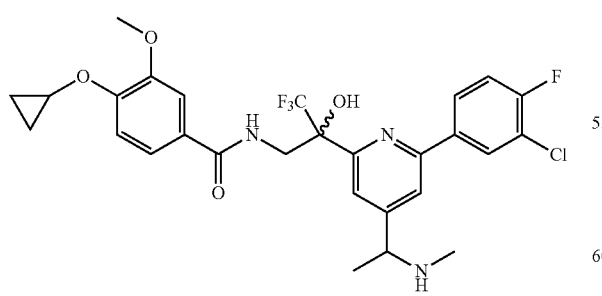

466

Compound 466 was prepared essentially as described in the preparation of 459 by using 1-(2,6-dichloropyridin-4-yl)ethanone. Compound 466 was obtained as white solid (20 mg, 18.5%). +ESI-MS: m/z 582.1 $[M+H]^+$.

Example 247

Preparation of Compound 467

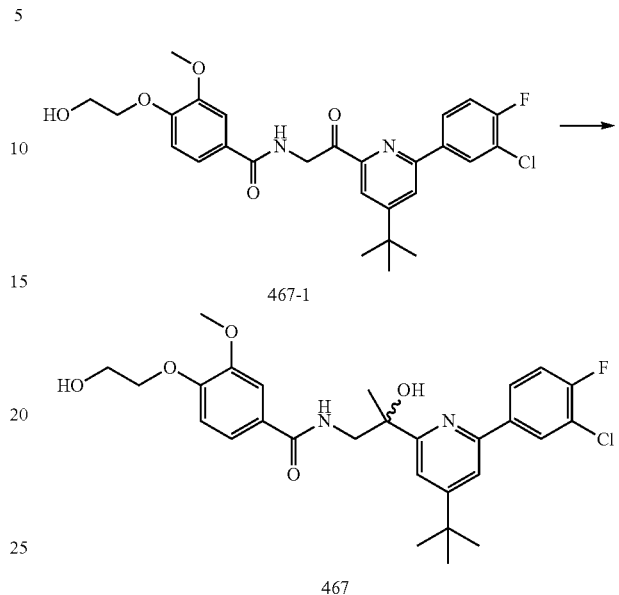

467-1

467

To a solution of 467-1 (60 mg, 0.12 mmol) in THF (4 mL) was added MeMgCl (1 mL, 3 M in ether) dropwise at 0° C., and the mixture was stirred at for 1 h. The reaction was quenched with sat. $NH_4Cl$ solution, and extracted with EA (3×10 mL). The combined organic phase was washed with brine, dried over anhydrous $Na_2SO_4$ and concentrated under reduced pressure. The residue was purified by prep-HPLC to give 467 (30 mg, 47%) as a white solid. +ESI-MS: m/z 531.3 $[M+H]^+$.

Example 248

Preparation of Compound 468

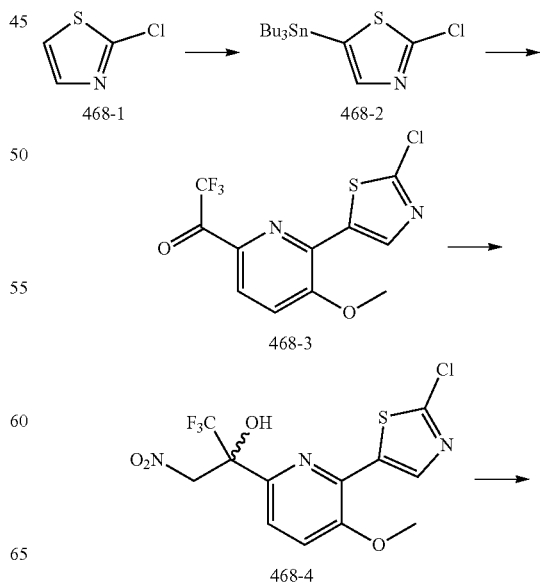

468-1

468-2

468-3

468-4

373
-continued

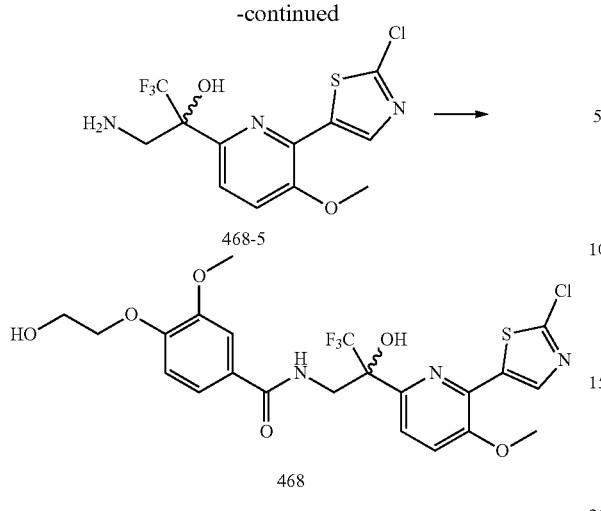

468-5

468

To a solution of 468-1 (2.4 g, 20 mmol) in anhydrous T (50 mL) was added n-BuLi (8 mL, 2.5M in hexane) at −78° C. under $N_2$, and the mixture was stirred for 0.5 h. The mixture was treated with tributylchlorostannane (6.5 g, 20 mmol) in portions, and stirred at −78° C. for 1 h. The reaction was quenched by water (50 mL), and extracted with EA (3×50 mL). The combined organic phase was washed with brine, dried over anhydrous $Na_2SO_4$ and concentrated under reduced pressure. The residue was purified by column chromatography (PE:EA 10:1) to give 468-2 (6 g, 74%).

A mixture of 468-2 (2.02 g, 5.0 mmol), Pd(dppf)Cl$_2$ (90 mg, 2 (50 mL eq.) and 1-(6-bromo-5-methoxypyridin-2-yl)-2,2,2-trifluoroethanone (1.5 g, 5 mL) was dissolved in dry DMF (10 mL) under $N_2$. The mixture was heated to 130° C. by microwave and stirred for 0.5 h. After cooling to r.t., the mixture was poured into water (50 mL) and extracted with EA (3×30 mL). The combined organic phase was washed with brine, dried over anhydrous $Na_2SO_4$ and concentrated under reduced pressure. The residue was purified by column chromatography (PE:EA 5:1) to give 468-3 (1.4 g, 82%).

Compound 468 was prepared essentially as described in the preparation of 424 by using 468-3. Crude 468 was purified by pre-HPLC to give 468 as a white solid (50 mg, 20%). +ESI-MS: m/z 547.9 [M+H]⁺.

Example 249

Preparation of Compound 469

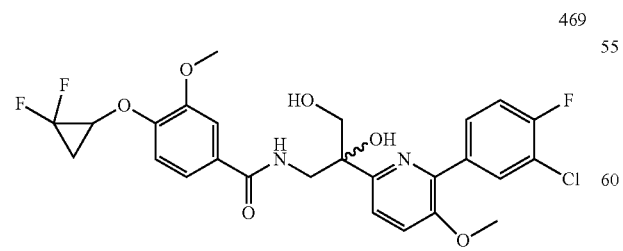

469

Compound 469 was prepared according to the method described in the preparation of 176. LCMS: m/z 553.10 [M+H]⁺.

374

Example 250

Preparation of Compound 135

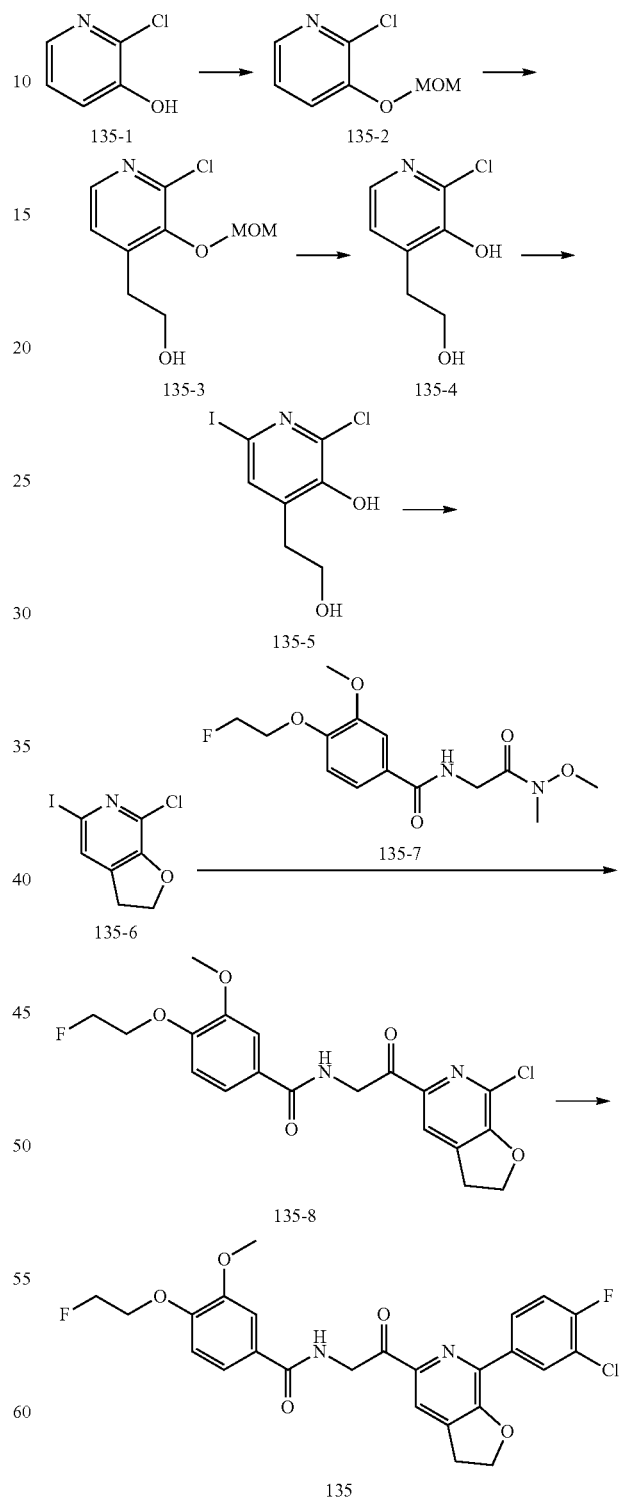

Compound 135-2 was prepared essentially as described in Granzhan et al., *Angew. Chem. Int'l Ed.* (2010) 49(32):

5515-5518, S5515/1-S5515/30, which is hereby incorporated by reference for the limited purpose of its description of the preparation of 135-2.

To a solution of 135-2 (10.0 g, 57.8 mmol) in anhydrous THF (60 mL) was added n-BuLi (35 mL, 2.5 M in hexane) dropwise at −78° C. under N₂. The mixture was stirred at −78° C. for 30 mins. under N₂ and oxirane (15.5 mL, 289 mmol) was added. The mixture was warmed to r.t. and stirred for 2 h. The reaction was quenched with H₂O, and extracted with EA (3×100 mL). The combined organic phase was washed with brine, dried over anhydrous Na₂SO₄ and concentrated under reduced pressure. The residue was purified by column chromatography (PE:EA 3:1) to give 135-3 (3.5 g, 28%). +ESI-MS: m/z 217.9 [M+H]⁺.

To a solution of 135-3 (3.5 g, 16.1 mmol) in MeOH (60 mL) was added conc. HCl solution (15 mL, 12 N) at r.t., and stirred at 60° C. for 5 h. The reaction was quenched with sat. NaHCO₃ solution, and extracted with EA (3×50 mL). The combined organic phase was washed with brine, dried over anhydrous Na₂SO₄ and concentrated under reduced pressure. The residue was purified by column chromatography (PE:EA 1:1) to give 135-4 (1.02 g, 36%).

To a solution of 135-4 (1.02 g, 5.7 mmol) and K₂CO₃ (1.5 g, 11.5 mmol) in a mixture of THF (10 mL) and H₂O (10 mL) was added I₂ (1.5 g, 6.0 mmol) in portions, and the mixture was stirred at r.t. for 30 mins. The reaction was quenched with sat. NaS₂O₃ solution, and extracted with EA (3×50 mL). The combined organic phase was washed with brine, dried over anhydrous Na₂SO₄ and concentrated under reduced pressure. The residue was purified by column chromatography (PE:EA 2:1) to give 135-5 (1.1 g, 62.5%).

To a solution of 135-5 (1.1 g, 3.7 mmol) and PPh₃ (1.5 g, 5.7 mmol) in anhydrous THF (10 mL) was added DIAD (1.2 g, 5.7 mmol) at r.t. under N₂. The mixture was heated to 70° C. for 1 h and then cooled to r.t. The reaction was quenched with H₂O, and extracted with EA (3×30 mL). The combined organic phase was washed with brine, dried over anhydrous Na₂SO₄ and concentrated under reduced pressure. The residue was purified by column chromatography (PE:EA 2:1) to give 135-6 (0.8 g, 78%). +ESI-MS: m/z 281.8 [M+H]⁺.

To a solution of 135-6 (0.8 g, 7.1 mmol) and 135-7 (2.2 g, 7.1 mmol) in THF (10 mL) was added i-PrMgBr (21 mL, 1.0 M in THF) dropwise under N₂, and the mixture was stirred at r.t. for 1 h. The reaction was quenched with sat. NH₄Cl solution and extracted with EA (3×30 mL). The combined organic phase was washed with brine, dried over anhydrous Na₂SO₄ and concentrated under reduced pressure. The residue was purified by column chromatography (PE:EA 1:1) to give 135-8 (1.2 g, 77%). +ESI-MS: m/z 408.9 [M+H]⁺.

To a solution of 135-8 (408 mg, 1.0 mmol), (3-chloro-4-fluorophenyl)boronic acid (175 mg, 1.0 mmol) and Cs₂CO₃ (276 mg, 2.0 mmol) in dioxane (5 mL) and water (1 mL) was added Pd(dppf)Cl₂ (82 mg, 0.1 mmol) under N₂. The mixture was heated to 120° C. under microwave irradiation and stirred for 30 mins. The mixture was cooled to r.t., poured into cold H₂O and extracted with EA (3×10 mL). The combined organic phase was washed with brine, dried over anhydrous Na₂SO₄ and concentrated under reduced pressure. The residue was purified by prep-HPLC to give 135 (80 mg) as a white solid. +ESI-MS: m/z 502.9 [M+H]⁺.

Example 251

Preparation of Compound 470

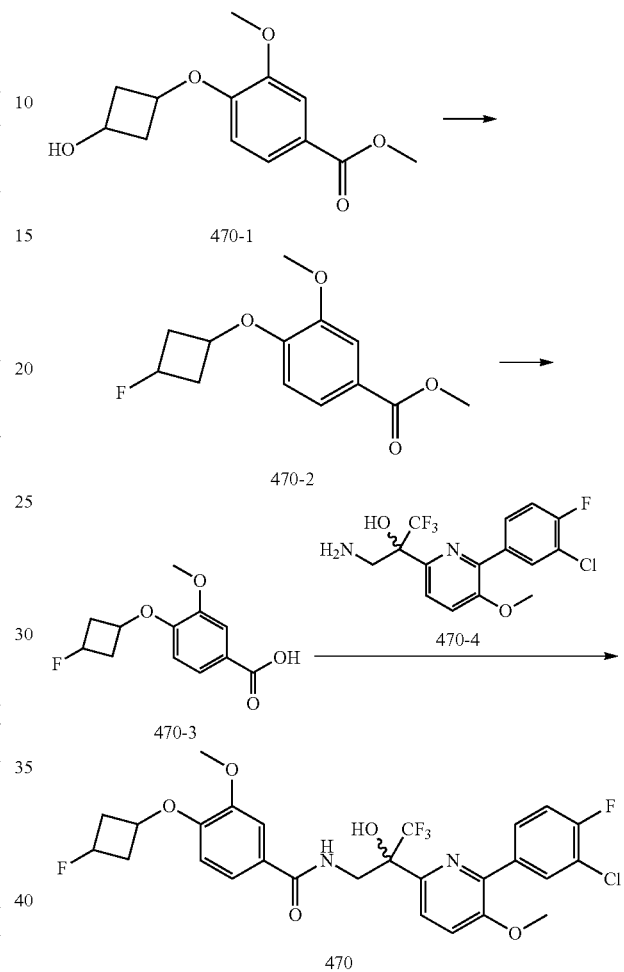

To a solution of 470-1 (1.7 g, 6.7 mmol) in DCM (10 mL) was added DAST (3 mL) at 0° C., and the mixture was stirred at 0° C. for 30 mins. The resulting was quenched with sat. NaHCO₃ solution at 0° C. and extracted by EA (3×20 mL). The combined organic phase was washed with brine, dried over anhydrous Na₂SO₄ and concentrated under reduced pressure. The residue was purified by column chromatography (PE:EA 15:1) to give 470-2 as a white solid (800 mg, 47.1%).

To a solution of 470-2 (254 mg, 1.0 mmol) in MeOH (5 mL) was added NaOH (5 mL, 2N), and the mixture was stirred at reflux for 1 h. The mixture was cooled to r.t. and acidified to pH 4~5 using HCl (2 M). The mixture was extracted with EA (3×20 mL). The combined organic phase was washed with brine, dried over anhydrous Na₂SO₄ and concentrated under reduced pressure to give 470-3 as a white solid (100 mg, 41.6%).

To a solution of 470-3 (100 mg, 0.42 mmol), HATU (190 mg, 0.5 mmol) and DIPEA (129 mg, 1.0 mmol) in anhydrous DCM (5 mL) was added 470-4 (140 mg, 0.39 mmol) at 25° C. The solution was stirred for 1 h and then quenched with aq. NaHCO₃ solution. The aqueous phase was extracted with DCM (2×10 mL). The combined organic phase was washed with brine, dried over anhydrous Na₂SO₄ and concentrated under reduced pressure. The residue was purified by prep-HPLC to give 470 as a white solid (60 mg, 24.5%). +ESI-MS: m/z 586.9 [M+H]⁺.

Example 252

Preparation of Compound 471

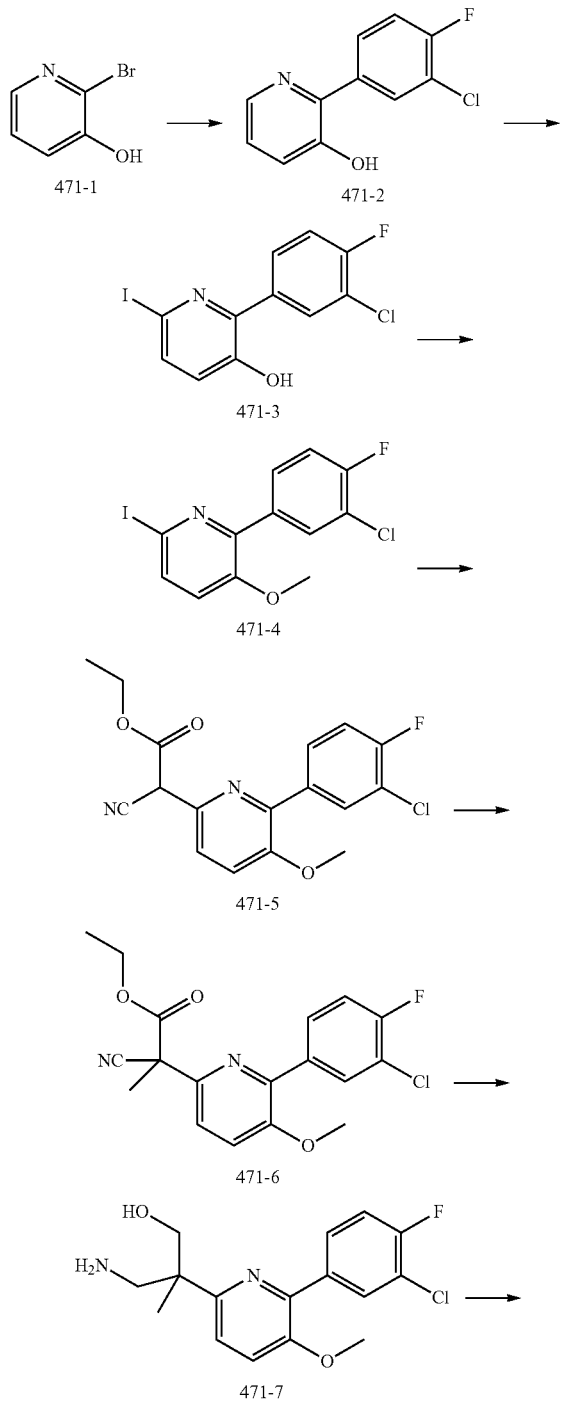

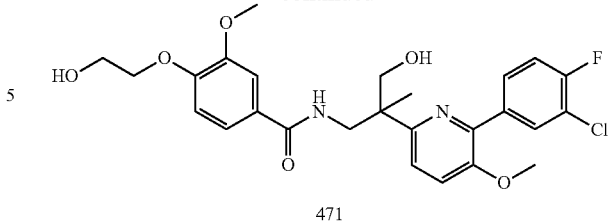

471

To a solution of bromide 471-1 (5.0 g, 28.9 mmol) and (3-chloro-4-fluorophenyl)boronic acid (5.5 g, 31.8 mmol) in dioxane (50 mL) were added Pd(dppf)Cl₂ (816 mg, 1.0 mmol) and a freshly prepared Cs₂CO₃ solution (11 g in 50 mL of water) under N₂. The mixture was stirred at 70° C. for 3 h. The solution was cooled to r.t., poured into ice water and extracted with EA (3×100 mL). The combined organic phase was washed with brine, dried over anhydrous Na₂SO₄ and concentrated under reduced pressure. The residue was purified by column chromatography (PE:EA 10:1~5:1) to give 471-2 (5.5 g) as a white solid.

To a solution of 471-2 (3.9 g, 17.4 mmol) and K₂CO₃ (3.0 g, 21.7 mmol) in DMF (50 mL) was added I₂ (1.4 g, 5.5 mmol) in portions at r.t., and the mixture was stirred for 2 h. The reaction was quenched with sat. Na₂S₂O₃ solution, and extracted with EA (3×50 mL). The combined organic phase was washed with brine, dried over anhydrous Na₂SO₄ and concentrated under reduced pressure. The residue was purified by column chromatography (PE:EA 50:1~25:1) to give 471-3 as a white solid (2.1 g, 50%). +ESI-MS: m/z 349.8 [M+H]⁺.

To a solution of 471-3 (2.0 g, 5.7 mmol) and K₂CO₃ (790 mg, 5.7 mmol) in DMF (25 mL) was added MeI (1.5 g, 11 mmol) dropwise at 0° C. The mixture was stirred at r.t. for 2 h. The reaction was quenched with water, and extracted with EA (3×50 mL). The combined organic phase was washed with brine, dried over anhydrous Na₂SO₄ and concentrated under reduced pressure. The residue was purified by column chromatography (PE:EA 50:1) to give 471-4 as a white solid (1.1 g, 55%).

To a solution of 471-4 (1.1 g, 3.0 mmol), picolinic acid hydrochloride (240 mg, 1.5 mmol), Cs₂CO₃ (2.8 g, 8.7 mmol) and CuI (165 mg, 0.75 mmol) in DMF (20 mL) was added ethyl 2-cyanoacetate (650 mg, 6.0 mmol) under N₂. The mixture was heated to 130° C. under microwave irradiation and stirred for 30 mins. The mixture was cooled to r.t., poured into water and extracted with EA (3×30 mL). The combined organic phase was washed with brine, dried over anhydrous Na₂SO₄ and concentrated under reduced pressure. The residue was purified by column chromatography (PE:EA 10:1~5:1) to give 471-5 as a yellow solid (720 mg, 65%). +ESI-MS: m/z 348.8 [M+H]⁺.

To a solution of 471-5 (720 mg, 2.04 mmol) in anhydrous DMF (15 mL) was added NaH (130 mg, 3.12 mmol) in portions at 0° C. After stirring for 30 mins., MeI (840 mg, 6 mmol) was added. The mixture was stirred at 0° C. for 2 h. The reaction was quenched with water, and extracted with EA (3×30 mL). The combined organic phase was washed with brine, dried over anhydrous Na₂SO₄ and concentrated under reduced pressure. The residue was purified by column chromatography (PE:EA 25:1) to give 471-6 as a white solid (468 mg, 65%). +ESI-MS: m/z 362.8 [M+H]⁺.

To a solution of 471-6 (460 mg, 1.27 mmol) in anhydrous THF (15 mL) was added LAH (250 mg, 5 mmol) at 0° C. under N₂, and the mixture stirred at 0° C. for 2 h. The reaction was quenched with water, and extracted with EA (3×30 mL). The combined organic phase was washed with brine, dried over anhydrous Na₂SO₄ and concentrated under reduced pressure. The residue was purified by prep-TLC to give 471-7 (150 mg, 36%). +ESI-MS: m/z 324.8 [M+H]⁺.

To a solution of 4-(2-hydroxyethoxy)-3-methoxybenzoic acid (60 mg, 0.3 mmol), HATU (70 mg, 0.5 mmol) and DIEA (300 mg, 0.7 mmol) in DCM (15 mL) was added amine 471-7 (100 mg, 0.3 mmol). After stirring at r.t. for 30 mins., the reaction was quenched with sat. NaHCO₃ solution, and extracted with DCM (3×10 mL). The combined organic phase was washed with brine, dried over anhydrous Na₂SO₄ and concentrated under reduced pressure. The residue was purified by prep-HPLC to give 471 as a white solid (55 mg, 32%). +ESI-MS: m/z 519.0 [M+H]⁺.

Example 253

Preparation of Compounds 509-513

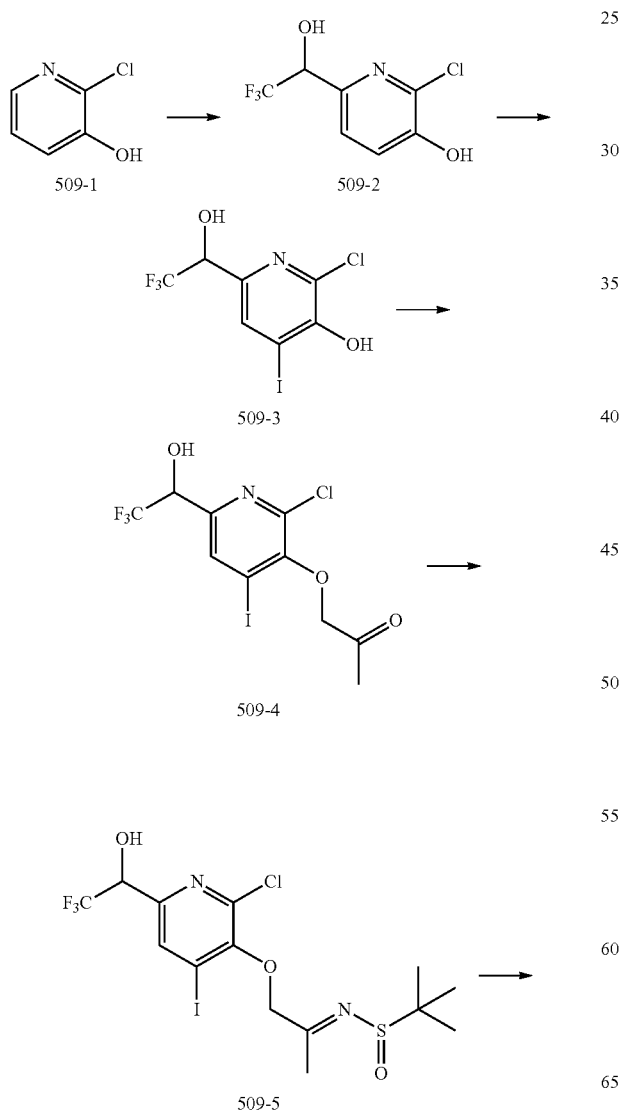

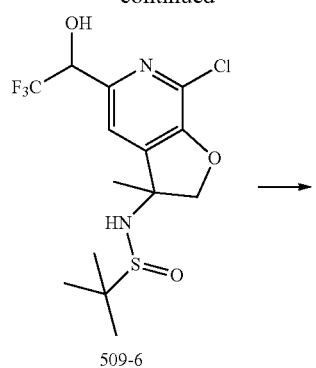

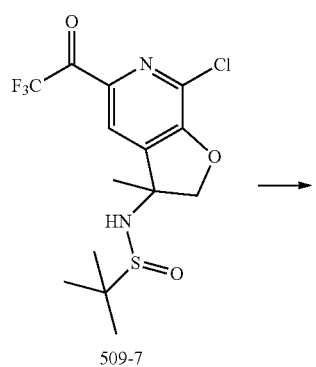

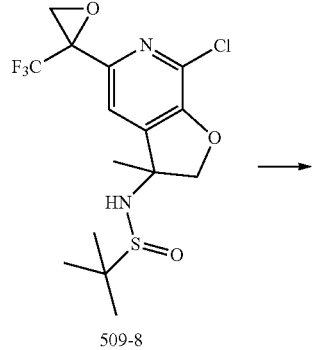

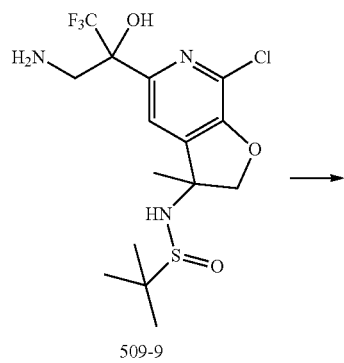

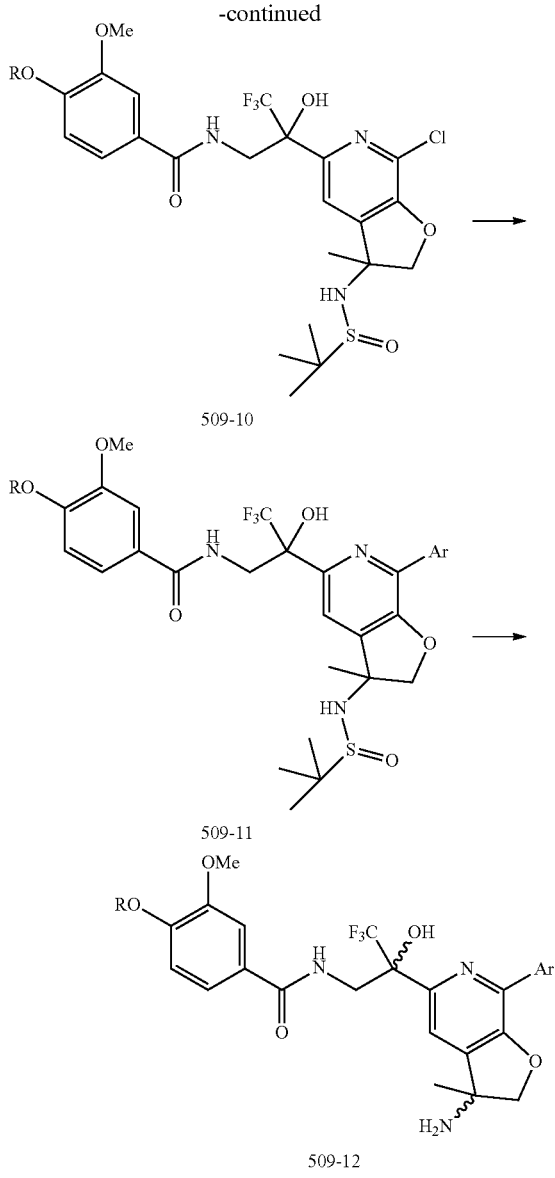

509-10

509-11

509-12

Potassium carbonate (29.8 g, 216 mmol) and trifluoroacetaldehyde ethyl hemiacetal (19 mL, 162 mmol) were sequentially added to a suspension of 509-1 (14.0 g, 108 mmol) in water (210 mL). The reaction was stirred at 100° C. overnight. Additional trifluoroacetaldehyde ethyl hemiacetal (19 mL, 162 mmol) was added. The reaction was stirred at 100° C. for 7 h, and further trifluoroacetaldehyde ethyl hemiacetal (19 mL, 162 mmol) was added. After 16 h at 100° C., the reaction was cooled to 0° C., neutralized with 1M aq. HCl solution and extracted with EtOAc. The organic portion was dried with $Na_2SO_4$, filtered and concentrated under reduced pressure. Chromatography of the residue (cyclohexane:EtOAc, 100:0 to 70:30) afforded 509-2 (24.0 g, 80% purity A/A UV).

Iodine (40.1 g, 158 mmol) was added to a solution of 509-2 (24.0 g) and potassium carbonate (28.9 g, 210 mmol) in water (350 mL). The mixture was stirred at r.t. overnight. A 1M aq. sodium thiosulfate solution was added. The mixture was treated with 3N aq. HCl until a white solid formed. EtOAc was added and the layers were separated. The aqueous phase was extracted with EtOAc (3×). The combined organic portions were dried with $Na_2SO_4$ and filtered. The solvents were removed under reduced pressure. Chromatography of the residue (cyclohexane:EtOAc, 100:0 to 70:30) afforded 509-3 as a white solid (21.0 g, 50% over two steps). UPLC/MS (ES$^+$) m/z: 354.03 [M+H]$^+$.

Chloroacetone (2.6 mL, 32.8 mmol) was added to a solution of 509-3 (10.5 g, 29.8 mmol) and potassium carbonate (6.18 g, 44.8 mmol) in acetone (170 mL). The reaction was stirred at 50° C. overnight. The volatiles were removed under reduced pressure, and the residue was partitioned between water and EtOAc. The layers were separated, and the organic portion was dried with $Na_2SO_4$, filtered and concentrated under reduced pressure. The residue was titrated with DCM, and the precipitate dried to afford 509-4 as a white solid (6.80 g, 55%). UPLC/MS (ES$^+$) m/z: 409.92 [M+H]$^+$. The supernatant was concentrated under reduced pressure, and the residue chromatographed (cyclohexane:EtOAc, 100:0 to 0:100) to afford unreacted 509-3 (1.20 g, 11%).

The reaction was performed in 8 batches. A mixture of 509-4 (841 mg, 2.05 mmol), 2-methylpropane-2-sulfinamide (273 mg, 2.26 mmol) and titanium(IV) ethoxide (1.03 g, 4.51 mmol) in THF (16 mL) was heated to 70° C. (sealed vial, degassed and purged with $N_2$). The mixture was stirred at 70° C. for 3 h. The 8 batches were unified. EtOAc and water were added. The mixture was stirred for 5 mins, and then filtered through a pad of celite. The layers were separated, and the aqueous portion was extracted with EtOAc. The combined organic portions were dried with $Na_2SO_4$ and filtered. The volatiles were removed under reduced pressure. Chromatography of the residue (cyclohexane:EtOAc, 50:50 to 0:100) afforded 509-5 (5.36 g, 63%). UPLC/MS (ES$^+$): m/z 513.10 [M+H]$^+$.

n-Butyllithium (1.6M solution in THF, 6.60 mL, 10.5 mmol) was added to a solution of EtMgBr (1M in THF, 5.23 mL, 5.23 mmol) in THF (15 mL), which had been precooled to 0° C. After 10 mins, the mixture was cooled to −78° C. A solution of 509-5 (2.68 g, 5.23 mmol) in THF (15 mL) was added dropwise. The reaction was stirred at −78° C. for 15 mins. The reaction was quenched with MeOH and diluted with EtOAc. The organic portion was washed with brine, and the aqueous portion extracted with EtOAc. The combined organic portions were dried with $Na_2SO_4$, filtered and concentrated under reduced pressure. Chromatography of the residue (cyclohexane:EtOAc, 100:0 to 50:50) afforded 509-6 as a yellow wax (2.60 g, 64%).

Dess-Martin periodinane (3.14 g, 7.46 mmol) was added to a stirred solution of 509-6 (2.60 g, 6.73 mmol) in DCM (36 mL). The reaction was stirred at r.t. under $N_2$ atmosphere for 3 h. The reaction was quenched with a 1:1 mixture of 2M aq. $Na_2S_2O_3$ and sat. aq. $NaHCO_3$. After 30 mins of vigorous stirring, the layers were separated. The organic portion was washed with brine, dried with $Na_2SO_4$, filtered and concentrated under reduced pressure. Chromatography of the residue (cyclohexane:EtOAc, 100:0 to 50:50) afforded 509-7 as a white solid (2.11 g, 81%). UPLC/MS (ES$^+$): m/z 385.16 [M+H]$^+$, 403.18 [M+$H_3$O]$^+$.

The reaction was performed in 2 batches. Trimethylsulfoxonium iodide (601 mg, 2.73 mmol) was added in 1 portion to a mixture of tBuOK (305 mg, 2.73 mmol) in $CH_3CN$ (50 mL), which had been previously degassed. The mixture was further degassed and stirred at r.t. for 30 mins. The solution containing the ylide was filtered from the solid and added to a solution of 509-7 (1.05 g, 2.73 mmol) in $CH_3CN$ (50 mL), which had been previously degassed. The reaction was stirred at r.t. for 1 h. The 2 batches were combined, and the volatiles were removed under reduced pressure. Chromatography of the residue (cyclohexane:EtOAc, 100:0 to 50:50) afforded 509-8 as a colorless wax (1.45 g, 66%). UPLC/MS (ES+): m/z 399.14 [M+H]+.

A solution of 509-8 (1.45 g, 3.64 mmol) in 7M $NH_3$-MeOH (800 mL) was stirred at r.t. for 2 h. The volatiles were removed under reduced pressure to afford 509-9 (1.43 g), which was used in the next step.

Method A: A mixture of 509-9 (750 mg), EDC (448 mg, 2.35 mmol), HOBT (317 mg, 2.35 mmol), TEA (500 uL, 3.60 mmol) and acid (1.80 mmol) in DCM (18 mL) was stirred at r.t. for 2 h. Water was added, and the mixture was stirred for 10 mins. The layers were separated, and the organic portion was dried with $Na_2SO_4$. The solvent was evaporated under reduced pressure. Chromatography of the residue (cyclohexane:EtOAc) afforded 509-10.

Method B: A solution of acid (0.120 mmol), HATU (44 mg) and DIPEA (110 uL) in DMF or DCM (1 mL) was stirred at r.t. for 15 mins. A solution of 509-9 (50 mg) in DMF (or DCM, 1 mL) was added to the reaction. The mixture was stirred at r.t. for 20 mins. The majority of the volatiles were removed under reduced pressure. The residue was taken up with EtOAc, and the organic portion was washed with 1M aq. NaOH and 1M aq. HCl, dried with $Na_2SO_4$, filtered and concentrated under reduced pressure to give 509-10.

A mixture of 509-10 (0.582 mmol), boronic acid (0.872 mmol), $K_3PO_4$ (247 mg, 1.16 mmol), $KH_2PO_4$ (158 mg, 1.16 mmol) and Pd(dbpf)$Cl_2$ (13.8 mg, 0.029 mmol) in a DME:EtOH:$H_2O$ mixture (5:3:1, 9 mL) was degassed and warmed to 50° C. for 6 h. DCM and water were added. The layers were separated, and the organic portion was dried with $Na_2SO_4$, filtered and concentrated under reduced pressure. Chromatography of the residue (cyclohexane:EtOAc) afforded 509-11.

A 4M HCl-dioxane solution (1 mL) was added to a solution of 509-11 (0.508 mmol) in MeOH (5 mL). After 15 mins, the volatiles were removed under reduced pressure. The residue was dissolved in DCM. The organic portion was washed with 5% aq. $NaHCO_3$ solution and water, dried with $Na_2SO_4$, filtered and concentrated under reduced pressure to afford 509-12.

509-9 ⟶

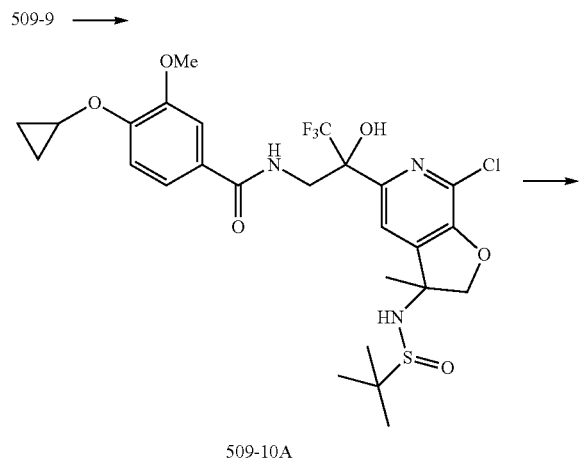

509-10A

-continued

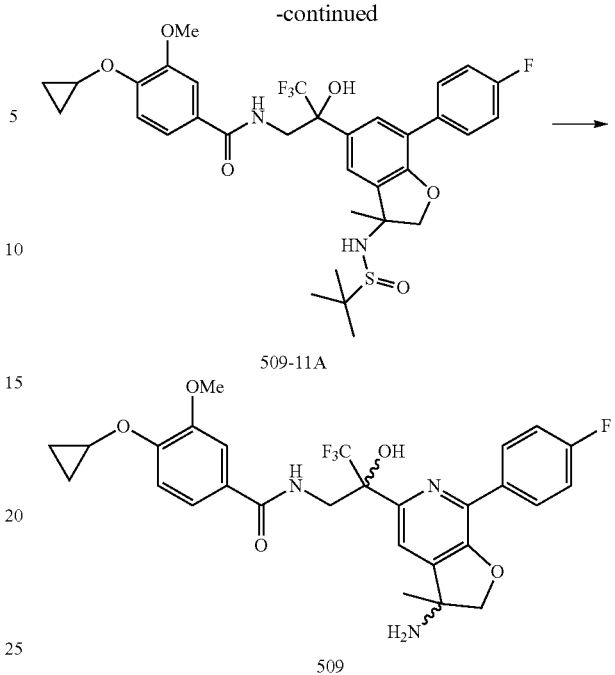

509-11A

509

Coupling of 509-9 with 4-cyclopropoxy-3-methoxybenzoic acid according to Method A afforded 509-10A as a white solid (85%). UPLC/MS (ES+): m/z 606.24 [M+H]+. Suzuki coupling of 509-10A with 4-fluorophenylboronic acid followed by sulfinamide hydrolysis afforded 509 as a white solid (53% over two steps). UPLC/MS (ES+): m/z 562.20 [M+H]+.

509 (53 mg) was dissolved in DCM. The solution was washed with sat. aq. $NaHCO_3$ solution, dried with $Na_2SO_4$, filtered and concentrated under reduced pressure. The amine was resolved by prep-HPLC [Chiralpak AD-H (25×3 cm, 5 um), mobile phase: n-hexane/(ethanol+0.1% ipa) 80:20% v/v, flow rate: 32 mL/min, UV detection DAD 220 nm]. Two fractions were recovered based on retention times: a mixture of 510, 512 and 513: $t_R$=21.0 min; and 511: white solid (7.3 mg, $t_R$=28.5 min). UPLC/MS (ES+): m/z 562.20 [M+H]+.

The mixture of 510, 512 and 513 was resolved by prep-HPLC [Chiralpak IC (25×3 cm, 5 um), mobile phase: n-hexane/(ethanol+0.1% ipa) 70/30% v/v, flow rate: 32 mL/min, UV detection DAD 220 nm]. Two fractions were recovered based on retention times: a mixture of 512 and 513: $t_R$=8.2 min; and 510: white solid (7.1 mg, $t_R$=10.6 min). UPLC/MS (ES+): m/z 562.20 [M+H]+.

The mixture of 512 and 513 was resolved by prep-HPLC [Chiralpak OJ-H (25×3 cm, 5 um), mobile phase: n-hexane/(ethanol/MeOH 1/1+0.1% ipa) 65/35% v/v, flow rate: 38 mL/min, UV detection DAD 220 nm]. Two fractions were recovered based on retention times: 512: white solid (6.0 mg, $t_R$=7.2 min). UPLC/MS (ES+): m/z 562.20 [M+H]+; and 513: white solid (6.0 mg, $t_R$=11.3 min). UPLC/MS (ES+): m/z 562.20 [M+H]+.

Alternatively, 509 (220 mg) was resolved by prep-HPLC [Chiralpak IC (25×2 cm, 5 um), mobile phase: n-hexane/(ethanol/methanol 1/1+0.1% ipa) 86/14% v/v, flow rate: 16 mL/min, UV detection DAD 220 nm]. Three fractions were recovered based on retention times: a mixture of 512 and 513: (104 mg, $t_R$=13.4 min); 511: (40 mg, 14%, $t_R$=15.0 min). UPLC/MS (ES+): m/z 562.20 [M+H]+; and 510: (35 mg, 12%, $t_R$=17.5 min). UPLC/MS (ES+): m/z 562.20 [M+H]+.

The mixture of 512 and 513: was resolved by prep-HPLC [Chiralcel OJ-H (25×3 cm, 5 um), mobile phase: n-hexane/(ethanol/methanol 1/1+0.1% ipa) 65/35% v/v, flow rate: 40 mL/min, UV detection DAD 220 nm]. Two fractions were recovered based on retention times: 512 (41 mg, 14%, $t_R$=7.5 min). UPLC/MS (ES$^+$): m/z 562.20 [M+H]$^+$; and 513 (46.6 mg, 16%, $t_R$=12.0 min). UPLC/MS (ES$^+$): m/z 562.20 [M+H]$^+$.

Example 254

Preparation of Compound 542

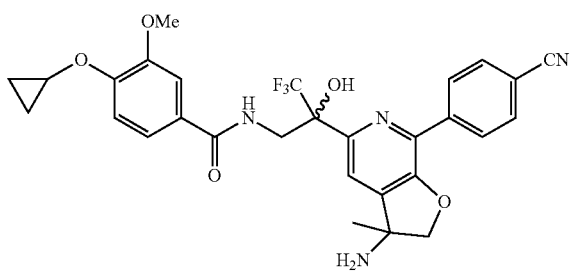 [SMILES: COc1cc(C(=O)NCC(O)(c2cc3c(c(-c4ccc(C#N)cc4)n2)OCC3(C)N)C(F)(F)F)ccc1OC1CC1]

Suzuki coupling of 509-10A with 4-cyanophenylboronic acid followed by hydrolysis of the resulting sulfinamide afforded 542 (78% over 2 steps). UPLC/MS (ES$^+$): m/z 569.40 [M+H]$^+$.

Example 255

Preparation of Compound 539

509-9 ⟶

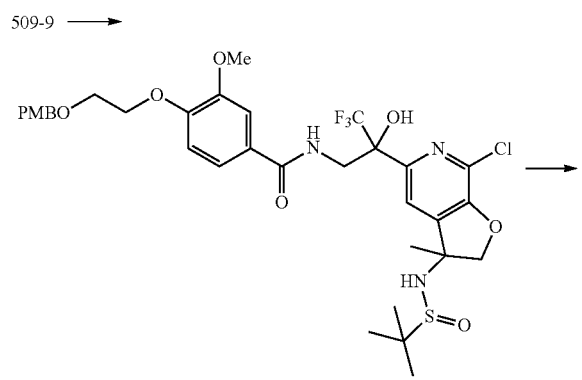

509-10B

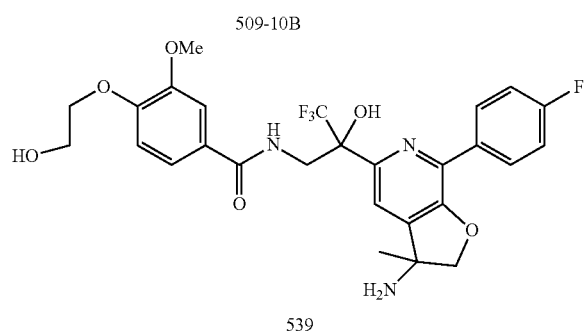

539

Coupling of 509-9 (50 mg) with 4-(2-(4-methoxybenzyloxy)ethoxy)-3-methoxybenzoic acid according to Method B afforded 509-10B. Suzuki coupling of 509-10B with 4-fluorophenylboronic acid followed by sulfinamide hydrolysis and PMB-group removal afforded 539 as an off-white solid (10 mg). UPLC/MS (ES$^+$): m/z 566.30 [M+H]$^+$.

Example 256

Preparation of Compound 543

509-9 ⟶

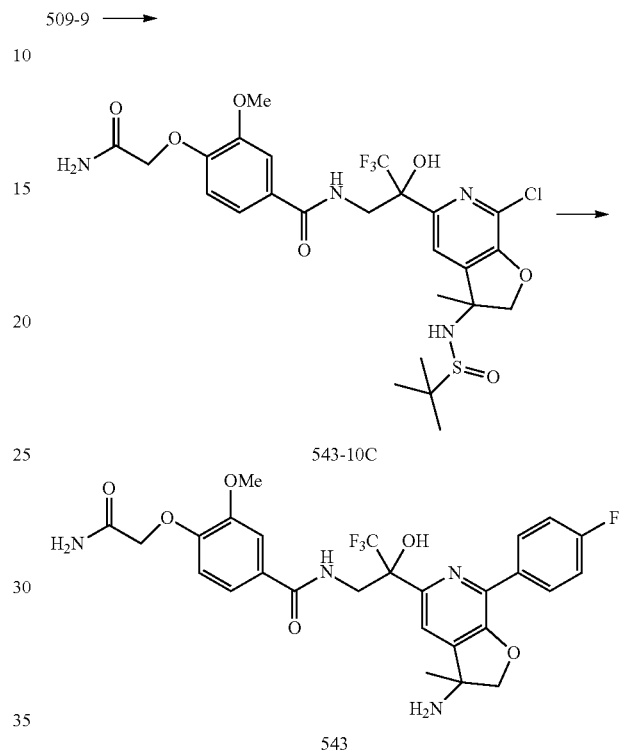

543-10C

543

Coupling of 509-9 (80 mg) with 4-(carbamoylmethoxy)-3-methoxybenzoic acid according to Method B afforded 509-10 C. Suzuki coupling of 509-10C with 4-fluorophenylboronic acid followed by sulfinamide hydrolysis afforded 543 as an off-white solid (8.7 mg). UPLC/MS (ES$^+$): m/z 579.40 [M+H]$^+$.

Example 257

Preparation of Compound 556

509-9 ⟶

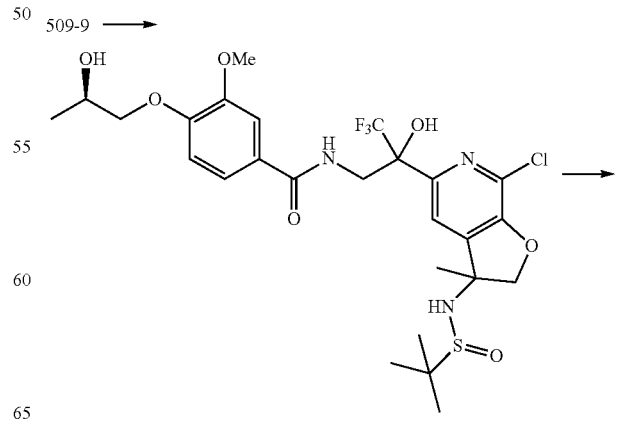

509-10D

-continued
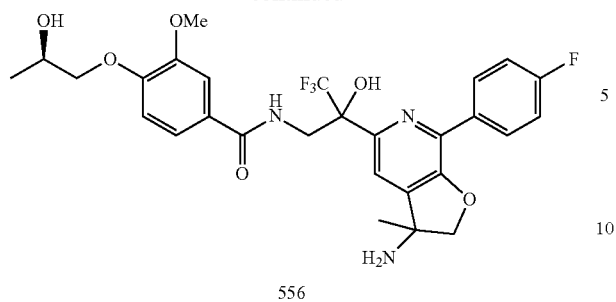
556
Coupling of 509-9 with 4-[(2R)-2-hydroxypropoxy]-3-methoxybenzoic acid according to Method A afforded 509-10D. UPLC/MS (ES+): m/z 624.20 [M+H]+. Suzuki coupling of 509-10D with 4-fluorophenylboronic acid followed by sulfinamide hydrolysis afforded 556 as an off-white solid (50% over 2 steps). UPLC/MS (ES+): m/z 580.33 [M+H]+.
Example 258
Preparation of Compounds 494, 498, 482 and 483
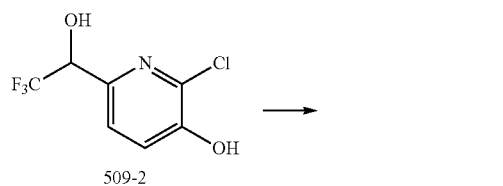
509-2
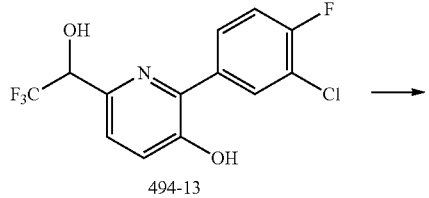
494-13
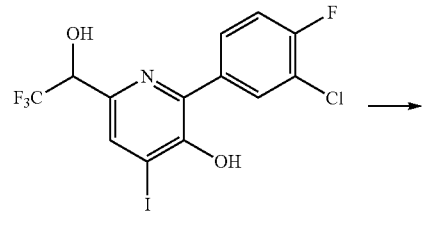
494-14
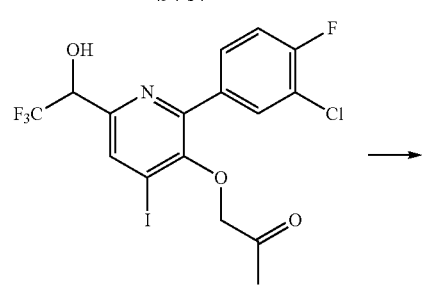
494-15
-continued
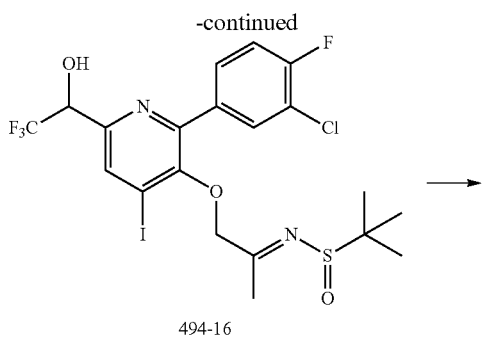
494-16
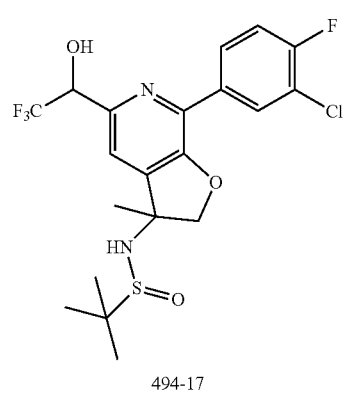
494-17
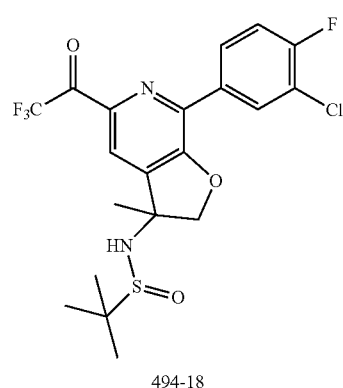
494-18
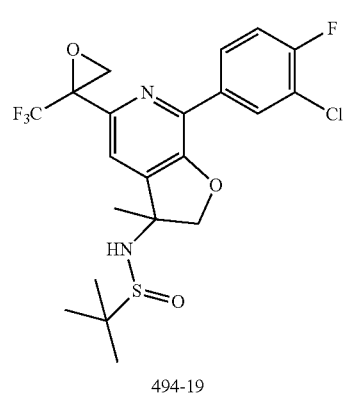
494-19

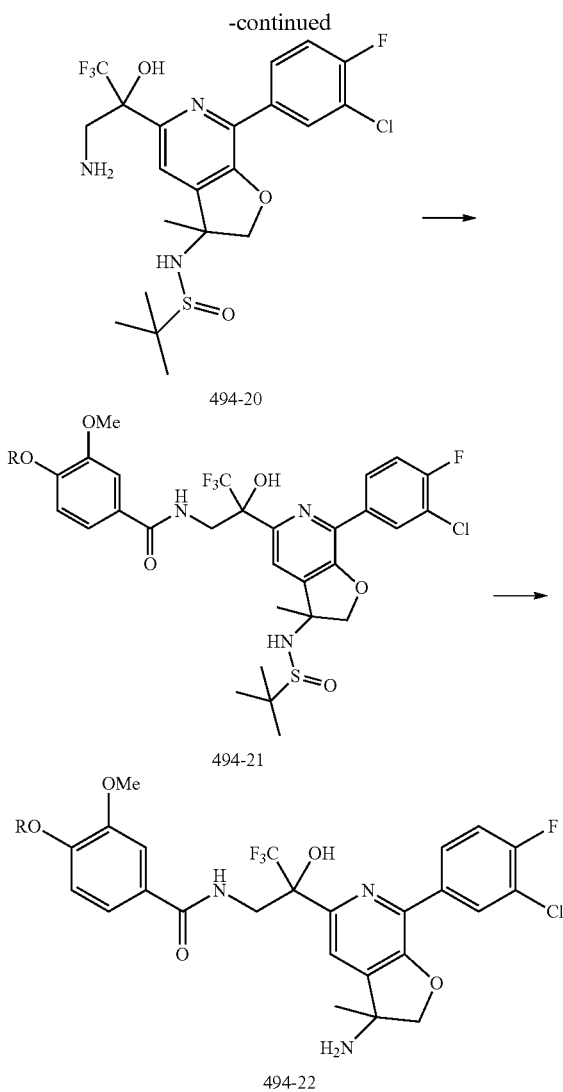

A mixture of 509-2 (5.00 g, 22.0 mmol), (3-chloro-4-fluorophenyl)boronic acid (7.66 g, 44.0 mmol), Pd(dppf)Cl$_2$ (1.60 g, 2.20 mmol) and Na$_2$CO$_3$ (2M aq solution, 22.0 mL, 44.0 mmol) in DCE (250 mL) was degassed and heated to reflux for 16 h. Additional Pd(dppf)Cl$_2$ (0.05 eq), (3-chloro-4-fluorophenyl)boronic acid (1 eq.) and aq Na$_2$CO$_3$ (1 eq) were added. The reaction was refluxed for 4 h and then water was added. The layers were separated, and the aqueous portion was extracted with EtOAc. The combined organic portions were dried with Na2SO$_4$, filtered and concentrated under reduced pressure. Chromatography of the residue (cyclohexane:DCM, 70:30 to 0:100) afforded 494-13 as a yellow solid (2.74 g). UPLC/MS (ES$^+$): m/z 322.10 [M+H]$^+$.

Iodine (1.77 g, 6.98 mmol) was added to a solution of 494-13 (2.24 g, 6.98 mmol) and potassium carbonate (2.89 g, 20.9 mmol) in water (100 mL). The mixture was stirred at r.t. for 30 mins. A 1M aq. sodium thiosulfate solution was added. The mixture was treated with 3N aq. HCl until a white solid formed. EtOAc was added, and the layers were separated. The aqueous phase was extracted with EtOAc. The combined organic portions were dried with Na$_2$SO$_4$ and filtered. The solvents were removed under reduced pressure. Chromatography of the residue (cyclohexane:EtOAc, 100:0 to 80:20) afforded 494-14 as a light yellow solid (2.80 g, 90%). UPLC/MS (ES$^+$): m/z 448.05 [M+H]$^+$.

Chloroacetone (548 µL, 6.89 mmol) was added to a solution of 494-14 (2.80 g, 6.26 mmol) and potassium carbonate (1.30 g, 9.40 mmol) in acetone (40 mL). The reaction was stirred at 50° C. for 24 h. The volatiles were removed under reduced pressure, and the residue was partitioned between water and EtOAc. The layers were separated, and the organic portion was dried with Na$_2$SO$_4$, filtered and concentrated under reduced pressure. Chromatography of the residue (cyclohexane:DCM, 60:40 to 30:70) afforded 494-15 as a white solid (2.38 g, 75%). UPLC/MS (ES$^+$): m/z 504.27 [M+H]$^+$.

A mixture of 494-15 (1.87 g, 3.72 mmol), 2-methylpropane-2-sulfinamide (495 mg, 4.09 mmol) and titanium(IV) ethoxide (1.86 g, 8.18 mmol) in THF (30 mL) was heated to 70° C. (sealed vial, degassed and purged with N$_2$). The mixture was stirred at 70° C. overnight. EtOAc and water were added. The mixture was filtered through a pad of celite. The layers were separated, and the organic portion was dried with Na$_2$SO$_4$ and filtered. The volatiles were removed under reduced pressure. Chromatography of the residue (cyclohexane:EtOAc, 80:20 to 20:80) afforded 494-16 as a light yellow solid (1.00 g, 45%). UPLC/MS (ES$^+$): m/z 607.07 [M+H]$^+$.

n-Buthyllithium (1.6 M solution in THF, 2.07 mL, 3.32 mmol) was added to a solution of EtMgBr (1 M solution in THF, 1.66 mL, 1.66 mmol) in THF (5 mL), which had been pre-cooled to 0° C. After 10 mins, the mixture was cooled to −78° C. A solution of 494-16 (1.00 g, 1.66 mmol) in THF (5 mL) was added dropwise, and the reaction was stirred at −78° C. for 15 mins. The reaction was quenched with MeOH and diluted with EtOAc. The organic portion was washed with brine, and the aqueous portion extracted with EtOAc. The combined organic portions were dried with Na$_2$SO$_4$, filtered and concentrated under reduced pressure. Chromatography of the residue (cyclohexane:EtOAc, 50:50 to 0:100) afforded 494-17 (775 mg, 70% purity A/A UV).

Dess-Martin periodinane (822 mg, 1.94 mmol) was added to a stirred solution of 494-17 (775 mg) in DCM (7 mL). The reaction was stirred at r.t. for 2 h and quenched with a 1:1 mixture of 2M aq. Na$_2$S$_2$O$_3$ and sat. aq. NaHCO$_3$. After 20 mins of vigorous stirring, the layers were separated. The aqueous portion was extracted with DCM. The combined organic portions were dried with Na$_2$SO$_4$, filtered and concentrated under reduced pressure. Chromatography of the residue (cyclohexane:EtOAc, 50:50 to 0:100) afforded 494-18 (480 mg, 60% over 2 steps).

Trimethylsulfoxonium iodide (57.5 mg, 0.261 mmol) was added in one portion to a mixture of tBuOK (29.2 mg, 0.261 mmol) in CH$_3$CN (5 mL), which had been previously degassed. The mixture was further degassed and stirred at r.t. for 30 mins. The solution containing the ylide was filtered from the solid and added to a solution 494-18 (125 mg, 0.261 mmol) in CH$_3$CN (4 mL), which had been previously degassed. The reaction was stirred at r.t. for 15 mins. The volatiles were removed under reduced pressure. Chromatography of the residue (cyclohexane:EtOAc, 80:20 to 0:100) afforded 494-19 as a colorless wax (51 mg, 40%). UPLC/MS (ES$^+$): m/z 493.20 [M+H]$^+$.

A solution of 494-19 (51 mg) in 7M NH$_3$-MeOH (30 mL) was stirred at r.t. for 18 h. The volatiles were removed under reduced pressure to afford 494-20 (62 mg), which was directly in the next step.

A mixture of acid (0.136 mmol), HATU (51.7 mg, 0.136 mmol) and DIPEA (43 uL, 0.246 mmol) in DCM (2 mL) was stirred at r.t. for 30 mins. A solution of 494-20 (62 mg) in DCM (2 mL) was added, and the mixture was stirred at r.t. for 1 h. The reaction was partitioned between DCM and water, and the layers were separated. The organic portion was washed with brine, dried with Na$_2$SO$_4$, filtered and concentrated under reduced pressure. Chromatography of the residue afforded 494-21.

A 4M HCl-dioxane solution (1 mL) was added to a solution of 494-21 (0.060 mmol) in MeOH (5 mL). After 30 mins, the volatiles were removed under reduced pressure. The residue was purified by reverse phase chromatography to afford 494-22.

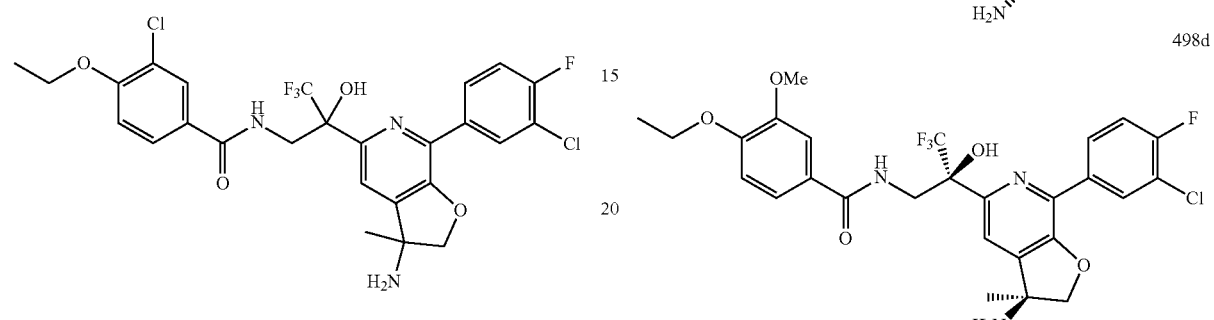

Coupling of 494-20 with 3-chloro-4-ethoxybenzoic acid followed by hydrolysis of the resulting sulfinamide afforded 494 (42% over 3 steps). UPLC/MS (ES$^+$): m/z 588.20 [M+H]$^+$.

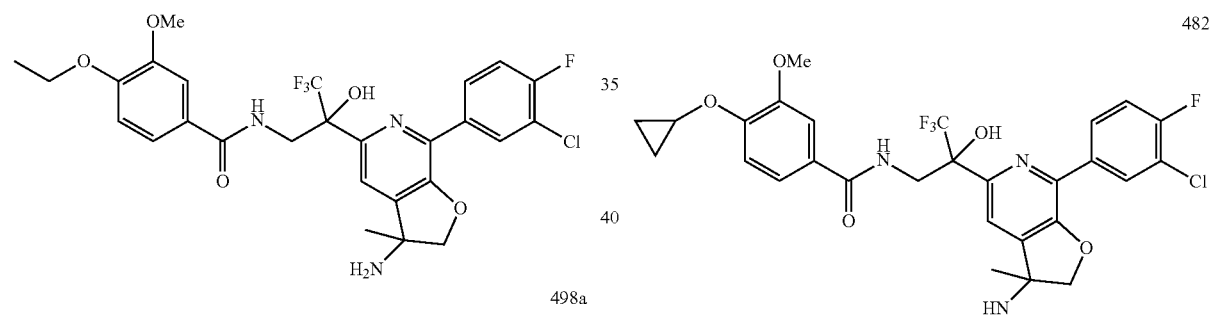

Coupling of 494-20 with 4-ethoxy-3-methoxybenzoic acid followed by hydrolysis of the resulting sulfinamide afforded 498 (28% over three steps). UPLC/MS (ES$^+$):m/z 584.30 [M+H]$^+$.

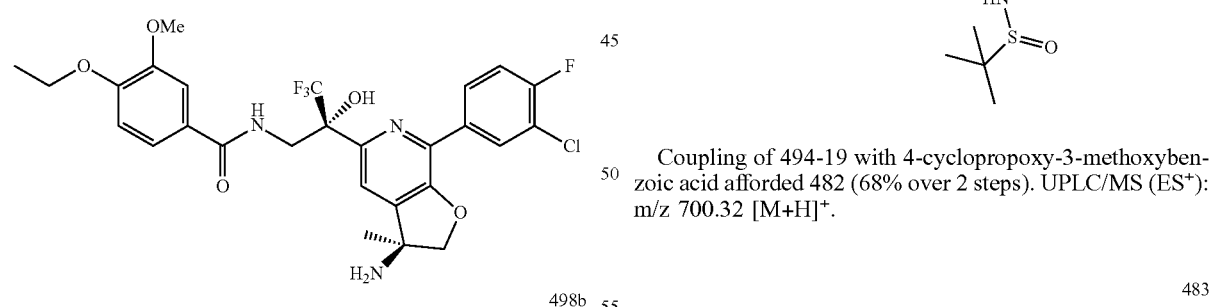

Coupling of 494-19 with 4-cyclopropoxy-3-methoxybenzoic acid afforded 482 (68% over 2 steps). UPLC/MS (ES$^+$): m/z 700.32 [M+H]$^+$.

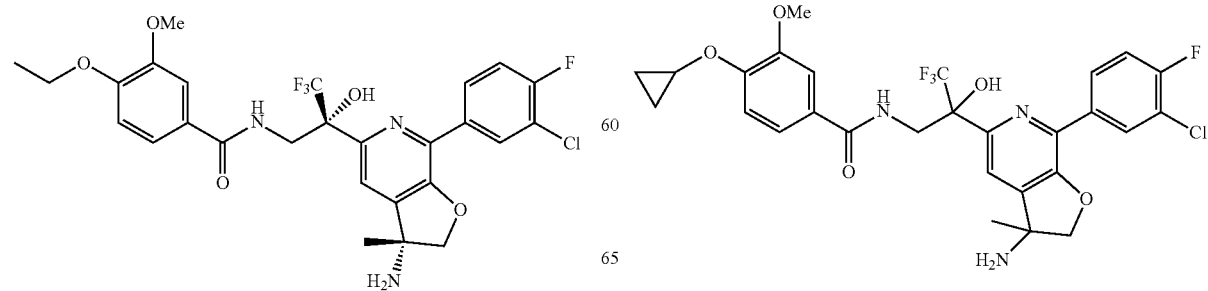

Hydrolysis of 482 according to general procedure afforded 483 as a white solid (formic acid salt, 76%). Alternatively, 483 was prepared by Suzuki coupling of 509-10A with 3-chloro-4-fluorophenylboronic acid and subsequent hydrolysis of the resulting sulfinamide (53% over 2 steps). UPLC/MS (ES+): m/z 596.29 [M+H]+.

483 (100 mg) was resolved by prep-HPLC [Chiralpak AD-H (25×2 cm, 5 um), mobile phase: n-hexane/(ethanol+0.1% ipa) 80/20% v/v, flow rate: 14 mL/min, UV detection DAD 220 nm]. Two fractions were recovered based on retention times: a mixture of 498a and 498b: 32 mg ($t_R$=14.3 min); and a mixture of 498c and 498d: 31 mg ($t_R$=19.0 min).

The mixture of 498a and 498b (32 mg) was resolved by prep-HPLC [Chiralcel OJ-H (25×2 cm, 5 um), mobile phase: n-hexane/(ethanol/methanol+0.1% ipa) 55/45% v/v, flow rate: 17 mL/min, UV detection DAD 220 nm]. Two fractions were recovered based on retention times: 498a: 9.3 mg ($t_R$=5.7 min). UPLC/MS (ES+): m/z 596.25 [M+H]+; and 498b: 10.2 mg ($t_R$=8.8 min). UPLC/MS (ES+): m/z 596.25 [M+H]+.

The mixture of 498c and 498d (31 mg) was resolved by prep-HPLC [Chiralpak IC (25×2 cm, 5 um), mobile phase: n-hexane/(2-propanol+0.1% ipa) 55/45% v/v, flow rate: 18 mL/min, UV detection DAD 220 nm]. Two fractions were recovered based on retention times: 498c: 10 mg ($t_R$=6.7 min). UPLC/MS (ES+): m/z 596.25 [M+H]+; and 498d: 8 mg ($t_R$=10.5 min). UPLC/MS (ES+): m/z 596.25 [M+H]+.

Example 259

Preparation of Compound 499

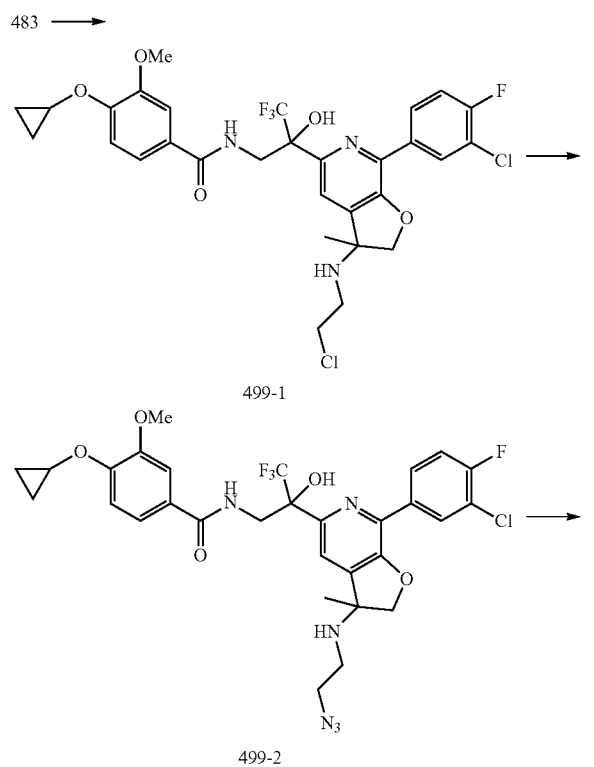

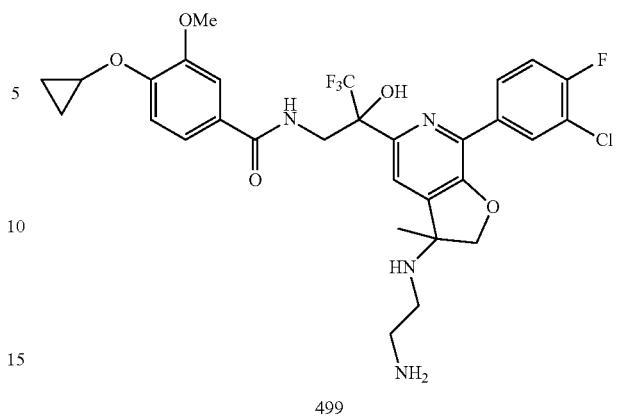

A solution of 483 (30 mg) and chloroacetaldehyde (50% aq. solution, 30 uL) in MeOH (1.5 mL) was stirred at r.t. for 1 h. NaBH3CN (2 mg) was added, and the mixture was stirred at r.t. for 18 h. The volatiles were removed under reduced pressure to afford a mixture of 499-1 and unreacted starting material (2:1), which was dissolved in DMF (1.5 mL). NaN3 (10 mg) was added. The reaction was stirred at 70° C. for 20 h. The volatiles were removed under reduced pressure. Chromatography of the residue (cyclohexane:EtOAc, 80:20 to 0:100) afforded 499-2 as a pale yellow oil (20 mg). UPLC/MS (ES+): m/z 665.30 [M+H]+.

A mixture of 499-2 (20 mg) and PPh3 (10 mg) in 2:1 THF—H2O (1.5 mL) was stirred while heating to 60° C. for 2 h. The volatiles were removed under reduced pressure. The residue was loaded on to an SCX column and eluted with 2M NH3-MeOH to afford 499 (7 mg). UPLC/MS (ES+): m/z 639.30 [M+H]+.

Example 260

Preparation of Compounds 530 and 531

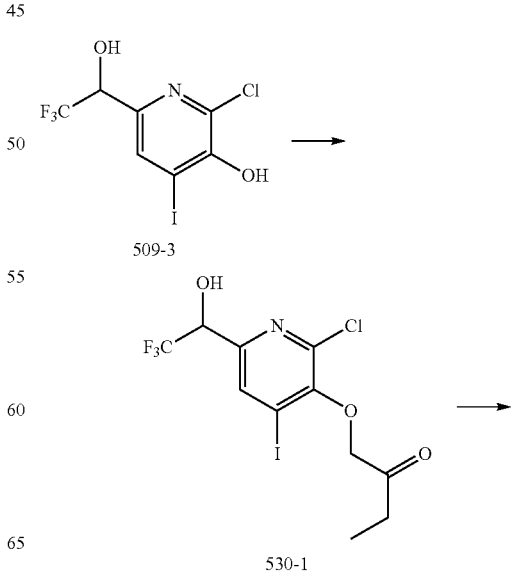

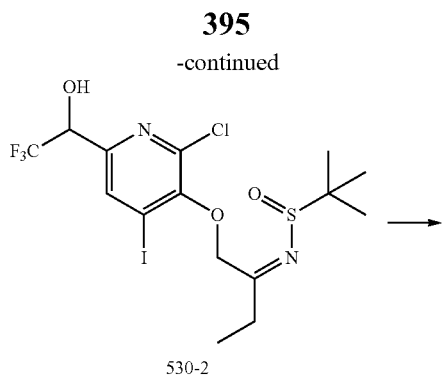
530-2
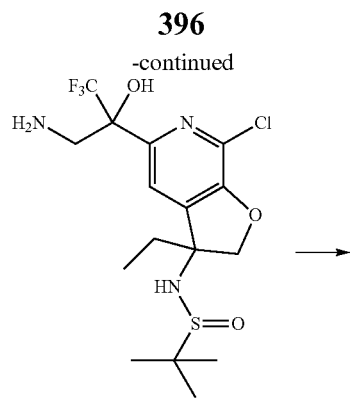
530-6
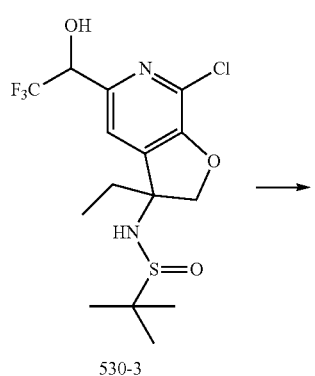
530-3
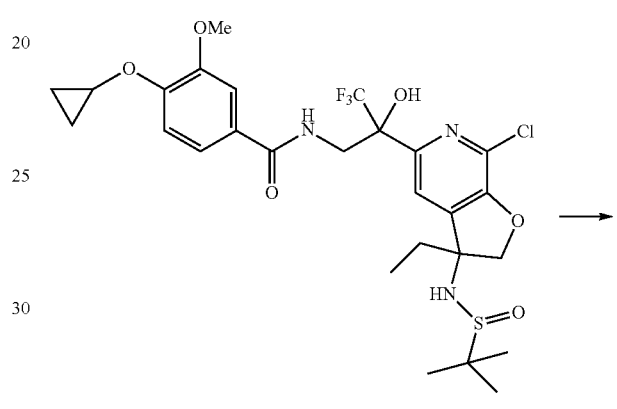
530-7
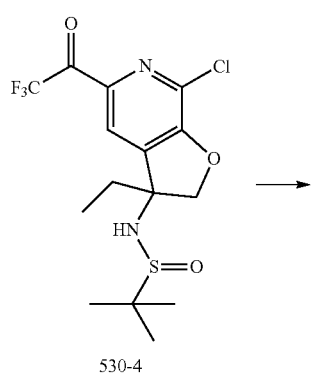
530-4
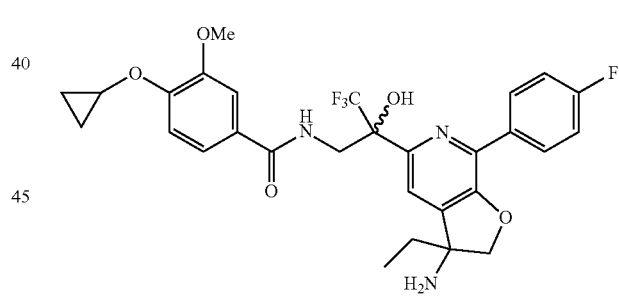
531
530-6 →
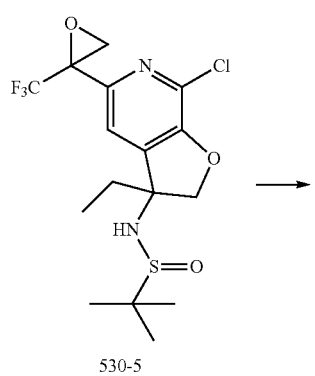
530-5
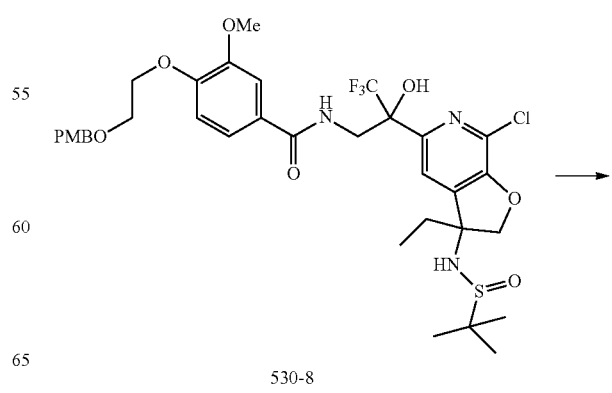
530-8

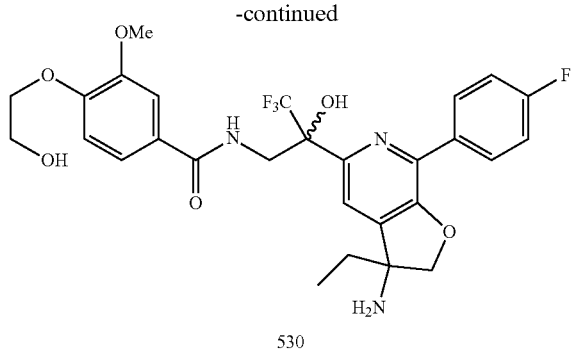

530

Compounds 530 and 531 were prepared by using a strategy that follows the procedure described for 509.

1-Bromo-2-butanone (300 mg, 1.98 mmol) was added to a solution of 509-3 (1.00 g, 2.84 mmol) and potassium carbonate (520 mg, 4.26 mmol) in acetone (16.5 mL). The reaction was stirred at 50° C. for 1 h. The volatiles were removed under reduced pressure, and the residue was partitioned between water and EtOAc. The layers were separated. The organic portion was dried with $Na_2SO_4$, filtered and concentrated under reduced pressure. The residue was triturated with DCM-cyclohexane to afford 530-1 as a white solid (1.02 g, 85%). UPLC/MS (ES$^+$): m/z 423.93 [M+H]$^+$.

The reaction was performed in 2 batches. A mixture of 530-1 (510 mg, 1.20 mmol), 2-methylpropane-2-sulfinamide (160 mg, 1.32 mmol) and titanium(IV) ethoxide (602 mg, 2.64 mmol) in THF (9.5 mL) was heated to 70° C. (sealed vial, degassed and purged with $N_2$). The mixture was stirred at 70° C. for 4 h. The 2 batches were unified, and EtOAc and water were added. The mixture was filtered through a pad of celite. The layers were separated and the aqueous portion was extracted with EtOAc. The combined organic portions were dried with $Na_2SO_4$ and filtered. The volatiles were removed under reduced pressure. Chromatography of the residue (cyclohexane:EtOAc, 95:5 to 60:40) afforded 530-2 (850 mg, 67%). UPLC/MS (ES$^+$): m/z 527.00 [M+H]$^+$.

EtMgBr (1M solution in THF, 1.61 mL, 1.61 mmol) was added to a solution of n-BuLi (1.6M solution in THF, 2.01 mL, 3.23 mmol) in dry THF (5 mL), which had been pre-cooled to 0° C. After 30 mins, the mixture was cooled to −78° C. A solution of 530-2 (850 mg, 1.61 mmol) in dry THF (4 mL) was added dropwise, and the reaction was stirred at −78° C. for 20 mins. The reaction was quenched with MeOH and diluted with EtOAc. The organic portion was washed with water and the aqueous portion extracted with EtOAc. The combined organic portions were dried with $Na_2SO_4$, filtered and concentrated under reduced pressure. Chromatography of the residue (cyclohexane:EtOAc, 100:0 to 30:70) afforded 530-3 as a white foam (441 mg).

Dess-Martin periodinane (932 mg, 2.20 mmol) was added to a stirred solution of 530-3 (441 mg) in DCM (5 mL). The reaction was stirred at r.t. for 1 h and quenched with a 1:1 mixture of 1M aq. $Na_2S_2O_3$ and 5% aq. $NaHCO_3$. After 20 min of vigorous stirring, the layers were separated. The aqueous portion was extracted with DCM. The combined organic portions were dried with $Na_2SO_4$, filtered and concentrated under reduced pressure. Chromatography of the residue (cyclohexane:EtOAc, 100:0 to 0:100) afforded 530-4 as a white foam (320 mg, 50% over two steps). UPLC/MS (ES$^+$): m/z 417.10 [M+H$_3$O]$^+$.

Trimethylsulfoxonium iodide (175 mg, 0.790 mmol) was added in one portion to a mixture of tBuOK (88 mg, 0.790 mmol) in $CH_3CN$ (15 mL), which had been previously degassed. The mixture was further degassed and stirred at r.t. for 30 mins. The solution containing the ylide was filtered from the solid and added to a solution 530-4 (317 mg, 0.790 mmol) in $CH_3CN$ (15 mL), which had been previously degassed. The reaction was stirred at r.t. for 1 h. The volatiles were removed under reduced pressure. Chromatography of the residue (cyclohexane:EtOAc, 100:0 to 50:50) afforded 530-5 as a colorless wax (207 mg, 64%). UPLC/MS (ES$^+$): m/z 413.12 [M+H]$^+$.

A solution of 530-5 (207 mg) in 7M $NH_3$-MeOH (142 mL) was stirred at r.t. for 2 h. The volatiles were removed under reduced pressure to afford crude 530-6 (203 mg) which was directly progressed to the next step.

A mixture of acid (0.233 mmol), HATU (86 mg, 0.252 mmol) and DIPEA (58 uL, 0.336 mmol) in DCM (2 mL) was stirred at r.t. for 30 mins. A solution of 530-6 (100 mg) in DCM (2 mL) was added. The mixture was stirred at r.t. for 1 h. The reaction was partitioned between DCM and water, and the layers were separated. The organic portion was washed with brine, dried with $Na_2SO_4$, filtered and concentrated under reduced pressure. The residue was purified by chromatography to give 530-7 or 530-8.

A mixture of 530-7 or 530-8 (0.134 mmol), 4-fluorophenylboronic acid (38 mg), $K_3PO_4$ (29 mg), $KH_2PO_4$ (18 mg) and Pd(dbpf)Cl$_2$ (17 mg) in a DME:EtOH:$H_2O$ mixture (10:5:3, 3.6 mL) was degassed and warmed to 50° C.-70° C. DCM and water were added. The layers were separated. The organic portion was dried with $Na_2SO_4$, filtered and concentrated under reduced pressure. The residue was purified by chromatography. A solution of sulfinamide (80 mg) in 4M HCl-dioxane was stirred at r.t. for 10 mins. The volatiles were removed under reduced pressure. The residue was purified by reverse phase chromatography.

Coupling of 530-6 with 4-cyclopropoxy-3-methoxybenzoic acid afforded 530-7, which was subjected to Suzuki coupling and sulfinamide hydrolysis as described herein to afford 531 as a white solid (formic acid salt, 25% overall). UPLC/MS (ES$^+$): m/z 576.30 [M+H]$^+$.

Coupling of 530-6 with 4-(2-(4-methoxybenzyloxy)ethoxy)-3-methoxybenzoic acid afforded 530-8, which was subjected to Suzuki coupling and protecting groups removal as described herein to afford 530 as a white powder (26% overall). UPLC/MS (ES$^+$): m/z 580.34 [M+H]$^+$.

Example 261

Preparation of Compounds 560, 565 and 568

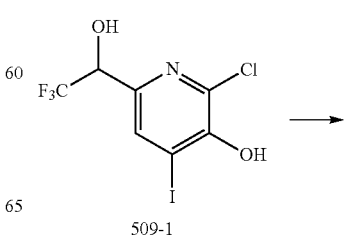

509-1

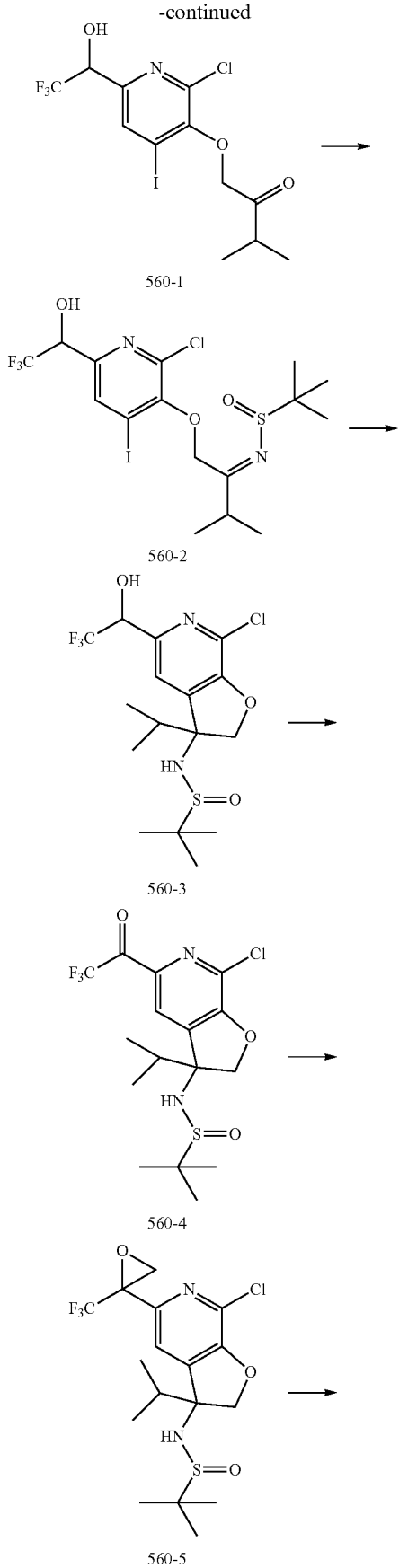
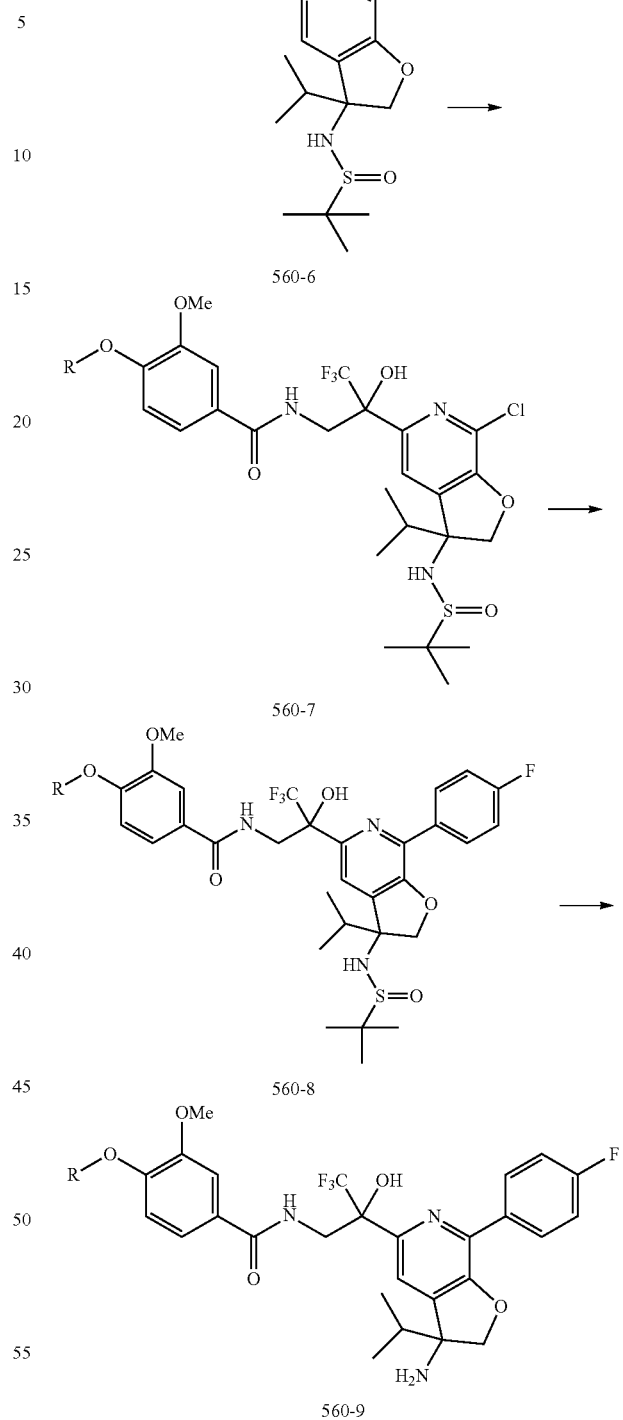
Compounds 560, 565 and 531 were prepared by using a strategy that follows the procedure described for 509.
1-Bromo-3-methylbutan-2-one (659 mg, 3.99 mmol) was added to a solution of 509-3 (2.01 g, 5.71 mmol) and potassium carbonate (1.18 g, 8.56 mmol) in acetone (34 mL). The reaction was stirred at 50° C. for 1 h. The volatiles were removed under reduced pressure and the residue was partitioned between water and EtOAc. The layers were separated. The organic portion was dried with Na₂SO₄, filtered and concentrated under reduced pressure. The residue was tritured with cyclohexane and the precipitate dried to afford 560-1 as a white solid (1.38 g, 55%). UPLC/MS (ES⁺): m/z 438.10 [M+H]⁺.

A mixture of 560-1 (1.38 g, 3.15 mmol), 2-methylpropane-2-sulfinamide (419 mg, 3.46 mmol) and titanium(IV) ethoxide (1.58 g, 6.93 mmol) in THF (25 mL) was heated to 70° C. (sealed vial, degassed and purged with N₂) and stirred at 70° C. for 4 h. EtOAc and water were added. The mixture was filtered through a pad of celite. The layers were separated. The organic portion was dried with Na₂SO₄ and filtered. The volatiles were removed under reduced pressure. Chromatography of the residue (cyclohexane:Et₂O, 90:10 to 60:40) afforded 560-2 (841 mg, 50%). UPLC/MS (ES⁺): m/z 541.10 [M+H]⁺.

n-Buthyllithium (1.6 M solution in THF, 1.93 mL, 3.10 mmol) was added to a solution of EtMgBr (1M solution in THF, 1.55 mL, 1.55 mmol) in THF (5 mL), which had been pre-cooled to 0° C. After 10 mins, the mixture was cooled to −78° C. A solution of 560-2 (841 mg, 1.55 mmol) in THF (4 mL) was added dropwise and the reaction was stirred at −78° C. for 20 min. The reaction was quenched with MeOH and diluted with EtOAc. The organic portion was washed with brine and the aqueous portion extracted with EtOAc. The combined organic portions were dried with Na₂SO₄, filtered and concentrated under reduced pressure. Chromatography of the residue (cyclohexane:EtOAc, 100:0 to 30:70) afforded 560-3 as a white foam (580 mg, 90%).

Dess-Martin periodinane (1.19 g, 2.80 mmol) was added to a stirred solution of 560-3 (580 mg, 1.40 mmol) in DCM (10 mL). The reaction was stirred at r.t. for 1 h and quenched with a 1:1 mixture of 2M aq. Na₂S₂O₃ and sat. aq. NaHCO₃. After 20 mins vigorous stirring, the layers were separated. The aqueous portion was extracted with DCM. The combined organic portions were dried with Na₂SO₄, filtered and concentrated under reduced pressure. Chromatography of the residue (cyclohexane:EtOAc, 100:0 to 0:100) afforded 560-4 as a white foam (520 mg, 90%).

Trimethylsulfoxonium iodide (277 mg, 1.26 mmol) was added in one portion to a mixture of tBuOK (141 mg, 1.26 mmol) in CH₃CN (20 mL), which had been previously degassed. The mixture was further degassed and stirred at r.t. for 30 mins. The solution containing the ylide was filtered from the solid and added to a solution 560-4 (520 mg, 1.26 mmol) in CH₃CN (20 mL), which had been previously degassed. The reaction was stirred at room temp for 15 min. Volatiles were removed under reduced pressure. Chromatography of the residue (cyclohexane:EtOAc, 80:20 to 50:50) afforded 560-5 as a colorless oil (311 mg, 58%). UPLC/MS (ES⁺): m/z 427.28 [M+H]⁺.

A solution of 560-5 (311 mg, 0.730 mmol) in 7M NH₃-MeOH (140 mL) was stirred at r.t. for 2 h. The volatiles were removed under reduced pressure to afford 560-6 (313 mg), which was directly progressed to the next step.

Method A:
A mixture of 560-6 (155 mg, 0.350 mmol), acid (0.350 mmol), EDC (86.3 mg, 0.450 mmol), HOBT (61.4 mg, 0.450 mmol) and TEA (97 µL, 0.700 mmol) in DCM (5 mL) was stirred at r.t. for 2 h. Water was added and the mixture was stirred at r.t. for 10 mins. The layers were separated, and the organic portion was washed with brine, dried with Na₂SO₄, filtered and concentrated under reduced pressure. Chromatography of the residue (cyclohexane:EtOAc) afforded 560-7.

Method B:
A mixture of acid (0.169 mmol), HATU (96.5 mg, 0.254 mmol), and DIPEA (59 uL, 0.338 mmol) in DMF (1 mL) was stirred at room temp for 30 min. A solution of aminol 560-6 (100 mg) in DMF (1 mL) was added and the reaction was stirred at room temp for 1 h. EtOAc was added and the organic portion was washed twice with sat. aq. NH₄Cl solution, dried (Na₂SO₄), filtered and concentrated under reduced pressure to afford 560-7, which was directly progressed to the next step.

A mixture of 560-7 (0.250 mmol), 4-fluorophenylboronic acid (104 mg, 0.740 mmol), K₃PO₄ (106 mg, 0.500 mmol), KH₂PO₄ (68 mg, 0.500 mmol) and Pd(dbpf)Cl₂ (11 mg, 0.017 mmol) in a DME:EtOH:H₂O mixture (5:3:1, 18 mL) was degassed and warmed to 80° C. After 3 h, EtOAc was added. The organic portion was washed with sat. aq. NH₄Cl solution, dried with Na₂SO₄, filtered and concentrated under reduced pressure. Chromatography of the residue (cyclohexane:EtOAc) afforded 560-8.

Method A:
Hydrochloric acid (4M solution in dioxane, 2 mL) was added to a solution of 560-8 (152 mg) in MeOH (4 mL). After 10 mins, the volatiles were removed under reduced pressure. The residue was purified by reverse phase chromatography to afford 560-9.

Method B:
A solution of 560-8 (0.089 mmol) in 4M HCl-dioxane (4 mL) was stirred at r.t. for 40 mins. The volatiles were removed under reduced pressure. The residue was purified by reverse phase chromatography (water-CH₃CN, 100:0 to 50:50) to afford 560-9.

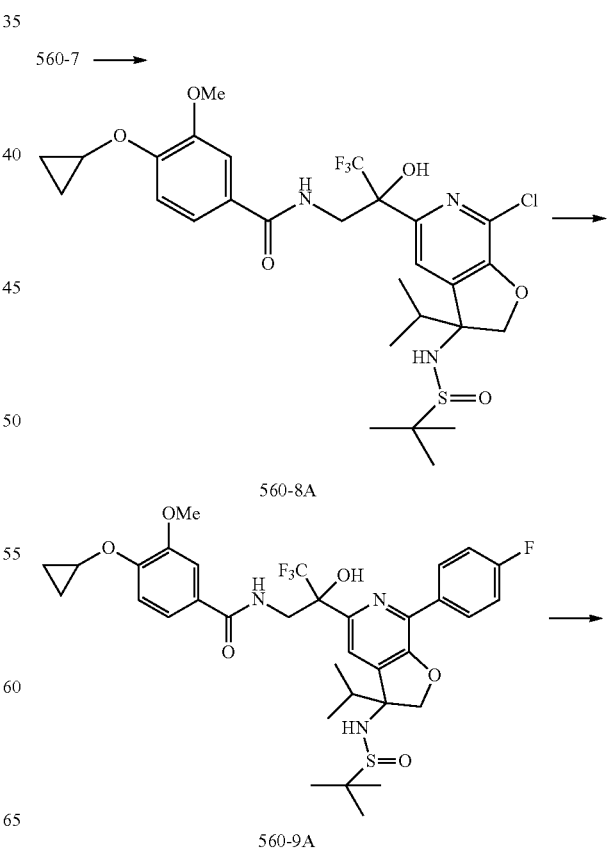

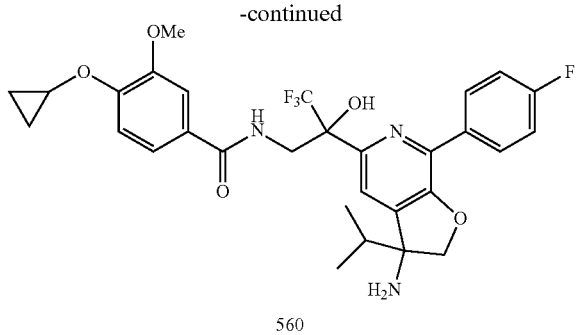

560

Coupling of 560-7 with 4-cyclopropoxy-3-methoxybenzoic acid according to Method A afforded 560-8A (70%). UPLC/MS (ES⁺): m/z 634.33 [M+H]⁺.

Suzuki coupling of 560-8A with 4-fluorophenylboronic acid followed by sulfinamide hydrolysis (Method A) afforded 560 as a white solid (43% over 2 steps). UPLC/MS (ES⁺): m/z 590.40 [M+H]⁺.

Coupling of 560-7 with 4-(2-(4-methoxybenzyloxy)ethoxy)-3-methoxybenzoic acid according to Method B afforded 560-8B which was progressed to the next step without any purification.

Suzuki coupling of 560-8B with 4-fluorophenylboronic acid followed by sulfinamide hydrolysis (Method B) afforded 565 as an off-white solid (13% overall). UPLC/MS (ES⁺): m/z 594.40 [M+H]⁺.

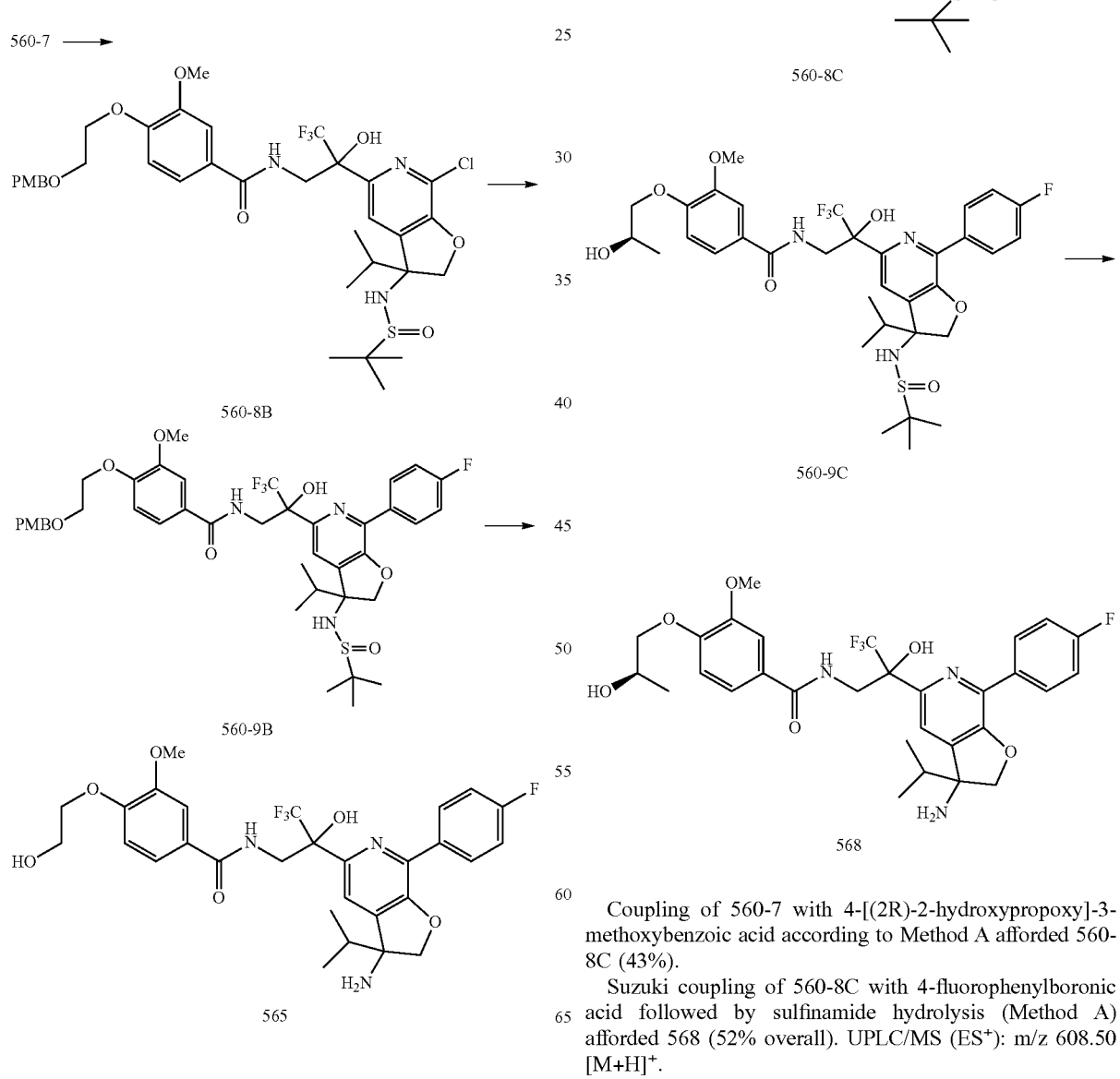

Coupling of 560-7 with 4-[(2R)-2-hydroxypropoxy]-3-methoxybenzoic acid according to Method A afforded 560-8C (43%).

Suzuki coupling of 560-8C with 4-fluorophenylboronic acid followed by sulfinamide hydrolysis (Method A) afforded 568 (52% overall). UPLC/MS (ES⁺): m/z 608.50 [M+H]⁺.

Example 262
Preparation of Compounds 473, 474 and 475
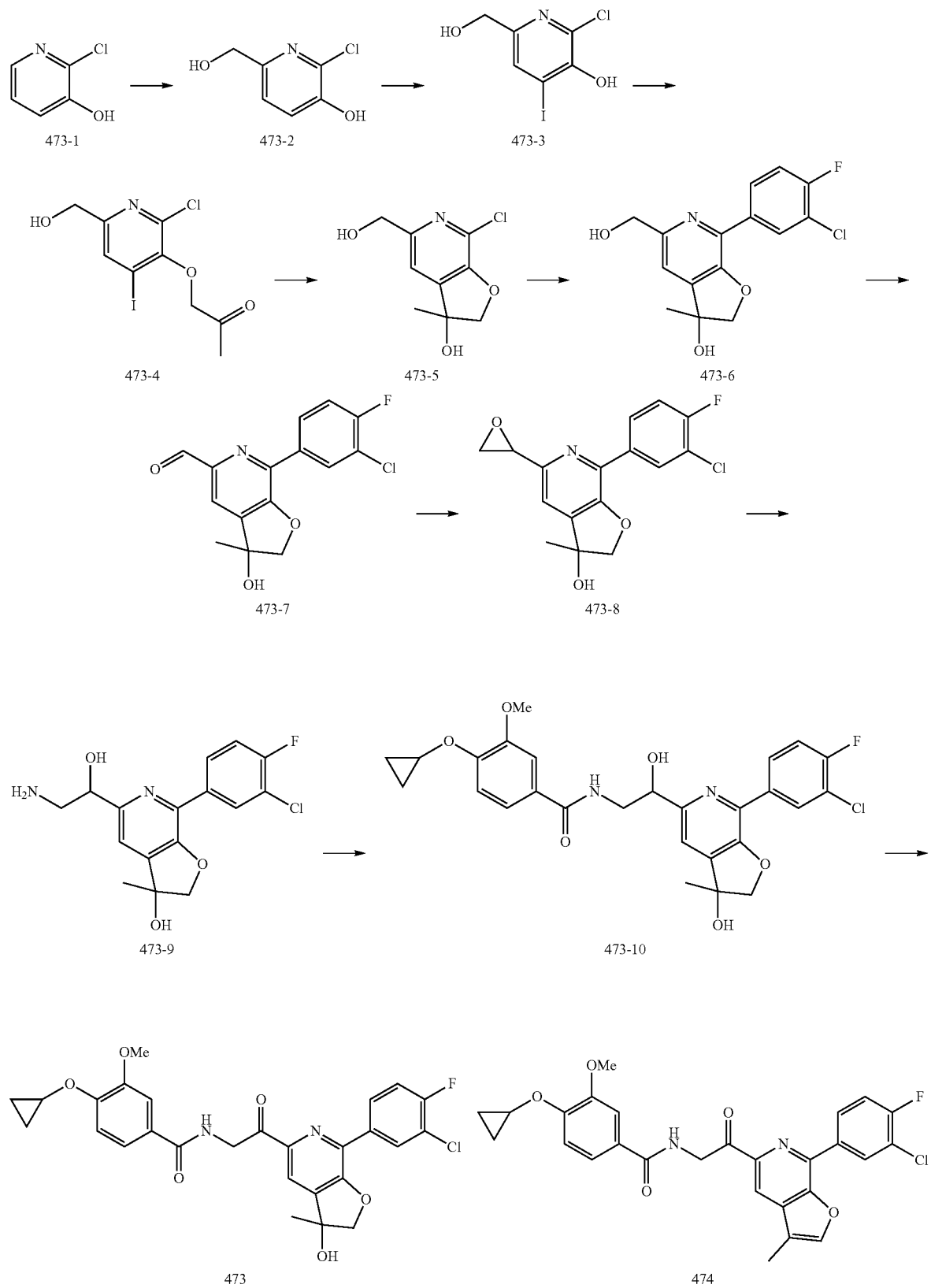

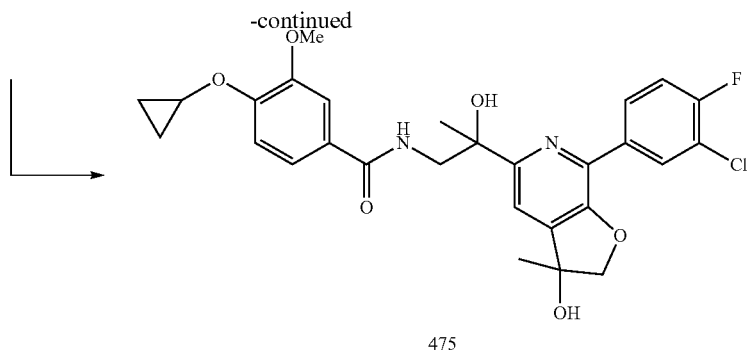

475

Formaldehyde (37% aq. solution, 30.4 mL, 407 mmol) was added in 4 portions to a mixture of 473-1 (15.0 g, 116 mmol) and NaHCO$_3$ (14.6 g, 174 mmol) in water (120 mL) which had been pre-heated to 90° C. The reaction was stirred at 90° C. for 16 h. Additional formaldehyde (37% aq. solution, 232 mmol) was added and the reaction was stirred at 90° C. for 1 h. After being cooled to r.t., the reaction was concentrated under reduced pressure. The crude 473-2 was directly used in the next step.

Iodine (25 g, 98.4 mmol) was added to a mixture of 473-2 (13 g) and K$_2$CO$_3$ (22.0 g, 159 mmol) in water (100 mL). The mixture was stirred at r.t. for 4 h. The reaction was poured in to a 1M aq. HCl solution, which had been pre-cooled to 0° C. The aqueous portion was extracted with EtOAc (3×). The combined organic portions were dried with Na$_2$SO$_4$ and filtered. The volatiles were removed under reduced pressure. Chromatography of the residue (cyclohexane:EtOAc, 100:0 to 0:100) afforded 473-3 as an off-white solid (5.4 g). $^1$H NMR (400 MHz, DMSO-d$_6$) δ ppm 4.41 (s, 2H), 7.77 (s, 1H), 10.37 (s, 1H).

Chloroacetone (750 uL) was added to a mixture of 473-3 (2.41 g) and K$_2$CO$_3$ (1.69 g) in acetone (50 mL). The mixture was warmed to 50° C. and stirred at 50° C. for 16 h. The volatiles were removed under reduced pressure. The residue was partitioned between EtOAc and water. The layers were separated and the aqueous portion was extracted with EtOAc. The combined organic portions were dried with Na$_2$SO$_4$ and filtered. The volatiles were removed under reduced pressure. Trituration of the residue with DCM:cyclohexane afforded 473-4 as a white solid (2.33 g). UPLC/MS (ES$^+$): m/z 342.00 [M+H]$^+$.

EtMgBr (1M solution in 2-methyltetrahydrofuran, 4.39 mL, 4.39 mmol) was added to a solution of n-BuLi (1.6 M solution in hexane, 5.48 mL, 8.78 mmol) in THF (10 mL), which had been pre-cooled to 0° C. After 10 mins, the mixture was cooled to −78° C. A solution of 473-4 (1.35 g, 3.96 mmol) in THF (8 mL) was added dropwise and the reaction was stirred at −78° C. for 2 h. The reaction was quenched with MeOH and diluted with EtOAc. The organic portion was washed with water, dried with Na$_2$SO$_4$, filtered and concentrated under reduced pressure. Chromatography of the residue (cyclohexane:EtOAc, 70:30 to 0:100) afforded 473-5 (619 mg, 72%). UPLC/MS (ES$^+$): m/z 216.10 [M+H]$^+$.

Alcohol 473-5 was split in 2 batches (2×305 mg) which were separately processed as described below. The 2 reactions were unified for work-up and purification procedures. A mixture of 473-5 (305 mg, 1.42 mmol), (3-chloro-4-fluorophenyl)boronic acid (617 mg, 3.54 mmol), Pd(dppf)Cl$_2$ (104 mg, 0.142 mmol) and sodium carbonate (2M aq. solution, 2.49 mL, 5.00 mmol) in DCE (10 mL) was degassed and stirred with heating to 100° C. under microwave irradiation for 1.5 h. DCM and water were added. The layers were separated and the aqueous portion was extracted with DCM. The combined organic portions were dried with Na$_2$SO$_4$ and filtered. The volatiles were removed under reduced pressure. Chromatography of the residue (cyclohexane:EtOAc, 50:50 to 0:100) afforded 473-6 (315 mg, 35%) and some unreacted 473-5 (94 mg). 473-6: $^1$H NMR (400 MHz, CDCl$_3$) δ ppm 1.74 (s, 3H), 4.48 (d, J=10.3 Hz, 1H), 4.66 (d, J=10.3 Hz, 1H), 4.75 (d, J=14.1 Hz, 1H), 4.79 (d, J=14.1 Hz, 1H), 7.22 (s, 1H), 7.23 (t, J=8.7 Hz, 1H), 8.18 (ddd, J=8.7, 4.7, 2.3 Hz, 1H), 8.36 (dd, J=7.3, 2.3 Hz, 1H).

Dess-Martin periodinane (365 mg, 0.861 mmol) was added to a stirred solution of 473-6 (315 mg, 1.02 mmol) in DCM (5 mL). The reaction was stirred at r.t. for 1.5 h. A 1:1 1M aq. Na$_2$S$_2$O$_3$:sat. aq. NaHCO$_3$ mixture was added to the reaction and the mixture was stirred at r.t. for 20 mins. The layers were separated and the aqueous portion was extracted with DCM. The combined organic portions were dried with Na$_2$SO$_4$ and filtered. The volatiles were removed under reduced pressure. Chromatography of the residue (cyclohexane-EtOAc, 90:10 to 0:100) afforded 473-7 (266 mg, 85%). $^1$H NMR (400 MHz, CDCl$_3$) δ ppm 1.57 (s, 3H), 4.60 (d, J=10.3 Hz, 1H), 4.82 (d, J=10.3 Hz, 1H), 7.30 (t, J=8.7 Hz, 1H), 8.02 (s, 1H), 8.32 (ddd, J=8.7, 4.6, 2.3 Hz, 1H), 8.50 (dd, J=7.3, 2.3 Hz, 1H), 10.11 (s, 1H).

Trimethylsulfoxonium iodide (191 mg, 0.866 mmol) was added to a solution of tBuOK (97 mg, 0.866 mmol) in DMSO (3 mL). The mixture was stirred at r.t. for 30 mins. A solution of 473-7 (266 mg, 0.866 mmol) in DMSO (3 mL) was added and the mixture was stirred at r.t. for 30 mins. The reaction was diluted with EtOAc and water. The layers were separated and the aqueous portion was extracted with EtOAc. The combined organic portions were washed with brine, dried with Na$_2$SO$_4$, filtered and concentrated under reduced pressure. Chromatography of the residue (cyclohexane:EtOAc, 80:20 to 0:100) afforded 473-8 (81 mg, 29%). $^1$H NMR (400 MHz, CDCl$_3$) δ ppm 1.75 (2×s, 3H), 3.00-3.04 (m, 1H), 3.24 (dd, J=5.1, 4.4 Hz, 1H), 4.11-4.15 (m, 1H) 4.48 (d, J=10.0 Hz, 1H), 4.68 (d, J=10.0 Hz, 1H), 7.20-7.28 (m, 2H), 8.21-8.28 (m, 1H), 8.40-8.46 (m, 1H).

A solution of 473-8 (81 mg, 0.252 mmol) in 7M NH$_3$-MeOH (50 mL) was stirred at r.t. for 20 h. The volatiles were removed under reduced pressure. Crude 473-9 was directly used in to the next step.

A mixture of 4-cyclopropoxy-3-methoxybenzoic acid (63 mg, 0.302 mmol), HATU (144 mg, 0.378 mmol) and DIPEA (88 uL, 0.504 mmol) in DMF (1 mL) was stirred at r.t. for 30 mins. A solution of 473-9 in DMF (2 mL) was added and the mixture was stirred at r.t. for 1 h. EtOAc was added The organic portion was washed with brine, dried with Na$_2$SO$_4$, filtered and concentrated under reduced pressure. Chromatography of the residue (EtOAc:MeOH, 100:0 to 80:20) afforded 473-10 (82 mg). UPLC/MS (ES+): m/z 529.30 [M+H]+.

Dess-Martin periodinane (65 mg, 1.57 mmol) was added to a solution of 473-10 (80 mg, 0.151 mmol) in DCM (5 mL). The reaction was stirred at r.t. for 10 mins. A 1:1 1M aq. $Na_2S_2O_3$:sat. aq. $NaHCO_3$ mixture was added. The mixture was stirred at r.t. for 20 mins. The layers were separated and the aqueous portion was extracted with DCM. The combined organic portions were dried with $Na_2SO_4$ and filtered. The volatiles were removed under reduced pressure. Chromatography of the residue (cyclohexane:EtOAc, 70:30 to 0:100) afforded 473 (24 mg, 18% over 3 steps) and 474 (19 mg, 15% over 3 steps). 473: white solid; UPLC/MS (ES+): m/z 527.30 [M+H]+. 474: off-white solid; UPLC/MS (ES+): m/z 509.30 [M+H]+.

MeMgBr (3M solution in $Et_2O$, 30 uL, 0.090 mmol) was added to a solution of 473 (16 mg, 0.030 mmol) in THF (2.5 mL). The reaction was stirred at r.t. under $N_2$ atmosphere for 30 mins. EtOAc and water were added. The layers were separated and the aqueous portion extracted with EtOAc. The combined organic portions were dried with $Na_2SO_4$ and filtered. The volatiles were removed under reduced pressure. Chromatography of the residue (cyclohexane:EtOAc, 30:70 to 0:100) afforded 475 as a white solid (6 mg, 37%). UPLC/MS (ES+): m/z 543.30 [M+H]+.

Example 263

Preparation of Compounds 479 and 480

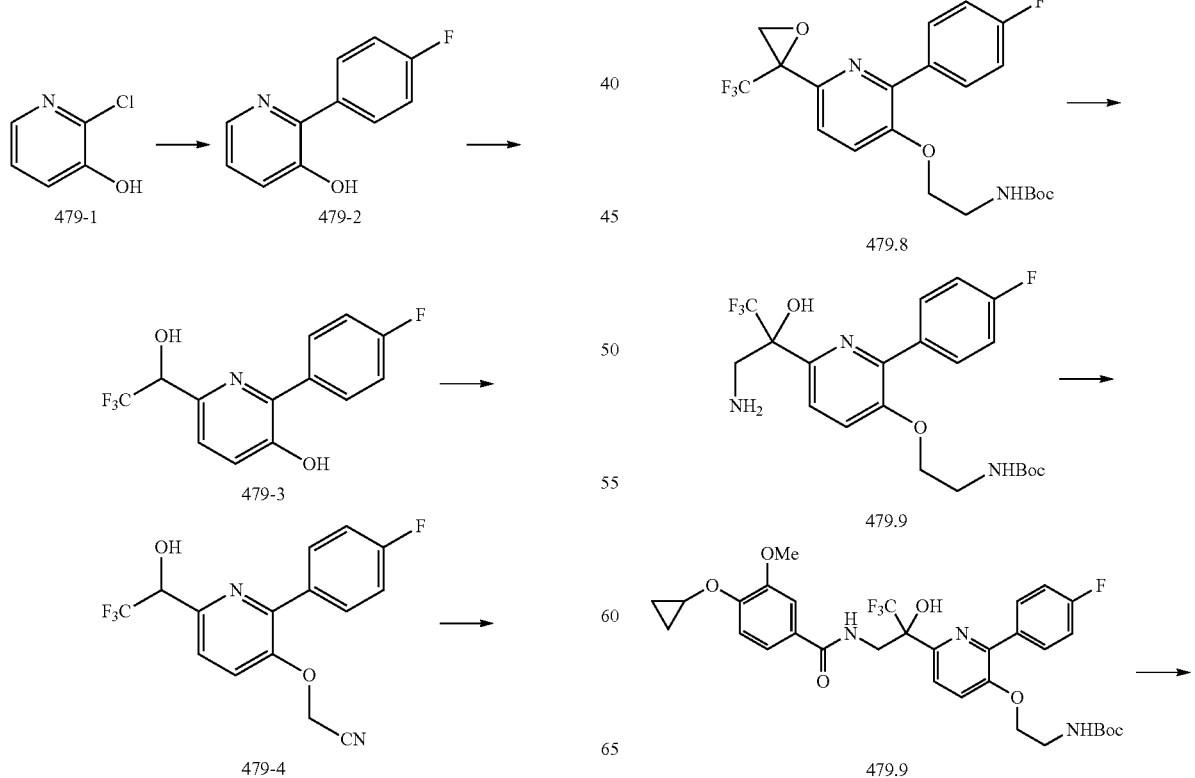

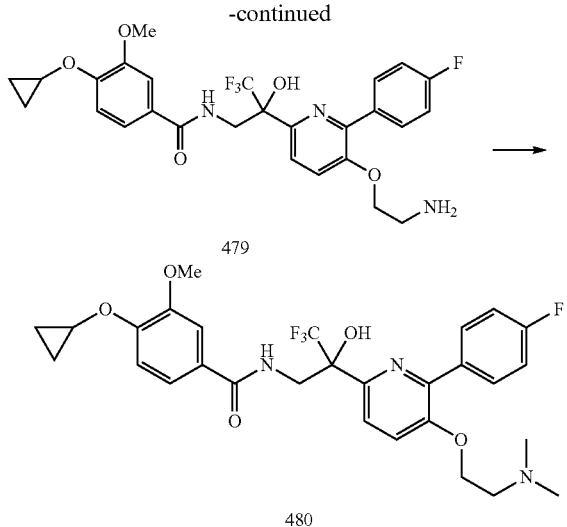

479

480

A mixture of 479-1 (1.00 g, 7.75 mmol), (4-fluorophenyl) boronic acid (2.17 g, 15.5 mmol), Pd(dppf)Cl$_2$ (566 mg, 0.775 mmol) and sodium carbonate (2M aq solution, 7.75 mL, 15.5 mmol) in DCE (70 mL) was degassed and stirred with heating to 85° C. overnight. Water and DCM were added. The layers were separated and the organic phase was concentrated under reduced pressure. Chromatography of the residue (cyclohexane:EtOAc, 100:0 to 50:50) afforded 479-2 as a white solid (990 mg, 67%). $^1$H NMR (400 MHz, DMSO-d$_6$) δ ppm 7.16-7.29 (m, 3H), 7.34 (dd, J=8.2, 1.4 Hz, 1H), 8.04-8.12 (m, 2H), 8.15 (dd, J=4.4, 1.4 Hz, 1H), 10.22 (s, 1H).

Potassium carbonate (1.15 g, 8.34 mmol) and trifluoroacetaldehyde ethyl hemiacetal (740 uL, 6.26 mmol) were added to a suspension of 479-2 (790 mg, 4.17 mmol) in water (15 mL). The mixture was stirred at 100° C. overnight. Additional trifluoroacetaldehyde ethyl hemiacetal (327 uL, 2.70 mmol) was added and the reaction was stirred at 100° C. overnight. The reaction was cooled to 0°, neutralized with 1M aq HCl solution and extracted with EtOAc. The organic portion was dried with Na$_2$SO$_4$, filtered and concentrated under reduced pressure. Chromatography of the residue (cyclohexane:EtOAc, 100:0 to 50:50) afforded 479-3 as a white solid (1.08 g, 90%). $^1$H NMR (400 MHz, DMSO-d$_6$) δ ppm 5.00-5.14 (m, 1H), 6.83 (d, J=6.3 Hz, 1H), 7.23-7.30 (m, 2H), 7.42 (s, 2H), 8.07-8.15 (m, 2H), 10.48 (s, 1H).

NaH (195 mg, 4.87 mmol) was added to a stirred solution of 479-3 (1.08 g, 3.75 mmol) in DMF (11 mL), which had been pre-cooled to 0° C. The mixture was stirred at 0° C. for 10 mins, then warmed to r.t. and stirred for 30 mins. The reaction was cooled to 0° C. and chloroacetonitrile (260 uL, 4.13 mmol) was added dropwise. The mixture was allowed to gradually reach r.t. and stirring was continued for 20 h. EtOAc and sat. aq. NH$_4$Cl were added. The layers were separated. The organic portion was washed with brine, dried with Na$_2$SO$_4$, filtered and concentrated under reduced pressure. Chromatography of the residue (cyclohexane:EtOAc, 100:0 to 50:50) afforded 479-4 as a colorless wax (1.10 g, 90%). $^1$H NMR (400 MHz, DMSO-d$_6$) δ ppm 5.12-5.25 (m, 1H), 5.33 (s, 2H), 7.02 (d, J=6.0 Hz, 1H), 7.30-7.37 (m, 2H), 7.67 (d, J=8.7 Hz, 1H), 7.83 (d, J=8.7 Hz, 1H), 7.91-7.98 (m, 2H).

LiAlH$_4$ (1M solution in THF, 3.17 mL, 3.17 mmol) was added dropwise to a stirred solution of 479-4 (940 mg, 2.80 mmol) in THF (20 mL) which had been pre-cooled to 0° C. The mixture was warmed to r.t. and stirred for 30 mins. The reaction was cooled to 0° C. Water (3 mL) was slowly added, followed by 1N aq. NaOH solution (3 mL) and more water (9 mL). EtOAc was then added, and the layers were separated. The organic portion was washed with brine, dried with Na$_2$SO$_4$, filtered and concentrated under reduced pressure. The crude 479-5 was directly used in the next step.

Di-tert-butyl dicarbonate (610 mg, 2.80 mmol) and DMAP (34.0 mg, 0.280 mmol) were added to a solution of 479-5 in DCM (10 mL). After 2 h, water was added and the layers were separated. The organic portion was dried with Na$_2$SO$_4$, filtered and concentrated under reduced pressure. Chromatography of the residue (cyclohexane:EtOAc, 100:0 to 50:50) afforded a di-protected compound. This di-protected compound was dissolved in CH$_3$CN (2 mL). A 1M aq. NaOH solution (2 mL) was added and the reaction was stirred at 50° C. for 1 h. Most of the solvents were removed under reduced pressure and the pH of the resulting solution was adjusted to 7 with 1M aq. HCl. The aqueous portion was extracted with EtOAc. The organic layer was dried with Na$_2$SO$_4$, filtered and evaporated under reduced pressure. Chromatography of the residue (cyclohexane:EtOAc, 100:0 to 50:50) afforded 479-6 as a white solid (235 mg). UPLC/MS (ES$^+$): m/z 431.38 [M+H]$^+$.

Dess-Martin periodinane (274 mg, 0.640 mmol) was added to a stirred solution of 479-6 (235 mg, 0.540 mmol) in DCM (9 mL). The reaction was stirred at r.t. under N$_2$ atmosphere overnight and quenched with a 1:1 2M aq. Na$_2$S$_2$O$_3$:sat. aq. NaHCO$_3$ mixture. After 30 mins, the layers were separated. The organic portion was washed with brine, dried with Na$_2$SO$_4$, filtered and concentrated under reduced pressure. Chromatography of the residue (cyclohexane:EtOAc, 100:0 to 50:50) afforded 479-7 as a white solid (144 mg, 62%). UPLC/MS (ES$^+$): m/z 447.29 [M+H$_3$O]$^+$.

Trimethylsulfoxonium iodide (57.0 mg, 0.260 mmol) was added to a solution of tBuOK (29.0 mg, 0.260 mmol) in DMSO (3 mL). The mixture was stirred at r.t. for 30 mins. A solution of 479-7 (112 mg, 0.260 mmol) in THF (3 mL) was added, and the mixture was stirred at r.t. for 30 mins. The mixture was diluted with EtOAc and water, and the layers were separated. The aqueous layer was extracted with EtOAc. The combined organic portions were washed with brine, dried with Na$_2$SO$_4$, filtered and concentrated under reduced pressure. Chromatography of the residue (cyclohexane:EtOAc, 100:0 to 50:50) afforded 479-8 (44 mg) and unreacted 479-7 (53 mg). 479-8: UPLC/MS (ES$^+$): m/z 443.29 [M+H]$^+$.

A solution of 479-8 (44 mg) in 7M NH$_3$-MeOH (2 mL) was stirred with heating to 45° C. for 40 mins. The volatiles were removed under reduced pressure. Crude 479-9 (45 mg) was directly used in the next step.

A mixture of 479-9 (45 mg), EDC (23 mg, 0.12 mmol), HOBT (17 mg, 0.12 mmol), TEA (33 uL, 0.24 mmol) and 4-cyclopropoxy-3-methoxybenzoic acid (20 mg, 0.098 mmol) in DCM (1 mL) was stirred at r.t. for 2 h. Water was added, and the mixture was stirred for 10 mins. The layers were separated. The organic portion was dried with Na$_2$SO$_4$, filtered and concentrated under reduced pressure. Chromatography (cyclohexane:EtOAc, 100:0 to 40:60) afforded 479-10 as a white solid (53 mg). UPLC/MS (ES$^+$): m/z 650.40 [M+H]$^+$.

TFA (350 uL) was added to a solution of 479-10 (53 mg, 0.081 mmol) in DCM (2 mL). The mixture was stirred at r.t. for 30 mins. Water was added, and the layers were separated. The organic portion was dried with Na$_2$SO$_4$, filtered and concentrated under reduced pressure. The residue was purified by reverse phase chromatography (water:CH$_3$CN, 100:0 to 40:60) to afford 479 (A/1587/35/1) as a white solid (30 mg, 67%). UPLC/MS (ES+): m/z 550.32 [M+H]+.

Formaldehyde (37% aq. solution, 3 uL) was added to a solution of 479 (17 mg, 0.030 mmol) in MeOH (200 uL). The mixture was stirred at r.t. for 3 h. Sodium cyanoborohydride (1.8 mg, 0.030 mmol) was added, and the reaction was stirred at r.t. for 10 mins. The solvents were removed under reduced pressure. Water and DCM were added. The layers were separated. The organic portion was dried with Na$_2$SO$_4$, filtered and concentrated under reduced pressure. Chromatography of the residue (DCM:MeOH, 100:0 to 90:10) afforded 480 as a white solid (2 mg, 10%). UPLC/MS (ES+): m/z 578.40 [M+H]+.

Example 264

Preparation of Compounds 506 and 507

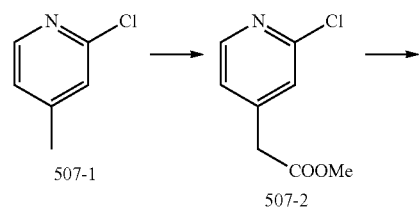

507-1 → 507-2

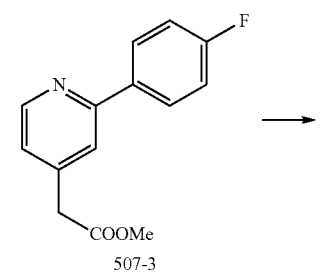

507-3

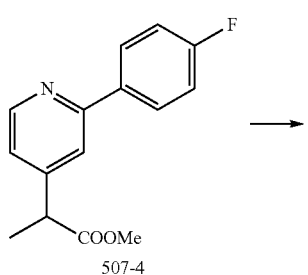

507-4

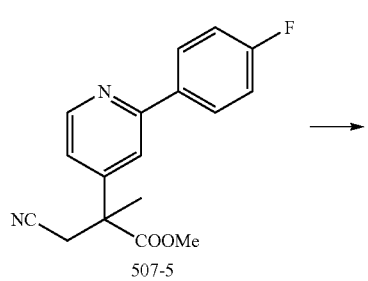

507-5

-continued

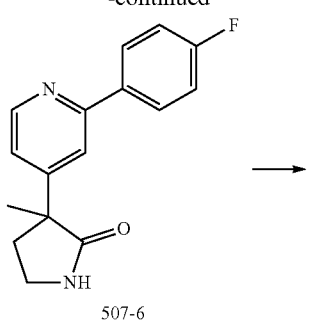

507-6

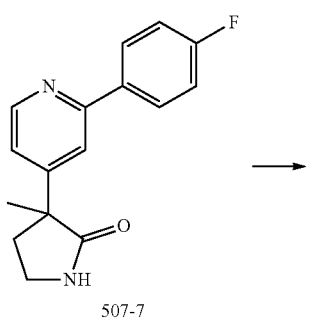

507-7

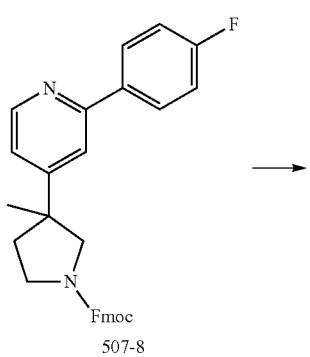

507-8

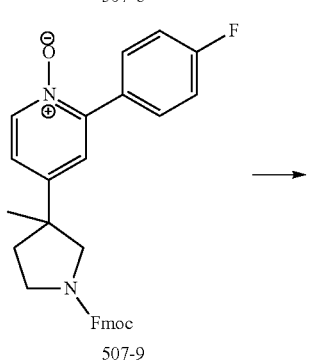

507-9

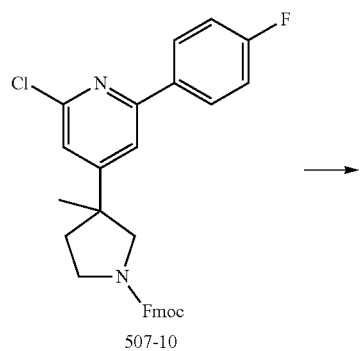

507-10

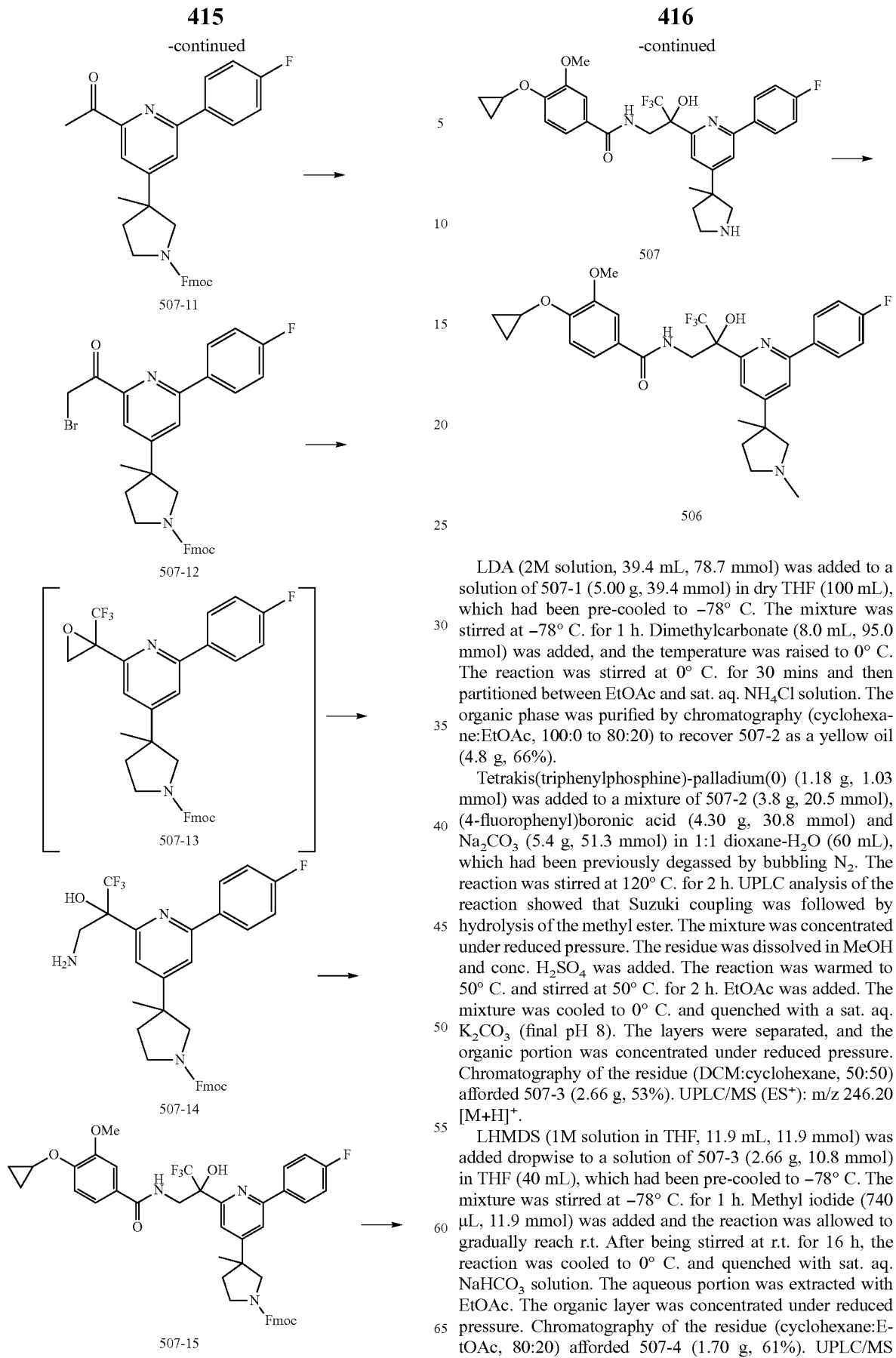

LDA (2M solution, 39.4 mL, 78.7 mmol) was added to a solution of 507-1 (5.00 g, 39.4 mmol) in dry THF (100 mL), which had been pre-cooled to −78° C. The mixture was stirred at −78° C. for 1 h. Dimethylcarbonate (8.0 mL, 95.0 mmol) was added, and the temperature was raised to 0° C. The reaction was stirred at 0° C. for 30 mins and then partitioned between EtOAc and sat. aq. NH$_4$Cl solution. The organic phase was purified by chromatography (cyclohexane:EtOAc, 100:0 to 80:20) to recover 507-2 as a yellow oil (4.8 g, 66%).

Tetrakis(triphenylphosphine)-palladium(0) (1.18 g, 1.03 mmol) was added to a mixture of 507-2 (3.8 g, 20.5 mmol), (4-fluorophenyl)boronic acid (4.30 g, 30.8 mmol) and Na$_2$CO$_3$ (5.4 g, 51.3 mmol) in 1:1 dioxane-H$_2$O (60 mL), which had been previously degassed by bubbling N$_2$. The reaction was stirred at 120° C. for 2 h. UPLC analysis of the reaction showed that Suzuki coupling was followed by hydrolysis of the methyl ester. The mixture was concentrated under reduced pressure. The residue was dissolved in MeOH and conc. H$_2$SO$_4$ was added. The reaction was warmed to 50° C. and stirred at 50° C. for 2 h. EtOAc was added. The mixture was cooled to 0° C. and quenched with a sat. aq. K$_2$CO$_3$ (final pH 8). The layers were separated, and the organic portion was concentrated under reduced pressure. Chromatography of the residue (DCM:cyclohexane, 50:50) afforded 507-3 (2.66 g, 53%). UPLC/MS (ES$^+$): m/z 246.20 [M+H]$^+$.

LHMDS (1M solution in THF, 11.9 mL, 11.9 mmol) was added dropwise to a solution of 507-3 (2.66 g, 10.8 mmol) in THF (40 mL), which had been pre-cooled to −78° C. The mixture was stirred at −78° C. for 1 h. Methyl iodide (740 µL, 11.9 mmol) was added and the reaction was allowed to gradually reach r.t. After being stirred at r.t. for 16 h, the reaction was cooled to 0° C. and quenched with sat. aq. NaHCO$_3$ solution. The aqueous portion was extracted with EtOAc. The organic layer was concentrated under reduced pressure. Chromatography of the residue (cyclohexane:EtOAc, 80:20) afforded 507-4 (1.70 g, 61%). UPLC/MS (ES$^+$): m/z 260.10 [M+H]$^+$.

LHMDS (1M solution in THF, 7.22 mL, 7.22 mmol) was added dropwise to a solution of 507-4 (1.70 g, 6.56 mmol) in THF (12 mL), which had been pre-cooled to −78° C. The mixture was stirred at −78° C. for 1 h. A solution of bromoacetonitrile (503 uL, 7.22 mmol) in THF (12 mL) was added, and the reaction was allowed to gradually reach r.t. After being stirred at r.t. for 2 h, the reaction was cooled to 0° C. and quenched with sat. aq. $NH_4Cl$ solution. The aqueous portion was extracted with EtOAc. The organic layer was concentrated under reduced pressure. Chromatography of the residue (cyclohexane:EtOAc, 50:50) afforded 507-5 (1.91 g, 98%). $^1H$ NMR (400 MHz, DMSO-$d_6$) δ ppm 1.76 (s, 3H), 3.37 (d, J=17.0 Hz, 1H), 3.44 (d, J=17.0 Hz, 1H), 3.72 (s, 3H), 7.31-7.40 (m, 3H), 7.90 (d, J=1.5 Hz, 1H), 8.15-8.23 (m, 2H), 8.68 (d, J=5.3 Hz, 1H).

Nickel Raney (0.600 mmol) was added to a solution of 507-5 (1.91 g, 6.40 mmol) in MeOH (50 mL). The reaction was stirred at 60° C. under $H_2$ atmosphere (5 bar) for 3 h. The reaction was filtered through a pad of celite and the solution was refluxed for 4 h. DIPEA (1 eq.) was added, and the mixture was refluxed for 30 mins. The volatiles were removed under reduced pressure. The residue was dissolved in EtOAc. The organic portion was washed with sat. aq. $NaHCO_3$ solution, dried and concentrated under reduced pressure. Chromatography of the residue (EtOAc:MeOH, 100:0 to 95:5) afforded 507-6 (870 mg, 50%). UPLC/MS ($ES^+$): m/z 271.20 $[M+H]^+$.

$LiAlH_4$ (2M solution in THF, 3.03 mL, 6.06 mmol) was added to a solution of 507-6 (820 mg, 3.03 mmol) in THF (18 mL), which had been pre-cooled to 0° C. The reaction was stirred at r.t. for 1 h, then warmed to 70° C. and stirred at 70° C. for 30 mins. The reaction was cooled to 0° C. and $Na_2SO_4 \cdot 10H_2O$ and $Et_2O$ were added. The mixture was filtered through a pad of celite, and the solution concentrated under reduced pressure. Crude 507-7 (720 mg) was directly used in the next step.

A mixture of 507-7 (720 mg) and sat. aq. $NaHCO_3$ solution (16 mL) in dioxane (9 mL) was cooled to 0° C. A solution of FmocCl (764 mg, 2.95 mmol) in dioxane (9 mL) was added, and the reaction was allowed to reach r.t. After 1 h, the reaction was diluted with EtOAc. The organic portion was washed with water and brine, dried and concentrated under reduced pressure. Chromatography of the residue (cyclohexane:EtOAc, 50:50) afforded 507-8 (1.10 g, 49% over 2 steps). UPLC/MS ($ES^+$): m/z 479.40 $[M+H]^+$.

m-Chloroperbenzoic acid (797 mg, 4.62 mmol) was added to a solution of 507-8 (1.10 g, 2.31 mmol) in DCM (30 mL). The reaction was stirred at r.t. overnight. EtOAc was added. The organic phase was washed with sat. aq. $K_2CO_3$ sol and concentrated under reduced pressure. Crude 507-9 (1.17 g) was directly used in the next step.

A mixture of 507-9 (1.17 g) and $POCl_3$ (50 mL) was stirred at 60° C. for 12 h. The volatiles were removed under reduced pressure. EtOAc and water were added, and the mixture was basified by adding sat. aq. $KHCO_3$ solution (final pH 8). The layers were separated, and the organic portion was concentrated under reduced pressure. Chromatography of the residue (cyclohexane:EtOAc, 90:10 to 0:100, then EtOAc:MeOH, 80:20) afforded 507-10 (700 mg, 58%) and unreacted starting material 507-9 (300 mg). 507-10: UPLC/MS ($ES^+$): m/z 513.27 $[M+H]^+$.

Tributyl[1-ethoxyethenyl]stannane (552 uL, 1.63 mmol) and $Pd(PPh_3)Cl_2$ (199 mg, 0.284 mmol) were sequentially added to a solution of 507-10 (700 mg, 1.36 mmol) in dioxane (4 mL), which had been previously degassed by bubbling $N_2$. The mixture was further degassed and stirred at 100° C. for 1 h. After being cooled to r.t., the mixture was partitioned between EtOAc and sat. aq. KF solution. The layers were separated. The organic portion was washed with 1M aq. HCl solution, dried and concentrated under reduced pressure. Chromatography of the residue (cyclohexane:EtOAc, 80:20) afforded 507-11 (670 mg, 95%). UPLC/MS ($ES^+$): m/z 521.32 $[M+H]^+$.

Hydrobromic acid (33% solution in AcOH, 377 uL, 2.08 mmol) and bromine (53 uL, 1.04 mmol) were added to a solution of 507-11 (541 mg, 1.04 mmol) in dioxane (10 mL), which had been pre-cooled to 0° C. The reaction was stirred at r.t. for 2 h. Additional bromine (0.5 eq., 27 μL) was added and stirring was prolonged for 2 h. The reaction was quenched with water and neutralized with sat. aq. $NaHCO_3$ solution. The aqueous portion was extracted with DCM. The organic layer was dried with $Na_2SO_4$ and concentrated under reduced pressure. Chromatography of the residue (DCM:EtOAc, 60:40) afforded 507-12.

$TMSCF_3$ (430 mg, 3.00 mmol) and CsF (91 mg) were sequentially added to a solution of 507-12 (90 mg) in THF (12 mL). The reaction was stirred at r.t. for 20 mins. The mixture was partitioned between EtOAc and 1M aq. HCl solution. The layers were separated, and the organic portion was concentrated under reduced pressure. Crude 507-13 was directly used in the next step.

A solution of 507-13 in ammonia (7M solution in MeOH, 5 mL) was stirred at r.t. for 1.5 h. The volatiles were removed under reduced pressure. Chromatography of the residue (cyclohexane:EtOAc-MeOH, 60:30:10) afforded 507-14 (44 mg). UPLC/MS ($ES^+$): m/z 606.40 $[M+H]^+$.

A solution of 4-cyclopropoxy-3-methoxybenzoic acid (20.0 mg, 0.095 mmol), DIPEA (50 uL, 0.270 mmol) and HATU (39.0 mg, 0.102 mmol) in DCM (4 mL) was stirred at r.t. for 30 mins. A solution of 507-14 (41.0 mg, 0.068 mmol) in DCM (1 mL) was added. The reaction was stirred for 16 h, quenched with MeOH (10 mL) and stirred for 1 h. The volatiles were removed under reduced pressure. Chromatography of the residue (cyclohexane:EtOAc, 100:0 to 60:40) afforded 507-15 as a colorless oil (23 mg, 42%). UPLC/MS ($ES^+$): m/z 796.50 $[M+H]^+$.

Morpholine (1 mL) was added to a solution of 507-15 (23 mg, 0.029 mmol) in DMF (1 mL), and the solution was stirred for 1 h. The volatiles were removed under reduced pressure. Chromatography of the residue (NH-cartridge, cyclohexane:EtOAc:MeOH, 100:0:0 to 60:30:10) afforded 507 (10 mg, 60%). UPLC/MS ($ES^+$): m/z 574.30 $[M+H]^+$.

Formaldehyde (37% aq. solution, 30 uL, 0.350 mmol) and $NaBH(OAc)_3$ (22.0 mg, 0.105 mmol) were added to a solution of 507 (4.0 mg, 0.007 mmol) in DCM (2 mL). The reaction was vigorously stirred overnight, quenched with 1M aq. NaOH solution and extracted with DCM. The volatiles were removed under reduced pressure. The residue was purified by SCX-chromatography to afford 506 as a colorless oil (2.4 mg, 58%). UPLC/MS ($ES^+$): m/z 588.50 $[M+H]^+$.

Example 265

Preparation of Compounds 519, 520, 521, 527 and 523

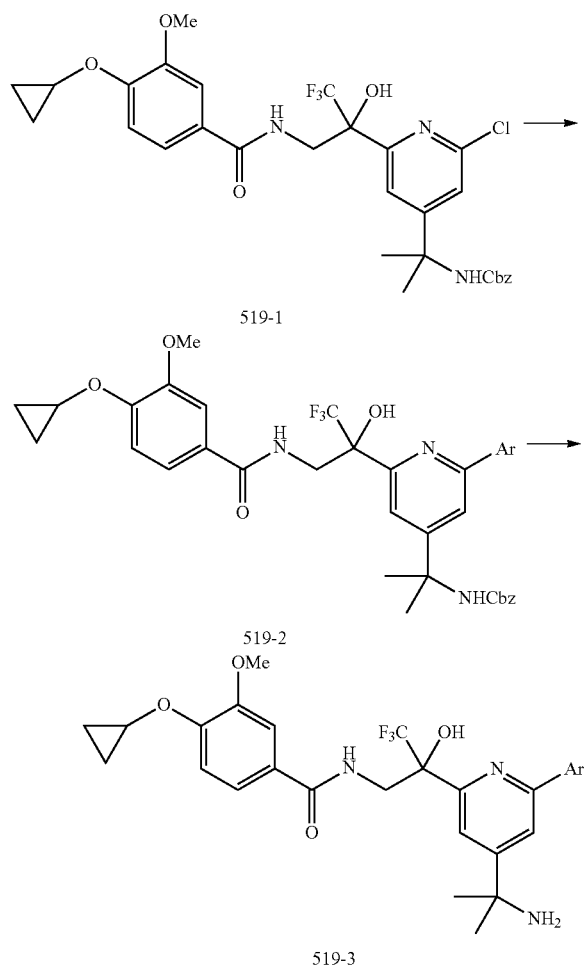

General Suzuki Coupling Conditions

Method A:

A mixture of 519-1 (70 mg, 0.112 mmol), boronate/boronic acid (0.170 mmol), KH$_2$PO$_4$ (15.3 mg, 0.112 mmol), K$_3$PO$_4$ (24.0 mg, 0.112 mmol) and Pd(dbpf)Cl$_2$ (7.5 mg, 0.011 mmol) in DME:H$_2$O:EtOH (1:0.5:0.3, 1.8 mL) was degassed and heated to 50° C. for 24 h. The mixture was partitioned between Et$_2$O and water. The organic portion was concentrated under reduced pressure. Chromatography of the residue (cyclohexane:EtOAc) afforded 519-2.

Method B:

A mixture of 519-1 (90 mg, 0.145 mmol), boronic acid (0.322 mmol), Pd$_2$(dba)$_3$ (15 mg, 0.016 mmol), PCy$_3$ (10 mg, 0.038 mmol) and K$_3$PO$_4$ (85 mg, 0.402 mmol) in dioxane (1 mL)-water (300 uL) was degassed and heated to 100° C. for 12 h. The volatiles were removed under reduced pressure. Chromatography of the residue (cyclohexane:EtOAc) afforded 519-2.

Protecting Group(s)-Removal:

Method A:

Aqueous HCl (6M solution, 4 mL) was added to a solution of 519-2 (0.056 mmol) in isopropanol (2.5 mL). The reaction was heated to 95° C. for 3 h. The volatiles were removed under reduced pressure. The residue was purified by reverse phase chromatography to afford 519-3.

Method B:

A mixture of 519-2 (0.047 mmol) and Pd/C (9 mg) in MeOH (4.7 mL) was stirred under H$_2$ atmosphere for 5 h. The mixture was filtered from the catalyst, and the solution was treated with 1M HCl solution in Et$_2$O. The volatiles were removed under reduced pressure. The residue was triturated with Et$_2$O to afford 519-3 as its hydrochloride salt.

Method C:

TMSCl (32 uL) and NaI (39 mg) were sequentially added to a solution of 519-2 (0.089 mmol) in CH$_3$CN (4 mL). The reaction was stirred at r.t. for 1 h, warmed to 45° C. and stirred at that temp for 16 h. Additional TMSCl (64 uL) and NaI (80 mg) were added, and the reaction was stirred at 45° C. for 5 h. The volatiles were removed under reduced pressure. The residue was partitioned between EtOAc and a 1:1 mixture of 5% aq. NaHCO$_3$:1M aq. Na$_2$S$_2$O$_3$. The layers were separated, and the aqueous portion was extracted with EtOAc. The combined organic portions were dried with Na$_2$SO$_4$, filtered and concentrated under reduced pressure. The residue was purified by reverse phase chromatography to give 519-3.

Method D:

Hydrobromic acid (33% solution in AcOH, 30 uL) was added to a solution of 519-2 (20 mg) in 4M HCl-dioxane (2 mL). The reaction was warmed to 70° C. When complete Cbz-removal was observed by UPLC, the reaction was concentrated under reduced pressure. The residue purified by reverse phase chromatography to afford 519-3.

Method E:

A mixture of 519-2 (9.1 mg) in 4M HCl-dioxane (2 mL) was warmed to 70° C. (or 100° C.). When complete Cbz-removal was observed by UPLC, the reaction was concentrated under reduced pressure, and the residue purified by reverse phase chromatography to afford 519-3.

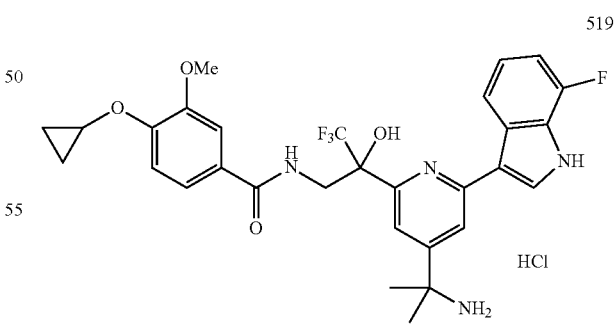

Suzuki coupling of 519-1 with 1-((2-(trimethylsilyl)ethoxy)methyl)-7-fluoro-3-(4,4,5,5-tetramethyl-1,3,2-dioxaborolan-2-yl)-1H-indole (Method A) followed by protecting groups removal according to Method A afforded 519 as its hydrochloride salt (white solid, 16% overall). UPLC/MS (ES$^+$): m/z 587.36 [M+H]$^+$.

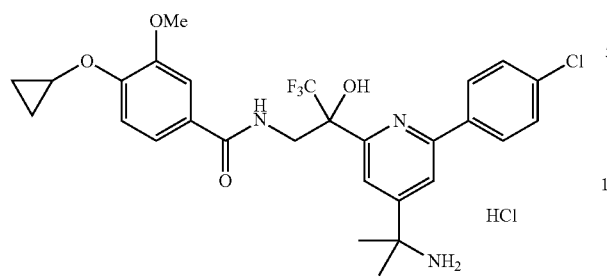

520

Suzuki coupling of 519-1 with 4-chlorophenylboronic acid (Method A) followed by Cbz-removal according to Method A afforded 520 as its hydrochloride salt (white solid, 24% overall). UPLC/MS (ES$^+$): m/z 564.30 [M+H]$^+$.

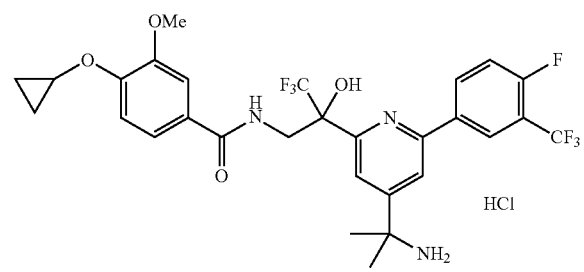

521

Suzuki coupling of 519-1 with 4-fluoro-3-(trifluoromethyl)phenylboronic acid (Method A) followed by Cbz-removal according to Method B afforded 521 as its hydrochloride salt (45% overall). UPLC/MS (ES$^+$): m/z 616.38 [M+H]$^+$.

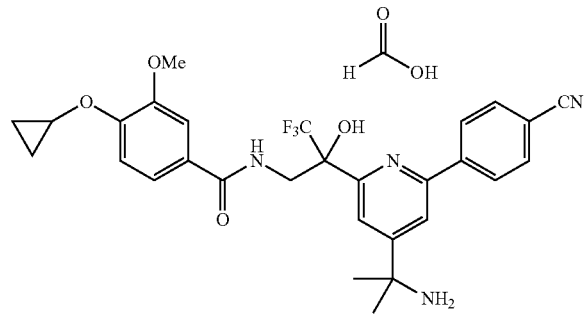

527

Suzuki coupling of 519-1 with 4-cyanophenylboronic acid (Method A) followed by Cbz-removal according to Method C afforded 527 as its formic acid salt (white solid, 37% overall). UPLC/MS (ES$^+$): m/z 555.40 [M+H]$^+$.

523

Suzuki coupling of 519-1 with 4-(trifluoromethyl)phenylboronic acid (Method A) followed by Cbz-removal according to Method B afforded 523 (5% overall). UPLC/MS (ES$^+$): m/z 598.30 [M+H]$^+$.

Example 266

Preparation of Compound 524

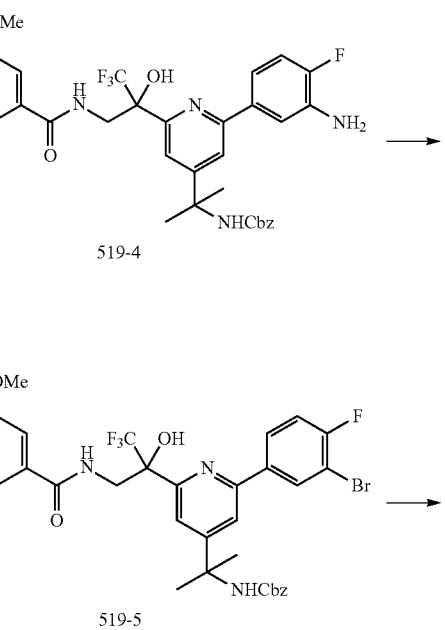

423

-continued

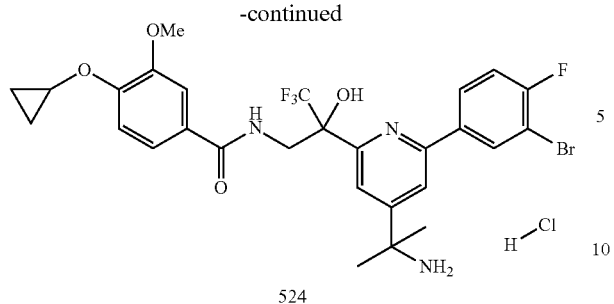

524

Suzuki coupling of 519-1 (310 mg) with 2-(4-fluoro-3-nitrophenyl)-5,5-dimethyl-1,3,2-dioxaborinane (Method A of Example 265) afforded 519-2A (35 mg). UPLC/MS (ES+): m/z 727.30 [M+H]+.

Iron powder (8 mg, 0.144 mmol) was added to a solution of 519-2A (35 mg, 0.05 mmol) in 2:2:1 EtOH:AcOH—$H_2O$ (2.5 mL). The mixture was heated to 80° C. for 1 h. The reaction was filtered through a pad of celite, and the volatiles were evaporated under reduced pressure. The crude was partitioned between EtOAc and aq. $NaHCO_3$ solution, and the organic portion was purified by chromatography to afford 519-4 (30 mg). UPLC/MS (ES+): m/z 697.40 [M+H]+.

Aniline 519-4 (30 mg) was dissolved in $CH_3CN$ (2 mL) under $N_2$ atmosphere. t-BuONO (14 mg, 0.129 mmol) was added. The mixture was stirred at r.t. for 30 mins. CuBr (6.2 mg, 0.043 mmol) was added, and the mixture was stirred for 2.5 h. The reaction was partitioned between DCM and sat. aq. $NH_4Cl$ solution. The organic phase was purified by chromatography to recover 519-5 (12 mg).

Deprotection of 519-5 according to Method A of Example 265 afforded 524 as its hydrochloride salt (1.2 mg). UPLC/MS (ES+): m/z 626.30 [M+H]+.

Example 267

Preparation of Compounds 557 and 567

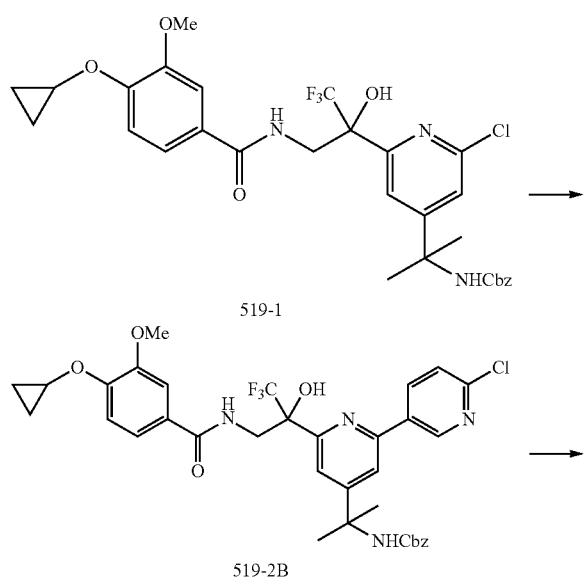

519-1

519-2B

424

-continued

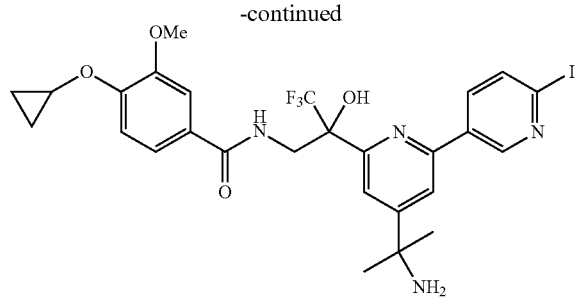

557

Suzuki coupling of 519-1 with 2-chloropyridine-5-boronic acid (Method B of Example 265) followed by treatment of the resulting Cbz-protected amine with TMSCl/NaI according to Method C of Example 265 afforded 557 (5% overall). UPLC/MS (ES+): m/z found 657.32 [M+H]+.

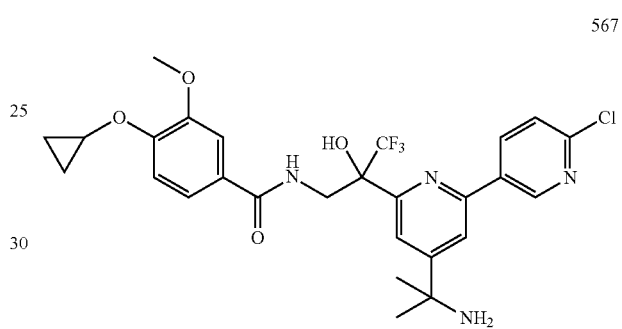

567

Deprotection of 519-2B according to Method E of Example 265 afforded 567 (16%). UPLC/MS (ES+): m/z 565.40 [M+H]+.

Example 268

Preparation of Compound 558

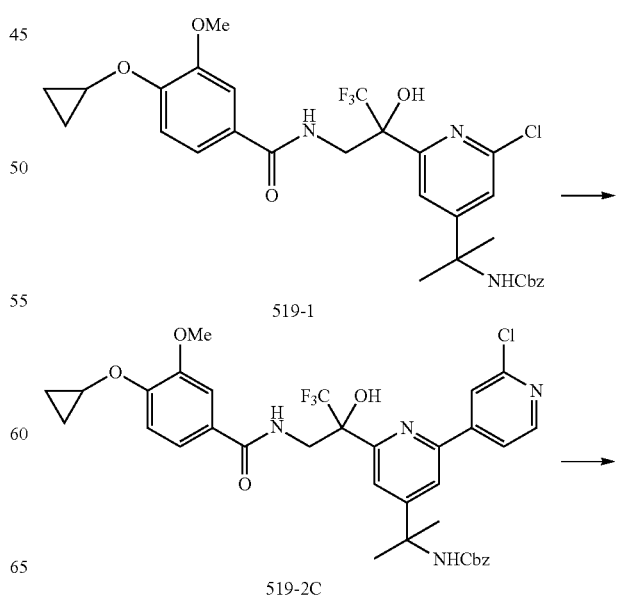

519-1

519-2C

-continued

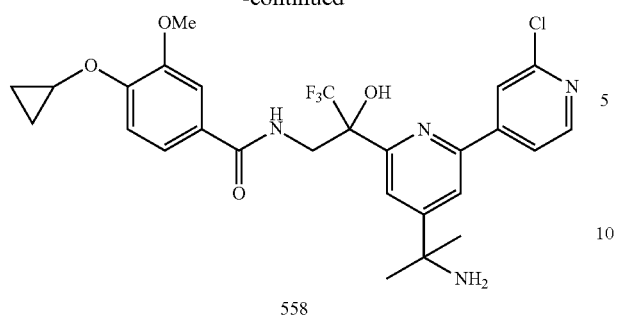
558

Suzuki coupling of 519-1 with 2-chloropyridine-4-boronic acid (Method B of Example 265) followed by Cbz-removal according to Method D of Example 265 afforded 558 (3% overall). UPLC/MS (ES$^+$): m/z 565.30 [M+H]$^+$.

Example 269

Preparation of Compound 559

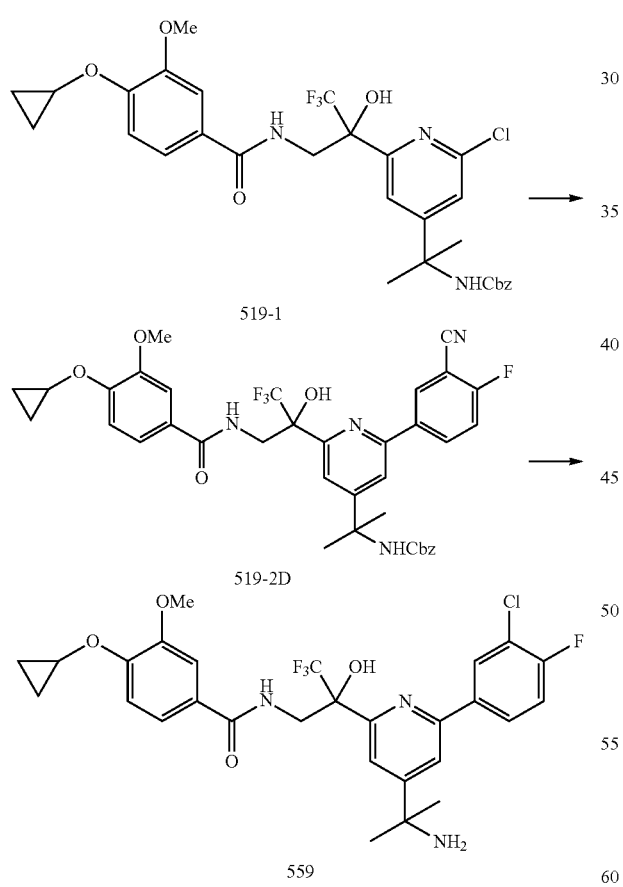

Suzuki coupling of 519-1 with 3-cyano-4-fluorophenylboronic acid (Method A of Example 265) followed by Cbz-removal according to Method D of Example 265 afforded 559 (10% overall). UPLC/MS (ES$^+$): m/z 573.42 [M+H]$^+$.

Example 270

Preparation of Compound 514

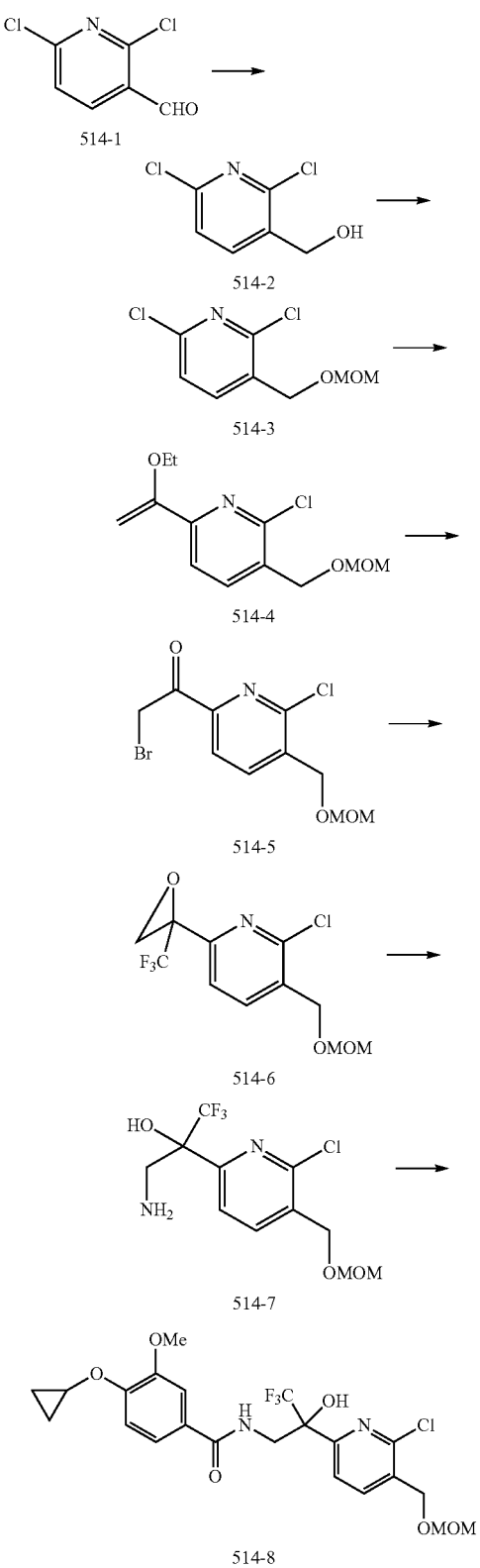

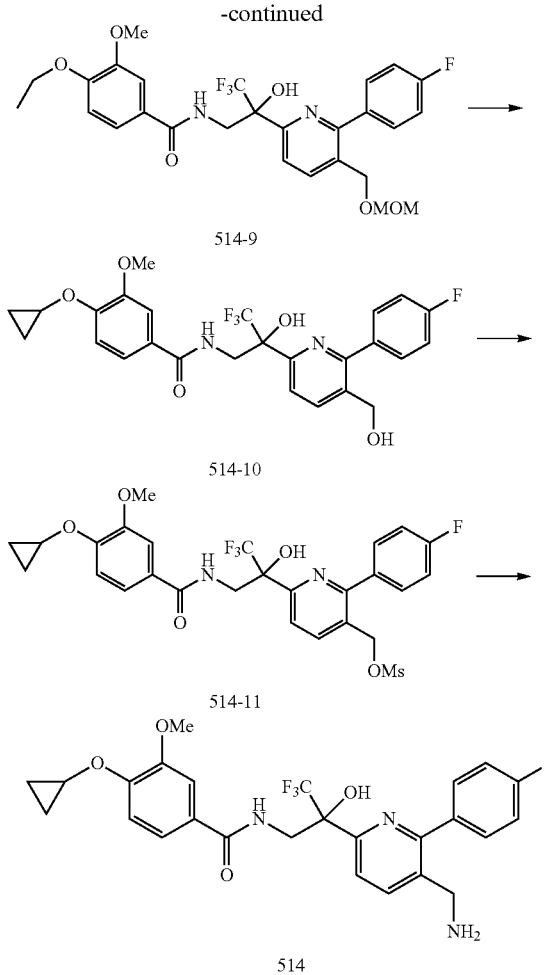

NBS (888 mg, 4.99 mmol) was added to a solution of 514-4 in THF (40 mL), which had been pre-cooled to 0° C. The reaction was stirred at 0° C. for 1 h, then warmed to r.t., and stirred for 2 h. EtOAc was added. The organic portion was washed with water, dried with Na$_2$SO$_4$, filtered and concentrated under reduced pressure. Chromatography of the residue (cyclohexane:EtOAc, 100:0 to 70:30) afforded 514-5 (1.11 g).

CF$_3$TMS (6 mL) was added to a solution of 514-5 (1.11 g) in THF (15 mL). CsF (2.74 g, 18.0 mmol) was added in 1 portion. After 1 h, the reaction was partitioned between EtOAc and sat. aq. NH$_4$Cl solution. The layers were separated, and the aqueous portion was extracted with EtOAc. The combined organic portions were dried with Na$_2$SO$_4$, filtered and concentrated under reduced pressure. Crude 514-6 was directly used in the next step.

A solution of 514-6 and 7M NH$_3$-MeOH (50 mL) was stirred at r.t. for 16 h. The volatiles were removed under reduced pressure. The residue was purified by reverse phase chromatography (water:CH$_3$CN, 100:0 to 50:50) to afford 514-7 (214 mg). UPLC/MS (ES$^+$): m/z 315.30 [M+H]$^+$.

A mixture of 514-7 (291 mg, 0.928 mmol), EDC (212 mg, 1.11 mmol), HOBT (150 mg, 1.11 mmol), TEA (310 uL, 2.23 mmol) and 4-cyclopropoxy-3-methoxybenzoic acid (193 mg, 0.924 mmol) in DCM (6 mL) was stirred at r.t. for 2 h. A 1M aq. HCl solution was added, and the mixture was stirred for 2 mins. The layers were separated. The organic portion was washed with 1M aq. NaOH solution, and concentrated under reduced pressure. Chromatography of the residue (cyclohexane:EtOAc, 70:30) afforded 514-8 (140 mg, 30%). UPLC/MS (ES$^+$): m/z 505.20 [M+H]$^+$.

A mixture of 514-8 (67.6 mg, 0.134 mmol), 4-fluorophenylboronic acid (28 mg, 0.201 mmol), KH$_2$PO$_4$ (21 mg, 0.134 mmol), K$_3$PO$_4$ (29.0 mg, 0.134 mmol) and Pd(dbpf)Cl$_2$ (9 mg, 0.013 mmol) in DME-H$_2$O-EtOH (5:3:1, 5 mL) was degassed and heated to 50° C. for 48 h. The mixture was partitioned between DCM and water. The organic portion was concentrated under reduced pressure. Chromatography of the residue (cyclohexane:EtOAc, 70:30) afforded 514-9 (50.7 mg). $^1$H NMR (400 MHz, CDCl$_3$) δ ppm 0.80-0.90 (m, 4H), 3.36 (s, 3H), 3.72-3.81 (m, 1H), 3.85 (s, 3H), 3.97 (dd, J=14.0, 3.5 Hz, 1H), 4.58 (s, 2H), 4.62-4.73 (m, 3H), 6.43 (dd, J=7.9, 3.5 Hz, 1H), 6.67 (s, 1H), 7.08 (dd, J=8.3, 1.8 Hz, 1H), 7.14-7.22 (m, 3H), 7.25 (d, J=1.8 Hz, 1H), 7.53-7.61 (m, 2H), 7.78 (d, J=8.1 Hz, 1H), 8.05 (d, J=8.1 Hz, 1H).

A solution of 514-9 (50.7 mg, 0.09 mmol) in 1:1 DCM-TFA (700 μL) was stirred at r.t. for 12 h. The reaction was diluted with DCM. The organic portion was washed with 2M aq. NaOH solution and concentrated under reduced pressure. Crude 514-10 (45 mg) was directly used in the next step. UPLC/MS (ES$^+$): m/z 521.30 [M+H]$^+$.

TEA (19 μL, 0.136 mmol) and MsCl (10 μL, 0.133 mL) were sequentially added to a solution of 514-10 (45 mg) in DCM (1 mL), which had been pre-cooled to 0° C. The reaction was allowed to reach r.t., stirred for 12 h and diluted with DCM. The organic portion was washed with water, dried with Na$_2$SO$_4$, filtered and concentrated under reduced pressure. Crude 514-11 (36 mg) was directly used in the next step.

A solution of 514-11 (36 mg) in 7M NH$_3$-MeOH (1 mL) was stirred at r.t. for 12 h. The volatiles were removed under reduced pressure. The residue was purified by reverse phase chromatography (water:CH$_3$CN, 100:0 to 67:33) to afford 514 (19.6 mg). UPLC/MS (ES$^+$): m/z 520.30 [M+H]$^+$.

NaBH$_4$ (808 mg, 21.3 mmol) was added to a solution of 514-1 (3.10 g, 17.7 mmol) in MeOH (22 mL), which had been pre-cooled to 0° C. The mixture was allowed to reach r.t. and stirring was prolonged for 30 mins. 1M aq. HCl solution was added, and the organic solvent was removed under reduced pressure. The aqueous phase was extracted with DCM (3×). The combined organic portions were dried with Na$_2$SO$_4$ and filtered. The volatiles were removed under reduced pressure to afford 514-2 (3.01 g). UPLC/MS (ES$^+$): m/z 178.00 [M+H]$^+$.

Chloromethyl methyl ether (704 μL, 9.27 mmol) and TEA (1.75 mL, 12.6 mmol) were added to a solution of 514-2 (1.5 g) in DCM (12 mL). The reaction was warmed to 45° C. When complete conversion was observed by UPLC, the reaction was cooled to r.t., diluted with DCM and washed with water. The organic portion was concentrated under reduced pressure. Chromatography of the residue (cyclohexane:EtOAc, 70:30) afforded 514-3 (1.48 g). UPLC/MS (ES$^+$): m/z 222.00 [M+H]$^+$.

A mixture of 514-3 (1.38 g, 6.24 mmol), Pd(PPh$_3$)Cl$_2$ (438 mg, 0.624 mmol) and tributyl[1-ethoxyethenyl]stannane (2.11 mL, 6.24 mmol) in dioxane (40 mL) was degassed, warmed to 90° C. and stirred at that temp for 3 h. After being cooled to r.t., the reaction was diluted with EtOAc. The organic portion was washed with a sat. aq. KF solution and water, dried with Na$_2$SO$_4$, filtered and concentrated under reduced pressure to afford crude 514-4, which was directly used in the next step.

Example 271

Preparation of Compound 538

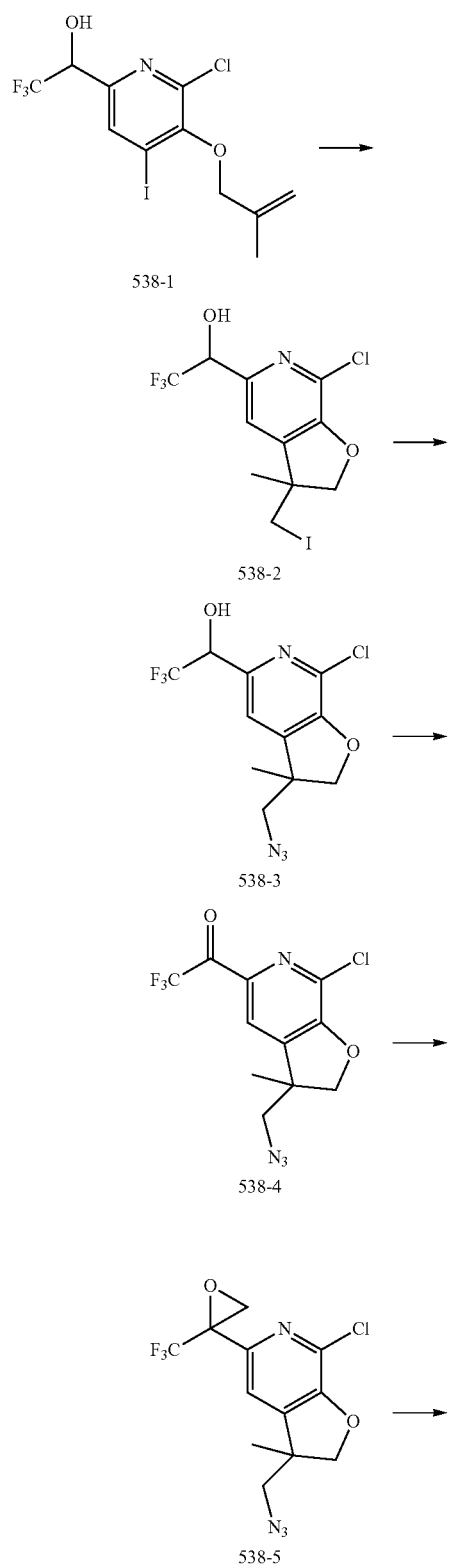

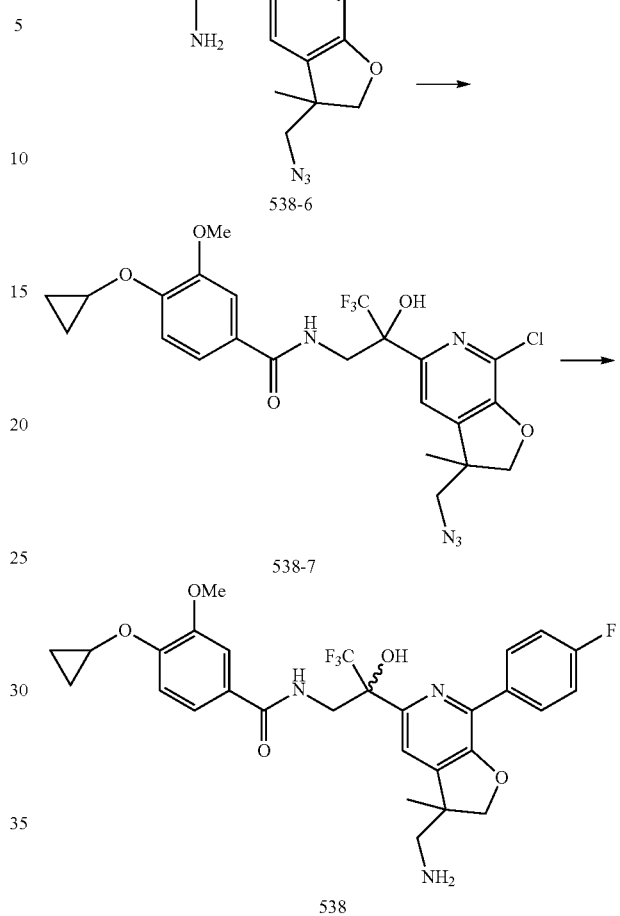

A 0.2 M solution of 538-1 (465 mg, 1.14 mmol) in toluene (5.7 mL) was degassed (mw vial). Pd(Q-phos)$_2$ (80 mg, 0.052 mmol) was added. The vial was sealed, purged with N$_2$ and heated to 100° C. for 6 h. Additional Pd(Q-phos)$_2$ (30 mg) was added. The vial was purged with N$_2$ and heated to 100° C. for 4 h. The mixture was directly purified by chromatography on silica gel (cyclohexane:EtOAc, 95:5 to 70:30) to afford 538-2 (414 mg, 96%). UPLC/MS (ES$^+$): m/z 408.10 [M+H]$^+$.

A mixture of 538-2 (340 mg) and NaN$_3$ (288 mg) in DMF (4 mL) was heated to 65° C. and stirred at that temp for 16 h. The volatiles were removed under reduced pressure. The crude residue was partitioned between EtOAc and sat. aq. NH$_4$Cl solution. The layers were separate. The organic portion was dried with Na$_2$SO$_4$, filtered and concentrated under reduced pressure to afford 538-3 (245 mg). UPLC/MS (ES$^+$): m/z 323.10 [M+H]$^+$.

Dess-Martin periodinane (484 mg, 1.14 mmol) was added to a solution of 538-3 (245 mg) in DCM (4 mL). The reaction was stirred at r.t. for 1 h and quenched with a 1:1 1M aq. Na$_2$S$_2$O$_3$:5% aq. NaHCO$_3$. The mixture was vigorously stirred for 1 h. The layers were separated, and the aqueous portion was extracted with DCM. The combined organic portions were dried with Na$_2$SO$_4$, filtered and concentrated under reduced pressure. Chromatography of the residue (cyclohexane:EtOAc) afforded 538-4 (206 mg). UPLC/MS (ES$^+$): m/z 339.10 [M+H$_3$O]$^+$.

Trimethylsulfoxonium iodide (141 mg, 0.643 mmol) was added in one portion to a mixture of tBuOK (72 mg, 0.643 mg) in CH₃CN (4 mL), which had been previously degassed. After 20 mins, the solution was filtered from the solid and added to a solution of 538-4 (206 mg) in CH₃CN (4 mL), which had been previously degassed. The reaction was stirred at r.t. for 15 mins. The volatiles were removed under reduced pressure. Chromatography of the residue (cyclohexane:EtOAc, 100:0 to 50:50) afforded 538-5. UPLC/MS (ES⁺): m/z 335.10 [M+H]⁺.

A solution of 538-5 (100 mg) in 7M NH₃-MeOH (60 mL) was stirred at r.t. for 1 h. The volatiles were removed under reduced pressure to afford crude 538-6 (108 mg), which was directly used in the next step. UPLC/MS (ES⁺): m/z 352.10 [M+H]⁺.

A mixture of 538-6 (108 mg), EDC (89 mg, 0.462 mmol), HOBT (63 mg, 0.462 mmol), 4-cyclopropoxy-3-methoxy-benzoic acid (64 mg, 0.307 mmol) and TEA (86 uL, 0.616 mmol) in DCM (4 mL) was stirred at r.t. for 16 h. The reaction was diluted with DCM. The organic portion was washed with 1M aq. HCl solution (2×), dried with Na₂SO₄, filtered and concentrated under reduced pressure. Chromatography of the residue (cyclohexane:EtOAc, 100:0 to 50:50) afforded 538-7 (136 mg). UPLC/MS (ES⁺): m/z 542.20 [M+H]⁺.

Pd(dbpf)Cl₂ (16 mg, 0.025 mmol) was added to a mixture of 538-7 (136 mg), K₃PO₄ (107 mg, 0.503 mmol), KH₂PO₄ (68 mg, 0.503 mmol) and 4-fluorophenylboronic acid (74 mg, 0.503 mmol) in 5:3:1 DME:EtOH:H₂O (2.7 mL), which had been previously degassed. The reaction was warmed to 65° C. and stirred at that temp for 10 h. The mixture was cooled to r.t. and stirred for 72 h. The reaction was diluted with EtOAc and washed with sat. aq. NH₄Cl solution. The organic portion was dried with Na₂SO₄, filtered and concentrated under reduced pressure. The residue was purified by reverse phase chromatography (water/0.1% HCOOH: CH₃CN/0.1% HCOOH, 100:0 to 50:50) to afford 538 as a white solid (formic acid salt, 33 mg, dr 1:1). UPLC/MS (ES⁺): m/z 576.40 [M+H]⁺.

Example 272

Preparation of Compound 522

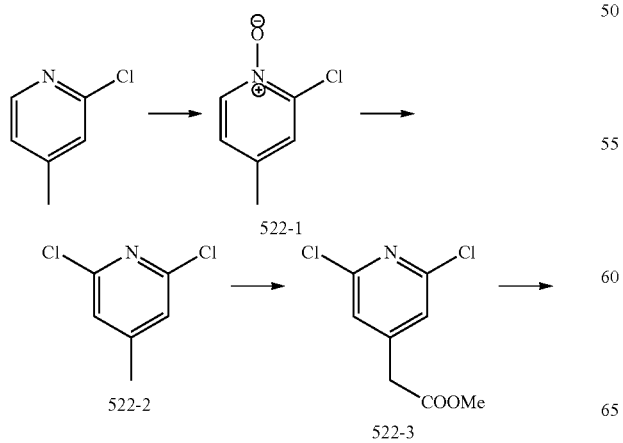

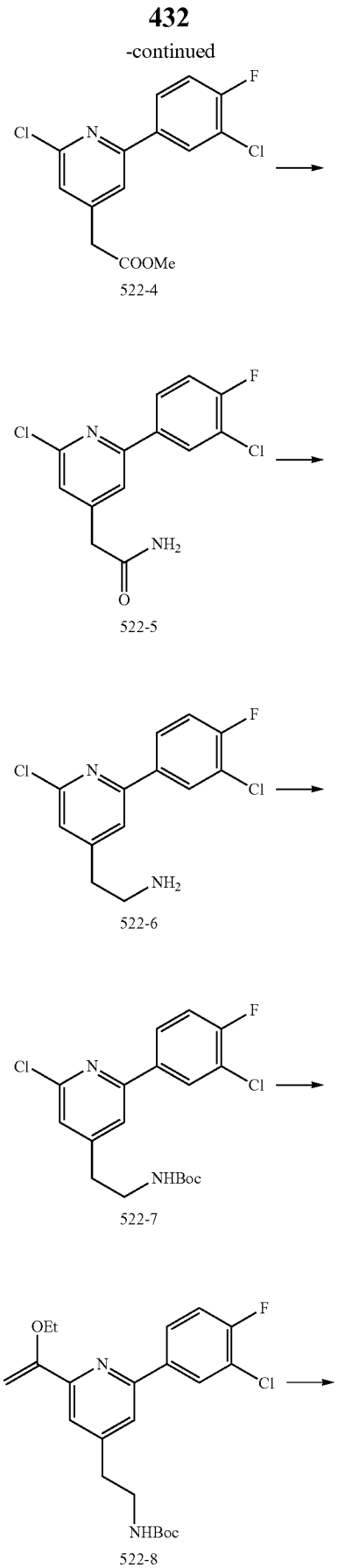

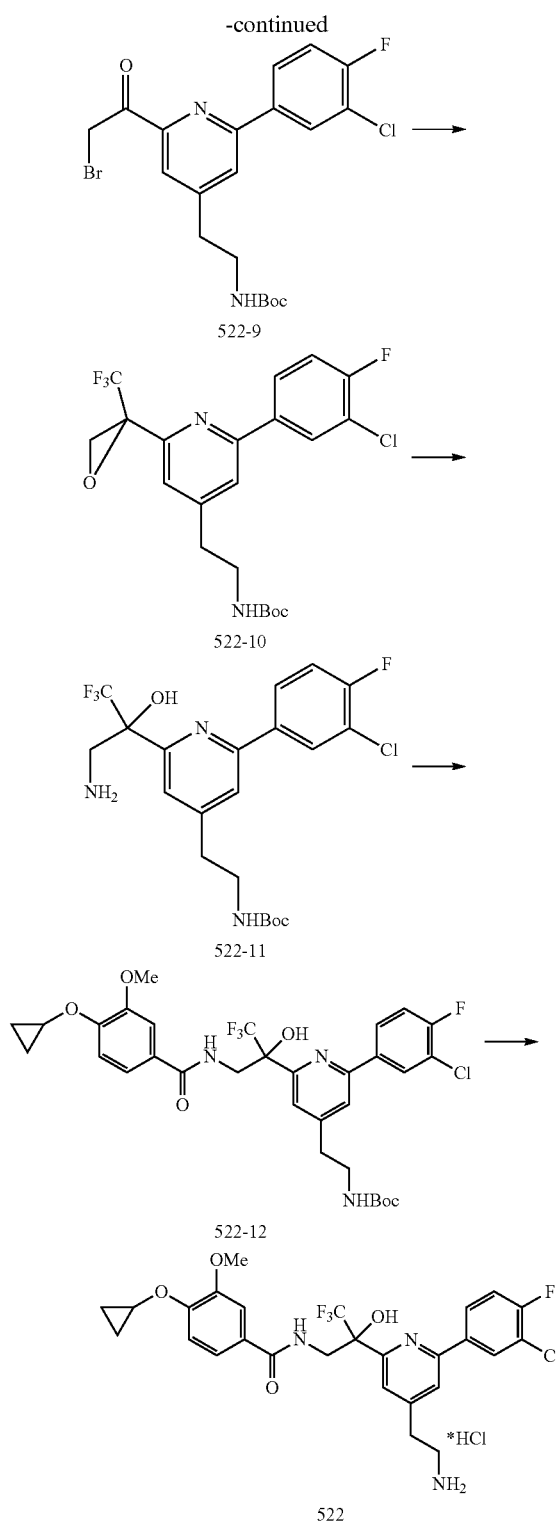

the residue (DCM:MeOH, 100:0 to 80:20) afforded 522-1 as a yellow oil (9.50 g, 42%). UPLC/MS (ES+): m/z 144.00 [M+H]+.

POCl3 (130 mL) was added to a solution of 522-1 (9.50 g, 66.0 mmol) in toluene (20 mL). The reaction was heated to 70° C. and stirred at that temp for 20 h. The volatiles were removed under reduced pressure. The residue was poured into ice. The mixture neutralized with sat. aq. K2CO3 solution and extracted with DCM (3×). The combined organic portions were dried with Na2SO4, filtered and concentrated under reduced pressure. Chromatography of the residue afforded 522-2 (3.80 g, 36%). UPLC/MS (ES+): m/z 162.10 [M+H]+.

A freshly prepared solution of LDA solution (1M in THF-hexane, 44.6 mL, 44.6 mmol) was added to a solution of 522-2 (3.61 g, 22.3 mmol) in THF (110 mL), which had been pre-cooled to −78° C. The reaction was stirred at −78° C. for 1 h. Dimethylcarbonate (4.5 mL, 53.5 mmol) was added. The reaction was allowed to reach 0° C., stirred at that temp for 1 h and quenched with water. The volatiles removed under reduced pressure. The residue was taken up with EtOAc. The organic portion was washed with sat. aq. NH4Cl solution, dried with Na2SO4, filtered and concentrated under reduced pressure. Chromatography of the residue (cyclohexane:EtOAc, 100:0 to 60:40) afforded 522-3 as a yellow oil (3.0 g, 61%). UPLC/MS (ES+): m/z 220.0 [M+H]+.

A mixture of 522-3 (450 mg, 2.00 mmol), 3-chloro-4-fluorophenylboronic acid (285 mg, 1.60 mmol), NaHCO3 (515 mg, 6.10 mmol) and Pd(PPh3)4 (95 mg, 0.080 mmol) in 2:1 THF:water (9 mL) was degassed and heated to 50° C. After 2 h, 3-chloro-4-fluorophenyl boronic acid (0.2 eq.) was added, and the mixture was stirred at 50° C. for 2 h. After being cooled to r.t., the reaction was diluted with DCM. The organic portion was washed with sat. aq. NaHCO3 solution, dried with Na2SO4, filtered and concentrated under reduced pressure. The residue was purified by reverse phase chromatography (water:CH3CN, 70:30 to 10:90) to afford 522-4 as a yellow oil (180 mg, 29%). UPLC/MS (ES+): m/z 314.10 [M+H]+.

522-4 (860 mg, 2.70 mmol) was dissolved in 7M NH3-MeOH (14 mL) at 0° C. The reaction was stirred at r.t. for 3 h and at 40° C. for 20 h. The volatiles were removed under reduced pressure to afford crude 522-5 (775 mg), which was directly used in the next step.

Borane-THF complex (1M solution in THF, 7.77 mL, 7.77 mmol) was added to a solution of 522-5 (775 mg) in THF (14 mL). The reaction was refluxed for 3 h. Additional borane-THF complex (4 eq., 2 aliquots) was added, and the mixture was refluxed overnight. The reaction was quenched with 2M aq. HCl solution, and the mixture was stirred for 30 mins. The aqueous portion was basified with sat. aq. NaHCO3 solution and extracted with EtOAc. The organic portion was washed with brine, dried with Na2SO4, filtered and concentrated under reduced pressure. The residue was loaded on to a SCX-column and eluted with 2M NH3-MeOH to give 522-6 (610 mg, 82%). UPLC/MS (ES+): m/z 285.10 [M+H]+.

Triethylamine (590 uL, 4.26 mmol) and Boc2O (700 mg, 3.20 mmol) were sequentially added to a solution of 522-6 (610 mg, 2.13 mmol) in DCM (11 mL). The mixture was stirred at r.t. for 1 h, diluted with DCM and washed with 0.5M aq. HCl solution. The organic portion was dried with Na2SO4, filtered and concentrated under reduced pressure. Chromatography of the residue (cyclohexane:EtOAc, 90:10 to 50:50) afforded 522-7 as a white solid (580 mg, 71%). UPLC/MS (ES+): m/z 385.20 [M+H]+.

meta-Chloroperbenzoic acid (56.0 g, 328 mmol) was added in several portions to a solution of 2-chloro-4-methylpyridine (20.0 g, 156 mmol) in DCM (520 mL). The mixture was refluxed for 8 h and diluted with DCM. The organic portion was washed with sat. aq. K2CO3 solution. The aqueous portion was extracted with EtOAc. The combined organic portions were dried with Na2SO4, filtered and concentrated under reduced pressure. Chromatography of A mixture of 522-7 (580 mg, 1.50 mmol), Pd(PPh₃)Cl₂ (105 mg, 0.150 mmol) and tributyl[1-ethoxyethenyl]stannane (560 uL, 1.65 mmol) in dioxane (8 mL) was degassed, warmed to 100° C. and stirred at that temp for 6 h. After being cooled to r.t., a sat. aq. KF solution was added. The mixture was stirred for 10 mins, and the aqueous portion was extracted with EtOAc. The organic phase was dried with Na₂SO₄, filtered and concentrated under reduced pressure to afford crude 522-8, which was directly used in the next step.

N-Bromosuccinimide (293 mg, 1.65 mmol) was added to a solution of 522-8 in THF (8 mL), which had been pre-cooled to 0° C. The reaction was stirred at 0° C. for 1 h, quenched with water and extracted with EtOAc. The organic portion was dried with Na₂SO₄, filtered and concentrated under reduced pressure. Chromatography of the residue (cyclohexane:EtOAc, 90:10 to 50:50) afforded 522-9 as a white solid (330 mg, 47% over 2 steps). ¹H NMR (400 MHz, CDCl₃) δ ppm 1.45 (s, 9H), 3.00 (t, J=6.5 Hz, 2H), 3.50 (q, J=6.5 Hz, 2H), 4.58-4.69 (m, 1H), 4.95 (s, 2H), 7.30 (t, J=8.0 Hz, 1H), 7.79 (br. s., 1H), 7.92 (s, 1H), 7.95-8.02 (m, 1H), 8.15 (dd, J=6.9, 2.1 Hz, 1H).

CF₃TMS (1.03 mL, 7.00 mmol) was added to a solution of 522-9 (330 mg, 0.700 mmol) in THF (5 mL). CsF (531 mg, 3.50 mmol) was added in one portion. After 1 h, the reaction was partitioned between EtOAc and sat. aq. NH₄Cl solution. The layers were separated, and the aqueous portion was extracted with EtOAc. The combined organic portions were dried with Na₂SO₄, filtered and concentrated under reduced pressure. The crude 522-10 was directly used in the next step.

A solution of 522-10 and 7M NH3-MeOH (10 mL) was stirred at r.t. for 3 h. The volatiles were removed under reduced pressure. The residue was purified by reverse phase chromatography (water:CH₃CN, 95:5 to 30:70) to afford 522-11 (56 mg).

A mixture of 4-cyclopropoxy-3-methoxybenzoic acid (49.0 mg, 0.230 mmol), HATU (108 mg, 0.280 mmol) and DIPEA (122 uL, 0.700 mmol) in DCM (1 mL) was stirred at r.t. for 30 mins. A solution of 522-11 (56 mg) in DCM (1 mL) was added, and the reaction was stirred at r.t. for 2 h and quenched with water. EtOAc was added. The organic portion was washed with 1M aq. HCl solution, 2M aq. NaOH solution and brine, dried with Na₂SO₄, filtered and concentrated under reduced pressure. Chromatography of the residue (cyclohexane:EtOAc, 90:10 to 40:60) afforded 522-12 (65 mg).

A solution of 522-12 in 4M HCl-dioxane (1 mL) was stirred at 0° C. for 1 h. The volatiles were removed under reduced pressure. The residue was purified by reverse phase chromatography (water:CH₃CN, 95:5 to 40:60) to afford 522 (14 mg). UPLC/MS (ES⁺): m/z 568.30 [M+H]⁺.

Example 273

Preparation of Compound 477

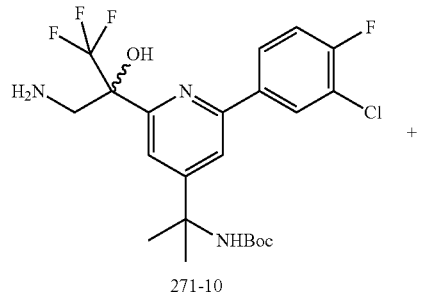

271-10

+

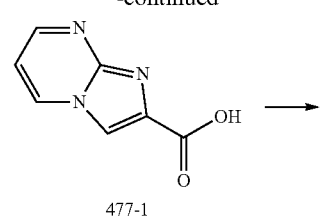

477-1

-continued

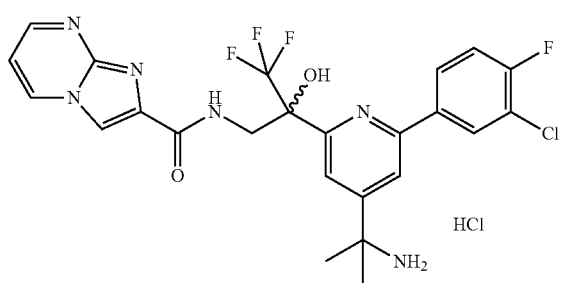

477

A mixture of 271-10 (50 mg, 0.1 mmol), 477-1 (16 mg, 0.1 mmol) and TEA (1 mmol) was dissolved in anhydrous DCM (4 mL) with stirring. The mixture was treated with HATU (38 mg, 0.1 mmol) in 1 portion. After stirring at r.t. for 30 mins, TFA (1 mL) was added. The solution was stirred at r.t. for 2 h. The mixture was concentrated to dryness. The residue was purified by reverse prep-HPLC to afford 477 (28 mg, 48%) as a white solid. +ESI-MS: m/z 537.1 [M+H]⁺.

Example 274

Preparation of Compound 478

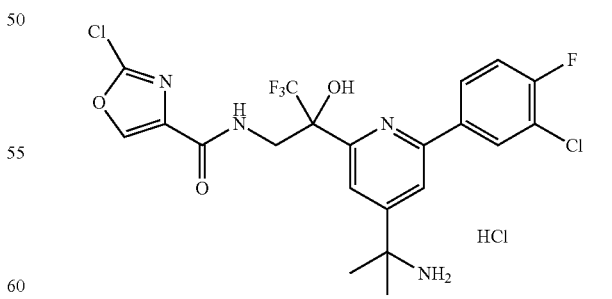

478

Compound 478 was prepared following the general procedure for preparing 477 by using 2-chlorooxazole-4-carboxylic acid and 271-10. Crude 478 was purified by prep-HPLC and obtained as a white solid (20 mg, 36%). +ESI-MS: m/z 520.9 [M+H]⁺.

Example 275

Preparation of Compound 485

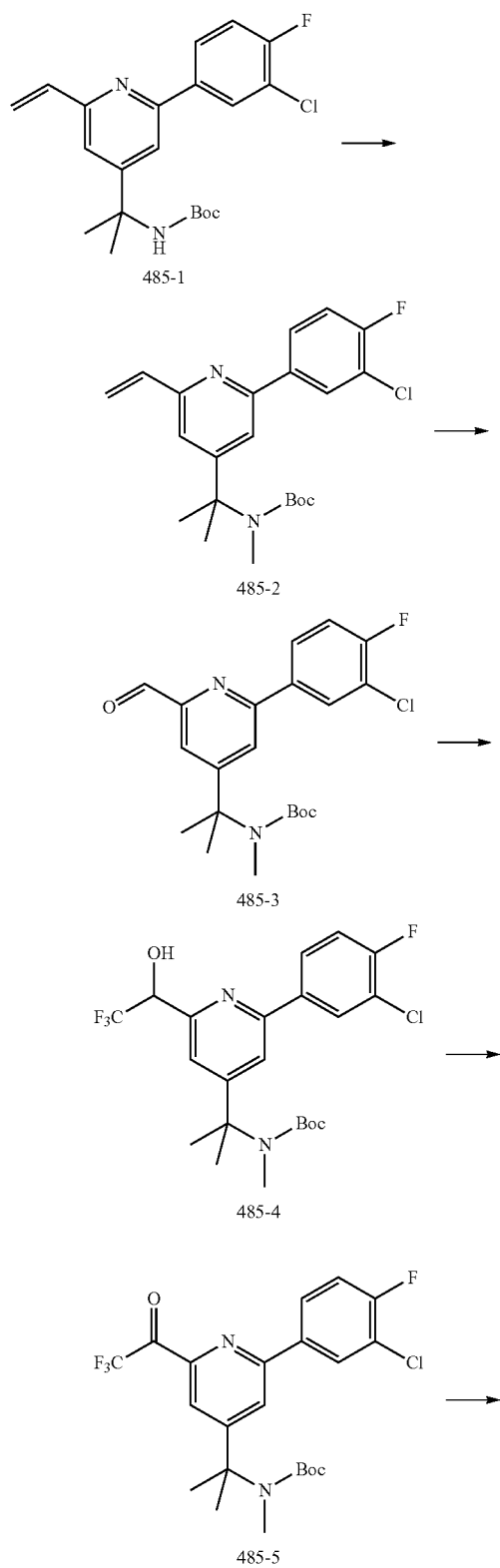

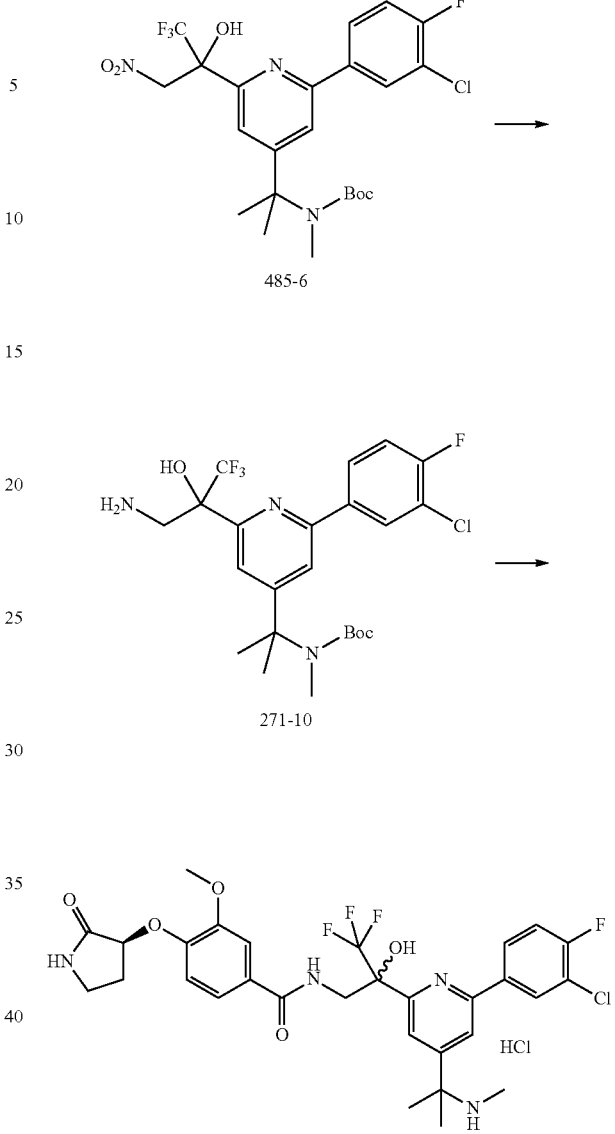

To a solution of 485-1 (6 g, 15.4 mmol) in anhydrous DMF (95 mL) was added NaH (640 mg, 16 mmol, 60% in mineral oil) in small portions at r.t. After stirring for 10 mins, a solution of MeI (2.3 g, 16 mmol) in DMF (5 mL) was added dropwise, and the reaction was stirred for 1 h. After complete conversion of 485-1, the mixture was quenched with water, and extracted with EtOAc (150 mL×2). The organic layer was dried over anhydrous $Na_2SO_4$ and concentrated under reduced pressure. The residue was purified by chromatography using (PE:EtOAc: 100:0 to 80:20) to afford 485-2 (5.8 g, 93.5%).

Compound 485 (white solid, 27 mg) was prepared following the general procedure for preparing 272 using 485-2 and (S)-3-methoxy-4-((2-oxopyrrolidin-3-yl)oxy)benzoic acid. +ESI-MS: m/z 639.1 [M+H]$^+$.

Example 276
Preparation of Compound 486
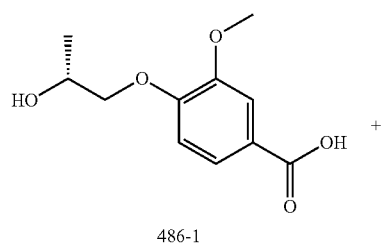
486-1
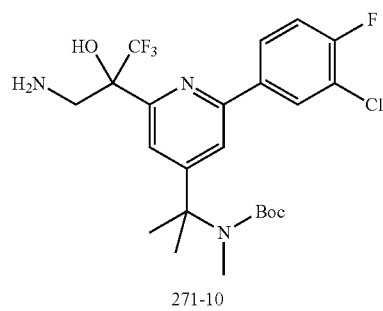
271-10
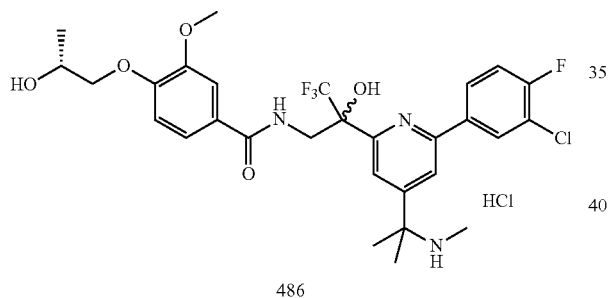
486
Compound 486 (white solid, 34 mg) was prepared following the general procedure for preparing 485 by using 486-1 and 271-10. +ESI-MS: m/z 614.1 [M+H]$^+$.
Example 277
Preparation of Compound 487
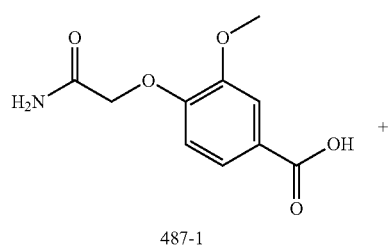
487-1
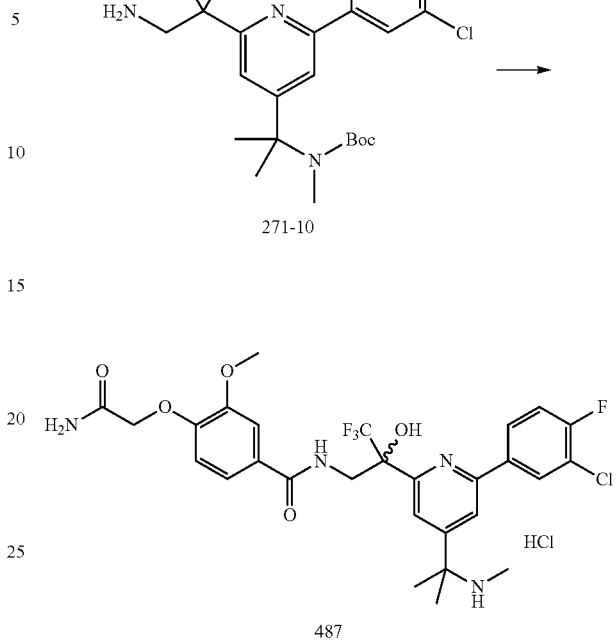
271-10
487
Compound 487 (white solid, 27.5 mg) was prepared following the general procedure for preparing 485 by using 487-1 and 271-10. +ESI-MS: m/z 613.1 [M+H]$^+$.
Example 278
Preparation of Compound 488
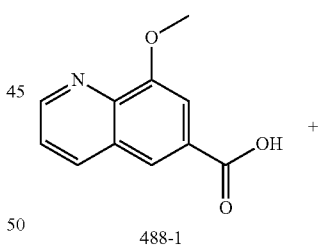
488-1
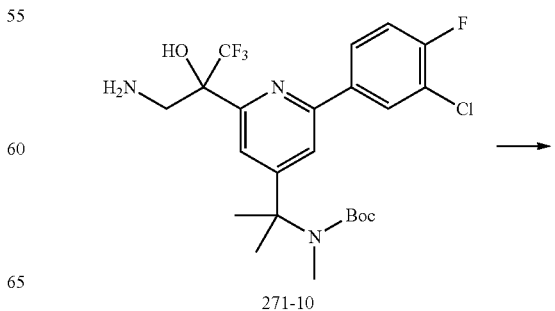
271-10

-continued

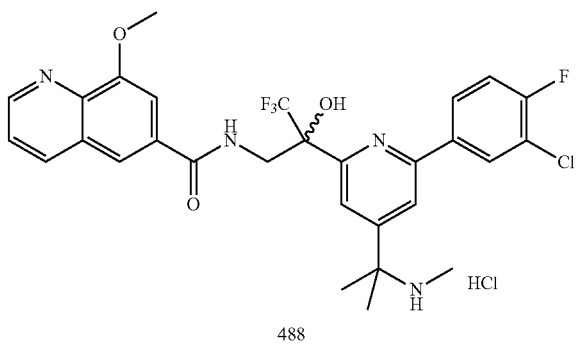

488

Compound 488 (white solid, 26 mg) was prepared following the general procedure for preparing 485 by using 488-1 and 271-10. +ESI-MS: m/z 591.1 [M+H]⁺.

Example 279

Preparation of Compound 489

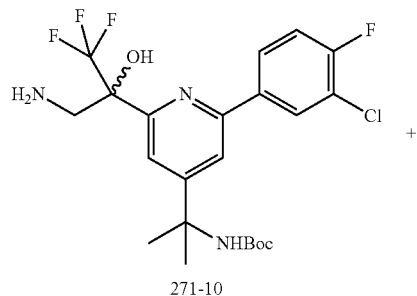

271-10

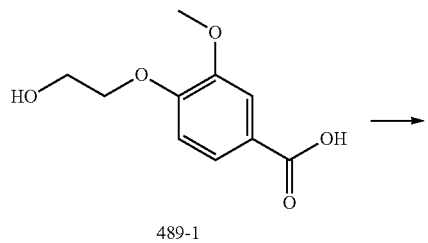

489-1

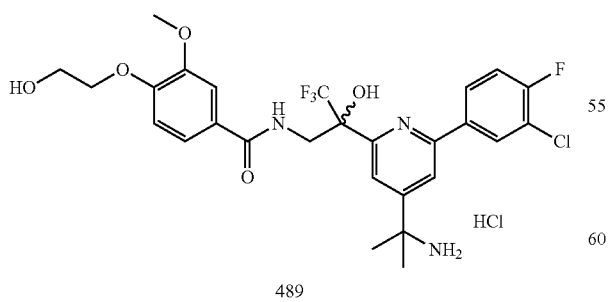

489

Compound 489 (white solid, 23 mg) was prepared following the general procedure for preparing 485 by using 489-1 and 271-10. +ESI-MS: m/z 586.0 [M+H]⁺.

Example 280

Preparation of Compound 490

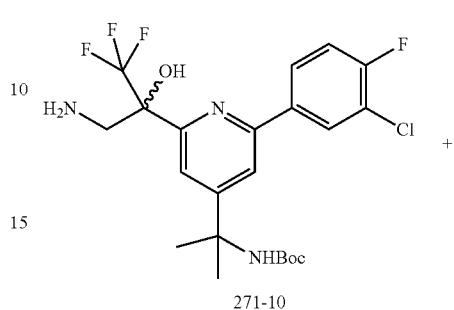

271-10

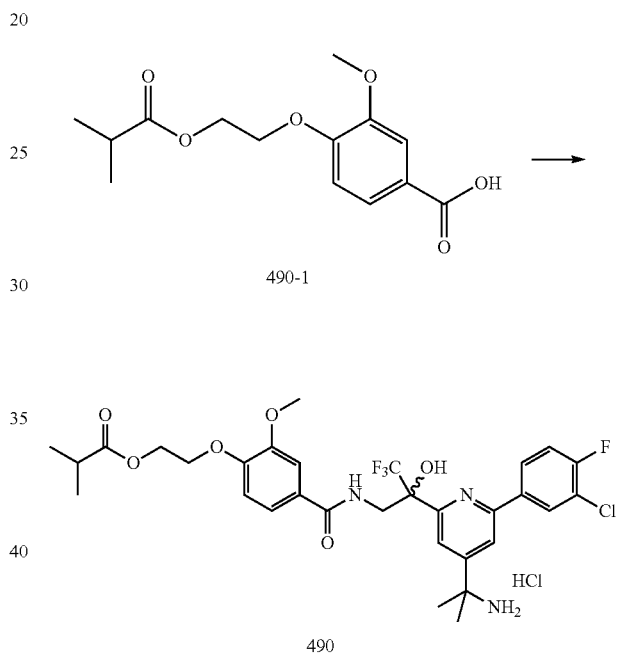

490

Compound 490 (white solid, 41 mg) was prepared following the general procedure for preparing 485 by using 490-1 and 271-10. +ESI-MS: m/z 656.0 [M+H]⁺.

Example 281

Preparation of Compound 491

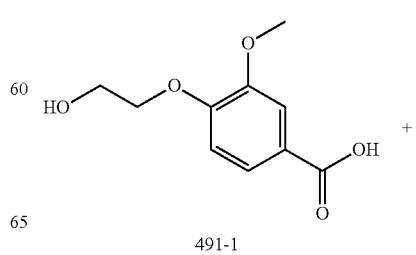

491-1

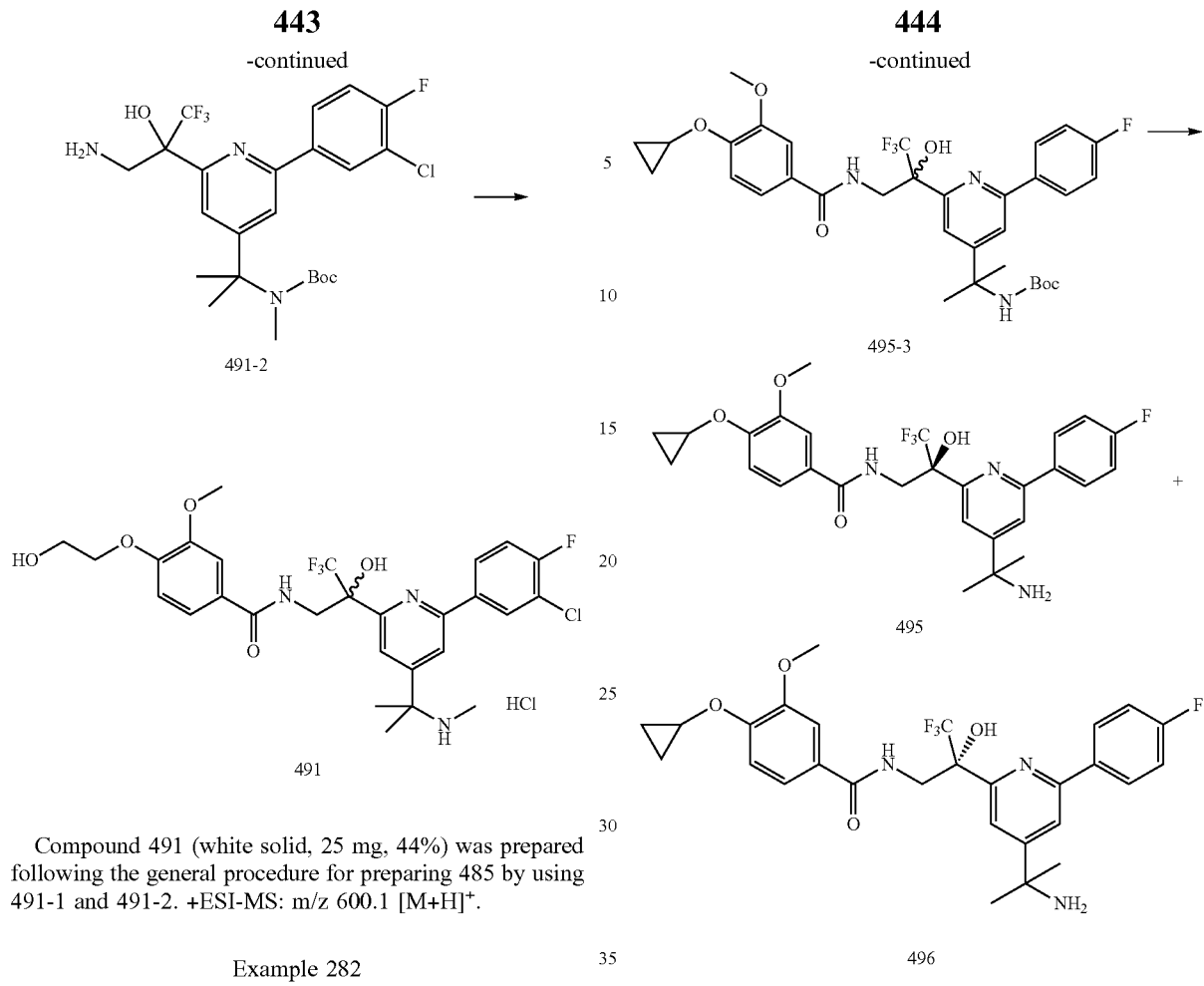

Compound 491 (white solid, 25 mg, 44%) was prepared following the general procedure for preparing 485 by using 491-1 and 491-2. +ESI-MS: m/z 600.1 [M+H]⁺.

Example 282

Preparation of Compounds 495 and 496

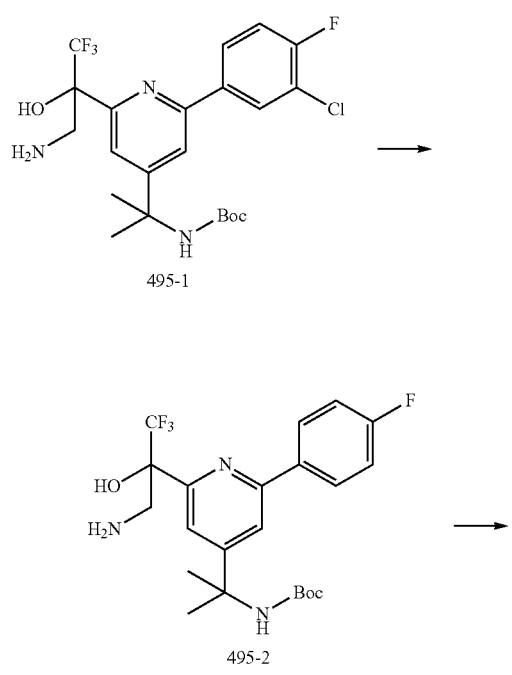

To a solution of 495-1 (850 mg, 1.73 mmol) in MeOH (50 mL) was added Pd/C (210 mg, 5%) under $N_2$ at r.t. The suspension was purged with hydrogen for several times. The mixture was stirred under hydrogen (15 psi) at r.t. for 12 h. After complete conversion of 495-1, the mixture was filtered through a pad of Celite, and the filtrate was concentrated to dryness. The residue was 495-2 (750 mg, 94.6%), which was used directly without further purification. +ESI-MS: m/z 458.2 [M+H]⁺.

A mixture of 495-2 (750 mg, 1.64 mmol), carboxyl acid 3 (340 mg, 1.64 mmol) and TEA (1 mmol) is dissolved in anhydrous DMF (10 mL) with stirring. The solution was treated with HATU (623 mg, 1.64 mmol) in one portion. After stirring at r.t. for 1-2 h, the mixture was poured into cold water and extracted with EA (20 mL×3). The combined organic layers were washed with brine, dried over anhydrous $Na_2SO_4$, and concentrated under reduced pressure. The residue was purified by column chromatography using PE:EA=1:1 as the eluent to give 495-3 as an oil (910 mg, 86%). +ESI-MS: m/z 648.1 [M+H]⁺.

To a stirring solution of 495-3 (910 mg, 1.41 mmol) in DCM (10 mL) was added TFA (5 mL) dropwise at r.t. The reaction was stirred for 30 mins and concentrated to dryness under reduced pressure. The residue was neutralized by sat. sodium carbonate solution and extracted with EA (15 mL×2). The combined organic layers were washed with brine, dried over anhydrous $Na_2SO_4$, and concentrated under reduced pressure. The residue was purified by prep-HPLC and separated by SFC to give 495 (93 mg) and 496 (82 mg) as a white solid.

495: +ESI-MS: m/z 548.1 [M+H]⁺; and 496: +ESI-MS: m/z 548.1 [M+H]⁺.

Example 283

Preparation of Compound 497

314 →

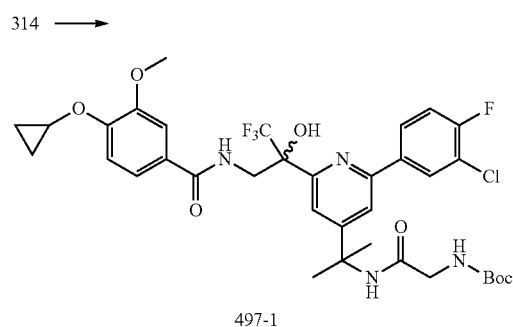

497-1

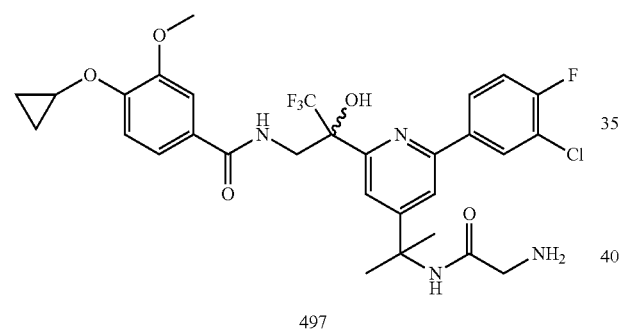

497

To a stirring solution of 314 (116 mg, 0.2 mmol), 2-((tert-butoxycarbonyl)amino)acetic acid (35 mg, 0.20 mmol) and DIPEA (90 mg, 0.7 mmol) in anhydrous DCM (5 mL) was added HATU (76 mg, 0.2 mmol) in one portion at 25° C. The solution was stirred for 1 h. The mixture was diluted with water and DCM. The organic layers were washed with brine, dried over anhydrous Na₂SO₄ and concentrated under reduced pressure to give crude 497-1 (110 mg), which used directly without purification. +ESI-MS: m/z 739.1 [M+H]⁺.

To a stirring solution of crude 497-1 (110 mg) in EA (10 mL) was added HCl:EA (4 M, 5 mL) at r.t. The reaction was stirred for 30 mins with TLC monitoring. After conversion of 497-1, the reaction was quenched with sat. sodium bicarbonate solution, and extracted with EA (10 mL×3). The combined organic layers were washed with brine, dried over anhydrous Na₂SO₄ and concentrated to dryness. The residue was purified by prep-HPLC to give 497 (50 mg, 52.6%) as a white solid. +ESI-MS: m/z 639.2 [M+H]⁺.

Example 284

Preparation of Compound 500

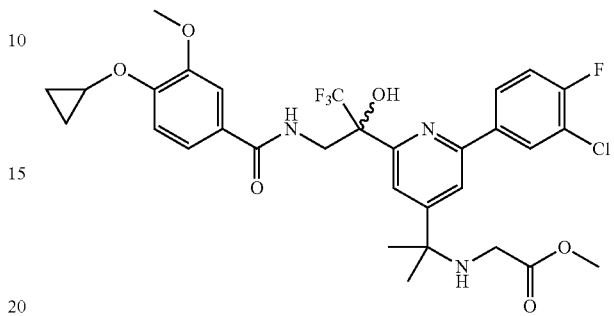

500

To a solution of 314 (58 mg, 0.1 mmol) and K₂CO₃ (27 mg, 0.2 mmol) in DMF (1 mL) was added methyl 2-bromoacetate (23 mg, 0.15 mmol) at r.t. The mixture was heated to 60° C. and stirred for 2 h. The reaction was cooled to r.t. and diluted with H₂O and EA. The combined organic layer was dried over Na₂SO₄ and concentrated under reduced pressure. The residue was purified by prep-HPLC to give 500 as a white solid (30 mg, 46.2%). +ESI-MS: m/z 654.1 [M+H]⁺.

Example 285

Preparation of Compound 501

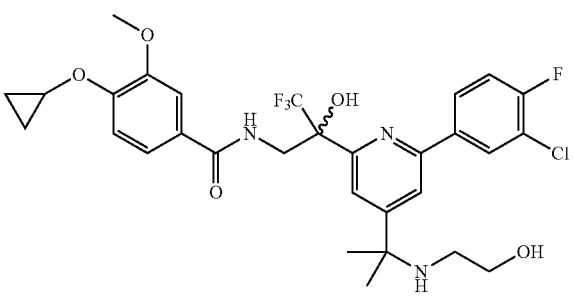

501

To a solution of 500 (90 mg, 0.14 mmol) in MeOH (10 mL) was added NH₃:MeOH (7M, 10 mL). The vial was sealed and heated to 60° C. for 2 h. The reaction was cooled to r.t. and diluted with H₂O (20 mL) and EA (20 mL). The combined organic layers were washed with brine, dried over anhydrous Na₂SO₄ and concentrated to dryness. The residue was purified by prep-HPLC to give 501 as a white solid (49 mg, 54.7%). +ESI-MS: m/z 639.1 [M+H]⁺.

Example 286

Preparation of Compound 502

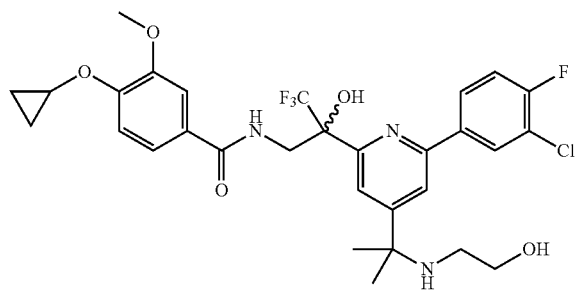

To a solution of 500 (65 mg, 0.1 mmol) in co-solvent of THF (2 mL) and MeOH (2 mL) was added LiBH$_4$ (10 mg, 0.5 mmol) at r.t. The mixture was stirred at r.t. for 30 mins. The reaction was quenched with H$_2$O and extracted with EA (10 mL×2). The combined organic layers were washed with brine, dried over anhydrous Na$_2$SO$_4$ and concentrated to dryness at low pressure. The residue was purified by prep-HPLC to give 502 as a white solid (40 mg, 64.5%). +ESI-MS: m/z 626.0 [M+H]$^+$.

Example 287

Preparation of Compound 503

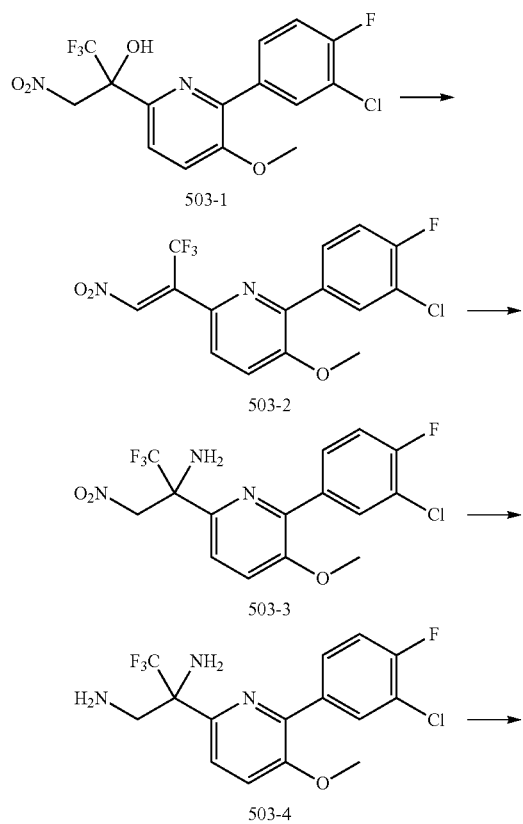

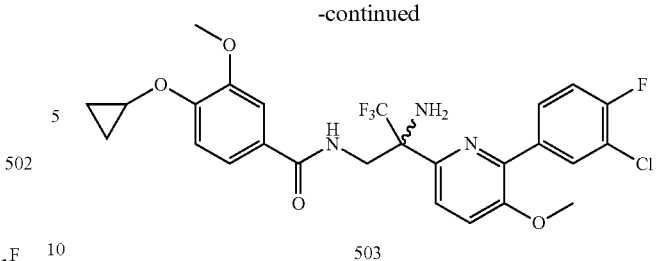

To a solution of 503-1 (1.0 g, 2.5 mmol) in toluene (8 mL) was added pyridine (590 mg, 7.5 mmol) at 0° C. The mixture was stirred at 0° C. for 5 mins and SOCl$_2$ (820 mg, 7.0 mmol) was added dropwise. After addition, the mixture was stirred at 0° C. for 30 mins. The reaction was quenched with H$_2$O and extracted with EA (10 mL×3). The combined organic layers were washed with brine, dried over anhydrous Na$_2$SO$_4$ and concentrated to dryness. The residue was purified by column chromatography using PE:EA=5:1 as the eluent to give 503-2 as a solid (0.8 g, 85.1%). +ESI-MS: m/z 377.1 [M+H]$^+$.

To a solution of 503-2 (0.8 g, 2.1 mmol) in DMSO (6 mL) was added ammonia water (1 mL) at 0° C. The mixture was stirred at r.t. for 30 mins. The mixture was diluted with H$_2$O and extracted with EA (10 mL×3). The combined organic layers were washed with brine, dried over anhydrous Na$_2$SO$_4$ and concentrated to dryness. The residue was purified by column chromatography using PE:EA=3:1 as the eluent to give 503-3 as a solid (650 mg, 78.7%). +ESI-MS: m/z 394.1 [M+H]$^+$.

To a solution of 503-3 (650 mg, 1.7 mmol) in MeOH (10 mL) was added Raney Ni (0.7 g) under N$_2$. The suspension was degassed under vacuum and purged with H$_2$ for several times. The reaction was stirred under H$_2$ (balloon) at r.t. for 30 mins. The mixture was filtered through a pad of Celite, and the filtrate was concentrated to give 503-4 (550 mg), which was used directly without purification.

To a solution of 503-4 (37 mg, 0.10 mmol), 4-cyclopropoxy-3-methoxybenzoic acid (21 mg, 0.10 mmol) and DIPEA (39 mg, 0.3 mmol) in anhydrous DCM (3 mL) was added HATU (39 mg, 0.10 mmol) in one portion at 25° C. The solution was stirred at this temperature for 1 h. The reaction was diluted with H$_2$O and extracted with DCM (10 mL×2). The combined organic layers were washed with brine, dried over anhydrous Na$_2$SO$_4$ and concentrated to dryness at low pressure. The residue was purified by prep-HPLC to give 503 as a white solid (35 mg, 63.6%). +ESI-MS: m/z 553.9 [M+H]$^+$.

Example 288

Preparation of Compound 504

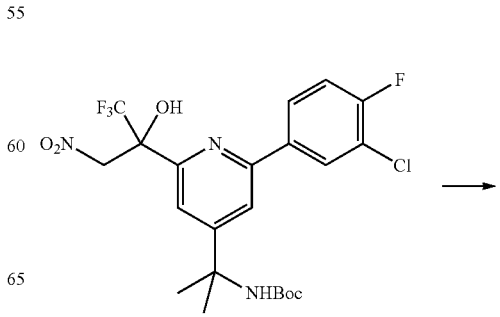

449
-continued
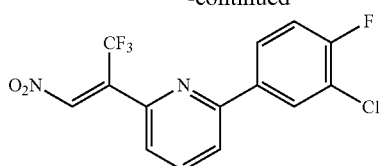
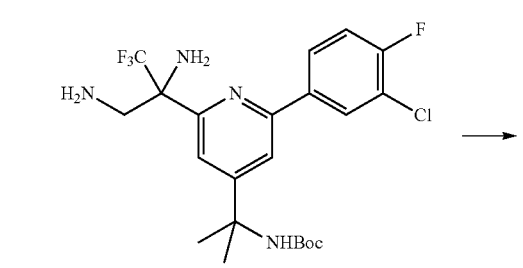
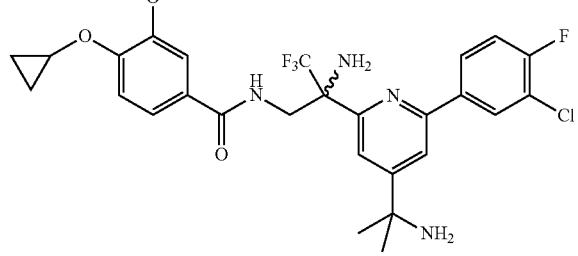
504
Compound 504 (white solid, 49 mg) was prepared following the general procedure for preparing 503 by using 503-1. +ESI-MS: m/z 581.2 [M+H]$^+$.
450
Example 289
Preparation of Compound 505
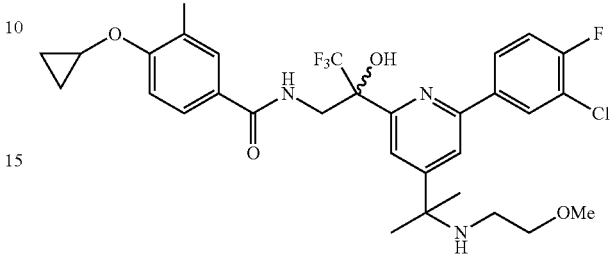
505
Compound 505 (white solid, 9 mg) was prepared following the general procedure for preparing 500 by using 314 and 1-bromo-2-methoxyethane as starting material. +ESI-MS: m/z 640.1 [M+H]$^+$.
Example 290
Preparation of Compound 508
314 ⟶
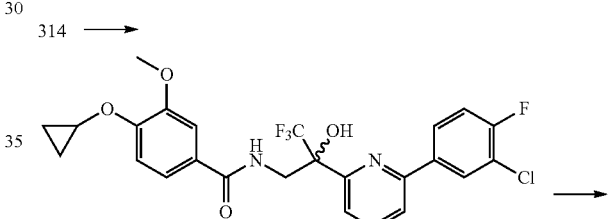
508-1
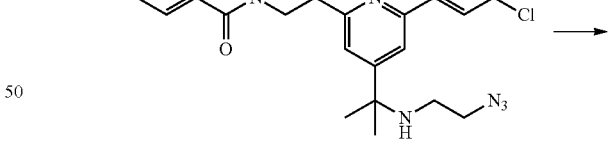
508-2
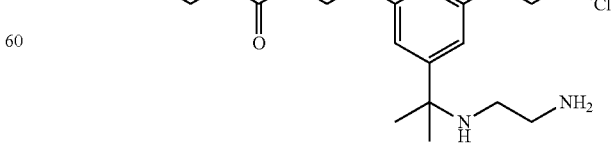
508

To a solution of 314 (290 mg, 0.5 mmol) in THF (5 mL) was added 2-chloroacetaldehyde (0.5 g, 40% in H₂O) at r.t. The mixture was stirred for 30 mins and NaBH₃CN (160 mg, 2.5 mmol) was added. The mixture was stirred at r.t. for 30 mins. The reaction was quenched with H₂O and extracted with EA (10 mL×3). The combined organic layers were washed with brine, dried over anhydrous Na₂SO₄ and concentrated to dryness. The residue was purified by column chromatography using PE:EA=1:1 as the eluent to give 508-1 as a solid (210 mg, 65.4%).

To a solution of 508-1 (210 mg, 0.33 mmol) in DMSO (5 mL) was added NaN₃ (60 mg, 0.92 mmol) at r.t. The mixture was stirred at 60° C. for 30 mins. The mixture was cooled to r.t. and diluted with H₂O and EA (10 mL×3). The combined organic layers were washed with brine, dried over anhydrous Na₂SO₄ and concentrated to give crude 508-2 (190 mg) as a pale yellow solid, which was used directly without purification. +ESI-MS: m/z 651.1 [M+H]⁺.

To a solution of 508-2 (190 mg, 0.29 mmol) in MeOH (15 mL) was added Pd/C (0.2 g) under N₂ at r.t. The suspension was degassed under vacuum and purged with H₂ for several times. The mixture was stirred under H₂ balloon for 30 mins at r.t. The mixture was filtered through a pad of Celite, and the filtrate was concentrated under reduced pressure. The residue was purified by prep-HPLC to give 508 as a white solid (101 mg, 55.5%). +ESI-MS: m/z 625.0 [M+H]⁺.

Example 291

Preparation of Compound 515

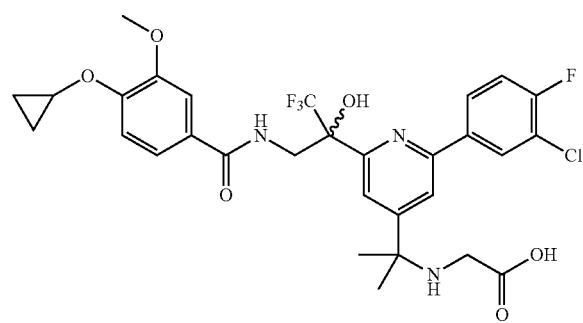

515

To a solution of 500 (180 mg, 0.28 mmol) in MeOH (5 ml) was added a solution of NaOH (50 mg, 1.25 mmol) in H₂O (5 mL) at r.t. The mixture was stirred at 60° C. for 1 h. MeOH was evaporated, and the aqueous phase was acidified to pH=1 by addition of 1 N HCl solution. The solution was extracted with EA (10 mL×3). The combined organic layers were washed with brine, dried over anhydrous Na₂SO₄ and concentrated at low pressure. The residue was purified by prep-HPLC to give 515 as a white solid (80 mg, 45.0%). +ESI-MS: m/z 640.0 [M+H]⁺.

Example 292

Preparation of Compound 516

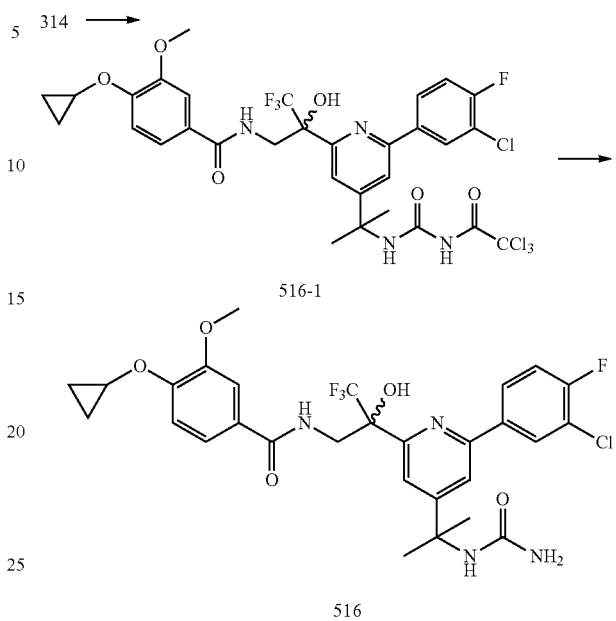

To a solution of 314 (100 mg, 0.17 mmol) in DCM (2 mL) was added CCl₃CONCO (36 mg, 0.189 mmol) at 0° C. The solution was stirred for 20 mins. The solution was diluted with DCM (10 mL) and H₂O (10 mL). The organic phase was separated and concentrated under reduced pressure to give crude 516-1 (78 mg, 60.0%), which was used directly without purification.

To a solution of 516-1 (78 mg, crude) in MeOH (1 mL) was added sat. NaHCO₃ solution (1 mL) and stirred at r.t. for 1 h. The mixture was extracted with EA (10 mL×3). The combined organic layers were washed by brine, dried over anhydrous Na₂SO₄ and concentrated at low pressure. The residue was purified by prep-HPLC to give 516 (28 mg, 44.4%) as a white solid. +ESI-MS: m/z 625.1 [M+H]⁺.

Example 293

Preparation of Compound 517

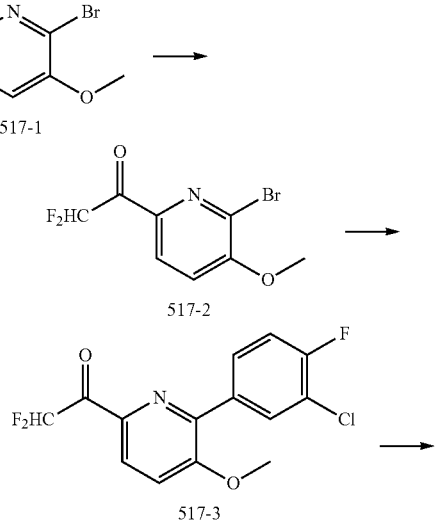

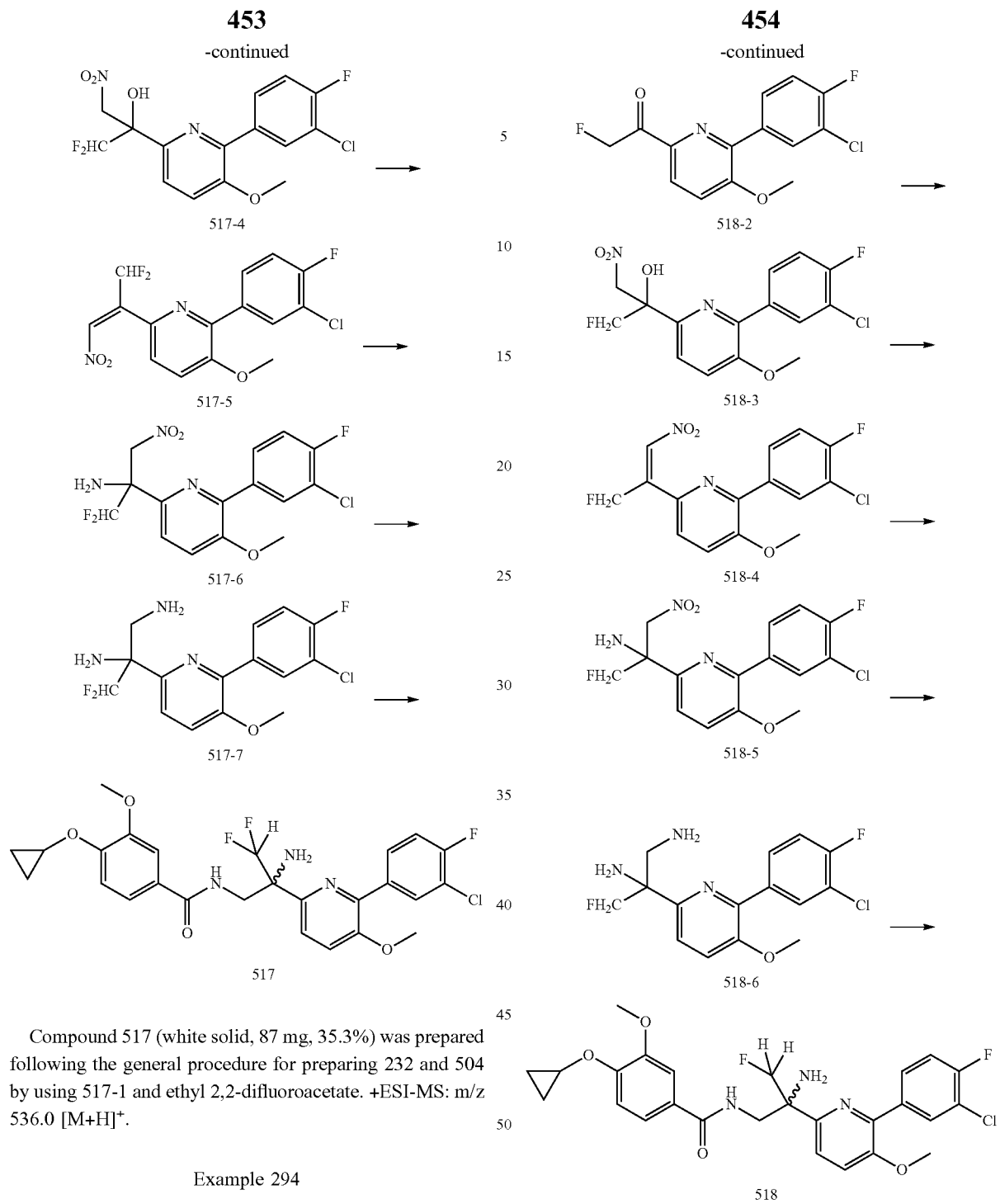

Compound 517 (white solid, 87 mg, 35.3%) was prepared following the general procedure for preparing 232 and 504 by using 517-1 and ethyl 2,2-difluoroacetate. +ESI-MS: m/z 536.0 [M+H]⁺.

Example 294

Preparation of Compound 518

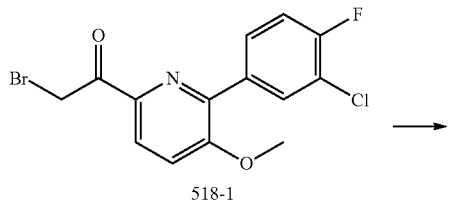

To a solution of 518-1 (3.56 g, 10.0 mmol) and CsF (3.0 g, 20.0 mmol) in MeCN (15 mL) was added 18-crown-6 (3.6 g, 13.6 mmol) at r.t. The mixture was heated to 100° C. and stirred at 100° C. for 5 h. The mixture was cooled to r.t., and the solid was removed by filtration. The filtrate was concentrated and purified by column chromatography using PE:EA=5:1 as the eluent to give 518-2 as a solid (2.01 g, 67.3%). +ESI-MS: m/z 297.9 [M+H]⁺.

Compound 518 (white solid, 21 mg, 45.3%) was prepared following the general procedure for preparing 503 by using 518-2. +ESI-MS: m/z 518.0 [M+H]⁺.

Example 295

Preparation of Compound 525

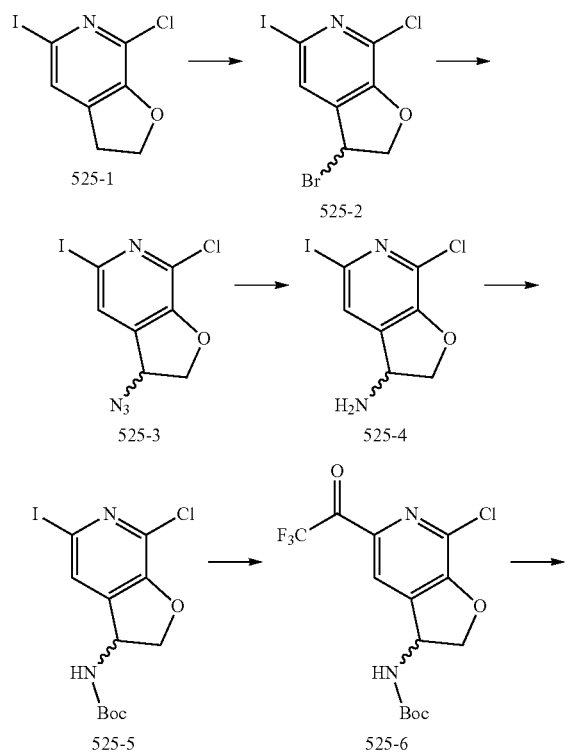

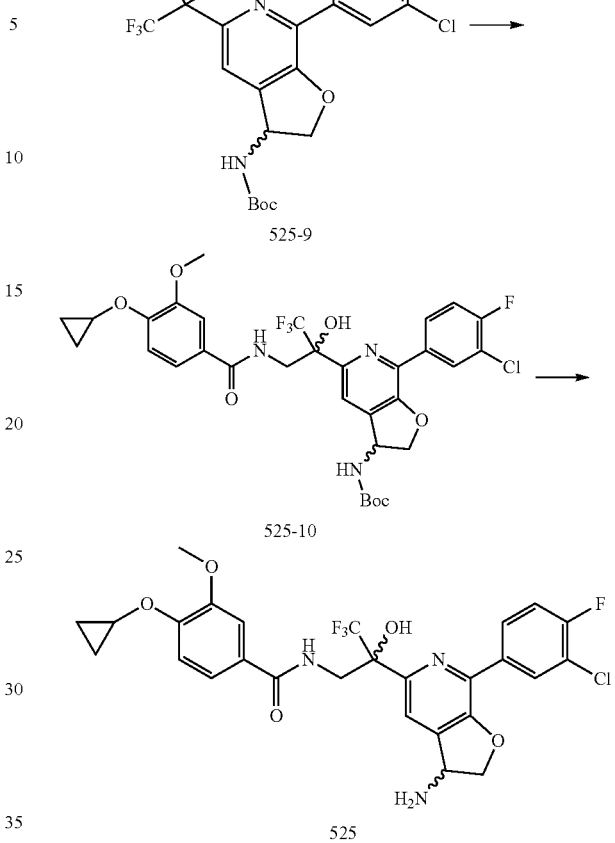

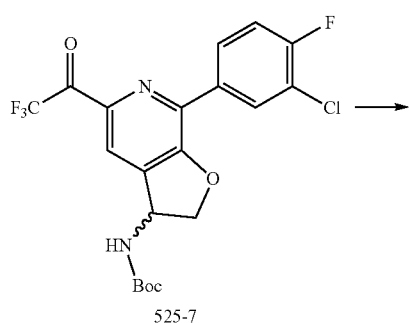

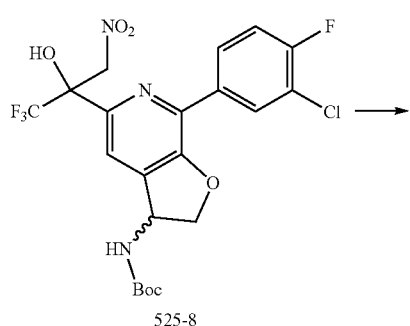

To a solution of 525-1 (2.8 g, 10.0 mmol) and AIBN (168 mg, 1.0 mmol) in CCl$_4$ (20 mL) was added NBS (1.9 g, 10.7 mmol) at r.t. The mixture was heated to 70° C. and stirred for 3 h. The mixture was cooled to r.t. and concentrated under reduced pressure. The residue was purified by column chromatography using PE:EA=15:1 as the eluent to give 525-2 as a solid (2.5 g, 69.8%). +ESI-MS: m/z 359.9 [M+H]$^+$.

To a solution of 525-2 (2.5 g, 7.0 mmol) in DMSO (15 mL) was added NaN$_3$ (1.1 g, 16.9 mmol) at r.t. The reaction was heated to 60° C. and stirred for 1 h. The reaction was cooled to r.t. The mixture was diluted with H$_2$O and extracted with EA (60 mL×3). The organic layers were dried over anhydrous Na$_2$SO$_4$, and concentrated under reduced pressure. The residue was purified by column chromatography using PE:EA=1:1 as the eluent to give 525-3 as a solid (1.8 g, 81.8%). +ESI-MS: m/z 322.8 [M+H]$^+$.

To a solution of 525-3 (1.8 g, 5.6 mmol) in MeOH (15 mL) was added SnCl$_2$.2H$_2$O (2.5 g, 11.1 mmol) at r.t. The mixture was stirred for 1 h with TLC monitoring. After 525-3 was consumed, the reaction was quenched with sat. NaHCO$_3$ and extracted with EA (30 mL×2). The combined organic solution was dried over anhydrous Na$_2$SO$_4$, and concentrated under reduced pressure. Crude 525-4 (1.0 g) was used directly without further purification.

To a solution of 525-4 (1.0 g, 3.4 mmol) in DCM (15 mL) was added Boc$_2$O (1.4 g, 6.4 mmol) at r.t. The mixture was stirred at r.t. for 3 h and then concentrated to dryness. The residue was purified by chromatography using PE:EA=5:1 as the eluent to give 525-5 as a solid (0.8 g, 61.5%).

To a solution of 525-5 (0.8 g, 2.0 mmol) and CF$_3$COOEt (1.7 g, 11.9 mmol) in THF (10 mL) was added isopropylmagnesium chloride (4 mL, 2.0 M in THF) dropwise at r.t. under N$_2$. The mixture was stirred at r.t. for 30 mins. The reaction was quenched with aq. NH$_4$Cl and extracted with EA (20 mL×3). The combined organic solution was dried over anhydrous Na$_2$SO$_4$, and concentrated under reduced pressure. Crude 525-6 (0.6 g) was used directly without purification.

Compound 525 (white solid, 130 mg) was prepared following the general procedure for preparing 272 using 525-6. +ESI-MS: m/z 582.1 [M+H]$^+$.

Example 296

Preparation of Compound 526

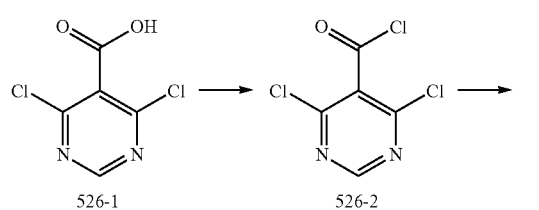

526-1          526-2

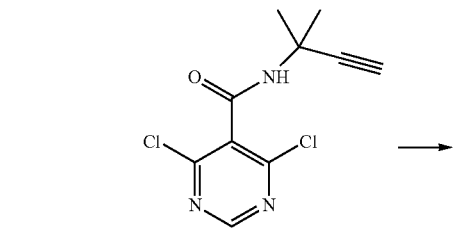

526-3

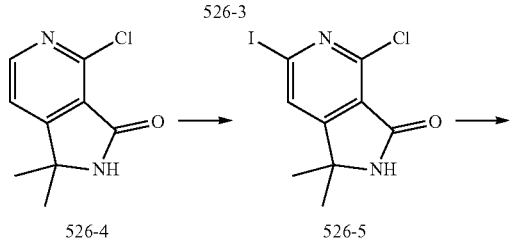

526-4          526-5

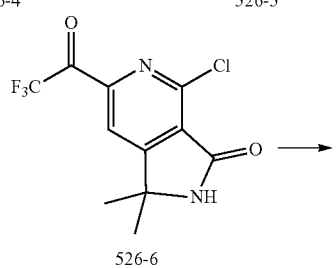

526-6

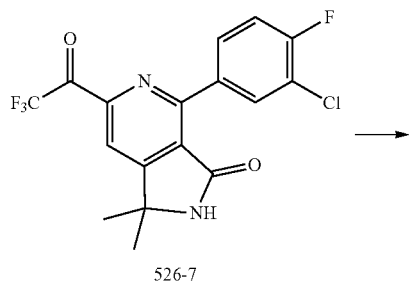

526-7

-continued

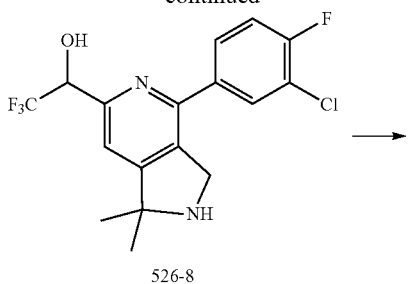

526-8

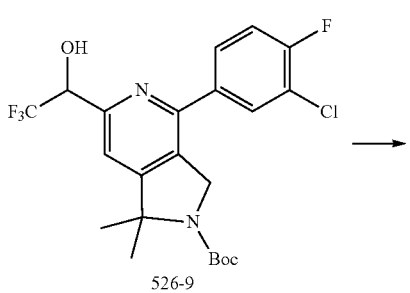

526-9

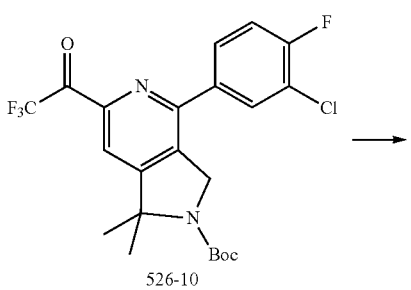

526-10

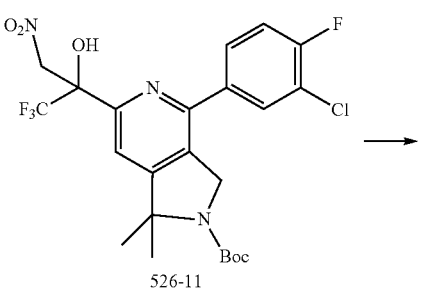

526-11

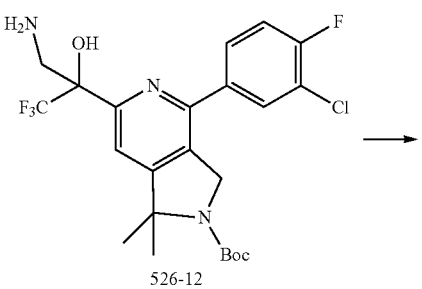

526-12

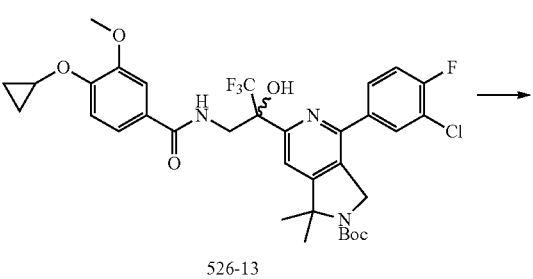

526-13

-continued

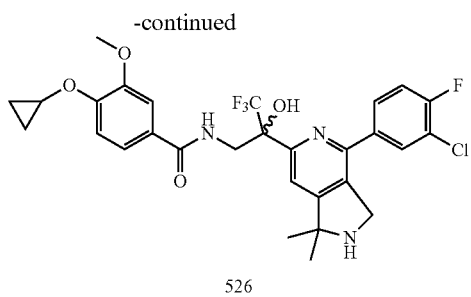

526

To a solution of 526-1 (10 g, 0.05 mol) in anhydrous DCM (100 mL) was added oxalyl dichloride (12.7 g, 0.1 mmol) and several drops of DMF. The mixture was stirred for 1 h and evaporated under reduced pressure to give 526-2.

To a solution of 2-methylbut-3-yn-2-amine (4.4 g, 52.5 mmol) and $Et_3N$ (10.1 g, 0.1 mmol) in anhydrous DCM (100 mL) was added a solution of crude 526-2 in DCM (50 mL) dropwise at r.t. The solution was stirred for 1 h, washed with water and brine (50 mL), dried with anhydrous $Na_2SO_4$ and concentrated to give 526-3. The residue was used directly without further purification.

526-3 (2.58 g, 10 mmol) in $PhNO_2$ (10 mL) was put in a microwave tube. The solution was heated to 210° C. by microwave irradiation and stirred for 5 mins. The reaction was cooled to r.t. and concentrated at low pressure. The residue was purified by column chromatography using PE:EA=10:1~1:1 to give 526-4 (610 mg, 31.1%). +ESI-MS: m/z 197.1 $[M+H]^+$.

To a stirring solution of DMAE (1.068 g, 12 mmol) in THF (10 mL) was added n-BuLi (10 mL, 25 mmol) at −78° C. After 5 mins, a solution of 526-4 (588 mg, 3 mmol) in anhydrous THF (3 mL) was added dropwise at −78° C. The mixture was stirred for 10 mins and a solution of $I_2$ (6.35 g, 25 mmol) in THF was added dropwise at −78° C. After 20 mins, the reaction was quenched with sat. aq. $Na_2SO_3$. The solution was extracted with EA (50 mL×2). The organic phase was washed with brine and dried over anhydrous $Na_2SO_4$. The organic phase was concentrated at low pressure, and the residue was purified by column chromatography using PE:EA=1:1 as the eluent to give 526-5 (650 mg, 51.0%). +ESI-MS: m/z 322.9 $[M+H]^+$.

To a solution of 526-5 (642 mg, 2 mmol) and $CF_3COOEt$ (468 mg, 4 mmol) in anhydrous THF (5 mL) was added iPrMgCl (3 mL, 6 mmol) dropwise at r.t. The solution was stirred for 10 mins. The reaction was quenched with water and extracted with EA (20 mL×2). The combined organic phase was washed with brine, dried over anhydrous $Na_2SO_4$, and concentrated to dryness. The residue was purified by column chromatography using PE:EA=1:1 as the eluent to give 526-6 (302 mg, 51.3%).

To a solution of 526-6 (300 mg, 1.03 mmol) in $DME/H_2O$ (4 mL/1 mL), $Cs_2CO_3$ (502 mg, 1.55 mmol), (3-chloro-4-fluorophenyl)boronic acid (270 mg, 1.87 mmol) and $Pd(dppf)Cl_2$ (50 mg, 65 mmol) were added at r.t. under $N_2$. The vial was sealed and heated to 100° C. for 40 mins by microwave irradiation. After cooling to r.t., the mixture was diluted with EA (10 mL) and brine (10 mL). The aqueous layer was extracted with EA (10 mL×2). The combined organic layers were washed with brine (10 mL), dried over anhydrous $Na_2SO_4$, and concentrated under reduced pressure. The residue was purified by column chromatography using PE:EA=1:1 as the eluent to give 526-7 (310 mg, 73.7%). +ESI-MS: m/z 386.9 $[M+H]^+$.

To a solution of 526-7 (310 mg, 0.76 mmol) in dry THF (5 mL) was added $BH_3.Me_2S$ (1 mL, 10 mmol) at r.t. The solution was stirred in a pre-heated 80° C. oil bath for 2 h. The solution was cooled to r.t., and the reaction was quenched with $H_2O$. The mixture was extracted with EA (20 mL×2). The combined organic phase was washed with brine, dried over anhydrous $Na_2SO_4$ and concentrated under reduced pressure. The residue was purified by column chromatography using EA as the eluent to give 526-8 (140 mg, 49.2%) as a gray solid.

To a solution of 526-8 (140 mg, 0.37 mmol) in toluene (3 mL) was added $Et_3N$ (75 mg, 0.74 mmol) and $Boc_2O$ (87 mg, 0.44 mmol) at r.t. The solution was stirred in a pre-heated 100° C. oil bath for 3 h. The solution was cooled to r.t. and diluted with EA (20 mL) and water (20 mL). The organic phase was washed with brine, dried over anhydrous $Na_2SO_4$ and concentrated under reduced pressure. The residue was purified by column chromatography using PE:EA=5:1 as the eluent to give 526-9 (90 mg, 51.0%). +ESI-MS: m/z 474.9 $[M+H]^+$.

To a stirred solution of 526-9 (90 mg, 0.189 mmol) in DMSO (2 mL) was added IBX (212 mg, 0.75 mmol) in one portion, and stirred at 40° C. for 2 h. The solution was poured into aq. $NaHCO_3$ and extracted with EA (10 mL×2). The combined organic phase was washed with brine, dried over anhydrous $Na_2SO_4$ and concentrated under reduced pressure. The residue was purified by column chromatography using 0~30% EA in PE as the eluent to give 526-10 (60 mg, 66.7%).

Compound 526 (white solid, 4 mg, 13.7%) was prepared following the general procedure for preparing 272 using 526-10. +ESI-MS: m/z 594.1 $[M+H]^+$.

Example 297

Preparation of Compound 528

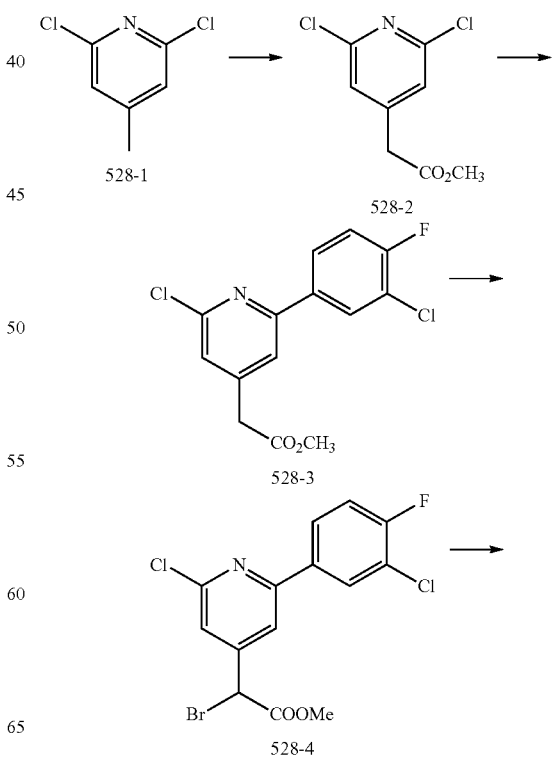

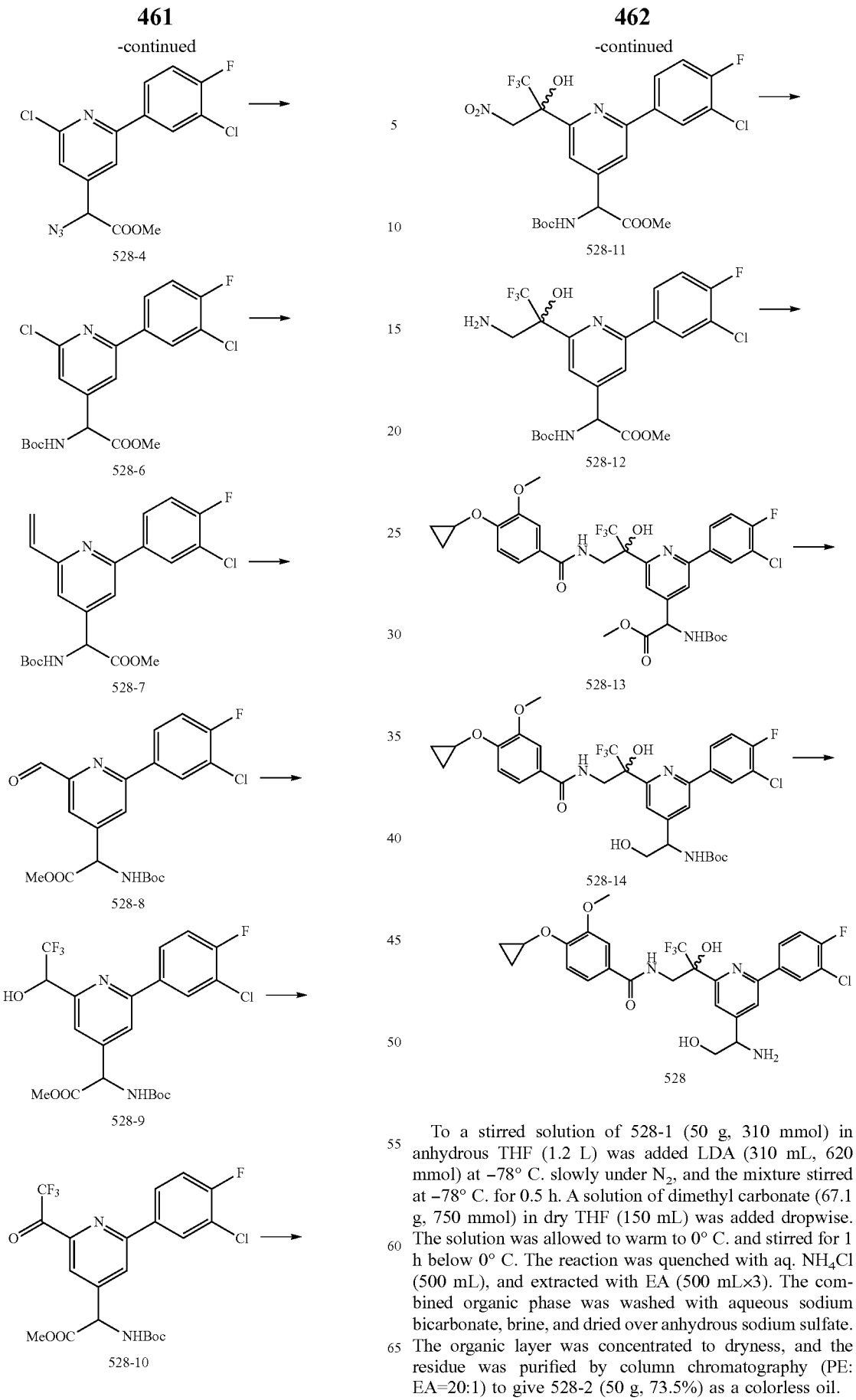

To a stirred solution of 528-1 (50 g, 310 mmol) in anhydrous THF (1.2 L) was added LDA (310 mL, 620 mmol) at −78° C. slowly under N$_2$, and the mixture stirred at −78° C. for 0.5 h. A solution of dimethyl carbonate (67.1 g, 750 mmol) in dry THF (150 mL) was added dropwise. The solution was allowed to warm to 0° C. and stirred for 1 h below 0° C. The reaction was quenched with aq. NH$_4$Cl (500 mL), and extracted with EA (500 mL×3). The combined organic phase was washed with aqueous sodium bicarbonate, brine, and dried over anhydrous sodium sulfate. The organic layer was concentrated to dryness, and the residue was purified by column chromatography (PE: EA=20:1) to give 528-2 (50 g, 73.5%) as a colorless oil.

To a solution of crude 528-2 (50 g, 230 mmol) in dioxane:H$_2$O (6:1) (1 L) was added (3-chloro-4-fluorophenyl) boronic acid (40 g, 230 mmol), Cs$_2$CO$_3$ (223.3 g, 680 mmol) and Pd(dppf)Cl$_2$ (16.8 g, 23 mmol) under N$_2$. The mixture was degassed for 3 times and refilled with N$_2$. The reaction was stirred at 80° C. in a pre-heated oil bath for 4 h. After cooling to r.t., the mixture was diluted with water (1.5 L) and extracted with EA (1 L×3). The combined organic layers were washed with brine, dried over anhydrous sodium sulfate, and concentrated under reduced pressure. The residue was purified by column chromatography (PE: EA=20:1~15:1) to yield 528-3 (42 g, 58.7%) as a light yellow solid.

To a solution of 528-3 (9.39 g, 30.00 mmol) in HOAc (100 mL) was added Br$_2$ (5.28 g, 33 mmol) dropwise at r.t. The mixture was heated at 60° C. for 5 h. The reaction was cooled to r.t. and concentrated under reduced pressure to dryness. The residue was used directly without further purification. +ESI-MS: m/z 393.7 [M+H]$^+$.

To a solution of crude 528-4 (10.0 g) in MeOH (100 mL) was added NaN$_3$ (3.3 g, 50.8 mmol) at 25° C., and the mixture was stirred at 25° C. for 1 h. The mixture was diluted with H$_2$O (150 mL), and extracted with and EA (150 mL×3). The combined organic layers were washed with brine, dried over anhydrous Na$_2$SO$_4$ and concentrated under reduced pressure. The residue was purified by column chromatography using PE:EA =20:1~5:1 as the eluent to give 528-5 (8.02 g, 88%).

To a solution of 528-5 (8.02 g, 22.6 mmol) and Boc$_2$O (14.8 g, 67.77 mmol) in MeOH (100 mL) was added Pd/C (3.0 g, 10%) under N$_2$. The suspension was degassed and purged with H$_2$ for several times. The mixture was stirred under H$_2$ balloon at 25° C. for 3 h. TLC showed that the starting material was consumed completely. The mixture was filtered through a pad of Celite, and the filtrate was concentrated under reduced pressure. The residue was purified by column chromatography using PE:EA=50:1~5:1 to give 528-6 (5.5 g). +ESI-MS: m/z 428.9 [M+H]$^+$.

528-13 (white solid, 80 mg) was prepared following the general procedure for preparing 272 using 528-6. +ESI-MS: m/z 712.1 [M+H]$^+$.

To a solution of 528-13 (80.00 mg crude) in a co-solvent of MeOH (5 mL) and THF (5 mL) was added NaBH$_4$ (40 mg, 1.05 mmol), and the mixture was stirred at 25° C. for 2 h. The reaction was quenched by H$_2$O and extracted by EA (10 mL×3). The combined organic layers were washed with brine, dried over anhydrous Na$_2$SO$_4$ and concentrated at low pressure. The residue was purified by prep-TLC to give 528-14 (51 mg). +ESI-MS: m/z 684.1 [M+H]$^+$.

Compound 528 (white solid, 18 mg, 39.9%) was prepared following the general procedure for preparing 272 using 528-14. +ESI-MS: m/z 584.0 [M+H]$^+$.

Example 298

Preparation of Compound 529

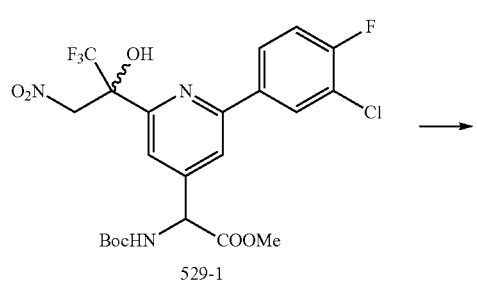
529-1

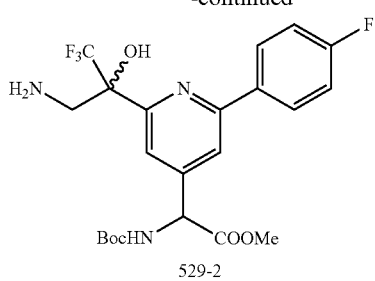
529-2

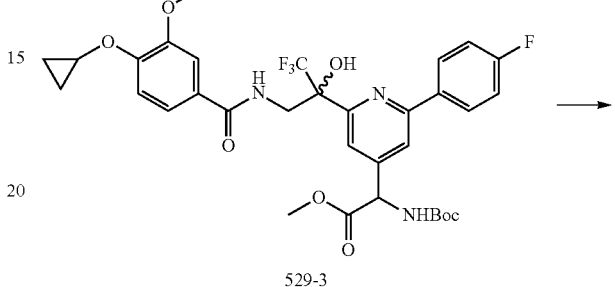
529-3

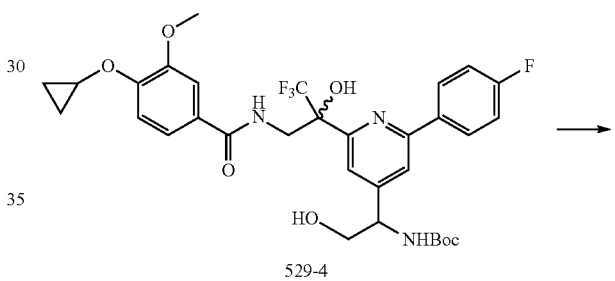
529-4

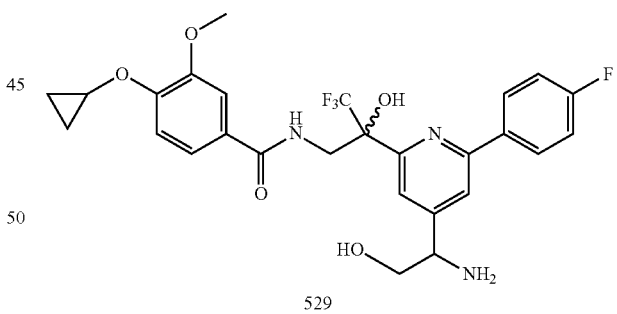
529

To a solution of 529-1 (150.00 mg) in MeOH (50 mL) was added Ra—Ni (0.15 g) under N$_2$. The suspension was degassed and purged with H$_2$ for several times. The mixture was stirred under H$_2$ balloon at 25° C. for 2H. TLC (PE: EA=1:1) showed that the starting material was consumed. The mixture was filtered, and the filtrate was concentrated to give 529-2 (90 mg, crude), which was used directly without further purification.

Compound 529 (white solid, 13 mg) was prepared following the general procedure for preparing 528 by using 529-2. +ESI-MS: m/z 550.1 [M+H]$^+$.

Example 299
Preparation of Compound 532
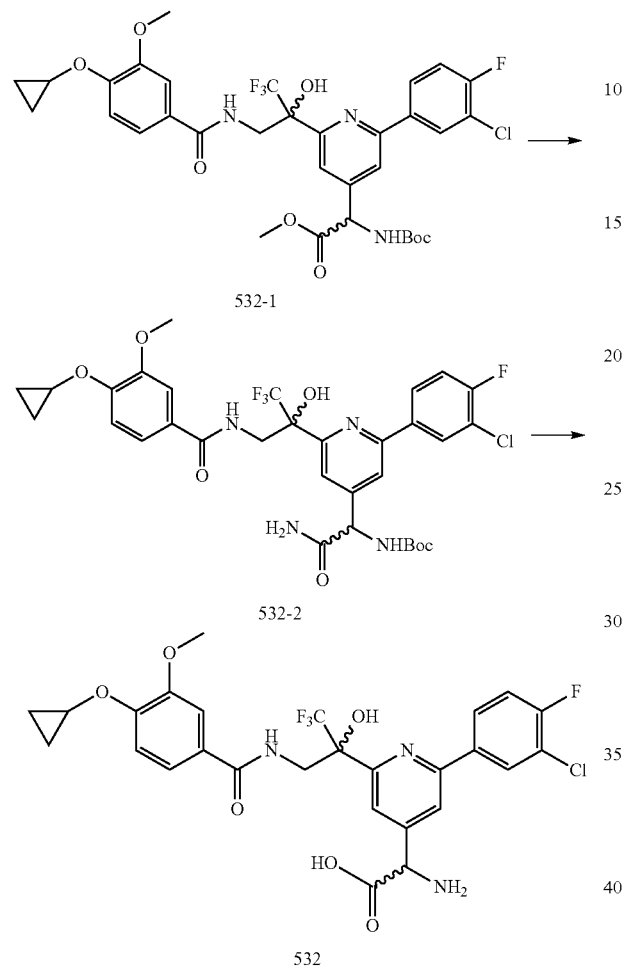
Compound 532 (white solid, 13 mg) was prepared following the general procedure for preparing 501 and 272 by using 532-1. +ESI-MS: m/z 597.1 [M+H]$^+$.
Example 300
Preparation of Compound 533
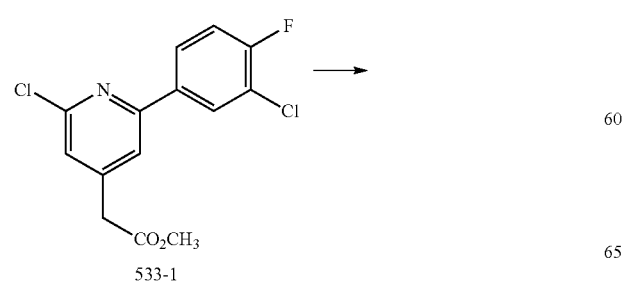
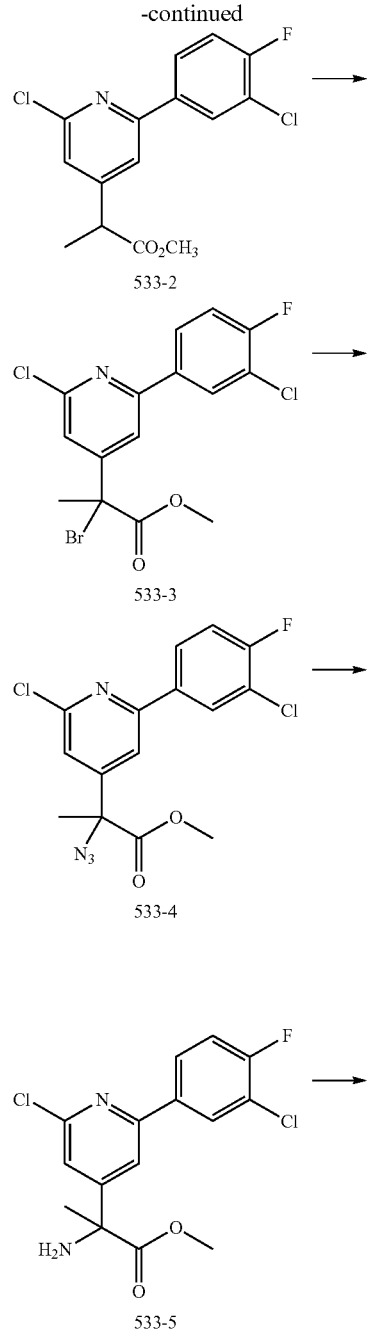

-continued

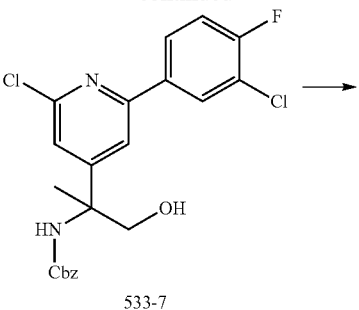
533-7

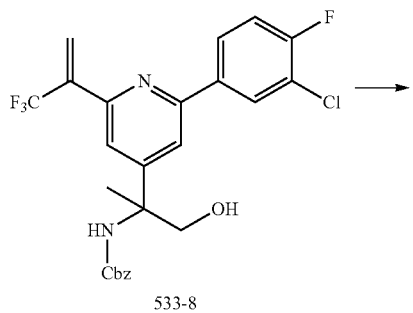
533-8

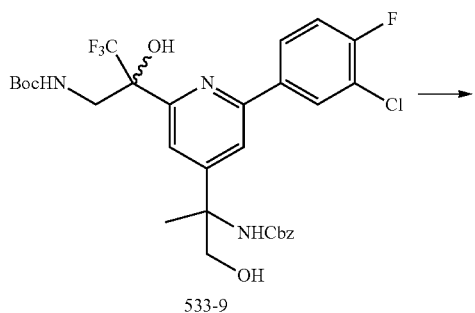
533-9

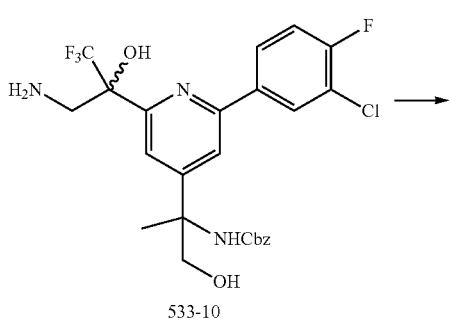
533-10

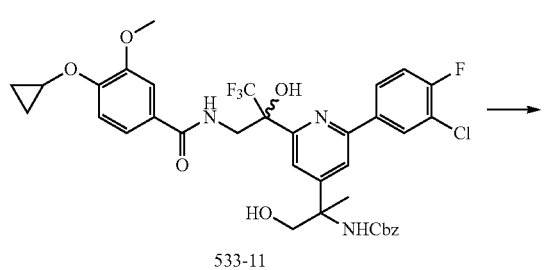
533-11

-continued

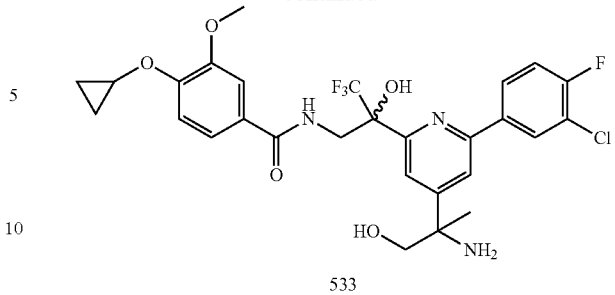
533

To a solution of 533-1 (10 g, 31.9 mmol) in anhydrous THF (100 mL) was added LiHMDS (63.9 mL, 63.9 mmol) dropwise, and stirred at −78° C. for 30 mins. A solution of MeI (9.07 g, 63.9 mmol) in dry THF (50 mL) was added dropwise. The mixture was warmed to 0° C. and stirred at 0° C. for 1 h. The reaction was quenched with water (100 mL) and extracted with EA (150 mL×3). The combined organic layers were washed with brine, dried over anhydrous sodium sulfate, and concentrated in vacuum to dryness. The residue was purified by column chromatography (PE:EA=10:1) to yield 533-2 (3.5 g, 32%) as a light yellow solid.

533-4 (crude, yellow oil) was prepared following the general procedure for preparing 501 by using 2. +ESI-MS: m/z 369.0 [M+H]+.

To a solution of 533-4 (500.00 mg, 1.35 mmol) in MeOH (30 mL) was added $SnCl_2 \cdot 2H_2O$ (760.40 mg, 3.39 mmol) in one portion at r.t. under $N_2$, and the mixture was stirred for 2 h. TLC showed that the reaction was completed. The mixture was diluted with water (20 mL). The solution was extracted with EA (30 mL×3). The combined organic phase was washed with brine, dried over anhydrous $Na_2SO_4$, and concentrated under reduced pressure. The residue was used in the next step without purification.

To a solution of 533-5 (0.5 g, 1.46 mmol) and CbzCl (745.56 mg, 4.37 mmol) in DCM (15 mL) was added $NaHCO_3$ (489.61 mg, 5.83 mmol) in one portion, and the mixture was stirred at r.t. for 1 h. The solution was poured into ice-water (15 mL) and stirred for 20 mins. The aqueous phase was extracted with EA (40 mL×3). The combined organic phase was washed with brine, dried over anhydrous $Na_2SO_4$, filtered and concentrated under reduced pressure. The residue was purified by column chromatography (PE:EA=30:1~10:1) to afford 533-6 (0.4 g) as a yellow solid. +ESI-MS: m/z 477.1 [M+H]+.

To a solution of 533-6 (0.4 g, 0.84 mol) in THF (40 mL) was added $LiBH_4$ (55 mg, 2.5 mmol) in one portion, and the mixture stirred at r.t. for 1 h. TLC showed that the reaction was completed. The mixture was poured into ice-water (15 mL) and stirred for 20 mins. The aqueous phase was extracted with EA (40 mL×3). The combined organic phase was washed with brine, dried over anhydrous $Na_2SO_4$, filtered and concentrated at low pressure. The residue was purified by column chromatography (PE:EA=30:1~2:1) to afford 533-7 (320.00 mg, 85%) as a yellow solid. +ESI-MS: m/z 448.6 [M+H]+.

To a solution of 533-7 (320 mg, 0.71 mmol) in DME (5 mL) and $H_2O$ (1 mL) were added 4,4,6-trimethyl-2-[1-(trifluoromethyl)vinyl]-1,3,2-dioxaborinane (320 mg, 1.42 mmol), $Cs_2CO_3$ (0.7 g, 2.13 mmol), and $Pd(dppf)Cl_2$ (52 mg, 0.07 mol) under $N_2$. The reaction flask was sealed and stirred at 110° C. by microwave irradiation for 1 h. The reaction was cooled to r.t., and diluted with EA and water. The organic phase was washed with brine, dried over anhydrous Na$_2$SO$_4$ and concentrated under reduced pressure. The residue was purified by column chromatography using 3-20% of EA in PE as the eluent to give 533-8 (220 mg, 60%). +ESI-MS: m/z 508.9 [M+H]$^+$.

To a mixture of 533-8 (100.00 mg, 0.2 mmol) in t-BuOH (1.5 mL) and H$_2$O (0.5 mL), were added K$_2$OsO$_4$H$_2$O (11 mg, 0.06 mmol) and BocHN-OTs (113 mg, 0.39 mmol), and the mixture was stirred at r.t. overnight. The mixture was poured into ice-water, stirred for 20 mins and extracted with EA (10 mL×3). The combined organic phase was washed with brine, dried over anhydrous Na$_2$SO$_4$, filtered and concentrated under reduced pressure. The residue was purified by column chromatography using PE:EA=30:1~20:1 as the eluent to give 533-9 (50 mg, 40%) as a yellow solid. +ESI-MS: m/z 642.1 [M+H]$^+$.

To a solution of 533-9 (50.00 mg, 0.078 mmol) in DCM (2 mL) was added TFA (1 mL). The mixture was stirred at r.t. for 1 h. The solution was poured into ice-water (5 mL) and neutralized with sat. NaHCO$_3$ solution. The aqueous phase was extracted with EA (5 mL×3). The combined organic phase was washed with brine, dried over anhydrous Na$_2$SO$_4$, filtered and concentrated under reduced pressure. The residue was purified by column chromatography using EA as the eluent to give 533-10 (30.00 mg, 71%) as a yellow solid. +ESI-MS: m/z 542.1 [M+H]$^+$.

533-11 (yellow solid, 30 mg, 74%) was prepared following the general procedure for preparing 272 using 533-11. +ESI-MS: m/z 732.3 [M+H]$^+$.

To a solution of 533-11 (30 mg) in CH$_3$CN (1 mL) was added one drop of TMSI at r.t. The mixture was stirred at r.t. for 10 mins. The mixture was poured into water, neutralized with sat. NaHCO$_3$ solution and extracted with EA (10 mL×3). The combined organic layers were washed with brine, dried over anhydrous Na$_2$SO$_4$, filtered and concentrated under reduced pressure. The residue was purified by prep-HPLC to give 533 (23.00 mg) as a white solid. +ESI-MS: m/z 597.9 [M+H]$^+$.

Example 301

Preparation of Compound 534

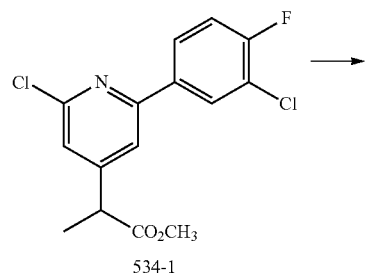

534-1

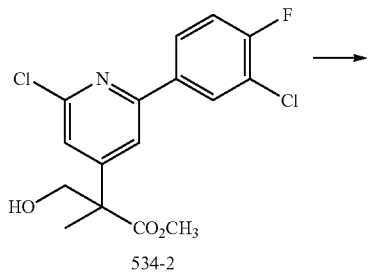

534-2

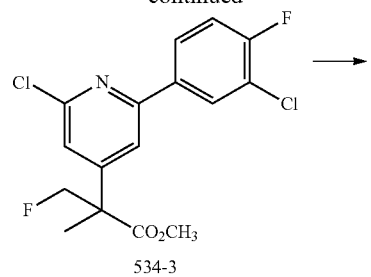

534-3

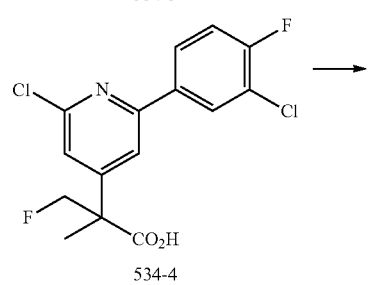

534-4

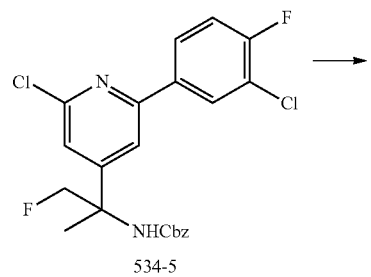

534-5

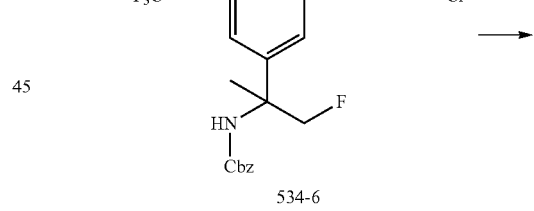

534-6

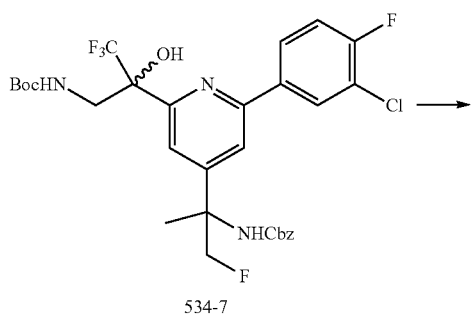

534-7

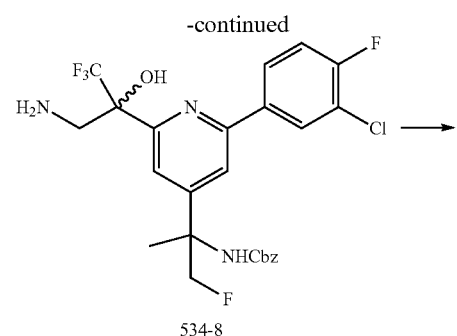

534-8

534-9

534

To a solution of 534-1 (6 g, 18.3 mmol) and TEA (18.5 g, 183 mmol) in THF (60 mL) was added aq. HCHO (15 g, 183 mmol) at 25° C. under $N_2$. The mixture was stirred at 25° C. for 2 h. TLC (PE:EA=5:1) showed that the reaction was completed. The mixture was diluted with water and extracted with EA (100 mL×3). The combined organic phase was washed with brine, dried over anhydrous $Na_2SO_4$, filtered and concentrated under reduced pressure. The residue was purified by column chromatography using PE:EA=30:1~5:1 as the eluent to afford 534-2 (5.1 g, 77%) as a white oil. +ESI-MS: m/z 358.1 [M+H]$^+$.

To a solution of 534-2 (1.76 g, 4.91 mmol) in DCM (20 mL) was added DAST (7.91 g, 49.10 mmol) dropwise at −78° C. under $N_2$. The mixture was slowly warmed to 25° C., and stirred for 12 h. TLC (PE:EA=5:1) showed that the reaction was completed. The mixture was cooled to 0° C. and quenched with sat. $NaHCO_3$ solution. The aqueous phase was extracted with EA (20 mL×3). The combined organic phase was washed with brine, dried over anhydrous $Na_2SO_4$, filtered and concentrated at low pressure. The residue was purified by column chromatography using PE:EA=100:1~60:1 as the eluent to afford 534-3 (0.6 g, 34%) as a white oil. +ESI-MS: m/z 360.1 [M+H]$^+$.

To a solution of 534-3 (590 mg, 1.64 mmol) in MeOH (6 mL) was added a solution of NaOH (260 mg, 6.6 mmol) in $H_2O$ (6 mL) at r.t. The mixture was heated to 60° C. and stirred for 2 h. The mixture was cooled to r.t., and the organic solvent was removed under reduced pressure. The pH of aqueous phase was adjusted to ~3 using 2M HCl and extracted with EA (30 mL×3). The combined organic layers were washed with brine, dried over anhydrous $Na_2SO_4$, filtered and concentrated in vacuum to give 534-4 (503 mg, 88%) as a white solid.

To a solution of 534-4 (438 mg, 1.27 mmol), DIPEA (655 mg, 5.07 mmol) and BnOH (274 mg, 2.53 mmol) in toluene (5 mL) was added DPPA (698 mg, 2.54 mmol) at r.t. under $N_2$. The mixture was heated to 80° C. and stirred for 12 h. The mixture was cooled to r.t. and concentrated under reduced pressure. The residue was purified by column chromatography using PE:EA=30:1~5:1 as the eluent to afford 534-5 (450.00 mg, 78.52%) as a white solid.

Compound 534 (white solid, 21 mg, 45.9%) was prepared following the general procedure for preparing 533 using 534-5. +ESI-MS: m/z 600.0 [M+H]$^+$.

Example 302

Preparation of Compound 535

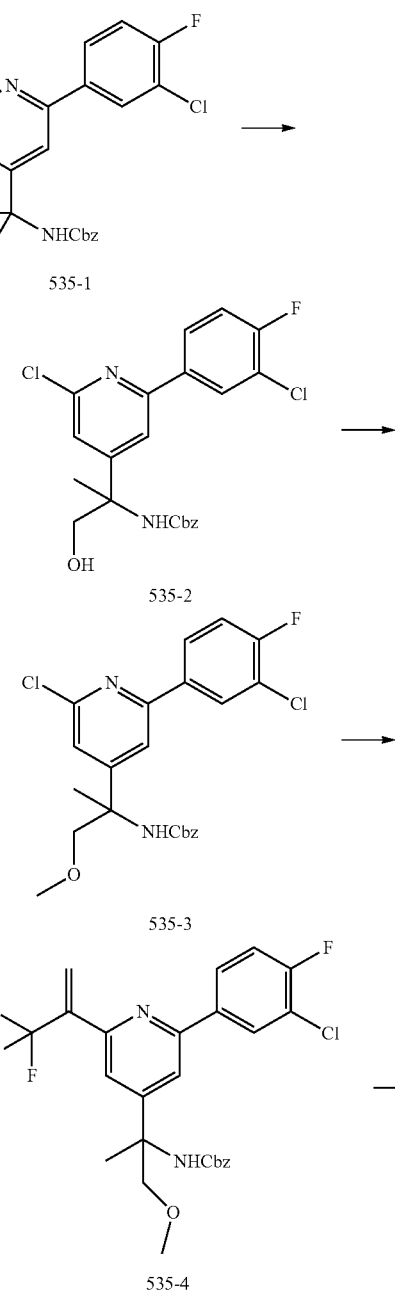

535-1

535-2

535-3

535-4

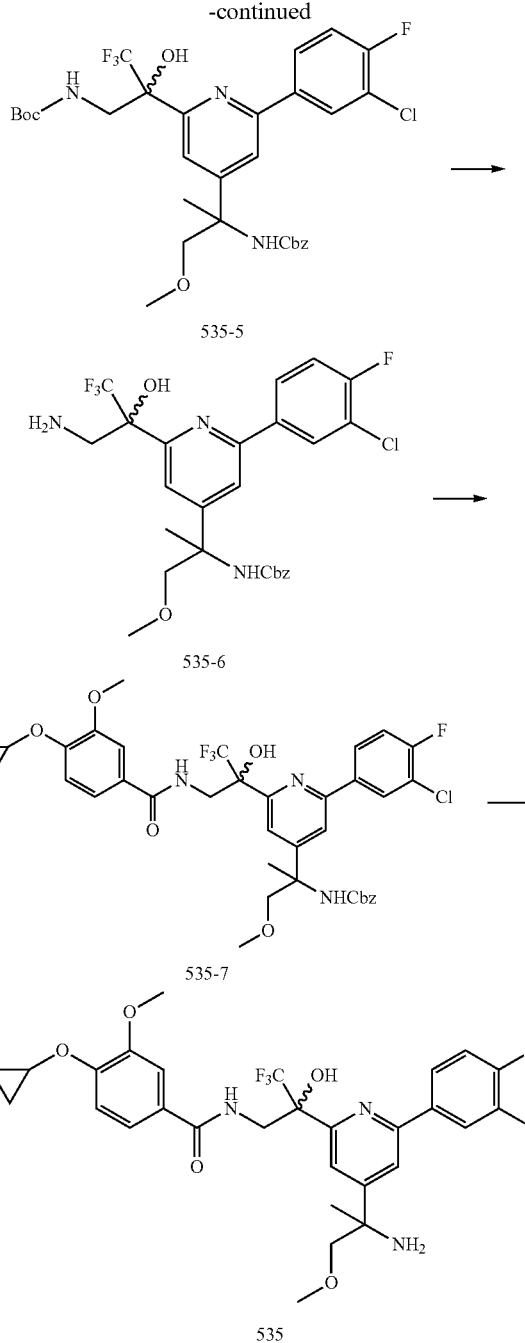

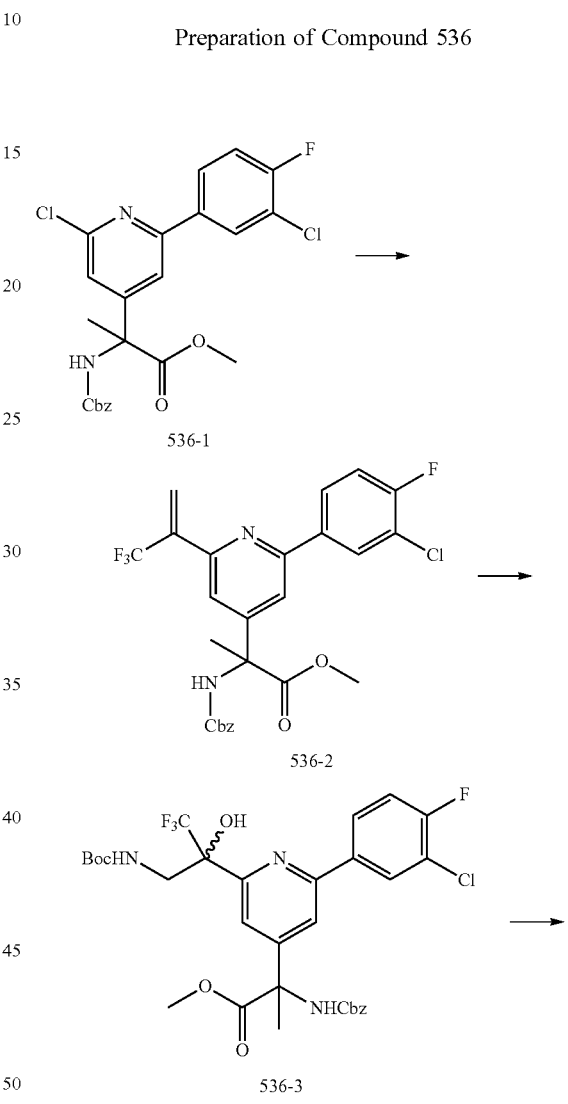

chromatography using PE:EA=10:1 as the eluent to give 535-3 (450 mg, 31%). +ESI-MS: m/z 463.1 [M+H]$^+$.

Compound 535 (white solid, 11 mg, 22%) was prepared following the general procedure for preparing 533 using 535-3. +ESI-MS: m/z 612.1 [M+H]$^+$.

Example 303

Preparation of Compound 536

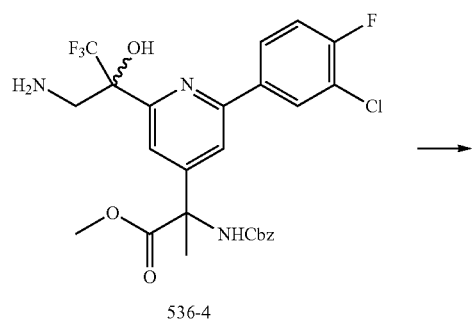

To a solution of 535-1 (2.0 g, 4.2 mmol) in MeOH (20 mL) was added NaBH$_4$ (476 mg, 12.6 mmol) at r.t. in small portions. The solution was stirred for 30 mins and quenched with H$_2$O. The mixture was extracted with EA (50 mL). The organic phase was washed with brine, dried over anhydrous Na$_2$SO$_4$, filtered and concentrated in vacuum. The residue was purified by column chromatography using PE:EA=1:1 to give 535-2 (1.6 g, 85%) as a white solid. +ESI-MS: m/z 449.1 [M+H]$^+$.

To a solution of 535-2 (1.40 g, 3.1 mmol) in THF (20 mL) were added Ag$_2$O (723 mg, 3.1 mmol) and MeI (1.77 g, 12.5 mmol) at r.t. The mixture was sealed and heated to 40° C. The reaction was stirred overnight and concentrated to dryness at low pressure. The residue was purified by column

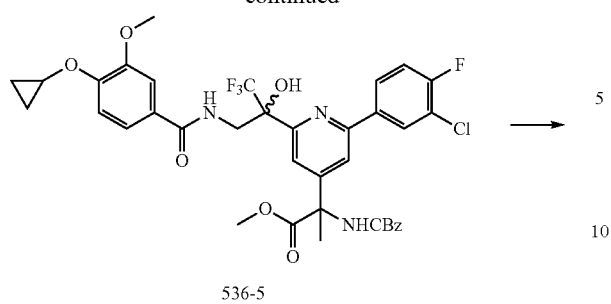
536-5
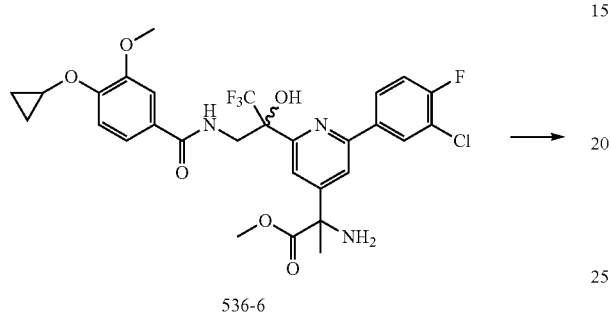
536-6
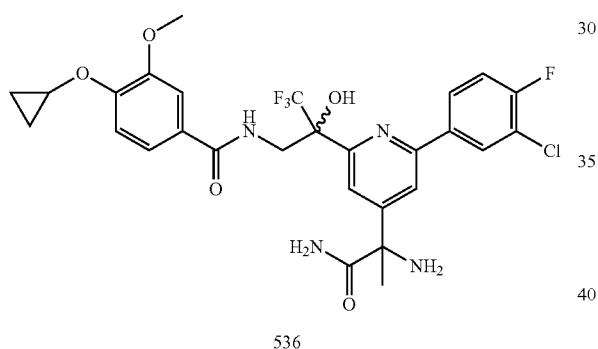
536
Compound 536 (white solid, 65 mg, 83%) was prepared following the general procedure for preparing 533 and 501 using 536-1. +ESI-MS: m/z 611.2 [M+H]$^+$.
Example 304
Preparation of Compound 537
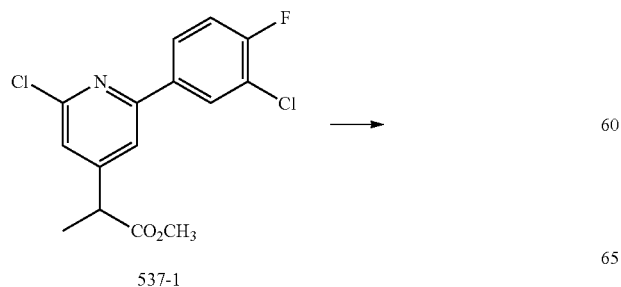
537-1
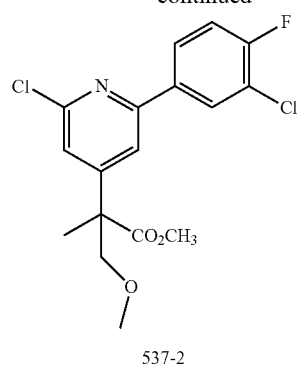
537-2
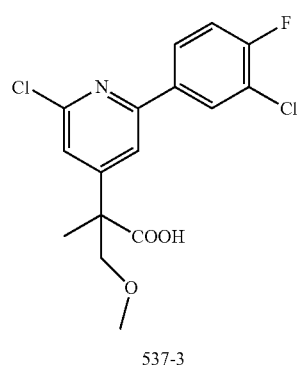
537-3
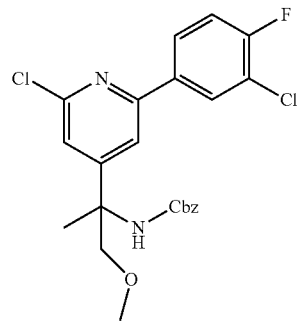
537-4
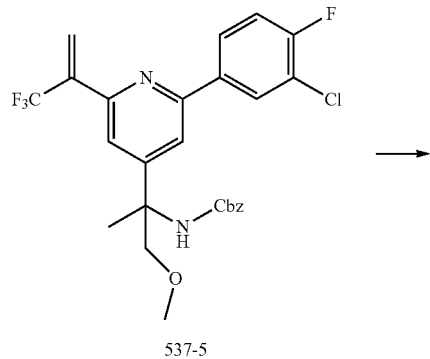
537-5

-continued

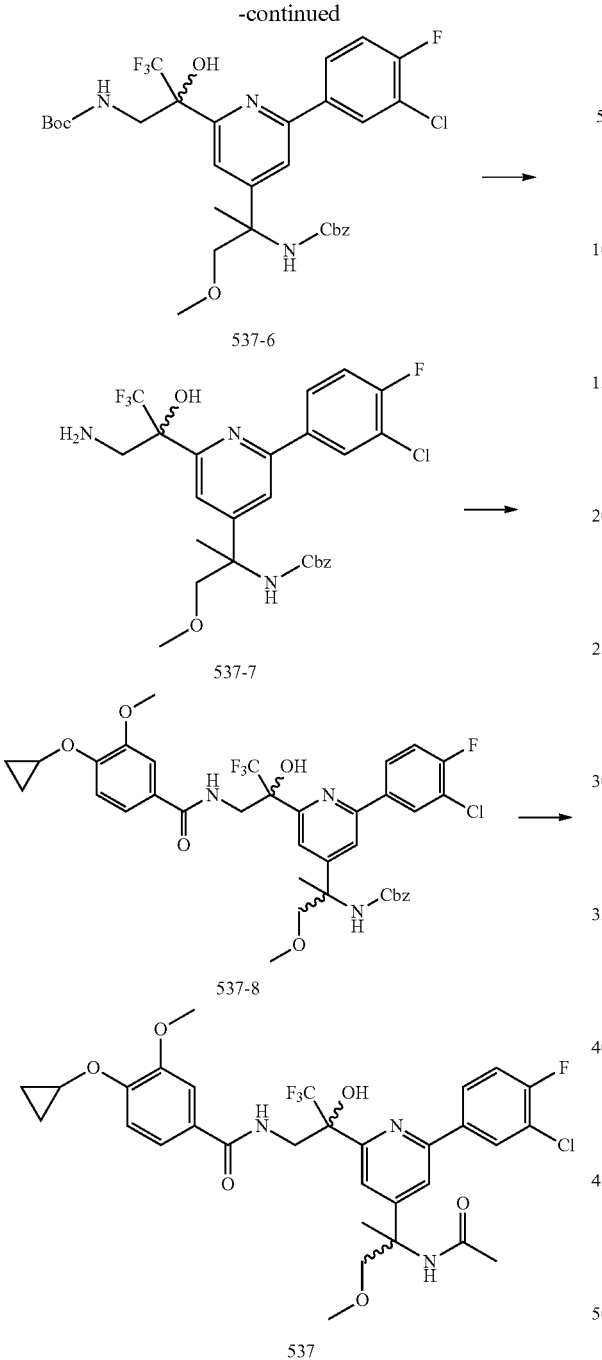

To a solution of 537-1 (0.7 g, 2.1 mmol) in THF (8 mL) was added LiHMDS (3.2 mL 1 M in THF) at −78° C. in a period of 1 minute under N$_2$. After stirring at −78° C. for 10 minutes, a solution of MOMCl (340 mg, 4.2 mmol) in THF (2 mL) was added at −78° C. in a period of 1 min under N$_2$. The reaction mixture was warmed to room temperature and stirred for 20 minutes. LCMS showed that 537-1 was consumed completely. The reaction was quenched by water and extracted with EA (20 mL×3). The combined organic phase was washed with brine, dried over anhydrous Na$_2$SO$_4$, filtered and concentrated under reduced pressure to give 537-2 (720 mg, 82%) as colorless oil. +ESI-MS: m/z 372.1 [M+H]$^+$.

537-8 (white solid, 45 mg, 78%) was prepared following the general procedure for preparing 533 using 537-2. +ESI-MS: m/z 746.1 [M+H]$^+$.

To a solution of 537-8 (45 mg, 0.06 mmol) in TFA (1 mL) was added HBr/HOAc (1 mL, 40%) at r.t. The reaction mixture was stirred at room temperature until all starting material was consumed (followed by LCMS). The resulting mixture was concentrated under reduced pressure. The residue was neutralized with aqueous NaHCO$_3$ and extracted with EA. The combined organic phase was concentrated under reduced pressure. The residue was purified by Pre-HPLC to afford 537 (9 mg, 16.3%) as a white solid. +ESI-MS: m/z 654.1 [M+H]$^+$.

Example 305

Preparation of Compound 540

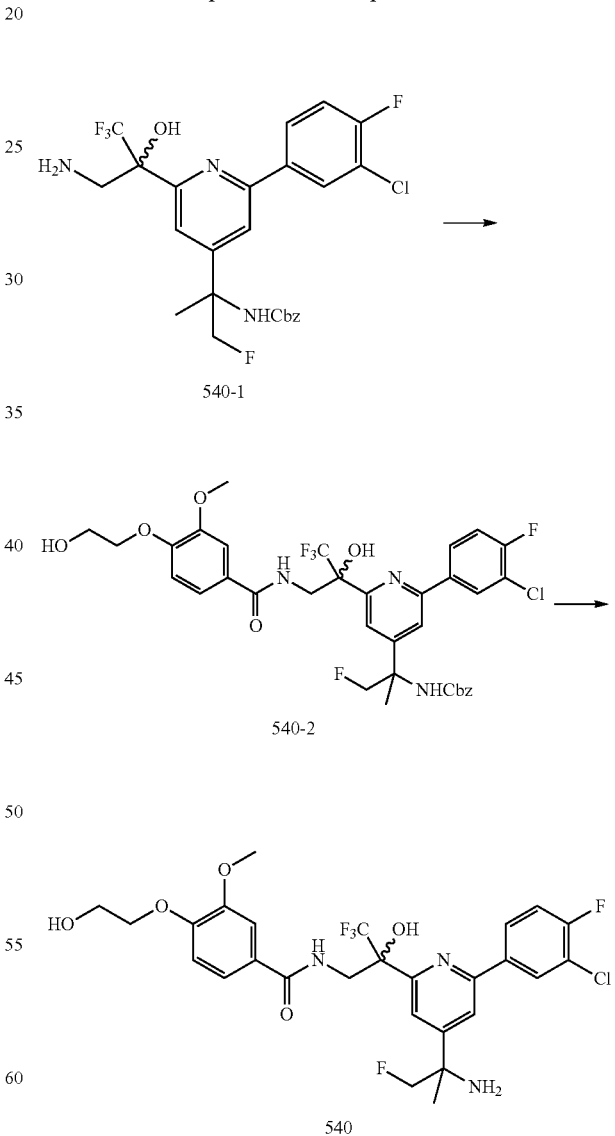

Compound 540 (white solid, 175 mg, 718.4%) was prepared following the general procedure for preparing 534 using 540-1. +ESI-MS: m/z/z 604.1 [M+H]$^+$.

Example 306
Preparation of Compound 541
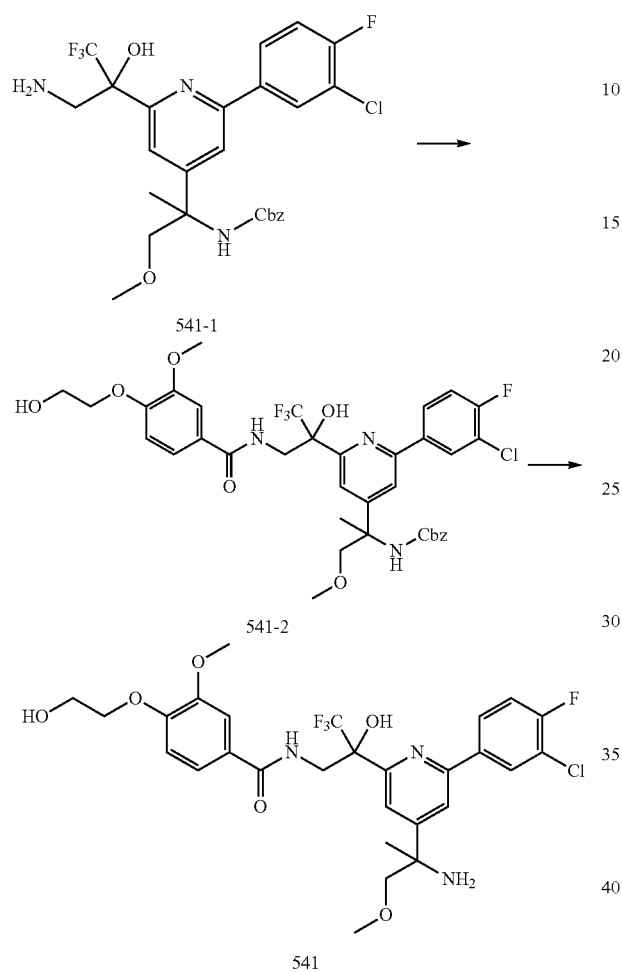
Compound 541 (white solid, 13 mg, 18.4%) was prepared following the general procedure for preparing 537 and 528 using 541-1. +ESI-MS: m/z 616.0 [M+H]$^+$.
Example 307
Preparation of Compound 544
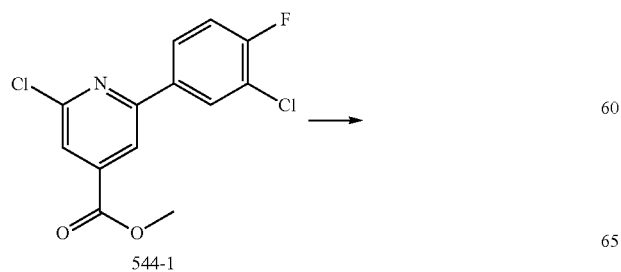
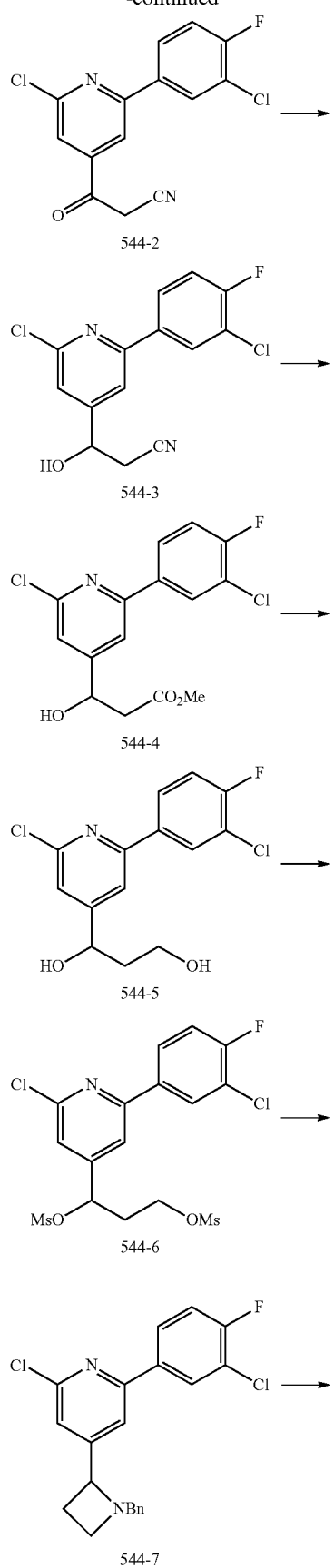

-continued

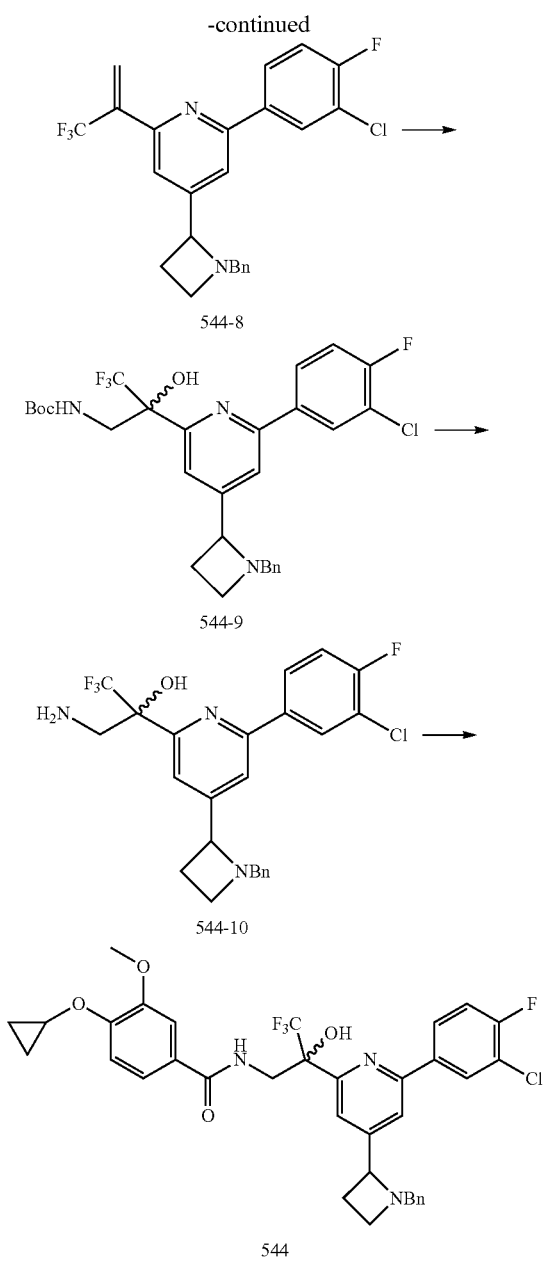

544-8

544-9

544-10

544

To a solution of CH₃CN (24.6 g, 600 mmol) in toluene (200 mL) was added n-BuLi (120 mL, 2.5 M in hexane) dropwise at −78° C. under N₂. The mixture was stirred at −78° C. for 30 mins. The mixture was treated with a solution of 544-1 (36.0 g, 120 mmol) in toluene (200 mL). The mixture was warmed to r.t. and stirred for 2 h. The reaction was quenched with sat. aq. NH₄Cl, and extracted with EA (4×200 mL). The combined organic layer was washed with brine, dried over anhydrous Na₂SO₄ and concentrated at low pressure. The residue was purified by column chromatography to give 544-2 as a white solid (31.5 g, 85.0%). +ESI-MS: m/z 308.9 [M+H]⁺.

To a solution of 544-2 (30.9 g, 100 mmol) in MeOH (600 mL) was added NaBH₄ (19 g, 500 mmol) in portions at 0° C., and stirred at 0° C. for 4 h. The mixture was quenched with water, and extracted with EA (4×300 mL). The combined organic layer was washed with brine, dried over anhydrous Na₂SO₄, filtered and concentrated under reduced pressure. The residue was further purified by column chromatography to afford 544-3 as a light yellow solid (28.0 g, 90.0%). +ESI-MS: m/z 310.9 [M+H]⁺.

To a solution of 544-3 (5 g, 16.08 mmol) in MeOH (100 mL) was added SOCl₂ (20 mL) at 0° C. dropwise. The mixture was heated to reflux and stirred for 48 h. The mixture was cooled to r.t. The solution was neutralized with sat. aq. NaHCO₃, and extracted with EA (4×300 mL). The combined organic layer was washed with brine, dried over anhydrous Na₂SO₄, filtered and concentrated under reduced pressure. The residue was purified by column chromatography to afford 544-4 as a light yellow solid (3.32 g, 60.0%).

Compound 544-5 (light yellow solid, 2.65 g, 90%) was prepared was prepared following the general procedure for preparing 544-3 using 544-4. +ESI-MS: m/z 315.7 [M+H]⁺.

To a solution of 544-5 (2.65 g, 8.38 mmol) and TEA (2.54 g, 25.15 mmol) in DCM (20 mL) was added MsCl (2.88 g, 25.15 mmol) at 0° C. The mixture was stirred at r.t. for 2 h. The reaction was quenched with sat. aq. NaHCO₃ and extracted with EA (4×100 mL). The combined organic layer was washed with brine, dried over anhydrous Na₂SO₄, filtered and concentrated at low pressure. The residue was purified by column chromatography to afford 544-6 as a light yellow solid (3.2 g, 80.8%).

To a solution of 544-6 (3.2 g, 8.4 mmol) in toluene (50 mL) were added BnNH₂ (5.4 g, 50.3 mmol), K₂CO₃ (6.9 g, 50.3 mmol), and KI (100 mg) at r.t. The mixture was stirred at 160° C. for 6 h. The mixture was cooled to r.t. and diluted with water. The solution was extracted with EA (4×100 mL). The combined organic layer was washed with brine, dried over anhydrous Na₂SO₄, filtered and concentrated at low pressure. The residue was purified by column chromatography to afford 544-7 as a light yellow solid (1.1 g, 33.9%). +ESI-MS: m/z 386.9 [M+H]⁺.

Compound 544 (white solid, 450 mg, 40.3%) was prepared was prepared following the general procedure for preparing 528 using 544-7. +ESI-MS: m/z 670.3

Example 308

Preparation of Compounds 545 and 546

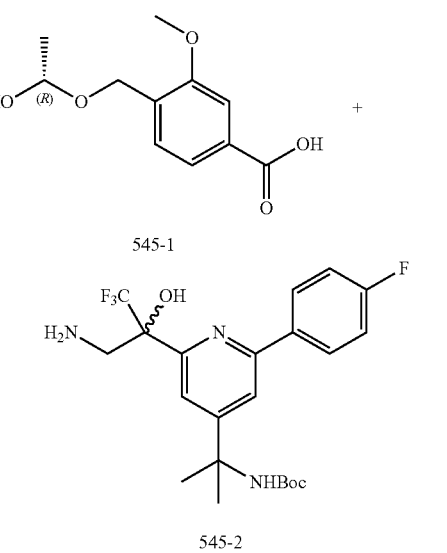

545-1

545-2

483
-continued
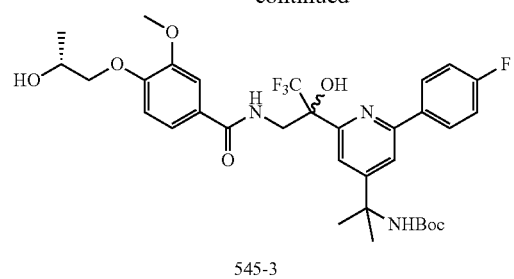
545-3
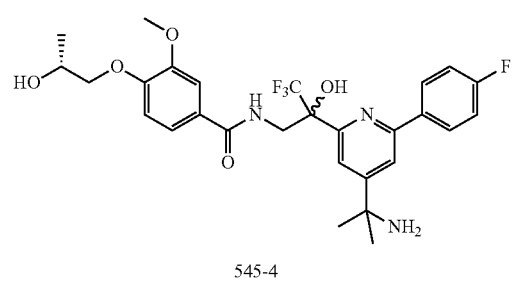
545-4
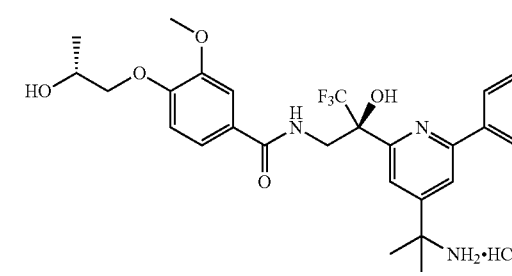
545
+
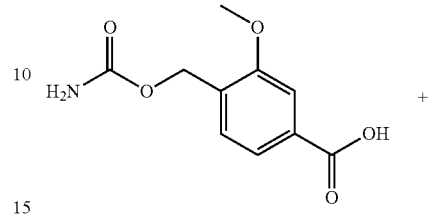
546
Compounds 545 (white solid, 112 mg) and 546 (white solid, 107 mg) was prepared following the general procedure for preparing 495 and 496 using 545-1 and 545-2. 545: +ESI-MS: m/z 566.2 [M+H]⁺; and 546: +ESI-MS: m/z 566.2 [M+H]⁺.
484
Example 309
Preparation of Compounds 547 and 548
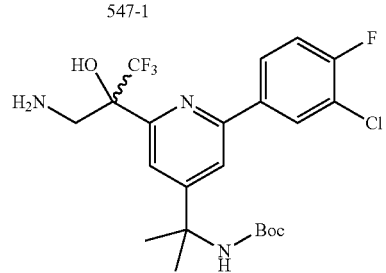
547-1
547-2
547-3
547-4
547
+

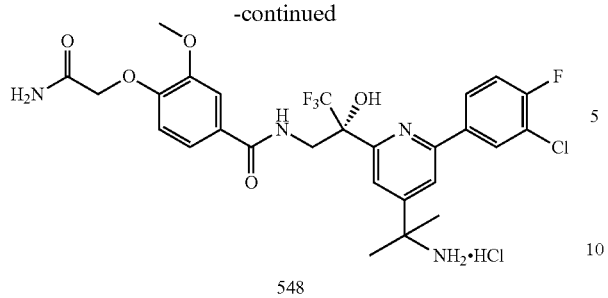

548

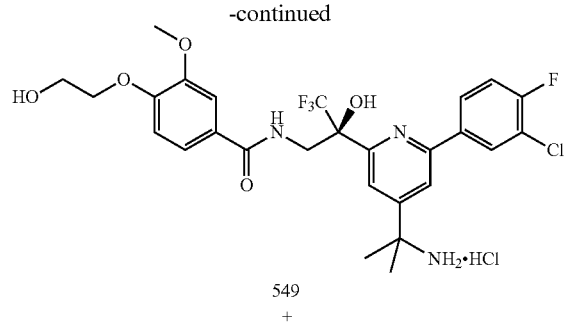

549
+

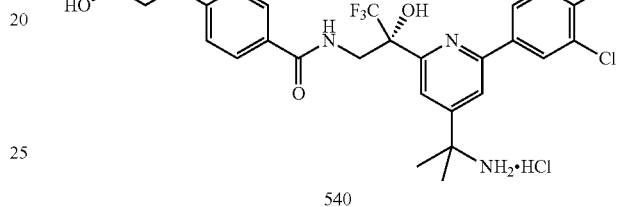

540

Compounds 547 (white solid, 45 mg) and 548 (white solid, 48 mg) was prepared following the general procedure for preparing 271 and 272 using 547-1 and 547-2. 547: +ESI-MS: m/z 599.1 [M+H]$^+$; and 548: +ESI-MS: m/z 599.1 [M+H]$^+$.

Example 310

Preparation of Compounds 549 and 550

Compounds 549 (white solid, 102 mg) and 550 (white solid, 108 mg) was prepared following the general procedure for preparing 271 and 272 using 549-1 and 549-2. 549: +ESI-MS: m/z 585.9 [M+H]$^+$; and 550: +ESI-MS: m/z 586.0 [M+H]$^+$.

Example 311

Preparation of Compounds 551 and 552

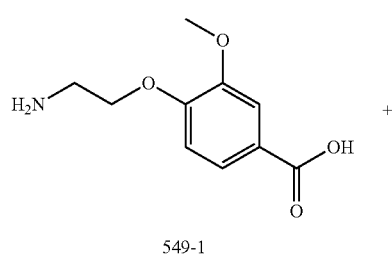

549-1

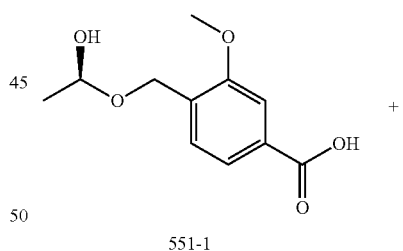

551-1

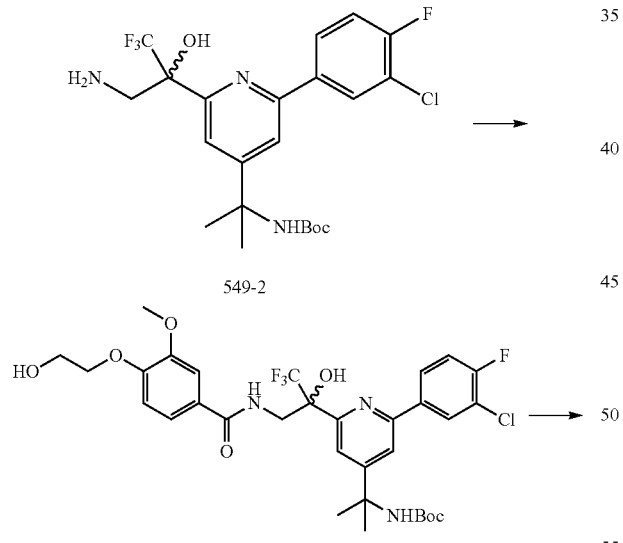

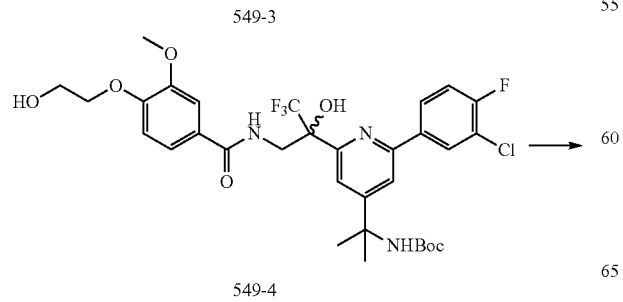

549-4

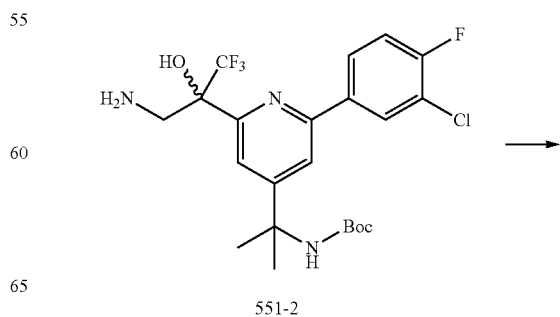

551-2

487
-continued
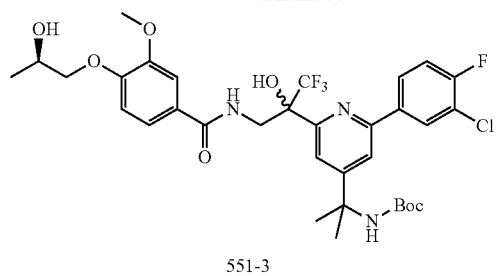
551-3
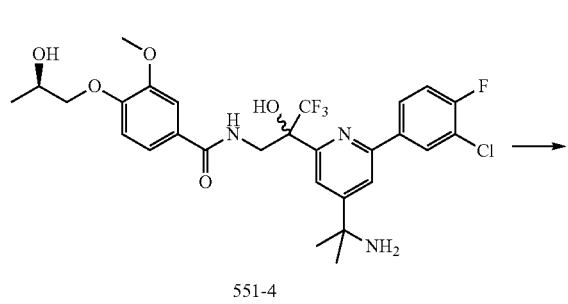
551-4
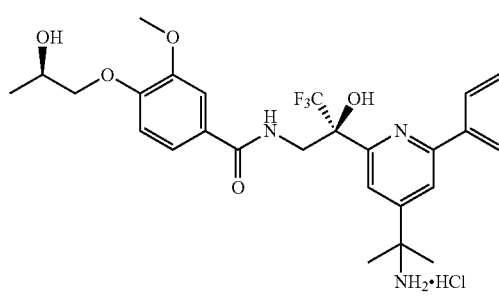
551
+
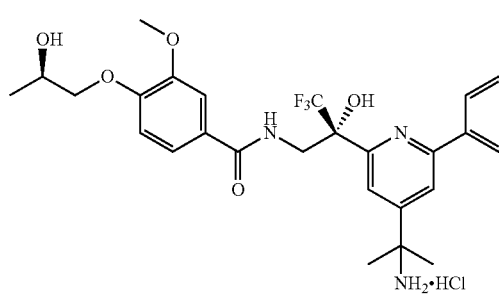
552
Compounds 551 (white solid, 78 mg) and 552 (white solid, 72 mg) was prepared following the general procedure for preparing 271 and 272 using 551-1 and 551-2. 551: +ESI-MS: m/z 600.2 [M+H]$^+$; and 552: +ESI-MS: m/z 600.2 [M+H]$^+$.
488
Example 312
Preparation of Compounds 553 and 554
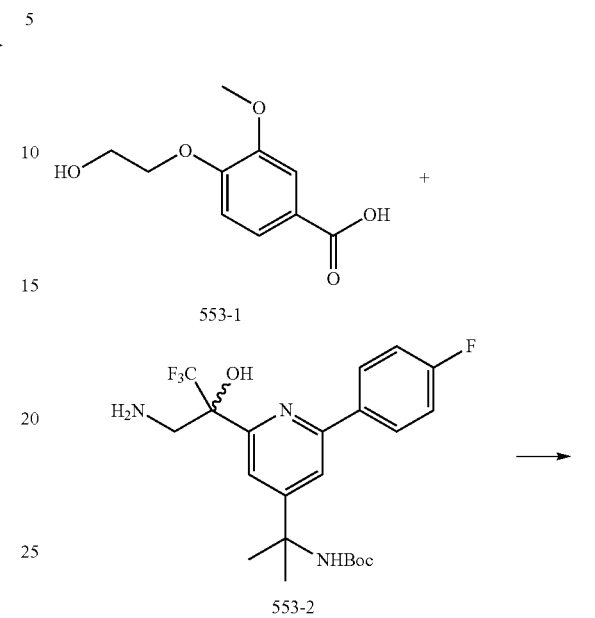
553-1
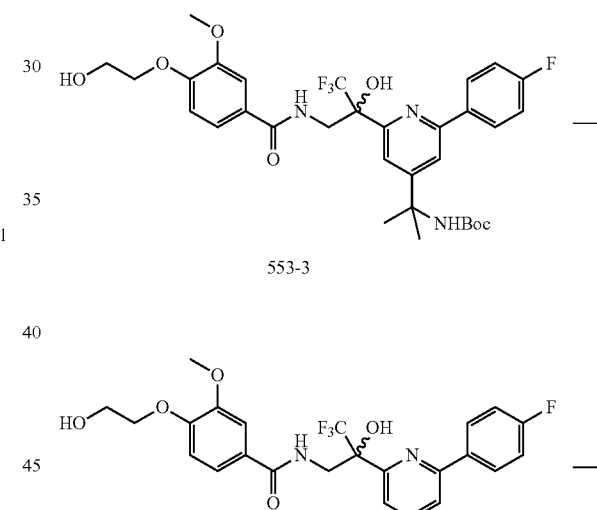
553-2
553-3
553-4
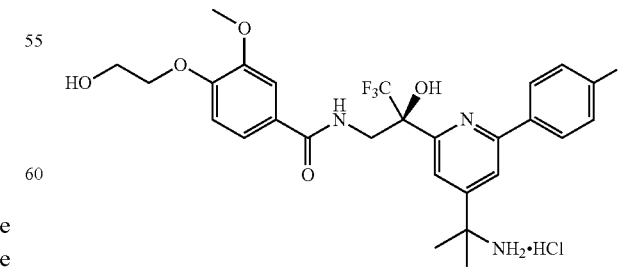
553
+

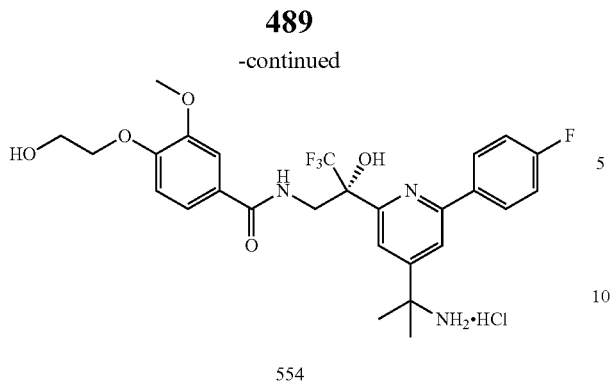
Compounds 553 (white solid, 35 mg) and 554 (white solid, 45 mg) was prepared following the general procedure for preparing 495 and 496 using 553-1 and 553-2. 553: +ESI-MS: m/z 552.2 [M+H]$^+$; and 554: +ESI-MS: m/z 552.1 [M+H]$^+$.
Example 313
Preparation of Compound 555
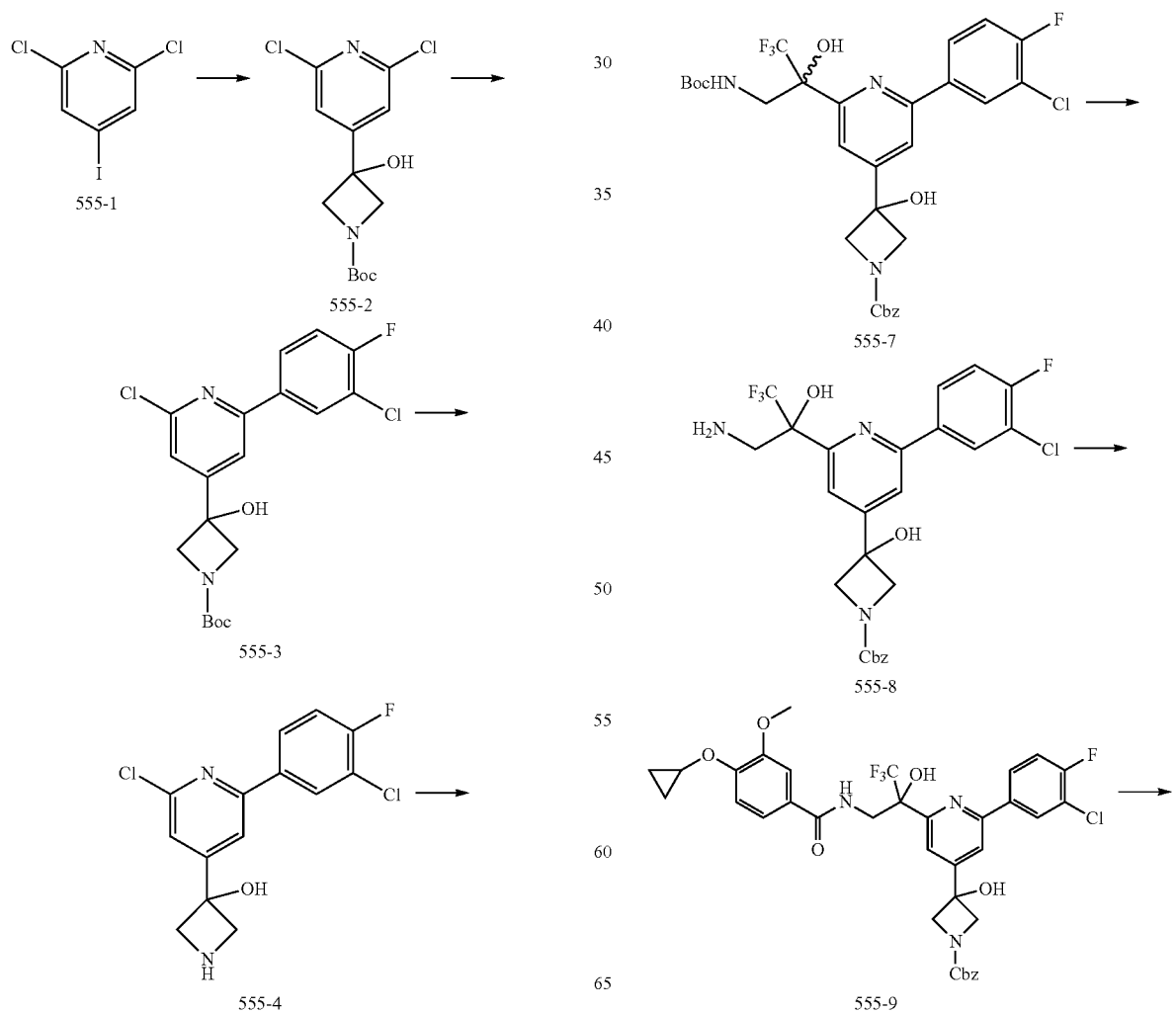

491

-continued

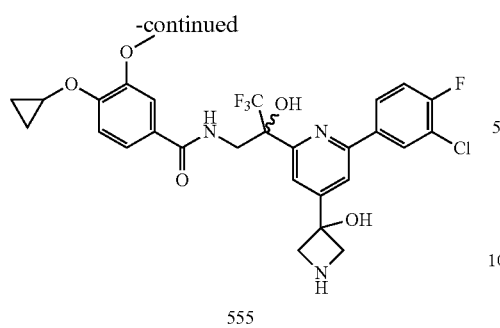

555

To a solution of 555-1 (2.74 g, 10 mmol) in anhydrous THF (30 mL) was added n-BuLi (4.8 mL, 2.5 M in hexane) dropwise at −78° C. under N₂. The mixture was stirred at −78° C. for 20 mins, and then treated with a solution of tert-butyl 3-oxoazetidine-1-carboxylate (1.71 g, 10.00 mmol) in anhydrous THF (5 mL) at −78° C. The solution was stirred for 30 mins at −78° C. The reaction was quenched with water and extracted with EA (3×50 mL). The combined organic phase was washed with brine, dried over anhydrous Na₂SO₄, filtered and concentrated under reduced pressure. The residue was purified by column chromatography using PE:EA=9:1 as the eluent to afford 555-2 (1.05 g, 33%). +ESI-MS: m/z 319.1 [M+H]⁺.

To a solution of 555-2 (0.8 g, 2.52 mmol) and (3-chloro-4-fluorophenyl) boronic acid (440 mg, 2.52 mmol) in dioxane:H₂O (10:1 mL) were added Cs₂CO₃ (1.23 g, 3.78 mmol) and Pd(dppf)Cl₂ (185.00 mg, 0.25 mmol) under N₂. The mixture was heated to 80° C. in an oil bath and stirred for 1 h. The mixture was cooled to r.t., poured into H₂O (20 mL) and extracted with EA (3×30 mL). The combined organic phase was washed with brine, dried over anhydrous Na₂SO₄ and concentrated under reduced pressure. The residue was purified by column chromatography using PE:EA=9:1 as the eluent to afford 555-3 (780 mg). +ESI-MS: m/z 413.1 [M+H]⁺.

To a solution of 555-3 (780 mg, 1.89 mmol) in DCM (8 mL) was added TFA (2 mL), and the mixture stirred at r.t. for 30 mins. The mixture was concentrated under reduced pressure, and the residue was dissolved in DCM (10 mL) and Et₃N (572 mg, 5.65 mmol). CbzCl (643 mg, 3.77 mmol) was added slowly at r.t., and the mixture was stirred for 2 h. The solution was washed with brine, dried over anhydrous Na₂SO₄ and concentrated under reduce pressure. The residue was purified by column chromatography using PE:EA=4:1 as the eluent to give 555-5 (720.00 mg). +ESI-MS: m/z 447.1 [M+H]⁺.

Compound 555 (white solid, 3.5 mg, 16.3%) was prepared following the general procedure for preparing 533 using 555-5. +ESI-MS: m/z 595.9[M+H]⁺.

492

Example 314

Preparation of Compounds 561 and 562

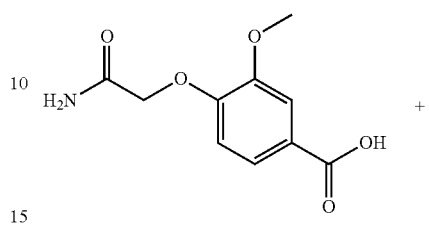

561-1

+

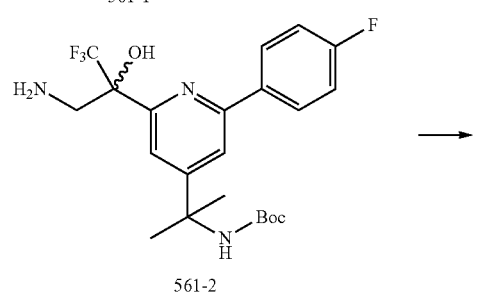

561-2

561-3

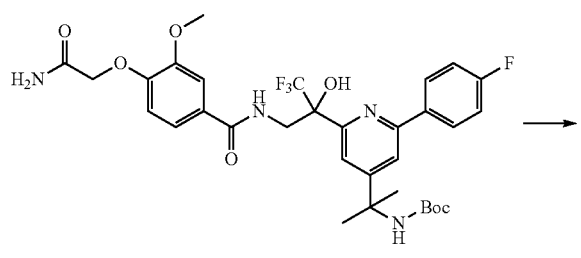

561-4

561

+

493
-continued
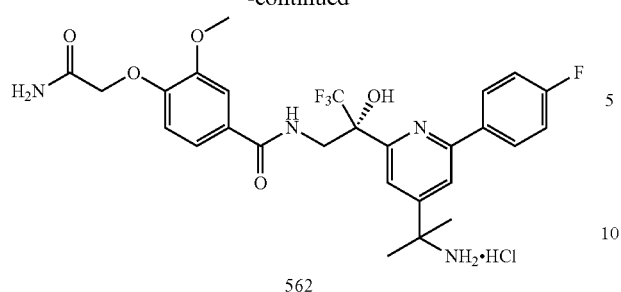
562
Compounds 561 (white solid, 50 mg) and 562 (white solid, 48 mg) was prepared following the general procedure for preparing 495 and 496 using 561-1 and 561-2. 561: +ESI-MS: m/z 565.1 [M+H]$^+$; and 562: +ESI-MS: m/z 565.1 [M+H]$^+$.
Example 315
Preparation of Compound 563
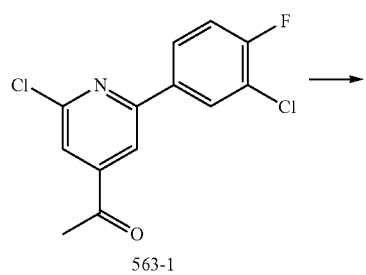
563-1
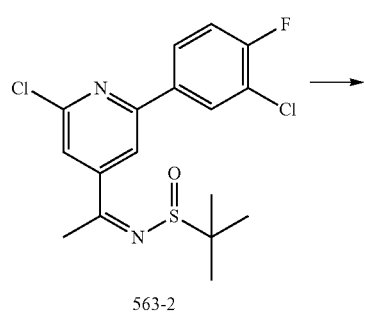
563-2
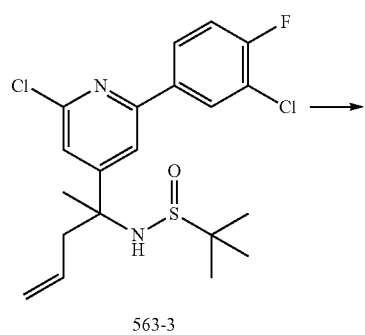
563-3
494
-continued
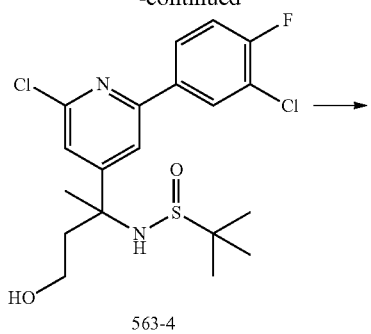
563-4
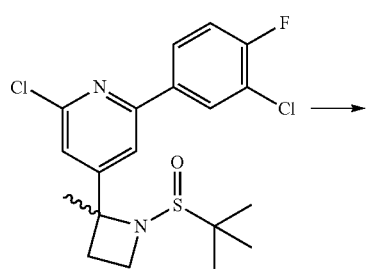
563-5
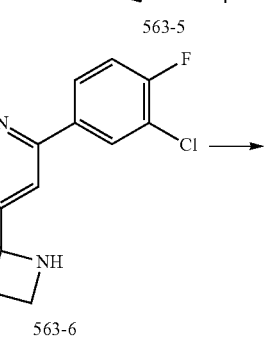
563-6
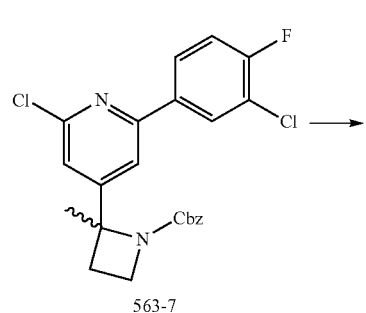
563-7
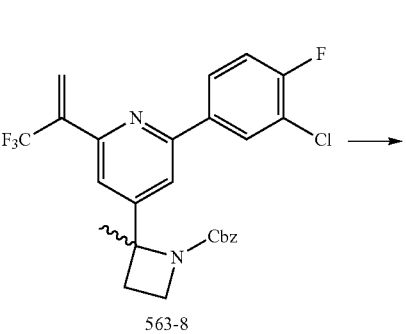
563-8

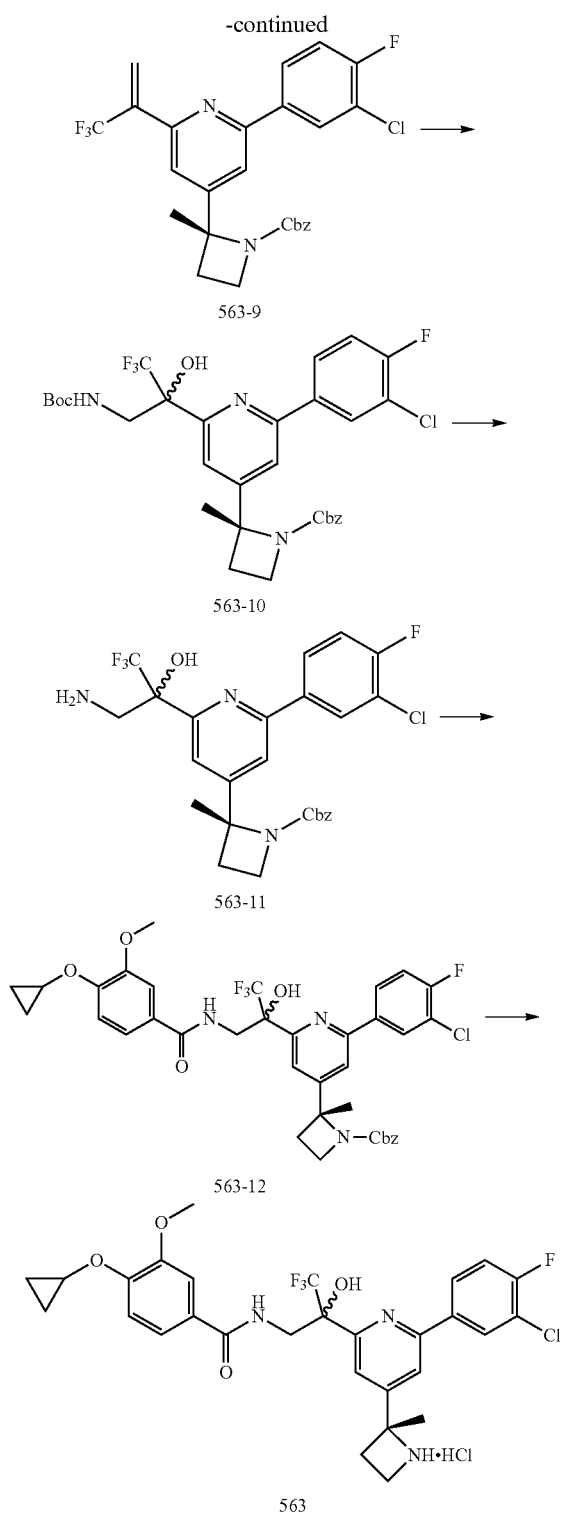

filtered through a pad of Celite, and the cake was washed with EA. The aqueous was extracted with EA. The combined organic layers were washed with brine, dried over anhydrous $Na_2SO_4$, filtered and concentrated under reduced pressure. The residue was purified by column chromatography to give 563-2 (3.50 g, 85.6%). +ESI-MS: m/z 387.0 $[M+H]^+$.

To a solution of 563-2 (3.50 g, 9.0 mmol) in anhydrous THF (15 mL) was added allylmagnesium bromide (13.6 mL, 1.0 M in THF) at −78° C. under $N_2$, and the mixture was stirred at −78° C. for 1 h. The mixture was allowed to warm to 25° C. and stirred for another 1 h. The reaction was quenched with aq. $NH_4Cl$ solution and extracted with EA (3×30 mL). The combined organic phase was washed with brine, dried over anhydrous $Na_2SO_4$, filtered and concentrated under reduced pressure. The residue was purified column chromatography to afford 563-3 (1.20 g, 31%) as a yellow solid. +ESI-MS: m/z 429.1 $[M+H]^+$.

Ozone was bubbled into a solution of 563-3 (1.2 g, 2.8 mmol) in anhydrous MeOH (30 mL) at −78° C. for 10 mins. After excess $O_3$ was purged by nitrogen, $NaBH_4$ (420 mg 11.2 mmol) was added at 25° C. in portions. The solution was stirred for 30 mins at r.t. The reaction was quenched with $H_2O$ and extracted with EA (3×60 mL). The combined organic layers were washed with brine, dried over anhydrous $Na_2SO_4$ and concentrated under reduced pressure. The residue was purified by column chromatography using PE:EA=2:1 as the eluent to give 563-4 (1.02 g, 83%) as a solid. +ESI-MS: m/z 433.1 $[M+H]^+$.

To a solution of 563-4 (1.01 g, 2.5 mmol) and $PPh_3$ (1.0 g, 3.8 mmol) in anhydrous THF (20 mL) was added DIAD (870 mg, 4.3 mmol) dropwise at 25° C. under $N_2$. The mixture was heated to 70° C. and stirred for 4 h. The mixture was cooled to 25° C. and concentrated under reduced pressure. The residue was purified by column chromatography to afford 563-5 (902 mg, 85%) as a solid.

To a solution of 563-5 (902 mg 2.2 mmol) in dioxane (8 mL) was added conc. HCl (1 mL, 12 M) in one portion, and stirred at 25° C. for 1 h. The mixture was concentrated to give 563-6 (750 mg), which was used for the next step without further purification.

563-6 (750 mg) and $NaHCO_3$ (607 mg, 7.2 mmol) were dissolved in DCM (10 mL) and $H_2O$ (1 mL). The solution was treated with CbzCl (617 mg 3.6 mmol) at r.t. The mixture was stirred at r.t. for 1 h. The mixture was diluted with water and extracted with EA (3×30 mL). The combined organic phase was washed with brine, dried over anhydrous $Na_2SO_4$, filtered and concentrated under reduced pressure. The residue was purified by column chromatography to afford 563-7 (990 mg, 93%). +ESI-MS: m/z 444.9 $[M+H]^+$.

563-8 (white solid, 1.1 g, 16.3%) was prepared following the general procedure for preparing 533 using 563-7. +ESI-MS: m/z 595.9 $[M+H]^+$. 563-9 (402 mg) was obtained by SFC separation of 563-8 (1.1 g).

Compound 563 (white solid, 20 mg, 33%) was prepared following the general procedure for preparing 533 using 563-9. +ESI-MS: m/z 593.9 $[M+H]^+$.

A solution of 563-1 (3.00 g, 10.56 mmol) and tetraethoxytitanium (7.23 g, 31.68 mmol) in anhydrous THF (60 mL) was stirred for 5 mins. The solution was treated with 2-methylpropane-2-sulfinamide (1.92 g, 15.84 mmol) and stirred at 70° C. for 5 h. The mixture was cooled to r.t., and the reaction was quenched with sat. aq. $NaHCO_3$ until white titanium salts precipitate was formed. The suspension was

Example 316
Preparation of Compound 564
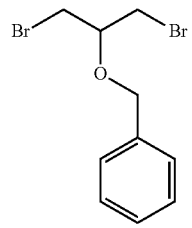
564-3
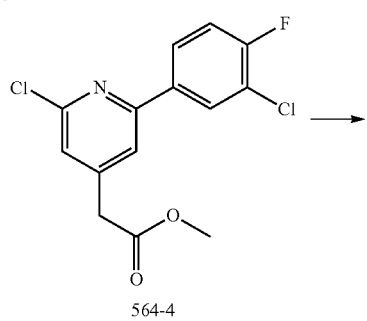
564-4
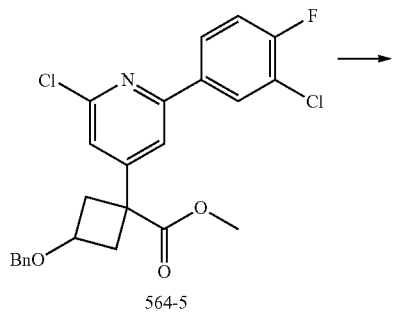
564-5
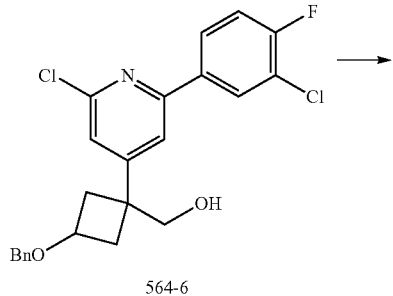
564-6
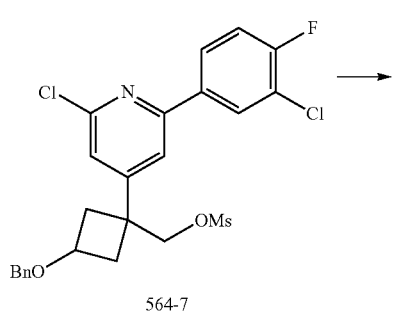
564-7
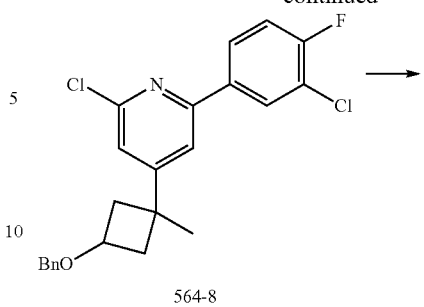
564-8
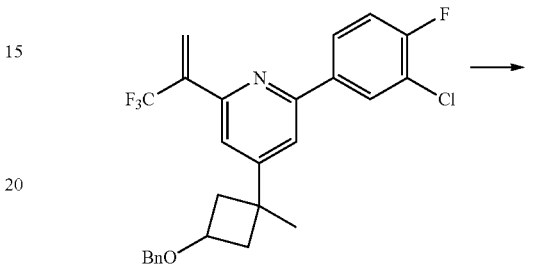
564-9
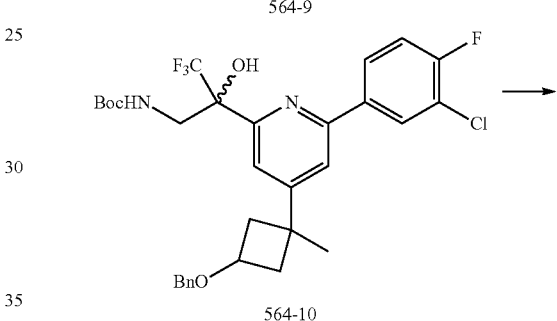
564-10
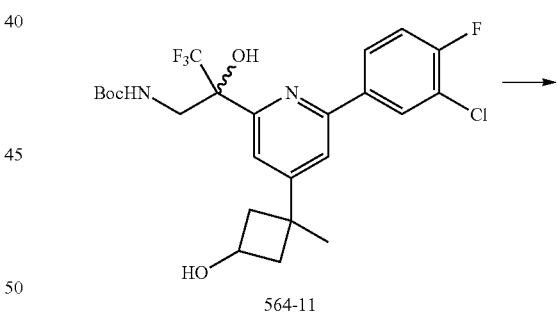
564-11
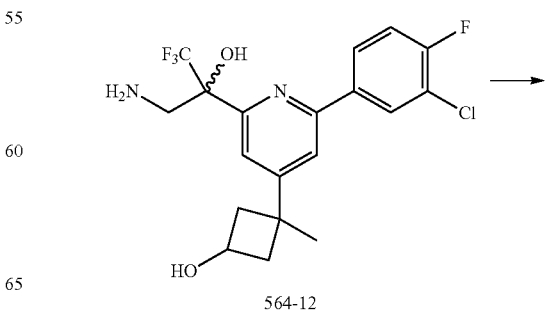
564-12

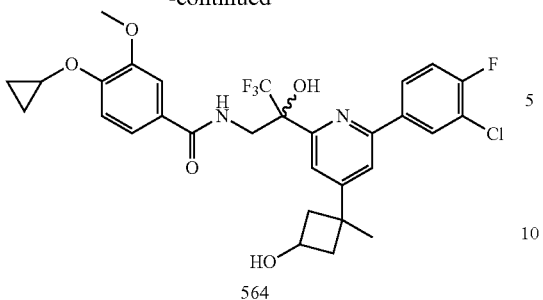

564-3 was prepared as described in Franck, D. et al., Bioorganic & *Medicinal Chemistry* (2013) 21(3):643-652.

To a solution of 564-4 (11.22 g, 35.7 mmol) in anhydrous THF (200 mL) was added LiHMDS (286 mL 1 M in THF) in portions at −78° C. under $N_2$. The mixture was stirred at −78° C. for 30 mins. The mixture was treated with a solution of 564-3 (22 g, 71.4 mmol) in anhydrous THF (50 mL) dropwise. The mixture was warmed to r.t. and stirred for 3 h. The reaction was quenched with ice-water (150 mL). The aqueous phase was extracted with EA (3×200 mL). The combined organic phase was washed with brine, dried over anhydrous $Na_2SO_4$ and concentrated under reduced pressure. The residue was purified by column chromatography using PE:EA=30:1~10:1 as the eluent to afford 564-5 (11.0 g, 70% purity) as a light yellow oil. +ESI-MS: m/z 460.0 $[M+H]^+$.

To a solution of 564-5 (11.0 g, 23.9 mmol) in anhydrous THF (60 mL) was added $LiAlH_4$ (907 mg, 23.9 mmol) in portions at 0° C. under $N_2$. The mixture was stirred at 0° C. for 30 mins. The reaction was quenched by ice-water and filtered via a pad of Celite. The filtrate was extracted with EA (3×100 mL). The combined organic phase was washed with brine, dried with anhydrous $Na_2SO_4$ and concentrated under reduced pressure. The residue was purified by column chromatography using PE:EA=30:1~20:1 as the eluent to afford 564-6 (3.8 g, 28% yield, 81% purity) as a light yellow oil. +ESI-MS: m/z 432.1 $[M+H]^+$.

To a solution of 564-6 (0.8 g, 2.34 mmol) and TEA (0.71 g, 7.01 mmol) in DCM (10 mL) was added MSCl (270 mg, 2.34 mmol) dropwise at 0° C., and the mixture was stirred at 20° C. for 30 mins. The mixture was poured into ice-water (50 mL) and extracted with EA (3×20 mL). The combined organic phase was washed with brine, dried with anhydrous $Na_2SO_4$, filtered and concentrated under reduced pressure to afford 564-7 (0.6 g, crude) as a yellow oil, which was used for next step directly. +ESI-MS: m/z 509.9 $[M+H]^+$.

To a solution of crude 564-7 (0.6 g, 1.43 mmol,) in DMSO (6 mL) was added $NaBH_4$ (270 mg, 7.14 mmol) in one portion at r.t. under $N_2$. The mixture was stirred at 50-60° C. for 12 h. The reaction was cooled to r.t., quenched with ice-water and extracted with EA (3×20 mL). The combined organic phase was washed with brine, dried with anhydrous $Na_2SO_4$, filtered and concentrated under reduced pressure. The residue was purified by column chromatography using PE:EA=30:1~8:1 as the eluent to afford 564-8 (0.3 g, 78% purity) as a yellow solid. +ESI-MS: m/z 415.9 $[M+H]^+$.

Compound 564 (white solid, 2.7 mg) was prepared following the general procedure for preparing 533 using 564-8. +ESI-MS: m/z 609.1 $[M+H]^+$.

Example 317

Preparation of Compound 569

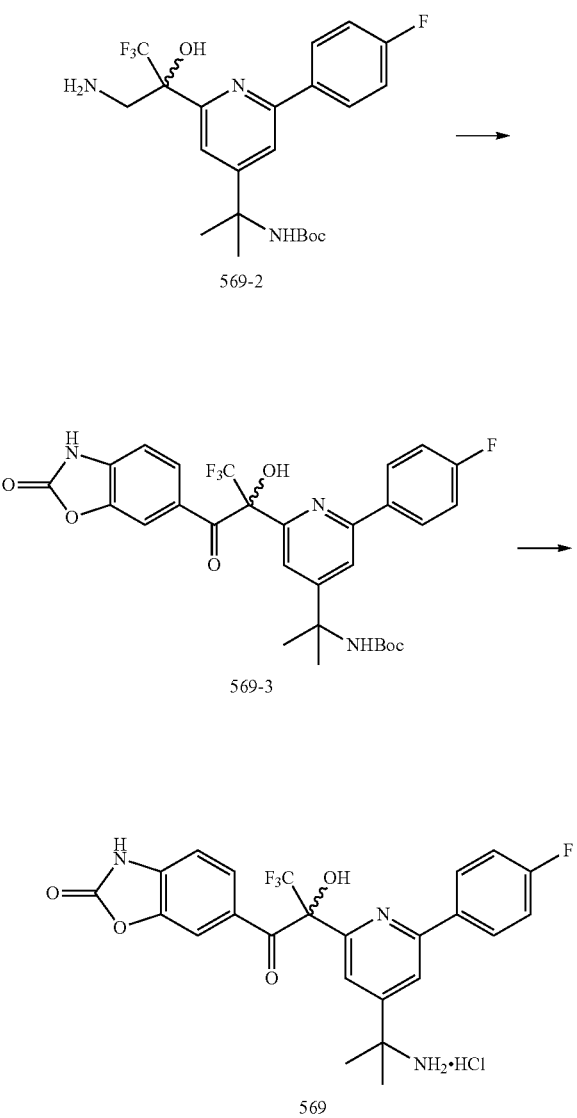

Compound 569 (white solid, 53 mg, 74%) was prepared following the general procedure for preparing 495 using 569-1 and 569-2. +ESI-MS: m/z 519.1 $[M+H]^+$.

Example 318
Preparation of Compound 570
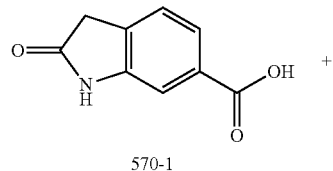
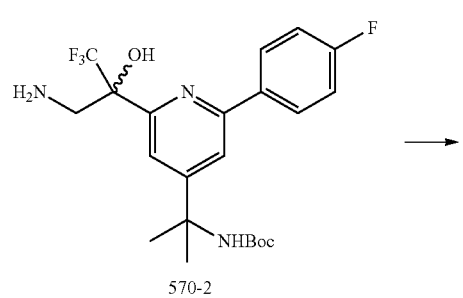
Compound 570 (white solid, 25 mg, 32%) was prepared following the general procedure for preparing 495 using 570-1 and 570-2. +ESI-MS: m/z 517.1 [M+H]$^+$.
Example 319
Preparation of Compound 571
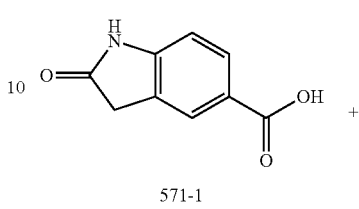
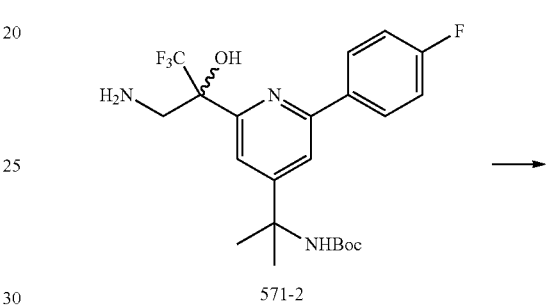
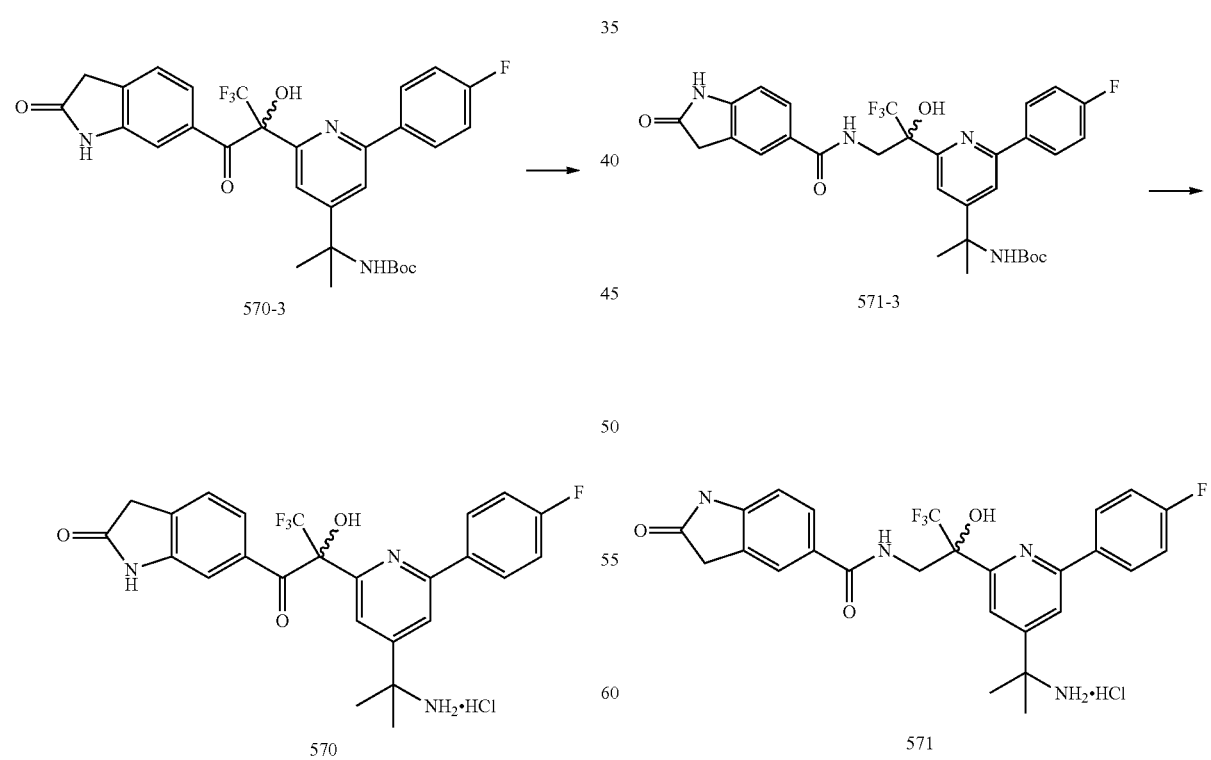
Compound 571 (white solid, 21 mg, 23%) was prepared following the general procedure for preparing 495 using 571-1 and 571-2. +ESI-MS: m/z 517.1 [M+H]$^+$.

Example 320
Preparation of Compounds 604a-d
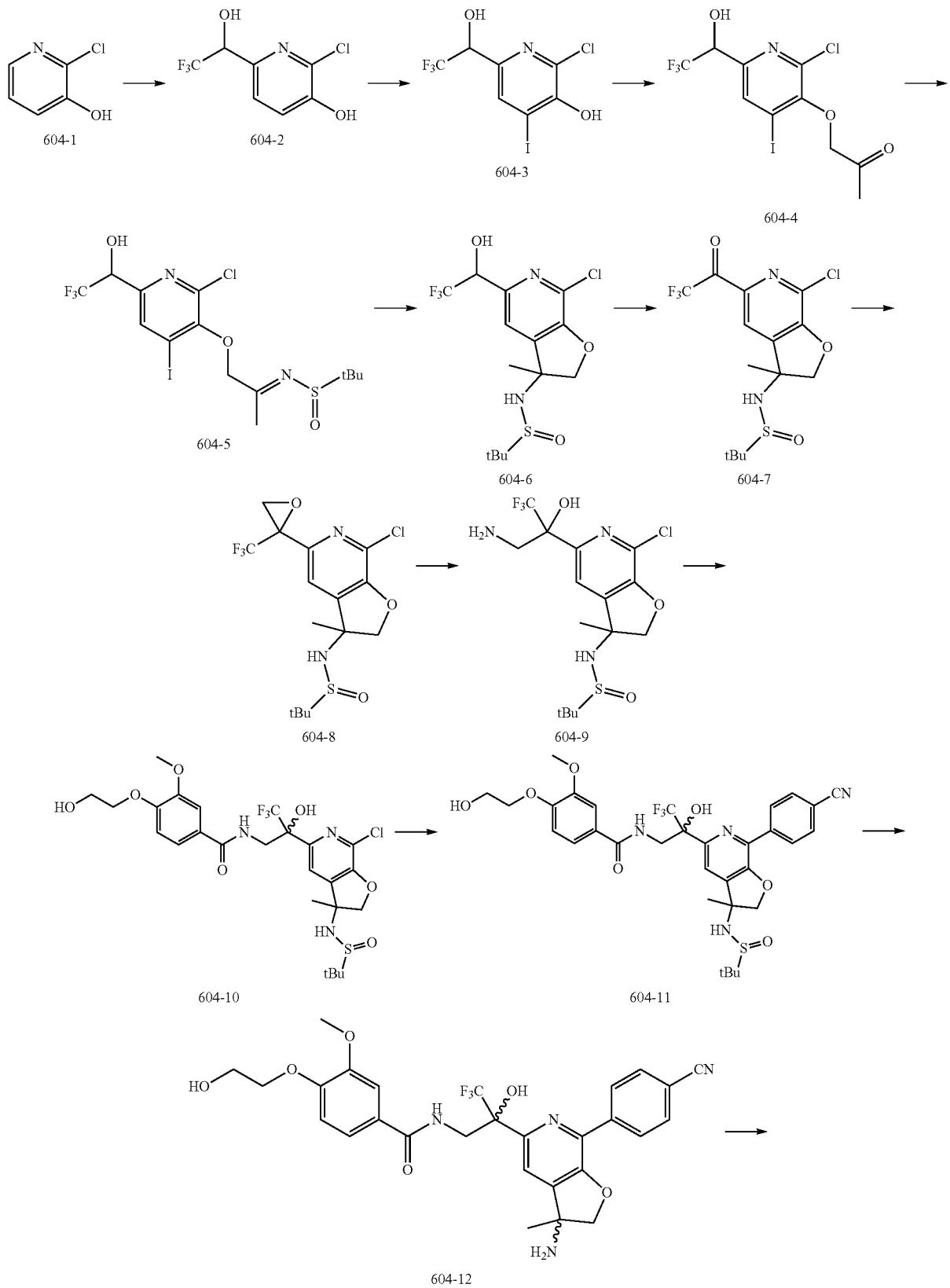

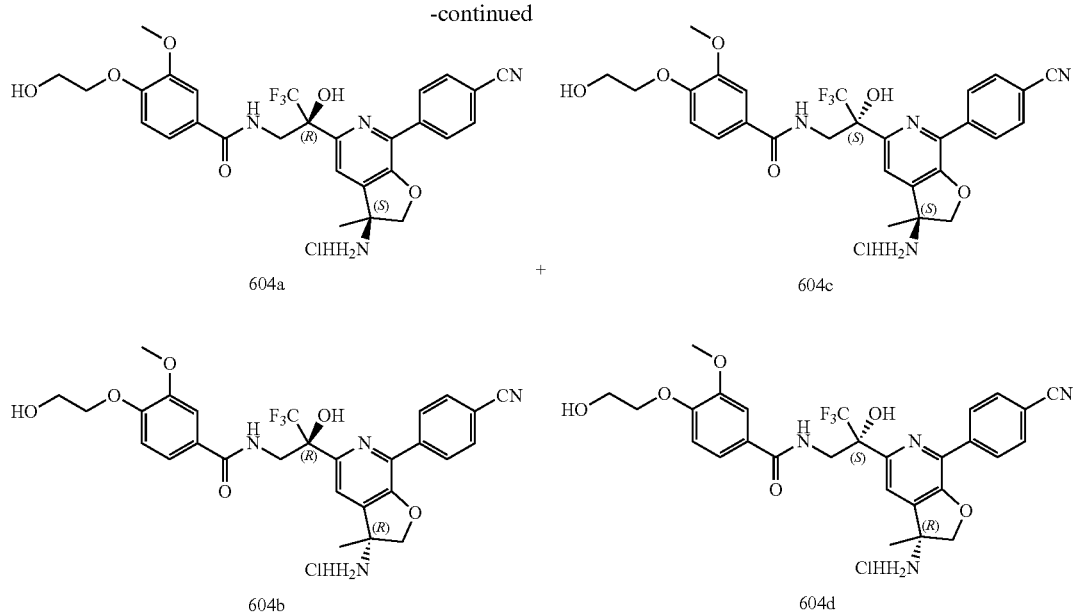

604a

604c

604b

604d

To a mixture of 604-1 (12.0 g, 92.6 mmol) and 2,2,2-trifluoroethane-1,1-diol (32.3 g, 277.9 mmol) in H$_2$O (25 mL) was added K$_2$CO$_3$ (25.6 g, 185.2 mmol, 2.00 eq.) in one portion at r.t. The flask was sealed, heated to 125° C. and stirred for 16 h. The mixture was cooled to 0° C., neutralized with 1M HCl solution, and extracted with EA (3×100 mL). The combined organic phase was dried over anhydrous Na$_2$SO$_4$, filtered and concentrated under reduced pressure. The residue was washed with DCM and PE to afford 604-2 (17.0 g, 81%) as a white solid.

To a stirring solution of 604-2 (130 g, 571.2 mmol) and Na$_2$CO$_3$ (121 g, 1.1 mol) in H$_2$O (800 mL) was added I$_2$ (174 g, 685.5 mmol) in portions. The mixture was stirred at 25° C. for 48 h. A sat. sodium sulfite solution (500 mL) was used to quench the reaction. The mixture was acidified with 3M HCl and diluted with EA (1 L). The organic phase was separated, and the aqueous phase was extracted with EA (3×500 mL). The combined organic phase was dried over anhydrous Na$_2$SO$_4$, filtered and concentrated under reduced pressure. The residue was purified by column chromatography by using PE:EA=1:1 as the eluent to afford 604-3 (180 g, 89%) as a white solid.

To a solution of 604-3 (88 g, 249 mmol) and 1-chloropropan-2-one (55.9 g, 605.0 mmol) in DMF (200 mL) was added NaHCO$_3$ (62.7 g, 746.1 mmol) in one portion at r.t. under N$_2$. The mixture was stirred at 25° C. for 25 h, and the solid was removed by filtration. The filtrate was concentrated to dryness under reduced pressure, and the residue was dissolved in DCM and triturated with PE to afford 604-4 (66 g, 65%) as a white solid.

A mixture of 604-4 (9.0 g, 22 mmol), 2-methylpropane-2-sulfinamide (S-configuration, 2.66 g, 22 mmol) and titanium(IV) ethoxide (10.5 g, 46.1 mmol) in anhydrous THF (18.00 mL) was heated to 80° C. (sealed vial, degassed and purged with N$_2$) and stirred for 1 h. EA (150 mL) and water (10 mL) were added with stirring. The mixture was stirred for 5 mins and filtered through a pad of celite. The filtrate was concentrated under reduced pressure, and the residue was purified by column chromatography on silica gel using EA:DCM=1:9 as the eluent to afford 604-5 (6.8 g, 60%).

To a solution of EtMgBr (4.4 mL, 13.2 mmol, 3 M in ether) in dry THF (50 mL) was added n-BuLi (10.6 mL, 26.5 mmol, 2.5 M in hexane), and the mixture was stirred at 0° C. After stirring for 10 mins, the mixture was cooled down to −78° C. A solution of 604-5 (6.8 g, 13.26 mmol) in dry THF (50 mL) was added dropwise, and the reaction was stirred at −78° C. for 15 mins. The reaction was quenched with H$_2$O (50 mL) and extracted with EA (2×100 mL). The combined organic phase was washed with brine, dried over anhydrous Na$_2$SO$_4$, filtered and concentrated under reduced pressure. The residue was purified by column chromatography (eluent: 0-10% EA in DCM) to afford 604-6 (3.10 g, 60%).

To a stirring solution of 604-6 (6.8, 17.6 mmol) in DCM (50 mL) was added Dess-Martin reagent (8.95 g, 21.1 mmol), and the mixture was stirred at r.t. under N$_2$ for 1 h. The reaction was quenched with sat. aq. Na$_2$SO$_3$ solution and sat. aq. NaHCO$_3$ solution. After 30 mins of stirring vigorously, the organic layers were separated, and the aqueous layer was extracted with EA (2×100 mL). The combined organic phase was washed with brine, dried over anhydrous Na$_2$SO$_4$, filtered and concentrated under reduced pressure. The residue was purified by column chromatography (eluent: 0-10% EA in DCM) to afford 604-7 (5.1 g 75.4%).

To a solution of t-BuOK (1.64 g, 14.58 mmol) in CH$_3$CN (150 mL) was added Me$_3$SOI (3.21 g, 14.58 mmol). The mixture was degassed and stirred at r.t. for 30 mins. The solution containing the ylide was filtered from the solid and added to a solution of 604-7 (5.1 g, 13.25 mmol) in CH$_3$CN (150 mL), which had been previously degassed. The reaction was stirred at r.t. for 1 h. The volatiles were removed under reduced pressure. The residue was purified by column chromatography using DCM:EA=9:1 as the eluent to give 604-8 (3.2 g, 60.5%).

To a solution of 604-8 (3.2 g, 8.02 mmol) in MeOH (300 mL) was added ammonia water (10 mL) in one portion. The solution was stirred at 25° C. for 18 h. The volatiles were removed under reduced pressure to afford crude 604-9 (3.1 g, 93%).

To a solution of 4-(2-hydroxyethoxy)-3-methoxybenzoic acid (460 mg, 2.17 mmol) in DCM (6 mL) was added HATU (985 mg, 2.59 mmol) and DIPEA (558 mg, 4.32 mmol) in one portion at r.t. After stirring for 10 mins, 604-9 (900 mg, 2.16 mmol) was added. The mixture was stirred for 1 h at r.t. The solution was washed with brine, dried over anhydrous Na$_2$SO$_4$, filtered and concentrated under reduced pressure. The residue was purified by column chromatography (eluent: 10-100% EA in PE) to give 604-10 (890 mg, 67.5%).

604-10 (300 mg, 0.49 mmol), (4-cyanophenyl)boronic acid (88 mg, 0.6 mmol) and Cs$_2$CO$_3$ (240 mg, 0.74 mmol) were taken up into a microwave tube in co-solvent DME: H$_2$O (12 mL, v:v=5:1). The solution was degassed and Pd(PPh$_3$)$_4$ (57 mg, 0.05 mmol, 0.10 eq.) was added. The sealed tube was heated to 110° C. by microwave irradiation and stirred for 1 h. The solution was cooled to r.t. and poured into water. The mixture was extracted with EA (2×20 mL). The combined organic layers were washed with brine (20 mL), dried over anhydrous Na$_2$SO$_4$, filtered and concentrated under reduced pressure. The residue was purified by column chromatography using EA as the eluent to give 604-11 (320 mg, 96.2%).

To a solution of 604-11 (300 mg, 0.44 mmol) in dioxane (3 mL) was added HCl/dioxane (1 mL, 4M) at r.t. The mixture was stirred at r.t. until all the starting material was consumed. The mixture was concentrated under reduced pressure. The residue was dissolved in EA, and basified by a sat. NaHCO$_3$ solution. The organic phase was washed with brine, dried over anhydrous Na$_2$SO$_4$, filtered and concentrated under reduced pressure to afford crude 604-12 (~200 mg, 71% yield, 90% purity).

604-12 (~200.00 mg, 90% purity) was separated by SFC ("Column: Chiralcel OJ-H 250×4.6 mm I.D., 5 um Mobile phase: methanol (0.05% DEA) in CO2 from 5% to 40% Flow rate: 2.35 mL/min Wavelength: 220 nm") to give peak 1, peak 2, peak 3 and peak 4. The solution of peak 1 in CH$_3$CN and water was treated with HCl (2 M, 0.2 mL) and lyophilized to give 604a (25 mg). +ESI-MS: m/z 573.1 [M+H]$^+$. The solution of peak 2 in CH$_3$CN and water was treated with HCl (2 M, 0.2 mL) and lyophilized to give 604b (25 mg). +ESI-MS: m/z 573.1 [M+H]$^+$. The solution of peak 3 in CH$_3$CN and water was treated with HCl (2 M, 0.2 mL) and lyophilized to give 604c (19 mg). +ESI-MS: m/z 573.1 [M+H]$^+$. The solution of peak 4 in CH$_3$CN and water was treated with HCl (2 M, 0.2 mL) and lyophilized to give 604d (22 mg). +ESI-MS: m/z 573.3 [M+H]$^+$.

Example 321

Preparation of Compounds 605a-d

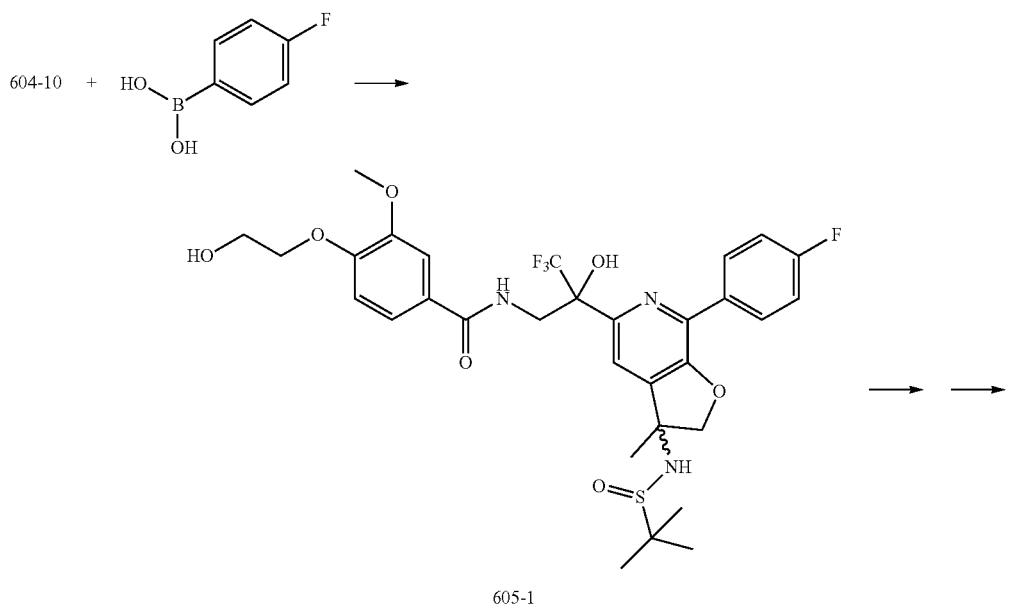

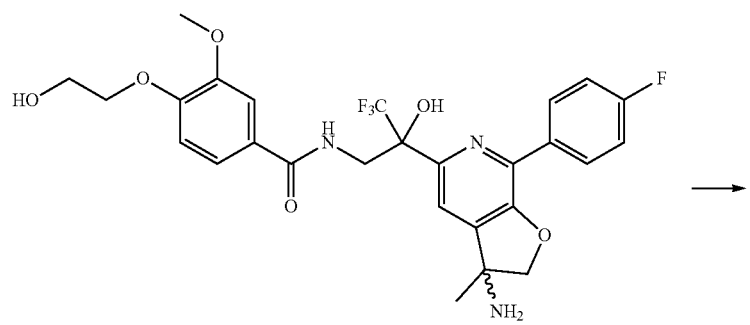

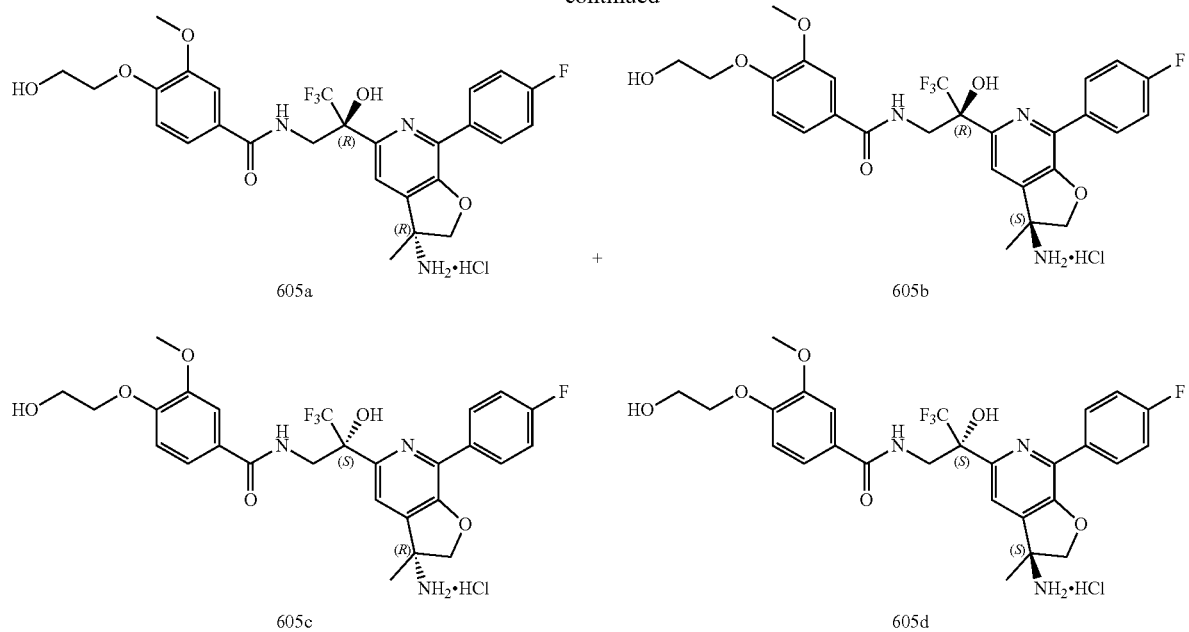

605a

605b

605c

605d

To a solution of 604-10 (400 mg, 0.66 mmol) and (4-fluorophenyl)boronic acid (138 mg, 984 mmol) in DME (3 mL) and H$_2$O (1 mL) was added Pd(dppf)Cl$_2$ (24 mg, 0.033 mmol) and Cs$_2$CO$_3$ (641 mg, 2.0 mmol) in a microwave tube under N$_2$. The reaction mixture was heated to 100° C. and stirred for 1 hour. After cooling to room temperature, the reaction mixture was poured into water (30 mL) and stirred for 5 mins. The aqueous phase was extracted with EA (30 mL×3). The combined organic phase was washed with brine, dried over anhydrous Na$_2$SO$_4$, filtered and concentrated under reduced pressure. The residue was purified by column chromatography using EA as eluent to give 605-1 (310 mg) as a white solid. +ESI-MS: m/z 670.1 [M+H]$^+$.

Compounds 605a, 605b, 605c and 605d was prepared following the general procedure for preparing 605a using 605-1. The crude was purified by prep-HPLC and SFC separation. 605a (white solid, 20 mg): m/z 566.2 [M+H]$^+$, 605b (white solid, 18 mg): m/z 566.1 [M+H]$^+$, 605c (white solid, 12.8 mg): m/z 566.1 [M+H]$^+$ and 605d (white solid, 12.7 mg): m/z 566.2 [M+H]$^+$.

Example 322

Preparation of Compounds 629-632

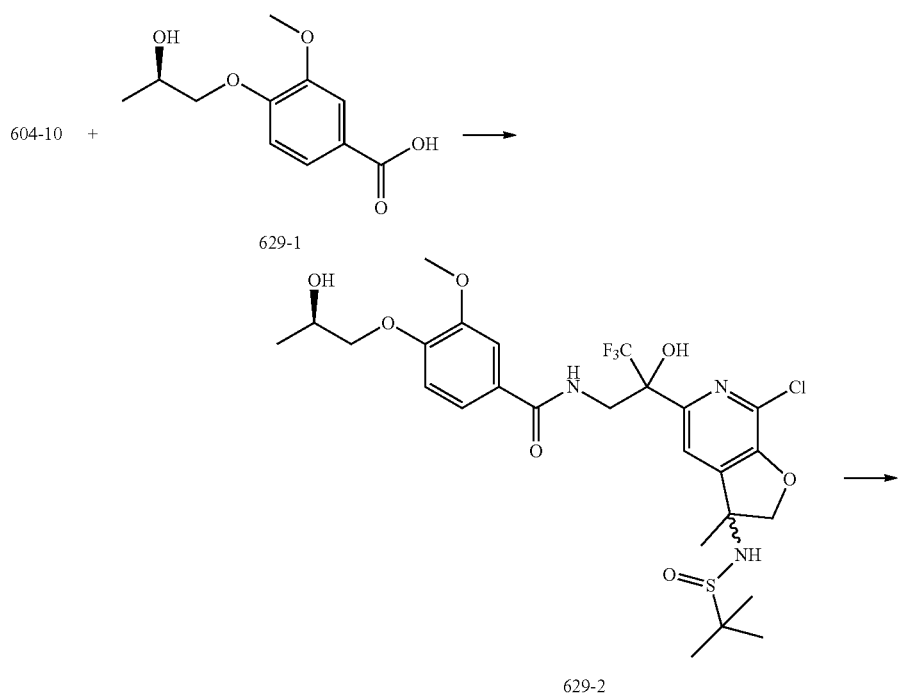

604-10 +

629-1

629-2

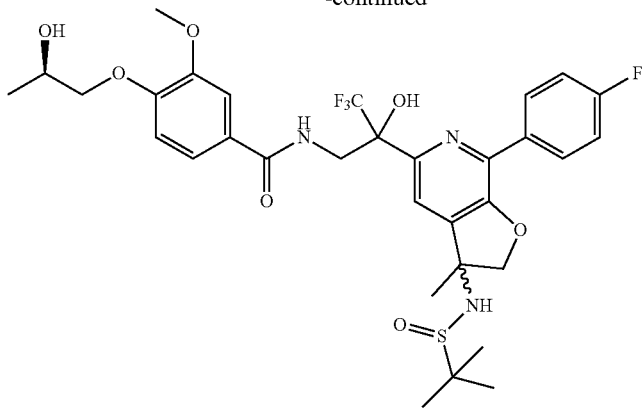
629-3
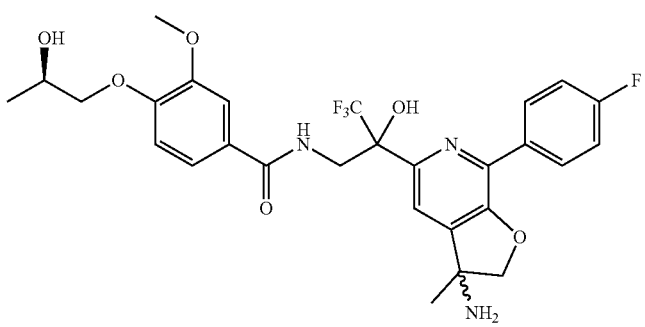
629-4
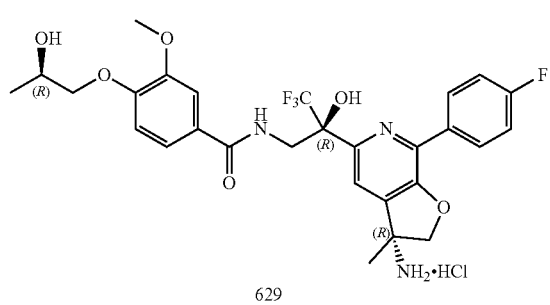
629
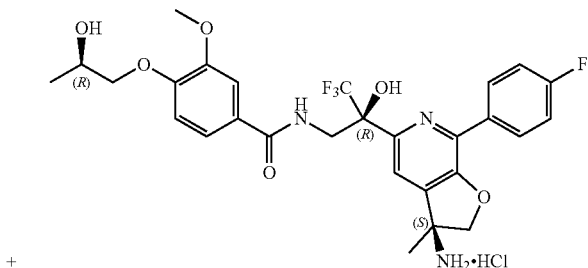
630
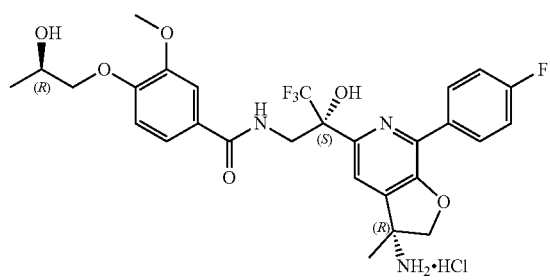
631
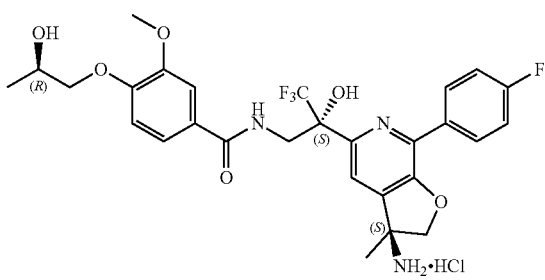
632
Compounds 629, 630, 631 and 632 was prepared following the general procedure for preparing 605d using 604-10, 629-1 and (4-fluorophenyl)boronic acid. 629 (white solid, 14.1 mg): m/z 580.1 [M+H]+, 630 (white solid, 18.6 mg): m/z 580.1 [M+H]+, 631 (white solid, 25.8 mg): m/z 580.1 [M+H]+ and 632 (white solid, 34.5 mg): m/z 580.1 [M+H]+.

Example 323
Preparation of Compounds 633a-633b
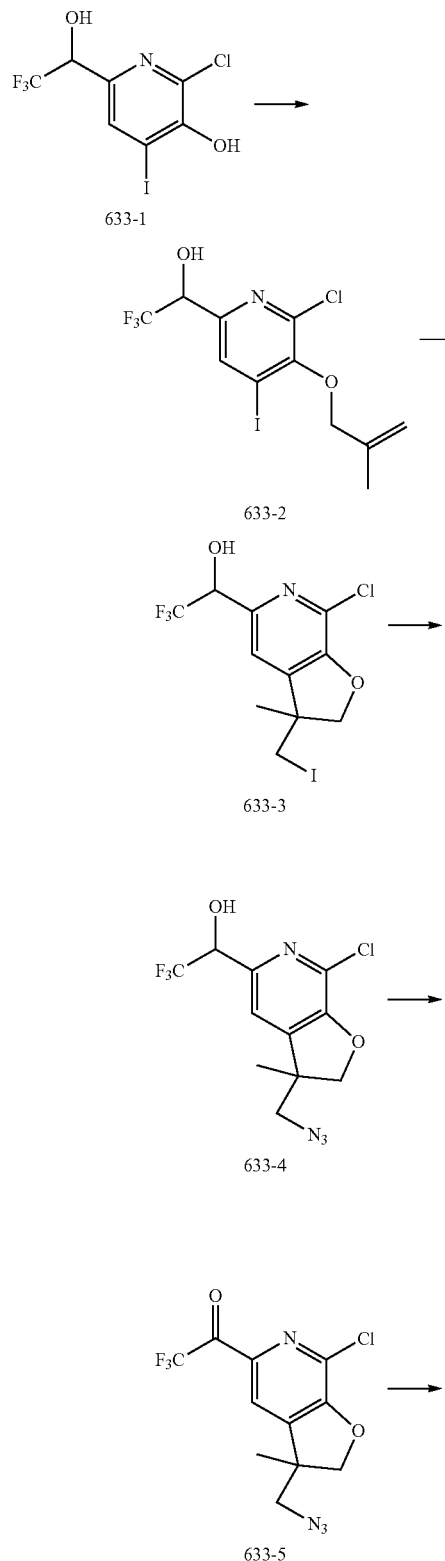
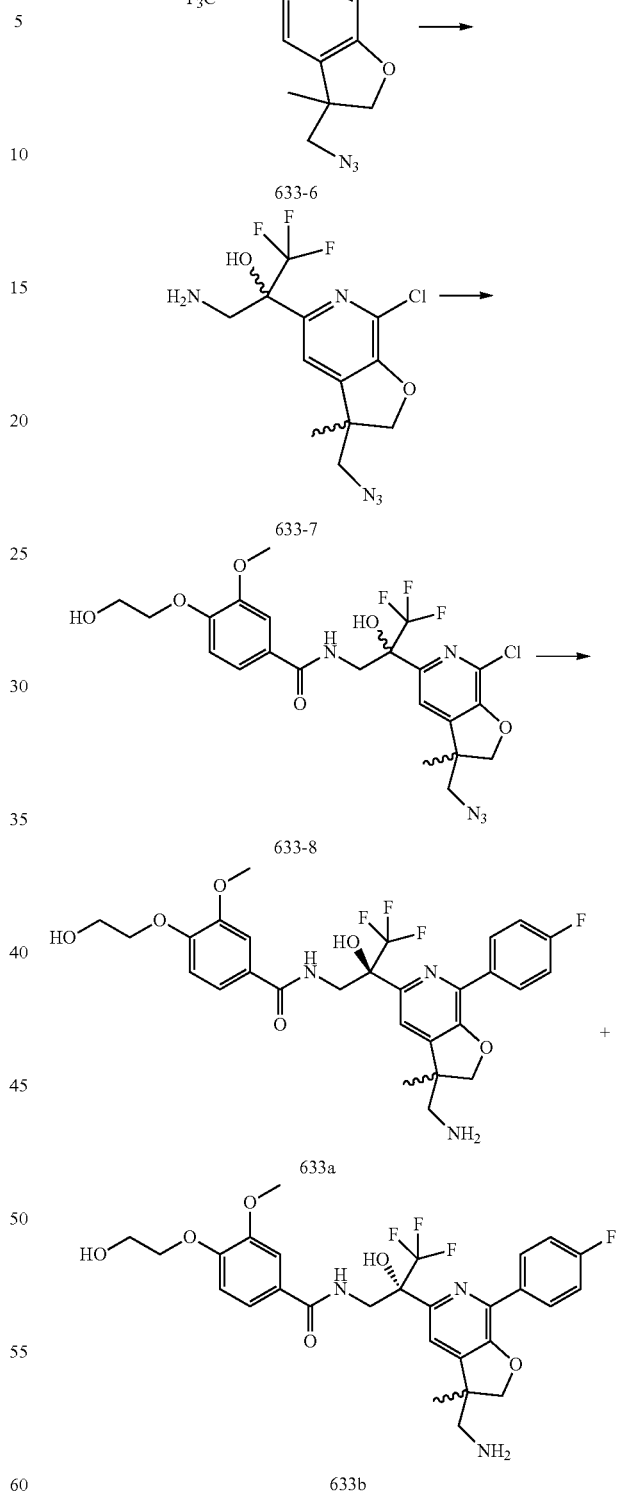
633-1 (9.0 g, 25.5 mmol) and NaHCO₃ (6.4 g, 76.4 mmol) were dissolved in DMF (80 mL). 3-bromo-2-methylprop-1-ene (4.5 g, 33.1 mmol) was added by syringe, and the mixture was heated to 70° C. for 3 h. After cooling to r.t, the reaction was quenched with H₂O and extracted with EA.

The organic phase was washed with brine, dried over anhydrous MgSO4, filtered and concentrated under reduced pressure. The residue was purified by flash chromatography (eluent:PE:EA=30:1~8:1) to give 633-2 (8.02 g, 77%) as a white solid. +ESI-MS: m/z 407.8 [M+H]$^+$.

A sealed tube was charged with a solution of 633-2 (7.0 g, 17.2 mmol) in toluene (50 mL). Pd$_2$(dba)$_3$ (580.0 mg, 1.0 mmol) and Q-phos (1.0 g, 1.4 mmol) was added under N$_2$. The sealed tube was stirred at 100° C. in an oil bath. After stirring for 7 h, the mixture was cooled to r.t. and concentrated at low pressure. The residue was purified by flash chromatography using 2-5% EA in PE as the eluent to afford 633-3 (3.5 g, 50%) as a solid.

To a solution of 633-3 (3.5 g, 8.6 mmol) in DMF (50 mL) was added NaN$_3$ (12.4 g, 190.7 mmol) at r.t. The solution was heated to 70° C. and stirred for 16 h. The mixture was cooled to r.t. and quenched by pouring into water. The mixture was extracted with EA (3×50 mL). The combined organic layers were washed with brine, dried over anhydrous MgSO4, filtered and concentrated under reduced pressure. The residue was purified by column chromatography using 5-12% EA in PE as the eluent to give 633-4 (2.4 g, 86.6%) as an oil. +ESI-MS: m/z 322.9 [M+H]$^+$.

633-8 was prepared following the general procedure for preparing 604a using 633-4.

633-8 (500 mg, 0.92 mmol), (4-fluorophenyl)boronic acid (167 mg, 1.2 mmol), Cs$_2$CO$_3$ (450 mg, 1.4 mmol) and Pd(PPh$_3$)$_4$ (106 mg, 0.092 mmol) were taken up into a microwave tube in a co-solvent of dioxane (15 mL) and H$_2$O (3 mL). The sealed tube was heated at 110° C. by microwave irradiation and stirred for 1 h. LCMS showed that ~30% of the desired product was formed. The solution was concentrated under reduced pressure, and the residue was purified by TLC and further purified by prep-HPLC to give pure 633a (~80 mg) and 633b (~70 mg). 633a: +ESI-MS: m/z 580.2 [M+H]$^+$ and 633b: +ESI-MS: m/z 580.1 [M+H]$^+$.

Example 324

Preparation of Compound 638

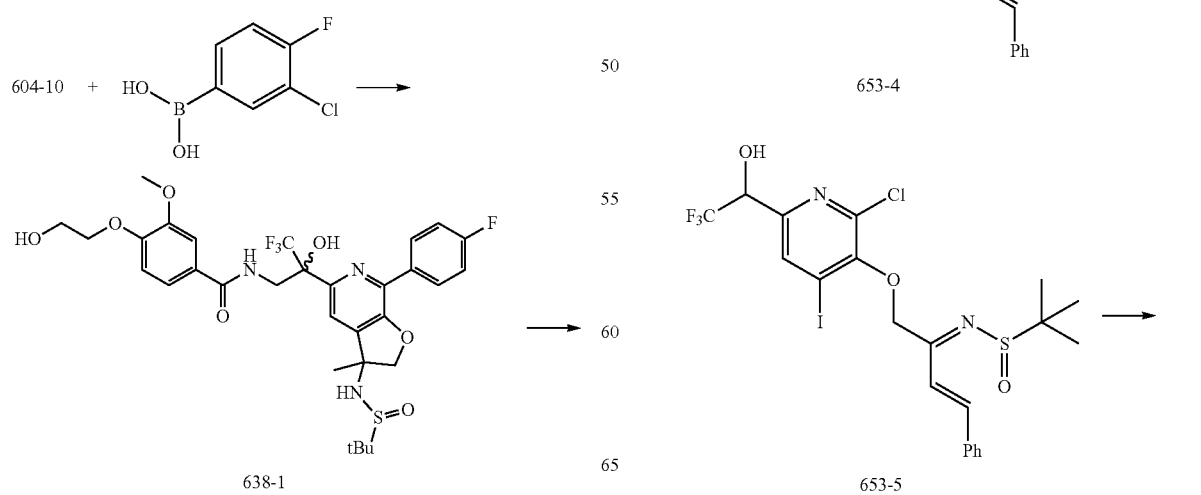

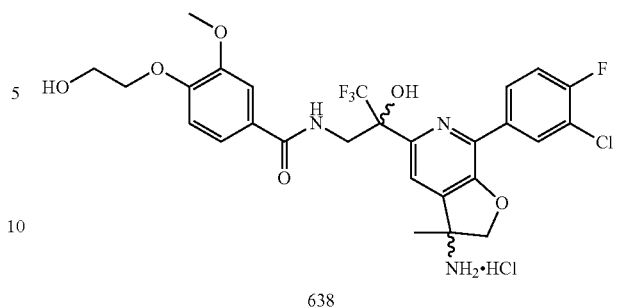

Compound 638 (white solid, 15 mg) was prepared following the general procedure for preparing 604a using 604-10 and (3-chloro-4-fluorophenyl)boronic acid. +ESI-MS: m/z 600.1 [M+H]$^+$.

Example 325

Preparation of Compounds 653 and 654

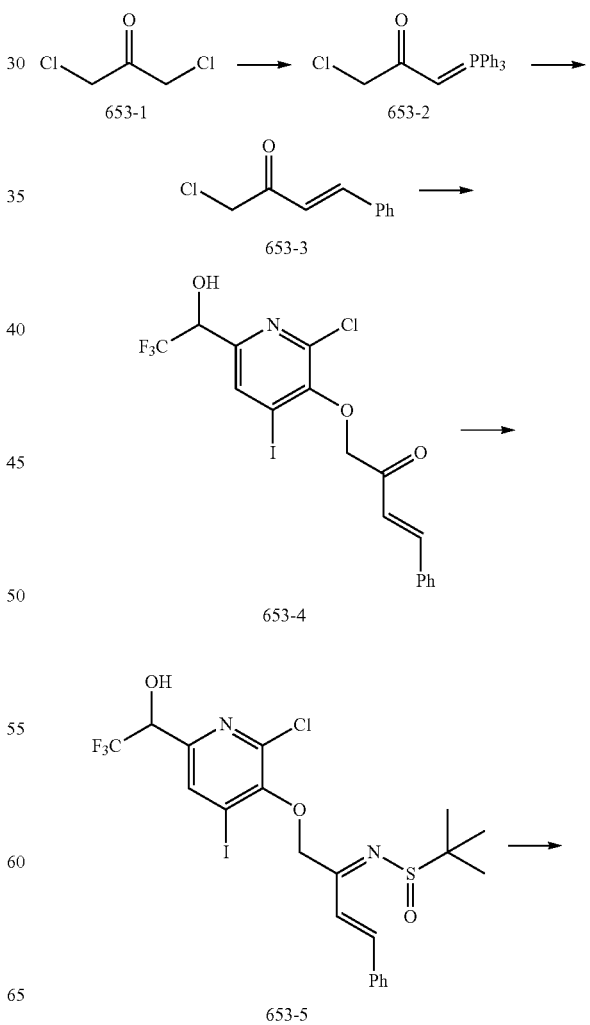

517
-continued
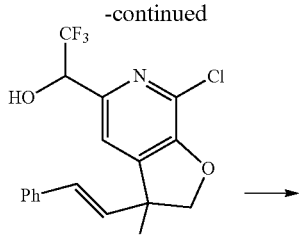
653-6
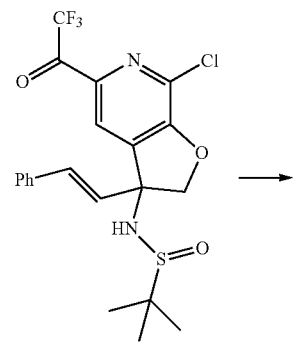
653-7
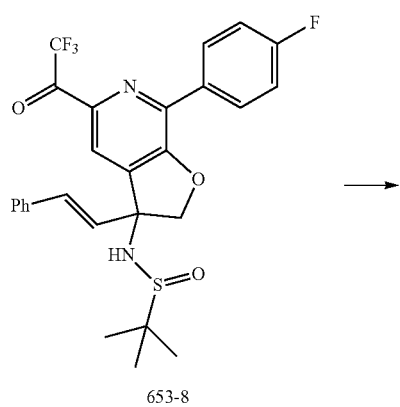
653-8
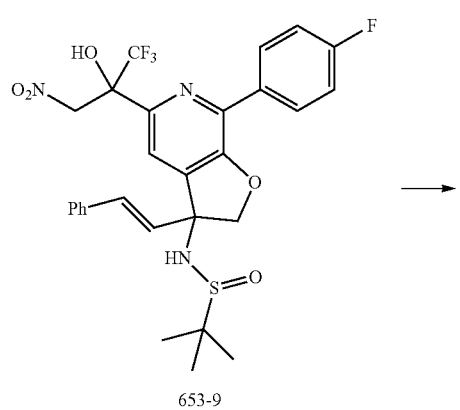
653-9
518
-continued
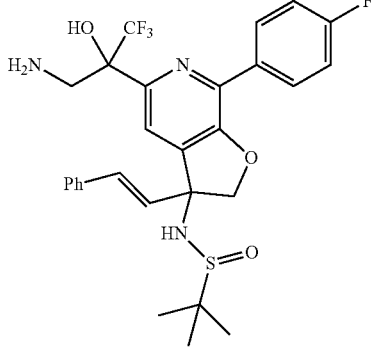
653-10
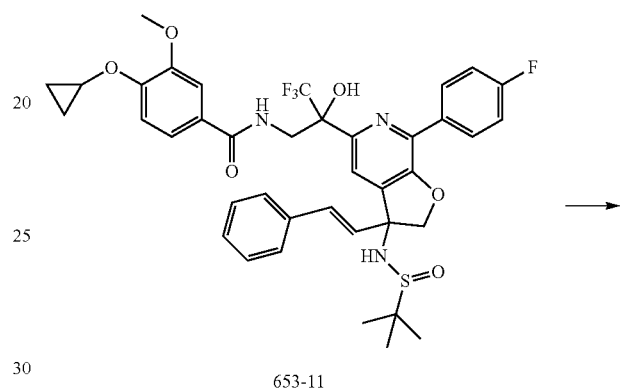
653-11
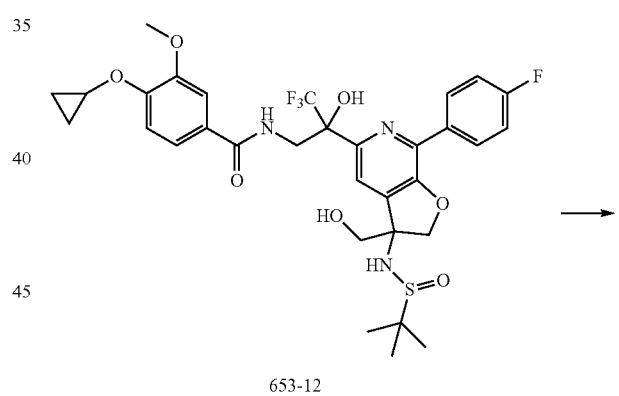
653-12
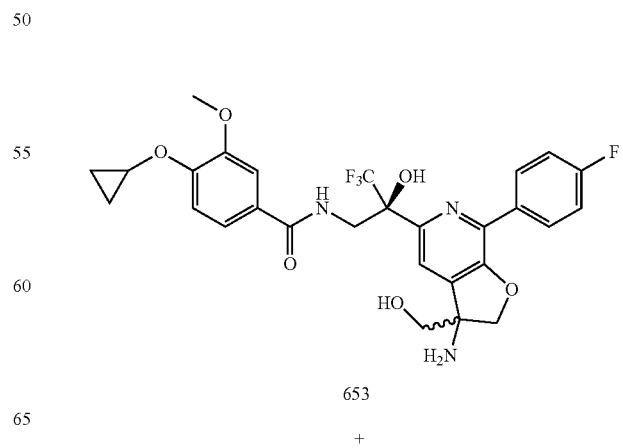
653
+

-continued

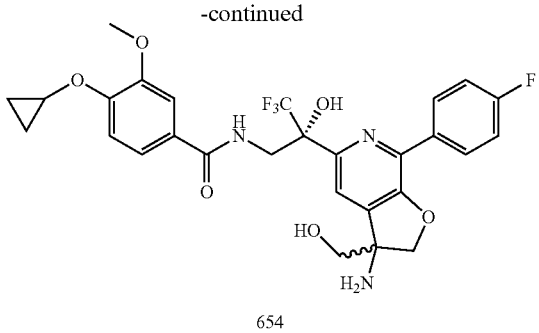

654

2-chloro-4-iodo-6-(2,2,2-trifluoro-1-hydroxyethyl)pyridin-3-ol was prepared as provided in Hénichart, J. et al., *J. Het. Chem.* (1986), 23(5):1531-1533.

To a solution of 2-chloro-4-iodo-6-(2,2,2-trifluoro-1-hydroxyethyl)pyridin-3-ol (16 g, 45.3 mmol) in $CH_3CN$ (150 mL) was added $K_2CO_3$ (12.5 g, 90.5 mmol) in one portion. After stirring at r.t. for 5 mins, a solution of 653-3 (9.8 g, 54.3 mmol) in $CH_3CN$ (10 mL) was added slowly under $N_2$. The mixture was stirred at 90° C. for 1 h in a pre-heated oil bath. After cooling to r.t., the mixture was poured into water (150 mL) and stirred for 5 mins. The mixture was extracted with EA (2×150 mL). The combined organic phase was washed with brine, dried with anhydrous $Na_2SO_4$, filtered and concentrated in vacuum. The residue was purified by column chromatography using 2-5% EA in PE as the eluent to afford 653-4 (10.9 g, 49%) as a yellow solid.

653-8 was prepared following the general procedure for preparing 604a using 653-4.

To a solution of 653-8 (1.0 g, 1.9 mmol) in $CH_3NO_2$ (15 mL) was added TEA (2.0 mL) in one portion at r.t. The reaction mixture was stirred for 2 h and concentrated under reduced pressure. The residue was purified by column chromatography using 10-20% EA in PE as the eluent to afford 653-9 (0.8 g, 72%) as a yellow solid. +ESI-MS: m/z 593.9 $[M+H]^+$.

To a solution of 653-9 (400 mg, 0.67 mmol) in EtOH (10 mL) and $H_2O$ (10 mL) was added Fe (188 mg, 3.4 mmol) powder and $NH_4Cl$ (180 mg, 3.4 mmol) in one portion. The mixture was stirred at 80° C. for 2 h. After cooling to r.t., the mixture was poured into water (20 mL) and extracted with EA (3×10 mL). The combined organic phase was washed with brine, dried with anhydrous $Na_2SO_4$, filtered and concentrated in vacuum. The residue was purified by column chromatography using EA as the eluent to afford 653-10 (250 mg, 66%) as a yellow solid. +ESI-MS: m/z 564.1 $[M+H]^+$.

To a solution of 4-cyclopropoxy-3-methoxybenzoic acid (75 mg, 0.36 mmol) in DMF (6.0 mL) was added HATU (137 mg, 0.36 mmol) and DIPEA (47 mg, 0.36 mmol). After stirring at r.t. for 5 mins, 653-10 (203 mg, 0.36 mmol) was added. The mixture was stirred for 1 h and then poured into water. The mixture was extracted with EA (2×10 mL). The combined organic phase was washed with brine, dried with anhydrous $Na_2SO_4$, filtered and concentrated in vacuum. The residue was purified by column chromatography using EA as the eluent to afford 653-11 (120 mg, 44.2%) as a yellow solid. +ESI-MS: m/z 754.2 $[M+H]^+$.

Ozone was bubbled into a solution of 653-11 (120 mg, 0.16 mmol) in anhydrous MeOH (10 mL) at −78° C. for 6 mins. After excess $O_3$ was purged by $N_2$, $NaBH_4$ (18.1 mg, 0.48 mmol) was added at r.t. The reaction was stirred for 0.5 h and quenched with water. The mixture was extracted with EA (2×10 mL), dried over sodium sulfate, concentrated to give the crude product. The residue was purified by column chromatography using EA as the eluent to afford 653-12 (70 mg, 65%) as a yellow solid. +ESI-MS: m/z 682.1 $[M+H]^+$.

To a solution of 653-12 (70 mg, 0.1 mmol) in MeOH (10 mL) was added HCl/dioxane (3 mL, 4 M). The mixture was stirred at r.t. for 20 mins. The mixture was concentrated under reduced pressure. The residue was purified by prep-HPLC to afford 653 (12 mg) and 654 (18 mg) as white solids. 653: +ESI-MS: m/z 578.1 $[M+H]^+$ and 654: +ESI-MS: m/z 578.1 $[M+H]^+$.

Example 326

Preparation of Compound 606

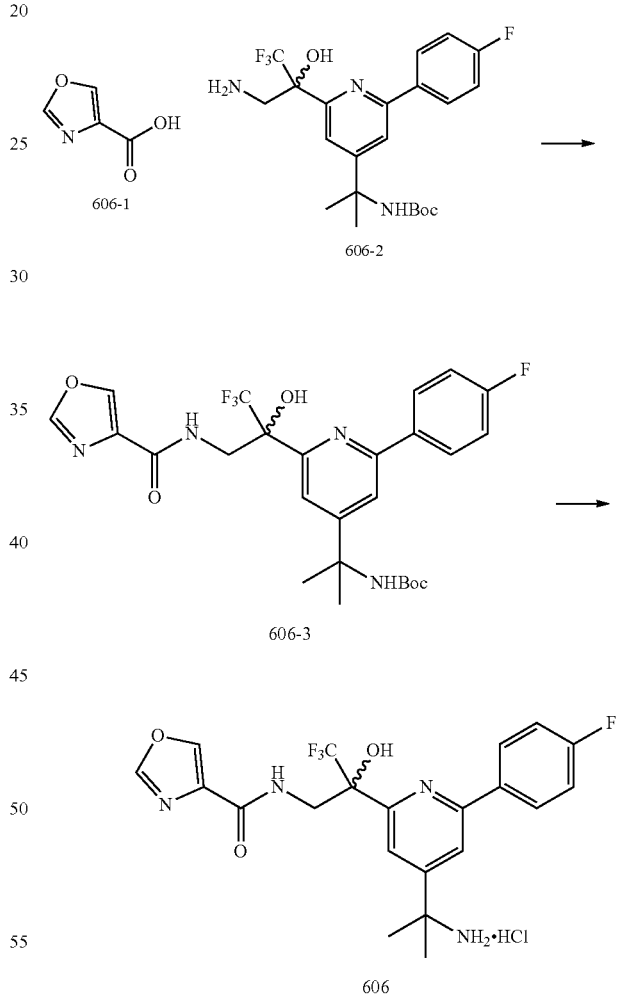

A mixture of 606-2 (45 mg, 0.1 mmol), 606-1 (16 mg, 0.1 mmol) and TEA (1 mmol) is dissolved in anhydrous DCM (4 mL) with stirring. The solution was treated with HATU (38 mg, 0.1 mmol) in one portion. After stirring at r.t. for 30 mins, TFA (1 mL) was added. The solution was stirred at r.t. for 2 h. The mixture was concentrated to dryness. The residue was isolated by acidic prep-HPLC to afford 606 (26 mg, 45%) as a white solid. +ESI-MS: m/z 452.0 $[M+H]^+$.

Example 327

Preparation of Compound 607

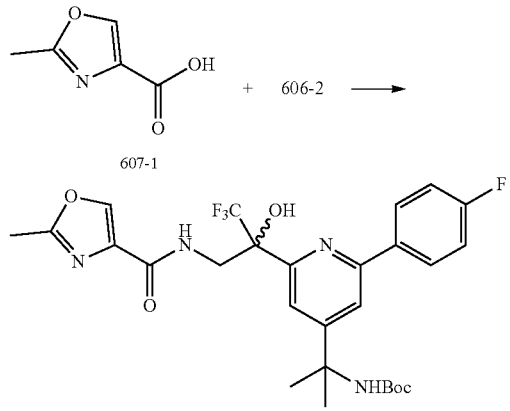

Compound 607 was prepared following the general procedure for preparing 606 using 607-1 and 606-2. The crude product was purified by prep-HPLC to give 607 (66 mg, 75%) as a white solid (66 mg, 75%). +ESI-MS: m/z 466.9 [M+H]$^+$.

Example 328

Preparation of Compound 608

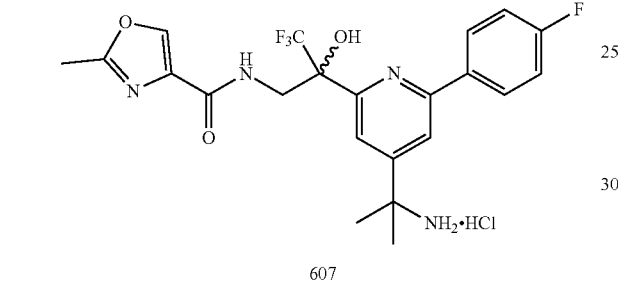

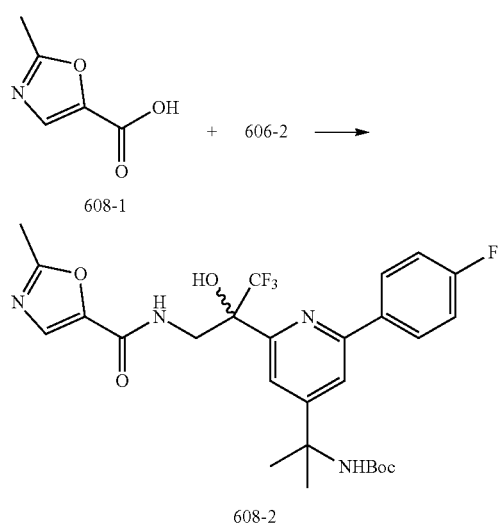

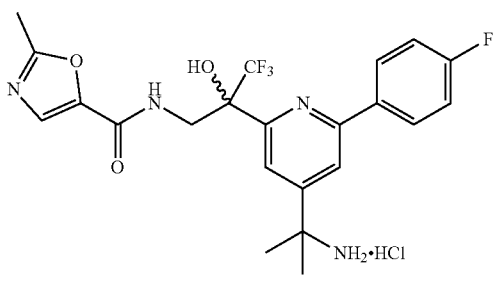

Compound 608 was prepared following the general procedure for preparing 606 using 608-1 and 606-2. The crude product was purified by prep-HPLC to give 608 (46.5 mg, 84%) as a white solid. +ESI-MS: m/z 466.9 [M+H]$^+$.

Example 329

Preparation of Compound 609

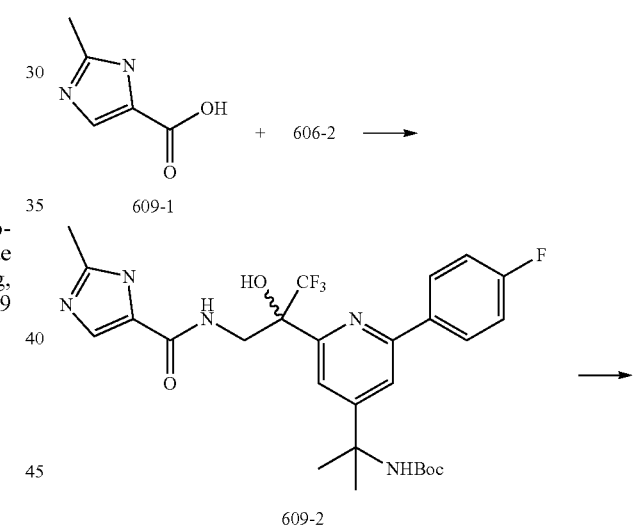

Compound 609 was prepared following the general procedure for preparing 606 using 609-1 and 606-2. The crude product was purified by prep-HPLC to give 609 (13.5 mg, 34%) as a white solid. +ESI-MS: m/z 465.9 [M+H]$^+$.

Example 330

Preparation of Compound 610

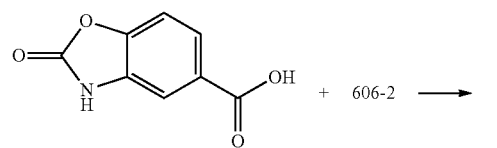

610-1

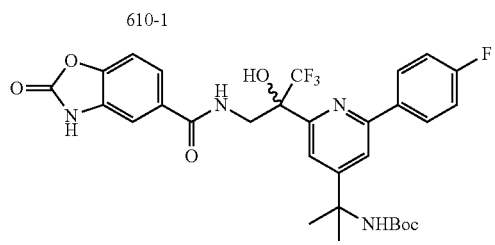

610-2

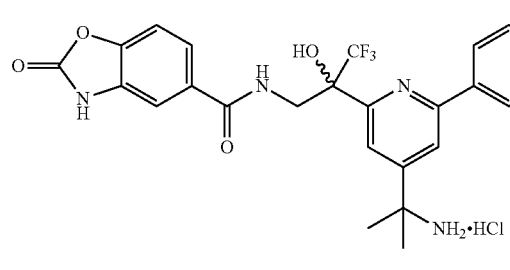

610

Compound 610 was prepared following the general procedure for preparing 606 using 610-1 and 606-2. The crude product was purified by prep-HPLC to give 610 (34 mg, 57%) as a white solid. +ESI-MS: m/z 518.9 [M+H]$^+$.

Example 331

Preparation of Compound 613

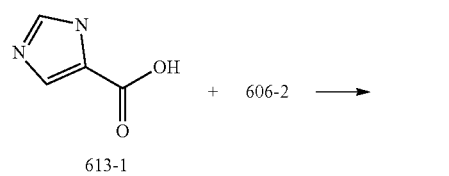

613-1

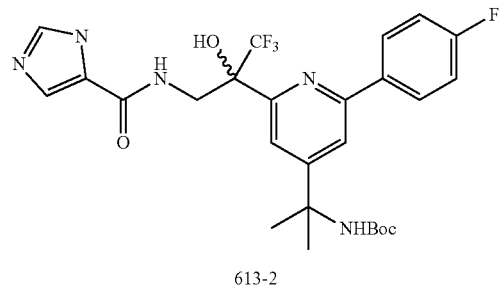

613-2

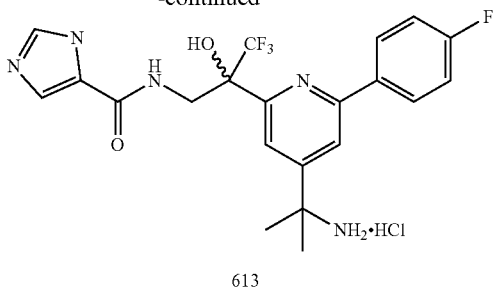

613

Compound 613 was prepared following the general procedure for preparing 606 using 613-1 and 606-2. The crude product was purified by prep-HPLC to give 613 (29 mg, 50%) as a white solid. +ESI-MS: m/z 451.9 [M+H]$^+$.

Example 332

Preparation of Compounds 623a and 623b

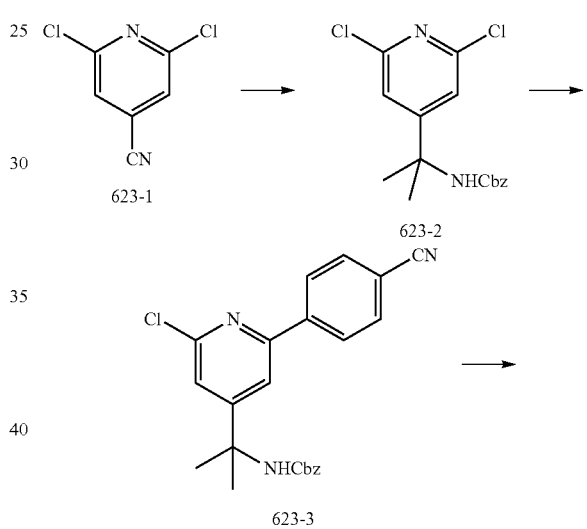

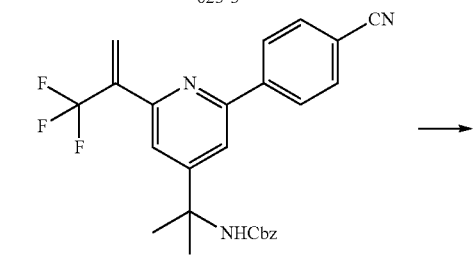

623-4

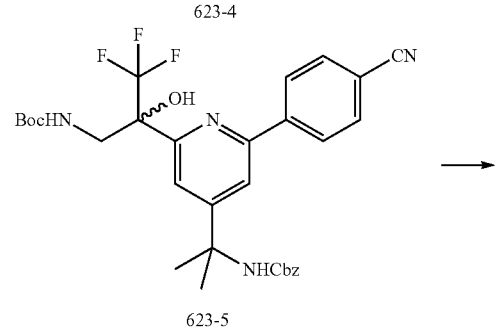

623-5

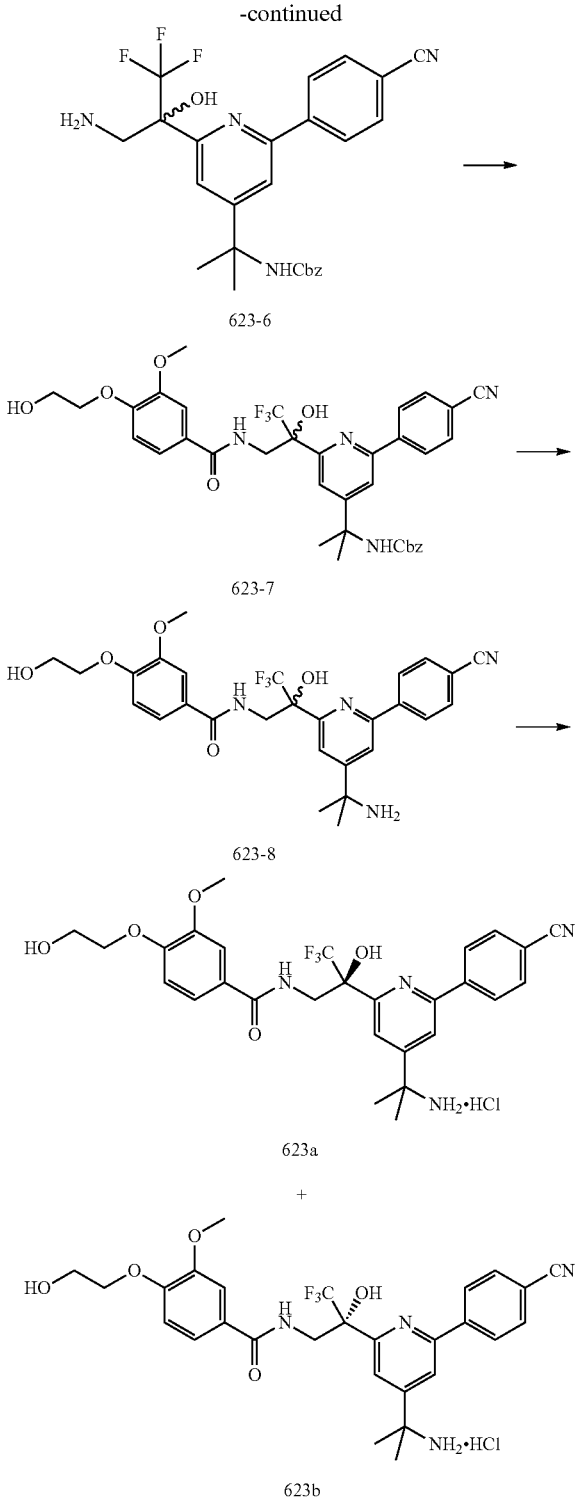

623-6

623-7

623-8

623a

+

623b

To a solution of 623-1 (20 g, 116 mmol) in anhydrous toluene (200 mL) was added MeMgBr (3 M, 115.61 mL) slowly at 0° C. under N$_2$. After addition and stirring for 30 mins, Ti(i-PrO)$_4$ (36.1 g, 127.2 mmol) was added dropwise The mixture was heated at 100° C. for 30 mins. After cooling to r.t., copious quantities of diatomite was added to the mixture. The mixture was basified with aqueous NaOH solution (2 M) and filtered through a pad of diatomite. The cake was washed with EA, and the filtrate was separated and concentrated to provide crude 2-(2,6-dichloro-4-pyridyl)propan-2-amine (~25 g).

Crude 2-(2,6-dichloro-4-pyridyl)propan-2-amine was dissolved in anhydrous DCM (250 mL). The solution was treated with CbzCl (20.79 g, 121.90 mmol) and DIPEA (31.51 g, 243.80 mmol). The mixture was stirred at r.t. overnight. The mixture was washed with brine, dried over anhydrous Na$_2$SO$_4$ and concentrated to dryness under reduced pressure. The residue was purified by column chromatography using 3-10% EA in PE as the eluent to give 623-2 (15 g, 36% yield over 3 steps) as a white solid. +ESI-MS: m/z 338.8 [M+H]$^+$.

To a stirring solution of 623-2 (5.0 g, 14.7 mmol) in dioxane (100 mL) and water (10 mL) were added (4-cyanophenyl)boronic acid (2.17 g, 14.7 mmol), Cs$_2$CO$_3$ (9.6 g, 29.5 mmol), and Pd(dppf)Cl2 (1.08 g, 1.47 mmol) under N$_2$. The mixture was stirred at 80° C. for 1 h under N$_2$. After cooling to r.t., the mixture was diluted with EA (100 mL) and water (100 mL). The combined organic phase was washed with brine, dried over anhydrous Na$_2$SO$_4$ and concentrated to dryness under reduced pressure. The residue was purified by column chromatography using 3-20% EA in PE as the eluent to give 623-3 (2.0 g, 33% yield) as a white solid.

Compound 623-8 was prepared following the general procedure for preparing 533 using 623-3. Racemic 623-8 was separated by SFC and prep-HPLC to afford 623a (62 mg) and 623b (29 mg) as white solids. 623a: +ESI-MS: m/z 559.4 [M+H]$^+$ and 623b: +ESI-MS: m/z 559.0 [M+H]$^+$.

Example 333

Preparation of Compounds 624a and 624b

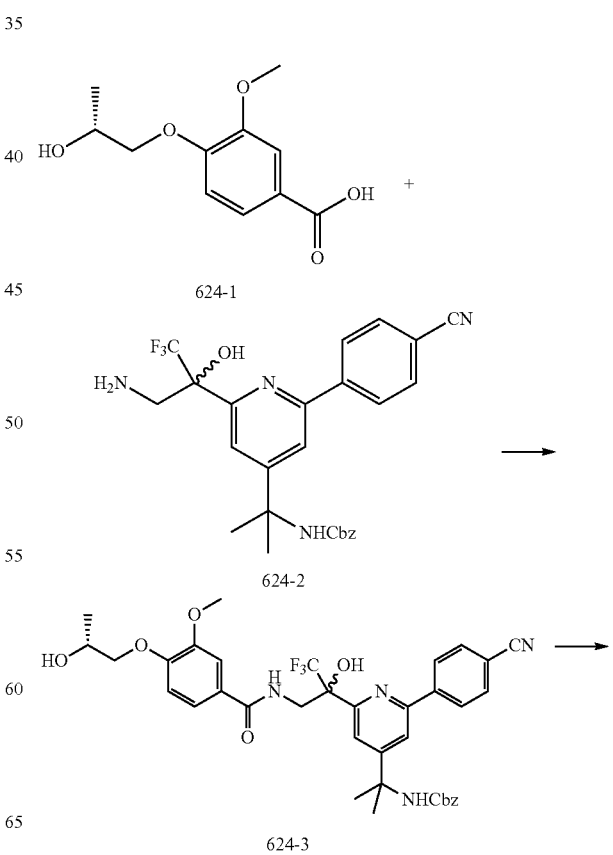

624-1

624-2

624-3

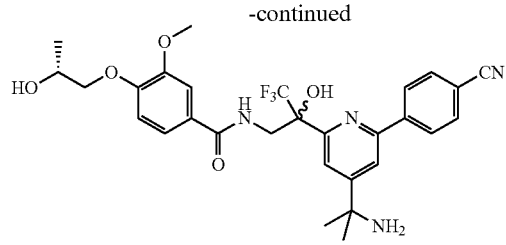
624-4
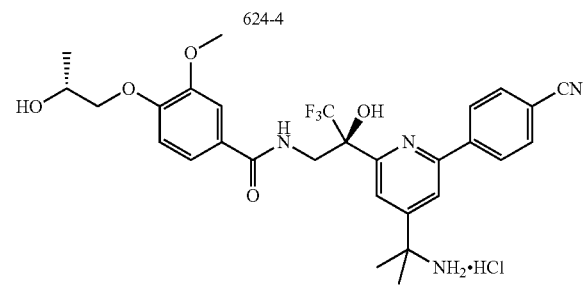
624a
+
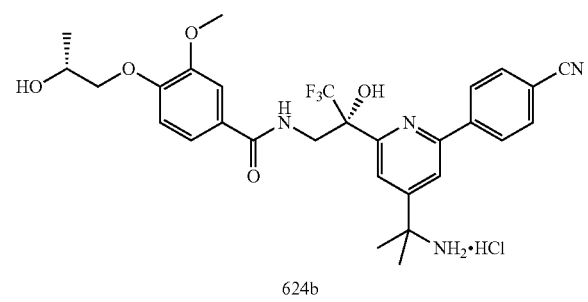
624b
Compounds 624a (white solid, 62 mg) and 624b (white solid, 62 mg) were prepared following the general procedure for preparing 623a and 623b using 624-1 and 624-2. 624a: +ESI-MS: m/z 573.1 [M+H]⁺ and 624b: +ESI-MS: m/z 573.1 [M+H]⁺.
Example 334
Preparation of Compound 625
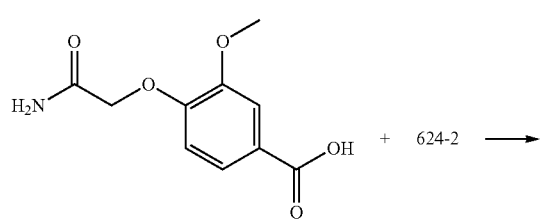
625-1
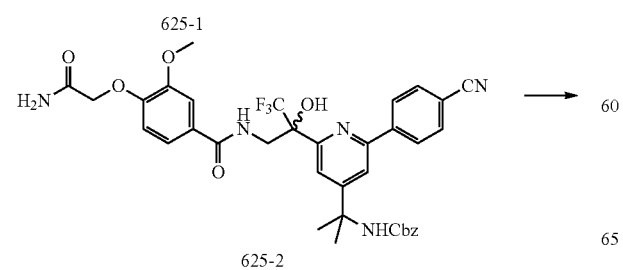
625-2
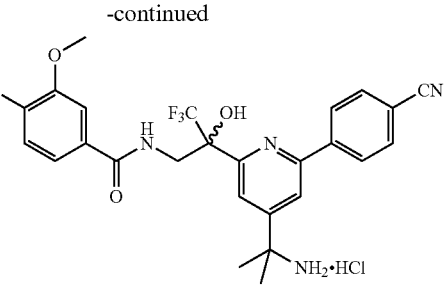
625
Compound 625 (white solid, 32 mg) was prepared following the general procedure for preparing 623a and 623b using 625-1 and 624-2. +ESI-MS: m/z 572.1 [M+H]⁺.
Example 335
Preparation of Compound 634
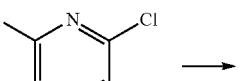
634-1
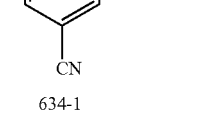
634-2
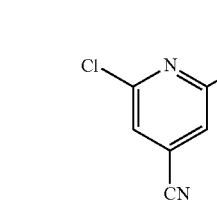
634-3
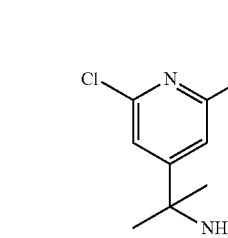
634-4

529
-continued
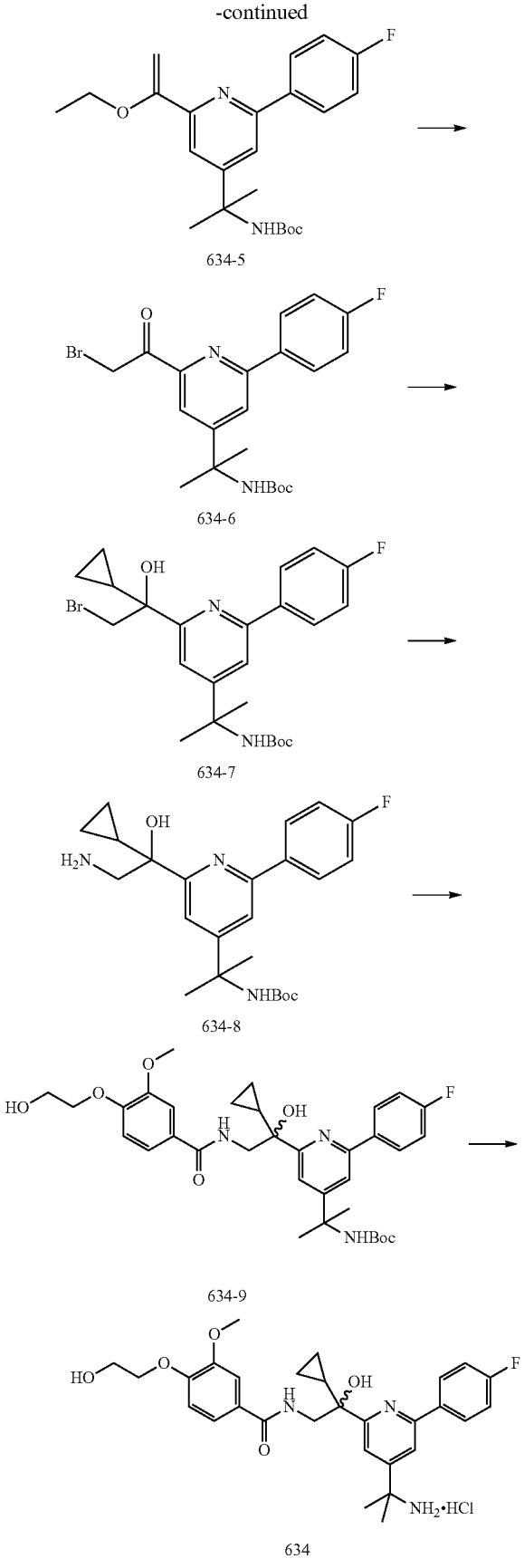
530
Compound 634 (white solid, 10 mg) was prepared following the general procedure for preparing 406 using 634-1 and 634-2. +ESI-MS: m/z 524.1 [M+H]$^+$.
Example 336
Preparation of Compound 639
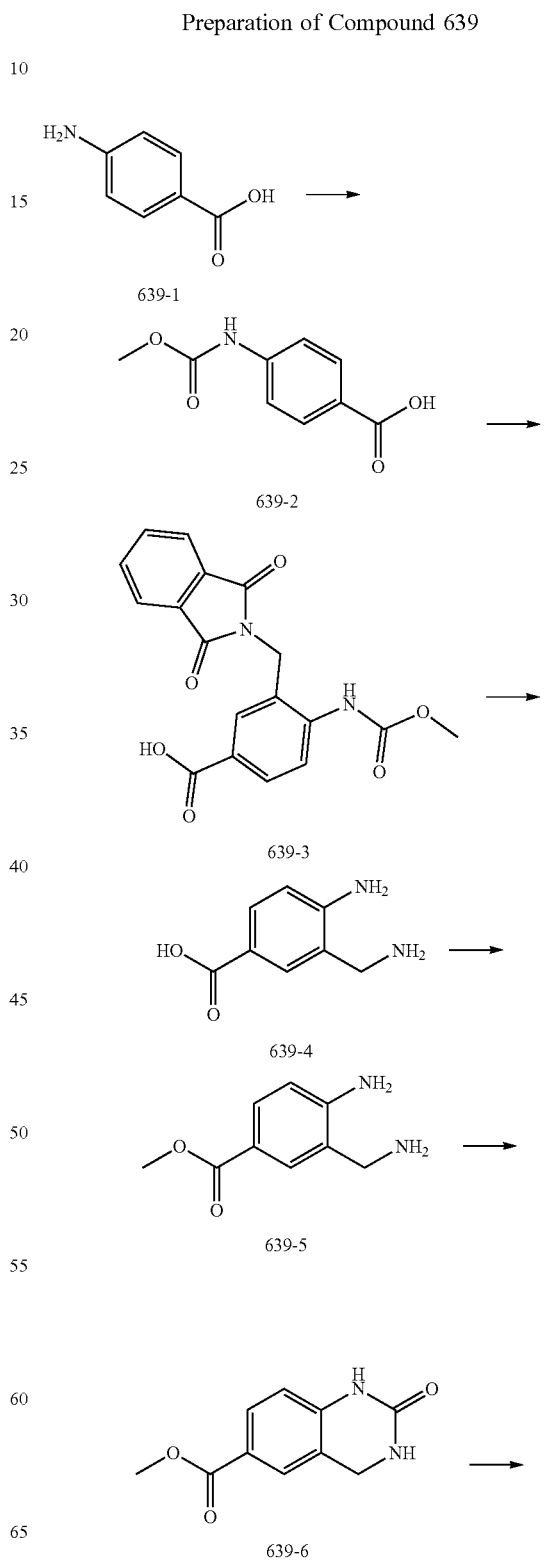

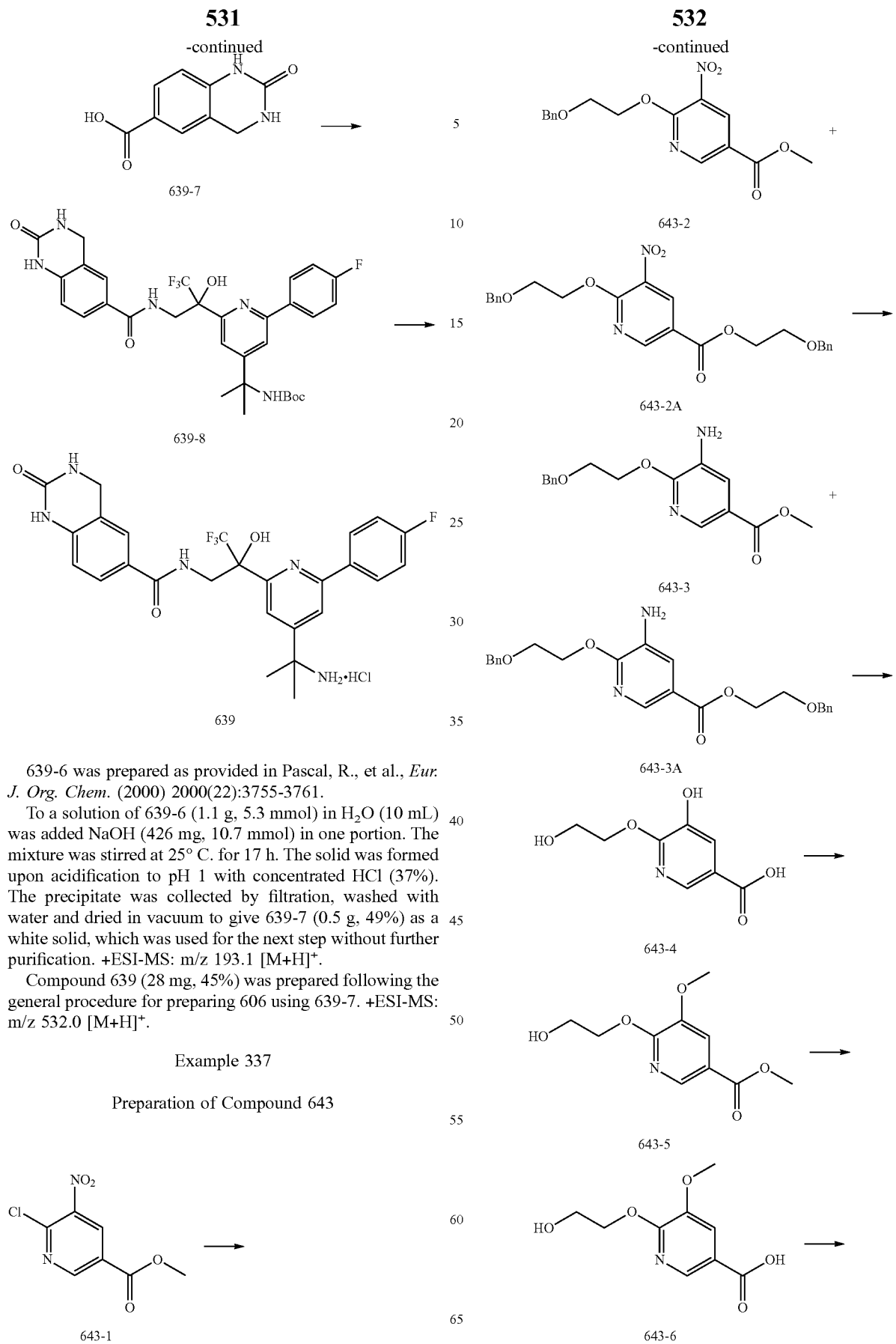

639-6 was prepared as provided in Pascal, R., et al., *Eur. J. Org. Chem.* (2000) 2000(22):3755-3761.

To a solution of 639-6 (1.1 g, 5.3 mmol) in H$_2$O (10 mL) was added NaOH (426 mg, 10.7 mmol) in one portion. The mixture was stirred at 25° C. for 17 h. The solid was formed upon acidification to pH 1 with concentrated HCl (37%). The precipitate was collected by filtration, washed with water and dried in vacuum to give 639-7 (0.5 g, 49%) as a white solid, which was used for the next step without further purification. +ESI-MS: m/z 193.1 [M+H]$^+$.

Compound 639 (28 mg, 45%) was prepared following the general procedure for preparing 606 using 639-7. +ESI-MS: m/z 532.0 [M+H]$^+$.

Example 337

Preparation of Compound 643

533
-continued

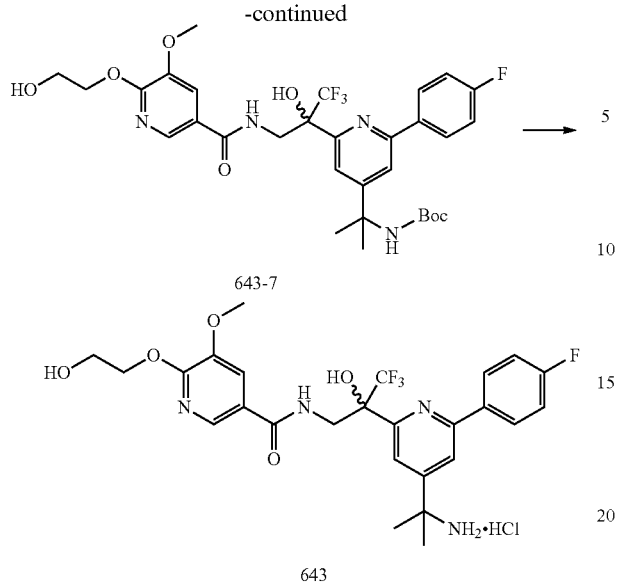

To a solution of 643-1 (1.5 g, 6.9 mmol) in DMF (20 mL) was added 2-benzyloxyl ethanol (6.3 g, 41 mmol) at 25° C. The solution was stirred for 6 h and then poured into $H_2O$ (20 mL). The mixture was extracted with EA (2×40 mL). The combined organic phase was washed with brine, dried over anhydrous $Na_2SO_4$ and concentrated under reduced pressure. The residue was purified by column chromatography using 5~10% EA in PE as the eluent to give a mixture of 643-2 and 643-2A (1.50 g).

To a solution of 643-2A and 643-2A (1.50 g, crude mixture) in $EtOH/H_2O$ (20/10 mL) were added Fe (1.5 g, 26.7 mmol) and $NH_4Cl$ (1.5 g, 28 mmol) at 25° C. The solution was heated to 80° C. and stirred for 2 h. The mixture was filtered, and the filtrate was concentrated to give a mixture of 643-3 and 643-3A (1.20 g, crude). The products were used for the next step without further purification.

A mixture of 643-3 and 643-3A (1.2 g, crude) in $H_2SO_4/H_2O$ (1:1) (10 mL) was cooled to −5° C. $NaNO_2$ (376 mg, 5.45 mmol) was added in portions at −5° C. The solution was stirred at −5° C. for 0.5 h. The solution was heated to 120° C. After stirring 0.5 h at 120° C., the solution was poured into ice water (20 mL) and extracted with EA (2×20 mL). The organic phase was concentrated at low pressure. The residue was purified by chromatography to give 643-4 (0.3 g, crude).

To a solution of 643-4 (0.3 g, crude) in DMF (5 mL), $K_2CO_3$ (320 mg, 2.3 mmol) was added dropwise $CH_3I$ (2.14 g, 15.1 mmol) at r.t. The solution was stirred for 3 h. The mixture was poured into $H_2O$ (10 mL) and extracted with EA (2×20 mL). The combined organic phase was washed with brine, dried over anhydrous $Na_2SO_4$ and concentrated under reduced pressure to give crude 643-5 (210 mg), which was used in the next step directly.

To a mixture of 643-5 (210 mg, crude) in MeOH (2 mL) was added an aq. NaOH solution (2 mL, 2 M) in one portion at 25° C. The mixture was heated to 60° C. and stirred for 2 h. The mixture was cooled to r.t. and acidified to pH=3-4 by the addition of 1 M aqueous HCl. The mixture was extracted with EA (3×10 mL). The combined organic phase was washed with brine, dried over anhydrous $Na_2SO_4$ and concentrated under reduced pressure. The residue was purified by prep-TLC (EA) to afford 643-6 (110 mg, 56%).

534

Compound 643 (white solid, 14 mg, 24%) was prepared following the general procedure for preparing 606 using 643-6. +ESI-MS: m/z 553.1 $[M+H]^+$.

Example 338

Preparation of Compound 644

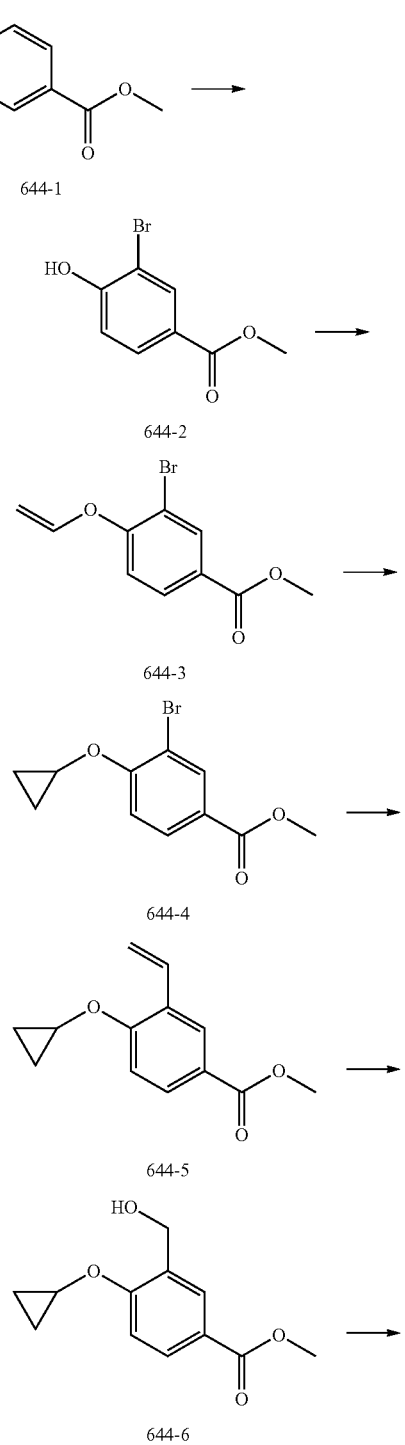

535

-continued

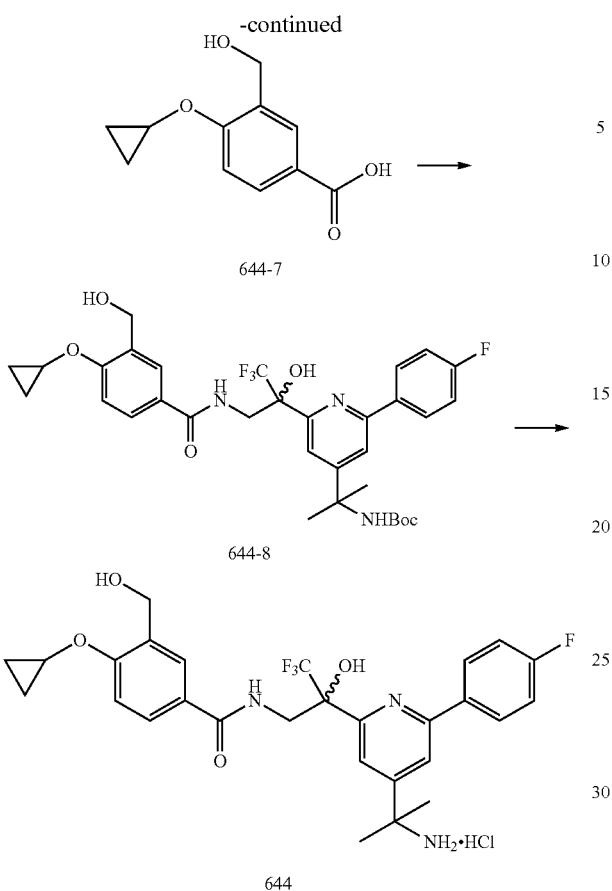

644-2 was prepared as provided in PCT Publication No. WO 2013/007663, published Jan. 17, 2013

644-4 was prepared following the general procedure for preparing 272 using 644-2.

A mixture of 644-4 (1.5 g, 5.5 mmol), potassium vinyl trifluoroborate (1.6 g, 11.1 mmol), $Cs_2CO_3$ (1.8 g, 5.5 mmol) and $Pd(dppf)Cl_2$ (0.4 g, 0.5 mmol) in i-PrOH (10 mL) was de-gassed. The mixture was heated to 80° C. for 15 h under $N_2$. After cooling to r.t, the mixture was concentrated under reduced pressure. The residue was purified by column chromatography using 5-20% DCM in PE to give 644-5 (0.9 g, 74.5%).

Ozone was bubbled into a solution of 644-5 (0.87 g, 4 mmol) in anhydrous MeOH (10 mL) at −78° C. for 10 mins. After the excess ozone was purged by $N_2$, $NaBH_4$ (304 mg, 8 mmol) was added at 25° C. The solution was stirred at 25° C. for 30 mins. The reaction was quenched with $H_2O$ and extracted with EA (3×20 mL). The combined organic solutions were washed with brine, dried over anhydrous $Na_2SO_4$ and concentrated under reduced pressure. The residue was purified by column chromatography 10-25% DCM in PE to give 644-6 (0.7 g, 79%) as a solid.

To a solution of 644-6 (0.5 g, 2.3 mmol) in MeOH (3 mL) was added NaOH (0.5 g, 12.5 mmol) in $H_2O$ (3 mL). After stirring at 60° C. for 1 h, the mixture was acidified to pH=3-4 by addition of 2 M HCl solution. The mixture was extracted with EA (3×10 mL). The combined organic solutions were washed with brine, dried over $Na_2SO_4$ and concentrated under reduced pressure to give 644-7 (0.4 g, 85.3%).

Compound 644 (white solid, 27 mg, 42%) was prepared following the general procedure for preparing 606 using 644-7. +ESI-MS: m/z 548.0 [M+H]⁺.

536

Example 339

Preparation of Compound 657

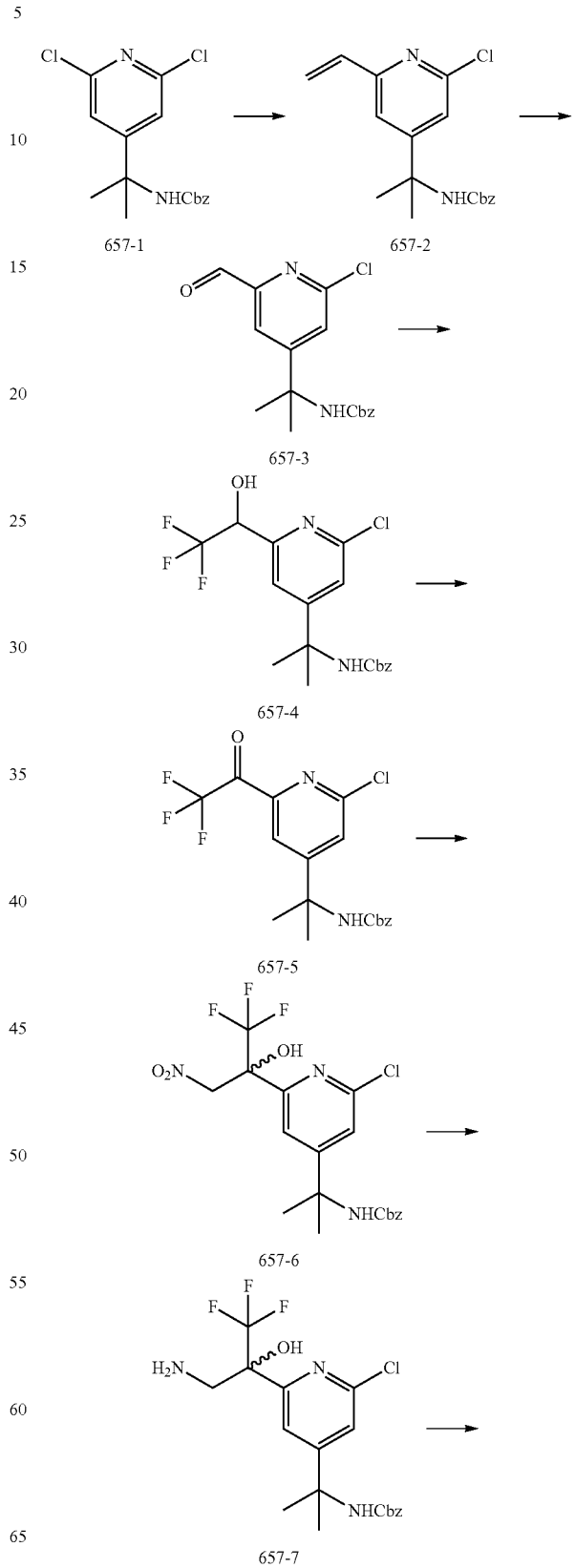

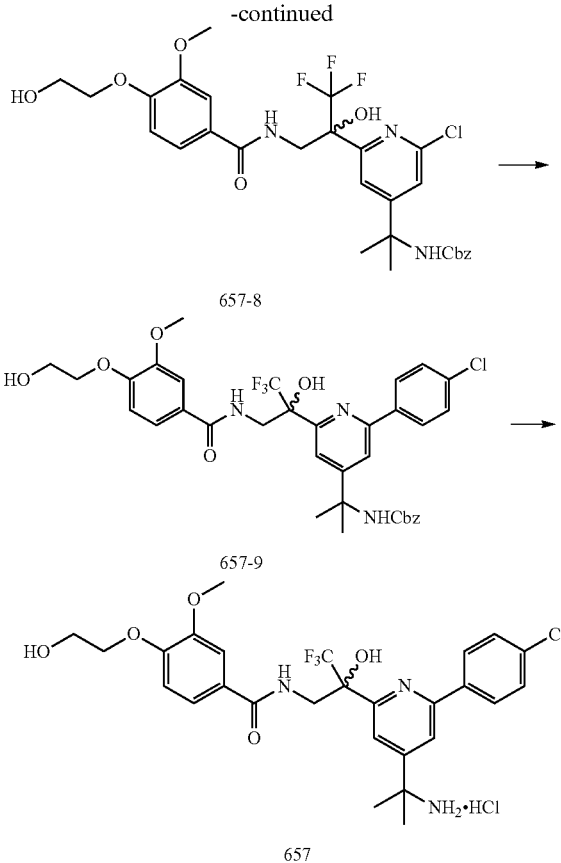

657-8

657-9

657

657-6 was prepared following the general procedure for preparing 606 using 657-1.

To a stirring solution of 657-6 (2 g, 4.3 mmol) in EtOH (40 mL) were added SnCl$_2$·2H$_2$O (3.9 g, 17.3 mmol) and conc. HCl (5.4 mL, 12 M). After stirring at 60° C. for 12 h, the mixture was cooled to r.t., and EtOH was removed under reduced pressure. The residue was diluted with water (10 mL) and neutralized by sat. aq. Na$_2$CO$_3$ solution. The aqueous phase was extracted with EA (3×30 mL). The combined organic phase was washed with brine, dried over anhydrous Na$_2$SO$_4$, filtered and concentrated under reduced pressure. The residue was purified by column chromatography using 50-100% EA in PE as the eluent to afford 657-7 (0.82 g, 44%) as a yellow oil. +ESI-MS: m/z 432.3 [M+H]$^+$.

To a solution of 4-(2-hydroxyethoxy)-3-methoxybenzoic acid (1.5 g, 7.2 mmol) in anhydrous DMF (30 mL) were added HATU (2.7 g, 7.2 mmol) and DIEA (2.3 g, 18 mmol). After stirring at 25° C. for 30 mins, a solution of 657-7 (2.5 g, 6.0 mmol) in DMF (5 mL) was added dropwise. The mixture was stirred at 25° C. for 1-2 h. The solution was poured into water (50 mL), and extracted with EA (3×30 mL). The combined organic phase was washed with brine, dried over anhydrous Na$_2$SO$_4$, filtered and concentrated under reduced pressure. The residue was purified by column chromatography using DCM:MeOH=200:1~80:1 as the eluent to afford 657-8 (2.2 g, 59%) as yellow oil.

657-8 (100 mg, 0.16 mmol), 4-Cl-phenyl boronic acid (50 mg, 0.32 mmol) and Cs$_2$CO$_3$ (156 mg, 0.48 mmol) were taken up into a microwave tube in co-solvent dioxane:H$_2$O (1.2 mL, v:v=5:1). The solution was degassed and Pd(dppf)Cl$_2$ (3.5 mg, 0.05 mmol) was added. The sealed tube was heated to 110° C. by microwave irradiation and stirred for 1 h. The solution was cooled to r.t. and poured into water (10 mL). The mixture was extracted with EA (3×5 mL). The combined organic layers were washed with brine, dried over anhydrous Na$_2$SO$_4$, filtered and concentrated under reduced pressure. The residue was purification by prep-TLC to give 657-9 (49 mg, 44%)

To a solution of 657-9 (49 mg) in CH$_3$CN (1 mL) was added one drop of TMSI at r.t., and the mixture stirred at r.t. for 10 mins. The mixture was poured into water, neutralized with sat. NaHCO$_3$ solution, and extracted with EA (3×10 mL). The combined organic layers were washed with brine, dried over anhydrous Na$_2$SO$_4$, filtered and concentrated under reduced pressure. The residue was purified by prep-HPLC to give 657 (15 mg) as a white solid. +ESI-MS: m/z 567.9 [M+H]$^+$.

Example 340

Preparation of Compound 658

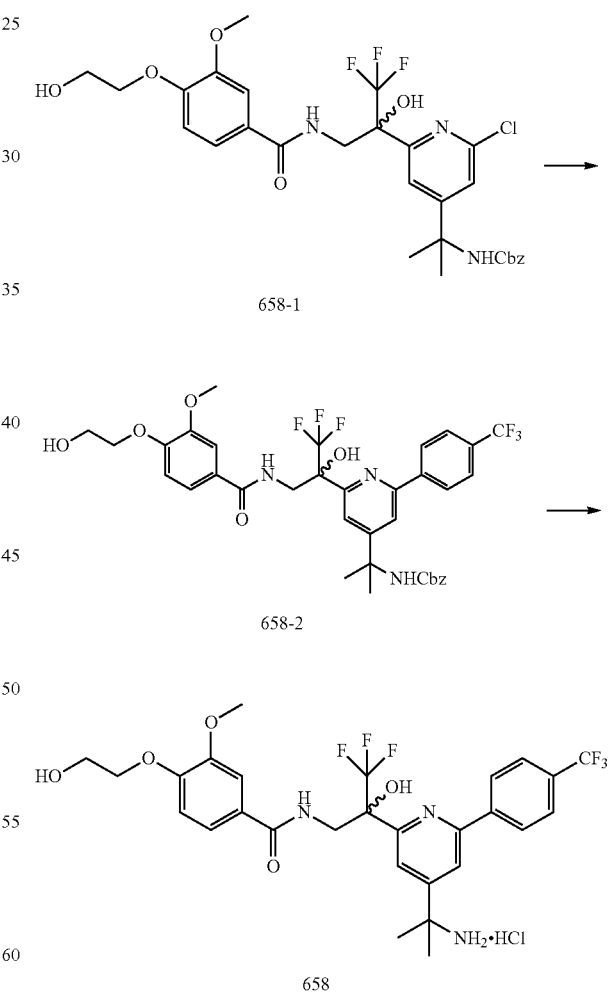

658-1

658-2

658

Compound 658 (white solid, 8 mg) was prepared following the general procedure for preparing 657 using 658-1 and 4-CF$_3$-phenyl boronic acid. The crude product was purified by prep-HPLC. +ESI-MS: m/z 602.1 [M+H]$^+$.

539

Example 341

Preparation of Compound 659

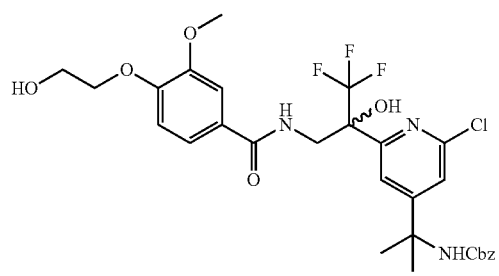

659-1

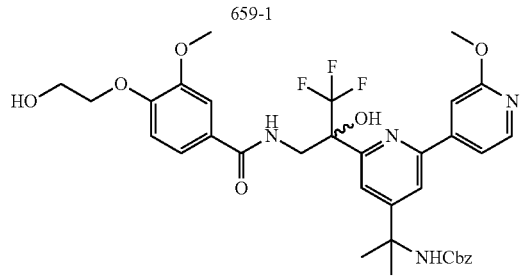

659-2

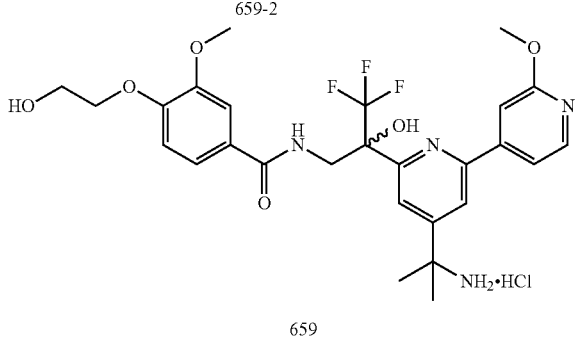

659

Compound 659 (white solid, 11 mg) was prepared following the general procedure for preparing 657 using 659-1 and 2-methoxy-4-pyridyl boronic acid. The crude product was purified by prep-HPLC. +ESI-MS: m/z 565.1 [M+H]$^+$.

Example 342

Preparation of Compound 660

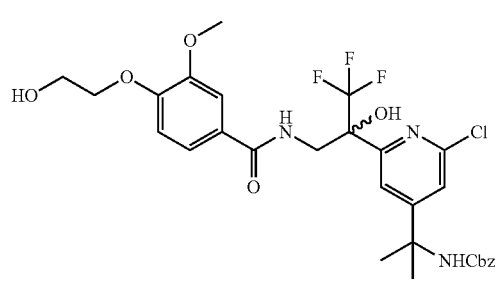

660-1

540

-continued

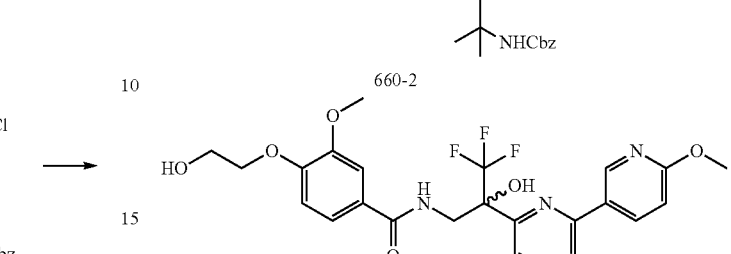

660-2

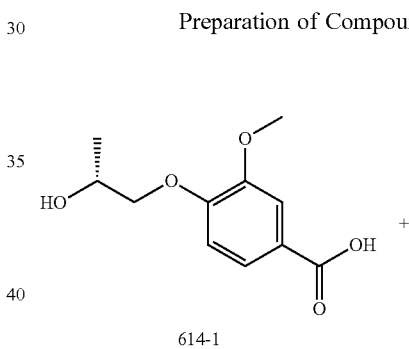

660

Compound 659 (white solid, 10 mg) was prepared following the general procedure for preparing 657 using 660-1 and 2-methoxy-4-pyridyl boronic acid. The crude product was purified by prep-HPLC. +ESI-MS: m/z 565.1 [M+H]$^+$.

Example 343

Preparation of Compound 614

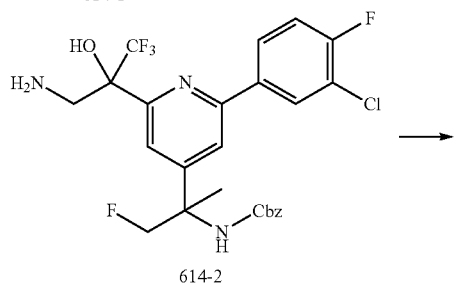

614-1

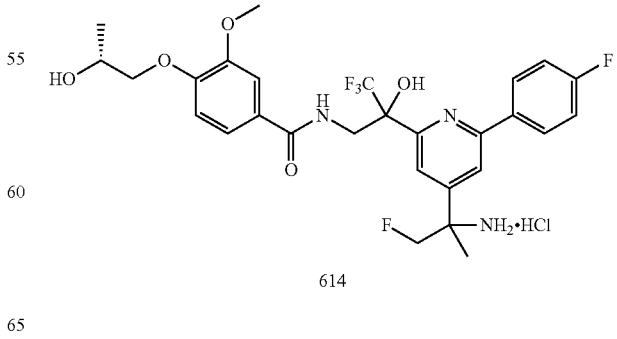

614-2

614

A mixture of 614-1 (23 mg, 0.1 mmol), 614-2 (50 mg, 0.1 mmol) and TEA (1 mmol) were dissolved in DCM (4 mL).

HATU (38 mg, 0.1 mmol) was added, and the mixture was stirred for 30 mins. The mixture was diluted with brine (5 mL), and the aqueous phase was extracted with DCM (2×5 mL). The combined organic layer was washed with brine, dried over anhydrous Na$_2$SO$_4$ and concentrated under reduced pressure. The residue was dissolved in MeOH (10 mL) and hydrogenated over Pd/C (10 mg, 10%) at 15 psi for 17 h. The catalyst was removed by filtration, and the cake was washed with MeOH (5 mL). The combined filtrates was concentrated and purified by prep-HPLC to give 614 (28 mg, 45%). +ESI-MS: m/z 584.0 [M+H]$^+$.

Example 344

Preparation of Compound 615

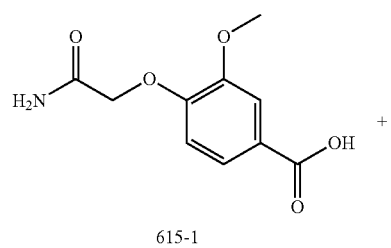

615-1

Example 345

Preparation of Compound 626

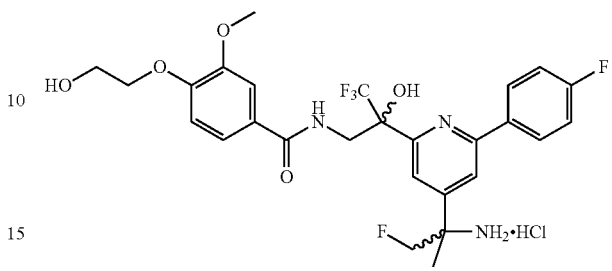

To a solution of 540 (160 mg, 0.26 mmol) in MeOH (2 mL) was added Pd/C (150 mg) under N$_2$. The suspension was degassed under vacuum and purged with H$_2$ several times. The mixture was stirred at 25° C. for 12 h. The mixture was filtered through a pad of Celite, and the pad was washed with MeOH. The combined filtrates were concentrated under reduced pressure. The residue was purified by prep-HPLC of acidity with HCl to give 626 (69 mg, 43%). +ESI-MS: m/z 570.0 [M+H]$^+$.

Example 346

Preparation of Compound 627

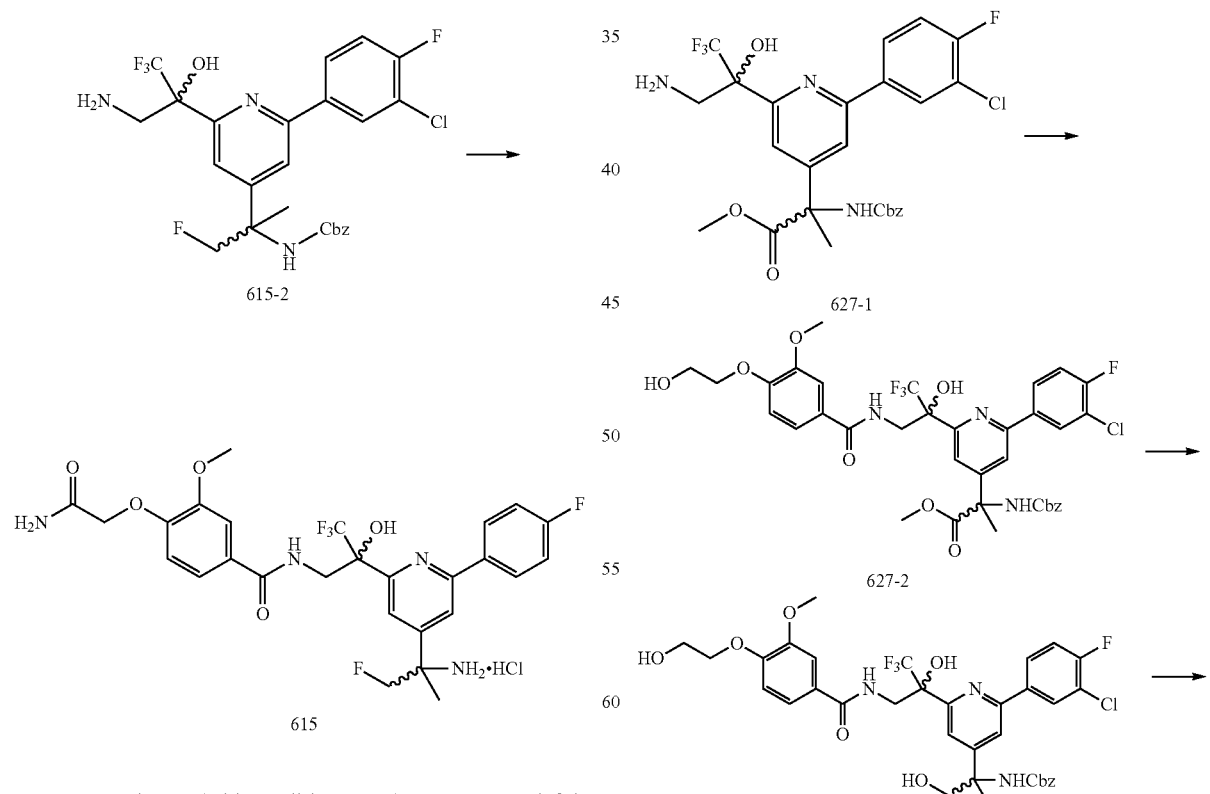

Compound 615 (white solid, 43 mg) was prepared following the general procedure for preparing 614 using 615-1 and 615-2. The crude product was purified by prep-HPLC. +ESI-MS: m/z 583.1 [M+H]$^+$.

543

-continued

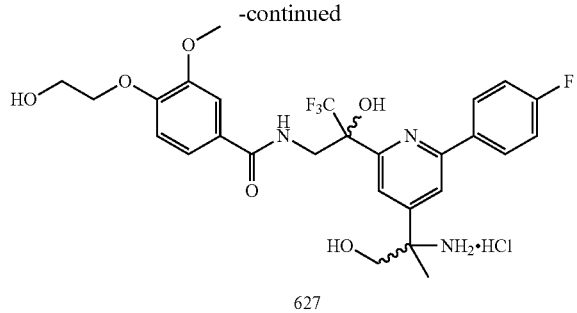

627

A mixture of 627-1 (66 mg, 0.3 mmol), 627-2 (150 mg, 0.3 mmol) and TEA (1 mmol) were dissolved in DCM (4 mL). HATU (120 mg, 0.2 mmol) was added, and the mixture was stirred for 30 mins. The reaction was diluted with brine (5 mL), and the aqueous phase was extracted with DCM (2×5 mL). The combined organic layer was washed with brine, dried over anhydrous $Na_2SO_4$ and concentrated under reduced pressure to give crude 627-2, which was used in next step without further purification. +ESI-MS: m/z 764.1 $[M+H]^+$.

To a solution of 627-2 (0.7 g, crude) in MeOH (20 mL) was added $LiBH_4$ (59 mg, 2.8 mmol) in one portion at r.t. The mixture was stirred for 1 h. The reaction was quenched with 2N HCl solution and extracted with EA (3×20 mL). The combined organic layer was washed with brine, dried over anhydrous $Na_2SO_4$ and concentrated under reduced pressure. The residue was purified by column chromatography using PE:EA=30:1~3:1 as the eluent to afford 627-3 (0.6, 89%) as an oil. +ESI-MS: m/z 736.0 $[M+H]^+$.

Compound 627 (white solid, 180 mg) was prepared following the general procedure for preparing 540 using 627-3. +ESI-MS: m/z 568.1 $[M+H]^+$.

Example 347

Preparation of Compounds 655 and 656

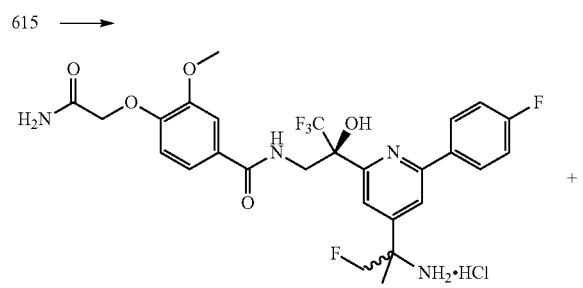

544

Compound 615 (30 mg) was separated by SFC to give solutions of peak 1 and peak 2. The two peaks were acidified by aq. HCl (2 M) and lyophilized to give 655 (9.2 mg) and 656 (8.9 mg) as a white solid. 655: +ESI-MS: m/z 583.1 $[M+H]^+$ and 656: +ESI-MS: m/z 583.1 $[M+H]^+$.

Example 348

Preparation of Compound 622

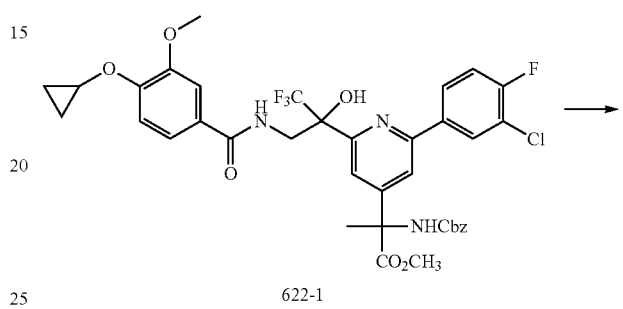

622-1 (white solid, 610 mg) was prepared following the general procedure for preparing 536. +ESI-MS: m/z 760.1 $[M+H]^+$.

Compound 622 (12 mg,) was prepared following the general procedure for preparing 581 using 622-1. LCMS: m/z 592.15 $[M+H]^+$.

Example 349

Preparation of Compound 650

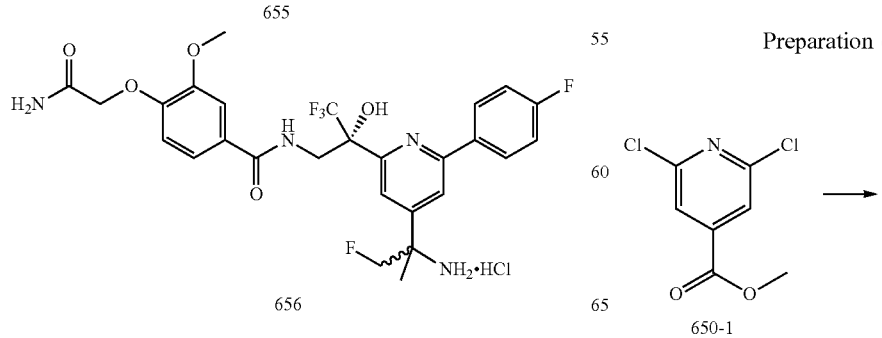

650-1

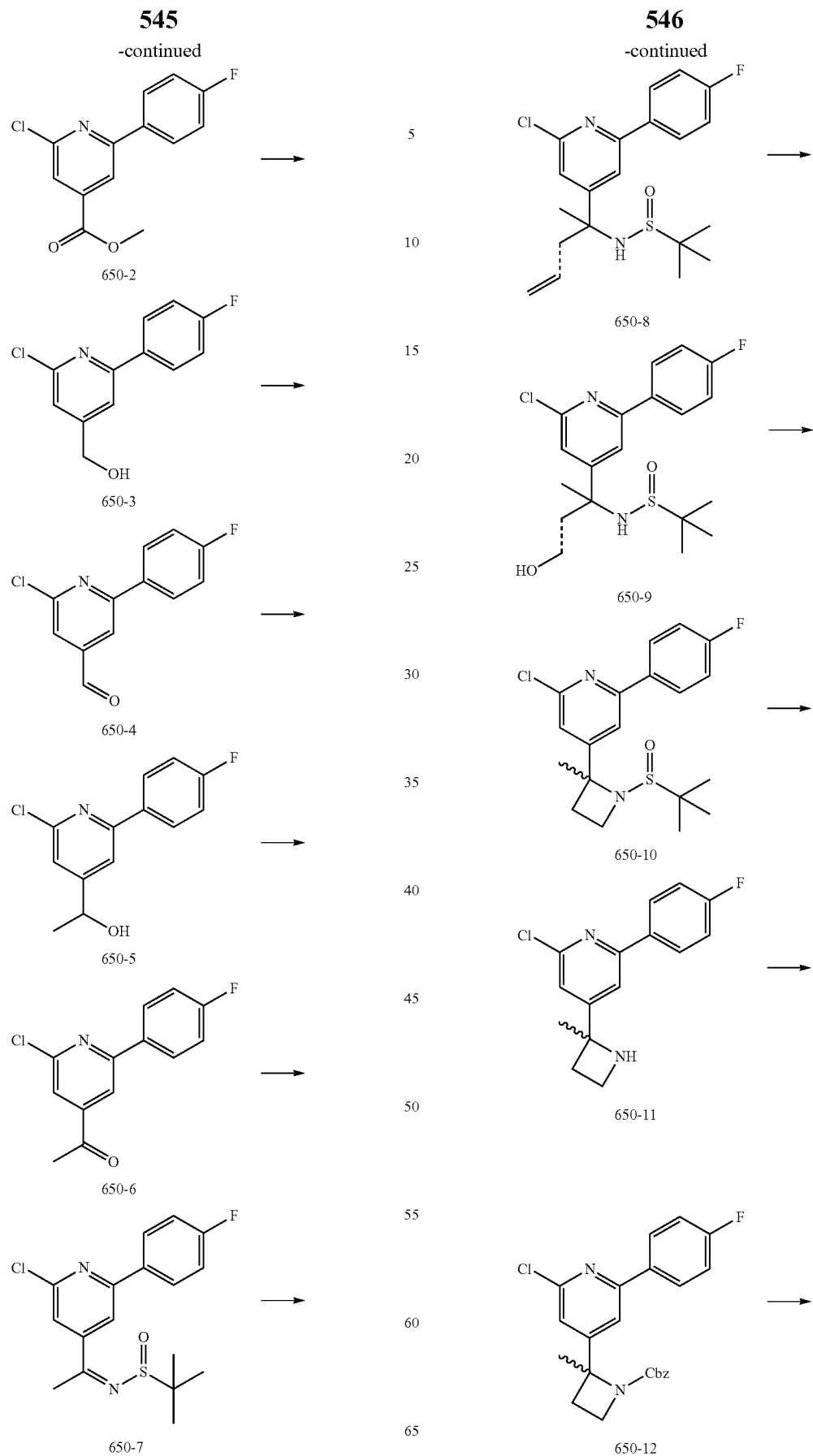

-continued

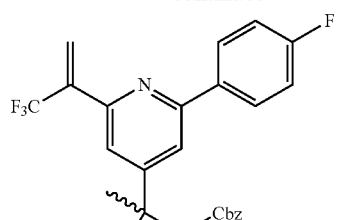

650-13

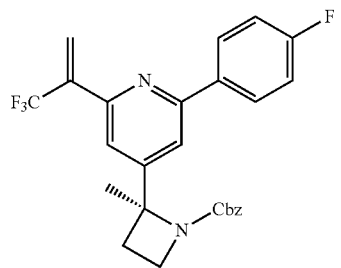

650-14

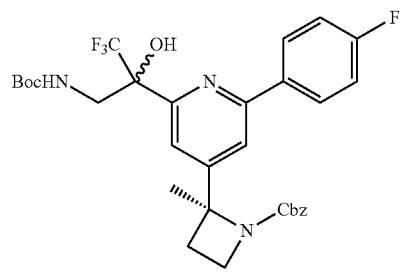

650-15

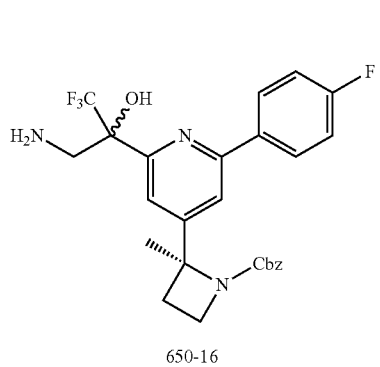

650-16

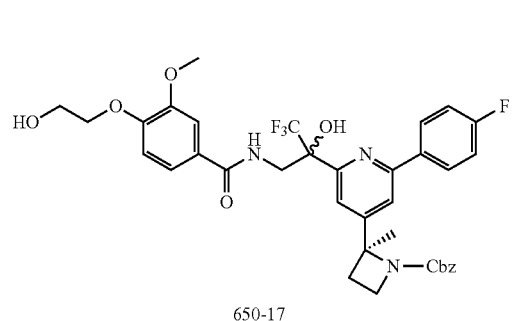

650-17

-continued

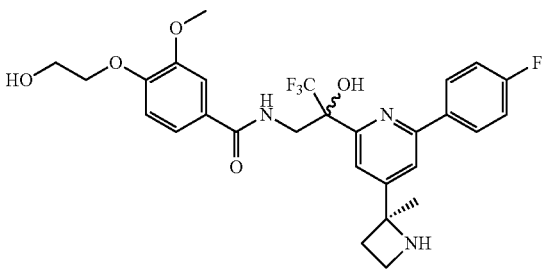

650

650-17 (white solid, 210 mg) was prepared following the general procedure for preparing 563 using 650-1 and 4-F-phenyl boronic acid. +ESI-MS: m/z 698.1 [M+H]$^+$.

To a stirring mixture of 650-17 (200 mg, 0.28 mmol) in CH$_3$CN (2 mL) were added NaI (215 mg, 1.4 mmol) and TMSCl (152 mg, 1.4 mmol). The mixture was stirred at 65° C. for 20 mins. The mixture was cooled to r.t. and diluted with EtOAc. The reaction was quenched with a 10% aqueous solution of Na$_2$S$_2$O$_3$. The layers were separated, and the aqueous layer was extracted with EtOAc. The combined organic layers were dried over Na$_2$SO$_4$, filtered and concentrated under reduced pressure. The crude product mixture was purified via prep-HPLC to afford 650 (10 mg) as a white solid. LCMS 564.20 m/z [M+H]$^+$.

Example 350

Preparation of Compound 667

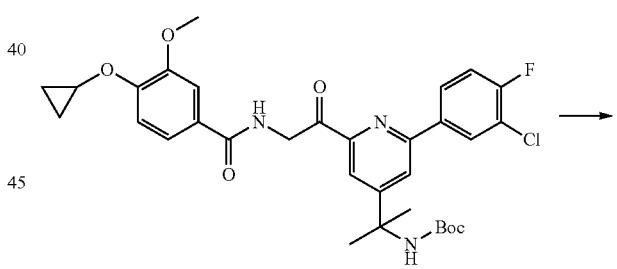

667-1

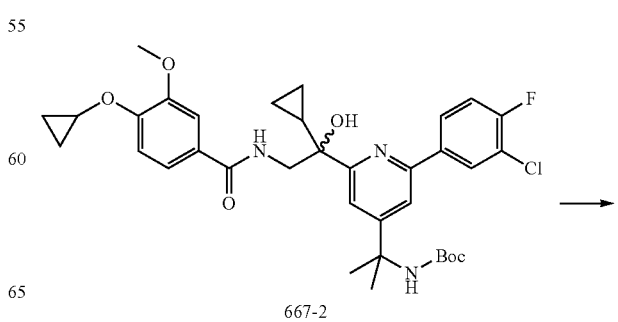

667-2

-continued

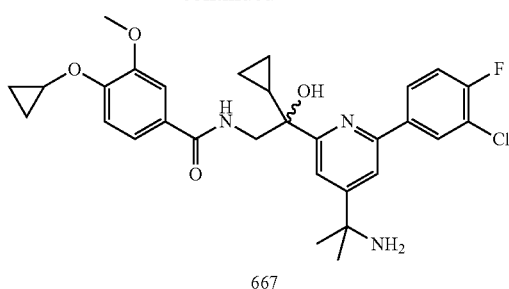

667

To a solution of 667-1 (100 mg, 0.16 mmol) in THF (1 mL) was added cyclopropylmagnesium chloride (2 mL, 1 mmol) dropwise at r.t. The mixture was stirred for 2 h. The reaction was quenched with aq. NH$_4$Cl and extracted with EA (3×10 mL). The combined organic phase was washed with brine, dried over Na$_2$SO$_4$ and concentrated under reduced pressure. The residue was purified by prep-TLC (PE:EA=1:1) to give 667-2 (62 mg, 58.4%).

To a solution of 667-2 (62 mg, 0.1 mmol) in DCM (2 mL) was added TFA (2 mL) at r.t. The mixture was stirred for 30 mins. The mixture was neutralized by aq. NaHCO$_3$ solution and extracted by EA (3×10 mL). The combined organic layers were washed with brine, dried over Na$_2$SO$_4$ and concentrated under reduced pressure. The residue was purified by prep-HPLC to give 667 (9 mg, 16.3%) as a white solid. +ESI-MS: m/z 554.0

Example 351

Preparation of Compound 603

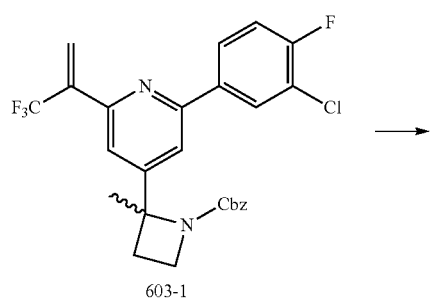

603-1

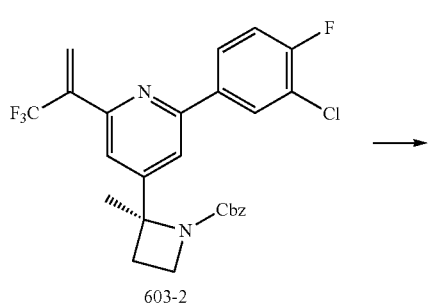

603-2

-continued

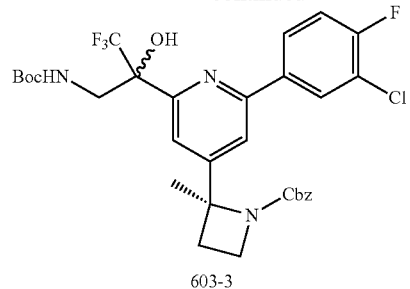

603-3

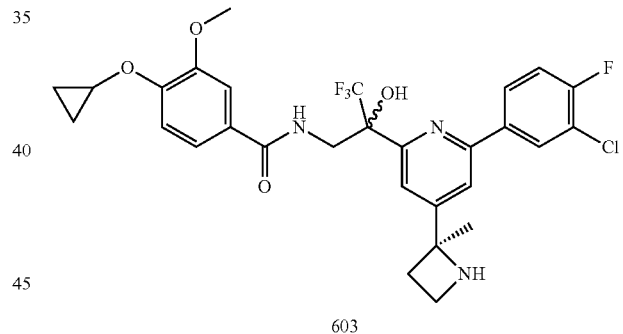

603-4

603-5

603

Enantiomer 603-2 (270 mg) was obtained by SFC separation of racemic 603-1 (1.1 g).

To a stirring mixture of 603-2 (270 mg 0.8 mmol) in 2-methylpropan-2-ol (6 mL):H$_2$O (2 mL) at 0° C. were added BocN-OTs (308 mg 1.07 mmol) and K$_2$OsO$_4$—H$_2$O (60 mg, 0.16 mmol) at r.t. The mixture was stirred at r.t. for 30 h. The mixture was diluted with water and extracted with DCM (3×10 mL). The combined organic phase was washed with brine, dried over Na$_2$SO$_4$ and concentrated under reduced pressure. The residue was purified by column chromatography using PE:EA=1:1 as the eluent to afford 603-3 (~200 mg, ~60%). +ESI-MS: m/z 638.1 [M+H]$^+$.

To a mixture of 603-3 (200 mg, 0.32 mmol) in DCM (6 mL) was added TFA (3 mL) at r.t. The mixture was stirred for 30 mins, neutralized with aqueous NaHCO$_3$ and extracted with EA (3×10 mL). The combined organic layers were washed by brine, dried over Na$_2$SO$_4$ and concentrated under reduced pressure to give crude 603-4 (110 mg), which was used without further purification. +ESI-MS: m/z 538.1 [M+H]⁺.

To a solution of 4-(cyclopropoxy)-3-methoxy-benzoic acid (37 mg, 0.17 mmol), HATU (100 mg 0.26 mmol) and DIPEA (57 mg, 0.44 mmol) in anhydrous DMF (3 mL) was added 603-4 (110 mg crude) at r.t. The solution was stirred for 5 h at r.t. with TLC monitoring. The mixture was diluted with 1.0 N aqueous NaHCO₃ solution and extracted with EA (3×10 mL). The combined organic layers were washed by brine, dried over anhydrous Na₂SO₄, and concentrated under reduced pressure. The residue was purified by column chromatography using PE:EA=1:1 as the eluent and prep-HPLC to give 603-5 (43 mg, 28.7%). +ESI-MS: m/z 728.1 [M+H]⁺.

To a stirring mixture of 603-5 (15 mg, 0.041 mmol) in CH₃CN (1 mL) at r.t. were added NaI (32 mg, 0.2 mmol) and TMSCl (22 mg, 0.2 mmol). The mixture was stirred at 55° C. for 15 mins. The mixture was diluted with EtOAc and washed with a 10% aq. Na₂S₂O₃ solution. The organic layer was washed with brine, dried over Na₂SO₄, filtered and concentrated under reduced pressure. The reaction was concentrated and the crude product was purified by prep-HPLC to provide 603. +ESI-MS: m/z 594.20 [M+H]⁺.

Example 352

Preparation of Compound 575

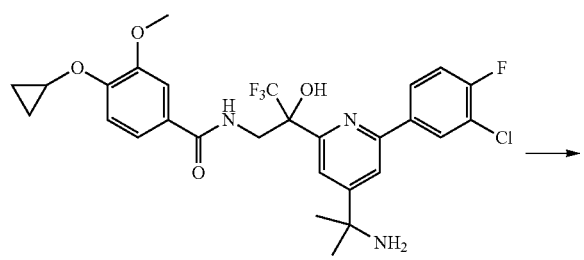

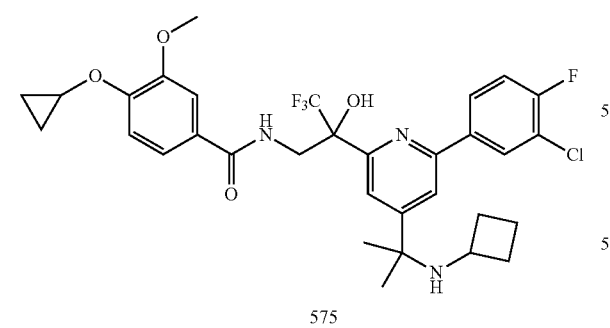

575

Cyclobutanone (17 μL, 0.22 mmol) and sodium cyanoborohydride (47 mg, 0.22 mmol) were added to a solution of 314 (43 mg, 0.074 mmol) every 30 mins for 6 h. The mixture was diluted with EtOAc, washed with 1N HCl and brine, dried over MgSO₄ and concentrated under reduced pressure. The crude product was purified by reverse phase HPLC to give 575 (14 mg, 23%). LCMS: m/z 637.20 [M+H]⁺.

Example 353

Preparation of Compound 577

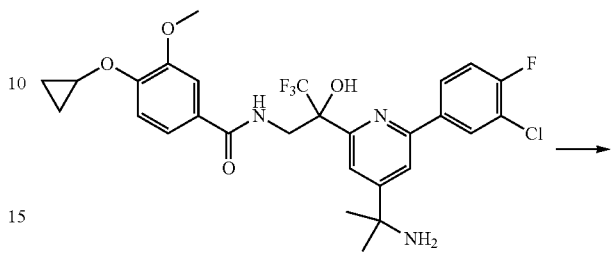

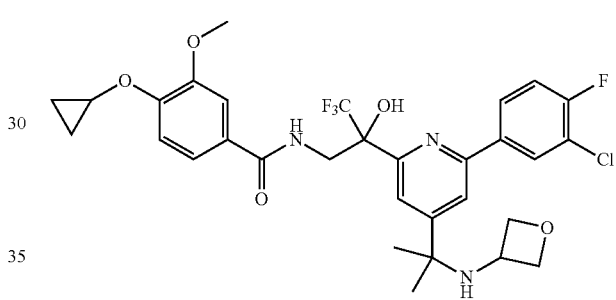

577

Compound 577 was prepared following the general procedure for preparing 575. LCMS: m/z 639.10 [M+H]⁺.

Example 354

Preparation of Compound 581

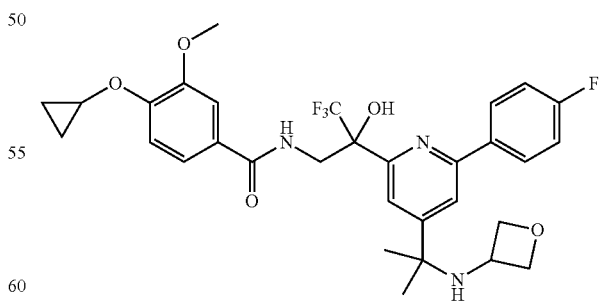

577 (12 mg, 0.019 mmol) was hydrogenated over 10% Pd/C (3 mg) in EtOH (2 mL) for 1 h. The catalyst was removed by filtration and the crude product was purified by reverse-phase HPLC to give 581 (8 mg, 66%). LCMS: m/z 604.20 [M+H]⁺.

Example 355

Preparation of Compound 576

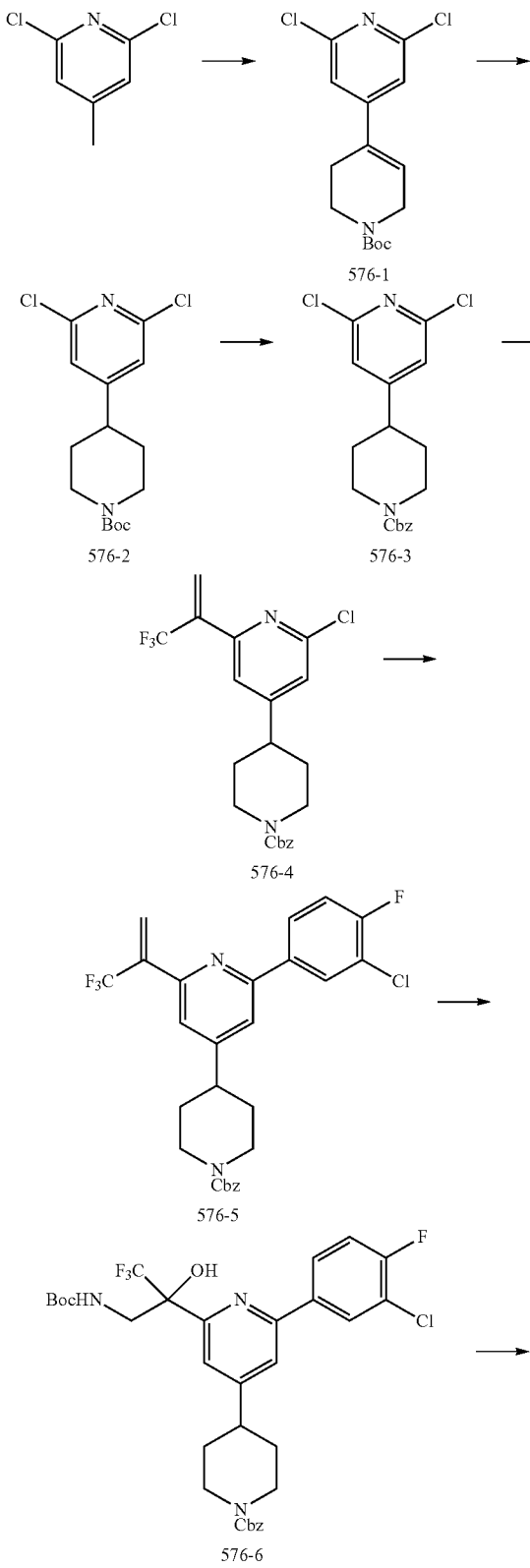

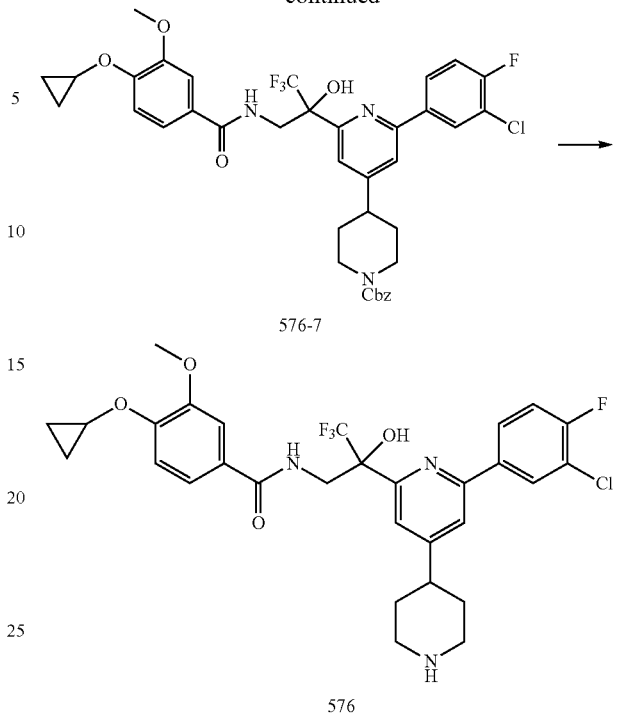

Pd(dppf)Cl$_2$ (66 mg, 0.091 mmol) was added to a solution of 2,4-dichloro-4-iodopyridine (0.50 g, 1.8 mmol), (1-(tert-Butoxycarbonyl)-1,2,3,6-tetrahydropyridin-4-yl)boronic acid (0.54 g, 1.8 mmol) and cesium carbonate (1.8 g, 5.5 mmol) in dimethoxyethane (10 mL) and water (1 mL). The mixture was heated under microwave irradiation at 110° C. for 1 h. The mixture was diluted with EA, washed with brine, dried over anhydrous Na$_2$SO$_4$ and concentrated. The residue was purified by chromatography on silica gel (EA: hexane) to give 576-1 (0.47 g, 72%). LCMS: m/z 329.00 [M+H]$^+$.

A solution of 576-1 (0.83 g, 2.5 mmol) and platinum oxide (83 mg) in EtOH was stirred under H$_2$ atmosphere for 1 h. The mixture was filtered to remove catalyst and concentrated. The product (0.80 g, 96%) was used without further purification. LCMS: m/z 331.05 [M+H]$^+$.

HCl (4N in dioxane, 3 mL) was added to 576-2 (0.80 g, 2.4 mmol). The mixture was stirred at r.t. for 30 mins and concentrated under reduced pressure. The crude product was dissolved in CH$_2$Cl$_2$ (10 mL), and DIEA (1.1 mL, 6.0 mmol) and benzyl chloroformate (0.41 mL, 2.9 mmol) were added. The reaction was stirred at r.t. for 1 h. The mixture was diluted with EA, washed with 1N HCl and brine, dried over anhydrous Na$_2$SO$_4$ and concentrated. The residue was purified by chromatography on silica gel (EA:hexane) to give 576-3 (0.49 g, 54%). LCMS: m/z 365.05 [M+H]$^+$.

Pd(dppf)Cl$_2$ (0.45 g, 0.61 mmol) was added to a solution of 576-3 (0.49 g, 1.3 mmol), 1-(trifluoromethyl)vinylboronic acid hexylene glycol ester (0.30 g, 1.3 mmol), Cs$_2$CO$_3$ (1.3 g, 4.0 mmol) in DME (3 mL) and water (0.3 mL). The reaction vessel was heated under microwave irradiation for 20 mins at 110° C. The mixture was diluted with EA. The organic phase was washed with water and brine, dried over anhydrous Na$_2$SO$_4$ and concentrated. The residue was purified by chromatography on silica gel (EA:hexane) to give 576-4 (0.23 g, 41%). LCMS: m/z 425.05 [M+H]$^+$.

Pd(dppf)Cl$_2$ (20 mg, 0.027 mmol) was added to a solution of 576-4 (0.23 g, 0.54 mmol), 3-chloro-4-fluorophenyl boronic acid (95 mg, 0.54 mmol), Cs$_2$CO$_3$ (0.53 g, 1.6 mmol) in DME (2 mL) and water (0.2 mL). The reaction vessel was heated under microwave irradiation at 110° C. for 1 h. The mixture was diluted with EA. The organic phase was washed with water and brine, dried over anhydrous Na$_2$SO$_4$ and concentrated. The residue was purified by chromatography on silica gel (EA:hexane) to give 576-4 (0.11 g, 38%). LCMS: m/z 519.10 [M+H]$^+$.

Potassium osmate (11 mg, 0.029 mmol) was added to a solution of 576-5 (0.11 g, 0.21 mmol) and tert-butyl (tosyloxy)carbamate (91 mg, 0.33 mmol) in t-butanol (1 mL) and water (0.33 mL). The solution was stirred overnight at r.t. The crude mixture was purified by chromatography on silica gel (EA:hexane) to give 576-6 (0.12 g, 85%). LCMS: m/z 652.20 [M+H]$^+$.

HCl (2 mL, 4N in dioxane) was added to 576-6 (0.12 g, 0.18 mmol), and the mixture was stirred at r.t. for 2 h. The solvent was removed by evaporation and the amine salt was re-dissolved in DMF (1 mL). 4-cyclopropoxy-3-methoxybenzoic acid (57 mg, 0.28 mmol), HATU (0.14 g, 0.37 mmol) and DIEA (0.14 mL, 0.74 mmol) were added, and the mixture was stirred at r.t. for 2 h. The mixture was diluted with EA. The organic phase was washed with 1N HCl, water and brine, dried over anhydrous Na$_2$SO$_4$ and concentrated. The residue was purified by chromatography on silica gel (EA:hexane) to give 576-7 (35 mg, 26%). LCMS: m/z 742.20 [M+H]$^+$.

Chlorotrimethylsilane (23 µL, 0.24 mmol) was added dropwise to a solution of 576-7 (35 mg, 0.047 mmol) and NaI (28 mg, 0.24 mmol) in CH$_3$CN (1 mL), and the mixture was stirred for 30 mins. The mixture was diluted with EA, washed with Na$_2$S$_2$O$_3$ and brine, dried and concentrated. The crude product was purified by reverse-phase HPLC to provide 576 (13 mg, 37%). LCMS: m/z 609.15 [M+H]$^+$.

Example 356

Preparation of Compound 579

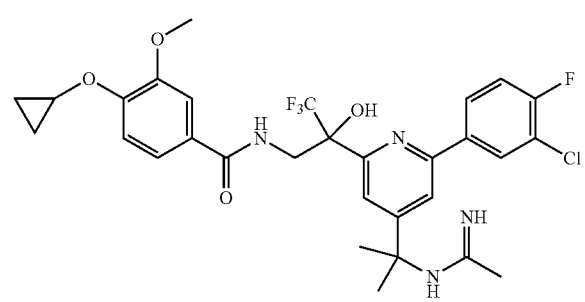 [SMILES: COc1cc(C(=O)NCC(O)(c2cc(C(C)(C)NC(C)=N)cc(-c3ccc(F)c(Cl)c3)n2)C(F)(F)F)ccc1OC1CC1]

Ethyl acetimidate hydrochloride (150 mg, 1.2 mmol) was added to a solution of 314 (50 mg, 0.086 mmol) in EtOH (3 mL). The mixture heated at reflux for 24 h. The mixture was diluted with EA, washed with brine, dried and concentrated. The crude product was purified by reverse phase HPLC to give 579 (8 mg, 16%). LCMS: m/z 624.15 [M+H]$^+$.

Example 357

Preparation of Compound 585

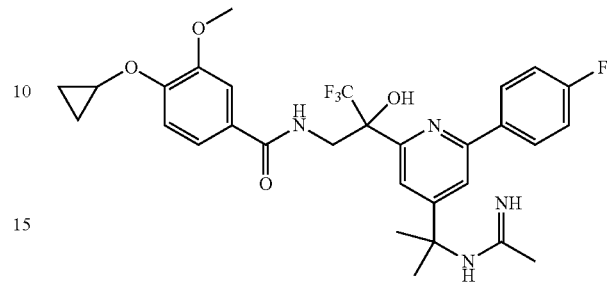

Compound 585 was prepared following the general procedure for preparing 579 using 318 and ethyl acetimidate. LCMS: m/z 590.20 [M+H]$^+$.

Example 358

Preparation of Compound 580

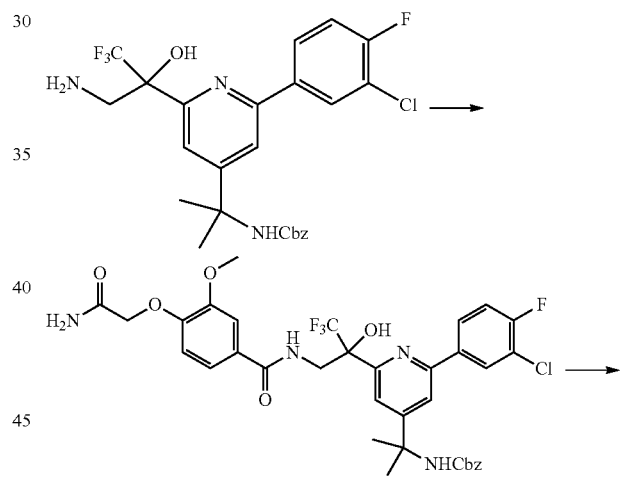

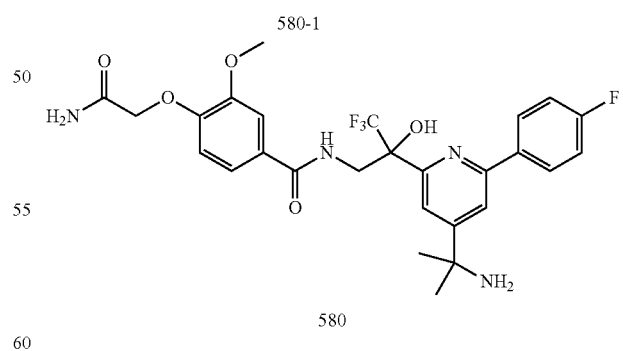

Benzyl(2-2(3-amino-1,1,1-trifluoro-2-hydroxypropan-2-yl)-6-(3-chloro-4-fluorophenyl)pyridine-4-yl)propan-2-yl) carbamate was coupled with 4-(2-amino-2-oxoethoxy)-3-methoxybenzoic acid following the general procedure for 576-7. 580-1 was hydrogenated following the general procedure for preparing 581. LCMS: m/z 565.15 [M+H]$^+$.

Example 359

Preparation of Compound 586

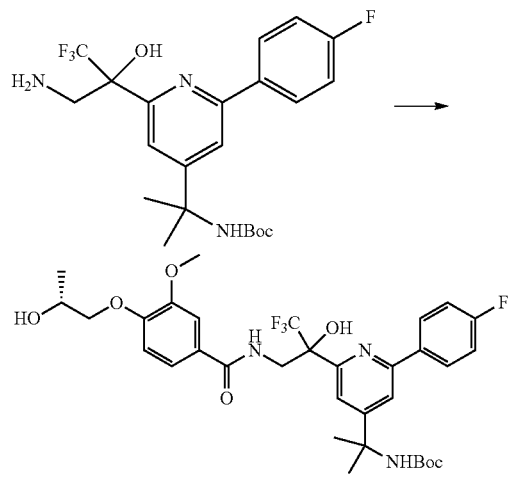

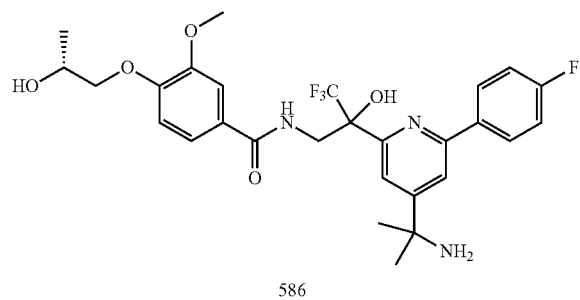

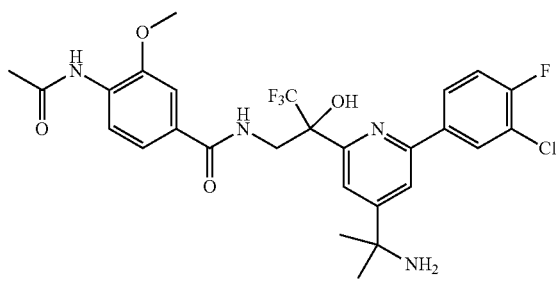 [SMILES: COc1cc(C(=O)NCC(O)(c2cc(C(C)(C)N)cc(-c3ccc(F)c(Cl)c3)n2)C(F)(F)F)ccc1NC(C)=O]

586-1 was prepared following the general procedure for 576-7. HCl in dioxane (3 mL) was added to 568-1 (92 mg, 0.18 mmol), and the mixture was stirred at r.t. for 3 h. The mixture was concentrated, and the crude product purified by reverse-phase HPLC to provide 586 (43 mg, 47%). LCMS: m/z 566.20 [M+H]$^+$.

Example 360

Preparation of Compound 592

Compound 592 was prepared following the general procedure for 586 using 4-acetamido-3-methoxybenzoic acid. LCMS: m/z 583.15 [M+H]$^+$.

Example 361

Preparation of Compound 593

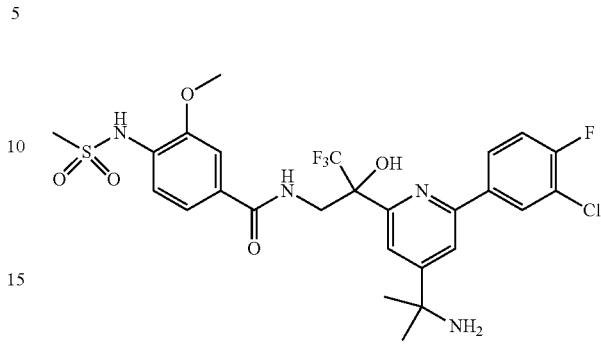

Compound 593 was prepared following the general procedure for 586. LCMS: m/z 619.00 [M+H]$^+$.

Example 362

Preparation of Compound 596

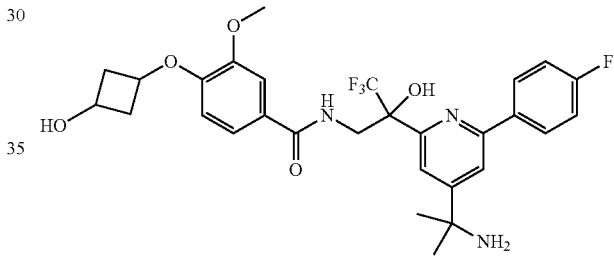

Compound 596 was prepared following the general procedure for 586 using 4-(3-hydroxycyclobutoxy)-3-methoxybenzoic acid. LCMS: m/z 578.20 [M+H]$^+$.

Example 363

Preparation of Compound 616

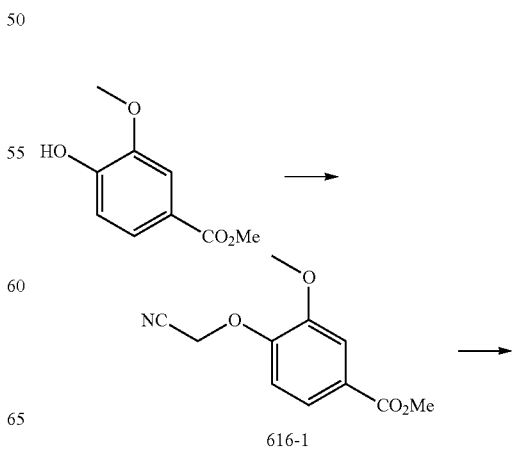

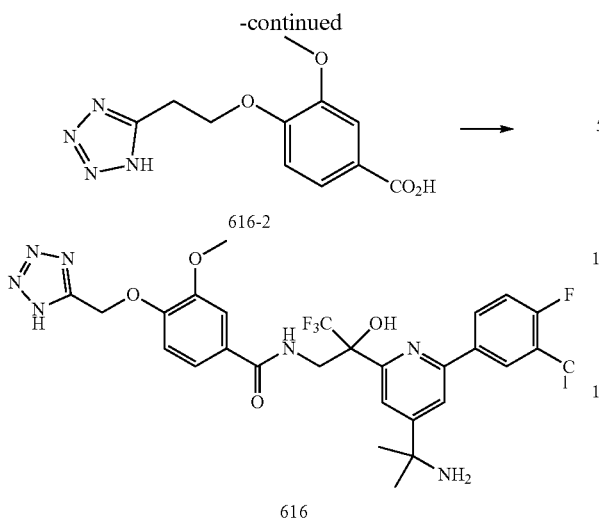

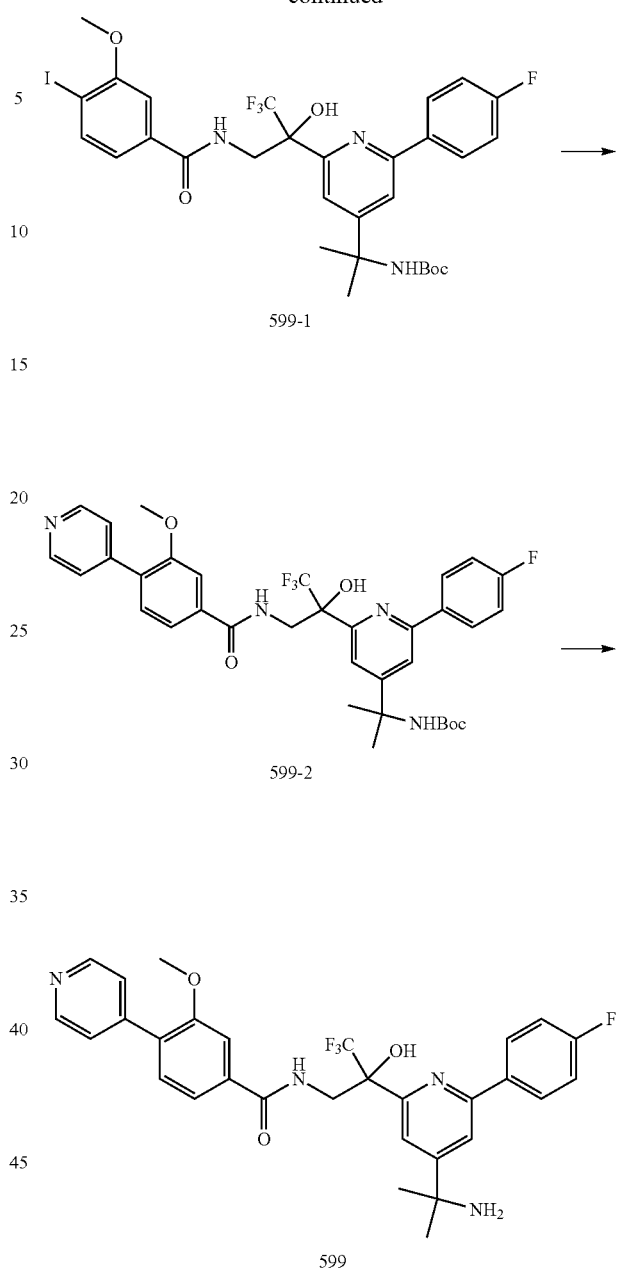

To a stirring mixture of methyl 4-hydroxy-3-methoxybenzoate (1 g, 5.49 mmol) in DMF (5 mL) at r.t. were added $K_2CO_3$ (1.14 g, 8.24 mmol) and 2-bromoacetonitrile. The mixture was stirred at r.t. for several hours and then diluted with EtOAc and water. The layers were separated, and the aqueous layer was extracted with EtOAc. The combined organic layers were washed with brine, dried over $Na_2SO_4$, filtered and concentrated under reduced pressure. The crude product mixture was purified via a silica gel chromatography to afford 616-1 as a white solid.

To a stirring mixture of 616-1 (190 mg, 0.856 mmol) in DMF (2 mL) were added $NaN_3$ (71.5 mg, 1.1 mmol) and $NH_4Cl$ (59 mg, 1.1 mmol). The mixture was carried out under microwave irradiation for 45 mins at 100° C. The mixture was diluted with EtOAc and water, and the layers were separated. To the aqueous layer was added a 10% aqueous HCl solution until a white precipitation was formed. The tetrazole-product was filtered off, and then dissolved directly in aq. NaOH solution (1.5 mL, 2N). The mixture was heated at 80° C. for 30 mins. The mixture was cooled to r.t. and acidified with a 10% aq. HCl solution. The white solid was filtered off and dry under reduced pressure. Crude 616-2 was used without further purification. LCMS: m/z 265.05 [M+H]+.

Compound 616 was prepared following the general procedure for 586 using 616-2. LCMS: m/z 624.15 [M+H]+.

Example 364

Preparation of Compound 599

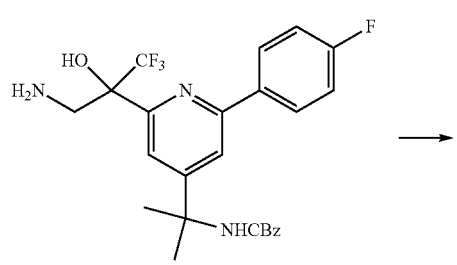

599-1 was prepared following the general procedure for 576-7. Pd(dppf)Cl$_2$ (12 mg, 0.016 mmol) was added to a solution of 599-1 (0.23 g, 0.32 mmol), pyridine-4-boronic acid (65 mg, 0.016 mmol) and cesium carbonate (0.31 g, 0.96 mmol) in dimethoxyethane (2 mL) and water (0.2 mL). The mixture was heated under microwave irradiation at 110° C. for 20 mins. The mixture was diluted with EA, washed with brine, dried and concentrated. The residue was purified by chromatography on silica gel (EA:hexane) to give 599-2 (0.11 g, 500).

599-2 was prepared following the general procedure for 586 to give 599. LCMS: m/z 569.20 [M+H]g, 17%). LCMS: m/z 642.15 [M+H]+.

Example 365

Preparation of Compound 601

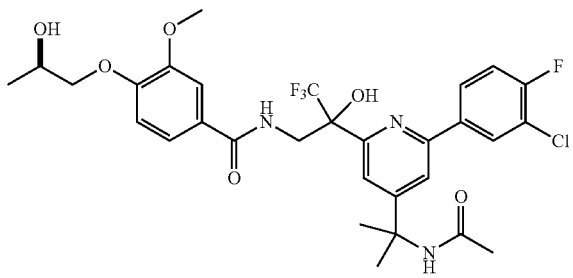 [SMILES: COc1cc(C(=O)NCC(O)(c2cc(C(C)(C)NC(C)=O)cc(-c3ccc(F)c(Cl)c3)n2)C(F)(F)F)ccc1OC[C@@H](C)O]

DIEA (87 µL, 0.50 mmol) was added to a solution of 317 (0.10 g, 0.16 mmol), acetic acid (20 mL, 0.33 mmol) and HATU (0.14 g, 0.35 mmol) in DMF. The mixture was stirred at r.t. for 1 h. The crude product was purified by reverse phase HPLC to provide 601 (17 mg, 17%). LCMS: m/z 642.15 [M+H]$^+$.

Example 366

Preparation of Compound 611

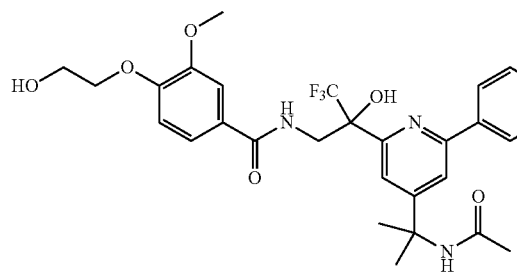

Compound 611 was prepared following the general procedure for 601 using 320. LCMS: m/z 594.20 [M+H]$^+$.

Example 367

Preparation of Compound 612

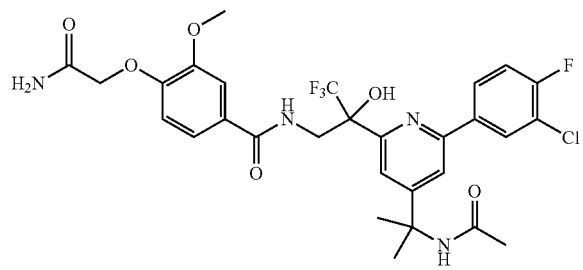 [SMILES: COc1cc(C(=O)NCC(O)(c2cc(C(C)(C)NC(C)=O)cc(-c3ccc(F)c(Cl)c3)n2)C(F)(F)F)ccc1OCC(N)=O]

Compound 612 was prepared following the general procedure for 601 using 322. LCMS: m/z 641.15 [M+H]$^+$.

Example 368

Preparation of Compound 621

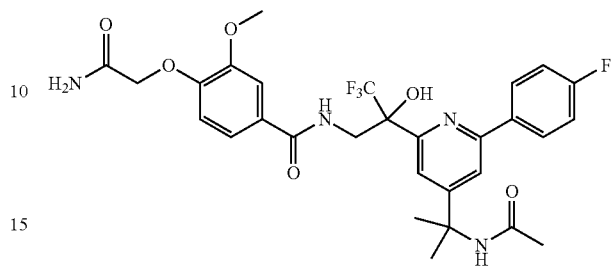

Compound 621 was prepared following the general procedure for 601 using 580. LCMS: m/z 607.20 [M+H]$^+$.

Example 369

Preparation of Compound 620

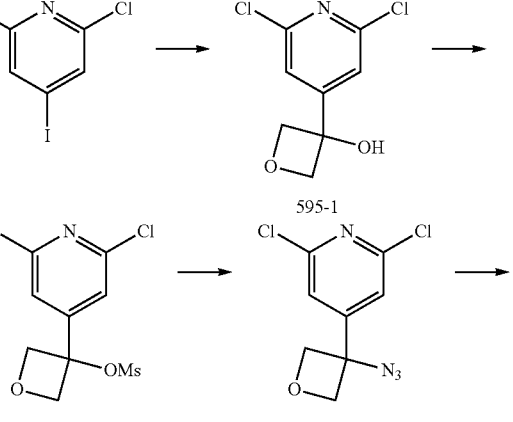

Compound 620 was prepared following the general procedure for 601 using 586. LCMS: m/z 608.2 [M+H]$^+$.

Example 370

Preparation of Compound 595

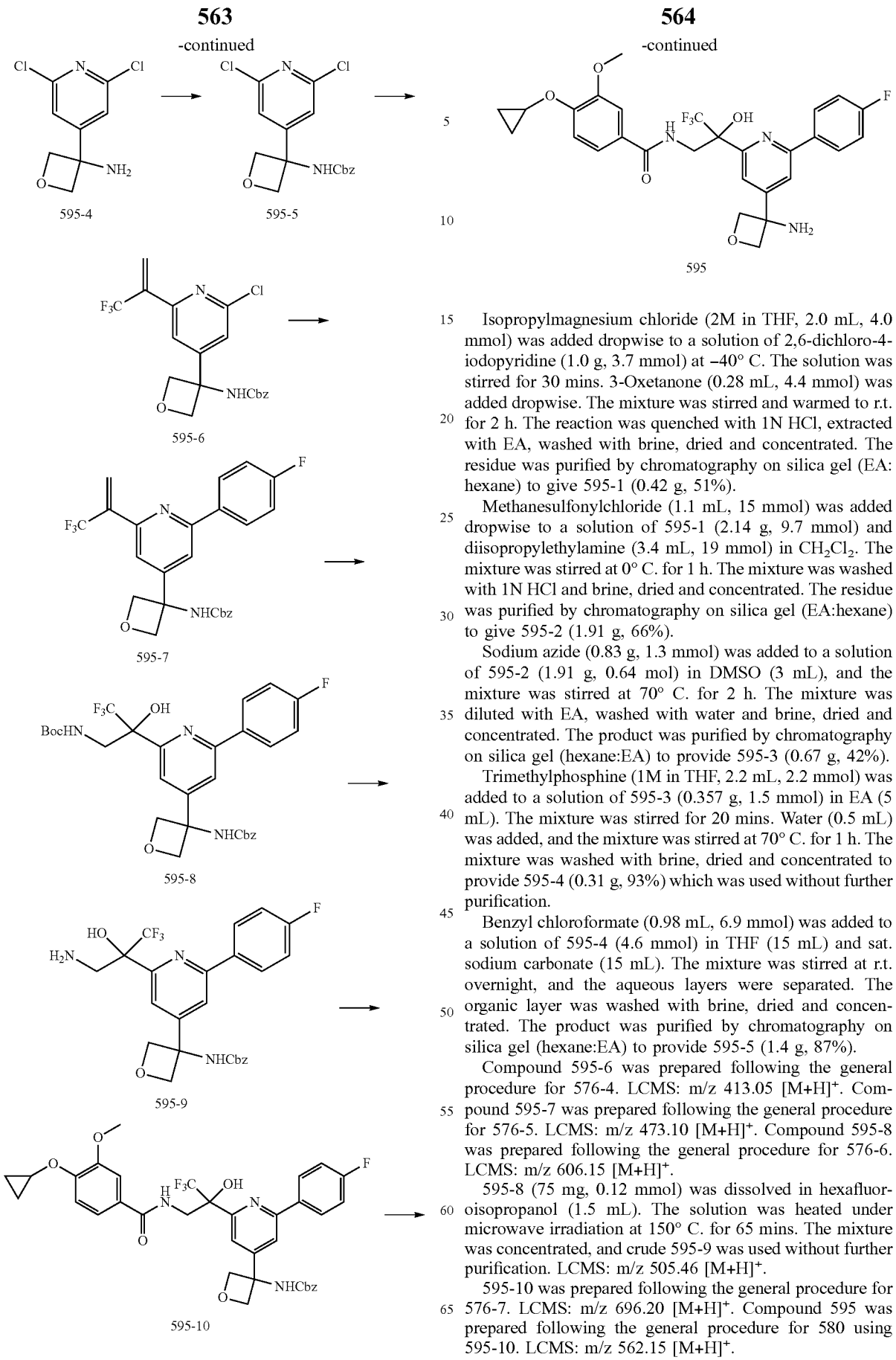

Isopropylmagnesium chloride (2M in THF, 2.0 mL, 4.0 mmol) was added dropwise to a solution of 2,6-dichloro-4-iodopyridine (1.0 g, 3.7 mmol) at −40° C. The solution was stirred for 30 mins. 3-Oxetanone (0.28 mL, 4.4 mmol) was added dropwise. The mixture was stirred and warmed to r.t. for 2 h. The reaction was quenched with 1N HCl, extracted with EA, washed with brine, dried and concentrated. The residue was purified by chromatography on silica gel (EA: hexane) to give 595-1 (0.42 g, 51%).

Methanesulfonylchloride (1.1 mL, 15 mmol) was added dropwise to a solution of 595-1 (2.14 g, 9.7 mmol) and diisopropylethylamine (3.4 mL, 19 mmol) in $CH_2Cl_2$. The mixture was stirred at 0° C. for 1 h. The mixture was washed with 1N HCl and brine, dried and concentrated. The residue was purified by chromatography on silica gel (EA:hexane) to give 595-2 (1.91 g, 66%).

Sodium azide (0.83 g, 1.3 mmol) was added to a solution of 595-2 (1.91 g, 0.64 mol) in DMSO (3 mL), and the mixture was stirred at 70° C. for 2 h. The mixture was diluted with EA, washed with water and brine, dried and concentrated. The product was purified by chromatography on silica gel (hexane:EA) to provide 595-3 (0.67 g, 42%).

Trimethylphosphine (1M in THF, 2.2 mL, 2.2 mmol) was added to a solution of 595-3 (0.357 g, 1.5 mmol) in EA (5 mL). The mixture was stirred for 20 mins. Water (0.5 mL) was added, and the mixture was stirred at 70° C. for 1 h. The mixture was washed with brine, dried and concentrated to provide 595-4 (0.31 g, 93%) which was used without further purification.

Benzyl chloroformate (0.98 mL, 6.9 mmol) was added to a solution of 595-4 (4.6 mmol) in THF (15 mL) and sat. sodium carbonate (15 mL). The mixture was stirred at r.t. overnight, and the aqueous layers were separated. The organic layer was washed with brine, dried and concentrated. The product was purified by chromatography on silica gel (hexane:EA) to provide 595-5 (1.4 g, 87%).

Compound 595-6 was prepared following the general procedure for 576-4. LCMS: m/z 413.05 [M+H]⁺. Compound 595-7 was prepared following the general procedure for 576-5. LCMS: m/z 473.10 [M+H]⁺. Compound 595-8 was prepared following the general procedure for 576-6. LCMS: m/z 606.15 [M+H]⁺.

595-8 (75 mg, 0.12 mmol) was dissolved in hexafluoroisopropanol (1.5 mL). The solution was heated under microwave irradiation at 150° C. for 65 mins. The mixture was concentrated, and crude 595-9 was used without further purification. LCMS: m/z 505.46 [M+H]⁺.

595-10 was prepared following the general procedure for 576-7. LCMS: m/z 696.20 [M+H]⁺. Compound 595 was prepared following the general procedure for 580 using 595-10. LCMS: m/z 562.15 [M+H]⁺.

Example 371

Preparation of Compound 602

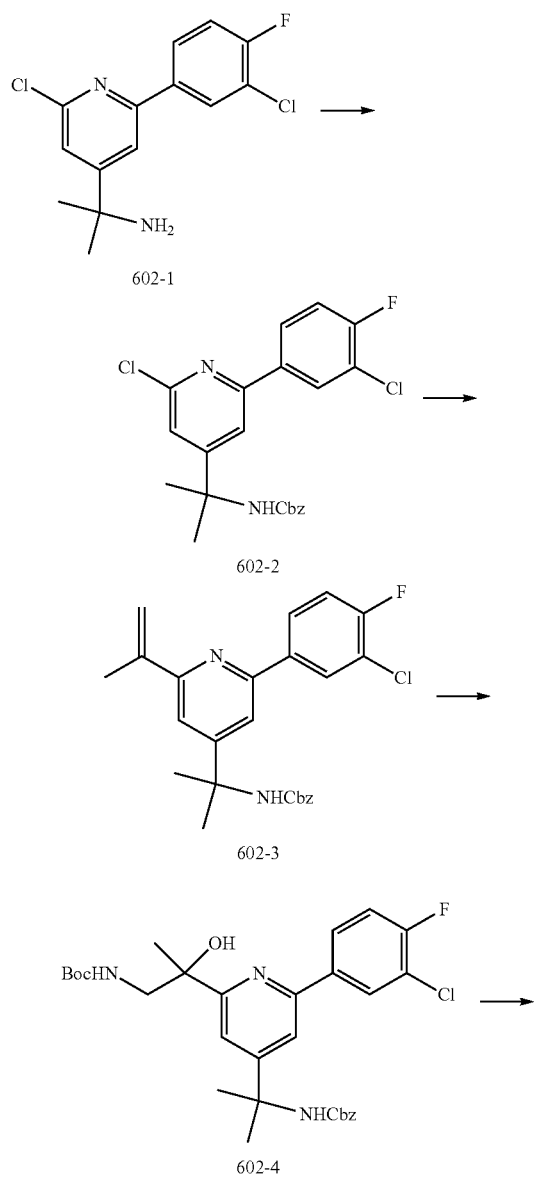

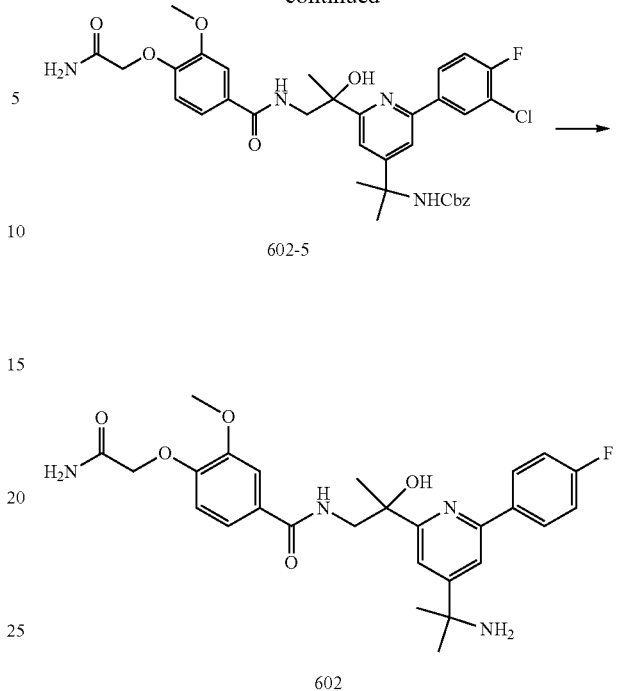

Benzyl chloroformate (0.61 mL, 4.3 mmol) was added dropwise to a solution of 602-1 (0.86 g, 2.9 mmol) and diisopropylethylamine (1.0 mL, 5.7 mmol) in $CH_2Cl_2$ (10 mL). The mixture was stirred at r.t. overnight. The mixture was washed with 1N HCl and brine, dried and concentrated. Crude 602-2 (0.73 g, 58%) was purified by chromatography (hexane:EA). LCMS: m/z 433.05 $[M+H]^+$.

602-3 was prepared following the general procedure for 576-4. LCMS: m/z 439.10 $[M+H]^+$. 602-4 was prepared following the general procedure for 576-6. LCMS: m/z 572.15$[M+H]^+$. 602-5 was prepared following the general procedure for 576-7. LCMS: m/z 679.20 $[M+H]^+$. Compound 602 was prepared following the general procedure for 580 using 602-5. LCMS: m/z 511.15 $[M+H]^+$.

Example 372

Preparation of Compound 578

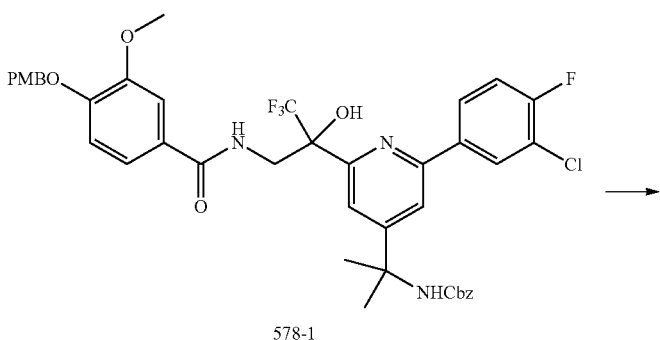

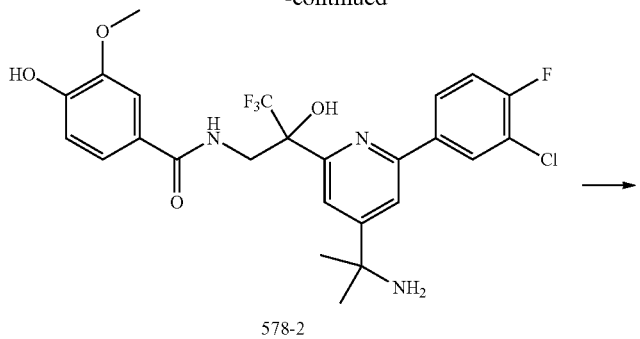

578-2

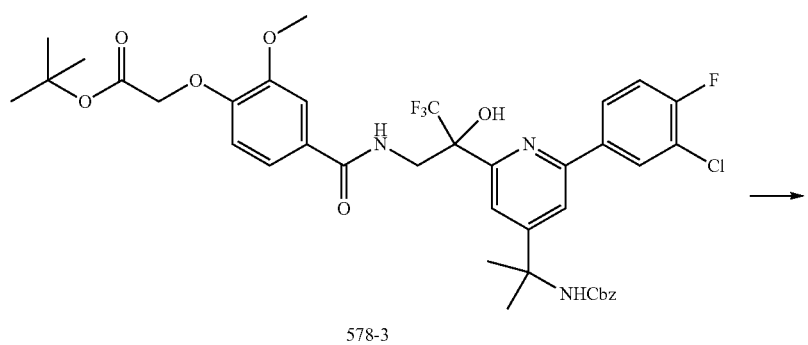

578-3

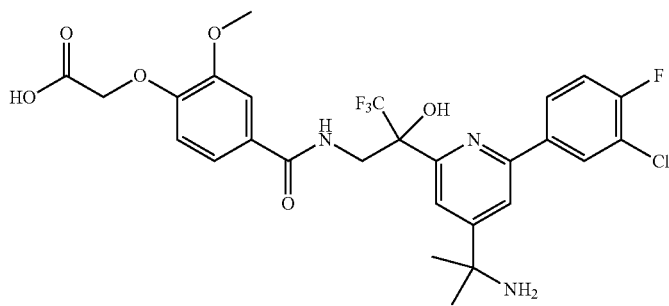

578

Trifluoroacetic acid (0.3 mL) was added to 578-1 (55 mg, 0.069 mmol) in CH$_2$Cl$_2$, and the mixture was stirred at r.t. for 4 mins. The reaction was quenched with cold sodium bicarbonate and extracted with CH$_2$Cl$_2$. The combined organic extracts were washed with brine, dried, concentrated and used without further purification.

Potassium carbonate (50 mg, 0.35 mmol) was added to a solution of 578-2 (0.069 mmol) and tert-butyl bromoacetate (30 µL, 0.21 mmol) in DMF (1 mL). The mixture was heated at 55° C. for 1 h. The mixture was diluted with EA, and washed with water and brine. The crude product was purified by column chromatography (hexane:EA) to provide 578-3. LCMS: m/z 790.20 [M+H]$^+$.

Compound 578 was prepared following the general procedure for 576 using 578-3. LCMS: m/z 600.15 [M+H]$^+$.

Example 373

Preparation of Compound 619

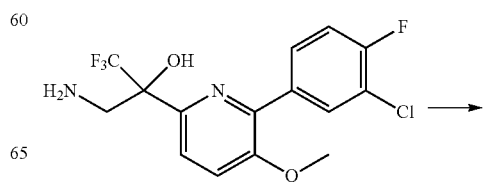

-continued

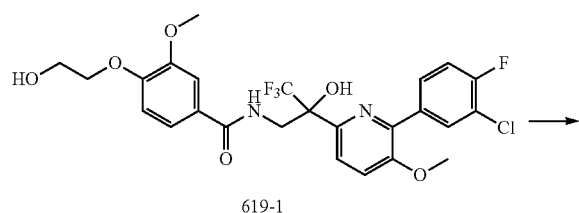

619-1

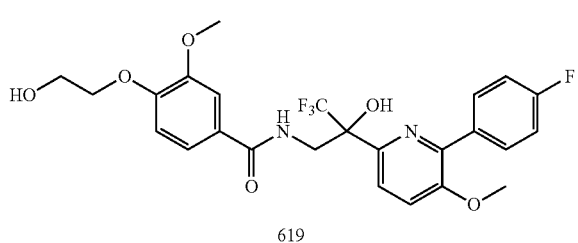

619

619-1 was prepared following the general procedure for 576. Compound 619 was prepared following the general procedure for 580. LCMS: m/z 525.15 [M+H]⁺.

Example 374

Preparation of Compound 635

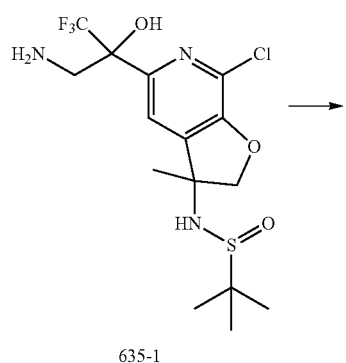

635-1

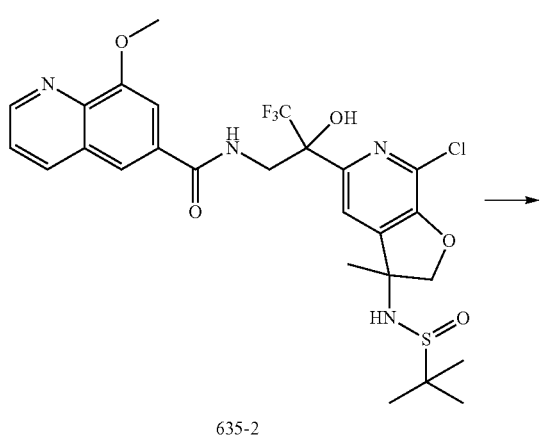

635-2

-continued

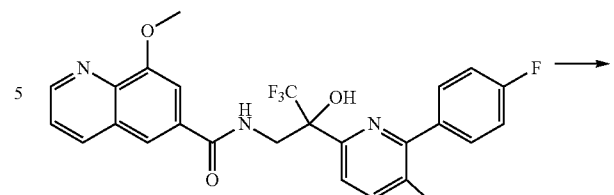

635-3

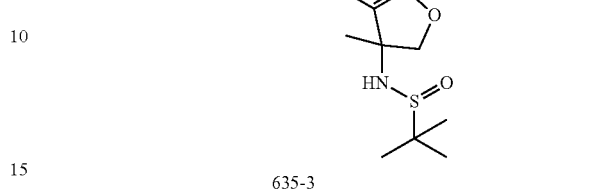

635

DIEA (90 µL, 0.52 mmol) was added to a solution of 635-1 (72 mg, 0.17 mmol), 8-methoxyquinoline-6-carboxylic acid (45 mg, 0.21 mmol) and HATU (98 mg, 0.26 mmol). The mixture was stirred at r.t. for 2 h. The mixture was purified by reverse-phase HPLC to provide 635-2 (50 mg, 48%). LCMS: m/z 601.10 [M+H]⁺.

Pd(dppf)Cl₂ (3 mg, 0.0041 mmol) was added to a solution of 635-2 (50 mg, 0.083 mmol), 4-fluorophenyl boronic acid (17 mg, 0.12 mmol), K₃PO₄ (0.11 mg, 0.22 mmol), KH₂PO₄ (45 mg, 0.22 mmol) in DME (1 mL), EtOH (0.6 mL) and water (0.2 mL). The solution was heated under microwave irradiation at 110° C. for 4 h. The mixture was diluted with EA, washed with brine, dried and concentrated. Crude 635-3 was purified by silica gel chromatography (MeOH:EtOAc). LCMS: m/z 661.20 [M+H]⁺.

635-3 (27 mg) was dissolved in MeOH (1 mL). To this stirring mixture was added a solution of HCl in dioxane (0.2 mL). The mixture was stirred at r.t. for 5 mins. The mixture was concentrated, and 635 (5 mg, 25%) was purified by reverse-phase HPLC. LCMS: m/z 557.15 [M+H]⁺.

Example 375

Preparation of Compound 637

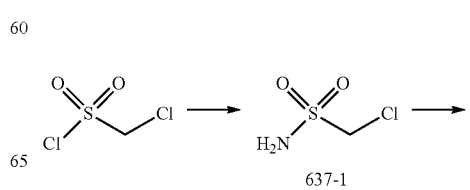

637-1

571

-continued

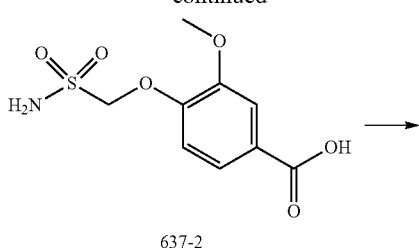

637-2

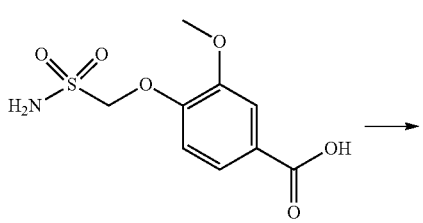

637-3

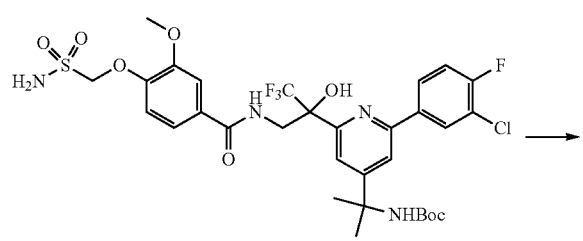

637-4

572

-continued

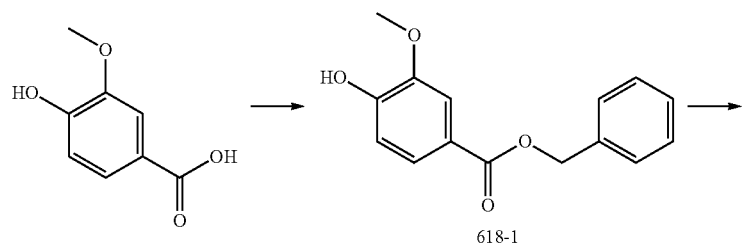

637

Chloromethanesulfonyl chloride (0.4 mL, 4.4 mmol) was added dropwise to a solution of ammonia (0.5 M in dioxane, 8.8 mL, 4.4 mmol) and DIEA (0.92 mL, 5.3 mmol) at 0° C. The solution was stirred for 1 h. The reaction was washed with 1N HCl and brine, dried and concentrated. The crude product was used without further purification.

Potassium carbonate (1.2 g, 8.8 mmol) was added to a solution of methyl vanillate (0.40 g, 2.2 mmol) and 637-1 (4.4 mmol) in DMF (2.0 mL). The mixture was stirred at 65° C. overnight. The reaction was diluted with EA, washed with water and brine, dried and concentrated. The crude product was purified by silica gel chromatography (hexane: EA) to provide 637-2 (50 mg, 8%).

NaOH (2N, 1 mL) was added to a solution of 637-2 (50 mg, 0.18 mmol) in MeOH (3 mL). The mixture was stirred at r.t. overnight. The mixture was acidified by the addition of 2N HCl and extracted with EA. The organic extracts were washed with brine, dried and concentrated. Crude 637-3 was used without further purification.

637-4 was prepared following the general procedure for 576-7. Compound 637 was prepared following the general procedure for 586. LCMS: m/z 635.15

Example 376

Preparation of Compound 618

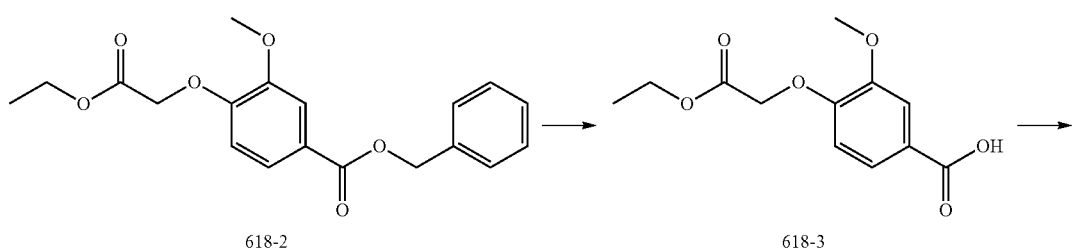

-continued

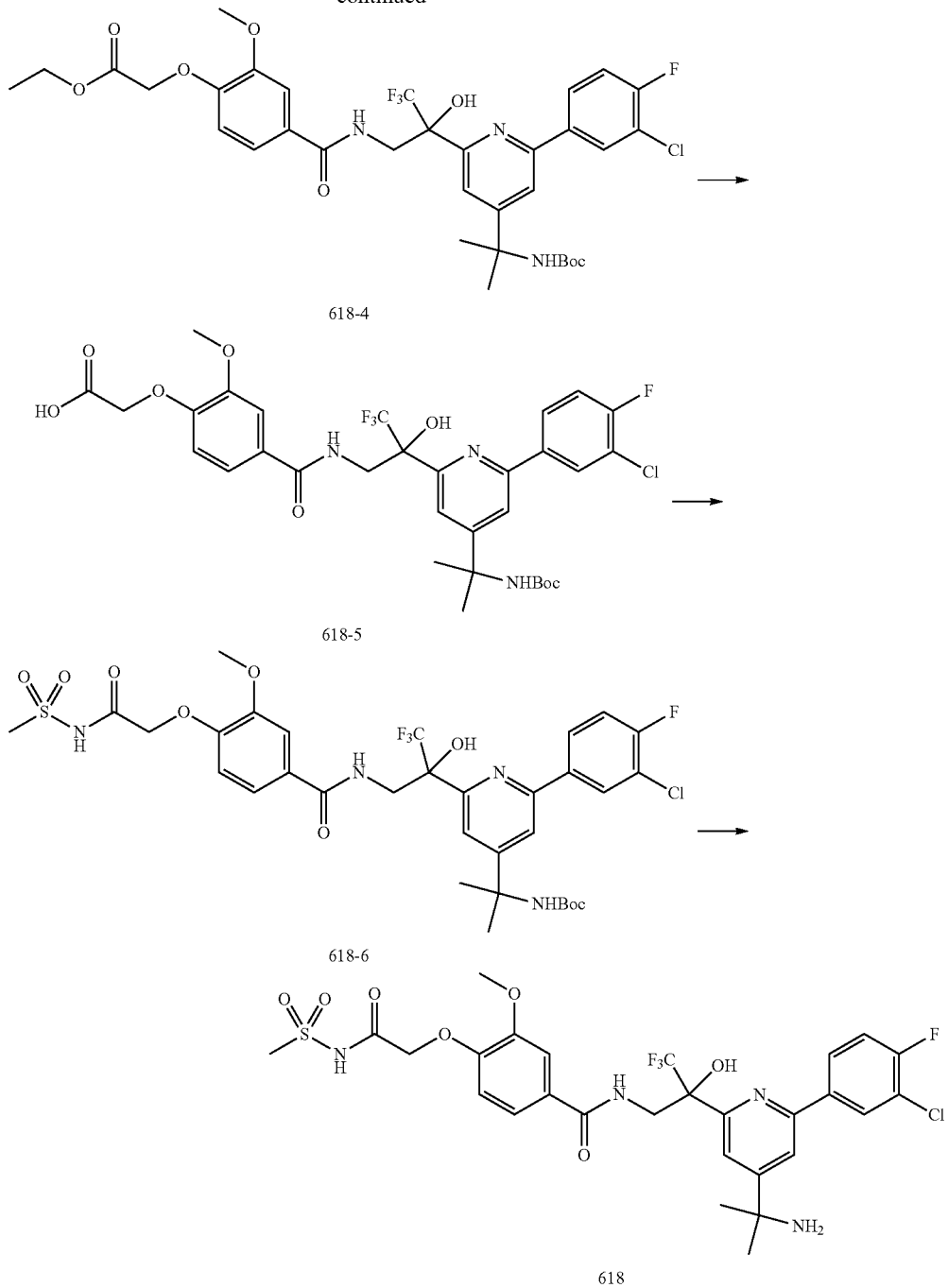

Cesium carbonate (1.0 g, 5.9 mmol) as added to vanillic acid (2.0 g, 12 mmol) suspended in 90% aq. MeOH (20 mL). The mixture was stirred at r.t. for 30 mins. The solvents were removed and the crude product was dried by co-evaporating (2×) with toluene. The cesium salt was re-dissolved in DMF (15 mL). Benzyl bromide was added, and the mixture was stirred at r.t. overnight. The mixture was diluted with EA, washed with water and brine, dried and concentrated. The product was purified by silica gel chromatography (hexane:EA) to yield 618-1 (0.4 g, 12%).

Ethyl bromoacetate (0.34 mL, 3.1 mmol) was added to a solution of 618-1 (0.4 g, 1.5 mmol) and potassium carbonate (0.64 g, 4.6 mmol) in DMF (3 mL). The mixture was stirred at r.t. for 3 h. The mixture was washed with water and brine, dried and concentrated. The crude product was purified by column chromatography (hexane:EA) to yield 618-2 (0.177 g, 34%).

618-2 (0.177 g 0.51 mmol) was hydrogenated over 10% Pd/C (35 mg) in EtOH for 45 mins. The catalyst was removed by filtration, and the mixture was concentrated to yield 618-3 (0.13 g, 100%), which was used without further purification.

618-4 was prepared following the general procedure for 576-7. LCMS: m/z 728.20 [M+H]$^+$. NaOH (2N, 2 mL) was added to a solution of 618-4 (0.302 g, 0.43 mmol) in MeOH (10 mL). The mixture was stirred overnight at r.t. The mixture was acidified with 1N HCl and extracted with EA. The organic extracts were washed with brine, dried and concentrated to yield 618-5 (0.29 g, 92%). LCMS: m/z 700.20 [M+H]⁺.

DMAP was added to a solution of 618-5 (50 mg, 0.071 mmol), methyl sulfonamide (10 mg, 0.11 mmol) and EDCI (16 mg, 0.086 mmol) in DMF (1 mL). The mixture was stirred at r.t. overnight. The product was purified by reverse-phase HPLC to yield 618-6 (27 mg). LCMS: m/z 777.05 [M+H]⁺. Compound 618 was prepared following the general procedure for 586. LCMS: m/z 677.05 [M+H]⁺.

Example 377

Preparation of Compound 617

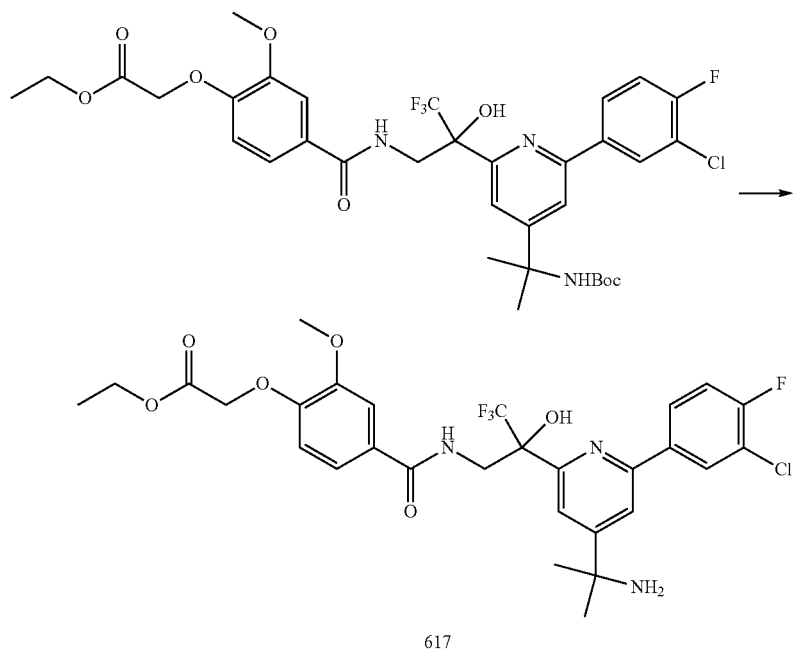

Compound 617 was prepared following the general procedure for 586. LCMS: m/z 628.15 [M+H]⁺.

Example 378

Preparation of Compound 641

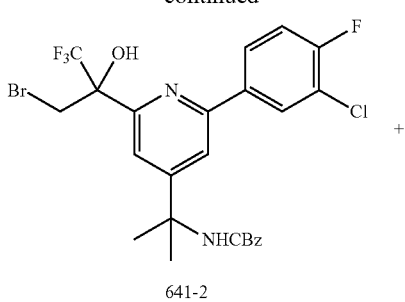

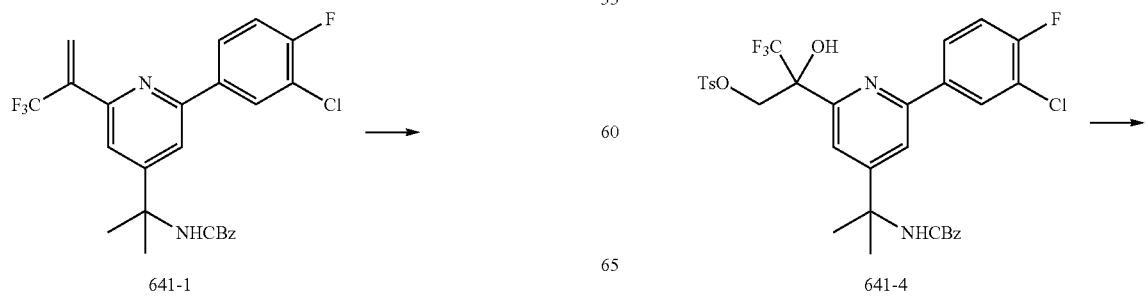

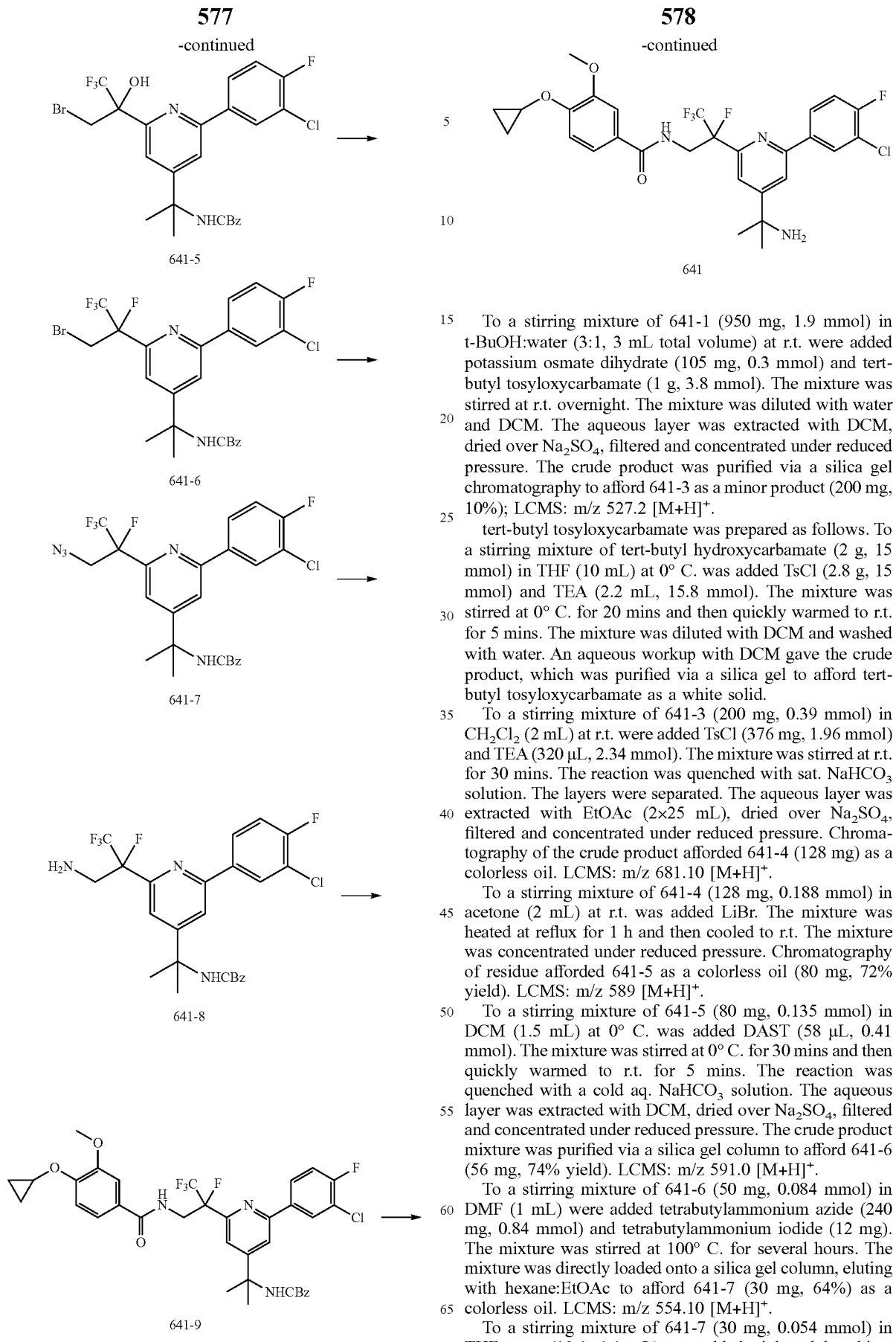

To a stirring mixture of 641-1 (950 mg, 1.9 mmol) in t-BuOH:water (3:1, 3 mL total volume) at r.t. were added potassium osmate dihydrate (105 mg, 0.3 mmol) and tert-butyl tosyloxycarbamate (1 g, 3.8 mmol). The mixture was stirred at r.t. overnight. The mixture was diluted with water and DCM. The aqueous layer was extracted with DCM, dried over $Na_2SO_4$, filtered and concentrated under reduced pressure. The crude product was purified via a silica gel chromatography to afford 641-3 as a minor product (200 mg, 10%); LCMS: m/z 527.2 [M+H]$^+$.

tert-butyl tosyloxycarbamate was prepared as follows. To a stirring mixture of tert-butyl hydroxycarbamate (2 g, 15 mmol) in THF (10 mL) at 0° C. was added TsCl (2.8 g, 15 mmol) and TEA (2.2 mL, 15.8 mmol). The mixture was stirred at 0° C. for 20 mins and then quickly warmed to r.t. for 5 mins. The mixture was diluted with DCM and washed with water. An aqueous workup with DCM gave the crude product, which was purified via a silica gel to afford tert-butyl tosyloxycarbamate as a white solid.

To a stirring mixture of 641-3 (200 mg, 0.39 mmol) in $CH_2Cl_2$ (2 mL) at r.t. were added TsCl (376 mg, 1.96 mmol) and TEA (320 µL, 2.34 mmol). The mixture was stirred at r.t. for 30 mins. The reaction was quenched with sat. $NaHCO_3$ solution. The layers were separated. The aqueous layer was extracted with EtOAc (2×25 mL), dried over $Na_2SO_4$, filtered and concentrated under reduced pressure. Chromatography of the crude product afforded 641-4 (128 mg) as a colorless oil. LCMS: m/z 681.10 [M+H]$^+$.

To a stirring mixture of 641-4 (128 mg, 0.188 mmol) in acetone (2 mL) at r.t. was added LiBr. The mixture was heated at reflux for 1 h and then cooled to r.t. The mixture was concentrated under reduced pressure. Chromatography of residue afforded 641-5 as a colorless oil (80 mg, 72% yield). LCMS: m/z 589 [M+H]$^+$.

To a stirring mixture of 641-5 (80 mg, 0.135 mmol) in DCM (1.5 mL) at 0° C. was added DAST (58 µL, 0.41 mmol). The mixture was stirred at 0° C. for 30 mins and then quickly warmed to r.t. for 5 mins. The reaction was quenched with a cold aq. $NaHCO_3$ solution. The aqueous layer was extracted with DCM, dried over $Na_2SO_4$, filtered and concentrated under reduced pressure. The crude product mixture was purified via a silica gel column to afford 641-6 (56 mg, 74% yield). LCMS: m/z 591.0 [M+H]$^+$.

To a stirring mixture of 641-6 (50 mg, 0.084 mmol) in DMF (1 mL) were added tetrabutylammonium azide (240 mg, 0.84 mmol) and tetrabutylammonium iodide (12 mg). The mixture was stirred at 100° C. for several hours. The mixture was directly loaded onto a silica gel column, eluting with hexane:EtOAc to afford 641-7 (30 mg, 64%) as a colorless oil. LCMS: m/z 554.10 [M+H]$^+$.

To a stirring mixture of 641-7 (30 mg, 0.054 mmol) in THF:water (10:1, 1.1 mL) was added triphenylphosphine, polymer-bound (142 mg, 0.54 mmol). The mixture was stirred at 70° C. for 30 mins and then cooled to r.t. The mixture was filtered through a plug of celite. The plug was washed several times with EtOAc. The crude mixture was concentrated under reduced pressure, and the crude product was used in the next step without further purification.

To a stirring mixture of 4-cyclopropoxy-3-methoxybenzoic acid in DMF (1 mL) were added HATU (21 mg, 0.054 mmol) and DIPEA (15 μL, 0.11 mmol). The mixture was stirred at r.t. for 5 mins. A solution of 641-8 in DMF (0.5 mL) was added. The mixture was stirred at r.t. for 10 mins. The reaction was quenched with a 10% aq. solution of NaHCO$_3$ (10 mL). The mixture was diluted with DCM, and an aqueous work up with DCM was followed. The crude product was purified via prep-HPLC to afford 641-9 (20 mg, 52%, 2 steps) as a white solid. LCMS: m/z 718.2 [M+H]$^+$.

To a stirring mixture of 641-9 (20 mg, 0.0286 mmol) in AcCN (1 mL) at r.t. were added NaI (22 mg, 0.143 mmol) and TMSCl (19 mg, 0.143 mmol). The mixture was warmed to 60° C. until the starting materials were consumed. The mixture was cooled to r.t. and diluted with CH$_2$Cl$_2$. The mixture was washed with a 10% aq. solution of Na$_2$S$_2$O$_3$. The aqueous layer was extracted with DCM (2×10 mL), dried over Na$_2$SO$_4$, filtered and concentrated under reduced pressure. The crude product was further purified via prep-HPLC to afford 641. LCMS: m/z 584.15 [M+H]$^+$.

Example 379

Preparation of Compound 573

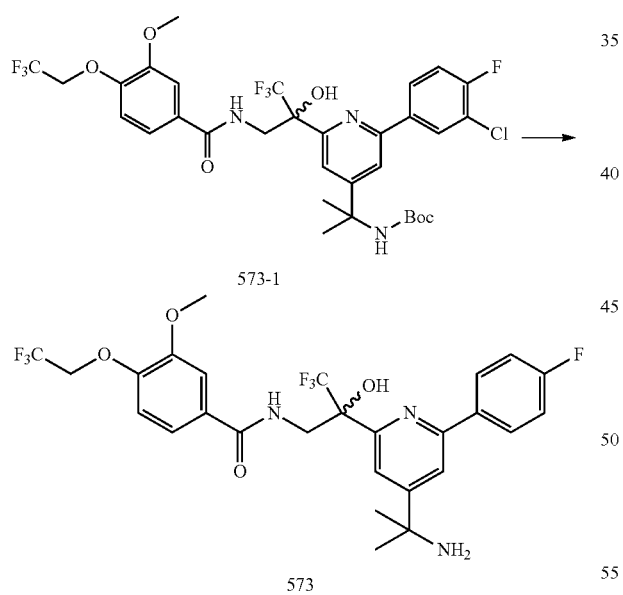

To a stirring solution of 573-1 (30 mg, 0.41 mmol) in EtOAc:EtOH (5 mL:5 mL) was added Pd/C (20 mg). The mixture was placed under a H$_2$ balloon. The mixture was stirred for several hours until the starting material was consumed. The crude mixture was filtered through a plug of celite, and the plug was washed with EtOAc (2×20 mL). The mixture was concentrated under reduced pressure, which was used without further purification.

The N-Boc protected amine was dissolved in a 4N HCl in dioxane. The mixture was stirred overnight at r.t. The crude product mixture was concentrated under reduced pressure. The crude product mixture was purified via a prep-HPLC to afford 573 as a white solid. LCMS: m/z 590.15 [M+H]$^+$.

Example 380

Preparation of Compound 598

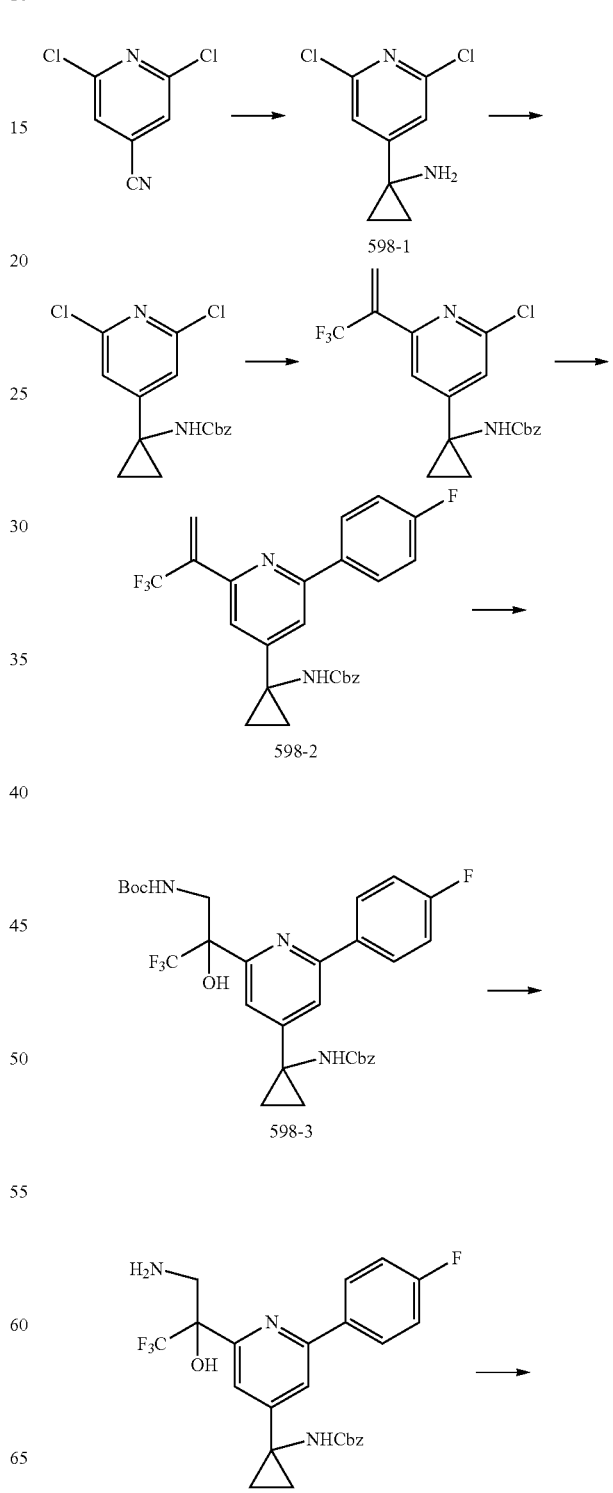

-continued

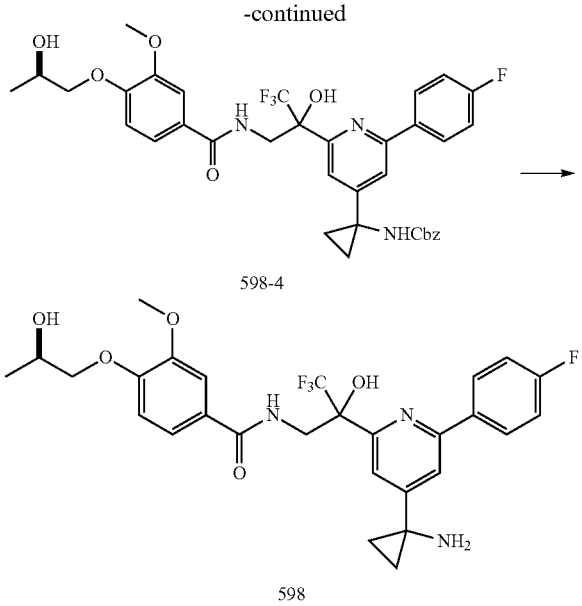

To a stirring mixture of 2,6-dichloroisonicotinonitrile (1 g, 5.78 mmol) in Et₂O at r.t. under Ar was added Ti(OiPr)₄ (1.97 mL, 6.65 mmol). The mixture was stirred for 10 mins and then cooled to 0° C. A solution of EtMgBr (3.54 mL, 12.14 mmol) in 2-methyltetrafuran was added over 10 mins. The mixture was stirred at r.t. for 1 h, and then cooled to 0° C. BF₃.OEt (1.3 mL, 10.58 mmol) was added. The mixture was warmed to r.t. and stir for 30 mins. The reaction was quenched with 1N HCl (5 mL) and then 2N NaOH (10 mL). The mixture was diluted with DCM. The aqueous layer was extracted with DCM, dried over MgSO4, filtered and concentrated under reduced pressure. Chromatography of the residue afford 598-1 (100 mg, 8.5%) as a colorless oil. LCMS: m/z 203.1 [M+H]⁺.

To a stirring mixture of 598-1 (100 mg, 0.49 mmol) in DCM (1 mL) at 0° C. were added CBzCl (84.2 mg, 0.49 mmol) and DIPEA (86 µL, 0.49 mmol). The mixture was warmed to r.t. for 20 mins. The reaction was quenched with a cold sat. NaHCO₃ solution. The aqueous layer was extracted with DCM, dried over Na₂SO₄, filtered and concentrated under reduced pressure. Chromatography of the residue afford N—CBz protected amine (100 mg, 60%). LCMS: m/z 337.0 [M+H]⁺.

To a stirring mixture of benzyl (1-(2,6-dichloropyridin-4-yl)cyclopropyl)carbamate (100 mg, 0.297 mmol) in DME (2 mL, deoxygenated prior to using) were added 4,4,6-trimethyl-2-(3,3,3-trifluoroprop-1-en-2-yl)-1,3,2-dioxaborinane (132 mg, 0.59 mmol), a solution of Cs₂CO₃ (290 mg, 0.89 mmol in 0.3 mL of water) and PdCl₂(dppf) (45 mg, 0.062 mmol). The mixture was heated under microwave irradiation for 1 h at 110° C. The crude product mixture was diluted with EtOAc and water. An aqueous workup with EtOAc was followed. The crude product was purified via a silica gel chromatography to afford desired product. The mixtures was used in the next step without further purification (70 mg). LCMS: m/z 397.10 [M+H]⁺.

To a stirring mixture of products from the previous step (70 mg, 0.176 mmol) in DME (1.5 mL, deoxygenated prior to using) were added 4-fluorophenylboronic acid (36 mg, 0.259 mmol), a solution of Cs₂CO₃ (171 mg, 0.52 mmol in 0.3 mL of water), and PdCl₂(dppf) (26 mg, 0.035 mmol). The mixture was carried out under microwave irradiation at 110° C. for 1 h. The crude product was diluted with EtOAc and water. The aqueous layer was extracted with EtOAc, dried over MgSO₄, filtered and concentrated under reduced pressure. The crude product was purified via a silica gel chromatography to yield benzyl (1-(2-(4-fluorophenyl)-6-(3,3,3-trifluoroprop-1-en-2-yl)pyridin-4-yl)cyclopropyl) carbamate as the desired product. LCMS: m/z 457. [M+H]⁺.

To a stirring mixture of 598-2 (50 mg, 0.085 mmol) in t-BuOH:water (3:1, 1.3 mL) at r.t. were added potassium osmate dihydrate (8 mg, 0.0215 mmol) and tert-butyl tosyloxycarbamate (62 mg, 0.215 mmol). The mixture was stirred at r.t. overnight, and then diluted with water and DCM. The aqueous layer was extracted with DCM, dried over MgSO₄, filtered and concentrated under reduced pressure. The crude product was purified via a silica gel chromatography to afford 598-3 (24 mg, 37%). LCMS: m/z 590.20 [M+H]⁺.

The N-Boc protected amine was dissolved in a solution of HCl in dioxane (2 mL, 4N) at r.t. The mixture was stirred at r.t. until the starting material was consumed. The mixture was concentrated under reduced pressure to afford the crude amino alcohol, which was used without further purification. LCMS: m/z 490.10 [M+H]⁺.

To a stirring mixture of (R)-4-(2-hydroxypropoxy)-3-methoxybenzoic acid (9 mg, 0.04 mmol) in DMF (0.5 mL) were added HATU (15.2 mg, 0.04 mmol) and DIPEA (17 µL, 0.1 mmol). The mixture was stirred at r.t. for 10 mins. A solution of the crude amino alcohol in DMF (0.2 mL) was added. The mixture was stirred at r.t. for 10 mins. The reaction was quenched with a 10% aq. NaHCO₃ solution (1 mL). The mixture was diluted with DCM, and an aqueous work up with DCM was followed. The crude product was purified via prep-HPLC to afford benzyl (1-(2-(4-fluorophenyl)-6-(1,1,1-trifluoro-2-hydroxy-3-(4-((R)-2-hydroxypropoxy)-3-methoxybenzamido)propan-2-yl)pyridin-4-yl) cyclopropyl)carbamate (7 mg, 24% 2 steps) as a white solid. LCMS: m/z 698.2 [M+H]⁺.

To a stirring mixture of 598-4 (7 mg, 0.01 mmol) in AcCN (0.5 mL) at r.t. were added NaI (7.5 mg, 0.05 mmol) and TMSCl (5.4 mg, 0.05 mmol). The mixture was warmed to 60° C. until the starting material was consumed. The mixture was cooled to r.t. and diluted with CH₂Cl₂. The mixture was washed with a 10% aq. Na₂S₂O₃ solution. The aqueous layer was extracted with DCM (2×10 mL), dried over Na₂SO₄, filtered and concentrated under reduced pressure. The crude product was further purified via prep-HPLC to afford 598. LCMS: m/z 564.20 [M+H]⁺.

Example 381

Preparation of Compound 600

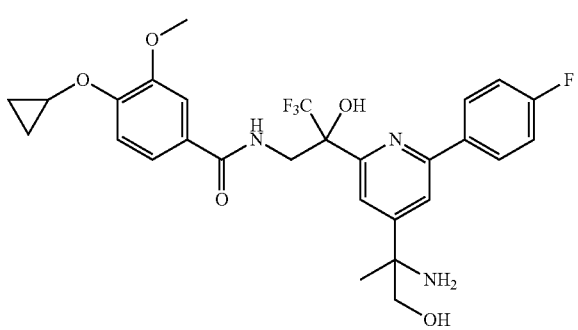 [SMILES: COc1cc(C(=O)NCC(O)(c2cc(C(C)(N)CO)cc(-c3ccc(F)cc3)n2)C(F)(F)F)ccc1OC1CC1]

583

To a stirring solution of 533 (10 mg, 0.016 mmol) in EtOAc:EtOH (5 mL:1 mL) was added Pd/C (15 mg). The mixture was placed under a H₂ balloon. The mixture was stirred for several hours until the starting material was consumed. The crude mixture was filtered through a plug of celite, and the plug was washed several times with EtOAc (2×20 mL). The mixture was concentrated under reduced pressure and purified via prep-HPLC to afford 600 as a white solid (3 mg, 32%). LCMS: m/z 564.2 [M+H]⁺.

Example 382

Preparation of Compound 594

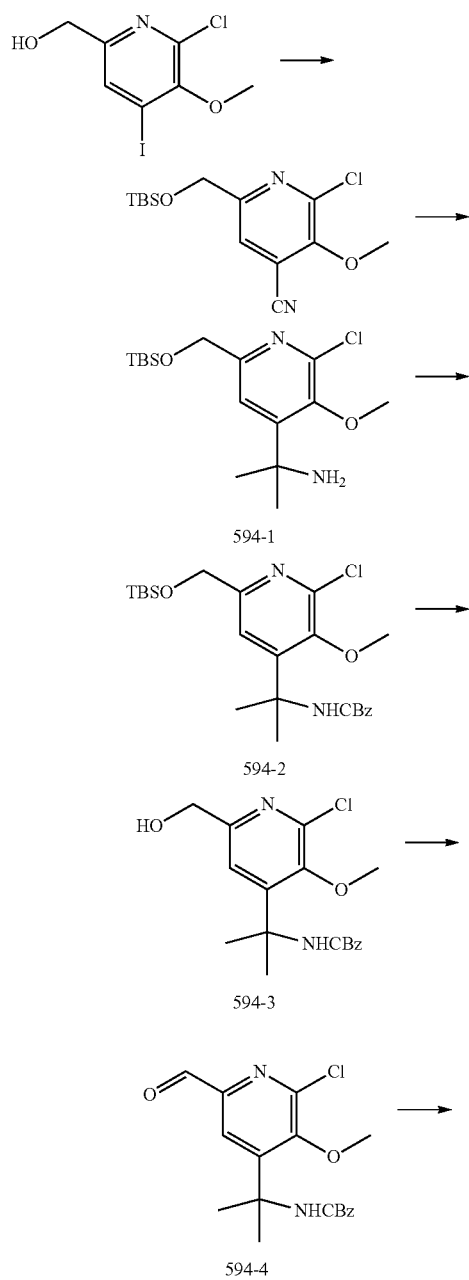

584

-continued

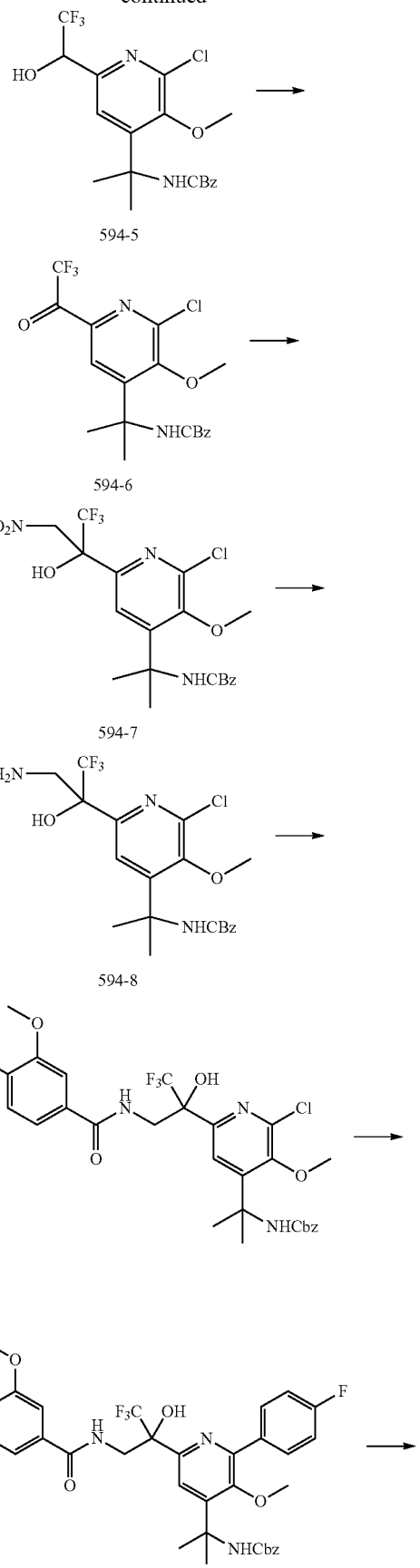

-continued

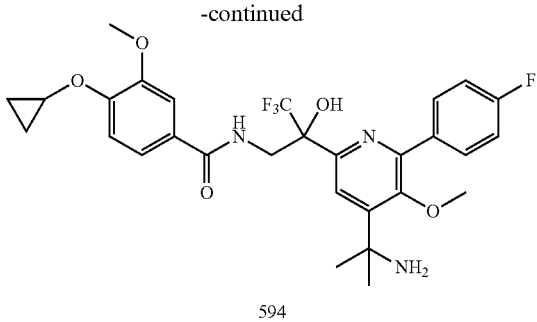

594

Iodomethane (0.66 mL, 11 mmol) was added dropwise to a solution of 2-chloro-3-hydroxy-6-(hydroxymethyl)-4-iodopyridine (2.03 g, 7.1 mmol) and potassium carbonate (2.0 g, 14 mmol) in DMF (8 mL). The mixture was stirred at r.t. for 1 h. The mixture was diluted with EA, washed with water and brine, dried and concentrated. The product (1.77 g, 64%) crystallized upon standing.

DIPEA (2.0 mL, 12 mmol) was added dropwise to a solution of (6-chloro-4-iodo-5-methoxypyridin-2-yl)methanol (1.77 g, 5.91 mmol), tert-butylchlorodimethylsilane (1.3 g, 8.9 mmol) and a catalytic amount of imidazole in $CH_2Cl_2$ (10 mL). The mixture was stirred at r.t. overnight. The mixture was diluted with $CH_2Cl_2$, washed with 1N HCl and brine, dried and concentrated. The crude product was purified by column chromatography (hexane:EA) to yield the product (2.18 g, 75%) as a white solid.

Copper cyanide (1.0 g, 12 mmol) was added to a solution of 6-(((tert-butyldimethyl silyl)oxy)methyl)-2-chloro-4-iodo-3-methoxypyridine (1.0 g, 2.4 mmol) in dimethyl acetamide (3 mL). The mixture was heated at 140° C. for 2 h, and then diluted with DCM. A 10% aq. solution of $NH_4OH$ was added. The mixture was stirred at r.t. for 20 mins, and the layers were separated. An aqueous work up with EtOAc was followed. Chromatography of residue afforded 6-(((tert-butyldimethylsilyl)oxy)methyl)-2-chloro-3-methoxyisonicotinonitrile (520 mg, 70%) as a colorless oil.

To a stirring mixture of 6-(((tert-butyldimethylsilyl)oxy)methyl)-2-chloro-3-methoxyisonicotinonitrile (520 mg, 1.66 mmol) in $Et_2O$ (3.9 mL) at 0° C. was added a solution of MeMgBr in 2-methyltetrafuran (1.47 mL, 4.71 mmol). After 1 h of stirring at r.t., $Ti(OiPr)_4$ was added. The mixture was heated at reflux for 2 h and then diluted with $CH_2Cl_2$. The mixture was cooled to r.t., and copious quantities of Celite were added. The crude mixture was basified with a solution of NaOH (2 mL, 2N) and filtered through a plug of Celite. The plug was washed several times with DCM. The filtrate was washed with a 10% aq. HCl solution. The layers were separated, and the organic layer was washed with sat. $NaHCO_3$ solution. The aqueous layer was extracted with EtOAc (2×25 mL). The organic layers were dried over $Na_2SO_4$, filtered and concentrated under reduced pressure. Chromatography of residue afforded 594-1 (147 mg, 26%) as a colorless oil. LCMS: m/z 345.15 $[M+H]^+$.

To a stirring mixture of 594-1 (147 mg, 0.45 mmol) in DCM (1.5 mL) at 0° C. were added CBzCl (114 mg, 0.67 mmol) and DIPEA (233 µL, 0.49 mmol). The mixture was warmed to r.t. for 10 mins. The reaction was quenched with a cold sat. $NaHCO_3$ solution. The aqueous layer was extracted with DCM, dried over $Na_2SO_4$, filtered and concentrated under reduced pressure. Chromatography of the residue afford 594-2 (110 mg, 57%) as a white solid.

To a stirring mixture of 594-2 (110 mg, 0.25 mmol) in THF (762 µL) at rt was added dropwise a solution of TBAF (0.85 mL) in THF. The mixture was stirred at r.t. until the starting material was consumed. Silica gel was added, and the mixture was stirred at r.t. for 10 mins. resulting mixture was concentrated under reduced pressure. Chromatography of the residue 594-3, which was used without further purification. LCMS: m/z 365.05 $[M+H]^+$.

To a stirring mixture of 594-3 (110 mg, ~0.3 mmol) in $CH_2Cl_2$ (1.3 mL) at r.t. was added and Dess-Martin periodinane (383 mg, 0.9 mmol). The mixture was stirred at r.t. until the alcohol was consumed. The reaction was quenched with a 5% $NaHSO_3$ solution and a sat. $NaHCO_3$ solution. The aqueous layer was extracted with EtOAc (2×25 mL). The organic layers were dried with $Na_2SO_4$, filtered and concentrated under reduced pressure. The crude product mixture was purified via a silica gel column to afford 594-4 (90 mg, 55% 2 steps). LCMS: m/z 363.05 $[M+H]^+$.

To a stirring mixture of 594-4 (90 mg, 0.248 mmol) in DMF (0.5 mL) were added $TMSCF_3$ (53 mg, 0.37 mmol) and a TBAF solution in THF (37 µL). The mixture was stirred at r.t. for 1 h. Silica gel was added, and the mixture was stirred for 10 mins. The crude mixture was concentrated under reduced pressure. Chromatography of the residue afford 594-5 (86 mg, 80%). LCMS: m/z 433.05 $[M+H]^+$.

To a stirring mixture of 594-5 (86 mg, 0.198 mmol) in $CH_2Cl_2$ (1.0 mL) at r.t. was added the Dess-Martin periodinane reagent (421 mg, 0.99 mmol). The mixture was stirred at r.t. until the alcohol was consumed. The reaction was quenched with a 5% aqueous solution of $NaHSO_3$ and a sat. $NaHCO_3$ solution. The aqueous layer was extracted with EtOAc (2×25 mL). The organic layers were dried with $Na_2SO_4$, filtered and concentrated under reduced pressure. The crude product mixture was purified via a silica gel column to afford 594-6 (80 mg, 90%). LCMS: m/z 449.05 $[M+H_2O+H]^+$.

To a stirring mixture of 594-6 (30 mg, 0.074 mmol) in $MeNO_2$ (0.5 mL) was added TEA (20 µL, 0.147 mmol). The mixture was stirred at r.t. for 30 mins, and then diluted with DCM and washed with water. The aqueous layer was extracted with DCM, dried over $Na_2SO_4$, filtered and concentrated under reduced pressure. Chromatography of the residue afford 594-7 (30 mg, 82%) as a white solid. LCMS: m/z 492.05 $[M+H]^+$.

To a stirring mixture of 594-7 (30 mg, 0.061 mmol) in EtOAc (0.3 mL) at r.t. was added $SnCl_2.2H_2O$ (166 mg, 0.74 mmol). The mixture was heated at reflux for 1 h and then cooled to r.t. The mixture was concentrated under reduced pressure. The crude product mixture was directly loaded into a silica gel column to afford 594-8. LCMS: m/z 462.05 $[M+H]^+$.

To a stirring mixture of 4-cyclopropoxy-3-methoxybenzoic acid (12.6 mg, 0.06 mmol) in DMF (0.5 mL) were added HATU (23 mg, 0.06 mmol) and DIPEA (16 µL, 0.09 mmol). The mixture was stirred at r.t. for 10 mins. A solution of 594-8 in DMF (0.2 mL) was added, and the mixture was stirred at r.t. for 10 mins. The reaction was quenched with a 10% aq. $NaHCO_3$ solution(10 mL). The mixture was diluted with DCM and an aqueous work up with DCM was followed. The crude product was purified via prep-HPLC to afford benzyl (2-(2-chloro-6-(3-(4-cyclopropoxy-3-methoxybenzamido)-1,1,1-trifluoro-2-hydroxypropan-2-yl)-3-methoxypyridin-4-yl)propan-2-yl)carbamate (30 mg, quantitative) as a white solid. LCMS: m/z 652.15 $[M+H]^+$.

To a stirring mixture of benzyl (2-(2-chloro-6-(3-(4-cyclopropoxy-3-methoxybenzamido)-1,1,1-trifluoro-2-hydroxypropan-2-yl)-3-methoxypyridin-4-yl)carbamate (30 mg, 0.046 mmol) in DME (2 mL, deoxygenated prior to using) were added 4-fluorophenyl boronic acid (8 mg, 0.055 mmol), a solution of Cs₂CO₃ (45 mg, 0.14 mmol in 0.3 mL of water) and PdCl₂(dppf) (5 mg, 0.007 mmol). The mixture was stirred at 110° C. under microwave reaction conditions for 1 h. The crude product mixture was diluted with EtOAc and water. An aqueous workup with EtOAc was followed. The crude product mixture was purified via a silica gel chromatography to afford the product and unreacted starting material (25 mg). LCMS: m/z 712.20 [M+H]⁺.

To a stirring solution of N-Cbz protected amine and unreacted starting material from the previous step (25 mg) in EtOAc:i-PrOH:HOAc (5 mL:1 mL:1 mL) was added Pd/C (20 mg). The mixture was placed under a H₂ balloon. The mixture was stirred for several hours until the starting material was consumed. The crude mixture was filtered through a plug of celite, and the plug was washed with EtOAc (2×20 mL). The mixture was concentrated under reduced pressure. The crude product mixture was purified via HPLC to afford 594 as a white solid. LCMS: m/z 578.15 [M+H]⁺.

Example 383

Preparation of Compounds 582, 583 and 589

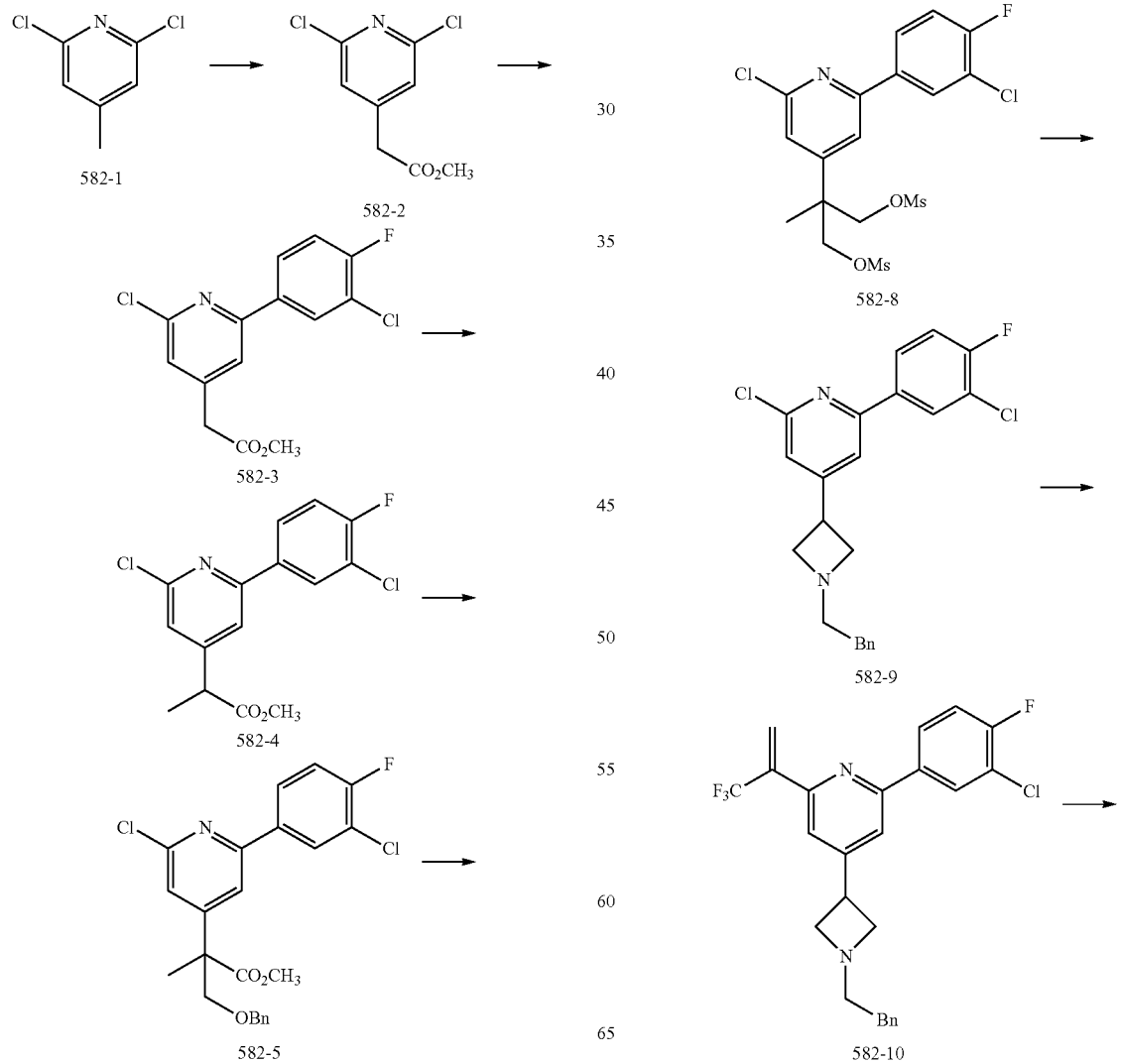

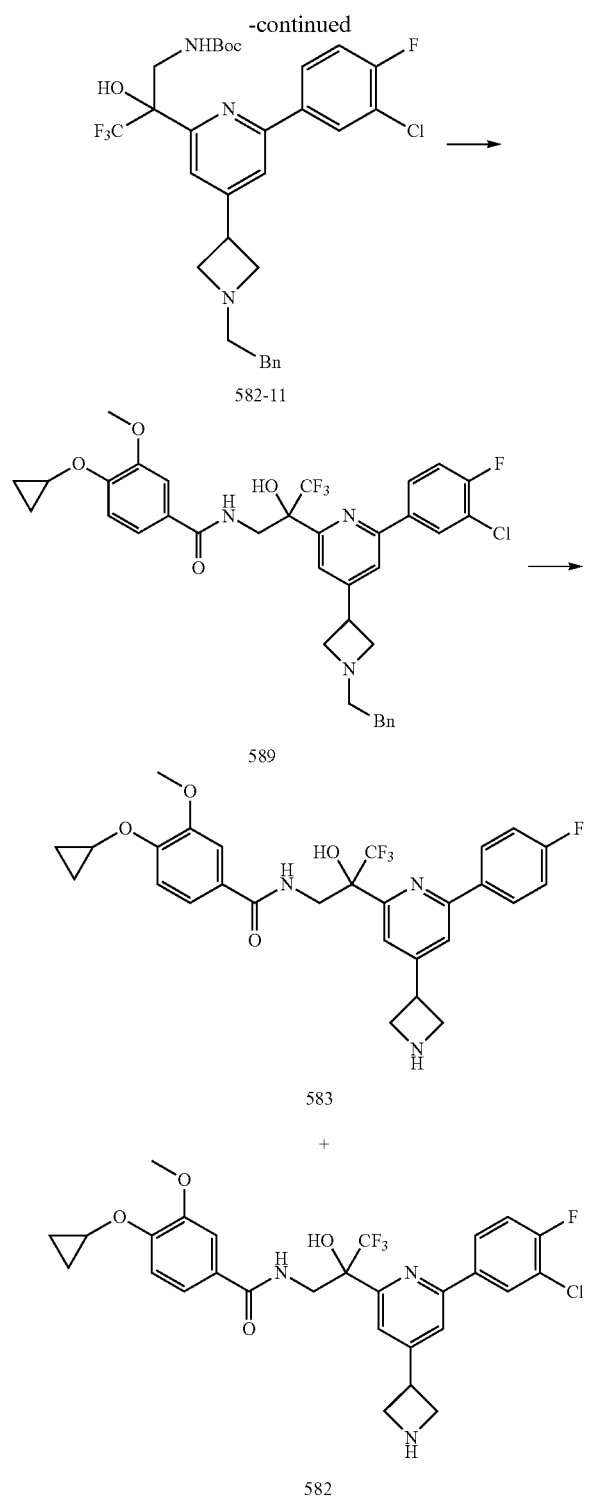

dried over sodium sulfate. The organic layer was concentrated to dryness, and the residue was purified by column chromatography (PE:EA=20:1) to give 582-2 (50 g, 73.5%) as a colorless oil.

To a solution of crude 582-2 (50 g, 230 mmol) in dioxane:$H_2O$ (6:1) (1 L) was added 4-fluoro-3-chloro-phenyl boronic acid (40 g, 230 mmol), $Cs_2CO_3$ (223.3 g, 680 mmol) and Pd(dppf)$Cl_2$ (16.8 g, 23 mmol) under $N_2$. The mixture was degassed (3×) and refilled with $N_2$. The mixture was stirred at 80° C. in a pre-heated oil bath for 4 h. After cooling to r.t., the mixture was diluted with water (1.5 L) and extracted with EA (3×1 L). The combined organic layers were washed with brine, dried over sodium sulfate and concentrated in vacuum to dryness. The residue was purified by column chromatography (PE:EA=20:1~15:1) to yield 582-3 (42 g, 58.7%) as a light yellow solid.

To a solution of 582-3 (10 g, 31.9 mmol) in anhydrous THF (100 mL) was added LiHMDS (63.9 mL, 63.9 mmol) dropwise at −78° C. The mixture was stirred at −78° C. for 30 mins. A solution of MeI (9.07 g, 63.9 mmol) in dry THF (50 mL) was added dropwise. The mixture was warmed to 0° C. and stirred at 0° C. for 1 h. The reaction was quenched with water (100 mL) and extracted with EA (3×150 mL). The combined organic layers were washed with brine, dried over sodium sulfate and concentrated in vacuum to dryness. The residue was purified by column chromatography (PE:EA=10:1) to yield 582-4 (3.5 g, 32%) as a light yellow solid.

To a solution of 582-4 (3.2 g, 10.22 mmol) in anhydrous THF (20 mL) was added NaHMDS (20.44 mL, 20.44 mmol) dropwise at −78° C. The mixture was stirred at −78° C. for 30 mins. A solution of BnOCH$_2$Cl (3.19 g, 20.44 mmol) in dry THF (10 mL) was added dropwise. The mixture was warmed to 0° C. and stirred for 1 h. The reaction was quenched with water (50 mL) and extracted with EA (3×50 mL). The combined organic layers were washed with brine, dried over sodium sulfate and concentrated in vacuum to dryness. The residue was purified by column chromatography (PE:EA=10:1) to yield 582-5 (2.7 g, 59%) as a yellow oil.

To a stirred solution of 582-5 (16.22 g, 36.29 mmol) in anhydrous THF (150 mL) was added LiAlH$_4$ (1.38 g, 36.29 mmol) powder in portions under $N_2$ at 0° C. for a period of 10~15 mins. The mixture was stirred at 0° C. for 0.5 h. The reaction was quenched with water (100 mL) and filtered via a plug of celite. The filtrate was extracted with EA (3×100 mL). The combined organic layers were washed with brine, dried over sodium sulfate and concentrated in vacuum to dryness. The residue was purified by column chromatography (PE:EA=3:1) to give 582-6 (13.5 g, 89%) as a yellow oil.

To a stirred solution of 582-6 (5 g, 11.93 mmol) in anhydrous DCM (50 mL) was added FeCl$_3$ (19.4 g, 119.3 mmol) powder in one portion at r.t. The mixture was stirred at r.t. for 1 h. The mixture was diluted with water (100 mL) and filtered via a bed of celite bed. The filtrate was extracted with EA (2×150 mL). The combined organic layers were To a stirred solution of 582-1 (50 g, 310 mmol) in anhydrous THF (1.2 L) was added LDA (310 mL, 620 mmol) at −78° C. under $N_2$. The mixture was stirred at −78° C. for 0.5 h. A solution of dimethyl carbonate (67.1 g, 750 mmol) in dry THF (150 mL) was added dropwise. The solution was warmed to 0° C. and stirred for 1 h below 0° C. The reaction was quenched with aq. NH$_4$Cl (500 mL), extracted with EA (3×1 L). The combined organic phase was washed with a. sodium bicarbonate (1 L) and brine, and washed with brine, dried over sodium sulfate and concentrated in vacuum to dryness. The residue was purified by column chromatography (PE:EA=1:1) to give 582-7 (3.6 g, 92%) as a brown oil.

To a stirred solution of 582-7 (3.5 g, 10.6 mmol) in anhydrous DCM (20 mL) was added TEA (5.4 g, 53 mmol) at r.t. MsCl (4.8 g, 42.4 mmol) was added dropwise, and the mixture was stirred at r.t. for 1 h. The solution was washed with water (20 mL) and brine (20 mL), and then concentrated to dryness. The residue was purified by column chromatography (PE:EA=5:1) to give 582-8 (3.6 g, 69%) as a yellow oil.

582-8 (480 mg, 0.987 mmol) was dissolved in benzyl amine (3 mL). The mixture was heated under microwave irradiation at 135° C. for 5 h. The crude mixture was cooled to r.t. and directly loaded into a silica gel column to afford a mixture of products. This mixture was further purified via prep-HPLC to afford 582-9 (100 mg, 25% yield) as a colorless oil; LCMS: m/z 401.05 [M+H]$^+$.

To a stirring mixture of 582-9 (100 mg, 0.249 mmol) in DME (2 mL, deoxygenated prior to using) were added 4,4,6-trimethyl-2-(3,3,3-trifluoroprop-1-en-2-yl)-1,3,2-dioxaborinane (111 mg, 0.498 mmol), a solution of Cs$_2$CO$_3$ (243 mg, 0.75 mmol in 0.5 mL of water) and PdCl$_2$(dppf) (36 mg, 0.005 mmol). The mixture was stirred at 110° C. for 2 h under microwave reaction conditions. The crude product mixture was diluted with EtOAc and water. An aqueous workup with EtOAc was followed. The crude product mixture was purified via a silica gel chromatography to afford 582-10 (114 mg, quantitative yield). LCMS: m/z 461.05 [M+H]$^+$.

To a stirring mixture of 582-10 (26 mg, 0.056 mmol) in t-BuOH:water (3:1, 1.3 mL total volume) at r.t. were added potassium osmate dihydrate (3 mg, 0.008 mmol) and tert-butyl tosyloxycarbamate (32 mg, 0.112 mmol). The mixture was stirred at r.t. overnight. The mixture was diluted with water and diluted with DCM. The aqueous layer was extracted with DCM, dried over Na$_2$SO$_4$, filtered and concentrated under reduced pressure. The crude product mixture was purified via a silica gel chromatography to afford 582-11 (15 mg, 45%). LCMS: m/z 594.2 [M+H]$^+$.

The N-Boc protected amine was dissolved in HCl in dioxane (3 mL, 4N). The mixture was stirred at r.t. for several hours until the starting material was consumed. The crude product was concentrated under reduced pressure and directly used in the next step without further purification. Coupling of the crude amine with 4-cyclopropoxy-3-methoxybenzoic acid following the general procedure for 598 afforded 589 as a white solid. LCMS: m/z 684.20 [M+H]$^+$.

To a stirring solution of 589 (38 mg, 0.064 mmol) in EtOAc:iPrOH:HOAc (5 mL:1 mL:1 mL) was added a 10% Pd/C (40 mg). The mixture was placed under a H$_2$ balloon. The mixture was stirred for several hours until the starting material was consumed. The crude mixture was filtered through a plug of celite, and the plug was washed with EtOAc (2×20 mL). The mixture was concentrated under reduced pressure and purified via prep-HPLC to afford 583 and 582. 583: LCMS: m/z 560.15 [M+H]$^+$ and 582: LCMS: m/z 594.15 [M+H]$^+$.

Example 384

Preparation of Compound 590

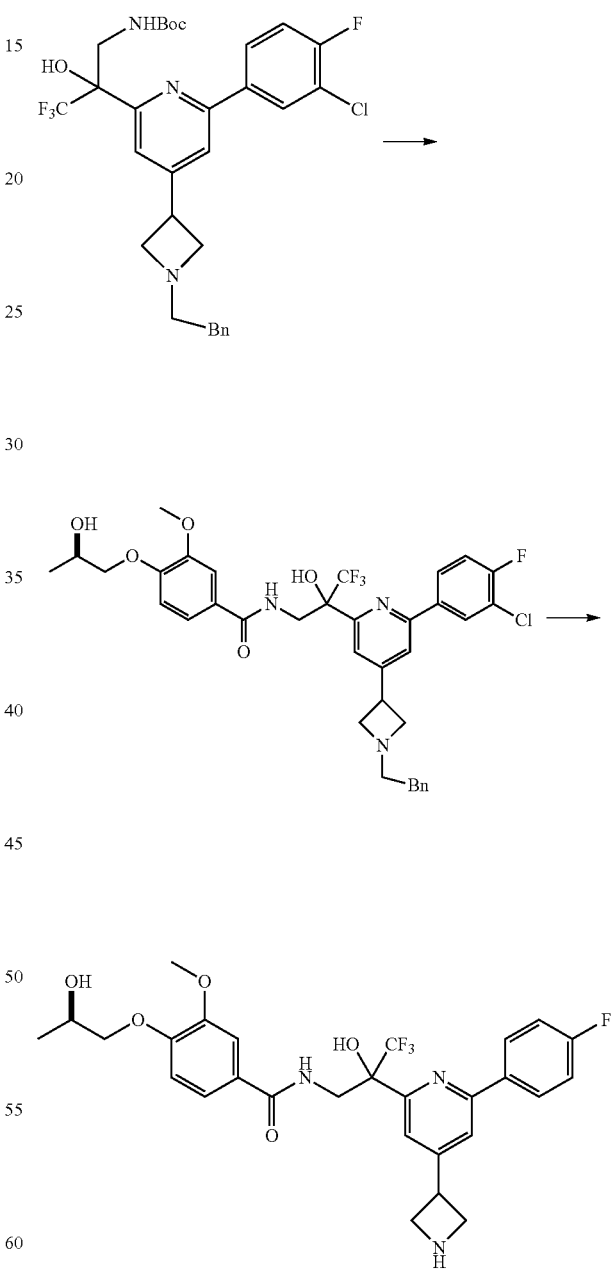

Compound 590 was prepared following the general procedure for 583 using (R)-4-(2-hydroxypropoxy)-3-methoxybenzoic acid and HATU. LCMS: m/z 578.15 [M+H]$^+$.

Example 385

Preparation of Compound 584

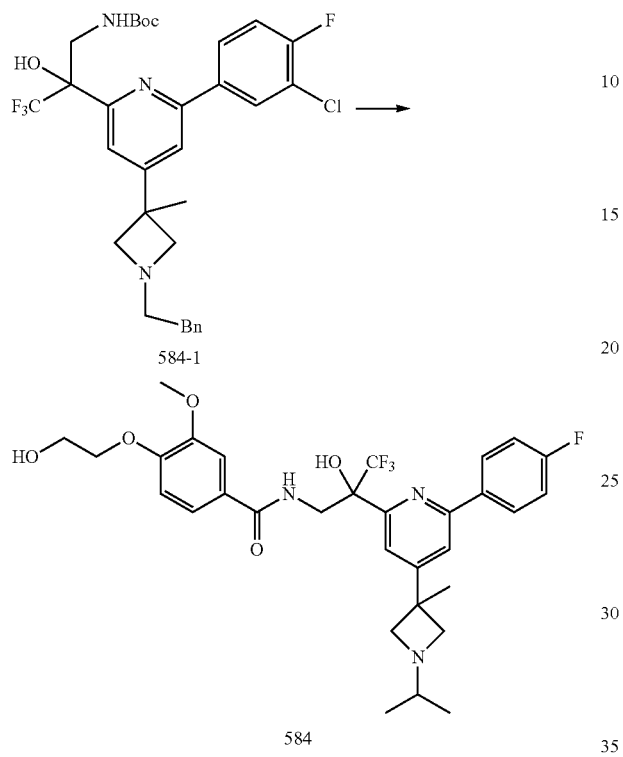

584-1 was prepared following the general procedure for 583 using 3-methoxy-4-(2-((4-methoxybenzyl)oxy)ethoxy)benzoic acid and HATU.

To a stirring mixture of 584-1 in DCM (1 mL) was added TFA (0.2 mL). The mixture was stirred at r.t. for 5 mins, and then diluted with DCM. The reaction quenched with a cold NaHCO$_3$ solution. The aqueous layer was extracted with DCM, dried with Na$_2$SO$_4$, filtered and concentrated under reduced pressure. The crude product mixture was purified via prep-HPLC to afford 584 as a white solid. LCMS: m/z 606.25 [M+H]$^+$.

Example 386

Preparation of Compound 588

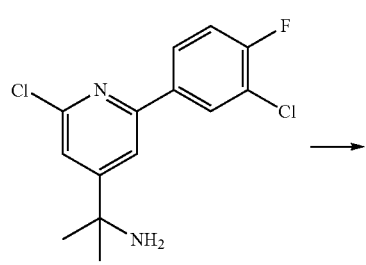

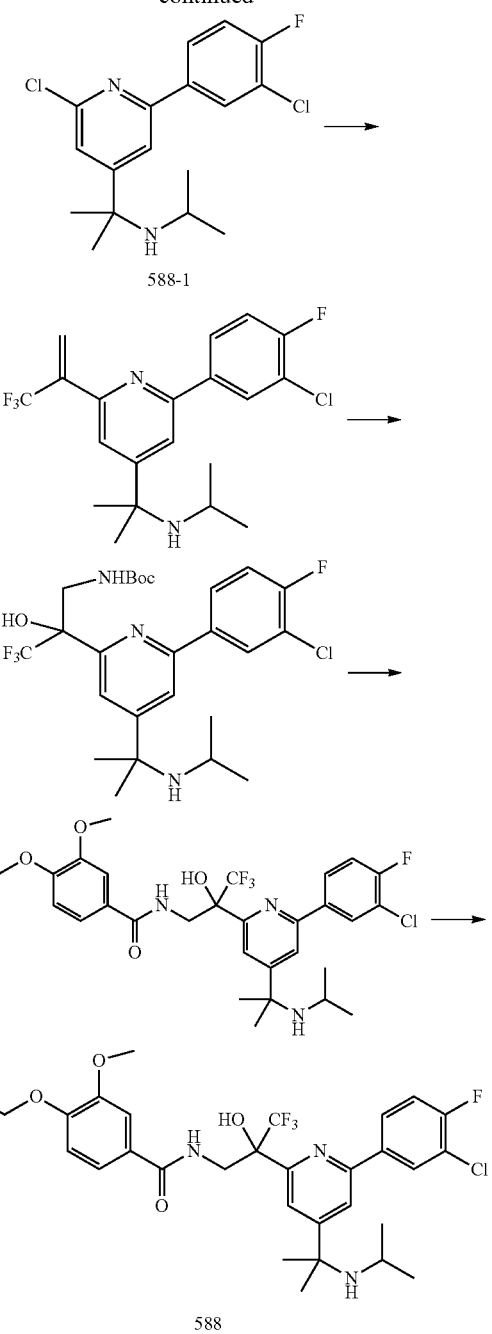

To a stirring mixture of 2-(2-chloro-6-(3-chloro-4-fluorophenyl)pyridin-4-yl)propan-2-amine (200 mg, 0.67 mmol) in DCE (1 mL) at r.t. were added acetone (78 mg, 1.33 mmol), HOAc (10 mg) and Na(OAc)$_3$BH (280 mg). The mixture was stirred at r.t. overnight. The mixture was diluted with DCM, and the reaction quenched with a cold NaHCO$_3$ solution. The aqueous layer was extracted with DCM, dried with Na$_2$SO$_4$, filtered and concentrated under reduced pressure. The crude product mixture was purified via a silica gel column to afford 588-1 (180 mg, 79%) as a colorless oil. LCMS: m/z 341.0 [M+H]$^+$.

Compound 588 was prepared following the general procedure for 582 and 583. LCMS: m/z 607.2 [M+H]$^+$.

Example 387

Preparation of Compound 597

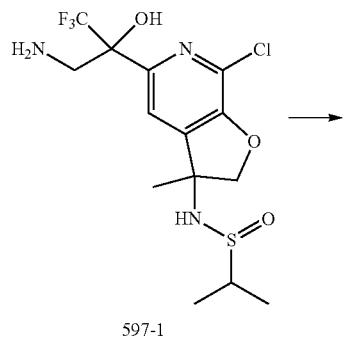

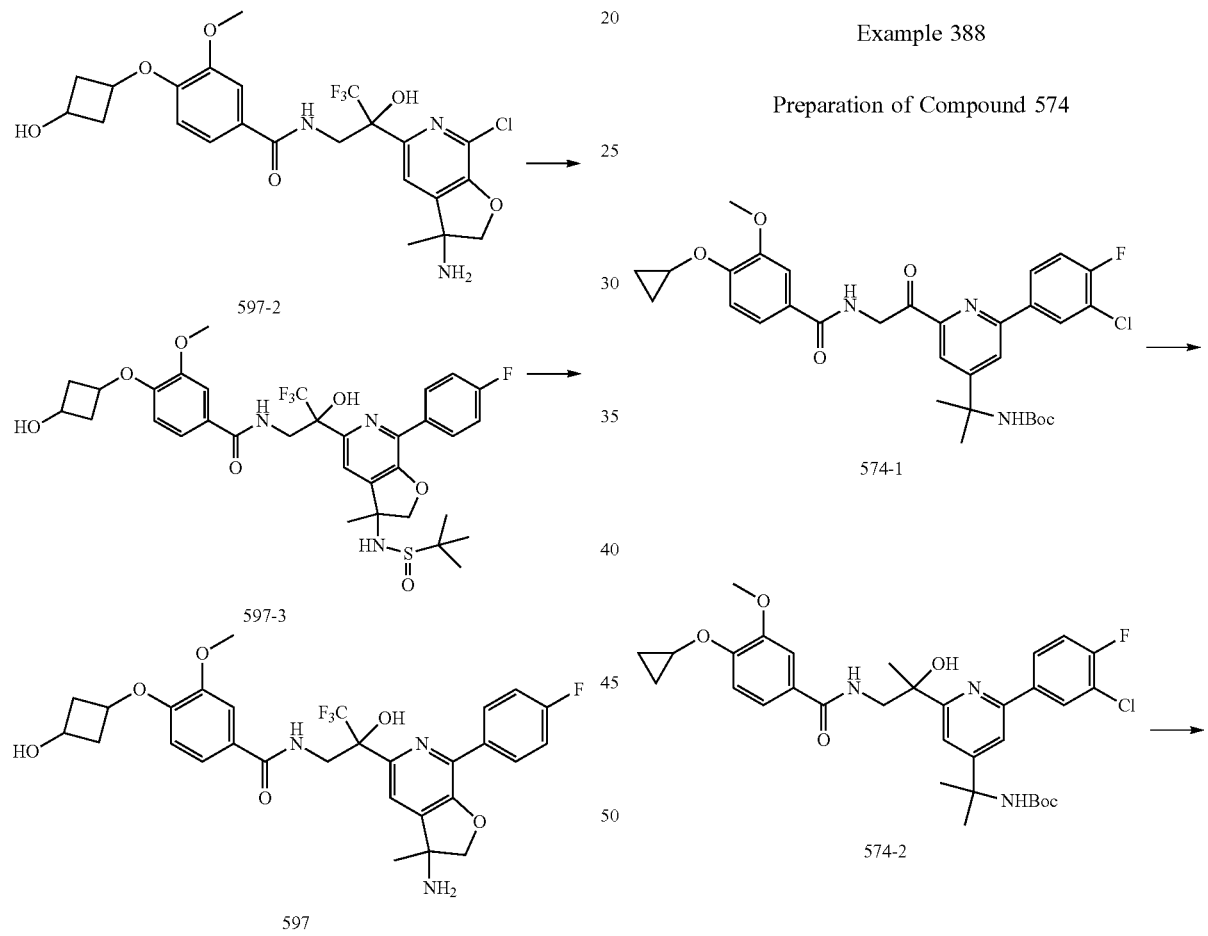

To a stirring mixture of 4-(3-hydroxycyclobutoxy)-3-methoxybenzoic acid (70 mg, 0.168 mmol) in DMF (1 mL) were added HATU (64 mg, 0.168 mmol) and DIPEA (60 μL, 0.336 mmol). The mixture was stirred at r.t. for 5 mins. A solution of 597-1 in DMF (0.5 mL) was added, and the mixture was stirred at r.t. for 10 mins. The reaction was quenched with a 10% aq. solution of NaHCO$_3$ (1 mL). The mixture was diluted with DCM, and an aqueous work up with DCM was followed. The crude product was purified via prep-HPLC to afford 597-2 (80 mg, 75%) as a white solid. LCMS: m/z 636.15 [M+H]$^+$.

To a stirring mixture of 597-2 (40 mg, 0.063 mmol) in DME:EtOH:H$_2$O (1.5 mL:0.5 mL:0.2 mL, deoxygenated prior to using) were added 4-fluorophenylboronic acid (9 mg, 0.063 mmol), K$_3$PO$_4$·7H$_2$O (64 mg, 0.19 mmol), KH$_2$PO$_4$ (25 mg, 0.16 mmol) and PdCl$_2$(dppf) (7.5 mg, 0.01 mmol). The mixture was carried out under microwave irradiation at 110° C. for 5 h. The crude product mixture was diluted with EtOAc and water. An aqueous workup with EtOAc was followed. The crude product mixture was purified via a silica gel chromatography to afford 597-3. LCMS: m/z 696.20 [M+H]$^+$.

To a stirring mixture of 597-3 in MeOH (5 mL) at r.t. was added a solution of HCl in dioxane (4N, 1 mL). The mixture was stirred for 10 mins, and then concentrated under reduced pressure. The crude product was purified via HPLC to afford 597 (30 mg, 70%) as a white solid. LCMS: m/z 592.1 [M+H]$^+$.

Example 388

Preparation of Compound 574

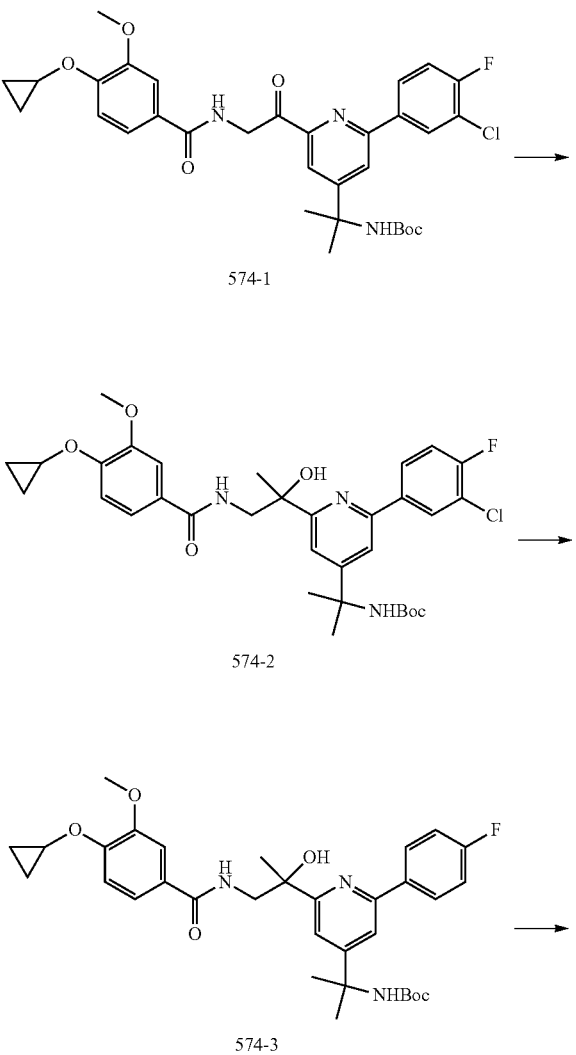

-continued

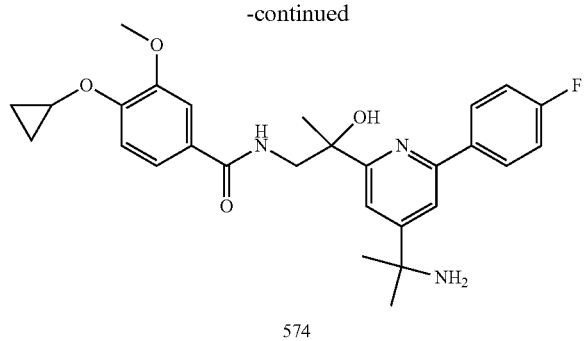

574

To a stirring mixture of 574-1 (130 mg, 0.21 mmol) in THF (2 mL) at r.t. was added dropwise a solution of MeMgBr in toluene (0.91 mL, 1.27 mmol). The mixture was stirred at r.t. for 2 h, and then diluted with EtOAc. The reaction quenched with a sat. NH$_4$Cl solution. The layers were separated, and the aqueous layer was extracted with EtOAc. The combined organic layers were washed with brine, dried over Na$_2$SO$_4$, filtered and concentrated under reduced pressure. The crude product was purified via a silica gel chromatography to afford a mixture that included 574-2. LCMS: m/z 628.20 [M+H]$^+$.

574-2 (40 mg) was hydrogenated over 10% Pd/C (35 mg) in EtOAc:EtOH (5 mL each) for 2 h. The catalyst was removed by filtration, and the crude product was used in the next step without further purification. LCMS: m/z 594.25 [M+H]$^+$.

To HCl in dioxane (5 mL, 4N) was added 574-3 (20 mg), and the mixture was stirred at r.t. for 3 h. The mixture was concentrated, and the crude product was purified by prep-HPLC to provide 574. LCMS: m/z 494.20 [M+H]$^+$.

Example 389

Preparation of Compound 572

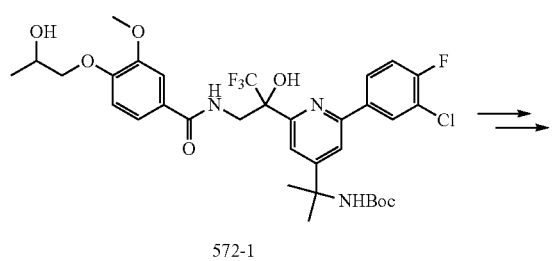

572-1

572

To a stirring mixture of 572-1 (25 mg, 0.0357 mmol) in pyridine (1 mL) was added a solution of isopropylchloroformate (110 μL, 0.101 mmol) in toluene. The mixture was stirred at r.t. for 2 h. The mixture was diluted with DCM, and the reaction quenched with a sat. NaHCO$_3$ solution. The layers were separated, and the aqueous layer was extracted with EtOAc. The combined organic layers were washed with brine, dried over Na$_2$SO$_4$, filtered and concentrated under reduced pressure. The crude product was purified via a silica gel chromatography to afford 572-2 as a colorless oil. LCMS: m/z 786.25 [M+H]$^+$.

To a stirring mixture of 572-2 (22 mg, 0.032 mmol) in AcCN (1 mL) at 0° C. were added NaI (24 mg, 0.15 mmol) and TMSCl (25 μL, 0.15 mmol). The mixture was stirred for an 10 mins, and then warmed to r.t. The mixture was diluted with EtOAc and washed with a 10% aq. Na$_2$S$_2$O$_3$ solution. The organic layer were washed with brine, dried over Na$_2$SO$_4$, filtered and concentrated under reduced pressure. The mixture was concentrated, and the crude product purified by prep-HPLC to provide 572. LCMS: m/z 686.2 [M+H]$^+$.

Example 390

Preparation of Compound 591

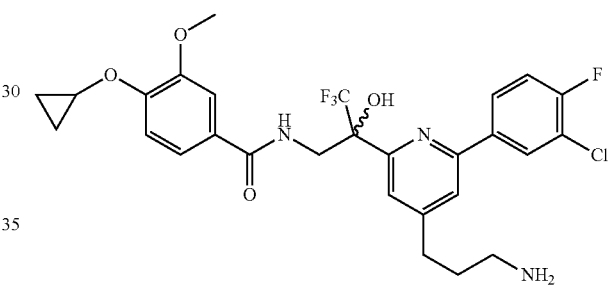

To a stirring mixture of 544 (50 mg, 0.075 mmol) in HOAc:EtOAc (6 mL, 5:1) was added Pd/C (30 mg). The mixture was placed under a H$_2$ balloon for several hours. The mixture was filtered through a plug of Celite, and the plug was washed several times with EtOAc. The filtrate was concentrated under reduced pressure and purified via prep-HPLC to afford 544. LCMS: m/z 582.10 [M+H]$^+$.

Example 391

Preparation of Compound 640

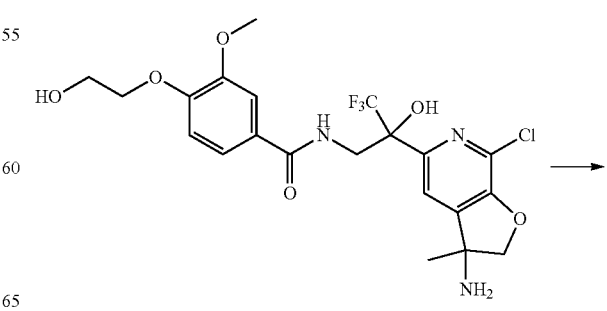

640-1

-continued

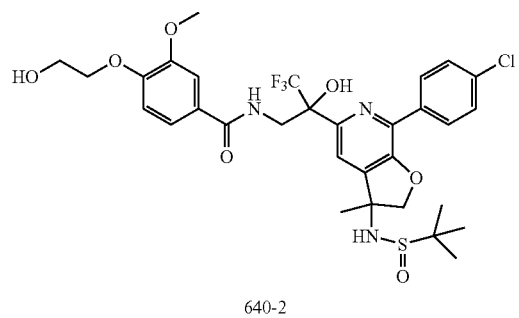

640-2

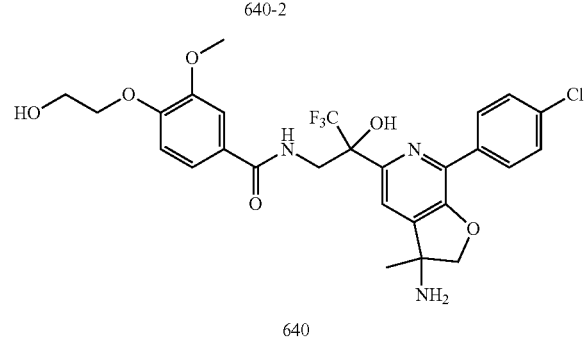

640

Suzuki coupling of 640-1 (50 mg) with 4-chlorophenyl-boronic acid followed by sulfinamide hydrolysis afforded 640 (20 mg) as a white solid. LCMS: m/z 582.15 [M+H]$^+$.

Example 392

Preparation of Compound 646

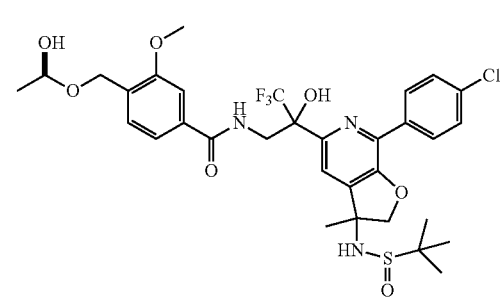

646-1

-continued

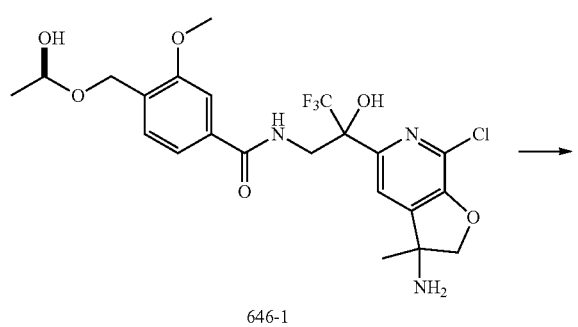

646

Compound 646 (white solid, 11.6 mg) was prepared following the general procedure for 640 using 646-1 (25 mg). LCMS: m/z 596.10 [M+H]$^+$.

Example 393

Preparation of Compound 666

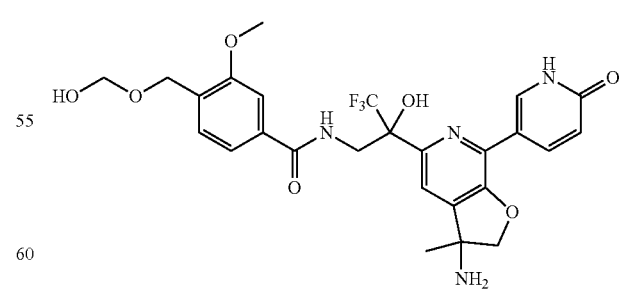

Compound 666 (white solid, 6.7 mg) was prepared following the general procedure for 640 using 646-1 (20 mg) and 4-chloro-3-fluorophenyl boronic acid. LCMS: m/z 614.15 [M+H]$^+$.

Example 394

Preparation of Compound 649

Compound 649 (white solid, 19.6 mg) was prepared following the general procedure for 640 using 640-1 (40 mg) and (6-oxo-1,6-dihydropyridin-3-yl)boronic acid. LCMS: m/z 565.15 [M+H]$^+$.

Example 395
Preparation of Compound 665
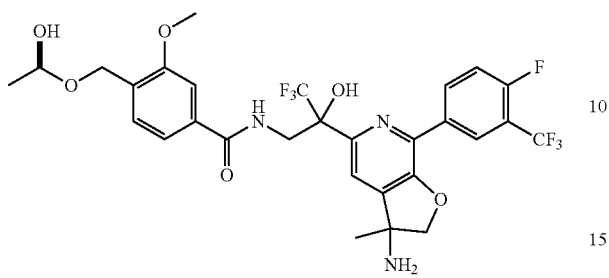
Compound 649 (white solid, 9.2 mg) was prepared following the general procedure for 640 using 646-1 (35 mg) and (4-fluoro-3-(trifluoromethyl)phenyl)boronic acid. LCMS: m/z 648.15 [M+H]$^+$.
Example 396
Preparation of Compound 628
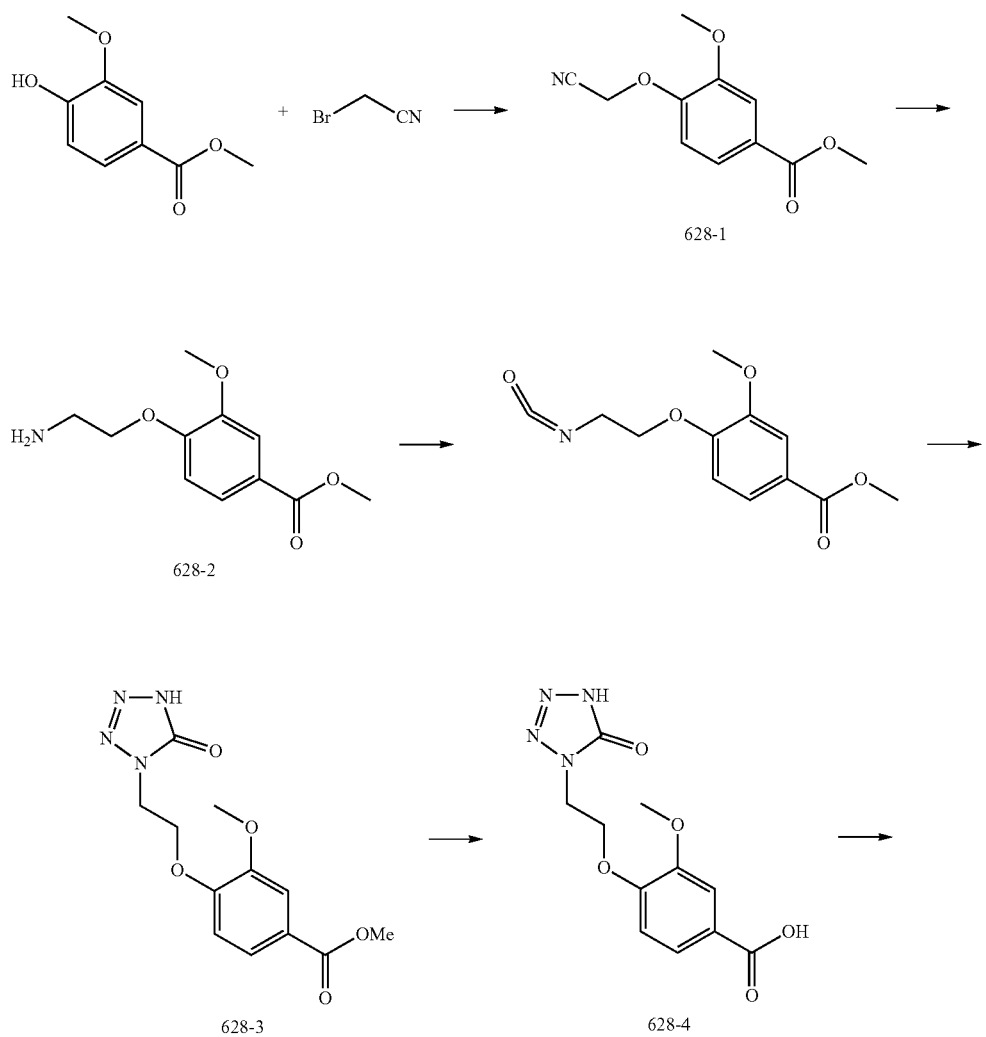

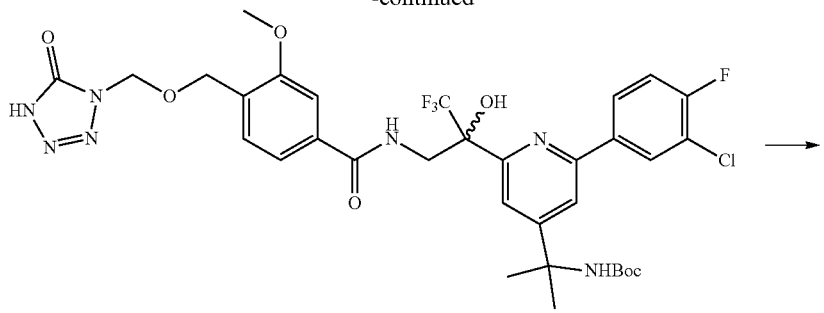

628-5

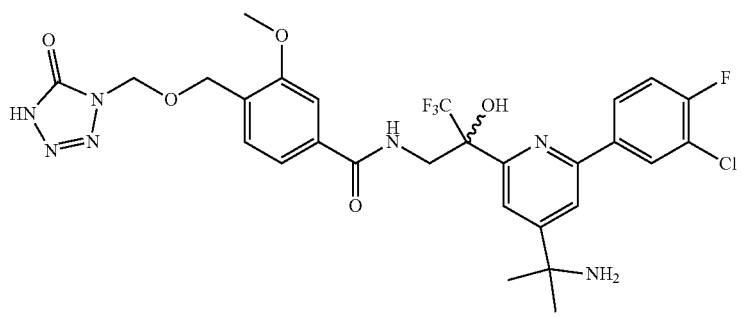

628

To a stirring mixture of methyl-4-methoxybenzoate (1 g, 5.49 mmol) in DMF (5 mL) at r.t. was added K₂CO₃ (1.14 g, 8.24 mmol) and 2-bromoacetonitrile (653 mg, 5.49 mmol). The mixture was stirred at r.t. for 3 h, and then diluted with EtOAc and water. The aqueous layer was extracted with EtOAc. The organic layers were dried over Na₂SO₄, filtered and concentrated under reduced pressure. The crude product was purified via a silica gel chromatography to afford 628-1 as a white solid.

To a stirring mixture of 628-1 (600 mg, 2.72 mmol) in THF (6 mL) was added dropwise a solution of borane and DMS complex in THF (0.26 mL, 2.72 mmol) at r.t. The mixture was slowly warmed to 60° C. for 1 h. The mixture was cooled to r.t. and diluted with EtOAc. The reaction was quenched with an aq. solution of HCl (1N). The mixture was stirred at r.t. for 10 mins and then neutralized with a sat. NaHCO₃ solution. The layers were separated, and the aqueous layer was extracted with EtOAc. The organic layers were dried over Na₂SO₄, filtered and concentrated under reduced pressure. The crude product was purified via a silica gel chromatography to afford 628-2 as a white solid. LCMS: m/z 226.1 [M+H]⁺.

To a stirring mixture of 628-2 (40 mg, 0.177 mmol) in DCM (0.6 mL) at 0° C. were added diphosgene (32 mg, 0.177 mmol) and DIPEA (42 µL, 0.27 mmol). The mixture was warmed to r.t. for 20 mins and then concentrated under reduced pressure. The crude product was dissolved in toluene (0.5 mL), and azidotrimethylsilane (0.14 mL) and 1 drop of BF₃.OEt₂ were added. The mixture was heated at reflux for 1 h. The crude mixture was cooled to r.t. and diluted with DCM. The reaction was quenched with water, and extracted with DCM. The organic layers were dried over Na₂SO₄, filtered and concentrated under reduced pressure. The crude product was purified via a silica gel chromatography to afford 628-3 as a white solid (18 mg, 36% in 2 steps).

628-3 was dissolved in a solution of HCl in dioxane (1 mL). An aqueous solution of HCl (6N, 1 mL) was added, and the mixture was heated at 80° C. overnight. The mixture was cooled to r.t. and diluted with EtOAc. The aqueous layer was extracted with EtOAc. The organic layers were dried over Na₂SO₄, filtered and concentrated under reduced pressure. The crude product was purified via prep-HPLC to afford 628-4 as a white solid. LCMS: m/z 302.85 [M+Na]⁺.

To a stirring mixture of tert-butyl (2-(2-(3-amino-1,1,1-trifluoro-2-hydroxypropan-2-yl)-6-(3-chloro-4-fluorophenyl)pyridin-4-yl)propan-2-yl)carbamate (8 mg, 0.0163 mmol) and 628-4 (from the previous step) in DCM (0.3 mL) were added EDCI (6.2 mg, 0.032 mmol), HOAt (4.5 mg, 0.033 mmol) and TEA (20 µL). The mixture was stirred for 5 mins, and the reaction was quenched with 2 drops of a solution of HCl (1N). The organic layer was transferred to a different flask and concentrated under reduced pressure. The crude product was purified via prep-HPLC to afford the desired product as a white solid; LCMS: m/z 754.20 [M+H]⁺.

628-5 was dissolved in a solution of HCl in dioxane (5 mL, 4N). The mixture was stirred at r.t. until the starting material was consumed. The crude mixture was concentrated under reduced pressure and purified via prep-HPLC to afford 628 as a white solid (8.5 mg). LCMS: m/z 654.1 [M+H]⁺.

Example 397

Preparation of Compound 636

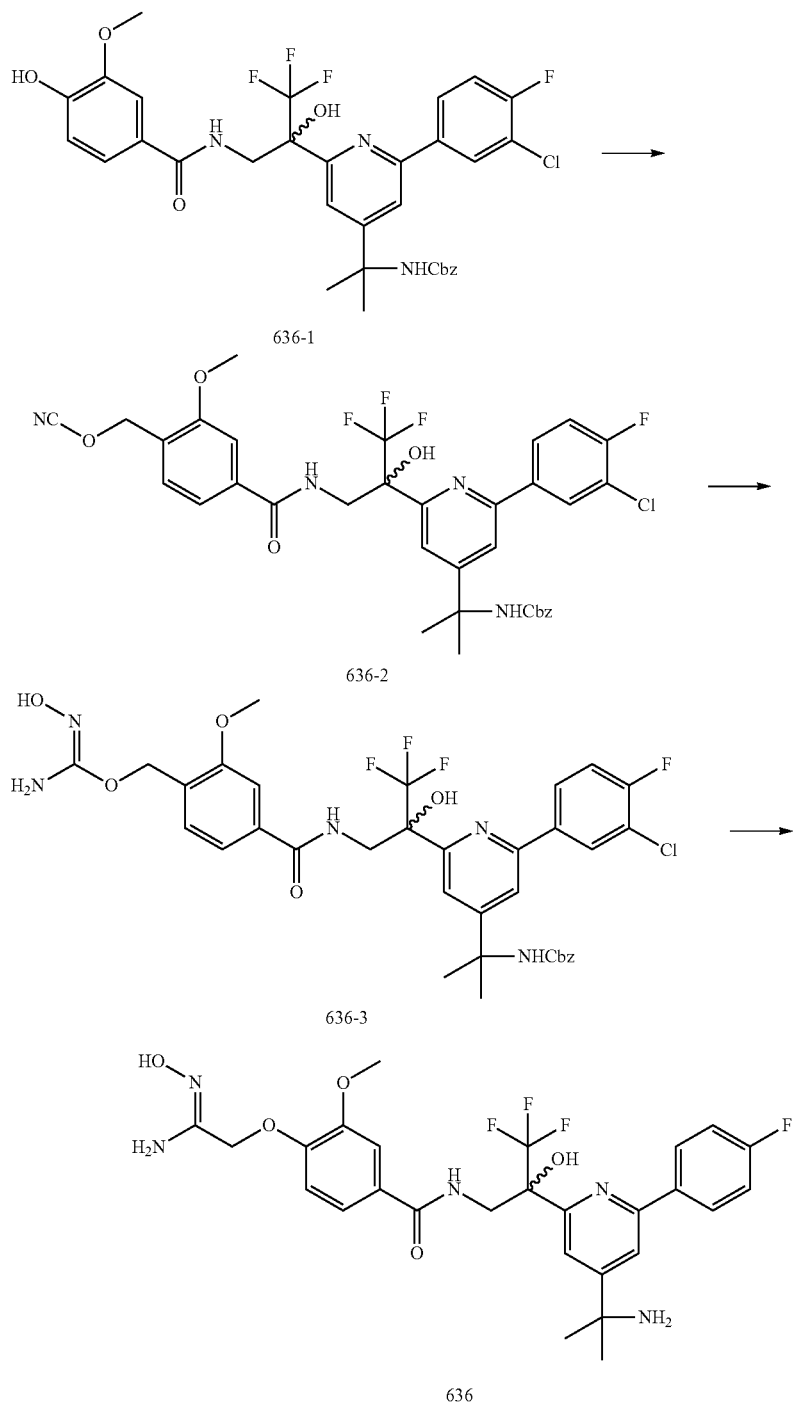

The crude product was purified via a silica gel column to afford 636-2 as a colorless oil (40 mg). LCMS: m/z 715.15 [M+H]$^+$.

To a stirring mixture of 636-1 (130 mg, 0.192 mmol) in DMF (1 mL) were added K$_2$CO$_3$ (80 mg, 0.576 mmol) and 2-bromoacetonitrile (46 mg, 0.38 mmol). The mixture was stirred at r.t. until the starting material was consumed. The mixture was diluted with EtOAc and washed with brine. The aqueous layer was extracted with EtOAc, dried over Na$_2$SO$_4$, filtered and concentrated under reduced pressure.

To a stirring mixture of 636-2 (20 mg, 0.028 mmol) in pyridine (0.3 mL) was added NH$_2$OH.HCl (10 mg). The mixture was stirred at reflux for several hours. The mixture was cooled to r.t., diluted with toluene and concentrated under reduced pressure. This process was repeated twice. The crude product was purified via a silica gel column to afford 636-3 as a colorless oil (10 mg).

To a stirring mixture of 636-3 (10 mg, 0.013 mmol) in EtOAc:HOAc:EtOH (5:1:1, 7 mL) was added Pd/C (20 mg). The mixture was placed under a H₂ balloon for several hours. The mixture was filtered through a plug of Celite, and the plug was washed several times with EtOAc. The filtrate was concentrated under reduced pressure and purified via prep-HPLC to afford 636 (4.0 mg) as a white solid. LCMS: m/z 580.15 [M+H]⁺.

Example 398

Preparation of Compound 652

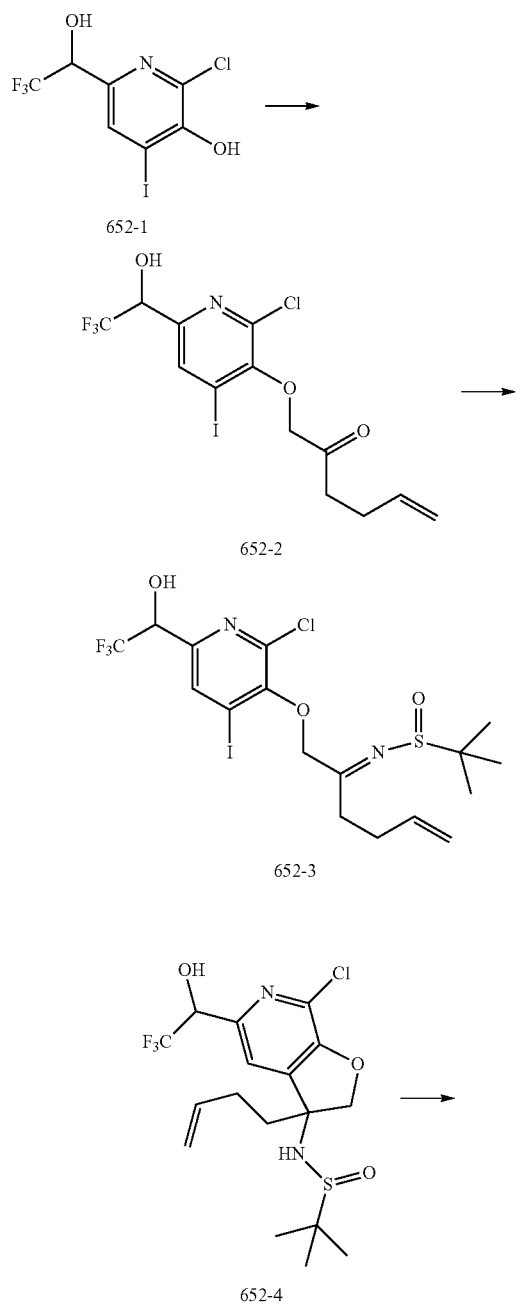

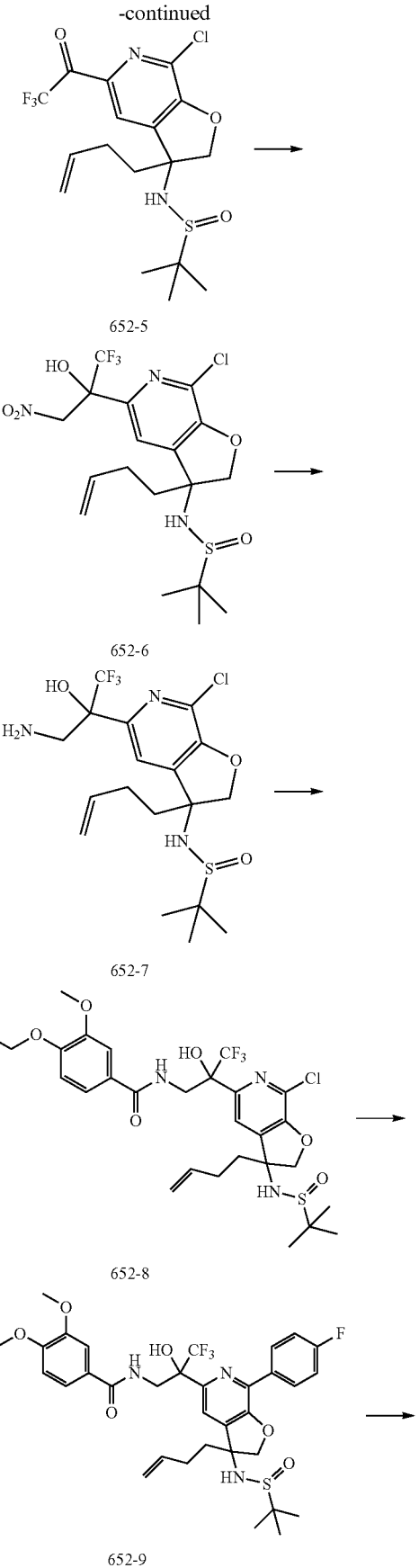

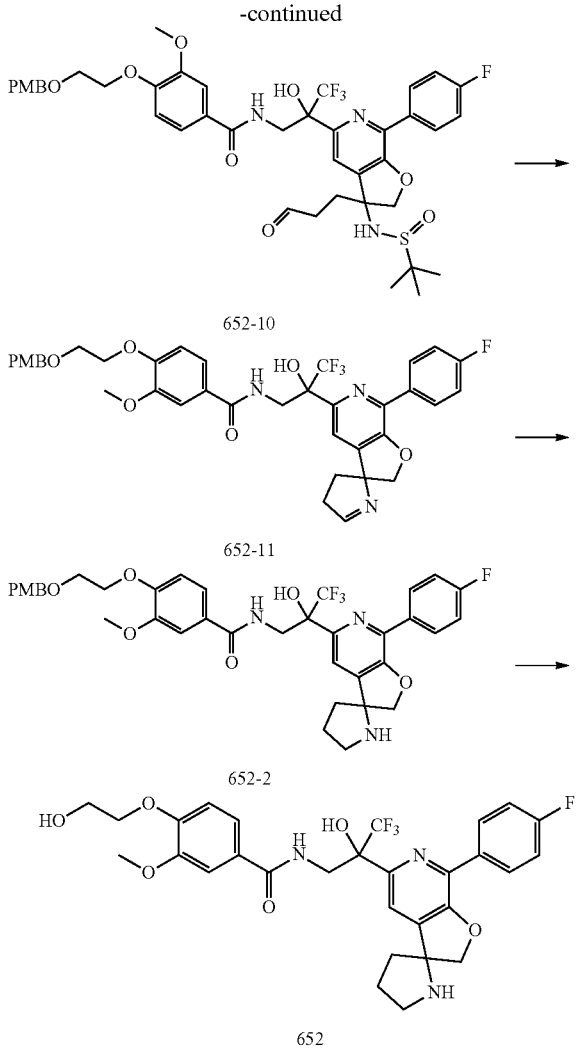

To a stirring mixture of 652-1 (750 mg, 2.12 mmol) were added 1-chlorohex-5-en-2-one (390 mg, 2.33 mmol) and potassium carbonate (410 mg, 2.97 mmol) in acetone (4.0 mL). The mixture was stirred at 50° C. for 2 h. The volatiles were removed under reduced pressure, and the residue was partitioned between water and EtOAc. The layers were separated, and the organic layers were dried with $Na_2SO_4$, filtered and concentrated under reduced pressure. The crude product was purified via a silica gel column to afford 652-2 as a white solid (480 mg, 50%). LCMS: m/z 449.90 [M+H]$^+$.

A mixture of 652-2 (420 mg, 1.18 mmol), 2-methylpropane-2-sulfinamide (157 mg, 1.31 mmol) and titanium(IV) ethoxide (770 μL, 2.6 mmol) in THF (7 mL) was heated to 70° C. (sealed vial, degassed and purged with $N_2$). The mixture was stirred 70° C. for 3 h. The mixture was diluted with EtOAc and water was added. The mixture was stirred for 5 mins and then filtered through a pad of celite. The layers were separated, and the aqueous layer was extracted with EtOAc. The combined organic layers were dried with $Na_2SO_4$ and filtered. The volatiles were removed under reduced pressure. Crude 652-3 was used in the next step without further purification. LCMS: m/z 552.95 [M+H]$^+$.

n-Buthyllithium (2.5 M solution in hexane, 0.64 mL, 1.6 mmol) was added to a solution of ethylmagnesium bromide (3.42 M in 2-Me THF, 0.24 mL, 0.8 mmol) in THF (2.5 mL), which had been pre-cooled to 0° C. After 10 mins, the mixture was cooled to −78° C. A solution of 652-3 (460 mg, 0.83 mmol) in THF (1 mL) was added dropwise, and the mixture was stirred at −78° C. for 15 mins. The reaction was quenched with MeOH and diluted with EtOAc. The organic layer was washed with brine, and the aqueous layer was extracted with EtOAc. The combined organic layers were dried over $Na_2SO_4$, filtered and concentrated under reduced pressure. Chromatography of the residue afforded 652-4 as a brownish oil. LCMS: m/z 427.05 [M+H]$^+$.

To a stirring mixture of 652-4 (180 mg, 0.42 mmol) in DCM (2 mL) was added Dess-Martin reagent (537 mg, 1.26 mmol). The mixture was stirred at r.t. until the starting material was consumed. The mixture was diluted with EtOAc. The reaction quenched with 5% of $NaHSO_3$ and a sat. $NaHCO_3$ solution. The layers were separated, and the aqueous layer was extracted with EtOAc. The combined organic layers were dried over $Na_2SO_4$, filtered and concentrated under reduced pressure. The crude product was purified via a silica gel column to afford 652-5 as a white solid. LCMS: m/z 443.1 [M+H+$H_2O$]$^+$.

To a stirring mixture of 652-5 (135 mg, 0.305 mmol) in nitromethane (0.5 mL) at r.t. was added TEA (63 μL, 0.46 mmol). The mixture was stirred at r.t. for 30 mins and then diluted with DCM. The reaction was quenched with a sat. $NaHCO_3$ solution. The layers were separated, and the aqueous layer was extracted with DCM. The combined organic layers were dried over $Na_2SO_4$, filtered and concentrated under reduced pressure. The crude product was purified via a silica gel column to afford 652-6 as a white solid (140 mg, 94%). LCMS: m/z 486.05 [M+H]$^+$.

To a stirring mixture of 652-6 (50 mg, 0.1 mmol) in EtOH:water (10:1, 1.1 mL) was added Fe (28 mg, 0.5 mmol) and $NH_4Cl$ (27 mg, 0.5 mmol). The mixture was heated at 80° C. for 30 mins and then cooled to r.t. The mixture was diluted with DCM (5 mL), and the reaction was quenched with a solution of NaOH (2N, 1 mL). The layers were separated, and the aqueous layer was extracted with DCM (2×5 mL). The combined organic layers were dried over $Na_2SO_4$, filtered and concentrated under reduced pressure. The crude product was purified via a silica gel column to afford 652-7 as a white solid. LCMS: m/z 456.1 [M+H]$^+$.

To a stirring mixture of 3-methoxy-4-(2-((4-methoxybenzyl)oxy)ethoxy)benzoic acid (14.5 mg, 0.044 mmol) in DMF (0.2 mL) were added HATU (17 mg, 0.044 mmol) and DIPEA (17 μL, 0.088 mmol). The mixture was stirred at r.t. for 5 mins. A solution of 652-7 (20 mg, 0.044 mmol) in DMF (0.1 mL) was added, and the mixture was stirred at for 10 mins. The reaction was quenched with a 10% aq. solution of $NaHCO_3$ (1 mL). The mixture was diluted with DCM, and an aqueous work up with DCM was followed. The crude product was purified via prep-HPLC to afford 652-8 (6.5 mg, 19%) as a white solid. LCMS: m/z 770.25 [M+H]$^+$.

To a stirring mixture of 652-8 (6.5 mg, 0.008 mmol) in DME:EtOH:$H_2O$ (1.0 mL:0.3 mL:0.1 mL, deoxygenated prior to using) were added 4-fluorophenylboronic acid (9 mg, 0.063 mmol), $K_3PO_4 \cdot 7H_2O$ (14.3 mg, 0.04 mmol), $KH_2PO_4$ (5.5 mg, 0.04 mmol) and $PdCl_2(dppf)$ (6.0 mg, 0.008 mmol). The mixture was carried out under microwave irradiation at 110° C. for 5 h. The crude product was concentrated under reduced pressure and purified via a silica gel chromatography to afford 652-9. LCMS: m/z 830.2 [M+H]$^+$.

To a stirring mixture of 652-9 in t-BuOH:$H_2O$ (3:1, 0.4 mL) were added $K_2OsO_4 \cdot 2H_2O$ (1 mg). The mixture was stirred for 2 h and $NaIO_4$ (5 mg) was added. The mixture was stirred at r.t. overnight. The mixture was loaded directly into a silica gel column to afford 652-10. LCMS: m/z 832.3 [M+H]+.

To a stirring mixture of 652-10 in MeOH (1.0 mL) was added a solution of HCl in dioxane (0.2 mL). The mixture was stirred for 10 mins at r.t. and concentrated under reduced pressure. Crude 652-11 was used in the next step without further purification.

652-11 was dissolved in MeOH (0.5 mL) was added NaBH$_4$ (1.6 mg). The mixture was stirred at r.t. for 10 mins and then diluted with EtOAc. The reaction was quenched with a sat. NaHCO$_3$ solution. The layers were separated, and the aqueous layer was extracted with EtOAc. The combined organic layers were dried over Na$_2$SO$_4$, filtered and concentrated under reduced pressure. Crude 652-12 was used in the next step without further purification.

To a stirring mixture of 652-12 in DCM (1.0 mL) was added TFA (0.1 mL). The mixture was stirred at r.t. until the starting material was consumed. The mixture was diluted with DCM, and the reaction was quenched with a cold sat. NaHCO$_3$ solution. The layers were separated, and the aqueous layer was extracted with EtOAc. The combined organic layers were dried over Na$_2$SO$_4$, filtered and concentrated under reduced pressure. The crude product was purified via prep-HPLC to afford 652 as a white solid (1.0 mg). LCMS: m/z 592.20 [M+H]+.

Example 399

Preparation of Compound 645

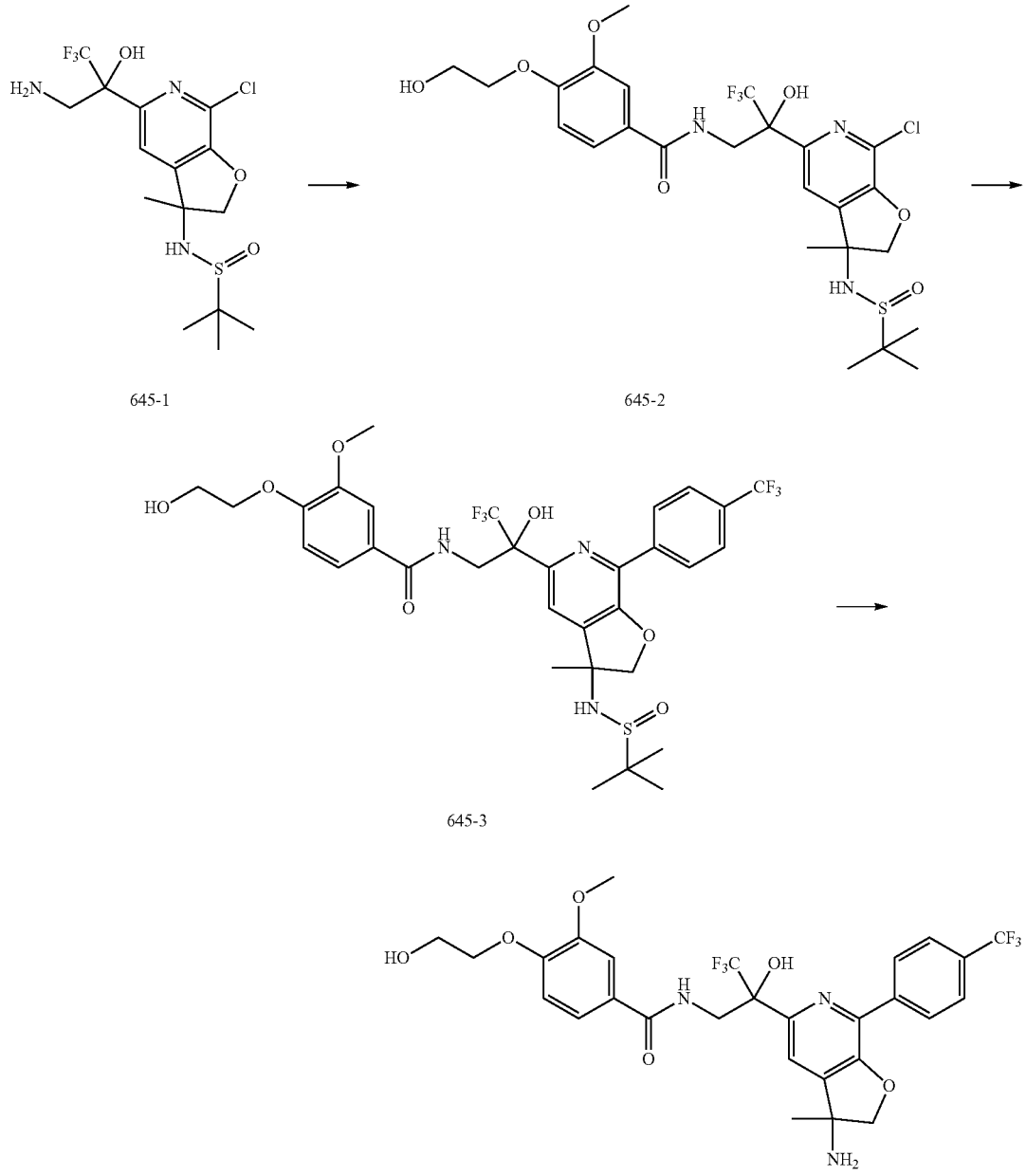

645-2 was prepared following the general procedure for 635-2. LCMS: m/z 610.10 [M+H]+. 645-3 was prepared following the general procedure for 635-3. LCMS: m/z 720.20 [M+H]+. Compound 645 (15.7 mg) was prepared following the general procedure for 635 using 645-3 (45 mg, 0.063 mmol). LCMS: m/z 616.15 [M+H]+.

Example 400

Preparation of Compound 662

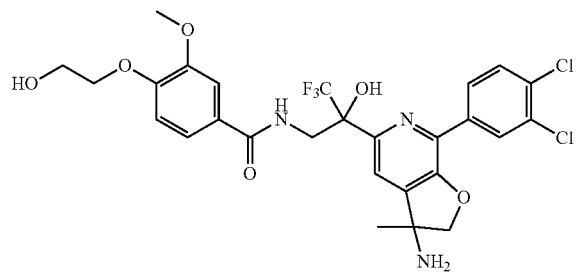 [SMILES: COc1cc(C(=O)NCC(O)(c2cc3c(c(-c4ccc(Cl)c(Cl)c4)n2)OCC3(C)N)C(F)(F)F)ccc1OCCO]

Compound 662 (5.7 mg) was prepared following the general procedure for 645. LCMS: m/z 616.10 [M+H]+.

Example 401

Preparation of Compound 663

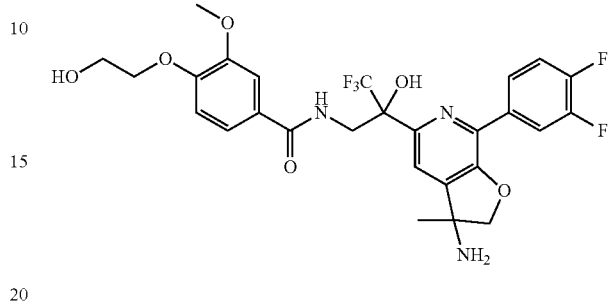

Compound 663 (11.4 mg) was prepared following the general procedure for 645. LCMS: m/z 584.15 [M+H]+.

Example 402

Preparation of Compound 647

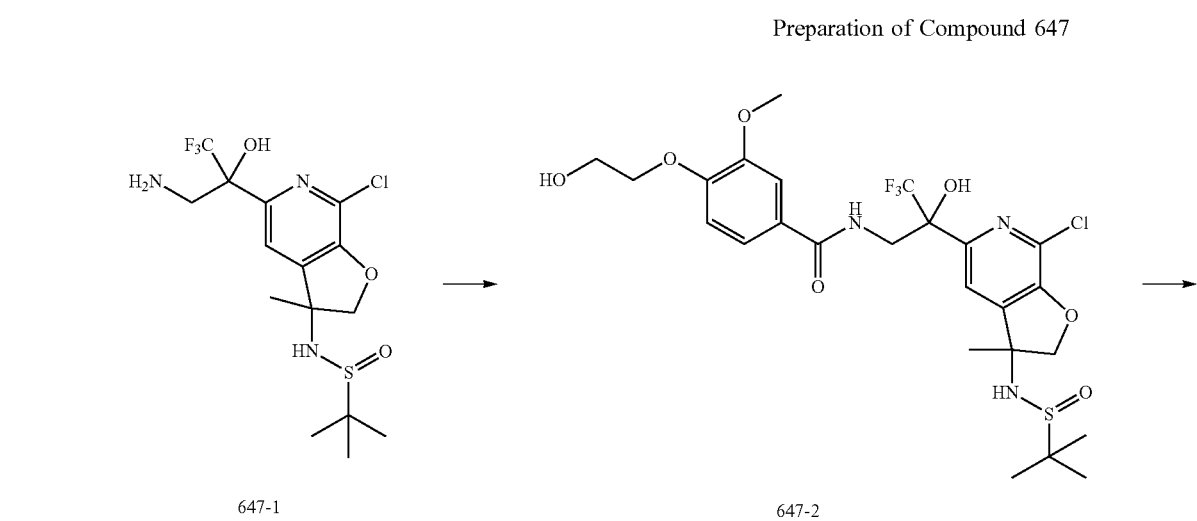

647-1             647-2

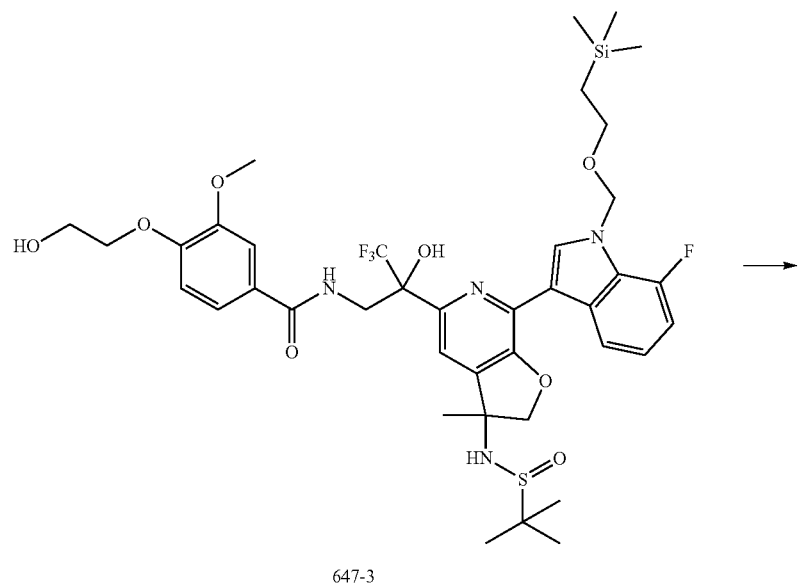

647-3

-continued
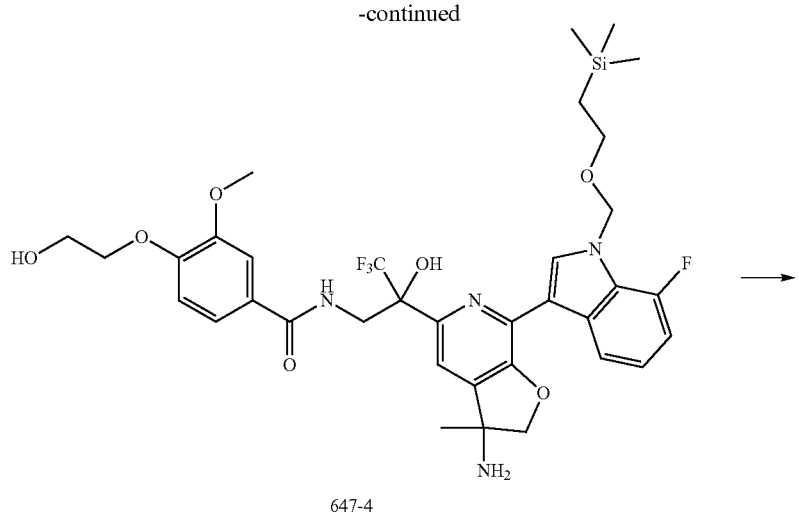
647-4
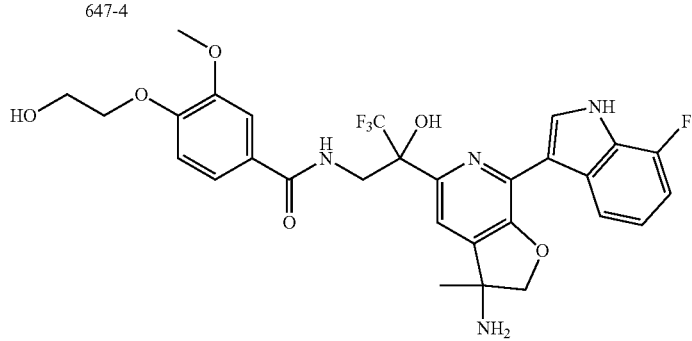
647
647-3 was prepared following the general procedure for 635-3. LCMS: m/z 839.25 [M+H]⁺. 647-4 was prepared following the general procedure for 635. 647-4 (51 mg, 0.084 mmol) was treated with TBAF (1M in THF, 0.1 mL, 0.1 mol) in THF (2 mL) at 70° C. for 2 h. The mixture was concentrated, and the crude product purified by silica gel chromatography (CH₂Cl₂:MeOH:NH₃) to provide 647 (10 mg, 19%). LCMS: m/z 605.15
Example 403
Preparation of Compound 648
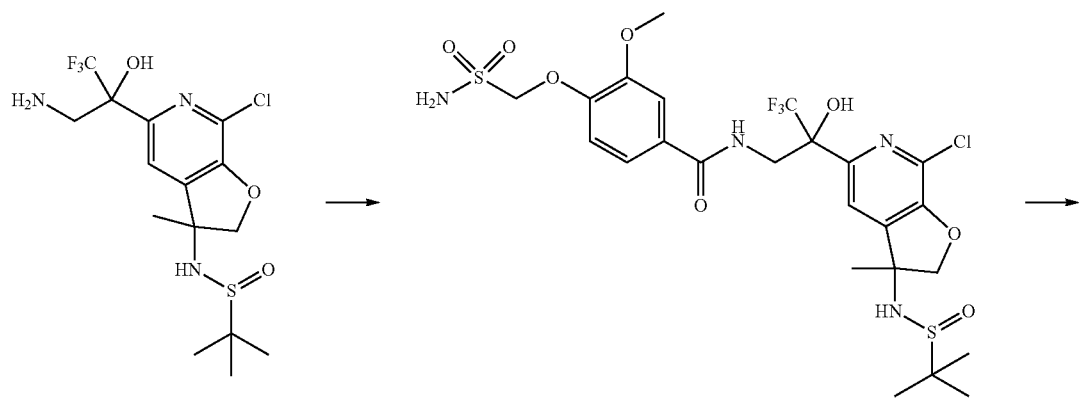
648-1
648-2

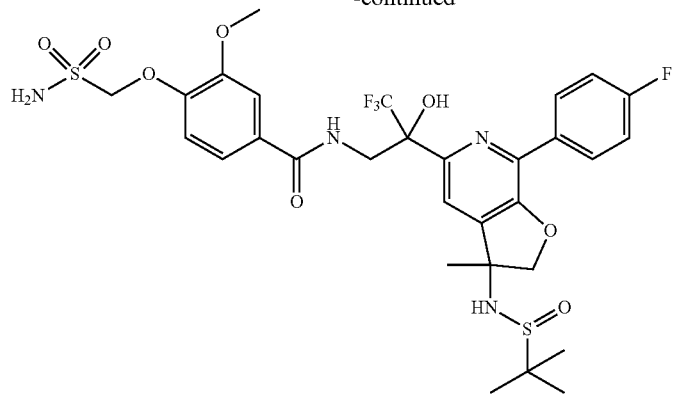
648-3
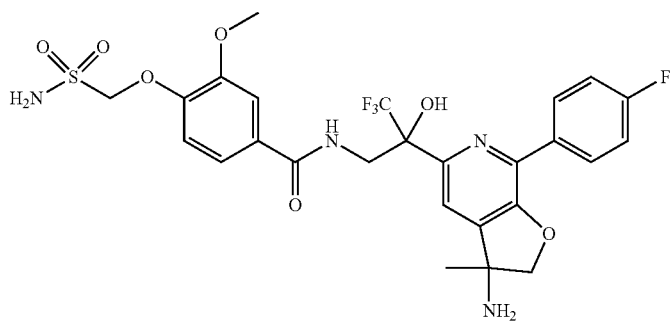
648
648-2 was prepared following the general procedure for 637-4. LCMS: m/z 629.05 [M+H]⁺. 648-3 was prepared following the general procedure for 635-3. LCMS: m/z 719.15 [M+H]⁺. Compound 648 (13.5 mg) was prepared following the general procedure for 635 using 648-3 (27 mg, 0.038 mmol). LCMS: m/z 615.15 [M+H]⁺.
Example 404
Preparation of Compound 651
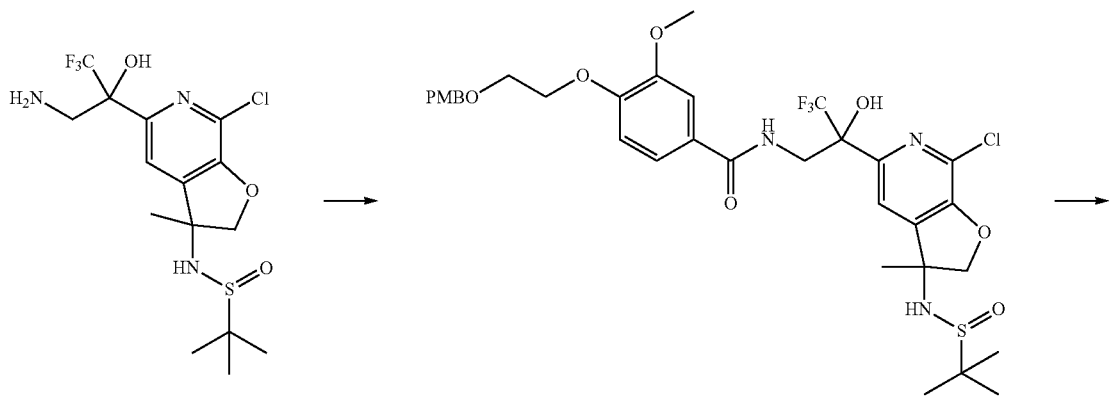
651-1                           651-2

-continued

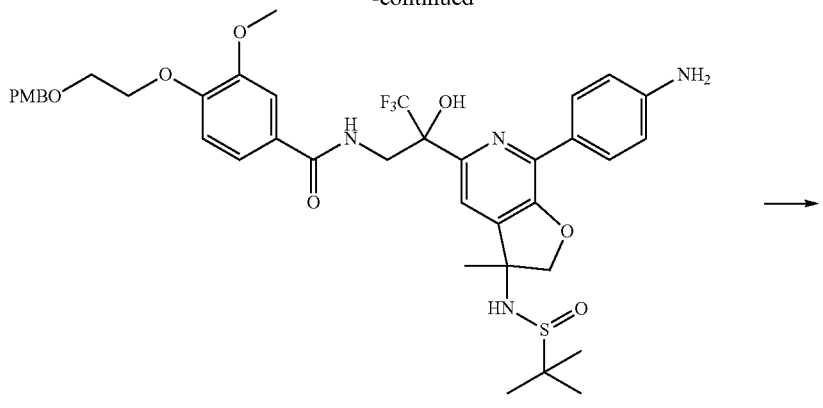

651-3

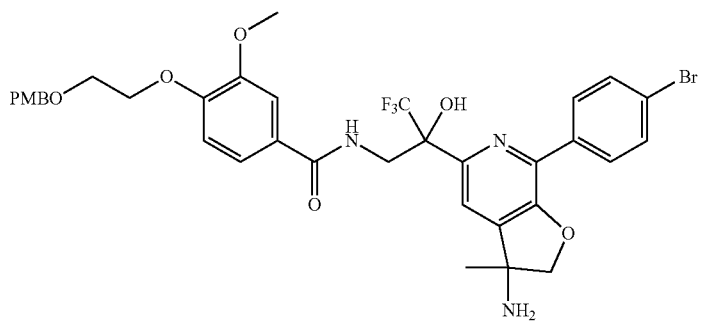

651-4

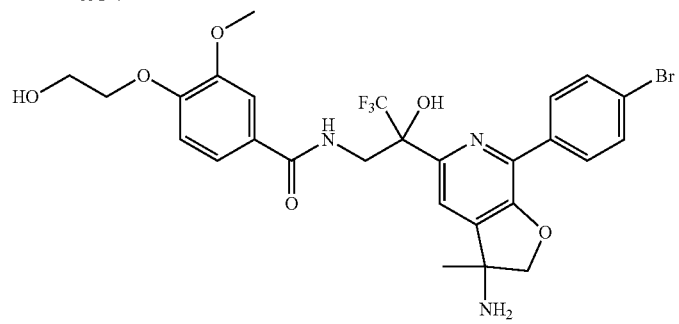

651

651-2 was prepared following the general procedure for 637-2. LCMS: m/z 730.20 [M+H]⁺. 651-3 was prepared following the general procedure for 637-3. LCMS: m/z 787.30 [M+H]⁺.

A solution of 651-3 (15 mg, 0.019 mmol) in CH₃CN (0.5 mL) was added dropwise to a solution of isopentyl nitrite (4 uL, 0.029 mmol) and copper bromide (3 mg, 0.023 mmol) in CH₃CN (1 mL) at 65° C. The mixture was stirred at 65° C. for 1 h and then cooled to 0° C. The reaction was quenched with the addition of 1N HC. The aqueous layer was basified with sodium bicarbonate and extracted with EA. The product was used without further purification to provide 651-4. LCMS: m/z 748.15 [M+H]⁺.

Trifluoroacetic acid (0.1 mL) was added to a solution of 651-4 in CH₂Cl₂ (0.9 mL), and the reaction was stirred at r.t. for 5 mins. The mixture was cooled to 0° C. The reaction was quenched with bicarbonate and extracted with EA. The product was purified by reverse-phase HPLC to yield 651 (4.0 mg). LCMS: m/z 628.05 [M+H]⁺.

Example 405

Preparation of Compound 661

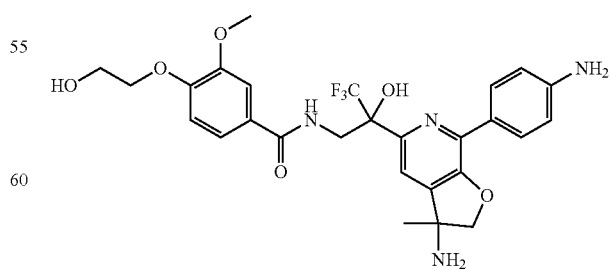

Compound 661 was prepared following the general procedure for 651. LCMS: m/z 563.15 [M+H]⁺.

Example 406

Preparation of Compound 493

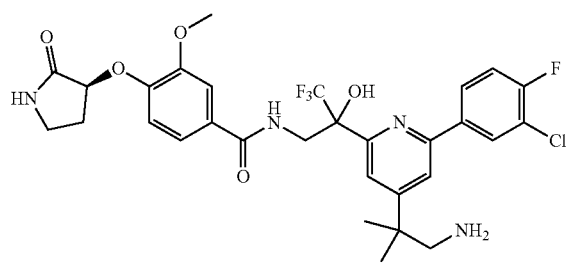 [SMILES: COc1cc(C(=O)NCC(O)(c2cc(C(C)(C)CN)cc(-c3ccc(F)c(Cl)c3)n2)C(F)(F)F)ccc1O[C@H]1CCNC1=O]

Compound 493 was prepared following the general procedure for 397 using (S)-3-methoxy-4-((2-oxopyrrolidin-3-yl)oxy)benzoic acid. LCMS: m/z 640.15 [M+H]$^+$.

Example 407

Preparation of Compound 587

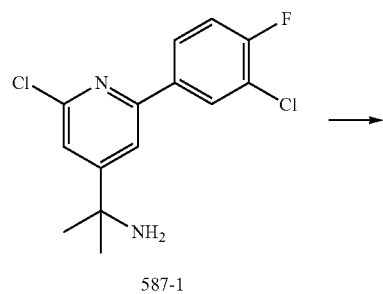

587-1

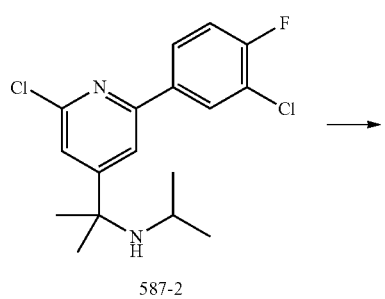

587-2

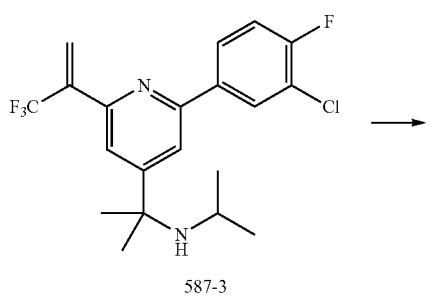

587-3

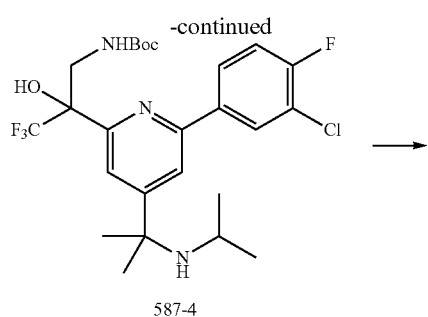

587-4

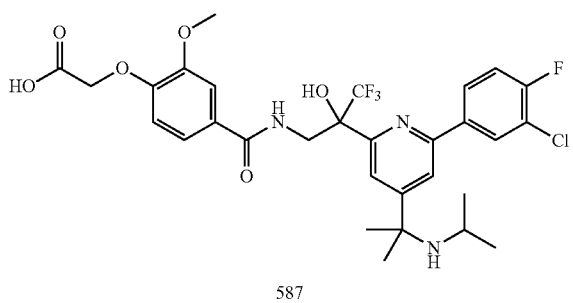

587

To a stirring mixture of 587-1 (200 mg, 0.67 mmol) in DCE (1 mL) at r.t. were added acetone (78 mg, 1.33 mmol), HOAc (10 mg), and Na(OAc)$_3$BH (280 mg). The mixture was stirred at r.t. overnight. The mixture was diluted with DCM, and the reaction was quenched with a cold NaHCO$_3$ solution. The aqueous layer was extracted with DCM, dried over Na$_2$SO$_4$, filtered and concentrated under reduced pressure. The crude product was purified via a silica gel column to afford 587-1 (180 mg, 79%) as a colorless oil. LCMS: m/z 341.0 [M+H]$^+$.

Compound 587 (35 mg) was prepared in 4 steps from 587-2 (180 mg). LCMS: m/z 641.15 [M+H]$^+$.

Example 408

Preparation of Compound 664

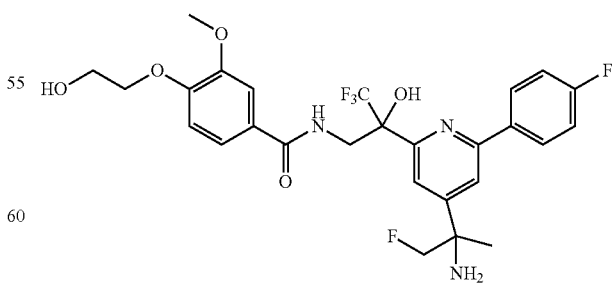

Compound 664 is a single diastereomer of 626 and was obtained by chiral separation of 626 via SFC system. +ESI-MS: m/z 570.15 [M+H]$^+$

Example 409

Preparation of Compound 642

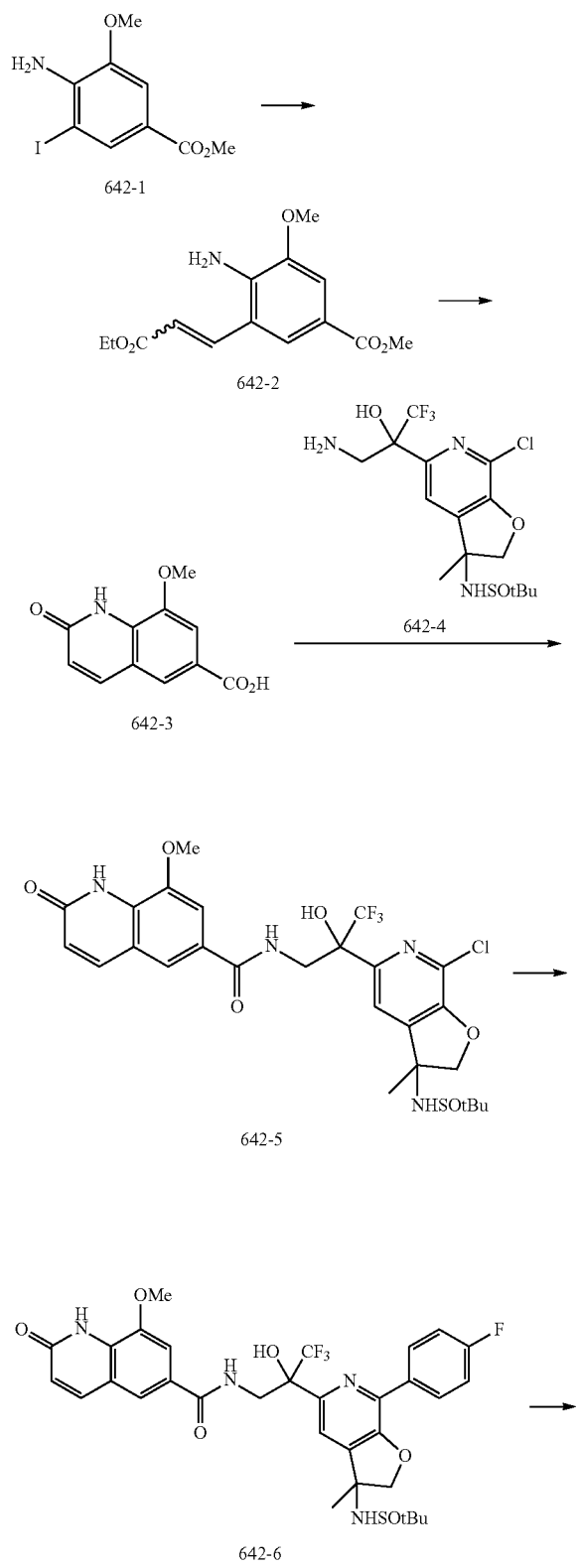

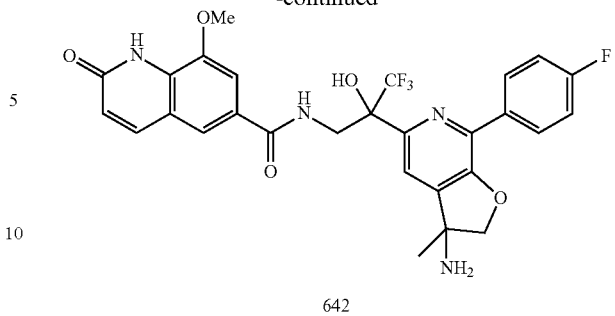

To a stirring mixture of 642-1 (540 mg, 1.76 mmol) in DMF (5 mL, deoxygenated prior to use) were added Pd(OAc)$_2$ (119 mg, 0.17 mmol), PPh$_3$ (102 mg, 0.387 mmol), TEA (0.3 mL, 2.11 mmol) and ethyl acrylate (0.42 mL, 3.87 mmol). The mixture was stirred at 85° C. overnight. The mixture was diluted with EtOAc and washed with brine. The layers were separated, and the aqueous layer was extracted with EtOAc. The organic layers were dried over Na$_2$SO$_4$, filtered and concentrated under reduced pressure. The crude product was purified via a silica gel chromatography to afford 642-2 as a yellow solid (410 mg, 83%). LCMS: m/z 280.05 [M+H]$^+$.

To a stirring mixture of 642-2 in a solution of HCl in dioxane (3 mL) was added concentrated HCl (1 mL). The mixture was stirred at 90° C. overnight. The crude product was cooled to r.t. and concentrated under reduced pressure to afford 642-3 as a brown solid. The solid was dissolved in toluene and concentrated under reduced pressure (2×). Crude 642-3 was used in the next step without further purification. LCMS: m/z 220.0 [M+H]$^+$.

To a stirring mixture of 642-3 (63 mg, 0.144 mmol) in DMF (0.5 mL) were added EDCI (33 mg, 0.173 mmol), HOAt (23 mg, 0.173 mmol) and TEA (41 µL, 0.088 mmol). The mixture was stirred at r.t. for 5 mins. A solution of 642-4 (60 mg, 0.144 mmol) in DMF (0.5 mL) was added. The mixture was stirred r.t. for 10 mins. The reaction was quenched with a 10% aq. solution of NaHCO$_3$ (1 mL). The mixture was diluted with DCM, and an aqueous work up with DCM was followed. The crude product was purified via prep-HPLC to afford 642-5 (20 mg) as a white solid. LCMS: m/z 617.1 [M+H]$^+$.

To a stirring mixture of 642-5 (20 mg, 0.032 mmol) in DME:EtOH:H$_2$O (1.0 mL:0.3 mL:0.1 mL, deoxygenated prior to using) were added 4-fluorophenylboronic acid (9 mg, 0.063 mmol), K$_3$PO$_4$·7H$_2$O (43 mg, 0.128 mmol), KH$_2$PO$_4$ (17.4 mg, 0.128 mmol) and PdCl$_2$(dppf) (20 mg). The mixture was carried out under microwave irradiation at 110° C. for 5 h. The crude product was concentrated under reduced pressure, and then purified via a silica gel chromatography to afford 642-6 as a brownish oil. LCMS: m/z 677.15 [M+H]$^+$.

To a stirring mixture of 642-6 in MeOH (1 mL) at r.t. was added a solution of HCl in dioxane (0.2 mL, 4N). The mixture was stirred at r.t. for 5 mins and then concentrated under reduced pressure. The crude product was purified via prep-HPLC to afford 642 (8.5 mg) as a white solid. LCMS: m/z 573.1 [M+H]$^+$.

Example 410

Preparation of Compound 476

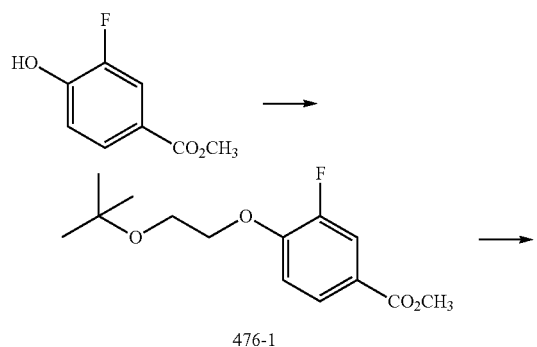

476-1

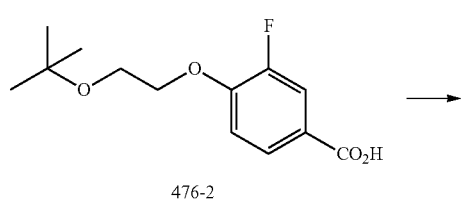

476-2

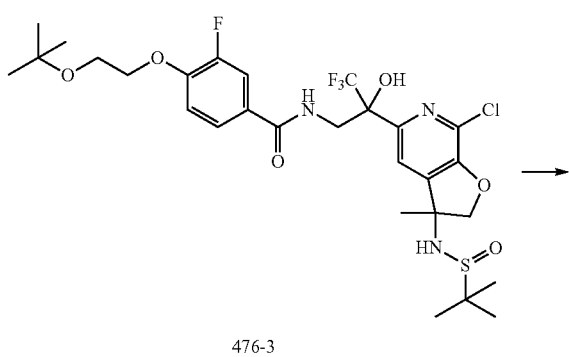

476-3

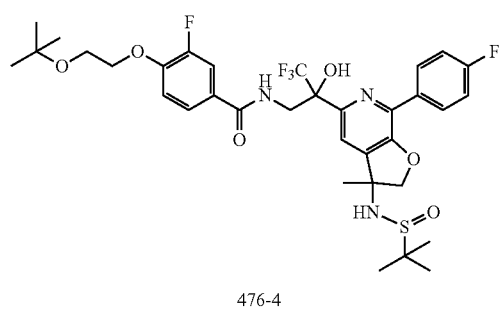

476-4

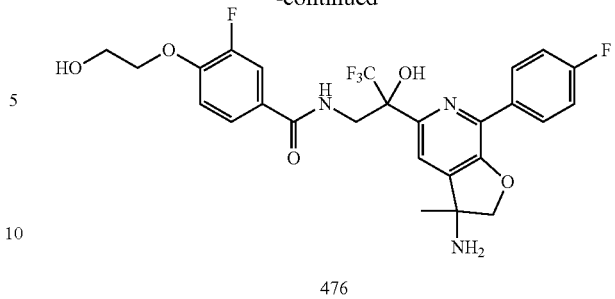

476

Diisopropylazadicarboxylate (0.29 mL, 1.5 mmol) was added to a solution of methyl 3-fluoro-4-hydroxybenzoate (0.21 g, 1.2 mmol, ethyl glycol mono-tert-butyl ether (0.32 mL, 2.5 mmol) and polymer bound triphenylphosphine (1.1 g, 1.9 mmol) in THF (5 mL). The mixture was stirred at r.t. for 1 h. The resin was removed by filtration, and the mixture was concentrated. The product was purified by column chromatography (hexane:EA) to 476-1 (0.34 g, 98%).

NaOH (2N, 3 mL) was added to a solution of 476-1 (0.34 g, 1.2 mmol) in MeOH (10 mL), and the mixture was heated at reflux for 1.5 h. The mixture was acidified with 1N HCl and extracted with EA. The organic extracts were washed with brine, dried and concentrated to obtain 476-2 (0.29 g, 91%).

476-3 was prepared following the general procedure for 635-2 using 476-2. 476-4 was prepared following the general procedure for 635-3 using 476-3.

HCl (4N in dioxane, 1 mL) was added to a solution of 476-4 (32 mg, 0.049 mmol) in $CH_2Cl_2$ (1 mL), and the mixture was stirred at r.t. for 5 h. The mixture was concentrated and the crude product purified by HPLC to yield 476. LCMS: m/z 555.05

Example 411

Preparation of Compound 481

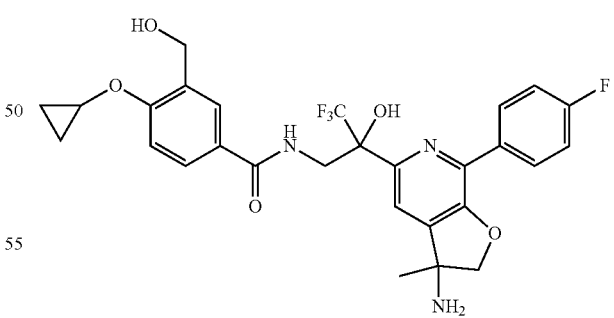

Compound 481 (8.7 mg) was prepared following the general procedure for 645. LCMS: m/z 562.15 [M+H]+.

Example 412

The following compounds were prepared following one or more of the methods provided herein.

| No. | Structure | MS |
|---|---|---|
| 472 | 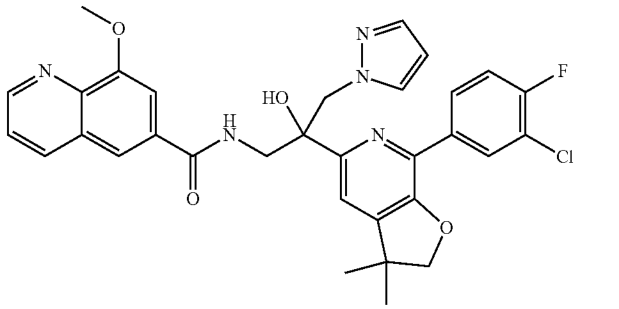 [SMILES: COc1cc(C(=O)NCC(O)(Cn2cccn2)c2cc3c(c(-c4ccc(F)c(Cl)c4)n2)OCC3(C)C)cc2cccnc12] | nd |
| 484 | 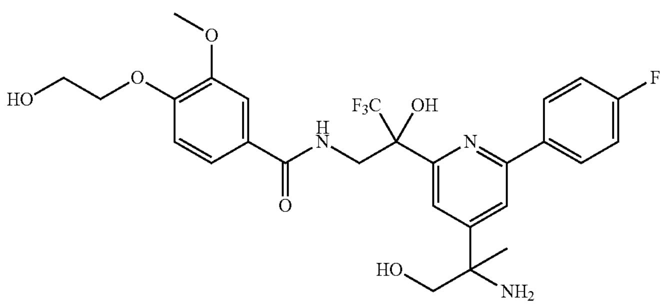 | 568.0 [M + H]+ |
| 492 | 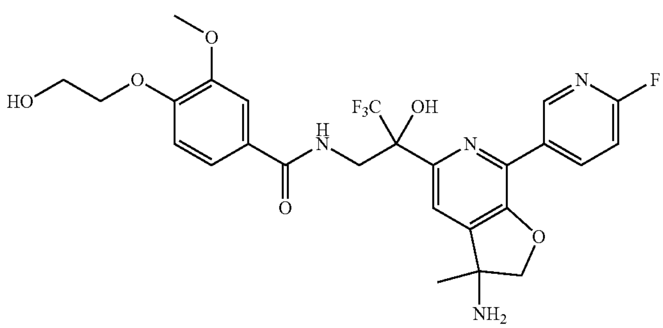 [SMILES: COc1cc(C(=O)NCC(O)(c2cc3c(c(-c4ccc(F)nc4)n2)OCC3(C)N)C(F)(F)F)ccc1OCCO] | 567.0 [M + H]+ |
| 668 | 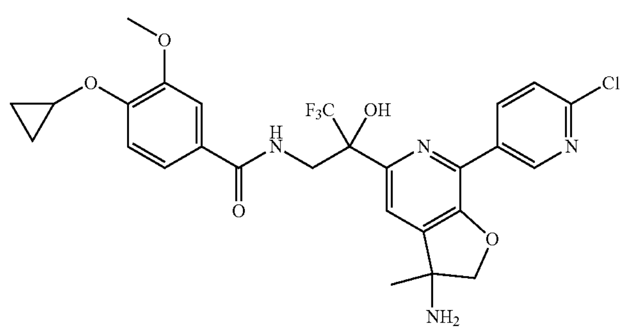 [SMILES: COc1cc(C(=O)NCC(O)(c2cc3c(c(-c4ccc(Cl)nc4)n2)OCC3(C)N)C(F)(F)F)ccc1OC1CC1] | 579.2 [M + H]+ |

-continued

| No. | Structure | MS |
|---|---|---|
| 669 | 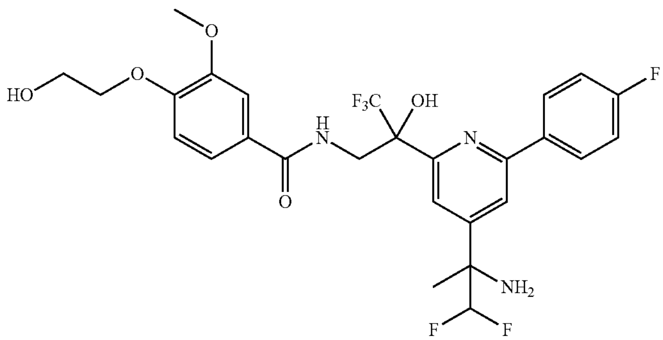 [SMILES: COc1cc(C(=O)NCC(O)(c2cc(C(C)(N)C(F)F)cc(-c3ccc(F)cc3)n2)C(F)(F)F)ccc1OCCO] | 610.1 [M + Na]+ |
| 670 | 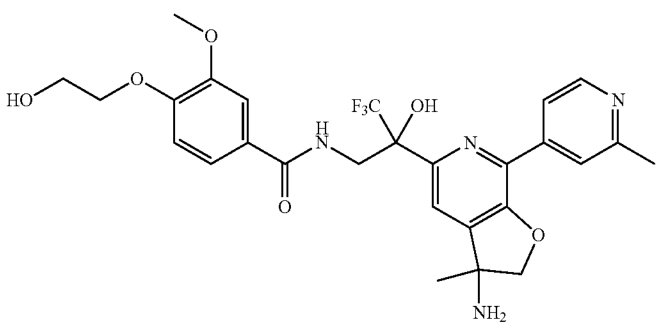 [SMILES: COc1cc(C(=O)NCC(O)(c2cc3c(c(-c4ccnc(C)c4)n2)OCC3(C)N)C(F)(F)F)ccc1OCCO] | 563 [M + H]+ |
| 671 | 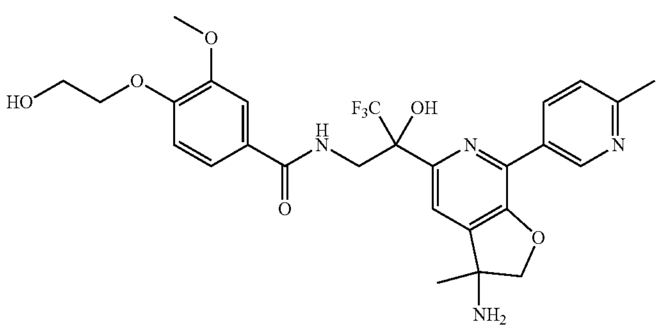 [SMILES: COc1cc(C(=O)NCC(O)(c2cc3c(c(-c4ccc(C)nc4)n2)OCC3(C)N)C(F)(F)F)ccc1OCCO] | 563.0 [M + H]+ |
| 672 | 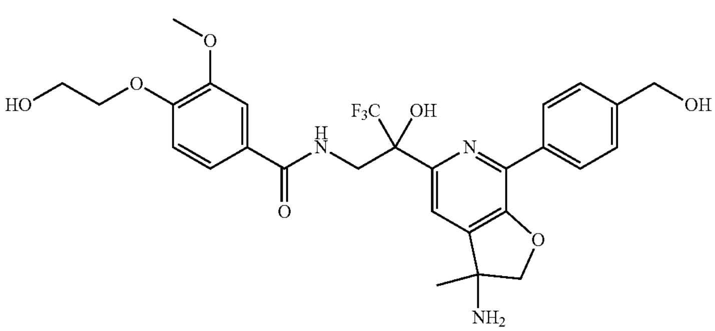 [SMILES: COc1cc(C(=O)NCC(O)(c2cc3c(c(-c4ccc(CO)cc4)n2)OCC3(C)N)C(F)(F)F)ccc1OCCO] | 578.0 [M + H]+ |

-continued

| No. | Structure | MS |
|---|---|---|
| 673 | 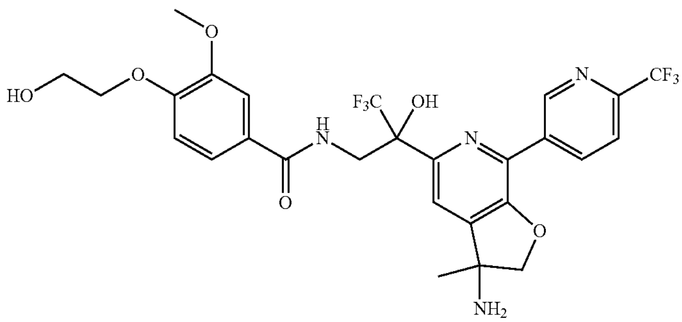 [SMILES: COc1cc(C(=O)NCC(O)(c2cc3c(c(-c4ccc(C(F)(F)F)nc4)n2)OCC3(C)N)C(F)(F)F)ccc1OCCO] | 617.1 [M + H]+ |
| 674 | 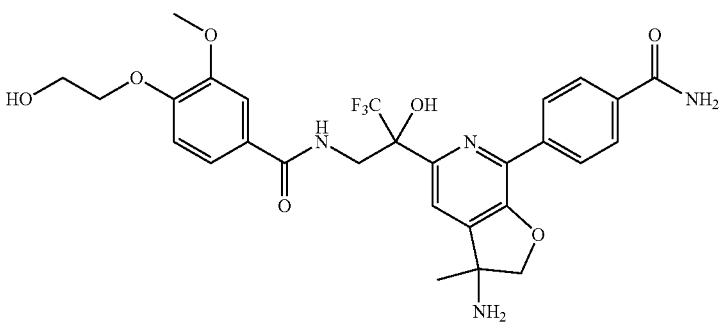 [SMILES: COc1cc(C(=O)NCC(O)(c2cc3c(c(-c4ccc(C(N)=O)cc4)n2)OCC3(C)N)C(F)(F)F)ccc1OCCO] | 591.1 [M + H]+ |
| 675 | 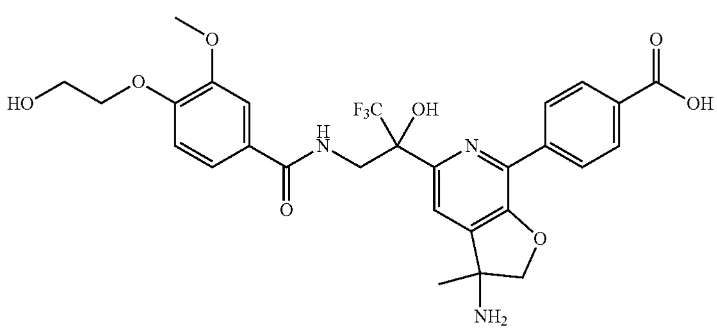 [SMILES: COc1cc(C(=O)NCC(O)(c2cc3c(c(-c4ccc(C(=O)O)cc4)n2)OCC3(C)N)C(F)(F)F)ccc1OCCO] | 614.0 [M + Na]+ |
| 676 | 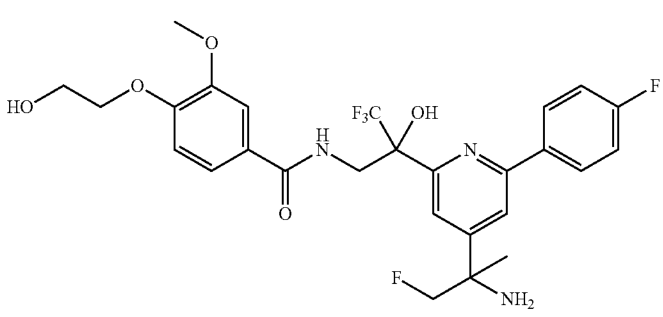 [SMILES: COc1cc(C(=O)NCC(O)(c2cc(C(C)(N)CF)cc(-c3ccc(F)cc3)n2)C(F)(F)F)ccc1OCCO] | 570.1 [M + H]+ |

-continued
| No. | Structure | MS |
|---|---|---|
| 677 | 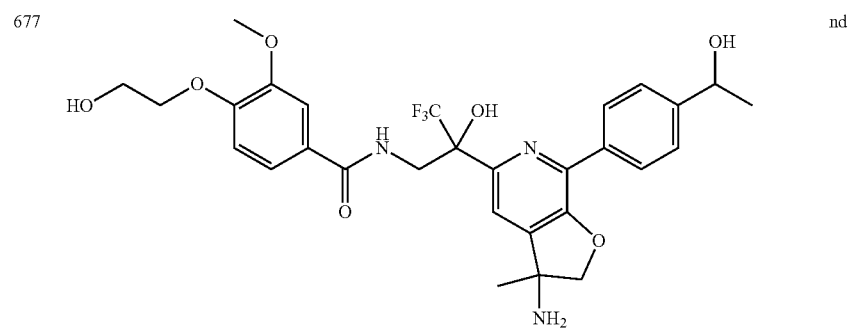 | nd |
| 678 | 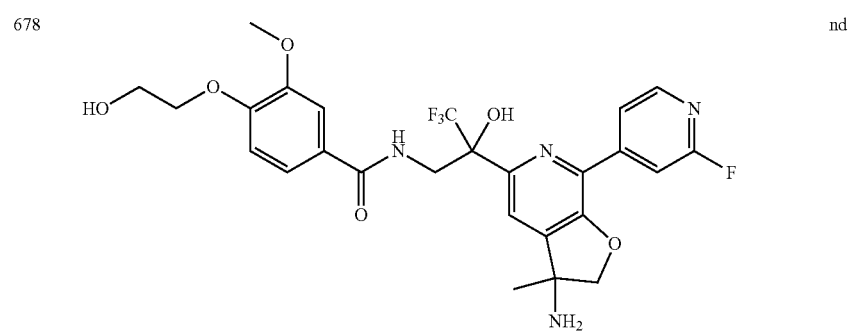 | nd |
| 679 | 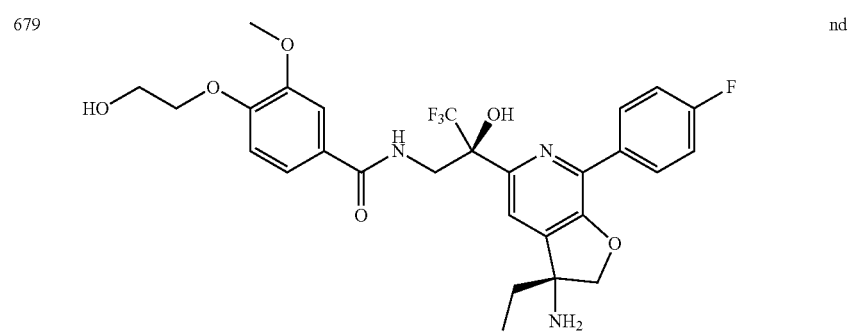 | nd |
| 680 | 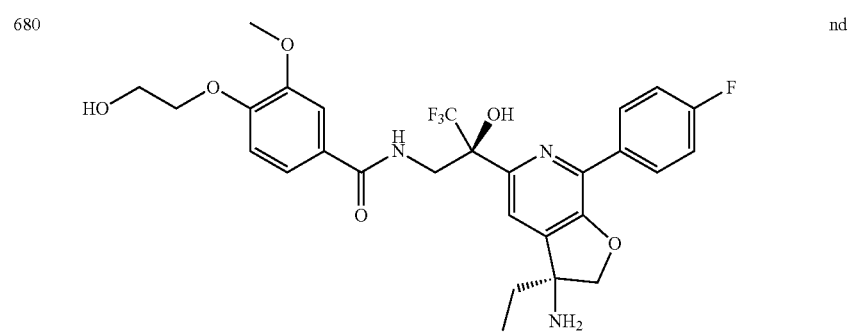 | nd |

| No. | Structure | MS |
|---|---|---|
| 681 | 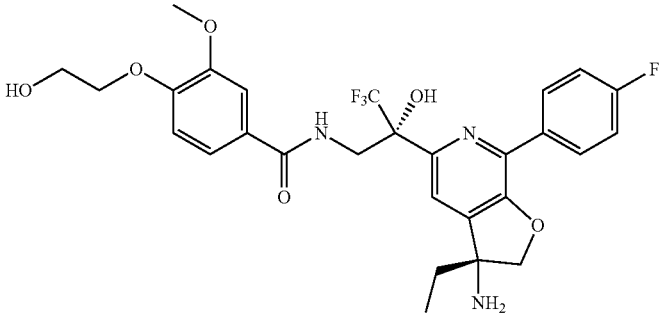 [SMILES: CC[C@]1(N)COc2c1cc([C@@](O)(CNC(=O)c1ccc(OCCO)c(OC)c1)C(F)(F)F)nc2-c1ccc(F)cc1] | nd |
| 682 | 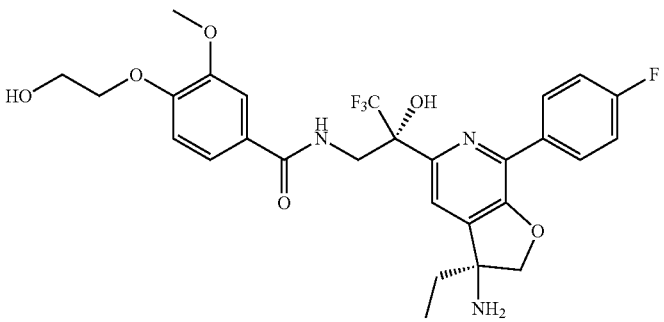 [SMILES: CC[C@@]1(N)COc2c1cc([C@@](O)(CNC(=O)c1ccc(OCCO)c(OC)c1)C(F)(F)F)nc2-c1ccc(F)cc1] | nd |

Example A

RSV Antiviral Assay

CPE reduction assays are performed as described by Sidwell and Huffman et al., *Appl. Microbiol.* (1971) 22(5): 797-801 with slight modifications. HEp-2 cells (ATCC #, CCL-23) are seeded at a density of 1,500 cells/30 μl/well into the 384-well cell plate(s) (Corning #3701) one day prior to the assay. Compounds are added into 384-well cell plates by Labcyte POD 810 Plate Assembler system. Each of the test compounds is provided to duplicate wells of a 384-well cell plate at final concentrations starting from 100 μM or 1 μM using 1/3 stepwise dilutions for 9 points. Quick-thaw Respiratory Syncytial Virus (RSV) long strain (ATCC #VR-26) stock in a 37° C. water bath. Place on ice until ready to use. Viruses are diluted to the concentration of 100 $TCID_{50}$/30 μL with medium and 30 μl diluted RSV are added into related wells of 384-well cell plates. For each plate, sixteen wells are set aside as uninfected, untreated cell controls (CC), and nine wells per test plate receive virus only as a control for virus replication (VC). The final DMSO concentration of all wells is 1%. Place the plates at 37° C., 5% $CO_2$ for 5 days.

After 5 days incubation, observe the CPE of cells in all wells. Cell controls should be natural and have no cell fusion; Cells in the virus control wells should exhibit signs of virus cytopathology (giant cell formation, syncytia). Six μl of cell counting kit-8 reagent (CCK-8, Dojindo Molecular Technologies Inc., CK04-20) are added to each well, which allows colorimetric assays to determine the number of viable cells through the dehydrogenase activity detection. After 3-4 hour incubation, the absorbance of each well is measured with a spectrophotometric plate reader at 450 nm wavelength, using a 630 nm filter as background according to manufacturer's instruction. The 50% effective concentration ($EC_{50}$) is calculated by using regression analysis, based on the mean O.D. at each concentration of compound.

Compounds of Formula (I) are active in the assay against the RSV virus as demonstrated in Tables A and B. Table A includes compounds with an $EC_{50}$ value that is less than 1 μM. Table B includes compounds with an $EC_{50}$ value that is equal to or higher than 1 μM and less than 50 M. Other tested compounds disclosed herein had an $EC_{50}$ value of 50 μM or greater.

TABLE A

| Compound |
|---|
| 101 |
| 115 |
| 116 |
| 116b |
| 117 |
| 117b |
| 118 |
| 118b |
| 119 |
| 120 |
| 120b |
| 122 |
| 122a |
| 123 |
| 124 |
| 125 |
| 126 |
| 127 |
| 130 |
| 135 |
| 140 |
| 142 |
| 143 |
| 166 |
| 167 |

TABLE A-continued

| Compound |
|---|
| 176 |
| 181 |
| 182 |
| 184 |
| 185 |
| 189 |
| 191 |
| 192 |
| 193 |
| 194 |
| 195 |
| 198 |
| 199 |
| 200 |
| 202 |
| 204 |
| 205 |
| 208 |
| 209 |
| 210 |
| 211 |
| 212 |
| 213 |
| 214 |
| 217 |
| 218 |
| 219 |
| 220 |
| 221 |
| 222 |
| 223 |
| 224 |
| 226 |
| 227 |
| 228 |
| 232 |
| 234 |
| 235 |
| 237 |
| 238 |
| 239 |
| 240 |
| 241 |
| 243 |
| 244 |
| 245 |
| 246 |
| 248 |
| 249 |
| 250 |
| 255 |
| 256 |
| 257 |
| 258 |
| 259 |
| 260 |
| 261 |
| 262 |
| 263 |
| 267 |
| 270 |
| 272 |
| 273 |
| 274 |
| 281 |
| 282 |
| 283 |
| 284 |
| 285 |
| 287 |
| 289 |
| 292 |
| 294 |
| 296 |
| 297 |
| 298 |
| 299 |
| 303 |
| 304 |
| 305 |
| 308 |
| 309 |
| 310 |
| 312 |
| 314 |
| 315 |
| 317 |
| 318 |
| 320 |
| 321 |
| 322 |
| 323 |
| 324 |
| 325 |
| 326 |
| 327 |
| 328 |
| 330 |
| 331 |
| 333 |
| 334 |
| 335 |
| 336 |
| 338 |
| 339 |
| 340 |
| 342 |
| 343 |
| 344 |
| 345 |
| 346 |
| 347 |
| 348 |
| 349 |
| 353 |
| 356 |
| 357 |
| 358 |
| 359 |
| 360 |
| 361 |
| 362 |
| 364 |
| 365 |
| 366 |
| 368 |
| 369 |
| 370 |
| 371 |
| 372 |
| 373 |
| 383 |
| 384 |
| 385 |
| 387 |
| 388 |
| 391 |
| 392 |
| 394 |
| 396 |
| 400 |
| 403 |
| 405 |
| 406 |
| 409 |
| 411 |
| 413 |
| 414 |
| 415 |
| 418 |
| 419 |
| 421 |
| 423 |
| 424 |
| 425 |
| 426 |

TABLE A-continued

| Compound |
|---|
| 428 |
| 429 |
| 431 |
| 433 |
| 434 |
| 435 |
| 436 |
| 442 |
| 443 |
| 444 |
| 445 |
| 447 |
| 448 |
| 449 |
| 451 |
| 452 |
| 453 |
| 454 |
| 455 |
| 456 |
| 459 |
| 460 |
| 461 |
| 462 |
| 464 |
| 465 |
| 466 |
| 467 |
| 469 |
| 470 |
| 473 |
| 474 |
| 475 |
| 476 |
| 479 |
| 482 |
| 483 |
| 485 |
| 486 |
| 487 |
| 488 |
| 489 |
| 490 |
| 491 |
| 494 |
| 495 |
| 496 |
| 497 |
| 498 |
| 498d |
| 499 |
| 500 |
| 501 |
| 502 |
| 503 |
| 504 |
| 505 |
| 507 |
| 508 |
| 510 |
| 514 |
| 515 |
| 516 |
| 517 |
| 518 |
| 519 |
| 520 |
| 521 |
| 525 |
| 526 |
| 527 |
| 528 |
| 529 |
| 530 |
| 531 |
| 532 |
| 533 |
| 534 |

TABLE A-continued

| Compound |
|---|
| 535 |
| 536 |
| 537 |
| 538 |
| 539 |
| 540 |
| 541 |
| 542 |
| 543 |
| 545 |
| 546 |
| 547 |
| 548 |
| 550 |
| 551 |
| 552 |
| 553 |
| 554 |
| 556 |
| 557 |
| 558 |
| 559 |
| 560 |
| 562 |
| 563 |
| 565 |
| 568 |
| 569 |
| 570 |
| 571 |
| 574 |
| 575 |
| 577 |
| 579 |
| 580 |
| 583 |
| 586 |
| 587 |
| 590 |
| 591 |
| 592 |
| 593 |
| 594 |
| 595 |
| 596 |
| 597 |
| 598 |
| 599 |
| 604d |
| 605a |
| 605b |
| 605d |
| 610 |
| 611 |
| 612 |
| 614 |
| 615 |
| 619 |
| 620 |
| 621 |
| 623b |
| 624b |
| 626 |
| 627 |
| 628 |
| 629 |
| 630 |
| 631 |
| 632 |
| 633b |
| 634 |
| 635 |
| 638 |
| 640 |
| 642 |
| 643 |
| 644 |
| 645 |

TABLE A-continued

| Compound |
|---|
| 646 |
| 650 |
| 653 |
| 654 |
| 656 |
| 662 |
| 663 |
| 664 |
| 665 |
| 666 |
| 667 |

TABLE B

| Compound |
|---|
| 100 |
| 102 |
| 104 |
| 106 |
| 107 |
| 108 |
| 109 |
| 111 |
| 112 |
| 113 |
| 114 |
| 116a |
| 117a |
| 118a |
| 120a |
| 121 |
| 122b |
| 129 |
| 131 |
| 132 |
| 133 |
| 134 |
| 137 |
| 145 |
| 148 |
| 149 |
| 150 |
| 161 |
| 165 |
| 174 |
| 175 |
| 177 |
| 178 |
| 179 |
| 186 |
| 187 |
| 190 |
| 196 |
| 197 |
| 206 |
| 207 |
| 215 |
| 216 |
| 229 |
| 233 |
| 236 |
| 251 |
| 252 |
| 253 |
| 254 |
| 264 |
| 265 |
| 266 |
| 268 |
| 275 |
| 276 |
| 277 |
| 278 |
| 279 |

TABLE B-continued

| Compound |
|---|
| 280 |
| 283 |
| 286 |
| 290 |
| 302 |
| 313 |
| 337 |
| 368 |
| 404 |
| 407 |
| 410 |
| 416 |
| 417 |
| 432 |
| 437 |
| 438 |
| 440 |
| 450 |
| 463 |
| 471 |
| 477 |
| 478 |
| 484 |
| 492 |
| 549 |
| 561 |
| 604b |
| 604a |
| 605c |
| 607 |
| 608 |
| 609 |
| 623a |
| 624a |
| 633a |
| 637 |
| 639 |
| 655 |
| 673 |

Example B

Cytotoxicity Determination

In order to determine the compound cytotoxicity, in parallel, each of the compounds is applied to duplicate wells in a 384-well cell plate at serial final concentrations starting from 100 μM using 1/2 stepwise dilutions for 7 points without addition of virus. Incubate the cells at 37° C., 5% $CO_2$ for 5 days. Add 6 μL CCK-8 into each well and incubate in a $CO_2$ incubator at 37° C. for 3-4 hours. Read the plates to obtain the optical densities which are used to calculate 50% cytotoxicity concentration ($CC_{50}$).

Compounds of Formula (I) are not cytotoxic as shown in Tables C and D. Table C includes compounds with a $CC_{50}$ value that is greater than 100 μM. Table D includes compounds with a $CC_{50}$ value that is equal to or less than 100 μM and greater than 10 μM. Other tested compounds disclosed herein had a $CC_{50}$ value of less than 10 μM.

TABLE C

| Compound |
|---|
| 108 |
| 109 |
| 116a |
| 117b |
| 120 |
| 120b |
| 121 |

TABLE C-continued

| Compound |
|---|
| 123 |
| 135 |
| 150 |
| 175 |
| 176 |
| 177 |
| 178 |
| 179 |
| 180 |
| 181 |
| 182 |
| 183 |
| 187 |
| 189 |
| 190 |
| 191 |
| 192 |
| 194 |
| 195 |
| 196 |
| 199 |
| 205 |
| 206 |
| 209 |
| 213 |
| 220 |
| 228 |
| 229 |
| 233 |
| 234 |
| 236 |
| 244 |
| 245 |
| 247 |
| 248 |
| 287 |
| 291 |
| 292 |
| 294 |
| 302 |
| 303 |
| 304 |
| 331 |
| 335 |
| 345 |
| 353 |
| 358 |
| 370 |
| 373 |
| 387 |
| 403 |
| 404 |
| 405 |
| 406 |
| 408 |
| 419 |
| 420 |
| 421 |
| 427 |
| 439 |
| 441 |
| 446 |
| 447 |
| 451 |
| 470 |
| 474 |
| 484 |
| 492 |
| 561 |
| 562 |
| 580 |
| 604a |
| 604b |
| 608 |
| 611 |
| 612 |
| 613 |
| 615 |
| 616 |
| 620 |
| 621 |
| 623a |
| 623b |
| 624a |
| 624b |
| 625 |
| 627 |
| 628 |
| 634 |
| 643 |
| 653 |
| 655 |
| 670 |
| 671 |
| 672 |
| 673 |
| 674 |
| 675 |

TABLE D

| Compound |
|---|
| 100 |
| 101 |
| 102 |
| 104 |
| 106 |
| 107 |
| 110 |
| 111 |
| 112 |
| 113 |
| 114 |
| 115 |
| 116 |
| 116b |
| 117 |
| 117a |
| 118 |
| 118a |
| 118b |
| 119 |
| 120a |
| 122 |
| 122a |
| 122b |
| 124 |
| 125 |
| 126 |
| 127 |
| 129 |
| 130 |
| 131 |
| 132 |
| 133 |
| 134 |
| 137 |
| 140 |
| 142 |
| 143 |
| 145 |
| 148 |
| 149 |
| 161 |
| 163 |
| 165 |
| 166 |
| 167 |
| 174 |
| 184 |
| 185 |
| 186 |

TABLE D-continued

| Compound |
|---|
| 193 |
| 197 |
| 200 |
| 202 |
| 204 |
| 207 |
| 208 |
| 210 |
| 211 |
| 212 |
| 214 |
| 215 |
| 216 |
| 217 |
| 218 |
| 219 |
| 221 |
| 222 |
| 223 |
| 224 |
| 226 |
| 227 |
| 232 |
| 235 |
| 237 |
| 238 |
| 239 |
| 240 |
| 241 |
| 242 |
| 243 |
| 246 |
| 249 |
| 250 |
| 251 |
| 252 |
| 253 |
| 254 |
| 255 |
| 256 |
| 257 |
| 258 |
| 259 |
| 260 |
| 261 |
| 262 |
| 263 |
| 264 |
| 265 |
| 266 |
| 267 |
| 268 |
| 269 |
| 270 |
| 277 |
| 278 |
| 279 |
| 283 |
| 285 |
| 286 |
| 288 |
| 289 |
| 290 |
| 293 |
| 295 |
| 296 |
| 297 |
| 298 |
| 299 |
| 305 |
| 308 |
| 309 |
| 310 |
| 312 |
| 313 |
| 315 |
| 317 |
| 318 |
| 320 |
| 321 |
| 322 |
| 326 |
| 327 |
| 328 |
| 330 |
| 333 |
| 334 |
| 336 |
| 337 |
| 338 |
| 339 |
| 340 |
| 342 |
| 343 |
| 344 |
| 346 |
| 347 |
| 348 |
| 349 |
| 356 |
| 357 |
| 359 |
| 360 |
| 361 |
| 362 |
| 364 |
| 365 |
| 366 |
| 368 |
| 369 |
| 371 |
| 372 |
| 383 |
| 384 |
| 385 |
| 386 |
| 388 |
| 391 |
| 392 |
| 396 |
| 400 |
| 407 |
| 409 |
| 410 |
| 411 |
| 412 |
| 413 |
| 414 |
| 415 |
| 416 |
| 417 |
| 418 |
| 422 |
| 423 |
| 424 |
| 425 |
| 426 |
| 428 |
| 429 |
| 430 |
| 431 |
| 432 |
| 433 |
| 434 |
| 435 |
| 436 |
| 437 |
| 438 |
| 440 |
| 442 |
| 443 |
| 444 |
| 445 |
| 448 |
| 449 |
| 450 |

TABLE D-continued

| Compound |
|---|
| 452 |
| 453 |
| 454 |
| 455 |
| 456 |
| 457 |
| 458 |
| 459 |
| 460 |
| 461 |
| 462 |
| 463 |
| 464 |
| 465 |
| 466 |
| 467 |
| 468 |
| 469 |
| 471 |
| 473 |
| 475 |
| 476 |
| 477 |
| 479 |
| 482 |
| 483 |
| 485 |
| 486 |
| 487 |
| 488 |
| 489 |
| 490 |
| 491 |
| 495 |
| 496 |
| 498 |
| 498d |
| 500 |
| 501 |
| 502 |
| 503 |
| 504 |
| 507 |
| 510 |
| 514 |
| 515 |
| 516 |
| 517 |
| 518 |
| 525 |
| 526 |
| 527 |
| 528 |
| 529 |
| 530 |
| 531 |
| 532 |
| 533 |
| 534 |
| 535 |
| 536 |
| 537 |
| 538 |
| 539 |
| 540 |
| 541 |
| 542 |
| 543 |
| 545 |
| 546 |
| 547 |
| 548 |
| 549 |
| 550 |
| 551 |
| 552 |
| 553 |
| 554 |
| 556 |
| 557 |
| 558 |
| 559 |
| 560 |
| 563 |
| 565 |
| 568 |
| 569 |
| 570 |
| 571 |
| 574 |
| 575 |
| 577 |
| 578 |
| 579 |
| 583 |
| 586 |
| 587 |
| 590 |
| 592 |
| 593 |
| 594 |
| 595 |
| 596 |
| 597 |
| 598 |
| 599 |
| 604c |
| 605a |
| 605b |
| 605c |
| 605d |
| 606 |
| 607 |
| 609 |
| 610 |
| 614 |
| 617 |
| 619 |
| 626 |
| 629 |
| 630 |
| 631 |
| 632 |
| 633a |
| 633b |
| 635 |
| 637 |
| 638 |
| 639 |
| 640 |
| 642 |
| 644 |
| 645 |
| 646 |
| 650 |
| 654 |
| 656 |
| 662 |
| 663 |
| 664 |
| 665 |
| 666 |

Example C

RSV Polymerase Inhibition Assay

Standard RSV polymerase assays were conducted in the presence of 10 nM recombinant RSV complex in a reaction buffer containing Tris-HCl pH7.5, 6 mM $MgCl_2$, and other additives and substrates including RNA oligonucleotides and radionucleotides. Standard reactions were incubated in 96-well plate format for 2 h at 30° C., in the presence of increasing concentration of inhibitor. The reaction was stopped with 90 µL of 0.1M EDTA, and the reaction product was transferred to a "reading" 96-well plate. After washing of the plate, radiolabeled RNA products were detected according to standard procedures with a Trilux Topcount scintillation counter. The compound concentration at which the enzyme-catalyzed rate was reduced by 50% ($IC_{50}$) was calculated by fitting the data to a non-linear regression (sigmoidal). The $IC_{50}$ values were derived from the mean of several independent experiments and are shown in Tables E and F.

Table E includes compounds with an $IC_{50}$ of <1 µM. Table F includes compounds with an $IC_{50}$<10 µM. Table G includes compounds with an $IC_{50}$ value of <100 µM.

TABLE E

| Compound |
| --- |
| 101 |
| 115 |
| 116 |
| 116b |
| 117 |
| 117b |
| 118 |
| 118b |
| 119 |
| 120 |
| 120b |
| 122 |
| 122a |
| 123 |
| 125 |
| 126 |
| 127 |
| 128 |
| 130 |
| 140 |
| 141 |
| 142 |
| 143 |
| 147 |
| 166 |
| 167 |
| 176 |
| 179 |
| 181 |
| 182 |
| 183 |
| 184 |
| 185 |
| 189 |
| 190 |
| 191 |
| 192 |
| 193 |
| 194 |
| 195 |
| 196 |
| 197 |
| 198 |
| 199 |
| 200 |
| 202 |
| 204 |
| 205 |
| 207 |
| 208 |
| 209 |
| 210 |
| 211 |
| 212 |
| 213 |
| 214 |
| 215 |
| 217 |
| 218 |

TABLE E-continued

| Compound |
| --- |
| 219 |
| 221 |
| 220 |
| 222 |
| 223 |
| 224 |
| 225 |
| 226 |
| 227 |
| 228 |
| 232 |
| 233 |
| 234 |
| 235 |
| 236 |
| 237 |
| 238 |
| 239 |
| 240 |
| 241 |
| 243 |
| 244 |
| 245 |
| 246 |
| 248 |
| 249 |
| 250 |
| 251 |
| 252 |
| 254 |
| 255 |
| 256 |
| 257 |
| 258 |
| 259 |
| 260 |
| 261 |
| 262 |
| 263 |
| 264 |
| 266 |
| 267 |
| 270 |
| 271 |
| 272 |
| 273 |
| 274 |
| 275 |
| 276 |
| 278 |
| 279 |
| 280 |
| 281 |
| 282 |
| 283 |
| 284 |
| 285 |
| 287 |
| 289 |
| 292 |
| 297 |
| 298 |
| 299 |
| 301 |
| 302 |
| 303 |
| 304 |
| 305 |
| 306 |
| 307 |
| 308 |
| 309 |
| 310 |
| 311 |
| 312 |
| 314 |
| 315 |
| 316 |

TABLE E-continued

| Compound |
|---|
| 317 |
| 318 |
| 319 |
| 320 |
| 321 |
| 322 |
| 323 |
| 324 |
| 325 |
| 326 |
| 327 |
| 328 |
| 329 |
| 330 |
| 331 |
| 332 |
| 333 |
| 334 |
| 335 |
| 336 |
| 337 |
| 338 |
| 339 |
| 340 |
| 341 |
| 342 |
| 343 |
| 344 |
| 345 |
| 346 |
| 347 |
| 348 |
| 349 |
| 353 |
| 354 |
| 355 |
| 356 |
| 357 |
| 358 |
| 359 |
| 360 |
| 361 |
| 362 |
| 364 |
| 365 |
| 366 |
| 367 |
| 369 |
| 370 |
| 371 |
| 372 |
| 373 |
| 375 |
| 376 |
| 378 |
| 379 |
| 380 |
| 383 |
| 384 |
| 385 |
| 386 |
| 387 |
| 388 |
| 389 |
| 390 |
| 391 |
| 392 |
| 393 |
| 394 |
| 395 |
| 396 |
| 397 |
| 398 |
| 399 |
| 400 |
| 402 |
| 403 |
| 405 |

TABLE E-continued

| Compound |
|---|
| 406 |
| 409 |
| 411 |
| 413 |
| 415 |
| 418 |
| 419 |
| 421 |
| 423 |
| 424 |
| 425 |
| 428 |
| 431 |
| 432 |
| 434 |
| 435 |
| 436 |
| 437 |
| 440 |
| 442 |
| 443 |
| 444 |
| 445 |
| 447 |
| 448 |
| 449 |
| 451 |
| 452 |
| 453 |
| 454 |
| 455 |
| 456 |
| 459 |
| 460 |
| 461 |
| 462 |
| 463 |
| 464 |
| 465 |
| 466 |
| 467 |
| 469 |
| 470 |
| 473 |
| 474 |
| 475 |
| 476 |
| 479 |
| 481 |
| 482 |
| 483 |
| 485 |
| 486 |
| 487 |
| 488 |
| 489 |
| 491 |
| 493 |
| 494 |
| 495 |
| 496 |
| 497 |
| 498 |
| 498c |
| 498d |
| 499 |
| 500 |
| 501 |
| 501 |
| 502 |
| 503 |
| 504 |
| 505 |
| 506 |
| 507 |
| 508 |
| 509 |
| 510 |

TABLE E-continued

| Compound |
|---|
| 511 |
| 514 |
| 515 |
| 516 |
| 517 |
| 518 |
| 519 |
| 520 |
| 521 |
| 522 |
| 523 |
| 524 |
| 525 |
| 526 |
| 527 |
| 528 |
| 529 |
| 530 |
| 531 |
| 532 |
| 533 |
| 534 |
| 535 |
| 536 |
| 537 |
| 538 |
| 539 |
| 540 |
| 541 |
| 452 |
| 543 |
| 545 |
| 546 |
| 547 |
| 548 |
| 549 |
| 550 |
| 551 |
| 552 |
| 553 |
| 554 |
| 555 |
| 556 |
| 557 |
| 558 |
| 559 |
| 560 |
| 562 |
| 563 |
| 565 |
| 567 |
| 568 |
| 569 |
| 570 |
| 571 |
| 573 |
| 574 |
| 575 |
| 576 |
| 577 |
| 578 |
| 579 |
| 580 |
| 581 |
| 582 |
| 583 |
| 584 |
| 585 |
| 586 |
| 588 |
| 589 |
| 590 |
| 591 |
| 593 |
| 594 |
| 595 |
| 596 |
| 598 |
| 599 |
| 600 |
| 601 |
| 602 |
| 603 |
| 604d |
| 605a |
| 605c |
| 605d |
| 610 |
| 611 |
| 612 |
| 614 |
| 615 |
| 617 |
| 618 |
| 619 |
| 620 |
| 621 |
| 622 |
| 623b |
| 624b |
| 625 |
| 626 |
| 627 |
| 628 |
| 629 |
| 630 |
| 631 |
| 632 |
| 633a |
| 633b |
| 634 |
| 635 |
| 636 |
| 637 |
| 638 |
| 639 |
| 640 |
| 641 |
| 642 |
| 643 |
| 644 |
| 645 |
| 646 |
| 647 |
| 648 |
| 650 |
| 651 |
| 652 |
| 653 |
| 654 |
| 655 |
| 656 |
| 657 |
| 658 |
| 662 |
| 663 |
| 664 |
| 665 |
| 666 |
| 667 |
| 668 |
| 669 |
| 676 |

TABLE F

| Compound |
|---|
| 109 |
| 114 |
| 120a |
| 122b |
| 124 |

TABLE F-continued

| Compound |
|---|
| 145 |
| 146 |
| 148 |
| 149 |
| 150 |
| 151 |
| 153 |
| 154 |
| 165 |
| 168 |
| 174 |
| 175 |
| 177 |
| 187 |
| 188 |
| 203 |
| 216 |
| 247 |
| 253 |
| 265 |
| 268 |
| 277 |
| 286 |
| 290 |
| 294 |
| 296 |
| 300 |
| 313 |
| 350 |
| 352 |
| 363 |
| 377 |
| 404 |
| 416 |
| 417 |
| 426 |
| 438 |
| 450 |
| 471 |
| 477 |
| 478 |
| 480 |
| 484 |
| 490 |
| 492 |
| 498b |
| 512 |
| 513 |
| 561 |
| 564 |
| 572 |
| 592 |
| 597 |
| 604a |
| 604b |
| 604c |
| 607 |
| 608 |
| 609 |
| 613 |
| 616 |
| 623a |
| 624a |
| 659 |
| 660 |
| 672 |
| 673 |

TABLE G

| Compound |
|---|
| 116a |
| 117a |
| 118a |
| 135 |
| 144 |
| 161 |
| 178 |
| 180 |
| 186 |
| 201 |
| 230 |
| 242 |
| 295 |
| 368 |
| 382 |
| 407 |
| 408 |
| 412 |
| 420 |
| 422 |
| 427 |
| 430 |
| 439 |
| 441 |
| 446 |

Example D

RSV Assay

The RSV subgenomic replicon 395 HeLa and APC126 were licensed from Apath (Brooklyn, N.Y.) and were originally developed by Dr. Mark Meeples of Center for Vaccines & Immunity, the Research Institute at Nationwide Children's Hospital in Columbus, Ohio. To generate subgenomic RSV replicon, three glycoprotein genes, those for SH, G, and F, from a full-length recombinant GFP-expressing (rg) RSV antigenomic cDNA were deleted. In their place, a blasticidin S deaminase (bsd) gene was inserted. Through multiple steps, the RSV replicon was established in HeLa cells (395 Hela) or BHK cells (APC126). Both 395 HeLa and APC126 cells were cultured in Dulbecco's Modified Eagle Medium (DMEM) containing 4500 mg/L D-glucose, L-glutamine, and 110 mg/L sodium pyruvate (Invitrogen, Cat. #11995-040). The medium was further supplemented with 10% (v/v) fetal bovine serum (FBS) (Mediatech, Cat. #35-010-CV), 1% (v/v) penicillin/streptomycin (Mediatech, Cat. #30-002-CI), and 10 µg/mL of Blasticidin (BSD) (Invivogen, Cat. code ant-bl-1). Cells were maintained at 37° C. in a humidified 5% $CO_2$ atmosphere.

Determination of 50% inhibitory concentration ($EC_{50}$), 90% inhibitory concentration ($EC_{90}$) and 50% cytotoxic concentration ($CC_{50}$) in RSV replicon cells were performed by the following procedure. On the first day, 5000 RSV replicon cells per well were plated in a 96-well plate. On the following day, compounds to be tested were solubilized in 100% DMSO to 100× the desired final testing concentration. Each compound was serially diluted (1:3) up to 9 distinct concentrations. Compounds in 100% DMSO were reduced to 10% (v/v) DMSO by diluting 1:10 in cell culture media. A 10 µL sample of the compounds diluted to 10% (v/v) DMSO with cell culture media was used to treat the RSV replicon cells in 96-well format. The final DMSO concentration was 1% (v/v). Cells were incubated with compounds for 7 days (for 395Hela) or 3 days (for APC126) at 37° C. in a 5% $CO_2$ atmosphere. In each assay, positive control that was previously characterized in the RSV replicon assay was included.

The *Renilla* Luciferase Assay System (Promega, Cat. #E2820) was used to measure anti-RSV replicon activity. Assay plates were set up as stated above. Luminescence was recorded using a Perkin Elmer multilabel counter Victor3V. $EC_{50}$, the concentration of the drug required for reducing RSV replicon RNA by 50% in relation to the untreated cell control value, was calculated from the plot of percentage reductions of the optical density (OD) value against the drug concentrations using the Microsoft Excel forecast function.

395 HeLa or APC126 cell proliferation assay (Promega; CellTiter-Glo Luminescent Cell Viability Assay, Cat. #G7572) was used to measure cell viability. The CellTiter-Glo® Luminescent Cell Viability Assay is a homogeneous method to determine the number of viable cells in culture based on quantitation of the ATP present, which signals the presence of metabolically active cells. Assay plates were set up in the same format as noted above for the replicon assay. CellTiter-Glo reagent (100 µL) was added to each well and incubated at room temperature for 8 minutes. Luminescence was recorded using a Perkin Elmer multilabel counter Victor3V. The $CC_{50}$, the concentration of the drug required for reducing viable cells by 50% in relation to the untreated cell control value, was calculated from the plot of percentage reductions of the luminescence value against the drug concentrations using the Microsoft Excel forecast function.

Table H includes compounds with an $EC_{50}$ value that is less than 1 µM. Table I includes compounds with an $EC_{50}$ value that is equal to or higher than 1 µM and less than 50 µM. Other tested compounds disclosed herein had an $EC_{50}$ value of 50 µM or greater.

TABLE H

| Compound |
|---|
| 106 |
| 115 |
| 116 |
| 116b |
| 117 |
| 117b |
| 118 |
| 118b |
| 119 |
| 120 |
| 120b |
| 122 |
| 122a |
| 123 |
| 124 |
| 125 |
| 126 |
| 130 |
| 140 |
| 141 |
| 143 |
| 147 |
| 166 |
| 176 |
| 184 |
| 189 |
| 191 |
| 192 |
| 193 |
| 194 |
| 195 |
| 198 |
| 200 |
| 202 |
| 204 |
| 205 |
| 208 |
| 209 |
| 211 |

TABLE H-continued

| Compound |
|---|
| 218 |
| 223 |
| 224 |
| 226 |
| 228 |
| 232 |
| 237 |
| 239 |
| 240 |
| 241 |
| 243 |
| 244 |
| 245 |
| 246 |
| 248 |
| 249 |
| 250 |
| 255 |
| 260 |
| 271 |
| 272 |
| 273 |
| 275 |
| 281 |
| 282 |
| 283 |
| 284 |
| 289 |
| 292 |
| 298 |
| 302 |
| 303 |
| 304 |
| 306 |
| 307 |
| 308 |
| 309 |
| 310 |
| 311 |
| 312 |
| 314 |
| 315 |
| 316 |
| 317 |
| 318 |
| 319 |
| 320 |
| 321 |
| 322 |
| 323 |
| 324 |
| 325 |
| 326 |
| 327 |
| 328 |
| 330 |
| 331 |
| 333 |
| 334 |
| 335 |
| 336 |
| 338 |
| 339 |
| 341 |
| 342 |
| 343 |
| 344 |
| 345 |
| 346 |
| 347 |
| 348 |
| 349 |
| 354 |
| 355 |
| 356 |
| 357 |
| 358 |
| 359 |

TABLE H-continued

| Compound |
|---|
| 360 |
| 361 |
| 362 |
| 363 |
| 364 |
| 365 |
| 366 |
| 369 |
| 370 |
| 371 |
| 372 |
| 373 |
| 376 |
| 379 |
| 380 |
| 383 |
| 384 |
| 385 |
| 386 |
| 387 |
| 388 |
| 389 |
| 390 |
| 391 |
| 392 |
| 393 |
| 394 |
| 395 |
| 396 |
| 397 |
| 398 |
| 400 |
| 403 |
| 405 |
| 406 |
| 409 |
| 411 |
| 413 |
| 415 |
| 418 |
| 419 |
| 421 |
| 423 |
| 424 |
| 425 |
| 428 |
| 431 |
| 434 |
| 436 |
| 437 |
| 442 |
| 443 |
| 444 |
| 445 |
| 447 |
| 448 |
| 449 |
| 452 |
| 453 |
| 454 |
| 455 |
| 456 |
| 459 |
| 460 |
| 462 |
| 466 |
| 467 |
| 470 |
| 483 |
| 485 |
| 486 |
| 487 |
| 488 |
| 489 |
| 490 |
| 491 |
| 493 |
| 494 |

TABLE H-continued

| Compound |
|---|
| 496 |
| 497 |
| 498 |
| 498d |
| 499 |
| 500 |
| 501 |
| 502 |
| 503 |
| 504 |
| 505 |
| 506 |
| 507 |
| 508 |
| 509 |
| 510 |
| 511 |
| 514 |
| 515 |
| 516 |
| 519 |
| 520 |
| 521 |
| 523 |
| 524 |
| 525 |
| 526 |
| 527 |
| 528 |
| 529 |
| 530 |
| 531 |
| 532 |
| 533 |
| 534 |
| 535 |
| 536 |
| 538 |
| 539 |
| 540 |
| 542 |
| 543 |
| 545 |
| 546 |
| 547 |
| 548 |
| 550 |
| 551 |
| 552 |
| 554 |
| 555 |
| 556 |
| 558 |
| 560 |
| 561 |
| 562 |
| 563 |
| 564 |
| 567 |
| 569 |
| 571 |
| 572 |
| 574 |
| 575 |
| 576 |
| 577 |
| 578 |
| 579 |
| 580 |
| 581 |
| 583 |
| 584 |
| 585 |
| 586 |
| 588 |
| 589 |
| 590 |
| 594 |

TABLE H-continued

Compound 595
596
598
600
601
602
603
604d
605d
611
612
614
615
621
622
623b
624b
626
627
630
633b
634
635
636
637
638
640
641
642
643
644
645
646
647
650
651
653
659
663
664
665
667
672
675

TABLE I

Compound 127
128
163
168
220
313
332
375
378
438
461

Example 15

Combination Studies

RSV with *Renilla* Reporter

RSV expressing *Renilla* luciferase (A2-RL-line1 9F) was generated by Dr. Martin Moore of Emory University, Atlanta, Ga., USA. The in vitro viral kinetics of A2-RL-line19F is similar to that of wild type RSV (See Hotard, A. L., *Virology* (2012) 434(1):129-136).

Host cell HEp-2 was purchased from ATCC (Cat. #CCL-23) and cells were cultured in DMEM/Ham's F-12 50/50 1× containing L-glutamine and 15 mM HEPES (Mediatech, Cat. #10-092-CM). The medium was further supplemented with 5% (v/v) FBS (Mediatech, Cat. #35-010-CV) and 1% (v/v) penicillin/streptomycin (Mediatech, Cat. #30-002-CI). HEp-2 cells were maintained at 37° C. in a humidified 5% $CO_2$ atmosphere.

Drug Treatment and Viral Dosing

To determine the effect of a combination of compounds, the following procedure was followed. On the first day, 20,000 HEp-2 cells were plated per well in a 96-well plate. On the following day, test articles were solubilized in 100% DMSO (for chemicals) or 1×PBS (for biologics) to 200× the desired final testing concentration. Subsequently, Compound (A), or a pharmaceutically acceptable salt thereof, was serially diluted (1:3) to 9 distinct concentrations "horizontally" in a 96-well plate, and Compound (B), or a pharmaceutically acceptable salt thereof, was serially diluted (1:3) to 7 distinct concentrations "vertically" in 96-well plate. The serially diluted 200× test articles were then diluted 1:10 into cell culture media to generate 20× test articles. A 5 µL aliquot of the 20× test articles was added in a checkerboard fashion to the cells with 90 µL existing media. Space was also allotted for titrations of each of the compounds alone to be used as reference controls. After 12 hour pre-incubation of test articles, A2-RL-line1 9F at an MOI of 0.5 was added to the plate and further incubated for 2 days at 37° C. in a 5% $CO_2$.

Determination of Anti-RSV Activity

The *Renilla* Luciferase Assay System (Promega, Cat. # E2820) was used to measure anti-RSV replicon activity. Assay plates were set up as stated above. Luminescence was recorded using a Perkin Elmer multilabel counter Victor3V.

Cell Viability Assay

Promega CellTiter-Glo Luminescent Cell Viability Assay, Cat. #G7572) was used to measure cell viability. The CellTiter-Glo® Luminescent Cell Viability Assay is a homogeneous method to determine the number of viable cells in culture based on quantitation of the adenosine triphosphate (ATP) present, which signals the presence of metabolically active cells. Assay plates were set up in the same format the anti-RSV assay, except that no virus was added to the cell viability assay. A 100-µL aliquot of CellTiter-Glo reagent was added to each well and incubated at room temperature for 8 minutes. Luminescence was recorded using a Perkin Elmer multilabel counter Victor3V.

Data Analysis

Each experiment was performed at N=5 for both anti-RSV activity and cell viability. Mean percent inhibition of the replicon values from the 5 experiments was generated and for anti-RSV activity, it was analyzed using two drug interaction analysis models, Isobologram Analysis and/or Prichard's Model.

Isobologram Analysis

The effects of drug-drug combinations were evaluated by the Loewe additivity model in which the experimental data were analyzed using CalcuSyn (Biosoft, Ferguson, Mo.), a computer program based on the method of Chou and Talalay. The combination index (CI) value and the isobologram for each experimental combination were calculated. CI values of <1, 1, and >1 indicate synergy, additive effect, and antagonism, respectively. Under the synergy category, CI<0.1 is considered very strong synergism; CI 0.1-0.3 strong synergism; CI 0.3-0.7 synergism and CI 0.7-0.85 moderate synergism. The isobologram analysis, which graphically represents additive, synergistic, and antagonistic drug effects, was also used to model the interaction of antiviral activities. In this representation, an effective concentration (EC) value of one drug is plotted on one axis and corresponding EC value of a second drug is plotted on the second axis; the line connecting these two points represents the amount of each drug in a combination that would be required to reach the equivalent EC value, given that their effects are additive.

Prichard's Model (MacSynergy II)

MacSynergy II software was kindly provided by Dr. M. Prichard (University of Michigan). This program allows the three-dimensional examination of drug interactions of all data points generated from the checkerboard combination of two inhibitors with Bliss-Independence model. Confidence bounds are determined from replicate data. If the 95% confidence limits (CL) do not overlap the theoretic additive surface, then the interaction between the two drugs differs significantly from additive. The volumes of synergy or antagonism can be determined and graphically depicted in three dimensions and represent the relative quantity of synergism or antagonism per change in the two drug concentrations. Synergy and antagonism volumes are based on the Bliss independence model, which assumes that both compounds act independently on different targets. A set of predicted fractional responses faAB under the Bliss independence model is calculated as faAB=faA+faB −faA•faB with faA andfaB representing the fraction of possible responses, e.g. % inhibition, of compounds A and B at amounts dA and dB, respectively, and describes the % inhibition of a combination of compounds A and B at amount (dA+dB). If faAB >faA +faB −faA•faB then we have Bliss synergy; if faAB <faA+faB −faA•faB then we have Bliss antagonism. The 95% synergy/antagonism volumes are the summation of the differences between the observed inhibition and the 95% confidence limit on the prediction of faAB under the Bliss independence model. MacSynergy II was used for data analysis.

MacSynergy II Volume Descriptions: <25 $\mu M^2\%$=Additive; 25-50 $\mu M^2\%$=Minor synergism; 50-100 $\mu M^2\%$=Significant synergism; and >100 $\mu M^2\%$=Strong synergism. For the combination of 574 and BMS-433771 (a fusion protein inhibitor) had a synergy volume of 24.9 $\mu M^2\%$ (additive/minor synergism).

Example F

Parainfluenza Virus-3 (PIV-3) Plaque Assay

MA-104 cells are grown in 24-well plates to a confluency of 90% in the presence of minimal essential medium (MEM) supplemented with 10% fetal bovine serum and antibiotics (C-EMEM). The cells are then washed twice with non-complete minimal essential medium (NC-EMEM). Test articles are dissolved in DMSO to a stock concentration of 10 mM.

An aliquot of 0.5 mL of the test article at various concentrations are then inoculated in triplicate wells and are incubated for 60 mins at 37° C. with 5% $CO_2$ for the diffusion of test article into MA-104 cells. After the incubation period, a stock of human PIV type 3 are thawed and diluted with NC-EMEM to achieve a viral concentration of $10^4$ pfu/mL. An aliquot of 0.1 mL are then inoculated into all the wells except for the negative and test article toxicity control wells. Upon infection, the plates are incubated for 72 h at 37° C. at 5% $CO_2$. After incubation, the plates are examined under microscopy to record cytotoxicity. The supernatants are collected for viral quantification using a standard plaque assay using MA-104 cells as the indicator cells.

To perform the plaques assay, MA-104 cells are grown to confluence in 24-well plates. The cells are washed with serum-free medium prior to inoculation of duplicate wells with serial 10-fold dilutions of supernatant sample. After 1 h incubation at 37° C., the samples are aspirated and 1.0 mL of methyl cellulose overlay media are added to each well. After 6 days of culture, the cells are fixed and stained with 0.06% crystal violet in 1% glutaraldehyde and viral plaques are enumerated. The data are analyzed with Prism software with $EC_{50}$ defined as drug concentration that reduced the viral load 50% from the viral control (VC).

Example G

Human Metapneumovirus (hMPV) $TCID_{50}$ Assay

LLC-MK2 cells are grown in 24-well plates to a confluency of 90% in the presence of minimal essential medium (MEM) supplemented with 10% fetal bovine serum and antibiotics (C-EMEM). The cells are then washed twice with non-complete minimal essential medium (NC-EMEM). Test articles are dissolved in DMSO to a stock concentration of 10 mM.

An aliquot of 0.5 mL of the test article at various concentrations are then inoculated in triplicate wells and are incubated for 60 mins at 37° C. with 5% $CO_2$ for the diffusion of test article into LLC-MK2 cells. After the incubation period, a stock of human metapneumovirus are thawed and diluted with NC-EMEM to achieve a viral concentration of $10^4$ pfu/mL. An aliquot of 0.1 mL are then inoculated into all the wells except for the negative and test article toxicity control wells. Upon infection, the plates are incubated for 7 days at 37° C. at 5% $CO_2$. After incubation, the plates are examined under microscopy to record cytotoxicity. The supernatants are collected for viral quantification using a standard $TCID_{50}$ assay using LLC-MK2 cells as the indicator cells. The data are analyzed with Prism software with $EC_{50}$ defined as drug concentration that reduced the viral load 50% from the viral control (VC).

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

A-L-Y    (I)

wherein: L is Formula (Ib1):

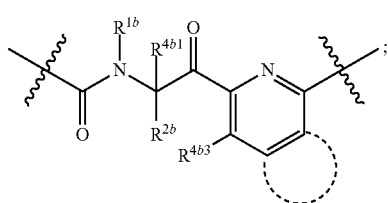

(Ib1)

wherein the dashed semi-circle along with the two carbon atoms to which it is connected form an optionally substituted cycloalkenyl, an optionally substituted aryl, an optionally substituted heteroaryl or an optionally substituted heterocyclyl;

$R^{4b3}$ is selected from the group consisting of hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy;

A is selected from the group consisting of an optionally substituted cycloalkyl, an optionally substituted cycloalkenyl, an optionally substituted aryl, an optionally substituted aryl(C$_{1-2}$ alkyl), an optionally substituted heteroaryl and an optionally substituted heterocyclyl;

Y is selected from the group consisting of an optionally substituted cycloalkyl, an optionally substituted cycloalkenyl, an optionally substituted aryl, an optionally substituted heteroaryl and an optionally substituted heterocyclyl;

R$^{1b}$ is hydrogen or an unsubstituted C$_{1-4}$ alkyl; and

R$^{2b}$ and R$^{2b1}$ are each independently selected from the group consisting of hydrogen, an optionally substituted C$_{1-4}$ alkyl, an optionally substituted aryl(C$_{1-6}$ alkyl), an optionally substituted heterocyclyl(C$_{1-6}$ alkyl), an alkoxyalkyl, an aminoalkyl, a hydroxyalkyl and hydroxy; or R$^{2b1}$ is hydrogen, and R$^{1b}$ and R$^{2b}$ are joined together with the atoms to which they are attached to form an optionally substituted 5 membered heterocyclyl or an optionally substituted 6 membered heterocyclyl.

2. The compound of claim 1, or a pharmaceutically acceptable salt thereof, wherein

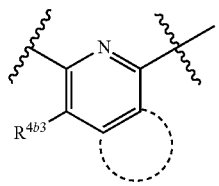

is an optionally substituted

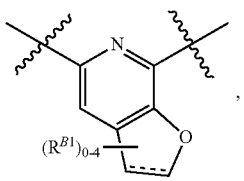, an optionally substituted

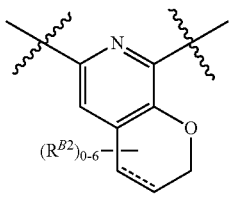

or an optionally substituted

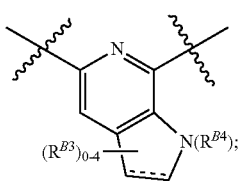

wherein each ----- is independently absent or a bond; each R$^{B1}$, each R$^{B2}$ and each R$^{B3}$ is independently an unsubstituted C$_{1-6}$ alkyl, halogen, hydroxy, amino, mono-substituted amino, di-substituted amino or —NH—S(=O)C$_{1-4}$ alkyl; and R$^{B4}$ is hydrogen or an unsubstituted C$_{1-6}$ alkyl.

3. The compound of claim 1, or a pharmaceutically acceptable salt thereof, wherein R$^{1b}$ is hydrogen.

4. The compound of claim 1, or a pharmaceutically acceptable salt thereof, wherein R$^{1b}$ is unsubstituted C$_{1-4}$ alkyl.

5. The compound of claim 1, or a pharmaceutically acceptable salt thereof, wherein R$^{2b}$ and R$^{2b1}$ are both hydrogen.

6. The compound of claim 1, or a pharmaceutically acceptable salt thereof, wherein A is an optionally substituted aryl.

7. The compound of claim 6, or a pharmaceutically acceptable salt thereof, wherein A is an optionally substituted phenyl.

8. The compound of claim 7, or a pharmaceutically acceptable salt thereof, wherein A is a phenyl substituted with one or more substituents selected from the group consisting of: an unsubstituted C$_{1-4}$ alkyl, a substituted C$_{1-4}$ alkyl, cycloalkyl, hydroxy, an unsubstituted C$_{1-4}$ alkoxy, a substituted C$_{1-4}$ alkoxy, halogen, haloalkyl, an optionally substituted haloalkoxy, nitro, amino, mono-substituted amino, di-substituted amine, —O-amido, sulfenyl, alkyoxyalkyl, an optionally substituted aryl, an optionally substituted mono-cyclic heteroaryl, an optionally substituted mono-cyclic heterocyclyl, an optionally substituted aryl (C$_{1-4}$ alkyl), an optionally substituted monocyclic heteroaryl (C$_{1-4}$ alkyl), an optionally substituted monocyclic heterocyclyl(C$_{1-4}$ alkyl), hydroxyalkyl and aminoalkyl.

9. The compound of claim 7, or a pharmaceutically acceptable salt thereof, wherein A is a phenyl substituted with one or more substituents selected from the group consisting of: methyl, ethyl, propyl, butyl, hydroxy, methoxy, ethoxy, n-propoxy, iso-propoxy, n-butoxy, iso-butoxy, t-butoxy, phenoxy, bromo, chloro, fluoro, trifluoromethyl, difluoromethoxy, trifluoromethoxy, cyano, N,N-di-methyl-amine, N,N-di-ethyl-amine, N-methyl-N-ethyl-amine, N-methyl-amino, N-ethyl-amino, amino, N-amido, N-sulfonamido, alkylthio, an optionally substituted phenyl, an optionally substituted imidazole, an optionally substituted morpholinyl, an optionally substituted pyrazole, an optionally substituted pyrrolidinyl, an optionally substituted pyridinyl, an optionally substituted piperidinyl, an optionally substituted piperidinone, an optionally substituted pyrrolidinone, an optionally substituted pyrimidine, an optionally substituted pyrazine, an optionally substituted 1,2,4-oxadiazole, —(CH$_2$)$_{1-4}$—OH, —(CH$_2$)$_{1-2}$—NH(CH$_3$), an optionally substituted —(CH$_2$)$_{1-2}$-imidazole, an optionally substituted —(CH$_2$)$_{1-2}$-pyrrolidinone, an optionally substituted —(CH$_2$)$_{1-2}$-imidazolidinone, —O(CH$_2$)$_2$—NH$_2$, —O(CH$_2$)$_2$—NH(CH$_3$), —O(CH$_2$)$_2$—N(CH$_3$)$_2$, —O—(CH$_2$)$_{2-4}$OH, —O(CH$_2$)$_2$OCH$_3$, an optionally substituted —O(CH$_2$)$_{0-2}$-cyclopentanone, an optionally substituted —O(CH$_2$)$_{0-2}$pyrrolidinone, an optionally substituted —O(CH$_2$)$_{0-2}$-morpholinyl, an optionally substituted —O(CH$_2$)$_{0-2}$-triazole, an optionally substituted —O(CH$_2$)$_{0-2}$-imidazole, an optionally substituted —O(CH$_2$)$_{0-2}$-pyrazole, an optionally substituted —O(CH$_2$)$_{0-2}$-tetrahydrofuran, an optionally substituted —O(CH$_2$)$_{0-2}$-pyrrolidinone, an optionally substituted —O(CH$_2$)$_{0-2}$-tetrazole, an optionally substituted —O(CH$_2$)$_{0-2}$-tetrazolone,

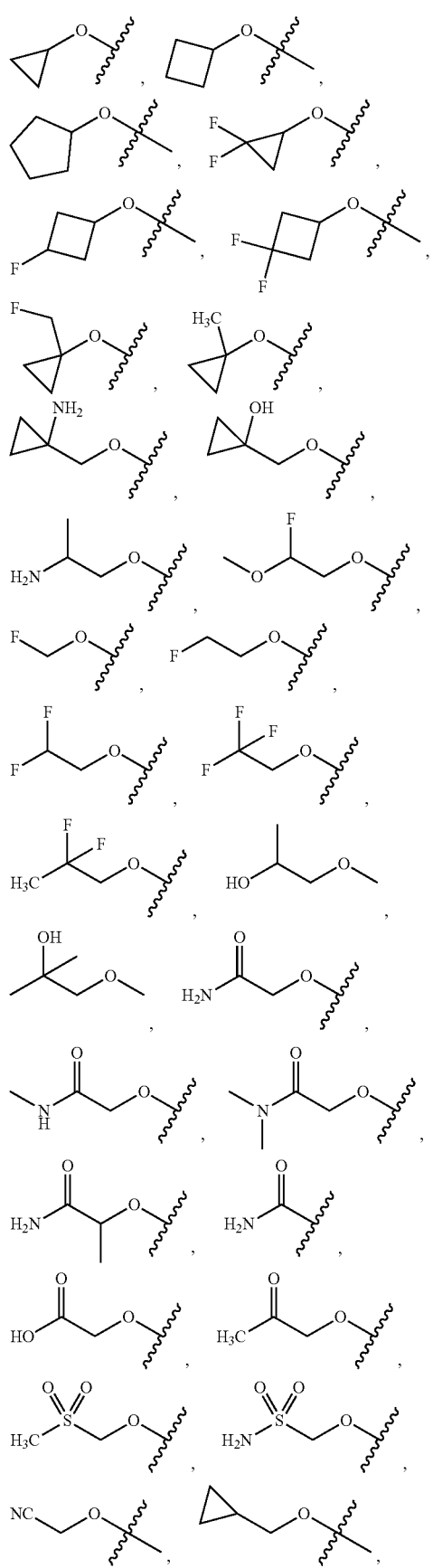

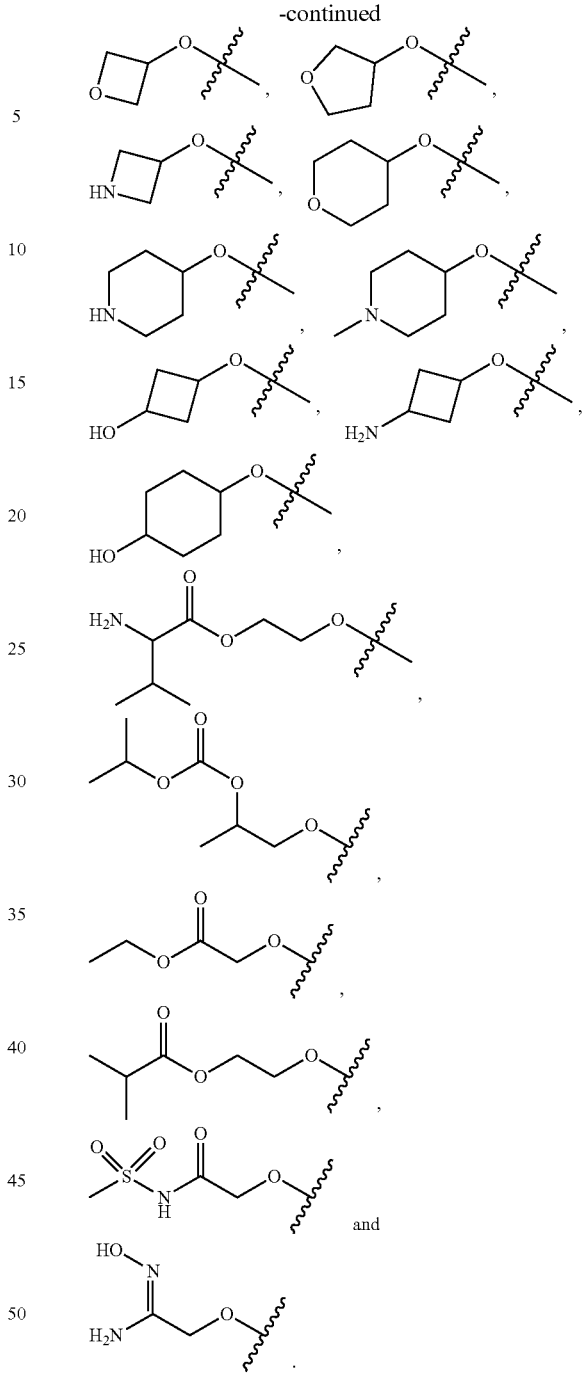

10. The compound of claim 7, or a pharmaceutically acceptable salt thereof, wherein A is a di-substituted phenyl.

11. The compound of claim 1, or a pharmaceutically acceptable salt thereof, wherein Y is an optionally substituted aryl.

12. The compound of claim 11, or a pharmaceutically acceptable salt thereof, wherein Y is a mono-substituted phenyl.

13. The compound of claim 11, or a pharmaceutically acceptable salt thereof, wherein Y is a di-substituted phenyl.

14. The compound of claim 1, or a pharmaceutically acceptable salt thereof, wherein Y is unsubstituted.

15. The compound of claim 1, or a pharmaceutically acceptable salt thereof, wherein Y is substituted with one or more $R^B$, wherein each $R^B$ is independently selected from the group consisting of: cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, alkoxyalkyl, $C_{1-4}$ haloalkyl, haloalkoxy, an unsubstituted acyl, an optionally substituted —C-carboxy, an optionally substituted —C-amido, sulfonyl, carbonyl, amino, mono-substituted amine, di-substituted amine and

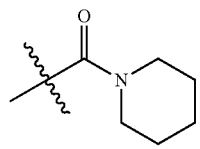

16. The compound of claim 1, or a pharmaceutically acceptable salt thereof, wherein Y is an optionally substituted benzothiophene.

17. The compound of claim 1, or a pharmaceutically acceptable salt thereof, wherein Y is an optionally substituted benzofuran or an optionally substituted indole.

18. The compound of claim 1, or a pharmaceutically acceptable salt thereof, wherein the compound is:

217

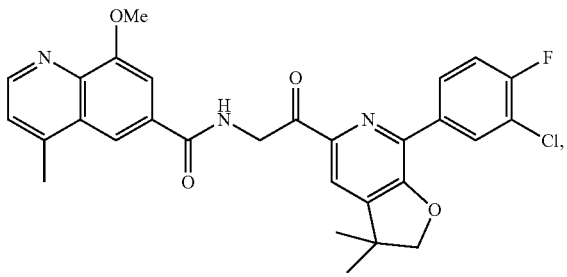

229

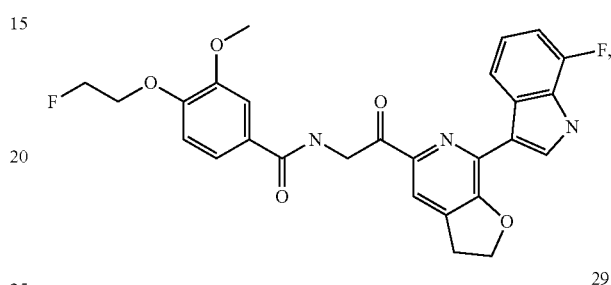

287

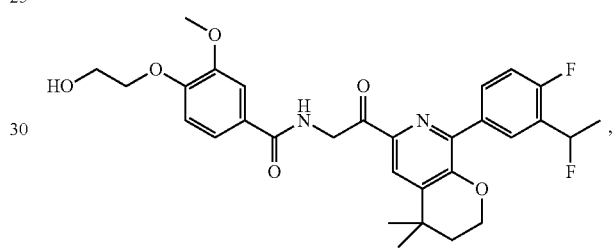

298

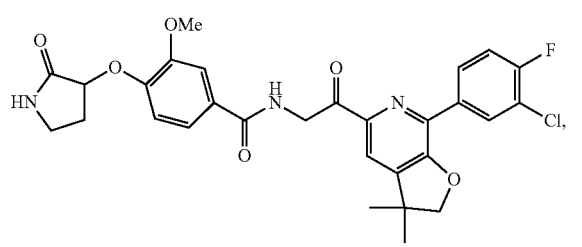

220

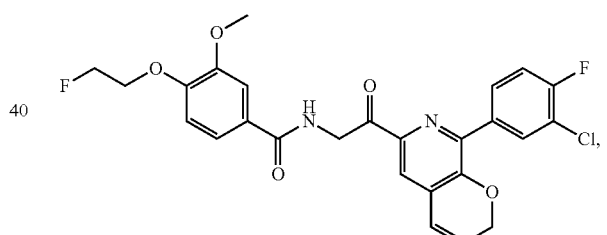

302

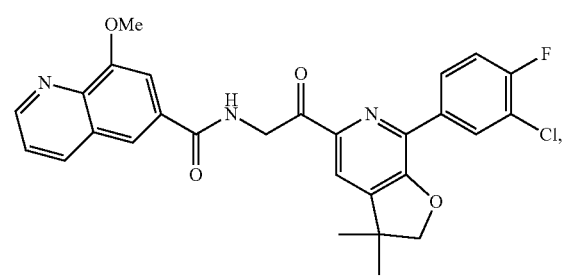

222

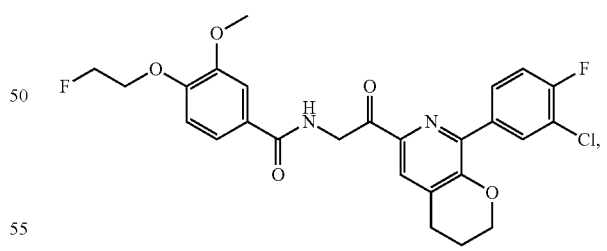

303

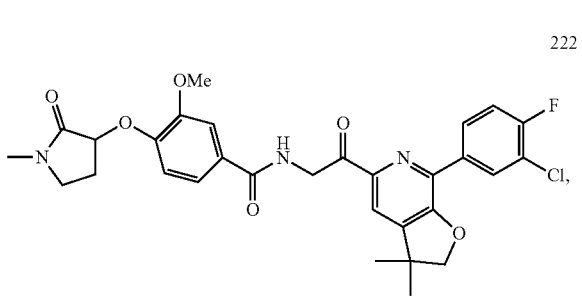

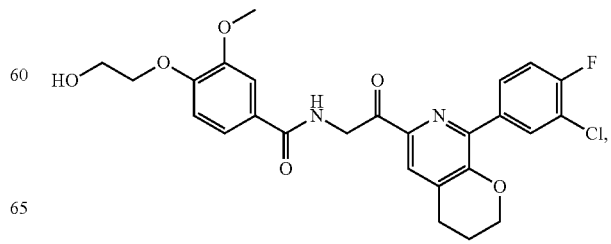

304

-continued

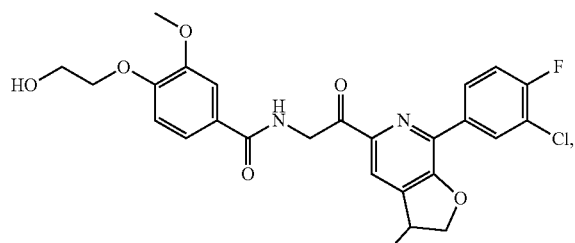

305

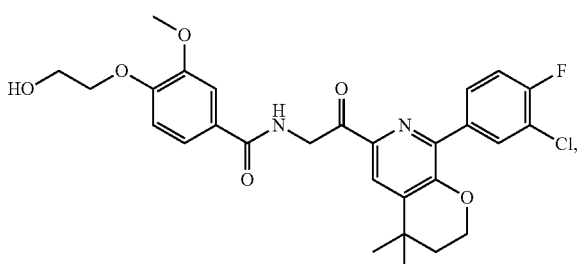

311

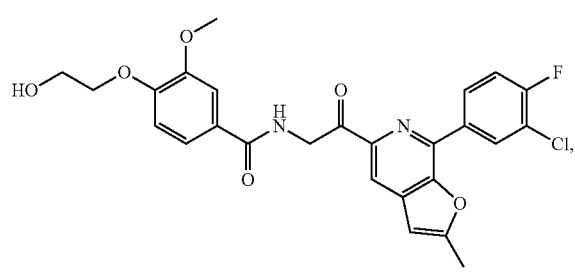

401

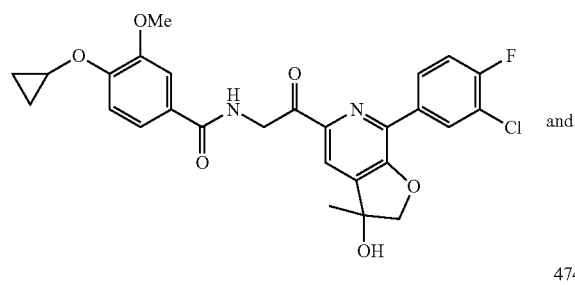

473

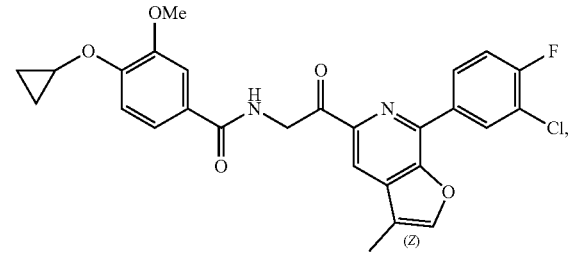

474 or a pharmaceutically acceptable salt thereof.

19. The compound of claim 1, or a pharmaceutically acceptable salt thereof, wherein the compound is:

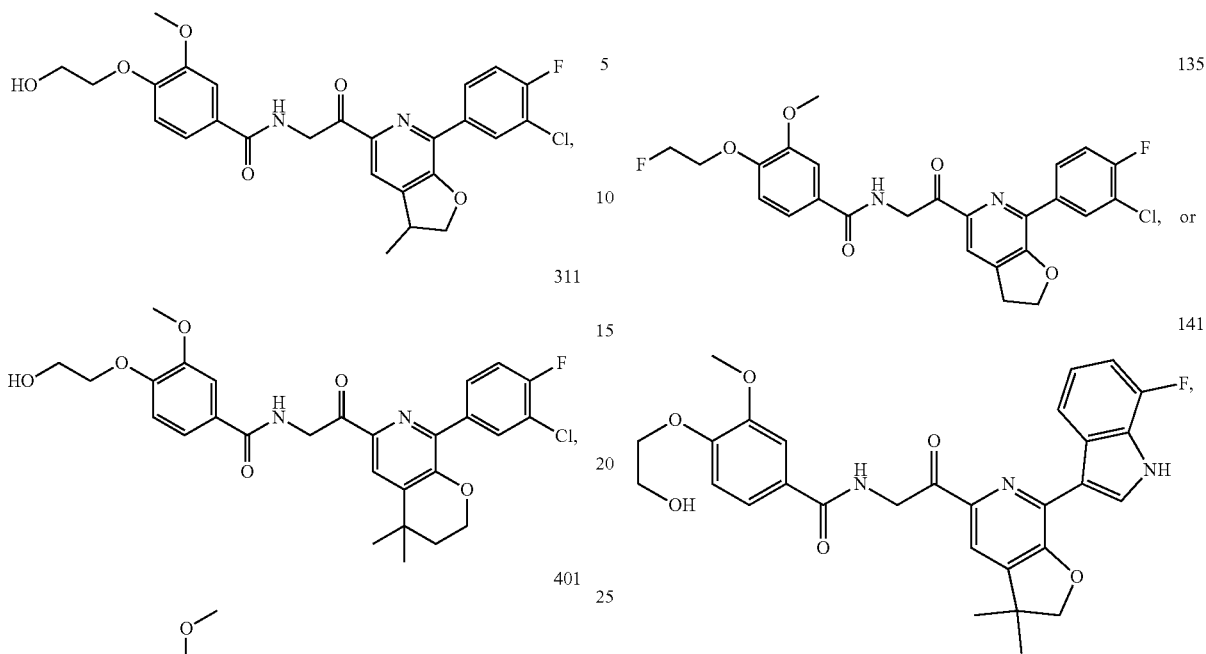

or a pharmaceutically acceptable salt thereof.

20. A pharmaceutical composition comprising an effective amount of a compound of claim 1, or a pharmaceutically acceptable salt thereof, and a pharmaceutically acceptable carrier, diluent, excipient, or combination thereof.

21. A method of ameliorating or treating a paramyxovirus infection, comprising administering to a subject suffering from the paramyxovirus infection an effective amount of a compound of claim 1, or a pharmaceutically acceptable salt thereof.

22. A method of ameliorating or treating a paramyxovirus infection, comprising contacting a cell infected with the paramyxovirus with an effective amount of a compound of claim 1, or a pharmaceutically acceptable salt thereof.

23. The method of claim 21, wherein the paramyxovirus infection is a human respiratory syncytial virus infection.

24. A method for inhibiting viral replication of a paramyxovirus, comprising contacting a cell infected with the paramyxovirus with an effective amount of a compound of claim 1, or a pharmaceutically acceptable salt thereof.

25. The method of claim 24, further comprising contacting the cell with an effective amount with one or more additional anti-RSV agents, wherein each of the one or more additional anti-RSV agents is selected from the group consisting of an anti-RSV antibody, a fusion protein inhibitor, an N-protein inhibitor, an RSV polymerase inhibitor, an IMPDH inhibitor, an interferon and any other compound that inhibits RSV virus, and pharmaceutically acceptable salts thereof.

* * * * *